(12) United States Patent
Gakhal et al.

(10) Patent No.: US 12,144,869 B2
(45) Date of Patent: *Nov. 19, 2024

(54) ANTI-ROR1 ANTIBODY CONJUGATES, COMPOSITIONS COMPRISING ANTI ROR1 ANTIBODY CONJUGATES, AND METHODS OF MAKING AND USING ANTI-ROR1 ANTIBODY CONJUGATES

(71) Applicant: Sutro Biopharma, Inc., South San Francisco, CA (US)

(72) Inventors: Amandeep Gakhal, San Mateo, CA (US); Abigail Yu, San Jose, CA (US); Ryan Stafford, Foster City, CA (US); Jeffrey Hanson, Oakland, CA (US); Alice Yam, Belmont, CA (US); Krishna Bajjuri, Union City, CA (US); Andreas Maderna, Walnut Creek, CA (US); Cristina Abrahams, Burlingame, CA (US); Xiaofan Li, Belmont, CA (US); Gang Yin, South San Francisco, CA (US); Miao Wen, Union City, CA (US); Kristin Bedard, Bellevue, WA (US); Daniel Calarese, Millbrae, CA (US); Helena Kiefel, South San Francisco, CA (US)

(73) Assignee: SUTRO BIOPHARMA, INC., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/345,892

(22) Filed: Jun. 30, 2023

(65) Prior Publication Data

US 2024/0058465 A1 Feb. 22, 2024

Related U.S. Application Data

(60) Provisional application No. 63/495,635, filed on Apr. 12, 2023, provisional application No. 63/489,926, filed on Mar. 13, 2023, provisional application No. 63/487,706, filed on Mar. 1, 2023, provisional application No. 63/382,262, filed on Nov. 3, 2022, provisional application No. 63/389,741, filed on Jul. 15, 2022, provisional application No. 63/357,442, filed on Jun. 30, 2022.

(51) Int. Cl.
*A61K 47/68* (2017.01)
*A61K 31/502* (2006.01)
*A61P 35/00* (2006.01)

(52) U.S. Cl.
CPC ........ *A61K 47/6869* (2017.08); *A61K 31/502* (2013.01); *A61K 47/6803* (2017.08); *A61K 47/6805* (2017.08); *A61K 47/6809* (2017.08); *A61K 47/6849* (2017.08); *A61K 47/6889* (2017.08); *A61P 35/00* (2018.01)

(58) Field of Classification Search
CPC combination set(s) only.
See application file for complete search history.

(56) References Cited

U.S. PATENT DOCUMENTS

2018/0079811 A1* 3/2018 Molloy ................... A61P 17/00
2021/0155692 A1* 5/2021 Bailey ................ C07K 16/2818

FOREIGN PATENT DOCUMENTS

| WO | WO 2016/123582 A1 | 8/2016 | |
|----|----|----|----|
| WO | WO 2017/072361 A1 | 5/2017 | |
| WO | WO 2018/237335 A1 | 12/2018 | |
| WO | WO-2020227105 A1 * | 11/2020 | ......... A61K 47/6803 |
| WO | WO 2022/011075 A1 | 1/2022 | |
| WO | WO 2024/006272 A1 | 1/2024 | |

OTHER PUBLICATIONS

Almagro JC et al., Progress and Challenges in the Design and Clinical Development of Antibodies for Cancer Therapy Front. Immunol. 2018; 8:1751 (Year: 2018).*

Chiu ML et al. Antibody Structure and Function: The Basis for Engineering Therapeutics. Antibodies 2019 8, 55, 1-80 (Year: 2019).*

Xu Y et al. RP-HPLC DAR Characterization of Site-Specific Antibody Drug Conjugates Produced in a Cell-Free Expression System. (Org. Process Res. Dev. 2016, 20, 6, 1034-1043) (Year: 2016).*

Bonaventure P et al. A selective orexin-1 receptor antagonist attenuates stress-induced hyperarousal without hypnotic effects. (Journal of Pharmacology and Experimental Therapeutics 352.3 (2015): 590-601 (Year: 2015).*

NIH NLM MeSH, https://www.ncbi.nlm.nih.gov/mesh/67009863, 2024 (Year: 2024).*

(Continued)

*Primary Examiner* — Karen A. Canella
*Assistant Examiner* — John J Skoko, III
(74) *Attorney, Agent, or Firm* — SQUIRE PATTON BOGGS (US)

(57) ABSTRACT

The present disclosure relates to antibodies and antibody conjugates, for instance antibody drug conjugates, with binding specificity for receptor tyrosine kinase orphan receptor 1 (ROR1) and its isoforms and homologs, and compositions comprising the antibodies or antibody conjugates, including pharmaceutical compositions. Also provided are methods of producing the antibodies and antibody conjugates and compositions thereof as well as methods of using the antibodies and antibody conjugates and compositions thereof, such as in therapeutic and diagnostic methods.

24 Claims, 61 Drawing Sheets

Specification includes a Sequence Listing.

(56) References Cited

OTHER PUBLICATIONS

Invitation to Pay Additional Fees and, Where Applicable, Protest fee dated Oct. 23, 2023 for the PCT Application No. PCT/US2023/026769; 18 pages.
Notification of Transmittal of the International Search Report and the Written Opinion of the International Searching Authority dated Dec. 14, 2023 for the PCT Application No. PCT/US2023/026769; 24 pages.
U.S. Appl. No. 18/349,337 Pending Claims, filed Dec. 18, 2023; 38 pages.
Freise and Wu, "In vivo imaging with antibodies and engineered fragments", Molecular Immunology, 2015, vol. 67, pp. 142-152.
Jeffrey et al., "Development and Properties of fl-Glucuronide Linkers for Monoclonal Antibody—Drug Conjugates", Bioconjugate Chemistry, American Chemical, US, vol. 17, No. 3, May 1, 2006, pp. 831-840, XP002423719; DOI: 10.1021/BC0600214.
Li et al., "The promising role of antibody drug conjugate in cancer therapy: Combining targeting ability with cytotoxicity effectively", Cancer Medicine, 2021, vol. 10, pp. 4677-4696.
Lowe et al., "Aggregation, Stability, And Formulation of Human Antibody Therapeutics", Advances in Protein Chemistry and Structural Biology, 2011, vol. 84, pp. 41-61.
Snyder et al., "Metabolism of an Oxime-Linked Antibody Drug Conjugate, AGS62P1, and Characterization of Its Identified Metabolite", Molevular Pharmaceutics, 2018, vol. 15, pp. 2384-2390.
Zimmerman et al., "Production of Site-Specific Antibody—Drug Conjugates Using Optimized Non-Natural Amino Acids in a Cell-Free Expression System", Bioconjugate Chemistry, 2014, vol. 25, pp. 351-361.

\* cited by examiner

FIG. 2

| Column # | 62 | 63 | 64 | 65 | 66 | 67 | 68 | 69 | 70 | 71 | 72 | 73 | 74 | 75 | 76 | 77 | 78 | 79 | 80 | 81 | 82 | 83 | 84 | 85 | 86 | 87 | 88 | 89 | 90 | 91 | 92 | 93 | 94 | 95 | 96 | 97 | 98 | 99 | 100 | 101 | 102 | 103 | 104 | 105 | 106 | 107 | 108 | 109 | 110 | 111 | 112 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| 1987-C05 | D | S | V | K | G | R | F | T | I | S | A | D | T | S | K | N | T | A | Y | L | Q | M | N | S | L | R | A | E | D | T | A | V | Y | Y | C | A | R | D | Y | - | - | - | - | - | - | G | V | F | D | Y |
| 2188-D11 | D | S | V | K | G | R | F | T | I | S | A | D | T | S | K | N | T | A | Y | L | Q | M | N | S | L | R | A | E | D | T | A | V | Y | Y | C | A | R | D | Y | - | - | - | - | - | - | G | V | F | D | Y |
| 2188-B04 | D | S | V | K | G | R | F | T | I | S | A | D | T | S | K | N | T | A | Y | L | Q | M | N | S | L | R | A | E | D | T | A | V | Y | Y | C | A | R | D | Y | - | - | - | - | - | - | G | V | F | D | Y |
| 2188-C09 | D | S | V | T | G | R | F | T | I | S | A | D | T | S | K | N | T | A | Y | L | Q | M | N | S | L | R | A | E | D | T | A | V | Y | Y | C | A | R | D | Y | - | - | - | - | - | - | G | V | F | D | Y |
| 2188-G03 | D | S | V | K | G | R | F | T | I | S | A | D | T | S | K | N | T | A | Y | L | Q | M | N | S | L | R | A | E | D | T | A | V | Y | Y | C | A | R | D | F | - | - | - | - | - | - | G | V | F | D | Y |
| 2188-E03 | D | S | V | K | G | R | F | T | I | S | A | D | T | S | K | N | T | A | Y | L | Q | M | N | S | L | R | A | E | D | T | A | V | Y | Y | C | A | R | D | Y | - | - | - | - | - | - | G | V | Y | D | Y |
| 2188-B11 | D | S | V | K | G | R | F | T | I | S | A | D | T | S | K | N | T | A | Y | L | Q | M | N | S | L | R | A | E | D | T | A | V | Y | Y | C | A | R | D | Y | - | - | - | - | - | - | G | V | F | D | Y |
| 2188-E07 | D | S | V | K | G | R | F | T | I | S | A | D | T | S | K | S | T | A | Y | L | Q | M | N | S | L | R | A | E | D | T | A | V | Y | Y | C | A | R | D | Y | - | - | - | - | - | - | G | V | Y | D | Y |
| 2188-B02 | D | S | V | K | G | R | F | T | I | S | A | D | T | S | K | N | T | A | Y | L | Q | M | N | S | L | R | A | E | D | T | A | V | Y | Y | C | A | R | D | Y | - | - | - | - | - | - | G | V | F | D | Y |
| 2188-C07 | D | S | V | K | G | R | F | T | I | S | A | D | T | S | K | N | T | A | Y | L | Q | M | N | S | L | R | A | E | D | T | A | V | Y | Y | C | A | R | D | Y | - | - | - | - | - | - | G | V | F | D | Y |
| 2188-A03 | D | S | V | K | G | R | F | T | I | S | A | D | T | S | K | N | T | A | Y | L | Q | M | N | S | L | R | A | E | D | T | A | V | Y | Y | C | A | R | D | Y | - | - | - | - | - | - | G | V | F | D | Y |
| 2188-F03 | D | S | V | K | G | R | F | T | I | S | A | D | T | S | K | N | T | A | Y | L | Q | M | N | S | L | R | A | E | D | T | A | V | Y | Y | C | A | R | D | Y | - | - | - | - | - | - | G | V | L | D | Y |
| 2188-D03 | D | S | V | K | G | R | F | T | I | S | A | D | T | S | K | N | T | A | Y | L | Q | M | N | S | L | R | A | E | D | T | A | V | Y | Y | C | A | R | D | Y | - | - | - | - | - | - | G | V | F | D | Y |
| 2188-C04 | D | S | V | R | G | R | F | T | I | S | A | D | T | S | K | N | T | A | Y | L | Q | M | N | S | L | R | A | E | D | T | A | V | Y | Y | C | A | R | D | Y | - | - | - | - | - | - | G | V | F | D | Y |
| 2188-D10 | D | S | V | K | G | R | F | T | I | S | A | D | T | S | K | N | T | A | Y | L | Q | M | N | S | L | R | A | E | D | T | A | V | Y | Y | C | A | R | D | Y | - | - | - | - | - | - | G | V | F | D | Y |
| 2188-A06 | D | S | V | K | G | R | F | T | I | S | A | D | T | S | K | N | T | A | Y | L | Q | M | N | S | L | R | A | E | D | T | A | V | Y | Y | C | A | R | D | Y | - | - | - | - | - | - | G | V | F | D | Y |
| 2188-C11 | D | S | V | K | G | R | F | T | I | S | A | D | T | S | K | N | T | A | Y | L | Q | M | N | S | L | R | A | E | D | T | A | V | Y | Y | C | A | R | D | Y | - | - | - | - | - | - | G | V | F | D | Y |
| 2188-F01 | D | S | V | K | G | R | F | T | I | S | A | D | T | S | K | N | T | A | Y | L | Q | M | N | S | L | R | A | E | D | T | A | V | Y | Y | C | A | R | D | F | - | - | - | - | - | - | G | V | F | D | Y |
| 2188-E11 | D | S | V | K | G | R | F | T | I | S | A | D | T | S | K | N | T | A | Y | L | Q | M | N | S | L | R | A | E | D | T | A | V | Y | Y | C | A | R | D | Y | - | - | - | - | - | - | G | V | F | D | Y |
| 2188-A07 | D | S | V | K | G | R | F | T | I | S | A | D | T | S | K | N | T | A | Y | L | Q | M | N | S | L | R | A | E | D | T | A | V | Y | Y | C | A | R | D | Y | - | - | - | - | - | - | G | V | F | D | Y |
| 2188-C01 | D | S | V | K | G | R | F | T | I | S | A | D | T | S | K | N | T | A | Y | L | Q | T | K | S | L | R | A | E | D | T | A | V | Y | Y | C | A | R | D | Y | - | - | - | - | - | - | G | V | F | D | Y |
| 2188-F08 | D | S | V | K | G | R | F | T | I | S | A | D | T | S | K | N | T | A | Y | L | Q | M | N | S | L | R | A | E | D | T | A | V | Y | Y | C | A | R | D | Y | - | - | - | - | - | - | G | V | F | D | Y |
| 2188-E04 | D | S | V | K | G | R | F | T | I | S | A | D | T | S | K | N | T | A | Y | L | Q | M | D | S | L | R | A | E | D | T | A | V | Y | Y | C | A | R | D | Y | - | - | - | - | - | - | G | V | F | D | Y |
| 2188-B01 | D | S | V | K | G | R | F | T | I | S | A | D | T | S | K | N | T | A | Y | L | Q | M | N | S | L | R | A | G | D | T | A | V | Y | Y | C | A | R | D | Y | - | - | - | - | - | - | G | V | F | D | Y |
| 2188-F11 | D | S | V | K | G | R | F | T | I | S | A | D | T | S | K | N | T | A | Y | L | Q | M | N | S | L | R | A | E | D | T | A | V | Y | Y | C | A | R | D | Y | - | - | - | - | - | - | G | V | F | D | Y |
| 2188-B08 | D | S | V | K | G | R | F | T | I | S | A | D | T | S | K | N | T | A | Y | L | Q | M | N | S | L | R | A | E | D | T | A | V | Y | Y | C | A | R | D | Y | - | - | - | - | - | - | G | V | F | D | Y |
| 2188-C10 | D | S | V | K | G | R | F | T | I | S | A | D | T | S | K | N | T | A | Y | L | Q | M | N | S | L | R | A | E | D | T | A | V | Y | Y | C | A | R | D | Y | - | - | - | - | - | - | G | V | F | D | Y |
| 2188-C02 | D | S | V | K | G | R | F | T | I | S | A | D | T | S | K | N | T | A | Y | L | Q | M | N | S | L | R | A | E | D | T | A | V | Y | Y | C | A | R | D | Y | - | - | - | - | - | - | G | V | F | D | Y |
| 2188-B07 | D | S | V | K | G | R | F | T | A | S | A | D | T | S | K | N | T | A | Y | L | Q | M | N | S | L | R | A | E | D | T | A | V | Y | Y | C | A | R | D | Y | - | - | - | - | - | - | G | V | F | D | Y |
| 2188-A11 | D | S | V | K | G | R | F | T | I | S | A | D | T | S | K | N | T | A | Y | L | Q | M | N | S | L | R | A | E | D | T | A | V | Y | Y | C | A | R | D | Y | - | - | - | - | - | - | G | V | F | D | Y |
| 2188-D01 | D | S | V | K | G | R | F | T | I | S | A | D | T | S | K | N | T | A | Y | L | Q | M | N | S | L | R | A | E | D | T | A | V | Y | Y | C | A | R | D | Y | - | - | - | - | - | - | G | V | F | D | Y |
| 2188-E09 | D | S | V | K | G | R | F | T | I | S | A | D | T | S | K | N | T | A | Y | L | Q | M | N | S | L | R | A | E | D | T | A | V | Y | Y | C | A | R | D | Y | - | - | - | - | - | - | G | V | F | D | Y |
| 2188-E06 | D | S | V | K | G | R | F | T | I | S | A | D | T | S | K | N | T | A | Y | L | Q | M | D | S | L | R | A | E | D | T | A | V | Y | Y | C | A | R | D | Y | - | - | - | - | - | - | G | V | F | D | Y |
| 2188-B03 | D | S | V | K | G | R | F | T | I | S | A | D | T | S | K | N | T | A | Y | L | Q | M | N | S | L | R | A | E | D | T | A | V | Y | Y | C | A | R | D | Y | - | - | - | - | - | - | G | V | Y | D | Y |

FIG. 2 (Cont. 1)

| Column # | 113 | 114 | 115 | 116 | 117 | 118 | 119 | 120 | 121 | 122 | 123 |
|---|---|---|---|---|---|---|---|---|---|---|---|
| 1987-C05 | W | G | Q | G | T | L | V | T | V | S | S |
| 2188-D11 | W | G | Q | G | T | L | V | T | V | S | S |
| 2188-B04 | W | G | Q | G | T | L | V | T | V | S | S |
| 2188-C09 | W | G | Q | G | T | L | V | T | V | S | S |
| 2188-G03 | W | G | Q | G | T | L | V | T | V | S | S |
| 2188-E03 | W | G | Q | G | T | L | V | T | V | S | S |
| 2188-B11 | W | G | Q | G | T | L | V | T | V | S | S |
| 2188-E07 | W | G | Q | G | T | L | V | T | V | S | S |
| 2188-B02 | W | G | Q | G | T | L | V | T | V | S | S |
| 2188-C07 | W | G | Q | G | T | L | V | T | V | S | S |
| 2188-A03 | W | G | Q | G | T | L | V | T | V | S | S |
| 2188-F03 | W | G | Q | G | T | L | V | T | V | S | S |
| 2188-D03 | W | G | Q | G | T | L | V | T | V | S | S |
| 2188-C04 | W | G | Q | G | T | L | V | T | V | S | S |
| 2188-D10 | W | G | Q | G | T | L | V | T | V | S | S |
| 2188-A06 | W | G | Q | G | T | L | V | T | V | S | S |
| 2188-C11 | W | G | Q | G | T | L | V | T | V | S | S |
| 2188-F01 | W | G | Q | G | T | L | V | T | V | S | S |
| 2188-E11 | W | G | Q | G | T | L | V | T | V | S | S |
| 2188-A07 | W | G | Q | G | T | L | V | T | V | S | S |
| 2188-C01 | W | G | Q | G | T | L | V | T | V | S | S |
| 2188-F08 | W | G | Q | G | T | L | V | T | V | S | S |
| 2188-E04 | W | G | Q | G | T | L | V | T | V | S | S |
| 2188-B01 | W | G | Q | G | T | L | V | T | V | S | S |
| 2188-B07 | W | G | Q | G | T | L | V | T | V | S | S |
| 2188-F11 | W | G | R | G | T | L | V | T | V | S | S |
| 2188-B08 | W | G | Q | G | T | L | V | T | V | S | S |
| 2188-C10 | W | G | Q | G | T | L | V | T | V | S | S |
| 2188-C02 | W | G | Q | G | T | L | V | T | V | S | S |
| 2188-A11 | W | G | Q | G | T | L | V | T | V | S | S |
| 2188-D01 | W | G | Q | G | T | L | V | T | V | S | S |
| 2188-E09 | W | G | Q | G | T | L | V | T | V | S | S |
| 2188-E06 | W | G | Q | G | T | L | V | T | V | S | S |
| 2188-B03 | W | G | Q | G | T | L | V | T | V | S | S |

| Column # | 113 | 114 | 115 | 116 | 117 | 118 | 119 | 120 | 121 | 122 | 123 |
|---|---|---|---|---|---|---|---|---|---|---|---|
| 2188-F06 | W | G | Q | G | T | L | V | T | V | S | S |
| 2188-D02 | W | G | Q | G | T | L | V | T | V | S | S |
| 2188-B06 | W | G | Q | G | T | L | V | T | V | S | S |
| 2188-D09 | W | G | Q | G | T | L | V | T | V | S | S |
| 2188-F02 | W | G | Q | G | T | L | V | T | V | S | S |
| 2188-E10 | W | G | Q | G | T | L | V | T | V | S | S |
| 2188-A09 | W | G | Q | G | T | L | V | T | V | S | S |
| 2188-D04 | W | G | Q | G | T | L | V | T | V | S | S |
| 2188-A05 | W | G | Q | G | T | L | V | T | V | S | S |
| 2188-E01 | W | G | Q | G | T | L | V | T | V | S | S |
| 2188-G01 | W | G | Q | G | T | L | V | T | V | S | S |
| 2188-B09 | W | G | Q | G | T | L | V | T | V | S | S |
| 2188-F07 | W | G | Q | G | T | L | V | T | V | S | S |
| 2188-D08 | W | G | Q | G | T | L | V | T | V | S | S |
| 2188-D05 | W | G | Q | G | T | L | V | T | V | S | S |
| 2188-C03 | W | G | Q | G | T | L | V | T | V | S | S |
| 2188-E08 | W | G | Q | G | T | L | V | T | V | S | S |
| 2188-C06 | W | G | Q | G | T | L | V | T | V | S | S |
| 2188-A08 | W | G | Q | G | T | L | V | T | V | S | S |
| 2188-B10 | W | G | Q | G | T | L | V | T | V | S | S |
| 2188-G02 | W | G | Q | G | T | L | V | T | V | S | S |
| 2188-C05 | W | G | Q | G | T | L | V | T | V | S | S |
| 2188-A10 | W | G | Q | G | T | L | V | T | V | S | S |
| 2188-G04 | W | G | Q | G | T | L | V | T | V | S | S |
| 2188-C08 | W | G | Q | G | T | L | V | T | V | S | S |
| 2188-E05 | W | G | Q | G | T | L | V | T | V | S | S |
| 2188-A02 | W | G | Q | G | T | L | V | T | V | S | S |
| 2188-F04 | W | G | Q | G | T | L | V | T | V | S | S |
| 2188-F05 | W | G | Q | G | T | L | V | T | V | S | S |
| 2188-D07 | W | G | Q | G | T | L | V | T | V | S | S |
| 2188-E02 | W | G | Q | G | T | L | V | T | V | S | S |
| 2188-D06 | W | G | Q | G | T | L | V | T | V | S | S |

| Column # | 113 | 114 | 115 | 116 | 117 | 118 | 119 | 120 | 121 | 122 | 123 |
|---|---|---|---|---|---|---|---|---|---|---|---|
| 2188-F09 | W | G | Q | G | T | L | V | T | V | S | S |
| 2188-F10 | W | G | Q | G | T | L | V | T | V | S | S |
| 2188-B05 | W | G | Q | G | T | L | V | T | V | S | S |
| 1943-C02 | W | G | Q | G | T | L | V | T | V | S | S |
| 2193-D04 | W | G | Q | G | T | L | V | T | V | S | S |
| 2193-E10 | W | G | Q | G | T | L | V | T | V | S | S |
| 2193-E06 | W | G | Q | G | T | L | V | T | V | S | S |
| 2193-E04 | W | G | Q | G | T | L | V | T | V | S | S |
| 2193-B09 | W | G | Q | G | T | L | V | T | V | S | S |
| 2193-D11 | W | G | Q | G | T | L | V | T | V | S | S |
| 2193-B02 | W | G | Q | G | T | L | V | T | V | S | S |
| 2193-D05 | W | G | Q | G | T | L | V | T | V | S | S |
| 2193-E11 | W | G | Q | G | T | L | V | T | V | S | S |
| 2193-D06 | W | G | Q | G | T | L | V | T | V | S | S |
| 2193-C02 | W | G | Q | G | T | L | V | T | V | S | S |
| 2193-B03 | W | G | Q | G | T | L | V | T | V | S | S |
| 2193-A02 | W | G | Q | G | T | L | V | T | V | S | S |
| 2193-E05 | W | G | Q | G | T | L | V | T | V | S | S |
| 2193-A06 | W | G | Q | G | T | L | V | T | V | S | S |
| 2193-C04 | W | G | Q | G | T | L | V | T | V | S | S |
| 2193-E08 | W | G | Q | G | T | L | V | T | V | S | S |
| 2193-B10 | W | G | Q | G | T | L | V | T | V | S | S |
| 2193-D08 | W | G | Q | G | T | L | V | T | V | S | S |
| 2193-B08 | W | G | Q | G | T | L | V | T | V | S | S |
| 2193-C05 | W | G | Q | G | T | L | V | T | V | S | S |
| 2193-D10 | W | G | Q | G | T | L | V | T | V | S | S |
| 2193-D03 | W | G | Q | G | T | L | V | T | V | S | S |
| 2193-A09 | W | G | R | G | T | L | V | T | V | S | S |
| 2193-A10 | W | G | Q | G | T | L | V | T | V | S | S |
| 2193-E07 | W | G | Q | G | T | L | V | T | V | S | S |
| 2193-A07 | W | G | Q | G | T | L | V | T | V | S | S |
| 2193-E03 | W | G | Q | G | T | L | V | T | V | S | S |
| 2193-C08 | W | G | Q | G | T | L | V | T | V | S | S |
| 2193-B11 | W | G | Q | G | T | L | V | T | V | S | S |

| Column # | 62 | 63 | 64 | 65 | 66 | 67 | 68 | 69 | 70 | 71 | 72 | 73 | 74 | 75 | 76 | 77 | 78 | 79 | 80 | 81 | 82 | 83 | 84 | 85 | 86 | 87 | 88 | 89 | 90 | 91 | 92 | 93 | 94 | 95 | 96 | 97 | 98 | 99 | 100 | 101 | 102 | 103 | 104 | 105 | 106 | 107 | 108 | 109 | 110 | 111 | 112 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| 2193-A03 | D | S | V | K | G | R | F | T | I | S | A | D | T | S | K | N | T | A | Y | L | Q | M | N | S | L | R | A | E | D | T | A | V | Y | Y | C | A | R | S | R | W | S | R | V | L | W | S | Y | V | F | D | Y |
| 2193-D02 | D | S | V | K | G | R | F | T | I | S | A | D | T | S | K | N | T | A | Y | L | Q | M | N | S | L | R | A | E | D | T | A | V | Y | Y | C | A | R | S | R | W | F | R | V | L | W | S | Y | V | F | D | Y |
| 2193-B06 | D | S | V | K | G | R | F | T | I | S | A | D | T | S | K | N | T | A | Y | L | Q | M | N | S | L | R | A | E | D | T | A | V | Y | Y | C | A | R | S | R | W | F | R | V | L | W | S | Y | V | F | D | Y |
| 2193-B01 | D | S | V | K | G | R | F | T | I | S | A | D | T | S | K | N | T | A | Y | L | Q | M | N | S | L | R | A | E | D | T | A | V | Y | Y | C | A | R | S | R | W | F | R | V | L | W | S | Y | V | L | D | Y |
| 2193-D09 | D | S | V | K | G | R | F | T | I | S | A | D | T | S | K | N | T | A | Y | L | Q | M | N | S | L | R | A | E | D | T | A | V | Y | Y | C | A | R | S | R | W | F | R | V | L | W | S | Y | V | F | D | Y |
| 2193-E09 | D | S | V | K | G | R | F | T | I | S | A | D | T | S | K | N | T | A | Y | L | Q | M | N | S | L | R | A | E | D | T | A | V | Y | Y | C | A | R | S | R | W | F | R | V | L | W | S | Y | V | F | D | Y |
| 2193-B07 | D | S | V | K | G | R | F | T | I | S | A | D | T | S | K | N | T | A | Y | L | Q | M | N | S | L | R | A | E | D | T | A | V | Y | Y | C | A | R | S | R | W | Y | R | A | L | W | I | Y | – | F | D | Y |
| 2193-C06 | D | S | V | K | G | R | F | T | I | S | A | D | T | S | K | N | T | A | Y | L | Q | M | N | S | L | R | A | E | D | T | A | V | Y | Y | C | A | R | S | R | W | F | R | V | L | W | S | Y | V | F | D | Y |
| 2193-B05 | D | S | V | K | G | R | F | T | I | S | A | D | T | S | K | N | T | A | Y | L | Q | M | N | S | L | R | A | E | D | T | A | V | Y | Y | C | A | R | S | R | W | Y | R | V | L | W | S | Y | V | F | D | Y |
| 2193-A11 | D | S | V | K | G | R | F | T | I | S | A | D | T | S | K | N | T | A | Y | L | Q | M | N | S | L | R | A | E | D | T | A | V | Y | Y | C | A | R | S | R | W | W | R | V | L | W | S | Y | V | F | D | Y |
| 2193-E02 | D | S | V | K | G | R | F | T | I | S | A | D | T | S | K | N | T | A | Y | L | Q | M | N | S | L | R | A | E | D | T | A | V | Y | Y | C | A | R | S | R | W | F | R | V | L | W | S | Y | V | F | D | Y |
| 2193-A08 | D | S | V | K | G | R | F | T | I | S | A | D | T | S | K | N | T | A | Y | L | Q | M | N | S | L | R | A | E | D | T | A | V | Y | Y | C | A | R | S | R | W | F | R | V | L | W | S | Y | V | F | D | Y |
| 2193-C11 | D | S | V | R | G | R | F | T | I | S | A | D | T | S | K | N | T | A | Y | L | Q | M | N | S | L | R | A | E | D | T | A | V | Y | Y | C | A | R | S | R | W | L | R | V | L | W | S | F | V | L | D | Y |
| 2193-A01 | D | S | L | K | G | R | F | T | I | S | A | D | T | S | K | N | T | A | Y | L | Q | M | N | S | L | R | A | E | D | T | A | V | Y | Y | C | A | R | S | R | W | F | R | V | L | W | S | Y | V | F | D | Y |
| 2193-D07 | D | S | V | K | G | R | F | T | I | S | A | D | T | S | K | N | T | A | Y | L | Q | M | N | S | L | R | A | E | D | T | A | V | Y | Y | C | A | R | S | R | W | Y | R | V | L | W | S | Y | V | F | D | Y |
| 2193-A05 | D | S | V | K | G | R | F | T | I | S | A | D | T | S | K | N | T | A | Y | L | Q | M | N | S | L | R | A | E | D | T | A | V | Y | Y | C | A | R | S | R | W | S | R | V | L | W | T | Y | V | F | D | Y |
| 2193-C03 | D | S | V | K | G | R | F | T | I | S | A | D | T | S | K | S | T | A | Y | L | Q | M | N | S | L | R | A | E | D | T | A | V | Y | Y | C | A | R | S | R | W | F | R | V | L | W | S | Y | V | F | D | Y |
| 2193-C09 | D | S | V | K | G | R | F | T | I | S | A | D | T | S | K | N | T | A | Y | L | Q | M | N | S | L | R | A | E | D | T | A | V | Y | Y | C | A | R | S | R | W | L | R | V | L | W | S | Y | V | F | D | Y |
| 2193-D01 | D | S | V | K | G | R | F | T | I | S | A | D | T | S | K | N | T | A | Y | L | Q | M | N | S | L | R | A | E | D | T | A | V | Y | Y | C | A | R | S | R | W | Y | R | V | L | W | T | Y | V | F | D | Y |
| 2193-E01 | D | S | V | K | G | R | F | T | I | S | A | D | T | S | K | N | T | A | Y | L | Q | M | N | S | L | R | A | E | G | T | A | V | Y | Y | C | A | R | S | R | W | F | R | V | L | W | S | Y | G | F | D | Y |
| 2193-C07 | D | S | V | K | G | R | F | T | I | S | A | D | T | S | K | N | T | A | Y | L | Q | M | N | S | L | R | A | E | D | T | A | V | Y | Y | C | A | R | S | R | W | F | R | V | L | W | S | F | V | F | D | Y |
| 2193-B04 | D | S | V | K | G | R | F | T | I | S | A | D | T | S | K | N | T | A | Y | L | Q | M | N | S | L | R | A | E | D | T | A | V | Y | Y | C | A | R | S | R | W | Y | R | V | L | W | S | Y | V | Y | D | Y |
| 2193-C10 | D | S | V | K | G | R | F | T | I | S | A | D | T | S | K | N | T | A | Y | L | Q | T | N | S | L | R | A | E | D | T | A | V | Y | Y | C | A | R | S | R | W | F | R | V | L | W | S | R | P | F | D | Y |
| 2193-C01 | D | S | M | K | G | R | F | T | I | S | A | D | T | S | K | N | T | A | Y | L | Q | M | N | S | L | R | A | E | D | T | A | V | Y | Y | C | A | R | D | H | R | R | – | – | – | Y | V | R | P | F | D | Y |
| 2193-A04 | D | S | V | K | G | R | F | T | I | S | A | D | T | S | K | N | T | A | Y | L | Q | M | N | S | L | R | A | E | D | T | A | V | Y | Y | C | A | R | D | S | R | R | – | – | – | Y | V | R | P | F | D | Y |
| 1944-A07 | D | S | V | K | G | R | F | T | I | S | A | D | T | S | K | N | T | A | Y | L | Q | M | N | S | L | R | A | E | D | T | A | V | Y | Y | C | A | R | D | S | R | R | – | – | – | Y | V | R | P | M | D | Y |
| 2194-A02 | D | S | V | K | G | R | F | T | I | S | A | D | T | S | K | N | T | A | Y | L | Q | M | N | S | L | R | A | E | D | T | A | V | Y | Y | C | A | R | D | S | R | R | – | – | – | Y | V | R | P | F | D | Y |
| 2194-A05 | D | S | V | K | G | R | F | T | I | S | A | D | T | S | K | N | T | A | Y | L | Q | M | N | S | L | R | A | E | D | T | A | V | Y | Y | C | A | R | D | S | R | R | – | – | – | Y | V | R | P | F | D | Y |
| 2194-B04 | D | S | V | K | G | R | F | T | I | S | A | D | T | S | K | N | T | A | Y | L | Q | M | N | S | L | R | A | E | D | T | A | V | Y | Y | C | A | R | D | S | R | R | – | – | – | Y | V | R | P | L | D | Y |
| 2194-A09 | D | S | V | K | G | R | F | N | I | S | A | D | T | S | K | N | T | A | Y | L | Q | M | N | S | L | R | A | E | D | T | A | V | Y | Y | C | A | R | D | S | R | R | – | – | – | Y | V | R | P | F | D | Y |
| 2194-A01 | D | S | V | K | G | R | F | T | I | S | A | D | T | S | K | N | T | A | Y | L | Q | M | N | S | L | R | A | E | D | T | A | V | Y | Y | C | A | R | D | S | R | R | – | – | – | Y | V | R | P | F | D | Y |
| 2194-B03 | D | S | V | K | G | R | F | T | I | S | A | D | T | S | K | N | T | A | Y | L | Q | M | N | S | L | R | A | E | D | T | A | V | Y | Y | C | A | R | D | S | R | R | – | – | – | Y | V | R | P | F | D | Y |
| 2194-B02 | D | S | V | K | G | R | F | T | I | S | A | D | T | S | K | N | T | A | Y | L | Q | M | N | S | L | R | A | E | D | T | A | V | Y | Y | C | A | R | D | S | R | R | – | – | – | Y | V | R | P | F | D | Y |
| 2194-A03 | D | S | V | K | G | R | F | T | I | S | A | D | T | S | K | N | T | A | Y | L | Q | M | N | S | L | R | A | E | D | T | A | V | Y | Y | C | A | R | D | S | R | R | – | – | – | Y | V | R | P | L | D | Y |

FIG. 5 (Cont. 1)

| Column # | 113 | 114 | 115 | 116 | 117 | 118 | 119 | 120 | 121 | 122 | 123 |
|---|---|---|---|---|---|---|---|---|---|---|---|
| 2193-A03 | W | G | Q | G | T | L | V | T | V | S | S |
| 2193-D02 | W | G | Q | G | T | L | V | T | V | S | S |
| 2193-B06 | W | G | Q | G | T | L | V | T | V | S | S |
| 2193-B01 | W | G | Q | G | T | L | V | T | V | S | S |
| 2193-D09 | W | G | Q | G | T | P | V | T | V | S | S |
| 2193-E09 | W | G | Q | G | T | L | V | T | V | S | S |
| 2193-B07 | W | G | Q | G | T | L | V | T | V | S | S |
| 2193-C06 | W | G | Q | G | T | L | V | T | V | S | S |
| 2193-B05 | W | G | Q | G | T | L | V | T | V | S | S |
| 2193-A11 | W | G | Q | G | T | L | V | T | V | S | S |
| 2193-E02 | W | G | Q | G | T | L | V | T | V | S | S |
| 2193-A08 | W | G | Q | G | T | L | V | T | V | S | S |
| 2193-C11 | W | G | Q | G | T | L | V | T | V | S | S |
| 2193-A01 | W | G | Q | G | T | L | V | T | V | S | S |
| 2193-D07 | W | G | Q | G | T | L | V | T | V | S | S |
| 2193-A05 | W | G | Q | G | T | L | V | T | V | S | S |
| 2193-C03 | W | G | Q | G | T | L | V | T | V | S | S |
| 2193-C09 | W | G | Q | G | T | L | V | T | V | S | S |
| 2193-D01 | W | G | Q | G | T | L | V | T | V | S | S |
| 2193-E01 | W | G | Q | G | T | L | V | T | V | S | S |
| 2193-C07 | W | G | Q | G | T | L | V | T | V | S | S |
| 2193-B04 | W | G | Q | G | T | L | V | T | V | S | S |
| 2193-C10 | W | G | Q | G | T | L | V | T | V | S | S |
| 2193-C01 | W | G | Q | G | T | L | V | T | V | S | S |
| 2193-A04 | W | G | Q | G | T | L | V | T | V | S | S |
| 1944-A07 | W | G | Q | G | T | L | V | T | V | S | S |
| 2194-A02 | W | G | Q | G | T | L | V | T | V | S | S |
| 2194-A05 | W | G | Q | G | T | L | V | T | V | S | S |
| 2194-B04 | W | G | Q | G | T | L | V | T | V | S | S |
| 2194-A09 | W | G | Q | G | T | L | V | T | V | S | S |
| 2194-A01 | W | G | Q | G | T | L | V | T | V | S | S |
| 2194-B03 | W | G | Q | G | T | L | V | T | V | S | S |
| 2194-B02 | W | G | Q | G | T | L | V | T | V | S | S |
| 2194-A03 | W | G | Q | G | T | L | V | T | V | S | S |

| Column # | Sequence (positions 1–61) |
|---|---|
| 2194-A11 | E V Q L V E S G G G L V Q P G G S L R L S C A A S G F N I T Q Y I H W V R Q A P G K G L E W V G Y I S P N S G Y T H D A |
| 2194-A08 | E V Q L V E S G G G L V Q P G G S L R L S C A A S G F N I T G Y Y H W V R Q A P G K G L E W V G Y I A P S S G Y T Y D A |
| 2194-A04 | E V Q L V E S G G G L V Q P G G S L R L S C A A S G F N I T G Y Y I H W V R Q A P G K G L E W V G Y I S P L A G N S T H H A |
| 2194-A10 | E V Q L V E S G G G L V Q P G G S L R L S C A A S G F N I T G Y Y I H W V R Q A P A K G L E W V G Y I S P N S G N T H I A |
| 2194-A07 | E V Q L V E S G G G L V Q P G G S L R L S C A A S G F N I T D Y Y I H W V R Q A P G K G L E W V G Y I S P L A G N T Y H A |
| 2194-B01 | E V Q L V E S G G G L V Q P G G S L R L S C A A S G F N I T A S Y Y H W V R Q A P G K G L E W V G S I S P L A S G A T S K A |
| 2194-A06 | E V Q L V E S G G G L V Q P G G S L R L S C A A S G F N I T G Y Y H W V R Q A P G K G L E W V G Q I S P N S G A T H D A |
| 2196-C01 | E V Q L V E S G G G L V Q P G G S L R L S C A A S G F N I T D Y Y H W V R Q A P G K G L E W V G Y I S P N S G A T H Y Q A |
| 2196-A02 | E V Q L V E S G G G L V Q P G G S L R L S C A A S G F N I T D Y Y H W V R Q A P G K G L E W V G F I S P N S G A T Y S A |
| 2196-B03 | E V Q L V E S G G G L V Q P G G S L R L S C A A S G F N I T G N Y Y H W V R Q A P G K G L E W V G Q I S P N S G W T Y Y A |
| 2196-A05 | E V Q L V E S G G G L V Q P G G S L R L S C A A S G F N I T G P Y Y H W V R Q A P G K G L E W V G Q Y P N N S G Y T Y L A |
| 2196-C02 | E V Q L V E S G G G L V Q P G G S L R L S C A A S G F N I T G Y Y H W V R Q A P G K G L E W V G Y I S P N S G H T Y Q A |
| 2196-B11 | E V Q L V E S G G G L V Q P G G S L R L S C A A S G F N I T G Y Y H W V R Q A P G R G L E W V G Q I S P N S G S T H E A |
| 2196-B08 | E V Q L V E S G G G L V Q P G G S L R L S C A A S G F N I T G Y Y H W V R Q A P G K G L E W V G Y I S P N S G A T H Y A |
| 2196-A04 | E V Q L V E S G G G L V Q P G G S L R L S C A A S G F N I T G Y Y H W V R Q A P G E G L E W V G Q I S P N S G S T H Q A |
| 2196-A03 | E V Q L V E S G G G L V Q P G G S L R L S C A A S G F N I T G Y Y H W V R Q A P G K G L E W V G Y I S P N S G A T Y H A |
| 2196-B07 | E V Q L V A P G Q P G G S L R L S C A A S G F N I T G Y Y H W V R Q A P G K G L E W V G Y I S P N S G Y T Y Y A |
| 2196-A06 | E V Q L V E S G G G L V Q P G G S L R L S C A A S G F N I T G Y Y H W V R Q A P G K G L E W V G Y I S P N S G Y T Y L A |
| 2196-A01 | E V Q L V E S G G G L V Q P G G S L R L S C A A S G F N I T G Y Y H W V R Q A P G K G L E W V G Q I S P N S G A T H Y A |
| 2196-B01 | E V Q L V E S G G G L V Q P G G S L R L S C A A S G F N I T G Y Y H W V R Q A P G K G L E W V G Q I S P N S G S T Y K A |
| 2196-A09 | E V Q L V E S G G G L V Q P G G S L R L S C A A S G F N I T G Y Y H W V R Q A P G K G L E W V G Y I S P N S G G T T H Y A |
| 2196-A08 | E V Q L V E S G G G L V Q P G G S L R L S C A A S G F N I T G Y Y H W V R Q A P G K G L E W V G Y I S P N S G A T H Y A |
| 2196-A10 | E V Q L V E S G G G L V Q P G G S L R L S C A A S G F N I T G Y Y H W V R Q A P G K G L E W V G Q I S P N S G S T Y H A |
| 2196-B06 | E V Q L V E S G G G L V Q P G G S L R L S C A A S G F N I T E Y Y H W V R Q A P G K G L E W V G Q I S P N S G G S T Y N A |
| 2196-B09 | E V Q L V E S G G G L V Q P G G S L R L S C A A S G F N I T G Y Y H W V R Q A P G K G L E W V G Y I A P L N S G S T Y Y A |
| 2196-C03 | E V Q L V E S G G G L V Q P G G S L R L S C A A S G F N I T G Y Y H W V R Q A P G K G L E W V G Q I S P N S G S T Y D A |
| 2196-C04 | E V Q L V E S G G G L V Q P G G S L R L S C A A S G F N I T T E Y Y H W V R Q A P G K G L E W V G Q Y P N N S G G Q T Y Y A |
| 2196-A07 | E V Q L V E S G G G L V Q P G G S L R L S C A A S G F N I T G Y Y H W V R Q A P G K G L E W V G Y I A P N S G A T Y D A |
| 2196-A11 | E V Q L V E S G G G L V Q P G G S L R L S C A A S G F N I T G Y Y H W V R Q A P G K G L E W V G Y I S P N S G Y T Y Q A |
| 2196-B02 | E V Q L V E S G G G L V Q P G G S L R L S C A A S G F N I T T E Y Y H W V R Q A P G K G L E W V G Q I S P N S G A T Y Y A |
| 2196-B04 | E V Q L V E S G G G L V Q P G G S L R L S C A A S G F N I T G Y Y H W V R Q A P G K G L E W V G Y I S P N S G T T Y D A |
| 2196-B10 | E V Q L V E S G G G L V Q P G G S L R L S C A A S G F N I T G Y Y H W V R Q A P G K G L E W V G S I T P L S G A T S K A |

| Column # | 113 | 114 | 115 | 116 | 117 | 118 | 119 | 120 | 121 | 122 | 123 |
|---|---|---|---|---|---|---|---|---|---|---|---|
| 2194-A11 | W | G | Q | G | T | L | V | T | V | S | S |
| 2194-A08 | W | G | Q | G | T | L | V | T | V | S | S |
| 2194-A04 | W | G | Q | G | T | L | V | T | V | S | S |
| 2194-A10 | W | G | Q | S | T | L | V | T | V | S | S |
| 2194-A07 | W | G | Q | G | T | L | V | T | V | S | S |
| 2194-B01 | W | G | Q | G | T | L | V | T | V | S | S |
| 2194-A06 | W | G | Q | G | T | L | V | T | V | S | S |
| 2196-C01 | W | G | Q | G | T | L | V | T | V | S | S |
| 2196-A02 | W | G | Q | G | T | L | V | T | V | S | S |
| 2196-B03 | W | G | Q | G | T | L | V | T | V | S | S |
| 2196-A05 | W | G | Q | G | T | L | V | T | V | S | S |
| 2196-C02 | W | G | Q | G | T | L | V | T | V | S | S |
| 2196-B11 | W | G | Q | G | T | L | V | T | V | S | S |
| 2196-B08 | W | G | Q | G | T | L | V | T | V | S | S |
| 2196-A04 | W | G | Q | G | T | L | V | T | V | S | S |
| 2196-A03 | W | G | Q | G | T | L | V | T | V | S | S |
| 2196-B07 | W | G | Q | G | T | L | V | T | V | S | S |
| 2196-A06 | W | G | Q | G | T | L | V | T | V | S | S |
| 2196-B05 | W | G | Q | G | T | L | V | T | V | S | S |
| 2196-A01 | W | G | Q | G | T | L | V | T | V | S | S |
| 2196-B01 | W | G | Q | G | T | L | V | T | V | S | S |
| 2196-A09 | W | G | Q | G | T | L | V | T | V | S | S |
| 2196-A08 | W | G | Q | G | T | L | V | T | V | S | S |
| 2196-A10 | W | G | Q | G | T | L | V | T | V | S | S |
| 2196-B06 | W | G | Q | G | T | L | V | T | V | S | S |
| 2196-B09 | W | G | Q | G | T | L | V | T | V | S | S |
| 2196-C03 | W | G | R | G | T | L | V | T | V | S | S |
| 2196-C04 | W | G | Q | G | T | L | V | T | V | S | S |
| 2196-A07 | W | G | Q | G | T | L | V | T | V | S | S |
| 2196-A11 | W | G | Q | G | T | L | V | T | V | S | S |
| 2196-B02 | W | G | Q | G | T | L | V | T | V | S | S |
| 2196-B04 | W | G | Q | G | T | L | V | T | V | S | S |
| 2196-B10 | W | G | Q | G | T | L | V | T | V | S | S |

FIG. 6 (Cont. 2)

| Column # | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 | 35 | 36 | 37 | 38 | 39 | 40 | 41 | 42 | 43 | 44 | 45 | 46 | 47 | 48 | 49 | 50 | 51 | 52 | 53 | 54 | 55 | 56 | 57 | 58 | 59 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| TRASTUZUMAB | D | I | Q | M | T | Q | S | P | S | S | L | S | A | S | V | G | D | R | V | T | I | T | C | R | A | S | Q | D | - | - | V | N | T | - | A | V | A | W | Y | Q | Q | K | P | G | K | A | P | K | L | L | I | Y | S | A | S | F | L | Y | S |
| SP34 | - | Q | A | V | V | T | Q | E | S | A | L | T | T | S | P | G | E | T | V | T | L | T | C | R | S | S | T | G | A | V | T | T | S | N | Y | A | N | W | V | Q | E | K | P | D | H | L | F | T | G | L | I | I | G | T | N | K | R | A | P |
| 2037-B10 | - | Q | T | V | V | T | Q | E | P | S | L | T | V | S | P | G | G | T | V | T | L | T | C | R | S | S | T | G | A | V | T | T | S | G | Y | Y | P | N | W | L | Q | Q | K | P | G | Q | A | P | R | G | L | I | G | G | T | K | F | L | A |
| HUCHT1-LC3 | D | I | Q | M | T | Q | S | P | S | T | L | S | A | S | V | G | D | R | V | T | I | T | C | R | A | S | Q | D | - | I | R | N | - | Y | L | N | W | Y | Q | Q | K | P | G | K | A | P | K | L | L | I | Y | Y | T | S | R | L | H | S |
| HOKT3-LC1 | D | I | Q | M | T | Q | S | P | S | S | L | S | A | S | V | G | D | R | V | T | I | T | C | S | A | S | S | S | - | - | V | - | S | - | Y | M | N | W | Y | Q | Q | K | P | G | K | A | P | K | R | L | I | Y | D | T | S | K | L | A | S |
| HSP34-LC3 | - | Q | T | V | V | T | Q | E | P | S | L | T | V | S | P | G | G | T | V | T | L | T | C | G | S | S | T | G | A | V | T | S | G | Y | Y | P | N | W | F | Q | Q | K | P | G | Q | A | P | R | G | L | I | I | G | T | K | F | L | A | P |

| Column # | 60 | 61 | 62 | 63 | 64 | 65 | 66 | 67 | 68 | 69 | 70 | 71 | 72 | 73 | 74 | 75 | 76 | 77 | 78 | 79 | 80 | 81 | 82 | 83 | 84 | 85 | 86 | 87 | 88 | 89 | 90 | 91 | 92 | 93 | 94 | 95 | 96 | 97 | 98 | 99 | 100 | 101 | 102 | 103 | 104 | 105 | 106 | 107 | 108 | 109 | 110 | 111 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| TRASTUZUMAB | G | V | P | S | R | F | S | G | S | R | S | G | T | D | F | T | L | T | I | S | S | L | Q | P | E | D | F | A | T | Y | Y | C | Q | Q | H | Y | T | T | P | P | T | F | G | Q | G | T | K | V | E | I | K | - |
| SP34 | G | V | P | A | R | F | S | G | S | L | I | G | D | K | A | A | L | T | I | T | G | A | Q | T | E | D | E | A | I | Y | F | C | A | L | W | Y | S | N | L | W | V | F | G | G | G | T | K | L | T | V | L | - |
| 2037-B10 | G | T | P | A | R | F | S | G | S | L | L | G | G | K | A | A | L | T | L | S | G | V | Q | P | E | D | E | A | E | Y | Y | C | A | L | W | Y | S | N | R | W | V | F | G | G | G | T | K | L | T | V | T | G |
| HUCHT1-LC3 | G | V | P | S | R | F | S | G | S | G | S | G | T | E | Y | T | L | T | I | S | S | L | Q | P | D | D | F | A | T | Y | Y | C | Q | Q | G | N | T | L | P | W | T | F | G | Q | G | T | K | V | E | I | K | - |
| HOKT3-LC1 | G | V | P | S | R | F | S | G | S | G | S | G | T | E | Y | T | L | T | I | S | S | L | Q | P | E | D | F | A | T | Y | Y | C | Q | Q | W | S | S | N | P | F | T | F | G | Q | G | T | K | L | E | I | K | - |
| HSP34-LC3 | G | T | P | A | R | F | S | G | S | L | L | G | G | K | A | A | L | T | L | S | G | V | Q | P | E | D | E | A | E | Y | Y | C | A | L | W | Y | S | N | R | W | V | F | G | G | G | T | Q | L | T | V | T | G |

FIG. 7

SEQUENCE LISTING

```
Sequence total quantity: 1053
SEQ ID NO: 1            moltype = AA  length = 937
FEATURE                 Location/Qualifiers
REGION                  1..937
                        note = misc_feature - Human (hROR1) From UniProt Q01973
source                  1..937
                        mol_type = protein
                        organism = Homo sapiens
SEQUENCE: 1
MHRPRRRGTR PPLLALLAAL LLAARGAAAQ ETELSVSAEL VPTSSWNISS ELNKDSYLTL   60
DEPMNNITTS LGQTAELHCK VSGNPPPTIR WFKNDAPVVQ EPRRLSFRST IYGSRLRIRN  120
LDTTDTGYFQ CVATNGKEVV SSTGVLFVKF GPPPTASPGY SDEYEEDGFC QPYRGIACAR  180
FIGNRTVYME SLHMQGEIEN QITAAFTMIG TSSHLSDKCS QFAIPSLCHY AFPYCDETSS  240
VPKPRDLCRD ECEILENVLC QTEYIFARSN PMILMRLKLP NCEDLPQPES PEAANCIRIG  300
IPMADPINKN HKCYNSTGVD YRGTVSVTKS GRQCQPWNSQ YPHTHTFTAL RFPELNGGHS  360
YCRNPGNQKE APWCFTLDEN FKSDLCDIPA CDSKDSKEKN KMEILYILVP SVAIPLAIAL  420
LFFFICVCRN NQKSSSAPVQ RQPKHVRGQN VEMSMLNAYK PKSKAKELPL SAVRFMEELG  480
ECAFGKIYKG HLYLPGMDHA QLVAIKTLKD YNNPQQWTEF QQEASLMAEL HHPNIVCLLG  540
AVTQEQPVCM LFEYINQGDL HEFLIMRSPH SDVGCSSDED GTVKSSLDHG DFLHIAIQIA  600
AGMEYLSSHF FVHKDLAARN ILIGEQLHVK ISDLGLSREI YSADYYRVQS KSLLPIRWMP  660
PEAIMYGKFS SDSDIWSFGV VLWEIFSFGL QPYYGFSNQE VIEMVRKRQL LPCSEDCPPR  720
MYSLMTECWN EIPSRRPRFK DIHVRLRSWE GLSSHTSSTT PSGGNATTQT TSLSASPVSN  780
LSNPRYPNYM FPSQGITPQG QIAGFIGPPI PQNQRFIPIN GYPIPPGYAA FPAAHYQPTG  840
PPRVIQHCPP PKSRSPSSAS GSTSTGHVTS LPSSGSNQEA NIPLLPHMSI PNHPGGMGIT  900
VFGNKSQKPY KIDSKQASLL GDANIHGHTE SMISAEL                          937

SEQ ID NO: 2            moltype = AA  length = 937
FEATURE                 Location/Qualifiers
REGION                  1..937
                        note = misc_feature - Cynomolgus ROR1 From UniProt F6RUP2
source                  1..937
                        mol_type = protein
                        organism = Macaca fascicularis
SEQUENCE: 2
MHRPRRRGTR PPLLALLAAL LLAARGAAAQ ETELSVSAEL VPTSSWNISS ELNKDSYLTL   60
DEPMNNITTS LGQTAELHCK VSGNPPPTIR WFKNDAPVVQ EPRRLSFRST IYGSRLRIRN  120
LDTTDTGYFQ CVATNGKEVV SSTGVLFVKF GPPPTASPGY SDEYEEDGFC QPYRGIACAR  180
FIGNRTVYME SLHMQGEIEN QITAAFTMIG TSSHLSDKCS QFAIPSLCHY AFPYCDETSS  240
VPKPRDLCRD ECEILENVLC QTEYIFARSN PMILMRLKLP NCEDLPQPES PEAANCIRIG  300
IPMADPINKN HKCYNSTGVD YRGTVSVTKS GRQCQPWNSQ YPHTHTFTAL RFPELNGGHS  360
YCRNPGNQKE APWCFTLDEN FKSDLCDIPA CDSKDSKEKN KMEILYILVP SVAIPLAIAL  420
LFFFICVCRN NQKSSSPPVQ RQPKHVRGQN VEMSMLNAYK PKSKAKELPL SAVRFMEELG  480
ECAFGKIYKG HLYLPGMDHA QLVAIKTLKD YNNPQQWTEF QQEASLMAEL HHPNIVCLLG  540
AVTQEQPVCM LFEYMNQGDL HEFLIMRSPH SDVGCSSDED GTVKSSLDHG DFLHIAIQIA  600
AGMEYLSSHF FVHKDLAARN ILIGEQLHVK ISDLGLSREI YSADYYRVQS KSLLPIRWMP  660
PEAIMYGKFS SDSDIWSFGV VLWEIFSFGL QPYYGFSNQE VIEMVRKRQL LPCSEDCPPR  720
MYSLMTECWN EIPSRRPRFK DIHVRLRSWE GLSSHTSSTT PSGGNATTQT TSLSASPVSN  780
LSNPRYPNYI FPSQGITPQG QIAGFIGPPI PQNQRFIPIN GYPIPPGYAA FPAAHYQPTG  840
PPRVIQHCPP PKSRSPSSAS GSTSTGHVTS LPSSGSNQEA NIPLLPHMSI PNHPGGMGIT  900
VFGNKSQKPY KIDAKQASLL GDANIHGHTE SMISAEL                          937

SEQ ID NO: 3            moltype = AA  length = 937
FEATURE                 Location/Qualifiers
REGION                  1..937
                        note = misc_feature - Murine ROR1 From UniProt Q9Z139
source                  1..937
                        mol_type = protein
                        organism = Mus musculus
SEQUENCE: 3
MHRPRRRGTR PPPLALLAAL LLAARGADAQ ETELSVSAEL VPTSSWNTSS EIDKGSYLTL   60
DEPMNNITTS LGQTAELHCK VSGNPPPSIR WFKNDAPVVQ EPRRISFRAT NYGSRLRIRN  120
LDTTDTGYFQ CVATNGKKVV STTGVLFVKF GPPPTASPGS SDEYEEDGFC QPYRGIACAR  180
FIGNRTVYME SLHMQGEIEN QITAAFTMIG TSSHLSDKCS QFAIPSLCHY AFPYCDETSS  240
VPKPRDLCRD ECEVLENVLC QTEYIFARSN PMILMRLKLP NCEDLPQPES PEAANCIRIG  300
```

```
IPMADPINKN HKCYNSTGVD YRGTVSVTKS GRQCQPWNSQ YPHTHSFTAL RFPELNGGHS    360
YCRNPGNQKE APWCFTLDEN FKSDLCDIPA CDSKDSKEKN KMEILYILVP SVAIPLAIAF    420
LFFFICVCRN NQKSSSPPVQ RQPKPVRGQN VEMSMLNAYK PKSKAKELPL SAVRFMEELG    480
ECTFGKIYKG HLYLPGMDHA QLVAIKTLKD YNNPQQWTEF QQEASLMAEL HHPNIVCLLG    540
AVTQEQPVCM LFEYMNQGDL HEFLIMRSPH SDVGCSSDED GTVKSSLDHG DPLHIAIQIA    600
AGMEYLSSHF FVHKDLAARN ILIGEQLHVK ISDLGLSREI YSADYYRVQS KSSLPIRWMP    660
PEAIMYGKFS SDSDIWSFGV VLWEIFSFGL QPYYGFSNQE VIEMVRKRQL LPCSEDCPPR    720
MYSLMTECWN EIPSRRPRFK DIHVRLRSWE GLSSHTSSTT PSGGNATTQT TSLSASPVSN    780
LSNPRFPNYM FPSQGITPQG QIAGFIGPAI PQNQRFIPIN GYPIPPGYAA FPAAHYQPAG    840
PPRVIQHCPP PKSRSPSSAS GSTSTGHVAS LPSSGSNQEA NVPLLPHMSI PNHPGGMGIT    900
VFGNKSQKPY KIDSKQSSLL GDSHIHGHTE SMISAEV                             937

SEQ ID NO: 4           moltype = AA   length = 7
FEATURE                Location/Qualifiers
REGION                 1..7
                       note = Synthetic: 1987-C05; CDR-H1; Chothia
source                 1..7
                       mol_type = protein
                       organism = synthetic construct
SEQUENCE: 4
GFNISDY                                                              7

SEQ ID NO: 5           moltype = AA   length = 7
FEATURE                Location/Qualifiers
REGION                 1..7
                       note = Synthetic: 2188-D11; CDR-H1; Chothia
source                 1..7
                       mol_type = protein
                       organism = synthetic construct
SEQUENCE: 5
GFNIRDY                                                              7

SEQ ID NO: 6           moltype = AA   length = 7
FEATURE                Location/Qualifiers
REGION                 1..7
                       note = Synthetic: 2188-B04; CDR-H1; Chothia
source                 1..7
                       mol_type = protein
                       organism = synthetic construct
SEQUENCE: 6
GFNITWY                                                              7

SEQ ID NO: 7           moltype = AA   length = 7
FEATURE                Location/Qualifiers
REGION                 1..7
                       note = Synthetic: 2188-C09; CDR-H1; Chothia
source                 1..7
                       mol_type = protein
                       organism = synthetic construct
SEQUENCE: 7
GFNINSY                                                              7

SEQ ID NO: 8           moltype = AA   length = 7
FEATURE                Location/Qualifiers
REGION                 1..7
                       note = Synthetic: 2188-G03; CDR-H1; Chothia
source                 1..7
                       mol_type = protein
                       organism = synthetic construct
SEQUENCE: 8
GFNIVDY                                                              7

SEQ ID NO: 9           moltype = AA   length = 7
FEATURE                Location/Qualifiers
REGION                 1..7
                       note = Synthetic: 2188-E03; CDR-H1; Chothia
source                 1..7
                       mol_type = protein
                       organism = synthetic construct
SEQUENCE: 9
GFNIRDY                                                              7

SEQ ID NO: 10          moltype = AA   length = 7
FEATURE                Location/Qualifiers
REGION                 1..7
                       note = Synthetic: 2188-B11; CDR-H1; Chothia
source                 1..7
                       mol_type = protein
                       organism = synthetic construct
```

```
SEQUENCE: 10
GFNINRY                                                                          7

SEQ ID NO: 11            moltype = AA  length = 7
FEATURE                  Location/Qualifiers
REGION                   1..7
                         note = Synthetic: 2188-E07; CDR-H1; Chothia
source                   1..7
                         mol_type = protein
                         organism = synthetic construct
SEQUENCE: 11
GFNIGDY                                                                          7

SEQ ID NO: 12            moltype = AA  length = 7
FEATURE                  Location/Qualifiers
REGION                   1..7
                         note = Synthetic: 2188-B02; CDR-H1; Chothia
source                   1..7
                         mol_type = protein
                         organism = synthetic construct
SEQUENCE: 12
GFNISSY                                                                          7

SEQ ID NO: 13            moltype = AA  length = 7
FEATURE                  Location/Qualifiers
REGION                   1..7
                         note = Synthetic: 2188-C07; CDR-H1; Chothia
source                   1..7
                         mol_type = protein
                         organism = synthetic construct
SEQUENCE: 13
GFNIVRY                                                                          7

SEQ ID NO: 14            moltype = AA  length = 7
FEATURE                  Location/Qualifiers
REGION                   1..7
                         note = Synthetic: 2188-A03; CDR-H1; Chothia
source                   1..7
                         mol_type = protein
                         organism = synthetic construct
SEQUENCE: 14
GFNIRDY                                                                          7

SEQ ID NO: 15            moltype = AA  length = 7
FEATURE                  Location/Qualifiers
REGION                   1..7
                         note = Synthetic: 2188-F03; CDR-H1; Chothia
source                   1..7
                         mol_type = protein
                         organism = synthetic construct
SEQUENCE: 15
GFNISDY                                                                          7

SEQ ID NO: 16            moltype = AA  length = 7
FEATURE                  Location/Qualifiers
REGION                   1..7
                         note = Synthetic: 2188-D03; CDR-H1; Chothia
source                   1..7
                         mol_type = protein
                         organism = synthetic construct
SEQUENCE: 16
GFNISDY                                                                          7

SEQ ID NO: 17            moltype = AA  length = 7
FEATURE                  Location/Qualifiers
REGION                   1..7
                         note = Synthetic: 2188-C04; CDR-H1; Chothia
source                   1..7
                         mol_type = protein
                         organism = synthetic construct
SEQUENCE: 17
GFNINSY                                                                          7

SEQ ID NO: 18            moltype = AA  length = 7
FEATURE                  Location/Qualifiers
REGION                   1..7
                         note = Synthetic: 2188-D10; CDR-H1; Chothia
source                   1..7
                         mol_type = protein
```

```
                        organism = synthetic construct
SEQUENCE: 18
GFNISDY                                                                 7

SEQ ID NO: 19           moltype = AA   length = 7
FEATURE                 Location/Qualifiers
REGION                  1..7
                        note = Synthetic: 2188-A06; CDR-H1; Chothia
source                  1..7
                        mol_type = protein
                        organism = synthetic construct
SEQUENCE: 19
GFNIKSY                                                                 7

SEQ ID NO: 20           moltype = AA   length = 7
FEATURE                 Location/Qualifiers
REGION                  1..7
                        note = Synthetic: 2188-C11; CDR-H1; Chothia
source                  1..7
                        mol_type = protein
                        organism = synthetic construct
SEQUENCE: 20
GFNIKSY                                                                 7

SEQ ID NO: 21           moltype = AA   length = 7
FEATURE                 Location/Qualifiers
REGION                  1..7
                        note = Synthetic: 2188-F01; CDR-H1; Chothia
source                  1..7
                        mol_type = protein
                        organism = synthetic construct
SEQUENCE: 21
GFNIRYY                                                                 7

SEQ ID NO: 22           moltype = AA   length = 7
FEATURE                 Location/Qualifiers
REGION                  1..7
                        note = Synthetic: 2188-E11; CDR-H1; Chothia
source                  1..7
                        mol_type = protein
                        organism = synthetic construct
SEQUENCE: 22
GFNISHY                                                                 7

SEQ ID NO: 23           moltype = AA   length = 7
FEATURE                 Location/Qualifiers
REGION                  1..7
                        note = Synthetic: 2188-A07; CDR-H1; Chothia
source                  1..7
                        mol_type = protein
                        organism = synthetic construct
SEQUENCE: 23
GFNIHHY                                                                 7

SEQ ID NO: 24           moltype = AA   length = 7
FEATURE                 Location/Qualifiers
REGION                  1..7
                        note = Synthetic: 2188-C01; CDR-H1; Chothia
source                  1..7
                        mol_type = protein
                        organism = synthetic construct
SEQUENCE: 24
GFNIISY                                                                 7

SEQ ID NO: 25           moltype = AA   length = 7
FEATURE                 Location/Qualifiers
REGION                  1..7
                        note = Synthetic: 2188-F08; CDR-H1; Chothia
source                  1..7
                        mol_type = protein
                        organism = synthetic construct
SEQUENCE: 25
GFNIPDF                                                                 7

SEQ ID NO: 26           moltype = AA   length = 7
FEATURE                 Location/Qualifiers
REGION                  1..7
                        note = Synthetic: 2188-E04; CDR-H1; Chothia
source                  1..7
```

```
                            mol_type = protein
                            organism = synthetic construct
SEQUENCE: 26
GFNISDY                                                                         7

SEQ ID NO: 27               moltype = AA   length = 7
FEATURE                     Location/Qualifiers
REGION                      1..7
                            note = Synthetic: 2188-B01; CDR-H1; Chothia
source                      1..7
                            mol_type = protein
                            organism = synthetic construct
SEQUENCE: 27
GFNINSH                                                                         7

SEQ ID NO: 28               moltype = AA   length = 7
FEATURE                     Location/Qualifiers
REGION                      1..7
                            note = Synthetic: 2188-F11; CDR-H1; Chothia
source                      1..7
                            mol_type = protein
                            organism = synthetic construct
SEQUENCE: 28
GFNITGY                                                                         7

SEQ ID NO: 29               moltype = AA   length = 7
FEATURE                     Location/Qualifiers
REGION                      1..7
                            note = Synthetic: 2188-B08; CDR-H1; Chothia
source                      1..7
                            mol_type = protein
                            organism = synthetic construct
SEQUENCE: 29
GFNIDSY                                                                         7

SEQ ID NO: 30               moltype = AA   length = 7
FEATURE                     Location/Qualifiers
REGION                      1..7
                            note = Synthetic: 2188-C10; CDR-H1; Chothia
source                      1..7
                            mol_type = protein
                            organism = synthetic construct
SEQUENCE: 30
GFNINSY                                                                         7

SEQ ID NO: 31               moltype = AA   length = 7
FEATURE                     Location/Qualifiers
REGION                      1..7
                            note = Synthetic: 2188-C02; CDR-H1; Chothia
source                      1..7
                            mol_type = protein
                            organism = synthetic construct
SEQUENCE: 31
GFNIERY                                                                         7

SEQ ID NO: 32               moltype = AA   length = 7
FEATURE                     Location/Qualifiers
REGION                      1..7
                            note = Synthetic: 2188-B07; CDR-H1; Chothia
source                      1..7
                            mol_type = protein
                            organism = synthetic construct
SEQUENCE: 32
GFNIHSH                                                                         7

SEQ ID NO: 33               moltype = AA   length = 7
FEATURE                     Location/Qualifiers
REGION                      1..7
                            note = Synthetic: 2188-A11; CDR-H1; Chothia
source                      1..7
                            mol_type = protein
                            organism = synthetic construct
SEQUENCE: 33
GFNISDY                                                                         7

SEQ ID NO: 34               moltype = AA   length = 7
FEATURE                     Location/Qualifiers
REGION                      1..7
                            note = Synthetic: 2188-D01; CDR-H1; Chothia
```

```
source                      1..7
                            mol_type = protein
                            organism = synthetic construct
SEQUENCE: 34
GFNIKSY                                                                       7

SEQ ID NO: 35               moltype = AA  length = 7
FEATURE                     Location/Qualifiers
REGION                      1..7
                            note = Synthetic: 2188-E09; CDR-H1; Chothia
source                      1..7
                            mol_type = protein
                            organism = synthetic construct
SEQUENCE: 35
GFNISDF                                                                       7

SEQ ID NO: 36               moltype = AA  length = 7
FEATURE                     Location/Qualifiers
REGION                      1..7
                            note = Synthetic: 2188-E06; CDR-H1; Chothia
source                      1..7
                            mol_type = protein
                            organism = synthetic construct
SEQUENCE: 36
GFNIGDY                                                                       7

SEQ ID NO: 37               moltype = AA  length = 7
FEATURE                     Location/Qualifiers
REGION                      1..7
                            note = Synthetic: 2188-B03; CDR-H1; Chothia
source                      1..7
                            mol_type = protein
                            organism = synthetic construct
SEQUENCE: 37
GFNISSY                                                                       7

SEQ ID NO: 38               moltype = AA  length = 7
FEATURE                     Location/Qualifiers
REGION                      1..7
                            note = Synthetic: 2188-F06; CDR-H1; Chothia
source                      1..7
                            mol_type = protein
                            organism = synthetic construct
SEQUENCE: 38
GFNILDY                                                                       7

SEQ ID NO: 39               moltype = AA  length = 7
FEATURE                     Location/Qualifiers
REGION                      1..7
                            note = Synthetic: 2188-D02; CDR-H1; Chothia
source                      1..7
                            mol_type = protein
                            organism = synthetic construct
SEQUENCE: 39
GFNISDY                                                                       7

SEQ ID NO: 40               moltype = AA  length = 7
FEATURE                     Location/Qualifiers
REGION                      1..7
                            note = Synthetic: 2188-B06; CDR-H1; Chothia
source                      1..7
                            mol_type = protein
                            organism = synthetic construct
SEQUENCE: 40
GFNIHSY                                                                       7

SEQ ID NO: 41               moltype = AA  length = 7
FEATURE                     Location/Qualifiers
REGION                      1..7
                            note = Synthetic: 2188-D09; CDR-H1; Chothia
source                      1..7
                            mol_type = protein
                            organism = synthetic construct
SEQUENCE: 41
GFNIRDY                                                                       7

SEQ ID NO: 42               moltype = AA  length = 7
FEATURE                     Location/Qualifiers
REGION                      1..7
```

```
source                      note = Synthetic: 2188-F02; CDR-H1; Chothia
                            1..7
                            mol_type = protein
                            organism = synthetic construct
SEQUENCE: 42
GFNISDY                                                                          7

SEQ ID NO: 43               moltype = AA  length = 7
FEATURE                     Location/Qualifiers
REGION                      1..7
                            note = Synthetic: 2188-E10; CDR-H1; Chothia
source                      1..7
                            mol_type = protein
                            organism = synthetic construct
SEQUENCE: 43
GFNIGDF                                                                          7

SEQ ID NO: 44               moltype = AA  length = 7
FEATURE                     Location/Qualifiers
REGION                      1..7
                            note = Synthetic: 2188-A09; CDR-H1; Chothia
source                      1..7
                            mol_type = protein
                            organism = synthetic construct
SEQUENCE: 44
GFNIINY                                                                          7

SEQ ID NO: 45               moltype = AA  length = 7
FEATURE                     Location/Qualifiers
REGION                      1..7
                            note = Synthetic: 2188-D04; CDR-H1; Chothia
source                      1..7
                            mol_type = protein
                            organism = synthetic construct
SEQUENCE: 45
GFNISDY                                                                          7

SEQ ID NO: 46               moltype = AA  length = 7
FEATURE                     Location/Qualifiers
REGION                      1..7
                            note = Synthetic: 2188-A05; CDR-H1; Chothia
source                      1..7
                            mol_type = protein
                            organism = synthetic construct
SEQUENCE: 46
GFNIKRY                                                                          7

SEQ ID NO: 47               moltype = AA  length = 7
FEATURE                     Location/Qualifiers
REGION                      1..7
                            note = Synthetic: 2188-E01; CDR-H1; Chothia
source                      1..7
                            mol_type = protein
                            organism = synthetic construct
SEQUENCE: 47
GFNIGDY                                                                          7

SEQ ID NO: 48               moltype = AA  length = 7
FEATURE                     Location/Qualifiers
REGION                      1..7
                            note = Synthetic: 2188-G01; CDR-H1; Chothia
source                      1..7
                            mol_type = protein
                            organism = synthetic construct
SEQUENCE: 48
GFNISDY                                                                          7

SEQ ID NO: 49               moltype = AA  length = 7
FEATURE                     Location/Qualifiers
REGION                      1..7
                            note = Synthetic: 2188-B09; CDR-H1; Chothia
source                      1..7
                            mol_type = protein
                            organism = synthetic construct
SEQUENCE: 49
GFNINSY                                                                          7

SEQ ID NO: 50               moltype = AA  length = 7
FEATURE                     Location/Qualifiers
```

```
REGION                  1..7
                        note = Synthetic: 2188-F07; CDR-H1; Chothia
source                  1..7
                        mol_type = protein
                        organism = synthetic construct
SEQUENCE: 50
GFNISDY                                                                    7

SEQ ID NO: 51           moltype = AA  length = 7
FEATURE                 Location/Qualifiers
REGION                  1..7
                        note = Synthetic: 2188-D08; CDR-H1; Chothia
source                  1..7
                        mol_type = protein
                        organism = synthetic construct
SEQUENCE: 51
GFNIRDY                                                                    7

SEQ ID NO: 52           moltype = AA  length = 7
FEATURE                 Location/Qualifiers
REGION                  1..7
                        note = Synthetic: 2188-D05; CDR-H1; Chothia
source                  1..7
                        mol_type = protein
                        organism = synthetic construct
SEQUENCE: 52
GFNISEY                                                                    7

SEQ ID NO: 53           moltype = AA  length = 7
FEATURE                 Location/Qualifiers
REGION                  1..7
                        note = Synthetic: 2188-C03; CDR-H1; Chothia
source                  1..7
                        mol_type = protein
                        organism = synthetic construct
SEQUENCE: 53
GFNINSY                                                                    7

SEQ ID NO: 54           moltype = AA  length = 7
FEATURE                 Location/Qualifiers
REGION                  1..7
                        note = Synthetic: 2188-E08; CDR-H1; Chothia
source                  1..7
                        mol_type = protein
                        organism = synthetic construct
SEQUENCE: 54
GFNIIDF                                                                    7

SEQ ID NO: 55           moltype = AA  length = 7
FEATURE                 Location/Qualifiers
REGION                  1..7
                        note = Synthetic: 2188-C06; CDR-H1; Chothia
source                  1..7
                        mol_type = protein
                        organism = synthetic construct
SEQUENCE: 55
GFNINSY                                                                    7

SEQ ID NO: 56           moltype = AA  length = 7
FEATURE                 Location/Qualifiers
REGION                  1..7
                        note = Synthetic: 2188-A08; CDR-H1; Chothia
source                  1..7
                        mol_type = protein
                        organism = synthetic construct
SEQUENCE: 56
GFNIHNF                                                                    7

SEQ ID NO: 57           moltype = AA  length = 7
FEATURE                 Location/Qualifiers
REGION                  1..7
                        note = Synthetic: 2188-B10; CDR-H1; Chothia
source                  1..7
                        mol_type = protein
                        organism = synthetic construct
SEQUENCE: 57
GFNINSY                                                                    7

SEQ ID NO: 58           moltype = AA  length = 7
```

```
FEATURE                 Location/Qualifiers
REGION                  1..7
                        note = Synthetic: 2188-G02; CDR-H1; Chothia
source                  1..7
                        mol_type = protein
                        organism = synthetic construct
SEQUENCE: 58
GFNIVGY                                                                  7

SEQ ID NO: 59           moltype = AA  length = 7
FEATURE                 Location/Qualifiers
REGION                  1..7
                        note = Synthetic: 2188-C05; CDR-H1; Chothia
source                  1..7
                        mol_type = protein
                        organism = synthetic construct
SEQUENCE: 59
GFNINSF                                                                  7

SEQ ID NO: 60           moltype = AA  length = 7
FEATURE                 Location/Qualifiers
REGION                  1..7
                        note = Synthetic: 2188-A10; CDR-H1; Chothia
source                  1..7
                        mol_type = protein
                        organism = synthetic construct
SEQUENCE: 60
GFNINSY                                                                  7

SEQ ID NO: 61           moltype = AA  length = 7
FEATURE                 Location/Qualifiers
REGION                  1..7
                        note = Synthetic: 2188-G04; CDR-H1; Chothia
source                  1..7
                        mol_type = protein
                        organism = synthetic construct
SEQUENCE: 61
GFNIFDY                                                                  7

SEQ ID NO: 62           moltype = AA  length = 7
FEATURE                 Location/Qualifiers
REGION                  1..7
                        note = Synthetic: 2188-C08; CDR-H1; Chothia
source                  1..7
                        mol_type = protein
                        organism = synthetic construct
SEQUENCE: 62
GFNIKSH                                                                  7

SEQ ID NO: 63           moltype = AA  length = 7
FEATURE                 Location/Qualifiers
REGION                  1..7
                        note = Synthetic: 2188-E05; CDR-H1; Chothia
source                  1..7
                        mol_type = protein
                        organism = synthetic construct
SEQUENCE: 63
GFNISDY                                                                  7

SEQ ID NO: 64           moltype = AA  length = 7
FEATURE                 Location/Qualifiers
REGION                  1..7
                        note = Synthetic: 2188-A02; CDR-H1; Chothia
source                  1..7
                        mol_type = protein
                        organism = synthetic construct
SEQUENCE: 64
GFNIKSY                                                                  7

SEQ ID NO: 65           moltype = AA  length = 7
FEATURE                 Location/Qualifiers
REGION                  1..7
                        note = Synthetic: 2188-F04; CDR-H1; Chothia
source                  1..7
                        mol_type = protein
                        organism = synthetic construct
SEQUENCE: 65
GFNISDF                                                                  7
```

```
SEQ ID NO: 66           moltype = AA  length = 7
FEATURE                 Location/Qualifiers
REGION                  1..7
                        note = Synthetic: 2188-F05; CDR-H1; Chothia
source                  1..7
                        mol_type = protein
                        organism = synthetic construct
SEQUENCE: 66
GFNISDY                                                                    7

SEQ ID NO: 67           moltype = AA  length = 7
FEATURE                 Location/Qualifiers
REGION                  1..7
                        note = Synthetic: 2188-D07; CDR-H1; Chothia
source                  1..7
                        mol_type = protein
                        organism = synthetic construct
SEQUENCE: 67
GFNISDF                                                                    7

SEQ ID NO: 68           moltype = AA  length = 7
FEATURE                 Location/Qualifiers
REGION                  1..7
                        note = Synthetic: 2188-E02; CDR-H1; Chothia
source                  1..7
                        mol_type = protein
                        organism = synthetic construct
SEQUENCE: 68
GFNIPDY                                                                    7

SEQ ID NO: 69           moltype = AA  length = 7
FEATURE                 Location/Qualifiers
REGION                  1..7
                        note = Synthetic: 2188-D06; CDR-H1; Chothia
source                  1..7
                        mol_type = protein
                        organism = synthetic construct
SEQUENCE: 69
GFNIRDY                                                                    7

SEQ ID NO: 70           moltype = AA  length = 7
FEATURE                 Location/Qualifiers
REGION                  1..7
                        note = Synthetic: 2188-F09; CDR-H1; Chothia
source                  1..7
                        mol_type = protein
                        organism = synthetic construct
SEQUENCE: 70
GFNIRDY                                                                    7

SEQ ID NO: 71           moltype = AA  length = 7
FEATURE                 Location/Qualifiers
REGION                  1..7
                        note = Synthetic: 2188-F10; CDR-H1; Chothia
source                  1..7
                        mol_type = protein
                        organism = synthetic construct
SEQUENCE: 71
GFNISVF                                                                    7

SEQ ID NO: 72           moltype = AA  length = 7
FEATURE                 Location/Qualifiers
REGION                  1..7
                        note = Synthetic: 2188-B05; CDR-H1; Chothia
source                  1..7
                        mol_type = protein
                        organism = synthetic construct
SEQUENCE: 72
GFNIPDY                                                                    7

SEQ ID NO: 73           moltype = AA  length = 7
FEATURE                 Location/Qualifiers
REGION                  1..7
                        note = Synthetic: 1943-C02; CDR-H1; Chothia
source                  1..7
                        mol_type = protein
                        organism = synthetic construct
SEQUENCE: 73
GFNINDY                                                                    7
```

```
SEQ ID NO: 74             moltype = AA  length = 7
FEATURE                   Location/Qualifiers
REGION                    1..7
                          note = Synthetic: 2193-D04; CDR-H1; Chothia
source                    1..7
                          mol_type = protein
                          organism = synthetic construct
SEQUENCE: 74
GFNINGF                                                                   7

SEQ ID NO: 75             moltype = AA  length = 7
FEATURE                   Location/Qualifiers
REGION                    1..7
                          note = Synthetic: 2193-E10; CDR-H1; Chothia
source                    1..7
                          mol_type = protein
                          organism = synthetic construct
SEQUENCE: 75
GFNIYDY                                                                   7

SEQ ID NO: 76             moltype = AA  length = 7
FEATURE                   Location/Qualifiers
REGION                    1..7
                          note = Synthetic: 2193-E06; CDR-H1; Chothia
source                    1..7
                          mol_type = protein
                          organism = synthetic construct
SEQUENCE: 76
GFNIDDY                                                                   7

SEQ ID NO: 77             moltype = AA  length = 7
FEATURE                   Location/Qualifiers
REGION                    1..7
                          note = Synthetic: 2193-E04; CDR-H1; Chothia
source                    1..7
                          mol_type = protein
                          organism = synthetic construct
SEQUENCE: 77
GFNINDR                                                                   7

SEQ ID NO: 78             moltype = AA  length = 7
FEATURE                   Location/Qualifiers
REGION                    1..7
                          note = Synthetic: 2193-B09; CDR-H1; Chothia
source                    1..7
                          mol_type = protein
                          organism = synthetic construct
SEQUENCE: 78
GFNINNS                                                                   7

SEQ ID NO: 79             moltype = AA  length = 7
FEATURE                   Location/Qualifiers
REGION                    1..7
                          note = Synthetic: 2193-D11; CDR-H1; Chothia
source                    1..7
                          mol_type = protein
                          organism = synthetic construct
SEQUENCE: 79
GFNINAY                                                                   7

SEQ ID NO: 80             moltype = AA  length = 7
FEATURE                   Location/Qualifiers
REGION                    1..7
                          note = Synthetic: 2193-B02; CDR-H1; Chothia
source                    1..7
                          mol_type = protein
                          organism = synthetic construct
SEQUENCE: 80
GFNIKNS                                                                   7

SEQ ID NO: 81             moltype = AA  length = 7
FEATURE                   Location/Qualifiers
REGION                    1..7
                          note = Synthetic: 2193-D05; CDR-H1; Chothia
source                    1..7
                          mol_type = protein
                          organism = synthetic construct
SEQUENCE: 81
```

-continued

```
GFNINDH                                                               7

SEQ ID NO: 82           moltype = AA  length = 7
FEATURE                 Location/Qualifiers
REGION                  1..7
                        note = Synthetic: 2193-E11; CDR-H1; Chothia
source                  1..7
                        mol_type = protein
                        organism = synthetic construct SEQUENCE: 82
GFNINDY                                                               7

SEQ ID NO: 83           moltype = AA  length = 7
FEATURE                 Location/Qualifiers
REGION                  1..7
                        note = Synthetic: 2193-D06; CDR-H1; Chothia
source                  1..7
                        mol_type = protein
                        organism = synthetic construct SEQUENCE: 83
GFNIRDY                                                               7

SEQ ID NO: 84           moltype = AA  length = 7
FEATURE                 Location/Qualifiers
REGION                  1..7
                        note = Synthetic: 2193-C02; CDR-H1; Chothia
source                  1..7
                        mol_type = protein
                        organism = synthetic construct SEQUENCE: 84
GFNISDY                                                               7

SEQ ID NO: 85           moltype = AA  length = 7
FEATURE                 Location/Qualifiers
REGION                  1..7
                        note = Synthetic: 2193-B03; CDR-H1; Chothia
source                  1..7
                        mol_type = protein
                        organism = synthetic construct SEQUENCE: 85
GFNIRDY                                                               7

SEQ ID NO: 86           moltype = AA  length = 7
FEATURE                 Location/Qualifiers
REGION                  1..7
                        note = Synthetic: 2193-A02; CDR-H1; Chothia
source                  1..7
                        mol_type = protein
                        organism = synthetic construct SEQUENCE: 86
GFNIHAS                                                               7

SEQ ID NO: 87           moltype = AA  length = 7
FEATURE                 Location/Qualifiers
REGION                  1..7
                        note = Synthetic: 2193-E05; CDR-H1; Chothia
source                  1..7
                        mol_type = protein
                        organism = synthetic construct SEQUENCE: 87
GFNIKRS                                                               7

SEQ ID NO: 88           moltype = AA  length = 7
FEATURE                 Location/Qualifiers
REGION                  1..7
                        note = Synthetic: 2193-A06; CDR-H1; Chothia
source                  1..7
                        mol_type = protein
                        organism = synthetic construct SEQUENCE: 88
GFNINAY                                                               7

SEQ ID NO: 89           moltype = AA  length = 7
FEATURE                 Location/Qualifiers
REGION                  1..7
                        note = Synthetic: 2193-C04; CDR-H1; Chothia
source                  1..7
                        mol_type = protein
                        organism = synthetic construct
```

```
SEQUENCE: 89
GFNINTS                                                                          7

SEQ ID NO: 90           moltype = AA  length = 7
FEATURE                 Location/Qualifiers
REGION                  1..7
                        note = Synthetic: 2193-E08; CDR-H1; Chothia
source                  1..7
                        mol_type = protein
                        organism = synthetic construct
SEQUENCE: 90
GFNINEY                                                                          7

SEQ ID NO: 91           moltype = AA  length = 7
FEATURE                 Location/Qualifiers
REGION                  1..7
                        note = Synthetic: 2193-B10; CDR-H1; Chothia
source                  1..7
                        mol_type = protein
                        organism = synthetic construct
SEQUENCE: 91
GFNIADY                                                                          7

SEQ ID NO: 92           moltype = AA  length = 7
FEATURE                 Location/Qualifiers
REGION                  1..7
                        note = Synthetic: 2193-D08; CDR-H1; Chothia
source                  1..7
                        mol_type = protein
                        organism = synthetic construct
SEQUENCE: 92
GFNIKRS                                                                          7

SEQ ID NO: 93           moltype = AA  length = 7
FEATURE                 Location/Qualifiers
REGION                  1..7
                        note = Synthetic: 2193-B08; CDR-H1; Chothia
source                  1..7
                        mol_type = protein
                        organism = synthetic construct
SEQUENCE: 93
GFNIKDY                                                                          7

SEQ ID NO: 94           moltype = AA  length = 7
FEATURE                 Location/Qualifiers
REGION                  1..7
                        note = Synthetic: 2193-C05; CDR-H1; Chothia
source                  1..7
                        mol_type = protein
                        organism = synthetic construct
SEQUENCE: 94
GFNIKHS                                                                          7

SEQ ID NO: 95           moltype = AA  length = 7
FEATURE                 Location/Qualifiers
REGION                  1..7
                        note = Synthetic: 2193-D10; CDR-H1; Chothia
source                  1..7
                        mol_type = protein
                        organism = synthetic construct
SEQUENCE: 95
GFNINVS                                                                          7

SEQ ID NO: 96           moltype = AA  length = 7
FEATURE                 Location/Qualifiers
REGION                  1..7
                        note = Synthetic: 2193-D03; CDR-H1; Chothia
source                  1..7
                        mol_type = protein
                        organism = synthetic construct
SEQUENCE: 96
GFNINDH                                                                          7

SEQ ID NO: 97           moltype = AA  length = 7
FEATURE                 Location/Qualifiers
REGION                  1..7
                        note = Synthetic: 2193-A09; CDR-H1; Chothia
source                  1..7
                        mol_type = protein
```

```
                        organism = synthetic construct
SEQUENCE: 97
GFNIGKH                                                                           7

SEQ ID NO: 98           moltype = AA  length = 7
FEATURE                 Location/Qualifiers
REGION                  1..7
                        note = Synthetic: 2193-A10; CDR-H1; Chothia
source                  1..7
                        mol_type = protein
                        organism = synthetic construct
SEQUENCE: 98
GFNIGDY                                                                           7

SEQ ID NO: 99           moltype = AA  length = 7
FEATURE                 Location/Qualifiers
REGION                  1..7
                        note = Synthetic: 2193-E07; CDR-H1; Chothia
source                  1..7
                        mol_type = protein
                        organism = synthetic construct
SEQUENCE: 99
GFNINKV                                                                           7

SEQ ID NO: 100          moltype = AA  length = 7
FEATURE                 Location/Qualifiers
REGION                  1..7
                        note = Synthetic: 2193-A07; CDR-H1; Chothia
source                  1..7
                        mol_type = protein
                        organism = synthetic construct
SEQUENCE: 100
GFNINAS                                                                           7

SEQ ID NO: 101          moltype = AA  length = 7
FEATURE                 Location/Qualifiers
REGION                  1..7
                        note = Synthetic: 2193-E03; CDR-H1; Chothia
source                  1..7
                        mol_type = protein
                        organism = synthetic construct
SEQUENCE: 101
GFNITAS                                                                           7

SEQ ID NO: 102          moltype = AA  length = 7
FEATURE                 Location/Qualifiers
REGION                  1..7
                        note = Synthetic: 2193-C08; CDR-H1; Chothia
source                  1..7
                        mol_type = protein
                        organism = synthetic construct
SEQUENCE: 102
GFNIHY                                                                            7

SEQ ID NO: 103          moltype = AA  length = 7
FEATURE                 Location/Qualifiers
REGION                  1..7
                        note = Synthetic: 2193-B11; CDR-H1; Chothia
source                  1..7
                        mol_type = protein
                        organism = synthetic construct
SEQUENCE: 103
GFNITGS                                                                           7

SEQ ID NO: 104          moltype = AA  length = 7
FEATURE                 Location/Qualifiers
REGION                  1..7
                        note = Synthetic: 2193-A03; CDR-H1; Chothia
source                  1..7
                        mol_type = protein
                        organism = synthetic construct
SEQUENCE: 104
GFNIANY                                                                           7

SEQ ID NO: 105          moltype = AA  length = 7
FEATURE                 Location/Qualifiers
REGION                  1..7
                        note = Synthetic: 2193-D02; CDR-H1; Chothia
source                  1..7
```

```
                            mol_type = protein
                            organism = synthetic construct
SEQUENCE: 105
GFNIKDY                                                              7

SEQ ID NO: 106              moltype = AA   length = 7
FEATURE                     Location/Qualifiers
REGION                      1..7
                            note = Synthetic: 2193-B06; CDR-H1; Chothia
source                      1..7
                            mol_type = protein
                            organism = synthetic construct
SEQUENCE: 106
GFNIDGY                                                              7

SEQ ID NO: 107              moltype = AA   length = 7
FEATURE                     Location/Qualifiers
REGION                      1..7
                            note = Synthetic: 2193-B01; CDR-H1; Chothia
source                      1..7
                            mol_type = protein
                            organism = synthetic construct
SEQUENCE: 107
GFNIGGY                                                              7

SEQ ID NO: 108              moltype = AA   length = 7
FEATURE                     Location/Qualifiers
REGION                      1..7
                            note = Synthetic: 2193-D09; CDR-H1; Chothia
source                      1..7
                            mol_type = protein
                            organism = synthetic construct
SEQUENCE: 108
GFNINGY                                                              7

SEQ ID NO: 109              moltype = AA   length = 7
FEATURE                     Location/Qualifiers
REGION                      1..7
                            note = Synthetic: 2193-E09; CDR-H1; Chothia
source                      1..7
                            mol_type = protein
                            organism = synthetic construct
SEQUENCE: 109
GFNIGAY                                                              7

SEQ ID NO: 110              moltype = AA   length = 7
FEATURE                     Location/Qualifiers
REGION                      1..7
                            note = Synthetic: 2193-B07; CDR-H1; Chothia
source                      1..7
                            mol_type = protein
                            organism = synthetic construct
SEQUENCE: 110
GFNINNS                                                              7

SEQ ID NO: 111              moltype = AA   length = 7
FEATURE                     Location/Qualifiers
REGION                      1..7
                            note = Synthetic: 2193-C06; CDR-H1; Chothia
source                      1..7
                            mol_type = protein
                            organism = synthetic construct
SEQUENCE: 111
GFNIIVH                                                              7

SEQ ID NO: 112              moltype = AA   length = 7
FEATURE                     Location/Qualifiers
REGION                      1..7
                            note = Synthetic: 2193-B05; CDR-H1; Chothia
source                      1..7
                            mol_type = protein
                            organism = synthetic construct
SEQUENCE: 112
GFNINQY                                                              7

SEQ ID NO: 113              moltype = AA   length = 7
FEATURE                     Location/Qualifiers
REGION                      1..7
                            note = Synthetic: 2193-A11; CDR-H1; Chothia
```

-continued

```
source                      1..7
                            mol_type = protein
                            organism = synthetic construct
SEQUENCE: 113
GFNIDAY                                                                   7

SEQ ID NO: 114              moltype = AA  length = 7
FEATURE                     Location/Qualifiers
REGION                      1..7
                            note = Synthetic: 2193-E02; CDR-H1; Chothia
source                      1..7
                            mol_type = protein
                            organism = synthetic construct
SEQUENCE: 114
GFNIKDY                                                                   7

SEQ ID NO: 115              moltype = AA  length = 7
FEATURE                     Location/Qualifiers
REGION                      1..7
                            note = Synthetic: 2193-A08; CDR-H1; Chothia
source                      1..7
                            mol_type = protein
                            organism = synthetic construct
SEQUENCE: 115
GFNIIDS                                                                   7

SEQ ID NO: 116              moltype = AA  length = 7
FEATURE                     Location/Qualifiers
REGION                      1..7
                            note = Synthetic: 2193-C11; CDR-H1; Chothia
source                      1..7
                            mol_type = protein
                            organism = synthetic construct
SEQUENCE: 116
GFNIADS                                                                   7

SEQ ID NO: 117              moltype = AA  length = 7
FEATURE                     Location/Qualifiers
REGION                      1..7
                            note = Synthetic: 2193-A01; CDR-H1; Chothia
source                      1..7
                            mol_type = protein
                            organism = synthetic construct
SEQUENCE: 117
GFNINDH                                                                   7

SEQ ID NO: 118              moltype = AA  length = 7
FEATURE                     Location/Qualifiers
REGION                      1..7
                            note = Synthetic: 2193-D07; CDR-H1; Chothia
source                      1..7
                            mol_type = protein
                            organism = synthetic construct
SEQUENCE: 118
GFNIIDY                                                                   7

SEQ ID NO: 119              moltype = AA  length = 7
FEATURE                     Location/Qualifiers
REGION                      1..7
                            note = Synthetic: 2193-A05; CDR-H1; Chothia
source                      1..7
                            mol_type = protein
                            organism = synthetic construct
SEQUENCE: 119
GFNIKGY                                                                   7

SEQ ID NO: 120              moltype = AA  length = 7
FEATURE                     Location/Qualifiers
REGION                      1..7
                            note = Synthetic: 2193-C03; CDR-H1; Chothia
source                      1..7
                            mol_type = protein
                            organism = synthetic construct
SEQUENCE: 120
GFNINYS                                                                   7

SEQ ID NO: 121              moltype = AA  length = 7
FEATURE                     Location/Qualifiers
REGION                      1..7
```

```
source                    note = Synthetic: 2193-C09; CDR-H1; Chothia
                          1..7
                          mol_type = protein
                          organism = synthetic construct
SEQUENCE: 121
GFNINHS                                                                   7

SEQ ID NO: 122            moltype = AA  length = 7
FEATURE                   Location/Qualifiers
REGION                    1..7
                          note = Synthetic: 2193-D01; CDR-H1; Chothia
source                    1..7
                          mol_type = protein
                          organism = synthetic construct
SEQUENCE: 122
GFNINDS                                                                   7

SEQ ID NO: 123            moltype = AA  length = 7
FEATURE                   Location/Qualifiers
REGION                    1..7
                          note = Synthetic: 2193-E01; CDR-H1; Chothia
source                    1..7
                          mol_type = protein
                          organism = synthetic construct
SEQUENCE: 123
GFNIKGK                                                                   7

SEQ ID NO: 124            moltype = AA  length = 7
FEATURE                   Location/Qualifiers
REGION                    1..7
                          note = Synthetic: 2193-C07; CDR-H1; Chothia
source                    1..7
                          mol_type = protein
                          organism = synthetic construct
SEQUENCE: 124
GFNIKDQ                                                                   7

SEQ ID NO: 125            moltype = AA  length = 7
FEATURE                   Location/Qualifiers
REGION                    1..7
                          note = Synthetic: 2193-B04; CDR-H1; Chothia
source                    1..7
                          mol_type = protein
                          organism = synthetic construct
SEQUENCE: 125
GFNISNS                                                                   7

SEQ ID NO: 126            moltype = AA  length = 7
FEATURE                   Location/Qualifiers
REGION                    1..7
                          note = Synthetic: 2193-C10; CDR-H1; Chothia
source                    1..7
                          mol_type = protein
                          organism = synthetic construct
SEQUENCE: 126
GFNINNA                                                                   7

SEQ ID NO: 127            moltype = AA  length = 7
FEATURE                   Location/Qualifiers
REGION                    1..7
                          note = Synthetic: 2193-C01; CDR-H1; Chothia
source                    1..7
                          mol_type = protein
                          organism = synthetic construct
SEQUENCE: 127
GLNINDH                                                                   7

SEQ ID NO: 128            moltype = AA  length = 7
FEATURE                   Location/Qualifiers
REGION                    1..7
                          note = Synthetic: 2193-A04; CDR-H1; Chothia
source                    1..7
                          mol_type = protein
                          organism = synthetic construct
SEQUENCE: 128
GFNIISY                                                                   7

SEQ ID NO: 129            moltype = AA  length = 7
FEATURE                   Location/Qualifiers
```

```
REGION              1..7
                    note = Synthetic: 1944-A07; CDR-H1; Chothia
source              1..7
                    mol_type = protein
                    organism = synthetic construct
SEQUENCE: 129
GFNITGY                                                                    7

SEQ ID NO: 130      moltype = AA  length = 7
FEATURE             Location/Qualifiers
REGION              1..7
                    note = Synthetic: 2194-A02; CDR-H1; Chothia
source              1..7
                    mol_type = protein
                    organism = synthetic construct
SEQUENCE: 130
GFNITGY                                                                    7

SEQ ID NO: 131      moltype = AA  length = 7
FEATURE             Location/Qualifiers
REGION              1..7
                    note = Synthetic: 2194-A05; CDR-H1; Chothia
source              1..7
                    mol_type = protein
                    organism = synthetic construct
SEQUENCE: 131
GFNIKEY                                                                    7

SEQ ID NO: 132      moltype = AA  length = 7
FEATURE             Location/Qualifiers
REGION              1..7
                    note = Synthetic: 2194-B04; CDR-H1; Chothia
source              1..7
                    mol_type = protein
                    organism = synthetic construct
SEQUENCE: 132
GFNITGY                                                                    7

SEQ ID NO: 133      moltype = AA  length = 7
FEATURE             Location/Qualifiers
REGION              1..7
                    note = Synthetic: 2194-A09; CDR-H1; Chothia
source              1..7
                    mol_type = protein
                    organism = synthetic construct
SEQUENCE: 133
GFNITGY                                                                    7

SEQ ID NO: 134      moltype = AA  length = 7
FEATURE             Location/Qualifiers
REGION              1..7
                    note = Synthetic: 2194-A01; CDR-H1; Chothia
source              1..7
                    mol_type = protein
                    organism = synthetic construct
SEQUENCE: 134
GFNITGY                                                                    7

SEQ ID NO: 135      moltype = AA  length = 7
FEATURE             Location/Qualifiers
REGION              1..7
                    note = Synthetic: 2194-B03; CDR-H1; Chothia
source              1..7
                    mol_type = protein
                    organism = synthetic construct
SEQUENCE: 135
GFNITSY                                                                    7

SEQ ID NO: 136      moltype = AA  length = 7
FEATURE             Location/Qualifiers
REGION              1..7
                    note = Synthetic: 2194-B02; CDR-H1; Chothia
source              1..7
                    mol_type = protein
                    organism = synthetic construct
SEQUENCE: 136
GFNISGY                                                                    7

SEQ ID NO: 137      moltype = AA  length = 7
```

```
FEATURE                 Location/Qualifiers
REGION                  1..7
                        note = Synthetic: 2194-A03; CDR-H1; Chothia
source                  1..7
                        mol_type = protein
                        organism = synthetic construct
SEQUENCE: 137
GFNITGY                                                                 7

SEQ ID NO: 138          moltype = AA  length = 7
FEATURE                 Location/Qualifiers
REGION                  1..7
                        note = Synthetic: 2194-A11; CDR-H1; Chothia
source                  1..7
                        mol_type = protein
                        organism = synthetic construct
SEQUENCE: 138
GFNITQY                                                                 7

SEQ ID NO: 139          moltype = AA  length = 7
FEATURE                 Location/Qualifiers
REGION                  1..7
                        note = Synthetic: 2194-A08; CDR-H1; Chothia
source                  1..7
                        mol_type = protein
                        organism = synthetic construct
SEQUENCE: 139
GFNITGY                                                                 7

SEQ ID NO: 140          moltype = AA  length = 7
FEATURE                 Location/Qualifiers
REGION                  1..7
                        note = Synthetic: 2194-A04; CDR-H1; Chothia
source                  1..7
                        mol_type = protein
                        organism = synthetic construct
SEQUENCE: 140
GFNITGY                                                                 7

SEQ ID NO: 141          moltype = AA  length = 7
FEATURE                 Location/Qualifiers
REGION                  1..7
                        note = Synthetic: 2194-A10; CDR-H1; Chothia
source                  1..7
                        mol_type = protein
                        organism = synthetic construct
SEQUENCE: 141
GFNITQY                                                                 7

SEQ ID NO: 142          moltype = AA  length = 7
FEATURE                 Location/Qualifiers
REGION                  1..7
                        note = Synthetic: 2194-A07; CDR-H1; Chothia
source                  1..7
                        mol_type = protein
                        organism = synthetic construct
SEQUENCE: 142
GFNFTDY                                                                 7

SEQ ID NO: 143          moltype = AA  length = 7
FEATURE                 Location/Qualifiers
REGION                  1..7
                        note = Synthetic: 2194-B01; CDR-H1; Chothia
source                  1..7
                        mol_type = protein
                        organism = synthetic construct
SEQUENCE: 143
GFNIASY                                                                 7

SEQ ID NO: 144          moltype = AA  length = 7
FEATURE                 Location/Qualifiers
REGION                  1..7
                        note = Synthetic: 2194-A06; CDR-H1; Chothia
source                  1..7
                        mol_type = protein
                        organism = synthetic construct
SEQUENCE: 144
GFNITDY                                                                 7
```

```
SEQ ID NO: 145          moltype = AA  length = 7
FEATURE                 Location/Qualifiers
REGION                  1..7
                        note = Synthetic: 2196-C01; CDR-H1; Chothia
source                  1..7
                        mol_type = protein
                        organism = synthetic construct
SEQUENCE: 145
GFNIIGY                                                                    7

SEQ ID NO: 146          moltype = AA  length = 7
FEATURE                 Location/Qualifiers
REGION                  1..7
                        note = Synthetic: 2196-A02; CDR-H1; Chothia
source                  1..7
                        mol_type = protein
                        organism = synthetic construct
SEQUENCE: 146
GFNITGY                                                                    7

SEQ ID NO: 147          moltype = AA  length = 7
FEATURE                 Location/Qualifiers
REGION                  1..7
                        note = Synthetic: 2196-B03; CDR-H1; Chothia
source                  1..7
                        mol_type = protein
                        organism = synthetic construct
SEQUENCE: 147
GFNITGY                                                                    7

SEQ ID NO: 148          moltype = AA  length = 7
FEATURE                 Location/Qualifiers
REGION                  1..7
                        note = Synthetic: 2196-A05; CDR-H1; Chothia
source                  1..7
                        mol_type = protein
                        organism = synthetic construct
SEQUENCE: 148
GFNITNY                                                                    7

SEQ ID NO: 149          moltype = AA  length = 7
FEATURE                 Location/Qualifiers
REGION                  1..7
                        note = Synthetic: 2196-C02; CDR-H1; Chothia
source                  1..7
                        mol_type = protein
                        organism = synthetic construct
SEQUENCE: 149
GFNITGY                                                                    7

SEQ ID NO: 150          moltype = AA  length = 7
FEATURE                 Location/Qualifiers
REGION                  1..7
                        note = Synthetic: 2196-B11; CDR-H1; Chothia
source                  1..7
                        mol_type = protein
                        organism = synthetic construct
SEQUENCE: 150
GFNITGY                                                                    7

SEQ ID NO: 151          moltype = AA  length = 7
FEATURE                 Location/Qualifiers
REGION                  1..7
                        note = Synthetic: 2196-B08; CDR-H1; Chothia
source                  1..7
                        mol_type = protein
                        organism = synthetic construct
SEQUENCE: 151
GFNITGY                                                                    7

SEQ ID NO: 152          moltype = AA  length = 7
FEATURE                 Location/Qualifiers
REGION                  1..7
                        note = Synthetic: 2196-A04; CDR-H1; Chothia
source                  1..7
                        mol_type = protein
                        organism = synthetic construct
SEQUENCE: 152
GFNISPY                                                                    7
```

```
SEQ ID NO: 153          moltype = AA   length = 7
FEATURE                 Location/Qualifiers
REGION                  1..7
                        note = Synthetic: 2196-A03; CDR-H1; Chothia
source                  1..7
                        mol_type = protein
                        organism = synthetic construct
SEQUENCE: 153
GFNITQY                                                                   7

SEQ ID NO: 154          moltype = AA   length = 7
FEATURE                 Location/Qualifiers
REGION                  1..7
                        note = Synthetic: 2196-B07; CDR-H1; Chothia
source                  1..7
                        mol_type = protein
                        organism = synthetic construct
SEQUENCE: 154
GFNITGY                                                                   7

SEQ ID NO: 155          moltype = AA   length = 7
FEATURE                 Location/Qualifiers
REGION                  1..7
                        note = Synthetic: 2196-A06; CDR-H1; Chothia
source                  1..7
                        mol_type = protein
                        organism = synthetic construct
SEQUENCE: 155
GFNITGY                                                                   7

SEQ ID NO: 156          moltype = AA   length = 7
FEATURE                 Location/Qualifiers
REGION                  1..7
                        note = Synthetic: 2196-B05; CDR-H1; Chothia
source                  1..7
                        mol_type = protein
                        organism = synthetic construct
SEQUENCE: 156
GFNITGY                                                                   7

SEQ ID NO: 157          moltype = AA   length = 7
FEATURE                 Location/Qualifiers
REGION                  1..7
                        note = Synthetic: 2196-A01; CDR-H1; Chothia
source                  1..7
                        mol_type = protein
                        organism = synthetic construct
SEQUENCE: 157
GFNITGY                                                                   7

SEQ ID NO: 158          moltype = AA   length = 7
FEATURE                 Location/Qualifiers
REGION                  1..7
                        note = Synthetic: 2196-B01; CDR-H1; Chothia
source                  1..7
                        mol_type = protein
                        organism = synthetic construct
SEQUENCE: 158
GFNITGY                                                                   7

SEQ ID NO: 159          moltype = AA   length = 7
FEATURE                 Location/Qualifiers
REGION                  1..7
                        note = Synthetic: 2196-A09; CDR-H1; Chothia
source                  1..7
                        mol_type = protein
                        organism = synthetic construct
SEQUENCE: 159
GFNITGY                                                                   7

SEQ ID NO: 160          moltype = AA   length = 7
FEATURE                 Location/Qualifiers
REGION                  1..7
                        note = Synthetic: 2196-A08; CDR-H1; Chothia
source                  1..7
                        mol_type = protein
                        organism = synthetic construct
SEQUENCE: 160
```

```
GFNITGY                                                             7

SEQ ID NO: 161       moltype = AA  length = 7
FEATURE              Location/Qualifiers
REGION               1..7
                     note = Synthetic: 2196-A10; CDR-H1; Chothia
source               1..7
                     mol_type = protein
                     organism = synthetic construct
SEQUENCE: 161
GFNITGY                                                             7

SEQ ID NO: 162       moltype = AA  length = 7
FEATURE              Location/Qualifiers
REGION               1..7
                     note = Synthetic: 2196-B06; CDR-H1; Chothia
source               1..7
                     mol_type = protein
                     organism = synthetic construct
SEQUENCE: 162
GFNITGY                                                             7

SEQ ID NO: 163       moltype = AA  length = 7
FEATURE              Location/Qualifiers
REGION               1..7
                     note = Synthetic: 2196-B09; CDR-H1; Chothia
source               1..7
                     mol_type = protein
                     organism = synthetic construct
SEQUENCE: 163
GFNITEY                                                             7

SEQ ID NO: 164       moltype = AA  length = 7
FEATURE              Location/Qualifiers
REGION               1..7
                     note = Synthetic: 2196-C03; CDR-H1; Chothia
source               1..7
                     mol_type = protein
                     organism = synthetic construct
SEQUENCE: 164
GFNITGY                                                             7

SEQ ID NO: 165       moltype = AA  length = 7
FEATURE              Location/Qualifiers
REGION               1..7
                     note = Synthetic: 2196-C04; CDR-H1; Chothia
source               1..7
                     mol_type = protein
                     organism = synthetic construct
SEQUENCE: 165
GFNITGY                                                             7

SEQ ID NO: 166       moltype = AA  length = 7
FEATURE              Location/Qualifiers
REGION               1..7
                     note = Synthetic: 2196-A07; CDR-H1; Chothia
source               1..7
                     mol_type = protein
                     organism = synthetic construct
SEQUENCE: 166
GFNITGY                                                             7

SEQ ID NO: 167       moltype = AA  length = 7
FEATURE              Location/Qualifiers
REGION               1..7
                     note = Synthetic: 2196-A11; CDR-H1; Chothia
source               1..7
                     mol_type = protein
                     organism = synthetic construct
SEQUENCE: 167
GFNITGY                                                             7

SEQ ID NO: 168       moltype = AA  length = 7
FEATURE              Location/Qualifiers
REGION               1..7
                     note = Synthetic: 2196-B02; CDR-H1; Chothia
source               1..7
                     mol_type = protein
                     organism = synthetic construct
```

```
SEQUENCE: 168
GFNITQY                                                                   7

SEQ ID NO: 169         moltype = AA  length = 7
FEATURE                Location/Qualifiers
REGION                 1..7
                       note = Synthetic: 2196-B04; CDR-H1; Chothia
source                 1..7
                       mol_type = protein
                       organism = synthetic construct
SEQUENCE: 169
GFNITEY                                                                   7

SEQ ID NO: 170         moltype = AA  length = 7
FEATURE                Location/Qualifiers
REGION                 1..7
                       note = Synthetic: 2196-B10; CDR-H1; Chothia
source                 1..7
                       mol_type = protein
                       organism = synthetic construct
SEQUENCE: 170
GFNITGY                                                                   7

SEQ ID NO: 171         moltype = AA  length = 5
FEATURE                Location/Qualifiers
REGION                 1..5
                       note = Synthetic: 1987-C05; CDR-H1; Kabat
source                 1..5
                       mol_type = protein
                       organism = synthetic construct
SEQUENCE: 171
DYDIH                                                                     5

SEQ ID NO: 172         moltype = AA  length = 5
FEATURE                Location/Qualifiers
REGION                 1..5
                       note = Synthetic: 2188-D11; CDR-H1; Kabat
source                 1..5
                       mol_type = protein
                       organism = synthetic construct
SEQUENCE: 172
DYDIH                                                                     5

SEQ ID NO: 173         moltype = AA  length = 5
FEATURE                Location/Qualifiers
REGION                 1..5
                       note = Synthetic: 2188-B04; CDR-H1; Kabat
source                 1..5
                       mol_type = protein
                       organism = synthetic construct
SEQUENCE: 173
WYDIH                                                                     5

SEQ ID NO: 174         moltype = AA  length = 5
FEATURE                Location/Qualifiers
REGION                 1..5
                       note = Synthetic: 2188-C09; CDR-H1; Kabat
source                 1..5
                       mol_type = protein
                       organism = synthetic construct
SEQUENCE: 174
SYDIH                                                                     5

SEQ ID NO: 175         moltype = AA  length = 5
FEATURE                Location/Qualifiers
REGION                 1..5
                       note = Synthetic: 2188-G03; CDR-H1; Kabat
source                 1..5
                       mol_type = protein
                       organism = synthetic construct
SEQUENCE: 175
DYDIH                                                                     5

SEQ ID NO: 176         moltype = AA  length = 5
FEATURE                Location/Qualifiers
REGION                 1..5
                       note = Synthetic: 2188-E03; CDR-H1; Kabat
source                 1..5
                       mol_type = protein
```

```
                              -continued organism = synthetic construct
SEQUENCE: 176
DYDIH                                                                          5

SEQ ID NO: 177                moltype = AA  length = 5
FEATURE                       Location/Qualifiers
REGION                        1..5
                              note = Synthetic: 2188-B11; CDR-H1; Kabat
source                        1..5
                              mol_type = protein
                              organism = synthetic construct
SEQUENCE: 177
RYDIH                                                                          5

SEQ ID NO: 178                moltype = AA  length = 5
FEATURE                       Location/Qualifiers
REGION                        1..5
                              note = Synthetic: 2188-E07; CDR-H1; Kabat
source                        1..5
                              mol_type = protein
                              organism = synthetic construct
SEQUENCE: 178
DYGIH                                                                          5

SEQ ID NO: 179                moltype = AA  length = 5
FEATURE                       Location/Qualifiers
REGION                        1..5
                              note = Synthetic: 2188-B02; CDR-H1; Kabat
source                        1..5
                              mol_type = protein
                              organism = synthetic construct
SEQUENCE: 179
SYDIH                                                                          5

SEQ ID NO: 180                moltype = AA  length = 5
FEATURE                       Location/Qualifiers
REGION                        1..5
                              note = Synthetic: 2188-C07; CDR-H1; Kabat
source                        1..5
                              mol_type = protein
                              organism = synthetic construct
SEQUENCE: 180
RYDIH                                                                          5

SEQ ID NO: 181                moltype = AA  length = 5
FEATURE                       Location/Qualifiers
REGION                        1..5
                              note = Synthetic: 2188-A03; CDR-H1; Kabat
source                        1..5
                              mol_type = protein
                              organism = synthetic construct
SEQUENCE: 181
DYDIH                                                                          5

SEQ ID NO: 182                moltype = AA  length = 5
FEATURE                       Location/Qualifiers
REGION                        1..5
                              note = Synthetic: 2188-F03; CDR-H1; Kabat
source                        1..5
                              mol_type = protein
                              organism = synthetic construct
SEQUENCE: 182
DYDIH                                                                          5

SEQ ID NO: 183                moltype = AA  length = 5
FEATURE                       Location/Qualifiers
REGION                        1..5
                              note = Synthetic: 2188-D03; CDR-H1; Kabat
source                        1..5
                              mol_type = protein
                              organism = synthetic construct
SEQUENCE: 183
DYDIH                                                                          5

SEQ ID NO: 184                moltype = AA  length = 5
FEATURE                       Location/Qualifiers
REGION                        1..5
                              note = Synthetic: 2188-C04; CDR-H1; Kabat
source                        1..5
```

-continued

```
                        mol_type = protein
                        organism = synthetic construct
SEQUENCE: 184
SYDIH                                                                   5

SEQ ID NO: 185          moltype = AA   length = 5
FEATURE                 Location/Qualifiers
REGION                  1..5
                        note = Synthetic: 2188-D10; CDR-H1; Kabat
source                  1..5
                        mol_type = protein
                        organism = synthetic construct
SEQUENCE: 185
DYDIH                                                                   5

SEQ ID NO: 186          moltype = AA   length = 5
FEATURE                 Location/Qualifiers
REGION                  1..5
                        note = Synthetic: 2188-A06; CDR-H1; Kabat
source                  1..5
                        mol_type = protein
                        organism = synthetic construct
SEQUENCE: 186
SYDIH                                                                   5

SEQ ID NO: 187          moltype = AA   length = 5
FEATURE                 Location/Qualifiers
REGION                  1..5
                        note = Synthetic: 2188-C11; CDR-H1; Kabat
source                  1..5
                        mol_type = protein
                        organism = synthetic construct
SEQUENCE: 187
SYDIH                                                                   5

SEQ ID NO: 188          moltype = AA   length = 5
FEATURE                 Location/Qualifiers
REGION                  1..5
                        note = Synthetic: 2188-F01; CDR-H1; Kabat
source                  1..5
                        mol_type = protein
                        organism = synthetic construct
SEQUENCE: 188
YYDIH                                                                   5

SEQ ID NO: 189          moltype = AA   length = 5
FEATURE                 Location/Qualifiers
REGION                  1..5
                        note = Synthetic: 2188-E11; CDR-H1; Kabat
source                  1..5
                        mol_type = protein
                        organism = synthetic construct
SEQUENCE: 189
HYDIH                                                                   5

SEQ ID NO: 190          moltype = AA   length = 5
FEATURE                 Location/Qualifiers
REGION                  1..5
                        note = Synthetic: 2188-A07; CDR-H1; Kabat
source                  1..5
                        mol_type = protein
                        organism = synthetic construct
SEQUENCE: 190
HYDIH                                                                   5

SEQ ID NO: 191          moltype = AA   length = 5
FEATURE                 Location/Qualifiers
REGION                  1..5
                        note = Synthetic: 2188-C01; CDR-H1; Kabat
source                  1..5
                        mol_type = protein
                        organism = synthetic construct
SEQUENCE: 191
SYDIH                                                                   5

SEQ ID NO: 192          moltype = AA   length = 5
FEATURE                 Location/Qualifiers
REGION                  1..5
                        note = Synthetic: 2188-F08; CDR-H1; Kabat
```

```
source                  1..5
                        mol_type = protein
                        organism = synthetic construct
SEQUENCE: 192
DFEIH                                                                    5

SEQ ID NO: 193          moltype = AA   length = 5
FEATURE                 Location/Qualifiers
REGION                  1..5
                        note = Synthetic: 2188-E04; CDR-H1; Kabat
source                  1..5
                        mol_type = protein
                        organism = synthetic construct
SEQUENCE: 193
DYDIH                                                                    5

SEQ ID NO: 194          moltype = AA   length = 5
FEATURE                 Location/Qualifiers
REGION                  1..5
                        note = Synthetic: 2188-B01; CDR-H1; Kabat
source                  1..5
                        mol_type = protein
                        organism = synthetic construct
SEQUENCE: 194
SHDIH                                                                    5

SEQ ID NO: 195          moltype = AA   length = 5
FEATURE                 Location/Qualifiers
REGION                  1..5
                        note = Synthetic: 2188-F11; CDR-H1; Kabat
source                  1..5
                        mol_type = protein
                        organism = synthetic construct
SEQUENCE: 195
GYDIH                                                                    5

SEQ ID NO: 196          moltype = AA   length = 5
FEATURE                 Location/Qualifiers
REGION                  1..5
                        note = Synthetic: 2188-B08; CDR-H1; Kabat
source                  1..5
                        mol_type = protein
                        organism = synthetic construct
SEQUENCE: 196
SYDIH                                                                    5

SEQ ID NO: 197          moltype = AA   length = 5
FEATURE                 Location/Qualifiers
REGION                  1..5
                        note = Synthetic: 2188-C10; CDR-H1; Kabat
source                  1..5
                        mol_type = protein
                        organism = synthetic construct
SEQUENCE: 197
SYDIH                                                                    5

SEQ ID NO: 198          moltype = AA   length = 5
FEATURE                 Location/Qualifiers
REGION                  1..5
                        note = Synthetic: 2188-C02; CDR-H1; Kabat
source                  1..5
                        mol_type = protein
                        organism = synthetic construct
SEQUENCE: 198
RYDIH                                                                    5

SEQ ID NO: 199          moltype = AA   length = 5
FEATURE                 Location/Qualifiers
REGION                  1..5
                        note = Synthetic: 2188-B07; CDR-H1; Kabat
source                  1..5
                        mol_type = protein
                        organism = synthetic construct
SEQUENCE: 199
SHDIH                                                                    5

SEQ ID NO: 200          moltype = AA   length = 5
FEATURE                 Location/Qualifiers
REGION                  1..5
```

```
SEQ ID NO: 200                          moltype = AA  length = 5
FEATURE                                 Location/Qualifiers
REGION                                  1..5
                                        note = Synthetic: 2188-A11; CDR-H1; Kabat
source                                  1..5
                                        mol_type = protein
                                        organism = synthetic construct
SEQUENCE: 200
DYDIH                                                                           5

SEQ ID NO: 201                          moltype = AA  length = 5
FEATURE                                 Location/Qualifiers
REGION                                  1..5
                                        note = Synthetic: 2188-D01; CDR-H1; Kabat
source                                  1..5
                                        mol_type = protein
                                        organism = synthetic construct
SEQUENCE: 201
SYDIH                                                                           5

SEQ ID NO: 202                          moltype = AA  length = 5
FEATURE                                 Location/Qualifiers
REGION                                  1..5
                                        note = Synthetic: 2188-E09; CDR-H1; Kabat
source                                  1..5
                                        mol_type = protein
                                        organism = synthetic construct
SEQUENCE: 202
DFDIH                                                                           5

SEQ ID NO: 203                          moltype = AA  length = 5
FEATURE                                 Location/Qualifiers
REGION                                  1..5
                                        note = Synthetic: 2188-E06; CDR-H1; Kabat
source                                  1..5
                                        mol_type = protein
                                        organism = synthetic construct
SEQUENCE: 203
DYDIH                                                                           5

SEQ ID NO: 204                          moltype = AA  length = 5
FEATURE                                 Location/Qualifiers
REGION                                  1..5
                                        note = Synthetic: 2188-B03; CDR-H1; Kabat
source                                  1..5
                                        mol_type = protein
                                        organism = synthetic construct
SEQUENCE: 204
SYDIH                                                                           5

SEQ ID NO: 205                          moltype = AA  length = 5
FEATURE                                 Location/Qualifiers
REGION                                  1..5
                                        note = Synthetic: 2188-F06; CDR-H1; Kabat
source                                  1..5
                                        mol_type = protein
                                        organism = synthetic construct
SEQUENCE: 205
DYDIH                                                                           5

SEQ ID NO: 206                          moltype = AA  length = 5
FEATURE                                 Location/Qualifiers
REGION                                  1..5
                                        note = Synthetic: 2188-D02; CDR-H1; Kabat
source                                  1..5
                                        mol_type = protein
                                        organism = synthetic construct
SEQUENCE: 206
DYDIH                                                                           5

SEQ ID NO: 207                          moltype = AA  length = 5
FEATURE                                 Location/Qualifiers
REGION                                  1..5
                                        note = Synthetic: 2188-B06; CDR-H1; Kabat
source                                  1..5
                                        mol_type = protein
                                        organism = synthetic construct
SEQUENCE: 207
SYDIH                                                                           5

SEQ ID NO: 208                          moltype = AA  length = 5
FEATURE                                 Location/Qualifiers
```

```
REGION                  1..5
                        note = Synthetic: 2188-D09; CDR-H1; Kabat
source                  1..5
                        mol_type = protein
                        organism = synthetic construct
SEQUENCE: 208
DYDIH                                                                      5

SEQ ID NO: 209          moltype = AA  length = 5
FEATURE                 Location/Qualifiers
REGION                  1..5
                        note = Synthetic: 2188-F02; CDR-H1; Kabat
source                  1..5
                        mol_type = protein
                        organism = synthetic construct
SEQUENCE: 209
DYDIH                                                                      5

SEQ ID NO: 210          moltype = AA  length = 5
FEATURE                 Location/Qualifiers
REGION                  1..5
                        note = Synthetic: 2188-E10; CDR-H1; Kabat
source                  1..5
                        mol_type = protein
                        organism = synthetic construct
SEQUENCE: 210
DFDIH                                                                      5

SEQ ID NO: 211          moltype = AA  length = 5
FEATURE                 Location/Qualifiers
REGION                  1..5
                        note = Synthetic: 2188-A09; CDR-H1; Kabat
source                  1..5
                        mol_type = protein
                        organism = synthetic construct
SEQUENCE: 211
NYDIH                                                                      5

SEQ ID NO: 212          moltype = AA  length = 5
FEATURE                 Location/Qualifiers
REGION                  1..5
                        note = Synthetic: 2188-D04; CDR-H1; Kabat
source                  1..5
                        mol_type = protein
                        organism = synthetic construct
SEQUENCE: 212
DYDIH                                                                      5

SEQ ID NO: 213          moltype = AA  length = 5
FEATURE                 Location/Qualifiers
REGION                  1..5
                        note = Synthetic: 2188-A05; CDR-H1; Kabat
source                  1..5
                        mol_type = protein
                        organism = synthetic construct
SEQUENCE: 213
RYDIH                                                                      5

SEQ ID NO: 214          moltype = AA  length = 5
FEATURE                 Location/Qualifiers
REGION                  1..5
                        note = Synthetic: 2188-E01; CDR-H1; Kabat
source                  1..5
                        mol_type = protein
                        organism = synthetic construct
SEQUENCE: 214
DYDIH                                                                      5

SEQ ID NO: 215          moltype = AA  length = 5
FEATURE                 Location/Qualifiers
REGION                  1..5
                        note = Synthetic: 2188-G01; CDR-H1; Kabat
source                  1..5
                        mol_type = protein
                        organism = synthetic construct
SEQUENCE: 215
DYDIH                                                                      5

SEQ ID NO: 216          moltype = AA  length = 5
```

```
                         -continued

FEATURE                  Location/Qualifiers
REGION                   1..5
                         note = Synthetic: 2188-B09; CDR-H1; Kabat
source                   1..5
                         mol_type = protein
                         organism = synthetic construct
SEQUENCE: 216
SYDIH                                                                    5

SEQ ID NO: 217           moltype = AA  length = 5
FEATURE                  Location/Qualifiers
REGION                   1..5
                         note = Synthetic: 2188-F07; CDR-H1; Kabat
source                   1..5
                         mol_type = protein
                         organism = synthetic construct
SEQUENCE: 217
DYDIH                                                                    5

SEQ ID NO: 218           moltype = AA  length = 5
FEATURE                  Location/Qualifiers
REGION                   1..5
                         note = Synthetic: 2188-D08; CDR-H1; Kabat
source                   1..5
                         mol_type = protein
                         organism = synthetic construct
SEQUENCE: 218
DYDIH                                                                    5

SEQ ID NO: 219           moltype = AA  length = 5
FEATURE                  Location/Qualifiers
REGION                   1..5
                         note = Synthetic: 2188-D05; CDR-H1; Kabat
source                   1..5
                         mol_type = protein
                         organism = synthetic construct
SEQUENCE: 219
EYDIH                                                                    5

SEQ ID NO: 220           moltype = AA  length = 5
FEATURE                  Location/Qualifiers
REGION                   1..5
                         note = Synthetic: 2188-C03; CDR-H1; Kabat
source                   1..5
                         mol_type = protein
                         organism = synthetic construct
SEQUENCE: 220
SYDIH                                                                    5

SEQ ID NO: 221           moltype = AA  length = 5
FEATURE                  Location/Qualifiers
REGION                   1..5
                         note = Synthetic: 2188-E08; CDR-H1; Kabat
source                   1..5
                         mol_type = protein
                         organism = synthetic construct
SEQUENCE: 221
DFDIH                                                                    5

SEQ ID NO: 222           moltype = AA  length = 5
FEATURE                  Location/Qualifiers
REGION                   1..5
                         note = Synthetic: 2188-C06; CDR-H1; Kabat
source                   1..5
                         mol_type = protein
                         organism = synthetic construct
SEQUENCE: 222
SYDIH                                                                    5

SEQ ID NO: 223           moltype = AA  length = 5
FEATURE                  Location/Qualifiers
REGION                   1..5
                         note = Synthetic: 2188-A08; CDR-H1; Kabat
source                   1..5
                         mol_type = protein
                         organism = synthetic construct
SEQUENCE: 223
NFDIH                                                                    5
```

```
SEQ ID NO: 224         moltype = AA  length = 5
FEATURE                Location/Qualifiers
REGION                 1..5
                       note = Synthetic: 2188-B10; CDR-H1; Kabat
source                 1..5
                       mol_type = protein
                       organism = synthetic construct
SEQUENCE: 224
SYDIH                                                                    5

SEQ ID NO: 225         moltype = AA  length = 5
FEATURE                Location/Qualifiers
REGION                 1..5
                       note = Synthetic: 2188-G02; CDR-H1; Kabat
source                 1..5
                       mol_type = protein
                       organism = synthetic construct
SEQUENCE: 225
GYDIH                                                                    5

SEQ ID NO: 226         moltype = AA  length = 5
FEATURE                Location/Qualifiers
REGION                 1..5
                       note = Synthetic: 2188-C05; CDR-H1; Kabat
source                 1..5
                       mol_type = protein
                       organism = synthetic construct
SEQUENCE: 226
SFDIH                                                                    5

SEQ ID NO: 227         moltype = AA  length = 5
FEATURE                Location/Qualifiers
REGION                 1..5
                       note = Synthetic: 2188-A10; CDR-H1; Kabat
source                 1..5
                       mol_type = protein
                       organism = synthetic construct
SEQUENCE: 227
SYDIH                                                                    5

SEQ ID NO: 228         moltype = AA  length = 5
FEATURE                Location/Qualifiers
REGION                 1..5
                       note = Synthetic: 2188-G04; CDR-H1; Kabat
source                 1..5
                       mol_type = protein
                       organism = synthetic construct
SEQUENCE: 228
DYDIH                                                                    5

SEQ ID NO: 229         moltype = AA  length = 5
FEATURE                Location/Qualifiers
REGION                 1..5
                       note = Synthetic: 2188-C08; CDR-H1; Kabat
source                 1..5
                       mol_type = protein
                       organism = synthetic construct
SEQUENCE: 229
SHDIH                                                                    5

SEQ ID NO: 230         moltype = AA  length = 5
FEATURE                Location/Qualifiers
REGION                 1..5
                       note = Synthetic: 2188-E05; CDR-H1; Kabat
source                 1..5
                       mol_type = protein
                       organism = synthetic construct
SEQUENCE: 230
DYDIH                                                                    5

SEQ ID NO: 231         moltype = AA  length = 5
FEATURE                Location/Qualifiers
REGION                 1..5
                       note = Synthetic: 2188-A02; CDR-H1; Kabat
source                 1..5
                       mol_type = protein
                       organism = synthetic construct
SEQUENCE: 231
SYDIH                                                                    5
```

```
SEQ ID NO: 232           moltype = AA  length = 5
FEATURE                  Location/Qualifiers
REGION                   1..5
                         note = Synthetic: 2188-F04; CDR-H1; Kabat
source                   1..5
                         mol_type = protein
                         organism = synthetic construct
SEQUENCE: 232
DFDIH                                                                      5

SEQ ID NO: 233           moltype = AA  length = 5
FEATURE                  Location/Qualifiers
REGION                   1..5
                         note = Synthetic: 2188-F05; CDR-H1; Kabat
source                   1..5
                         mol_type = protein
                         organism = synthetic construct
SEQUENCE: 233
DYDIH                                                                      5

SEQ ID NO: 234           moltype = AA  length = 5
FEATURE                  Location/Qualifiers
REGION                   1..5
                         note = Synthetic: 2188-D07; CDR-H1; Kabat
source                   1..5
                         mol_type = protein
                         organism = synthetic construct
SEQUENCE: 234
DFDIH                                                                      5

SEQ ID NO: 235           moltype = AA  length = 5
FEATURE                  Location/Qualifiers
REGION                   1..5
                         note = Synthetic: 2188-E02; CDR-H1; Kabat
source                   1..5
                         mol_type = protein
                         organism = synthetic construct
SEQUENCE: 235
DYEIH                                                                      5

SEQ ID NO: 236           moltype = AA  length = 5
FEATURE                  Location/Qualifiers
REGION                   1..5
                         note = Synthetic: 2188-D06; CDR-H1; Kabat
source                   1..5
                         mol_type = protein
                         organism = synthetic construct
SEQUENCE: 236
DYDIH                                                                      5

SEQ ID NO: 237           moltype = AA  length = 5
FEATURE                  Location/Qualifiers
REGION                   1..5
                         note = Synthetic: 2188-F09; CDR-H1; Kabat
source                   1..5
                         mol_type = protein
                         organism = synthetic construct
SEQUENCE: 237
DYDIH                                                                      5

SEQ ID NO: 238           moltype = AA  length = 5
FEATURE                  Location/Qualifiers
REGION                   1..5
                         note = Synthetic: 2188-F10; CDR-H1; Kabat
source                   1..5
                         mol_type = protein
                         organism = synthetic construct
SEQUENCE: 238
VFDIH                                                                      5

SEQ ID NO: 239           moltype = AA  length = 5
FEATURE                  Location/Qualifiers
REGION                   1..5
                         note = Synthetic: 2188-B05; CDR-H1; Kabat
source                   1..5
                         mol_type = protein
                         organism = synthetic construct
SEQUENCE: 239
```

```
DYDIH                                                                        5

SEQ ID NO: 240          moltype = AA  length = 5
FEATURE                 Location/Qualifiers
REGION                  1..5
                        note = Synthetic: 1943-C02; CDR-H1; Kabat
source                  1..5
                        mol_type = protein
                        organism = synthetic construct
SEQUENCE: 240
DYYIH                                                                        5

SEQ ID NO: 241          moltype = AA  length = 5
FEATURE                 Location/Qualifiers
REGION                  1..5
                        note = Synthetic: 2193-D04; CDR-H1; Kabat
source                  1..5
                        mol_type = protein
                        organism = synthetic construct
SEQUENCE: 241
GFYIH                                                                        5

SEQ ID NO: 242          moltype = AA  length = 5
FEATURE                 Location/Qualifiers
REGION                  1..5
                        note = Synthetic: 2193-E10; CDR-H1; Kabat
source                  1..5
                        mol_type = protein
                        organism = synthetic construct
SEQUENCE: 242
DYYIH                                                                        5

SEQ ID NO: 243          moltype = AA  length = 5
FEATURE                 Location/Qualifiers
REGION                  1..5
                        note = Synthetic: 2193-E06; CDR-H1; Kabat
source                  1..5
                        mol_type = protein
                        organism = synthetic construct
SEQUENCE: 243
DYYIH                                                                        5

SEQ ID NO: 244          moltype = AA  length = 5
FEATURE                 Location/Qualifiers
REGION                  1..5
                        note = Synthetic: 2193-E04; CDR-H1; Kabat
source                  1..5
                        mol_type = protein
                        organism = synthetic construct
SEQUENCE: 244
DRYIH                                                                        5

SEQ ID NO: 245          moltype = AA  length = 5
FEATURE                 Location/Qualifiers
REGION                  1..5
                        note = Synthetic: 2193-B09; CDR-H1; Kabat
source                  1..5
                        mol_type = protein
                        organism = synthetic construct
SEQUENCE: 245
NSYIH                                                                        5

SEQ ID NO: 246          moltype = AA  length = 5
FEATURE                 Location/Qualifiers
REGION                  1..5
                        note = Synthetic: 2193-D11; CDR-H1; Kabat
source                  1..5
                        mol_type = protein
                        organism = synthetic construct
SEQUENCE: 246
AYYIH                                                                        5

SEQ ID NO: 247          moltype = AA  length = 5
FEATURE                 Location/Qualifiers
REGION                  1..5
                        note = Synthetic: 2193-B02; CDR-H1; Kabat
source                  1..5
                        mol_type = protein
                        organism = synthetic construct
```

```
SEQUENCE: 247
NSYIH                                                                         5

SEQ ID NO: 248          moltype = AA   length = 5
FEATURE                 Location/Qualifiers
REGION                  1..5
                        note = Synthetic: 2193-D05; CDR-H1; Kabat
source                  1..5
                        mol_type = protein
                        organism = synthetic construct
SEQUENCE: 248
DHYIH                                                                         5

SEQ ID NO: 249          moltype = AA   length = 5
FEATURE                 Location/Qualifiers
REGION                  1..5
                        note = Synthetic: 2193-E11; CDR-H1; Kabat
source                  1..5
                        mol_type = protein
                        organism = synthetic construct
SEQUENCE: 249
DYYIH                                                                         5

SEQ ID NO: 250          moltype = AA   length = 5
FEATURE                 Location/Qualifiers
REGION                  1..5
                        note = Synthetic: 2193-D06; CDR-H1; Kabat
source                  1..5
                        mol_type = protein
                        organism = synthetic construct
SEQUENCE: 250
DYYIH                                                                         5

SEQ ID NO: 251          moltype = AA   length = 5
FEATURE                 Location/Qualifiers
REGION                  1..5
                        note = Synthetic: 2193-C02; CDR-H1; Kabat
source                  1..5
                        mol_type = protein
                        organism = synthetic construct
SEQUENCE: 251
DYYIH                                                                         5

SEQ ID NO: 252          moltype = AA   length = 5
FEATURE                 Location/Qualifiers
REGION                  1..5
                        note = Synthetic: 2193-B03; CDR-H1; Kabat
source                  1..5
                        mol_type = protein
                        organism = synthetic construct
SEQUENCE: 252
DYYIH                                                                         5

SEQ ID NO: 253          moltype = AA   length = 5
FEATURE                 Location/Qualifiers
REGION                  1..5
                        note = Synthetic: 2193-A02; CDR-H1; Kabat
source                  1..5
                        mol_type = protein
                        organism = synthetic construct
SEQUENCE: 253
ASYIH                                                                         5

SEQ ID NO: 254          moltype = AA   length = 5
FEATURE                 Location/Qualifiers
REGION                  1..5
                        note = Synthetic: 2193-E05; CDR-H1; Kabat
source                  1..5
                        mol_type = protein
                        organism = synthetic construct
SEQUENCE: 254
RSYIH                                                                         5

SEQ ID NO: 255          moltype = AA   length = 5
FEATURE                 Location/Qualifiers
REGION                  1..5
                        note = Synthetic: 2193-A06; CDR-H1; Kabat
source                  1..5
                        mol_type = protein
```

```
                              -continued

SEQUENCE: 255
AYYIH                                                                      5

SEQ ID NO: 256          moltype = AA  length = 5
FEATURE                 Location/Qualifiers
REGION                  1..5
                        note = Synthetic: 2193-C04; CDR-H1; Kabat
source                  1..5
                        mol_type = protein
                        organism = synthetic construct
SEQUENCE: 256
TSYIH                                                                      5

SEQ ID NO: 257          moltype = AA  length = 5
FEATURE                 Location/Qualifiers
REGION                  1..5
                        note = Synthetic: 2193-E08; CDR-H1; Kabat
source                  1..5
                        mol_type = protein
                        organism = synthetic construct
SEQUENCE: 257
EYYIH                                                                      5

SEQ ID NO: 258          moltype = AA  length = 5
FEATURE                 Location/Qualifiers
REGION                  1..5
                        note = Synthetic: 2193-B10; CDR-H1; Kabat
source                  1..5
                        mol_type = protein
                        organism = synthetic construct
SEQUENCE: 258
DYYVH                                                                      5

SEQ ID NO: 259          moltype = AA  length = 5
FEATURE                 Location/Qualifiers
REGION                  1..5
                        note = Synthetic: 2193-D08; CDR-H1; Kabat
source                  1..5
                        mol_type = protein
                        organism = synthetic construct
SEQUENCE: 259
RSYIH                                                                      5

SEQ ID NO: 260          moltype = AA  length = 5
FEATURE                 Location/Qualifiers
REGION                  1..5
                        note = Synthetic: 2193-B08; CDR-H1; Kabat
source                  1..5
                        mol_type = protein
                        organism = synthetic construct
SEQUENCE: 260
DYYIH                                                                      5

SEQ ID NO: 261          moltype = AA  length = 5
FEATURE                 Location/Qualifiers
REGION                  1..5
                        note = Synthetic: 2193-C05; CDR-H1; Kabat
source                  1..5
                        mol_type = protein
                        organism = synthetic construct
SEQUENCE: 261
HSYIH                                                                      5

SEQ ID NO: 262          moltype = AA  length = 5
FEATURE                 Location/Qualifiers
REGION                  1..5
                        note = Synthetic: 2193-D10; CDR-H1; Kabat
source                  1..5
                        mol_type = protein
                        organism = synthetic construct
SEQUENCE: 262
VSYIH                                                                      5

SEQ ID NO: 263          moltype = AA  length = 5
FEATURE                 Location/Qualifiers
REGION                  1..5
                        note = Synthetic: 2193-D03; CDR-H1; Kabat
source                  1..5
```

```
                                  mol_type = protein
                                  organism = synthetic construct
SEQUENCE: 263
DHYIH                                                                         5

SEQ ID NO: 264            moltype = AA   length = 5
FEATURE                   Location/Qualifiers
REGION                    1..5
                          note = Synthetic: 2193-A09; CDR-H1; Kabat
source                    1..5
                          mol_type = protein
                          organism = synthetic construct
SEQUENCE: 264
KHHIH                                                                         5

SEQ ID NO: 265            moltype = AA   length = 5
FEATURE                   Location/Qualifiers
REGION                    1..5
                          note = Synthetic: 2193-A10; CDR-H1; Kabat
source                    1..5
                          mol_type = protein
                          organism = synthetic construct
SEQUENCE: 265
DYYIH                                                                         5

SEQ ID NO: 266            moltype = AA   length = 5
FEATURE                   Location/Qualifiers
REGION                    1..5
                          note = Synthetic: 2193-E07; CDR-H1; Kabat
source                    1..5
                          mol_type = protein
                          organism = synthetic construct
SEQUENCE: 266
KVYIH                                                                         5

SEQ ID NO: 267            moltype = AA   length = 5
FEATURE                   Location/Qualifiers
REGION                    1..5
                          note = Synthetic: 2193-A07; CDR-H1; Kabat
source                    1..5
                          mol_type = protein
                          organism = synthetic construct
SEQUENCE: 267
ASDIH                                                                         5

SEQ ID NO: 268            moltype = AA   length = 5
FEATURE                   Location/Qualifiers
REGION                    1..5
                          note = Synthetic: 2193-E03; CDR-H1; Kabat
source                    1..5
                          mol_type = protein
                          organism = synthetic construct
SEQUENCE: 268
ASYIH                                                                         5

SEQ ID NO: 269            moltype = AA   length = 5
FEATURE                   Location/Qualifiers
REGION                    1..5
                          note = Synthetic: 2193-C08; CDR-H1; Kabat
source                    1..5
                          mol_type = protein
                          organism = synthetic construct
SEQUENCE: 269
HYYIH                                                                         5

SEQ ID NO: 270            moltype = AA   length = 5
FEATURE                   Location/Qualifiers
REGION                    1..5
                          note = Synthetic: 2193-B11; CDR-H1; Kabat
source                    1..5
                          mol_type = protein
                          organism = synthetic construct
SEQUENCE: 270
GSYIH                                                                         5

SEQ ID NO: 271            moltype = AA   length = 5
FEATURE                   Location/Qualifiers
REGION                    1..5
                          note = Synthetic: 2193-A03; CDR-H1; Kabat
```

```
source                     1..5
                           mol_type = protein
                           organism = synthetic construct
SEQUENCE: 271
NYHIH                                                                5

SEQ ID NO: 272             moltype = AA  length = 5
FEATURE                    Location/Qualifiers
REGION                     1..5
                           note = Synthetic: 2193-D02; CDR-H1; Kabat
source                     1..5
                           mol_type = protein
                           organism = synthetic construct
SEQUENCE: 272
DYYIH                                                                5

SEQ ID NO: 273             moltype = AA  length = 5
FEATURE                    Location/Qualifiers
REGION                     1..5
                           note = Synthetic: 2193-B06; CDR-H1; Kabat
source                     1..5
                           mol_type = protein
                           organism = synthetic construct
SEQUENCE: 273
GYYIH                                                                5

SEQ ID NO: 274             moltype = AA  length = 5
FEATURE                    Location/Qualifiers
REGION                     1..5
                           note = Synthetic: 2193-B01; CDR-H1; Kabat
source                     1..5
                           mol_type = protein
                           organism = synthetic construct
SEQUENCE: 274
GYYIH                                                                5

SEQ ID NO: 275             moltype = AA  length = 5
FEATURE                    Location/Qualifiers
REGION                     1..5
                           note = Synthetic: 2193-D09; CDR-H1; Kabat
source                     1..5
                           mol_type = protein
                           organism = synthetic construct
SEQUENCE: 275
GYYIH                                                                5

SEQ ID NO: 276             moltype = AA  length = 5
FEATURE                    Location/Qualifiers
REGION                     1..5
                           note = Synthetic: 2193-E09; CDR-H1; Kabat
source                     1..5
                           mol_type = protein
                           organism = synthetic construct
SEQUENCE: 276
AYYIH                                                                5

SEQ ID NO: 277             moltype = AA  length = 5
FEATURE                    Location/Qualifiers
REGION                     1..5
                           note = Synthetic: 2193-B07; CDR-H1; Kabat
source                     1..5
                           mol_type = protein
                           organism = synthetic construct
SEQUENCE: 277
NSYIH                                                                5

SEQ ID NO: 278             moltype = AA  length = 5
FEATURE                    Location/Qualifiers
REGION                     1..5
                           note = Synthetic: 2193-C06; CDR-H1; Kabat
source                     1..5
                           mol_type = protein
                           organism = synthetic construct
SEQUENCE: 278
VHYIH                                                                5

SEQ ID NO: 279             moltype = AA  length = 5
FEATURE                    Location/Qualifiers
REGION                     1..5
```

```
                        note = Synthetic: 2193-B05; CDR-H1; Kabat
source                  1..5
                        mol_type = protein
                        organism = synthetic construct
SEQUENCE: 279
QYYIH                                                                    5

SEQ ID NO: 280          moltype = AA  length = 5
FEATURE                 Location/Qualifiers
REGION                  1..5
                        note = Synthetic: 2193-A11; CDR-H1; Kabat
source                  1..5
                        mol_type = protein
                        organism = synthetic construct
SEQUENCE: 280
AYYIH                                                                    5

SEQ ID NO: 281          moltype = AA  length = 5
FEATURE                 Location/Qualifiers
REGION                  1..5
                        note = Synthetic: 2193-E02; CDR-H1; Kabat
source                  1..5
                        mol_type = protein
                        organism = synthetic construct
SEQUENCE: 281
DYYIH                                                                    5

SEQ ID NO: 282          moltype = AA  length = 5
FEATURE                 Location/Qualifiers
REGION                  1..5
                        note = Synthetic: 2193-A08; CDR-H1; Kabat
source                  1..5
                        mol_type = protein
                        organism = synthetic construct
SEQUENCE: 282
DSYIH                                                                    5

SEQ ID NO: 283          moltype = AA  length = 5
FEATURE                 Location/Qualifiers
REGION                  1..5
                        note = Synthetic: 2193-C11; CDR-H1; Kabat
source                  1..5
                        mol_type = protein
                        organism = synthetic construct
SEQUENCE: 283
DSYIH                                                                    5

SEQ ID NO: 284          moltype = AA  length = 5
FEATURE                 Location/Qualifiers
REGION                  1..5
                        note = Synthetic: 2193-A01; CDR-H1; Kabat
source                  1..5
                        mol_type = protein
                        organism = synthetic construct
SEQUENCE: 284
DHYIH                                                                    5

SEQ ID NO: 285          moltype = AA  length = 5
FEATURE                 Location/Qualifiers
REGION                  1..5
                        note = Synthetic: 2193-D07; CDR-H1; Kabat
source                  1..5
                        mol_type = protein
                        organism = synthetic construct
SEQUENCE: 285
DYNIH                                                                    5

SEQ ID NO: 286          moltype = AA  length = 5
FEATURE                 Location/Qualifiers
REGION                  1..5
                        note = Synthetic: 2193-A05; CDR-H1; Kabat
source                  1..5
                        mol_type = protein
                        organism = synthetic construct
SEQUENCE: 286
GYYIH                                                                    5

SEQ ID NO: 287          moltype = AA  length = 5
FEATURE                 Location/Qualifiers
```

```
REGION                  1..5
                        note = Synthetic: 2193-C03; CDR-H1; Kabat
source                  1..5
                        mol_type = protein
                        organism = synthetic construct
SEQUENCE: 287
YSYIH                                                                      5

SEQ ID NO: 288          moltype = AA  length = 5
FEATURE                 Location/Qualifiers
REGION                  1..5
                        note = Synthetic: 2193-C09; CDR-H1; Kabat
source                  1..5
                        mol_type = protein
                        organism = synthetic construct
SEQUENCE: 288
HSYIH                                                                      5

SEQ ID NO: 289          moltype = AA  length = 5
FEATURE                 Location/Qualifiers
REGION                  1..5
                        note = Synthetic: 2193-D01; CDR-H1; Kabat
source                  1..5
                        mol_type = protein
                        organism = synthetic construct
SEQUENCE: 289
DSYIH                                                                      5

SEQ ID NO: 290          moltype = AA  length = 5
FEATURE                 Location/Qualifiers
REGION                  1..5
                        note = Synthetic: 2193-E01; CDR-H1; Kabat
source                  1..5
                        mol_type = protein
                        organism = synthetic construct
SEQUENCE: 290
GKYIH                                                                      5

SEQ ID NO: 291          moltype = AA  length = 5
FEATURE                 Location/Qualifiers
REGION                  1..5
                        note = Synthetic: 2193-C07; CDR-H1; Kabat
source                  1..5
                        mol_type = protein
                        organism = synthetic construct
SEQUENCE: 291
DQDIH                                                                      5

SEQ ID NO: 292          moltype = AA  length = 5
FEATURE                 Location/Qualifiers
REGION                  1..5
                        note = Synthetic: 2193-B04; CDR-H1; Kabat
source                  1..5
                        mol_type = protein
                        organism = synthetic construct
SEQUENCE: 292
NSYIH                                                                      5

SEQ ID NO: 293          moltype = AA  length = 5
FEATURE                 Location/Qualifiers
REGION                  1..5
                        note = Synthetic: 2193-C10; CDR-H1; Kabat
source                  1..5
                        mol_type = protein
                        organism = synthetic construct
SEQUENCE: 293
NAYIH                                                                      5

SEQ ID NO: 294          moltype = AA  length = 5
FEATURE                 Location/Qualifiers
REGION                  1..5
                        note = Synthetic: 2193-C01; CDR-H1; Kabat
source                  1..5
                        mol_type = protein
                        organism = synthetic construct
SEQUENCE: 294
DHYIH                                                                      5

SEQ ID NO: 295          moltype = AA  length = 5
```

```
                        -continued

FEATURE                 Location/Qualifiers
REGION                  1..5
                        note = Synthetic: 2193-A04; CDR-H1; Kabat
source                  1..5
                        mol_type = protein
                        organism = synthetic construct
SEQUENCE: 295
SYYIH                                                                    5

SEQ ID NO: 296          moltype = AA  length = 5
FEATURE                 Location/Qualifiers
REGION                  1..5
                        note = Synthetic: 1944-A07; CDR-H1; Kabat
source                  1..5
                        mol_type = protein
                        organism = synthetic construct
SEQUENCE: 296
GYYIH                                                                    5

SEQ ID NO: 297          moltype = AA  length = 5
FEATURE                 Location/Qualifiers
REGION                  1..5
                        note = Synthetic: 2194-A02; CDR-H1; Kabat
source                  1..5
                        mol_type = protein
                        organism = synthetic construct
SEQUENCE: 297
GYYIH                                                                    5

SEQ ID NO: 298          moltype = AA  length = 5
FEATURE                 Location/Qualifiers
REGION                  1..5
                        note = Synthetic: 2194-A05; CDR-H1; Kabat
source                  1..5
                        mol_type = protein
                        organism = synthetic construct
SEQUENCE: 298
EYHIH                                                                    5

SEQ ID NO: 299          moltype = AA  length = 5
FEATURE                 Location/Qualifiers
REGION                  1..5
                        note = Synthetic: 2194-B04; CDR-H1; Kabat
source                  1..5
                        mol_type = protein
                        organism = synthetic construct
SEQUENCE: 299
GYHIH                                                                    5

SEQ ID NO: 300          moltype = AA  length = 5
FEATURE                 Location/Qualifiers
REGION                  1..5
                        note = Synthetic: 2194-A09; CDR-H1; Kabat
source                  1..5
                        mol_type = protein
                        organism = synthetic construct
SEQUENCE: 300
GYYIH                                                                    5

SEQ ID NO: 301          moltype = AA  length = 5
FEATURE                 Location/Qualifiers
REGION                  1..5
                        note = Synthetic: 2194-A01; CDR-H1; Kabat
source                  1..5
                        mol_type = protein
                        organism = synthetic construct
SEQUENCE: 301
GYYIH                                                                    5

SEQ ID NO: 302          moltype = AA  length = 5
FEATURE                 Location/Qualifiers
REGION                  1..5
                        note = Synthetic: 2194-B03; CDR-H1; Kabat
source                  1..5
                        mol_type = protein
                        organism = synthetic construct
SEQUENCE: 302
SYYIH                                                                    5
```

```
SEQ ID NO: 303         moltype = AA  length = 5
FEATURE                Location/Qualifiers
REGION                 1..5
                       note = Synthetic: 2194-B02; CDR-H1; Kabat
source                 1..5
                       mol_type = protein
                       organism = synthetic construct
SEQUENCE: 303
GYYIH                                                                      5

SEQ ID NO: 304         moltype = AA  length = 5
FEATURE                Location/Qualifiers
REGION                 1..5
                       note = Synthetic: 2194-A03; CDR-H1; Kabat
source                 1..5
                       mol_type = protein
                       organism = synthetic construct
SEQUENCE: 304
GYYIH                                                                      5

SEQ ID NO: 305         moltype = AA  length = 5
FEATURE                Location/Qualifiers
REGION                 1..5
                       note = Synthetic: 2194-A11; CDR-H1; Kabat
source                 1..5
                       mol_type = protein
                       organism = synthetic construct
SEQUENCE: 305
QYYIH                                                                      5

SEQ ID NO: 306         moltype = AA  length = 5
FEATURE                Location/Qualifiers
REGION                 1..5
                       note = Synthetic: 2194-A08; CDR-H1; Kabat
source                 1..5
                       mol_type = protein
                       organism = synthetic construct
SEQUENCE: 306
GYHIH                                                                      5

SEQ ID NO: 307         moltype = AA  length = 5
FEATURE                Location/Qualifiers
REGION                 1..5
                       note = Synthetic: 2194-A04; CDR-H1; Kabat
source                 1..5
                       mol_type = protein
                       organism = synthetic construct
SEQUENCE: 307
GYYIH                                                                      5

SEQ ID NO: 308         moltype = AA  length = 5
FEATURE                Location/Qualifiers
REGION                 1..5
                       note = Synthetic: 2194-A10; CDR-H1; Kabat
source                 1..5
                       mol_type = protein
                       organism = synthetic construct
SEQUENCE: 308
QYYIH                                                                      5

SEQ ID NO: 309         moltype = AA  length = 5
FEATURE                Location/Qualifiers
REGION                 1..5
                       note = Synthetic: 2194-A07; CDR-H1; Kabat
source                 1..5
                       mol_type = protein
                       organism = synthetic construct
SEQUENCE: 309
DYYIH                                                                      5

SEQ ID NO: 310         moltype = AA  length = 5
FEATURE                Location/Qualifiers
REGION                 1..5
                       note = Synthetic: 2194-B01; CDR-H1; Kabat
source                 1..5
                       mol_type = protein
                       organism = synthetic construct
SEQUENCE: 310
SYYIH                                                                      5
```

```
SEQ ID NO: 311          moltype = AA   length = 5
FEATURE                 Location/Qualifiers
REGION                  1..5
                        note = Synthetic: 2194-A06; CDR-H1; Kabat
source                  1..5
                        mol_type = protein
                        organism = synthetic construct
SEQUENCE: 311
DYYIH                                                                    5

SEQ ID NO: 312          moltype = AA   length = 5
FEATURE                 Location/Qualifiers
REGION                  1..5
                        note = Synthetic: 2196-C01; CDR-H1; Kabat
source                  1..5
                        mol_type = protein
                        organism = synthetic construct
SEQUENCE: 312
GYYIH                                                                    5

SEQ ID NO: 313          moltype = AA   length = 5
FEATURE                 Location/Qualifiers
REGION                  1..5
                        note = Synthetic: 2196-A02; CDR-H1; Kabat
source                  1..5
                        mol_type = protein
                        organism = synthetic construct
SEQUENCE: 313
GYYIH                                                                    5

SEQ ID NO: 314          moltype = AA   length = 5
FEATURE                 Location/Qualifiers
REGION                  1..5
                        note = Synthetic: 2196-B03; CDR-H1; Kabat
source                  1..5
                        mol_type = protein
                        organism = synthetic construct
SEQUENCE: 314
GYYIH                                                                    5

SEQ ID NO: 315          moltype = AA   length = 5
FEATURE                 Location/Qualifiers
REGION                  1..5
                        note = Synthetic: 2196-A05; CDR-H1; Kabat
source                  1..5
                        mol_type = protein
                        organism = synthetic construct
SEQUENCE: 315
NYYIH                                                                    5

SEQ ID NO: 316          moltype = AA   length = 5
FEATURE                 Location/Qualifiers
REGION                  1..5
                        note = Synthetic: 2196-C02; CDR-H1; Kabat
source                  1..5
                        mol_type = protein
                        organism = synthetic construct
SEQUENCE: 316
GYHIH                                                                    5

SEQ ID NO: 317          moltype = AA   length = 5
FEATURE                 Location/Qualifiers
REGION                  1..5
                        note = Synthetic: 2196-B11; CDR-H1; Kabat
source                  1..5
                        mol_type = protein
                        organism = synthetic construct
SEQUENCE: 317
GYYIH                                                                    5

SEQ ID NO: 318          moltype = AA   length = 5
FEATURE                 Location/Qualifiers
REGION                  1..5
                        note = Synthetic: 2196-B08; CDR-H1; Kabat
source                  1..5
                        mol_type = protein
                        organism = synthetic construct
SEQUENCE: 318
```

```
GYYIH                                                                            5

SEQ ID NO: 319          moltype = AA  length = 5
FEATURE                 Location/Qualifiers
REGION                  1..5
                        note = Synthetic: 2196-A04; CDR-H1; Kabat
source                  1..5
                        mol_type = protein
                        organism = synthetic construct
SEQUENCE: 319
PYYIH                                                                            5

SEQ ID NO: 320          moltype = AA  length = 5
FEATURE                 Location/Qualifiers
REGION                  1..5
                        note = Synthetic: 2196-A03; CDR-H1; Kabat
source                  1..5
                        mol_type = protein
                        organism = synthetic construct
SEQUENCE: 320
QYHIH                                                                            5

SEQ ID NO: 321          moltype = AA  length = 5
FEATURE                 Location/Qualifiers
REGION                  1..5
                        note = Synthetic: 2196-B07; CDR-H1; Kabat
source                  1..5
                        mol_type = protein
                        organism = synthetic construct
SEQUENCE: 321
GYHIH                                                                            5

SEQ ID NO: 322          moltype = AA  length = 5
FEATURE                 Location/Qualifiers
REGION                  1..5
                        note = Synthetic: 2196-A06; CDR-H1; Kabat
source                  1..5
                        mol_type = protein
                        organism = synthetic construct
SEQUENCE: 322
GYYIH                                                                            5

SEQ ID NO: 323          moltype = AA  length = 5
FEATURE                 Location/Qualifiers
REGION                  1..5
                        note = Synthetic: 2196-B05; CDR-H1; Kabat
source                  1..5
                        mol_type = protein
                        organism = synthetic construct
SEQUENCE: 323
GYYIH                                                                            5

SEQ ID NO: 324          moltype = AA  length = 5
FEATURE                 Location/Qualifiers
REGION                  1..5
                        note = Synthetic: 2196-A01; CDR-H1; Kabat
source                  1..5
                        mol_type = protein
                        organism = synthetic construct
SEQUENCE: 324
GYYIH                                                                            5

SEQ ID NO: 325          moltype = AA  length = 5
FEATURE                 Location/Qualifiers
REGION                  1..5
                        note = Synthetic: 2196-B01; CDR-H1; Kabat
source                  1..5
                        mol_type = protein
                        organism = synthetic construct
SEQUENCE: 325
GYYIH                                                                            5

SEQ ID NO: 326          moltype = AA  length = 5
FEATURE                 Location/Qualifiers
REGION                  1..5
                        note = Synthetic: 2196-A09; CDR-H1; Kabat
source                  1..5
                        mol_type = protein
                        organism = synthetic construct
```

```
SEQUENCE: 326
GYYIH                                                                      5

SEQ ID NO: 327          moltype = AA   length = 5
FEATURE                 Location/Qualifiers
REGION                  1..5
                        note = Synthetic: 2196-A08; CDR-H1; Kabat
source                  1..5
                        mol_type = protein
                        organism = synthetic construct
SEQUENCE: 327
GYYIH                                                                      5

SEQ ID NO: 328          moltype = AA   length = 5
FEATURE                 Location/Qualifiers
REGION                  1..5
                        note = Synthetic: 2196-A10; CDR-H1; Kabat
source                  1..5
                        mol_type = protein
                        organism = synthetic construct
SEQUENCE: 328
GYYIH                                                                      5

SEQ ID NO: 329          moltype = AA   length = 5
FEATURE                 Location/Qualifiers
REGION                  1..5
                        note = Synthetic: 2196-B06; CDR-H1; Kabat
source                  1..5
                        mol_type = protein
                        organism = synthetic construct
SEQUENCE: 329
GYYIH                                                                      5

SEQ ID NO: 330          moltype = AA   length = 5
FEATURE                 Location/Qualifiers
REGION                  1..5
                        note = Synthetic: 2196-B09; CDR-H1; Kabat
source                  1..5
                        mol_type = protein
                        organism = synthetic construct
SEQUENCE: 330
EYYIH                                                                      5

SEQ ID NO: 331          moltype = AA   length = 5
FEATURE                 Location/Qualifiers
REGION                  1..5
                        note = Synthetic: 2196-C03; CDR-H1; Kabat
source                  1..5
                        mol_type = protein
                        organism = synthetic construct
SEQUENCE: 331
GYYIH                                                                      5

SEQ ID NO: 332          moltype = AA   length = 5
FEATURE                 Location/Qualifiers
REGION                  1..5
                        note = Synthetic: 2196-C04; CDR-H1; Kabat
source                  1..5
                        mol_type = protein
                        organism = synthetic construct
SEQUENCE: 332
GYYIH                                                                      5

SEQ ID NO: 333          moltype = AA   length = 5
FEATURE                 Location/Qualifiers
REGION                  1..5
                        note = Synthetic: 2196-A07; CDR-H1; Kabat
source                  1..5
                        mol_type = protein
                        organism = synthetic construct
SEQUENCE: 333
GYYIH                                                                      5

SEQ ID NO: 334          moltype = AA   length = 5
FEATURE                 Location/Qualifiers
REGION                  1..5
                        note = Synthetic: 2196-A11; CDR-H1; Kabat
source                  1..5
                        mol_type = protein
```

```
                              organism = synthetic construct
SEQUENCE: 334
GYYIH                                                                       5

SEQ ID NO: 335          moltype = AA  length = 5
FEATURE                 Location/Qualifiers
REGION                  1..5
                        note = Synthetic: 2196-B02; CDR-H1; Kabat
source                  1..5
                        mol_type = protein
                        organism = synthetic construct
SEQUENCE: 335
QYYIH                                                                       5

SEQ ID NO: 336          moltype = AA  length = 5
FEATURE                 Location/Qualifiers
REGION                  1..5
                        note = Synthetic: 2196-B04; CDR-H1; Kabat
source                  1..5
                        mol_type = protein
                        organism = synthetic construct
SEQUENCE: 336
EYYIH                                                                       5

SEQ ID NO: 337          moltype = AA  length = 5
FEATURE                 Location/Qualifiers
REGION                  1..5
                        note = Synthetic: 2196-B10; CDR-H1; Kabat
source                  1..5
                        mol_type = protein
                        organism = synthetic construct
SEQUENCE: 337
GYYIH                                                                       5

SEQ ID NO: 338          moltype = AA  length = 6
FEATURE                 Location/Qualifiers
REGION                  1..6
                        note = Synthetic: 1987-C05; CDR-H2; Chothia
source                  1..6
                        mol_type = protein
                        organism = synthetic construct
SEQUENCE: 338
DPDDGS                                                                      6

SEQ ID NO: 339          moltype = AA  length = 6
FEATURE                 Location/Qualifiers
REGION                  1..6
                        note = Synthetic: 2188-D11; CDR-H2; Chothia
source                  1..6
                        mol_type = protein
                        organism = synthetic construct
SEQUENCE: 339
DPDDGS                                                                      6

SEQ ID NO: 340          moltype = AA  length = 6
FEATURE                 Location/Qualifiers
REGION                  1..6
                        note = Synthetic: 2188-B04; CDR-H2; Chothia
source                  1..6
                        mol_type = protein
                        organism = synthetic construct
SEQUENCE: 340
NPDDGD                                                                      6

SEQ ID NO: 341          moltype = AA  length = 6
FEATURE                 Location/Qualifiers
REGION                  1..6
                        note = Synthetic: 2188-C09; CDR-H2; Chothia
source                  1..6
                        mol_type = protein
                        organism = synthetic construct
SEQUENCE: 341
NPHDGD                                                                      6

SEQ ID NO: 342          moltype = AA  length = 6
FEATURE                 Location/Qualifiers
REGION                  1..6
                        note = Synthetic: 2188-G03; CDR-H2; Chothia
source                  1..6
```

```
                           mol_type = protein
                           organism = synthetic construct
SEQUENCE: 342
DPRDGS                                                                  6

SEQ ID NO: 343             moltype = AA  length = 6
FEATURE                    Location/Qualifiers
REGION                     1..6
                           note = Synthetic: 2188-E03; CDR-H2; Chothia
source                     1..6
                           mol_type = protein
                           organism = synthetic construct
SEQUENCE: 343
DPDDGS                                                                  6

SEQ ID NO: 344             moltype = AA  length = 6
FEATURE                    Location/Qualifiers
REGION                     1..6
                           note = Synthetic: 2188-B11; CDR-H2; Chothia
source                     1..6
                           mol_type = protein
                           organism = synthetic construct
SEQUENCE: 344
NPDDGD                                                                  6

SEQ ID NO: 345             moltype = AA  length = 6
FEATURE                    Location/Qualifiers
REGION                     1..6
                           note = Synthetic: 2188-E07; CDR-H2; Chothia
source                     1..6
                           mol_type = protein
                           organism = synthetic construct
SEQUENCE: 345
DPEDGF                                                                  6

SEQ ID NO: 346             moltype = AA  length = 6
FEATURE                    Location/Qualifiers
REGION                     1..6
                           note = Synthetic: 2188-B02; CDR-H2; Chothia
source                     1..6
                           mol_type = protein
                           organism = synthetic construct
SEQUENCE: 346
NPDDGD                                                                  6

SEQ ID NO: 347             moltype = AA  length = 6
FEATURE                    Location/Qualifiers
REGION                     1..6
                           note = Synthetic: 2188-C07; CDR-H2; Chothia
source                     1..6
                           mol_type = protein
                           organism = synthetic construct
SEQUENCE: 347
NPDDGD                                                                  6

SEQ ID NO: 348             moltype = AA  length = 6
FEATURE                    Location/Qualifiers
REGION                     1..6
                           note = Synthetic: 2188-A03; CDR-H2; Chothia
source                     1..6
                           mol_type = protein
                           organism = synthetic construct
SEQUENCE: 348
NPDDGD                                                                  6

SEQ ID NO: 349             moltype = AA  length = 6
FEATURE                    Location/Qualifiers
REGION                     1..6
                           note = Synthetic: 2188-F03; CDR-H2; Chothia
source                     1..6
                           mol_type = protein
                           organism = synthetic construct
SEQUENCE: 349
DPDDGS                                                                  6

SEQ ID NO: 350             moltype = AA  length = 6
FEATURE                    Location/Qualifiers
REGION                     1..6
                           note = Synthetic: 2188-D03; CDR-H2; Chothia
```

```
source                  1..6
                        mol_type = protein
                        organism = synthetic construct
SEQUENCE: 350
DPHDGS                                                                    6

SEQ ID NO: 351          moltype = AA  length = 6
FEATURE                 Location/Qualifiers
REGION                  1..6
                        note = Synthetic: 2188-C04; CDR-H2; Chothia
source                  1..6
                        mol_type = protein
                        organism = synthetic construct
SEQUENCE: 351
NPEDGD                                                                    6

SEQ ID NO: 352          moltype = AA  length = 6
FEATURE                 Location/Qualifiers
REGION                  1..6
                        note = Synthetic: 2188-D10; CDR-H2; Chothia
source                  1..6
                        mol_type = protein
                        organism = synthetic construct
SEQUENCE: 352
DPRDGA                                                                    6

SEQ ID NO: 353          moltype = AA  length = 6
FEATURE                 Location/Qualifiers
REGION                  1..6
                        note = Synthetic: 2188-A06; CDR-H2; Chothia
source                  1..6
                        mol_type = protein
                        organism = synthetic construct
SEQUENCE: 353
NPDDGD                                                                    6

SEQ ID NO: 354          moltype = AA  length = 6
FEATURE                 Location/Qualifiers
REGION                  1..6
                        note = Synthetic: 2188-C11; CDR-H2; Chothia
source                  1..6
                        mol_type = protein
                        organism = synthetic construct
SEQUENCE: 354
NPDDGD                                                                    6

SEQ ID NO: 355          moltype = AA  length = 6
FEATURE                 Location/Qualifiers
REGION                  1..6
                        note = Synthetic: 2188-F01; CDR-H2; Chothia
source                  1..6
                        mol_type = protein
                        organism = synthetic construct
SEQUENCE: 355
DPDDGW                                                                    6

SEQ ID NO: 356          moltype = AA  length = 6
FEATURE                 Location/Qualifiers
REGION                  1..6
                        note = Synthetic: 2188-E11; CDR-H2; Chothia
source                  1..6
                        mol_type = protein
                        organism = synthetic construct
SEQUENCE: 356
DPGDGA                                                                    6

SEQ ID NO: 357          moltype = AA  length = 6
FEATURE                 Location/Qualifiers
REGION                  1..6
                        note = Synthetic: 2188-A07; CDR-H2; Chothia
source                  1..6
                        mol_type = protein
                        organism = synthetic construct
SEQUENCE: 357
NPDDGD                                                                    6

SEQ ID NO: 358          moltype = AA  length = 6
FEATURE                 Location/Qualifiers
REGION                  1..6
```

-continued

```
                         note = Synthetic: 2188-C01; CDR-H2; Chothia
source                   1..6
                         mol_type = protein
                         organism = synthetic construct
SEQUENCE: 358
DPHDGS                                                                    6

SEQ ID NO: 359           moltype = AA   length = 6
FEATURE                  Location/Qualifiers
REGION                   1..6
                         note = Synthetic: 2188-F08; CDR-H2; Chothia
source                   1..6
                         mol_type = protein
                         organism = synthetic construct
SEQUENCE: 359
EPDDGA                                                                    6

SEQ ID NO: 360           moltype = AA   length = 6
FEATURE                  Location/Qualifiers
REGION                   1..6
                         note = Synthetic: 2188-E04; CDR-H2; Chothia
source                   1..6
                         mol_type = protein
                         organism = synthetic construct
SEQUENCE: 360
DPQDGS                                                                    6

SEQ ID NO: 361           moltype = AA   length = 6
FEATURE                  Location/Qualifiers
REGION                   1..6
                         note = Synthetic: 2188-B01; CDR-H2; Chothia
source                   1..6
                         mol_type = protein
                         organism = synthetic construct
SEQUENCE: 361
NPDDGD                                                                    6

SEQ ID NO: 362           moltype = AA   length = 6
FEATURE                  Location/Qualifiers
REGION                   1..6
                         note = Synthetic: 2188-F11; CDR-H2; Chothia
source                   1..6
                         mol_type = protein
                         organism = synthetic construct
SEQUENCE: 362
DPEDGA                                                                    6

SEQ ID NO: 363           moltype = AA   length = 6
FEATURE                  Location/Qualifiers
REGION                   1..6
                         note = Synthetic: 2188-B08; CDR-H2; Chothia
source                   1..6
                         mol_type = protein
                         organism = synthetic construct
SEQUENCE: 363
NPDDGD                                                                    6

SEQ ID NO: 364           moltype = AA   length = 6
FEATURE                  Location/Qualifiers
REGION                   1..6
                         note = Synthetic: 2188-C10; CDR-H2; Chothia
source                   1..6
                         mol_type = protein
                         organism = synthetic construct
SEQUENCE: 364
NPDDGD                                                                    6

SEQ ID NO: 365           moltype = AA   length = 6
FEATURE                  Location/Qualifiers
REGION                   1..6
                         note = Synthetic: 2188-C02; CDR-H2; Chothia
source                   1..6
                         mol_type = protein
                         organism = synthetic construct
SEQUENCE: 365
NPDDGD                                                                    6

SEQ ID NO: 366           moltype = AA   length = 6
FEATURE                  Location/Qualifiers
```

```
                      REGION                 1..6
                                             note = Synthetic: 2188-B07; CDR-H2; Chothia
                      source                 1..6
                                             mol_type = protein
                                             organism = synthetic construct
SEQUENCE: 366
NPDDGD                                                                              6

SEQ ID NO: 367        moltype = AA   length = 6
FEATURE               Location/Qualifiers
REGION                1..6
                      note = Synthetic: 2188-A11; CDR-H2; Chothia
source                1..6
                      mol_type = protein
                      organism = synthetic construct
SEQUENCE: 367
DPKDGA                                                                              6

SEQ ID NO: 368        moltype = AA   length = 6
FEATURE               Location/Qualifiers
REGION                1..6
                      note = Synthetic: 2188-D01; CDR-H2; Chothia
source                1..6
                      mol_type = protein
                      organism = synthetic construct
SEQUENCE: 368
NPYDGD                                                                              6

SEQ ID NO: 369        moltype = AA   length = 6
FEATURE               Location/Qualifiers
REGION                1..6
                      note = Synthetic: 2188-E09; CDR-H2; Chothia
source                1..6
                      mol_type = protein
                      organism = synthetic construct
SEQUENCE: 369
DPQDGW                                                                              6

SEQ ID NO: 370        moltype = AA   length = 6
FEATURE               Location/Qualifiers
REGION                1..6
                      note = Synthetic: 2188-E06; CDR-H2; Chothia
source                1..6
                      mol_type = protein
                      organism = synthetic construct
SEQUENCE: 370
DPEDGA                                                                              6

SEQ ID NO: 371        moltype = AA   length = 6
FEATURE               Location/Qualifiers
REGION                1..6
                      note = Synthetic: 2188-B03; CDR-H2; Chothia
source                1..6
                      mol_type = protein
                      organism = synthetic construct
SEQUENCE: 371
DPGDGA                                                                              6

SEQ ID NO: 372        moltype = AA   length = 6
FEATURE               Location/Qualifiers
REGION                1..6
                      note = Synthetic: 2188-F06; CDR-H2; Chothia
source                1..6
                      mol_type = protein
                      organism = synthetic construct
SEQUENCE: 372
DPDDGA                                                                              6

SEQ ID NO: 373        moltype = AA   length = 6
FEATURE               Location/Qualifiers
REGION                1..6
                      note = Synthetic: 2188-D02; CDR-H2; Chothia
source                1..6
                      mol_type = protein
                      organism = synthetic construct
SEQUENCE: 373
DPEDGA                                                                              6

SEQ ID NO: 374        moltype = AA   length = 6
```

```
                            -continued

FEATURE             Location/Qualifiers
REGION              1..6
                    note = Synthetic: 2188-B06; CDR-H2; Chothia
source              1..6
                    mol_type = protein
                    organism = synthetic construct
SEQUENCE: 374
NPDDGD                                                                    6

SEQ ID NO: 375      moltype = AA  length = 6
FEATURE             Location/Qualifiers
REGION              1..6
                    note = Synthetic: 2188-D09; CDR-H2; Chothia
source              1..6
                    mol_type = protein
                    organism = synthetic construct
SEQUENCE: 375
DPGDGS                                                                    6

SEQ ID NO: 376      moltype = AA  length = 6
FEATURE             Location/Qualifiers
REGION              1..6
                    note = Synthetic: 2188-F02; CDR-H2; Chothia
source              1..6
                    mol_type = protein
                    organism = synthetic construct
SEQUENCE: 376
DPSDGS                                                                    6

SEQ ID NO: 377      moltype = AA  length = 6
FEATURE             Location/Qualifiers
REGION              1..6
                    note = Synthetic: 2188-E10; CDR-H2; Chothia
source              1..6
                    mol_type = protein
                    organism = synthetic construct
SEQUENCE: 377
DPRDGA                                                                    6

SEQ ID NO: 378      moltype = AA  length = 6
FEATURE             Location/Qualifiers
REGION              1..6
                    note = Synthetic: 2188-A09; CDR-H2; Chothia
source              1..6
                    mol_type = protein
                    organism = synthetic construct
SEQUENCE: 378
NPDDGD                                                                    6

SEQ ID NO: 379      moltype = AA  length = 6
FEATURE             Location/Qualifiers
REGION              1..6
                    note = Synthetic: 2188-D04; CDR-H2; Chothia
source              1..6
                    mol_type = protein
                    organism = synthetic construct
SEQUENCE: 379
DPADGS                                                                    6

SEQ ID NO: 380      moltype = AA  length = 6
FEATURE             Location/Qualifiers
REGION              1..6
                    note = Synthetic: 2188-A05; CDR-H2; Chothia
source              1..6
                    mol_type = protein
                    organism = synthetic construct
SEQUENCE: 380
NPDDGD                                                                    6

SEQ ID NO: 381      moltype = AA  length = 6
FEATURE             Location/Qualifiers
REGION              1..6
                    note = Synthetic: 2188-E01; CDR-H2; Chothia
source              1..6
                    mol_type = protein
                    organism = synthetic construct
SEQUENCE: 381
DPQDGA                                                                    6
```

```
SEQ ID NO: 382          moltype = AA  length = 6
FEATURE                 Location/Qualifiers
REGION                  1..6
                        note = Synthetic: 2188-G01; CDR-H2; Chothia
source                  1..6
                        mol_type = protein
                        organism = synthetic construct
SEQUENCE: 382
DPNDGA                                                                    6

SEQ ID NO: 383          moltype = AA  length = 6
FEATURE                 Location/Qualifiers
REGION                  1..6
                        note = Synthetic: 2188-B09; CDR-H2; Chothia
source                  1..6
                        mol_type = protein
                        organism = synthetic construct
SEQUENCE: 383
DPKDGW                                                                    6

SEQ ID NO: 384          moltype = AA  length = 6
FEATURE                 Location/Qualifiers
REGION                  1..6
                        note = Synthetic: 2188-F07; CDR-H2; Chothia
source                  1..6
                        mol_type = protein
                        organism = synthetic construct
SEQUENCE: 384
DPNDGS                                                                    6

SEQ ID NO: 385          moltype = AA  length = 6
FEATURE                 Location/Qualifiers
REGION                  1..6
                        note = Synthetic: 2188-D08; CDR-H2; Chothia
source                  1..6
                        mol_type = protein
                        organism = synthetic construct
SEQUENCE: 385
DPDDGA                                                                    6

SEQ ID NO: 386          moltype = AA  length = 6
FEATURE                 Location/Qualifiers
REGION                  1..6
                        note = Synthetic: 2188-D05; CDR-H2; Chothia
source                  1..6
                        mol_type = protein
                        organism = synthetic construct
SEQUENCE: 386
DPHDGW                                                                    6

SEQ ID NO: 387          moltype = AA  length = 6
FEATURE                 Location/Qualifiers
REGION                  1..6
                        note = Synthetic: 2188-C03; CDR-H2; Chothia
source                  1..6
                        mol_type = protein
                        organism = synthetic construct
SEQUENCE: 387
NPDDGD                                                                    6

SEQ ID NO: 388          moltype = AA  length = 6
FEATURE                 Location/Qualifiers
REGION                  1..6
                        note = Synthetic: 2188-E08; CDR-H2; Chothia
source                  1..6
                        mol_type = protein
                        organism = synthetic construct
SEQUENCE: 388
DPQDGS                                                                    6

SEQ ID NO: 389          moltype = AA  length = 6
FEATURE                 Location/Qualifiers
REGION                  1..6
                        note = Synthetic: 2188-C06; CDR-H2; Chothia
source                  1..6
                        mol_type = protein
                        organism = synthetic construct
SEQUENCE: 389
NPDDGD                                                                    6
```

```
SEQ ID NO: 390            moltype = AA   length = 6
FEATURE                   Location/Qualifiers
REGION                    1..6
                          note = Synthetic: 2188-A08; CDR-H2; Chothia
source                    1..6
                          mol_type = protein
                          organism = synthetic construct
SEQUENCE: 390
NPFDGD                                                                    6

SEQ ID NO: 391            moltype = AA   length = 6
FEATURE                   Location/Qualifiers
REGION                    1..6
                          note = Synthetic: 2188-B10; CDR-H2; Chothia
source                    1..6
                          mol_type = protein
                          organism = synthetic construct
SEQUENCE: 391
NPHDGD                                                                    6

SEQ ID NO: 392            moltype = AA   length = 6
FEATURE                   Location/Qualifiers
REGION                    1..6
                          note = Synthetic: 2188-G02; CDR-H2; Chothia
source                    1..6
                          mol_type = protein
                          organism = synthetic construct
SEQUENCE: 392
DPNDGA                                                                    6

SEQ ID NO: 393            moltype = AA   length = 6
FEATURE                   Location/Qualifiers
REGION                    1..6
                          note = Synthetic: 2188-C05; CDR-H2; Chothia
source                    1..6
                          mol_type = protein
                          organism = synthetic construct
SEQUENCE: 393
DPRDGS                                                                    6

SEQ ID NO: 394            moltype = AA   length = 6
FEATURE                   Location/Qualifiers
REGION                    1..6
                          note = Synthetic: 2188-A10; CDR-H2; Chothia
source                    1..6
                          mol_type = protein
                          organism = synthetic construct
SEQUENCE: 394
NPEDGD                                                                    6

SEQ ID NO: 395            moltype = AA   length = 6
FEATURE                   Location/Qualifiers
REGION                    1..6
                          note = Synthetic: 2188-G04; CDR-H2; Chothia
source                    1..6
                          mol_type = protein
                          organism = synthetic construct
SEQUENCE: 395
DPRDGS                                                                    6

SEQ ID NO: 396            moltype = AA   length = 6
FEATURE                   Location/Qualifiers
REGION                    1..6
                          note = Synthetic: 2188-C08; CDR-H2; Chothia
source                    1..6
                          mol_type = protein
                          organism = synthetic construct
SEQUENCE: 396
NPDDGD                                                                    6

SEQ ID NO: 397            moltype = AA   length = 6
FEATURE                   Location/Qualifiers
REGION                    1..6
                          note = Synthetic: 2188-E05; CDR-H2; Chothia
source                    1..6
                          mol_type = protein
                          organism = synthetic construct
SEQUENCE: 397
```

```
                                           -continued

EPWDGS                                                                   6

SEQ ID NO: 398          moltype = AA  length = 6
FEATURE                 Location/Qualifiers
REGION                  1..6
                        note = Synthetic: 2188-A02; CDR-H2; Chothia
source                  1..6
                        mol_type = protein
                        organism = synthetic construct
SEQUENCE: 398
NPEDGD                                                                   6

SEQ ID NO: 399          moltype = AA  length = 6
FEATURE                 Location/Qualifiers
REGION                  1..6
                        note = Synthetic: 2188-F04; CDR-H2; Chothia
source                  1..6
                        mol_type = protein
                        organism = synthetic construct
SEQUENCE: 399
DPDDGA                                                                   6

SEQ ID NO: 400          moltype = AA  length = 6
FEATURE                 Location/Qualifiers
REGION                  1..6
                        note = Synthetic: 2188-F05; CDR-H2; Chothia
source                  1..6
                        mol_type = protein
                        organism = synthetic construct
SEQUENCE: 400
DPRDGA                                                                   6

SEQ ID NO: 401          moltype = AA  length = 6
FEATURE                 Location/Qualifiers
REGION                  1..6
                        note = Synthetic: 2188-D07; CDR-H2; Chothia
source                  1..6
                        mol_type = protein
                        organism = synthetic construct
SEQUENCE: 401
DPTDGA                                                                   6

SEQ ID NO: 402          moltype = AA  length = 6
FEATURE                 Location/Qualifiers
REGION                  1..6
                        note = Synthetic: 2188-E02; CDR-H2; Chothia
source                  1..6
                        mol_type = protein
                        organism = synthetic construct
SEQUENCE: 402
EPHDGS                                                                   6

SEQ ID NO: 403          moltype = AA  length = 6
FEATURE                 Location/Qualifiers
REGION                  1..6
                        note = Synthetic: 2188-D06; CDR-H2; Chothia
source                  1..6
                        mol_type = protein
                        organism = synthetic construct
SEQUENCE: 403
DPNDGA                                                                   6

SEQ ID NO: 404          moltype = AA  length = 6
FEATURE                 Location/Qualifiers
REGION                  1..6
                        note = Synthetic: 2188-F09; CDR-H2; Chothia
source                  1..6
                        mol_type = protein
                        organism = synthetic construct
SEQUENCE: 404
DPNDGS                                                                   6

SEQ ID NO: 405          moltype = AA  length = 6
FEATURE                 Location/Qualifiers
REGION                  1..6
                        note = Synthetic: 2188-F10; CDR-H2; Chothia
source                  1..6
                        mol_type = protein
                        organism = synthetic construct
```

```
SEQUENCE: 405
DPNDGA                                                                         6

SEQ ID NO: 406          moltype = AA  length = 6
FEATURE                 Location/Qualifiers
REGION                  1..6
                        note = Synthetic: 2188-B05; CDR-H2; Chothia
source                  1..6
                        mol_type = protein
                        organism = synthetic construct
SEQUENCE: 406
DPDDGW                                                                         6

SEQ ID NO: 407          moltype = AA  length = 6
FEATURE                 Location/Qualifiers
REGION                  1..6
                        note = Synthetic: 1943-C02; CDR-H2; Chothia
source                  1..6
                        mol_type = protein
                        organism = synthetic construct
SEQUENCE: 407
DPNSGS                                                                         6

SEQ ID NO: 408          moltype = AA  length = 6
FEATURE                 Location/Qualifiers
REGION                  1..6
                        note = Synthetic: 2193-D04; CDR-H2; Chothia
source                  1..6
                        mol_type = protein
                        organism = synthetic construct
SEQUENCE: 408
DPNGGS                                                                         6

SEQ ID NO: 409          moltype = AA  length = 6
FEATURE                 Location/Qualifiers
REGION                  1..6
                        note = Synthetic: 2193-E10; CDR-H2; Chothia
source                  1..6
                        mol_type = protein
                        organism = synthetic construct
SEQUENCE: 409
DPVNGS                                                                         6

SEQ ID NO: 410          moltype = AA  length = 6
FEATURE                 Location/Qualifiers
REGION                  1..6
                        note = Synthetic: 2193-E06; CDR-H2; Chothia
source                  1..6
                        mol_type = protein
                        organism = synthetic construct
SEQUENCE: 410
DPKNGS                                                                         6

SEQ ID NO: 411          moltype = AA  length = 6
FEATURE                 Location/Qualifiers
REGION                  1..6
                        note = Synthetic: 2193-E04; CDR-H2; Chothia
source                  1..6
                        mol_type = protein
                        organism = synthetic construct
SEQUENCE: 411
DPSLGS                                                                         6

SEQ ID NO: 412          moltype = AA  length = 6
FEATURE                 Location/Qualifiers
REGION                  1..6
                        note = Synthetic: 2193-B09; CDR-H2; Chothia
source                  1..6
                        mol_type = protein
                        organism = synthetic construct
SEQUENCE: 412
DPNNGS                                                                         6

SEQ ID NO: 413          moltype = AA  length = 6
FEATURE                 Location/Qualifiers
REGION                  1..6
                        note = Synthetic: 2193-D11; CDR-H2; Chothia
source                  1..6
                        mol_type = protein
```

```
                               -continued
                             organism = synthetic construct
SEQUENCE: 413
DPNTGS                                                              6

SEQ ID NO: 414               moltype = AA  length = 6
FEATURE                      Location/Qualifiers
REGION                       1..6
                             note = Synthetic: 2193-B02; CDR-H2; Chothia
source                       1..6
                             mol_type = protein
                             organism = synthetic construct
SEQUENCE: 414
DPTRGS                                                              6

SEQ ID NO: 415               moltype = AA  length = 6
FEATURE                      Location/Qualifiers
REGION                       1..6
                             note = Synthetic: 2193-D05; CDR-H2; Chothia
source                       1..6
                             mol_type = protein
                             organism = synthetic construct
SEQUENCE: 415
DPNSGS                                                              6

SEQ ID NO: 416               moltype = AA  length = 6
FEATURE                      Location/Qualifiers
REGION                       1..6
                             note = Synthetic: 2193-E11; CDR-H2; Chothia
source                       1..6
                             mol_type = protein
                             organism = synthetic construct
SEQUENCE: 416
EPNSGA                                                              6

SEQ ID NO: 417               moltype = AA  length = 6
FEATURE                      Location/Qualifiers
REGION                       1..6
                             note = Synthetic: 2193-D06; CDR-H2; Chothia
source                       1..6
                             mol_type = protein
                             organism = synthetic construct
SEQUENCE: 417
DPHSGS                                                              6

SEQ ID NO: 418               moltype = AA  length = 6
FEATURE                      Location/Qualifiers
REGION                       1..6
                             note = Synthetic: 2193-C02; CDR-H2; Chothia
source                       1..6
                             mol_type = protein
                             organism = synthetic construct
SEQUENCE: 418
DPQSGS                                                              6

SEQ ID NO: 419               moltype = AA  length = 6
FEATURE                      Location/Qualifiers
REGION                       1..6
                             note = Synthetic: 2193-B03; CDR-H2; Chothia
source                       1..6
                             mol_type = protein
                             organism = synthetic construct
SEQUENCE: 419
DPVSGS                                                              6

SEQ ID NO: 420               moltype = AA  length = 6
FEATURE                      Location/Qualifiers
REGION                       1..6
                             note = Synthetic: 2193-A02; CDR-H2; Chothia
source                       1..6
                             mol_type = protein
                             organism = synthetic construct
SEQUENCE: 420
DPKSGS                                                              6

SEQ ID NO: 421               moltype = AA  length = 6
FEATURE                      Location/Qualifiers
REGION                       1..6
                             note = Synthetic: 2193-E05; Chothia
source                       1..6
```

```
                              -continued mol_type = protein
                              organism = synthetic construct
SEQUENCE: 421
DPNGSS                                                                  6

SEQ ID NO: 422                moltype = AA   length = 6
FEATURE                       Location/Qualifiers
REGION                        1..6
                              note = Synthetic: 2193-A06; CDR-H2; Chothia
source                        1..6
                              mol_type = protein
                              organism = synthetic construct
SEQUENCE: 422
DPDSGS                                                                  6

SEQ ID NO: 423                moltype = AA   length = 6
FEATURE                       Location/Qualifiers
REGION                        1..6
                              note = Synthetic: 2193-C04; CDR-H2; Chothia
source                        1..6
                              mol_type = protein
                              organism = synthetic construct
SEQUENCE: 423
DPKSGS                                                                  6

SEQ ID NO: 424                moltype = AA   length = 6
FEATURE                       Location/Qualifiers
REGION                        1..6
                              note = Synthetic: 2193-E08; CDR-H2; Chothia
source                        1..6
                              mol_type = protein
                              organism = synthetic construct
SEQUENCE: 424
DPHSGS                                                                  6

SEQ ID NO: 425                moltype = AA   length = 6
FEATURE                       Location/Qualifiers
REGION                        1..6
                              note = Synthetic: 2193-B10; CDR-H2; Chothia
source                        1..6
                              mol_type = protein
                              organism = synthetic construct
SEQUENCE: 425
DPNSGY                                                                  6

SEQ ID NO: 426                moltype = AA   length = 6
FEATURE                       Location/Qualifiers
REGION                        1..6
                              note = Synthetic: 2193-D08; CDR-H2; Chothia
source                        1..6
                              mol_type = protein
                              organism = synthetic construct
SEQUENCE: 426
DPSGGS                                                                  6

SEQ ID NO: 427                moltype = AA   length = 6
FEATURE                       Location/Qualifiers
REGION                        1..6
                              note = Synthetic: 2193-B08; CDR-H2; Chothia
source                        1..6
                              mol_type = protein
                              organism = synthetic construct
SEQUENCE: 427
DPSPGA                                                                  6

SEQ ID NO: 428                moltype = AA   length = 6
FEATURE                       Location/Qualifiers
REGION                        1..6
                              note = Synthetic: 2193-C05; CDR-H2; Chothia
source                        1..6
                              mol_type = protein
                              organism = synthetic construct
SEQUENCE: 428
DPHNGS                                                                  6

SEQ ID NO: 429                moltype = AA   length = 6
FEATURE                       Location/Qualifiers
REGION                        1..6
                              note = Synthetic: 2193-D10; CDR-H2; Chothia
```

```
source                  1..6
                        mol_type = protein
                        organism = synthetic construct
SEQUENCE: 429
DPNSGF                                                                     6

SEQ ID NO: 430          moltype = AA   length = 6
FEATURE                 Location/Qualifiers
REGION                  1..6
                        note = Synthetic: 2193-D03; CDR-H2; Chothia
source                  1..6
                        mol_type = protein
                        organism = synthetic construct
SEQUENCE: 430
DPNTGS                                                                     6

SEQ ID NO: 431          moltype = AA   length = 6
FEATURE                 Location/Qualifiers
REGION                  1..6
                        note = Synthetic: 2193-A09; CDR-H2; Chothia
source                  1..6
                        mol_type = protein
                        organism = synthetic construct
SEQUENCE: 431
DPKGGS                                                                     6

SEQ ID NO: 432          moltype = AA   length = 6
FEATURE                 Location/Qualifiers
REGION                  1..6
                        note = Synthetic: 2193-A10; CDR-H2; Chothia
source                  1..6
                        mol_type = protein
                        organism = synthetic construct
SEQUENCE: 432
DPKSGY                                                                     6

SEQ ID NO: 433          moltype = AA   length = 6
FEATURE                 Location/Qualifiers
REGION                  1..6
                        note = Synthetic: 2193-E07; CDR-H2; Chothia
source                  1..6
                        mol_type = protein
                        organism = synthetic construct
SEQUENCE: 433
DPTIGS                                                                     6

SEQ ID NO: 434          moltype = AA   length = 6
FEATURE                 Location/Qualifiers
REGION                  1..6
                        note = Synthetic: 2193-A07; CDR-H2; Chothia
source                  1..6
                        mol_type = protein
                        organism = synthetic construct
SEQUENCE: 434
DPNTGT                                                                     6

SEQ ID NO: 435          moltype = AA   length = 6
FEATURE                 Location/Qualifiers
REGION                  1..6
                        note = Synthetic: 2193-E03; CDR-H2; Chothia
source                  1..6
                        mol_type = protein
                        organism = synthetic construct
SEQUENCE: 435
DPKGGS                                                                     6

SEQ ID NO: 436          moltype = AA   length = 6
FEATURE                 Location/Qualifiers
REGION                  1..6
                        note = Synthetic: 2193-C08; CDR-H2; Chothia
source                  1..6
                        mol_type = protein
                        organism = synthetic construct
SEQUENCE: 436
DPYPGS                                                                     6

SEQ ID NO: 437          moltype = AA   length = 6
FEATURE                 Location/Qualifiers
REGION                  1..6
```

```
                        note = Synthetic: 2193-B11; CDR-H2; Chothia
source                  1..6
                        mol_type = protein
                        organism = synthetic construct
SEQUENCE: 437
DPKSGF                                                                         6

SEQ ID NO: 438          moltype = AA   length = 6
FEATURE                 Location/Qualifiers
REGION                  1..6
                        note = Synthetic: 2193-A03; CDR-H2; Chothia
source                  1..6
                        mol_type = protein
                        organism = synthetic construct
SEQUENCE: 438
DPKSGS                                                                         6

SEQ ID NO: 439          moltype = AA   length = 6
FEATURE                 Location/Qualifiers
REGION                  1..6
                        note = Synthetic: 2193-D02; CDR-H2; Chothia
source                  1..6
                        mol_type = protein
                        organism = synthetic construct
SEQUENCE: 439
DPESGS                                                                         6

SEQ ID NO: 440          moltype = AA   length = 6
FEATURE                 Location/Qualifiers
REGION                  1..6
                        note = Synthetic: 2193-B06; CDR-H2; Chothia
source                  1..6
                        mol_type = protein
                        organism = synthetic construct
SEQUENCE: 440
DPHPGS                                                                         6

SEQ ID NO: 441          moltype = AA   length = 6
FEATURE                 Location/Qualifiers
REGION                  1..6
                        note = Synthetic: 2193-B01; CDR-H2; Chothia
source                  1..6
                        mol_type = protein
                        organism = synthetic construct
SEQUENCE: 441
DPRSGY                                                                         6

SEQ ID NO: 442          moltype = AA   length = 6
FEATURE                 Location/Qualifiers
REGION                  1..6
                        note = Synthetic: 2193-D09; CDR-H2; Chothia
source                  1..6
                        mol_type = protein
                        organism = synthetic construct
SEQUENCE: 442
DPNSGS                                                                         6

SEQ ID NO: 443          moltype = AA   length = 6
FEATURE                 Location/Qualifiers
REGION                  1..6
                        note = Synthetic: 2193-E09; CDR-H2; Chothia
source                  1..6
                        mol_type = protein
                        organism = synthetic construct
SEQUENCE: 443
DPGSGY                                                                         6

SEQ ID NO: 444          moltype = AA   length = 6
FEATURE                 Location/Qualifiers
REGION                  1..6
                        note = Synthetic: 2193-B07; CDR-H2; Chothia
source                  1..6
                        mol_type = protein
                        organism = synthetic construct
SEQUENCE: 444
DPNSGS                                                                         6

SEQ ID NO: 445          moltype = AA   length = 6
FEATURE                 Location/Qualifiers
```

```
REGION                  1..6
                        note = Synthetic: 2193-C06; CDR-H2; Chothia
source                  1..6
                        mol_type = protein
                        organism = synthetic construct
SEQUENCE: 445
DPISGS                                                                       6

SEQ ID NO: 446          moltype = AA  length = 6
FEATURE                 Location/Qualifiers
REGION                  1..6
                        note = Synthetic: 2193-B05; CDR-H2; Chothia
source                  1..6
                        mol_type = protein
                        organism = synthetic construct
SEQUENCE: 446
DPIGGS                                                                       6

SEQ ID NO: 447          moltype = AA  length = 6
FEATURE                 Location/Qualifiers
REGION                  1..6
                        note = Synthetic: 2193-A11; CDR-H2; Chothia
source                  1..6
                        mol_type = protein
                        organism = synthetic construct
SEQUENCE: 447
DPKSGS                                                                       6

SEQ ID NO: 448          moltype = AA  length = 6
FEATURE                 Location/Qualifiers
REGION                  1..6
                        note = Synthetic: 2193-E02; CDR-H2; Chothia
source                  1..6
                        mol_type = protein
                        organism = synthetic construct
SEQUENCE: 448
DPTSGS                                                                       6

SEQ ID NO: 449          moltype = AA  length = 6
FEATURE                 Location/Qualifiers
REGION                  1..6
                        note = Synthetic: 2193-A08; CDR-H2; Chothia
source                  1..6
                        mol_type = protein
                        organism = synthetic construct
SEQUENCE: 449
DPNAGS                                                                       6

SEQ ID NO: 450          moltype = AA  length = 6
FEATURE                 Location/Qualifiers
REGION                  1..6
                        note = Synthetic: 2193-C11; CDR-H2; Chothia
source                  1..6
                        mol_type = protein
                        organism = synthetic construct
SEQUENCE: 450
DPKSGS                                                                       6

SEQ ID NO: 451          moltype = AA  length = 6
FEATURE                 Location/Qualifiers
REGION                  1..6
                        note = Synthetic: 2193-A01; CDR-H2; Chothia
source                  1..6
                        mol_type = protein
                        organism = synthetic construct
SEQUENCE: 451
DPTSGS                                                                       6

SEQ ID NO: 452          moltype = AA  length = 6
FEATURE                 Location/Qualifiers
REGION                  1..6
                        note = Synthetic: 2193-D07; CDR-H2; Chothia
source                  1..6
                        mol_type = protein
                        organism = synthetic construct
SEQUENCE: 452
GPADGS                                                                       6

SEQ ID NO: 453          moltype = AA  length = 6
```

```
FEATURE              Location/Qualifiers
REGION               1..6
                     note = Synthetic: 2193-A05; CDR-H2; Chothia
source               1..6
                     mol_type = protein
                     organism = synthetic construct
SEQUENCE: 453
DPNSGS                                                                     6

SEQ ID NO: 454       moltype = AA  length = 6
FEATURE              Location/Qualifiers
REGION               1..6
                     note = Synthetic: 2193-C03; CDR-H2; Chothia
source               1..6
                     mol_type = protein
                     organism = synthetic construct
SEQUENCE: 454
EPKSGS                                                                     6

SEQ ID NO: 455       moltype = AA  length = 6
FEATURE              Location/Qualifiers
REGION               1..6
                     note = Synthetic: 2193-C09; CDR-H2; Chothia
source               1..6
                     mol_type = protein
                     organism = synthetic construct
SEQUENCE: 455
DPISGS                                                                     6

SEQ ID NO: 456       moltype = AA  length = 6
FEATURE              Location/Qualifiers
REGION               1..6
                     note = Synthetic: 2193-D01; CDR-H2; Chothia
source               1..6
                     mol_type = protein
                     organism = synthetic construct
SEQUENCE: 456
DPTSGP                                                                     6

SEQ ID NO: 457       moltype = AA  length = 6
FEATURE              Location/Qualifiers
REGION               1..6
                     note = Synthetic: 2193-E01; CDR-H2; Chothia
source               1..6
                     mol_type = protein
                     organism = synthetic construct
SEQUENCE: 457
DPKSGS                                                                     6

SEQ ID NO: 458       moltype = AA  length = 6
FEATURE              Location/Qualifiers
REGION               1..6
                     note = Synthetic: 2193-C07; CDR-H2; Chothia
source               1..6
                     mol_type = protein
                     organism = synthetic construct
SEQUENCE: 458
DPTRGA                                                                     6

SEQ ID NO: 459       moltype = AA  length = 6
FEATURE              Location/Qualifiers
REGION               1..6
                     note = Synthetic: 2193-B04; CDR-H2; Chothia
source               1..6
                     mol_type = protein
                     organism = synthetic construct
SEQUENCE: 459
EPKNGS                                                                     6

SEQ ID NO: 460       moltype = AA  length = 6
FEATURE              Location/Qualifiers
REGION               1..6
                     note = Synthetic: 2193-C10; CDR-H2; Chothia
source               1..6
                     mol_type = protein
                     organism = synthetic construct
SEQUENCE: 460
DPRSGS                                                                     6
```

```
SEQ ID NO: 461           moltype = AA  length = 6
FEATURE                  Location/Qualifiers
REGION                   1..6
                         note = Synthetic: 2193-C01; CDR-H2; Chothia
source                   1..6
                         mol_type = protein
                         organism = synthetic construct
SEQUENCE: 461
DPKSGS                                                                   6

SEQ ID NO: 462           moltype = AA  length = 6
FEATURE                  Location/Qualifiers
REGION                   1..6
                         note = Synthetic: 2193-A04; CDR-H2; Chothia
source                   1..6
                         mol_type = protein
                         organism = synthetic construct
SEQUENCE: 462
DPNSGS                                                                   6

SEQ ID NO: 463           moltype = AA  length = 6
FEATURE                  Location/Qualifiers
REGION                   1..6
                         note = Synthetic: 1944-A07; CDR-H2; Chothia
source                   1..6
                         mol_type = protein
                         organism = synthetic construct
SEQUENCE: 463
SPNSGS                                                                   6

SEQ ID NO: 464           moltype = AA  length = 6
FEATURE                  Location/Qualifiers
REGION                   1..6
                         note = Synthetic: 2194-A02; CDR-H2; Chothia
source                   1..6
                         mol_type = protein
                         organism = synthetic construct
SEQUENCE: 464
SPLAGN                                                                   6

SEQ ID NO: 465           moltype = AA  length = 6
FEATURE                  Location/Qualifiers
REGION                   1..6
                         note = Synthetic: 2194-A05; CDR-H2; Chothia
source                   1..6
                         mol_type = protein
                         organism = synthetic construct
SEQUENCE: 465
SPNSGS                                                                   6

SEQ ID NO: 466           moltype = AA  length = 6
FEATURE                  Location/Qualifiers
REGION                   1..6
                         note = Synthetic: 2194-B04; CDR-H2; Chothia
source                   1..6
                         mol_type = protein
                         organism = synthetic construct
SEQUENCE: 466
SPLAGN                                                                   6

SEQ ID NO: 467           moltype = AA  length = 6
FEATURE                  Location/Qualifiers
REGION                   1..6
                         note = Synthetic: 2194-A09; CDR-H2; Chothia
source                   1..6
                         mol_type = protein
                         organism = synthetic construct
SEQUENCE: 467
TPLSGA                                                                   6

SEQ ID NO: 468           moltype = AA  length = 6
FEATURE                  Location/Qualifiers
REGION                   1..6
                         note = Synthetic: 2194-A01; CDR-H2; Chothia
source                   1..6
                         mol_type = protein
                         organism = synthetic construct
SEQUENCE: 468
SPLAGN                                                                   6
```

```
SEQ ID NO: 469         moltype = AA  length = 6
FEATURE                Location/Qualifiers
REGION                 1..6
                       note = Synthetic: 2194-B03; CDR-H2; Chothia
source                 1..6
                       mol_type = protein
                       organism = synthetic construct
SEQUENCE: 469
SPLAGN                                                                        6

SEQ ID NO: 470         moltype = AA  length = 6
FEATURE                Location/Qualifiers
REGION                 1..6
                       note = Synthetic: 2194-B02; CDR-H2; Chothia
source                 1..6
                       mol_type = protein
                       organism = synthetic construct
SEQUENCE: 470
SPLAGN                                                                        6

SEQ ID NO: 471         moltype = AA  length = 6
FEATURE                Location/Qualifiers
REGION                 1..6
                       note = Synthetic: 2194-A03; CDR-H2; Chothia
source                 1..6
                       mol_type = protein
                       organism = synthetic construct
SEQUENCE: 471
TPNSGT                                                                        6

SEQ ID NO: 472         moltype = AA  length = 6
FEATURE                Location/Qualifiers
REGION                 1..6
                       note = Synthetic: 2194-A11; CDR-H2; Chothia
source                 1..6
                       mol_type = protein
                       organism = synthetic construct
SEQUENCE: 472
SPNSGY                                                                        6

SEQ ID NO: 473         moltype = AA  length = 6
FEATURE                Location/Qualifiers
REGION                 1..6
                       note = Synthetic: 2194-A08; CDR-H2; Chothia
source                 1..6
                       mol_type = protein
                       organism = synthetic construct
SEQUENCE: 473
APSSGY                                                                        6

SEQ ID NO: 474         moltype = AA  length = 6
FEATURE                Location/Qualifiers
REGION                 1..6
                       note = Synthetic: 2194-A04; CDR-H2; Chothia
source                 1..6
                       mol_type = protein
                       organism = synthetic construct
SEQUENCE: 474
SPLAGN                                                                        6

SEQ ID NO: 475         moltype = AA  length = 6
FEATURE                Location/Qualifiers
REGION                 1..6
                       note = Synthetic: 2194-A10; CDR-H2; Chothia
source                 1..6
                       mol_type = protein
                       organism = synthetic construct
SEQUENCE: 475
SPNSGS                                                                        6

SEQ ID NO: 476         moltype = AA  length = 6
FEATURE                Location/Qualifiers
REGION                 1..6
                       note = Synthetic: 2194-A07; CDR-H2; Chothia
source                 1..6
                       mol_type = protein
                       organism = synthetic construct
SEQUENCE: 476
```

-continued

```
SPLAGN                                                                          6

SEQ ID NO: 477          moltype = AA  length = 6
FEATURE                 Location/Qualifiers
REGION                  1..6
                        note = Synthetic: 2194-B01; CDR-H2; Chothia
source                  1..6
                        mol_type = protein
                        organism = synthetic construct
SEQUENCE: 477
SPLAGN                                                                          6

SEQ ID NO: 478          moltype = AA  length = 6
FEATURE                 Location/Qualifiers
REGION                  1..6
                        note = Synthetic: 2194-A06; CDR-H2; Chothia
source                  1..6
                        mol_type = protein
                        organism = synthetic construct
SEQUENCE: 478
SPLAGN                                                                          6

SEQ ID NO: 479          moltype = AA  length = 6
FEATURE                 Location/Qualifiers
REGION                  1..6
                        note = Synthetic: 2196-C01; CDR-H2; Chothia
source                  1..6
                        mol_type = protein
                        organism = synthetic construct
SEQUENCE: 479
TPLSGA                                                                          6

SEQ ID NO: 480          moltype = AA  length = 6
FEATURE                 Location/Qualifiers
REGION                  1..6
                        note = Synthetic: 2196-A02; CDR-H2; Chothia
source                  1..6
                        mol_type = protein
                        organism = synthetic construct
SEQUENCE: 480
SPNSGA                                                                          6

SEQ ID NO: 481          moltype = AA  length = 6
FEATURE                 Location/Qualifiers
REGION                  1..6
                        note = Synthetic: 2196-B03; CDR-H2; Chothia
source                  1..6
                        mol_type = protein
                        organism = synthetic construct
SEQUENCE: 481
SPNSGA                                                                          6

SEQ ID NO: 482          moltype = AA  length = 6
FEATURE                 Location/Qualifiers
REGION                  1..6
                        note = Synthetic: 2196-A05; CDR-H2; Chothia
source                  1..6
                        mol_type = protein
                        organism = synthetic construct
SEQUENCE: 482
SPNSGA                                                                          6

SEQ ID NO: 483          moltype = AA  length = 6
FEATURE                 Location/Qualifiers
REGION                  1..6
                        note = Synthetic: 2196-C02; CDR-H2; Chothia
source                  1..6
                        mol_type = protein
                        organism = synthetic construct
SEQUENCE: 483
SPNSGW                                                                          6

SEQ ID NO: 484          moltype = AA  length = 6
FEATURE                 Location/Qualifiers
REGION                  1..6
                        note = Synthetic: 2196-B11; CDR-H2; Chothia
source                  1..6
                        mol_type = protein
                        organism = synthetic construct
```

```
SEQUENCE: 484
SPNSGY                                                                          6

SEQ ID NO: 485          moltype = AA  length = 6
FEATURE                 Location/Qualifiers
REGION                  1..6
                        note = Synthetic: 2196-B08; CDR-H2; Chothia
source                  1..6
                        mol_type = protein
                        organism = synthetic construct
SEQUENCE: 485
SPNSGY                                                                          6

SEQ ID NO: 486          moltype = AA  length = 6
FEATURE                 Location/Qualifiers
REGION                  1..6
                        note = Synthetic: 2196-A04; CDR-H2; Chothia
source                  1..6
                        mol_type = protein
                        organism = synthetic construct
SEQUENCE: 486
YPISGH                                                                          6

SEQ ID NO: 487          moltype = AA  length = 6
FEATURE                 Location/Qualifiers
REGION                  1..6
                        note = Synthetic: 2196-A03; CDR-H2; Chothia
source                  1..6
                        mol_type = protein
                        organism = synthetic construct
SEQUENCE: 487
SPNSGS                                                                          6

SEQ ID NO: 488          moltype = AA  length = 6
FEATURE                 Location/Qualifiers
REGION                  1..6
                        note = Synthetic: 2196-B07; CDR-H2; Chothia
source                  1..6
                        mol_type = protein
                        organism = synthetic construct
SEQUENCE: 488
SPNSGA                                                                          6

SEQ ID NO: 489          moltype = AA  length = 6
FEATURE                 Location/Qualifiers
REGION                  1..6
                        note = Synthetic: 2196-A06; CDR-H2; Chothia
source                  1..6
                        mol_type = protein
                        organism = synthetic construct
SEQUENCE: 489
SPNSGS                                                                          6

SEQ ID NO: 490          moltype = AA  length = 6
FEATURE                 Location/Qualifiers
REGION                  1..6
                        note = Synthetic: 2196-B05; CDR-H2; Chothia
source                  1..6
                        mol_type = protein
                        organism = synthetic construct
SEQUENCE: 490
SPNSGA                                                                          6

SEQ ID NO: 491          moltype = AA  length = 6
FEATURE                 Location/Qualifiers
REGION                  1..6
                        note = Synthetic: 2196-A01; CDR-H2; Chothia
source                  1..6
                        mol_type = protein
                        organism = synthetic construct
SEQUENCE: 491
SPNSGY                                                                          6

SEQ ID NO: 492          moltype = AA  length = 6
FEATURE                 Location/Qualifiers
REGION                  1..6
                        note = Synthetic: 2196-B01; CDR-H2; Chothia
source                  1..6
                        mol_type = protein
```

```
                        organism = synthetic construct
SEQUENCE: 492
SPNSGY                                                                    6

SEQ ID NO: 493          moltype = AA  length = 6
FEATURE                 Location/Qualifiers
REGION                  1..6
                        note = Synthetic: 2196-A09; CDR-H2; Chothia
source                  1..6
                        mol_type = protein
                        organism = synthetic construct
SEQUENCE: 493
SPNSGA                                                                    6

SEQ ID NO: 494          moltype = AA  length = 6
FEATURE                 Location/Qualifiers
REGION                  1..6
                        note = Synthetic: 2196-A08; CDR-H2; Chothia
source                  1..6
                        mol_type = protein
                        organism = synthetic construct
SEQUENCE: 494
SPNSGS                                                                    6

SEQ ID NO: 495          moltype = AA  length = 6
FEATURE                 Location/Qualifiers
REGION                  1..6
                        note = Synthetic: 2196-A10; CDR-H2; Chothia
source                  1..6
                        mol_type = protein
                        organism = synthetic construct
SEQUENCE: 495
SPNSGA                                                                    6

SEQ ID NO: 496          moltype = AA  length = 6
FEATURE                 Location/Qualifiers
REGION                  1..6
                        note = Synthetic: 2196-B06; CDR-H2; Chothia
source                  1..6
                        mol_type = protein
                        organism = synthetic construct
SEQUENCE: 496
SPNSGS                                                                    6

SEQ ID NO: 497          moltype = AA  length = 6
FEATURE                 Location/Qualifiers
REGION                  1..6
                        note = Synthetic: 2196-B09; CDR-H2; Chothia
source                  1..6
                        mol_type = protein
                        organism = synthetic construct
SEQUENCE: 497
SPNSGS                                                                    6

SEQ ID NO: 498          moltype = AA  length = 6
FEATURE                 Location/Qualifiers
REGION                  1..6
                        note = Synthetic: 2196-C03; CDR-H2; Chothia
source                  1..6
                        mol_type = protein
                        organism = synthetic construct
SEQUENCE: 498
SPNSGS                                                                    6

SEQ ID NO: 499          moltype = AA  length = 6
FEATURE                 Location/Qualifiers
REGION                  1..6
                        note = Synthetic: 2196-C04; CDR-H2; Chothia
source                  1..6
                        mol_type = protein
                        organism = synthetic construct
SEQUENCE: 499
APLSGS                                                                    6

SEQ ID NO: 500          moltype = AA  length = 6
FEATURE                 Location/Qualifiers
REGION                  1..6
                        note = Synthetic: 2196-A07; CDR-H2; Chothia
source                  1..6
```

```
                            mol_type = protein
                            organism = synthetic construct
SEQUENCE: 500
SPNSGS                                                                    6

SEQ ID NO: 501              moltype = AA   length = 6
FEATURE                     Location/Qualifiers
REGION                      1..6
                            note = Synthetic: 2196-A11; CDR-H2; Chothia
source                      1..6
                            mol_type = protein
                            organism = synthetic construct
SEQUENCE: 501
SPNSGT                                                                    6

SEQ ID NO: 502              moltype = AA   length = 6
FEATURE                     Location/Qualifiers
REGION                      1..6
                            note = Synthetic: 2196-B02; CDR-H2; Chothia
source                      1..6
                            mol_type = protein
                            organism = synthetic construct
SEQUENCE: 502
SPNSGQ                                                                    6

SEQ ID NO: 503              moltype = AA   length = 6
FEATURE                     Location/Qualifiers
REGION                      1..6
                            note = Synthetic: 2196-B04; CDR-H2; Chothia
source                      1..6
                            mol_type = protein
                            organism = synthetic construct
SEQUENCE: 503
SPNSGA                                                                    6

SEQ ID NO: 504              moltype = AA   length = 6
FEATURE                     Location/Qualifiers
REGION                      1..6
                            note = Synthetic: 2196-B10; CDR-H2; Chothia
source                      1..6
                            mol_type = protein
                            organism = synthetic construct
SEQUENCE: 504
TPLSGA                                                                    6

SEQ ID NO: 505              moltype = AA   length = 17
FEATURE                     Location/Qualifiers
REGION                      1..17
                            note = Synthetic: 1987-C05; CDR-H2; Kabat
source                      1..17
                            mol_type = protein
                            organism = synthetic construct
SEQUENCE: 505
GIDPDDGSTD YADSVKG                                                       17

SEQ ID NO: 506              moltype = AA   length = 17
FEATURE                     Location/Qualifiers
REGION                      1..17
                            note = Synthetic: 2188-D11; CDR-H2; Kabat
source                      1..17
                            mol_type = protein
                            organism = synthetic construct
SEQUENCE: 506
LIDPDDGSTD EADSVKG                                                       17

SEQ ID NO: 507              moltype = AA   length = 17
FEATURE                     Location/Qualifiers
REGION                      1..17
                            note = Synthetic: 2188-B04; CDR-H2; Kabat
source                      1..17
                            mol_type = protein
                            organism = synthetic construct
SEQUENCE: 507
WINPDDGDTY YADSVKG                                                       17

SEQ ID NO: 508              moltype = AA   length = 17
FEATURE                     Location/Qualifiers
REGION                      1..17
                            note = Synthetic: 2188-C09; CDR-H2; Kabat
```

```
source                     1..17
                           mol_type = protein
                           organism = synthetic construct
SEQUENCE: 508
WINPHDGDTY YADSVKG                                                        17

SEQ ID NO: 509             moltype = AA   length = 17
FEATURE                    Location/Qualifiers
REGION                     1..17
                           note = Synthetic: 2188-G03; CDR-H2; Kabat
source                     1..17
                           mol_type = protein
                           organism = synthetic construct
SEQUENCE: 509
GIDPRDGSTD YADSVKG                                                        17

SEQ ID NO: 510             moltype = AA   length = 17
FEATURE                    Location/Qualifiers
REGION                     1..17
                           note = Synthetic: 2188-E03; CDR-H2; Kabat
source                     1..17
                           mol_type = protein
                           organism = synthetic construct
SEQUENCE: 510
GIDPDDGSTD YADSVKG                                                        17

SEQ ID NO: 511             moltype = AA   length = 17
FEATURE                    Location/Qualifiers
REGION                     1..17
                           note = Synthetic: 2188-B11; CDR-H2; Kabat
source                     1..17
                           mol_type = protein
                           organism = synthetic construct
SEQUENCE: 511
WINPDDGDTF LADSVKG                                                        17

SEQ ID NO: 512             moltype = AA   length = 17
FEATURE                    Location/Qualifiers
REGION                     1..17
                           note = Synthetic: 2188-E07; CDR-H2; Kabat
source                     1..17
                           mol_type = protein
                           organism = synthetic construct
SEQUENCE: 512
GIDPEDGFTV HADSVKG                                                        17

SEQ ID NO: 513             moltype = AA   length = 17
FEATURE                    Location/Qualifiers
REGION                     1..17
                           note = Synthetic: 2188-B02; CDR-H2; Kabat
source                     1..17
                           mol_type = protein
                           organism = synthetic construct
SEQUENCE: 513
WINPDDGDTY LADSVKG                                                        17

SEQ ID NO: 514             moltype = AA   length = 17
FEATURE                    Location/Qualifiers
REGION                     1..17
                           note = Synthetic: 2188-C07; CDR-H2; Kabat
source                     1..17
                           mol_type = protein
                           organism = synthetic construct
SEQUENCE: 514
WINPDDGDTY YADSVKG                                                        17

SEQ ID NO: 515             moltype = AA   length = 17
FEATURE                    Location/Qualifiers
REGION                     1..17
                           note = Synthetic: 2188-A03; CDR-H2; Kabat
source                     1..17
                           mol_type = protein
                           organism = synthetic construct
SEQUENCE: 515
WINPDDGDTY YADSVKG                                                        17

SEQ ID NO: 516             moltype = AA   length = 17
FEATURE                    Location/Qualifiers
REGION                     1..17
```

```
                        note = Synthetic: 2188-F03; CDR-H2; Kabat
source                  1..17
                        mol_type = protein
                        organism = synthetic construct
SEQUENCE: 516
GIDPDDGSTD YADSVKG                                                        17

SEQ ID NO: 517          moltype = AA  length = 17
FEATURE                 Location/Qualifiers
REGION                  1..17
                        note = Synthetic: 2188-D03; CDR-H2; Kabat
source                  1..17
                        mol_type = protein
                        organism = synthetic construct
SEQUENCE: 517
GIDPHDGSTD YADSVKG                                                        17

SEQ ID NO: 518          moltype = AA  length = 17
FEATURE                 Location/Qualifiers
REGION                  1..17
                        note = Synthetic: 2188-C04; CDR-H2; Kabat
source                  1..17
                        mol_type = protein
                        organism = synthetic construct
SEQUENCE: 518
WINPEDGDTY HADSVKG                                                        17

SEQ ID NO: 519          moltype = AA  length = 17
FEATURE                 Location/Qualifiers
REGION                  1..17
                        note = Synthetic: 2188-D10; CDR-H2; Kabat
source                  1..17
                        mol_type = protein
                        organism = synthetic construct
SEQUENCE: 519
RIDPRDGATD YADSVKG                                                        17

SEQ ID NO: 520          moltype = AA  length = 17
FEATURE                 Location/Qualifiers
REGION                  1..17
                        note = Synthetic: 2188-A06; CDR-H2; Kabat
source                  1..17
                        mol_type = protein
                        organism = synthetic construct
SEQUENCE: 520
WINPDDGDTY HADSVKG                                                        17

SEQ ID NO: 521          moltype = AA  length = 17
FEATURE                 Location/Qualifiers
REGION                  1..17
                        note = Synthetic: 2188-C11; CDR-H2; Kabat
source                  1..17
                        mol_type = protein
                        organism = synthetic construct
SEQUENCE: 521
WINPDDGDTY LADSVKG                                                        17

SEQ ID NO: 522          moltype = AA  length = 17
FEATURE                 Location/Qualifiers
REGION                  1..17
                        note = Synthetic: 2188-F01; CDR-H2; Kabat
source                  1..17
                        mol_type = protein
                        organism = synthetic construct
SEQUENCE: 522
LIDPDDGWTV SADSVKG                                                        17

SEQ ID NO: 523          moltype = AA  length = 17
FEATURE                 Location/Qualifiers
REGION                  1..17
                        note = Synthetic: 2188-E11; CDR-H2; Kabat
source                  1..17
                        mol_type = protein
                        organism = synthetic construct
SEQUENCE: 523
GIDPGDGATD HADSVKG                                                        17

SEQ ID NO: 524          moltype = AA  length = 17
FEATURE                 Location/Qualifiers
```

```
REGION                  1..17
                        note = Synthetic: 2188-A07; CDR-H2; Kabat
source                  1..17
                        mol_type = protein
                        organism = synthetic construct
SEQUENCE: 524
WINPDDGDTY YADSVKG                                                  17

SEQ ID NO: 525          moltype = AA   length = 17
FEATURE                 Location/Qualifiers
REGION                  1..17
                        note = Synthetic: 2188-C01; CDR-H2; Kabat
source                  1..17
                        mol_type = protein
                        organism = synthetic construct
SEQUENCE: 525
LIDPHDGSTD SADSVKG                                                  17

SEQ ID NO: 526          moltype = AA   length = 17
FEATURE                 Location/Qualifiers
REGION                  1..17
                        note = Synthetic: 2188-F08; CDR-H2; Kabat
source                  1..17
                        mol_type = protein
                        organism = synthetic construct
SEQUENCE: 526
RIEPDDGATD YADSVKG                                                  17

SEQ ID NO: 527          moltype = AA   length = 17
FEATURE                 Location/Qualifiers
REGION                  1..17
                        note = Synthetic: 2188-E04; CDR-H2; Kabat
source                  1..17
                        mol_type = protein
                        organism = synthetic construct
SEQUENCE: 527
GIDPQDGSTD YADSVKG                                                  17

SEQ ID NO: 528          moltype = AA   length = 17
FEATURE                 Location/Qualifiers
REGION                  1..17
                        note = Synthetic: 2188-B01; CDR-H2; Kabat
source                  1..17
                        mol_type = protein
                        organism = synthetic construct
SEQUENCE: 528
WINPDDGDTY YADSVKG                                                  17

SEQ ID NO: 529          moltype = AA   length = 17
FEATURE                 Location/Qualifiers
REGION                  1..17
                        note = Synthetic: 2188-F11; CDR-H2; Kabat
source                  1..17
                        mol_type = protein
                        organism = synthetic construct
SEQUENCE: 529
GIDPEDGATD YADSVKG                                                  17

SEQ ID NO: 530          moltype = AA   length = 17
FEATURE                 Location/Qualifiers
REGION                  1..17
                        note = Synthetic: 2188-B08; CDR-H2; Kabat
source                  1..17
                        mol_type = protein
                        organism = synthetic construct
SEQUENCE: 530
WINPDDGDTF YADSVKG                                                  17

SEQ ID NO: 531          moltype = AA   length = 17
FEATURE                 Location/Qualifiers
REGION                  1..17
                        note = Synthetic: 2188-C10; CDR-H2; Kabat
source                  1..17
                        mol_type = protein
                        organism = synthetic construct
SEQUENCE: 531
WINPDDGDTY HADSVKG                                                  17

SEQ ID NO: 532          moltype = AA   length = 17
```

```
                           -continued

FEATURE               Location/Qualifiers
REGION                1..17
                      note = Synthetic: 2188-C02; CDR-H2; Kabat
source                1..17
                      mol_type = protein
                      organism = synthetic construct
SEQUENCE: 532
WINPDDGDTY YADSVKG                                              17

SEQ ID NO: 533        moltype = AA  length = 17
FEATURE               Location/Qualifiers
REGION                1..17
                      note = Synthetic: 2188-B07; CDR-H2; Kabat
source                1..17
                      mol_type = protein
                      organism = synthetic construct
SEQUENCE: 533
WINPDDGDTY YADSVKG                                              17

SEQ ID NO: 534        moltype = AA  length = 17
FEATURE               Location/Qualifiers
REGION                1..17
                      note = Synthetic: 2188-A11; CDR-H2; Kabat
source                1..17
                      mol_type = protein
                      organism = synthetic construct
SEQUENCE: 534
LIDPKDGATD SADSVKG                                              17

SEQ ID NO: 535        moltype = AA  length = 17
FEATURE               Location/Qualifiers
REGION                1..17
                      note = Synthetic: 2188-D01; CDR-H2; Kabat
source                1..17
                      mol_type = protein
                      organism = synthetic construct
SEQUENCE: 535
WINPYDGDTY YADSVKG                                              17

SEQ ID NO: 536        moltype = AA  length = 17
FEATURE               Location/Qualifiers
REGION                1..17
                      note = Synthetic: 2188-E09; CDR-H2; Kabat
source                1..17
                      mol_type = protein
                      organism = synthetic construct
SEQUENCE: 536
EIDPQDGWTV HADSVKG                                              17

SEQ ID NO: 537        moltype = AA  length = 17
FEATURE               Location/Qualifiers
REGION                1..17
                      note = Synthetic: 2188-E06; CDR-H2; Kabat
source                1..17
                      mol_type = protein
                      organism = synthetic construct
SEQUENCE: 537
GIDPEDGATD IADSVKG                                              17

SEQ ID NO: 538        moltype = AA  length = 17
FEATURE               Location/Qualifiers
REGION                1..17
                      note = Synthetic: 2188-B03; CDR-H2; Kabat
source                1..17
                      mol_type = protein
                      organism = synthetic construct
SEQUENCE: 538
AIDPGDGATD YADSVKG                                              17

SEQ ID NO: 539        moltype = AA  length = 17
FEATURE               Location/Qualifiers
REGION                1..17
                      note = Synthetic: 2188-F06; CDR-H2; Kabat
source                1..17
                      mol_type = protein
                      organism = synthetic construct
SEQUENCE: 539
GIDPDDGATD YADSVKG                                              17
```

```
SEQ ID NO: 540           moltype = AA  length = 17
FEATURE                  Location/Qualifiers
REGION                   1..17
                         note = Synthetic: 2188-D02; CDR-H2; Kabat
source                   1..17
                         mol_type = protein
                         organism = synthetic construct
SEQUENCE: 540
GIDPEDGATD YADSVKG                                                          17

SEQ ID NO: 541           moltype = AA  length = 17
FEATURE                  Location/Qualifiers
REGION                   1..17
                         note = Synthetic: 2188-B06; CDR-H2; Kabat
source                   1..17
                         mol_type = protein
                         organism = synthetic construct
SEQUENCE: 541
WINPDDGDTY HADSVKG                                                          17

SEQ ID NO: 542           moltype = AA  length = 17
FEATURE                  Location/Qualifiers
REGION                   1..17
                         note = Synthetic: 2188-D09; CDR-H2; Kabat
source                   1..17
                         mol_type = protein
                         organism = synthetic construct
SEQUENCE: 542
GIDPGDGSTD YADSVKG                                                          17

SEQ ID NO: 543           moltype = AA  length = 17
FEATURE                  Location/Qualifiers
REGION                   1..17
                         note = Synthetic: 2188-F02; CDR-H2; Kabat
source                   1..17
                         mol_type = protein
                         organism = synthetic construct
SEQUENCE: 543
WIDPSDGSTE HADSVKG                                                          17

SEQ ID NO: 544           moltype = AA  length = 17
FEATURE                  Location/Qualifiers
REGION                   1..17
                         note = Synthetic: 2188-E10; CDR-H2; Kabat
source                   1..17
                         mol_type = protein
                         organism = synthetic construct
SEQUENCE: 544
GIDPRDGATD YADSVKG                                                          17

SEQ ID NO: 545           moltype = AA  length = 17
FEATURE                  Location/Qualifiers
REGION                   1..17
                         note = Synthetic: 2188-A09; CDR-H2; Kabat
source                   1..17
                         mol_type = protein
                         organism = synthetic construct
SEQUENCE: 545
WINPDDGDTY YADSVKG                                                          17

SEQ ID NO: 546           moltype = AA  length = 17
FEATURE                  Location/Qualifiers
REGION                   1..17
                         note = Synthetic: 2188-D04; CDR-H2; Kabat
source                   1..17
                         mol_type = protein
                         organism = synthetic construct
SEQUENCE: 546
GIDPADGSTD YADSVKG                                                          17

SEQ ID NO: 547           moltype = AA  length = 17
FEATURE                  Location/Qualifiers
REGION                   1..17
                         note = Synthetic: 2188-A05; CDR-H2; Kabat
source                   1..17
                         mol_type = protein
                         organism = synthetic construct
SEQUENCE: 547
WINPDDGDTY YADSVKG                                                          17
```

```
SEQ ID NO: 548          moltype = AA   length = 17
FEATURE                 Location/Qualifiers
REGION                  1..17
                        note = Synthetic: 2188-E01; CDR-H2; Kabat
source                  1..17
                        mol_type = protein
                        organism = synthetic construct
SEQUENCE: 548
GIDPQDGATD YADSVKG                                                      17

SEQ ID NO: 549          moltype = AA   length = 17
FEATURE                 Location/Qualifiers
REGION                  1..17
                        note = Synthetic: 2188-G01; CDR-H2; Kabat
source                  1..17
                        mol_type = protein
                        organism = synthetic construct
SEQUENCE: 549
GIDPNDGATD YADSVKG                                                      17

SEQ ID NO: 550          moltype = AA   length = 17
FEATURE                 Location/Qualifiers
REGION                  1..17
                        note = Synthetic: 2188-B09; CDR-H2; Kabat
source                  1..17
                        mol_type = protein
                        organism = synthetic construct
SEQUENCE: 550
VIDPKDGWTD HADSVKG                                                      17

SEQ ID NO: 551          moltype = AA   length = 17
FEATURE                 Location/Qualifiers
REGION                  1..17
                        note = Synthetic: 2188-F07; CDR-H2; Kabat
source                  1..17
                        mol_type = protein
                        organism = synthetic construct
SEQUENCE: 551
GIDPNDGSTD HADSVKG                                                      17

SEQ ID NO: 552          moltype = AA   length = 17
FEATURE                 Location/Qualifiers
REGION                  1..17
                        note = Synthetic: 2188-D08; CDR-H2; Kabat
source                  1..17
                        mol_type = protein
                        organism = synthetic construct
SEQUENCE: 552
GIDPDDGATD EADSVKG                                                      17

SEQ ID NO: 553          moltype = AA   length = 17
FEATURE                 Location/Qualifiers
REGION                  1..17
                        note = Synthetic: 2188-D05; CDR-H2; Kabat
source                  1..17
                        mol_type = protein
                        organism = synthetic construct
SEQUENCE: 553
GIDPHDGWTD HADSVKG                                                      17

SEQ ID NO: 554          moltype = AA   length = 17
FEATURE                 Location/Qualifiers
REGION                  1..17
                        note = Synthetic: 2188-C03; CDR-H2; Kabat
source                  1..17
                        mol_type = protein
                        organism = synthetic construct
SEQUENCE: 554
WINPDDGDTY YADSVKG                                                      17

SEQ ID NO: 555          moltype = AA   length = 17
FEATURE                 Location/Qualifiers
REGION                  1..17
                        note = Synthetic: 2188-E08; CDR-H2; Kabat
source                  1..17
                        mol_type = protein
                        organism = synthetic construct
SEQUENCE: 555
```

```
                                         -continued
GIDPQDGSTD LADSVKG                                                              17

SEQ ID NO: 556          moltype = AA  length = 17
FEATURE                 Location/Qualifiers
REGION                  1..17
                        note = Synthetic: 2188-C06; CDR-H2; Kabat
source                  1..17
                        mol_type = protein
                        organism = synthetic construct
SEQUENCE: 556
WINPDDGDTY LADSVKG                                                              17

SEQ ID NO: 557          moltype = AA  length = 17
FEATURE                 Location/Qualifiers
REGION                  1..17
                        note = Synthetic: 2188-A08; CDR-H2; Kabat
source                  1..17
                        mol_type = protein
                        organism = synthetic construct
SEQUENCE: 557
WINPFDGDTY YADSVKG                                                              17

SEQ ID NO: 558          moltype = AA  length = 17
FEATURE                 Location/Qualifiers
REGION                  1..17
                        note = Synthetic: 2188-B10; CDR-H2; Kabat
source                  1..17
                        mol_type = protein
                        organism = synthetic construct
SEQUENCE: 558
WINPHDGDTY HADSVKG                                                              17

SEQ ID NO: 559          moltype = AA  length = 17
FEATURE                 Location/Qualifiers
REGION                  1..17
                        note = Synthetic: 2188-G02; CDR-H2; Kabat
source                  1..17
                        mol_type = protein
                        organism = synthetic construct
SEQUENCE: 559
GIDPNDGATD YADSVKG                                                              17

SEQ ID NO: 560          moltype = AA  length = 17
FEATURE                 Location/Qualifiers
REGION                  1..17
                        note = Synthetic: 2188-C05; CDR-H2; Kabat
source                  1..17
                        mol_type = protein
                        organism = synthetic construct
SEQUENCE: 560
GIDPRDGSTD SADSVKG                                                              17

SEQ ID NO: 561          moltype = AA  length = 17
FEATURE                 Location/Qualifiers
REGION                  1..17
                        note = Synthetic: 2188-A10; CDR-H2; Kabat
source                  1..17
                        mol_type = protein
                        organism = synthetic construct
SEQUENCE: 561
WINPEDGDTS HADSVKG                                                              17

SEQ ID NO: 562          moltype = AA  length = 17
FEATURE                 Location/Qualifiers
REGION                  1..17
                        note = Synthetic: 2188-G04; CDR-H2; Kabat
source                  1..17
                        mol_type = protein
                        organism = synthetic construct
SEQUENCE: 562
GIDPRDGSTD HADSVKG                                                              17

SEQ ID NO: 563          moltype = AA  length = 17
FEATURE                 Location/Qualifiers
REGION                  1..17
                        note = Synthetic: 2188-C08; CDR-H2; Kabat
source                  1..17
                        mol_type = protein
                        organism = synthetic construct
```

```
SEQUENCE: 563
WINPDDGDTY HADSVKG                                                    17

SEQ ID NO: 564         moltype = AA  length = 17
FEATURE                Location/Qualifiers
REGION                 1..17
                       note = Synthetic: 2188-E05; CDR-H2; Kabat
source                 1..17
                       mol_type = protein
                       organism = synthetic construct
SEQUENCE: 564
GIEPWDGSTD HADSVKG                                                    17

SEQ ID NO: 565         moltype = AA  length = 17
FEATURE                Location/Qualifiers
REGION                 1..17
                       note = Synthetic: 2188-A02; CDR-H2; Kabat
source                 1..17
                       mol_type = protein
                       organism = synthetic construct
SEQUENCE: 565
WINPEDGDTY YADSVKG                                                    17

SEQ ID NO: 566         moltype = AA  length = 17
FEATURE                Location/Qualifiers
REGION                 1..17
                       note = Synthetic: 2188-F04; CDR-H2; Kabat
source                 1..17
                       mol_type = protein
                       organism = synthetic construct
SEQUENCE: 566
GIDPDDGATD YADSVKG                                                    17

SEQ ID NO: 567         moltype = AA  length = 17
FEATURE                Location/Qualifiers
REGION                 1..17
                       note = Synthetic: 2188-F05; CDR-H2; Kabat
source                 1..17
                       mol_type = protein
                       organism = synthetic construct
SEQUENCE: 567
GIDPRDGATD SADSVKG                                                    17

SEQ ID NO: 568         moltype = AA  length = 17
FEATURE                Location/Qualifiers
REGION                 1..17
                       note = Synthetic: 2188-D07; CDR-H2; Kabat
source                 1..17
                       mol_type = protein
                       organism = synthetic construct
SEQUENCE: 568
GIDPTDGATD YADSVKG                                                    17

SEQ ID NO: 569         moltype = AA  length = 17
FEATURE                Location/Qualifiers
REGION                 1..17
                       note = Synthetic: 2188-E02; CDR-H2; Kabat
source                 1..17
                       mol_type = protein
                       organism = synthetic construct
SEQUENCE: 569
GIEPHDGSTD YADSVKG                                                    17

SEQ ID NO: 570         moltype = AA  length = 17
FEATURE                Location/Qualifiers
REGION                 1..17
                       note = Synthetic: 2188-D06; CDR-H2; Kabat
source                 1..17
                       mol_type = protein
                       organism = synthetic construct
SEQUENCE: 570
GIDPNDGATD YADSVKG                                                    17

SEQ ID NO: 571         moltype = AA  length = 17
FEATURE                Location/Qualifiers
REGION                 1..17
                       note = Synthetic: 2188-F09; CDR-H2; Kabat
source                 1..17
                       mol_type = protein
```

```
                          -continued organism = synthetic construct
SEQUENCE: 571
AIDPNDGSTD YADSVKG                                                    17

SEQ ID NO: 572            moltype = AA  length = 17
FEATURE                   Location/Qualifiers
REGION                    1..17
                          note = Synthetic: 2188-F10; CDR-H2; Kabat
source                    1..17
                          mol_type = protein
                          organism = synthetic construct
SEQUENCE: 572
GIDPNDGATD HADSVKG                                                    17

SEQ ID NO: 573            moltype = AA  length = 17
FEATURE                   Location/Qualifiers
REGION                    1..17
                          note = Synthetic: 2188-B05; CDR-H2; Kabat
source                    1..17
                          mol_type = protein
                          organism = synthetic construct
SEQUENCE: 573
VIDPDDGWTH YADSVKG                                                    17

SEQ ID NO: 574            moltype = AA  length = 17
FEATURE                   Location/Qualifiers
REGION                    1..17
                          note = Synthetic: 1943-C02; CDR-H2; Kabat
source                    1..17
                          mol_type = protein
                          organism = synthetic construct
SEQUENCE: 574
AIDPNSGSTD YADSVKG                                                    17

SEQ ID NO: 575            moltype = AA  length = 17
FEATURE                   Location/Qualifiers
REGION                    1..17
                          note = Synthetic: 2193-D04; CDR-H2; Kabat
source                    1..17
                          mol_type = protein
                          organism = synthetic construct
SEQUENCE: 575
AIDPNGGSTV YADSVKG                                                    17

SEQ ID NO: 576            moltype = AA  length = 17
FEATURE                   Location/Qualifiers
REGION                    1..17
                          note = Synthetic: 2193-E10; CDR-H2; Kabat
source                    1..17
                          mol_type = protein
                          organism = synthetic construct
SEQUENCE: 576
AIDPVNGSTN NADSVKG                                                    17

SEQ ID NO: 577            moltype = AA  length = 17
FEATURE                   Location/Qualifiers
REGION                    1..17
                          note = Synthetic: 2193-E06; CDR-H2; Kabat
source                    1..17
                          mol_type = protein
                          organism = synthetic construct
SEQUENCE: 577
VIDPKNGSTV YADSVKG                                                    17

SEQ ID NO: 578            moltype = AA  length = 17
FEATURE                   Location/Qualifiers
REGION                    1..17
                          note = Synthetic: 2193-E04; CDR-H2; Kabat
source                    1..17
                          mol_type = protein
                          organism = synthetic construct
SEQUENCE: 578
VIDPSLGSTI DADSVKG                                                    17

SEQ ID NO: 579            moltype = AA  length = 17
FEATURE                   Location/Qualifiers
REGION                    1..17
                          note = Synthetic: 2193-B09; CDR-H2; Kabat
source                    1..17
```

```
                          mol_type = protein
                          organism = synthetic construct
SEQUENCE: 579
IIDPNNGSTA YADSVKG                                                       17

SEQ ID NO: 580            moltype = AA  length = 17
FEATURE                   Location/Qualifiers
REGION                    1..17
                          note = Synthetic: 2193-D11; CDR-H2; Kabat
source                    1..17
                          mol_type = protein
                          organism = synthetic construct
SEQUENCE: 580
AIDPNTGSTV DADSVKG                                                       17

SEQ ID NO: 581            moltype = AA  length = 17
FEATURE                   Location/Qualifiers
REGION                    1..17
                          note = Synthetic: 2193-B02; CDR-H2; Kabat
source                    1..17
                          mol_type = protein
                          organism = synthetic construct
SEQUENCE: 581
TIDPTRGSTV HADSVKG                                                       17

SEQ ID NO: 582            moltype = AA  length = 17
FEATURE                   Location/Qualifiers
REGION                    1..17
                          note = Synthetic: 2193-D05; CDR-H2; Kabat
source                    1..17
                          mol_type = protein
                          organism = synthetic construct
SEQUENCE: 582
AIDPNSGSTV YADSVKG                                                       17

SEQ ID NO: 583            moltype = AA  length = 17
FEATURE                   Location/Qualifiers
REGION                    1..17
                          note = Synthetic: 2193-E11; CDR-H2; Kabat
source                    1..17
                          mol_type = protein
                          organism = synthetic construct
SEQUENCE: 583
GIEPNSGATV FADSVKG                                                       17

SEQ ID NO: 584            moltype = AA  length = 17
FEATURE                   Location/Qualifiers
REGION                    1..17
                          note = Synthetic: 2193-D06; CDR-H2; Kabat
source                    1..17
                          mol_type = protein
                          organism = synthetic construct
SEQUENCE: 584
AIDPHSGSTV YADSVKG                                                       17

SEQ ID NO: 585            moltype = AA  length = 17
FEATURE                   Location/Qualifiers
REGION                    1..17
                          note = Synthetic: 2193-C02; CDR-H2; Kabat
source                    1..17
                          mol_type = protein
                          organism = synthetic construct
SEQUENCE: 585
TIDPQSGSTV YADSVKG                                                       17

SEQ ID NO: 586            moltype = AA  length = 17
FEATURE                   Location/Qualifiers
REGION                    1..17
                          note = Synthetic: 2193-B03; CDR-H2; Kabat
source                    1..17
                          mol_type = protein
                          organism = synthetic construct
SEQUENCE: 586
AIDPVSGSTL FADSVKG                                                       17

SEQ ID NO: 587            moltype = AA  length = 17
FEATURE                   Location/Qualifiers
REGION                    1..17
                          note = Synthetic: 2193-A02; CDR-H2; Kabat
```

```
SEQ ID NO: 587                         
  source           1..17
                   mol_type = protein
                   organism = synthetic construct
SEQUENCE: 587
AIDPKSGSTY YADSVKG                                                      17

SEQ ID NO: 588   moltype = AA  length = 17
FEATURE          Location/Qualifiers
REGION           1..17
                 note = Synthetic: 2193-E05; CDR-H2; Kabat
source           1..17
                 mol_type = protein
                 organism = synthetic construct
SEQUENCE: 588
SIDPNGSSTH YADSVKG                                                      17

SEQ ID NO: 589   moltype = AA  length = 17
FEATURE          Location/Qualifiers
REGION           1..17
                 note = Synthetic: 2193-A06; CDR-H2; Kabat
source           1..17
                 mol_type = protein
                 organism = synthetic construct
SEQUENCE: 589
AIDPDSGSTH NADSVKG                                                      17

SEQ ID NO: 590   moltype = AA  length = 17
FEATURE          Location/Qualifiers
REGION           1..17
                 note = Synthetic: 2193-C04; CDR-H2; Kabat
source           1..17
                 mol_type = protein
                 organism = synthetic construct
SEQUENCE: 590
AIDPKSGSTN FADSVKG                                                      17

SEQ ID NO: 591   moltype = AA  length = 17
FEATURE          Location/Qualifiers
REGION           1..17
                 note = Synthetic: 2193-E08; CDR-H2; Kabat
source           1..17
                 mol_type = protein
                 organism = synthetic construct
SEQUENCE: 591
AIDPHSGSTN FADSVKG                                                      17

SEQ ID NO: 592   moltype = AA  length = 17
FEATURE          Location/Qualifiers
REGION           1..17
                 note = Synthetic: 2193-B10; CDR-H2; Kabat
source           1..17
                 mol_type = protein
                 organism = synthetic construct
SEQUENCE: 592
AIDPNSGYTV KADSVKG                                                      17

SEQ ID NO: 593   moltype = AA  length = 17
FEATURE          Location/Qualifiers
REGION           1..17
                 note = Synthetic: 2193-D08; CDR-H2; Kabat
source           1..17
                 mol_type = protein
                 organism = synthetic construct
SEQUENCE: 593
AIDPSGGSTN HADSVKG                                                      17

SEQ ID NO: 594   moltype = AA  length = 17
FEATURE          Location/Qualifiers
REGION           1..17
                 note = Synthetic: 2193-B08; CDR-H2; Kabat
source           1..17
                 mol_type = protein
                 organism = synthetic construct
SEQUENCE: 594
AIDPSPGATL DADSVKG                                                      17

SEQ ID NO: 595   moltype = AA  length = 17
FEATURE          Location/Qualifiers
REGION           1..17
```

```
                        note = Synthetic: 2193-C05; CDR-H2; Kabat
source                  1..17
                        mol_type = protein
                        organism = synthetic construct
SEQUENCE: 595
AIDPHNGSTA SADSVKG                                                    17

SEQ ID NO: 596          moltype = AA  length = 17
FEATURE                 Location/Qualifiers
REGION                  1..17
                        note = Synthetic: 2193-D10; CDR-H2; Kabat
source                  1..17
                        mol_type = protein
                        organism = synthetic construct
SEQUENCE: 596
TIDPNSGFTV HADSVKG                                                    17

SEQ ID NO: 597          moltype = AA  length = 17
FEATURE                 Location/Qualifiers
REGION                  1..17
                        note = Synthetic: 2193-D03; CDR-H2; Kabat
source                  1..17
                        mol_type = protein
                        organism = synthetic construct
SEQUENCE: 597
AIDPNTGSTV NADSVKG                                                    17

SEQ ID NO: 598          moltype = AA  length = 17
FEATURE                 Location/Qualifiers
REGION                  1..17
                        note = Synthetic: 2193-A09; CDR-H2; Kabat
source                  1..17
                        mol_type = protein
                        organism = synthetic construct
SEQUENCE: 598
VIDPKGGSTV YADSVKG                                                    17

SEQ ID NO: 599          moltype = AA  length = 17
FEATURE                 Location/Qualifiers
REGION                  1..17
                        note = Synthetic: 2193-A10; CDR-H2; Kabat
source                  1..17
                        mol_type = protein
                        organism = synthetic construct
SEQUENCE: 599
AIDPKSGYTV YADSVKG                                                    17

SEQ ID NO: 600          moltype = AA  length = 17
FEATURE                 Location/Qualifiers
REGION                  1..17
                        note = Synthetic: 2193-E07; CDR-H2; Kabat
source                  1..17
                        mol_type = protein
                        organism = synthetic construct
SEQUENCE: 600
SIDPTIGSTH FADSVKG                                                    17

SEQ ID NO: 601          moltype = AA  length = 17
FEATURE                 Location/Qualifiers
REGION                  1..17
                        note = Synthetic: 2193-A07; CDR-H2; Kabat
source                  1..17
                        mol_type = protein
                        organism = synthetic construct
SEQUENCE: 601
AIDPNTGTTN YADSVKG                                                    17

SEQ ID NO: 602          moltype = AA  length = 17
FEATURE                 Location/Qualifiers
REGION                  1..17
                        note = Synthetic: 2193-E03; CDR-H2; Kabat
source                  1..17
                        mol_type = protein
                        organism = synthetic construct
SEQUENCE: 602
AIDPKGGSTR FADSVKG                                                    17

SEQ ID NO: 603          moltype = AA  length = 17
FEATURE                 Location/Qualifiers
```

```
REGION                  1..17
                        note = Synthetic: 2193-C08; CDR-H2; Kabat
source                  1..17
                        mol_type = protein
                        organism = synthetic construct
SEQUENCE: 603
AIDPYPGSTY NADSVKG                                                          17

SEQ ID NO: 604          moltype = AA  length = 17
FEATURE                 Location/Qualifiers
REGION                  1..17
                        note = Synthetic: 2193-B11; CDR-H2; Kabat
source                  1..17
                        mol_type = protein
                        organism = synthetic construct
SEQUENCE: 604
AIDPKSGFTS YADSVKG                                                          17

SEQ ID NO: 605          moltype = AA  length = 17
FEATURE                 Location/Qualifiers
REGION                  1..17
                        note = Synthetic: 2193-A03; CDR-H2; Kabat
source                  1..17
                        mol_type = protein
                        organism = synthetic construct
SEQUENCE: 605
AIDPKSGSTV HADSVKG                                                          17

SEQ ID NO: 606          moltype = AA  length = 17
FEATURE                 Location/Qualifiers
REGION                  1..17
                        note = Synthetic: 2193-D02; CDR-H2; Kabat
source                  1..17
                        mol_type = protein
                        organism = synthetic construct
SEQUENCE: 606
AIDPESGSTV YADSVKG                                                          17

SEQ ID NO: 607          moltype = AA  length = 17
FEATURE                 Location/Qualifiers
REGION                  1..17
                        note = Synthetic: 2193-B06; CDR-H2; Kabat
source                  1..17
                        mol_type = protein
                        organism = synthetic construct
SEQUENCE: 607
AIDPHPGSTV YADSVKG                                                          17

SEQ ID NO: 608          moltype = AA  length = 17
FEATURE                 Location/Qualifiers
REGION                  1..17
                        note = Synthetic: 2193-B01; CDR-H2; Kabat
source                  1..17
                        mol_type = protein
                        organism = synthetic construct
SEQUENCE: 608
AIDPRSGYTV YADSVKG                                                          17

SEQ ID NO: 609          moltype = AA  length = 17
FEATURE                 Location/Qualifiers
REGION                  1..17
                        note = Synthetic: 2193-D09; CDR-H2; Kabat
source                  1..17
                        mol_type = protein
                        organism = synthetic construct
SEQUENCE: 609
AIDPNSGSTN FADSVKG                                                          17

SEQ ID NO: 610          moltype = AA  length = 17
FEATURE                 Location/Qualifiers
REGION                  1..17
                        note = Synthetic: 2193-E09; CDR-H2; Kabat
source                  1..17
                        mol_type = protein
                        organism = synthetic construct
SEQUENCE: 610
AIDPGSGYTV PADSVKG                                                          17

SEQ ID NO: 611          moltype = AA  length = 17
```

```
FEATURE                 Location/Qualifiers
REGION                  1..17
                        note = Synthetic: 2193-B07; CDR-H2; Kabat
source                  1..17
                        mol_type = protein
                        organism = synthetic construct
SEQUENCE: 611
AIDPNSGSTL SADSVKG                                                               17

SEQ ID NO: 612          moltype = AA  length = 17
FEATURE                 Location/Qualifiers
REGION                  1..17
                        note = Synthetic: 2193-C06; CDR-H2; Kabat
source                  1..17
                        mol_type = protein
                        organism = synthetic construct
SEQUENCE: 612
AIDPISGSTQ WADSVKG                                                               17

SEQ ID NO: 613          moltype = AA  length = 17
FEATURE                 Location/Qualifiers
REGION                  1..17
                        note = Synthetic: 2193-B05; CDR-H2; Kabat
source                  1..17
                        mol_type = protein
                        organism = synthetic construct
SEQUENCE: 613
AIDPIGGSTH LADSVKG                                                               17

SEQ ID NO: 614          moltype = AA  length = 17
FEATURE                 Location/Qualifiers
REGION                  1..17
                        note = Synthetic: 2193-A11; CDR-H2; Kabat
source                  1..17
                        mol_type = protein
                        organism = synthetic construct
SEQUENCE: 614
AIDPKSGSTV YADSVKG                                                               17

SEQ ID NO: 615          moltype = AA  length = 17
FEATURE                 Location/Qualifiers
REGION                  1..17
                        note = Synthetic: 2193-E02; CDR-H2; Kabat
source                  1..17
                        mol_type = protein
                        organism = synthetic construct
SEQUENCE: 615
SIDPTSGSTV IADSVKG                                                               17

SEQ ID NO: 616          moltype = AA  length = 17
FEATURE                 Location/Qualifiers
REGION                  1..17
                        note = Synthetic: 2193-A08; CDR-H2; Kabat
source                  1..17
                        mol_type = protein
                        organism = synthetic construct
SEQUENCE: 616
AIDPNAGSTV YADSVKG                                                               17

SEQ ID NO: 617          moltype = AA  length = 17
FEATURE                 Location/Qualifiers
REGION                  1..17
                        note = Synthetic: 2193-C11; CDR-H2; Kabat
source                  1..17
                        mol_type = protein
                        organism = synthetic construct
SEQUENCE: 617
VIDPKSGSTN YADSVKG                                                               17

SEQ ID NO: 618          moltype = AA  length = 17
FEATURE                 Location/Qualifiers
REGION                  1..17
                        note = Synthetic: 2193-A01; CDR-H2; Kabat
source                  1..17
                        mol_type = protein
                        organism = synthetic construct
SEQUENCE: 618
AIDPTSGSTV FADSVKG                                                               17
```

```
SEQ ID NO: 619          moltype = AA  length = 17
FEATURE                 Location/Qualifiers
REGION                  1..17
                        note = Synthetic: 2193-D07; CDR-H2; Kabat
source                  1..17
                        mol_type = protein
                        organism = synthetic construct
SEQUENCE: 619
AIGPADGSTV NADSVKG                                                        17

SEQ ID NO: 620          moltype = AA  length = 17
FEATURE                 Location/Qualifiers
REGION                  1..17
                        note = Synthetic: 2193-A05; CDR-H2; Kabat
source                  1..17
                        mol_type = protein
                        organism = synthetic construct
SEQUENCE: 620
VIDPNSGSTI FADSVKG                                                        17

SEQ ID NO: 621          moltype = AA  length = 17
FEATURE                 Location/Qualifiers
REGION                  1..17
                        note = Synthetic: 2193-C03; CDR-H2; Kabat
source                  1..17
                        mol_type = protein
                        organism = synthetic construct
SEQUENCE: 621
AIEPKSGSTA SADSVKG                                                        17

SEQ ID NO: 622          moltype = AA  length = 17
FEATURE                 Location/Qualifiers
REGION                  1..17
                        note = Synthetic: 2193-C09; CDR-H2; Kabat
source                  1..17
                        mol_type = protein
                        organism = synthetic construct
SEQUENCE: 622
AIDPISGSTV YADSVKG                                                        17

SEQ ID NO: 623          moltype = AA  length = 17
FEATURE                 Location/Qualifiers
REGION                  1..17
                        note = Synthetic: 2193-D01; CDR-H2; Kabat
source                  1..17
                        mol_type = protein
                        organism = synthetic construct
SEQUENCE: 623
AIDPTSGPTV YADSVKG                                                        17

SEQ ID NO: 624          moltype = AA  length = 17
FEATURE                 Location/Qualifiers
REGION                  1..17
                        note = Synthetic: 2193-E01; CDR-H2; Kabat
source                  1..17
                        mol_type = protein
                        organism = synthetic construct
SEQUENCE: 624
AIDPKSGSTA HADSVKG                                                        17

SEQ ID NO: 625          moltype = AA  length = 17
FEATURE                 Location/Qualifiers
REGION                  1..17
                        note = Synthetic: 2193-C07; CDR-H2; Kabat
source                  1..17
                        mol_type = protein
                        organism = synthetic construct
SEQUENCE: 625
AIDPTRGATV YADSVKG                                                        17

SEQ ID NO: 626          moltype = AA  length = 17
FEATURE                 Location/Qualifiers
REGION                  1..17
                        note = Synthetic: 2193-B04; CDR-H2; Kabat
source                  1..17
                        mol_type = protein
                        organism = synthetic construct
SEQUENCE: 626
AIEPKNGSTH HADSVKG                                                        17
```

```
SEQ ID NO: 627          moltype = AA   length = 17
FEATURE                 Location/Qualifiers
REGION                  1..17
                        note = Synthetic: 2193-C10; CDR-H2; Kabat
source                  1..17
                        mol_type = protein
                        organism = synthetic construct
SEQUENCE: 627
AIDPRSGSTI SADSVKG                                                        17

SEQ ID NO: 628          moltype = AA   length = 17
FEATURE                 Location/Qualifiers
REGION                  1..17
                        note = Synthetic: 2193-C01; CDR-H2; Kabat
source                  1..17
                        mol_type = protein
                        organism = synthetic construct
SEQUENCE: 628
TIDPKSGSTH VADSVKG                                                        17

SEQ ID NO: 629          moltype = AA   length = 17
FEATURE                 Location/Qualifiers
REGION                  1..17
                        note = Synthetic: 2193-A04; CDR-H2; Kabat
source                  1..17
                        mol_type = protein
                        organism = synthetic construct
SEQUENCE: 629
AIDPNSGSTL LADSVKG                                                        17

SEQ ID NO: 630          moltype = AA   length = 17
FEATURE                 Location/Qualifiers
REGION                  1..17
                        note = Synthetic: 1944-A07; CDR-H2; Kabat
source                  1..17
                        mol_type = protein
                        organism = synthetic construct
SEQUENCE: 630
YISPNSGSTY YADSVKG                                                        17

SEQ ID NO: 631          moltype = AA   length = 17
FEATURE                 Location/Qualifiers
REGION                  1..17
                        note = Synthetic: 2194-A02; CDR-H2; Kabat
source                  1..17
                        mol_type = protein
                        organism = synthetic construct
SEQUENCE: 631
YISPLAGNTY HADSVKG                                                        17

SEQ ID NO: 632          moltype = AA   length = 17
FEATURE                 Location/Qualifiers
REGION                  1..17
                        note = Synthetic: 2194-A05; CDR-H2; Kabat
source                  1..17
                        mol_type = protein
                        organism = synthetic construct
SEQUENCE: 632
YISPNSGSTY YADSVKG                                                        17

SEQ ID NO: 633          moltype = AA   length = 17
FEATURE                 Location/Qualifiers
REGION                  1..17
                        note = Synthetic: 2194-B04; CDR-H2; Kabat
source                  1..17
                        mol_type = protein
                        organism = synthetic construct
SEQUENCE: 633
YISPLAGNTY HADSVKG                                                        17

SEQ ID NO: 634          moltype = AA   length = 17
FEATURE                 Location/Qualifiers
REGION                  1..17
                        note = Synthetic: 2194-A09; CDR-H2; Kabat
source                  1..17
                        mol_type = protein
                        organism = synthetic construct
SEQUENCE: 634
```

-continued

```
YITPLSGATY RADSVKG                                                   17

SEQ ID NO: 635        moltype = AA   length = 17
FEATURE               Location/Qualifiers
REGION                1..17
                      note = Synthetic: 2194-A01; CDR-H2; Kabat
source                1..17
                      mol_type = protein
                      organism = synthetic construct
SEQUENCE: 635
YISPLAGNTY HADSVKG                                                   17

SEQ ID NO: 636        moltype = AA   length = 17
FEATURE               Location/Qualifiers
REGION                1..17
                      note = Synthetic: 2194-B03; CDR-H2; Kabat
source                1..17
                      mol_type = protein
                      organism = synthetic construct
SEQUENCE: 636
YISPLAGNTY HADSVKG                                                   17

SEQ ID NO: 637        moltype = AA   length = 17
FEATURE               Location/Qualifiers
REGION                1..17
                      note = Synthetic: 2194-B02; CDR-H2; Kabat
source                1..17
                      mol_type = protein
                      organism = synthetic construct
SEQUENCE: 637
YISPLAGNTY HADSVKG                                                   17

SEQ ID NO: 638        moltype = AA   length = 17
FEATURE               Location/Qualifiers
REGION                1..17
                      note = Synthetic: 2194-A03; CDR-H2; Kabat
source                1..17
                      mol_type = protein
                      organism = synthetic construct
SEQUENCE: 638
YITPNSGTTY SADSVKG                                                   17

SEQ ID NO: 639        moltype = AA   length = 17
FEATURE               Location/Qualifiers
REGION                1..17
                      note = Synthetic: 2194-A11; CDR-H2; Kabat
source                1..17
                      mol_type = protein
                      organism = synthetic construct
SEQUENCE: 639
YISPNSGYTT DADSVKG                                                   17

SEQ ID NO: 640        moltype = AA   length = 17
FEATURE               Location/Qualifiers
REGION                1..17
                      note = Synthetic: 2194-A08; CDR-H2; Kabat
source                1..17
                      mol_type = protein
                      organism = synthetic construct
SEQUENCE: 640
YIAPSSGYTY DADSVKG                                                   17

SEQ ID NO: 641        moltype = AA   length = 17
FEATURE               Location/Qualifiers
REGION                1..17
                      note = Synthetic: 2194-A04; CDR-H2; Kabat
source                1..17
                      mol_type = protein
                      organism = synthetic construct
SEQUENCE: 641
YISPLAGNTH HADSVKG                                                   17

SEQ ID NO: 642        moltype = AA   length = 17
FEATURE               Location/Qualifiers
REGION                1..17
                      note = Synthetic: 2194-A10; CDR-H2; Kabat
source                1..17
                      mol_type = protein
                      organism = synthetic construct
```

```
SEQUENCE: 642
YISPNSGSTH IADSVKG                                                    17

SEQ ID NO: 643         moltype = AA  length = 17
FEATURE                Location/Qualifiers
REGION                 1..17
                       note = Synthetic: 2194-A07; CDR-H2; Kabat
source                 1..17
                       mol_type = protein
                       organism = synthetic construct
SEQUENCE: 643
YISPLAGNTY HADSVKG                                                    17

SEQ ID NO: 644         moltype = AA  length = 17
FEATURE                Location/Qualifiers
REGION                 1..17
                       note = Synthetic: 2194-B01; CDR-H2; Kabat
source                 1..17
                       mol_type = protein
                       organism = synthetic construct
SEQUENCE: 644
YISPLAGNTY HADSVKG                                                    17

SEQ ID NO: 645         moltype = AA  length = 17
FEATURE                Location/Qualifiers
REGION                 1..17
                       note = Synthetic: 2194-A06; CDR-H2; Kabat
source                 1..17
                       mol_type = protein
                       organism = synthetic construct
SEQUENCE: 645
YISPLAGNTY HADSVKG                                                    17

SEQ ID NO: 646         moltype = AA  length = 17
FEATURE                Location/Qualifiers
REGION                 1..17
                       note = Synthetic: 2196-C01; CDR-H2; Kabat
source                 1..17
                       mol_type = protein
                       organism = synthetic construct
SEQUENCE: 646
SITPLSGATS KADSVKG                                                    17

SEQ ID NO: 647         moltype = AA  length = 17
FEATURE                Location/Qualifiers
REGION                 1..17
                       note = Synthetic: 2196-A02; CDR-H2; Kabat
source                 1..17
                       mol_type = protein
                       organism = synthetic construct
SEQUENCE: 647
QISPNSGATH DADSVKG                                                    17

SEQ ID NO: 648         moltype = AA  length = 17
FEATURE                Location/Qualifiers
REGION                 1..17
                       note = Synthetic: 2196-B03; CDR-H2; Kabat
source                 1..17
                       mol_type = protein
                       organism = synthetic construct
SEQUENCE: 648
YISPNSGATH YADSVKG                                                    17

SEQ ID NO: 649         moltype = AA  length = 17
FEATURE                Location/Qualifiers
REGION                 1..17
                       note = Synthetic: 2196-A05; CDR-H2; Kabat
source                 1..17
                       mol_type = protein
                       organism = synthetic construct
SEQUENCE: 649
YISPNSGATY QADSVKG                                                    17

SEQ ID NO: 650         moltype = AA  length = 17
FEATURE                Location/Qualifiers
REGION                 1..17
                       note = Synthetic: 2196-C02; CDR-H2; Kabat
source                 1..17
                       mol_type = protein
```

```
                        -continued
                        organism = synthetic construct
SEQUENCE: 650
FISPNSGWTY SADSVKG                                                  17

SEQ ID NO: 651          moltype = AA  length = 17
FEATURE                 Location/Qualifiers
REGION                  1..17
                        note = Synthetic: 2196-B11; CDR-H2; Kabat
source                  1..17
                        mol_type = protein
                        organism = synthetic construct
SEQUENCE: 651
QISPNSGYTY YADSVKG                                                  17

SEQ ID NO: 652          moltype = AA  length = 17
FEATURE                 Location/Qualifiers
REGION                  1..17
                        note = Synthetic: 2196-B08; CDR-H2; Kabat
source                  1..17
                        mol_type = protein
                        organism = synthetic construct
SEQUENCE: 652
QISPNSGYTY LADSVKG                                                  17

SEQ ID NO: 653          moltype = AA  length = 17
FEATURE                 Location/Qualifiers
REGION                  1..17
                        note = Synthetic: 2196-A04; CDR-H2; Kabat
source                  1..17
                        mol_type = protein
                        organism = synthetic construct
SEQUENCE: 653
QIYPISGHTY QADSVKG                                                  17

SEQ ID NO: 654          moltype = AA  length = 17
FEATURE                 Location/Qualifiers
REGION                  1..17
                        note = Synthetic: 2196-A03; CDR-H2; Kabat
source                  1..17
                        mol_type = protein
                        organism = synthetic construct
SEQUENCE: 654
YISPNSGSTH EADSVKG                                                  17

SEQ ID NO: 655          moltype = AA  length = 17
FEATURE                 Location/Qualifiers
REGION                  1..17
                        note = Synthetic: 2196-B07; CDR-H2; Kabat
source                  1..17
                        mol_type = protein
                        organism = synthetic construct
SEQUENCE: 655
YISPNSGATY YADSVKG                                                  17

SEQ ID NO: 656          moltype = AA  length = 17
FEATURE                 Location/Qualifiers
REGION                  1..17
                        note = Synthetic: 2196-A06; CDR-H2; Kabat
source                  1..17
                        mol_type = protein
                        organism = synthetic construct
SEQUENCE: 656
QISPNSGSTH QADSVKG                                                  17

SEQ ID NO: 657          moltype = AA  length = 17
FEATURE                 Location/Qualifiers
REGION                  1..17
                        note = Synthetic: 2196-B05; CDR-H2; Kabat
source                  1..17
                        mol_type = protein
                        organism = synthetic construct
SEQUENCE: 657
QISPNSGATY HADSVKG                                                  17

SEQ ID NO: 658          moltype = AA  length = 17
FEATURE                 Location/Qualifiers
REGION                  1..17
                        note = Synthetic: 2196-A01; CDR-H2; Kabat
source                  1..17
```

```
                        mol_type = protein
                        organism = synthetic construct
SEQUENCE: 658
QISPNSGYTY YADSVKG                                                        17

SEQ ID NO: 659          moltype = AA  length = 17
FEATURE                 Location/Qualifiers
REGION                  1..17
                        note = Synthetic: 2196-B01; CDR-H2; Kabat
source                  1..17
                        mol_type = protein
                        organism = synthetic construct
SEQUENCE: 659
QISPNSGYTY YADSVKG                                                        17

SEQ ID NO: 660          moltype = AA  length = 17
FEATURE                 Location/Qualifiers
REGION                  1..17
                        note = Synthetic: 2196-A09; CDR-H2; Kabat
source                  1..17
                        mol_type = protein
                        organism = synthetic construct
SEQUENCE: 660
QISPNSGATH YADSVKG                                                        17

SEQ ID NO: 661          moltype = AA  length = 17
FEATURE                 Location/Qualifiers
REGION                  1..17
                        note = Synthetic: 2196-A08; CDR-H2; Kabat
source                  1..17
                        mol_type = protein
                        organism = synthetic construct
SEQUENCE: 661
YISPNSGSTY KADSVKG                                                        17

SEQ ID NO: 662          moltype = AA  length = 17
FEATURE                 Location/Qualifiers
REGION                  1..17
                        note = Synthetic: 2196-A10; CDR-H2; Kabat
source                  1..17
                        mol_type = protein
                        organism = synthetic construct
SEQUENCE: 662
YISPNSGATH YADSVKG                                                        17

SEQ ID NO: 663          moltype = AA  length = 17
FEATURE                 Location/Qualifiers
REGION                  1..17
                        note = Synthetic: 2196-B06; CDR-H2; Kabat
source                  1..17
                        mol_type = protein
                        organism = synthetic construct
SEQUENCE: 663
QISPNSGSTY SADSVKG                                                        17

SEQ ID NO: 664          moltype = AA  length = 17
FEATURE                 Location/Qualifiers
REGION                  1..17
                        note = Synthetic: 2196-B09; CDR-H2; Kabat
source                  1..17
                        mol_type = protein
                        organism = synthetic construct
SEQUENCE: 664
YISPNSGSTY YADSVKG                                                        17

SEQ ID NO: 665          moltype = AA  length = 17
FEATURE                 Location/Qualifiers
REGION                  1..17
                        note = Synthetic: 2196-C03; CDR-H2; Kabat
source                  1..17
                        mol_type = protein
                        organism = synthetic construct
SEQUENCE: 665
QISPNSGSTY SADSVKG                                                        17

SEQ ID NO: 666          moltype = AA  length = 17
FEATURE                 Location/Qualifiers
REGION                  1..17
                        note = Synthetic: 2196-C04; CDR-H2; Kabat
```

```
source                  1..17
                        mol_type = protein
                        organism = synthetic construct
SEQUENCE: 666
FIAPLSGSTH NADSVKG                                                     17

SEQ ID NO: 667          moltype = AA   length = 17
FEATURE                 Location/Qualifiers
REGION                  1..17
                        note = Synthetic: 2196-A07; CDR-H2; Kabat
source                  1..17
                        mol_type = protein
                        organism = synthetic construct
SEQUENCE: 667
QISPNSGSTY YADSVKG                                                     17

SEQ ID NO: 668          moltype = AA   length = 17
FEATURE                 Location/Qualifiers
REGION                  1..17
                        note = Synthetic: 2196-A11; CDR-H2; Kabat
source                  1..17
                        mol_type = protein
                        organism = synthetic construct
SEQUENCE: 668
QISPNSGTTY DADSVKG                                                     17

SEQ ID NO: 669          moltype = AA   length = 17
FEATURE                 Location/Qualifiers
REGION                  1..17
                        note = Synthetic: 2196-B02; CDR-H2; Kabat
source                  1..17
                        mol_type = protein
                        organism = synthetic construct
SEQUENCE: 669
YISPNSGQTY DADSVKG                                                     17

SEQ ID NO: 670          moltype = AA   length = 17
FEATURE                 Location/Qualifiers
REGION                  1..17
                        note = Synthetic: 2196-B04; CDR-H2; Kabat
source                  1..17
                        mol_type = protein
                        organism = synthetic construct
SEQUENCE: 670
YISPNSGATY QADSVKG                                                     17

SEQ ID NO: 671          moltype = AA   length = 17
FEATURE                 Location/Qualifiers
REGION                  1..17
                        note = Synthetic: 2196-B10; CDR-H2; Kabat
source                  1..17
                        mol_type = protein
                        organism = synthetic construct
SEQUENCE: 671
SITPLSGATS KADSVKG                                                     17

SEQ ID NO: 672          moltype = AA   length = 7
FEATURE                 Location/Qualifiers
REGION                  1..7
                        note = Synthetic: 1987-C05; CDR-H3
source                  1..7
                        mol_type = protein
                        organism = synthetic construct
SEQUENCE: 672
DYGVFDY                                                                 7

SEQ ID NO: 673          moltype = AA   length = 7
FEATURE                 Location/Qualifiers
REGION                  1..7
                        note = Synthetic: 2188-D11; CDR-H3
source                  1..7
                        mol_type = protein
                        organism = synthetic construct
SEQUENCE: 673
DYGVFDY                                                                 7

SEQ ID NO: 674          moltype = AA   length = 7
FEATURE                 Location/Qualifiers
REGION                  1..7
```

```
                            note = Synthetic: 2188-B04; CDR-H3
source                      1..7
                            mol_type = protein
                            organism = synthetic construct
SEQUENCE: 674
DYGVFDY                                                                           7

SEQ ID NO: 675              moltype = AA  length = 7
FEATURE                     Location/Qualifiers
REGION                      1..7
                            note = Synthetic: 2188-C09; CDR-H3
source                      1..7
                            mol_type = protein
                            organism = synthetic construct
SEQUENCE: 675
DYGVFDY                                                                           7

SEQ ID NO: 676              moltype = AA  length = 7
FEATURE                     Location/Qualifiers
REGION                      1..7
                            note = Synthetic: 2188-G03; CDR-H3
source                      1..7
                            mol_type = protein
                            organism = synthetic construct
SEQUENCE: 676
DFGVFDY                                                                           7

SEQ ID NO: 677              moltype = AA  length = 7
FEATURE                     Location/Qualifiers
REGION                      1..7
                            note = Synthetic: 2188-E03; CDR-H3
source                      1..7
                            mol_type = protein
                            organism = synthetic construct
SEQUENCE: 677
DYGVYDY                                                                           7

SEQ ID NO: 678              moltype = AA  length = 7
FEATURE                     Location/Qualifiers
REGION                      1..7
                            note = Synthetic: 2188-B11; CDR-H3
source                      1..7
                            mol_type = protein
                            organism = synthetic construct
SEQUENCE: 678
DYGVFDY                                                                           7

SEQ ID NO: 679              moltype = AA  length = 7
FEATURE                     Location/Qualifiers
REGION                      1..7
                            note = Synthetic: 2188-E07; CDR-H3
source                      1..7
                            mol_type = protein
                            organism = synthetic construct
SEQUENCE: 679
DYGVYDY                                                                           7

SEQ ID NO: 680              moltype = AA  length = 7
FEATURE                     Location/Qualifiers
REGION                      1..7
                            note = Synthetic: 2188-B02; CDR-H3
source                      1..7
                            mol_type = protein
                            organism = synthetic construct
SEQUENCE: 680
DYGVFDY                                                                           7

SEQ ID NO: 681              moltype = AA  length = 7
FEATURE                     Location/Qualifiers
REGION                      1..7
                            note = Synthetic: 2188-C07; CDR-H3
source                      1..7
                            mol_type = protein
                            organism = synthetic construct
SEQUENCE: 681
DYGVFDY                                                                           7

SEQ ID NO: 682              moltype = AA  length = 7
FEATURE                     Location/Qualifiers
```

```
REGION                  1..7
                        note = Synthetic: 2188-A03; CDR-H3
source                  1..7
                        mol_type = protein
                        organism = synthetic construct
SEQUENCE: 682
DYGVFDY                                                                         7

SEQ ID NO: 683          moltype = AA  length = 7
FEATURE                 Location/Qualifiers
REGION                  1..7
                        note = Synthetic: 2188-F03; CDR-H3
source                  1..7
                        mol_type = protein
                        organism = synthetic construct
SEQUENCE: 683
DYGVFDY                                                                         7

SEQ ID NO: 684          moltype = AA  length = 7
FEATURE                 Location/Qualifiers
REGION                  1..7
                        note = Synthetic: 2188-D03; CDR-H3
source                  1..7
                        mol_type = protein
                        organism = synthetic construct
SEQUENCE: 684
DYGVYDY                                                                         7

SEQ ID NO: 685          moltype = AA  length = 7
FEATURE                 Location/Qualifiers
REGION                  1..7
                        note = Synthetic: 2188-C04; CDR-H3
source                  1..7
                        mol_type = protein
                        organism = synthetic construct
SEQUENCE: 685
DYGVYDY                                                                         7

SEQ ID NO: 686          moltype = AA  length = 7
FEATURE                 Location/Qualifiers
REGION                  1..7
                        note = Synthetic: 2188-D10; CDR-H3
source                  1..7
                        mol_type = protein
                        organism = synthetic construct
SEQUENCE: 686
DYGVFDY                                                                         7

SEQ ID NO: 687          moltype = AA  length = 7
FEATURE                 Location/Qualifiers
REGION                  1..7
                        note = Synthetic: 2188-A06; CDR-H3
source                  1..7
                        mol_type = protein
                        organism = synthetic construct
SEQUENCE: 687
DYGVFDY                                                                         7

SEQ ID NO: 688          moltype = AA  length = 7
FEATURE                 Location/Qualifiers
REGION                  1..7
                        note = Synthetic: 2188-C11; CDR-H3
source                  1..7
                        mol_type = protein
                        organism = synthetic construct
SEQUENCE: 688
DYGVFDY                                                                         7

SEQ ID NO: 689          moltype = AA  length = 7
FEATURE                 Location/Qualifiers
REGION                  1..7
                        note = Synthetic: 2188-F01; CDR-H3
source                  1..7
                        mol_type = protein
                        organism = synthetic construct
SEQUENCE: 689
DYGVFDY                                                                         7

SEQ ID NO: 690          moltype = AA  length = 7
```

```
FEATURE                Location/Qualifiers
REGION                 1..7
                       note = Synthetic: 2188-E11; CDR-H3
source                 1..7
                       mol_type = protein
                       organism = synthetic construct
SEQUENCE: 690
DYGVFDY                                                                       7

SEQ ID NO: 691         moltype = AA  length = 7
FEATURE                Location/Qualifiers
REGION                 1..7
                       note = Synthetic: 2188-A07; CDR-H3
source                 1..7
                       mol_type = protein
                       organism = synthetic construct
SEQUENCE: 691
DYGVFDY                                                                       7

SEQ ID NO: 692         moltype = AA  length = 7
FEATURE                Location/Qualifiers
REGION                 1..7
                       note = Synthetic: 2188-C01; CDR-H3
source                 1..7
                       mol_type = protein
                       organism = synthetic construct
SEQUENCE: 692
DYGVFDY                                                                       7

SEQ ID NO: 693         moltype = AA  length = 7
FEATURE                Location/Qualifiers
REGION                 1..7
                       note = Synthetic: 2188-F08; CDR-H3
source                 1..7
                       mol_type = protein
                       organism = synthetic construct
SEQUENCE: 693
DYGVFDY                                                                       7

SEQ ID NO: 694         moltype = AA  length = 7
FEATURE                Location/Qualifiers
REGION                 1..7
                       note = Synthetic: 2188-E04; CDR-H3
source                 1..7
                       mol_type = protein
                       organism = synthetic construct
SEQUENCE: 694
DFGVFDY                                                                       7

SEQ ID NO: 695         moltype = AA  length = 7
FEATURE                Location/Qualifiers
REGION                 1..7
                       note = Synthetic: 2188-B01; CDR-H3
source                 1..7
                       mol_type = protein
                       organism = synthetic construct
SEQUENCE: 695
DYGVLDY                                                                       7

SEQ ID NO: 696         moltype = AA  length = 7
FEATURE                Location/Qualifiers
REGION                 1..7
                       note = Synthetic: 2188-F11; CDR-H3
source                 1..7
                       mol_type = protein
                       organism = synthetic construct
SEQUENCE: 696
DYGVFDY                                                                       7

SEQ ID NO: 697         moltype = AA  length = 7
FEATURE                Location/Qualifiers
REGION                 1..7
                       note = Synthetic: 2188-B08; CDR-H3
source                 1..7
                       mol_type = protein
                       organism = synthetic construct
SEQUENCE: 697
DYGVFDY                                                                       7
```

```
SEQ ID NO: 698         moltype = AA  length = 7
FEATURE                Location/Qualifiers
REGION                 1..7
                       note = Synthetic: 2188-C10; CDR-H3
source                 1..7
                       mol_type = protein
                       organism = synthetic construct
SEQUENCE: 698
DYGVFDY                                                                       7

SEQ ID NO: 699         moltype = AA  length = 7
FEATURE                Location/Qualifiers
REGION                 1..7
                       note = Synthetic: 2188-C02; CDR-H3
source                 1..7
                       mol_type = protein
                       organism = synthetic construct
SEQUENCE: 699
DYGVFDY                                                                       7

SEQ ID NO: 700         moltype = AA  length = 7
FEATURE                Location/Qualifiers
REGION                 1..7
                       note = Synthetic: 2188-B07; CDR-H3
source                 1..7
                       mol_type = protein
                       organism = synthetic construct
SEQUENCE: 700
DYGVFDY                                                                       7

SEQ ID NO: 701         moltype = AA  length = 7
FEATURE                Location/Qualifiers
REGION                 1..7
                       note = Synthetic: 2188-A11; CDR-H3
source                 1..7
                       mol_type = protein
                       organism = synthetic construct
SEQUENCE: 701
DYGVFDY                                                                       7

SEQ ID NO: 702         moltype = AA  length = 7
FEATURE                Location/Qualifiers
REGION                 1..7
                       note = Synthetic: 2188-D01; CDR-H3
source                 1..7
                       mol_type = protein
                       organism = synthetic construct
SEQUENCE: 702
DYGVFDY                                                                       7

SEQ ID NO: 703         moltype = AA  length = 7
FEATURE                Location/Qualifiers
REGION                 1..7
                       note = Synthetic: 2188-E09; CDR-H3
source                 1..7
                       mol_type = protein
                       organism = synthetic construct
SEQUENCE: 703
DYGVFDY                                                                       7

SEQ ID NO: 704         moltype = AA  length = 7
FEATURE                Location/Qualifiers
REGION                 1..7
                       note = Synthetic: 2188-E06; CDR-H3
source                 1..7
                       mol_type = protein
                       organism = synthetic construct
SEQUENCE: 704
DYGVFDY                                                                       7

SEQ ID NO: 705         moltype = AA  length = 7
FEATURE                Location/Qualifiers
REGION                 1..7
                       note = Synthetic: 2188-B03; CDR-H3
source                 1..7
                       mol_type = protein
                       organism = synthetic construct
SEQUENCE: 705
DYGVYDY                                                                       7
```

```
SEQ ID NO: 706          moltype = AA   length = 7
FEATURE                 Location/Qualifiers
REGION                  1..7
                        note = Synthetic: 2188-F06; CDR-H3
source                  1..7
                        mol_type = protein
                        organism = synthetic construct
SEQUENCE: 706
DYGVFDY                                                                    7

SEQ ID NO: 707          moltype = AA   length = 7
FEATURE                 Location/Qualifiers
REGION                  1..7
                        note = Synthetic: 2188-D02; CDR-H3
source                  1..7
                        mol_type = protein
                        organism = synthetic construct
SEQUENCE: 707
DYGVFDY                                                                    7

SEQ ID NO: 708          moltype = AA   length = 7
FEATURE                 Location/Qualifiers
REGION                  1..7
                        note = Synthetic: 2188-B06; CDR-H3
source                  1..7
                        mol_type = protein
                        organism = synthetic construct
SEQUENCE: 708
DYGVFDY                                                                    7

SEQ ID NO: 709          moltype = AA   length = 7
FEATURE                 Location/Qualifiers
REGION                  1..7
                        note = Synthetic: 2188-D09; CDR-H3
source                  1..7
                        mol_type = protein
                        organism = synthetic construct
SEQUENCE: 709
DFGVFDY                                                                    7

SEQ ID NO: 710          moltype = AA   length = 7
FEATURE                 Location/Qualifiers
REGION                  1..7
                        note = Synthetic: 2188-F02; CDR-H3
source                  1..7
                        mol_type = protein
                        organism = synthetic construct
SEQUENCE: 710
DYGVFDY                                                                    7

SEQ ID NO: 711          moltype = AA   length = 7
FEATURE                 Location/Qualifiers
REGION                  1..7
                        note = Synthetic: 2188-E10; CDR-H3
source                  1..7
                        mol_type = protein
                        organism = synthetic construct
SEQUENCE: 711
DYGVFDY                                                                    7

SEQ ID NO: 712          moltype = AA   length = 7
FEATURE                 Location/Qualifiers
REGION                  1..7
                        note = Synthetic: 2188-A09; CDR-H3
source                  1..7
                        mol_type = protein
                        organism = synthetic construct
SEQUENCE: 712
DYGVFDY                                                                    7

SEQ ID NO: 713          moltype = AA   length = 7
FEATURE                 Location/Qualifiers
REGION                  1..7
                        note = Synthetic: 2188-D04; CDR-H3
source                  1..7
                        mol_type = protein
                        organism = synthetic construct
SEQUENCE: 713
```

-continued

DYGVYDY                                                                  7

SEQ ID NO: 714         moltype = AA  length = 7
FEATURE                Location/Qualifiers
REGION                 1..7
                       note = Synthetic: 2188-A05; CDR-H3
source                 1..7
                       mol_type = protein
                       organism = synthetic construct
SEQUENCE: 714
DYGVFDY                                                                  7

SEQ ID NO: 715         moltype = AA  length = 7
FEATURE                Location/Qualifiers
REGION                 1..7
                       note = Synthetic: 2188-E01; CDR-H3
source                 1..7
                       mol_type = protein
                       organism = synthetic construct
SEQUENCE: 715
DYGVFDY                                                                  7

SEQ ID NO: 716         moltype = AA  length = 7
FEATURE                Location/Qualifiers
REGION                 1..7
                       note = Synthetic: 2188-G01; CDR-H3
source                 1..7
                       mol_type = protein
                       organism = synthetic construct
SEQUENCE: 716
DYGVFDY                                                                  7

SEQ ID NO: 717         moltype = AA  length = 7
FEATURE                Location/Qualifiers
REGION                 1..7
                       note = Synthetic: 2188-B09; CDR-H3
source                 1..7
                       mol_type = protein
                       organism = synthetic construct
SEQUENCE: 717
DYGVFDY                                                                  7

SEQ ID NO: 718         moltype = AA  length = 7
FEATURE                Location/Qualifiers
REGION                 1..7
                       note = Synthetic: 2188-F07; CDR-H3
source                 1..7
                       mol_type = protein
                       organism = synthetic construct
SEQUENCE: 718
DYGVFDY                                                                  7

SEQ ID NO: 719         moltype = AA  length = 7
FEATURE                Location/Qualifiers
REGION                 1..7
                       note = Synthetic: 2188-D08; CDR-H3
source                 1..7
                       mol_type = protein
                       organism = synthetic construct
SEQUENCE: 719
DYGVFDY                                                                  7

SEQ ID NO: 720         moltype = AA  length = 7
FEATURE                Location/Qualifiers
REGION                 1..7
                       note = Synthetic: 2188-D05; CDR-H3
source                 1..7
                       mol_type = protein
                       organism = synthetic construct
SEQUENCE: 720
DYGVYDY                                                                  7

SEQ ID NO: 721         moltype = AA  length = 7
FEATURE                Location/Qualifiers
REGION                 1..7
                       note = Synthetic: 2188-C03; CDR-H3
source                 1..7
                       mol_type = protein
                       organism = synthetic construct

```
SEQUENCE: 721
DYGVFDY                                                                          7

SEQ ID NO: 722          moltype = AA  length = 7
FEATURE                 Location/Qualifiers
REGION                  1..7
                        note = Synthetic: 2188-E08; CDR-H3
source                  1..7
                        mol_type = protein
                        organism = synthetic construct
SEQUENCE: 722
DYGVFDY                                                                          7

SEQ ID NO: 723          moltype = AA  length = 7
FEATURE                 Location/Qualifiers
REGION                  1..7
                        note = Synthetic: 2188-C06; CDR-H3
source                  1..7
                        mol_type = protein
                        organism = synthetic construct
SEQUENCE: 723
DYGVFDY                                                                          7

SEQ ID NO: 724          moltype = AA  length = 7
FEATURE                 Location/Qualifiers
REGION                  1..7
                        note = Synthetic: 2188-A08; CDR-H3
source                  1..7
                        mol_type = protein
                        organism = synthetic construct
SEQUENCE: 724
DYGVFDY                                                                          7

SEQ ID NO: 725          moltype = AA  length = 7
FEATURE                 Location/Qualifiers
REGION                  1..7
                        note = Synthetic: 2188-B10; CDR-H3
source                  1..7
                        mol_type = protein
                        organism = synthetic construct
SEQUENCE: 725
DYGVFDY                                                                          7

SEQ ID NO: 726          moltype = AA  length = 7
FEATURE                 Location/Qualifiers
REGION                  1..7
                        note = Synthetic: 2188-G02; CDR-H3
source                  1..7
                        mol_type = protein
                        organism = synthetic construct
SEQUENCE: 726
DYGVFDY                                                                          7

SEQ ID NO: 727          moltype = AA  length = 7
FEATURE                 Location/Qualifiers
REGION                  1..7
                        note = Synthetic: 2188-C05; CDR-H3
source                  1..7
                        mol_type = protein
                        organism = synthetic construct
SEQUENCE: 727
DYGVFDY                                                                          7

SEQ ID NO: 728          moltype = AA  length = 7
FEATURE                 Location/Qualifiers
REGION                  1..7
                        note = Synthetic: 2188-A10; CDR-H3
source                  1..7
                        mol_type = protein
                        organism = synthetic construct
SEQUENCE: 728
DYGVFDY                                                                          7

SEQ ID NO: 729          moltype = AA  length = 7
FEATURE                 Location/Qualifiers
REGION                  1..7
                        note = Synthetic: 2188-G04; CDR-H3
source                  1..7
                        mol_type = protein
```

```
                        organism = synthetic construct
SEQUENCE: 729
DYGVYDY                                                                 7

SEQ ID NO: 730          moltype = AA  length = 7
FEATURE                 Location/Qualifiers
REGION                  1..7
                        note = Synthetic: 2188-C08; CDR-H3
source                  1..7
                        mol_type = protein
                        organism = synthetic construct
SEQUENCE: 730
DYGVFDY                                                                 7

SEQ ID NO: 731          moltype = AA  length = 7
FEATURE                 Location/Qualifiers
REGION                  1..7
                        note = Synthetic: 2188-E05; CDR-H3
source                  1..7
                        mol_type = protein
                        organism = synthetic construct
SEQUENCE: 731
DYGVFDY                                                                 7

SEQ ID NO: 732          moltype = AA  length = 7
FEATURE                 Location/Qualifiers
REGION                  1..7
                        note = Synthetic: 2188-A02; CDR-H3
source                  1..7
                        mol_type = protein
                        organism = synthetic construct
SEQUENCE: 732
DFGVFDY                                                                 7

SEQ ID NO: 733          moltype = AA  length = 7
FEATURE                 Location/Qualifiers
REGION                  1..7
                        note = Synthetic: 2188-F04; CDR-H3
source                  1..7
                        mol_type = protein
                        organism = synthetic construct
SEQUENCE: 733
DYGVFDY                                                                 7

SEQ ID NO: 734          moltype = AA  length = 7
FEATURE                 Location/Qualifiers
REGION                  1..7
                        note = Synthetic: 2188-F05; CDR-H3
source                  1..7
                        mol_type = protein
                        organism = synthetic construct
SEQUENCE: 734
DYGVFDY                                                                 7

SEQ ID NO: 735          moltype = AA  length = 7
FEATURE                 Location/Qualifiers
REGION                  1..7
                        note = Synthetic: 2188-D07; CDR-H3
source                  1..7
                        mol_type = protein
                        organism = synthetic construct
SEQUENCE: 735
DYGVFDY                                                                 7

SEQ ID NO: 736          moltype = AA  length = 7
FEATURE                 Location/Qualifiers
REGION                  1..7
                        note = Synthetic: 2188-E02; CDR-H3
source                  1..7
                        mol_type = protein
                        organism = synthetic construct
SEQUENCE: 736
DYGVYDY                                                                 7

SEQ ID NO: 737          moltype = AA  length = 7
FEATURE                 Location/Qualifiers
REGION                  1..7
                        note = Synthetic: 2188-D06; CDR-H3
source                  1..7
```

```
                         mol_type = protein
                         organism = synthetic construct
SEQUENCE: 737
DYGVFDY                                                                  7

SEQ ID NO: 738           moltype = AA  length = 7
FEATURE                  Location/Qualifiers
REGION                   1..7
                         note = Synthetic: 2188-F09; CDR-H3
source                   1..7
                         mol_type = protein
                         organism = synthetic construct
SEQUENCE: 738
DYGVFDY                                                                  7

SEQ ID NO: 739           moltype = AA  length = 7
FEATURE                  Location/Qualifiers
REGION                   1..7
                         note = Synthetic: 2188-F10; CDR-H3
source                   1..7
                         mol_type = protein
                         organism = synthetic construct
SEQUENCE: 739
DYGVFDY                                                                  7

SEQ ID NO: 740           moltype = AA  length = 7
FEATURE                  Location/Qualifiers
REGION                   1..7
                         note = Synthetic: 2188-B05; CDR-H3
source                   1..7
                         mol_type = protein
                         organism = synthetic construct
SEQUENCE: 740
DYGVFDY                                                                  7

SEQ ID NO: 741           moltype = AA  length = 14
FEATURE                  Location/Qualifiers
REGION                   1..14
                         note = Synthetic: 1943-C02; CDR-H3
source                   1..14
                         mol_type = protein
                         organism = synthetic construct
SEQUENCE: 741
SRWFRVLWSY VFDY                                                         14

SEQ ID NO: 742           moltype = AA  length = 14
FEATURE                  Location/Qualifiers
REGION                   1..14
                         note = Synthetic: 2193-D04; CDR-H3
source                   1..14
                         mol_type = protein
                         organism = synthetic construct
SEQUENCE: 742
SRWYRVLWSY AFDY                                                         14

SEQ ID NO: 743           moltype = AA  length = 14
FEATURE                  Location/Qualifiers
REGION                   1..14
                         note = Synthetic: 2193-E10; CDR-H3
source                   1..14
                         mol_type = protein
                         organism = synthetic construct
SEQUENCE: 743
SRWYRVLWSY VFDY                                                         14

SEQ ID NO: 744           moltype = AA  length = 14
FEATURE                  Location/Qualifiers
REGION                   1..14
                         note = Synthetic: 2193-E06; CDR-H3
source                   1..14
                         mol_type = protein
                         organism = synthetic construct
SEQUENCE: 744
SRWFRVLWSY VFDY                                                         14

SEQ ID NO: 745           moltype = AA  length = 14
FEATURE                  Location/Qualifiers
REGION                   1..14
                         note = Synthetic: 2193-E04; CDR-H3
```

```
source                    1..14
                          mol_type = protein
                          organism = synthetic construct
SEQUENCE: 745
SRWFRVLWSY VFDY                                                                  14

SEQ ID NO: 746            moltype = AA  length = 14
FEATURE                   Location/Qualifiers
REGION                    1..14
                          note = Synthetic: 2193-B09; CDR-H3
source                    1..14
                          mol_type = protein
                          organism = synthetic construct
SEQUENCE: 746
SRWYRVLWSY VLDY                                                                  14

SEQ ID NO: 747            moltype = AA  length = 14
FEATURE                   Location/Qualifiers
REGION                    1..14
                          note = Synthetic: 2193-D11; CDR-H3
source                    1..14
                          mol_type = protein
                          organism = synthetic construct
SEQUENCE: 747
SRWFRVLWSY VFDY                                                                  14

SEQ ID NO: 748            moltype = AA  length = 14
FEATURE                   Location/Qualifiers
REGION                    1..14
                          note = Synthetic: 2193-B02; CDR-H3
source                    1..14
                          mol_type = protein
                          organism = synthetic construct
SEQUENCE: 748
SRWFRVLWSY VFDY                                                                  14

SEQ ID NO: 749            moltype = AA  length = 14
FEATURE                   Location/Qualifiers
REGION                    1..14
                          note = Synthetic: 2193-D05; CDR-H3
source                    1..14
                          mol_type = protein
                          organism = synthetic construct
SEQUENCE: 749
SRWFRVLWSY VFDY                                                                  14

SEQ ID NO: 750            moltype = AA  length = 14
FEATURE                   Location/Qualifiers
REGION                    1..14
                          note = Synthetic: 2193-E11; CDR-H3
source                    1..14
                          mol_type = protein
                          organism = synthetic construct
SEQUENCE: 750
SRWYRVLWSY VFHY                                                                  14

SEQ ID NO: 751            moltype = AA  length = 14
FEATURE                   Location/Qualifiers
REGION                    1..14
                          note = Synthetic: 2193-D06; CDR-H3
source                    1..14
                          mol_type = protein
                          organism = synthetic construct
SEQUENCE: 751
SRWFRVLWSY VFDY                                                                  14

SEQ ID NO: 752            moltype = AA  length = 14
FEATURE                   Location/Qualifiers
REGION                    1..14
                          note = Synthetic: 2193-C02; CDR-H3
source                    1..14
                          mol_type = protein
                          organism = synthetic construct
SEQUENCE: 752
SRWFRVLWSF VFDY                                                                  14

SEQ ID NO: 753            moltype = AA  length = 14
FEATURE                   Location/Qualifiers
REGION                    1..14
```

```
                        note = Synthetic: 2193-B03; CDR-H3
source                  1..14
                        mol_type = protein
                        organism = synthetic construct
SEQUENCE: 753
SRWFRVLWSY VFDY                                                              14

SEQ ID NO: 754          moltype = AA  length = 14
FEATURE                 Location/Qualifiers
REGION                  1..14
                        note = Synthetic: 2193-A02; CDR-H3
source                  1..14
                        mol_type = protein
                        organism = synthetic construct
SEQUENCE: 754
SRWLRVLWSY IFDY                                                              14

SEQ ID NO: 755          moltype = AA  length = 14
FEATURE                 Location/Qualifiers
REGION                  1..14
                        note = Synthetic: 2193-E05; CDR-H3
source                  1..14
                        mol_type = protein
                        organism = synthetic construct
SEQUENCE: 755
SRWFRVLWSY VLDY                                                              14

SEQ ID NO: 756          moltype = AA  length = 14
FEATURE                 Location/Qualifiers
REGION                  1..14
                        note = Synthetic: 2193-A06; CDR-H3
source                  1..14
                        mol_type = protein
                        organism = synthetic construct
SEQUENCE: 756
SRWFRVLWSY IFDY                                                              14

SEQ ID NO: 757          moltype = AA  length = 14
FEATURE                 Location/Qualifiers
REGION                  1..14
                        note = Synthetic: 2193-C04; CDR-H3
source                  1..14
                        mol_type = protein
                        organism = synthetic construct
SEQUENCE: 757
SRWFRVLWSY VLDY                                                              14

SEQ ID NO: 758          moltype = AA  length = 14
FEATURE                 Location/Qualifiers
REGION                  1..14
                        note = Synthetic: 2193-E08; CDR-H3
source                  1..14
                        mol_type = protein
                        organism = synthetic construct
SEQUENCE: 758
SRWYRVLWSY VFDY                                                              14

SEQ ID NO: 759          moltype = AA  length = 14
FEATURE                 Location/Qualifiers
REGION                  1..14
                        note = Synthetic: 2193-B10; CDR-H3
source                  1..14
                        mol_type = protein
                        organism = synthetic construct
SEQUENCE: 759
SRWLRVLWSF VFDY                                                              14

SEQ ID NO: 760          moltype = AA  length = 14
FEATURE                 Location/Qualifiers
REGION                  1..14
                        note = Synthetic: 2193-D08; CDR-H3
source                  1..14
                        mol_type = protein
                        organism = synthetic construct
SEQUENCE: 760
TRWFRVLWSY VFDY                                                              14

SEQ ID NO: 761          moltype = AA  length = 14
FEATURE                 Location/Qualifiers
```

-continued

```
REGION                  1..14
                        note = Synthetic: 2193-B08; CDR-H3
source                  1..14
                        mol_type = protein
                        organism = synthetic construct
SEQUENCE: 761
SRWFRVLWSY ALDY                                                                 14

SEQ ID NO: 762          moltype = AA  length = 14
FEATURE                 Location/Qualifiers
REGION                  1..14
                        note = Synthetic: 2193-C05; CDR-H3
source                  1..14
                        mol_type = protein
                        organism = synthetic construct
SEQUENCE: 762
SRWFRVLWSY VIDY                                                                 14

SEQ ID NO: 763          moltype = AA  length = 14
FEATURE                 Location/Qualifiers
REGION                  1..14
                        note = Synthetic: 2193-D10; CDR-H3
source                  1..14
                        mol_type = protein
                        organism = synthetic construct
SEQUENCE: 763
SRWFRVLWSY VFDY                                                                 14

SEQ ID NO: 764          moltype = AA  length = 14
FEATURE                 Location/Qualifiers
REGION                  1..14
                        note = Synthetic: 2193-D03; CDR-H3
source                  1..14
                        mol_type = protein
                        organism = synthetic construct
SEQUENCE: 764
SRWSRVLWIY VFDY                                                                 14

SEQ ID NO: 765          moltype = AA  length = 14
FEATURE                 Location/Qualifiers
REGION                  1..14
                        note = Synthetic: 2193-A09; CDR-H3
source                  1..14
                        mol_type = protein
                        organism = synthetic construct
SEQUENCE: 765
SRWSRVLWSY VFDY                                                                 14

SEQ ID NO: 766          moltype = AA  length = 14
FEATURE                 Location/Qualifiers
REGION                  1..14
                        note = Synthetic: 2193-A10; CDR-H3
source                  1..14
                        mol_type = protein
                        organism = synthetic construct
SEQUENCE: 766
SRWFRVLWSY VFDY                                                                 14

SEQ ID NO: 767          moltype = AA  length = 14
FEATURE                 Location/Qualifiers
REGION                  1..14
                        note = Synthetic: 2193-E07; CDR-H3
source                  1..14
                        mol_type = protein
                        organism = synthetic construct
SEQUENCE: 767
SQWFRVLWSY VFDY                                                                 14

SEQ ID NO: 768          moltype = AA  length = 14
FEATURE                 Location/Qualifiers
REGION                  1..14
                        note = Synthetic: 2193-A07; CDR-H3
source                  1..14
                        mol_type = protein
                        organism = synthetic construct
SEQUENCE: 768
SRWFRVLWSY VFDY                                                                 14

SEQ ID NO: 769          moltype = AA  length = 14
```

```
FEATURE                 Location/Qualifiers
REGION                  1..14
                        note = Synthetic: 2193-E03; CDR-H3
source                  1..14
                        mol_type = protein
                        organism = synthetic construct
SEQUENCE: 769
SRWFRVLWSY VFDY                                                              14

SEQ ID NO: 770          moltype = AA   length = 14
FEATURE                 Location/Qualifiers
REGION                  1..14
                        note = Synthetic: 2193-C08; CDR-H3
source                  1..14
                        mol_type = protein
                        organism = synthetic construct
SEQUENCE: 770
SRWFRVLWSY VFDY                                                              14

SEQ ID NO: 771          moltype = AA   length = 14
FEATURE                 Location/Qualifiers
REGION                  1..14
                        note = Synthetic: 2193-B11; CDR-H3
source                  1..14
                        mol_type = protein
                        organism = synthetic construct
SEQUENCE: 771
SRWFRVLWSF VFDY                                                              14

SEQ ID NO: 772          moltype = AA   length = 14
FEATURE                 Location/Qualifiers
REGION                  1..14
                        note = Synthetic: 2193-A03; CDR-H3
source                  1..14
                        mol_type = protein
                        organism = synthetic construct
SEQUENCE: 772
SRWSRVLWTY VFDY                                                              14

SEQ ID NO: 773          moltype = AA   length = 14
FEATURE                 Location/Qualifiers
REGION                  1..14
                        note = Synthetic: 2193-D02; CDR-H3
source                  1..14
                        mol_type = protein
                        organism = synthetic construct
SEQUENCE: 773
SRWFRVLWSY VFDY                                                              14

SEQ ID NO: 774          moltype = AA   length = 14
FEATURE                 Location/Qualifiers
REGION                  1..14
                        note = Synthetic: 2193-B06; CDR-H3
source                  1..14
                        mol_type = protein
                        organism = synthetic construct
SEQUENCE: 774
SRWFRVLWTY VFDY                                                              14

SEQ ID NO: 775          moltype = AA   length = 14
FEATURE                 Location/Qualifiers
REGION                  1..14
                        note = Synthetic: 2193-B01; CDR-H3
source                  1..14
                        mol_type = protein
                        organism = synthetic construct
SEQUENCE: 775
SRWFRVLWSF VLDY                                                              14

SEQ ID NO: 776          moltype = AA   length = 14
FEATURE                 Location/Qualifiers
REGION                  1..14
                        note = Synthetic: 2193-D09; CDR-H3
source                  1..14
                        mol_type = protein
                        organism = synthetic construct
SEQUENCE: 776
SRWFRVLWSY VFDY                                                              14
```

```
SEQ ID NO: 777           moltype = AA  length = 14
FEATURE                  Location/Qualifiers
REGION                   1..14
                         note = Synthetic: 2193-E09; CDR-H3
source                   1..14
                         mol_type = protein
                         organism = synthetic construct
SEQUENCE: 777
SRWYRVLWSY VFDY                                                              14

SEQ ID NO: 778           moltype = AA  length = 14
FEATURE                  Location/Qualifiers
REGION                   1..14
                         note = Synthetic: 2193-B07; CDR-H3
source                   1..14
                         mol_type = protein
                         organism = synthetic construct
SEQUENCE: 778
SRWFRVLWSY IFDY                                                              14

SEQ ID NO: 779           moltype = AA  length = 14
FEATURE                  Location/Qualifiers
REGION                   1..14
                         note = Synthetic: 2193-C06; CDR-H3
source                   1..14
                         mol_type = protein
                         organism = synthetic construct
SEQUENCE: 779
SRWRRALWIY VFDY                                                              14

SEQ ID NO: 780           moltype = AA  length = 14
FEATURE                  Location/Qualifiers
REGION                   1..14
                         note = Synthetic: 2193-B05; CDR-H3
source                   1..14
                         mol_type = protein
                         organism = synthetic construct
SEQUENCE: 780
SRWYRVLWSY VFDY                                                              14

SEQ ID NO: 781           moltype = AA  length = 14
FEATURE                  Location/Qualifiers
REGION                   1..14
                         note = Synthetic: 2193-A11; CDR-H3
source                   1..14
                         mol_type = protein
                         organism = synthetic construct
SEQUENCE: 781
SRWFRVLWSY VFDY                                                              14

SEQ ID NO: 782           moltype = AA  length = 14
FEATURE                  Location/Qualifiers
REGION                   1..14
                         note = Synthetic: 2193-E02; CDR-H3
source                   1..14
                         mol_type = protein
                         organism = synthetic construct
SEQUENCE: 782
SRWWRVLWSY VFDY                                                              14

SEQ ID NO: 783           moltype = AA  length = 14
FEATURE                  Location/Qualifiers
REGION                   1..14
                         note = Synthetic: 2193-A08; CDR-H3
source                   1..14
                         mol_type = protein
                         organism = synthetic construct
SEQUENCE: 783
SRWFRVLWSY VFDY                                                              14

SEQ ID NO: 784           moltype = AA  length = 14
FEATURE                  Location/Qualifiers
REGION                   1..14
                         note = Synthetic: 2193-C11; CDR-H3
source                   1..14
                         mol_type = protein
                         organism = synthetic construct
SEQUENCE: 784
SRWFRVLWSY VFDY                                                              14
```

```
SEQ ID NO: 785         moltype = AA  length = 14
FEATURE                Location/Qualifiers
REGION                 1..14
                       note = Synthetic: 2193-A01; CDR-H3
source                 1..14
                       mol_type = protein
                       organism = synthetic construct
SEQUENCE: 785
SRWFRVLWSY VFDY                                                              14

SEQ ID NO: 786         moltype = AA  length = 14
FEATURE                Location/Qualifiers
REGION                 1..14
                       note = Synthetic: 2193-D07; CDR-H3
source                 1..14
                       mol_type = protein
                       organism = synthetic construct
SEQUENCE: 786
SRWLRVLWSY VFDY                                                              14

SEQ ID NO: 787         moltype = AA  length = 14
FEATURE                Location/Qualifiers
REGION                 1..14
                       note = Synthetic: 2193-A05; CDR-H3
source                 1..14
                       mol_type = protein
                       organism = synthetic construct
SEQUENCE: 787
SRWFRVLWSY VLDY                                                              14

SEQ ID NO: 788         moltype = AA  length = 14
FEATURE                Location/Qualifiers
REGION                 1..14
                       note = Synthetic: 2193-C03; CDR-H3
source                 1..14
                       mol_type = protein
                       organism = synthetic construct
SEQUENCE: 788
SRWYRVLWSY VLDY                                                              14

SEQ ID NO: 789         moltype = AA  length = 14
FEATURE                Location/Qualifiers
REGION                 1..14
                       note = Synthetic: 2193-C09; CDR-H3
source                 1..14
                       mol_type = protein
                       organism = synthetic construct
SEQUENCE: 789
SRWSRVLWSY VFDY                                                              14

SEQ ID NO: 790         moltype = AA  length = 14
FEATURE                Location/Qualifiers
REGION                 1..14
                       note = Synthetic: 2193-D01; CDR-H3
source                 1..14
                       mol_type = protein
                       organism = synthetic construct
SEQUENCE: 790
SRWFRVLWSY VFDY                                                              14

SEQ ID NO: 791         moltype = AA  length = 14
FEATURE                Location/Qualifiers
REGION                 1..14
                       note = Synthetic: 2193-E01; CDR-H3
source                 1..14
                       mol_type = protein
                       organism = synthetic construct
SEQUENCE: 791
SRWFRVLWTY VFDY                                                              14

SEQ ID NO: 792         moltype = AA  length = 14
FEATURE                Location/Qualifiers
REGION                 1..14
                       note = Synthetic: 2193-C07; CDR-H3
source                 1..14
                       mol_type = protein
                       organism = synthetic construct
SEQUENCE: 792
```

```
SRWYRVLWSF VFDY                                                                14

SEQ ID NO: 793          moltype = AA   length = 14
FEATURE                 Location/Qualifiers
REGION                  1..14
                        note = Synthetic: 2193-B04; CDR-H3
source                  1..14
                        mol_type = protein
                        organism = synthetic construct
SEQUENCE: 793
SRWFRVLWTY VFDY                                                                14

SEQ ID NO: 794          moltype = AA   length = 14
FEATURE                 Location/Qualifiers
REGION                  1..14
                        note = Synthetic: 2193-C10; CDR-H3
source                  1..14
                        mol_type = protein
                        organism = synthetic construct
SEQUENCE: 794
SRWFRVLWSF GFDY                                                                14

SEQ ID NO: 795          moltype = AA   length = 14
FEATURE                 Location/Qualifiers
REGION                  1..14
                        note = Synthetic: 2193-C01; CDR-H3
source                  1..14
                        mol_type = protein
                        organism = synthetic construct
SEQUENCE: 795
SRWFRVLWSY VFDY                                                                14

SEQ ID NO: 796          moltype = AA   length = 14
FEATURE                 Location/Qualifiers
REGION                  1..14
                        note = Synthetic: 2193-A04; CDR-H3
source                  1..14
                        mol_type = protein
                        organism = synthetic construct
SEQUENCE: 796
SRWFRVLWSY VYDY                                                                14

SEQ ID NO: 797          moltype = AA   length = 11
FEATURE                 Location/Qualifiers
REGION                  1..11
                        note = Synthetic: 1944-A07; CDR-H3
source                  1..11
                        mol_type = protein
                        organism = synthetic construct
SEQUENCE: 797
DSRRYVRPFD Y                                                                   11

SEQ ID NO: 798          moltype = AA   length = 11
FEATURE                 Location/Qualifiers
REGION                  1..11
                        note = Synthetic: 2194-A02; CDR-H3
source                  1..11
                        mol_type = protein
                        organism = synthetic construct
SEQUENCE: 798
DSRRYVRPFD Y                                                                   11

SEQ ID NO: 799          moltype = AA   length = 11
FEATURE                 Location/Qualifiers
REGION                  1..11
                        note = Synthetic: 2194-A05; CDR-H3
source                  1..11
                        mol_type = protein
                        organism = synthetic construct
SEQUENCE: 799
DHRRYVRPFD Y                                                                   11

SEQ ID NO: 800          moltype = AA   length = 11
FEATURE                 Location/Qualifiers
REGION                  1..11
                        note = Synthetic: 2194-B04; CDR-H3
source                  1..11
                        mol_type = protein
                        organism = synthetic construct
```

-continued

```
SEQUENCE: 800
DSRRYVRPLD Y                                                           11

SEQ ID NO: 801          moltype = AA  length = 11
FEATURE                 Location/Qualifiers
REGION                  1..11
                        note = Synthetic: 2194-A09; CDR-H3
source                  1..11
                        mol_type = protein
                        organism = synthetic construct
SEQUENCE: 801
DSRRYVRPFD Y                                                           11

SEQ ID NO: 802          moltype = AA  length = 11
FEATURE                 Location/Qualifiers
REGION                  1..11
                        note = Synthetic: 2194-A01; CDR-H3
source                  1..11
                        mol_type = protein
                        organism = synthetic construct
SEQUENCE: 802
DSRRYVRPMD Y                                                           11

SEQ ID NO: 803          moltype = AA  length = 11
FEATURE                 Location/Qualifiers
REGION                  1..11
                        note = Synthetic: 2194-B03; CDR-H3
source                  1..11
                        mol_type = protein
                        organism = synthetic construct
SEQUENCE: 803
DSRRYVRPFD Y                                                           11

SEQ ID NO: 804          moltype = AA  length = 11
FEATURE                 Location/Qualifiers
REGION                  1..11
                        note = Synthetic: 2194-B02; CDR-H3
source                  1..11
                        mol_type = protein
                        organism = synthetic construct
SEQUENCE: 804
DSRRYVRPLD Y                                                           11

SEQ ID NO: 805          moltype = AA  length = 11
FEATURE                 Location/Qualifiers
REGION                  1..11
                        note = Synthetic: 2194-A03; CDR-H3
source                  1..11
                        mol_type = protein
                        organism = synthetic construct
SEQUENCE: 805
DSRRYVRPLD Y                                                           11

SEQ ID NO: 806          moltype = AA  length = 11
FEATURE                 Location/Qualifiers
REGION                  1..11
                        note = Synthetic: 2194-A11; CDR-H3
source                  1..11
                        mol_type = protein
                        organism = synthetic construct
SEQUENCE: 806
DSRRYVRPFD Y                                                           11

SEQ ID NO: 807          moltype = AA  length = 11
FEATURE                 Location/Qualifiers
REGION                  1..11
                        note = Synthetic: 2194-A08; CDR-H3
source                  1..11
                        mol_type = protein
                        organism = synthetic construct
SEQUENCE: 807
DSRRYVRPFD Y                                                           11

SEQ ID NO: 808          moltype = AA  length = 11
FEATURE                 Location/Qualifiers
REGION                  1..11
                        note = Synthetic: 2194-A04; CDR-H3
source                  1..11
                        mol_type = protein
```

```
                                    -continued
                      organism = synthetic construct
SEQUENCE: 808
DSRRYVRPLD Y                                                              11

SEQ ID NO: 809        moltype = AA   length = 11
FEATURE               Location/Qualifiers
REGION                1..11
                      note = Synthetic: 2194-A10; CDR-H3
source                1..11
                      mol_type = protein
                      organism = synthetic construct
SEQUENCE: 809
DSRRYVRPFD Y                                                              11

SEQ ID NO: 810        moltype = AA   length = 11
FEATURE               Location/Qualifiers
REGION                1..11
                      note = Synthetic: 2194-A07; CDR-H3
source                1..11
                      mol_type = protein
                      organism = synthetic construct
SEQUENCE: 810
DSRRYVRPFD Y                                                              11

SEQ ID NO: 811        moltype = AA   length = 11
FEATURE               Location/Qualifiers
REGION                1..11
                      note = Synthetic: 2194-B01; CDR-H3
source                1..11
                      mol_type = protein
                      organism = synthetic construct
SEQUENCE: 811
DSRRYVRPFD Y                                                              11

SEQ ID NO: 812        moltype = AA   length = 11
FEATURE               Location/Qualifiers
REGION                1..11
                      note = Synthetic: 2194-A06; CDR-H3
source                1..11
                      mol_type = protein
                      organism = synthetic construct
SEQUENCE: 812
DSRRYVRPFD Y                                                              11

SEQ ID NO: 813        moltype = AA   length = 11
FEATURE               Location/Qualifiers
REGION                1..11
                      note = Synthetic: 2196-C01; CDR-H3
source                1..11
                      mol_type = protein
                      organism = synthetic construct
SEQUENCE: 813
DSRRYIRSWD Y                                                              11

SEQ ID NO: 814        moltype = AA   length = 11
FEATURE               Location/Qualifiers
REGION                1..11
                      note = Synthetic: 2196-A02; CDR-H3
source                1..11
                      mol_type = protein
                      organism = synthetic construct
SEQUENCE: 814
DSRRYVRGWD Y                                                              11

SEQ ID NO: 815        moltype = AA   length = 11
FEATURE               Location/Qualifiers
REGION                1..11
                      note = Synthetic: 2196-B03; CDR-H3
source                1..11
                      mol_type = protein
                      organism = synthetic construct
SEQUENCE: 815
DSRRYVRPFD Y                                                              11

SEQ ID NO: 816        moltype = AA   length = 11
FEATURE               Location/Qualifiers
REGION                1..11
                      note = Synthetic: 2196-A05; CDR-H3
source                1..11
```

```
                                   -continued
                              mol_type = protein
                              organism = synthetic construct
SEQUENCE: 816
DSRRYVRSWD Y                                                              11

SEQ ID NO: 817               moltype = AA  length = 11
FEATURE                      Location/Qualifiers
REGION                       1..11
                             note = Synthetic: 2196-C02; CDR-H3
source                       1..11
                             mol_type = protein
                             organism = synthetic construct
SEQUENCE: 817
DSRRYVRPFD Y                                                              11

SEQ ID NO: 818               moltype = AA  length = 11
FEATURE                      Location/Qualifiers
REGION                       1..11
                             note = Synthetic: 2196-B11; CDR-H3
source                       1..11
                             mol_type = protein
                             organism = synthetic construct
SEQUENCE: 818
DSRRYIRSWD Y                                                              11

SEQ ID NO: 819               moltype = AA  length = 11
FEATURE                      Location/Qualifiers
REGION                       1..11
                             note = Synthetic: 2196-B08; CDR-H3
source                       1..11
                             mol_type = protein
                             organism = synthetic construct
SEQUENCE: 819
DSRRYVRGWD Y                                                              11

SEQ ID NO: 820               moltype = AA  length = 11
FEATURE                      Location/Qualifiers
REGION                       1..11
                             note = Synthetic: 2196-A04; CDR-H3
source                       1..11
                             mol_type = protein
                             organism = synthetic construct
SEQUENCE: 820
ESRRYVGPFG Y                                                              11

SEQ ID NO: 821               moltype = AA  length = 11
FEATURE                      Location/Qualifiers
REGION                       1..11
                             note = Synthetic: 2196-A03; CDR-H3
source                       1..11
                             mol_type = protein
                             organism = synthetic construct
SEQUENCE: 821
DSRRYVRGWD Y                                                              11

SEQ ID NO: 822               moltype = AA  length = 11
FEATURE                      Location/Qualifiers
REGION                       1..11
                             note = Synthetic: 2196-B07; CDR-H3
source                       1..11
                             mol_type = protein
                             organism = synthetic construct
SEQUENCE: 822
DSRRYVRGWD Y                                                              11

SEQ ID NO: 823               moltype = AA  length = 11
FEATURE                      Location/Qualifiers
REGION                       1..11
                             note = Synthetic: 2196-A06; CDR-H3
source                       1..11
                             mol_type = protein
                             organism = synthetic construct
SEQUENCE: 823
DSRRYVRGWD Y                                                              11

SEQ ID NO: 824               moltype = AA  length = 11
FEATURE                      Location/Qualifiers
REGION                       1..11
                             note = Synthetic: 2196-B05; CDR-H3
```

```
source                   1..11
                         mol_type = protein
                         organism = synthetic construct
SEQUENCE: 824
DSRRYVRGWD Y                                                              11

SEQ ID NO: 825           moltype = AA   length = 11
FEATURE                  Location/Qualifiers
REGION                   1..11
                         note = Synthetic: 2196-A01; CDR-H3
source                   1..11
                         mol_type = protein
                         organism = synthetic construct
SEQUENCE: 825
DSRRYVRGWD Y                                                              11

SEQ ID NO: 826           moltype = AA   length = 11
FEATURE                  Location/Qualifiers
REGION                   1..11
                         note = Synthetic: 2196-B01; CDR-H3
source                   1..11
                         mol_type = protein
                         organism = synthetic construct
SEQUENCE: 826
DSRRYVRSWD Y                                                              11

SEQ ID NO: 827           moltype = AA   length = 11
FEATURE                  Location/Qualifiers
REGION                   1..11
                         note = Synthetic: 2196-A09; CDR-H3
source                   1..11
                         mol_type = protein
                         organism = synthetic construct
SEQUENCE: 827
DSRRYIRSWD Y                                                              11

SEQ ID NO: 828           moltype = AA   length = 11
FEATURE                  Location/Qualifiers
REGION                   1..11
                         note = Synthetic: 2196-A08; CDR-H3
source                   1..11
                         mol_type = protein
                         organism = synthetic construct
SEQUENCE: 828
DSRRYVRSWD Y                                                              11

SEQ ID NO: 829           moltype = AA   length = 11
FEATURE                  Location/Qualifiers
REGION                   1..11
                         note = Synthetic: 2196-A10; CDR-H3
source                   1..11
                         mol_type = protein
                         organism = synthetic construct
SEQUENCE: 829
DSRRYVRSWD Y                                                              11

SEQ ID NO: 830           moltype = AA   length = 11
FEATURE                  Location/Qualifiers
REGION                   1..11
                         note = Synthetic: 2196-B06; CDR-H3
source                   1..11
                         mol_type = protein
                         organism = synthetic construct
SEQUENCE: 830
DSRRYVLSWD Y                                                              11

SEQ ID NO: 831           moltype = AA   length = 11
FEATURE                  Location/Qualifiers
REGION                   1..11
                         note = Synthetic: 2196-B09; CDR-H3
source                   1..11
                         mol_type = protein
                         organism = synthetic construct
SEQUENCE: 831
DSRRYVRSWD Y                                                              11

SEQ ID NO: 832           moltype = AA   length = 11
FEATURE                  Location/Qualifiers
REGION                   1..11
```

```
                         note = Synthetic: 2196-C03; CDR-H3
source                   1..11
                         mol_type = protein
                         organism = synthetic construct
SEQUENCE: 832
DSRRYVLSWD Y                                                                    11

SEQ ID NO: 833           moltype = AA  length = 11
FEATURE                  Location/Qualifiers
REGION                   1..11
                         note = Synthetic: 2196-C04; CDR-H3
source                   1..11
                         mol_type = protein
                         organism = synthetic construct
SEQUENCE: 833
ESRRYVNPWD Y                                                                    11

SEQ ID NO: 834           moltype = AA  length = 11
FEATURE                  Location/Qualifiers
REGION                   1..11
                         note = Synthetic: 2196-A07; CDR-H3
source                   1..11
                         mol_type = protein
                         organism = synthetic construct
SEQUENCE: 834
DSRRYVRGWD Y                                                                    11

SEQ ID NO: 835           moltype = AA  length = 11
FEATURE                  Location/Qualifiers
REGION                   1..11
                         note = Synthetic: 2196-A11; CDR-H3
source                   1..11
                         mol_type = protein
                         organism = synthetic construct
SEQUENCE: 835
DSRRYVRGWD Y                                                                    11

SEQ ID NO: 836           moltype = AA  length = 11
FEATURE                  Location/Qualifiers
REGION                   1..11
                         note = Synthetic: 2196-B02; CDR-H3
source                   1..11
                         mol_type = protein
                         organism = synthetic construct
SEQUENCE: 836
DSRRYVRSWD Y                                                                    11

SEQ ID NO: 837           moltype = AA  length = 11
FEATURE                  Location/Qualifiers
REGION                   1..11
                         note = Synthetic: 2196-B04; CDR-H3
source                   1..11
                         mol_type = protein
                         organism = synthetic construct
SEQUENCE: 837
DSRRYVRGWD Y                                                                    11

SEQ ID NO: 838           moltype = AA  length = 11
FEATURE                  Location/Qualifiers
REGION                   1..11
                         note = Synthetic: 2196-B10; CDR-H3
source                   1..11
                         mol_type = protein
                         organism = synthetic construct
SEQUENCE: 838
DSRRYIRSWD Y                                                                    11

SEQ ID NO: 839           moltype = AA  length = 11
FEATURE                  Location/Qualifiers
REGION                   1..11
                         note = Synthetic: trastuzumab; CDR-L1
source                   1..11
                         mol_type = protein
                         organism = synthetic construct
SEQUENCE: 839
RASQDVNTAV A                                                                    11

SEQ ID NO: 840           moltype = AA  length = 14
FEATURE                  Location/Qualifiers
```

```
REGION                  1..14
                        note = Synthetic: SP34; CDR-L1
source                  1..14
                        mol_type = protein
                        organism = synthetic construct
SEQUENCE: 840
RSSTGAVTTS NYAN                                                              14

SEQ ID NO: 841          moltype = AA  length = 14
FEATURE                 Location/Qualifiers
REGION                  1..14
                        note = Synthetic: 2037-B10; CDR-L1
source                  1..14
                        mol_type = protein
                        organism = synthetic construct
SEQUENCE: 841
GSSTGAVTSG YYPN                                                              14

SEQ ID NO: 842          moltype = AA  length = 11
FEATURE                 Location/Qualifiers
REGION                  1..11
                        note = Synthetic: hUCHT1-LC3; CDR-L1
source                  1..11
                        mol_type = protein
                        organism = synthetic construct
SEQUENCE: 842
RASQDIRNYL N                                                                 11

SEQ ID NO: 843          moltype = AA  length = 10
FEATURE                 Location/Qualifiers
REGION                  1..10
                        note = Synthetic: hOKT3-LC1; CDR-L1
source                  1..10
                        mol_type = protein
                        organism = synthetic construct
SEQUENCE: 843
SASSSVSYMN                                                                   10

SEQ ID NO: 844          moltype = AA  length = 7
FEATURE                 Location/Qualifiers
REGION                  1..7
                        note = Synthetic: trastuzumab; CDR-L2
source                  1..7
                        mol_type = protein
                        organism = synthetic construct
SEQUENCE: 844
SASFLYS                                                                       7

SEQ ID NO: 845          moltype = AA  length = 7
FEATURE                 Location/Qualifiers
REGION                  1..7
                        note = Synthetic: SP34; CDR-L2
source                  1..7
                        mol_type = protein
                        organism = synthetic construct
SEQUENCE: 845
GTNKRAP                                                                       7

SEQ ID NO: 846          moltype = AA  length = 7
FEATURE                 Location/Qualifiers
REGION                  1..7
                        note = Synthetic: 2037-B10; CDR-L2
source                  1..7
                        mol_type = protein
                        organism = synthetic construct
SEQUENCE: 846
GTKFLAP                                                                       7

SEQ ID NO: 847          moltype = AA  length = 7
FEATURE                 Location/Qualifiers
REGION                  1..7
                        note = Synthetic: hUCHT1-LC3; CDR-L2
source                  1..7
                        mol_type = protein
                        organism = synthetic construct
SEQUENCE: 847
YTSRLHS                                                                       7

SEQ ID NO: 848          moltype = AA  length = 7
```

```
FEATURE                 Location/Qualifiers
REGION                  1..7
                        note = Synthetic: hOKT3-LC1; CDR-L2
source                  1..7
                        mol_type = protein
                        organism = synthetic construct
SEQUENCE: 848
DTSKLAS                                                                              7

SEQ ID NO: 849          moltype = AA   length = 9
FEATURE                 Location/Qualifiers
REGION                  1..9
                        note = Synthetic: trastuzumab; CDR-L3
source                  1..9
                        mol_type = protein
                        organism = synthetic construct
SEQUENCE: 849
QQHYTTPPT                                                                            9

SEQ ID NO: 850          moltype = AA   length = 9
FEATURE                 Location/Qualifiers
REGION                  1..9
                        note = Synthetic: SP34; CDR-L3
source                  1..9
                        mol_type = protein
                        organism = synthetic construct
SEQUENCE: 850
ALWYSNLWV                                                                            9

SEQ ID NO: 851          moltype = AA   length = 9
FEATURE                 Location/Qualifiers
REGION                  1..9
                        note = Synthetic: 2037-B10; CDR-L3
source                  1..9
                        mol_type = protein
                        organism = synthetic construct
SEQUENCE: 851
ALWYSNRWV                                                                            9

SEQ ID NO: 852          moltype = AA   length = 9
FEATURE                 Location/Qualifiers
REGION                  1..9
                        note = Synthetic: hUCHT1-LC3; CDR-L3
source                  1..9
                        mol_type = protein
                        organism = synthetic construct
SEQUENCE: 852
QQGNTLPWT                                                                            9

SEQ ID NO: 853          moltype = AA   length = 9
FEATURE                 Location/Qualifiers
REGION                  1..9
                        note = Synthetic: hOKT3-LC1; CDR-L3
source                  1..9
                        mol_type = protein
                        organism = synthetic construct
SEQUENCE: 853
QQWSSNPFT                                                                            9

SEQ ID NO: 854          moltype = AA   length = 116
FEATURE                 Location/Qualifiers
REGION                  1..116
                        note = Synthetic: 1987-C05; VH
source                  1..116
                        mol_type = protein
                        organism = synthetic construct
SEQUENCE: 854
EVQLVESGGG LVQPGGSLRL SCAASGFNIS DYDIHWVRQA PGKGLEWVGG IDPDDGSTDY                    60
ADSVKGRFTI SADTSKNTAY LQMNSLRAED TAVYYCARDY GVFDYWGQGT LVTVSS                       116

SEQ ID NO: 855          moltype = AA   length = 116
FEATURE                 Location/Qualifiers
REGION                  1..116
                        note = Synthetic: 2188-D11; VH
source                  1..116
                        mol_type = protein
                        organism = synthetic construct
SEQUENCE: 855
EVQLVESGGG LVQTGGSLRL SCAASGFNIR DYDIHWVRQA PGKGLEWVGL IDPDDGSTDE                    60
```

```
ADSVKGRFTI SADTSKNTAY LQMNSLRAED TAVYYCARDY GVFDYWGQGT LVTVSS        116

SEQ ID NO: 856           moltype = AA   length = 116
FEATURE                  Location/Qualifiers
REGION                   1..116
                         note = Synthetic: 2188-B04; VH
source                   1..116
                         mol_type = protein
                         organism = synthetic construct
SEQUENCE: 856
EVQLVESGGG LVQPGGSLRL SCAASGFNIT WYDIHWVRQA PGKGLEWVGW INPDDGDTYY    60
ADSVKGRFTI SADTSKNTAY LQMNSLRAED TAVYYCARDY GVFDYWGQGT LVTVSS        116

SEQ ID NO: 857           moltype = AA   length = 116
FEATURE                  Location/Qualifiers
REGION                   1..116
                         note = Synthetic: 2188-C09; VH
source                   1..116
                         mol_type = protein
                         organism = synthetic construct
SEQUENCE: 857
EVQLVESGGG LVQPGGSLRL SCAASGFNIN SYDIHWVRQA PGKGLEWVGW INPHDGDTYY    60
ADSVTGRFTI SADTSKNTAY LQMNSLRAED TAVYYCARDY GVFDYWGQGT LVTVSS        116

SEQ ID NO: 858           moltype = AA   length = 116
FEATURE                  Location/Qualifiers
REGION                   1..116
                         note = Synthetic: 2188-G03; VH
source                   1..116
                         mol_type = protein
                         organism = synthetic construct
SEQUENCE: 858
EVQLVESGGG LVQPGGSLRL SCAASGFNIV DYDIHWVRQA PGKGLEWVVG IDPRDGSTDY    60
ADSVKGRFTI SADTSKNTAY LQMNSLRAED TAVYYCARDF GVFDYWGQGT LVTVSS        116

SEQ ID NO: 859           moltype = AA   length = 116
FEATURE                  Location/Qualifiers
REGION                   1..116
                         note = Synthetic: 2188-E03; VH
source                   1..116
                         mol_type = protein
                         organism = synthetic construct
SEQUENCE: 859
EVQLVESGGG LVQPGGSLRL SCAASGFNIR DYDIHWVRQA PGKGLEWVAG IDPDDGSTDY    60
ADSVKGRFTI SADTSKNTAY LQMNSLRAED TAVYYCARDY GVYDYWGQGT LVTVSS        116

SEQ ID NO: 860           moltype = AA   length = 116
FEATURE                  Location/Qualifiers
REGION                   1..116
                         note = Synthetic: 2188-B11; VH
source                   1..116
                         mol_type = protein
                         organism = synthetic construct
SEQUENCE: 860
EVQLVESGGG LVQPGGSLRL SCAASGFNIN RYDIHWVRQA PGKGLEWVGW INPDDGDTFL    60
ADSVKGRFTI SADTSKSTAY LQMNSLRAED TAVYYCARDY GVFDYWGQGT LVTVSS        116

SEQ ID NO: 861           moltype = AA   length = 116
FEATURE                  Location/Qualifiers
REGION                   1..116
                         note = Synthetic: 2188-E07; VH
source                   1..116
                         mol_type = protein
                         organism = synthetic construct
SEQUENCE: 861
EVQLVESGGG LVQPGGSLRL SCAASGFNIG DYGIHWVRQA PGKGLEWVGG IDPEDGFTVH    60
ADSVKGRFTI SADTSKNTAY LQMNSLRAED TAVYYCARDY GVYDYWGQGT LVTVSS        116

SEQ ID NO: 862           moltype = AA   length = 116
FEATURE                  Location/Qualifiers
REGION                   1..116
                         note = Synthetic: 2188-B02; VH
source                   1..116
                         mol_type = protein
                         organism = synthetic construct
SEQUENCE: 862
EVQLVESGGG LVQPGGSLRL SCAASGFNIS SYDIHWVRQA PGKGLEWVGW INPDDGDTYL    60
ADSVKGRFTI SADTSKSTAY LQMNSLRAED TAVYYCARDY GVFDYWGQGT LVTVSS        116
```

```
SEQ ID NO: 863           moltype = AA  length = 116
FEATURE                  Location/Qualifiers
REGION                   1..116
                         note = Synthetic: 2188-C07; VH
source                   1..116
                         mol_type = protein
                         organism = synthetic construct
SEQUENCE: 863
EVQLVESGGG LVQPGGSLRL SCAASGFNIV RYDIHWVRQA PGKGLEWVGW INPDDGDTYY      60
ADSVKGRFTI SADTSKNTAY LQMNSLRAED TAVYYCARDY GVFDYWGQGT LVTVSS         116

SEQ ID NO: 864           moltype = AA  length = 116
FEATURE                  Location/Qualifiers
REGION                   1..116
                         note = Synthetic: 2188-A03; VH
source                   1..116
                         mol_type = protein
                         organism = synthetic construct
SEQUENCE: 864
EVQLVESGGG LVQPGGSLRL SCAASGFNIR DYDIHWVRQA PGKGLEWVGW INPDDGDTYY      60
ADSVKGRFTI SADTSKNTAY LQMNSLRAED TAVYYCARDY GVFDYWGQGT LVTVSS         116

SEQ ID NO: 865           moltype = AA  length = 116
FEATURE                  Location/Qualifiers
REGION                   1..116
                         note = Synthetic: 2188-F03; VH
source                   1..116
                         mol_type = protein
                         organism = synthetic construct
SEQUENCE: 865
EVQLVESGGG LVQPGGSLRL SCAASGFNIS DYDIHWVRQA PGKGLEWVSG IDPDDGSTDY      60
ADSVKGRFTI SADTSKNTAY LQMNSLRAED TAVYYCARDY GVFDYWGQGT LVTVSS         116

SEQ ID NO: 866           moltype = AA  length = 116
FEATURE                  Location/Qualifiers
REGION                   1..116
                         note = Synthetic: 2188-D03; VH
source                   1..116
                         mol_type = protein
                         organism = synthetic construct
SEQUENCE: 866
EVQLVESGGG LVQPGGSLRL SCAASGFNIS DYDIHWVRQA PGKGLEWVGG IDPHDGSTDY      60
ADSVKGRFTI SADTSKNTAY LQMNSLRAED TAVYYCARDY GVYDYWGQGT LVTVSS         116

SEQ ID NO: 867           moltype = AA  length = 116
FEATURE                  Location/Qualifiers
REGION                   1..116
                         note = Synthetic: 2188-C04; VH
source                   1..116
                         mol_type = protein
                         organism = synthetic construct
SEQUENCE: 867
EVQLVESGGG LVQPGGSLRL SCAASGFNIN SYDIHWVRQA PGKGLEWVGW INPEDGDTYH      60
ADSVRGRFTI SADTSKNTAY LQMNSLRAED TAVYYCARDY GVYDYWGQGT LVTVSS         116

SEQ ID NO: 868           moltype = AA  length = 116
FEATURE                  Location/Qualifiers
REGION                   1..116
                         note = Synthetic: 2188-D10; VH
source                   1..116
                         mol_type = protein
                         organism = synthetic construct
SEQUENCE: 868
EVQLVESGGG LVQPGGSLRL SCAASGFNIS DYDIHWVRQA PGKGLEWVGR IDPRDGATDY      60
ADSVKGRFTI SADTSKNTAY LQMNSLRAED TAVYYCARDY GVFDYWGQGT LVTVSS         116

SEQ ID NO: 869           moltype = AA  length = 116
FEATURE                  Location/Qualifiers
REGION                   1..116
                         note = Synthetic: 2188-A06; VH
source                   1..116
                         mol_type = protein
                         organism = synthetic construct
SEQUENCE: 869
EVQLVESGGG LVQPGGSLRL SCAASGFNIK SYDIHWVRQA PGKGLEWVGW INPDDGDTYH      60
ADSVKGRFTI SADTSKNTAY LQMNSLRAED TAVYYCARDY GVFDYWGQGT LVTVSS         116

SEQ ID NO: 870           moltype = AA  length = 116
FEATURE                  Location/Qualifiers
```

```
REGION                    1..116
                          note = Synthetic: 2188-C11; VH
source                    1..116
                          mol_type = protein
                          organism = synthetic construct
SEQUENCE: 870
EVQLVESGGG LVQPGGSLRL SCAASGFNIK SYDIHWVRQA PGKGLEWVGW INPDDGDTYL    60
ADSVKGRFTI SADTSKNTAY LQMNSLRAED TAVYYCARDY GVFDYWGQGT LVTVSS       116

SEQ ID NO: 871            moltype = AA  length = 116
FEATURE                   Location/Qualifiers
REGION                    1..116
                          note = Synthetic: 2188-F01; VH
source                    1..116
                          mol_type = protein
                          organism = synthetic construct
SEQUENCE: 871
EVQLVESGGG LVQPGGSLRL SCAASGFNIR YYDIHWVRQA PGKGLEWVGL IDPDDGWTVS    60
ADSVKGRFTI SADTSKNTAY LQMNSLRAED TAVYYCARDY GVFDYWGQGT LVTVSS       116

SEQ ID NO: 872            moltype = AA  length = 116
FEATURE                   Location/Qualifiers
REGION                    1..116
                          note = Synthetic: 2188-E11; VH
source                    1..116
                          mol_type = protein
                          organism = synthetic construct
SEQUENCE: 872
EVQLVESGGG LVQPGGSLRL SCAASGFNIS HYDIHWVRQA PGKGLEWVSG IDPGDGATDH    60
ADSVKGRFTI SADTSKNTAY LQMNSLRAED TAVYYCARDY GVFDYWGQGT LVTVSS       116

SEQ ID NO: 873            moltype = AA  length = 116
FEATURE                   Location/Qualifiers
REGION                    1..116
                          note = Synthetic: 2188-A07; VH
source                    1..116
                          mol_type = protein
                          organism = synthetic construct
SEQUENCE: 873
EVQLVESGGG LVQPGGSLRL SCAASGFNIH HYDIHWVRQA PGKGLEWVGW INPDDGDTYY    60
ADSVKGRFTI SADTSKNTAY LQMNSLRAED TAVYYCARDY GVFDYWGQGT LVTVSS       116

SEQ ID NO: 874            moltype = AA  length = 116
FEATURE                   Location/Qualifiers
REGION                    1..116
                          note = Synthetic: 2188-C01; VH
source                    1..116
                          mol_type = protein
                          organism = synthetic construct
SEQUENCE: 874
EVQLVESGGG LVQPGGSLRL SCAASGFNII SYDIHWVRQA PGKGLEWVSL IDPHDGSTDS    60
ADSVKGRFTI SADTSKNTAY LQMNSLRAED TAVYYCARDY GVFDYWGQGT LVTVSS       116

SEQ ID NO: 875            moltype = AA  length = 116
FEATURE                   Location/Qualifiers
REGION                    1..116
                          note = Synthetic: 2188-F08; VH
source                    1..116
                          mol_type = protein
                          organism = synthetic construct
SEQUENCE: 875
EVQLVESGGG LVQPGGSLRL SCAASGFNIP DFEIHWVRQA PGKGLEWVAR IEPDDGATDY    60
ADSVKGRFTI SADTSKNTAY LQMNSLRAED TAVYYCARDY GVFDYWGQGT LVTVSS       116

SEQ ID NO: 876            moltype = AA  length = 116
FEATURE                   Location/Qualifiers
REGION                    1..116
                          note = Synthetic: 2188-E04; VH
source                    1..116
                          mol_type = protein
                          organism = synthetic construct
SEQUENCE: 876
EVQLVESGGG LVQPGGSLRL SCAASGFNIS DYDIHWVRQA PGKGLEWVAG IDPQDGSTDY    60
ADSVKGRFTI SADTSKNTAY LQMNSLRAED AAVYYCARDF GVFDYWGQGT LVTVSS       116

SEQ ID NO: 877            moltype = AA  length = 116
FEATURE                   Location/Qualifiers
REGION                    1..116
                          note = Synthetic: 2188-B01; VH
```

```
                        source          1..116
                                        mol_type = protein
                                        organism = synthetic construct
SEQUENCE: 877
EVQLVESGGG LVQPGGSLRL SCAASGFNIN SHDIHWVRQA PGKGLEWVGW INPDDGDTYY    60
ADSVKGRFTI SADTSKNTAY LQMNSLRAED TAVYYCARDY GVLDYWGQGT LVTVSS       116

SEQ ID NO: 878          moltype = AA  length = 116
FEATURE                 Location/Qualifiers
REGION                  1..116
                        note = Synthetic: 2188-F11; VH
source                  1..116
                        mol_type = protein
                        organism = synthetic construct
SEQUENCE: 878
EVQLVESGGG LVQPGGSLRL SCAASGFNIT GYDIHWVRQA PGKGLEWVGG IDPEDGATDY    60
ADSVKGRFTI SADTSKNTAY LQMNSLRAED TAVYYCARDY GVFDYWGQGT LVTVSS       116

SEQ ID NO: 879          moltype = AA  length = 116
FEATURE                 Location/Qualifiers
REGION                  1..116
                        note = Synthetic: 2188-B08; VH
source                  1..116
                        mol_type = protein
                        organism = synthetic construct
SEQUENCE: 879
EVQLVESGGG LVQPGGSLRL SCAASGFNID SYDIHWVRQA PGKGLEWVGW INPDDGDTFY    60
ADSVKGRFTI SADTSKNTAY LQMDSLRAED TAVYYCARDY GVFDYWGQGT LVTVSS       116

SEQ ID NO: 880          moltype = AA  length = 116
FEATURE                 Location/Qualifiers
REGION                  1..116
                        note = Synthetic: 2188-C10; VH
source                  1..116
                        mol_type = protein
                        organism = synthetic construct
SEQUENCE: 880
EVQLVESGGG LVQPGGSLRL SCAASGFNIN SYDIHWVRQA PGKGLEWVGW INPDDGDTYH    60
ADSVKGRFTI SADTSKNTAY LQMNSLRAED TAVYYCARDY GVFDYWGQGT LVTVSS       116

SEQ ID NO: 881          moltype = AA  length = 116
FEATURE                 Location/Qualifiers
REGION                  1..116
                        note = Synthetic: 2188-C02; VH
source                  1..116
                        mol_type = protein
                        organism = synthetic construct
SEQUENCE: 881
EVQLVESGGG LVQPGGSLRL SCAASGFNIE RYDIHWVRQA PGKGLEWVGW INPDDGDTYY    60
ADSVKGRFTI SADTSKNTAY LQTKSLRAED TAVYYCARDY GVFDYWGQGT LVTVSS       116

SEQ ID NO: 882          moltype = AA  length = 116
FEATURE                 Location/Qualifiers
REGION                  1..116
                        note = Synthetic: 2188-B07; VH
source                  1..116
                        mol_type = protein
                        organism = synthetic construct
SEQUENCE: 882
EVQLVESGGG LVQPGGSLRL SCAASGFNIH SHDIHWVRQA PGKGLEWVGW INPDDGDTYY    60
ADSVKGRFAI SADTSKNTAY LQMNSLRAED TAVYYCARDY GVFDYWGRGT LVTVSS       116

SEQ ID NO: 883          moltype = AA  length = 116
FEATURE                 Location/Qualifiers
REGION                  1..116
                        note = Synthetic: 2188-A11; VH
source                  1..116
                        mol_type = protein
                        organism = synthetic construct
SEQUENCE: 883
EVQLVESGGG LVQPGGSLRL SCAASGFNIS DYDIHWVRQA PGKGLEWVSL IDPKDGATDS    60
ADSVKGRFTI SADTSKNTAY LQMNSLRAGD TAVYYCARDY GVFDYWGQGT LVTVSS       116

SEQ ID NO: 884          moltype = AA  length = 116
FEATURE                 Location/Qualifiers
REGION                  1..116
                        note = Synthetic: 2188-D01; VH
source                  1..116
                        mol_type = protein
```

```
                        organism = synthetic construct
SEQUENCE: 884
EVQLVESGGG LVQPGGSLRL SCAASGFNIK SYDIHWVRQA PGKGLEWVGW INPYDGDTYY    60
ADSVKGRFTI SADTSKNTAY LQMNSLRAED TAVYYCARDY GVFDYWGQGT LVTVSS       116

SEQ ID NO: 885          moltype = AA   length = 116
FEATURE                 Location/Qualifiers
REGION                  1..116
                        note = Synthetic: 2188-E09; VH
source                  1..116
                        mol_type = protein
                        organism = synthetic construct
SEQUENCE: 885
EVQLVESGGG LVQPGGSLRL SCAASGFNIS DFDIHWVRQA PGKGLEWVAE IDPQDGWTVH    60
ADSVKGRFTI SADTSKNTAY LQMNSLRAED TAVYYCARDY GVFDYWGQGT LVTVSS       116

SEQ ID NO: 886          moltype = AA   length = 116
FEATURE                 Location/Qualifiers
REGION                  1..116
                        note = Synthetic: 2188-E06; VH
source                  1..116
                        mol_type = protein
                        organism = synthetic construct
SEQUENCE: 886
EVQLVESGGG LVQPGGSLRL SCAASGFNIG DYDIHWVRQA PGKGLEWVGG IDPEDGATDI    60
ADSVKGRFTI SADTSKNTAY LQMDSLRAED TAVYYCARDY GVFDYWGQGT LVTVSS       116

SEQ ID NO: 887          moltype = AA   length = 116
FEATURE                 Location/Qualifiers
REGION                  1..116
                        note = Synthetic: 2188-B03; VH
source                  1..116
                        mol_type = protein
                        organism = synthetic construct
SEQUENCE: 887
EVQLVESGGG LVQPGGSLRL SCAASGFNIS SYDIHWVRQA PGKGLEWVGA IDPGDGATDY    60
ADSVKGRFTI SADTSKNTAY LQMNSLRAED TAVYYCARDY GVYDYWGQGT LVTVSS       116

SEQ ID NO: 888          moltype = AA   length = 116
FEATURE                 Location/Qualifiers
REGION                  1..116
                        note = Synthetic: 2188-F06; VH
source                  1..116
                        mol_type = protein
                        organism = synthetic construct
SEQUENCE: 888
EVQLVESGGG LVQPGGSLRL SCAASGFNIL DYDIHWVRQA PGKGLEWVGG IDPDDGATDY    60
ADSVKGRFTI SADTSKNTAY LQMNSLRAED TAVYYCARDY GVFDYWGQGT LVTVSS       116

SEQ ID NO: 889          moltype = AA   length = 116
FEATURE                 Location/Qualifiers
REGION                  1..116
                        note = Synthetic: 2188-D02; VH
source                  1..116
                        mol_type = protein
                        organism = synthetic construct
SEQUENCE: 889
EVQLVESGGG LVQPGGSLRL SCAASGFNIS DYDIHWVRQA PGKGLEWVGG IDPEDGATDY    60
ADSVKGRFTI SADTSKNTAY LQMNSLRAED TAVYYCARDY GVFDYWGQGT LVTVSS       116

SEQ ID NO: 890          moltype = AA   length = 116
FEATURE                 Location/Qualifiers
REGION                  1..116
                        note = Synthetic: 2188-B06; VH
source                  1..116
                        mol_type = protein
                        organism = synthetic construct
SEQUENCE: 890
EVQLVESGGG LVQPGGSLRL SCAASGFNIH SYDIHWVRQA PGEGLEWVGW INPDDGDTYH    60
ADSVKGRFTI SADTSKNTAY LQMNSLRAED TAVYYCARDY GVFDYWGQGT LVTVSS       116

SEQ ID NO: 891          moltype = AA   length = 116
FEATURE                 Location/Qualifiers
REGION                  1..116
                        note = Synthetic: 2188-D09; VH
source                  1..116
                        mol_type = protein
                        organism = synthetic construct
SEQUENCE: 891
```

```
EVQLVESGGG LVQPGGSLRL SCAASGFNIR DYDIHWVRQA PGKGLEWVVG IDPGDGSTDY    60
ADSVKGRFTI SADTSKNTAY LQMNSLRAED TAVYYCARDF GVFDYWGQGT LVTVSS       116

SEQ ID NO: 892            moltype = AA  length = 116
FEATURE                   Location/Qualifiers
REGION                    1..116
                          note = Synthetic: 2188-F02; VH
source                    1..116
                          mol_type = protein
                          organism = synthetic construct
SEQUENCE: 892
EVQLVESGGG LVQPGGSLRL SCAASGFNIS DYDIHWVRQA PGKGLEWVAW IDPSDGSTEH    60
ADSVKGRFTI SADTSKNTAY LQMSSLRAED TAVYYCARDY GVFDYWGQGT LVTVSS       116

SEQ ID NO: 893            moltype = AA  length = 116
FEATURE                   Location/Qualifiers
REGION                    1..116
                          note = Synthetic: 2188-E10; VH
source                    1..116
                          mol_type = protein
                          organism = synthetic construct
SEQUENCE: 893
EVQLVESGGG LVQPGGSLRL SCAASGFNIG DFDIHWVRQA PGKGLEWVGG IDPRDGATDY    60
ADSVKGRFTI SADTSKNTAY LQMNSLRAED TAVYYCARDY GVFDYWGQGT LVTVSS       116

SEQ ID NO: 894            moltype = AA  length = 116
FEATURE                   Location/Qualifiers
REGION                    1..116
                          note = Synthetic: 2188-A09; VH
source                    1..116
                          mol_type = protein
                          organism = synthetic construct
SEQUENCE: 894
EVQLVESGGG LVQPGGSLRL SCAASGFNII NYDIHWVRQA PGKGLEWVGW INPDDGDTYY    60
ADSVKGRFTI SADTSKNTAY LQMNSLRAED TAVYYCARDY GVFDYWGQGT LVTVSS       116

SEQ ID NO: 895            moltype = AA  length = 116
FEATURE                   Location/Qualifiers
REGION                    1..116
                          note = Synthetic: 2188-D04; VH
source                    1..116
                          mol_type = protein
                          organism = synthetic construct
SEQUENCE: 895
EVQLVESGGG LVQPGGSLRL SCAASGFNIS DYDIHWVRQA PGKGLEWVGG IDPADGSTDY    60
ADSVKGRFTI SADTSKNTAY LQMNSLRAED TAVYYCARDY GVYDYWGQGT LVTVSS       116

SEQ ID NO: 896            moltype = AA  length = 116
FEATURE                   Location/Qualifiers
REGION                    1..116
                          note = Synthetic: 2188-A05; VH
source                    1..116
                          mol_type = protein
                          organism = synthetic construct
SEQUENCE: 896
EVQLVESGGG LVQPGGSLRL SCAASGFNIK RYDIHWVRQA PGKGLEWVGW INPDDGDTYY    60
ADSVKGRFTI SADTSKNTAY LQMNSLRAED TAVYYCARDY GVFDYWGQGT LVTVSS       116

SEQ ID NO: 897            moltype = AA  length = 116
FEATURE                   Location/Qualifiers
REGION                    1..116
                          note = Synthetic: 2188-E01; VH
source                    1..116
                          mol_type = protein
                          organism = synthetic construct
SEQUENCE: 897
EVQLVESGGG LVQPGGSLRL SCAASGFNIG DYDIHWVRQA PGKGLEWVVG IDPQDGATDY    60
ADSVKGRFTI SADTSKNTAY LQMNSLRAED TAVYYCARDY GVFDYWGQGT LVTVSS       116

SEQ ID NO: 898            moltype = AA  length = 116
FEATURE                   Location/Qualifiers
REGION                    1..116
                          note = Synthetic: 2188-G01; VH
source                    1..116
                          mol_type = protein
                          organism = synthetic construct
SEQUENCE: 898
EVQLVESGGG LVQPGGSLRL SCAASGFNIS DYDIHWVRQA PGKGLEWVGG IDPNDGATDY    60
ADSVKGRFTI SADTSKNTAY LQMNSLRAED TAVYYCARDY GVFDYWGQGT LVTVSS       116
```

```
SEQ ID NO: 899          moltype = AA   length = 116
FEATURE                 Location/Qualifiers
REGION                  1..116
                        note = Synthetic: 2188-B09; VH
source                  1..116
                        mol_type = protein
                        organism = synthetic construct
SEQUENCE: 899
EVQLVESGGG LVQPGGSLRL SCAASGFNIN SYDIHWVRQA PGKGLEWVGV IDPKDGWTDH  60
ADSVKGRFTI SADTSKNTAY LQMNSLRTED TAVYYCARDY GVFDYWGQGT LVTVSS     116

SEQ ID NO: 900          moltype = AA   length = 116
FEATURE                 Location/Qualifiers
REGION                  1..116
                        note = Synthetic: 2188-F07; VH
source                  1..116
                        mol_type = protein
                        organism = synthetic construct
SEQUENCE: 900
EVQLVESGGG LVQPGGSLRL SCAASGFNIS DYDIHWVRQA PGKGLEWVGG IDPNDGSTDH  60
ADSVKGRFTI SADTSKNMAY LQMNSLRAED TAVYYCARDY GVFDYWGQGT LVTVSS     116

SEQ ID NO: 901          moltype = AA   length = 116
FEATURE                 Location/Qualifiers
REGION                  1..116
                        note = Synthetic: 2188-D08; VH
source                  1..116
                        mol_type = protein
                        organism = synthetic construct
SEQUENCE: 901
EVQLVESGGG LVQPGGSLRL SCAASGFNIR DYDIHWVRQA PGKGLEWVVG IDPDDGATDE  60
ADSVKGRFTI SADTSKNTAY LQMNSLRAED TAVYYCARDY GVFDYWGQGT LVTVSS     116

SEQ ID NO: 902          moltype = AA   length = 116
FEATURE                 Location/Qualifiers
REGION                  1..116
                        note = Synthetic: 2188-D05; VH
source                  1..116
                        mol_type = protein
                        organism = synthetic construct
SEQUENCE: 902
EVQLVESGGG LVQPGGSLRL SCAASGFNIS EYDIHWVRQA PGKGLEWVGG IDPHDGWTDH  60
ADSVKGRFTI SADTSKNTAY LQMNSLRAED TAVYYCARDY GVYDYWGQGT LVTVSS     116

SEQ ID NO: 903          moltype = AA   length = 116
FEATURE                 Location/Qualifiers
REGION                  1..116
                        note = Synthetic: 2188-C03; VH
source                  1..116
                        mol_type = protein
                        organism = synthetic construct
SEQUENCE: 903
EVQLVESGGG LVQPGGSLRL SCAASGFNIN SYDIHWVRQA PGKGLEWVGW INPDDGDTYY  60
ADSVKGRFTI SADTSKNTAY LQMNSLRAED TAVYYCARDY GVFDYWGQGT LVTVSS     116

SEQ ID NO: 904          moltype = AA   length = 116
FEATURE                 Location/Qualifiers
REGION                  1..116
                        note = Synthetic: 2188-E08; VH
source                  1..116
                        mol_type = protein
                        organism = synthetic construct
SEQUENCE: 904
EVQLVESGGG LVQPGGSLRL SCAASGFNII DFDIHWVRQA PGKGLEWVGG IDPQDGSTDL  60
ADSVKGRLTI SADTSKNTAY LQMNSLRAED TAVYYCARDY GVFDYWGQGT LVTVSS     116

SEQ ID NO: 905          moltype = AA   length = 116
FEATURE                 Location/Qualifiers
REGION                  1..116
                        note = Synthetic: 2188-C06; VH
source                  1..116
                        mol_type = protein
                        organism = synthetic construct
SEQUENCE: 905
EVQLVESGGG LVQPGGSLRL SCAASGFNIN SYDIHWVRQA PGKGLEWVGW INPDDGDTYL  60
ADSVKGRFTI SADTSKNTAY LQMNSLRAED TAVYYCARDY GVFDYWGQGT LVTVSS     116

SEQ ID NO: 906          moltype = AA   length = 116
```

```
FEATURE                 Location/Qualifiers
REGION                  1..116
                        note = Synthetic: 2188-A08; VH
source                  1..116
                        mol_type = protein
                        organism = synthetic construct
SEQUENCE: 906
EVQLVESGGG LVQPGGSLRL SCAASGFNIH NFDIHWVRQA PGKGLEWVGW INPFDGDTYY    60
ADSVKGRFTI SADTSKNTAY LRMNSLRAED TAAYYCARDY GVFDYWGQGT LVTVSS       116

SEQ ID NO: 907          moltype = AA   length = 116
FEATURE                 Location/Qualifiers
REGION                  1..116
                        note = Synthetic: 2188-B10; VH
source                  1..116
                        mol_type = protein
                        organism = synthetic construct
SEQUENCE: 907
EVQLVESGGG LVQPGGSLRL SCAASGFNIN SYDIHWVRQA PGKGLEWVGW INPHDGDTYH    60
ADSVKGRFTI SADTSKNTAY LQMNSLRAED TAVYYCARDY GVFDYWGQGT LVTVSS       116

SEQ ID NO: 908          moltype = AA   length = 116
FEATURE                 Location/Qualifiers
REGION                  1..116
                        note = Synthetic: 2188-G02; VH
source                  1..116
                        mol_type = protein
                        organism = synthetic construct
SEQUENCE: 908
EVQLVESGGG LVQPGGSLRL SCAASGFNIV GYDIHWVRQA PSKGLEWVGG IDPNDGATDY    60
ADSVKGRFTI SADTSKNTAY LQMNSLRAED TAVYYCARDY GVFDYWGQGT LVTVSS       116

SEQ ID NO: 909          moltype = AA   length = 116
FEATURE                 Location/Qualifiers
REGION                  1..116
                        note = Synthetic: 2188-C05; VH
source                  1..116
                        mol_type = protein
                        organism = synthetic construct
SEQUENCE: 909
EVQLVESGGG LVQPGGSLRL SCAASGFNIN SFDIHWVRQA PGKGLEWVGG IDPRDGSTDS    60
ADSVKGRFTI SADTSKNTAY LQMNSLRAED TAVYYCARDY GVFDYWGQGT LVTVSS       116

SEQ ID NO: 910          moltype = AA   length = 116
FEATURE                 Location/Qualifiers
REGION                  1..116
                        note = Synthetic: 2188-A10; VH
source                  1..116
                        mol_type = protein
                        organism = synthetic construct
SEQUENCE: 910
EVQLVESGGG LVQPGGSLRL SCAASGFNIN SYDIHWVRQA PGKGLEWVGW INPEDGDTSH    60
ADSVKGRFTI SADTSKNTAY LQMNSLRAED TAVYYCARDY GVFDYWGQGT LVTVSS       116

SEQ ID NO: 911          moltype = AA   length = 116
FEATURE                 Location/Qualifiers
REGION                  1..116
                        note = Synthetic: 2188-G04; VH
source                  1..116
                        mol_type = protein
                        organism = synthetic construct
SEQUENCE: 911
EVQLVESGGG LVQPGGSLRL SCAASGFNIF DYDIHWVRQA PGKGLEWVGG IDPRDGSTDH    60
ADSVKGRFTI SADTSKNTAY LQMNSLRAED TAVYYCARDY GVYDYWGQGT LVTVSS       116

SEQ ID NO: 912          moltype = AA   length = 116
FEATURE                 Location/Qualifiers
REGION                  1..116
                        note = Synthetic: 2188-C08; VH
source                  1..116
                        mol_type = protein
                        organism = synthetic construct
SEQUENCE: 912
EVQLVESGGG LVQPGGSLRL SCAASGFNIK SHDIHWVRQA PGKGLEWVGW INPDDGDTYH    60
ADSVKGRFTI SADTSKNTAY LQMNSLRAED TAVYYCARDY GVFDYWGQGT LVTVSS       116

SEQ ID NO: 913          moltype = AA   length = 116
FEATURE                 Location/Qualifiers
REGION                  1..116
```

```
                    note = Synthetic: 2188-E05; VH
source              1..116
                    mol_type = protein
                    organism = synthetic construct
SEQUENCE: 913
EVQLVESGGG LVQPGGSLRL SCAASGFNIS DYDIHWVRQA PGKGLEWVAG IEPWDGSTDH     60
ADSVKGRFTI SADTSKNTAY LQMNSLRAED TAVYYCARDY GVFDYWGQGT LVTVSS        116

SEQ ID NO: 914      moltype = AA  length = 116
FEATURE             Location/Qualifiers
REGION              1..116
                    note = Synthetic: 2188-A02; VH
source              1..116
                    mol_type = protein
                    organism = synthetic construct
SEQUENCE: 914
EVQLVESGGG LVQPGGSLRL SCAASGFNIK SYDIHWVRQA PGKGLEWVGW INPEDGDTYY     60
ADSVKGRFTI SADTSKNTAY LQMNSLRAED TAVYYCARDF GVFDYWGQGT LVTVSS        116

SEQ ID NO: 915      moltype = AA  length = 116
FEATURE             Location/Qualifiers
REGION              1..116
                    note = Synthetic: 2188-F04; VH
source              1..116
                    mol_type = protein
                    organism = synthetic construct
SEQUENCE: 915
EVQLVESGGS LVQPGGSLRL SCAASGFNIS DFDIHWVRQA PGKGLEWVSG IDPDDGATDY     60
ADSVKGRFTI SADTSKNTAY LQMNSLRAED TAVYYCARDY GVFDYWGQGT LVTVSS        116

SEQ ID NO: 916      moltype = AA  length = 116
FEATURE             Location/Qualifiers
REGION              1..116
                    note = Synthetic: 2188-F05; VH
source              1..116
                    mol_type = protein
                    organism = synthetic construct
SEQUENCE: 916
EVQLVESGGG LVQPGGSLRL SCAASGFNIS DYDIHWVRQA PGKGLEWVGG IDPRDGATDS     60
ADSVKGRFTI SADTSKNTAY LQMNSLRAED TAVYYCARDY GVFDYWGQGT LVTVSS        116

SEQ ID NO: 917      moltype = AA  length = 116
FEATURE             Location/Qualifiers
REGION              1..116
                    note = Synthetic: 2188-D07; VH
source              1..116
                    mol_type = protein
                    organism = synthetic construct
SEQUENCE: 917
EVQLVESGGG LVQPGGSLRL SCAASGFNIS DFDIHWVRQA PGKGLEWVVG IDPTDGATDY     60
ADSVKGRFTI SADTSKNTAY LQMNSLRAED TAVYYCARDY GVFDYWGQGT LVTVSS        116

SEQ ID NO: 918      moltype = AA  length = 116
FEATURE             Location/Qualifiers
REGION              1..116
                    note = Synthetic: 2188-E02; VH
source              1..116
                    mol_type = protein
                    organism = synthetic construct
SEQUENCE: 918
EVQLVESGGG LVQPGGSLRL SCAASGFNIP DYEIHWVRQA PGKGLEWVGG IEPHDGSTDY     60
ADSVKGRFTI SADTSKNTAY LQMNSLRAED TAVYYCARDY GVYDYWGQGT LVTVSS        116

SEQ ID NO: 919      moltype = AA  length = 116
FEATURE             Location/Qualifiers
REGION              1..116
                    note = Synthetic: 2188-D06; VH
source              1..116
                    mol_type = protein
                    organism = synthetic construct
SEQUENCE: 919
EVQLVESGGG LVQPGGSLRL SCAASGFNIR DYDIHWVRQA PGKGLEWVGG IDPNDGATDY     60
ADSVKGRFTI SADTSKNTAY LQMNSLRAED TAVYYCARDY GVFDYWGQGT LVTVSS        116

SEQ ID NO: 920      moltype = AA  length = 116
FEATURE             Location/Qualifiers
REGION              1..116
                    note = Synthetic: 2188-F09; VH
source              1..116
```

```
                            mol_type = protein
                            organism = synthetic construct
SEQUENCE: 920
EVQLVESGGD LVQPGGSLRL SCAASGFNIR DYDIHWVRQA PGKGLEWVSA IDPNDGSTDY    60
ADSVKGRFTI SADTSKNTAY LQMNSLRAED TAVYYCARDY GVFDYWGQGT LVTVSS       116

SEQ ID NO: 921          moltype = AA  length = 116
FEATURE                 Location/Qualifiers
REGION                  1..116
                        note = Synthetic: 2188-F10; VH
source                  1..116
                        mol_type = protein
                        organism = synthetic construct
SEQUENCE: 921
EVQLVESGGG LVQPGGSLRL SCAASGFNIS VFDIHWVRQA PGKGLEWVGG IDPNDGATDH    60
ADSVKGRFTI SADTSKNTAY LQMNSLRAED TAVYYCARDY GVFDYWGQGT LVTVSS       116

SEQ ID NO: 922          moltype = AA  length = 116
FEATURE                 Location/Qualifiers
REGION                  1..116
                        note = Synthetic: 2188-B05; VH
source                  1..116
                        mol_type = protein
                        organism = synthetic construct
SEQUENCE: 922
EVQLVESGGG LVQPGGSLRL SCAASGFNIP DYDIHWVRQA PGKGLEWVGV IDPDDGWTHY    60
ADSVKGRFTI SADTSKNTAY LQMNSLRAED TAVYYCARDY GVFDYWGQGT LVTVSS       116

SEQ ID NO: 923          moltype = AA  length = 123
FEATURE                 Location/Qualifiers
REGION                  1..123
                        note = Synthetic: 1943-C02; VH
source                  1..123
                        mol_type = protein
                        organism = synthetic construct
SEQUENCE: 923
EVQLVESGGG LAQPGGSLRL SCAAPGFNIN DYYIHWVRQA PGKGLEWVGA IDPNSGSTDY    60
ADSVKGRFAI SADTSKNTAY LQMNSLRAED TAVYYCARSR WFRVLWSYVF DYWGQGTLVT   120
VSS                                                                 123

SEQ ID NO: 924          moltype = AA  length = 123
FEATURE                 Location/Qualifiers
REGION                  1..123
                        note = Synthetic: 2193-D04; VH
source                  1..123
                        mol_type = protein
                        organism = synthetic construct
SEQUENCE: 924
EVQLVESGGG LVQPGGSLRL SCAASGFNIN GFYIHWVRQA PGKGLEWVGA IDPNGGSTVY    60
ADSVKGRFTI SADTSKNTAY LQMNSLRAED TAVYYCARSR WYRVLWSYAF DYWGQGTLVT   120
VSS                                                                 123

SEQ ID NO: 925          moltype = AA  length = 123
FEATURE                 Location/Qualifiers
REGION                  1..123
                        note = Synthetic: 2193-E10; VH
source                  1..123
                        mol_type = protein
                        organism = synthetic construct
SEQUENCE: 925
EVQLVESGGG LVQPGGSLRL SCAASGFNIY DYYIHWVRQA PGKGLEWVGA IDPVNGSTNN    60
ADSVKGRFTI SADTSKNTAY LQMNSLRAED TAVYYCARSR WYRVLWSYVF DYWGQGTLVT   120
VSS                                                                 123

SEQ ID NO: 926          moltype = AA  length = 123
FEATURE                 Location/Qualifiers
REGION                  1..123
                        note = Synthetic: 2193-E06; VH
source                  1..123
                        mol_type = protein
                        organism = synthetic construct
SEQUENCE: 926
EVQLVESGGG LVRPGGSLRL SCAASGFNID DYYIHWVRQA PGKGLEWVGV IDPKNGSTVY    60
ADSVKGRSTI SADTPKSTAY LQMNSLRAED TAVYYCARSR WFRVLWSYVF DYWGQGTLVT   120
VSS                                                                 123

SEQ ID NO: 927          moltype = AA  length = 123
FEATURE                 Location/Qualifiers
REGION                  1..123
```

```
                           note = Synthetic: 2193-E04; VH
source                     1..123
                           mol_type = protein
                           organism = synthetic construct
SEQUENCE: 927
EVQLVESGGG LVQPGGSLRL SCAASGFNIN DRYIHWVRQA PGKGLEWVGV IDPSLGSTID   60
ADSVKGRFTI SADTSRNTAY LQMNSLRAED TAVYYCARSR WFRVLWSYVF DYWGQGTLVT  120
VSS                                                                123

SEQ ID NO: 928             moltype = AA   length = 123
FEATURE                    Location/Qualifiers
REGION                     1..123
                           note = Synthetic: 2193-B09; VH
source                     1..123
                           mol_type = protein
                           organism = synthetic construct
SEQUENCE: 928
EVQLVESGGG LVQPGGSLRL SCAASGFNIN NSYIHWVRQA PGKGLEWVGI IDPNNGSTAY   60
ADSVKGRFTI SADTSKNTAY LQMNSLRAED TAVYYCARSR WYRVLWSYVL DYWGQGTLVT  120
VSS                                                                123

SEQ ID NO: 929             moltype = AA   length = 123
FEATURE                    Location/Qualifiers
REGION                     1..123
                           note = Synthetic: 2193-D11; VH
source                     1..123
                           mol_type = protein
                           organism = synthetic construct
SEQUENCE: 929
EVQLVESGGG SVQPGGSLRL SCAASGFNIN AYYIHWVRQA PGKGLEWVGA IDPNTGSTVD   60
ADSVKGRFTI SADTSKNTAY LQMNSLRAED TAVYYCARSR WFRVLWSYVF DYWGQGTLVT  120
VSS                                                                123

SEQ ID NO: 930             moltype = AA   length = 123
FEATURE                    Location/Qualifiers
REGION                     1..123
                           note = Synthetic: 2193-B02; VH
source                     1..123
                           mol_type = protein
                           organism = synthetic construct
SEQUENCE: 930
EVQLVESGGG LVQPGGSLRL SCAASGFNIK NSYIHWVRQA PGKGLEWVGT IDPTRGSTVH   60
ADSVKGRFTI SADTSKNTAY LQMNSLRAED TAVYYCARSR WFRVLWSYVF DYWGQGTLVT  120
VSS                                                                123

SEQ ID NO: 931             moltype = AA   length = 123
FEATURE                    Location/Qualifiers
REGION                     1..123
                           note = Synthetic: 2193-D05; VH
source                     1..123
                           mol_type = protein
                           organism = synthetic construct
SEQUENCE: 931
EVQLVESGGG LVQPGGSLRL SCAASGFNIN DHYIHWVRQA PGKGLEWVGA IDPNSGSTVY   60
ADSVKGRFTI SADTSKNTAY LQMNSLRAED TAVYYCARSR WFRVLWSYVF DYWGQGTLVT  120
VSS                                                                123

SEQ ID NO: 932             moltype = AA   length = 123
FEATURE                    Location/Qualifiers
REGION                     1..123
                           note = Synthetic: 2193-E11; VH
source                     1..123
                           mol_type = protein
                           organism = synthetic construct
SEQUENCE: 932
EVQLVESGGG LVQPGGSLRL SCAASGFNIN DYYIHWVRQA PGKGLEWVGG IEPNSGATVF   60
ADSVKGRFTI GADTSKNTAY LQMNSLRAED TAVYYCARSR WYRVLWSYVF HYWGQGTLVT  120
VSS                                                                123

SEQ ID NO: 933             moltype = AA   length = 123
FEATURE                    Location/Qualifiers
REGION                     1..123
                           note = Synthetic: 2193-D06; VH
source                     1..123
                           mol_type = protein
                           organism = synthetic construct
SEQUENCE: 933
EVQLVESGGG LVQPGGSLRL SCAASGFNIR DYYIHWVRQA PGKGLEWVRA IDPHSGSTVY   60
ADSVKGRFTI SADTSKNTAY LQMNSLRAED TAVYYCARSR WFRVLWSYVF DYWGQGTLVT  120
```

-continued

```
VSS                                                               123

SEQ ID NO: 934           moltype = AA   length = 123
FEATURE                  Location/Qualifiers
REGION                   1..123
                         note = Synthetic: 2193-C02; VH
source                   1..123
                         mol_type = protein
                         organism = synthetic construct
SEQUENCE: 934
EVQLVESGGG LVQPGGSLRL SCAASGFNIS DYYIHWVRQA PGKGLEWVGT IDPQSGSTVY    60
ADSVKGRFTI SADTSENTAY LQMNSLRAED TAVYYCARSR WFRVLWSFVF DYWGQGTLVT   120
VSS                                                               123

SEQ ID NO: 935           moltype = AA   length = 123
FEATURE                  Location/Qualifiers
REGION                   1..123
                         note = Synthetic: 2193-B03; VH
source                   1..123
                         mol_type = protein
                         organism = synthetic construct
SEQUENCE: 935
EVQLVESGGG LVQPGGSLRL SCAASGFNIR DYYIHWVRQA PGKGLEWVGA IDPVSGSTLF    60
ADSVKGRFTI SADTSKNTAY LQMNSLRAED TEVYYCARSR WFRVLWSYVF DYWGQGTLVT   120
VSS                                                               123

SEQ ID NO: 936           moltype = AA   length = 123
FEATURE                  Location/Qualifiers
REGION                   1..123
                         note = Synthetic: 2193-A02; VH
source                   1..123
                         mol_type = protein
                         organism = synthetic construct
SEQUENCE: 936
EVQLVESGGG LVQPGGSLRL SCAASGFNIH ASYIHWVRQA PGKGLEWVGA IDPKSGSTYY    60
ADSVKGRFTI SADTSKNTAY LQMNSLRAED TAVYYCARSR WLRVLWSYIF DYWGQGTLVT   120
VSS                                                               123

SEQ ID NO: 937           moltype = AA   length = 123
FEATURE                  Location/Qualifiers
REGION                   1..123
                         note = Synthetic: 2193-E05; VH
source                   1..123
                         mol_type = protein
                         organism = synthetic construct
SEQUENCE: 937
EVQLVESGGG LVQPGGSLRL SCAASGFNIK RSYIHWVRQA PGKGLEWVVS IDPNGSSTHY    60
ADSVKGRFTI SADTSKNTAY LQMNSLRAED TAVYYCARSR WFRVLWSYVL DYWGQGTLVT   120
VSS                                                               123

SEQ ID NO: 938           moltype = AA   length = 123
FEATURE                  Location/Qualifiers
REGION                   1..123
                         note = Synthetic: 2193-A06; VH
source                   1..123
                         mol_type = protein
                         organism = synthetic construct
SEQUENCE: 938
EVQLVESGGG LVQPGGSLRL SCAASGFNIN AYYIHWVRQA PGKGLEWVDA IDPDSGSTHN    60
ADSVKGRFTI SADTSKNTAY LQMNSLRAED TAVYYCARSR WFRVLWSYIF DYWGQGTLVT   120
VSS                                                               123

SEQ ID NO: 939           moltype = AA   length = 123
FEATURE                  Location/Qualifiers
REGION                   1..123
                         note = Synthetic: 2193-C04; VH
source                   1..123
                         mol_type = protein
                         organism = synthetic construct
SEQUENCE: 939
EVQLVESGGG LVQPGGSLRL SCAASGFNIN TSYIHWVRQA PGKGLEWVGA IDPKSGSTNF    60
ADSVKGRFTI SADASKNTAY LQMNSLRAED TAVYYCARSR WFRVLWSYVL DYWGQGTLVT   120
VSS                                                               123

SEQ ID NO: 940           moltype = AA   length = 123
FEATURE                  Location/Qualifiers
REGION                   1..123
                         note = Synthetic: 2193-E08; VH
source                   1..123
```

-continued

```
                            mol_type = protein
                            organism = synthetic construct
SEQUENCE: 940
EVQLVESGGG LVQPGGSLRL SCAASGFNIN EYYIHWVRQA PGKGLEWVGA IDPHSGSTNF    60
ADSVKGRFTI SADTSKNTAY LQMNSLRAED TAVYYCARSR WYRVLWSYVF DYWGQGTLVT   120
VSS                                                                  123

SEQ ID NO: 941              moltype = AA   length = 123
FEATURE                     Location/Qualifiers
REGION                      1..123
                            note = Synthetic: 2193-B10; VH
source                      1..123
                            mol_type = protein
                            organism = synthetic construct
SEQUENCE: 941
EVQLVESGGG LVQPGGSLRL SCAASGFNIA DYYVHWVRQA PGKGLEWVGA IDPNSGYTVK    60
ADSVKGRFTI SADTSKNTAY LQMNSLRAED TAVYYCARSR WLRVLWSFVF DYWGQGTLVT   120
VSS                                                                  123

SEQ ID NO: 942              moltype = AA   length = 123
FEATURE                     Location/Qualifiers
REGION                      1..123
                            note = Synthetic: 2193-D08; VH
source                      1..123
                            mol_type = protein
                            organism = synthetic construct
SEQUENCE: 942
EVQLVESGGG LVQPGGSLRL SCAASGFNIK RSYIHWVRQA PGKGLEWVVA IDPSGGSTNH    60
ADSVKGRFTI SADTSKNTAY LQMNSLRAED TAVYYCARTR WFRVLWSYVF DYWGQGTLVT   120
VSS                                                                  123

SEQ ID NO: 943              moltype = AA   length = 123
FEATURE                     Location/Qualifiers
REGION                      1..123
                            note = Synthetic: 2193-B08; VH
source                      1..123
                            mol_type = protein
                            organism = synthetic construct
SEQUENCE: 943
EVQLVESGGG LVQPGGSLRL SCAASGFNIK DYYIHWVRQA PGKGLEWVSA IDPSPGATLD    60
ADSVKGRFTI SADTSKNTAY LQMNSLRAED TAVYYCARSR WFRVLWSYAL DYWGQGTLVT   120
VSS                                                                  123

SEQ ID NO: 944              moltype = AA   length = 123
FEATURE                     Location/Qualifiers
REGION                      1..123
                            note = Synthetic: 2193-C05; VH
source                      1..123
                            mol_type = protein
                            organism = synthetic construct
SEQUENCE: 944
EVQLVESGGG LVQPGGSLRL SCAASGFNIK HSYIHWVRQA PGKGLEWVGA IDPHNGSTAS    60
ADSVKGRFTI SADTSKNTAY LQMNSLRAED TAVHYCARSR WFRVLWSYVI DYWGQGTLVT   120
VSS                                                                  123

SEQ ID NO: 945              moltype = AA   length = 123
FEATURE                     Location/Qualifiers
REGION                      1..123
                            note = Synthetic: 2193-D10; VH
source                      1..123
                            mol_type = protein
                            organism = synthetic construct
SEQUENCE: 945
EVQLVESGGG LVQPGGSLRL SCAASGFNIN VSYIHWVRQA PGKGLEWVAT IDPNSGFTVH    60
ADSVKGRFTI SADTSKNTAY LQMNSLRAED TAVYYCARSR WFRVLWSYVF DYWGQGTLVT   120
VSS                                                                  123

SEQ ID NO: 946              moltype = AA   length = 123
FEATURE                     Location/Qualifiers
REGION                      1..123
                            note = Synthetic: 2193-D03; VH
source                      1..123
                            mol_type = protein
                            organism = synthetic construct
SEQUENCE: 946
EVQLVESGGG LVQPGGSLRL SCAASGFNIN DHYIHWVRQA PGKGLEWVSA IDPNTGSTVN    60
ADSVKGRFTI SADTSKNTAY LQMNSLRAED TAVYYCARSR WSRVLWIYVF DYWGQGTLVT   120
VSS                                                                  123
```

```
SEQ ID NO: 947              moltype = AA   length = 123
FEATURE                     Location/Qualifiers
REGION                      1..123
                            note = Synthetic: 2193-A09; VH
source                      1..123
                            mol_type = protein
                            organism = synthetic construct
SEQUENCE: 947
EVQLVESGGG LVQPGGSLRL SCAASGFNIG KHHIHWVRQA PGKGLEWVGV IDPKGGSTVY   60
ADSVKGRFTI SADTSKNTAY LQMNSLRAED TAVYYCARSR WSRVLWSYVF DYWGQGTLVT  120
VSS                                                                123

SEQ ID NO: 948              moltype = AA   length = 123
FEATURE                     Location/Qualifiers
REGION                      1..123
                            note = Synthetic: 2193-A10; VH
source                      1..123
                            mol_type = protein
                            organism = synthetic construct
SEQUENCE: 948
EVQLVESGGG LVQPGGSLRL SCAASGFNIG DYYIHWVRQA PGKGLEWVGA IDPKSGYTVY   60
ADSVKGRFTI SADTSKNTAY LQMNSLRAED TAVYYCARSR WFRVLWSYVF DYWGQGTLVT  120
VSS                                                                123

SEQ ID NO: 949              moltype = AA   length = 123
FEATURE                     Location/Qualifiers
REGION                      1..123
                            note = Synthetic: 2193-E07; VH
source                      1..123
                            mol_type = protein
                            organism = synthetic construct
SEQUENCE: 949
EVQLVESGGG LVQPGGSLRL SCAASGFNIN KVYIHWVRQA PGKGLEWVVS IDPTIGSTHF   60
ADSVKGRFTI SADTSKSTAY LQMNSLRAED TAVYYCARSQ WFRVLWSYVF DYWGQGTLVT  120
VSS                                                                123

SEQ ID NO: 950              moltype = AA   length = 123
FEATURE                     Location/Qualifiers
REGION                      1..123
                            note = Synthetic: 2193-A07; VH
source                      1..123
                            mol_type = protein
                            organism = synthetic construct
SEQUENCE: 950
EVQLVESGGG LVQPGGSLRL SCAASGFNIN ASDIHWVRQA PGKGLGWVGA IDPNTGTTNY   60
ADSVKGRFTI SADTSKNTAY LQMNSLRAED TAVYYCARSR WFRVLWSYVF DYWGQGTLVT  120
VSS                                                                123

SEQ ID NO: 951              moltype = AA   length = 123
FEATURE                     Location/Qualifiers
REGION                      1..123
                            note = Synthetic: 2193-E03; VH
source                      1..123
                            mol_type = protein
                            organism = synthetic construct
SEQUENCE: 951
EVQLVESGGG LVQPGGSLRL SCAASGFNIT ASYIHWVRQA PGKGLEWVGA IDPKGGSTRF   60
ADSVKGRFTI SADTSKNTAY LQMNSLRAED TAVYYCARSR WFRVLWSYVF DYWGQGTLVT  120
VSS                                                                123

SEQ ID NO: 952              moltype = AA   length = 123
FEATURE                     Location/Qualifiers
REGION                      1..123
                            note = Synthetic: 2193-C08; VH
source                      1..123
                            mol_type = protein
                            organism = synthetic construct
SEQUENCE: 952
EVQLVESGSG LVQPGGSLRL SCAASGFNIN HYYIHWVRQA PGKGLEWVGA IDPYPGSTYN   60
ADSVKGRFTI SADTSKNTAY LQMNSLRAED TAVYYCARSR WFRVLWSYVF DYWGQGTLVT  120
VSS                                                                123

SEQ ID NO: 953              moltype = AA   length = 123
FEATURE                     Location/Qualifiers
REGION                      1..123
                            note = Synthetic: 2193-B11; VH
source                      1..123
                            mol_type = protein
                            organism = synthetic construct
```

```
SEQUENCE: 953
EVQLVESGGG LVQPGGSLRL SCAASGFNIT GSYIHWVRQA PGKGLEWVGA IDPKSGFTSY    60
ADSAKGRFTI SADTSKNTAY LQMNSLRAED TAVYYCARSR WFRVLWSFVF DYWGQGTLVT   120
VSS                                                                 123

SEQ ID NO: 954          moltype = AA  length = 123
FEATURE                 Location/Qualifiers
REGION                  1..123
                        note = Synthetic: 2193-A03; VH
source                  1..123
                        mol_type = protein
                        organism = synthetic construct
SEQUENCE: 954
EVQLVESGGG LVQPGGSLRL SCAASGFNIA NYHIHWVRQA PGKGLEWVGA IDPKSGSTVH    60
ADSVKGRFTI SADTSKNTAY LQMNSLRAED TAVYYCARSR WSRVLWTYVF DYWGQGTLVT   120
VSS                                                                 123

SEQ ID NO: 955          moltype = AA  length = 123
FEATURE                 Location/Qualifiers
REGION                  1..123
                        note = Synthetic: 2193-D02; VH
source                  1..123
                        mol_type = protein
                        organism = synthetic construct
SEQUENCE: 955
EVQLVESGGG LVQPGGSLRL SCAASGFNIK DYYIHWVRQA PGKGLEWVGA IDPESGSTVY    60
ADSVKGRFTI SADTSKNTAY LQMNSLRAED TAVYYCARSR WFRVLWSYVF DYWGQGTLVT   120
VSS                                                                 123

SEQ ID NO: 956          moltype = AA  length = 123
FEATURE                 Location/Qualifiers
REGION                  1..123
                        note = Synthetic: 2193-B06; VH
source                  1..123
                        mol_type = protein
                        organism = synthetic construct
SEQUENCE: 956
EVQLVESGGG LVQPGGSLRL SCAASGFNID GYYIHWVRQA PGKGLEWVAA IDPHPGSTVY    60
ADSVKGRFTI SADTSKNTAY LQMNSLRAED TAVYYCARSR WFRVLWTYVF DYWGQGTLVT   120
VSS                                                                 123

SEQ ID NO: 957          moltype = AA  length = 123
FEATURE                 Location/Qualifiers
REGION                  1..123
                        note = Synthetic: 2193-B01; VH
source                  1..123
                        mol_type = protein
                        organism = synthetic construct
SEQUENCE: 957
EVQLVESGGG LVQPGGSLRL SCAASGFNIG GYYIHWVRQA PGKGLEWVGA IDPRSGYTVY    60
ADSVKGRFTI SADTSKNTAY LQMNSLRAED TAVYYCARSR WFRVLWSFVL DYWGQGTLVT   120
VSS                                                                 123

SEQ ID NO: 958          moltype = AA  length = 123
FEATURE                 Location/Qualifiers
REGION                  1..123
                        note = Synthetic: 2193-D09; VH
source                  1..123
                        mol_type = protein
                        organism = synthetic construct
SEQUENCE: 958
EVQLVESGGG LVQPGGSLRL SCAASGFNIN GYYIHWVRQA PGKGLEWVSA IDPNSGSTNF    60
ADSVKGRFTI SADTSKNTAY LQMNSLRAED TAVYYCARSR WFRVLWSYVF DYWGQGTPVT   120
VSS                                                                 123

SEQ ID NO: 959          moltype = AA  length = 123
FEATURE                 Location/Qualifiers
REGION                  1..123
                        note = Synthetic: 2193-E09; VH
source                  1..123
                        mol_type = protein
                        organism = synthetic construct
SEQUENCE: 959
EVQLVESGGG LVQPGGSLRL PCAASGFNIG AYYIHWVRQA PGKGLEWVGA IDPSGYTVP     60
ADSVKGRFTI SADTSKNTAY LQMNSLRAED TAVYYCARSR WYRVLWSYVF DYWGQGTLVT   120
VSS                                                                 123

SEQ ID NO: 960          moltype = AA  length = 123
FEATURE                 Location/Qualifiers
```

```
REGION                    1..123
                          note = Synthetic: 2193-B07; VH
source                    1..123
                          mol_type = protein
                          organism = synthetic construct
SEQUENCE: 960
EVQLVESGGG LVQPGGSLRL SCAASGFNIN NSYIHWVRQA PGKGLEWVGA IDPNSGSTLS    60
ADSVKGRFTI SADTSKSTAY LQMNSLRAED TAVYYCARSR WFRVLWSYIF DYWGQGTLVT   120
VSS                                                                 123

SEQ ID NO: 961            moltype = AA   length = 123
FEATURE                   Location/Qualifiers
REGION                    1..123
                          note = Synthetic: 2193-C06; VH
source                    1..123
                          mol_type = protein
                          organism = synthetic construct
SEQUENCE: 961
EVQLVESGGG LVQPGGSLRL SCAASGFNII VHYIHWVRQA PGKGLEWVSA IDPISGSTQW    60
ADSVKGRFTI SADTSKNTAY LQMNSLRAED TAVYYCARSR WRRALWIYVF DYWGQGTLVT   120
VSS                                                                 123

SEQ ID NO: 962            moltype = AA   length = 123
FEATURE                   Location/Qualifiers
REGION                    1..123
                          note = Synthetic: 2193-B05; VH
source                    1..123
                          mol_type = protein
                          organism = synthetic construct
SEQUENCE: 962
EVQLVESGGG LVQPGGSLRL SCAASGFNIN QYYIHWVRQA PGEGLEWVGA IDPIGGSTHL    60
ADSVKGRFTI SADTSKNTAY LQMNSLRAED AAVYYCARSR WYRVLWSYVF DYWGQGTLVT   120
VSS                                                                 123

SEQ ID NO: 963            moltype = AA   length = 123
FEATURE                   Location/Qualifiers
REGION                    1..123
                          note = Synthetic: 2193-A11; VH
source                    1..123
                          mol_type = protein
                          organism = synthetic construct
SEQUENCE: 963
EVQLVESGGG LVQPGGSLRL SCAASGFNID AYYIHWVRQA PGKGLEWVGA IDPKSGSTVY    60
ADSVKGRFTT SADTSKNTAY LQMNSLRAED TAVYYCARSR WFRVLWSYVF DYWGQGTLVT   120
VSS                                                                 123

SEQ ID NO: 964            moltype = AA   length = 123
FEATURE                   Location/Qualifiers
REGION                    1..123
                          note = Synthetic: 2193-E02; VH
source                    1..123
                          mol_type = protein
                          organism = synthetic construct
SEQUENCE: 964
EVQLVESGGG LVQPGGSLRL SCAASGFNIK DYYIHWVRQA PGKGLEWVGS IDPTSGSTVI    60
ADSVKGRFTI SADTSKNTAY LQMNSLRAED TAVYYCARSR WWRVLWSYVF DYWGQGTLVT   120
VSS                                                                 123

SEQ ID NO: 965            moltype = AA   length = 123
FEATURE                   Location/Qualifiers
REGION                    1..123
                          note = Synthetic: 2193-A08; VH
source                    1..123
                          mol_type = protein
                          organism = synthetic construct
SEQUENCE: 965
EVQLVESGGG LVQPGGSLRL SCAASGFNII DSYIHWVRQA PGKGLEWVGA IDPNAGSTVY    60
ADSVRGRFTI SADTSKNTAY IQMNSLRAED TAVYYCARSR WFRVLWSYVF DYWGQGTLVT   120
VSS                                                                 123

SEQ ID NO: 966            moltype = AA   length = 123
FEATURE                   Location/Qualifiers
REGION                    1..123
                          note = Synthetic: 2193-C11; VH
source                    1..123
                          mol_type = protein
                          organism = synthetic construct
SEQUENCE: 966
EVQLVESGGG LVQPGGSLRL SCAASGFNIA DSYIHWVRQA PGKGLEWVAV IDPKSGSTNY    60
```

```
ADSVKGRFTI SADTSKNTAY LQMNSLRAED TAVYYCARSR WFRVLWSYVF DYWGQGTLVT    120
VSS                                                                 123

SEQ ID NO: 967          moltype = AA  length = 123
FEATURE                 Location/Qualifiers
REGION                  1..123
                        note = Synthetic: 2193-A01; VH
source                  1..123
                        mol_type = protein
                        organism = synthetic construct
SEQUENCE: 967
EVQLVESGGG LVQPGGSLRL SCAASGFNIN DHYIHWVRQA PGKGLEWVGA IDPTSGSTVF    60
ADSVKGRFTI SADTSKNTAY LQMNSLRAED TAVYYCARSR WFRVLWSYVF DYWGQGTLVT    120
VSS                                                                 123

SEQ ID NO: 968          moltype = AA  length = 123
FEATURE                 Location/Qualifiers
REGION                  1..123
                        note = Synthetic: 2193-D07; VH
source                  1..123
                        mol_type = protein
                        organism = synthetic construct
SEQUENCE: 968
EVQLVESGGG LVQPGGSLRL SCAASGFNII DYNIHWVRQA PGKGLEWVTA IGPADGSTVN    60
ADSLKGRFTI SADTSKNTAY LQMNSLRAED TAVYYCARSR WLRVLWSYVF DYWGQGTLVT    120
VSS                                                                 123

SEQ ID NO: 969          moltype = AA  length = 123
FEATURE                 Location/Qualifiers
REGION                  1..123
                        note = Synthetic: 2193-A05; VH
source                  1..123
                        mol_type = protein
                        organism = synthetic construct
SEQUENCE: 969
EVQLVESGGG LVQPGGSLRL SCAASGFNIK GYYIHWVRQA PGKGLEWVSV IDPNSGSTIF    60
ADSVKGRFTI SADTSKNTAY LQMNSLRAED TAVYYCARSR WFRVLWSYVL DYWGQGTLVT    120
VSS                                                                 123

SEQ ID NO: 970          moltype = AA  length = 123
FEATURE                 Location/Qualifiers
REGION                  1..123
                        note = Synthetic: 2193-C03; VH
source                  1..123
                        mol_type = protein
                        organism = synthetic construct
SEQUENCE: 970
EVQLVESGGG LVQPGGSLRL SCAASGFNIN YSYIHWVRQA PGKGLEWVGA IEPKSGSTAS    60
ADSVKGRFTI SADTSKNTAY LQMNSLRAED AAVYYCARSR WYRVLWSYVL DYWGQGTLVT    120
VSS                                                                 123

SEQ ID NO: 971          moltype = AA  length = 123
FEATURE                 Location/Qualifiers
REGION                  1..123
                        note = Synthetic: 2193-C09; VH
source                  1..123
                        mol_type = protein
                        organism = synthetic construct
SEQUENCE: 971
EVQLVESGGG LVQPGGPLRL SCAASGFNIN HSYIHWVRQA PGKGLEWVGA IDPISGSTVY    60
ADSVKGRFTI SADTSKNTAY LQMNSLRAED TAVYYCARSR WSRVLWSYVF DYWGQGTLVT    120
VSS                                                                 123

SEQ ID NO: 972          moltype = AA  length = 123
FEATURE                 Location/Qualifiers
REGION                  1..123
                        note = Synthetic: 2193-D01; VH
source                  1..123
                        mol_type = protein
                        organism = synthetic construct
SEQUENCE: 972
EVQLVESGGG LVQPGGSLRL SCAASGFNIN DSYIHWVRQA PGKGLEWVGA IDPTSGPTVY    60
ADSVKGRFTI SADTSKSTAY LQMNSLRAED TAVYYCARSR WFRVLWSYVF DYWGQGTLVT    120
VSS                                                                 123

SEQ ID NO: 973          moltype = AA  length = 123
FEATURE                 Location/Qualifiers
REGION                  1..123
                        note = Synthetic: 2193-E01; VH
```

```
source                   1..123
                         mol_type = protein
                         organism = synthetic construct
SEQUENCE: 973
EVQLVESGGG LVQPGGSLRL SCAASGFNIK GKYIHWVRQA PGKGLEWVGA IDPKSGSTAH   60
ADSVKGRFTI SADTSKNTAY LQMNSLRAED TAAYYCARSR WFRVLWTYVF DYWGQGTLVT  120
VSS                                                                123

SEQ ID NO: 974           moltype = AA  length = 123
FEATURE                  Location/Qualifiers
REGION                   1..123
                         note = Synthetic: 2193-C07; VH
source                   1..123
                         mol_type = protein
                         organism = synthetic construct
SEQUENCE: 974
EVQLVESGGG LVQPGGSLRL SCAASGFNIK DQDIHWVRQA PGKGLEWVGA IDPTRGATVY   60
ADSVKGRFTI SADTSKNTAY LQMNSLRAEG TAVYYCARSR WYRVLWSFVF DYWGQGTLVT  120
VSS                                                                123

SEQ ID NO: 975           moltype = AA  length = 123
FEATURE                  Location/Qualifiers
REGION                   1..123
                         note = Synthetic: 2193-B04; VH
source                   1..123
                         mol_type = protein
                         organism = synthetic construct
SEQUENCE: 975
EVQLVESGGG LVQPGGSLRL SCAASGFNIS NSYIHWVRQA PGKGLEWVGA IEPKNGSTHH   60
ADSVKGRFTI SADTSKNTAY LQMNSLRAED TAVYYCARSR WFRVLWTYVF DYWGQGTLVT  120
VSS                                                                123

SEQ ID NO: 976           moltype = AA  length = 123
FEATURE                  Location/Qualifiers
REGION                   1..123
                         note = Synthetic: 2193-C10; VH
source                   1..123
                         mol_type = protein
                         organism = synthetic construct
SEQUENCE: 976
EVQLVESGGG LVQPGGSLRL SCAASGFNIN NAYIHWVRQA PGKGLEWVGA IDPRSGSTIS   60
ADSMKGRFTI SADTSKNTAY LQMNSLRAED TAVYYCARSR WFRVLWSFGF DYWGQGTLVT  120
VSS                                                                123

SEQ ID NO: 977           moltype = AA  length = 123
FEATURE                  Location/Qualifiers
REGION                   1..123
                         note = Synthetic: 2193-C01; VH
source                   1..123
                         mol_type = protein
                         organism = synthetic construct
SEQUENCE: 977
EVQLVESGGG LVQPGGSLRL SCAASGLNIN DHYIHWVRQA PGKGLEWVGT IDPKSGSTHV   60
ADSVKGRFTI SADTSKNTAY LQMNSLRAED TAVYYCARSR WFRVLWSYVF DYWGQGTLVT  120
VSS                                                                123

SEQ ID NO: 978           moltype = AA  length = 123
FEATURE                  Location/Qualifiers
REGION                   1..123
                         note = Synthetic: 2193-A04; VH
source                   1..123
                         mol_type = protein
                         organism = synthetic construct
SEQUENCE: 978
EVQLVESGGG LVQPGGSLRL SCAASGFNII SYYIHWVRQA PGKGLEWVGA IDPNSGSTLL   60
ADSVKGRFTI SADTSKNTAY LQMNSLRAED TAVYYCARSR WFRVLWSYVY DYWGQGTLVT  120
VSS                                                                123

SEQ ID NO: 979           moltype = AA  length = 120
FEATURE                  Location/Qualifiers
REGION                   1..120
                         note = Synthetic: 1944-A07; VH
source                   1..120
                         mol_type = protein
                         organism = synthetic construct
SEQUENCE: 979
EVQLVESGGG LVQPGGSLRL SCAASGFNIT GYYIHWVRQA PGKGLEWVGY ISPNSGSTYY   60
ADSVKGRFTI SADTSKNTAY LQMNSLRAED TAVYYCARDS RRYVRPFDYW GQGTLVTVSS  120
```

```
SEQ ID NO: 980              moltype = AA  length = 120
FEATURE                     Location/Qualifiers
REGION                      1..120
                            note = Synthetic: 2194-A02; VH
source                      1..120
                            mol_type = protein
                            organism = synthetic construct
SEQUENCE: 980
EVQLVESGGG LVQPGGSLRL SCAASGFNIT GYYIHWVRQA PGKGLEWVGY ISPLAGNTYH    60
ADSVKGRFTI SADTSKNTAY LQMNSLRAED TAVYYCARDS RRYVRPFDYW GQGTLVTVSS   120

SEQ ID NO: 981              moltype = AA  length = 120
FEATURE                     Location/Qualifiers
REGION                      1..120
                            note = Synthetic: 2194-A05; VH
source                      1..120
                            mol_type = protein
                            organism = synthetic construct
SEQUENCE: 981
EVQLVESGGG LVQPGGSLRL SCAASGFNIK EYIHIHWVRQA PGKGLEWVGY ISPNSGSTYY    60
ADSVKGRFTI SADTSKNTAY LQMNSLRAED TAVYYCARDH RRYVRPFDYW GQGTLVTVSS   120

SEQ ID NO: 982              moltype = AA  length = 120
FEATURE                     Location/Qualifiers
REGION                      1..120
                            note = Synthetic: 2194-B04; VH
source                      1..120
                            mol_type = protein
                            organism = synthetic construct
SEQUENCE: 982
EVQLVESGGG LVQPGGSLRL SCAASGFNIT GYHIHWVRQA PGKGLEWVGY ISPLAGNTYH    60
ADSVKGRFTI SADTSKNTAY LQMNSLRAED TAVYYCTRDS RRYVRPLDYW GQGTLVTVSS   120

SEQ ID NO: 983              moltype = AA  length = 120
FEATURE                     Location/Qualifiers
REGION                      1..120
                            note = Synthetic: 2194-A09; VH
source                      1..120
                            mol_type = protein
                            organism = synthetic construct
SEQUENCE: 983
EVQLVESGGG LVQPGGSLRL SCAASGFNIT GYYIHWVRQA PGKGLEWVGY ITPLSGATYR    60
ADSVKGRFTI SADTSKNTAY LQMNSLRAED TAVYYCARDS RRYVRPFDYW GQGTLVTVSS   120

SEQ ID NO: 984              moltype = AA  length = 120
FEATURE                     Location/Qualifiers
REGION                      1..120
                            note = Synthetic: 2194-A01; VH
source                      1..120
                            mol_type = protein
                            organism = synthetic construct
SEQUENCE: 984
EVQLVESGGG LVQPGGSLRL SCAASGFNIT GYYIHWVRQA PGKGLEWVGY ISPLAGNTYH    60
ADSVKGRFNI SADTSKNTAY LQMNSLRAED TAVYYCARDS RRYVRPMDYW GQGTLVTVSS   120

SEQ ID NO: 985              moltype = AA  length = 120
FEATURE                     Location/Qualifiers
REGION                      1..120
                            note = Synthetic: 2194-B03; VH
source                      1..120
                            mol_type = protein
                            organism = synthetic construct
SEQUENCE: 985
EVQLVESGGG LVQPGGSLRL SCAASGFNIT SYYIHWVRQA PGKGLEWVGY ISPLAGNTYH    60
ADSVKGRFTI SADTSKNTAY LQMNSLRAED TAVYYCARDS RRYVRPFDYW GQGTLVTVSS   120

SEQ ID NO: 986              moltype = AA  length = 120
FEATURE                     Location/Qualifiers
REGION                      1..120
                            note = Synthetic: 2194-B02; VH
source                      1..120
                            mol_type = protein
                            organism = synthetic construct
SEQUENCE: 986
EVQLVESGGG LVQPGGSLRL SCAASGFNIS GYYIHWVRQT PGKGLEWVGY ISPLAGNTYH    60
ADSVKGRFTI SADTSKNTAY LQMNSLRAED TAVYYCARDS RRYVRPLDYW GQGTLVTVSS   120

SEQ ID NO: 987              moltype = AA  length = 120
FEATURE                     Location/Qualifiers
```

```
REGION                  1..120
                        note = Synthetic: 2194-A03; VH
source                  1..120
                        mol_type = protein
                        organism = synthetic construct
SEQUENCE: 987
EVQLVESGGG LVQPGGPLRL SCAASGFNIT GYYIHWVRQA PGKGLEWVGY ITPNSGTTYS   60
ADSVKGRFTI SADTSKNTAY LQMNSLRAED TAVYYCARDS RRYVRPLDYW GQGTLVTVSS  120

SEQ ID NO: 988          moltype = AA   length = 120
FEATURE                 Location/Qualifiers
REGION                  1..120
                        note = Synthetic: 2194-A11; VH
source                  1..120
                        mol_type = protein
                        organism = synthetic construct
SEQUENCE: 988
EVQLVESGGG LVQPGGSLRL SCAASGFNIT QYYIHWVRQA PGKGLEWVGY ISPNSGYTTD   60
ADSVKGRFTI SADTSKNTAY LQMNSLRAED TAVYYCARDS RRYVRPFDYW GQGTLVTVSS  120

SEQ ID NO: 989          moltype = AA   length = 120
FEATURE                 Location/Qualifiers
REGION                  1..120
                        note = Synthetic: 2194-A08; VH
source                  1..120
                        mol_type = protein
                        organism = synthetic construct
SEQUENCE: 989
EVQLVESGGG LVQPGGSLRL SCAASGFNIT GYHIHWVRQA PGKGLEWVGY IAPSSGYTYD   60
ADSVKGRFTI SADTSKNTAY LQMNSLRAED TAVYYCARDS RRYVRPFDYW GQGTLVTVSS  120

SEQ ID NO: 990          moltype = AA   length = 120
FEATURE                 Location/Qualifiers
REGION                  1..120
                        note = Synthetic: 2194-A04; VH
source                  1..120
                        mol_type = protein
                        organism = synthetic construct
SEQUENCE: 990
EVQLVESGGG LVQPGGSLRL SCAASGFNIT GYYIHWVRQA PGKGLEWVGY ISPLAGNTHH   60
ADSVKGRFTI SADTSKNTAY LQMNSLRAED TAVYYCARDS RRYVRPLDYW GQGTLVTVSS  120

SEQ ID NO: 991          moltype = AA   length = 120
FEATURE                 Location/Qualifiers
REGION                  1..120
                        note = Synthetic: 2194-A10; VH
source                  1..120
                        mol_type = protein
                        organism = synthetic construct
SEQUENCE: 991
EVQLVESGGG LVQPGGSLRL SCAASGFNIT QYYIHWVRQA PAKGLEWVGY ISPNSGSTHI   60
ADSVKGRFTI SADTSKNTAY LQMNSLRAED TAVYYCARDS RRYVRPFDYW GQSTLVTVSS  120

SEQ ID NO: 992          moltype = AA   length = 120
FEATURE                 Location/Qualifiers
REGION                  1..120
                        note = Synthetic: 2194-A07; VH
source                  1..120
                        mol_type = protein
                        organism = synthetic construct
SEQUENCE: 992
EVQLVESGGG LVQPGGSLRL SCAASGFNFT DYYIHWVRQA PGKGLEWVGY ISPLAGNTYH   60
ADSVKGRFTI SADTSKNTAY LQMNSLRAED TAVYYCARDS RRYVRPFDYW GQGTLVTVSS  120

SEQ ID NO: 993          moltype = AA   length = 120
FEATURE                 Location/Qualifiers
REGION                  1..120
                        note = Synthetic: 2194-B01; VH
source                  1..120
                        mol_type = protein
                        organism = synthetic construct
SEQUENCE: 993
EVQLVESGGG LVQPGGSLRL SCAASGFNIA SYYIHWVRQA PGKGLEWVGY ISPLAGNTYH   60
ADSVKGRFTI SADTSKNTAY LQMNSLRAED TAVYYCARDS RRYVRPFDYW GQGTLVTVSS  120

SEQ ID NO: 994          moltype = AA   length = 120
FEATURE                 Location/Qualifiers
REGION                  1..120
                        note = Synthetic: 2194-A06; VH
```

```
                        -continued source                  1..120
                        mol_type = protein
                        organism = synthetic construct
SEQUENCE: 994
EVQLVESGGG LVQPGGSLRL SCAASGFNIT DYYIHWVRQA PGKGLEWVGY ISPLAGNTYH    60
ADSVKGRFPI SADTSKNTAY LQMNSLRAED TAVYYCARDS RRYVRPFDYW GQGTLVTVSS   120

SEQ ID NO: 995          moltype = AA  length = 120
FEATURE                 Location/Qualifiers
REGION                  1..120
                        note = Synthetic: 2196-C01; VH
source                  1..120
                        mol_type = protein
                        organism = synthetic construct
SEQUENCE: 995
EVQLVESGGG LVQPGGSLRL SCAASGFNII GYYIHWVRQA PGKGLEWVGS ITPLSGATSK    60
ADSVKGRFTI SADTSKNTAY LQMNSLRAED TAVYYCARDS RRYIRSWDYW GQGTLVTVSS   120

SEQ ID NO: 996          moltype = AA  length = 120
FEATURE                 Location/Qualifiers
REGION                  1..120
                        note = Synthetic: 2196-A02; VH
source                  1..120
                        mol_type = protein
                        organism = synthetic construct
SEQUENCE: 996
EVQLVESGGG LVQPGGSLRL SCAASGFNIT GYYIHWVRQA PGKGLEWVGQ ISPNSGATHD    60
ADSVKGRFTI SADTSKNTAY LQMNSLRAED TAVYYCARDS RRYVRGWDYW GQGTLVTVSS   120

SEQ ID NO: 997          moltype = AA  length = 120
FEATURE                 Location/Qualifiers
REGION                  1..120
                        note = Synthetic: 2196-B03; VH
source                  1..120
                        mol_type = protein
                        organism = synthetic construct
SEQUENCE: 997
EVQLVESGGG LAQPGGSLRL SCAASGFNIT GYYIHWVRQA PGKGLEWVGY ISPNSGATHY    60
ADSVKGRFTI SADTSKNTAY LQMNSLRAED TAVYYCARDS RRYVRPFDYW GQGTLVTVSS   120

SEQ ID NO: 998          moltype = AA  length = 120
FEATURE                 Location/Qualifiers
REGION                  1..120
                        note = Synthetic: 2196-A05; VH
source                  1..120
                        mol_type = protein
                        organism = synthetic construct
SEQUENCE: 998
EVQLVESGGG LVQPGGSLRL SCAASGFNIT NYYIHWVRQA PGKGLEWVGY ISPNSGATYQ    60
ADSVKGRFTI SADTSKNTAY LQMNSLRAED TAVYYCARDS RRYVRSWDYW GQGTLVTVSS   120

SEQ ID NO: 999          moltype = AA  length = 120
FEATURE                 Location/Qualifiers
REGION                  1..120
                        note = Synthetic: 2196-C02; VH
source                  1..120
                        mol_type = protein
                        organism = synthetic construct
SEQUENCE: 999
EVQLVESGGG LVQPGGSLRL SCAASGFNIT GYHIHWVRQA PGKGLEWVGF ISPNSGWTYS    60
ADSVKGRFTI SADTSKNTAY LQMNSLRAED TAVYYCARDS RRYVRPFDYW GQGTLVTVSS   120

SEQ ID NO: 1000         moltype = AA  length = 120
FEATURE                 Location/Qualifiers
REGION                  1..120
                        note = Synthetic: 2196-B11; VH
source                  1..120
                        mol_type = protein
                        organism = synthetic construct
SEQUENCE: 1000
EVQLVESGGG LVQPGGSLRL SCAASGFNIT GYYIHWVRQA PGRGLEWVGQ ISPNSGYTYY    60
ADSVKGRFTI SADTSKNTAY LQMNSLRAED TAVYYCARDS RRYIRSWDYW GQGTLVTVSS   120

SEQ ID NO: 1001         moltype = AA  length = 120
FEATURE                 Location/Qualifiers
REGION                  1..120
                        note = Synthetic: 2196-B08; VH
source                  1..120
                        mol_type = protein
```

```
                            organism = synthetic construct
SEQUENCE: 1001
EVQLVESGGG LVQPGGSLRL SCAASGFNIT GYYIHWVRQA PGKGLEWVGQ ISPNSGYTYL   60
ADSVKGRFTI SADTSKNTAY LQMNSLRAED TAVYYCARDS RRYVRGWDYW GQGTLVTVSS  120

SEQ ID NO: 1002         moltype = AA   length = 120
FEATURE                 Location/Qualifiers
REGION                  1..120
                        note = Synthetic: 2196-A04; VH
source                  1..120
                        mol_type = protein
                        organism = synthetic construct
SEQUENCE: 1002
EVQLVESGGG LVQPGGSLRL SCAASGFNIS PYYIHWVRQA PGKGLEWVGQ IYPISGHTYQ   60
ADSVKGRFTI SADTSKNTAY LQMNSLRAED TAVYYCARES RRYVGPFGYW GQGTLVTVSS  120

SEQ ID NO: 1003         moltype = AA   length = 120
FEATURE                 Location/Qualifiers
REGION                  1..120
                        note = Synthetic: 2196-A03; VH
source                  1..120
                        mol_type = protein
                        organism = synthetic construct
SEQUENCE: 1003
EVQLVESGGG LVQPGGSLRL SCAASGFNIT QYHIHWVRQA PGKGLEWVGY ISPNSGSTHE   60
ADSVKGRFTI SADTSKNTAY LQMNSLRAED TAVYYCARDS RRYVRGWDYW GQGTLVTVSS  120

SEQ ID NO: 1004         moltype = AA   length = 120
FEATURE                 Location/Qualifiers
REGION                  1..120
                        note = Synthetic: 2196-B07; VH
source                  1..120
                        mol_type = protein
                        organism = synthetic construct
SEQUENCE: 1004
EVQLVESGGG LVQPGGSLRL SCAASGFNIT GYHIHWVRQA PGEGLEWVGY ISPNSGATYY   60
ADSVEGRFTI SADTSKNTAY LQMHSLRAED TAVYYCTRDS RRYVRGWDYW GQGTLVTVSS  120

SEQ ID NO: 1005         moltype = AA   length = 120
FEATURE                 Location/Qualifiers
REGION                  1..120
                        note = Synthetic: 2196-A06; VH
source                  1..120
                        mol_type = protein
                        organism = synthetic construct
SEQUENCE: 1005
EVQLVESGGG LVQPGGSLRL SCAASGFNIT GYYIHWVRQA PGKGLEWVGQ ISPNSGSTHQ   60
ADSVKGRFTI SADTSKNTAY LQMNSLRAGD TAVYYCARDS RRYVRGWDYW GQGTLVTVSS  120

SEQ ID NO: 1006         moltype = AA   length = 120
FEATURE                 Location/Qualifiers
REGION                  1..120
                        note = Synthetic: 2196-B05; VH
source                  1..120
                        mol_type = protein
                        organism = synthetic construct
SEQUENCE: 1006
EVQLVESGGG LVQPGGSLRL SCAASGFNIT GYYIHWVRQA PGKGLEWVGQ ISPNSGATYH   60
ADSVKGRFTI SADTSKNTAY LQMNSLRAED TAVYYCARDS RRYVRGWDYW GQGTLVTVSS  120

SEQ ID NO: 1007         moltype = AA   length = 120
FEATURE                 Location/Qualifiers
REGION                  1..120
                        note = Synthetic: 2196-A01; VH
source                  1..120
                        mol_type = protein
                        organism = synthetic construct
SEQUENCE: 1007
EVQLVESGGG LVQPGGSLRL SCAASGFNIT GYYIHWVRQA PGKGLEWVGQ ISPNSGYTYY   60
ADSVKGRFTI SADTSKNTAY LQMNSLRAED TAVYYCARDS RRYVRGWDYW GQGTLVTVSS  120

SEQ ID NO: 1008         moltype = AA   length = 120
FEATURE                 Location/Qualifiers
REGION                  1..120
                        note = Synthetic: 2196-B01; VH
source                  1..120
                        mol_type = protein
                        organism = synthetic construct
SEQUENCE: 1008
```

```
EVQLVESGGG LVQPGGSLRL SCAASGFNIT GYYIHWVRQA PGKGLEWVGQ ISPNSGYTYY    60
ADSVKGRFTI SADTSKNTTY LQMNSLRAED TAVYYCARDS RRYVRSWDYW GQGTLVTVSS   120

SEQ ID NO: 1009           moltype = AA   length = 120
FEATURE                   Location/Qualifiers
REGION                    1..120
                          note = Synthetic: 2196-A09; VH
source                    1..120
                          mol_type = protein
                          organism = synthetic construct
SEQUENCE: 1009
EVQLVESGGG LVQPGGSLRL SCAASGFNIT GYYIHWVRQA PGKGLEWVGQ ISPNSGATHY    60
ADSVKGRFTI SADTSKNTAY LQMNSLRAED TAVYYCARDS RRYIRSWDYW GQGTLVTVSS   120

SEQ ID NO: 1010           moltype = AA   length = 120
FEATURE                   Location/Qualifiers
REGION                    1..120
                          note = Synthetic: 2196-A08; VH
source                    1..120
                          mol_type = protein
                          organism = synthetic construct
SEQUENCE: 1010
EVQLVESGGG LVQPGGSLRL SCAASGFNIT GYYIHWVRQA PGKGLEWVGY ISPNSGSTYK    60
ADSVKGRFTI SADTSRNTAY LQMNSLRAED TAVYYCARDS RRYVRSWDYW GQGTLVTVSS   120

SEQ ID NO: 1011           moltype = AA   length = 120
FEATURE                   Location/Qualifiers
REGION                    1..120
                          note = Synthetic: 2196-A10; VH
source                    1..120
                          mol_type = protein
                          organism = synthetic construct
SEQUENCE: 1011
EVQLVESGGG LVQPGGSLRL SCAASGFNIT GYYIHWVRQA PGKGLEWVGY ISPNSGATHY    60
ADSVKGRFTI SADISKNTAY LQMNSLRAED TAVHYCARDS RRYVRSWDYW GQGTLVTVSS   120

SEQ ID NO: 1012           moltype = AA   length = 120
FEATURE                   Location/Qualifiers
REGION                    1..120
                          note = Synthetic: 2196-B06; VH
source                    1..120
                          mol_type = protein
                          organism = synthetic construct
SEQUENCE: 1012
EVQLVESGGG LVQPGGSLRL SCAASGFNIT GYYIHWVRQA PGKGLEWVGQ ISPNSGSTYS    60
ADSVKGRFTI SADTSKNTAY LQMNSLRAED TAVYYCARDS RRYVLSWDYW GQGTLVTVSS   120

SEQ ID NO: 1013           moltype = AA   length = 120
FEATURE                   Location/Qualifiers
REGION                    1..120
                          note = Synthetic: 2196-B09; VH
source                    1..120
                          mol_type = protein
                          organism = synthetic construct
SEQUENCE: 1013
EVQLVESGGG LVQPEGSLRL SCAASGFNIT EYYIHWVRQA PGKGLEWVGY ISPNSGSTYY    60
ADSVKGRFTI SADTSKNTAY LQMNSLRAED TAVYYCARDS RRYVRSWDYW GQGTLVTVSS   120

SEQ ID NO: 1014           moltype = AA   length = 120
FEATURE                   Location/Qualifiers
REGION                    1..120
                          note = Synthetic: 2196-C03; VH
source                    1..120
                          mol_type = protein
                          organism = synthetic construct
SEQUENCE: 1014
EVQLVESGGG LVQPGGSLRL SCAASGFNIT GYYIHWVRQA PGKGLEWVGQ ISPNSGSTYS    60
ADSVKGRFTI SADTSKNTAY LQMSSLRAED TAVYYCARDS RRYVLSWDYW GQGTLVTVSS   120

SEQ ID NO: 1015           moltype = AA   length = 120
FEATURE                   Location/Qualifiers
REGION                    1..120
                          note = Synthetic: 2196-C04; VH
source                    1..120
                          mol_type = protein
                          organism = synthetic construct
SEQUENCE: 1015
EVQLVESGGG LVQPGGSLRL SCAASGFNIT GYYIHWVRQA PGKGLEWVGF IAPLSGSTHN    60
ADSVKGRFTI SADTSKNTAY LQMNSLRAED TAVYYCARES RRYVNPWDYW GQGTLVTVSS   120
```

```
SEQ ID NO: 1016         moltype = AA  length = 120
FEATURE                 Location/Qualifiers
REGION                  1..120
                        note = Synthetic: 2196-A07; VH
source                  1..120
                        mol_type = protein
                        organism = synthetic construct
SEQUENCE: 1016
EVQLVESGGG LVQPGGSLRL SCAASGFNIT GYYIHWVRQA PGKGLEWVGQ ISPNSGSTYY   60
ADSVKGRFTI SADTSKNTAY LQMSSLRAED TAVYYCARDS RRYVRGWDYW GQGTLVTVSS  120

SEQ ID NO: 1017         moltype = AA  length = 120
FEATURE                 Location/Qualifiers
REGION                  1..120
                        note = Synthetic: 2196-A11; VH
source                  1..120
                        mol_type = protein
                        organism = synthetic construct
SEQUENCE: 1017
EVQLVESGGG LVQPGGSLRL SCAASGFNIT GYYIHWVRQA PGKGLEWVGQ ISPNSGTTYD   60
ADSVKGRFTI SADTSKNTAY LQMNSLRAED TAVYYCARDS RRYVRGWDYW GQGTLVTVSS  120

SEQ ID NO: 1018         moltype = AA  length = 120
FEATURE                 Location/Qualifiers
REGION                  1..120
                        note = Synthetic: 2196-B02; VH
source                  1..120
                        mol_type = protein
                        organism = synthetic construct
SEQUENCE: 1018
EVQLVESGGG LVQPGGSLRL SCAASGFNIT QYYIHWVRQA PGKGLEWVGY ISPNSGQTYD   60
ADSVKGRFTI SADTSKNTAY LQMNSLRAED TAVYYCARDS RRYVRSWDYW GQGTLVTVSS  120

SEQ ID NO: 1019         moltype = AA  length = 120
FEATURE                 Location/Qualifiers
REGION                  1..120
                        note = Synthetic: 2196-B04; VH
source                  1..120
                        mol_type = protein
                        organism = synthetic construct
SEQUENCE: 1019
EVQLVESGGG LVQPGGSLRL SCAASGFNIT EYYIHWVRQA PGKGLEWVGY ISPNSGATYQ   60
ADSVKGRFTI SADTSKNTAY LQMNSLRAED TAVYYCARDS RRYVRGWDYW GQGTLVTVSS  120

SEQ ID NO: 1020         moltype = AA  length = 120
FEATURE                 Location/Qualifiers
REGION                  1..120
                        note = Synthetic: 2196-B10; VH
source                  1..120
                        mol_type = protein
                        organism = synthetic construct
SEQUENCE: 1020
EVQLVESGGG LVQPGGSLRL SCAASGFNIT GYYIHWVRQA PGKGLEWVGS ITPLSGATSK   60
ADSVKGRFTI SADTSKNTAY LQMNSLRAED TAVYYCARDS RRYIRSWDYW GQGTLVTVSS  120

SEQ ID NO: 1021         moltype = AA  length = 107
FEATURE                 Location/Qualifiers
REGION                  1..107
                        note = Synthetic: trastuzumab; VL
source                  1..107
                        mol_type = protein
                        organism = synthetic construct
SEQUENCE: 1021
DIQMTQSPSS LSASVGDRVT ITCRASQDVN TAVAWYQQKP GKAPKLLIYS ASFLYSGVPS   60
RFSGSRSGTD FTLTISSLQP EDFATYYCQQ HYTTPPTFGQ GTKVEIK                107

SEQ ID NO: 1022         moltype = AA  length = 109
FEATURE                 Location/Qualifiers
REGION                  1..109
                        note = Synthetic: SP34 ; VL
source                  1..109
                        mol_type = protein
                        organism = synthetic construct
SEQUENCE: 1022
QAVVTQESAL TTSPGETVTL TCRSSTGAVT TSNYANWVQE KPDHLFTGLI GGTNKRAPGV   60
PARFSGSLIG DKAALTITGA QTEDEAIYFC ALWYSNLWVF GGGTKLTVL              109

SEQ ID NO: 1023         moltype = AA  length = 110
```

```
FEATURE                 Location/Qualifiers
REGION                  1..110
                        note = Synthetic: 2037-B10; VL
source                  1..110
                        mol_type = protein
                        organism = synthetic construct
SEQUENCE: 1023
QTVVTQEPSL TVSPGGTVTL TCGSSTGAVT SGYYPNWLQQ KPGQAPRGLI GGTKFLAPGT    60
PARFSGSLLG GKAALTLSGV QPEDEAEYYC ALWYSNRWVF GGGTQLTVTG              110

SEQ ID NO: 1024         moltype = AA  length = 107
FEATURE                 Location/Qualifiers
REGION                  1..107
                        note = Synthetic: hUCHT1-LC3; VL
source                  1..107
                        mol_type = protein
                        organism = synthetic construct
SEQUENCE: 1024
DIQMTQSPST LSASVGDRVT ITCRASQDIR NYLNWYQQKP GKAPKLLIYY TSRLHSGVPS    60
RFSGSGSGTE YTLTISSLQP DDFATYYCQQ GNTLPWTFGG GTKVEIK                 107

SEQ ID NO: 1025         moltype = AA  length = 106
FEATURE                 Location/Qualifiers
REGION                  1..106
                        note = Synthetic: hOKT3-LC1; VL
source                  1..106
                        mol_type = protein
                        organism = synthetic construct
SEQUENCE: 1025
DIQMTQSPSS LSASVGDRVT ITCSASSSVS YMNWYQQKPG KAPKRLIYDT SKLASGVPSR    60
FSGSGSGTEY TLTISSLQPE DFATYYCQQW SSNPFTFGQG TKLEIK                  106

SEQ ID NO: 1026         moltype = AA  length = 110
FEATURE                 Location/Qualifiers
REGION                  1..110
                        note = Synthetic: hSP34-LC3; VL
source                  1..110
                        mol_type = protein
                        organism = synthetic construct
SEQUENCE: 1026
QTVVTQEPSL TVSPGGTVTL TCGSSTGAVT SGYYPNWFQQ KPGQAPRGLI GGTKFLAPGT    60
PARFSGSLLG GKAALTLSGV QPEDEAEYYC ALWYSNRWVF GGGTQLTVTG              110

SEQ ID NO: 1027         moltype = AA  length = 330
FEATURE                 Location/Qualifiers
REGION                  1..330
                        note = Synthetic: Human IgG1 HC Constant
source                  1..330
                        mol_type = protein
                        organism = synthetic construct
SEQUENCE: 1027
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPELLGG   120
PSVFLFPPKP KDTLMISRTP EVTCVVVDVS HEDPEVKFNW YVDGVEVHNA KTKPREEQYN   180
STYRVVSVLT VLHQDWLNGK EYKCKVSNKA LPAPIEKTIS KAKGQPREPQ VYTLPPSREE   240
MTKNQVSLTC LVKGFYPSDI AVEWESNGQP ENNYKTTPPV LDSDGSFFLY SKLTVDKSRW   300
QQGNVFSCSV MHEALHNHYT QKSLSLSPGK                                   330

SEQ ID NO: 1028         moltype = AA  length = 107
FEATURE                 Location/Qualifiers
REGION                  1..107
                        note = Synthetic: Human IgG LC Constant Ckappa
source                  1..107
                        mol_type = protein
                        organism = synthetic construct
SEQUENCE: 1028
RTVAAPSVFI FPPSDEQLKS GTASVVCLLN NFYPREAKVQ WKVDNALQSG NSQESVTEQD    60
SKDSTYSLSS TLTLSKADYE KHKVYACEVT HQGLSSPVTK SFNRGEC                107

SEQ ID NO: 1029         moltype = AA  length = 323
FEATURE                 Location/Qualifiers
REGION                  1..323
                        note = Synthetic: Mouse IgG1 HC Constant
source                  1..323
                        mol_type = protein
                        organism = synthetic construct
SEQUENCE: 1029
AKTTPPSVYP LAPGSAAQTN SMVTLGCLVK GYFPEPVTVT WNSGSLSSGV HTFPAVLQSD    60
LYTLSSSVTV PSSTWPSETV TCNVAHPASS TKVDKKIVPR DCGCKPCICT VPEVSSVFIF   120
```

```
PPKPKDVLTI TLTPKVTCVV VDISKDDPEV QFSWFVDDVE VHTAQTQPRE EQFNSTFRSV    180
SELPIMHQDW LNGKEFKCRV NSAAFPAPIE KTISKTKGRP KAPQVYTIPP PKEQMAKDKV    240
SLTCMITDFF PEDITVEWQW NGQPAENYKN TQPIMDTDGS YFVYSKLNVQ KSNWEAGNTF    300
TCSVLHEGLH NHHTEKSLSH SPG                                           323

SEQ ID NO: 1030         moltype = AA  length = 107
FEATURE                 Location/Qualifiers
REGION                  1..107
                        note = Synthetic: Mouse IgG LC Constant Ckappa
source                  1..107
                        mol_type = protein
                        organism = synthetic construct
SEQUENCE: 1030
RADAAPTVSI FPPSSEQLTS GGASVVCFLN NFYPKDINVK WKIDGSERQN GVLNSWTDQD     60
SKDSTYSMSS TLTLTKDEYE RHNSYTCEAT HKTSTSPIVK SFNRNEC                  107

SEQ ID NO: 1031         moltype = AA  length = 108
FEATURE                 Location/Qualifiers
REGION                  1..108
                        note = Synthetic: Kappa LC
source                  1..108
                        mol_type = protein
                        organism = synthetic construct
SEQUENCE: 1031
HMTVAAPSVF IFPPSDEQLK SGTASVVCLL NNFYPREAKV QWKVDNALQS GNSQESVTEQ     60
DSKDSTYSLS STLTLSKADY EKHKVYACEV THQGLSSPVT KSFNRGEC                 108

SEQ ID NO: 1032         moltype = AA  length = 106
FEATURE                 Location/Qualifiers
REGION                  1..106
                        note = Synthetic: Lambda LD
source                  1..106
                        mol_type = protein
                        organism = synthetic construct
SEQUENCE: 1032
GQPKAAPSVT LFPPSSEELQ ANKATLVCLI SDFYPGAVTV AWKADSSPVK AGVETTTPSK     60
QSNNKYAASS YLSLTPEQWK SHRSYSCQVT HEGSTVEKTV APTECS                   106

SEQ ID NO: 1033         moltype = AA  length = 20
FEATURE                 Location/Qualifiers
REGION                  1..20
                        note = Synthetic: FlagHis Tag
source                  1..20
                        mol_type = protein
                        organism = synthetic construct
SEQUENCE: 1033
GSGDYKDDDD KGSGHHHHHH                                                 20

SEQ ID NO: 1034         moltype = AA  length = 15
FEATURE                 Location/Qualifiers
REGION                  1..15
                        note = Synthetic: Linker
source                  1..15
                        mol_type = protein
                        organism = synthetic construct
SEQUENCE: 1034
GGGGSGGGGS GGGGS                                                      15

SEQ ID NO: 1035         moltype = AA  length = 11
FEATURE                 Location/Qualifiers
REGION                  1..11
                        note = Synthetic: Linker
source                  1..11
                        mol_type = protein
                        organism = synthetic construct
SEQUENCE: 1035
AAGSDQEPKS S                                                          11

SEQ ID NO: 1036         moltype = AA  length = 445
FEATURE                 Location/Qualifiers
REGION                  1..445
                        note = Synthetic: 2188-D04 IgG HC Y180F404TAG
source                  1..445
                        mol_type = protein
                        organism = synthetic construct
SEQUENCE: 1036
MEVQLVESGG GLVQPGGSLR LSCAASGFNI SDYDIHWVRQ APGKGLEWVG GIDPADGSTD     60
YADSVKGRFT ISADTSKNTA YLQMNSLRAE DTAVYYCARD YGVYDYWGQG TLVTVSSAST    120
KGPSVFPLAP SSKSTSGGTA ALGCLVKDYF PEPVTVSWNS GALTSGVHTF PAVLQSSGLS    180
```

```
LSSVVTVPSS SLGTQTYICN VNHKPSNTKV DKKVEPKSCD KTHTCPPCPA PELLGGPSVF    240
LFPPKPKDTL MISRTPEVTC VVVDVSHEDP EVKFNWYVDG VEVHNAKTKP REEQYNSTYR    300
VVSVLTVLHQ DWLNGKEYKC KVSNKALPAP IEKTISKAKG QPREPQVYTL PPSREEMTKN    360
QVSLTCLVKG FYPSDIAVEW ESNGQPENNY KTTPPVLDSD GSFLYSKLTV DKSRWQQGNV    420
FSCSVMHEAL HNHYTQKSLS LSPGK                                         445

SEQ ID NO: 1037            moltype = AA   length = 446
FEATURE                    Location/Qualifiers
REGION                     1..446
                           note = Synthetic: 2188-D04 Y180TAG V262E
source                     1..446
                           mol_type = protein
                           organism = synthetic construct
SEQUENCE: 1037
MEVQLVESGG GLVQPGGSLR LSCAASGFNI SDYDIHWVRQ APGKGLEWVG GIDPADGSTD     60
YADSVKGRFT ISADTSKNTA YLQMNSLRAE DTAVYYCARD YGVYDYWGQG TLVTVSSAST    120
KGPSVFPLAP SSKSTSGGTA ALGCLVKDYF PEPVTVSWNS GALTSGVHTF PAVLQSSGLS    180
LSSVVTVPSS SLGTQTYICN VNHKPSNTKV DKKVEPKSCD KTHTCPPCPA PELLGGPSVF    240
LFPPKPKDTL MISRTPEVTC EVVDVSHEDP EVKFNWYVDG VEVHNAKTKP REEQYNSTYR    300
VVSVLTVLHQ DWLNGKEYKC KVSNKALPAP IEKTISKAKG QPREPQVYTL PPSREEMTKN    360
QVSLTCLVKG FYPSDIAVEW ESNGQPENNY KTTPPVLDSD GSFFLYSKLT VDKSRWQQGN    420
VFSCSVMHEA LHNHYTQKSL SLSPGK                                        446

SEQ ID NO: 1038            moltype = AA   length = 446
FEATURE                    Location/Qualifiers
REGION                     1..446
                           note = Synthetic: 2188-D04 IgG HC F404TAG
source                     1..446
                           mol_type = protein
                           organism = synthetic construct
SEQUENCE: 1038
MEVQLVESGG GLVQPGGSLR LSCAASGFNI SDYDIHWVRQ APGKGLEWVG GIDPADGSTD     60
YADSVKGRFT ISADTSKNTA YLQMNSLRAE DTAVYYCARD YGVYDYWGQG TLVTVSSAST    120
KGPSVFPLAP SSKSTSGGTA ALGCLVKDYF PEPVTVSWNS GALTSGVHTF PAVLQSSGLY    180
SLSSVVTVPS SSLGTQTYIC NVNHKPSNTK VDKKVEPKSC DKTHTCPPCP APELLGGPSV    240
FLFPPKPKDT LMISRTPEVT CVVVDVSHED PEVKFNWYVD GVEVHNAKTK PREEQYNSTY    300
RVVSVLTVLH QDWLNGKEYK CKVSNKALPA PIEKTISKAK GQPREPQVYT LPPSREEMTK    360
NQVSLTCLVK GFYPSDIAVE WESNGQPENN YKTTPPVLDS DGSFLYSKLT VDKSRWQQGN    420
VFSCSVMHEA LHNHYTQKSL SLSPGK                                        446

SEQ ID NO: 1039            moltype = AA   length = 446
FEATURE                    Location/Qualifiers
REGION                     1..446
                           note = Synthetic: 2188-D04_HC_F404TAG_Knob
source                     1..446
                           mol_type = protein
                           organism = synthetic construct
SEQUENCE: 1039
MEVQLVESGG GLVQPGGSLR LSCAASGFNI SDYDIHWVRQ APGKGLEWVG GIDPADGSTD     60
YADSVKGRFT ISADTSKNTA YLQMNSLRAE DTAVYYCARD YGVYDYWGQG TLVTVSSAST    120
KGPSVFPLAP SSKSTSGGTA ALGCLVKDYF PEPVTVSWNS GALTSGVHTF PAVLQSSGLY    180
SLSSVVTVPS SSLGTQTYIC NVNHKPSNTK VDKKVEPKSC DKTHTCPPCP APELLGGPSV    240
FLFPPKPKDT LMISRTPEVT CVVVDVSHED PEVKFNWYVD GVEVHNAKTK PREEQYNSTY    300
RVVSVLTVLH QDWLNGKEYK CKVSNKALPA PIEKTISKAK GQPREPQVYT LPPSREEMTK    360
NQVSLWCLVK GFYPSDIAVE WESNGQPENN YKTTPPVLDS DGSFLYSKLT VDKSRWQQGN    420
VFSCSVMHEA LHNHYTQKSL SLSPGK                                        446

SEQ ID NO: 1040            moltype = AA   length = 446
FEATURE                    Location/Qualifiers
REGION                     1..446
                           note = Synthetic: 2188-D04_HC_F404TAG_Hole
source                     1..446
                           mol_type = protein
                           organism = synthetic construct
SEQUENCE: 1040
MEVQLVESGG GLVQPGGSLR LSCAASGFNI SDYDIHWVRQ APGKGLEWVG GIDPADGSTD     60
YADSVKGRFT ISADTSKNTA YLQMNSLRAE DTAVYYCARD YGVYDYWGQG TLVTVSSAST    120
KGPSVFPLAP SSKSTSGGTA ALGCLVKDYF PEPVTVSWNS GALTSGVHTF PAVLQSSGLY    180
SLSSVVTVPS SSLGTQTYIC NVNHKPSNTK VDKKVEPKSC DKTHTCPPCP APELLGGPSV    240
FLFPPKPKDT LMISRTPEVT CVVVDVSHED PEVKFNWYVD GVEVHNAKTK PREEQYNSTY    300
RVVSVLTVLH QDWLNGKEYK CKVSNKALPA PIEKTISKAK GQPREPQVYT LPPSREEMTK    360
NQVSLSCAVK GFYPSDIAVE WESNGQPENN YKTTPPVLDS DGSFLVSKLT VDKSRWQQGN    420
VFSCSVMHEA LHNHYTQKSL SLSPGK                                        446

SEQ ID NO: 1041            moltype = AA   length = 450
FEATURE                    Location/Qualifiers
REGION                     1..450
                           note = Synthetic: 2194-A05_HC_F404TAG_Knob
source                     1..450
```

```
                        mol_type = protein
                        organism = synthetic construct
SEQUENCE: 1041
MEVQLVESGG GLVQPGGSLR LSCAASGFNI KEYHIHWVRQ APGKGLEWVG YISPNSGSTY    60
YADSVKGRFT ISADTSKNTA YLQMNSLRAE DTAVYYCARD HRRYVRPFDY WGQGTLVTVS   120
SASTKGPSVF PLAPSSKSTS GGTAALGCLV KDYFPEPVTV SWNSGALTSG VHTFPAVLQS   180
SGLYSLSSVV TVPSSSLGTQ TYICNVNHKP SNTKVDKKVE PKSCDKTHTC PPCPAPELLG   240
GPSVFLFPPK PKDTLMISRT PEVTCVVVDV SHEDPEVKFN WYVDGVEVHN AKTKPREEQY   300
NSTYRVVSVL TVLHQDWLNG KEYKCKVSNK ALPAPIEKTI SKAKGQPREP QVYTLPPSRE   360
EMTKNQVSLW CLVKGFYPSD IAVEWESNGQ PENNYKTTPP VLDSDGSFLY SKLTVDKSRW   420
QQGNVFSCSV MHEALHNHYT QKSLSLSPGK                                    450

SEQ ID NO: 1042         moltype = AA  length = 450
FEATURE                 Location/Qualifiers
REGION                  1..450
                        note = Synthetic: 1987-C06_HC_F404TAG_Hole
source                  1..450
                        mol_type = protein
                        organism = synthetic construct
SEQUENCE: 1042
MEVQLVESGG GLVQPGGSLR LSCAASGFNI KEYHIHWVRQ APGKGLEWVG YISPNSGSTY    60
YADSVKGRFT ISADTSKNTA YLQMNSLRAE DTAVYYCARD HRRYVRPFDY WGQGTLVTVS   120
SASTKGPSVF PLAPSSKSTS GGTAALGCLV KDYFPEPVTV SWNSGALTSG VHTFPAVLQS   180
SGLYSLSSVV TVPSSSLGTQ TYICNVNHKP SNTKVDKKVE PKSCDKTHTC PPCPAPELLG   240
GPSVFLFPPK PKDTLMISRT PEVTCVVVDV SHEDPEVKFN WYVDGVEVHN AKTKPREEQY   300
NSTYRVVSVL TVLHQDWLNG KEYKCKVSNK ALPAPIEKTI SKAKGQPREP QVYTLPPSRE   360
EMTKNQVSLW CLVKGFYPSD IAVEWESNGQ PENNYKTTPP VLDSDGSFLY SKLTVDKSRW   420
QQGNVFSCSV MHEALHNHYT QKSLSLSPGK                                    450

SEQ ID NO: 1043         moltype = AA  length = 446
FEATURE                 Location/Qualifiers
REGION                  1..446
                        note = Synthetic: 1943-C01_HC_F404TAG_Hole
source                  1..446
                        mol_type = protein
                        organism = synthetic construct
SEQUENCE: 1043
MEVQLVESGG GLVQPGGSLR LSCAASGFNI NGYDIHWVRQ APGKGLEWVG YIDPNDGATN    60
YADSVKGRFT ISADTSKNTA YLQMNSLRAE DTAVYYCARD YGVFDYWGQG TLVTVSSAST   120
KGPSVFPLAP SSKSTSGGTA ALGCLVKDYF PEPVTVSWNS GALTSGVHTF PAVLQSSGLY   180
SLSSVVTVPS SSLGTQTYIC NVNHKPSNTK VDKKVEPKSC DKTHTCPPCP APELLGGPSV   240
FLFPPKPKDT LMISRTPEVT CVVVDVSHED PEVKFNWYVD GVEVHNAKTK PREEQYNSTY   300
RVVSVLTVLH QDWLNGKEYK CKVSNKALPA PIEKTISKAK GQPREPQVYT LPPSREEMTK   360
NQVSLSCAVK GFYPSDIAVE WESNGQPENN YKTTPPVLDS DGSFLVSKLT VDKSRWQQGN   420
VFSCSVMHEA LHNHYTQKSL SLSPGK                                        446

SEQ ID NO: 1044         moltype = AA  length = 453
FEATURE                 Location/Qualifiers
REGION                  1..453
                        note = Synthetic: 2193-B09_HC_F404TAG_Hole
source                  1..453
                        mol_type = protein
                        organism = synthetic construct
SEQUENCE: 1044
MEVQLVESGG GLVQPGGSLR LSCAASGFNI NNSYIHWVRQ APGKGLEWVG IIDPNNGSTA    60
YADSVKGRFT ISADTSKNTA YLQMNSLRAE DTAVYYCARS RWYRVLWSYV LDYWGQGTLV   120
TVSSASTKGP SVFPLAPSSK STSGGTAALG CLVKDYFPEP VTVSWNSGAL TSGVHTFPAV   180
LQSSGLYSLS SVVTVPSSSL GTQTYICNVN HKPSNTKVDK KVEPKSCDKT HTCPPCPAPE   240
LLGGPSVFLF PPKPKDTLMI SRTPEVTCVV VDVSHEDPEV KFNWYVDGVE VHNAKTKPRE   300
EQYNSTYRVV SVLTVLHQDW LNGKEYKCKV SNKALPAPIE KTISKAKGQP REPQVYTLPP   360
SREEMTKNQV SLSCAVKGFY PSDIAVEWES NGQPENNYKT TPPVLDSDGS FLVSKLTVDK   420
SRWQQGNVFS CSVMHEALHN HYTQKSLSLS PGK                                453

SEQ ID NO: 1045         moltype = AA  length = 450
FEATURE                 Location/Qualifiers
REGION                  1..450
                        note = Synthetic: 2194-A05_HC_F404TAG_Hole
source                  1..450
                        mol_type = protein
                        organism = synthetic construct
SEQUENCE: 1045
MEVQLVESGG GLVQPGGSLR LSCAASGFNI KEYHIHWVRQ APGKGLEWVG YISPNSGSTY    60
YADSVKGRFT ISADTSKNTA YLQMNSLRAE DTAVYYCARD HRRYVRPFDY WGQGTLVTVS   120
SASTKGPSVF PLAPSSKSTS GGTAALGCLV KDYFPEPVTV SWNSGALTSG VHTFPAVLQS   180
SGLYSLSSVV TVPSSSLGTQ TYICNVNHKP SNTKVDKKVE PKSCDKTHTC PPCPAPELLG   240
GPSVFLFPPK PKDTLMISRT PEVTCVVVDV SHEDPEVKFN WYVDGVEVHN AKTKPREEQY   300
NSTYRVVSVL TVLHQDWLNG KEYKCKVSNK ALPAPIEKTI SKAKGQPREP QVYTLPPSRE   360
EMTKNQVSLS CAVKGFYPSD IAVEWESNGQ PENNYKTTPP VLDSDGSFLV SKLTVDKSRW   420
QQGNVFSCSV MHEALHNHYT QKSLSLSPGK                                    450
```

```
SEQ ID NO: 1046         moltype = AA  length = 453
FEATURE                 Location/Qualifiers
REGION                  1..453
                        note = Synthetic: 2186-B04_HC_F404TAG_Hole
source                  1..453
                        mol_type = protein
                        organism = synthetic construct
SEQUENCE: 1046
MEVQLVESGG GLVQPGGSLR LSCAASGFNI AGYAIHWVRQ APGKGLEWVG LITPTPGTSN   60
YADSVKGRFT ISVDTSKNTA YLQMNSLRAE DTAAYYCARD YRGVYLYSFY YDYWGQGTLV  120
TVSSASTKGP SVFPLAPSSK STSGGTAALG CLVKDYFPEP VTVSWNSGAL TSGVHTFPAV  180
LQSSGLYSLS SVVTVPSSSL GTQTYICNVN HKPSNTKVDK KVEPKSCDKT HTCPPCPAPE  240
LLGGPSVFLF PPKPKDTLMI SRTPEVTCVV VDVSHEDPEV KFNWYVDGVE VHNAKTKPRE  300
EQYNSTYRVV SVLTVLHQDW LNGKEYKCKV SNKALPAPIE KTISKAKGQP REPQVYTLPP  360
SREEMTKNQV SLSCAVKGFY PSDIAVEWES NGQPENNYKT TPPVLDSDGS FLVSKLTVDK  420
SRWQQGNVFS CSVMHEALHN HYTQKSLSLS PGK                              453

SEQ ID NO: 1047         moltype = AA  length = 453
FEATURE                 Location/Qualifiers
REGION                  1..453
                        note = Synthetic: 1987-C06_HC_F404TAG_Hole
source                  1..453
                        mol_type = protein
                        organism = synthetic construct
SEQUENCE: 1047
MEVQLVESGG GLVQPGGSLR LSCAASGFNI TSYGIHWVRQ APGKGLEWVG WIAPNSGNTY   60
YADSVKGRFT ISADTSKNTA YLQMNSLRAE DTAVYYCARD IVSTYSYYYL MDYWGQGTLV  120
TVSSASTKGP SVFPLAPSSK STSGGTAALG CLVKDYFPEP VTVSWNSGAL TSGVHTFPAV  180
LQSSGLYSLS SVVTVPSSSL GTQTYICNVN HKPSNTKVDK KVEPKSCDKT HTCPPCPAPE  240
LLGGPSVFLF PPKPKDTLMI SRTPEVTCVV VDVSHEDPEV KFNWYVDGVE VHNAKTKPRE  300
EQYNSTYRVV SVLTVLHQDW LNGKEYKCKV SNKALPAPIE KTISKAKGQP REPQVYTLPP  360
SREEMTKNQV SLSCAVKGFY PSDIAVEWES NGQPENNYKT TPPVLDSDGS FLVSKLTVDK  420
SRWQQGNVFS CSVMHEALHN HYTQKSLSLS PGK                              453

SEQ ID NO: 1048         moltype = AA  length = 444
FEATURE                 Location/Qualifiers
REGION                  1..444
                        note = Synthetic: 2188-D04 IgG HC Y180/F241/F404TAG
                          P011531_0
source                  1..444
                        mol_type = protein
                        organism = synthetic construct
SEQUENCE: 1048
MEVQLVESGG GLVQPGGSLR LSCAASGFNI SDYDIHWVRQ APGKGLEWVG GIDPADGSTD   60
YADSVKGRFT ISADTSKNTA YLQMNSLRAE DTAVYYCARD YGVYDYWGQG TLVTVSSAST  120
KGPSVFPLAP SSKSTSGGTA ALGCLVKDYF PEPVTVSWNS GALTSGVHTF PAVLQSSGLS  180
LSSVVTVPSS SLGTQTYICN VNHKPSNTKV DKKVEPKSCD KTHTCPPCPA PELLGGPSVL  240
FPPKPKDTLM ISRTPEVTCV VVDVSHEDPE VKFNWYVDGV EVHNAKTKPR EEQYNSTYRV  300
VSVLTVLHQD WLNGKEYKCK VSNKALPAPI EKTISKAKGQ PREPQVYTLP PSREEMTKNQ  360
VSLTCLVKGF YPSDIAVEWE SNGQPENNYK TTPPVLDSDG SFLYSKLTVD KSRWQQGNVF  420
SCSVMHEALH NHYTQKSLSL SPGK                                        444

SEQ ID NO: 1049         moltype = AA  length = 213
FEATURE                 Location/Qualifiers
REGION                  1..213
                        note = Synthetic: trastuzumab LC SerOpt
                          K42TAG/E161TAG/TCT162AGC
source                  1..213
                        mol_type = protein
                        organism = synthetic construct
SEQUENCE: 1049
MDIQMTQSPS SLSASVGDRV TITCRASQDV NTAVAWYQQK PGAPKLLIYS ASFLYSGVPS   60
RFSGSRSGTD FTLTISSLQP EDFATYYCQQ HYTTPPTFGQ GTKVEIKRTV AAPSVFIFPP  120
SDEQLKSGTA SVVCLLNNFY PREAKVQWKV DNALQSGNSQ SVTEQDSKDS TYSLSSTLTL  180
SKADYEKHKV YACEVTHQGL SSPVTKSFNR GEC                              213

SEQ ID NO: 1050         moltype = AA  length = 214
FEATURE                 Location/Qualifiers
REGION                  1..214
                        note = Synthetic: trastuzumab LC SerOpt K42TAG
source                  1..214
                        mol_type = protein
                        organism = synthetic construct
SEQUENCE: 1050
MDIQMTQSPS SLSASVGDRV TITCRASQDV NTAVAWYQQK PGAPKLLIYS ASFLYSGVPS   60
RFSGSRSGTD FTLTISSLQP EDFATYYCQQ HYTTPPTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                             214
```

```
SEQ ID NO: 1051        moltype = AA  length = 215
FEATURE                Location/Qualifiers
REGION                 1..215
                       note = Synthetic: Trastuzumab LC SerOpt
source                 1..215
                       mol_type = protein
                       organism = synthetic construct
SEQUENCE: 1051
MDIQMTQSPS SLSASVGDRV TITCRASQDV NTAVAWYQQK PGKAPKLLIY SASFLYSGVP    60
SRFSGSRSGT DFTLTISSLQ PEDFATYYCQ QHYTTPPTFG QGTKVEIKRT VAAPSVFIFP   120
PSDEQLKSGT ASVVCLLNNF YPREAKVQWK VDNALQSGNS QESVTEQDSK DSTYSLSSTL   180
TLSKADYEKH KVYACEVTHQ GLSSPVTKSF NRGEC                              215

SEQ ID NO: 1052        moltype = AA  length = 447
FEATURE                Location/Qualifiers
REGION                 1..447
                       note = Synthetic: 2188-D04 HC
source                 1..447
                       mol_type = protein
                       organism = synthetic construct
SEQUENCE: 1052
MEVQLVESGG GLVQPGGSLR LSCAASGFNI SDYDIHWVRQ APGKGLEWVG GIDPADGSTD    60
YADSVKGRFT ISADTSKNTA YLQMNSLRAE DTAVYYCARD YGVYDYWGQG TLVTVSSAST   120
KGPSVFPLAP SSKSTSGGTA ALGCLVKDYF PEPVTVSWNS GALTSGVHTF PAVLQSSGLY   180
SLSSVVTVPS SSLGTQTYIC NVNHKPSNTK VDKKVEPKSC DKTHTCPPCP APELLGGPSV   240
FLFPPKPKDT LMISRTPEVT CVVVDVSHED PEVKFNWYVD GVEVHNAKTK PREEQYNSTY   300
RVVSVLTVLH QDWLNGKEYK CKVSNKALPA PIEKTISKAK GQPREPQVYT LPPSREEMTK   360
NQVSLTCLVK GFYPSDIAVE WESNGQPENN YKTTPPVLDS DGSFFLYSKL TVDKSRWQQG   420
NVFSCSVMHE ALHNHYTQKS LSLSPGK                                       447

SEQ ID NO: 1053        moltype = AA  length = 215
FEATURE                Location/Qualifiers
REGION                 1..215
                       note = Synthetic: 2188-D04 LC
source                 1..215
                       mol_type = protein
                       organism = synthetic construct
SEQUENCE: 1053
MDIQMTQSPS SLSASVGDRV TITCRASQDV NTAVAWYQQK PGKAPKLLIY SASFLYSGVP    60
SRFSGSRSGT DFTLTISSLQ PEDFATYYCQ QHYTTPPTFG QGTKVEIKRT VAAPSVFIFP   120
PSDEQLKSGT ASVVCLLNNF YPREAKVQWK VDNALQSGNS QESVTEQDSK DSTYSLSSTL   180
TLSKADYEKH KVYACEVTHQ GLSSPVTKSF NRGEC                              215
```

ANTI-ROR1 ANTIBODY CONJUGATES, COMPOSITIONS COMPRISING ANTI ROR1 ANTIBODY CONJUGATES, AND METHODS OF MAKING AND USING ANTI-ROR1 ANTIBODY CONJUGATES

CROSS-REFERENCE TO RELATED APPLICATIONS

This application claims the benefit of U.S. Provisional Application No. 63/357,442 filed Jun. 30, 2022; U.S. Provisional Application No. 63/389,741 filed Jul. 15, 2022; U.S. Provisional Application No. 63/382,262 filed Nov. 3, 2022; U.S. Provisional Application No. 63/487,706 filed Mar. 1, 2023; U.S. Provisional Application No. 63/489,926 filed Mar. 13, 2023; and U.S. Provisional Application No. 63/495,635 filed Apr. 12, 2023. Each of these applications are incorporated for all purposes in their entirety.

This application incorporates by reference the computer readable sequence listing entitled "108843.00462 Sequence Listing" created Jul. 30, 2023 having 1.29 MB.

FIELD OF THE INVENTION

Provided herein are antibodies and antibody conjugates, for instance antibody drug conjugates, with binding specificity for receptor tyrosine kinase orphan receptor 1 (ROR1) and compositions comprising the antibodies or antibody conjugates, including pharmaceutical compositions. Also provided herein are methods of producing the antibodies and conjugates, and methods of using the antibodies or conjugates and compositions for therapy. The antibodies, conjugates, and compositions are useful in methods of treatment and prevention of cell proliferation and cancer, for example, by activating anti-tumor immunity; methods of detection of cell proliferation and cancer; and methods of diagnosis of cell proliferation and cancer. The antibodies, conjugates, and compositions are also useful in methods of treatment, prevention, detection, and diagnosis of autoimmune diseases, infectious diseases, and inflammatory conditions.

BACKGROUND

Receptor tyrosine kinase-like orphan receptor (ROR1) is a member of the receptor tyrosine kinases (RTK) family. *OMIM* entry 602336. Receptor tyrosine kinases function as cell surface receptors, and they have been postulated to play roles in the control of cell proliferation, differentiation, migration, and metabolism. Afzal & Jeffery, 2003, *Hum. Mutat.* 22:1-11. Based on conserved sequences from other receptor tyrosine kinases, ROR1 was initially identified in 1992. Masiakowski & Carroll, 1992, *J. Biol. Chem.* 267: 26181-26190. The ROR1 gene encodes a type I glycosylated membrane protein with a predicted length of 937 amino acids. See id.; *Entrez Gene* ID. 4919. The ROR1 gene has been mapped to chromosome 1p32-p31. Reddy et al., 1997, *Genomics* 41: 283-285. Expression of ROR1 has been observed in human heart, lung, and kidney, and also weakly in the central nervous system. Reddy et al. Truncated expression was observed in a variety of human cancers, including those originating from CNS or PNS neuroectoderm. Reddy, 1996, *Oncogene* 13:1555-1559. ROR1 knockout mice had no obvious skeletal or cardiac abnormalities, yet they died soon after birth due to respiratory dysfunction. Nomi et al., 2001, *Molec. Cell. Biol.* 21:8329-8335.

ROR1 has recently been shown to be expressed on cancer cells, including ovarian cancer cells, and on cancer stem cells. Zhang et al., 2014, *Proc. Natl. Acad. Sci. USA* 111: 17266-71. Treatment with a monoclonal antibody specific for ROR1 inhibited development of ovarian cancer cells, and ROR1 has been postulated as a target for cancer therapeutics. See id.

There is a need for improved methods of targeting and/or modulating the activity of ROR1. Given the specific expression of ROR1 in cancer cells and cancer stem cells, there is a need for improved therapeutics that can specifically target cells and tissues that express or overexpress ROR1. Antibody conjugates to ROR1 could be used to deliver therapeutic or diagnostic payload moieties to target cells expressing ROR1 for the treatment or diagnosis of such diseases.

SUMMARY

Provided herein are antibodies that selectively bind ROR1. In some embodiments, the antibodies bind human ROR1. In some embodiments, the antibodies also bind homologs of human ROR1.

In some embodiments, the antibodies comprise an illustrative CDR, $V_H$, or $V_L$ sequence provided in this disclosure, or a variant thereof. In some aspects, the variant is a variant with one or more conservative amino acid substitutions. In some aspects, the variant has sequence identity to the illustrative sequence or sequences.

Also provided are compositions and kits comprising the antibodies. In some embodiments, the compositions are pharmaceutical compositions. Any suitable pharmaceutical composition may be used. In some embodiments, the pharmaceutical composition is a composition for parenteral administration.

This disclosure also provides methods of using the anti-ROR1 antibodies provided herein. In some embodiments, the method is a method of treatment. In some embodiments, the method is a diagnostic method. In some embodiments, the method is an analytical method. In some embodiments, the method is a method of purifying and/or quantifying ROR1.

In some embodiments, the antibodies are used to treat a disease or condition. In some aspects, the disease or condition is selected from cancer, autoimmune disease, and infection.

Also provided herein are antibody conjugates that selectively bind receptor tyrosine kinase orphan receptor 1 (ROR1). The antibody conjugates comprise an antibody that binds ROR1 linked to one or more payload moieties. The antibody can be linked to the payload directly by a covalent bond or indirectly by way of a linker. ROR1 antibodies are described in detail herein, as are useful payload moieties, and useful linkers.

In another aspect, provided are compositions comprising the antibody conjugates. In some embodiments, the compositions are pharmaceutical compositions. Any suitable pharmaceutical composition may be used. In some embodiments, the pharmaceutical composition is a composition for parenteral administration. In a further aspect, provided herein are kits comprising the antibody conjugates or pharmaceutical compositions.

In another aspect, provide herein are methods of using the anti-ROR1 antibody conjugates. In some embodiments, the methods are methods of delivering one or more payload moieties to a target cell or tissue expressing ROR1. In some embodiments, the methods are methods of treatment. In some embodiments, the methods are diagnostic methods. In some embodiments, the methods are analytical methods. In some embodiments, the antibody conjugates are used to treat a disease or condition. In some aspects, the disease or condition is selected from a cancer, autoimmune disease, and infection. In certain embodiments, the anti-ROR1 antibody conjugates treat the disease or condition, for example cancer, by activating anti-tumor immunity or protective immunity.

In some embodiments, the antibody conjugates bind human ROR1. In some embodiments, the antibody conjugates also bind homologs of human ROR1. In some aspects, the antibody conjugates also bind homologs of cynomolgus monkey and/or mouse receptor ROR1.

These and other embodiments of the invention along with many of its features are described in more detail in conjunction with the text below and attached figures.

BRIEF DESCRIPTION OF THE FIGURES

Figure 2:
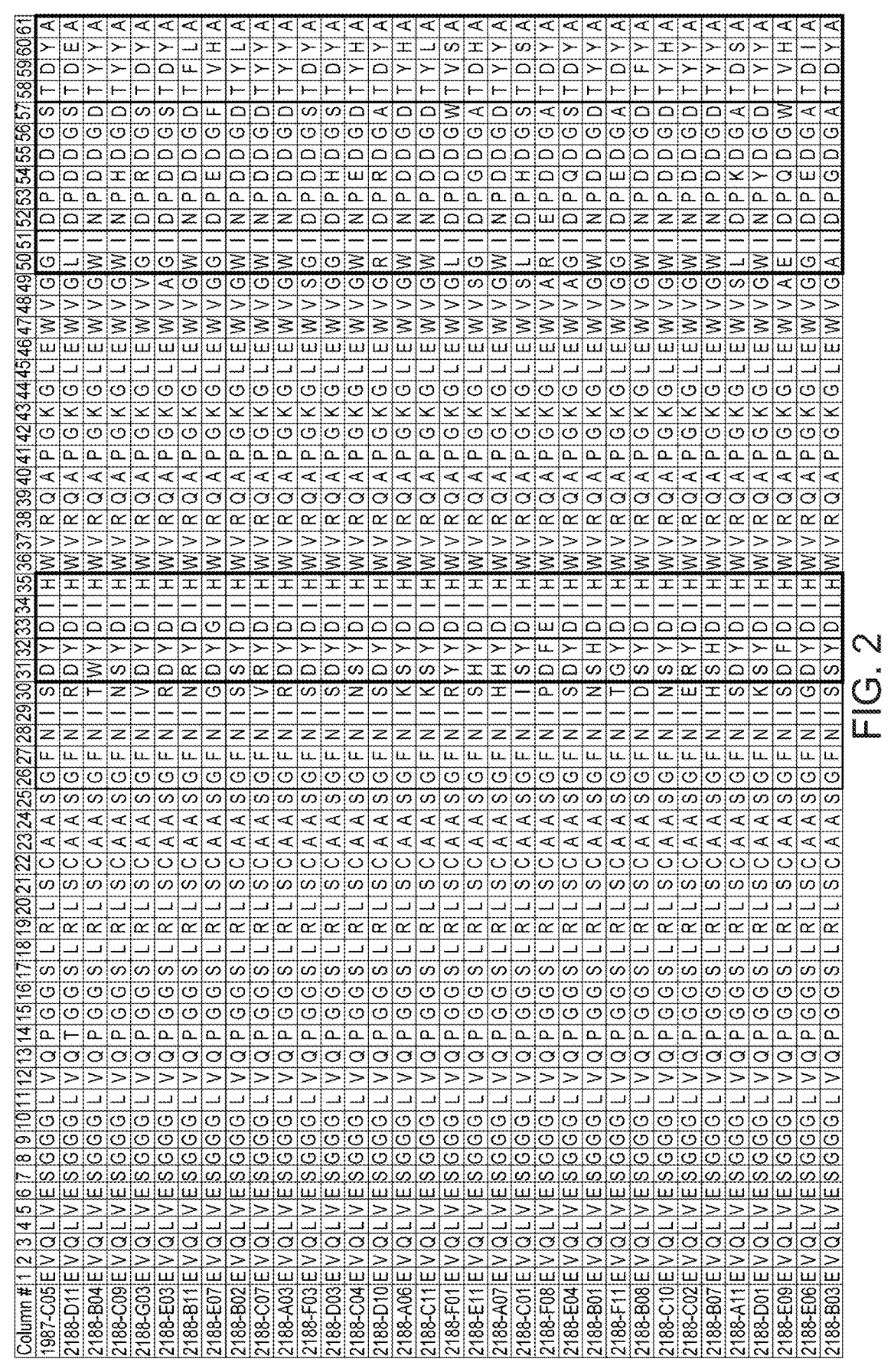
Figure 3:
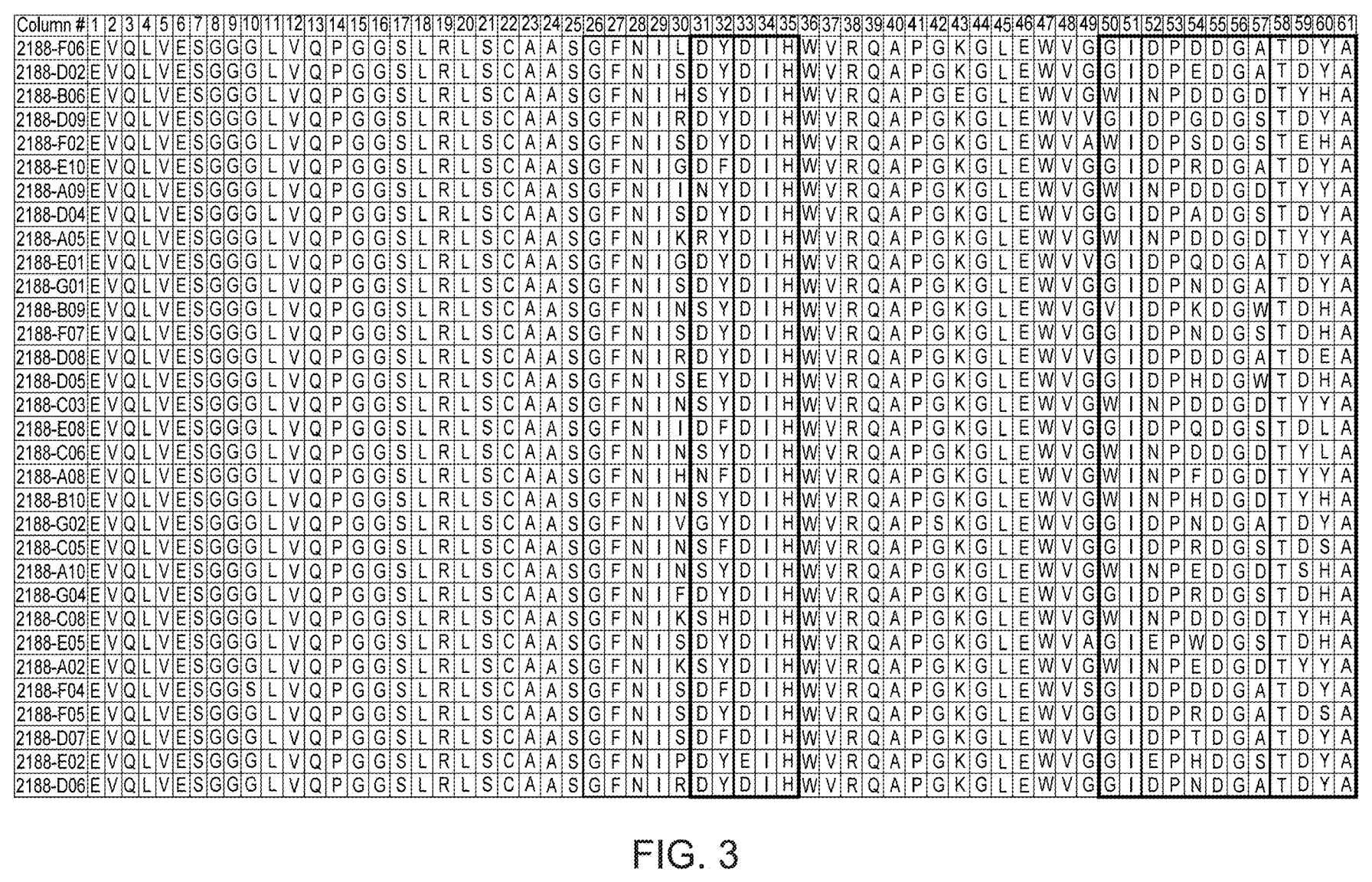
Figure 3:
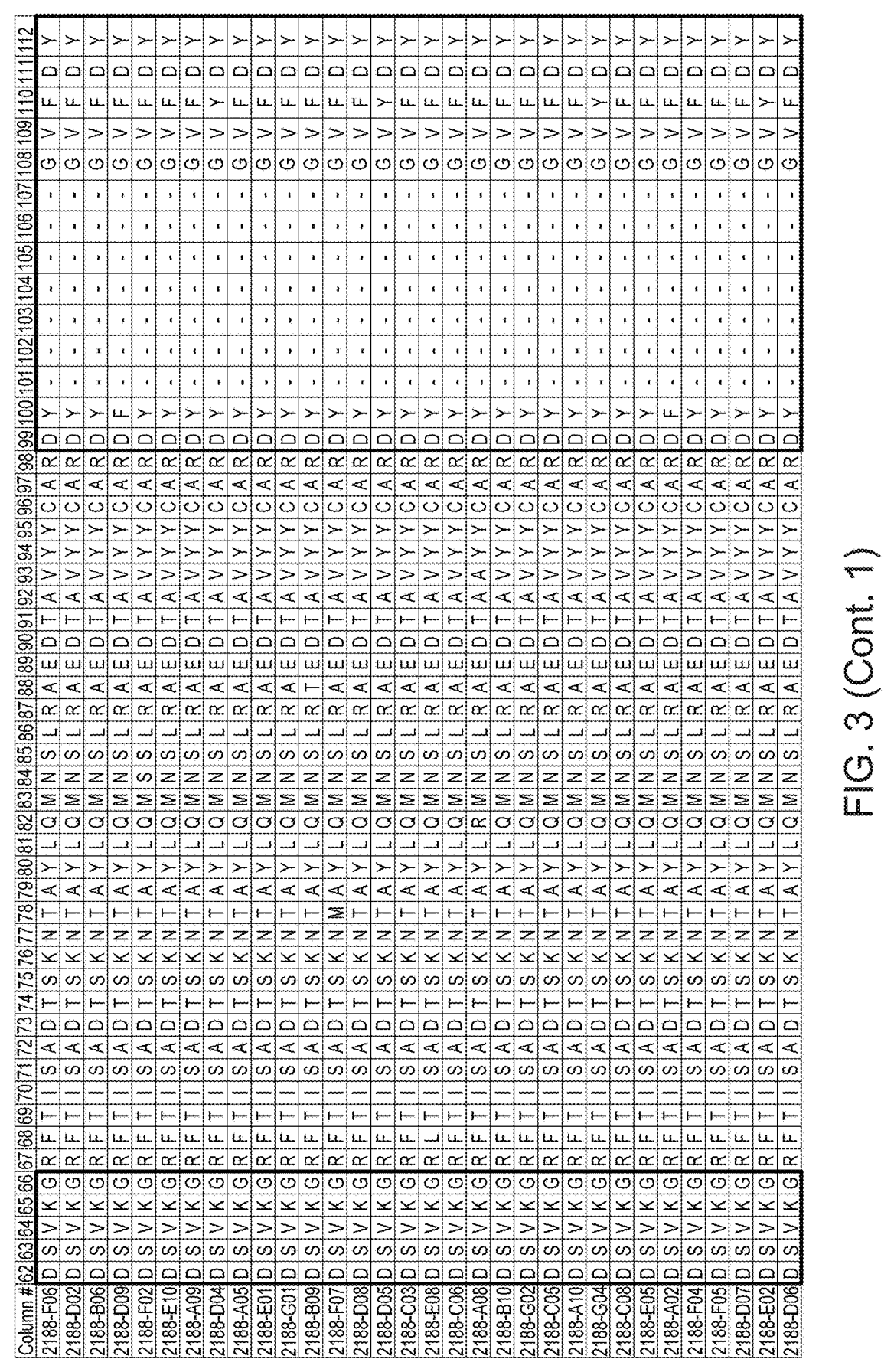
Figure 4:
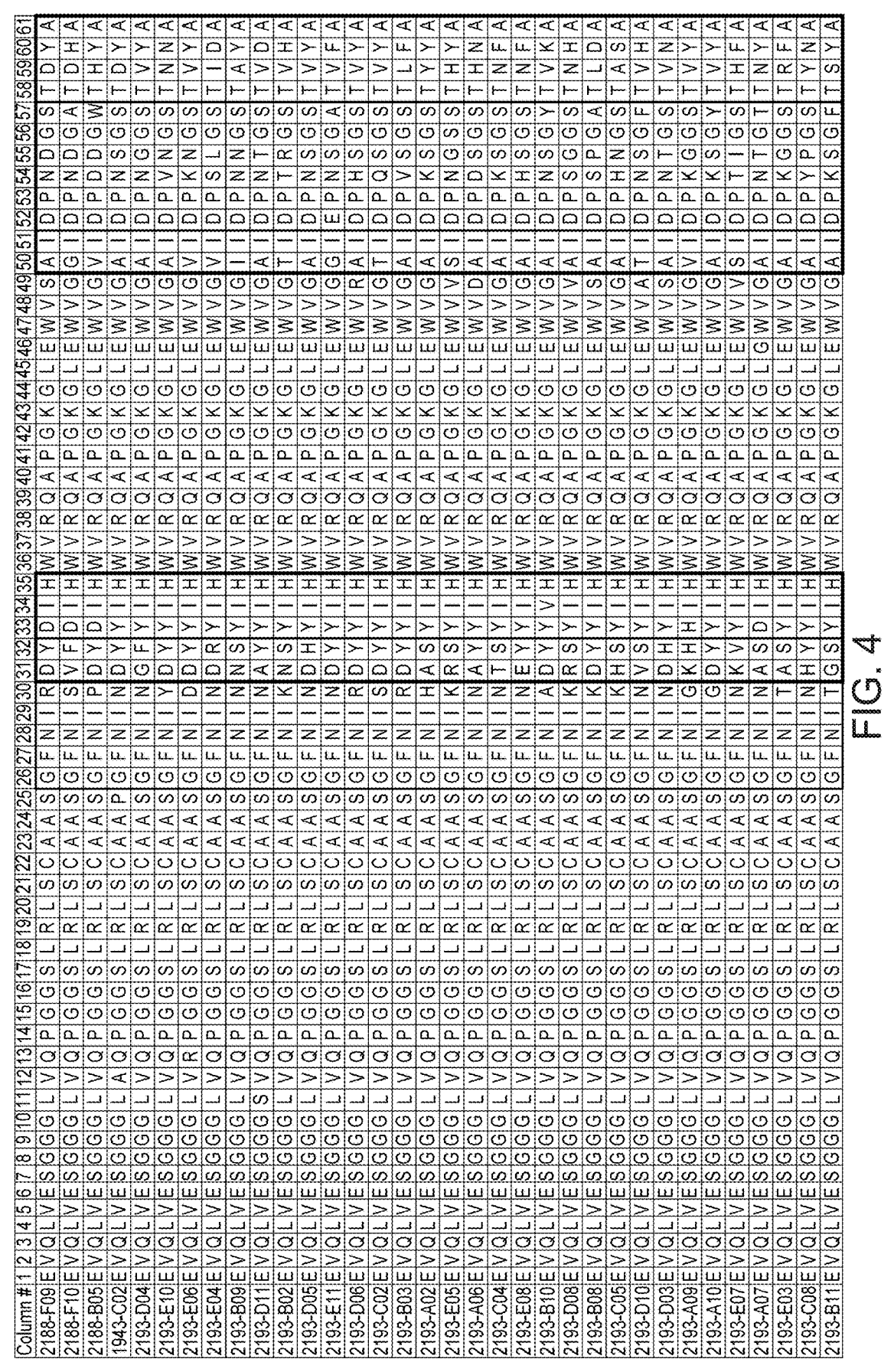
Figure 4:
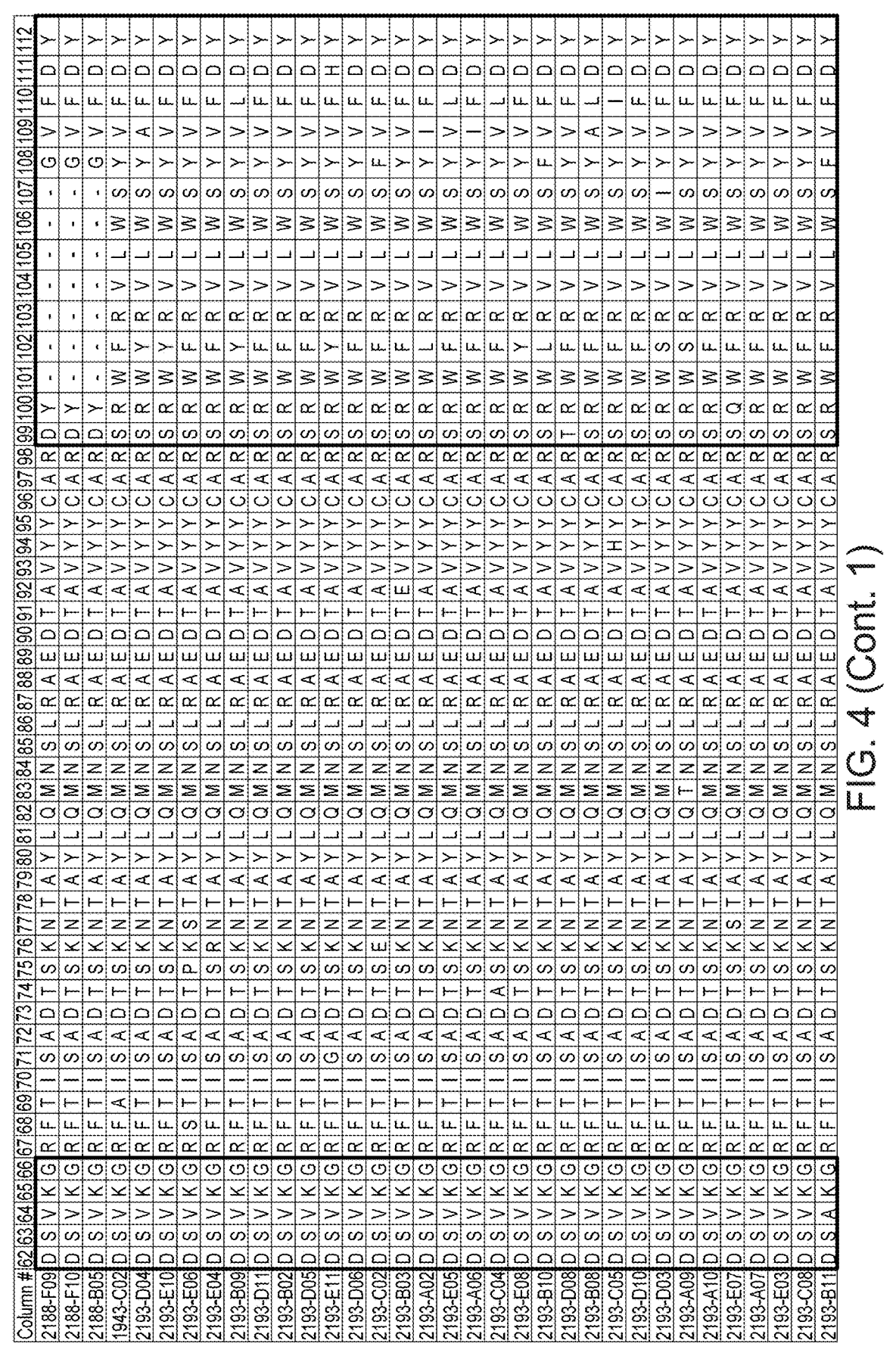
Figure 5:
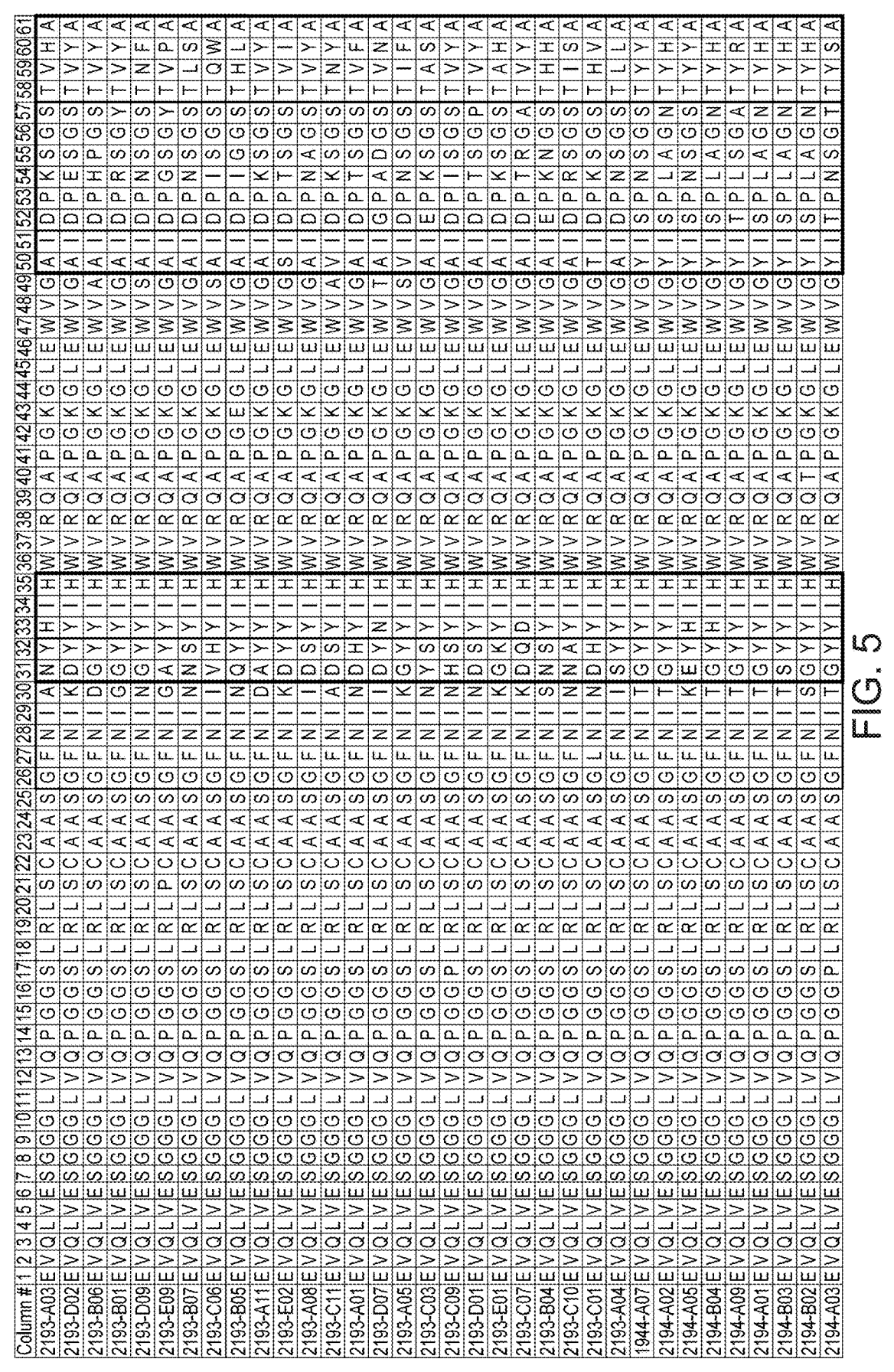
Figure 6:
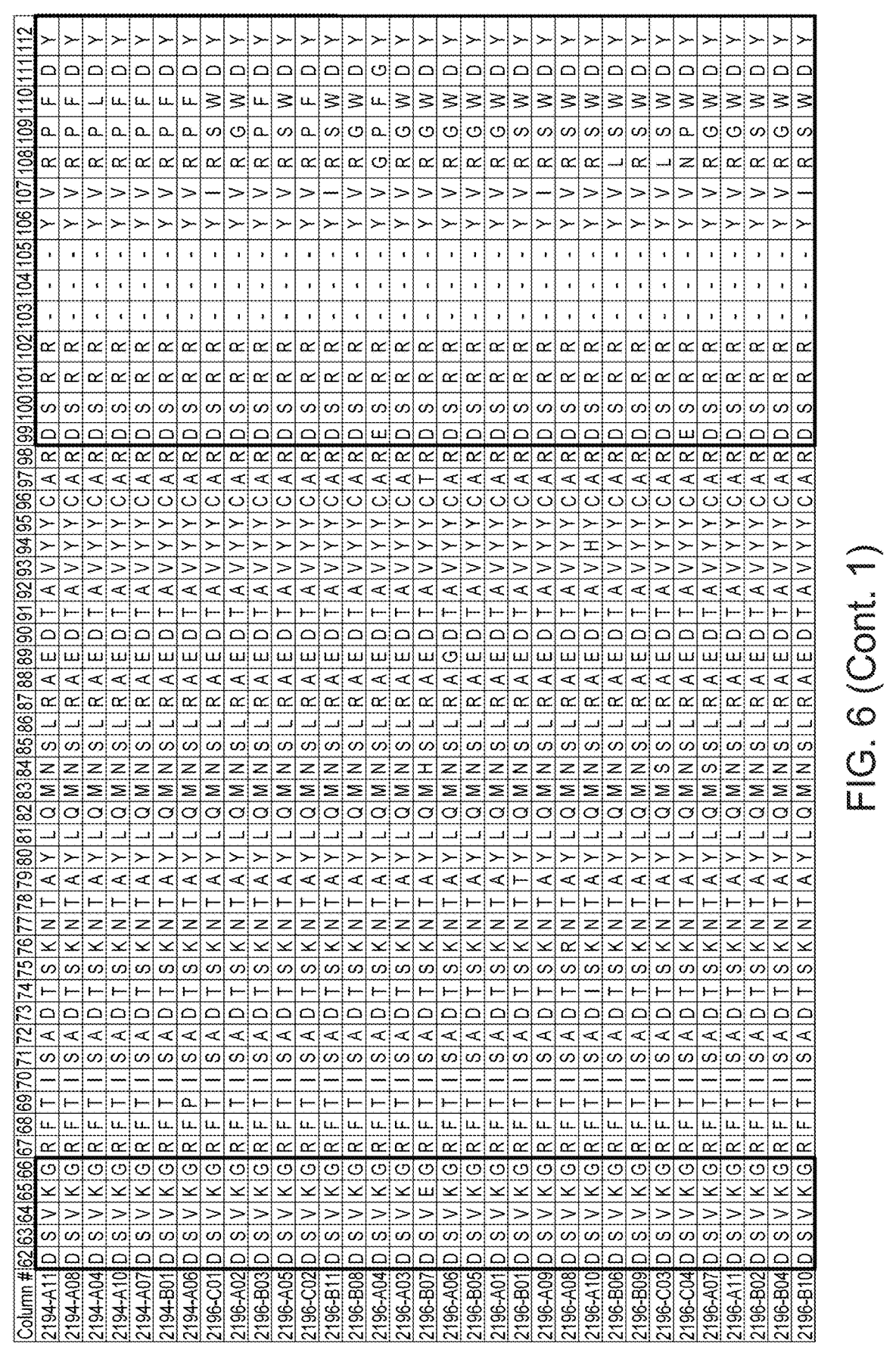

FIGS. 2-6 provide alignments of the VH sequences (SEQ ID NOs: 854-1020) from the variant antibodies provided herein. CDRs according to Chothia are highlighted, and CDRs according to Kabat are boxed.

FIG. 7 provides alignments of the VL sequences (SEQ ID NOs: 1021-1026) from trastuzumab and the variant antibodies provided herein. CDRs according to Chothia are highlighted, and CDRs according to Kabat are underlined.

DETAILED DESCRIPTION OF THE EMBODIMENTS

1. Definitions

Figure 1:
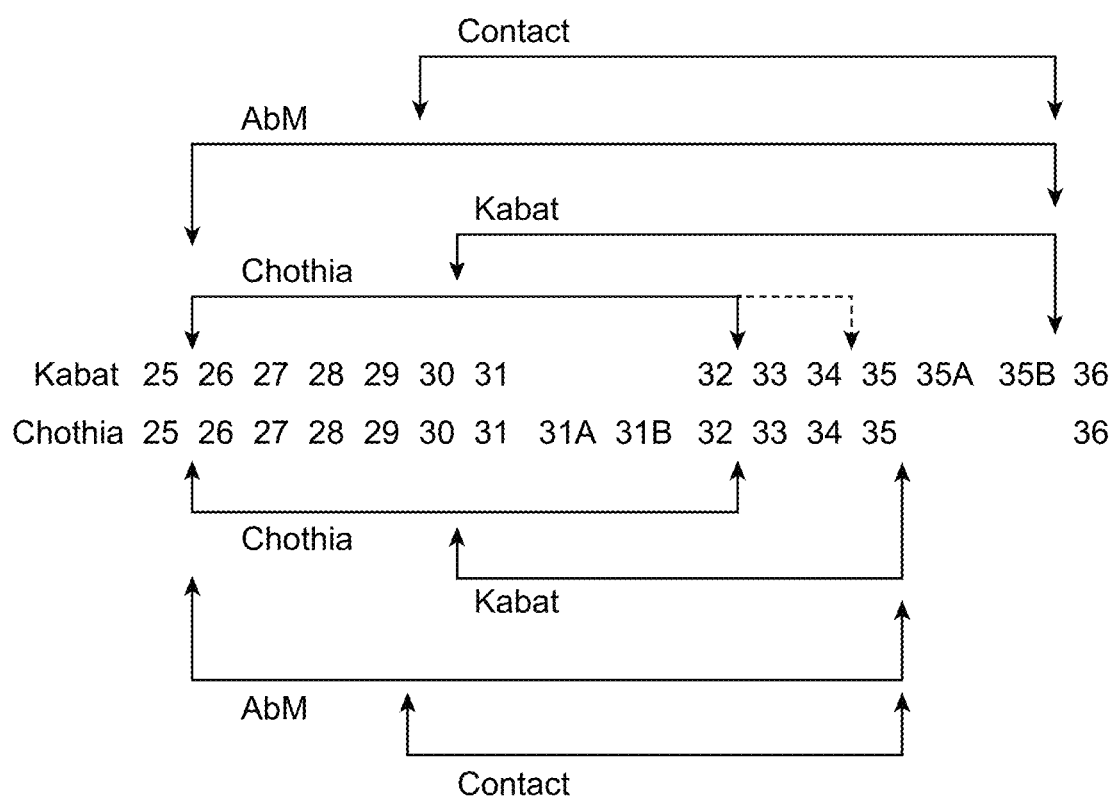
FIG. 1 provides a comparison of the Kabat and Chothia numbering systems for CDR-H1. Adapted from Martin A. C. R. (2010). Protein Sequence and Structure Analysis of Antibody Variable Domains. In R. Kontermann & S. Dübel (Eds.), *Antibody Engineering* vol. 2 (pp. 33-51). Springer-Verlag, Berlin Heidelberg.

Unless otherwise defined, all terms of art, notations and other scientific terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a difference over what is generally understood in the art. The techniques and procedures described or referenced herein are generally well understood and commonly employed using conventional methodologies by those skilled in the art, such as, for example, the widely utilized molecular cloning methodologies described in Sambrook et al., *Molecular Cloning: A Laboratory Manual* 2nd ed. (1989) Cold Spring Harbor Laboratory Press, Cold Spring Harbor, NY. As appropriate, procedures involving the use of commercially available kits and reagents are generally carried out in accordance with manufacturer-defined protocols and conditions unless otherwise noted.

As used herein, the singular forms "a," "an," and "the" include the plural referents unless the context clearly indicates otherwise.

The term "about" indicates and encompasses an indicated value and a range above and below that value. In certain embodiments, the term "about" indicates the designated value±10%, ±5%, or ±1%. In certain embodiments, the term "about" indicates the designated value±one standard deviation of that value.

The term "combinations thereof" includes every possible combination of elements to which the term refers to.

The terms "ROR1" and "receptor tyrosine kinase like orphan receptor 1" are used interchangeably herein. ROR1 is also known by synonyms, including NTRKR1 neurotrophic tyrosine kinase, receptor-related 1, and dJ537F10.1, among others. Unless specified otherwise, the terms include any variants, isoforms and species homologs of human ROR1 that are naturally expressed by cells, or that are expressed by cells transfected with a ROR1 or ROR1 gene. ROR1 proteins include, for example, human ROR1 (SEQ ID NO: 1). In some embodiments, ROR1 proteins include cynomolgus monkey ROR1 (SEQ ID NO: 2). In some embodiments, ROR1 proteins include murine ROR1 (SEQ ID NO: 3).

The term "immunoglobulin" refers to a class of structurally related proteins generally comprising two pairs of polypeptide chains: one pair of light (L) chains and one pair of heavy (H) chains. In an "intact immunoglobulin," all four of these chains are interconnected by disulfide bonds. The structure of immunoglobulins has been well characterized. See, e.g., Paul, *Fundamental Immunology* 7th ed., Ch. 5 (2013) Lippincott Williams & Wilkins, Philadelphia, PA. Briefly, each heavy chain typically comprises a heavy chain variable region ($V_H$) and a heavy chain constant region ($C_H$). The heavy chain constant region typically comprises three domains, abbreviated $C_{H1}$, $C_{H2}$, and $C_{H3}$. Each light chain typically comprises a light chain variable region ($V_L$) and a light chain constant region. The light chain constant region typically comprises one domain, abbreviated $C_L$.

The term "antibody" describes a type of immunoglobulin molecule and is used herein in its broadest sense. An antibody specifically includes intact antibodies (e.g., intact immunoglobulins), and antibody fragments. Antibodies comprise at least one antigen-binding domain. One example of an antigen-binding domain is an antigen binding domain formed by a $V_H$-$V_L$ dimer. A "ROR1 antibody," "anti-ROR1 antibody," "ROR1 Ab," "ROR1-specific antibody," "anti-ROR1 Ab," "ROR1 antibody," "anti-ROR1 antibody," "ROR1 Ab," "ROR1-specific antibody," or "anti-ROR1 Ab" is an antibody, as described herein, which binds specifically to ROR1 or ROR1. In some embodiments, the antibody binds the extracellular domain of ROR1.

The $V_H$ and $V_L$ regions may be further subdivided into regions of hypervariability ("hypervariable regions (HVRs);" also called "complementarity determining regions" (CDRs)) interspersed with regions that are more conserved. The more conserved regions are called framework regions (FRs). Each $V_H$ and $V_L$ generally comprises three CDRs and four FRs, arranged in the following order (from N-terminus to C-terminus): FR1-CDR1-FR2-CDR2-FR3-CDR3-FR4. The CDRs are involved in antigen binding, and influence antigen specificity and binding affinity of the antibody. See Kabat et al., *Sequences of Proteins of Immunological Interest* 5th ed. (1991) Public Health Service, National Institutes of Health, Bethesda, MD, incorporated by reference in its entirety.

The light chain from any vertebrate species can be assigned to one of two types, called kappa and lambda, based on the sequence of the constant domain.

The heavy chain from any vertebrate species can be assigned to one of five different classes (or isotypes): IgA, IgD, IgE, IgG, and IgM. These classes are also designated α, δ, ε, γ, and μ, respectively. The IgG and IgA classes are further divided into subclasses on the basis of differences in sequence and function. Humans express the following subclasses: IgG1, IgG2, IgG3, IgG4, IgA1, and IgA2.

The amino acid sequence boundaries of a CDR can be determined by one of skill in the art using any of a number of known numbering schemes, including those described by Kabat et al., supra ("Kabat" numbering scheme); Al-Lazikani et al., 1997, *J. Mol. Biol.*, 273:927-948 ("Chothia" numbering scheme); MacCallum et al., 1996, *J. Mol. Biol.* 262:732-745 ("Contact" numbering scheme); Lefranc et al., *Dev. Comp. Immunol.*, 2003, 27:55-77 ("IMGT" numbering scheme); and Honegge and Pluckthun, *J. Mol. Biol.*, 2001, 309:657-70 ("AHo" numbering scheme), each of which is incorporated by reference in its entirety.

Table 1 provides the positions of CDR-L1, CDR-L2, CDR-L3, CDR-H1, CDR-H2, and CDR-H3 as identified by the Kabat and Chothia schemes. For CDR-H1, residue numbering is provided using both the Kabat and Chothia numbering schemes.

TABLE 1

Residues in CDRs according to Kabat and Chothia numbering schemes.

| CDR | Kabat | Chothia |
|---|---|---|
| L1 | L24-L34 | L24-L34 |
| L2 | L50-L56 | L50-L56 |
| L3 | L89-L97 | L89-L97 |
| H1 (Kabat Numbering) | H31-H35B | H26-H32 or H34* |
| H1 (Chothia Numbering) | H31-H35 | H26-H32 |
| H2 | H50-H65 | H52-H56 |
| H3 | H95-H102 | H95-H102 |

*The C-terminus of CDR-H1, when numbered using the Kabat numbering convention, varies between H32 and H34, depending on the length of the CDR, as illustrated in FIG. 1.

Unless otherwise specified, the numbering scheme used for identification of a particular CDR herein is the Kabat/Chothia numbering scheme. Where the residues encompassed by these two numbering schemes diverge (e.g., CDR-H1 and/or CDR-H2), the numbering scheme is specified as either Kabat or Chothia. For convenience, CDR-H3 is sometimes referred to herein as either Kabat or Chothia. However, this is not intended to imply differences in sequence where they do not exist, and one of skill in the art can readily confirm whether the sequences are the same or different by examining the sequences.

CDRs may be assigned, for example, using antibody numbering software, such as Abnum, available at www.bioinf.org.uk/abs/abnum/, and described in Abhinandan and Martin, *Immunology*, 2008, 45:3832-3839, incorporated by reference in its entirety.

The "EU numbering scheme" is generally used when referring to a residue in an antibody heavy chain constant region (e.g., as reported in Kabat et al., supra). Unless stated otherwise, the EU numbering scheme is used to refer to residues in antibody heavy chain constant regions described herein.

An "antibody fragment" comprises a portion of an intact antibody, such as the antigen binding or variable region of an intact antibody. Antibody fragments include, for example, Fv fragments, Fab fragments, F(ab')$_2$ fragments, Fab' fragments, scFv (sFv) fragments, and scFv-Fc fragments.

"Fv" fragments comprise a non-covalently-linked dimer of one heavy chain variable domain and one light chain variable domain.

"Fab" fragments comprise, in addition to the heavy and light chain variable domains, the constant domain of the light chain and the first constant domain ($C_{H1}$) of the heavy chain. Fab fragments may be generated, for example, by recombinant methods or by papain digestion of a full-length antibody.

"F(ab')$_2$" fragments contain two Fab' fragments joined, near the hinge region, by disulfide bonds. F(ab')$_2$ fragments may be generated, for example, by recombinant methods or by pepsin digestion of an intact antibody. The F(ab') fragments can be dissociated, for example, by treatment with β-mercaptoethanol.

"Single-chain Fv" or "sFv" or "scFv" antibody fragments comprise a $V_H$ domain and a $V_L$ domain in a single polypeptide chain. The $V_H$ and $V_L$ are generally linked by a peptide linker. See Plückthun A. (1994). In some embodiments, the linker is SEQ ID NO: 1034. In some embodiments, the linker is SEQ ID NO: 1035. Antibodies from *Escherichia coli*. In Rosenberg M. & Moore G. P. (Eds.), *The Pharmacology of Monoclonal Antibodies* vol. 113 (pp. 269-315). Springer-Verlag, New York, incorporated by reference in its entirety.

"scFv-Fc" fragments comprise an scFv attached to an Fc domain. For example, an Fc domain may be attached to the C-terminus of the scFv. The Fc domain may follow the $V_H$ or $V_L$, depending on the orientation of the variable domains in the scFv (i.e., $V_H$-$V_L$ or $V_L$-$V_H$). Any suitable Fc domain known in the art or described herein may be used. In some cases, the Fc domain comprises an IgG1 Fc domain. In some embodiments, the IgG1 Fc domain comprises SEQ ID NO: 1027, or a portion thereof. SEQ ID NO: 1027 provides the sequence of $C_{H1}$, $C_{H2}$, and $C_{H3}$ of the human IgG1 constant region.

The term "monoclonal antibody" refers to an antibody from a population of substantially homogeneous antibodies. A population of substantially homogeneous antibodies comprises antibodies that are substantially similar and that bind the same epitope(s), except for variants that may normally arise during production of the monoclonal antibody. Such variants are generally present in only minor amounts. A monoclonal antibody is typically obtained by a process that includes the selection of a single antibody from a plurality of antibodies. For example, the selection process can be the selection of a unique clone from a plurality of clones, such as a pool of hybridoma clones, phage clones, yeast clones, bacterial clones, or other recombinant DNA clones. The selected antibody can be further altered, for example, to improve affinity for the target ("affinity maturation"), to humanize the antibody, to improve its production in cell culture, and/or to reduce its immunogenicity in a subject.

The term "chimeric antibody" refers to an antibody in which a portion of the heavy and/or light chain is derived from a particular source or species, while the remainder of the heavy and/or light chain is derived from a different source or species.

"Humanized" forms of non-human antibodies are chimeric antibodies that contain minimal sequence derived from the non-human antibody. A humanized antibody is generally a human immunoglobulin (recipient antibody) in which residues from one or more CDRs are replaced by residues from one or more CDRs of a non-human antibody (donor antibody). The donor antibody can be any suitable non-human antibody, such as a mouse, rat, rabbit, chicken, or non-human primate antibody having a desired specificity, affinity, or biological effect. In some instances, selected framework region residues of the recipient antibody are replaced by the corresponding framework region residues from the donor antibody. Humanized antibodies may also comprise residues that are not found in either the recipient antibody or the donor antibody. Such modifications may be made to further refine antibody function. For further details, see Jones et al., *Nature,* 1986, 321:522-525; Riechmann et al., *Nature,* 1988, 332:323-329; and Presta, *Curr. Op. Struct. Biol.,* 1992, 2:593-596, each of which is incorporated by reference in its entirety.

A "human antibody" is one which possesses an amino acid sequence corresponding to that of an antibody produced by a human or a human cell, or derived from a non-human source that utilizes a human antibody repertoire or human antibody-encoding sequences (e.g., obtained from human sources or designed de novo). Human antibodies specifically exclude humanized antibodies.

An "isolated antibody" is one that has been separated and/or recovered from a component of its natural environment. Components of the natural environment may include enzymes, hormones, and other proteinaceous or nonproteinaceous materials. In some embodiments, an isolated antibody is purified to a degree sufficient to obtain at least 15 residues of N-terminal or internal amino acid sequence, for example by use of a spinning cup sequenator. In some embodiments, an isolated antibody is purified to homogeneity by gel electrophoresis (e.g., SDS-PAGE) under reducing or nonreducing conditions, with detection by Coomassie blue or silver stain. An isolated antibody includes an antibody in situ within recombinant cells, since at least one component of the antibody's natural environment is not present. In some aspects, an isolated antibody is prepared by at least one purification step.

In some embodiments, an isolated antibody is purified to at least 80%, 85%, 90%, 95%, or 99% by weight. In some embodiments, an isolated antibody is purified to at least 80%, 85%, 90%, 95%, or 99% by volume. In some embodiments, an isolated antibody is provided as a solution comprising at least 85%, 90%, 95%, 98%, 99% to 100% by weight. In some embodiments, an isolated antibody is provided as a solution comprising at least 85%, 90%, 95%, 98%, 99% to 100% by volume.

"Affinity" refers to the strength of the sum total of non-covalent interactions between a single binding site of a molecule (e.g., an antibody) and its binding partner (e.g., an antigen). Unless indicated otherwise, as used herein, "binding affinity" refers to intrinsic binding affinity, which reflects a 1:1 interaction between members of a binding pair (e.g., antibody and antigen). The affinity of a molecule X for its partner Y can be represented by the dissociation constant ($K_D$). Affinity can be measured by common methods known in the art, including those described herein. Affinity can be determined, for example, using surface plasmon resonance (SPR) technology, such as a Biacore® instrument. In some embodiments, the affinity is determined at 25° C.

With regard to the binding of an antibody to a target molecule, the terms "specific binding," "specifically binds to," "specific for," "selectively binds," and "selective for" a particular antigen (e.g., a polypeptide target) or an epitope on a particular antigen mean binding that is measurably different from a non-specific or non-selective interaction. Specific binding can be measured, for example, by determining binding of a molecule compared to binding of a control molecule. Specific binding can also be determined by competition with a control molecule that mimics the antibody binding site on the target. In that case, specific binding is indicated if the binding of the antibody to the target is competitively inhibited by the control molecule.

The term "$k_d$" (sec$^{-1}$), as used herein, refers to the dissociation rate constant of a particular antibody-antigen interaction. This value is also referred to as the $k_{off}$ value.

The term "$k_a$" (M$^{-1}$×sec$^{-1}$), as used herein, refers to the association rate constant of a particular antibody-antigen interaction. This value is also referred to as the $k_{on}$ value.

The term "$K_D$" (M), as used herein, refers to the dissociation equilibrium constant of a particular antibody-antigen interaction. $K_D = k_d/k_a$.

The term "$K_A$" (M$^{-1}$), as used herein, refers to the association equilibrium constant of a particular antibody-antigen interaction. $K_A = k_a/k_d$.

An "affinity matured" antibody is one with one or more alterations in one or more CDRs or FRs that result in an improvement in the affinity of the antibody for its antigen, compared to a parent antibody which does not possess the alteration(s). In one embodiment, an affinity matured antibody has nanomolar or picomolar affinity for the target antigen. Affinity matured antibodies may be produced using a variety of methods known in the art. For example, Marks et al. (*Bio/Technology,* 1992, 10:779-783, incorporated by reference in its entirety) describes affinity maturation by $V_H$ and $V_L$ domain shuffling. Random mutagenesis of CDR and/or framework residues is described by, for example, Barbas et al. (*Proc. Nat. Acad. Sci. U.S.A.,* 1994, 91:3809-3813); Schier et al., *Gene,* 1995, 169:147-155; Yelton et al., *J. Immunol.,* 1995, 155:1994-2004; Jackson et al., *J. Immunol.,* 1995, 154:3310-33199; and Hawkins et al, *J. Mol. Biol.,* 1992, 226:889-896, each of which is incorporated by reference in its entirety.

When used herein in the context of two or more antibodies, the term "competes with" or "cross-competes with" indicates that the two or more antibodies compete for binding to an antigen (e.g., receptor tyrosine kinase orphan receptor 1, or ROR1). In one exemplary assay, ROR1 is coated on a plate and allowed to bind a first antibody, after which a second, labeled antibody is added. If the presence of the first antibody reduces binding of the second antibody, then the antibodies compete. In another exemplary assay, a first antibody is coated on a plate and allowed to bind the antigen, and then the second antibody is added. The term "competes with" also includes combinations of antibodies where one antibody reduces binding of another antibody, but where no competition is observed when the antibodies are added in the reverse order. However, in some embodiments, the first and second antibodies inhibit binding of each other, regardless of the order in which they are added. In some embodiments, one antibody reduces binding of another antibody to its antigen by at least 50%, at least 60%, at least 70%, at least 80%, or at least 90%.

The term "epitope" means a portion of an antigen capable of specific binding to an antibody. Epitopes frequently consist of surface-accessible amino acid residues and/or sugar side chains and may have specific three-dimensional structural characteristics, as well as specific charge characteristics. Conformational and non-conformational epitopes are distinguished in that the binding to the former but not the latter is lost in the presence of denaturing solvents. An epitope may comprise amino acid residues that are directly involved in the binding, and other amino acid residues, which are not directly involved in the binding. The epitope to which an antibody binds can be determined using known techniques for epitope determination such as, for example, testing for antibody binding to variants of ROR1 with different point-mutations.

Percent "identity" between a polypeptide sequence and a reference sequence, is defined as the percentage of amino acid residues in the polypeptide sequence that are identical to the amino acid residues in the reference sequence, after aligning the sequences and introducing gaps, if necessary, to achieve the maximum percent sequence identity. Alignment for purposes of determining percent amino acid sequence identity can be achieved in various ways that are within the skill in the art, for instance, using publicly available computer software such as BLAST, BLAST-2, ALIGN, MEGA-LIGN (DNASTAR), CLUSTALW, CLUSTAL OMEGA, or MUSCLE software. Those skilled in the art can determine appropriate parameters for aligning sequences, including any algorithms needed to achieve maximal alignment over the full length of the sequences being compared.

A "conservative substitution" or a "conservative amino acid substitution," refers to the substitution of an amino acid with a chemically or functionally similar amino acid. Conservative substitution tables providing similar amino acids are well known in the art. Polypeptide sequences having such substitutions are known as "conservatively modified variants." Such conservatively modified variants are in addition to and do not exclude polymorphic variants, interspecies homologs, and alleles. By way of example, the groups of amino acids provided in Tables 2-4 are, in some embodiments, considered conservative substitutions for one another.

TABLE 2

Selected groups of amino acids that are considered conservative substitutions for one another, in certain embodiments.

| | |
|---|---|
| Acidic Residues | D and E |
| Basic Residues | K, R, and H |
| Hydrophilic Uncharged Residues | S, T, N, and Q |
| Aliphatic Uncharged Residues | G, A, V, L, and I |
| Non-polar Uncharged Residues | C, M, and P |
| Aromatic Residues | F, Y, and W |
| Alcohol Group-Containing Residues | S and T |
| Aliphatic Residues | I, L, V, and M |
| Cycloalkenyl-associated Residues | F, H, W, and Y |
| Hydrophobic Residues | A, C, F, G, H, I, L, M, R, T, V, W, and Y |
| Negatively Charged Residues | D and E |
| Polar Residues | C, D, E, H, K, N, Q, R, S, and T |
| Positively Charged Residues | H, K, and R |
| Small Residues | A, C, D, G, N, P, S, T, and V |
| Very Small Residues | A, G, and S |
| Residues Involved in Turn Formation | A, C, D, E, G, H, K, N, Q, R, S, P, and T |
| Flexible Residues | Q, T, K, S, G, P, D, E, and R |

TABLE 3

Additional selected groups of amino acids that are considered conservative substitutions for one another, in certain embodiments.

| | |
|---|---|
| Group 1 | A, S, and T |
| Group 2 | D and E |
| Group 3 | N and Q |
| Group 4 | R and K |
| Group 5 | I, L, and M |
| Group 6 | F, Y, and W |

TABLE 4

Further selected groups of amino acids that are considered conservative substitutions for one another, in certain embodiments.

| | |
|---|---|
| Group A | A and G |
| Group B | D and E |
| Group C | N and Q |
| Group D | R, K, and H |
| Group E | I, L, M, V |
| Group F | F, Y, and W |
| Group G | S and T |
| Group H | C and M |

Additional conservative substitutions may be found, for example, in Creighton, *Proteins: Structures and Molecular Properties* 2nd ed. (1993) W. H. Freeman & Co., New York, NY. An antibody generated by making one or more conservative substitutions of amino acid residues in a parent antibody is referred to as a "conservatively modified variant."

The term "payload" refers to a molecular moiety that can be conjugated to an antibody. In particular embodiments, payloads are selected from the group consisting of therapeutic moieties and labelling moieties.

"Triple negative breast cancer" (TNBC) refers to a breast cancer characterized as estrogen receptor-negative, progesterone receptor-negative and human epidermal growth factor receptor-2-negative (HER2-negative). The TNBC can be BRCA1/2 wildtype or BRCA1/2 mutated. The determination of negative status of the estrogen, progesterone, and Her2/neu expression is readily determined by one of skill in the art, e.g., in accordance with the current accepted guidelines. For example, guidelines set forth by the American Society of Clinical Oncology (ASCO) and the College of American Pathologists (CAP) are widely accepted. The ASCO/CAP recommends testing by immunohistochemistry (IHC) or in situ hybridization (ISH) techniques. Further, a cancer is Her2 negative if a single test (or all tests) performed on a tumor specimen show: (a) IHC negative, IHC 1+ or IHC 0, or (b) ISH negative using single-probe ISH or dual-probe ISH. One of skill in the art would recognize that the triple negative cancer described herein does not include any cancer having an apparent histopathologic discordance as observed by the pathologist. Wolff, A C et al. *J Clin Oncol.* 2013 Nov. 1:31(31):3997-4013. Cancer is ER-negative or PR-negative if <1% of tumor cell nuclei are immunoreactive in the presence of evidence that the sample can express ER or PR (positive intrinsic controls are seen).

"PARP inhibitor-resistant" refers to the reduced effectiveness of PARP inhibitors in treating, curing, or improving triple negative breast cancer in a subject. In certain embodiments, the PARP inhibitor-resistance develops with prolonged exposure to one or more PARP inhibitors.

As used herein, the term "therapeutically effective amount" or "effective amount" refers to an amount of an antibody, antibody conjugate, or composition that when administered to a subject is effective to treat a disease or disorder. In some embodiments, a therapeutically effective amount or effective amount refers to an amount of an antibody, antibody conjugate, or composition that when administered to a subject is effective to prevent or ameliorate a disease or the progression of the disease, or result in amelioration of symptoms. A "therapeutically effective amount" can vary depending on, inter alia, the compound, the disease or disorder and its severity, and the age, weight, etc., of the subject to be treated.

As used herein, the term "inhibits growth" (e.g., referring to cells, such as tumor cells) is intended to include any measurable decrease in cell growth (e.g., tumor cell growth) when contacted with a ROR1 antibody or antibody conjugate described herein, as compared to the growth of the same cells not in contact with a ROR1 antibody. In some embodiments, growth may be inhibited by at least about 10%, 20%, 30%, 40%, 50%, 60%, 70%, 80%, 90%, 99%, or 100%. The decrease in cell growth can occur by a variety of mechanisms, including but not limited to antibody internalization, apoptosis, necrosis, and/or effector function-mediated activity.

In some chemical structures illustrated herein, certain substituents, chemical groups, and atoms are depicted with a curvy/wavy line (e.g., 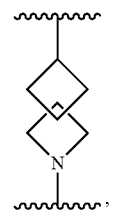) that intersects a bond or bonds to indicate the atom through which the substituents, chemical groups, and atoms are bonded. For example, in some structures, such as but not limited to

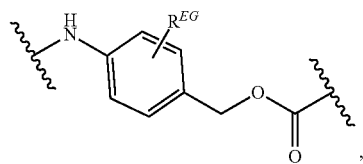

this curvy/wavy line indicates the atoms in the backbone of a conjugate or linker-payload structure to which the illustrated chemical entity is bonded. In some structures, such as but not limited to

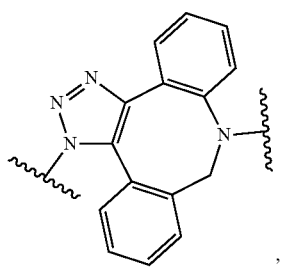 [SMILES: *N1Cc2ccccc2-c2c(nnn2*)-c2ccccc21]

this curvy/wavy line indicates the atoms in the antibody or antibody fragment as well as the atoms in the backbone of a conjugate or linker-payload structure to which the illustrated chemical entity is bonded.

Spiro compounds depicted with overlapping rings indicate that the rings can bond at any vertex. For instance, in the spiro group

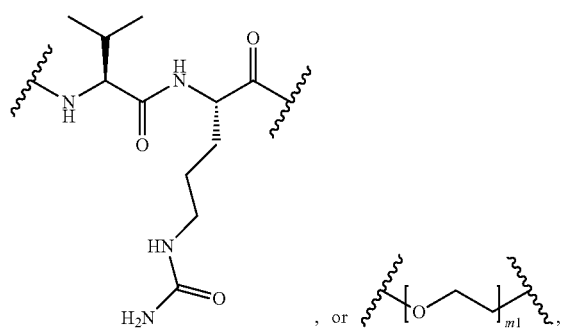

the two rings can bond at any of the three available vertex atoms in either ring.

When referring to the compounds provided herein, the following terms have the following meanings unless indicated otherwise. Unless defined otherwise, all technical and scientific terms used herein have the same meaning as is commonly understood by one of ordinary skill in the art. In the event that there is a plurality of definitions for a term herein, those in this section prevail unless stated otherwise.

"Alkoxy" and "alkoxyl," refer to the group —OR" where R" is alkyl or cycloalkyl. Alkoxy groups include, in certain embodiments, methoxy, ethoxy, n-propoxy, isopropoxy, n-butoxy, tert-butoxy, sec-butoxy, n-pentoxy, n-hexoxy, 1,2-dimethylbutoxy, and the like.

The term "alkoxyamine," as used herein, refers to the group -alkylene-O—$NH_2$, wherein alkylene is as defined herein. In some embodiments, alkoxyamine groups can react with aldehydes to form oxime residues. Examples of alkoxyamine groups include —$CH_2CH_2$—O—$NH_2$, —$CH_2$—O—$NH_2$, and —O—$NH_2$.

The term "alkyl," as used herein, unless otherwise specified, refers to a saturated straight or branched hydrocarbon. In certain embodiments, the alkyl group is a primary, secondary, or tertiary hydrocarbon. In certain embodiments, the alkyl group includes one to ten carbon atoms (i.e., $C_1$ to $C_{10}$ alkyl). In certain embodiments, the alkyl is a lower alkyl, for example, $C_{1-6}$alkyl, and the like. In certain embodiments, the alkyl group is selected from the group consisting of methyl, ethyl, propyl, isopropyl, butyl, isobutyl, sec-butyl, t-butyl, pentyl, isopentyl, neopentyl, hexyl, isohexyl, 3-methylpentyl, 2,2-dimethylbutyl, and 2,3-dimethylbutyl. In certain embodiments, "substituted alkyl" refers to an alkyl substituted with, for example, one, two, or three groups independently selected from a halogen (e.g., fluoro (F), chloro (Cl), bromo (Br), or iodo (I)), alkyl, —CN, —$NO_2$, amido, —C(O)—, —C(S)—, ester, carbamate, alkenyl, alkynyl, cycloalkyl, heterocycloalkyl, dialkylamino, haloalkyl, hydroxyl, amino, alkylamino, and alkoxy. In some embodiments, alkyl is unsubstituted.

The term "alkylene," as used herein, unless otherwise specified, refers to a divalent alkyl group, as defined herein. "Substituted alkylene" refers to an alkylene group substituted as described herein for alkyl. In some embodiments, alkylene is unsubstituted.

"Alkenyl" refers to an olefinically unsaturated hydrocarbon group, in certain embodiments, having up to about eleven carbon atoms or from two to six carbon atoms (e.g., "lower alkenyl"), which can be straight-chained or branched, and having at least one or from one to two sites of olefinic unsaturation. "Substituted alkenyl" refers to an alkenyl group substituted as described herein for alkyl.

"Alkenylene" refers to a divalent alkenyl as defined herein. Lower alkenylene is, for example, $C_2$-$C_6$-alkenylene.

"Alkynyl" refers to acetylenically unsaturated hydrocarbon groups, in certain embodiments, having up to about eleven carbon atoms or from two to six carbon atoms (e.g., "lower alkynyl"), which can be straight-chained or branched, and having at least one or from one to two sites of acetylenic unsaturation. Non-limiting examples of alkynyl groups include acetylene (—C≡CH), propargyl (—CH$_2$C≡CH), and the like. "Substituted alkynyl" refers to an alkynyl group substituted as described herein for alkyl.

"Alkynylene" refers to a divalent alkynyl as defined herein. Lower alkynylene is, for example, $C_2$-$C_6$-alkynylene.

"Amino" refers to —NH$_2$.

The term "alkylamino," as used herein, and unless otherwise specified, refers to the group —NHR" where R" is, for example, $C_{1-10}$alkyl, $C_{2-10}$ alkenyl, $C_{2-10}$ alkynyl, $C_{3-12}$ carbocycle, 3- to 12-membered heterocycle, $C_{1-10}$ haloalkyl, and the like as defined herein. In certain embodiments, alkylamino is $C_{1-6}$alkylamino.

The term "dialkylamino," as used herein, and unless otherwise specified, refers to the group —NR"R" where each R" is independently $C_{1-10}$alkyl, as defined herein. In certain embodiments, dialkylamino is, for example, di-$C_{1-6}$alkylamino, $C_{2-10}$ alkenyl, $C_{2-10}$ alkynyl, $C_{3-12}$ carbocycle, 3- to 12-membered heterocycle, $C_{1-10}$ haloalkyl, and the like.

The term "aryl," as used herein, and unless otherwise specified, refers to phenyl, biphenyl, or naphthyl. The term includes both substituted and unsubstituted moieties. An aryl group can be substituted with any described moiety including, but not limited to, one or more moieties (e.g., in some embodiments one, two, or three moieties) selected from the group consisting of halogen (e.g., fluoro (F), chloro (Cl), bromo (Br), or iodo (I)), alkyl, haloalkyl, hydroxyl, amino, alkylamino, arylamino, alkoxy, aryloxy, nitro, cyano, sulfonic acid, sulfate, phosphonic acid, phosphate, and phosphonate, wherein each moiety is independently either unprotected, or protected as necessary, as would be appreciated by those skilled in the art (see, e.g., Greene, et al., *Protective Groups in Organic Synthesis*, John Wiley and Sons, Second Edition, 1991); and wherein the aryl in the arylamino and aryloxy substituents are not further substituted.

The term "arylamino," as used herein, and unless otherwise specified, refers to an —NR'R" group where R' is hydrogen or $C_1$-$C_6$-alkyl; and R" is aryl, as defined herein.

The term "arylene," as used herein, and unless otherwise specified, refers to a divalent aryl group, as defined herein.

The term "aryloxy," as used herein, and unless otherwise specified, refers to an —OR group where R is aryl, as defined herein.

"Alkarylene" refers to an arylene group, as defined herein, wherein the aryl ring is substituted with one or two alkyl groups. "Substituted alkarylene" refers to an alkarylene, as defined herein, where the arylene group is further substituted, as defined herein for aryl.

"Aralkylene" refers to a —CH$_2$-arylene-, -arylene-CH$_2$—, or —CH$_2$-arylene-CH$_2$— group, where arylene is as defined herein. "Substituted aralkylene" refers to an aralkylene, as defined herein, where the aralkylene group is substituted, as defined herein for aryl.

"Carboxyl" or "carboxy" refers to —C(O)OH or —COOH.

The term "cycloalkyl" as used herein, unless otherwise specified, refers to a saturated cyclic hydrocarbon. In certain embodiments, the cycloalkyl group may be saturated, and/or bridged, and/or non-bridged, and/or a fused bicyclic group and/or a spirocyclic bicyclic group. In certain embodiments, the cycloalkyl group includes three to ten carbon atoms (i.e., $C_3$ to $C_{10}$ cycloalkyl). In some embodiments, the cycloalkyl has from three to fifteen carbons ($C_{3-15}$), from three to ten carbons ($C_{3-10}$), from three to seven carbons ($C_{3-7}$), or from three to six carbons ($C_3$-$C_6$) (i.e., "lower cycloalkyl"). In certain embodiments, the cycloalkyl group is cyclopropyl, cyclobutyl, cyclopentyl, cyclohexyl, cyclohexylmethyl, cycloheptyl, bicyclo[2.1.1]hexyl, bicyclo[2.2.1]heptyl, decalinyl, or adamantyl. Exemplary "cycloalkyl" or "carbocycles" include cyclopentyl, cyclohexyl, cyclohexenyl, adamantyl, phenyl, indanyl, and naphthyl. "Cycloalkyl" or "carbocycle" includes 3- to 10-membered monocyclic rings, 6- to 12-membered bicyclic rings, and 6- to 12-membered bridged rings. Each ring of a bicyclic cycloalkyl or carbocycle may be selected from saturated, unsaturated, and aromatic rings. A bicyclic cycloalkyl or carbocycle includes any combination of saturated, unsaturated and aromatic bicyclic rings, as valence permits. A bicyclic cycloalkyl or carbocycle includes any combination of ring sizes such as 4-5 fused ring systems, 5-5 fused ring systems, 5-6 fused ring systems, 6-6 fused ring systems, 5-7 fused ring systems, 6-7 fused ring systems, 5-8 fused ring systems, and 6-8 fused ring systems. Non-limiting examples of bridged bicyclic cycloalkyl or carbocycle groups include, but are not limited to, bicyclo[1.1.1]pentyl, bicyclo[2.1.1]hexyl, bicyclo[2.1.1]hexyl, bicyclo[3.1.1]heptyl, bicyclo[2.2.1]heptyl, bicyclo[3.2.1]octyl, bicyclo[2.2.2]octyl, bicyclo[3.3.1]nonyl, bicyclo[3.3.2]decyl, and 2-oxabicyclo[2.2.2]octyl. Non-limiting examples of spirocyclic cycloalkyl or carbocycle groups include, but are not limited to, spiro[3.3]heptyl, spiro[3.4]octyl, spiro[3.5]nonyl, spiro[3.6]decyl, spiro[4.4]nonyl, spiro[4.5]decyl, spiro[5.5]undecyl, spiro[5.6]dodecyl, and spiro[5.7]tridecyl.

The term "bicyclic ring system" includes 6-12 (e.g., 8-12 or 9-, 10-, or 11-) membered structures that form two rings, wherein the two rings have at least one atom in common (e.g., two atoms in common). Bicyclic rings can be fused, bridged, or spirocyclic. Bicyclic ring systems include bicycloaliphatics (e.g., bicycloalkyl or bicycloalkenyl), bicycloheteroaliphatics, bicyclic aryls, and bicyclic heteroaryls.

The term "bridged bicyclic ring system" refers to a bicyclic heterocycloaliphatic ring system or bicyclic cycloaliphatic ring system in which the rings are bridged. Examples of bridged bicyclic ring systems include, but are not limited to, adamantanyl, norbornanyl, bicyclo[1.1.1]pentyl, bicyclo[2.1.1]hexyl, bicyclo[2.1.1]hexyl, bicyclo[3.1.1]heptyl, bicyclo[2.2.1]heptyl, bicyclo[3.2.1]octyl, bicyclo[2.2.2]octyl, bicyclo[3.3.1]nonyl, bicyclo[3.3.2]decyl, 2-oxabicyclo[2.2.2]octyl, 6-azabicyclo[3.1.1]heptyl, 6-azabicyclo[3.1.1]heptyl, 1-azabicyclo[2.2.1]heptyl, 2-azabicyclo[2.2.1]heptyl, 7-azabicyclo[2.2.1]heptyl, 1-azabicyclo[2.2.2]octyl, 3-azabicyclo[3.2.1]octyl, and 2-oxabicyclo[3.1.1]heptyl, 2,6-dioxa-tricyclo[3.3.1.0$^{3,7}$]nonyl. A bridged bicyclic ring system can be optionally substituted with one or more substituents such as alkyl (including carboxyalkyl, hydroxyalkyl, and haloalkyl such as trifluoromethyl), alkenyl, alkynyl, cycloalkyl, (cycloalkyl)alkyl, heterocycloalkyl, (heterocycloalkyl)alkyl, aryl, heteroaryl, alkoxy, cycloalkyloxy, heterocycloalkyloxy, aryloxy, heteroaryloxy, aralkyloxy, heteroaralkyloxy, aroyl, heteroaroyl, nitro, carboxy, alkoxycarbonyl, alkylcarbonyloxy, aminocarbonyl, alkylcarbonylamino, cycloalkylcarbonylamino, (cycloalkylalkyl)carbonylamino, arylcarbonylamino, aralkylcarbonylamino, (heterocycloalkyl)carbonylamino, (heterocycloalkylalkyl)carbonylamino, heteroarylcarbonylamino, heteroaralkylcarbonylamino, cyano, halo, hydroxy, acyl, mercapto, alkylsulfanyl, sulfoxy, urea, thiourea, sulfamoyl, sulfamide, oxo, or carbamoyl.

The term "spiro bicyclic ring system" refers to a bicyclic heterocycloaliphatic ring system or bicyclic cycloaliphatic ring system in which 2 or 3 rings are linked together by one common atom. Spiro compounds depicted with overlapping rings indicate that the rings can bond at any vertex. For instance, in the spiro group

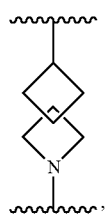

the two rings can bond at any of the three available vertex atoms in either ring.

The term "cycloalkylene," as used herein refers to a divalent cycloalkyl group, as defined herein. In certain embodiments, the cycloalkylene group is cyclopropylene

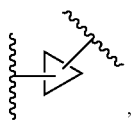

cyclobutylene

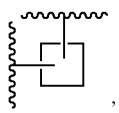

cyclopentylene

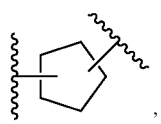

cyclohexylene

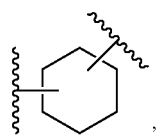

cycloheptylene

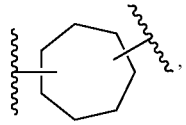

and the like. Lower cycloalkylene refers to a $C_3$-$C_6$-cycloalkylene.

The term "cycloalkylalkyl," as used herein, unless otherwise specified, refers to an alkyl group, as defined herein, substituted with one or two cycloalkyl, as defined herein.

The term "ester," as used herein, refers to —C(O)OR or —COOR where R is alkyl, as defined herein.

The term "fluorene" as used herein refers to

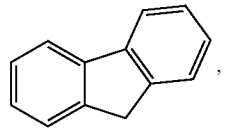 [SMILES: c1ccc2c(c1)Cc1ccccc1-2]

wherein any one or more carbons bearing one or more hydrogens can be substituted with a chemical functional group as described herein.

The term "haloalkyl" refers to an alkyl group, as defined herein, substituted with one or more halogen atoms (e.g., in some embodiments one, two, three, four, or five) which are independently selected.

The term "heteroalkyl" refers to an alkyl, as defined herein, in which one or more carbon atoms are replaced by heteroatoms. As used herein, "heteroalkenyl" refers to an alkenyl, as defined herein, in which one or more carbon atoms are replaced by heteroatoms. As used herein, "heteroalkynyl" refers to an alkynyl, as defined herein, in which one or more carbon atoms are replaced by heteroatoms. Suitable heteroatoms include, but are not limited to, nitrogen (N), oxygen (O), and sulfur (S) atoms. Heteroalkyl, heteroalkenyl, and heteroalkynyl are optionally substituted. Examples of heteroalkyl moieties include, but are not limited to, aminoalkyl, sulfonylalkyl, and sulfinylalkyl. Examples of heteroalkyl moieties also include, but are not limited to, methylamino, methylsulfonyl, and methylsulfinyl. "Substituted heteroalkyl" refers to heteroalkyl substituted with one, two, or three groups independently selected from halogen (e.g., fluoro (F), chloro (Cl), bromo (Br), or iodo (I)), alkyl, haloalkyl, hydroxyl, amino, alkylamino, and alkoxy. In some embodiments, a heteroalkyl group may comprise one, two, three, or four heteroatoms. Those of skill in the art will recognize that a 4-membered heteroalkyl may generally comprise one or two heteroatoms, a 5- or 6-membered heteroalkyl may generally comprise one, two, or three heteroatoms, and a 7- to 10-membered heteroalkyl may generally comprise one, two, three, or four heteroatoms.

The term "heteroalkylene," as used herein, refers to a divalent heteroalkyl, as defined herein. "Substituted heteroalkylene" refers to a divalent heteroalkyl, as defined herein, substituted as described for heteroalkyl.

The term "heterocycloalkyl" refers to a monovalent, monocyclic, or multicyclic non-aromatic ring system, wherein one or more of the ring atoms are heteroatoms independently selected from oxygen (O), sulfur (S), and nitrogen (N) (e.g., where the nitrogen or sulfur atoms may be optionally oxidized, and the nitrogen atoms may be optionally quaternized) and the remaining ring atoms of the non-aromatic ring are carbon atoms. In certain embodiments, heterocycloalkyl is a monovalent, monocyclic, or multicyclic fully-saturated ring system. In certain embodiments, the heterocycloalkyl group has from three to twenty, from three to fifteen, from three to ten, from three to eight, from four to seven, from four to eleven, or from five to six ring atoms. The heterocycloalkyl may be attached to a core structure at any heteroatom or carbon atom which results in the creation of a stable compound. In certain embodiments, the heterocycloalkyl is a monocyclic, bicyclic, tricyclic, or tetracyclic ring system, which may include a fused, and/or bridged bicyclic group, and/or a spirocyclic bicyclic group ring system and in which the nitrogen or sulfur atoms may be optionally oxidized, and/or the nitrogen atoms may be optionally quaternized. In some embodiments, heterocycloalkyl radicals include, but are not limited to, 2,5-diazabicyclo[2.2.2]octanyl, decahydroisoquinolinyl, dihydrobenzisoxazinyl, dihydrofuryl, dihydroisoindolyl, dihydropyranyl, dihydropyrazolyl, dihydropyrazinyl, dihydropyridinyl, dihydropyrimidinyl, dihydropyrrolyl, dioxolanyl, 1,4-dithianyl, furanonyl, imidazolidinyl, imidazolinyl, indolinyl, isothiazolidinyl, isoxazolidinyl, morpholinyl, octahydroindolyl, octahydroisoindolyl, oxazolidinonyl, oxazolidinyl, oxiranyl, piperazinyl, piperidinyl, 4-piperidonyl, pyrazolidinyl, pyrazolinyl, pyrrolidinyl, pyrrolinyl, quinuclidinyl, tetrahydrofuryl, tetrahydroisoquinolinyl, tetrahydropyranyl, tetrahydrothienyl, thiamorpholinyl, thiazolidinyl, tetrahydroquinolinyl, and 1,3,5-trithianyl. In certain embodiments, heterocycloalkyl may also be optionally substituted as described herein. In certain embodiments, heterocycloalkyl is substituted with one, two, or three groups independently selected from halogen (e.g., fluoro (F), chloro (Cl), bromo (Br), or iodo (I)), alkyl, haloalkyl, hydroxyl, amino, alkylamino, and alkoxy. In some embodiments, a heterocycloalkyl group may comprise one, two, three, or four heteroatoms. Those of skill in the art will recognize that a 4-membered heterocycloalkyl may generally comprise one or two heteroatoms, a 5- or 6-membered heterocycloalkyl may generally comprise one, two, or three heteroatoms, and a 7- to 10-membered heterocycloalkyl may generally comprise one, two, three, or four heteroatoms. In some embodiments, "heterocycloalkyl" or "heterocycle" radicals include, but are not limited to, 2,5-diazabicyclo[2.2.2]octanyl, decahydroisoquinolinyl, dihydrobenzisoxazinyl, dihydrofuryl, dihydroisoindolyl, dihydropyranyl, dihydropyrazolyl, dihydropyrazinyl, dihydropyridinyl, dihydropyrimidinyl, dihydropyrrolyl, dioxolanyl, 1,4-dithianyl, furanonyl, imidazolidinyl, imidazolinyl, indolinyl, isothiazolidinyl, isoxazolidinyl, morpholinyl, octahydroindolyl, octahydroisoindolyl, oxazolidinonyl, oxazolidinyl, oxiranyl, piperazinyl, piperidinyl, 4-piperidonyl, pyrazolidinyl, pyrazolinyl, pyrrolidinyl, pyrrolinyl, quinuclidinyl, tetrahydrofuryl, tetrahydroisoquinolinyl, tetrahydropyranyl, tetrahydrothienyl, thiamorpholinyl, thiazolidinyl, tetrahydroquinolinyl, and 1,3,5-trithianyl. Non-limiting examples of bridged heterocycloalkyl or heterocycle groups include, but are not limited to, 6-azabicyclo[3.1.1]heptyl, 6-azabicyclo[3.1.1]heptyl, 1-azabicyclo[2.2.1]heptyl, 2-azabicyclo[2.2.1]heptyl, 7-azabicyclo[2.2.1]heptyl, 1-azabicyclo[2.2.2]octyl, 3-azabicyclo[3.2.1]octyl, and 2-oxabicyclo[3.1.1]heptyl, 2,6-dioxa-tricyclo[3.3.1.0$^{3,7}$]nonyl. Non-limiting examples of spirocyclic heterocycloalkyl or heterocycle groups include, but are not limited to, 2,8-diazaspiro[4.5]decyl; 2,7-diazaspiro[3.5]nonyl; 3,9-diazaspiro[5.5]undecyl; 3-azaspiro[5.5]undecyl; 2-oxa-6-azaspiro[3.4]octyl; 2-oxa-9-azaspiro[5.5]undecyl; 3-oxa-9-azaspiro[5.5]undecyl; 7-azaspiro[3.5]nonyl; 2-azaspiro[3.5]nonyl; 7-oxaspiro[3.5]nonyl; and, 2-oxaspiro[3.5]nonyl.

"Heterocycloalkylene" refers to a divalent heterocycloalkyl as defined herein.

The term "heteroaryl" refers to a monovalent, monocyclic aromatic group and/or multicyclic aromatic group, wherein at least one aromatic ring contains one or more heteroatoms independently selected from oxygen, sulfur, and nitrogen within the ring. Each ring of a heteroaryl group can contain one or two oxygen atoms, one or two sulfur atoms, and/or one to four nitrogen atoms, provided that the total number of heteroatoms in each ring is four or less and each ring contains at least one carbon atom. In certain embodiments, the heteroaryl has from five to twenty, from five to fifteen, or from five to ten ring atoms. A heteroaryl may be attached to the rest of the molecule via a nitrogen or a carbon atom. In some embodiments, monocyclic heteroaryl groups include, but are not limited to, furanyl, imidazolyl, isothiazolyl, isoxazolyl, oxadiazolyl, oxazolyl, pyrazinyl, pyrazolyl, pyridazinyl, pyridyl, pyrimidinyl, pyrrolyl, triazolyl, thiadiazolyl, thiazolyl, thienyl, tetrazolyl, and triazinyl. Examples of bicyclic heteroaryl groups include, but are not limited to, benzofuranyl, benzimidazolyl, benzoisoxazolyl, benzopyranyl, benzothiadiazolyl, benzothiazolyl, benzothienyl, benzotriazolyl, benzoxazolyl, furopyridyl, imidazopyridinyl, imidazothiazolyl, indolizinyl, indolyl, indazolyl, isobenzofuranyl, isobenzothienyl, isoindolyl, isoquinolinyl, naphthyridinyl, oxazolopyridinyl, phthalazinyl, pteridinyl, purinyl, pyridopyridyl, pyrrolopyridyl, quinolinyl, quinoxalinyl, quinazolinyl, thiadiazolopyrimidyl, and thienopyridyl. Examples of tricyclic heteroaryl groups include, but are not limited to, acridinyl, benzindolyl, carbazolyl, dibenzofuranyl, perimidinyl, phenanthrolinyl, phenanthridinyl, phenarsazinyl, phenazinyl, phenothiazinyl, phenoxazinyl, and xanthenyl. In certain embodiments, heteroaryl may also be optionally substituted as described herein. "Substituted heteroaryl" is a heteroaryl substituted as defined for aryl.

The term "heteroarylene" refers to a divalent heteroaryl group, as defined herein. "Substituted heteroarylene" is a heteroarylene substituted as defined for aryl.

The term "protecting group," as used herein, and unless otherwise specified, refers to a group that is added to an oxygen, nitrogen, or phosphorus atom to prevent further reaction at the (protected) oxygen, nitrogen, or phosphorus, or for other purposes. A wide variety of oxygen and nitrogen protecting groups are known to those skilled in the art of organic synthesis (see, e.g., Greene, et al., Protective Groups in Organic Synthesis, John Wiley and Sons, Fourth Edition, 2006, which is incorporated herein by reference in its entirety).

"Pharmaceutically acceptable salt" refers to any salt of a compound provided herein which retains its biological properties and which is not toxic or otherwise undesirable for pharmaceutical use. Such salts may be derived from a variety of organic and inorganic counter-ions well known in the art. Such salts include, but are not limited to (1) acid addition salts formed with organic or inorganic acids such as hydrochloric, hydrobromic, sulfuric, nitric, phosphoric, sulfamic, acetic, trifluoroacetic, trichloroacetic, propionic, hexanoic, cyclopentylpropionic, glycolic, glutaric, pyruvic, lactic, malonic, succinic, sorbic, ascorbic, malic, maleic, fumaric, tartaric, citric, benzoic, 3-(4-hydroxybenzoyl)benzoic, picric, cinnamic, mandelic, phthalic, lauric, methanesulfonic, ethanesulfonic, 1,2-ethane-disulfonic, 2-hydroxyethanesulfonic, benzenesulfonic, 4-chlorobenzenesulfonic, 2-naphthalenesulfonic, 4-toluenesulfonic, camphoric, camphorsulfonic, 4-methylbicyclo[2.2.2]-oct-2-ene-1-carboxylic, glucoheptonic, 3-phenylpropionic, trimethylacetic, tert-butylacetic, lauryl sulfuric, gluconic, glutamic, hydroxynaphthoic, salicylic, stearic, cyclohexylsulfamic, quinic, and muconic acids, and the like; or (2) salts formed when an acidic proton present in the parent compound either (a) is replaced by a metal ion, for example, an alkali metal ion, an alkaline earth ion, or an aluminum ion, or alkali metal or alkaline earth metal hydroxides, such as sodium, potassium, calcium, magnesium, aluminum, lithium, zinc, and barium hydroxide, or ammonia; or (b) coordinates with an organic base, such as aliphatic, alicyclic, or aromatic organic amines, including, without limitation, ammonia, methylamine, dimethylamine, diethylamine, picoline, ethanolamine, diethanolamine, triethanolamine, ethylenediamine, lysine, arginine, ornithine, choline, N,N'-dibenzylethylene-diamine, chloroprocaine, procaine, N-benzylphenethylamine, N-methylglucamine piperazine, tris(hydroxymethyl)-aminomethane, tetramethylammonium hydroxide, and the like.

Pharmaceutically acceptable salts further include, by way of example and without limitation, sodium, potassium, calcium, magnesium, ammonium, and tetraalkylammonium salts, and the like, and when the compound contains a basic functionality, salts of non-toxic organic or inorganic acids, such as hydrohalides, for example, hydrochloride and hydrobromide, sulfate, phosphate, sulfamate, nitrate, acetate, trifluoroacetate, trichloroacetate, propionate, hexanoate, cyclopentylpropionate, glycolate, glutarate, pyruvate, lactate, malonate, succinate, sorbate, ascorbate, malate, maleate, fumarate, tartarate, citrate, benzoate, 3-(4-hydroxybenzoyl)benzoate, picrate, cinnamate, mandelate, phthalate, laurate, methanesulfonate (mesylate), ethanesulfonate, 1,2-ethane-di sulfonate, 2-hydroxyethanesulfonate, benzenesulfonate (besylate), 4-chlorobenzenesulfonate, 2-naphthalenesulfonate, 4-toluenesulfonate, camphorate, camphorsulfonate, 4-methylbicyclo[2.2.2]-oct-2-ene-1-carboxylate, glucoheptonate, 3-phenylpropionate, trimethylacetate, tert-butylacetate, lauryl sulfate, gluconate, glutamate, hydroxynaphthoate, salicylate, stearate, cyclohexylsulfamate, quinate, muconate, and the like.

The term "substantially free of" or "substantially in the absence of" with respect to a composition refers to a composition that includes at least 85% or 90% by weight, in certain embodiments 95%, 98%, 99%, or 100% by weight; or in certain embodiments, 95%, 98%, 99%, or 100% of the designated enantiomer or diastereomer of a compound. In certain embodiments, in the methods and compounds provided herein, the compounds are substantially free of one of two enantiomers. In certain embodiments, in the methods and compounds provided herein, the compounds are substantially free of one of two diastereomers. In certain embodiments, in the methods and compounds provided herein, the compounds are substantially free of enantiomers (i.e., the compounds are not a racemic or 50:50 mixture of compounds).

Similarly, the term "isolated" with respect to a composition refers to a composition that includes at least 85%, 90%, 95%, 98%, or 99% to 100% by weight, of the compound, the remainder comprising other chemical species, enantiomers, or diastereomers.

"Solvate" refers to a compound provided herein, or a salt thereof, that further includes a stoichiometric or non-stoichiometric amount of solvent bound by non-covalent intermolecular forces. Where the solvent is water, the solvate is a hydrate.

"Isotopic composition" refers to the amount of each isotope present for a given atom, and "natural isotopic composition" refers to the naturally occurring isotopic composition or abundance for a given atom. Atoms containing their natural isotopic composition may also be referred to herein as "non-enriched" atoms. Unless otherwise designated, the atoms of the compounds recited herein are meant to represent any stable isotope of that atom. For example, unless otherwise stated, when a position is designated specifically as hydrogen (H), the position is understood to have hydrogen at its natural isotopic composition.

"Isotopic enrichment" refers to the percentage of incorporation of an amount of a specific isotope at a given atom in a molecule in the place of that atom's natural isotopic abundance. For example, deuterium (D) enrichment of 1% at a given position means that 1% of the molecules in a given sample contain deuterium at the specified position. Because the naturally occurring distribution of deuterium is about 0.0156%, deuterium enrichment at any position in a compound synthesized using non-enriched starting materials is about 0.0156%. The isotopic enrichment of the compounds provided herein can be determined using conventional analytical methods known to one of ordinary skill in the art, including mass spectrometry and nuclear magnetic resonance spectroscopy.

"Isotopically enriched" refers to an atom having an isotopic composition other than the natural isotopic composition of that atom. "Isotopically enriched" may also refer to a compound containing at least one atom having an isotopic composition other than the natural isotopic composition of that atom.

As used herein, "alkyl," "alkylene," "alkylamino," "dialkylamino," "cycloalkyl," "aryl," "arylene," "alkoxy," "amino," "carboxyl," "heterocycloalkyl," "heteroaryl," "heteroarylene," "carboxyl," and "amino acid" groups optionally comprise deuterium (D) at one or more positions where hydrogen (H) atoms are present, and wherein the deuterium composition of the atom or atoms is other than the natural isotopic composition.

Also as used herein, "alkyl," "alkylene," "alkylamino," "dialkylamino," "cycloalkyl," "aryl," "arylene," "alkoxy," "amino," "carboxyl," "heterocycloalkyl," "heteroaryl," "heteroarylene," "carboxyl," and "amino acid" groups optionally comprise carbon-13 ($^{13}$C) at an amount other than the natural isotopic composition.

The term "macromolecule" or "macromolecular moiety" refers to a protein, peptide, antibody, nucleic acid, carbohydrate, or other large molecule composed of polymerized monomers. They include peptides of two or more residues, or ten or more residues. In certain embodiments, a macromolecule is at least 1000 Da in mass. In certain embodiments, a macromolecule has at least 1000 atoms. In certain embodiments, a macromolecule can be modified. For instance, a protein, peptide, or antibody can be modified with one or more carbohydrates and/or small molecule therapeutic compounds.

The term "amino acid" refers to the twenty common naturally occurring amino acids. Naturally occurring amino acids include alanine (Ala; A), arginine (Arg; R), asparagine (Asn; N), aspartic acid (Asp; D), cysteine (Cys; C); glutamic acid (Glu; E), glutamine (Gln; Q), Glycine (Gly; G); histidine (His; H), isoleucine (Ile; I), leucine (Leu; L), lysine (Lys; K), methionine (Met; M), phenylalanine (Phe; F), proline (Pro; P), serine (Ser; S), threonine (Thr; T), tryptophan (Trp; W), tyrosine (Tyr; Y), and valine (Val; V), and the less common pyrrolysine and selenocysteine. Natural amino acids also include citrulline. Naturally encoded amino acids include post-translational variants of the twenty-two naturally occurring amino acids such as prenylated amino acids, isoprenylated amino acids, myrisoylated amino acids, palmitoylated amino acids, N-linked glycosylated amino acids, O-linked glycosylated amino acids, phosphorylated amino acids, and acylated amino acids. The term "amino acid" also includes non-natural (or unnatural) or synthetic α-, β-, γ-, or δ-amino acids, and includes, but is not limited to, amino acids found in proteins, i.e., glycine, alanine, valine, leucine, isoleucine, methionine, phenylalanine, tryptophan, proline, serine, threonine, cysteine, tyrosine, asparagine, glutamine, aspartate, glutamate, lysine, arginine, and histidine. In certain embodiments, the amino acid is in the L-configuration. In certain embodiments, the amino acid is in the D-configuration. Alternatively, the amino acid can be a derivative of alanyl, valinyl, leucinyl, isoleucinyl, prolinyl, phenylalaninyl, tryptophanyl, methioninyl, glycinyl, serinyl, threoninyl, cysteinyl, tyrosinyl, asparaginyl, glutaminyl, aspartoyl, glutaroyl, lysinyl, argininyl, histidinyl, β-alanyl, β-valinyl, β-leucinyl, β-isoleucinyl, β-prolinyl, β-phenylalaninyl, β-tryptophanyl, β-methioninyl, β-glycinyl, β-serinyl, β-threoninyl, β-cysteinyl, β-tyrosinyl, β-asparaginyl, β-glutaminyl, β-aspartoyl, β-glutaroyl, β-lysinyl, β-argininyl, or β-histidinyl. Unnatural amino acids are not proteinogenic amino acids, or post-translationally modified variants thereof. In particular, the term unnatural amino acid refers to an amino acid that is not one of the twenty common amino acids or pyrrolysine or selenocysteine, or post-translationally modified variants thereof.

The term "conjugate" or "antibody conjugate" refers to a compound or drug moiety described herein linked to one or more macromolecular moieties. The macromolecular moiety is as defined herein or is any macromolecule deemed suitable to the person of skill in the art. The compound or drug moiety can be any compound or drug moiety described herein. The compound or drug moiety can be directly linked to the macromolecular moiety via a covalent bond, or the compound or drug moiety can be linked to the macromolecular moiety indirectly via a linker. Typically, the linker is covalently bonded to the macromolecular moiety and also covalently bonded to the compound or drug moiety.

"pAMF," "pAMF residue," or "pAMF mutation" refers to a variant phenylalanine residue (i.e., para-azidomethyl-L-phenylalanine) added or substituted into a polypeptide.

The term "linker" refers to a molecular moiety that is capable of forming at least two covalent bonds. Typically, a linker is capable of forming at least one covalent bond to a macromolecular moiety and at least another covalent bond to a compound or drug moiety. In certain embodiments, a linker can form more than one covalent bond to a macromolecular moiety. In certain embodiments, a linker can form more than one covalent bond to a compound or drug moiety or can form covalent bonds to more than one compound or drug moiety. After a linker forms a bond to a macromolecular moiety, or a compound or drug moiety, or both, the remaining structure (i.e. the residue of the linker ("linker residue") after one or more covalent bonds are formed) may still be referred to as a "linker" herein. The term "linker precursor" refers to a linker having one or more reactive groups capable of forming a covalent bond with a macromolecule, or compound or drug moiety, or both. A person of ordinary skill in the art, given the context of how the term linker is used, would understand whether "linker" means linker precursor with one reactive group, a linker precursor with more than one reactive groups, a linker residue which is covalently bonded to the macromolecule, a linker residue which is covalently bonded to a compound or drug moiety, and/or a linker residue which is covalently bonded to the macromolecule and is covalently bonded to a compound or drug moiety. In some embodiments, the linker is a cleavable linker. For example, a cleavable linker can be one that is released by a bio-labile or enzymatic function, which may or may not be engineered. In some embodiments, the linker is a non-cleavable linker. For example, a non-cleavable linker can be one that is released upon degradation of the macromolecular moiety.

As used herein, term "$EC_{50}$" refers to a dosage, concentration, or amount of a particular test compound that elicits a dose-dependent response at 50% of maximal expression of a particular response that is induced, provoked, or potentiated by the particular test compound.

As used herein, and unless otherwise specified, the term "$IC_{50}$" refers to an amount, concentration, or dosage of a particular test compound that achieves a 50% inhibition of a maximal response in an assay that measures such response.

As used herein, the terms "subject" and "patient" are used interchangeably. The terms "subject" and "subjects" refer to an animal, such as a mammal including a non-primate (e.g., a cow, pig, horse, cat, dog, rat, mouse, camel, avian, goat, and sheep) and a primate (e.g., a monkey, such as a cynomolgous monkey, a chimpanzee, and a human), and in certain embodiments, a human. In certain embodiments, the subject is a farm animal (e.g., a horse, a cow, a pig, etc.) or a pet (e.g., a dog or a cat). In certain embodiments, the subject is a human. In some embodiments, the subject has a disease that can be treated or diagnosed with an antibody or antibody conjugate provided herein. In some embodiments, the disease is gastric carcinoma, colorectal carcinoma, renal cell carcinoma, cervical carcinoma, non-small cell lung carcinoma, ovarian cancer, breast cancer, triple-negative breast cancer, endometrial cancer, prostate cancer, and/or a cancer of epithelial origin.

As used herein, the terms "therapeutic agent" and "therapeutic agents" refer to any agent(s) which can be used in the treatment or prevention of a disorder or one or more symptoms thereof. In certain embodiments, the term "therapeutic agent" includes an antibody or antibody conjugate provided herein. In certain embodiments, a therapeutic agent is an agent which is known to be useful for, or has been or is currently being used for the treatment or prevention of a disorder or one or more symptoms thereof.

"Treating" or "treatment" of any disease or disorder refers, in certain embodiments, to ameliorating a disease or disorder that exists in a subject. In another embodiment, "treating" or "treatment" includes ameliorating at least one physical parameter, which may be indiscernible by the subject. In yet another embodiment, "treating" or "treatment" includes modulating the disease or disorder, either physically (e.g., stabilization of a discernible symptom) or physiologically (e.g., stabilization of a physical parameter) or both. In yet another embodiment, "treating" or "treatment" includes delaying or preventing the onset of the disease or disorder, or delaying or preventing recurrence of the disease or disorder. In yet another embodiment, "treating" or "treatment" includes the reduction or elimination of either the disease or disorder, or retarding the progression of the disease or disorder or of one or more symptoms of the disease or disorder, or reducing the severity of the disease or disorder or of one or more symptoms of the disease or disorder.

As used herein, the terms "prophylactic agent" and "prophylactic agents" as used refer to any agent(s) which can be used in the prevention of a disorder or one or more symptoms thereof. In certain embodiments, the term "prophylactic agent" includes a compound, drug moiety, or conjugate provided herein. In certain other embodiments, the term "prophylactic agent" does not refer a compound, drug moiety, or conjugate provided herein. For example, a prophylactic agent is an agent which is known to be useful for, or has been or is currently being used to prevent or impede the onset, development, progression, and/or severity of a disorder.

As used herein, the phrase "prophylactically effective amount" refers to the amount of a therapy (e.g., prophylactic agent) which is sufficient to result in the prevention or reduction of the development, recurrence, or onset of one or more symptoms associated with a disorder or to enhance or improve the prophylactic effect(s) of another therapy (e.g., another prophylactic agent).

In some chemical structures illustrated herein, certain substituents, chemical groups, and atoms are depicted with a curvy/wavy/wiggly line (e.g.,

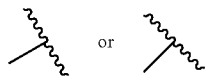

that intersects a bond or bonds to indicate the atom through which the substituents, chemical groups, and atoms are bonded. For example, in some structures, such as but not limited to,

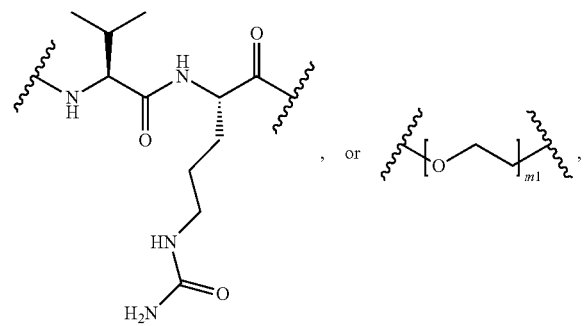

this curvy/wavy/wiggly line indicates the atoms in the backbone of a conjugate, compound, or drug moiety structure to which the illustrated chemical entity is bonded. In some structures, such as but not limited to

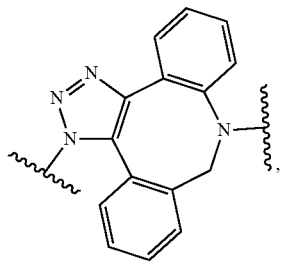 [SMILES: *N1Cc2ccccc2-c2c(nnn2*)-c2ccccc21]

this curvy/wavy/wiggly line indicates the atoms in the macromolecule as well as the atoms in the backbone of a conjugate, compound, or drug moiety structure to which the illustrated chemical entity is bonded.

As used herein, illustrations showing substituents bonded to a cyclic group (e.g., aromatic, heteroaromatic, fused ring, and saturated or unsaturated cycloalkyl or heterocycloalkyl) through a bond between ring atoms are meant to indicate, unless specified otherwise, that the cyclic group may be substituted with that substituent at any ring position in the cyclic group or on any ring in the fused ring group, according to techniques set forth herein or which are known in the field to which the instant disclosure pertains. For example, the group,

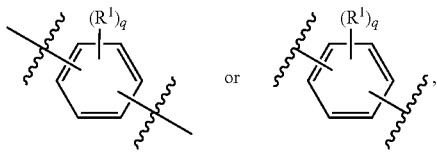

wherein subscript q is an integer from zero to four and in which the positions of substituent $R^1$ are described generically, i.e., not directly attached to any vertex of the bond line structure, i.e., specific ring carbon atom, includes the following, non-limiting examples of groups in which the substituent $R^1$ is bonded to a specific ring carbon atom:

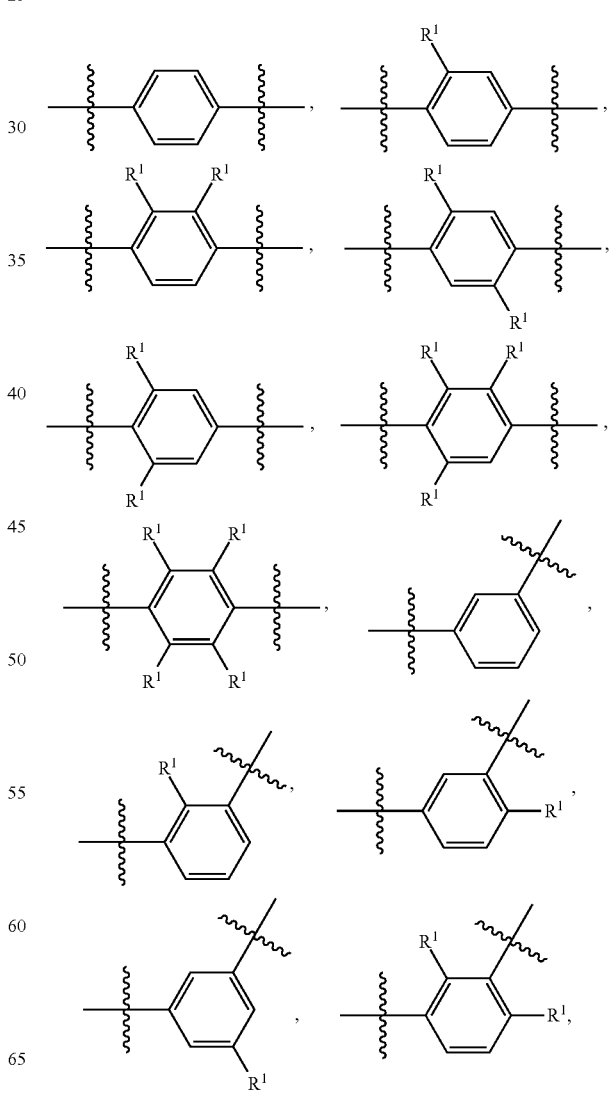

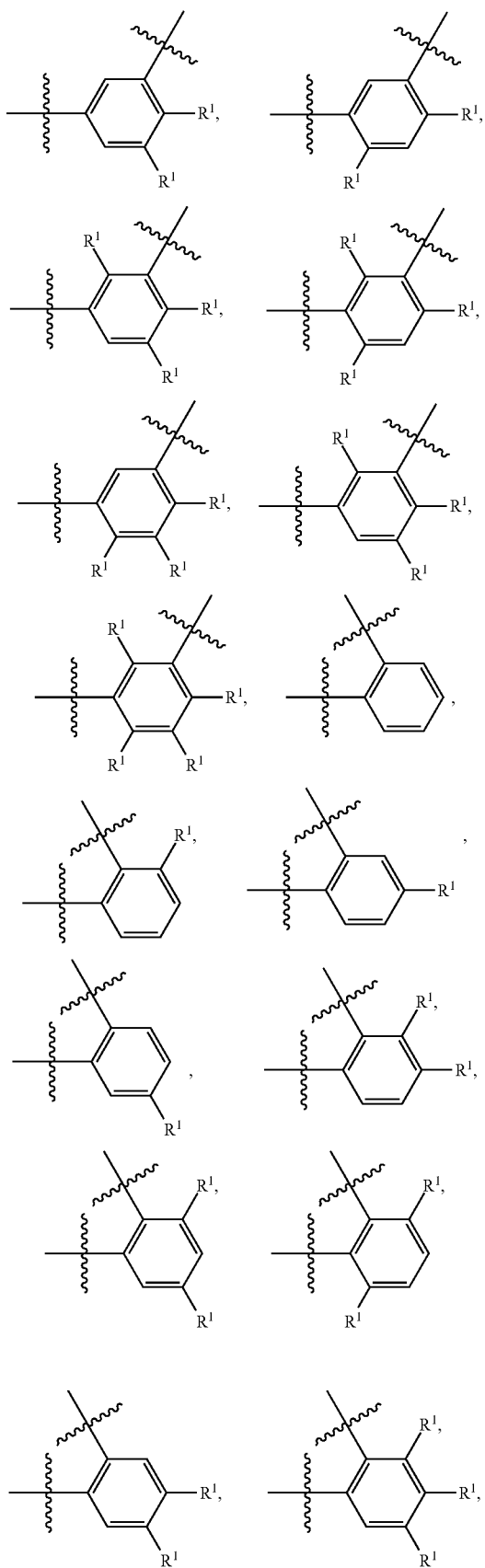

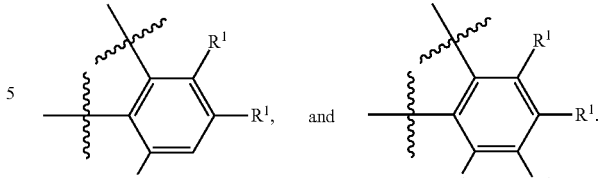

The term "carbocycle" as used herein, unless otherwise specified, refers to a saturated, unsaturated, or aromatic ring in which atom of the ring is carbon. In certain embodiments, the carbocycle group may be saturated, and/or bridged, and/or non-bridged, and/or a fused bicyclic group, and/or a spirocyclic bicyclic group. In certain embodiments, the carbocycle group includes three to ten carbon atoms (i.e., $C_3$ to $C_{10}$ carbocycle). In some embodiments, the carbocycle has from three to fifteen carbons ($C_{3-15}$), from three to ten carbons ($C_{3-10}$), from three to seven carbons ($C_{3-7}$), or from three to six carbons ($C_3$-$C_6$). In certain embodiments, the carbocycle group is cyclopropyl, cyclobutyl, cyclopentyl, cyclohexyl, cyclohexylmethyl, cycloheptyl, bicyclo[2.1.1]hexyl, bicyclo[2.2.1]heptyl, decalinyl, or adamantyl.

The term "heterocycle" refers to a saturated, unsaturated or aromatic ring comprising one or more heteroatoms. Exemplary heteroatoms include N, O, Si, P, B, and S atoms where the nitrogen or sulfur atoms may be optionally oxidized, and the nitrogen atoms may be optionally quaternized and the remaining ring atoms of the non-aromatic ring are carbon atoms. Heterocycles include 3- to 10-membered monocyclic rings, 6- to 12-membered bicyclic rings, and 6- to 12-membered bridged rings. In certain embodiments, heterocycle is a monovalent, monocyclic, or multicyclic fully-saturated ring system. In certain embodiments, the heterocycloalkyl or "heterocycle" group may be unsaturated, and/or bridged, and/or non-bridged, and/or a fused bicyclic group, and/or a spirocyclic bicyclic group.

The term "site-specific" refers to a modification of a polypeptide at a predetermined sequence location in the polypeptide. The modification is at a single, predictable residue of the polypeptide with little or no variation. In particular embodiments, a modified amino acid is introduced at that sequence location, for instance recombinantly or synthetically. Similarly, a moiety can be "site-specifically" linked to a residue at a particular sequence location in the polypeptide. In certain embodiments, a polypeptide can comprise more than one site-specific modification.

2. Conjugates

Provided herein are conjugates of antibodies to receptor tyrosine kinase orphan receptor 1 (ROR1). The conjugates comprise an antibody to ROR1 covalently linked directly or indirectly, via a linker, to a payload. In some embodiments, the conjugate comprises an antibody that specifically binds to receptor tyrosine kinase orphan receptor 1 (ROR1) linked site-specifically to at least one payload moiety, and the antibody comprises one or more non-natural amino acids. In certain embodiments, the antibody is linked to one payload. In further embodiments, the antibody is linked to more than one payload. In certain embodiments, the antibody is linked to two, three, four, five, six, seven, eight, nine, ten, or more payloads.

The payload can be any payload deemed useful by the practitioner of skill. In certain embodiments, the payload is a therapeutic moiety. In certain embodiments, the payload is a diagnostic moiety, e.g., a label. Useful payloads are described in the sections and examples below.

The linker can be any linker capable of forming at least one bond to the antibody and at least one bond to a payload. Useful linkers are described the sections and examples below.

In the conjugates provided herein, the antibody can be any antibody with binding specificity for ROR1. The ROR1 can be from any species. In certain embodiments, the ROR1 is a vertebrate ROR1. In certain embodiments, the ROR1 is a mammalian ROR1. In certain embodiments, the ROR1 is human ROR1. In certain embodiments, the ROR1 is mouse ROR1. In certain embodiments, the ROR1 is cynomolgus ROR1.

In certain embodiments, the antibody to ROR1 competes with an antibody described herein for binding. In certain embodiments, the antibody to ROR1 binds to the same epitope as an antibody described herein.

The antibody is typically a protein comprising multiple polypeptide chains. In certain embodiments, the antibody is a heterotetramer comprising two identical light (L) chains and two identical heavy (H) chains. Each light chain can be linked to a heavy chain by one covalent disulfide bond. Each heavy chain can be linked to the other heavy chain by one or more covalent disulfide bonds. Each heavy chain and each light chain can also have one or more intrachain disulfide bonds. As is known to those of skill in the art, each heavy chain typically comprises a variable domain ($V_H$) followed by a number of constant domains. Each light chain typically comprises a variable domain at one end ($V_L$) and a constant domain. As is known to those of skill in the art, antibodies typically have selective affinity for their target molecules, i.e., antigens.

The antibodies provided herein can have any antibody form known to those of skill in the art. They can be full-length, or fragments. Exemplary full-length antibodies include IgA, IgA1, IgA2, IgD, IgE, IgG, IgG1, IgG2, IgG3, IgG4, IgM, etc. Exemplary fragments include Fv, Fab, Fc, scFv, scFv-Fc, and etc.

In certain embodiments, the antibody of the conjugate comprises one, two, three, four, five, or six of the CDR sequences described herein. In certain embodiments, the antibody of the conjugate comprises a heavy chain variable domain ($V_H$) described herein. In certain embodiments, the antibody of the conjugate comprises a light chain variable domain ($V_L$) described herein. In certain embodiments, the antibody of the conjugate comprises a heavy chain variable domain ($V_H$) described herein and a light chain variable domain ($V_L$) described herein. In certain embodiments, the antibody of the conjugate comprises a paired heavy chain variable domain and a light chain variable domain described herein ($V_H$-$V_L$ pair).

In certain embodiments, the antibody of the conjugate comprises any of the amino acid sequences of the antibodies described above. In certain embodiments, the antibody comprises any of the amino acid sequences above with up to 10 amino acid substitutions. In certain embodiments, the antibody comprises any of the amino acid sequences above with up to 9 amino acid substitutions. In certain embodiments, the antibody comprises any of the amino acid sequences above with up to 8 amino acid substitutions. In certain embodiments, the antibody comprises any of the amino acid sequences above with up to 7 amino acid substitutions. In certain embodiments, the antibody comprises any of the amino acid sequences above with up to 6 amino acid substitutions. In certain embodiments, the antibody comprises any of the amino acid sequences above with up to 5 amino acid substitutions. In certain embodiments, the antibody comprises any of the amino acid sequences above with up to 4 amino acid substitutions. In certain embodiments, the antibody comprises any of the amino acid sequences above with up to 3 amino acid substitutions. In certain embodiments, the antibody comprises any of the amino acid sequences above with up to 2 amino acid substitutions. In certain embodiments, the antibody comprises any of the amino acid sequences above with up to 1 conservative amino acid substitution. In some embodiments, the amino acid substitutions are conservative amino acid substitutions. For example, in certain embodiments, the antibody comprises any of the amino acid sequences above with up to 10 conservative amino acid substitutions. In certain embodiments, the antibody comprises any of the amino acid sequences above with up to 9 conservative amino acid substitutions. In certain embodiments, the antibody comprises any of the amino acid sequences above with up to 8 conservative amino acid substitutions. In certain embodiments, the antibody comprises any of the amino acid sequences above with up to 7 conservative amino acid substitutions. In certain embodiments, the antibody comprises any of the amino acid sequences above with up to 6 conservative amino acid substitutions. In certain embodiments, the antibody comprises any of the amino acid sequences above with up to 5 conservative amino acid substitutions. In certain embodiments, the antibody comprises any of the amino acid sequences above with up to 4 conservative amino acid substitutions. In certain embodiments, the antibody comprises any of the amino acid sequences above with up to 3 conservative amino acid substitutions. In certain embodiments, the antibody comprises any of the amino acid sequences above with up to 2 conservative amino acid substitutions. In certain embodiments, the antibody comprises any of the amino acid sequences above with up to 1 conservative amino acid substitution.

In certain embodiments, the antibody conjugate can be formed from an antibody that comprises one or more reactive groups. In certain embodiments, the antibody conjugate can be formed from an antibody comprising all naturally encoded amino acids. Those of skill in the art will recognize that several naturally encoded amino acids include reactive groups capable of conjugation to a payload or to a linker. These reactive groups include cysteine side chains, lysine side chains, and amino-terminal groups. In these embodiments, the antibody conjugate can comprise a payload or linker linked to the residue of an antibody reactive group. In these embodiments, the payload precursor or linker precursor comprises a reactive group capable of forming a bond with an antibody reactive group. Typical reactive groups include maleimide groups, activated carbonates (including but not limited to, p-nitrophenyl ester), activated esters (including but not limited to, N-hydroxysuccinimide, p-nitrophenyl ester, and aldehydes). Particularly useful reactive groups include maleimide and succinimide, for instance N-hydroxysuccinimide, for forming bonds to cysteine and lysine side chains. Additional reactive groups include alkynes, for example strained alkynes, and azides, for forming bonds to non-natural amino acids incorporated in antibody polypeptide chains. Further reactive groups are described in the sections and examples below.

In certain embodiments, the antibody comprises one or more modified amino acids having a reactive group, as described herein. Typically, the modified amino acid is not a naturally encoded amino acid. These modified amino acids can comprise a reactive group useful for forming a covalent bond to a linker precursor or to a payload precursor. One of skill in the art can use the reactive group to link the polypeptide to any molecular entity capable of forming a covalent bond to the modified amino acid. Thus, provided herein are conjugates comprising an antibody comprising a modified amino acid residue linked to a payload directly or indirectly via a linker. Exemplary modified amino acids are described in the sections below. Generally, the modified amino acids have reactive groups capable of forming bonds to linkers or payloads with complementary reactive groups.

The non-natural amino acids are positioned at select locations in a polypeptide chain of the antibody. These locations were identified as providing optimum sites for substitution with the non-natural amino acids. Each site is capable of bearing a non-natural amino acid with optimum structure, function and/or methods for producing the antibody.

In certain embodiments, a site-specific position for substitution provides an antibody that is stable. Stability can be measured by any technique apparent to those of skill in the art.

In certain embodiments, a site-specific position for substitution provides an antibody that has optimal functional properties. For instance, the antibody can show little or no loss of binding affinity for its target antigen compared to an antibody without the site-specific non-natural amino acid. In certain embodiments, the antibody can show enhanced binding compared to an antibody without the site-specific non-natural amino acid.

In certain embodiments, a site-specific position for substitution provides an antibody that can be made advantageously. For instance, in certain embodiments, the antibody shows advantageous properties in its methods of synthesis, discussed below. In certain embodiments, the antibody can show little or no loss in yield in production compared to an antibody without the site-specific non-natural amino acid. In certain embodiments, the antibody can show enhanced yield in production compared to an antibody without the site-specific non-natural amino acid. In certain embodiments, the antibody can show little or no loss of tRNA suppression compared to an antibody without the site-specific non-natural amino acid. In certain embodiments, the antibody can show enhanced tRNA suppression in production compared to an antibody without the site-specific non-natural amino acid.

In certain embodiments, a site-specific position for substitution provides an antibody that has advantageous solubility. In certain embodiments, the antibody can show little or no loss in solubility compared to an antibody without the site-specific non-natural amino acid. In certain embodiments, the antibody can show enhanced solubility compared to an antibody without the site-specific non-natural amino acid.

In certain embodiments, a site-specific position for substitution provides an antibody that has advantageous expression. In certain embodiments, the antibody can show little or no loss in expression compared to an antibody without the site-specific non-natural amino acid. In certain embodiments, the antibody can show enhanced expression compared to an antibody without the site-specific non-natural amino acid.

In certain embodiments, a site-specific position for substitution provides an antibody that has advantageous folding. In certain embodiments, the antibody can show little or no loss in proper folding compared to an antibody without the site-specific non-natural amino acid. In certain embodiments, the antibody can show enhanced folding compared to an antibody without the site-specific non-natural amino acid.

In certain embodiments, a site-specific position for substitution provides an antibody that is capable of advantageous conjugation. As described below, several non-natural amino acids have side chains or functional groups that facilitate conjugation of the antibody to a second agent, either directly or via a linker. In certain embodiments, the antibody can show enhanced conjugation efficiency compared to an antibody without the same or other non-natural amino acids at other positions. In certain embodiments, the antibody can show enhanced conjugation yield compared to an antibody without the same or other non-natural amino acids at other positions. In certain embodiments, the antibody can show enhanced conjugation specificity compared to an antibody without the same or other non-natural amino acids at other positions.

The one or more non-natural amino acids are located at selected site-specific positions in at least one polypeptide chain of the antibody. The polypeptide chain can be any polypeptide chain of the antibody without limitation, including either light chain or either heavy chain. The site-specific position can be in any domain of the antibody, including any variable domain and any constant domain.

In certain embodiments, the antibodies provided herein comprise one non-natural amino acid at a site-specific position. In certain embodiments, the antibodies provided herein comprise two non-natural amino acids at site-specific positions. In certain embodiments, the antibodies provided herein comprise three non-natural amino acids at site-specific positions. In certain embodiments, the antibodies provided herein comprise more than three non-natural amino acids at site-specific positions. In certain embodiments, the antibodies provided herein comprise four non-natural amino acids at site-specific positions.

In certain embodiments, the antibodies provided herein comprise one or more non-natural amino acids each at a position selected from the group consisting of heavy chain or light chain residues HC-F404, HC-K121, HC-Y180, HC-F241, HC-221, LC-T22, LC-S7, LC-N152, LC-K42, LC-E161, LC-D170, HC-S136, HC-S25, HC-A40, HC-S119, HC-S190, HC-K222, HC-R19, HC-Y52, or HC-S70 according to the Kabat or Chothia or EU numbering scheme, or a post-translationally modified variant thereof. In certain embodiments, the antibodies provided herein comprise one or more non-natural amino acids each at a position selected from the group consisting of heavy chain or light chain residues HC-F404, HC-Y180, HC-F241, LC-K42, and LC-E161, according to the Kabat or Chothia or EU numbering scheme, or a post-translationally modified variant thereof. In certain embodiments, the antibodies provided herein comprise a non-natural amino acid at position HC-F404 according to the Kabat or Chothia or EU numbering scheme, or a post-translationally modified variant thereof. In certain embodiments, the antibodies provided herein comprise a non-natural amino acid at position HC-Y180, according to the Kabat or Chothia or EU numbering scheme, or a post-translationally modified variant thereof. In certain embodiments, the antibodies provided herein comprise non-natural amino acids at positions HC-F404 and HC-Y180, according to the Kabat or Chothia or EU numbering scheme, or a post-translationally modified variant thereof. In certain embodiments, the antibodies provided herein comprise a non-natural amino acid at position HC-F241 according to the Kabat or Chothia or EU numbering scheme, or a post-translationally modified variant thereof. In certain embodiments, the antibodies provided herein comprise a non-natural amino acid at position LC-K42 according to the Kabat or Chothia or EU numbering scheme, or a post-translationally modified variant thereof. In certain embodiments, the antibodies provided herein comprise a non-natural amino acid at position LC-E161 according to the Kabat or Chothia or EU numbering scheme, or a post-translationally modified variant thereof. In certain embodiments, the antibodies provided herein comprise non-natural amino acids at positions HC-F404, HC-Y180, and LC-K42, according to the Kabat or Chothia or EU numbering scheme, or a post-translationally modified variant thereof. In certain embodiments, the antibodies provided herein comprise non-natural amino acids at positions HC-F404, HC-Y180, LC-K42, and LC-E161, according to the Kabat or Chothia or EU numbering scheme, or a post-translationally modified variant thereof. In certain embodiments, the antibodies provided herein comprise non-natural amino acids at positions HC-F404, HC-Y180, and HC-F241, according to the Kabat or Chothia or EU numbering scheme, or a post-translationally modified variant thereof. In certain embodiments, the antibodies provided herein comprise non-natural amino acids at positions HC-F404, HC-Y180, HC-F241, and LC-K42, according to the Kabat or Chothia or EU numbering scheme, or a post-translationally modified variant thereof. In certain embodiments, the antibodies provided herein comprise non-natural amino acids at positions HC-F404, HC-Y180, HC-F241, and LC-K42, according to the Kabat or Chothia or EU numbering scheme, or a post-translationally modified variant thereof. In these designations, HC indicates a heavy chain residue, and LC indicates a light chain residue.

In some aspects, the present disclosure provides conjugates according to the following formula:

COMP—[LINK—PAY]$_{n2}$ or a pharmaceutically acceptable salt, solvate, stereoisomer, regioisomer, or tautomer thereof, wherein:
COMP is a residue of an anti-ROR1 antibody;
PAY is a payload moiety;
LINK is a linker; and
n2 is an integer from 1 to 10,
wherein COMP comprises one or more non-natural amino acids.

In certain embodiments, provided herein are conjugates according to Formula (C1) or (C2):

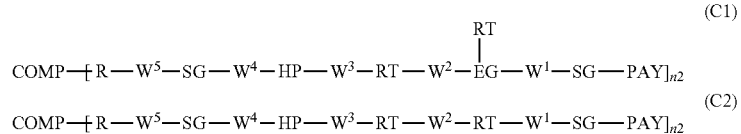

or a pharmaceutically acceptable salt, solvate, stereoisomer, regioisomer, or tautomer thereof, wherein:
COMP is a residue of an anti-ROR1 antibody;
PAY is a payload moiety;
$W^1$, $W^2$, $W^3$, $W^4$, and $W^5$ are each independently a single bond, absent, or a divalent attaching group;
EG is absent, or an eliminator group;
each RT is a release trigger group, in the backbone of Formula (C1) or (C2) or bonded to EG, wherein each RT is optional;

HP is a single bond, absent, or a divalent hydrophilic group;
each SG is a single bond, absent, or a divalent spacer group;
R is hydrogen, a terminal conjugating group, or a divalent residue of a terminal conjugating group; and
n2 is an integer from 1 to 10.

In some embodiments, a conjugate according to Formula (C1) or (C2) comprises n2 number of linked PAY moieties, wherein n2 is an integer from 1 to 10. In some embodiments, n2 is 2. In some embodiments, n2 is 3. In some embodiments, n2 is 4. In some embodiments, n2 is 5. In some embodiments, n2 is 6. In some embodiments, n2 is 7. In some embodiments, n2 is 8. In some embodiments, n2 is 10.

Attaching Groups

Attaching groups facilitate incorporation of eliminator groups, release trigger groups, hydrophobic groups, spacer groups, and/or conjugating groups into a compound. Useful attaching groups are known to, and are apparent to, those of skill in the art. Examples of useful attaching groups are provided herein. In certain embodiments, attaching groups are designated $W^1$, $W^2$, $W^3$, $W^4$, or $W^5$. In certain embodiments, an attaching group can comprise a divalent ketone, divalent ester, divalent ether, divalent amide, divalent amine, alkylene, arylene, sulfide, disulfide, carbonylene, or a combination thereof. In certain embodiments an attaching group can comprise —C(O)—, —O—, —C(O)NH—, —C(O)NH-alkyl-, —OC(O)NH—, —SC(O)NH—, —NH—, —NH-alkyl-, —N(CH$_3$)CH$_2$CH$_2$N(CH$_3$)—, —S—, —S—S—, —OCH$_2$CH$_2$O—, or the reverse (e.g. —NHC(O)—) thereof, or a combination thereof.

Eliminator Groups

Eliminator groups facilitate separation of a biologically active portion of a compound or conjugate described herein from the remainder of the compound or conjugate in vivo and/or in vitro. Eliminator groups can also facilitate separation of a biologically active portion of a compound or conjugate described herein in conjunction with a release trigger group. For example, the eliminator group and the release trigger group can react in a Releasing Reaction to release a biologically active portion of a compound or conjugate described herein from the compound or conjugate in vivo and/or in vitro. Upon initiation of the Releasing Reaction by the release trigger, the eliminator group cleaves the biologically active moiety, or a prodrug form of the biologically active moiety, and forms a stable, non-toxic entity that has no further effect on the activity of the biologically active moiety.

In certain embodiments, the eliminator group is designated EG herein. Useful eliminator groups include those described herein. In certain embodiments, the eliminator group is:

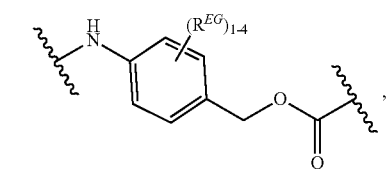

,

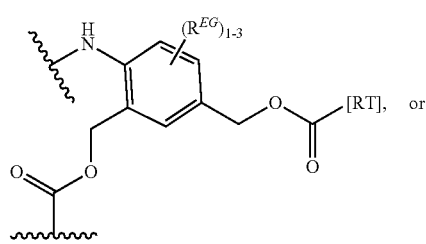

[RT], or

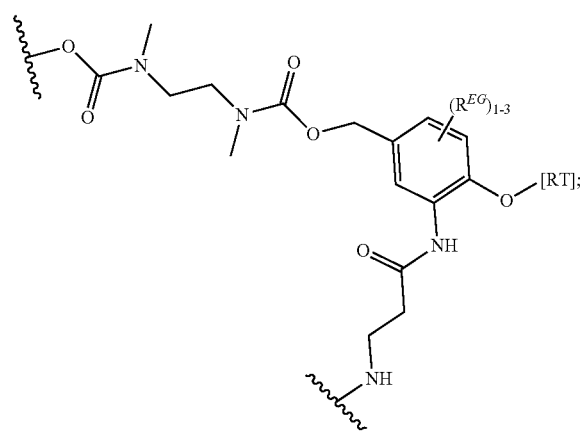

wherein $R^{EG}$ is selected from the group consisting of hydrogen, alkyl, biphenyl, —CF$_3$, —NO$_2$, —CN, fluoro, bromo, chloro, alkoxyl, alkylamino, dialkylamino, alkyl-C(O)O—, alkylamino-C(O)— and dialkylaminoC(O)—. In each structure, the phenyl ring can be bound to one, two, three, or in some cases, four $R^{EG}$ groups. In the second and third structures, those of skill will recognize that EG is bonded to an RT that is not within the backbone of formula (C1) as indicated in the above description of formula (C1). In some embodiments, $R^{EG}$ is selected from the group consisting of hydrogen, alkyl, biphenyl, —CF$_3$, alkoxyl, alkylamino, dialkylamino, alkyl-C(O)O—, alkylamino-C(O)— and dialkylaminoC(O)—. In further embodiments, $R^{EG}$ is selected from the group consisting of hydrogen, —NO$_2$, —CN, fluoro, bromo, and chloro. In certain embodiments, the eliminator group is

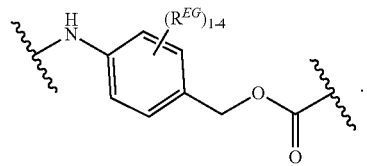

In certain embodiments, the eliminator group is

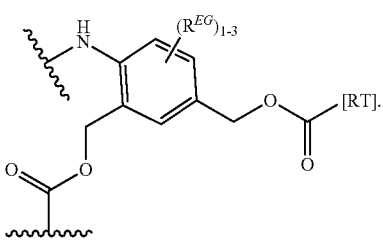

In certain embodiments, the eliminator group is

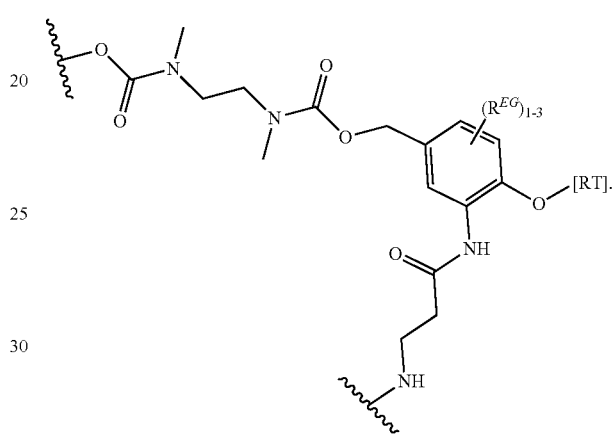

In some embodiments, provided herein is a conjugate according to Formula (C1) or (C2) or a pharmaceutically acceptable salt, solvate, stereoisomer, or tautomer thereof wherein EG comprises phenylene, carboxylene, amine, or a combination thereof. In some embodiments, the eliminator group is:

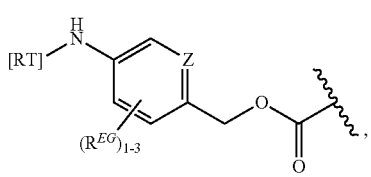

,

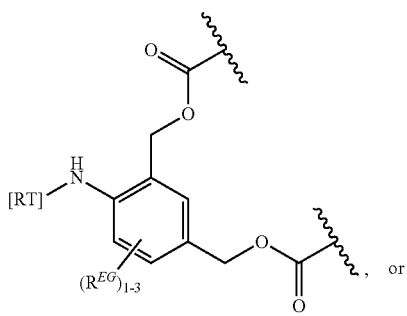

, or

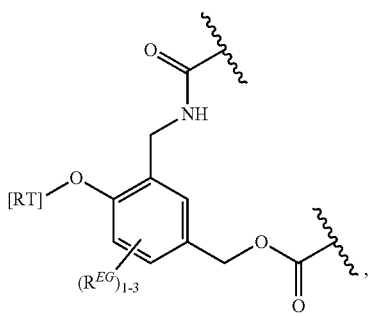

wherein Z may be CH or N, $R^{EG}$ is selected from the group consisting of hydrogen, alkyl, biphenyl, —CF$_3$, —NO$_2$, —CN, fluoro, bromo, chloro, alkoxyl, alkylamino, dialkylamino, alkyl-C(O)O—, alkylamino-C(O)— and dialkylaminoC(O)—. In each structure, the phenyl ring can be bound to one, two, three, or in some cases, four $R^{EG}$ groups. In the first and second structures, those of skill will recognize that EG is bonded to an RT that is not within the backbone of formula (C1) as indicated in the above description of formula (C1). In some embodiments, $R^{EG}$ is selected from the group consisting of hydrogen, alkyl, biphenyl, —CF$_3$, alkoxyl, alkylamino, dialkylamino, alkyl-C(O)O—, alkylamino-C(O)— and dialkylaminoC(O)—. In further embodiments, $R^{EG}$ is selected from the group consisting of hydrogen, —NO$_2$, —CN, fluoro, bromo, and chloro. In some embodiments, each $R^{EG}$ in the EG is hydrogen. In certain embodiments, the eliminator group is

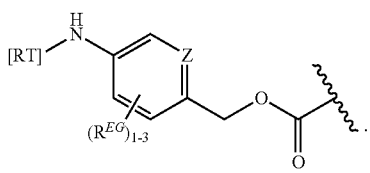

In certain embodiments, the eliminator group is

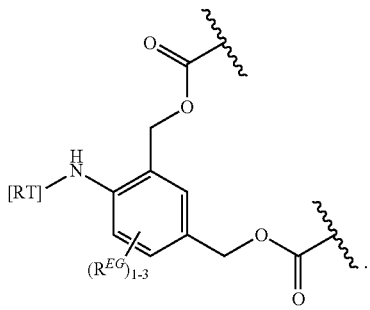

In certain embodiments, the eliminator group is

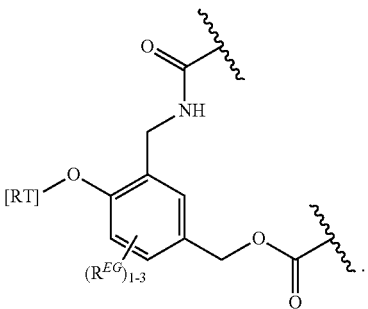

Release Trigger Groups

Release trigger groups facilitate separation of a biologically active portion of a compound or conjugate described herein from the remainder of the compound or conjugate in vivo and/or in vitro. Release trigger groups can also facilitate separation of a biologically active portion of a compound or conjugate described herein in conjunction with an eliminator group. For example, the eliminator group and the release trigger group can react in a Releasing Reaction to release a biologically active portion of a compound or conjugate described herein from the compound or conjugate in vivo and/or in vitro. In certain embodiment, the release trigger can act through a biologically-driven reaction with high tumor:nontumor specificity, such as the proteolytic action of an enzyme overexpressed in a tumor environment.

In certain embodiments, the release trigger group is designated RT herein. In certain embodiments, RT is divalent and bonded within the backbone of formula (C1). In other embodiments, RT is monovalent and bonded to EG as depicted above. Useful release trigger groups include those described herein. In certain embodiments, the release trigger group comprises a residue of a natural or non-natural amino acid or residue of a sugar ring. In certain embodiments, the release trigger group is:

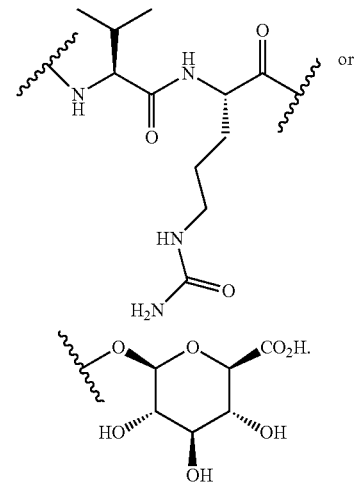

Those of skill will recognize that the first structure is divalent and can be bonded within the backbone of Formula (C1) or as depicted in Formula (C2), and that the second structure is monovalent and can be bonded to EG as depicted in formula (C1) above.

In certain embodiments, the release trigger group is

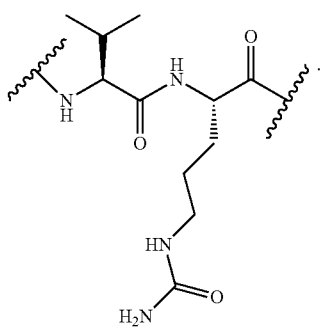 [SMILES: *N[C@H](C(=O)N[C@@H](CCCNC(N)=O)C(*)=O)C(C)C]

In certain embodiments, the release trigger group is

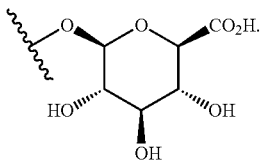 [SMILES: *O[C@H]1O[C@@H](C(=O)O)[C@H](O)[C@@H](O)[C@@H]1O]

In some embodiments, the release trigger group is a protease-cleavable $R_1$-Val-X peptide having the structure of:

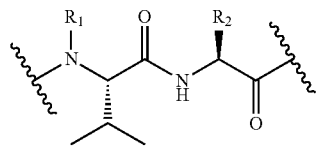

wherein $R_1$ is H or

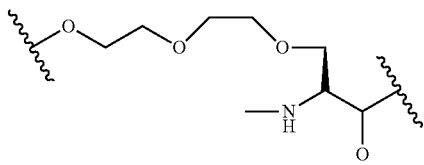

and $R_2$ is $CH_3$, $CH_2CH_2CO_2H$, or $(CH_2)_3NHCONH_2$; a legumain-cleavable Ala-Ala-Asn or Ala-Ala-Asp peptide having the structure of:

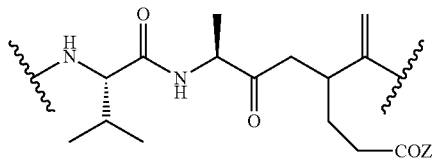

where Z is OH or $NH_2$; or a β-glucuronidase-cleavable β-glucuronide having the structure of:

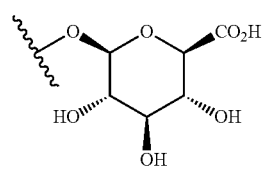 [SMILES: *O[C@H]1O[C@@H](C(=O)O)[C@H](O)[C@@H](O)[C@@H]1O]

or a Val-Lys-Gly peptide having the structure of:

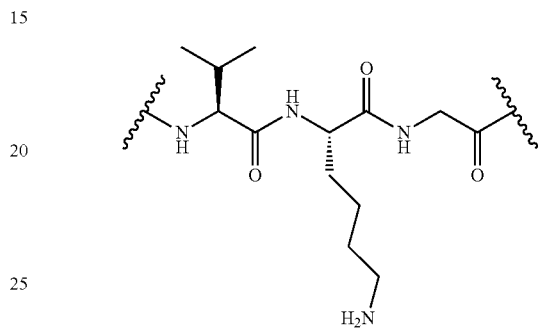

Those of skill will recognize that

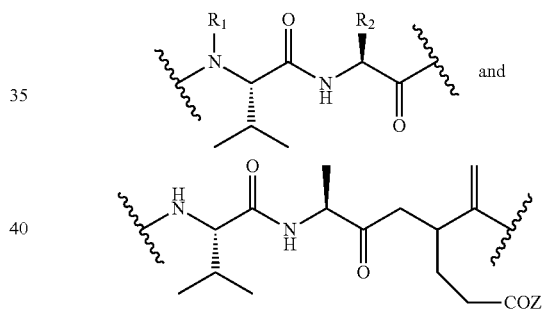

are divalent structures and can be bonded within the backbone of Formula (C1) or as depicted in Formula (C2). The structure

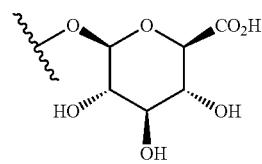 [SMILES: *O[C@H]1O[C@@H](C(=O)O)[C@H](O)[C@@H](O)[C@@H]1O]

is monovalent and can be bonded to EG as depicted in formula (C1) above.

In certain embodiments, the release trigger is selected from the group consisting of Val-Lys-Gly, Val-Ala-Asp, Ala-Ala-Ala, Val-Lys, Gly-Gly-Gly, Val-Ala, Gly-Gly-Phe-Gly, Val-Cit, Val-Cit, Val-Glu, Ala-Ala-Asn, and Gly. In certain embodiments, the release trigger further comprises a non-natural amino acid. In certain embodiments, the non-natural amino acid is according to

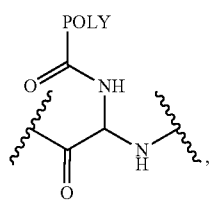

where POLY is a polymer, for instance a hydrophilic polymer. In certain embodiments, the non-natural amino acid is according to

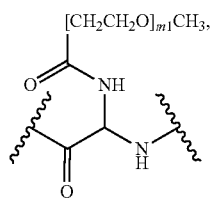

where m1 is an integer from 1 to 25, for instance 8, 9, 10, 11, 12, 13, 14, 15, 20, or 25.

Hydrophilic Groups

Hydrophilic groups facilitate increasing the hydrophilicity of the compounds described herein. It is believed that increased hydrophilicity allows for greater solubility in aqueous solutions, such as aqueous solutions found in biological systems. Hydrophilic groups can also function as spacer groups, which are described in further detail herein.

In certain embodiments, the hydrophilic group is designated HP herein. Useful hydrophilic groups include those described herein. In certain embodiments, the hydrophilic group is a divalent poly(ethylene glycol). In certain embodiments, the hydrophilic group is a divalent poly(ethylene glycol) according to the formula:

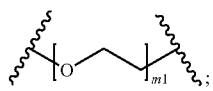

wherein m1 is an integer from 1 to 13, optionally 1 to 4, optionally 2 to 4, or optionally 4 to 8. In certain embodiments, m1 is 4. In certain embodiments, m1 is 12. In certain embodiments, m1 is 13.

In some embodiments, the hydrophilic group is a divalent poly(ethylene glycol) having the following formula:

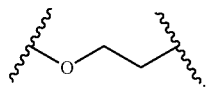

In some other embodiments, the hydrophilic group is a divalent poly(ethylene glycol) having the following formula:

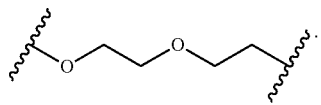 [SMILES: *CCOCCO*]

In other embodiments, the hydrophilic group is a divalent poly(ethylene glycol) having the following formula:

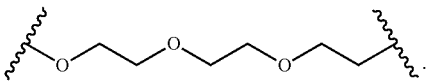 [SMILES: *CCOCCOCCO*]

In other embodiments, the hydrophilic group is a divalent poly(ethylene glycol) having the following formula:

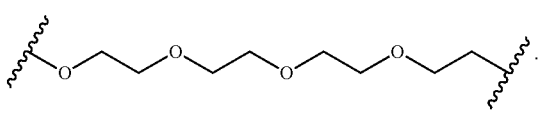 [SMILES: *CCOCCOCCOCCO*]

In some embodiments, the hydrophilic group is a sulfonic acid. In some embodiments, the hydrophilic group is the side chain of cysteic acid. In some embodiments, the hydrophilic group can bear a chain-presented sulfonic acid having the formula:

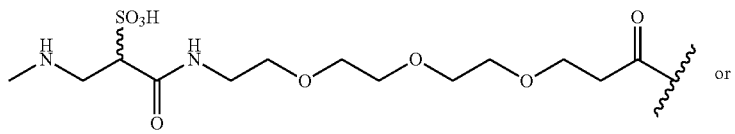 or

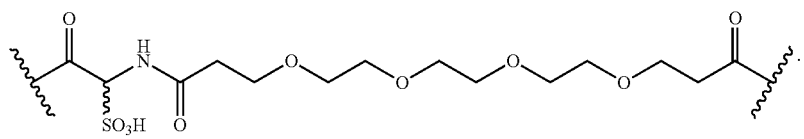.

In certain embodiments, the hydrophilic group is the side chain of a non-natural amino acid according to

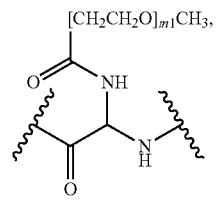

where m1 is an integer from 1 to 25, for instance 8, 9, 10, 11, 12, 13, 14, 15, 20, or 25.

Spacer Groups

Spacer groups facilitate spacing of the conjugating group from the other groups of the compounds described herein. This spacing can lead to more efficient conjugation of the compounds described herein to an antibody as well as more efficient cleavage of the active catabolite. The spacer group can also stabilize the conjugating group and lead to improved overall antibody-drug conjugate properties.

In certain embodiments, the spacer group is designated SP herein. Useful spacer groups include those described herein. In certain embodiments, the spacer group is:

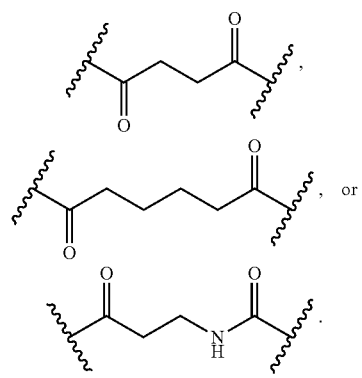

In certain embodiments, the spacer group, $W^4$, and the hydrophilic group combine to form a divalent poly(ethylene glycol) according to the formula:

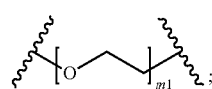

wherein m1 is an integer from 1 to 13, optionally 1 to 4, optionally 2 to 4, or optionally 4 to 8.

In some embodiments, the SP is

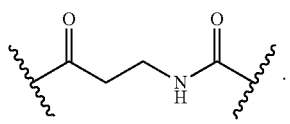 [SMILES: *C(=O)CCNC(*)=O]

In some embodiments, the divalent poly(ethylene glycol) has the following formula:

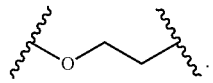

In some other embodiments, the divalent poly(ethylene glycol) has the following formula:

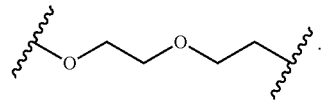

In other embodiments, the divalent poly(ethylene glycol) has the following formula:

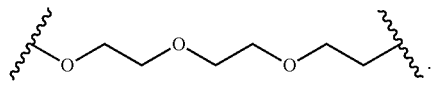 [SMILES: *CCOCCOCCO*]

In other embodiments, the divalent poly(ethylene glycol) has the following formula:

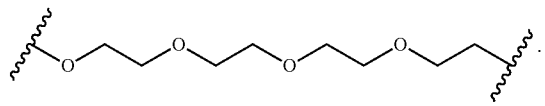 [SMILES: *CCOCCOCCOCCO*]

In some embodiments, the spacer group can bear a chain-presented sulfonic acid having the formula:

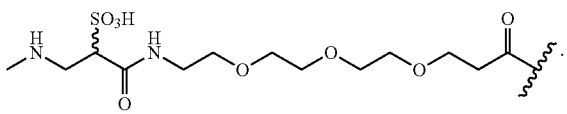 [SMILES: *C(=O)CCOCCOCCOCCNC(=O)C(CNC)S(=O)(=O)O]

In some embodiments, the spacer group is a diamine. In some embodiments, the spacer group is according to

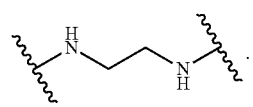 [SMILES: *NCCN*]

In some embodiments, the spacer group comprises fused rings or spiro rings. In some embodiments, the spacer group is according to

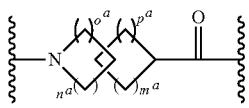

where each $n^a$, $m^a$, $o^a$, and $p^a$ is an integer independently selected from 1, 2, 3, 4, and 5. In some embodiments, the spacer group is according to

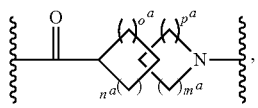

where each $n^a$, $m^a$, $o^a$, and $p^a$ is an integer independently selected from 1, 2, 3, 4, and 5. In some embodiments, the spacer group is selected from the group consisting of:

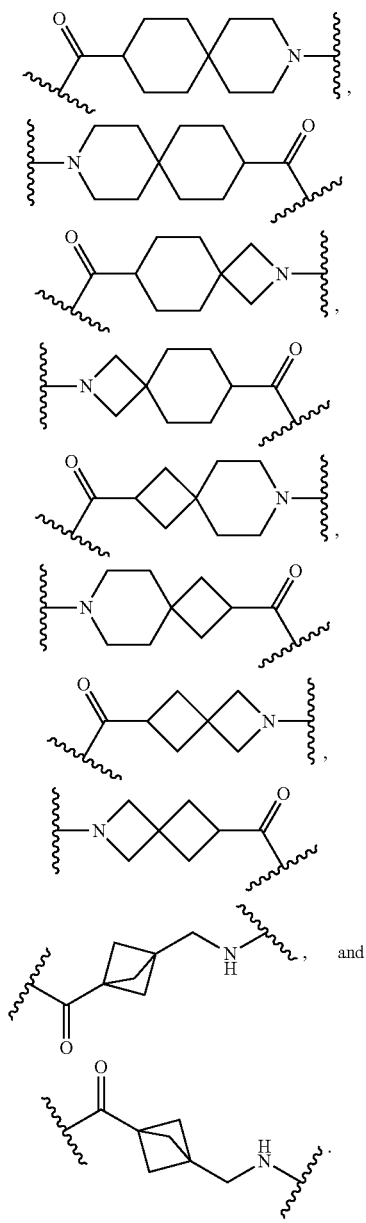

Conjugating Groups and Residues Thereof

Conjugating groups facilitate conjugation of the payloads described herein to a second compound, such as an antibody described herein. In certain embodiments, the conjugating group is designated R herein. Conjugating groups can react via any suitable reaction mechanism known to those of skill in the art. In certain embodiments, a conjugating group reacts through a [3+2] alkyne-azide cycloaddition reaction, inverse-electron demand Diels-Alder ligation reaction, thiol-electrophile reaction, or carbonyl-oxyamine reaction, as described in detail herein. In certain embodiments, the conjugating group comprises an alkyne, strained alkyne, tetrazine, thiol, para-acetyl-phenylalanine residue, oxyamine, maleimide, or azide. In certain embodiments, the conjugating group is:

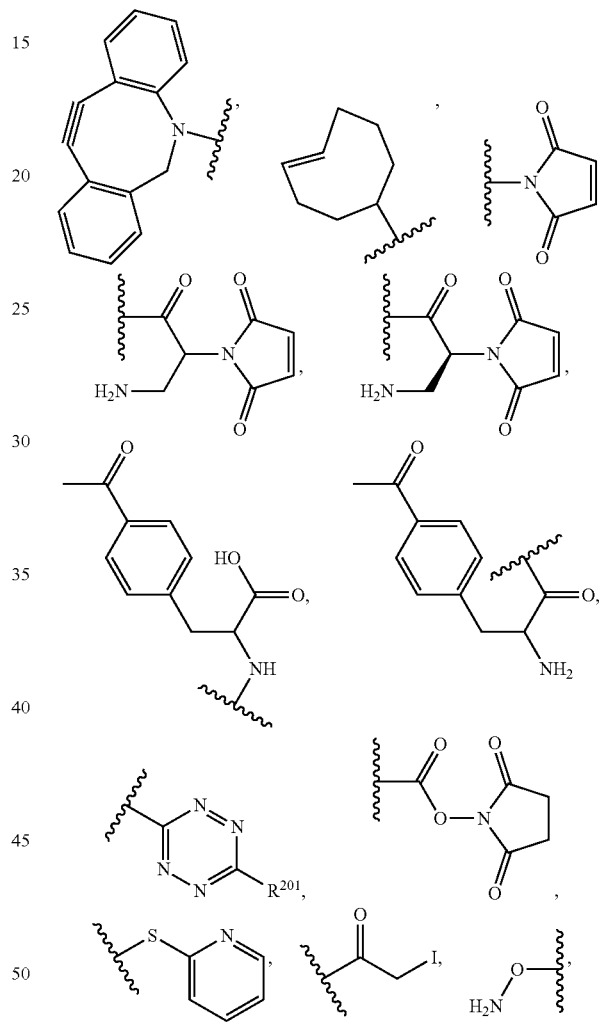

—$N_3$, or —SH; wherein $R^{201}$ is lower alkyl. In an embodiment, $R^{201}$ is methyl, ethyl, or propyl. In an embodiment, $R^{201}$ is methyl. Additional conjugating groups are described in, for example, U.S. Patent Publication No. 2014/0356385, U.S. Patent Publication No. 2013/0189287, U.S. Patent Publication No. 2013/0251783, U.S. Pat. Nos. 8,703,936, 9,145,361, 9,222,940, and 8,431,558.

After conjugation, a divalent residue of the conjugating group is formed and is bonded to the residue of an antibody. The structure of the divalent residue is determined by the type of conjugation reaction employed to form the conjugate.

In certain embodiments when a conjugate is formed through a [3+2] alkyne-azide cycloaddition reaction, the divalent residue of the conjugating group comprises a triazole ring or fused cyclic group comprising a triazole ring. In certain embodiment when a conjugate is formed through a strain-promoted [3+2] alkyne-azide cycloaddition (SPAAC) reaction, the divalent residue of the conjugating group is:

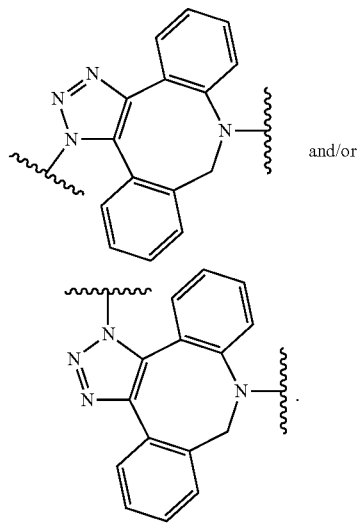

and/or

In certain embodiments when a conjugate is formed through a tetrazine inverse electron demand Diels-Alder ligation reaction, the divalent residue of the conjugating group comprises a fused bicyclic ring having at least two adjacent nitrogen atoms in the ring. In certain embodiments when a conjugate is formed through a tetrazine inverse electron demand Diels-Alder ligation reaction, the divalent residue of the conjugating group is:

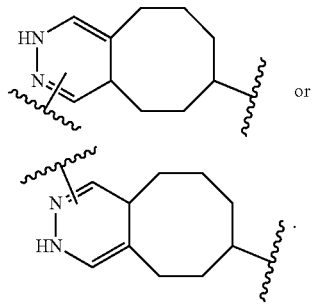

In certain embodiments when a conjugate is formed through a thiol-maleimide reaction, the divalent residue of the conjugating group comprises succinimidylene and a sulfur linkage. In certain embodiments when a conjugate is formed through a thiol-maleimide reaction, the divalent residue of the conjugating group is:

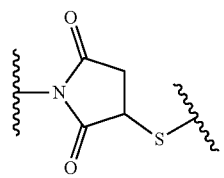

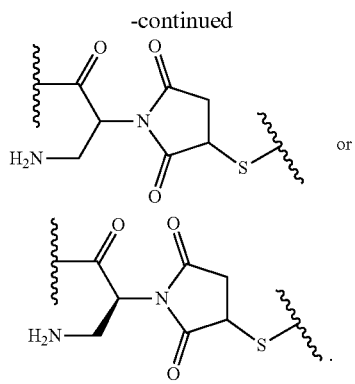

In certain embodiments, a conjugate is formed through a thiol-N-hydroxysuccinimide reaction using the following group:

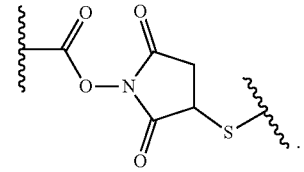 [SMILES: *SC1CC(=O)N(OC(*)=O)C1=O]

The reaction involved for formation of the conjugate comprises the following step:

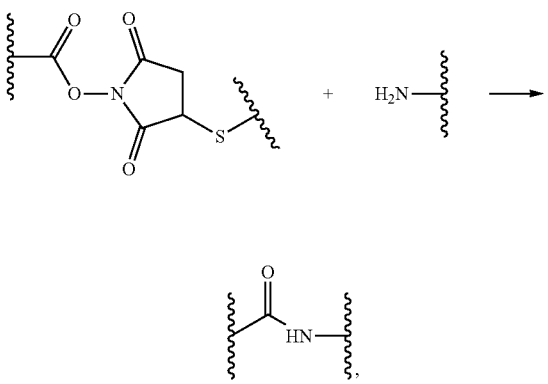

and the resulting divalent residue of the conjugating group is:

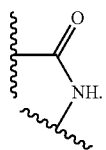

In certain embodiments when a conjugate is formed through a carbonyl-oxyamine reaction, the divalent residue of the conjugating group comprises a divalent residue of a non-natural amino acid. In certain embodiments when a conjugate is formed through a carbonyl-oxyamine reaction, the divalent residue of the conjugating group is:

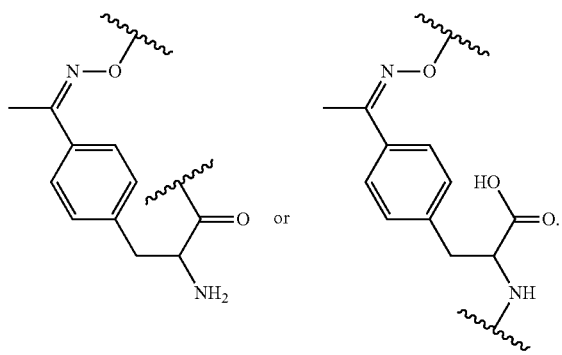 [SMILES: *O/N=C(/C)c1ccc(CC(N)C(*)=O)cc1 ; *NC(Cc1ccc(/C(C)=N\O*)cc1)C(=O)O]

In certain embodiments when a conjugate is formed through a carbonyl-oxyamine reaction, the divalent residue of the conjugating group comprises an oxime linkage. In certain embodiments when a conjugate is formed through a carbonyl-oxyamine reaction, the divalent residue of the conjugating group is:

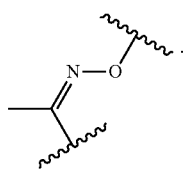 [SMILES: *O/N=C(\*)C]

In an embodiment, provided herein is a conjugate according to Formula (C1) or (C2), or a pharmaceutically acceptable salt, solvate, stereoisomer, or tautomer thereof; wherein R comprises a triazole ring. In an embodiment, provided herein is a conjugate according to Formula (C1) or (C2), or a pharmaceutically acceptable salt, solvate, stereoisomer, or tautomer thereof; wherein R is a triazole ring or fused cyclic group comprising a triazole ring. In an embodiment, provided herein is a conjugate according to Formula (C1) or (C2), or a pharmaceutically acceptable salt, solvate, stereoisomer, or tautomer thereof; wherein R is:

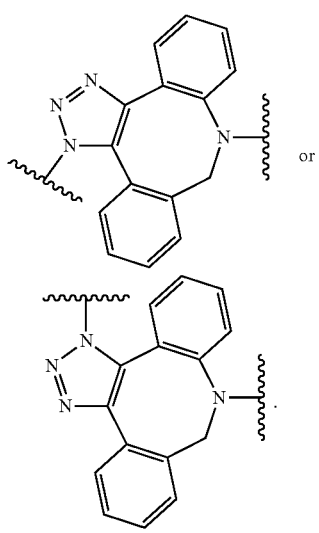

In an embodiment, provided herein is a conjugate according to Formula (C1) or (C2), or a pharmaceutically acceptable salt, solvate, stereoisomer, or tautomer thereof; wherein R comprises a fused bicyclic ring having at least two adjacent nitrogen atoms in the ring. In an embodiment, provided herein is a conjugate according to Formula (C1) or (C2), or a pharmaceutically acceptable salt, solvate, stereoisomer, or tautomer thereof; wherein R is:

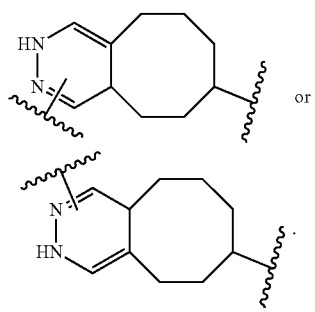

In an embodiment, provided herein is a conjugate according to Formula (C1) or (C2), or a pharmaceutically acceptable salt, solvate, stereoisomer, or tautomer thereof; wherein R comprises a sulfur linkage. In an embodiment, provided herein is a conjugate according to Formula (C1) or (C2), or a pharmaceutically acceptable salt, solvate, stereoisomer, or tautomer thereof; wherein R is:

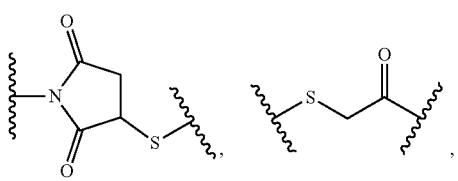

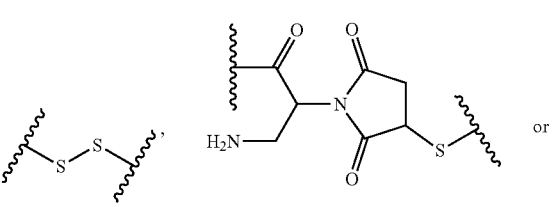

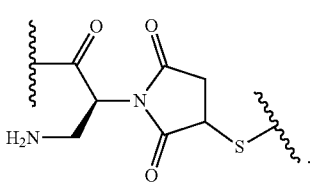

In an embodiment, provided herein is a conjugate according to Formula (C1) or (C2), or a pharmaceutically acceptable salt, solvate, or tautomer thereof; wherein R comprises a divalent residue of a non-natural amino acid. In an embodiment, provided herein is a conjugate according to Formula (C1) or (C2), or a pharmaceutically acceptable salt, solvate, stereoisomer, or tautomer thereof; wherein R is:

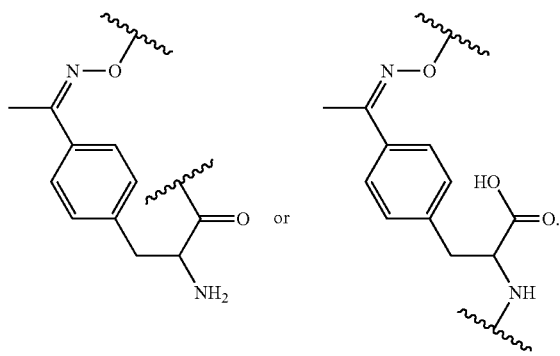 [SMILES: *O/N=C(/C)c1ccc(CC(N)C(*)=O)cc1 ; *NC(Cc1ccc(/C(C)=N\O*)cc1)C(=O)O]

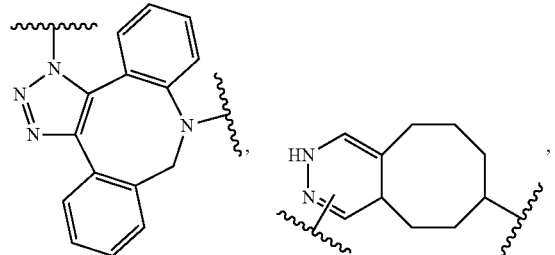

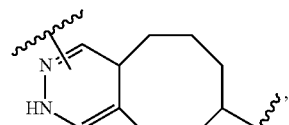

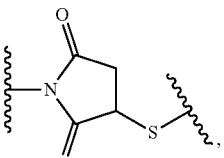

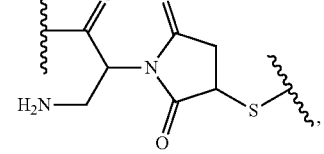

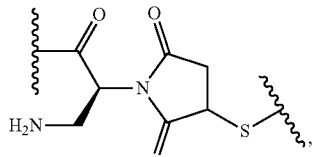

In an embodiment, provided herein is a conjugate according to Formula (C1) or (C2), or a pharmaceutically acceptable salt, solvate, stereoisomer, or tautomer thereof; wherein comprises an amide linkage. In an embodiment, provided herein is a conjugate according to Formula (C1) or (C2), or a pharmaceutically acceptable salt, solvate, stereoisomer, or tautomer thereof; wherein R is:

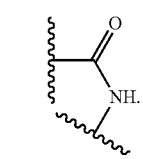 [SMILES: *NC(*)=O]

In an embodiment, provided herein is a conjugate according to Formula (C1) or (C2), or a pharmaceutically acceptable salt, solvate, stereoisomer, or tautomer thereof; wherein comprises an oxime linkage. In an embodiment, provided herein is a conjugate according to Formula (C1) or (C2), or a pharmaceutically acceptable salt, solvate, stereoisomer, or tautomer thereof; wherein R is:

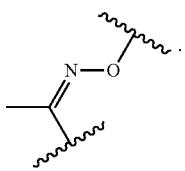 [SMILES: *O/N=C(\*)C]

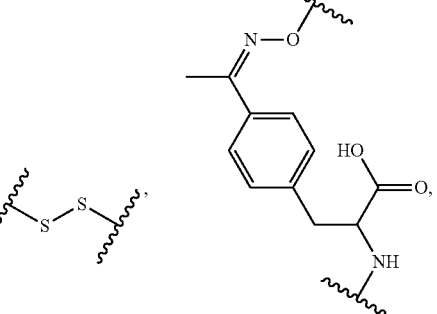

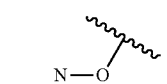

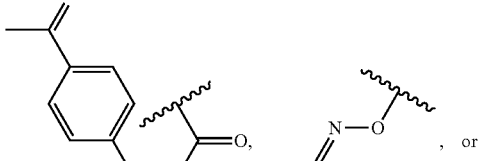

In an embodiment, provided herein is a conjugate according to Formula (C1) or (C2), or a pharmaceutically acceptable salt, solvate, stereoisomer, or tautomer thereof; wherein R is:

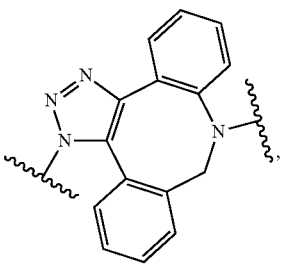

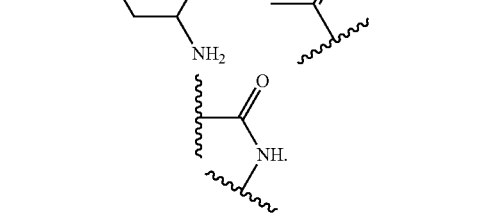

In an embodiment, provided herein is a compound according to Formula (C1) or (C2), or a pharmaceutically acceptable salt, solvate, stereoisomer, or tautomer thereof; wherein COMP is a residue of any compound known to be useful for conjugation to a payload, described herein, and an optional linker, described herein. In an embodiment, provided herein is a compound according to Formula (C1) or (C2), or a pharmaceutically acceptable salt, solvate, stereoisomer, or tautomer thereof; wherein COMP is a residue of an antibody chain.

In an aspect, provided herein is an antibody conjugate comprising payload, described herein, and an optional linker, described herein, linked to an anti-ROR1 antibody, wherein COMP is a residue of the antibody. In an embodiment, provided herein is an antibody conjugate according to Formula (C1) or (C2), or a pharmaceutically acceptable salt, solvate, stereoisomer, or tautomer thereof, wherein: COMP is a residue of the antibody; and R comprises a triazole ring or fused cyclic group comprising a triazole ring. In an embodiment, provided herein is an antibody conjugate according to Formula (C1) or (C2), or a pharmaceutically acceptable salt, solvate, stereoisomer, or tautomer thereof, wherein: COMP is a residue of the antibody; and R is:

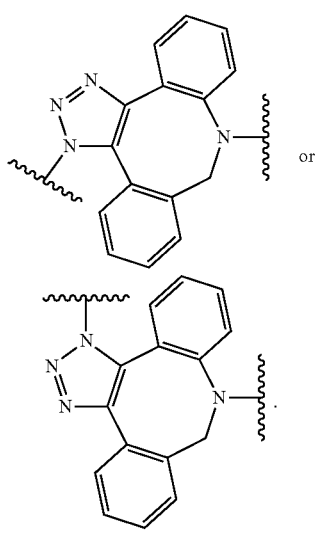

In an embodiment, provided herein is an antibody conjugate according to Formula (C1) or (C2), or a pharmaceutically acceptable salt, solvate, stereoisomer, or tautomer thereof, wherein: COMP is a residue of the antibody; and R comprises a fused bicyclic ring, wherein the fused bicyclic ring has at least two adjacent nitrogen atoms in the ring. In an embodiment, provided herein is an antibody conjugate according to Formula (C1) or (C2), or a pharmaceutically acceptable salt, solvate, stereoisomer, or tautomer thereof, wherein: COMP is a residue of the antibody; and R is:

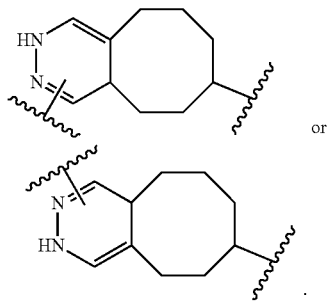

In an embodiment, provided herein is an antibody conjugate according to Formula (C1) or (C2), or a pharmaceutically acceptable salt, solvate, stereoisomer, or tautomer thereof, wherein: COMP is a residue of the polypeptide; and R comprises a sulfur linkage. In an embodiment, provided herein is an antibody conjugate according to Formula (C1) or (C2), or a pharmaceutically acceptable salt, solvate, stereoisomer, or tautomer thereof, wherein: COMP is a residue of the polypeptide; and R is:

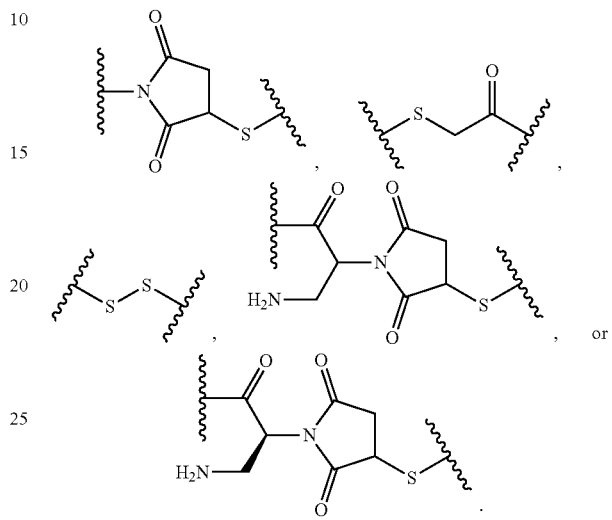

In an embodiment, provided herein is an antibody conjugate according to Formula (C1) or (C2), or a pharmaceutically acceptable salt, solvate, stereoisomer, or tautomer thereof, wherein: COMP is a residue of the polypeptide; and R comprises a divalent residue of a non-natural amino acid. In an embodiment, provided herein is an antibody conjugate according to Formula (C1) or (C2), or a pharmaceutically acceptable salt, solvate, stereoisomer, or tautomer thereof, wherein: COMP is a residue of the polypeptide; and R is:

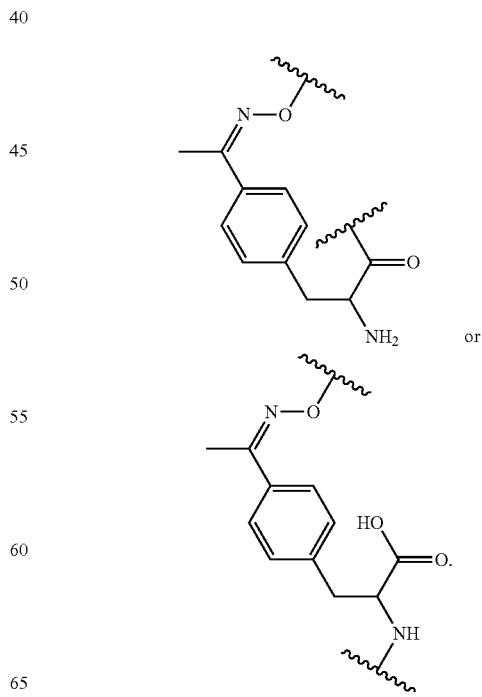

In an embodiment, provided herein is an antibody conjugate according to Formula (C1) or (C2), or a pharmaceutically acceptable salt, solvate, stereoisomer, or tautomer thereof, wherein: COMP is a residue of the polypeptide; and R comprises an amide linkage. In an embodiment, provided herein is an antibody conjugate according to Formula (C1) or (C2), or a pharmaceutically acceptable salt, solvate, stereoisomer, or tautomer thereof, wherein: COMP is a residue of the polypeptide; and R is:

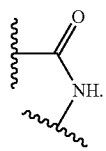 [SMILES: *NC(*)=O]

In an embodiment, provided herein is an antibody conjugate according to Formula (C1) or (C2), or a pharmaceutically acceptable salt, solvate, stereoisomer, or tautomer thereof, wherein: COMP is a residue of the polypeptide; and R comprises an amide linkage. In an embodiment, provided herein is an antibody conjugate according to Formula (C1) or (C2), or a pharmaceutically acceptable salt, solvate, stereoisomer, or tautomer thereof, wherein: COMP is a residue of the polypeptide; and R is:

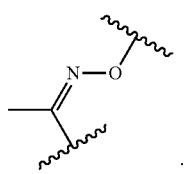 [SMILES: *O/N=C(\*)C]

In an aspect, provided herein is an antibody conjugate comprising a payload, described herein, and an optional linker, described herein, linked to an antibody according to Formula (C1) or (C2), or a pharmaceutically acceptable salt, solvate, stereoisomer, or tautomer thereof, wherein COMP is a residue of the antibody. In an embodiment, provided herein is an antibody conjugate according to Formula (C1) or (C2), or a pharmaceutically acceptable salt, solvate, stereoisomer, or tautomer thereof, wherein: COMP is a residue of the antibody; and R comprises a triazole ring or fused cyclic group comprising a triazole ring. In an embodiment, provided herein is an antibody conjugate according to Formula (C1) or (C2), or a pharmaceutically acceptable salt, solvate, stereoisomer, or tautomer thereof, wherein: COMP is a residue of the antibody; and R is:

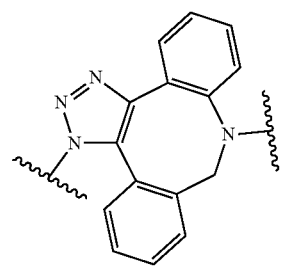

or

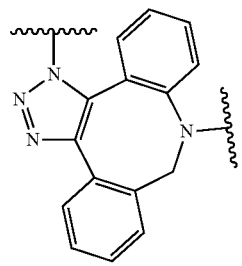

In an embodiment, provided herein is an antibody conjugate according to Formula (C1) or (C2), or a pharmaceutically acceptable salt, solvate, stereoisomer, or tautomer thereof, wherein: COMP is a residue of the antibody; and R comprises a fused bicyclic ring, wherein the fused bicyclic ring has at least two adjacent nitrogen atoms in the ring. In an embodiment, provided herein is an antibody conjugate according to Formula (C1) or (C2), or a pharmaceutically acceptable salt, solvate, stereoisomer, or tautomer thereof, wherein: COMP is a residue of the antibody; and R is:

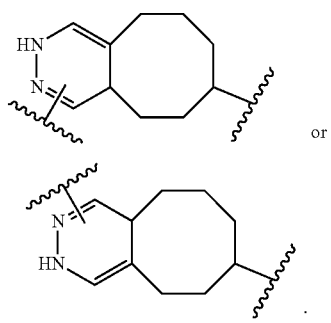

or

In an embodiment, provided herein is an antibody conjugate according to Formula (C1) or (C2), or a pharmaceutically acceptable salt, solvate, stereoisomer, or tautomer thereof, wherein: COMP is a residue of the antibody; and R comprises a sulfur linkage. In an embodiment, provided herein is an antibody conjugate according to Formula (C1) or (C2), or a pharmaceutically acceptable salt, solvate, stereoisomer, or tautomer thereof, wherein: COMP is a residue of the antibody; and R is:

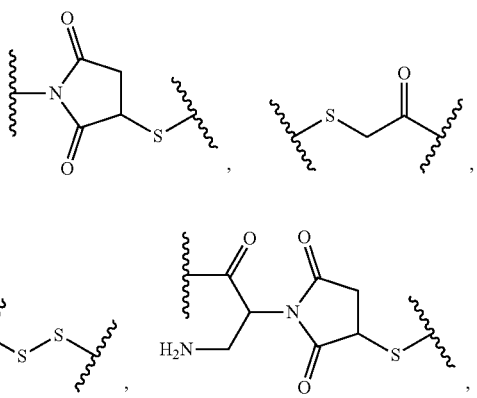

, or

-continued

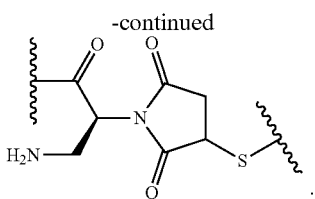

In an embodiment, provided herein is an antibody conjugate according to Formula (C1) or (C2), or a pharmaceutically acceptable salt, solvate, stereoisomer, or tautomer thereof, wherein: COMP is a residue of the antibody; and R comprises a divalent residue of a non-natural amino acid. In an embodiment, provided herein is an antibody conjugate according to Formula (C1) or (C2), or a pharmaceutically acceptable salt, solvate, stereoisomer, or tautomer thereof, wherein: COMP is a residue of the antibody; and R is:

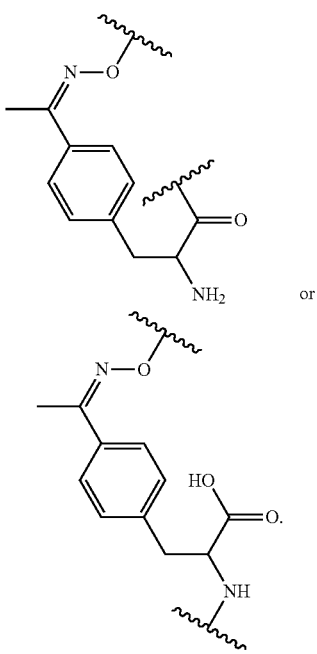

In an embodiment, provided herein is an antibody conjugate according to Formula (C1) or (C2), or a pharmaceutically acceptable salt, solvate, stereoisomer, or tautomer thereof, wherein: COMP is a residue of the antibody; and R comprises an amide linkage. In an embodiment, provided herein is an antibody conjugate according to Formula (C1) or (C2), or a pharmaceutically acceptable salt, solvate, stereoisomer, or tautomer thereof, wherein: COMP is a residue of the antibody; and R is:

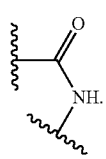

In an embodiment, provided herein is an antibody conjugate according to Formula (C1) or (C2), or a pharmaceutically acceptable salt, solvate, stereoisomer, or tautomer thereof, wherein: COMP is a residue of the antibody; and R comprises an oxime linkage. In an embodiment, provided herein is an antibody conjugate according to Formula (C1) or (C2), or a pharmaceutically acceptable salt, solvate, stereoisomer, or tautomer thereof, wherein: COMP is a residue of the antibody; and R is:

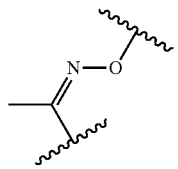

In an aspect, provided herein is an antibody conjugate comprising a payload, described herein, and an optional linker, described herein, linked to an antibody chain according to Formula (C1) or (C2), or a pharmaceutically acceptable salt, solvate, stereoisomer, or tautomer thereof, wherein COMP is a residue of the antibody chain. In an embodiment, provided herein is an antibody conjugate according to Formula (C1) or (C2), or a pharmaceutically acceptable salt, solvate, stereoisomer, or tautomer thereof, wherein: COMP is a residue of the antibody chain; and R comprises a triazole ring or fused cyclic group comprising a triazole ring. In an embodiment, provided herein is an antibody conjugate according to Formula (C1) or (C2), or a pharmaceutically acceptable salt, solvate, stereoisomer, or tautomer thereof, wherein: COMP is a residue of the antibody chain; and R is:

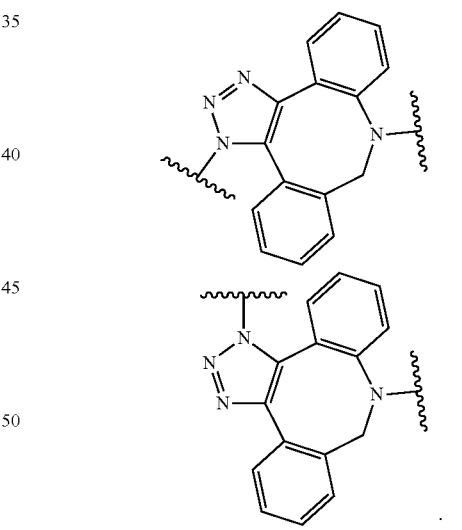

In an embodiment, provided herein is an antibody conjugate according to Formula (C1) or (C2), or a pharmaceutically acceptable salt, solvate, stereoisomer, or tautomer thereof, wherein: COMP is a residue of the antibody chain; and R comprises a fused bicyclic ring, wherein the fused bicyclic ring has at least two adjacent nitrogen atoms in the ring. In an embodiment, provided herein is an antibody conjugate according to Formula (C1) or (C2), or a pharmaceutically acceptable salt, solvate, stereoisomer, or tautomer thereof, wherein: COMP is a residue of the antibody chain; and R is:

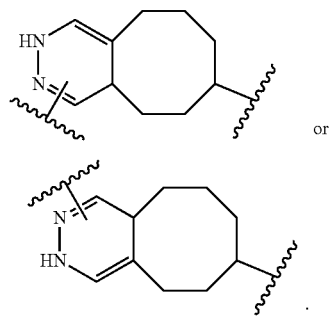

or

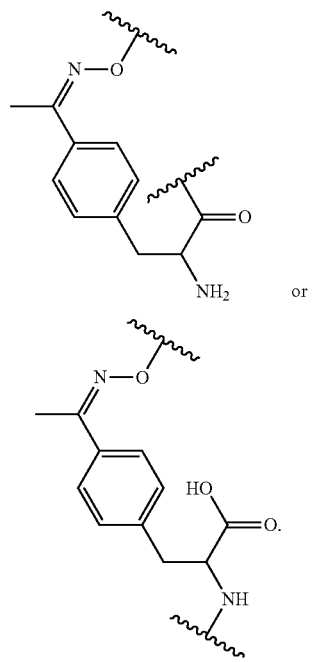

In an embodiment, provided herein is an antibody conjugate according to Formula (C1) or (C2), or a pharmaceutically acceptable salt, solvate, stereoisomer, or tautomer thereof, wherein: COMP is a residue of the antibody chain; and R comprises a sulfur linkage. In an embodiment, provided herein is an antibody conjugate according to Formula (C1) or (C2), or a pharmaceutically acceptable salt, solvate, stereoisomer, or tautomer thereof, wherein: COMP is a residue of the antibody chain; and R is:

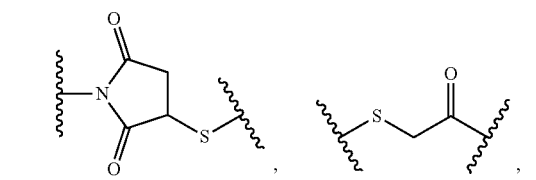

In an embodiment, provided herein is an antibody conjugate according to Formula (C1) or (C2), or a pharmaceutically acceptable salt, solvate, stereoisomer, or tautomer thereof, wherein: COMP is a residue of the antibody chain; and R comprises an amide linkage. In an embodiment, provided herein is an antibody conjugate according to Formula (C1) or (C2), or a pharmaceutically acceptable salt, solvate, stereoisomer, or tautomer thereof, wherein: COMP is a residue of the antibody chain; and R is:

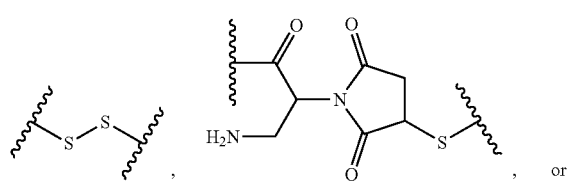

In an embodiment, provided herein is an antibody conjugate according to Formula (C1) or (C2), or a pharmaceutically acceptable salt, solvate, stereoisomer, or tautomer thereof, wherein: COMP is a residue of the antibody chain; and R comprises a divalent residue of a non-natural amino acid. In an embodiment, provided herein is an antibody conjugate according to Formula (C1) or (C2), or a pharmaceutically acceptable salt, solvate, stereoisomer, or tautomer thereof, wherein: COMP is a residue of the antibody chain; and R is:

In an embodiment, provided herein is an antibody conjugate according to Formula (C1) or (C2), or a pharmaceutically acceptable salt, solvate, stereoisomer, or tautomer thereof, wherein: COMP is a residue of the antibody chain; and R comprises an amide linkage. In an embodiment, provided herein is an antibody conjugate according to Formula (C1) or (C2), or a pharmaceutically acceptable salt, solvate, stereoisomer, or tautomer thereof, wherein: COMP is a residue of the antibody chain; and R is:

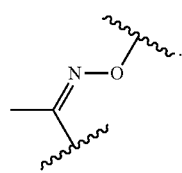 [SMILES: *O/N=C(\*)C]

Conjugates
In an embodiment, provided herein is a conjugate according to any of the following formulas, where COMP indicates a residue of the anti-ROR1 antibody and PAY indicates a payload moiety:
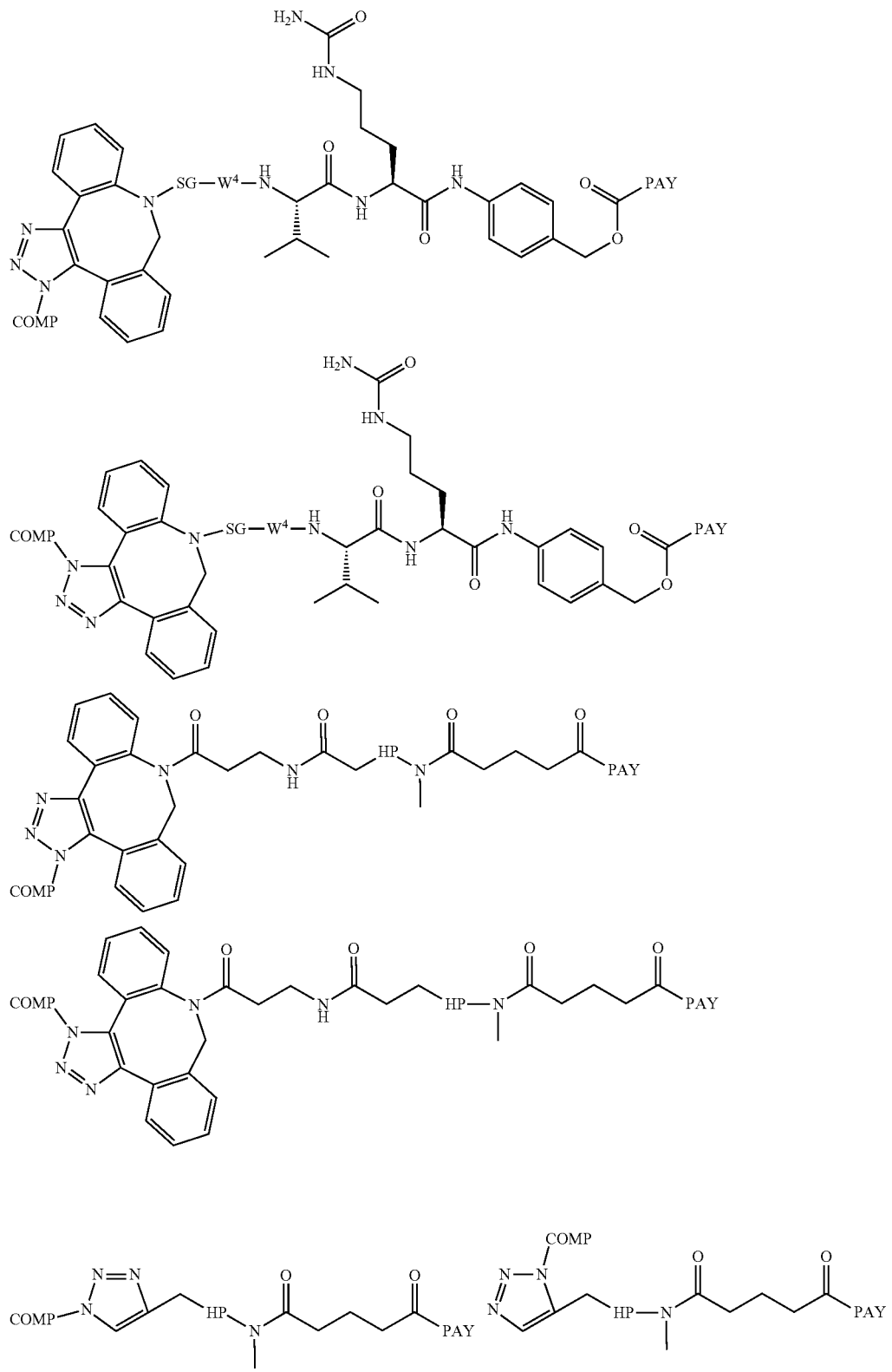

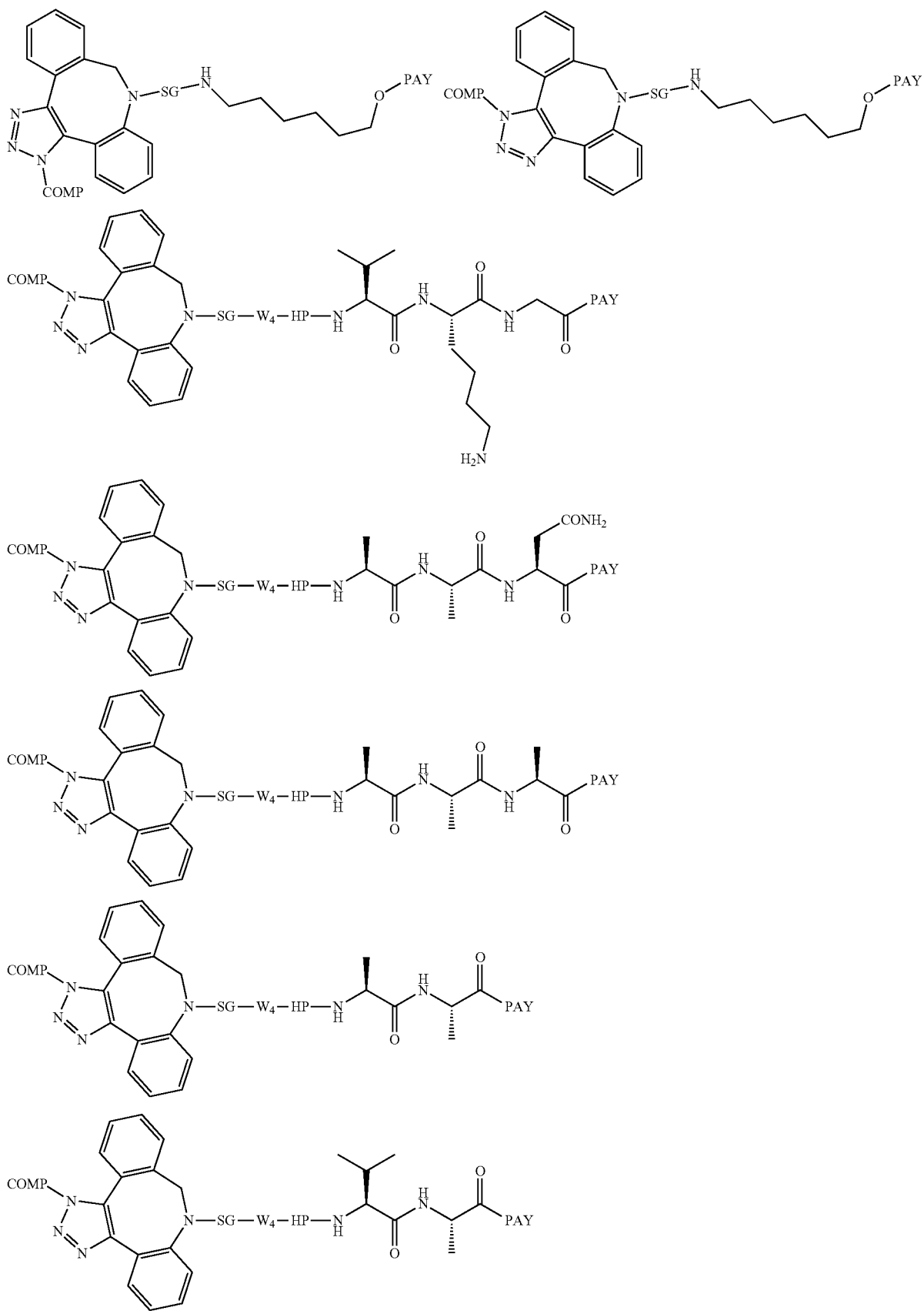

-continued

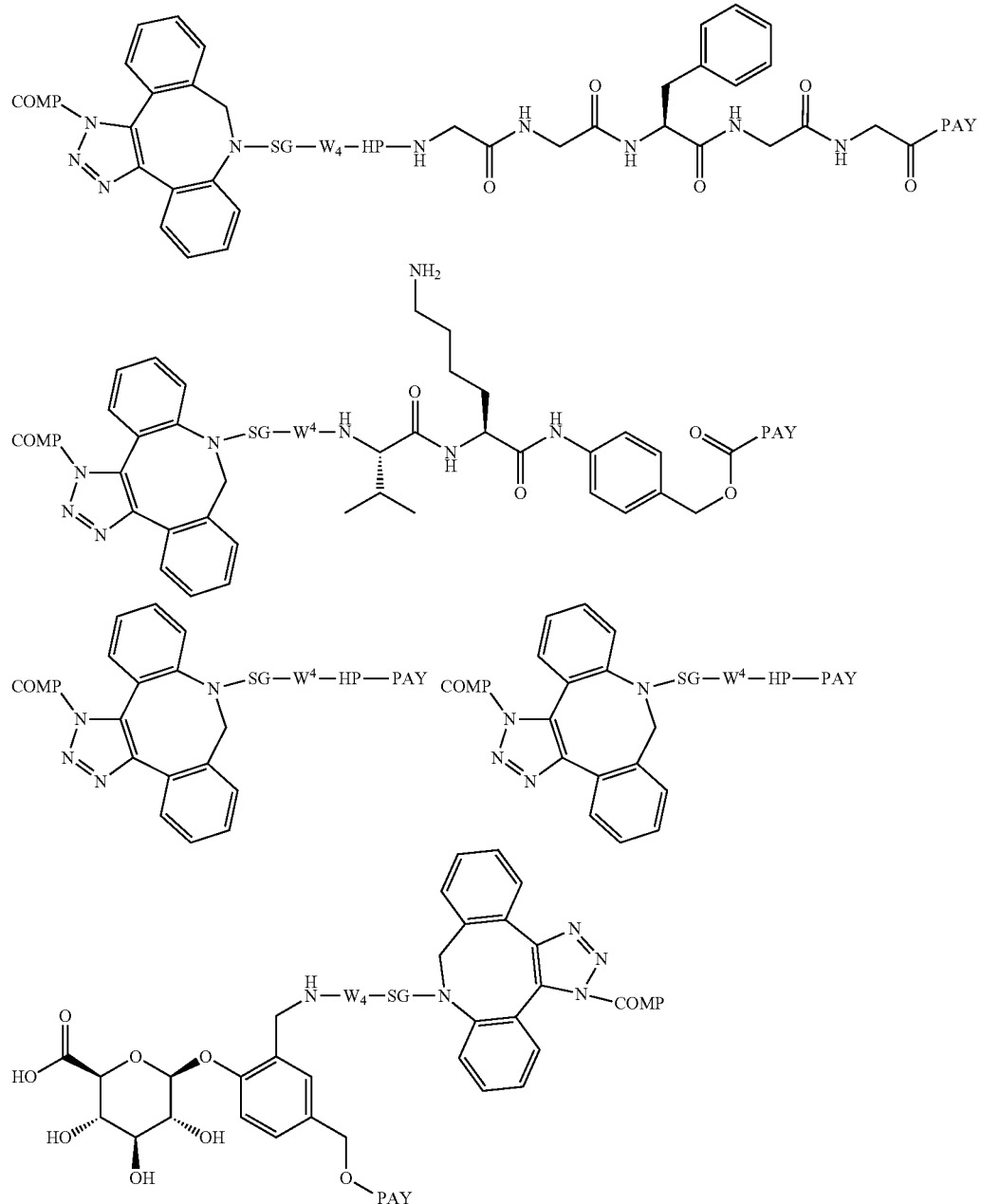

In an embodiment, provided herein is a conjugate according to any of the following formulas, where COMP indicates a residue of the anti-ROR1 antibody and PAY indicates a payload moiety:

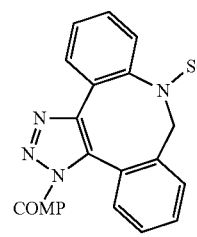 or 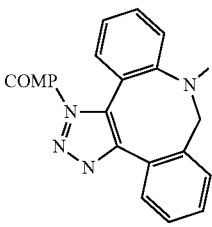

In an embodiment, provided herein is a conjugate according to any of the following formulas, where COMP indicates a residue of the anti-ROR1 antibody and PAY indicates a payload moiety:

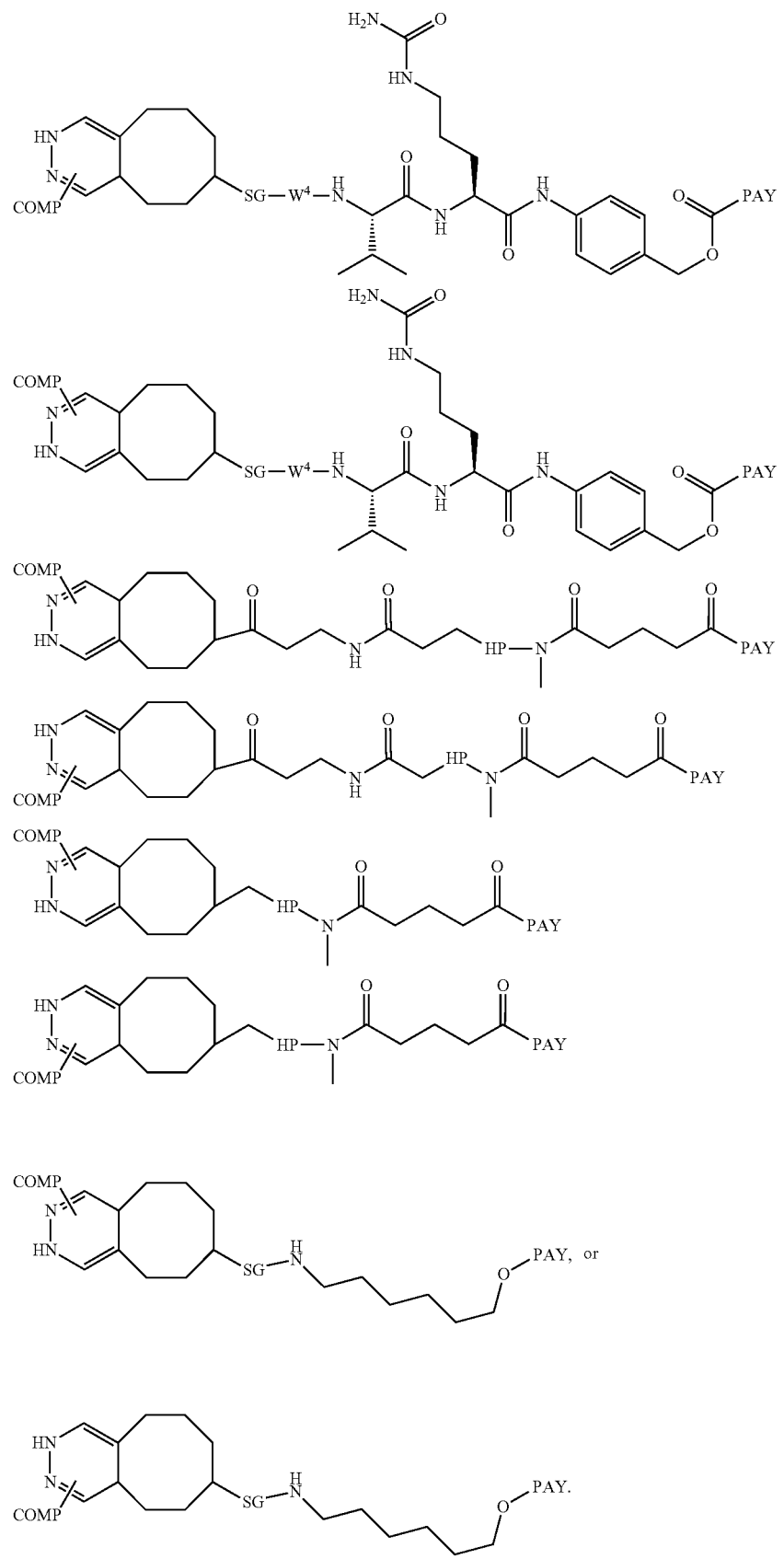

In an embodiment, provided herein is a conjugate according to any of Formulas 101a-104b, where COMP indicates a residue of the anti-ROR1 antibody and PAY indicates a payload moiety:
(101a)
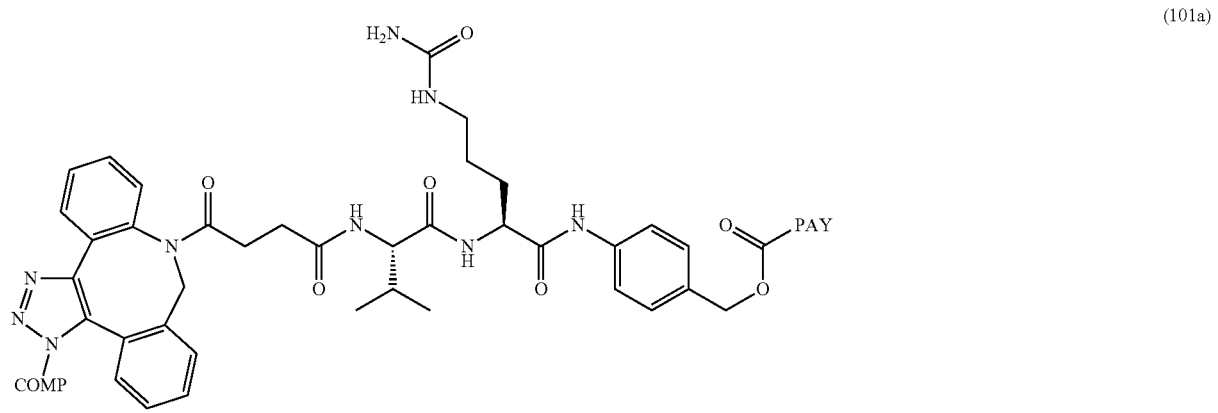
(101b)
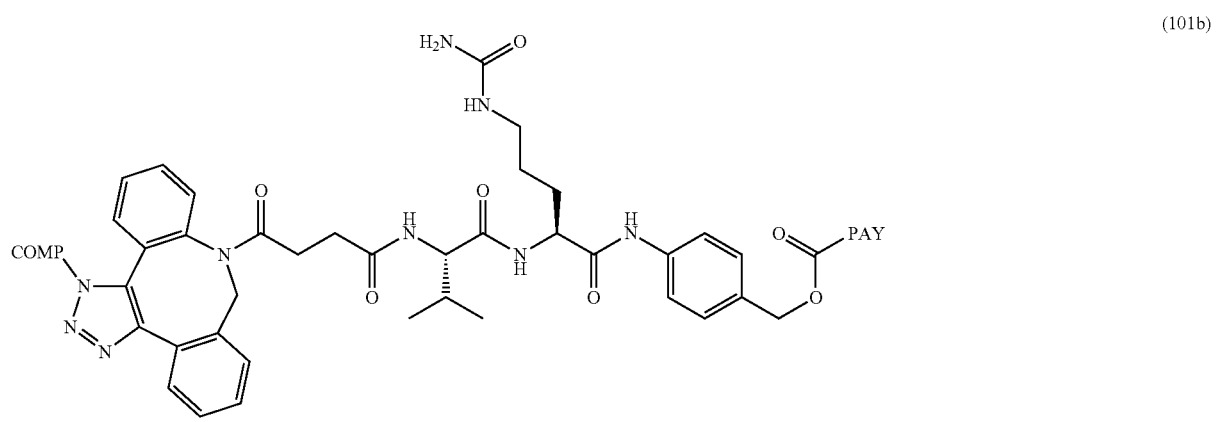
(102a)
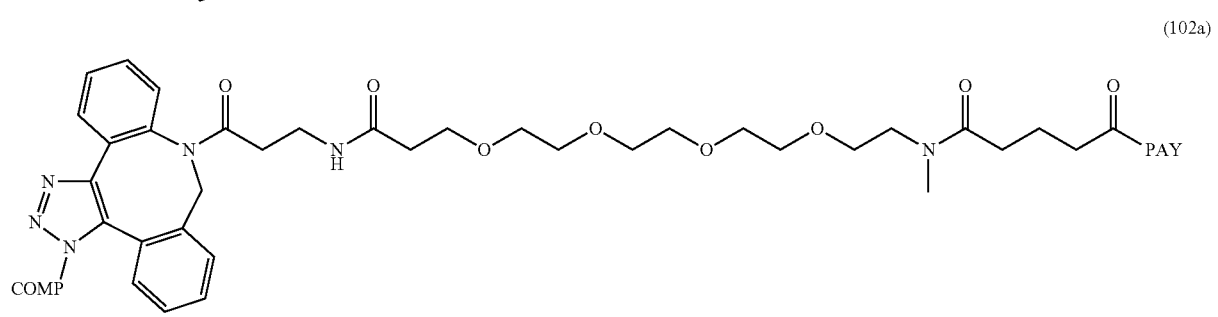
(102b)
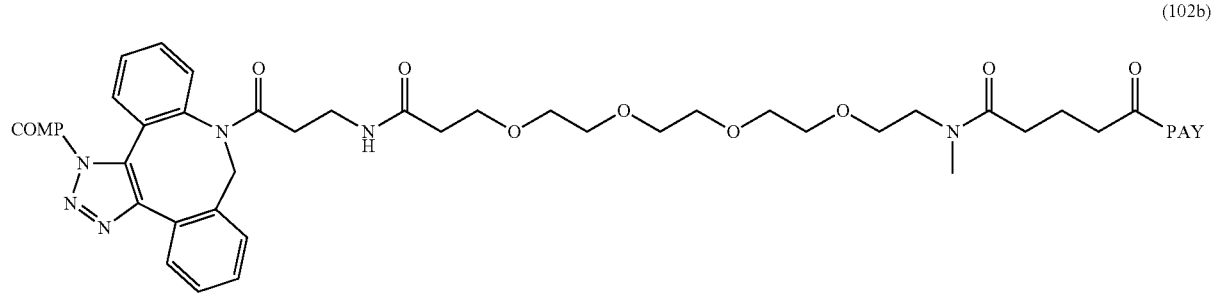
(103a)
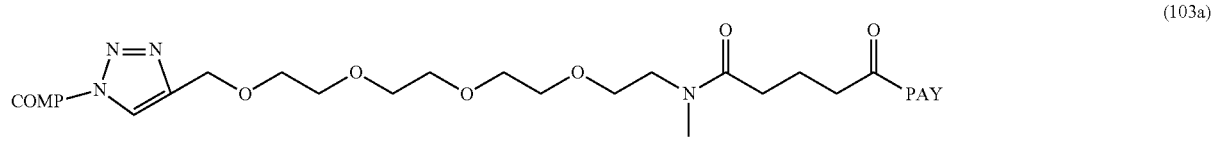

-continued

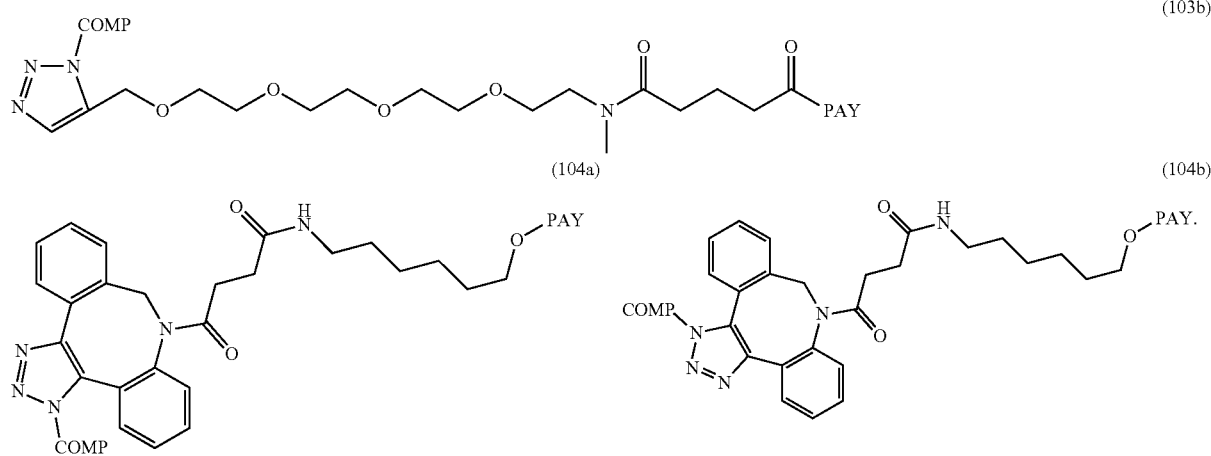

In any of the foregoing embodiments, the conjugate comprises n2 number of PAY moieties, wherein n2 is an integer from 1 to 10. In some embodiments, n2 is 2. In some embodiments, n2 is 3. In some embodiments, n2 is 4. In some embodiments, n2 is 5. In some embodiments, n2 is 6. In some embodiments, n2 is 7. In some embodiments, n2 is 8. In some embodiments, n2 is 9. In some embodiments, n2 is 10.

In some embodiments, provided herein are anti-ROR1 conjugates comprising a modified hemiasterlin and linker as described, for example, in PCT Publication No. WO 2016/123582. For example, the conjugate can have a structure comprising any of Formulas 1000-1000b, 1001-1001b, 1002-1002b, and I-XIXb-2, 101-111b, or 1-8b as described in PCT Publication No. WO 2016/2016/123582. Examples of conjugates comprising a modified hemiasterlin and linker are provided below.

In some embodiments, provided is a conjugate of Formula (I)

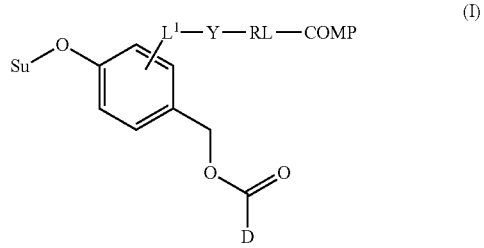

or a pharmaceutically acceptable salt thereof, wherein
COMP is a residue of an anti-ROR1 antibody provided herein;
$L^1$ is —$C_{1-6}$ alkylene-;
Y is —$X^1$—$C_{1-6}$ alkylene-$[X^1$—$C_{1-6}$ alkylene$]_n$-$[X^1]_p$, —, —$X^1$—$C_{2-6}$ alkenylene-$[X^1$—$C_{2-6}$ alkenylene$]_n$-$[X^1]_p$, —, —$X^1$—$C_{2-6}$ alkynylene-$[X^1$—$C_{2-6}$ alkynylene$]_n$-$[X^1]_p$, —, wherein at least one alkylene, alkenylene or alkynylene in Y is substituted with one or more substituents selected from $R^{50}$; and wherein the alkylene, alkenylene, or alkynylene in Y is optionally substituted with one or more substituents selected from $R^{51}$;

$R^{20}$ is —$C_{1-6}$ alkylene-$X^2$—$[C_{1-6}$ alkylene$]_m$-POLY, —$C_{2-6}$ alkenylene-$X^2$—$[C_{2-6}$ alkenylene$]_m$-POLY, or —$C_{2-6}$ alkynylene-$X^2$—$[C_{2-6}$ alkynylene$]_m$-POLY, wherein each alkylene, alkenylene or alkynylene of $R^{50}$ is optionally substituted with one or more substituents selected from halogen, —CN, —$NO_2$, —OH, —$N(R^{10})_2$, —$C(O)N(R^{10})_2$, —C(O)—, —C(S)—, —$C(O)OCH_2C_6H_5$, —$NHC(O)OCH_2C_6H_5$, $C_{1-10}$ alkyl, $C_{2-10}$ alkenyl, $C_{2-10}$ alkynyl, $C_{3-12}$ carbocycle, 3- to 12-membered heterocycle, and $C_{1-10}$ haloalkyl;

$R^{51}$ is independently selected from halogen, —CN, —$NO_2$, —OH, —$N(R^{10})_2$, —$C(O)N(R^{10})_2$, —C(O)—, —C(S)—, —$C(O)OCH_2C_6H_5$, —$NHC(O)OCH_2C_6H_5$, $C_{1-10}$ alkyl, $C_{2-10}$ alkenyl, $C_{2-10}$ alkynyl, $C_{3-12}$ carbocycle, 3- to 12-membered heterocycle, and $C_{1-10}$ haloalkyl;

$X^1$ and $X^2$ are independently selected from —C(O)— and —$N(R^{10})$ C(O)—;

$R^{10}$ is independently selected at each occurrence from hydrogen, $C_{1-10}$ alkyl, $C_{2-10}$ alkenyl, $C_{2-10}$ alkynyl, $C_{3-12}$ carbocycle, 3- to 12-membered heterocycle, and $C_{1-10}$ haloalkyl;

POLY is a water-soluble polymer;
n is an integer selected from zero, one, two, and three;
m is an integer selected from zero and one;
p is an integer selected from zero and one;
Su is a hexose form of a monosaccharide;
D is a drug moiety; and
RL is a reactive group residue.

In some embodiments, provided is a conjugate of Formula (II)

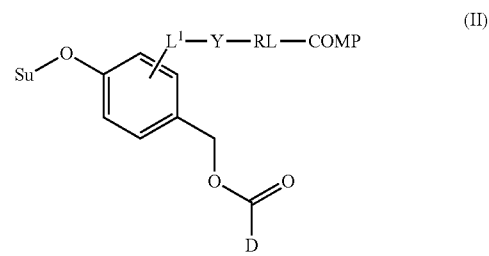

or a pharmaceutically acceptable salt thereof, wherein
COMP is a residue of an anti-ROR1 antibody provided herein;
$L^1$ is —$C_{1-6}$ alkylene-;
Y is —$X^1$—$C_{1-6}$ alkylene-[$X^1$—$C_{1-6}$ alkylene]$_n$-$X^1$—,
—$X^1$—$C_{2-6}$ alkenylene-[$X^1$—$C_{2-6}$ alkenylene]$_n$-$X^1$—,
—$X^1$—$C_{2-6}$ alkynylene-[$X^1$—$C_{2-6}$ alkynylene]$_n$-$X^1$—,
wherein at least one alkylene, alkenylene or alkynylene in Y is substituted with one or more substituents selected from $R^{50}$;
$R^{50}$ is —$C_{1-6}$ alkylene-$X^2$—[$C_{1-6}$ alkylene]$_m$-POLY, —$C_{2-6}$ alkenylene-$X^2$—[$C_{2-6}$ alkenylene]$_m$-POLY, or —$C_{2-6}$ alkynylene-$X^2$—[$C_{2-6}$ alkynylene]$_m$-POLY, wherein each alkylene, alkenylene or alkynylene of $R^{50}$ is optionally substituted with one or more substituents selected from halogen, —CN, —$NO_2$, —OH, —N($R^{10}$)$_2$, —C(O)N($R^{10}$)$_2$, —C(O)—, —C(S)—, —C(O)OCH$_2$C$_6$H$_5$, —NHC(O)OCH$_2$C$_6$H$_5$, $C_{1-10}$ alkyl, $C_{2-10}$ alkenyl, $C_{2-10}$ alkynyl, $C_{3-12}$ carbocycle, 3- to 12-membered heterocycle, and $C_{1-10}$ haloalkyl;
$X^1$ and $X^2$ are independently selected from —C(O)— and —N($R^{10}$) C(O)—;
$R^{10}$ is independently selected at each occurrence from hydrogen, $C_{1-10}$ alkyl, $C_{2-10}$ alkenyl, $C_{2-10}$ alkynyl, $C_{3-12}$ carbocycle, 3- to 12-membered heterocycle, and $C_{1-10}$ haloalkyl;
POLY is a water-soluble polymer;
n is an integer selected from zero, one, two, and three;
m is an integer selected from zero and one;
Su is a hexose form of a monosaccharide;
D is a drug moiety; and
RL is a reactive group residue.

In some embodiments, provided is a conjugate of Formula (IIA)

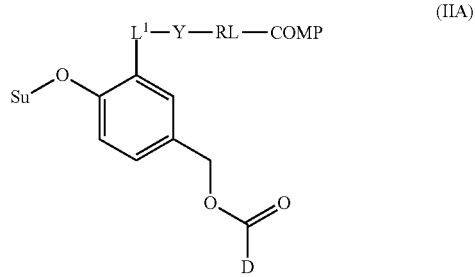

(IIA)

or a pharmaceutically acceptable salt thereof.

In some embodiments, the compound of Formula (II) is according to Formula (IIB)

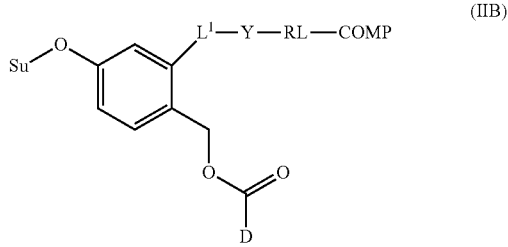

(IIB)

or a pharmaceutically acceptable salt thereof.

In some embodiments of Formula (I), (II), (IIA), or (IIB), $L^1$ is —$C_{1-3}$ alkylene-. In some embodiments, $L^1$ is —$CH_2$—. In some embodiments of Formula (I), (II), (IIA), or (IIB), $L^1$ is —$CH_2CH_2$—. In some embodiments, $L^1$ is —$CH_2CH_2CH_2$—.

In some embodiments of Formula (I), including any of the foregoing, p is 0. In some embodiments of Formula (I), including any of the foregoing, p is 1.

In some embodiments of Formula (I), (II), (IIA), or (IIB), including any of the foregoing, Y is —$X^1$—$C_{1-6}$ alkylene-[$X^1$—$C_{1-6}$ alkylene]n-$X^1$—, wherein at least one alkylene in Y is substituted with one or more substituents selected from $R^{50}$. In some embodiments of Formula (I), (II), (IIA), or (IIB), including any of the foregoing, Y is —$X^1$—$C_{1-6}$ alkylene-[$X^1$—$C_{1-6}$ alkylene]$_n$-, wherein at least one alkylene in Y is substituted with one or more substituents selected from $R^{50}$. In some embodiments of Formula (I), (II), (IIA), or (IIB), including any of the foregoing, Y is —$X^1$—$C_{2-6}$ alkenylene-[$X^1$—$C_{2-6}$ alkenylene]$_n$-$X^1$— wherein at least one alkenylene in Y is substituted with one or more substituents selected from $R^{50}$. In some embodiments of Formula (I), (II), (IIA), or (IIB), including any of the foregoing, Y is —$X^1$-$C_{2-6}$ alkenylene-[$X^1$—$C_{2-6}$ alkenylene]$_n$- wherein at least one alkenylene in Y is substituted with one or more substituents selected from $R^{50}$. In some embodiments of Formula (I), (II), (IIA), or (BB), including any of the foregoing, Y is —$X^1$—$C_{2-6}$ alkynylene-[$X^1$—$C_{2-6}$ alkynylene]$_n$-$X^1$— wherein at least one alkynylene in Y is substituted with one or more substituents selected from $R^{50}$. In some embodiments of Formula (I), (II), (IIA), or (BB), including any of the foregoing, Y is —$X^1$—$C_{2-6}$ alkynylene-[$X^1$—$C_{2-6}$ alkynylene]$_n$- wherein at least one alkynylene in Y is substituted with one or more substituents selected from $R^{50}$. In some embodiments of Formula (I), (II), (IIA), or (IIB), including any of the foregoing, n is zero. In some embodiments of Formula (I), (II), (IIA), or (IIB), n is one. In some embodiments of Formula (I), (II), (IIA), or (IIB), including any of the foregoing, n is two. In some embodiments, including any of the foregoing, n is three.

In certain embodiments of Formula (I), (II), (IIA), or (IIB), including any of the foregoing, Y is —$X^1$—$C_{1-4}$ alkylene-[$X^1$—$C_{1-4}$ alkylene]$_n$-$X^1$—, wherein at least one alkylene in Y is substituted with one or more substituents selected from $R^{50}$. In some embodiments of Formula (I), (II), (IIA), or (IIB), including any of the foregoing, n is zero. In some embodiments of Formula (I), (II), (IIA), or (IIB), including any of the foregoing, n is one. In some embodiments of Formula (I), (II), (IIA), or (IIB), including any of the foregoing, n is two. In some embodiments of Formula (I), (II), (IIA), or (IIB), including any of the foregoing, n is three.

In certain embodiments of Formula (I), (II), (IIA), or (IIB), including any of the foregoing, Y is —$X^1$—$C_{1-4}$ alkylene-$X^1$—$C_{1-4}$ alkylene-$X^1$—$C_{1-4}$ alkylene-$X^1$—$C_{1-4}$ alkylene-$X^1$—, wherein at least one alkylene in Y is substituted with one or more substituents selected from $R^{50}$. In certain embodiments of Formula (I), (II), (IIA), or (IIB), including any of the foregoing, Y is —$X^1$—$C_{1-4}$ alkylene-$X^1$—$C_{1-4}$ alkylene-$X^1$—$C_{1-4}$ alkylene-$X^1$—, wherein at least one alkylene in Y is substituted with one or more substituents selected from $R^{50}$. In certain embodiments of Formula (I), (II), (IIA), or (IIB), including any of the foregoing, Y is —$X^1$—$C_{1-4}$ alkylene-$X^1$—$C_{1-4}$ alkylene-$X^1$—, wherein at least one alkylene in Y is substituted with one or more substituents selected from $R^{50}$.

In certain embodiments of Formula (I), (II), (IIA), or (IIB), including any of the foregoing, $R^{50}$ is —$C_{1-6}$ alkylene-$X^2$—[$C_{1-6}$ alkylene]$_m$-POLY, wherein each alkylene of $R^{50}$ is optionally substituted with one or more substituents selected from halogen, —CN, —NO$_2$, —OH, —N(R$^{10}$)$_2$, —C(O)N(R$^{10}$)$_2$, —C(O)—, —C(S)—, —C(O)OCH$_2$C$_6$H$_5$, —NHC(O)OCH$_2$C$_6$H$_5$, C$_{1-10}$ alkyl, C$_{2-10}$ alkenyl, C$_{2-10}$ alkynyl, C$_{3-12}$ carbocycle, 3- to 12-membered heterocycle, and C$_{1-10}$ haloalkyl. In some embodiments of Formula (I), (II), (IIA), or (IIB), including any of the foregoing, R$^{50}$ is —C$_{1-4}$ alkylene-X$^2$—[C$_{1-4}$ alkylene]$_m$-POLY, wherein each alkylene of R$^{50}$ is optionally substituted with one or more substituents selected from halogen, —CN, —NO$_2$, —OH, —N(R$^{10}$)$_2$, —C(O)N(R$^{10}$)$_2$, —C(O)—, —C(S)—, —C(O)OCH$_2$C$_6$H$_5$, —NHC(O)OCH$_2$C$_6$H$_5$, C$_{1-10}$ alkyl, C$_{2-10}$ alkenyl, C$_{2-10}$ alkynyl, C$_{3-12}$ carbocycle, 3- to 12-membered heterocycle, and C$_{1-10}$ haloalkyl. In some embodiments of Formula (I), (II), (IIA), or (IIB), including any of the foregoing, each alkylene of R$^{50}$ is optionally substituted with one or more substituents selected from halogen, —OH, —N(R$^{10}$)$_2$, —C(O)N(R$^{10}$)$_2$, C$_{1-10}$ alkyl, C$_{2-10}$ alkenyl, C$_{2-10}$ alkynyl, C$_{3-12}$ carbocycle, 3- to 12-membered heterocycle, and C$_{1-10}$ haloalkyl. In some embodiments of Formula (I), (II), (IIA), or (IIB), including any of the foregoing, m is zero. In some embodiments of Formula (I), (II), (IIA), or (IIB), including any of the foregoing, m is one.

In certain embodiments of Formula (I), (II), (IIA), or (JIB), including any of the foregoing, R$^{50}$ is —C$_{2-6}$ alkenylene-X$^2$—[C$_{2-6}$ alkenylene]$_m$-POLY, wherein each alkenylene of R$^{50}$ is optionally substituted with one or more substituents selected from halogen, —CN, —NO$_2$, —OH, —N(R$^{10}$)$_2$, —C(O)N(R$^{10}$)$_2$, —C(O)—, —C(S)—, —C(O)OCH$_2$C$_6$H$_5$, —NHC(O)OCH$_2$C$_6$H$_5$, C$_{1-10}$ alkyl, C$_{2-10}$ alkenyl, C$_{2-10}$ alkynyl, C$_{3-12}$ carbocycle, 3- to 12-membered heterocycle, and C$_{1-10}$ haloalkyl. In some embodiments of Formula (I), (II), (IIA), or (IIB), including any of the foregoing, m is zero. In some embodiments of Formula (I), (II), (IIA), or (IIB), including any of the foregoing, m is one.

In certain embodiments of Formula (I), (II), (IIA), or (IIB), including any of the foregoing, R$^{50}$ is —C$_{2-6}$ alkynylene-X$^2$—[C$_{2-6}$ alkynylene]$_m$-POLY, wherein each alkynylene of R$^{50}$ is optionally substituted with one or more substituents selected from halogen, —CN, —NO$_2$, —OH, —N(R$^{10}$)$_2$, —C(O)N(R$^{10}$)$_2$, —C(O)—, —C(S)—, —C(O)OCH$_2$C$_6$H$_5$, —NHC(O)OCH$_2$C$_6$H$_5$, C$_{1-10}$ alkyl, C$_{2-10}$ alkenyl, C$_{2-10}$ alkynyl, C$_{3-12}$ carbocycle, 3- to 12-membered heterocycle, and C$_{1-10}$ haloalkyl. In come embodiments of Formula (I), (II), (IIA), or (IIB), including any of the foregoing, m is zero. In some embodiments of Formula (I), (II), (IIA), or (IIB), including any of the foregoing, m is one.

In certain embodiments of Formula (I), (II), (IIA), or (IIB), including any of the foregoing, POLY is polyethylene glycol (PEG), methoxypolyethylene glycol (mPEG), poly(propylene glycol) (PPG), copolymers of ethylene glycol and propylene glycol, poly(oxyethylated polyol), poly(olefinic alcohol), poly(vinylpyrrolidone), poly(hydroxyalkylmethacrylamide), poly(hydroxyalkylmethacrylate), poly(saccharides), poly(α-hydroxy acid), poly(vinyl alcohol), polyphosphazene, polyoxazolines (POZ), poly(N-acryloylmorpholine), polysarcosine, or a combination thereof. In some embodiments of Formula (I), (II), (IIA), or (IIB), including any of the foregoing, POLY is polyethylene glycol (PEG). In some embodiments of Formula (I), (II), (IIA), or (IIB), including any of the foregoing, POLY is methoxypolyethylene glycol (mPEG). In some embodiments of Formula (I), (II), (IIA), or (IIB), including any of the foregoing, POLY is poly(propylene glycol) (PPG). In some embodiments, POLY is copolymers of ethylene glycol and propylene glycol. In some embodiments of Formula (I), (II), (IIA), or (IIB), including any of the foregoing, POLY is poly(oxyethylated polyol). In some embodiments of Formula (I), (II), (IIA), or (IIB), including any of the foregoing, POLY is poly(olefinic alcohol). In some embodiments, POLY is poly(vinylpyrrolidone). In some embodiments of Formula (I), (II), (IIA), or (IIB), including any of the foregoing, POLY is poly(hydroxyalkylmethacrylamide). In some embodiments of Formula (I), (II), (IIA), or (IIB), including any of the foregoing, POLY is poly(hydroxyalkylmethacrylate). In some embodiments of Formula (I), (II), (IIA), or (IIB), including any of the foregoing, POLY is poly(saccharides). In some embodiments of Formula (I), (II), (IIA), or (IIB), including any of the foregoing, POLY is poly(α-hydroxy acid). In some embodiments of Formula (I), (II), (IIA), or (IIB), including any of the foregoing, POLY is poly(vinyl alcohol). In some embodiments of Formula (I), (II), (IIA), or (IIB), including any of the foregoing, POLY is polyphosphazene. In some embodiments of Formula (I), (II), (IIA), or (IIB), including any of the foregoing, POLY is polyoxazolines (POZ). In some embodiments of Formula (I), (II), (IIA), or (IIB), including any of the foregoing, POLY is poly(N-acryloylmorpholine). In some embodiments of Formula (I), (II), (IIA), or (IIB), including any of the foregoing, POLY is polysarcosine. In some embodiments of Formula (I), (II), (IIA), or (IIB), including any of the foregoing, POLY is a nonpeptidic, water-soluble polymer. In certain embodiments of Formula (I), (II), (IIA), or (IIB), including any of the foregoing, POLY includes a polyethylene glycol (PEG) or methoxypolyethylene glycol (mPEG). In certain embodiments of Formula (I), (II), (IIA), or (IIB), including any of the foregoing, POLY is

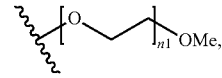

wherein ⌇ represents attachment to the remainder of the compound, and wherein n1 is an integer from one to twenty. In certain embodiments of Formula (I), (II), (IIA), or (IIB), including any of the foregoing, n1 is an integer between five to fifteen. In some embodiments of Formula (I), (II), (IIA), or (IIB), including any of the foregoing, n1 is one. In some embodiments of Formula (I), (II), (IIA), or (IIB), including any of the foregoing, n1 is two. In some embodiments of Formula (I), (II), (IIA), or (IIB), including any of the foregoing, n1 is three. In some embodiments of Formula (I), (II), (IIA), or (IIB), including any of the foregoing, n1 is four. In some embodiments of Formula (II), (IIA), or (IIB), including any of the foregoing, n1 is five. In some embodiments of Formula (I), (II), (IIA), or (IIB), including any of the foregoing, n1 is six. In some embodiment of Formula (I), (II), (IIA), or (IIB)s, n1 is seven. In some embodiments of Formula (I), (II), (IIA), or (IIB), including any of the foregoing, n1 is eight. In some embodiments of Formula (I), (II), (IIA), or (IIB), including any of the foregoing, n1 is nine. In some embodiments of Formula (I), (II), (IIA), or (IIB), including any of the foregoing, n1 is ten. In some embodiments of Formula (I), (II), (IIA), or (IIB), including any of the foregoing, n1 is eleven. In some embodiments of Formula (I), (II), (IIA), or (IIB), including any of the foregoing, n1 is twelve. In some embodiments of Formula (I), (II), (IIA), or (IIB), including any of the foregoing, n1 is thirteen. In some embodiments of Formula (I), (II), (IIA), or (IIB), including any of the foregoing, n1 is fourteen. In some embodiments of Formula (I), (II), (IIA), or (IIB), including any of the foregoing, n1 is fifteen. In some embodiments of Formula (I), (II), (IIA), or (IIB), including any of the foregoing, n1 is sixteen. In some embodiments of Formula (I), (II), (IIA), or (IIB), including any of the foregoing, n1 is seventeen. In some embodiments of Formula (I), (II), (IIA), or (IIB), n1 is eighteen. In some embodiments of Formula (I), (II), (IIA), or (IIB), including any of the foregoing, n1 is nineteen. In some embodiments of Formula (II), (IIA), or (IIB), including any of the foregoing, n1 is twenty. In some embodiments of Formula (I), (II), (IIA), or (IIB), including any of the foregoing, n1 is twenty-one. In some embodiments of Formula (I), (II), (IIA), or (IIB), including any of the foregoing, n1 is twenty-two. In some embodiments of Formula (I), (II), (IIA), or (IIB), including any of the foregoing, n1 is twenty-three. In some embodiments of Formula (I), (II), (IIA), or (IIB), including any of the foregoing, n1 is twenty-four. In some embodiments of Formula (I), (II), (IIA), or (IIB), including any of the foregoing, n1 is twenty-five. In some embodiments of Formula (I), (II), (IIA), or (IIB), including any of the foregoing, n1 is twenty-six. In some embodiments of Formula (I), (II), (IIA), or (IIB), including any of the foregoing, n1 is twenty-seven. In some embodiments of Formula (I), (II), (IIA), or (IIB), including any of the foregoing, n1 is twenty-eight. In some embodiments of Formula (I), (II), (IIA), or (IIB), including any of the foregoing, n1 is twenty-nine. In some embodiments of Formula (I), (II), (IIA), or (IIB), including any of the foregoing, n1 is thirty.

In certain embodiments, RL includes an alkyne, cyclooctyne, a strained alkene, a tetrazine, an amine, methylcyclopropene, a thiol, a para-acetyl-phenylalanine residue, an oxyamine, a maleimide, or an azide. In some embodiments, RL includes an alkyne. In some embodiments, RL includes an cyclooctyne. In some embodiments, RL includes a strained alkene. In some embodiments, RL includes a tetrazine. In some embodiments, RL includes an amine. In some embodiments, RL includes an methylcyclopropene. In some embodiments, RL includes a thiol. In some embodiments, RL includes a para-acetyl-phenylalanine residue. In some embodiments, RL includes an oxyamine. In some embodiments, RL includes a maleimide. In some embodiments, RL includes an azide. In certain embodiments, RL is selected from the group consisting of

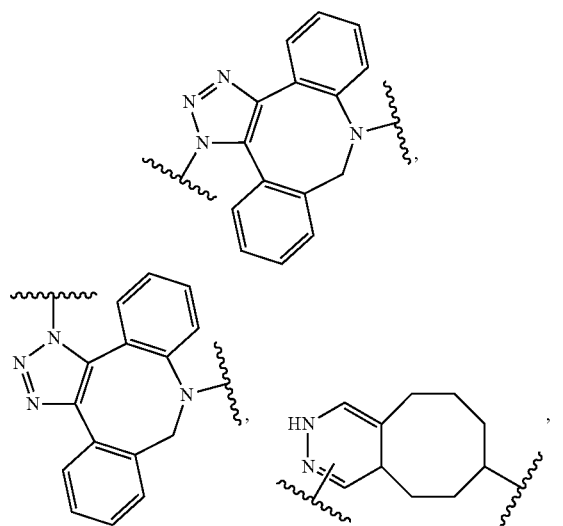

-continued

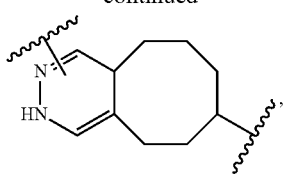

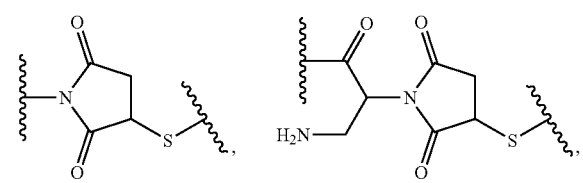

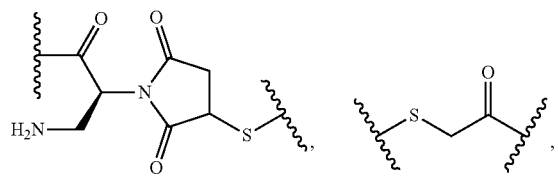

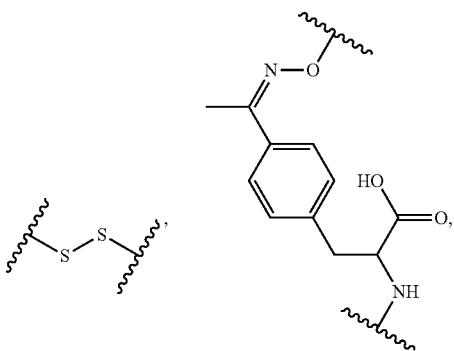

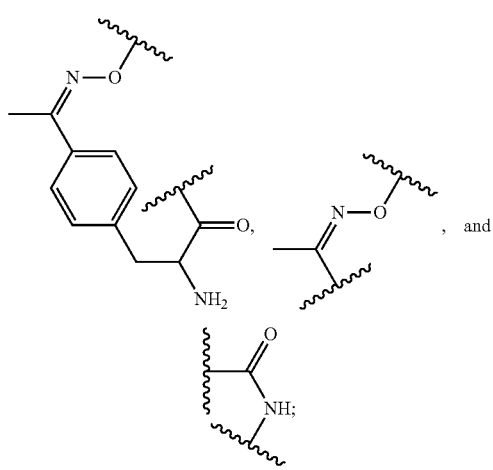

and $\zeta$ represents attachment to the remainder of the compound. In some embodiments, RL is

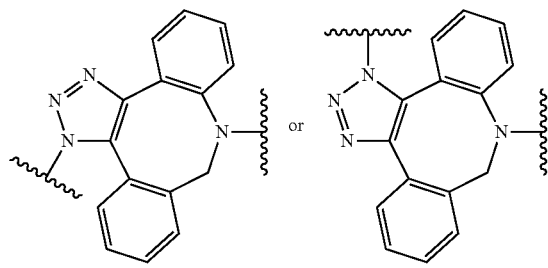 [SMILES: *N1Cc2ccccc2-c2c(nnn2*)-c2ccccc21 ; *N1Cc2ccccc2-c2nnn(*)c2-c2ccccc21] or and $\zeta$ represents attachment to the remainder of the compound. In one some embodiments, RL is

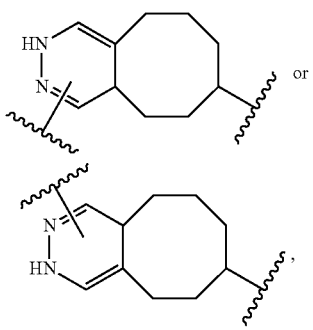, and $\zeta$ represents attachment to the remainder of the compound. In some embodiments, RL is

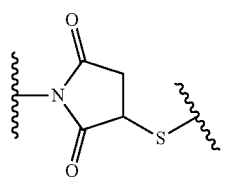 [SMILES: *SC1CC(=O)N(*)C1=O]

and $\zeta$ represents attachment to the remainder of the compound. In some embodiments, RL is

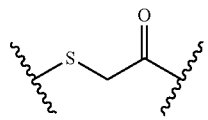 [SMILES: *SCC(*)=O]

and $\zeta$ represents attachment to the remainder of the compound. In some embodiments, RL is

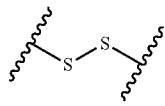 [SMILES: *SS*]

and $\zeta$ represents attachment to the remainder of the compound. In some embodiments, RL is

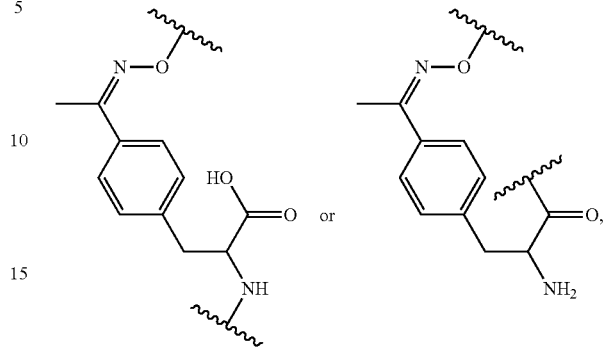 or wherein $\zeta$ represents attachment to the remainder of the compound. In some embodiments, RL is

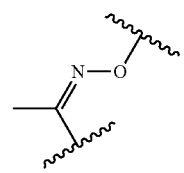 [SMILES: *O/N=C(\*)C]

and $\zeta$ represents attachment to the remainder of the compound. In some embodiments, RL is

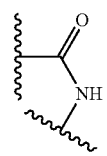

and $\zeta$ represents attachment to the remainder of the compound. In some embodiments, RL is

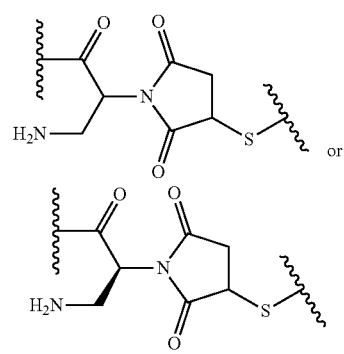 or and $\zeta$ represents attachment to the remainder of the compound. In some embodiments, Su is a sugar moiety. In some embodiments, Su is a hexose form of a monosaccharide. Su may be a glucuronic acid or mannose residue. In certain embodiments, Su is

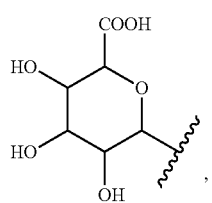

wherein $\xi$ represents attachment to the remainder of the compound. In certain embodiments, Su is

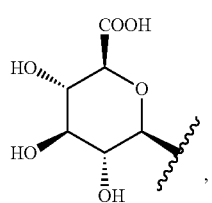

wherein $\xi$ represents attachment to the remainder of the compound.

In one aspect, provided herein is a conjugate of Formula (III):

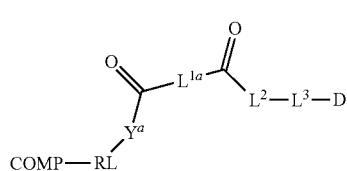

or a pharmaceutically acceptable salt and/or regioisomer thereof;
wherein
$L^{1a}$ is selected from

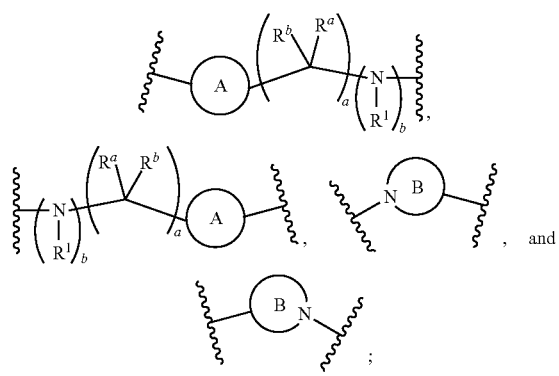

Ring A is an optionally substituted bridged, fused, or spirocyclic bicyclic carbocycle, or an optionally substituted bridged, fused, or spirocyclic bicyclic heterocycle, wherein the carbocycle or the heterocycle of Ring A are optionally substituted with one or more substituents selected from alkyl, alkenyl, alkynyl, cycloalkyl, halogen, alkoxy, —CN, —NO$_2$, —OH, —N(R$^2$R$^3$)$_2$, —C(O)—, —C(O)N(R$^2$R$^3$)$_2$, —C(O) OR$^2$, aminoalkyl, hydroxyalkyl, haloalkyl, aryl, arylalkyl, heteroaryl, and heteroarylalkyl;

Ring B is an optionally substituted N-linked bridged, fused, or spirocyclic bicyclic heterocycle, wherein Ring B is optionally substituted with one or more substituents selected from alkyl, alkenyl, alkynyl, cycloalkyl, halogen, alkoxy, —CN, —NO$_2$, —OH, —N(R$^2$R$^3$)$_2$, —C(O)—, —C(O)N(R$^2$R$^3$)$_2$, —C(O) OR$^2$, aminoalkyl, hydroxyalkyl, haloalkyl, aryl, arylalkyl, heteroaryl, and heteroarylalkyl;

R$^a$ and R$^b$ are independently selected from hydrogen, alkyl, alkenyl, alkynyl, cycloalkyl, halogen, alkoxy, —CN, —NO$_2$, —OH, —N(R$^2$R$^3$)$_2$, —C(O)N(R$^2$R$^3$)$_2$, —C(O)OR$^2$, aminoalkyl, hydroxyalkyl, haloalkyl, aryl, arylalkyl, heteroaryl, and heteroarylalkyl;

a is an integer independently selected from 0, 1, 2, 3, 4, 5, and 6;

R$^1$ is hydrogen or alkyl optionally substituted with one or more substituents selected from cycloalkyl, halogen, alkoxy, —CN, —NO$_2$, —OH, —N(R$^2$R$^3$)$_2$, —C(O)N(R$^2$R$^3$)$_2$, —C(O)OR$^2$, aryl, and heteroaryl;

R$^2$ and R$^3$ are independently selected from hydrogen, alkyl, cycloalkyl, aryl, arylalkyl, heteroaryl, and heteroarylalkyl;

Y$^a$ is *—C(O)—(CR$^a$R$^b$)$_c$—NH— or *—C(O)—(CR$^a$R$^b$)$_c$—, wherein * represents where Y$^a$ is bound to RL;

c is an integer selected from 1, 2, 3, 4, 5, or 6;

RL is a reactive group residue;

L$^2$ is absent or a linker comprising a hydrophilic polymer residue;

L$^3$ is absent, —C(O)-AA-, —C(O)-AA-Z—(CR$^a$R$^b$)$_a$—Z—(CR$^a$R$^b$)$_a$—C(O)—, —C(O)—Z—(CR$^a$R$^b$)$_a$—C(O)—Z-L$^4$-OC(O)—, —Z-AA-, -AA-, —C(O)—, —C(O)-AA-Z—(CR$^a$R$^b$)$_a$—, -AA-C(O)—, —C(O)—(CR$^a$R$^b$)$_a$—Z—(CR$^a$R$^b$)—Z-AA-C(O)—, —C(O)O-L$^4$-Z—C(O)—(CR$^a$R$^b$)$_a$—Z—C(O)—, -AA-Z—, or —(CR$^a$R$^b$)$_a$—Z-AA-C(O)—;

Z is selected from —NR$^2$— and —O—;

AA is an amino acid residue or a peptide residue;

L$^4$ is

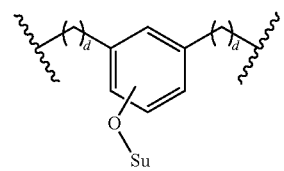

wherein Su is a hexose form of a monosaccharide;

d is an integer independently selected from 1, 2, and 3;

D is a drug moiety;

COMP is a residue of a ROR1 antibody; and $\xi$ represents attachment to the remainder of the compound.

In certain embodiments, the compound of Formula (III) is a compound of Formula (IIIA):

(IIIA)

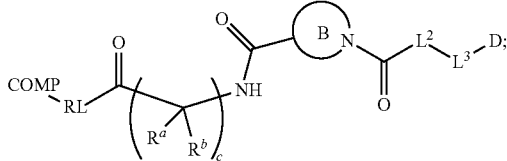

or a pharmaceutically acceptable salt and/or regioisomer thereof;

wherein integer c, RL, $R^a$, $R^b$, Ring B, $L^2$, $L^3$, D, and COMP are as defined herein.

In certain embodiments, the compound of Formula (IIIA) is selected from the following:

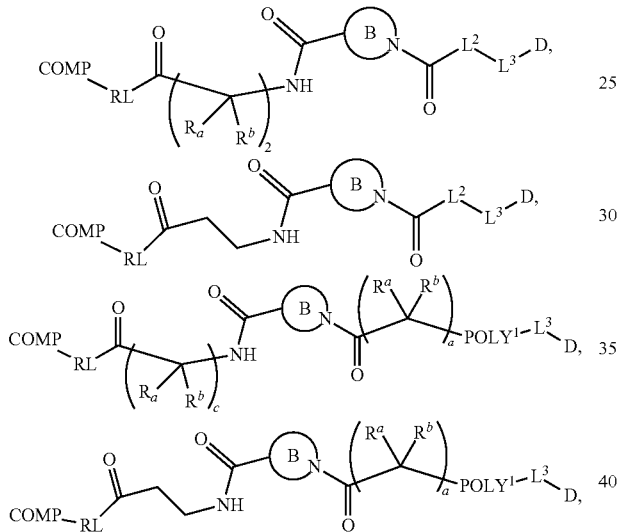

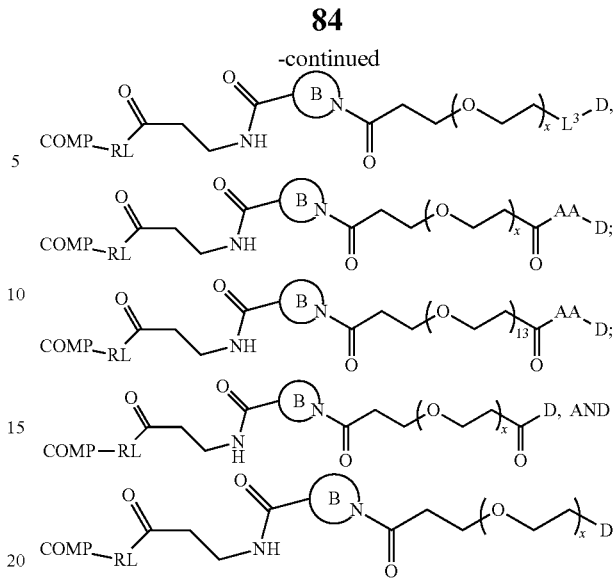

or a pharmaceutically acceptable salt and/or regioisomer thereof.

In certain embodiments, the compound of Formula (III) is a compound of Formula (IIIB):

(IIIB)

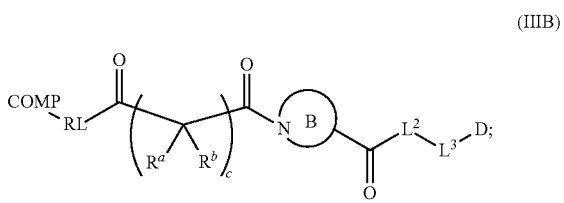

or a pharmaceutically acceptable salt and/or regioisomer thereof.

wherein integer c, RL, $R^a$, $R^b$, Ring B, $L^2$, $L^3$, D, and COMP are as defined herein.

In certain embodiments, the compound of Formula (TIM) is selected from the following:

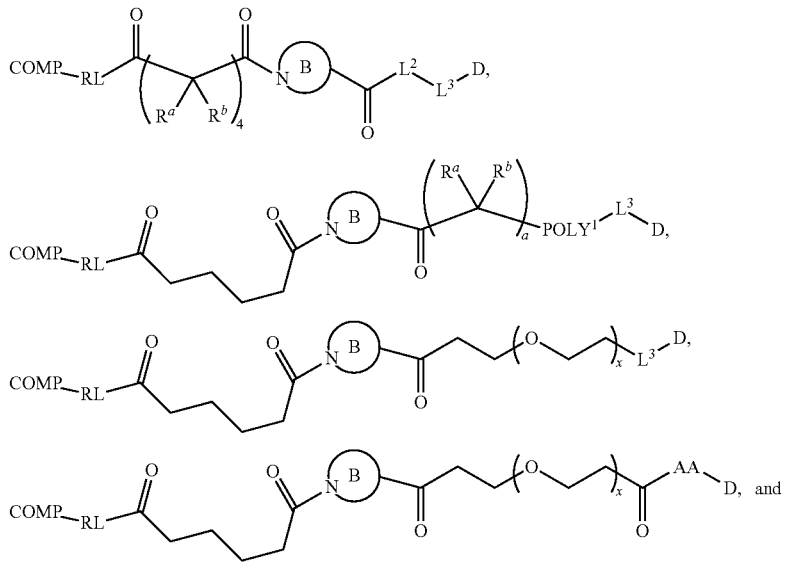

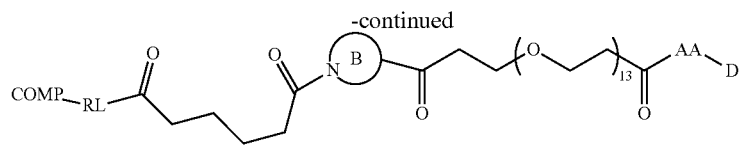

or a pharmaceutically acceptable salt and/or regioisomer thereof.

In certain embodiments, the compound of Formula (III) is a compound of Formula (IIIC):

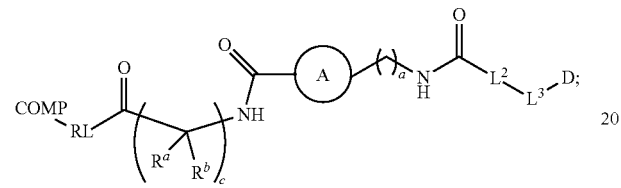

or a pharmaceutically acceptable salt and/or regioisomer thereof.

wherein integer a, integer c, RL, $R^a$, $R^b$, Ring A, $L^2$, $L^3$, D, and COMP are as defined herein.

In certain embodiments, the compound of Formula (IIIC) is selected from the following:

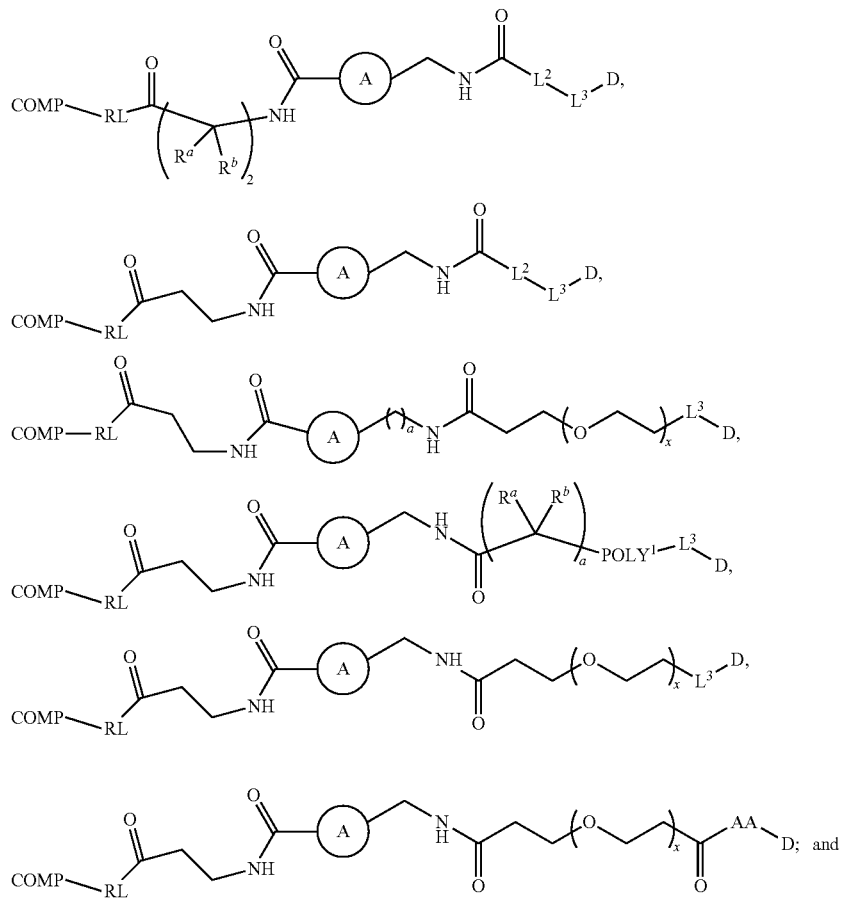

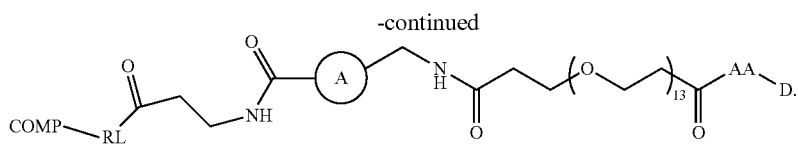

Or a pharmaceutically acceptable salt and/or regioisomer thereof.

In certain embodiments, the compound of Formula (III) is a compound of Formula (IIID):

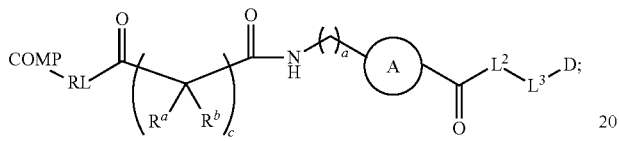

(IIID)

or a pharmaceutically acceptable salt and/or regioisomer thereof;

wherein integer a, integer c, RL, $R^a$, $R^b$, Ring A, $L^2$, $L^3$, D, and COMP are as defined herein.

In certain embodiments, the compound of Formula (MD) is selected from the following:

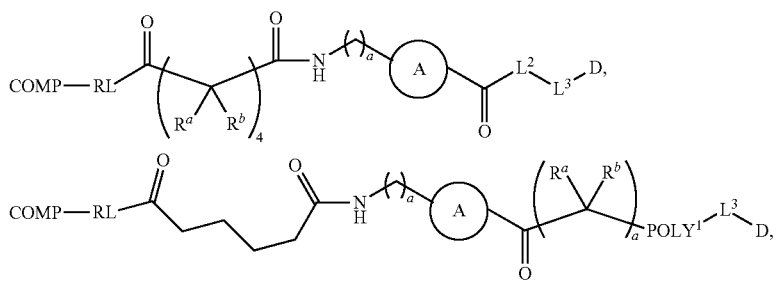

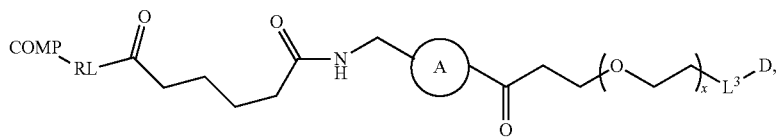

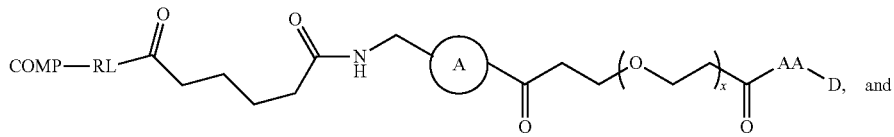

and

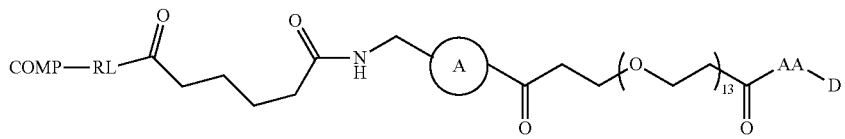

or a pharmaceutically acceptable salt and/or regioisomer thereof.

In certain embodiments, the compound of Formula (III) is a compound of Formula (IIIE)
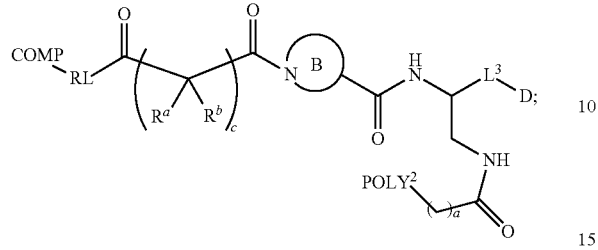
(IIIE)
or a pharmaceutically acceptable salt and/or regioisomer thereof;
wherein integer a, integer c, RL, $R^a$, $R^b$, Ring B, $L^3$, POLY$^2$, D, and COMP are as defined herein.
In certain embodiments, the compound of Formula (IIIE) is selected from the following:
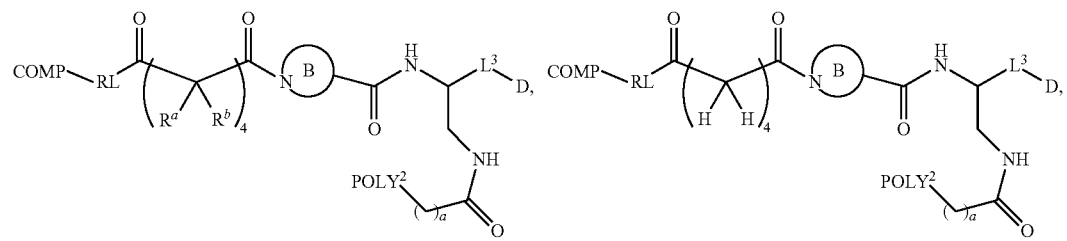
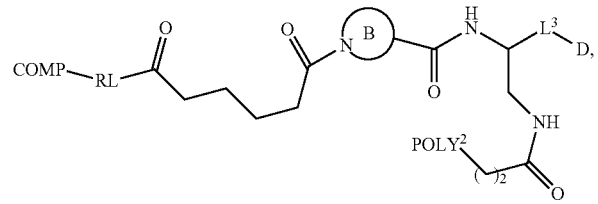
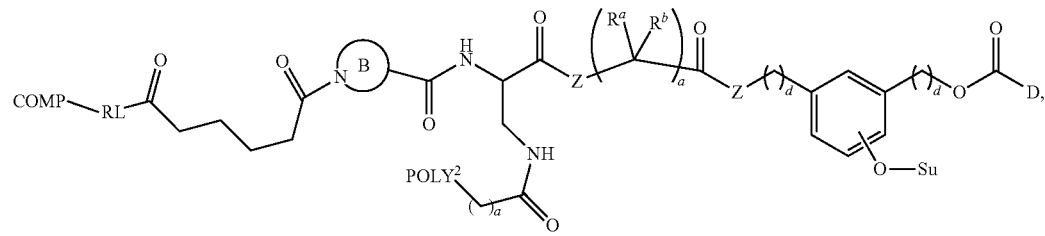
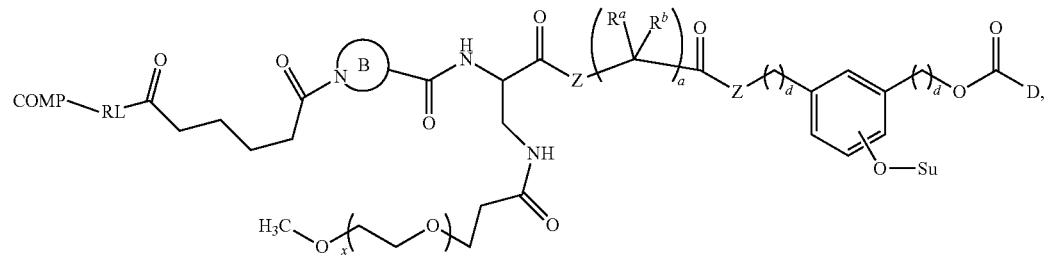
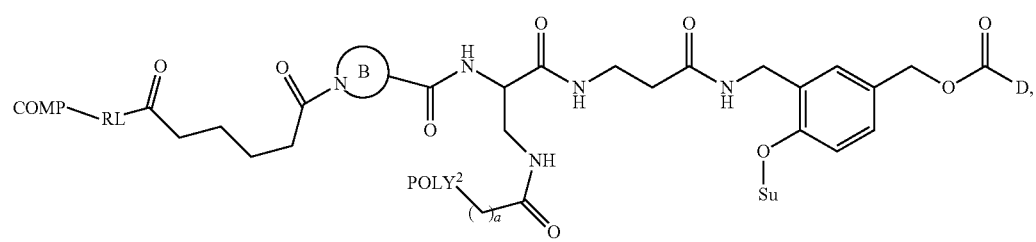

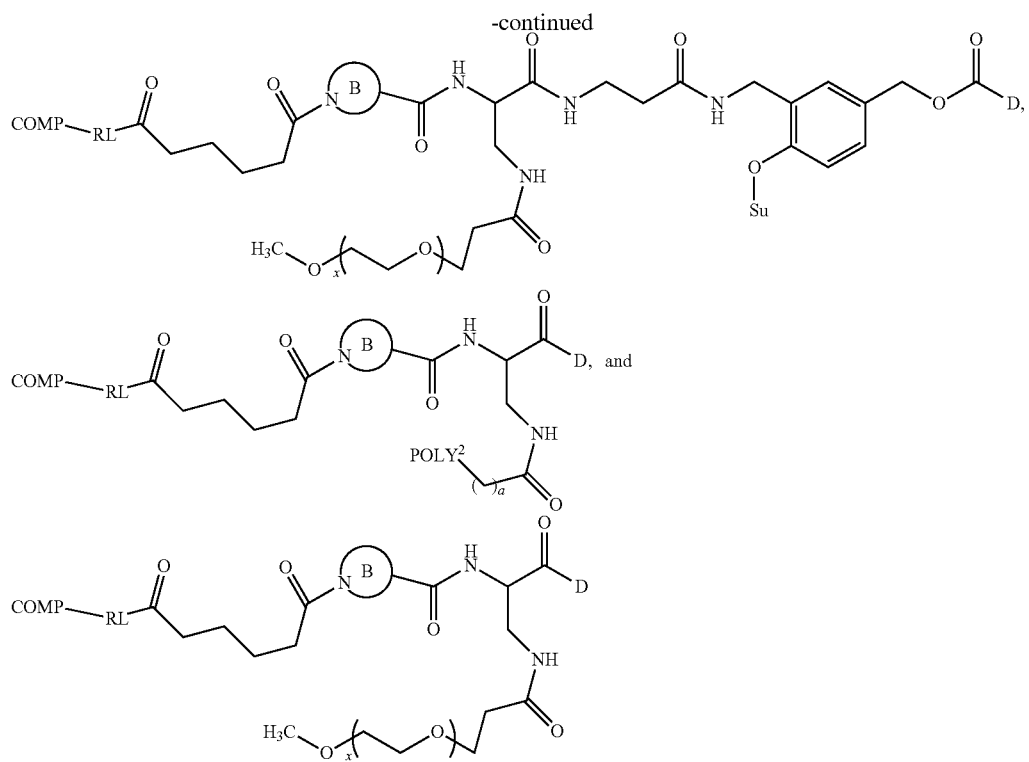

or a pharmaceutically acceptable salt and/or regioisomer thereof.

In certain embodiments, the compound of Formula (III) is a compound of Formula (IIIF):

(IIIF)

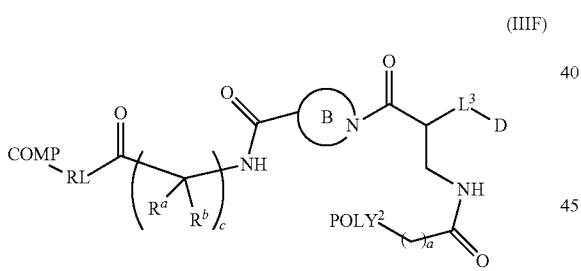

or a pharmaceutically acceptable salt and/or regioisomer thereof;

wherein integer a, integer c, RL, $R^a$, $R^b$, Ring B, $L^3$, POLY$^2$, D, and COMP are as defined herein.

In certain embodiments, the compound of Formula (IIIF) is selected from the following:

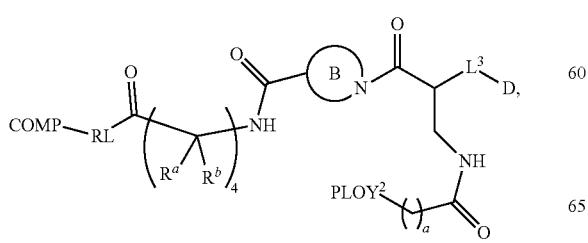

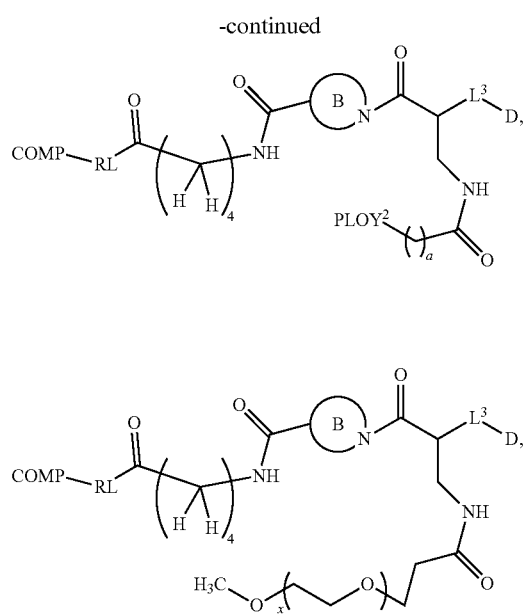

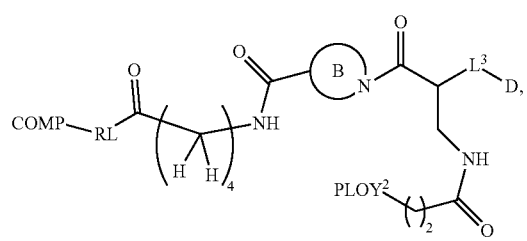

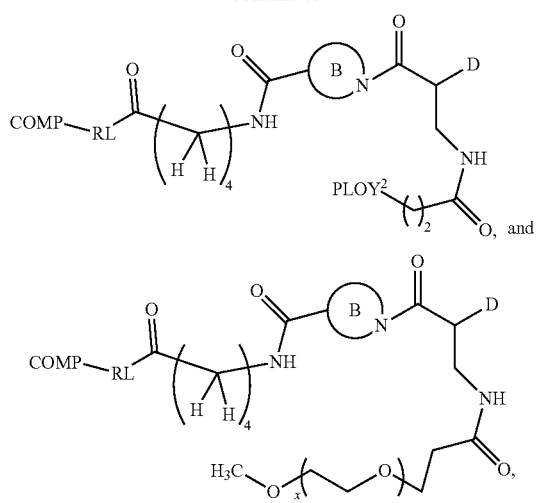

or a pharmaceutically acceptable salt and/or regioisomer thereof.

In certain embodiments, the compound of Formula (III) is a compound of Formula (IIIG):

(IIIG)

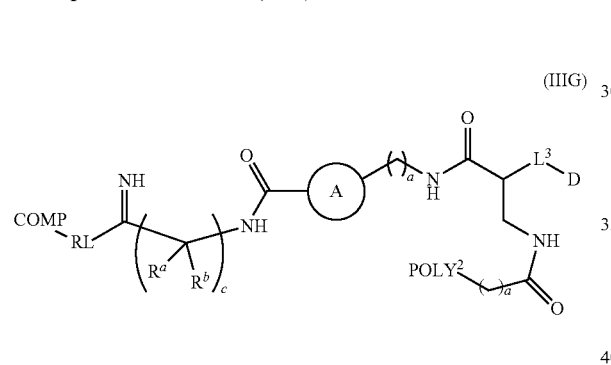

or a pharmaceutically acceptable salt and/or regioisomer thereof;

wherein integer a, integer c, RL, $R^a$, $R^b$, Ring A, $L^3$, $POLY^2$, D, and COMP are as defined herein.

In certain embodiments, the compound of Formula (IIIG) is selected from the following:

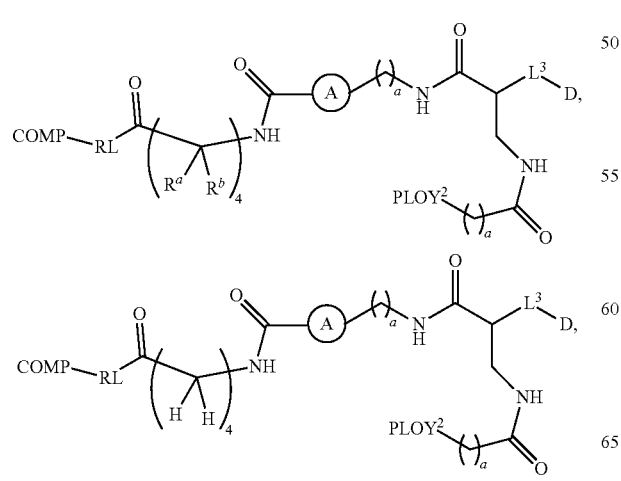

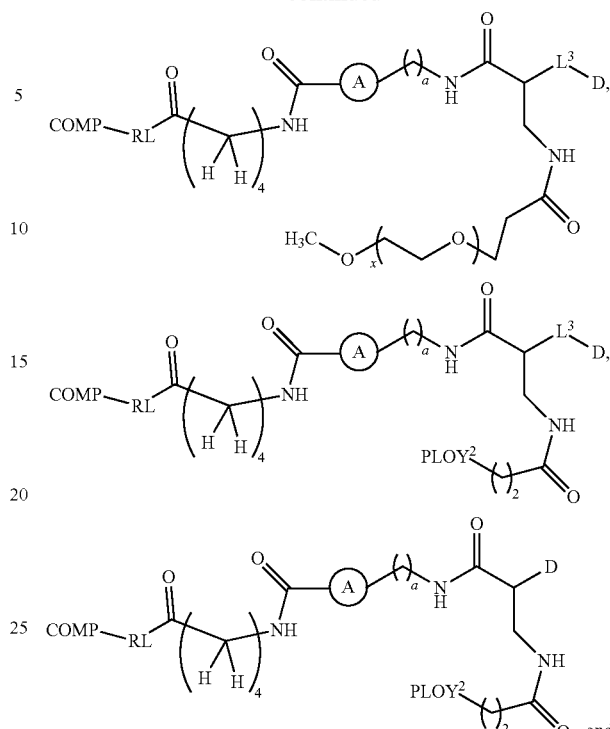

or a pharmaceutically acceptable salt and/or regioisomer thereof.

In certain embodiments, the compound of Formula (III) is a compound of Formula (IIIH):

(IIIH)

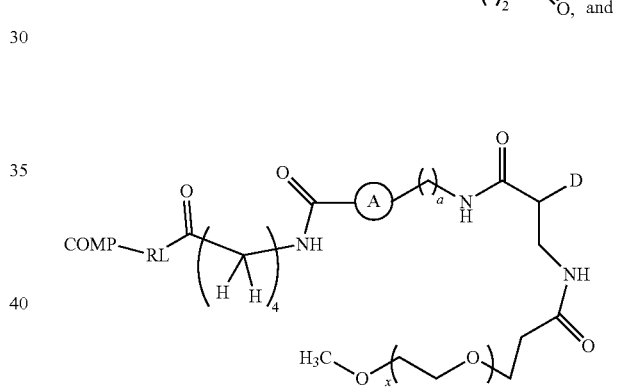

or a pharmaceutically acceptable salt and/or regioisomer thereof;

wherein integer a, integer c, RL, $R^a$, $R^b$, Ring A, $L^3$, $POLY^2$, D, and COMP are as defined herein.

In certain embodiments, the compound of Formula (IIIH) is selected from the following:

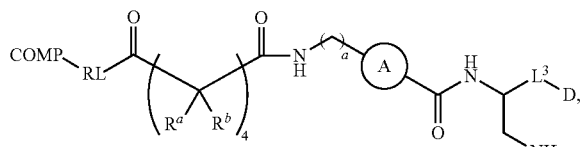

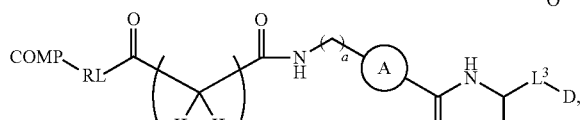

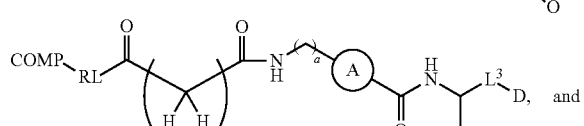

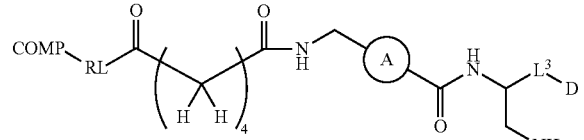

or a pharmaceutically acceptable salt and/or regioisomer thereof.

In one aspect, provided herein is a conjugate of Formula (V):

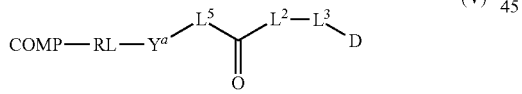

(V)

or a pharmaceutically acceptable salt and/or regioisomer thereof;
wherein
$L^5$ is a linker comprising an unnatural amino acid; and
RL, COMP, $Y^a$, $L^2$, $L^3$, and D are as defined herein.

In certain embodiments, the compound of Formula (V) is a compound of Formula (VA):

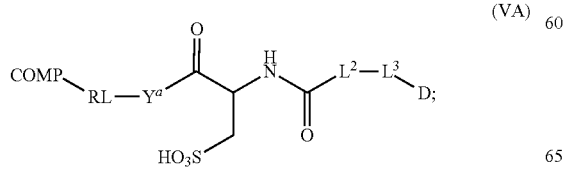

(VA)

or a pharmaceutically acceptable salt and/or regioisomer thereof;
wherein RL, COMP, $Y^a$, $L^2$, $L^3$, and D are as defined herein.

In certain embodiments, the compound of Formula (V) is a compound of Formula (VB):

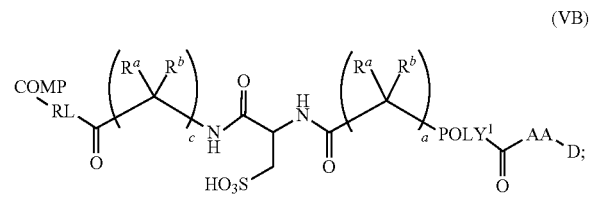

(VB)

or a pharmaceutically acceptable salt and/or regioisomer thereof;
wherein integer a, integer c, RL, COMP, $R^a$, $R^b$, $POLY^1$, AA, and D are as defined herein.

In certain embodiments, the compound of Formula (VB) is a compound of the formula:

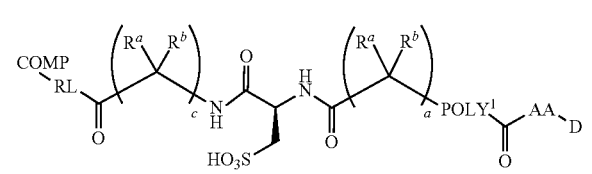

or a pharmaceutically acceptable salt and/or regioisomer thereof.

In certain embodiments of Formula (III)-(VB), including any of the foregoing, $L^{1a}$ is

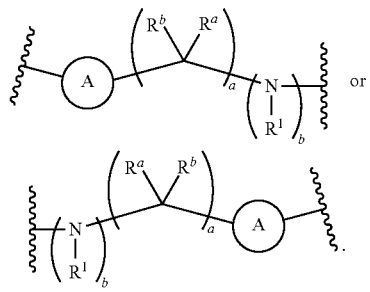

In certain embodiments of Formula (III)-(VB), including any of the foregoing, $L^{1a}$ is

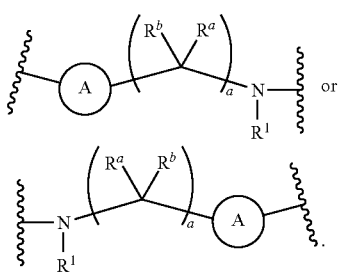

In certain embodiments of Formula (III)-(VB), including any of the foregoing, $L^{1a}$ is

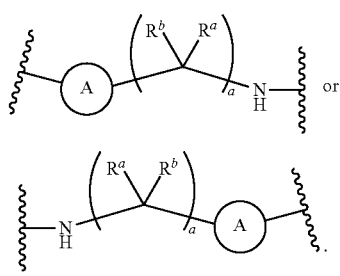
or

In certain embodiments of Formula (III)-(VB), including any of the foregoing, $L^{1a}$ is

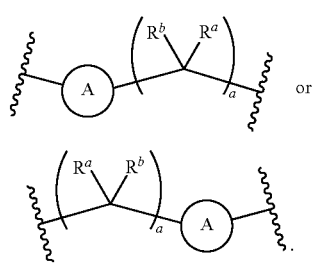
or

In certain embodiments of Formula (III)-(VB), including any of the foregoing, $L^{1a}$ is

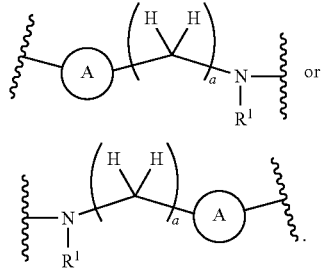
or

In certain embodiments of Formula (III)-(VB), including any of the foregoing, $L^{1a}$ is

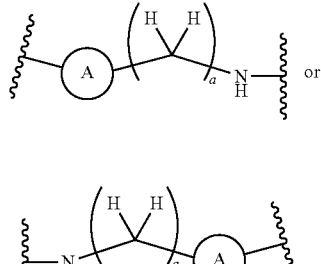

In certain embodiments of Formula (III)-(VB), including any of the foregoing, $L^{1a}$ is

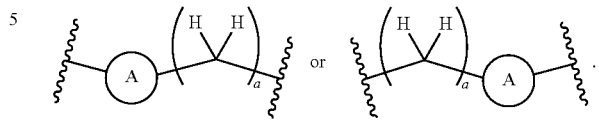

In certain embodiments of Formula (III)-(VB), including any of the foregoing, $L^{1a}$ is

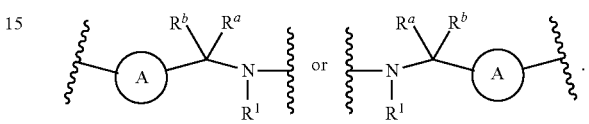

In certain embodiments of Formula (III)-(VB), including any of the foregoing, $L^{1a}$ is

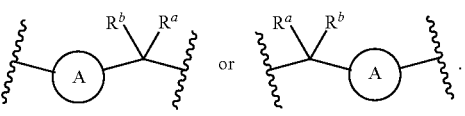

In certain embodiments of Formula (III)-(VB), including any of the foregoing, $L^{1a}$ is

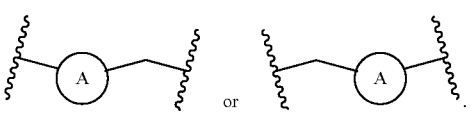

In certain embodiments of Formula (III)-(VB), including any of the foregoing, $L^{1a}$ is

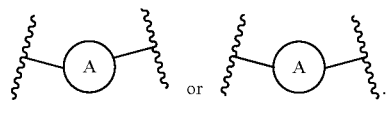

In certain embodiments of Formula (III)-(VB), including any of the foregoing, $L^{1a}$ is

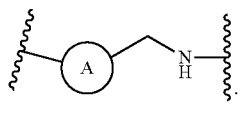

In certain embodiments of Formula (III)-(VB), including any of the foregoing, $L^{1a}$ is

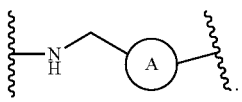

In certain embodiments of Formula (III)-(VB), including any of the foregoing, $L^{1a}$ is

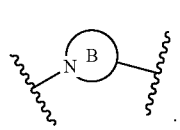

In certain embodiments of Formula (III)-(VB), including any of the foregoing, $L^{1a}$ is

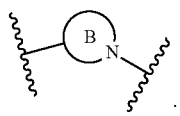

In certain embodiments of Formula (III)-(VB), including any of the foregoing, Ring B of $L^{1a}$ is an optionally substituted 5- to 12-membered N-linked bridged, fused, or spirocyclic bicyclic heterocycle containing 1, 2, or 3 heteroatoms independently selected from N, O, and S including the N to which the ring is attached, wherein Ring B is optionally substituted with one or more substituents selected from alkyl, alkenyl, alkynyl, cycloalkyl, halogen, alkoxy, —CN, —NO$_2$, —OH, —N(R$^2$R$^3$)$_2$, —C(O)—, —C(O)N(R$^2$R$^3$)$_2$, —C(O)OR$^2$, aminoalkyl, hydroxyalkyl, haloalkyl, aryl, arylalkyl, heteroaryl, and heteroarylalkyl. In certain embodiments of Formula (III)-(VB), including any of the foregoing, Ring B of $L^{1a}$ is an optionally substituted 5- to 12-membered N-linked spirocyclic bicyclic heterocycle containing 1, 2, or 3 heteroatoms independently selected from N, and S including the N to which the ring is attached.

In certain embodiments of Formula (III)-(VB), including any of the foregoing, Ring B of $L^{1a}$ is selected from

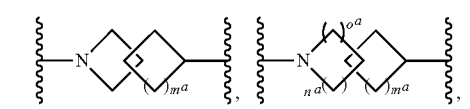

wherein $m^a$ is an integer selected from 1, 2, 3, 4, and 5; and each of $n^a$ and $o^a$ is an integer independently selected from 1, 2, and 3.

In certain embodiments of Formula (III)-(VB), including any of the foregoing, Ring B of $L^{1a}$ is

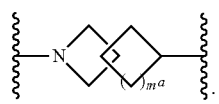

In certain embodiments of Formula (III)-(VB),

is selected from

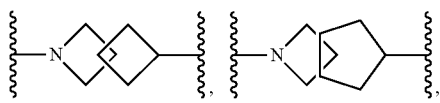

and

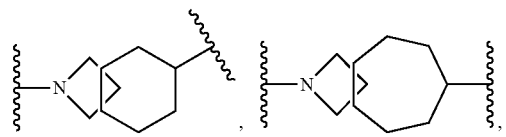

In certain embodiments of Formula (III)-(VB),

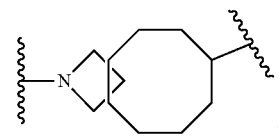

is selected from

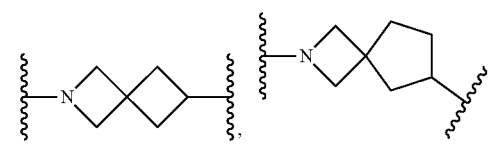

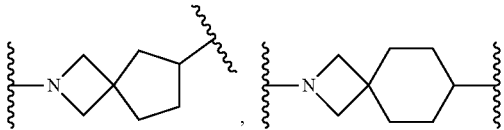

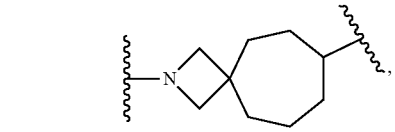

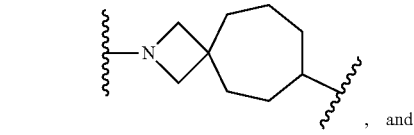

, and

-continued

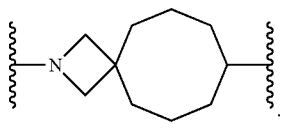

In certain embodiments of Formula (III)-(VB), Ring B of $L^{1a}$ is

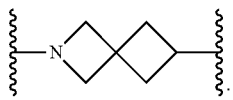 [SMILES: *C1CC2(C1)CN(*)C2]

In certain embodiments, Ring B is

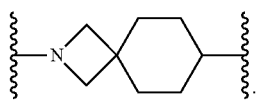

In certain embodiments of Formula (III)-(VB), including any of the foregoing, Ring B of $L^{1a}$ is

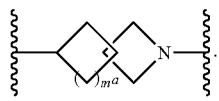

In certain embodiments of Formula (III)-(VB),

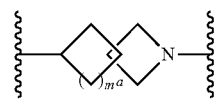

is selected from

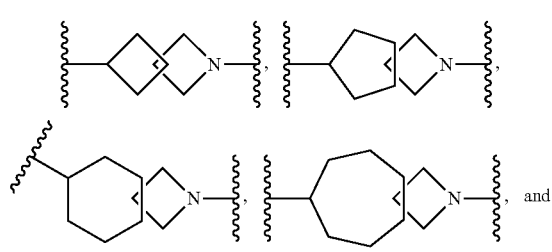

In certain embodiments of Formula (III)-(VB),

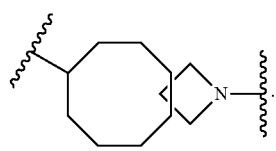

is selected from

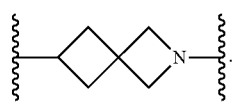

In certain embodiments of Formula (III)-(VB), Ring B of $L^{1a}$ is and

In certain embodiments of Formula (III)-(VB), Ring B of $L^{1a}$ is

In certain embodiments of Formula (III)-(VB), Ring B of $L^{1a}$ is

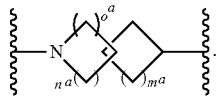

In certain embodiments of Formula (III)-(VB), including any of the foregoing, Ring B of $L^{1a}$ is In certain embodiments of Formula (III)-(VB),

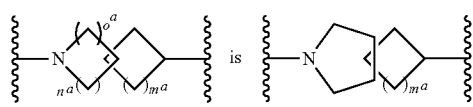

wherein $m^a$ is 1, 2, or 3. In certain embodiments of Formula (III)-(VB),

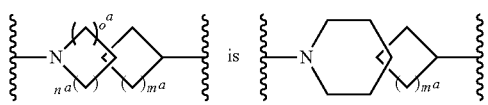

wherein $m^a$ is 1, 2, or 3. In certain embodiments of Formula (III)-(VB),

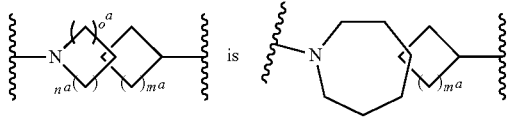

wherein $m^a$ is 1, 2, or 3. In certain embodiments of Formula (III)-(VB),

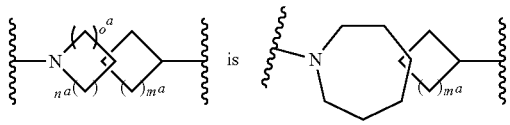

wherein $m^a$ is 1, 2, or 3.

In certain embodiments of Formula (III)-(VB),

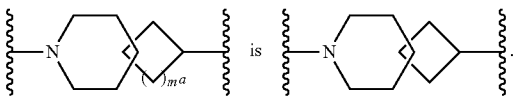

In certain embodiments of Formula (III)-(VB),

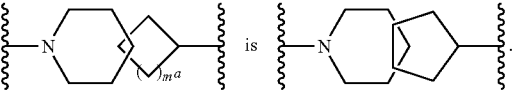

In certain embodiments of Formula (III)-(VB),

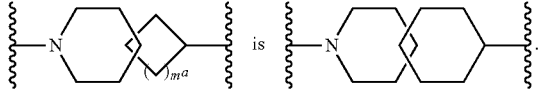

In certain embodiments of Formula (III)-(VB),

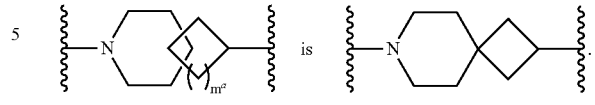

In certain embodiments of Formula (III)-(VB),

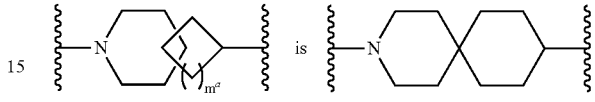

In certain embodiments of Formula (III)-(VB), including any of the foregoing, Ring B of $L^{1a}$ is

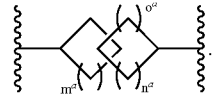

In certain embodiments of Formula (III)-(VB),

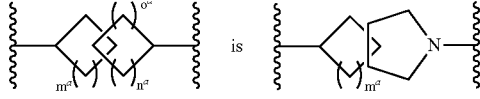

wherein $m^a$ is 1, 2, or 3. In certain embodiments of Formula (III)-(VB),

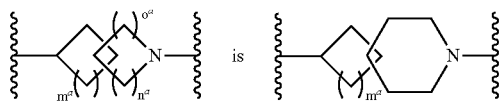

wherein $m^a$ is 1, 2, or 3. In certain embodiments of Formula (III)-(VB),

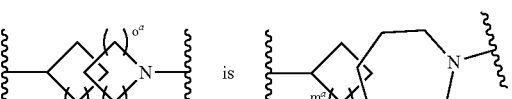

wherein $m^a$ is 1, 2, or 3. In certain embodiments of Formula (III)-(VB),

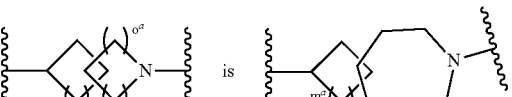

wherein $m^a$ is 1, 2, or 3.

In certain embodiments of Formula (III)-(VB),

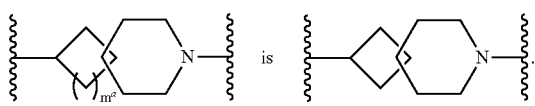

In certain embodiments of Formula (III)-(VB),

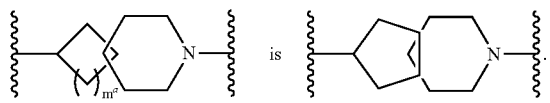

In certain embodiments of Formula (III)-(VB),

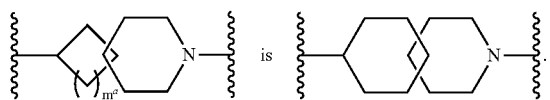

In certain embodiments,

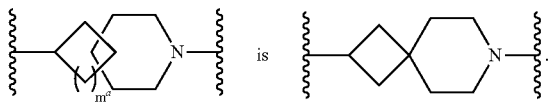

In certain embodiments of Formula (III)-(VB),

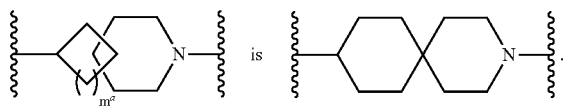

In certain embodiments of Formula (III)-(VB), including any of the foregoing, Ring B of $L^{1a}$ is

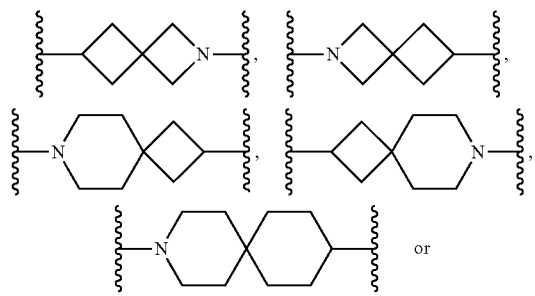

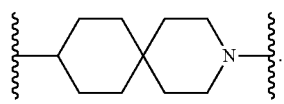

In certain embodiments of Formula (III)-(VB), including any of the foregoing, Ring B of $L^{1a}$ is selected from

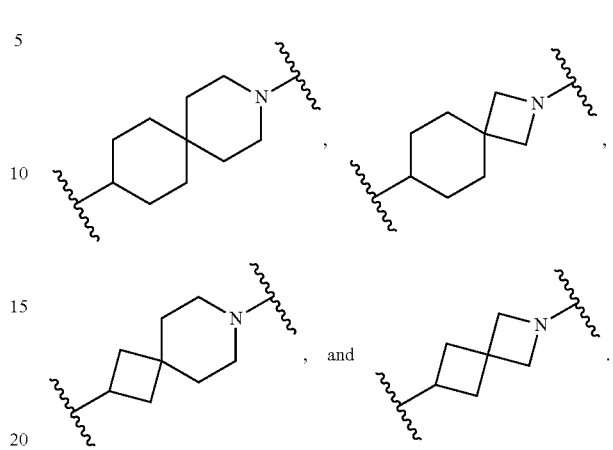

In certain embodiments of Formula (III)-(VB), including any of the foregoing, Ring B of $L^{1a}$ is selected from

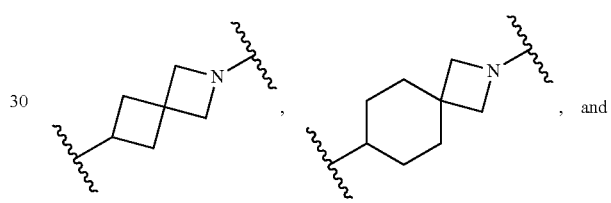

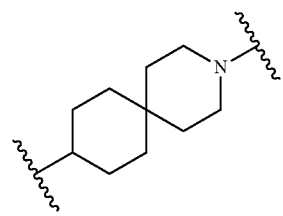

In certain embodiments of Formula (III)-(VB), including any of the foregoing, $L^{1a}$ is selected from

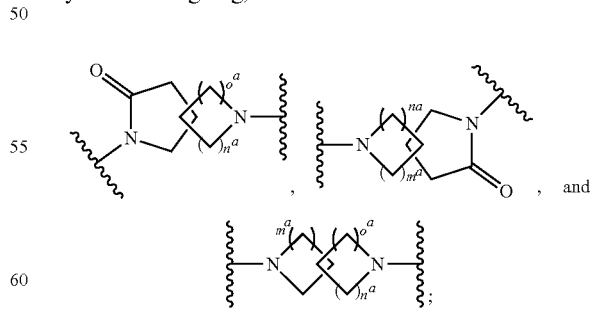

wherein $m^a$ is an integer selected from 1, 2, 3, 4, and 5; and each of $n^a$ and $o^a$ is an integer independently selected from 1, 2, and 3.

In certain embodiments of Formula (III)-(VB), including any of the foregoing, $L^{1a}$ is selected from

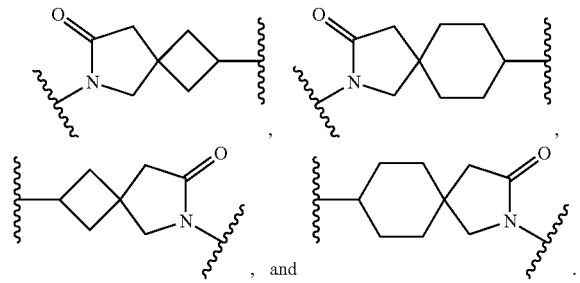

, and

In certain embodiments of Formula (III)-(VB), including any of the foregoing, Ring B of $L^{1a}$ is selected from

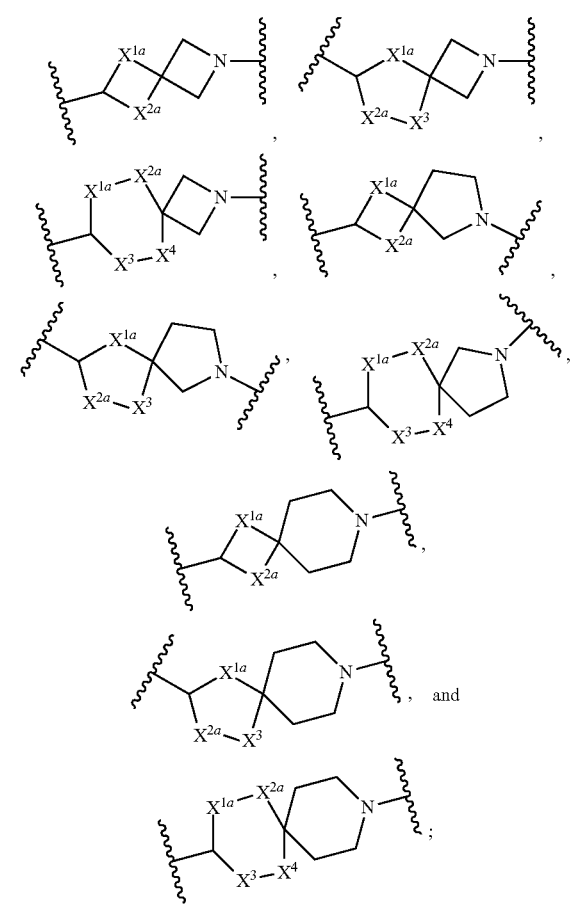

wherein $X^{1a}$, $X^{2a}$, $X^3$, and $X^4$ are independently selected from —C($R^4$)$_2$—, —NH—, —O—, and —S— wherein when $X^{1a}$, $X^{2a}$, and $X^3$ are present, at least one of $X^{1a}$-$X^3$ is —C($R^4$)$_2$— and when $X^{1a}$, $X^{2a}$, $X^3$, and $X^4$ are present, at least two of $X^{1a}$-$X^4$ are —C($R^4$)$_2$—; and $R^4$ is independently selected from hydrogen, $C_{1-6}$ alkyl, $C_{2-6}$ alkenyl, $C_{2-6}$ alkynyl, $C_{3-12}$ cycloalkyl, halogen, alkoxy, —CN, —NO$_2$, —OH, —N($R^2R^3$)$_2$, —C(O)N($R^2R^3$)$_2$, —C(O)OR$^2$, aminoalkyl, hydroxyalkyl, haloalkyl, aryl, arylalkyl, heteroaryl, and heteroarylalkyl; or two $R^4$ groups on the same carbon are taken together to form an oxo group In certain embodiments of Formula (III)-(VB), including any of the foregoing, Ring B of $L^{1a}$ is selected from

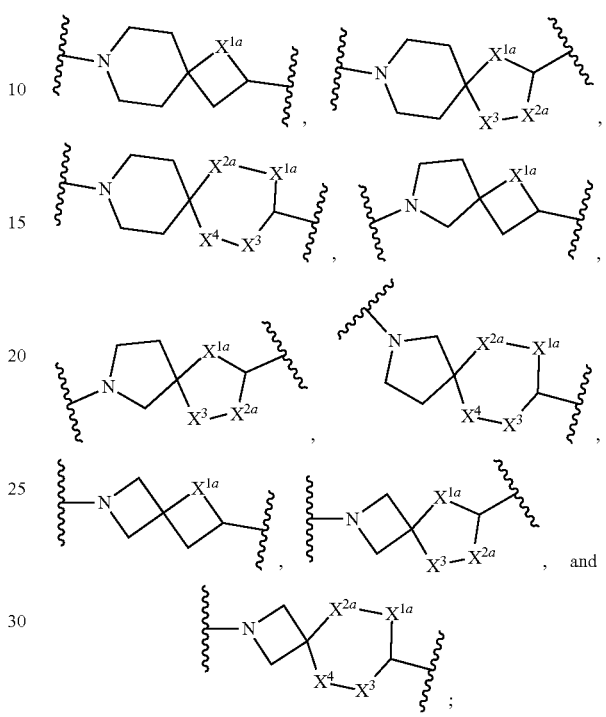

wherein $X^{1a}$, $X^{2a}$, $X^3$, and $X^4$ are independently selected from —C($R^4$)$_2$—, —NH—, —O—, and —S— wherein when $X^{1a}$, $X^{2a}$, and $X^3$ are present, at least one of $X^{1a}$-$X^3$ is —C($R^4$)$_2$— and when $X^{1a}$, $X^{2a}$, $X^3$, and $X^4$ are present, at least two of $X^{1a}$-$X^4$ are —C($R^4$)$_2$—; and $R^4$ is independently selected from hydrogen, $C_{1-6}$ alkyl, $C_{2-6}$ alkenyl, $C_{2-6}$ alkynyl, $C_{3-12}$ cycloalkyl, halogen, alkoxy, —CN, —NO$_2$, —OH, —N($R^2R^3$)$_2$, —C(O)N($R^2R^3$)$_2$, —C(O)OR$^2$, aminoalkyl, hydroxyalkyl, haloalkyl, aryl, arylalkyl, heteroaryl, and heteroarylalkyl; or two $R^4$ groups on the same carbon are taken together to form an oxo group.

In certain embodiments of Formula (III)-(VB), including any of the foregoing, Ring A of $L^{1a}$ is an optionally substituted bridged, fused, or spirocyclic bicyclic carbocycle, wherein the carbocycle or the heterocycle of Ring A are optionally substituted with one or more substituents selected from alkyl, alkenyl, alkynyl, cycloalkyl, halogen, alkoxy, —CN, —NO$_2$, —OH, —N($R^2R^3$)$_2$, —C(O)—, —C(O)N($R^2R^3$)$_2$, —C(O)OR$^2$, aminoalkyl, hydroxyalkyl, haloalkyl, aryl, arylalkyl, heteroaryl, and heteroarylalkyl. In certain embodiments, including any of the foregoing, Ring A of $L^{1a}$ is an optionally substituted $C_{4-12}$ bridged, fused, or spirocyclic bicyclic carbocycle. In certain embodiments of Formula (III)-(VB), including any of the foregoing, Ring A of $L^{1a}$ is an optionally substituted $C_{4-12}$ bridged bicyclic carbocycle. In certain embodiments of Formula (III)-(VB), including any of the foregoing, Ring A of $L^{1a}$ is an optionally substituted $C_{4-8}$ bridged bicyclic carbocycle.

In certain embodiments of Formula (III)-(VB), including any of the foregoing, Ring A of $L^{1a}$ is selected from

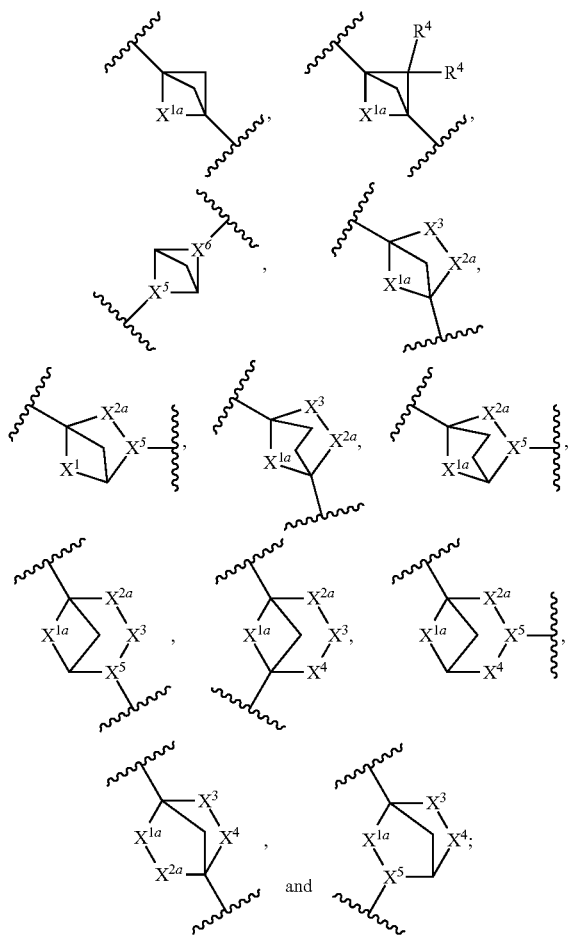

and

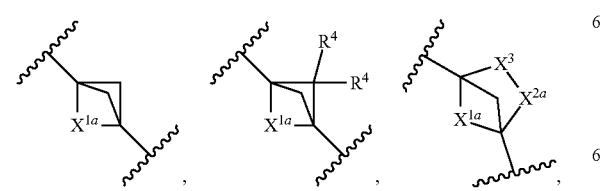

wherein $X^{1a}$, $X^{2a}$, $X^3$, and $X^4$ are independently selected from —C($R^4$)$_2$—, —NH—, —O—, and —S— wherein when $X^{1a}$, $X^{2a}$, and $X^3$ are present, at least one of $X^{1a}$-$X^3$ is —C($R^4$)$_2$— and when $X^{1a}$, $X^{2a}$, $X^3$, and $X^4$ are present, at least two of $X^{1a}$-$X^4$ are —C($R^4$)$_2$—;

$X^5$ is $CR^4$ or N; and $R^4$ is independently selected from hydrogen, $C_{1-6}$ alkyl, $C_{2-6}$ alkenyl, $C_{2-6}$ alkynyl, $C_{3-12}$ cycloalkyl, halogen, alkoxy, —CN, —NO$_2$, —OH, —N($R^2R^3$)$_2$, —C(O)N($R^2R^3$)$_2$, —C(O)OR$^2$, aminoalkyl, hydroxyalkyl, haloalkyl, aryl, arylalkyl, heteroaryl, and heteroarylalkyl; or two $R^4$ groups on the same carbon are taken together to form an oxo group.

In certain embodiments of Formula (III)-(VB), including any of the foregoing, Ring A of $L^{1a}$ is selected from

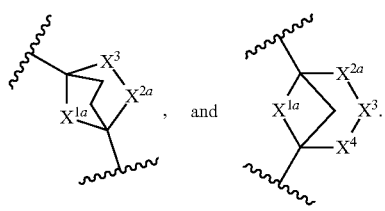

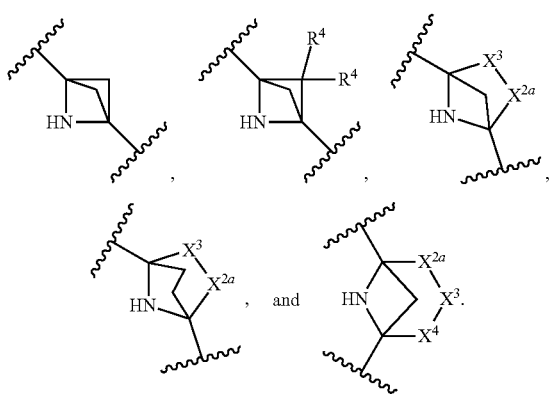

In certain embodiments of Formula (III)-(VB), including any of the foregoing, Ring A of $L^{1a}$ is selected from

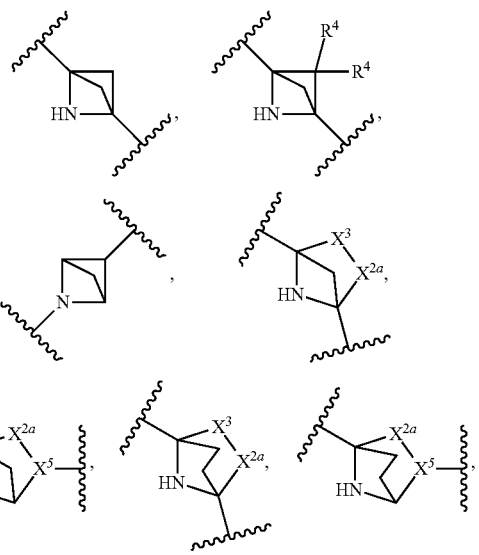

In certain embodiments of Formula (III)-(VB), including any of the foregoing, Ring A of $L^{1a}$ is selected from

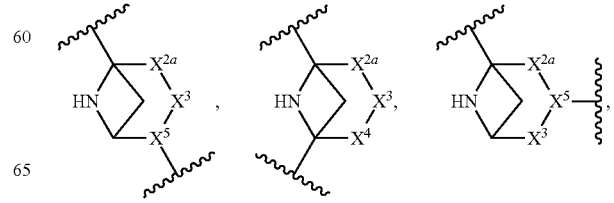

-continued

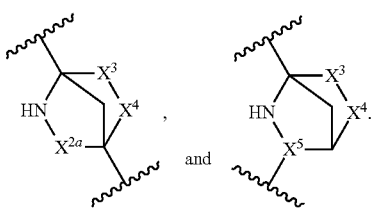

In certain embodiments of Formula (III)-(VB), including any of the foregoing, Ring A of $L^{1a}$ is selected from

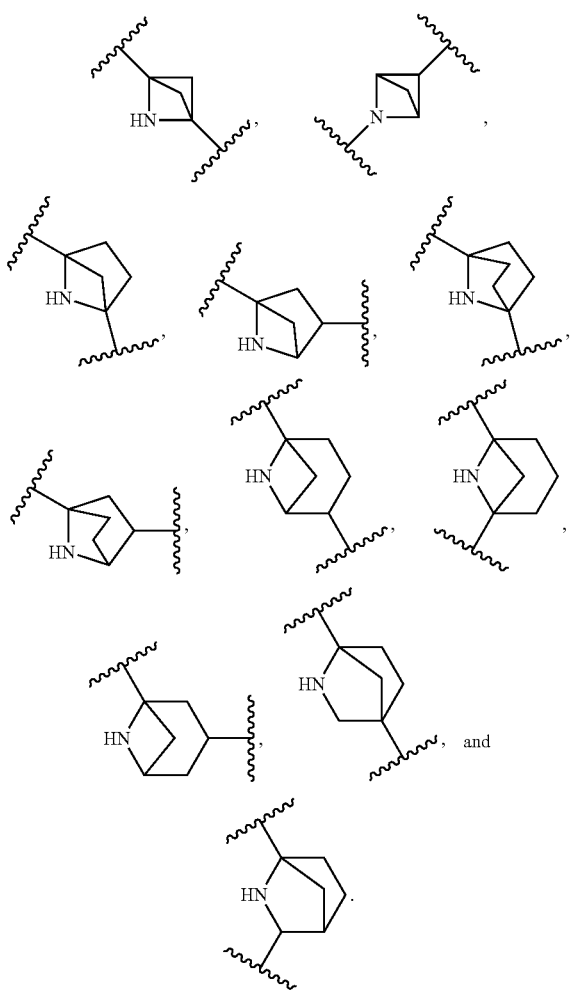

In certain embodiments of Formula (III)-(VB), including any of the foregoing, Ring A of $L^{1a}$ is

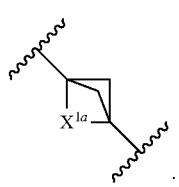

In certain embodiments of Formula (III)-(VB), including any of the foregoing, Ring A of $L^{1a}$ is

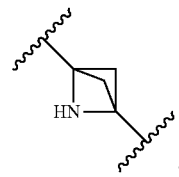

In certain embodiments of Formula (III)-(VB), including any of the foregoing, $X^{1a}$, $X^{2a}$, $X^3$, and/or $X^4$ is —$C(R^4)_2$—. In certain embodiments of Formula (III)-(VB), including any of the foregoing, $X^{1a}$ and $X^{2a}$ are —$C(R^4)_2$—. In certain embodiments of Formula (III)-(VB), including any of the foregoing, $X^{1a}$, $X^{2a}$, and $X^3$ are —$C(R^4)_2$—. In certain embodiments of Formula (III)-(VB), including any of the foregoing, $X^{1a}$, $X^{2a}$, $X^3$, and $X^4$ are —$C(R^4)_2$—. In certain embodiments of Formula (III)-(VB), including any of the foregoing, $X^{1a}$ is —NH—. In certain embodiments of Formula (III)-(VB), including any of the foregoing, $X^{2a}$ is NH—. In certain embodiments of Formula (III)-(VB), including any of the foregoing, $X^3$ is —NH—. In certain embodiments of Formula (III)-(VB), including any of the foregoing, $X^4$ is NH—. In certain embodiments, including any of the foregoing, $X^{1a}$ is —O—. In certain embodiments of Formula (III)-(VB), including any of the foregoing, $X^{2a}$ is —O—. In certain embodiments of Formula (III)-(VB), including any of the foregoing, $X^3$ is —O—. In certain embodiments of Formula (III)-(VB), including any of the foregoing, $X^4$ is —O—.

In certain embodiments of Formula (III)-(VB), including any of the foregoing, $L^{1a}$ is

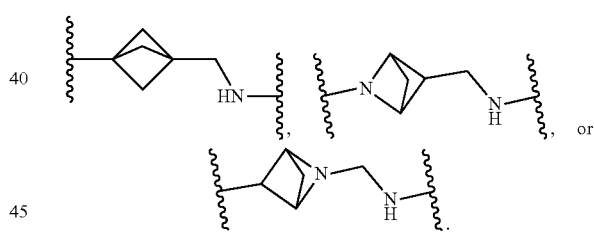

In certain embodiments, $L^{1a}$ is

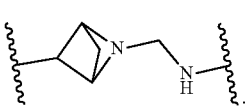 [SMILES: *NCN1C2CC1C2*]

In certain embodiments, including any of the foregoing, a is 0. In certain embodiments, including any of the foregoing, a is 1. In certain embodiments, including any of the foregoing, a is 2. In certain embodiments, including any of the foregoing, a is 3. In certain embodiments, including any of the foregoing, a is 4. In certain embodiments, including any of the foregoing, a is 5. In certain embodiments, including any of the foregoing, a is 6.

In certain embodiments of Formula (III)-(VB), b is 0. In certain embodiments, b is 1.

In certain embodiments of Formula (III)-(VB), b is 0 and a is 0. In certain embodiments of Formula (III)-(VB), b is 0 and a is 1. In certain embodiments of Formula (III)-(VB), b is 0 and a is 2. In certain embodiments of Formula (III)-(VB), b is 0 and a is 3. In certain embodiments of Formula (III)-(VB), b is 0 and a is 4. In certain embodiments of Formula (III)-(VB), b is 0 and a is 5. In certain embodiments of Formula (III)-(VB), b is 0 and a is 6. In certain embodiments of Formula (III)-(VB), b is 1 and a is 1. In certain embodiments of Formula (III)-(VB), b is 1 and a is 2. In certain embodiments of Formula (III)-(VB), b is 1 and a is 3. In certain embodiments of Formula (III)-(VB), b is 1 and a is 4. In certain embodiments of Formula (III)-(VB), b is 1 and a is 5. In certain embodiments of Formula (III)-(VB), b is 1 and a is 6.

In certain embodiments of Formula (III)-(VB), including any of the foregoing, $R^1$ is hydrogen. In certain embodiments of Formula (III)-(VB), including any of the foregoing, $R^1$ is unsubstituted alkyl. In certain embodiments of Formula (III)-(VB), including any of the foregoing, $R^1$ is methyl. In certain embodiments of Formula (III)-(VB), including any of the foregoing, $R^1$ is alkyl optionally substituted with one or more substituent selected from cycloalkyl, halogen, alkoxy, —CN, —$NO_2$, and —OH.

In certain embodiments of Formula (III)-(IVB), $L^5$ is a linker that comprises at least one amino acid selected from sulfoalanine, hydroxyproline (Hyp), beta-alanine, citrulline (Cit), ornithine (Orn), norleucine (Nle), 3-nitrotyrosine, nitroarginine, pyroglutamic acid (Pyr), naphtylalanine (Nal), 2,4-diaminobutyric acid (DAB), methionine sulfoxide, and methionine sulfone. In certain embodiments of Formula (III)-(IVB), $L^5$ is a linker that comprises

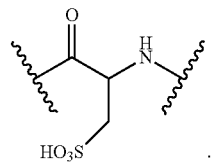

In certain embodiments of Formula (III)-(IVB), $L^5$ is a linker that comprises

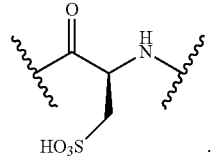 [SMILES: *N[C@@H](CS(=O)(=O)O)C(*)=O]

In certain embodiments of Formula (III)-(IVB), $L^5$ is

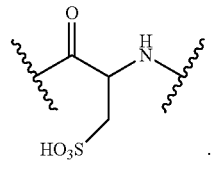

In certain embodiments of Formula (III)-(IVB), $L^5$ is

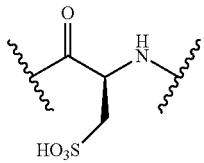

In certain embodiments, including any of the foregoing, $R^a$ is hydrogen and $R^b$ is selected from hydrogen, alkyl, alkenyl, alkynyl, cycloalkyl, halogen, alkoxy, —CN, —$NO_2$, —OH, —$N(R^2R^3)_2$, —$C(O)N(R^2R^3)_2$, —$C(O)OR^2$, aminoalkyl, hydroxyalkyl, haloalkyl, aryl, arylalkyl, heteroaryl, and heteroarylalkyl. In certain embodiments, including any of the foregoing, $R^a$ is hydrogen and $R^b$ is selected from hydrogen, alkyl, alkenyl, alkynyl, cycloalkyl, halogen, alkoxy, —CN, —$NO_2$, —OH, —$NH_2$, —C(O)$NH_2$, —C(O)OH, aminoalkyl, hydroxyalkyl, haloalkyl, aryl, arylalkyl, heteroaryl, and heteroarylalkyl. In certain embodiments, including any of the foregoing, $R^a$ is hydrogen and $R^b$ is selected from hydrogen, alkyl, halogen, alkoxy, —CN, —$NO_2$, —OH, —$NH_2$, —C(O)$NH_2$, and —C(O)OH. In certain embodiments, including any of the foregoing, $R^a$ and $R^b$ are both hydrogen.

In certain embodiments of Formula (III)-(VB), including any of the foregoing, $R^a$ is hydrogen; $R^b$ is selected from hydrogen, alkyl, halogen, alkoxy, —CN, —$NO_2$, —OH, —$NH_2$, —C(O)$NH_2$, and —C(O)OH; $R^1$ is hydrogen; a is 1; and b is 1. In certain embodiments of Formula (III)-(VB), including any of the foregoing, $R^a$ is hydrogen; $R^b$ is selected from hydrogen, alkyl, halogen, alkoxy, —CN, —$NO_2$, —OH, —$NH_2$, —C(O)$NH_2$, and —C(O)OH; $R^1$ is hydrogen; a is 2; and b is 1. In certain embodiments of Formula (III)-(VB), including any of the foregoing, $R^a$ is hydrogen; $R^b$ is selected from hydrogen, alkyl, halogen, alkoxy, —CN, —$NO_2$, —OH, —$NH_2$, —C(O)$NH_2$, and —C(O)OH; $R^1$ is hydrogen; a is 3; and b is 1.

In certain embodiments of Formula (III)-(VB), including any of the foregoing, $R^a$ is hydrogen; $R^b$ is selected from hydrogen, alkyl, halogen, alkoxy, —CN, —$NO_2$, —OH, —$NH_2$, —C(O)$NH_2$, and —C(O)OH; a is 1; and b is 0. In certain embodiments of Formula (III)-(VB), including any of the foregoing, $R^a$ is hydrogen; $R^b$ is selected from hydrogen, alkyl, halogen, alkoxy, —CN, —$NO_2$, —OH, —$NH_2$, —C(O)$NH_2$, and —C(O)OH; a is 2, and b is 0. In certain embodiments of Formula (III)-(VB), including any of the foregoing, $R^a$ is hydrogen; $R^b$ is selected from hydrogen, alkyl, halogen, alkoxy, —CN, —$NO_2$, —OH, —$NH_2$, —C(O)$NH_2$, and —C(O)OH; a is 3, and b is 0.

In certain embodiments of Formula (III)-(VB), including any of the foregoing, $R^a$ is hydrogen; $R^b$ is selected from hydrogen, alkyl, halogen, alkoxy, —CN, —$NO_2$, —OH, —$NH_2$, —C(O)$NH_2$, and —C(O)OH; $R^1$ is methyl; a is 1; and b is 1. In certain embodiments of Formula (III)-(VB), including any of the foregoing, $R^a$ is hydrogen; $R^b$ is selected from hydrogen, alkyl, halogen, alkoxy, —CN, —$NO_2$, —OH, —$NH_2$, —C(O)$NH_2$, and —C(O)OH; $R^1$ is methyl; a is 2; and b is 1. In certain embodiments of Formula (III)-(VB), including any of the foregoing, $R^a$ is hydrogen; $R^b$ is selected from hydrogen, alkyl, halogen, alkoxy, —CN, —$NO_2$, —OH, —$NH_2$, —C(O)$NH_2$, and —C(O)OH; $R^1$ is methyl; a is 3, and b is 1.

In certain embodiments, including any of the foregoing of Formula (III)-(VB), $R^a$ and R b are both hydrogen; $R^1$ is hydrogen; a is 1, and b is 1. In certain embodiments of Formula (III)-(VB), including any of the foregoing, $R^a$ and $R^b$ are both hydrogen; $R^1$ is hydrogen; a is 2, and b is 1. In certain embodiments of Formula (III)-(VB), including any of the foregoing, $R^a$ and $R^b$ are both hydrogen; $R^1$ is hydrogen; a is 3, and b is 1. In certain embodiments of Formula (III)-(VB), including any of the foregoing, $R^a$ and $R^b$ are both hydrogen; $R^1$ is hydrogen; a is 4, and b is 1. In certain embodiments of Formula (III)-(VB), including any of the foregoing, $R^a$ and $R^b$ are both hydrogen; $R^1$ is hydrogen; a is 5, and b is 1. In certain embodiments of Formula (III)-(VB), including any of the foregoing, $R^a$ and $R^b$ are both hydrogen; $R^1$ is hydrogen; a is 6, and b is 1.

In certain embodiments of Formula (III)-(VB), including any of the foregoing, $R^a$ and $R^b$ are both hydrogen; a is 1; and b is 0. In certain embodiments of Formula (III)-(VB), including any of the foregoing, $R^a$ and $R^b$ are both hydrogen; a is 2; and b is 0. In certain embodiments of Formula (III)-(VB), including any of the foregoing, $R^a$ and $R^b$ are both hydrogen; a is 3; and b is 0. In certain embodiments of Formula (III)-(VB), including any of the foregoing, $R^a$ and $R^b$ are both hydrogen; a is 4; and b is 0. In certain embodiments of Formula (III)-(VB), including any of the foregoing, $R^a$ and $R^b$ are both hydrogen; a is 5; and b is 0. In certain embodiments of Formula (III)-(VB), including any of the foregoing, $R^a$ and $R^b$ are both hydrogen; a is 6; and b is 0.

In certain embodiments of Formula (III)-(VB), including any of the foregoing, $R^a$ and $R^b$ are both hydrogen; $R^1$ is methyl; a is 1; and b is 0. In certain embodiments of Formula (III)-(VB), including any of the foregoing, $R^a$ and $R^b$ are both hydrogen; $R^1$ is methyl; a is 2; and b is 0. In certain embodiments of Formula (III)-(VB), including any of the foregoing, $R^a$ and $R^b$ are both hydrogen; $R^1$ is methyl; a is 3; and b is 0. In certain embodiments of Formula (III)-(VB), including any of the foregoing, $R^a$ and $R^b$ are both hydrogen; $R^1$ is methyl; a is 4; and b is 0. In certain embodiments of Formula (III)-(VB), including any of the foregoing, $R^a$ and $R^b$ are both hydrogen; $R^1$ is methyl; a is 5; and b is 0. In certain embodiments of Formula (III)-(VB), including any of the foregoing, $R^a$ and $R^b$ are both hydrogen; $R^1$ is methyl; a is 6; and b is 0.

In certain embodiments of Formula (III)-(IVB), including any of the foregoing, $R^a$ is hydrogen; $R^b$ is selected from hydrogen, alkyl, halogen, alkoxy, —CN, —NO$_2$, —OH, —NH$_2$, —C(O)NH$_2$, and —C(O)OH; a is 1; and c is 1. In certain embodiments of Formula (III)-(IVB), including any of the foregoing, $R^a$ is hydrogen; $R^b$ is selected from hydrogen, alkyl, halogen, alkoxy, —CN, —NO$_2$, —OH, —NH$_2$, —C(O)NH$_2$, and —C(O)OH; a is 2; and c is 1. In certain embodiments of Formula (III)-(IVB), including any of the foregoing, $R^a$ is hydrogen; $R^b$ is selected from hydrogen, alkyl, halogen, alkoxy, —CN, —NO$_2$, —OH, —NH$_2$, —C(O)NH$_2$, and —C(O)OH; a is 3; and c is 1.

In certain embodiments of Formula (III)-(IVB), including any of the foregoing, $Y^a$ is *—C(O)—(CR$^a$R$^b$)$_c$—NH— wherein * represents where $Y^a$ is bound to RL. In certain embodiments of Formula (III)-(IVB), including any of the foregoing, $Y^a$ is *—C(O)—(CH$_2$)$_c$—NH—. In certain embodiments of Formula (III)-(IVB), including any of the foregoing, $Y^a$ is *—C(O)—(CH$_2$)—NH—. In certain embodiments, including any of the foregoing, $Y^a$ is *—C(O)—(CH$_2$)$_2$—NH—. In certain embodiments of Formula (III)-(IVB), including any of the foregoing, $Y^a$ is *—C(O)—(CH$_2$)$_3$—NH—. In certain embodiments of Formula (III)-(IVB), including any of the foregoing, $Y^a$ is *—C(O)—(CH$_2$)$_4$—NH—. In certain embodiments of Formula (III)-(IVB), including any of the foregoing, $Y^a$ is *—C(O)—(CH$_2$)$_5$—NH—. In certain embodiments of Formula (III)-(IVB), including any of the foregoing, $Y^a$ is *—C(O)—(CH$_2$)$_6$—NH—.

In certain embodiments of Formula (III)-(IVB), including any of the foregoing, $Y^a$ is *—C(O)—(CR$^a$R$^b$)—NH—. In certain embodiments of Formula (III)-(IVB), including any of the foregoing, $Y^a$ is *—C(O)—(CR$^a$R$^b$)$_2$—NH—. In certain embodiments of Formula (III)-(IVB), including any of the foregoing, $Y^a$ is *—C(O)—(CR$^a$R$^b$)$_3$—NH—. In certain embodiments of Formula (III)-(IVB), including any of the foregoing, $Y^a$ is *—C(O)—(CR$^a$R$^b$)$_4$—NH—. In certain embodiments of Formula (III)-(IVB), including any of the foregoing, $Y^a$ is *—C(O)—(CR$^a$R$^b$)$_5$—NH—. In certain embodiments of Formula (III)-(IVB), including any of the foregoing, $Y^a$ is *—C(O)—(CR$^a$R$^b$)$_6$—NH—.

In certain embodiments of Formula (III)-(IVB), including any of the foregoing, $Y^a$ is *—C(O)—(CR$^a$R$^b$)$_c$—NH— wherein $R^a$ is hydrogen and $R^b$ is selected from hydrogen, alkyl, alkenyl, alkynyl, cycloalkyl, halogen, alkoxy, —CN, —NO$_2$, —OH, —N(R$^2$R$^3$)$_2$, —C(O)N(R$^2$R$^3$)$_2$, —C(O)OR$^2$, aminoalkyl, hydroxyalkyl, haloalkyl, aryl, arylalkyl, heteroaryl, and heteroarylalkyl. In certain embodiments of Formula (III)-(IVB), including any of the foregoing, $Y^a$ is *—C(O)—(CR$^a$R$^b$)$_2$—NH—, *—C(O)—(CR$^a$R$^b$)$_3$—NH—, or *—C(O)—(CR$^a$R$^b$)$_4$—NH— wherein $R^a$ is hydrogen and $R^b$ is selected from hydrogen, alkyl, alkenyl, alkynyl, cycloalkyl, halogen, alkoxy, —CN, —NO$_2$, —OH, —N(R$^2$R$^3$)$_2$, —C(O)N(R$^2$R$^3$)$_2$, —C(O)OR$^2$, aminoalkyl, hydroxyalkyl, haloalkyl, aryl, arylalkyl, heteroaryl, and heteroarylalkyl.

In certain embodiments of Formula (III)-(IVB), including any of the foregoing, $Y^a$ is *—C(O)—(CR$^a$R$^b$)$_c$— wherein * represents where $Y^a$ is bound to RL. In certain embodiments of Formula (III)-(IVB), including any of the foregoing, $Y^a$ is *—C(O)—(CH$_2$)$_c$—. In certain embodiments of Formula (III)-(IVB), including any of the foregoing, $Y^a$ is *—C(O)—(CH$_2$)—. In certain embodiments of Formula (III)-(IVB), including any of the foregoing, $Y^a$ is *—C(O)—(CH$_2$)$_2$—. In certain embodiments of Formula (III)-(IVB), including any of the foregoing, $Y^a$ is *—C(O)—(CH$_2$)$_3$—. In certain embodiments of Formula (III)-(IVB), including any of the foregoing, $Y^a$ is *—C(O)—(CH$_2$)$_4$—. In certain embodiments of Formula (III)-(IVB), including any of the foregoing of Formula (III)-(IVB), $Y^a$ is *—C(O)—(CH$_2$)$_5$—. In certain embodiments, including any of the foregoing, $Y^a$ is *—C(O)—(CH$_2$)$_6$—.

In certain embodiments, including any of the foregoing of Formula (III)-(IVB), $Y^a$ is *—C(O)—(CR$^a$R$^b$)—. In certain embodiments of Formula (III)-(IVB), including any of the foregoing, $Y^a$ is *—C(O)—(CR$^a$R$^b$)$_2$—. In certain embodiments of Formula (III)-(IVB), including any of the foregoing, $Y^a$ is *—C(O)—(CR$^a$R$^b$)$_3$—. In certain embodiments of Formula (III)-(IVB), including any of the foregoing, $Y^a$ is *—C(O)—(CR$^a$R$^b$)$_4$—. In certain embodiments of Formula (III)-(IVB), including any of the foregoing, $Y^a$ is *—C(O)—(CR$^a$R$^b$)$_5$—. In certain embodiments of Formula (III)-(IVB), including any of the foregoing, $Y^a$ is *—C(O)—(CR$^a$R$^b$)$_6$—.

In certain embodiments of Formula (III)-(IVB), including any of the foregoing, $Y^a$ is *—C(O)—(CR$^a$R$^b$)$_c$— wherein $R^a$ is hydrogen and $R^b$ is selected from hydrogen, alkyl, alkenyl, alkynyl, cycloalkyl, halogen, alkoxy, —CN, —NO$_2$, —OH, —N(R$^2$R$^3$)$_2$, —C(O)N(R$^2$R$^3$)$_2$, —C(O)OR$^2$, aminoalkyl, hydroxyalkyl, haloalkyl, aryl, arylalkyl, heteroaryl, and heteroarylalkyl. In certain embodiments of Formula (III)-(IVB), including any of the foregoing, $Y^a$ is *—C(O)—(CR$^a$R$^b$)$_2$—, *—C(O)—(CR$^a$R$^b$)$_3$—, or *—C (O)—(CR$^a$R$^b$)$_4$— wherein R$^a$ is hydrogen and R$^b$ is selected from hydrogen, alkyl, alkenyl, alkynyl, cycloalkyl, halogen, alkoxy, —CN, —NO$_2$, —OH, —N(R$^2$R$^3$)$_2$, —C(O)N (R$^2$R$^3$)$_2$, —C(O)OR$^2$, aminoalkyl, hydroxyalkyl, haloalkyl, aryl, arylalkyl, heteroaryl, and heteroarylalkyl.

In certain embodiments of Formula (III)-(IVB), including any of the foregoing, Y$^a$ is *—C(O)—(CH$_2$)$_2$—NH— or *—C(O)—(CH$_2$)$_4$—.

In certain embodiments of Formula (III)-(IVB), including any of the foregoing, L$^2$ is absent. In certain embodiments of Formula (III)-(IVB), including any of the foregoing, L$^2$ is a linker comprising a hydrophilic polymer residue.

In certain embodiments of Formula (III)-(IVB), including any of the foregoing, L$^2$ is —(CR$^a$R$^b$)$_a$-POLY$^1$-. In certain embodiments of Formula (III)-(IVB), including any of the foregoing, L$^2$ is —CH$_2$-POLY$^1$-. In certain embodiments of Formula (III)-(IVB), including any of the foregoing, L$^2$ is —(CH$_2$)$_2$-POLY$^1$-. In certain embodiments of Formula (III)-(IVB), including any of the foregoing, L$^2$ is —(CH$_2$)$_3$-POLY$^1$-. In certain embodiments of Formula (III)-(IVB), including any of the foregoing, L$^2$ is —(CH$_2$)$_4$-POLY$^1$-. In certain embodiments of Formula (III)-(IVB), including any of the foregoing, L$^2$ is —(CH$_2$)$_5$-POLY$^1$-. In certain embodiments of Formula (III)-(IVB), including any of the foregoing, L$^2$ is —(CH$_2$)$_6$-POLY$^1$-. In certain embodiments of Formula (III)-(IVB), including any of the foregoing, L$^2$ is —CR$^a$R$^b$-POLY$^1$-. In certain embodiments of Formula (III)-(IVB), including any of the foregoing, L$^2$ is —(CR$^a$R$^b$)$_2$-POLY$^1$-. In certain embodiments, including any of the foregoing, L$^2$ is —(CR$^a$R$^b$)$_3$-POLY$^1$-. In certain embodiments of Formula (III)-(IVB), including any of the foregoing, L$^2$ is —(CR$^a$R$^b$)$_4$-POLY$^1$-.

In certain embodiments of Formula (III)-(IVB), including any of the foregoing, L$^2$ is -POLY$^1$-.

In certain embodiments of Formula (III)-(IVB), including any of the foregoing, L$^2$ is —(CR$^a$R$^b$)$_a$-POLY$^1$-(CR$^a$R$^b$)$_a$—. In certain embodiments of Formula (III)-(IVB), including any of the foregoing, L$^2$ is —(CR$^a$R$^b$)$_a$-POLY$^1$-(CR$^a$R$^b$)$_a$— wherein a is independently selected from 0, 1, 2, 3, 4, or 6. In certain embodiments of Formula (III)-(IVB), including any of the foregoing, L$^2$ is —(CH$_2$)$_a$-POLY$^1$-(CH$_2$)$_a$— wherein a is independently selected from 0, 1, 2, 3, 4, 5, or 6. In certain embodiments of Formula (III)-(IVB), including any of the foregoing, L$^2$ is —(CH$_2$)$_a$-POLY$^1$-(CR$^a$R$^b$)$_a$— wherein a is selected from 1, 2, 3, 4, 5, or 6. In certain embodiments of Formula (III)-(IVB), including any of the foregoing, L$^2$ is —(CR$^a$R$^b$)$_a$-POLY$^1$-(CH$_2$)$_a$— wherein a is independently selected from 0, 1, 2, 3, 4, 5, or 6.

In certain embodiments of Formula (III)-(IVB), including any of the foregoing, POLY$^1$ is a divalent residue of a nonpeptidic, hydrophilic polymer. In certain embodiments of Formula (III)-(IVB), POLY$^1$ is a divalent residue of polyethylene glycol (PEG), poly(propylene glycol) (PPG), copolymers of ethylene glycol and propylene glycol, poly (oxyethylated polyol), poly(olefinic alcohol), poly(vinylpyrrolidone), poly(hydroxyalkylmethacrylamide), poly(hydroxyalkylmethacrylate), poly(saccharides), poly(α-hydroxy acid), poly(vinyl alcohol), polyphosphazene, polyoxazolines (POZ), poly(N-acryloylmorpholine), polysarcosine, or a combination thereof. In certain embodiments of Formula (III)-(IVB), including any of the foregoing, POLY$^1$ is a divalent residue of polyethylene glycol (PEG), poly(propylene glycol) (PPG), or a copolymer of ethylene glycol and propylene glycol.

In certain embodiments of Formula (III)-(IVB), including any of the foregoing, POLY$^1$ is a divalent residue of polyethylene glycol (PEG). In certain embodiments of Formula (III)-(IVB), including any of the foregoing, POLY$^1$ is a divalent residue of poly(propylene glycol) (PPG). In certain embodiments of Formula (III)-(IVB), including any of the foregoing, POLY$^1$ is a diavalent residue of copolymers of ethylene glycol and propylene glycol. In certain embodiments of Formula (III)-(IVB), including any of the foregoing, POLY$^1$ is a diavalent residue of poly(oxyethylated polyol). In certain embodiments of Formula (III)-(IVB), including any of the foregoing, POLY$^1$ is a diavalent residue of poly(olefinic alcohol). In certain embodiments of Formula (III)-(IVB), including any of the foregoing, POLY$^1$ is a diavalent residue of poly(vinylpyrrolidone). In certain embodiments of Formula (III)-(IVB), including any of the foregoing, POLY$^1$ is a diavalent residue of poly(hydroxyalkylmethacrylamide). In certain embodiments of Formula (III)-(IVB), including any of the foregoing, POLY$^1$ is a diavalent residue of poly(hydroxyalkylmethacrylate). In certain embodiments of Formula (III)-(IVB), including any of the foregoing, POLY$^1$ is a diavalent residue of poly(saccharides). In certain embodiments of Formula (III)-(IVB), including any of the foregoing, POLY$^1$ is a diavalent residue of poly(α-hydroxy acid). In certain embodiments of Formula (III)-(IVB), including any of the foregoing, POLY$^1$ is a diavalent residue of poly(vinyl alcohol). In certain embodiments of Formula (III)-(IVB), including any of the foregoing, POLY$^1$ is a diavalent residue of polyphosphazene. In certain embodiments of Formula (III)-(IVB), including any of the foregoing, POLY$^1$ is a diavalent residue of polyoxazolines (POZ). In certain embodiments of Formula (III)-(IVB), including any of the foregoing, POLY$^1$ is a diavalent residue of poly(N-acryloylmorpholine). In certain embodiments of Formula (III)-(IVB), including any of the foregoing, POLY$^1$ is a diavalent residue of polysarcosine.

In certain embodiments of Formula (III)-(IVB), including any of the foregoing, POLY$^1$ is

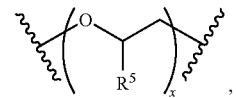

wherein R$^5$ is hydrogen or methyl, x is an integer from 1 to 100, inclusive, and ⁁ represents attachment to the remainder of the compound or conjugate. In certain embodiments of Formula (III)-(IVB), including any of the foregoing, x is an integer between 1 to 25. In certain embodiments of Formula (III)-(IVB), including any of the foregoing, x is an integer between 5 to 15. In some embodiments of Formula (III)-(IVB), including any of the foregoing, x is 1. In some embodiments of Formula (III)-(IVB), including any of the foregoing, x is 2. In some embodiments of Formula (III)-(IVB), including any of the foregoing, x is 3. In some embodiments of Formula (III)-(IVB), including any of the foregoing, x is 4. In some embodiments of Formula (III)-(IVB), including any of the foregoing, x is 5. In some embodiments of Formula (III)-(IVB), including any of the foregoing, x is 6. In some embodiments of Formula (III)-(IVB), including any of the foregoing, x is 7. In some embodiments of Formula (III)-(IVB), including any of the foregoing, x is 8. In some embodiments of Formula (III)-(IVB), including any of the foregoing, x is 9. In some embodiments of Formula (III)-(IVB), including any of the foregoing, x is 10. In some embodiments of Formula (III)-

(IVB), including any of the foregoing, x is 11. In some embodiments of Formula (III)-(IVB), including any of the foregoing, x is 12. In some embodiments of Formula (III)-(IVB), including any of the foregoing, x is 13. In some embodiments of Formula (III)-(IVB), including any of the foregoing, x is 14. In some embodiments of Formula (III)-(IVB), including any of the foregoing, x is 15. In some embodiments of Formula (III)-(IVB), including any of the foregoing, x is 16. In some embodiments of Formula (III)-(IVB), including any of the foregoing, x is 17. In some embodiments, including any of the foregoing, x is 18. In some embodiments of Formula (III)-(IVB), including any of the foregoing, x is 19. In some embodiments of Formula (III)-(IVB), including any of the foregoing, x is 20. In certain embodiments of Formula (III)-(IVB), including any of the foregoing, x is an integer between 25 and 50. In certain embodiments of Formula (III)-(IVB), including any of the foregoing, x is an integer between 35 and 45. In certain embodiments of Formula (III)-(IVB), including any of the foregoing, x is an integer between 50 and 75. In certain embodiments of Formula (III)-(IVB), including any of the foregoing, x is an integer between 55 and 65. In certain embodiments of Formula (III)-(IVB), including any of the foregoing, x is an integer between 75 and 100. In certain embodiments of Formula (III)-(IVB), including any of the foregoing, x is an integer between 85 and 95. In certain embodiments of Formula (III)-(IVB), including any of the foregoing, x is an integer in the range of 1 and 25, 20 and 45, 40 and 65, 60 and 85, 70 and 95, or 75 and 100.

In some embodiments of Formula (III)-(IVB), including any of the foregoing, $R^5$ is hydrogen. In some embodiments, including any of the foregoing, $R^5$ is methyl.

In certain embodiments of Formula (III)-(IVB), including any of the foregoing, $L^2$ is —$(CR^aR^b)_a$-POLY$^1$- wherein POLY$^1$ is

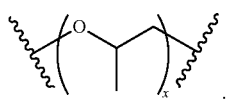

In certain embodiments of Formula (III)-(IVB), including any of the foregoing, $L^2$ is —$(CR^aR^b)_a$-POLY$^1$- wherein POLY$^1$ is

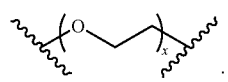

In certain embodiments of Formula (III)-(IVB), including any of the foregoing, $L^2$ is —$(CH_2)_a$-POLY$^1$- wherein POLY$^1$ is

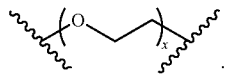

In certain embodiments of Formula (III)-(IVB), including any of the foregoing, $L^2$ is —$(CH_2)_2$-POLY$^1$- wherein POLY$^1$ is

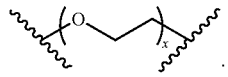

In certain embodiments of Formula (III)-(IVB), including any of the foregoing, $L^2$ is —$(CR^aR^b)_a$-POLY$^1$- wherein POLY$^1$ is

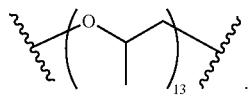

In certain embodiments of Formula (III)-(IVB), including any of the foregoing, $L^2$ is —$(CR^aR^b)_a$-POLY$^1$- wherein POLY$^1$ is

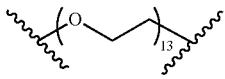

In certain embodiments of Formula (III)-(IVB), including any of the foregoing, $L^2$ is —$(CH_2)_2$-POLY$^1$- is

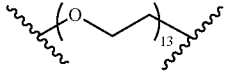

In certain embodiments of Formula (III)-(IVB), including any of the foregoing, $L^2$ is —$(CH_2)_2$-POLY$^1$- wherein POLY$^1$ is

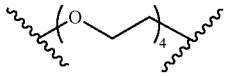

In certain embodiments of Formula (III)-(IVB), including any of the foregoing, $L^2$ is —$(CH_2)_2$-POLY$^1$- wherein POLY$^1$ is

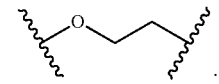

In certain embodiments of Formula (III)-(IVB), including any of the foregoing, $L^2$ is

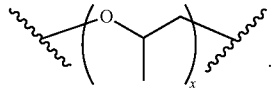

In certain embodiments, including any of the foregoing, $L^2$ is

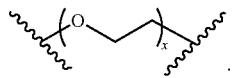

In certain embodiments of Formula (III)-(IVB), including any of the foregoing, $L^2$ is

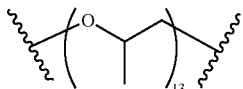

In certain embodiments of Formula (III)-(IVB), including any of the foregoing, $L^2$ is

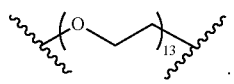

In certain embodiments of Formula (III)-(IVB), including any of the foregoing, $L^2$ is —$(CR^aR^b)_a$-POLY$^1$-$(CR^aR^b)_a$— wherein POLY$^1$ is

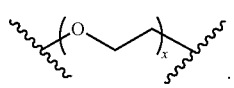

In certain embodiments of Formula (III)-(IVB), including any of the foregoing, $L^2$ is —$(CR^aR^b)_a$-POLY$^1$-$(CR^aR^b)_a$— wherein POLY$^1$ is

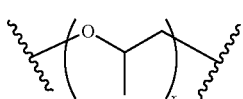

In certain embodiments of Formula (III)-(IVB), including any of the foregoing, $L^2$ is —$(CR^aR^b)_a$-POLY$^1$-$(CR^aR^b)_a$— wherein POLY$^1$ is

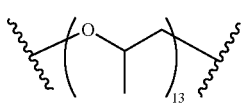

In certain embodiments of Formula (III)-(IVB), including any of the foregoing, $L^2$ is —$(CR^aR^b)_a$-POLY$^1$-$(CR^aR^b)_a$— wherein POLY$^1$ is

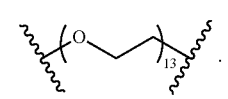

In certain embodiments of Formula (III)-(IVB), including any of the foregoing, $L^2$ is selected from

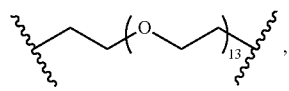

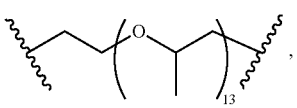

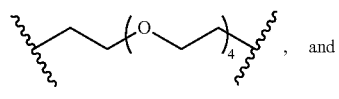

, and

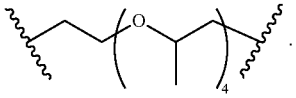

In certain embodiments of Formula (III)-(IVB), including any of the foregoing, $L^2$ is

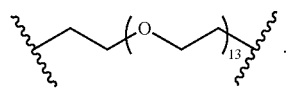

In certain embodiments of Formula (III)-(IVB), including any of the foregoing, $L^2$ is

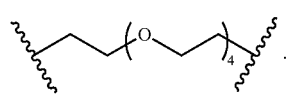

In certain embodiments of Formula (III)-(IVB), including any of the foregoing, $L^2$ is

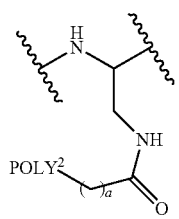

In certain embodiments of Formula (III)-(IVB), including any of the foregoing, $L^2$ is

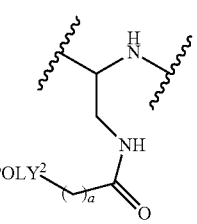

In certain embodiments of Formula (III)-(IVB), including any of the foregoing, $L^2$ is

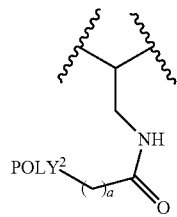

In certain embodiments of Formula (III)-(IVB), including any of the foregoing, $L^2$ is

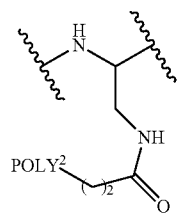

In certain embodiments of Formula (III)-(IVB), including any of the foregoing, $L^2$ is

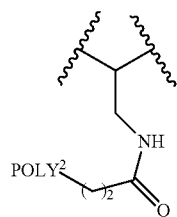

In certain embodiments of Formula (III)-(IVB), including any of the foregoing, POLY$^2$ is a residue of a nonpeptidic, hydrophilic polymer. In certain embodiments of Formula (III)-(IVB), POLY$^2$ is a residue of polyethylene glycol (PEG), methoxypolyethylene glycol (mPEG), poly(propylene glycol) (PPG), copolymers of ethylene glycol and propylene glycol, poly(oxyethylated polyol), poly(olefinic alcohol), poly(vinylpyrrolidone), poly(hydroxyalkylmethacrylamide), poly(hydroxyalkylmethacrylate), poly(saccharides), poly($\alpha$-hydroxy acid), poly(vinyl alcohol), polyphosphazene, polyoxazolines (POZ), poly(N-acryloylmorpholine), polysarcosine, or a combination thereof. In certain embodiments of Formula (III)-(IVB), including any of the foregoing, POLY$^2$ is a residue of polyethylene glycol (PEG), methoxypolyethylene glycol (mPEG), poly(propylene glycol) (PPG), or a copolymer of ethylene glycol and propylene glycol. In certain embodiments of Formula (III)-(IVB), including any of the foregoing, POLY$^2$ is a residue of methoxypolyethylene glycol (mPEG).

In certain embodiments of Formula (III)-(IVB), including any of the foregoing, POLY$^2$ is a residue of polyethylene glycol (PEG). In certain embodiments of Formula (III)-(IVB), including any of the foregoing, POLY$^2$ is a residue of poly(propylene glycol) (PPG). In certain embodiments, including any of the foregoing, POLY$^2$ is a residue of copolymers of ethylene glycol and propylene glycol. In certain embodiments of Formula (III)-(IVB), including any of the foregoing, POLY$^2$ is a residue of poly(oxyethylated polyol). In certain embodiments of Formula (III)-(IVB), including any of the foregoing, POLY$^2$ is a residue of poly(olefinic alcohol). In certain embodiments of Formula (III)-(IVB), including any of the foregoing, POLY$^2$ is a residue of poly(vinylpyrrolidone). In certain embodiments of Formula (III)-(IVB), including any of the foregoing, POLY$^2$ is a residue of poly(hydroxyalkylmethacrylamide). In certain embodiments of Formula (III)-(IVB), including any of the foregoing, POLY$^2$ is a residue of poly(hydroxyalkylmethacrylate). In certain embodiments of Formula (III)-(IVB), including any of the foregoing, POLY$^2$ is a residue of poly(saccharides). In certain embodiments of Formula (III)-(IVB), including any of the foregoing, POLY$^2$ is a residue of poly($\alpha$-hydroxy acid). In certain embodiments of Formula (III)-(IVB), including any of the foregoing, POLY$^2$ is a residue of poly(vinyl alcohol). In certain embodiments of Formula (III)-(IVB), including any of the foregoing, POLY$^2$ is a residue of polyphosphazene. In certain embodiments of Formula (III)-(IVB), including any of the foregoing, POLY$^2$ is a residue of polyoxazolines (POZ). In certain embodiments of Formula (III)-(IVB), including any of the foregoing, POLY$^2$ is a residue of poly(N-acryloylmorpholine). In certain embodiments of Formula (III)-(IVB), including any of the foregoing, POLY$^2$ is a residue of polysarcosine.

In certain embodiments of Formula (III)-(IVB), including any of the foregoing, POLY$^2$ is

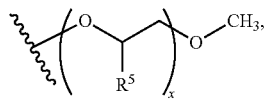

wherein $R^5$ is hydrogen or methyl, x is an integer from 1 to 100, inclusive, and ⁓ represents attachment to the remainder of the compound or conjugate. In certain embodiments of Formula (III)-(IVB), including any of the foregoing, x is an integer between 1 to 25. In certain embodiments of Formula (III)-(IVB), including any of the foregoing, x is an integer between 5 to 15. In some embodiments of Formula (III)-(IVB), including any of the foregoing, x is 1. In some embodiments of Formula (III)-(IVB), including any of the foregoing, x is 2. In some embodiments of Formula (III)-(IVB), including any of the foregoing, x is 3. In some embodiments of Formula (III)-(IVB), including any of the foregoing, x is 4. In some embodiments of Formula (III)-(IVB), including any of the foregoing, x is 5. In some embodiments of Formula (III)-(IVB), including any of the foregoing, x is 6. In some embodiments, including any of the foregoing, x is 7. In some embodiments of Formula (III)-(IVB), including any of the foregoing, x is 8. In some embodiments of Formula (III)-(IVB), including any of the foregoing, x is 9. In some embodiments of Formula (III)-(IVB), including any of the foregoing, x is 10. In some embodiments of Formula (III)-(IVB), including any of the foregoing, x is 11. In some embodiments of Formula (III)-(IVB), including any of the foregoing, x is 12. In some embodiments of Formula (III)-(IVB), including any of the foregoing, x is 13. In some embodiments of Formula (III)-(IVB), including any of the foregoing, x is 14. In some embodiments of Formula (III)-(IVB), including any of the foregoing, x is 15. In some embodiments of Formula (III)-

(IVB), including any of the foregoing, x is 16. In some embodiments of Formula (III)-(IVB), including any of the foregoing of Formula (III)-(IVB), x is 17. In some embodiments, including any of the foregoing of Formula (III)-(IVB), x is 18. In some embodiments of Formula (III)-(IVB), including any of the foregoing, x is 19. In some embodiments of Formula (III)-(IVB), including any of the foregoing, x is 20. In certain embodiments of Formula (III)-(IVB), including any of the foregoing, x is an integer between 25 and 50. In certain embodiments of Formula (III)-(IVB), including any of the foregoing, x is an integer between 35 and 45. In certain embodiments of Formula (III)-(IVB), including any of the foregoing, x is an integer between 50 and 75. In certain embodiments of Formula (III)-(IVB), including any of the foregoing, x is an integer between 55 and 65. In certain embodiments of Formula (III)-(IVB), including any of the foregoing, x is an integer between 75 and 100. In certain embodiments of Formula (III)-(IVB), including any of the foregoing, x is an integer between 85 and 95. In certain embodiments of Formula (III)-(IVB), including any of the foregoing, x is an integer in the range of 1 and 25, 20 and 45, 40 and 65, 60 and 85, 70 and 95, or 75 and 100.

In some embodiments of Formula (III)-(IVB), including any of the foregoing, $R^5$ is hydrogen. In some embodiments of Formula (III)-(IVB), including any of the foregoing, $R^5$ is methyl.

In certain embodiments of Formula (III)-(IVB), including any of the foregoing, $L^2$ is selected from the group consisting of

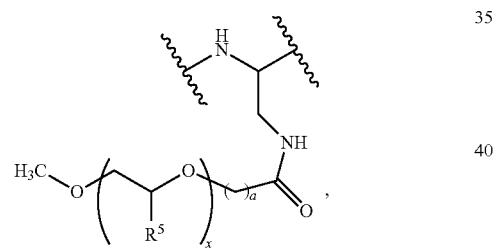

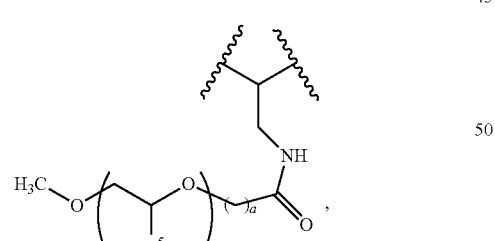

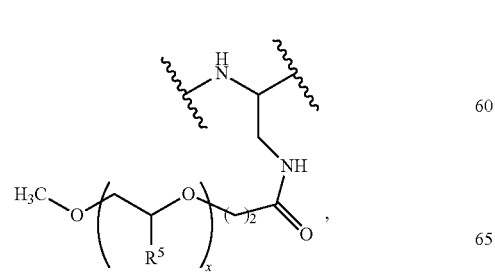

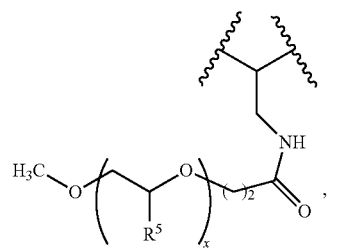

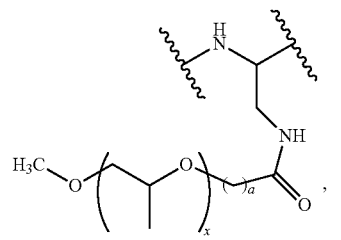

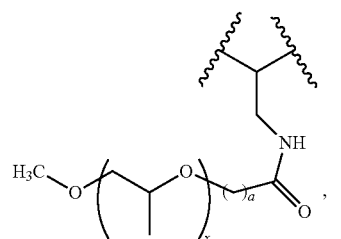

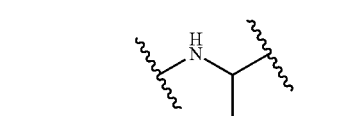, and

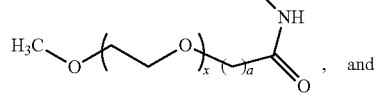.

In certain embodiments of Formula (III)-(IVB), including any of the foregoing, $L^2$ is selected from the group consisting of

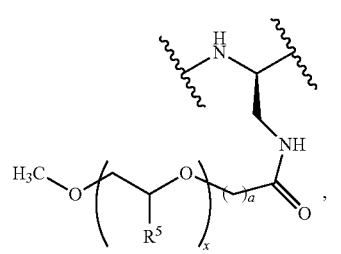

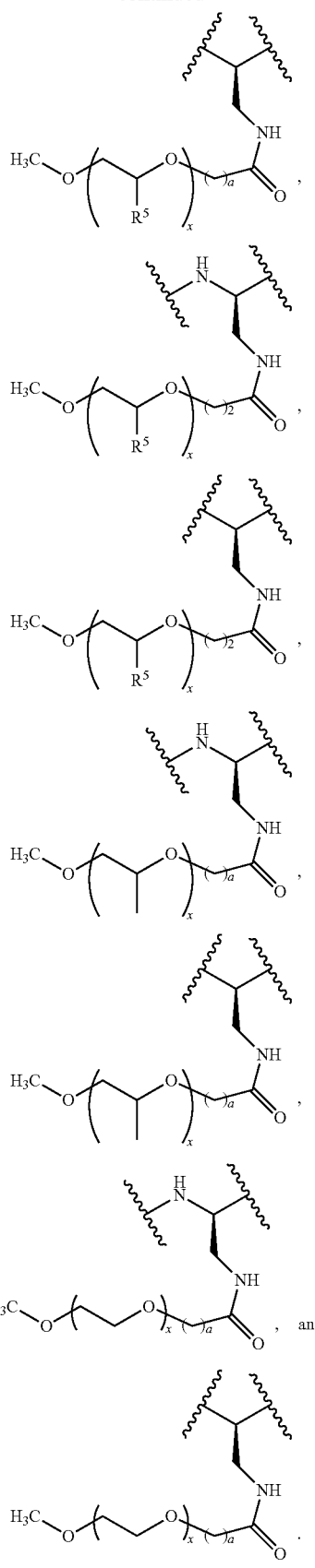

In certain embodiments of Formula (III)-(IVB), including any of the foregoing, $L^2$ is

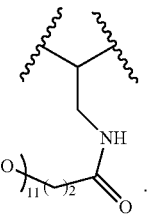

In certain embodiments of Formula (III)-(IVB), including any of the foregoing, $L^2$ is

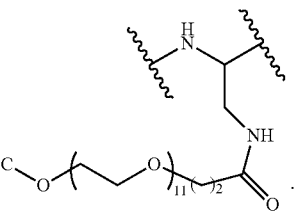

In certain embodiments of Formula (III)-(IVB), including any of the foregoing, $L^2$ is

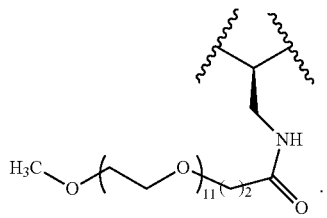

In certain embodiments of Formula (III)-(IVB), including any of the foregoing, $L^2$ is

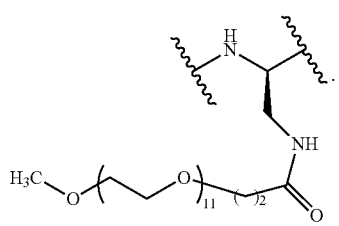

In certain embodiments of Formula (III)-(IVB), including any of the foregoing, $L^3$ is —C(O)-AA-.

In certain embodiments of Formula (III)-(IVB), including any of the foregoing, $L^3$ is —C(O)-AA-Z—$(CR^aR^b)_a$—Z—$(CR^aR^b)_a$—C(O)—. In certain embodiments of Formula (III)-(IVB), including any of the foregoing, $L^3$ is —C(O)-AA-NR$^2$—$(CR^aR^b)_a$—NR$^2$—$(CR^aR^b)_a$—C(O)—. In certain embodiments of Formula (III)-(IVB), including any of the foregoing, $L^3$ is —C(O)-AA-NH—$(CR^aR^b)_a$—NH—$(CR^aR^b)_a$—C(O)—. In certain embodiments of Formula (III)-(IVB), including any of the foregoing, $L^3$ is —C(O)-AA-NH—$(CH_2)_a$—NH—$(CH_2)_a$—C(O)—. In certain embodiments of Formula (III)-(IVB), including any of the foregoing, $L^3$ is —C(O)-AA-NH—$(CH_2)_a$—NH—$(CH_2)_a$—C(O)— wherein a is selected from 1, 2, and 3. In certain embodiments, including any of the foregoing, $L^3$ is —C(O)-AA-NH—$CH_2$—NH—$CH_2$—C(O)—

In certain embodiments of Formula (III)-(IVB), including any of the foregoing, $L^3$ is —C(O)-AA-Z—$(CR^aR^b)_a$. In certain embodiments, including any of the foregoing, $L^3$ is —C(O)-AA-NR$^2$—$(CH_2)_a$. In certain embodiments of Formula (III)-(IVB), including any of the foregoing, $L^3$ is —C(O)-AA-NH—$(CH_2)_2$.

In certain embodiments of Formula (III)-(IVB), including any of the foregoing, $L^3$ is -AA-. In certain embodiments, including any of the foregoing, $L^3$ is

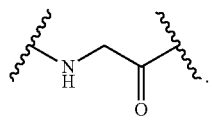 [SMILES: *NCC(*)=O]

In certain embodiments of Formula (III)-(IVB), including any of the foregoing, -AA- is an amino acid residue. In certain embodiments of Formula (III)-(IVB), including any of the foregoing, -AA- is a peptide residue. In certain embodiments of Formula (III)-(IVB), including any of the foregoing, -AA- is a dipeptide residue, a tripeptide residue, a tetrapeptide residue, or a pentapeptide residue. In certain embodiments of Formula (III)-(IVB), including any of the foregoing, -AA- comprises at least one amino acid residue selected from alanine, glycine, valine, and asparagine. In certain embodiments of Formula (III)-(IVB), including any of the foregoing, -AA- comprises at least one amino acid residue selected from alanine and glycine. In certain embodiments of Formula (III)-(IVB), including any of the foregoing, -AA- is selected from the group consisting of

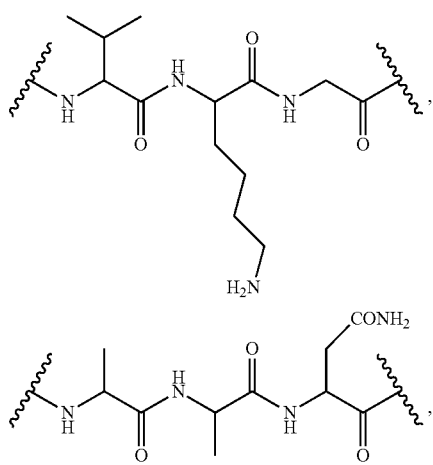

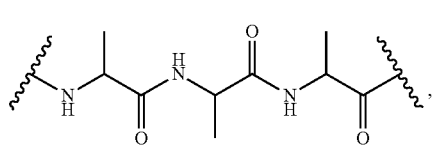

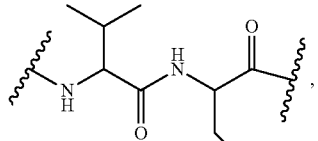

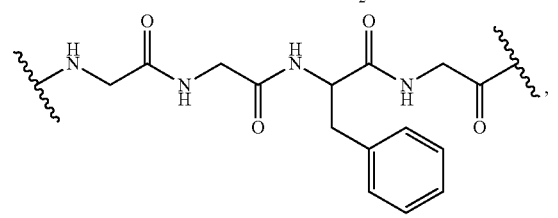

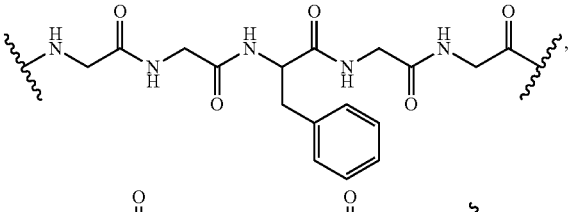

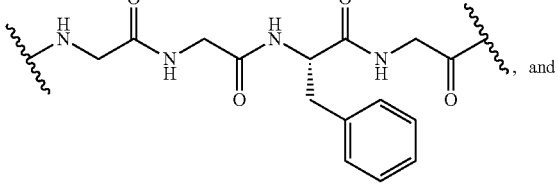

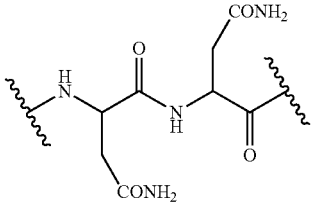

In certain embodiments of Formula (III)-(IVB), including any of the foregoing, -AA- is selected from the group consisting of

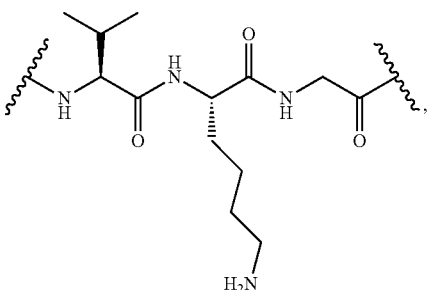

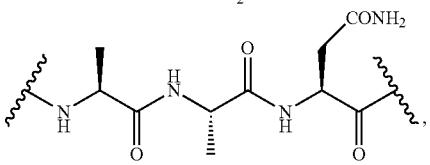

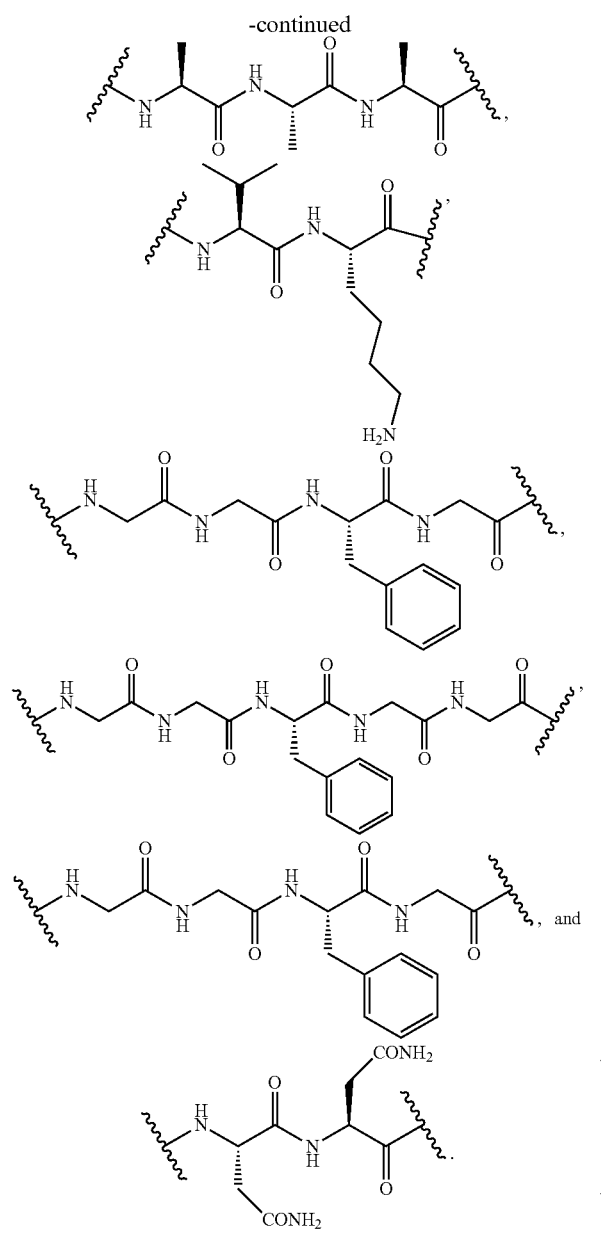

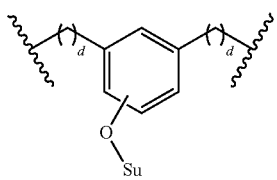

and Su is a hexose form of a monosaccharide and d is an integer independently selected from 1, 2, and 3. In certain embodiments of Formula (III)-(IVB), including any of the foregoing, $L^3$ is —C(O)—$NR^2$—$(CR^aR^b)_a$—C(O)—$NR^2$-$L^4$-OC(O)—. In certain embodiments of Formula (III)-(IVB), including any of the foregoing, $L^3$ is —C(O)—$NR^2$—$(CH_2)_2$—C(O)—$NR^2$-$L^4$-OC(O)—. In certain embodiments of Formula (III)-(IVB), including any of the foregoing, $L^3$ is —C(O)—NH—$(CR^aR^b)_a$—C(O)—NH-$L^4$-OC(O)—. In certain embodiments of Formula (III)-(IVB), including any of the foregoing, $L^3$ is —C(O)—NH—$(CH_2)_2$—C(O)—NH-$L^4$-OC(O)—.

In certain embodiments of Formula (III)-(IVB), including any of the foregoing, $L^4$ is

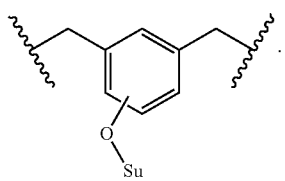

In certain embodiments of Formula (III)-(IVB), including any of the foregoing, $L^4$ is

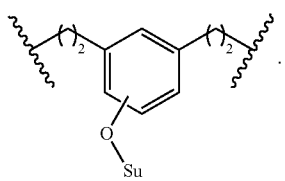

In certain embodiments of Formula (III)-(IVB), including any of the foregoing, $L^4$ is

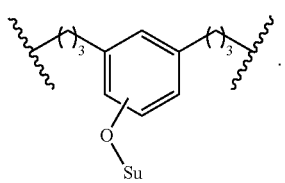

In some embodiments of Formula (III)-(IVB), including any of the foregoing, Su is a sugar moiety. In some embodiments, Su is a hexose form of a monosaccharide. Su may be a glucuronic acid or mannose residue. In certain embodiments of Formula (III)-(IVB), including any of the foregoing, Su is

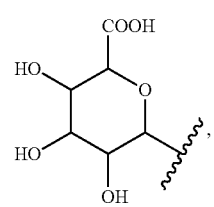

In certain embodiments of Formula (III)-(IVB), including any of the foregoing, $L^3$ is —C(O)—.

In certain embodiments of Formula (III)-(IVB), including any of the foregoing, $L^3$ is —C(O)—Z—$(CR^aR^b)_a$—C(O)—Z-$L^4$-OC(O)— wherein $L^4$ is wherein ⌇ represents attachment to the remainder of the compound. In certain embodiments of Formula (III)-(IVB), including any of the foregoing, Su is

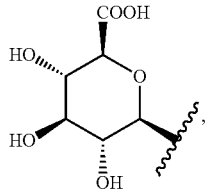

wherein ⌇ represents attachment to the remainder of the compound.

In certain embodiments of Formula (III)-(IVB), including any of the foregoing, $L^4$ is

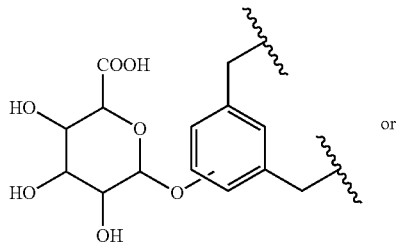

or

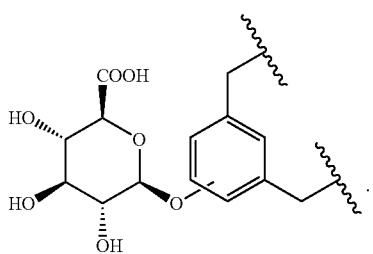

In certain embodiments of Formula (III)-(IVB), including any of the foregoing, $L^3$ is —C(O)—NH—$(CH_2)_2$—C(O)—NH-$L^4$-OC(O)— wherein $L^4$ is

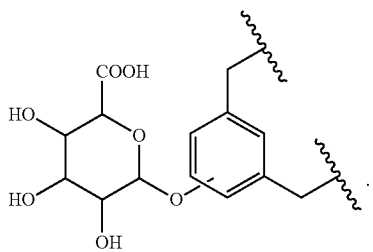

In certain embodiments of Formula (III)-(IVB), including any of the foregoing, $L^3$ is —C(O)—NH—$(CH_2)_2$—C(O)—NH-$L^4$-OC(O)— wherein $L^4$ is

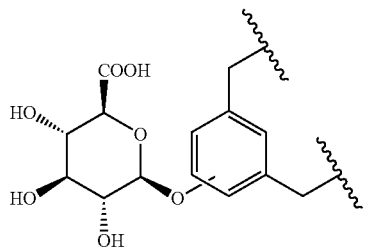

In certain embodiments of Formula (III)-(IVB), including any of the foregoing, $L^2$ is —$(CR^aR^b)_a$-POLY$^1$- and $L^3$ is —C(O)-AA-. In certain embodiments of Formula (III)-(IVB), including any of the foregoing, $L^2$ is —$(CR^aR^b)_a$-POLY$^1$-; $L^3$ is —C(O)-AA-; and, POLY$^1$ is

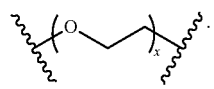

In certain embodiments of Formula (III)-(IVB), including any of the foregoing, $L^2$ is —$(CH_2)_a$-POLY$^1$-; $L^3$ is —C(O)-AA-; POLY$^1$ is

and x is an integer between 10 and 15. In certain embodiments of Formula (III)-(IVB), including any of the foregoing, $L^2$ is —$(CH_2)_2$-POLY$^1$-; $L^3$ is —C(O)-AA-; and, POLY$^1$ is

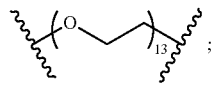

In certain embodiments of Formula (III)-(IVB), including any of the foregoing, $L^2$ is —$(CH_2)_2$-POLY$^1$-; $L^3$ is —C(O)-AA-; POLY$^1$ is

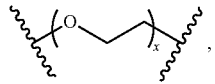

and AA is a dipeptide residue, a tripeptide residue, a tetrapeptide residue, or a pentapeptide residue.

In certain embodiments of Formula (III)-(IVB), including any of the foregoing, $L^2$ is —$(CR^aR^b)_a$-POLY$^1$- and $L^3$ is —C(O)-AA-Z—$(CR^aR^b)_a$—Z—$(CR^aR^b)_a$—C(O)—. In certain embodiments of Formula (III)-(IVB), including any of the foregoing, $L^2$ is —$(CR^aR^b)_a$-POLY$^1$-; $L^3$ is —C(O)-AA-Z—$(CR^aR^b)_a$—Z—$(CR^aR^b)_a$—C(O)—; POLY$^1$ is and Z is —NH—. In certain embodiments of Formula (III)-(IVB), including any of the foregoing, L² is —(CH₂)ₐ-POLY¹-; L³ is —C(O)-AA-NH—(CH₂)ₐ—NH—(CH₂)ₐ—C(O)—; POLY¹ is

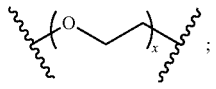

and x is an integer between 10 and 15. In certain embodiments of Formula (III)-(IVB), including any of the foregoing, L² is —(CH₂)₂-POLY¹-; L³ is —C(O)-AA-NH—CH₂—NH—CH₂—C(O)—; and, POLY¹ is

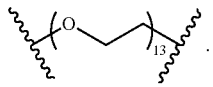

In certain embodiments of Formula (III)-(IVB), including any of the foregoing, L² is —(CH₂)₂-POLY¹-; L³ is —C(O)-AA-NH—CH₂—NH—CH₂—C(O)—; POLY¹ is

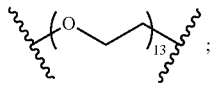

and AA is a dipeptide residue, a tripeptide residue, a tetrapeptide residue, or a pentapeptide residue.

In certain embodiments of Formula (III)-(IVB), including any of the foregoing, L² is —(CRᵃRᵇ)ₐ-POLY¹- and L³ is —C(O). In certain embodiments of Formula (III)-(IVB), including any of the foregoing, L² is —(CRᵃRᵇ)ₐ-POLY¹-; L³ is —C(O); and, POLY¹ is

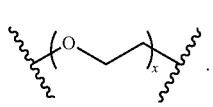

In certain embodiments of Formula (III)-(IVB), including any of the foregoing, L² is —(CH₂)ₐ-POLY¹-; L³ is —C(O); POLY¹ is

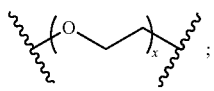

and x is an integer between 10 and 15. In certain embodiments of Formula (III)-(IVB), including any of the foregoing, L² is —(CH₂)₂-POLY¹-; L³ is —C(O); and, POLY¹ is

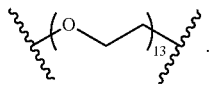

In certain embodiments of Formula (III)-(IVB), including any of the foregoing, L² is —(CH₂)₂-POLY¹-; L³ is —C(O); POLY¹ is

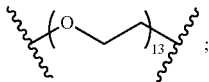

and AA is a dipeptide residue, a tripeptide residue, a tetrapeptide residue, or a pentapeptide residue.

In certain embodiments of Formula (III)-(IVB), including any of the foregoing, L² is —(CRᵃRᵇ)ₐ-POLY¹- and L³ is absent. In certain embodiments of Formula (III)-(IVB), including any of the foregoing, L² is —(CRᵃRᵇ)ₐ-POLY¹-; L³ is absent; and, POLY¹ is

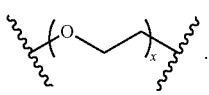

In certain embodiments of Formula (III)-(IVB), including any of the foregoing, L² is —(CH₂)ₐ-POLY¹-; L³ is absent; POLY¹ is

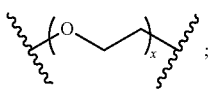

and x is an integer between 10 and 15. In certain embodiments of Formula (III)-(IVB), including any of the foregoing, L² is —(CH₂)₂-POLY¹-; L³ is absent; and, POLY¹ is

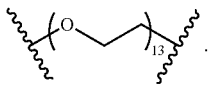

In certain embodiments of Formula (III)-(IVB), including any of the foregoing, L² is —(CH₂)₂-POLY¹-; L³ is absent; POLY¹ is

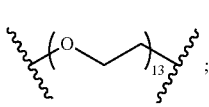

and AA is a dipeptide residue, a tripeptide residue, a tetrapeptide residue, or a pentapeptide residue.

In certain embodiments of Formula (III)-(IVB), including any of the foregoing, L² is —(CRᵃRᵇ)ₐ-POLY¹- and L³ is —C(O)-AA-Z—(CRᵃRᵇ)ₐ—. In certain embodiments of Formula (III)-(IVB), including any of the foregoing, L² is —(CRᵃRᵇ)ₐ-POLY¹-; L³ is —C(O)-AA-Z—(CRᵃRᵇ)ₐ—; and, POLY¹ is

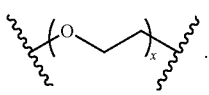

In certain embodiments of Formula (III)-(IVB), including any of the foregoing, L² is —(CH₂)ₐ-POLY¹-; —C(O)-AA-NR²—(CRᵃRᵇ)ₐ—; POLY¹ is

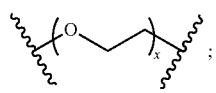

and x is an integer between 10 and 15. In certain embodiments of Formula (III)-(IVB), including any of the foregoing, $L^2$ is —$(CH_2)_2$-$POLY^1$-; $L^3$ is —C(O)-AA-NH—$(CR^aR^b)_a$—; and, $POLY^1$ is

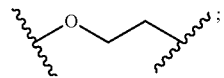

In certain embodiments of Formula (III)-(IVB), including any of the foregoing, $L^2$ is —$(CH_2)_2$-$POLY^1$-; $L^3$ is —C(O)-AA-NH—$(CR^aR^b)_a$—; $POLY^1$ is

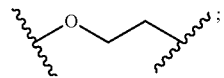

and AA is a dipeptide residue, a tripeptide residue, a tetrapeptide residue, or a pentapeptide residue.

Non-limiting examples of -$L^2$-$L^3$- include:

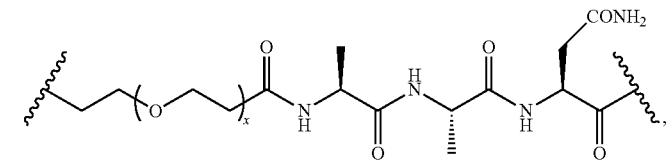

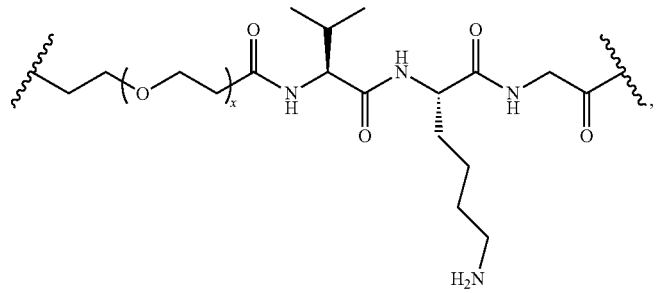

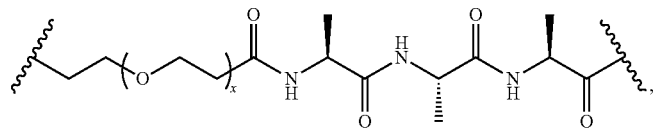

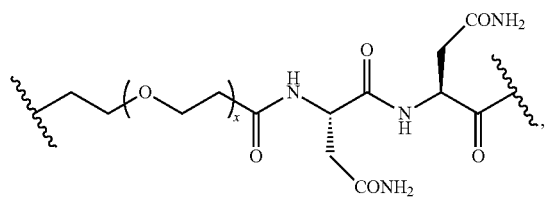

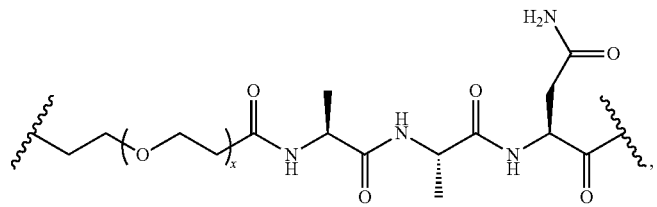

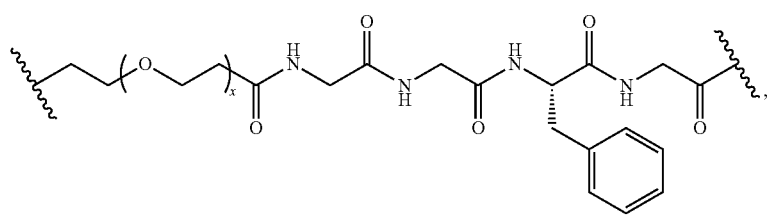

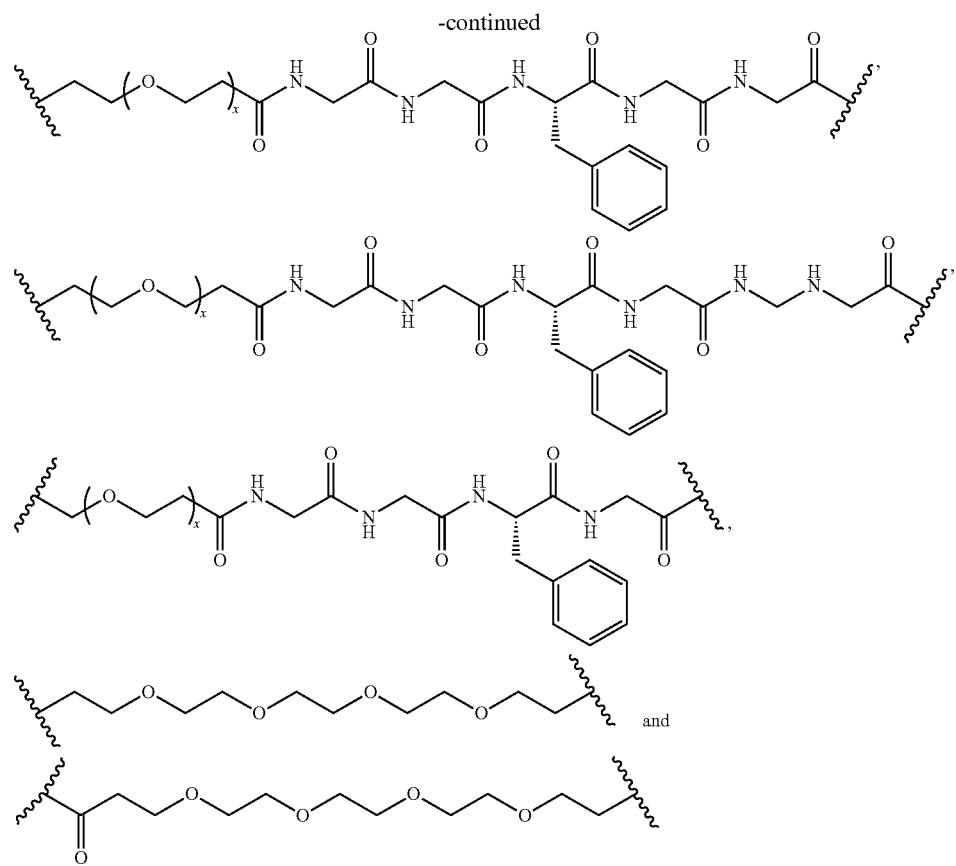
Additional non-limiting examples of -L²-L³- include:
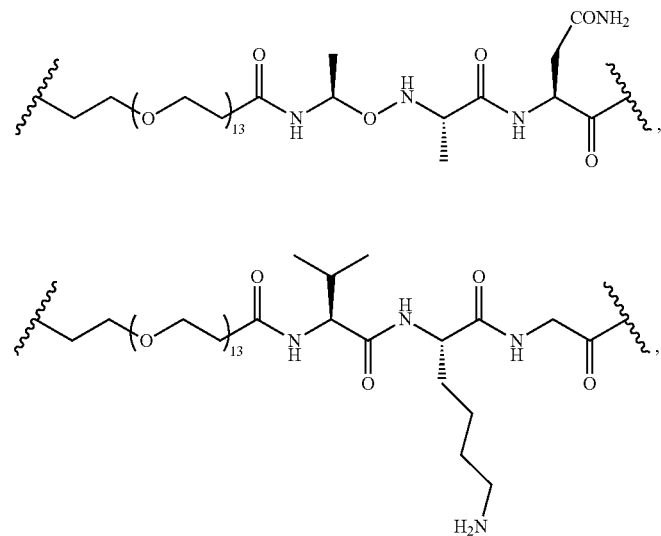
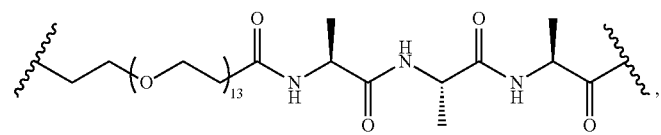

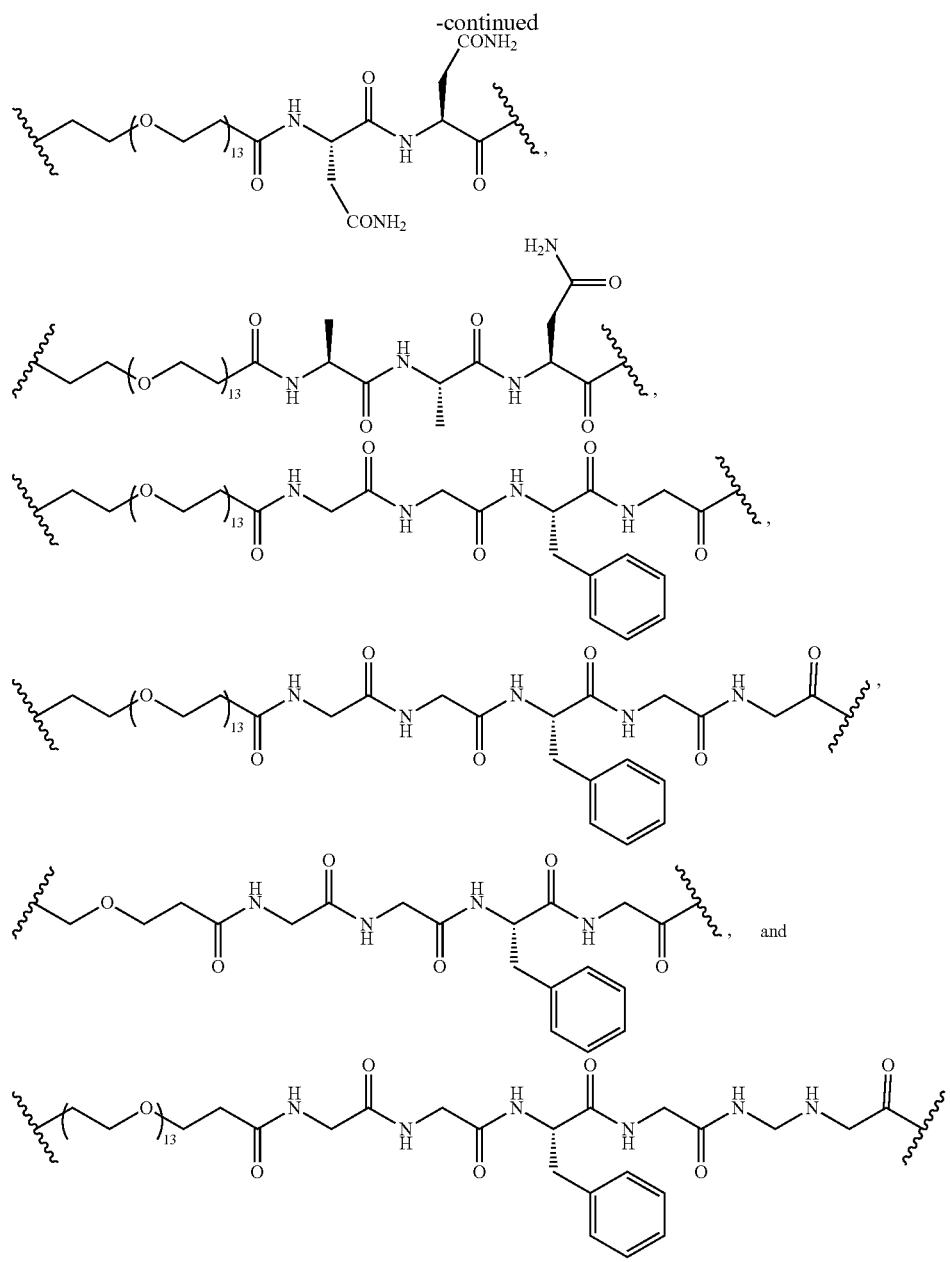
In certain embodiments of Formula (III)-(IVB), including any of the foregoing, $L^2$ is
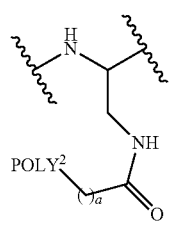
and $L^3$ is —C(O)—Z—(CR$^a$R$^b$)$_a$—C(O)—Z-L$^4$-OC(O)— wherein $L^4$ is
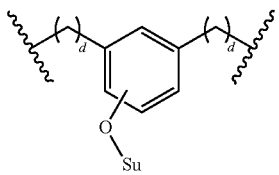
and Su is a hexose form of a monosaccharide and d is an integer independently selected from 1, 2, and 3. In certain embodiments of Formula (III)-(IVB), including any of the foregoing, $L^2$ is

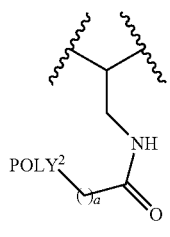

and $L^3$ is —C(O)—Z—$(CR^aR^b)_a$—C(O)—Z-$L^4$-OC(O)—.

In certain embodiments of Formula (III)-(IVB), including any of the foregoing, $L^2$ is

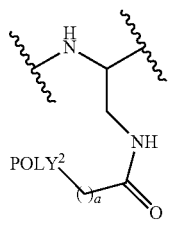

and $L^3$ is —C(O). In certain embodiments, including any of the foregoing, $L^2$ is

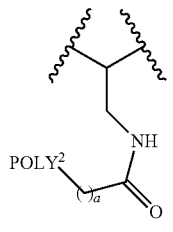

and $L^3$ is absent.

In certain embodiments of Formula (III)-(IVB), including any of the foregoing, $L^2$ is selected from the group consisting of

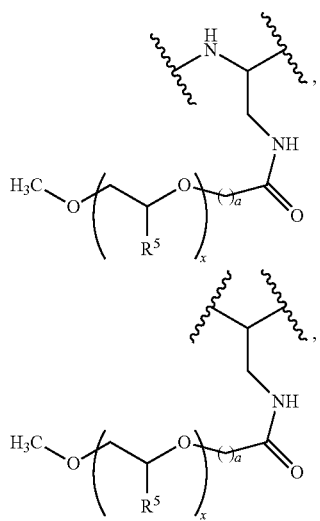

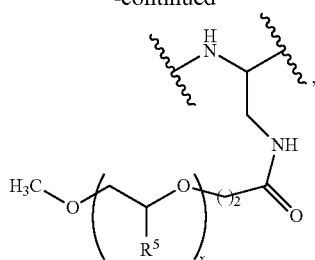

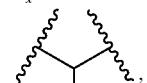

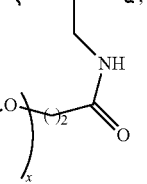

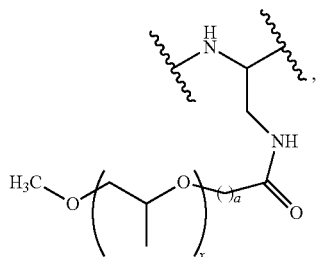

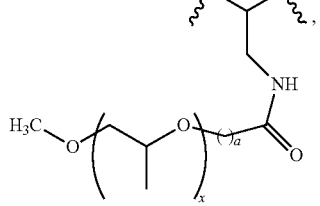

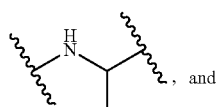, and

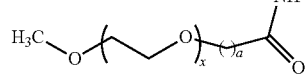

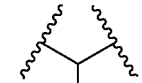

and $L^3$ is —C(O)—NH—$(CR^aR^b)_a$—C(O)—NH-$L^4$-OC(O)—.

In certain embodiments of Formula (III)-(IVB), including any of the foregoing, L² is selected from the group consisting of
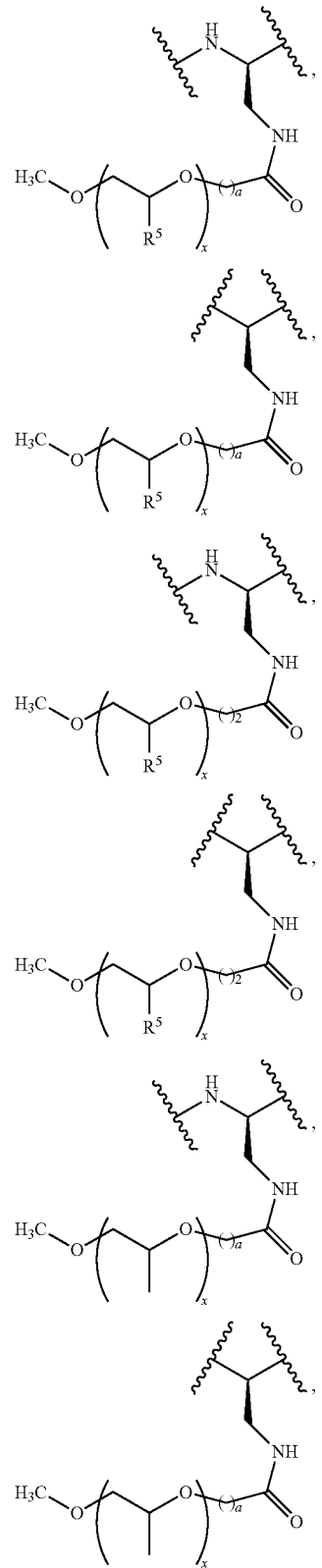
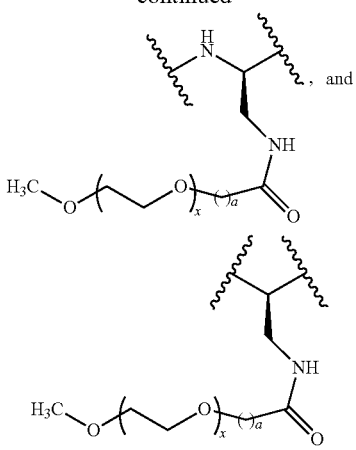
and L³ is —C(O)—NH—(CRᵃRᵇ)ₐ—C(O)—NH-L⁴-OC(O)—.
In certain embodiments of Formula (III)-(IVB), including any of the foregoing, L² is selected from the group consisting of and $L^3$ is —C(O)—NH—(CH$_2$)$_2$—C(O)—NH-$L^4$-OC(O)— wherein $L^4$ is

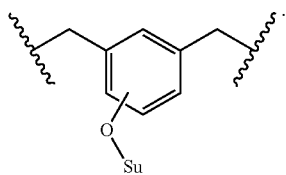

In certain embodiments of Formula (III)-(IVB), including any of the foregoing, $L^2$ is selected from the group consisting of

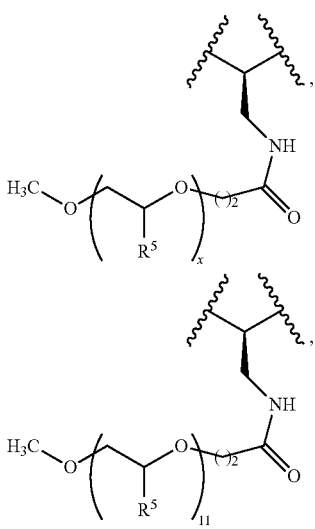

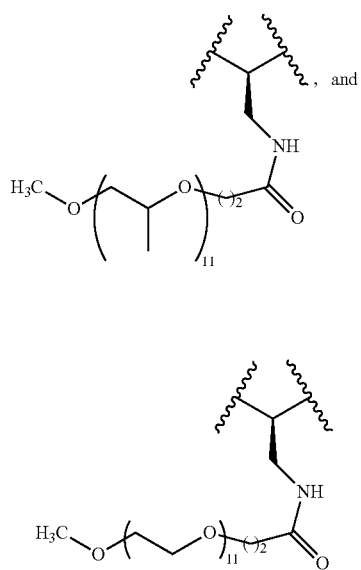

and $L^3$ is —C(O).

In certain embodiments, including any of the foregoing, D is a cytotoxic payload selected from a tubulin inhibitor, a DNA topoisomerase I inhibitor, and a DNA topoisomerase II inhibitor. In some embodiments, including any of the foregoing, D is a tubulin inhibitor. In some embodiments, including any of the foregoing, D is a DNA topoisomerase I inhibitor. In some embodiments, including any of the foregoing, D is a DNA topoisomerase I inhibitor selected from the group consisting of irinotecan, SN-38, topotecan, exatecan. In some embodiments, including any of the foregoing, D is irinotecan. In some embodiments, including any of the foregoing, D is SN-38. In some embodiments, including any of the foregoing, D is topotecan. In some embodiments, including any of the foregoing, D is exatecan. In some embodiments, including any of the foregoing, D is a DNA topoisomerase II inhibitor. In some embodiments, including any of the foregoing, D is a DNA topoisomerase II inhibitor selected from the group consisting of etoposide, teniposide, and tafluposide. In some embodiments, including any of the foregoing, D is etoposide. In some embodiments, including any of the foregoing, D is teniposide. In some embodiments, including any of the foregoing, D is tafluposide. In some embodiments, including any of the foregoing, D is selected from the group consisting of hemiasterlins, camptothecins, and anthracyclines. Anthracyclines may include PNU-159682 and EDA PNU-159682 derivatives. In some embodiments, including any of the foregoing, D is an anthracycline selected from the group consisting of daunorubicin, doxorubicin, epirubicin, idarubicin, mitoxantrone, and valrubicin. In some embodiments, including any of the foregoing, D is daunorubicin. In some embodiments, including any of the foregoing, D is doxorubicin. In some embodiments, including any of the foregoing, D is epirubicin. In some embodiments, including any of the foregoing, D is idarubicin. In some embodiments, including any of the foregoing, D is mitoxantrone. In some embodiments, including any of the foregoing, D is valrubicin. In some embodiments, including any of the foregoing, D is a hemiasterlin. In some embodiments, including any of the foregoing, D is a camptothecin. In some embodiments, including any of the foregoing, D is an anthracycline. In some embodiments, including any of the foregoing, D is PNU-159682. In some embodiments, including any of the foregoing, D is an EDA PNU compound. In some embodiments, including any of the foregoing, D is an EDA PNU-159682 derivative. In some embodiments, including any of the foregoing, D is hemiasterlin, exatecan, PNU-159682, or an EDA PNU-159682 derivative. In some embodiments, including any of the foregoing, D is hemiasterlin. In some embodiments, including any of the foregoing, D is exatecan. In some embodiments, including any of the foregoing, D is of PNU-159682. In some embodiments, including any of the foregoing, D is EDA PNU-159682 compound or derivative. In some embodiments, including any of the foregoing, D is not an immunestimulatory compound.

In some embodiments, including any of the foregoing, D is an alkylating agent. In some embodiments, including any of the foregoing, D is a bifunctional alkylator. In some embodiments, including any of the foregoing, D is a bifunctional alkylator selected from the group consisting of cyclophosphamide, mechlorethamine, chlorambucil, and melphalan. In some embodiments, including any of the foregoing, D is cyclophosphamide. In some embodiments, including any of the foregoing, D is mechlorethamine. In some embodiments, including any of the foregoing, D is chlorambucil. In some embodiments, including any of the foregoing, D is melphalan. In some embodiments, including any of the foregoing, D is a monofunctional alkylator. In some embodiments, including any of the foregoing, D is a monofunctional alkkylator selected from the group consisting of dacabazine, nitrosourea, and temozolomide. In some embodiments, including any of the foregoing, D is dacabazine. In some embodiments, including any of the foregoing, D is nitrosourea. In some embodiments, including any of the foregoing, D is temozolomide. In some embodiments, including any of the foregoing, D is a cytoskeletal disruptor (e.g., a taxane). In some embodiments, including any of the foregoing, D is a cytoskeletal disruptor selected from the group consisting of paclitaxel, docetaxel, abraxane, and taxotere. In some embodiments, including any of the foregoing, D is paclitaxel. In some embodiments, including any of the foregoing, D is docetaxel. In some embodiments, including any of the foregoing, D is abraxane. In some embodiments, including any of the foregoing, D is taxotere. In some embodiments, including any of the foregoing, D is an epothilone. In some embodiments, including any of the foregoing, D is an epothilone selected from the group consisting of epothilone A, epothilone B, epothilone C, epothilone D, and ixabepilone. In some embodiments, including any of the foregoing, D is epothilone A. In some embodiments, including any of the foregoing, D is epothilone B. In some embodiments, including any of the foregoing, D is epothilone C. In some embodiments, including any of the foregoing, D is epothilone D. In some embodiments, including any of the foregoing, D is ixabepilone. In some embodiments, including any of the foregoing, D is a histone deacetylase inhibitor. In some embodiments, including any of the foregoing, D is a histone deacetylase inhibitor selected from the group consisting of vorinostat and romidepsin. In some embodiments, including any of the foregoing, D is vorinostat. In some embodiments, including any of the foregoing, D is romidepsin. In some embodiments, including any of the foregoing, D is a kinase inhibitor. In some embodiments, including any of the foregoing, D is a kinase inhibitor selected from the group consisting of bortezomib, erlotinib, gefitinib, imatinib, vemurafenib, and vismodegib. In some embodiments, including any of the foregoing, D is bortezomib. In some embodiments, including any of the foregoing, D is erlotinib. In some embodiments, including any of the foregoing, D is gefitinib. In some embodiments, including any of the foregoing, D is imatinib. In some embodiments, including any of the foregoing, D is vemurafenib. In some embodiments, including any of the foregoing, D is vismodegib. In some embodiments, including any of the foregoing, D is a nucleotide analog and/or precursor analog. In some embodiments, including any of the foregoing, D is a nucleotide analog and/or precursor analog selected from the group consisting of azacitidine, azathioprine, capecitabine, cyatarabine, doxifluridine, fluorouracil, gemcitabine, hydroxyurea, mercaptopurine, methotrexate, and tioguanine (formerly thioguanine). In some embodiments, including any of the foregoing, D is azacitidine. In some embodiments, including any of the foregoing, D is azathioprine. In some embodiments, including any of the foregoing, D is capecitabine. In some embodiments, including any of the foregoing, D is cyatarabine. In some embodiments, including any of the foregoing, D is doxifluridine. In some embodiments, including any of the foregoing, D is fluorouracil. In some embodiments, including any of the foregoing, D is gemcitabine. In some embodiments, including any of the foregoing, D is hydroxyurea. In some embodiments, including any of the foregoing, D is mercaptopurine. In some embodiments, including any of the foregoing, D is methotrexate. In some embodiments, including any of the foregoing, D is tioguanine (formerly thioguanine). In some embodiments, including any of the foregoing, D is a peptide antibiotic. In some embodiments, including any of the foregoing, D is a peptide antibiotic selected from the group consisting of bleomycin and actinomycin. In some embodiments, including any of the foregoing, D is bleomycin. In some embodiments, including any of the foregoing, D is actinomycin. In some embodiments, including any of the foregoing, D is a platinum-based agent. In some embodiments, including any of the foregoing, D is a platinum-based agent selected from the group consisting of carboplatin, cisplatin, and oxaliplatin. In some embodiments, including any of the foregoing, D is carboplatin. In some embodiments, including any of the foregoing, D is cisplatin. In some embodiments, including any of the foregoing, D is oxaliplatin. In some embodiments, including any of the foregoing, D is a retinoid. In some embodiments, including any of the foregoing, D is a retinoid selected from the group consisting of tretinoin, alitretinoin, and bexarotene. In some embodiments, including any of the foregoing, D is tretinoin. In some embodiments, including any of the foregoing, D is alitretinoin. In some embodiments, including any of the foregoing, D is bexarotene. In some embodiments, including any of the foregoing, D is a vinca alkaloid and derivatives thereof. In some embodiments, including any of the foregoing, D is a vinca alkaloid and derivatives thereof selected from the group consisting of vinblastine, vincristine, vindesine, vinorelbine. In some embodiments, including any of the foregoing, D is a residue of vinblastine. In some embodiments, including any of the foregoing, D is vincristine. In some embodiments, including any of the foregoing, D is vindesine.

In any of the foregoing embodiments, the conjugate comprises n2 number of linker-payloads, wherein n2 is an integer from 1 to 10. In some embodiments, n2 is 2. In some embodiments, n2 is 3. In some embodiments, n2 is 4. In some embodiments, n2 is 5. In some embodiments, n2 is 6. In some embodiments, n2 is 7. In some embodiments, n2 is 8. In some embodiments, n2 is 9. In some embodiments, n2 is 10.

In some embodiments, provided herein are anti-ROR1 conjugates having the structure of any of Conjugates A-MM in the table below. In some embodiments, n2 is an integer from 1 to 8. In some embodiments, n2 is 2. In some embodiments, n2 is 4. In some embodiments, n2 is 6. In some embodiments, n2 is 8. The present disclosure encompasses each and every regioisomer of the conjugate structures depicted below.

151 152
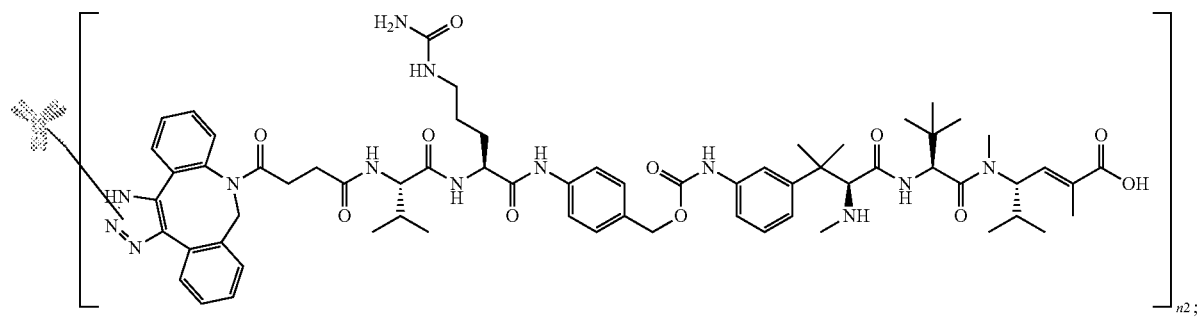
A
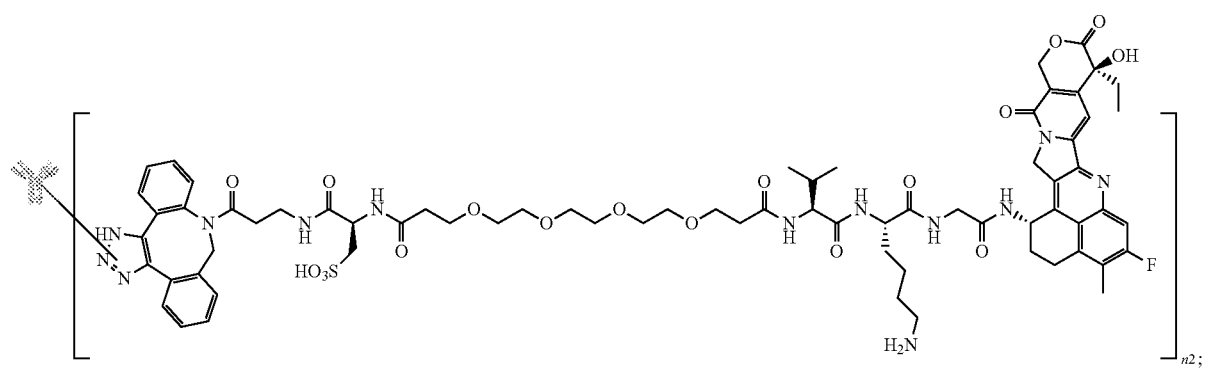
B
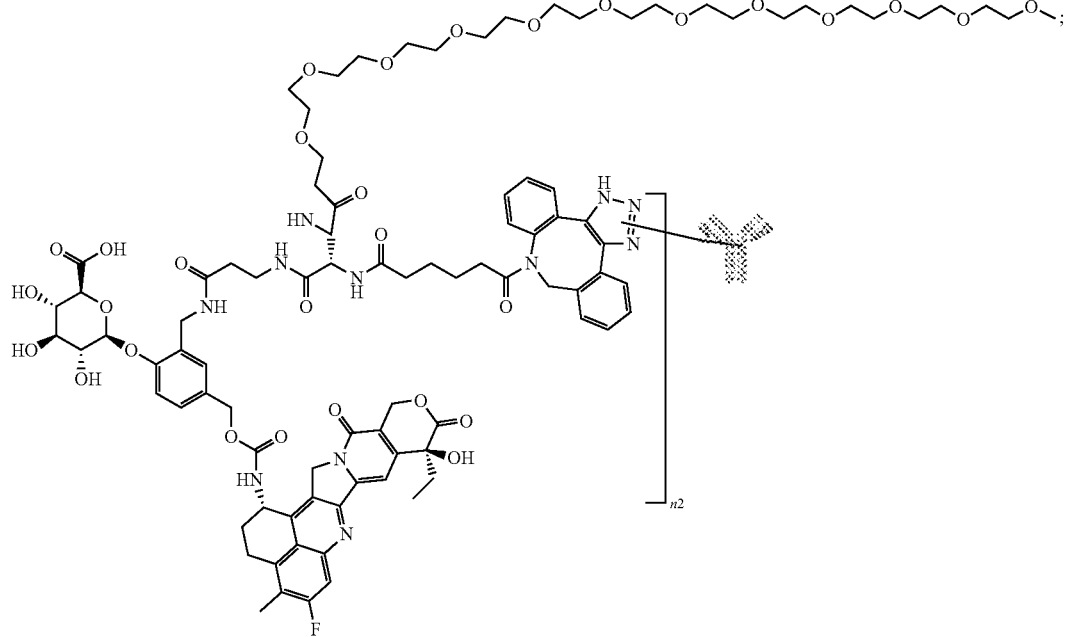
C

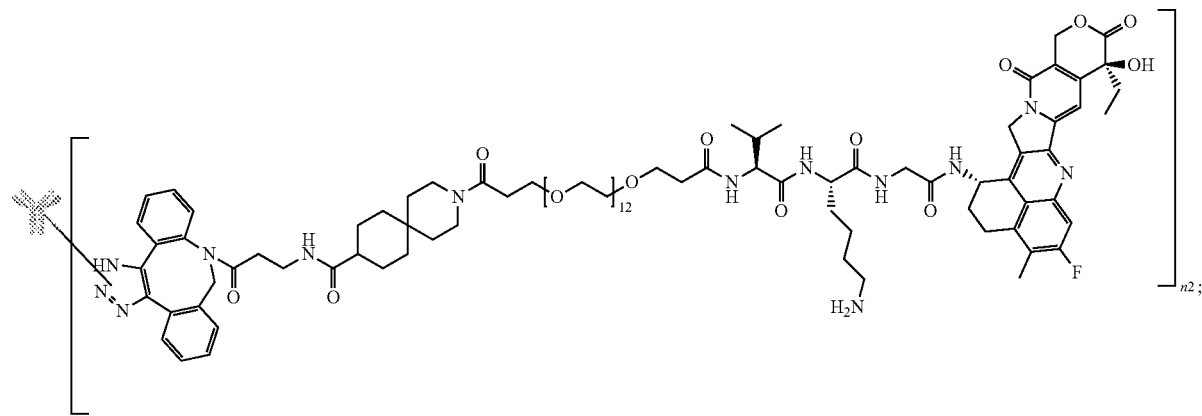
D
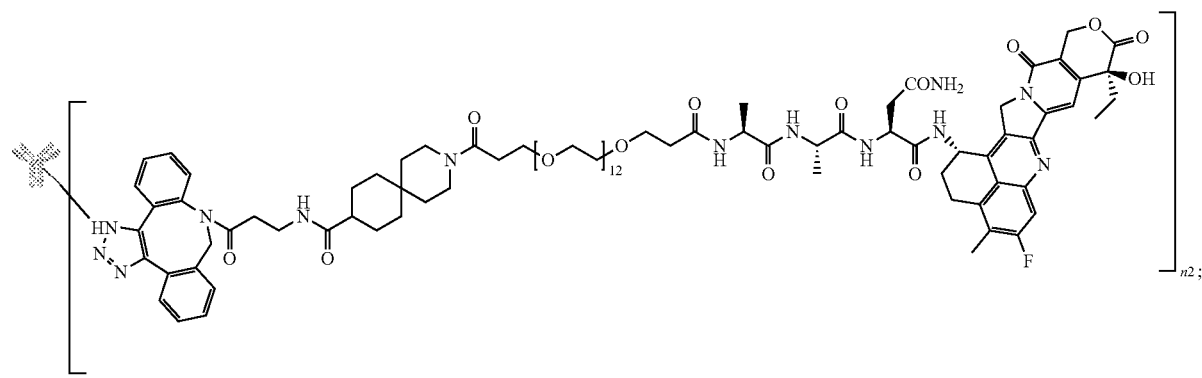
E
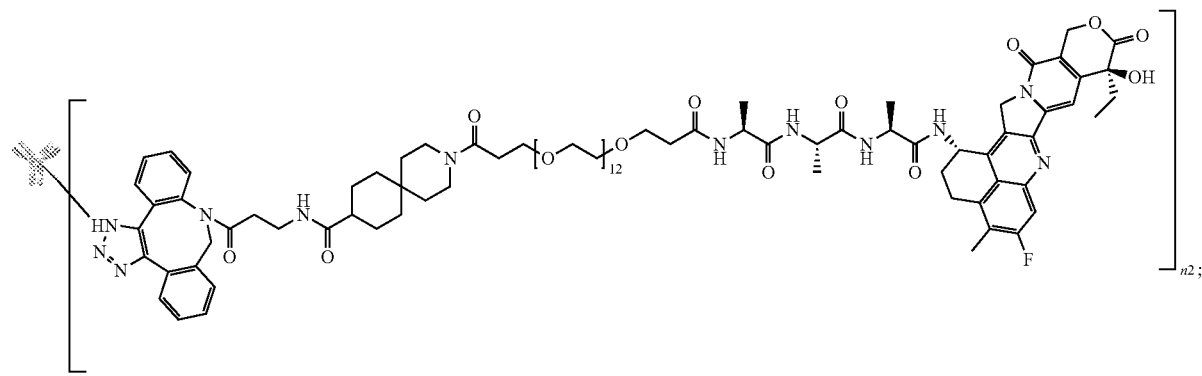
F
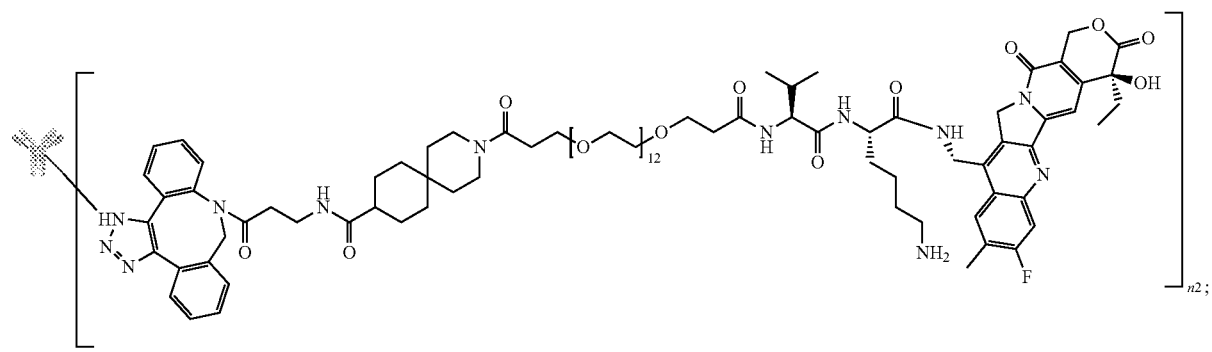
G

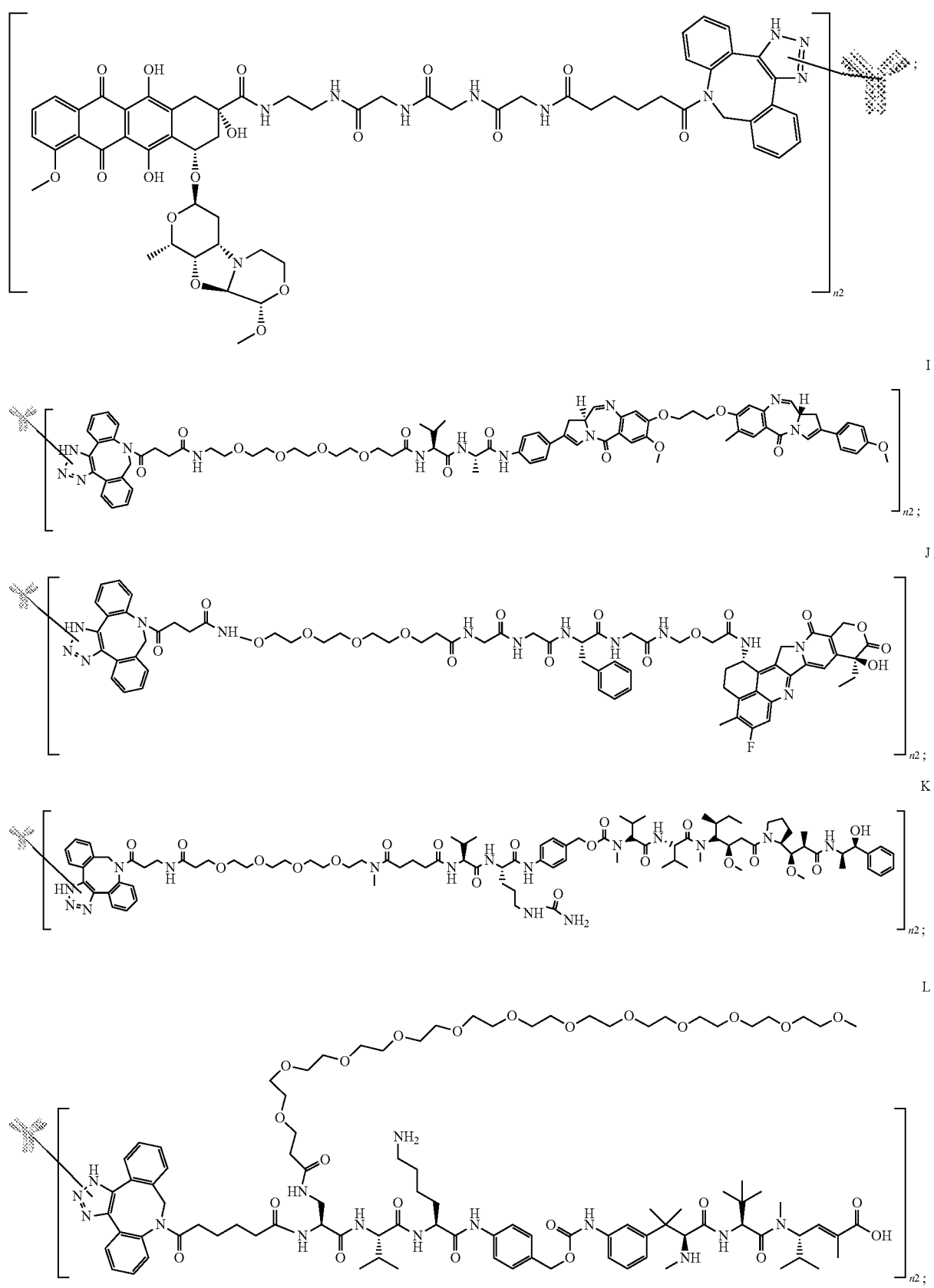

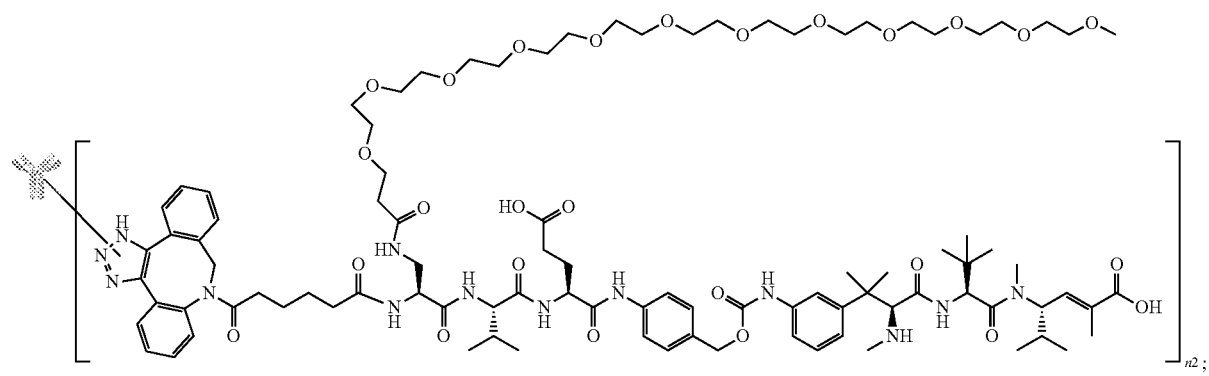
M
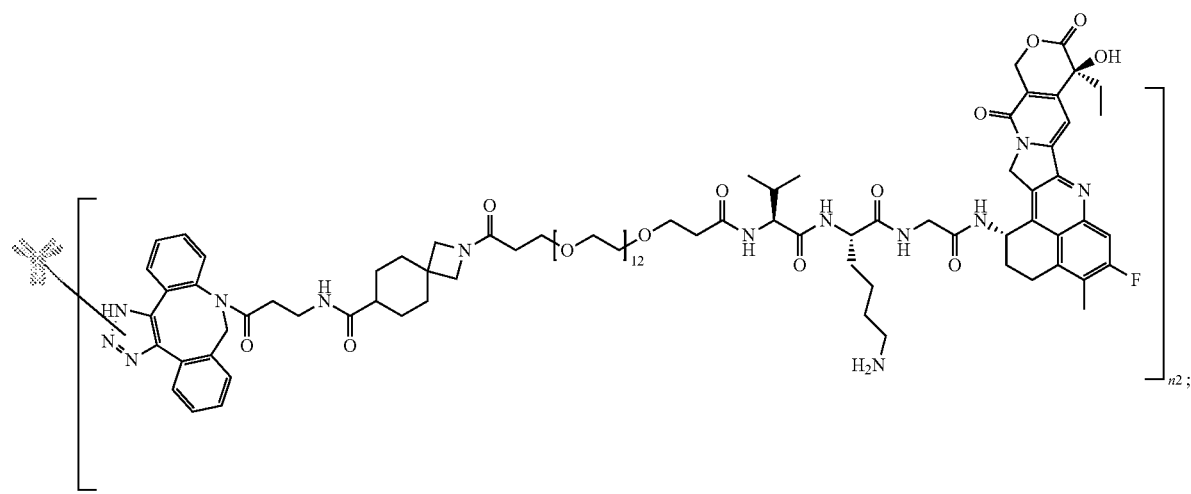
N
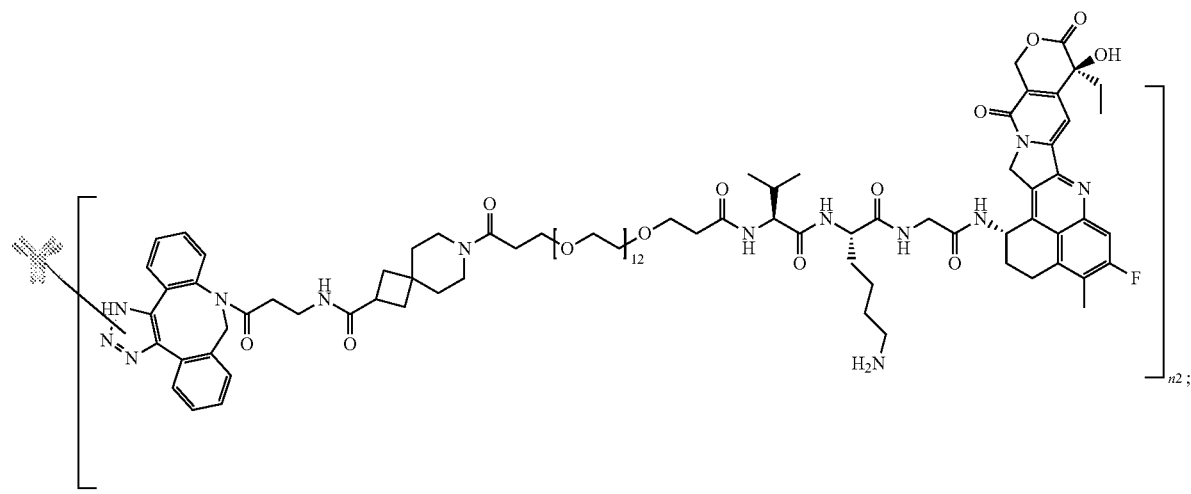
O

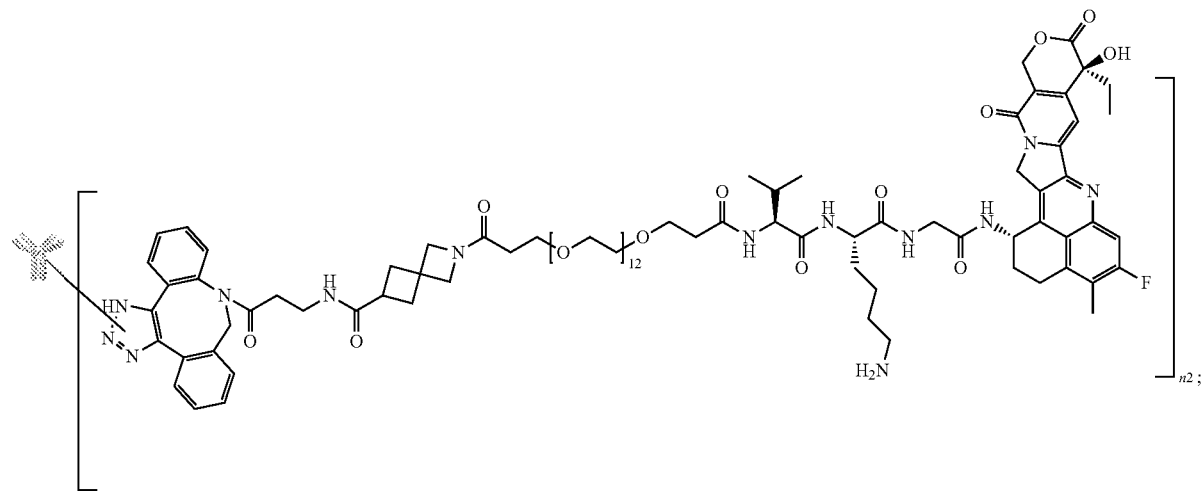
P
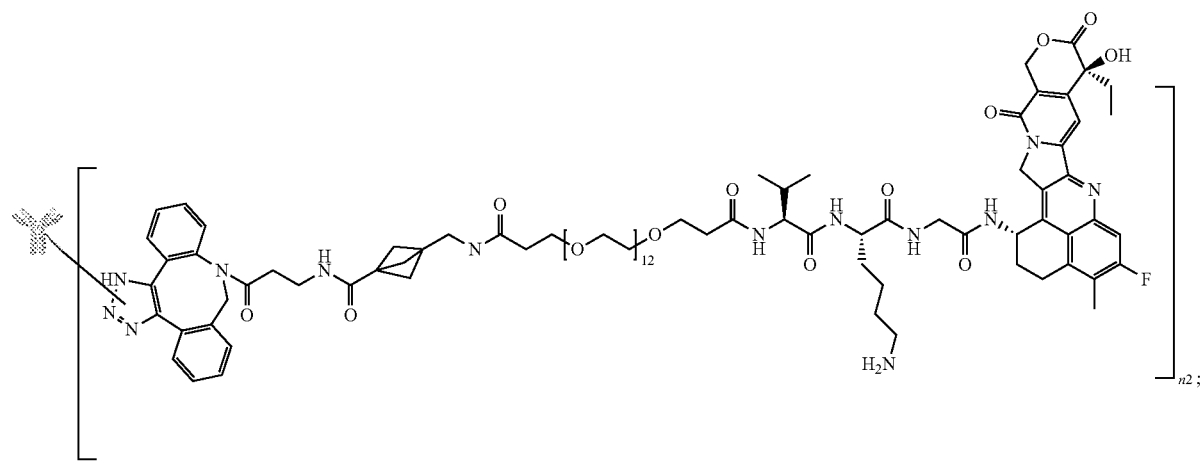
Q
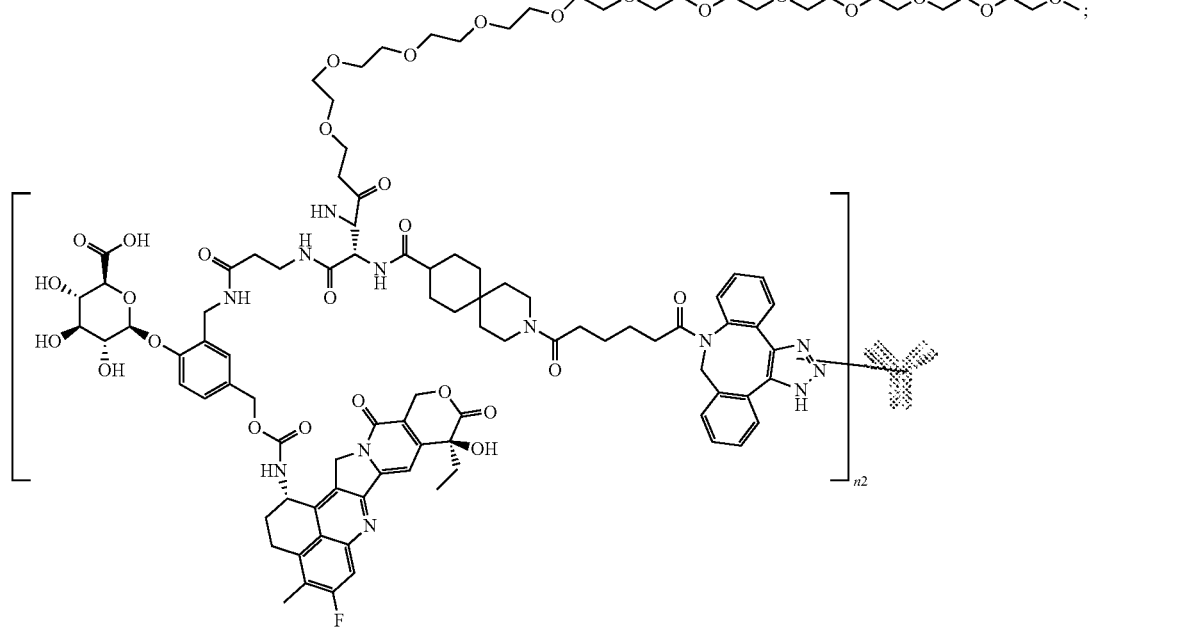
R

-continued
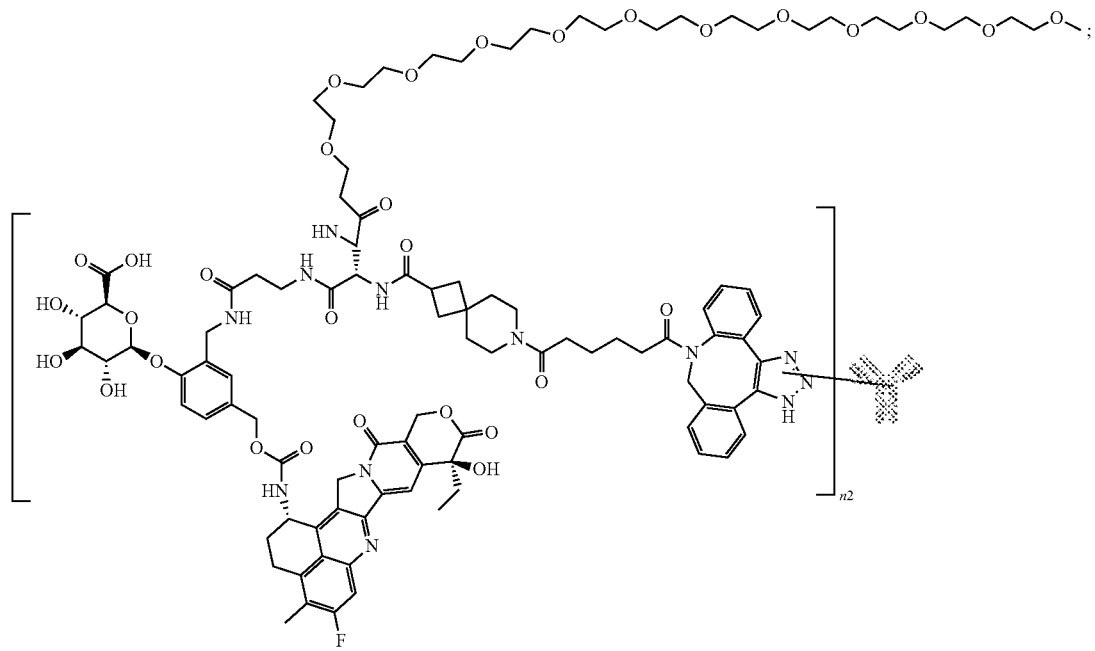
S
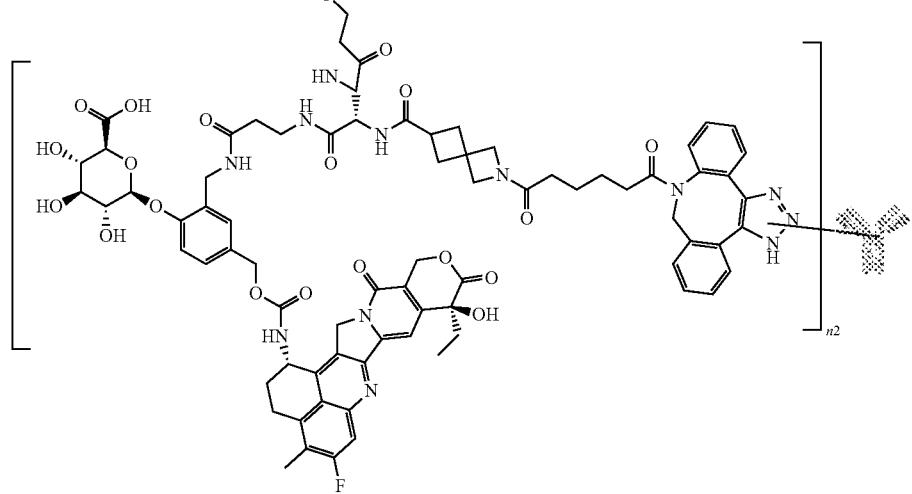
T
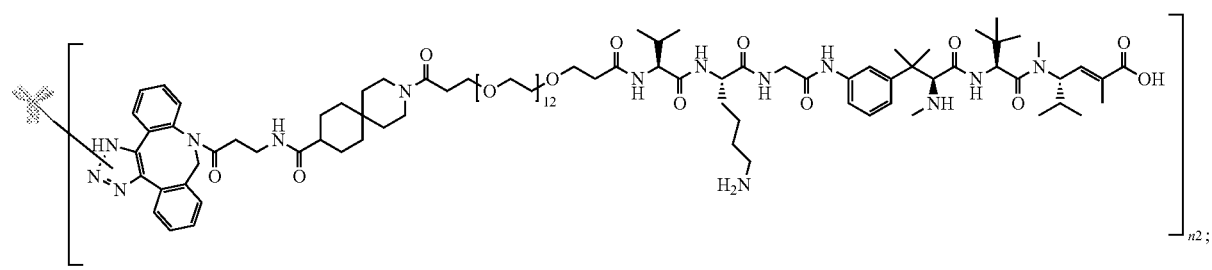
U

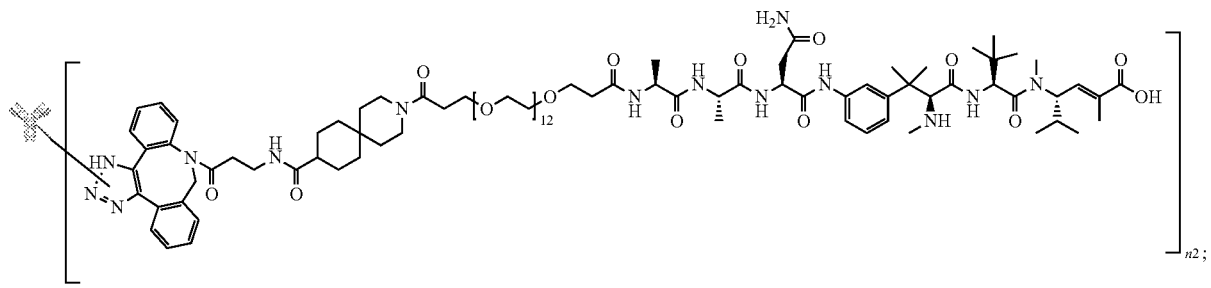
V
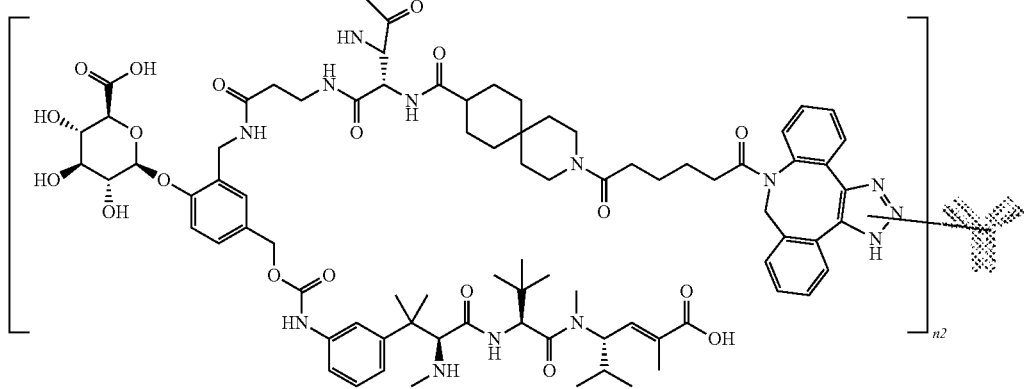
W
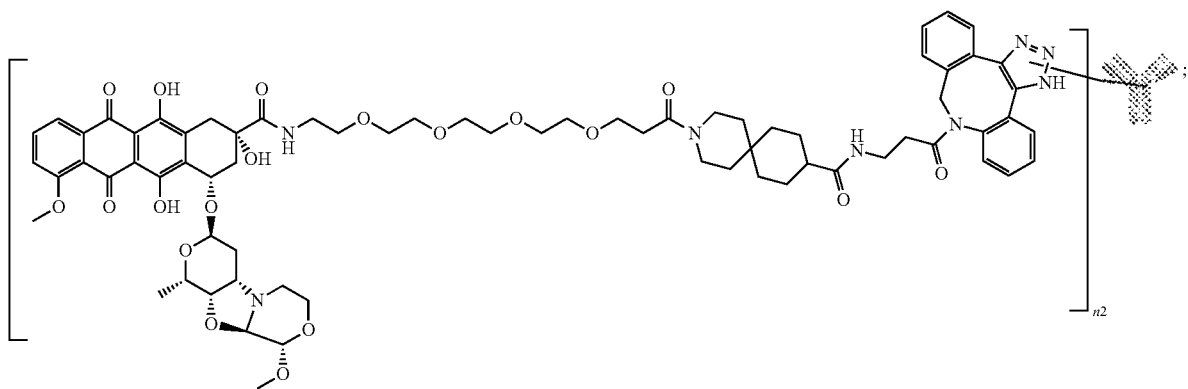
X

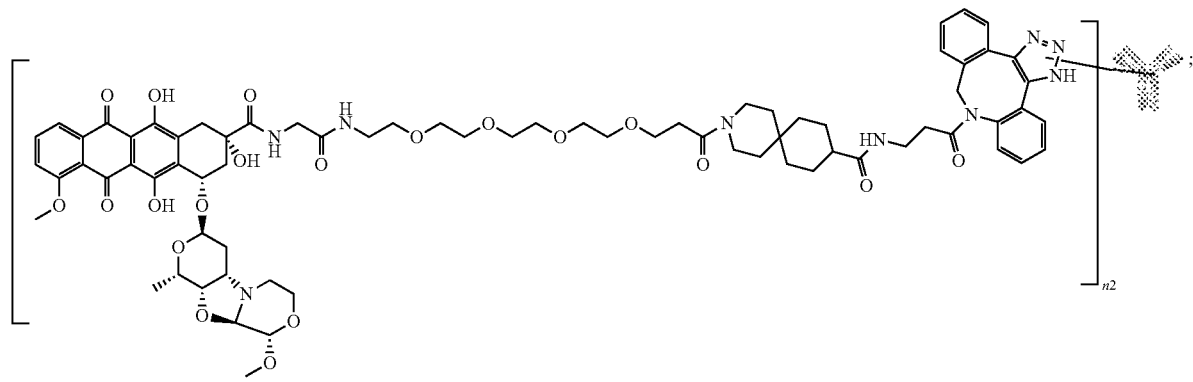
Y
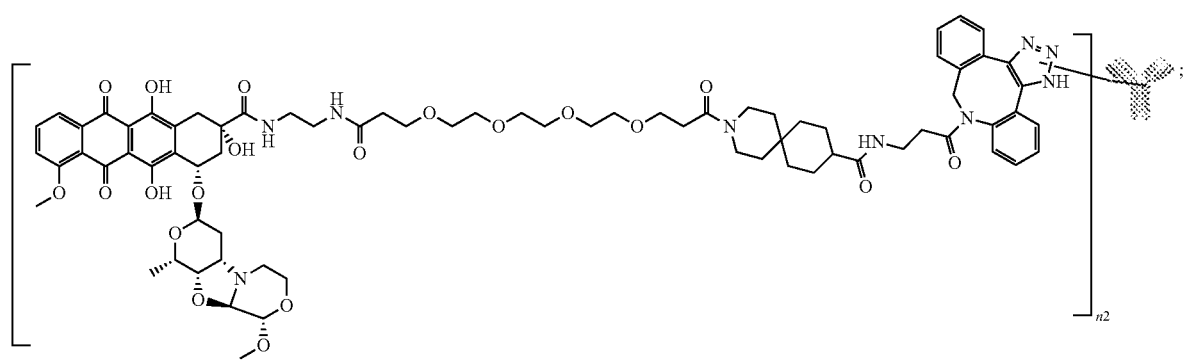
Z
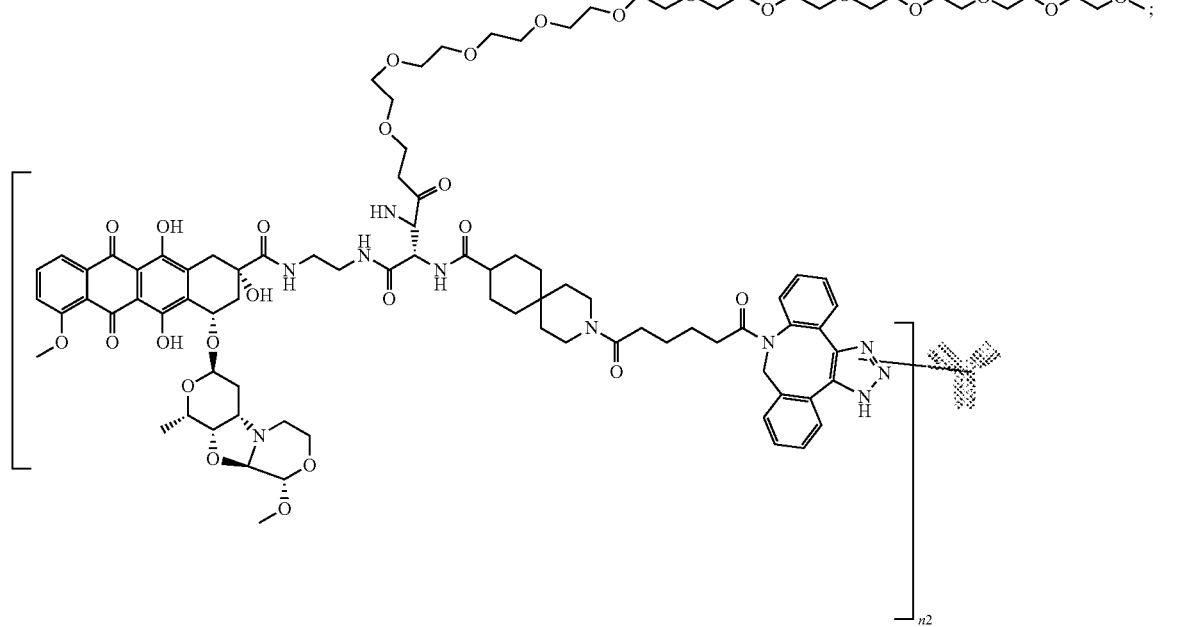
AA

-continued
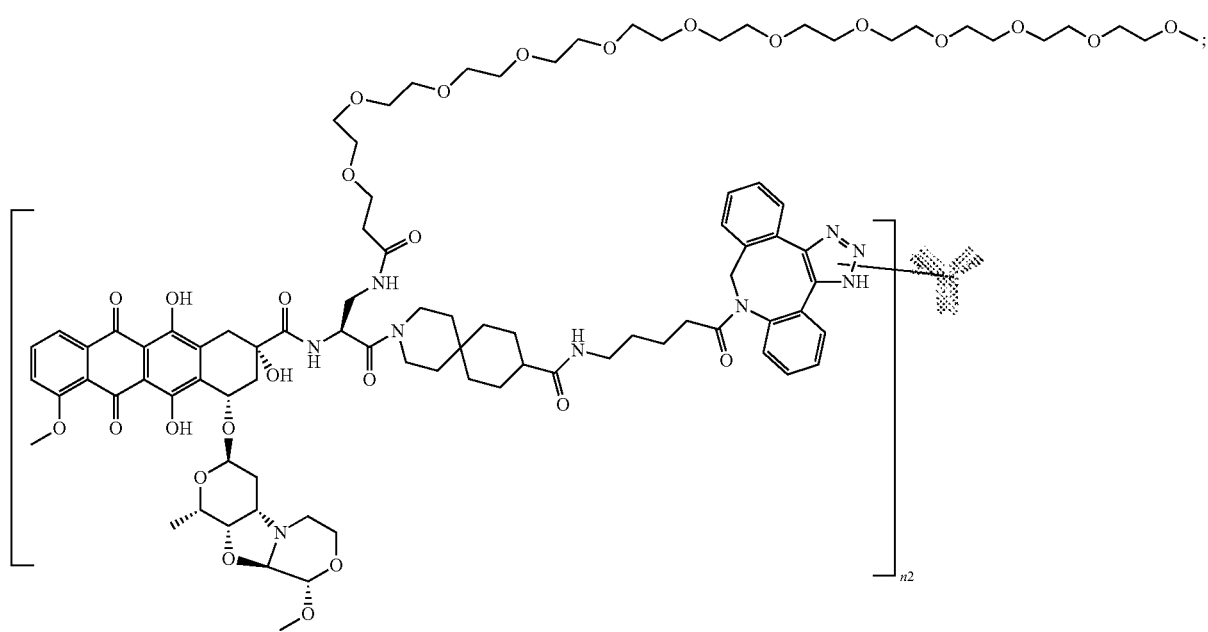
BB
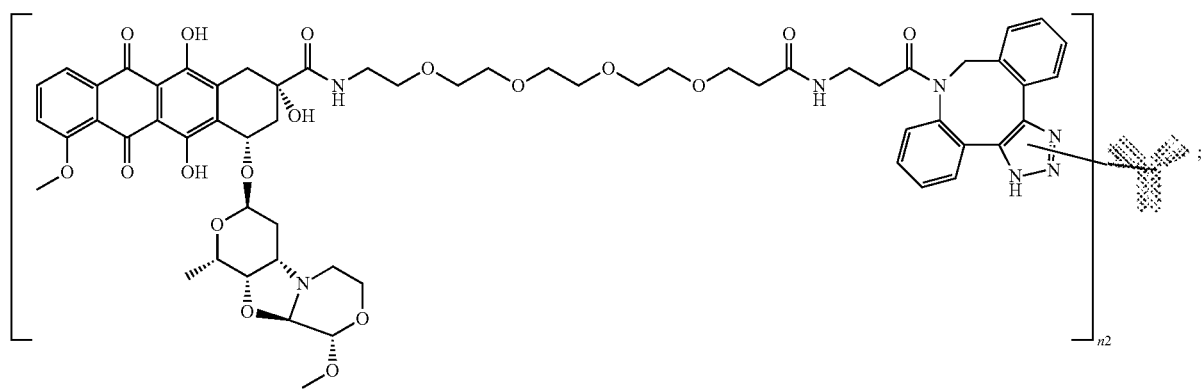
CC
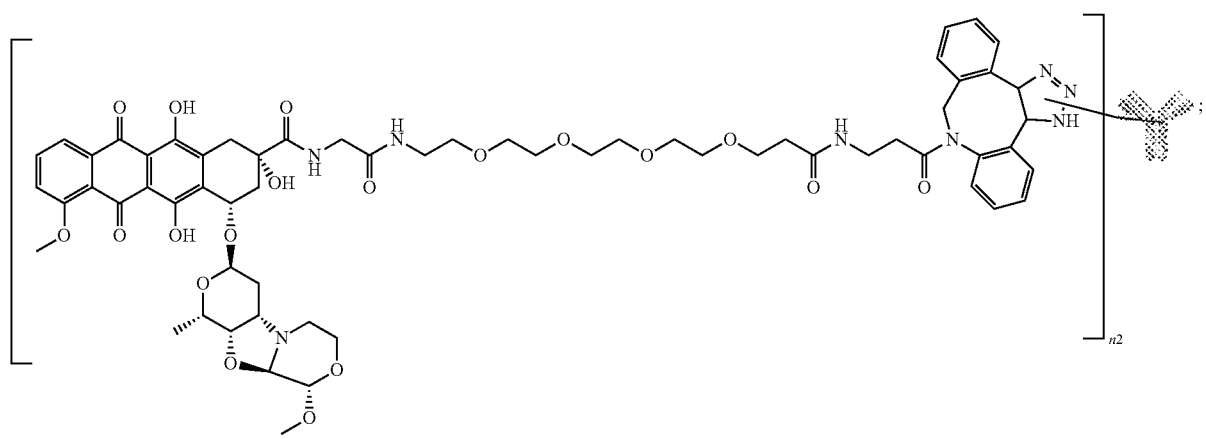
DD

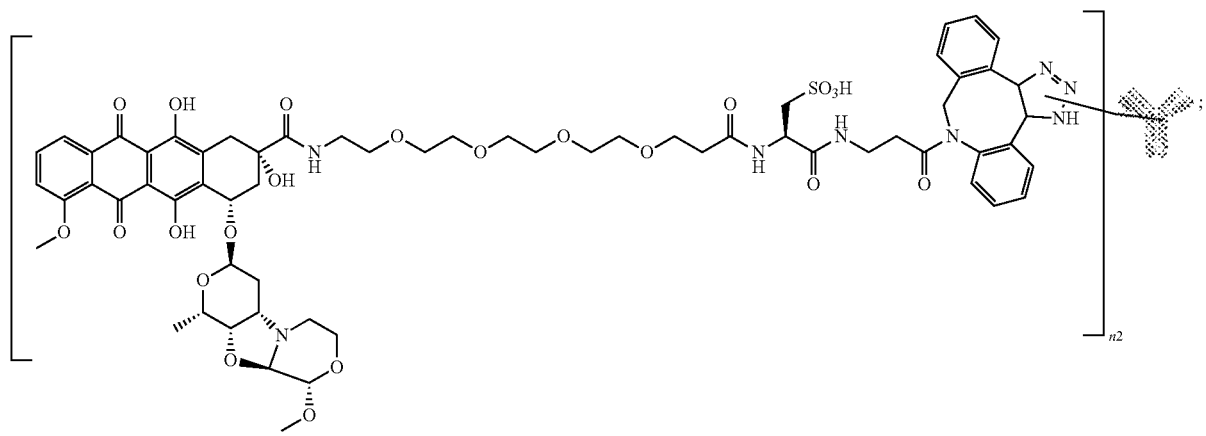
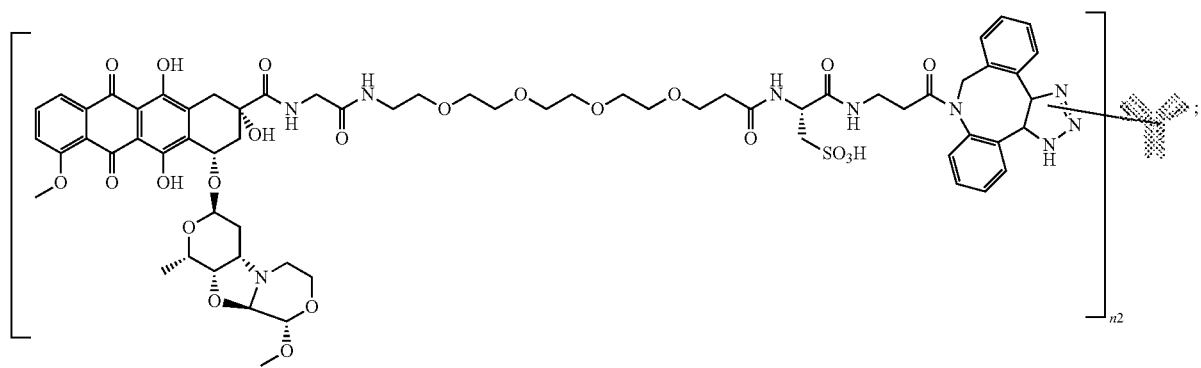
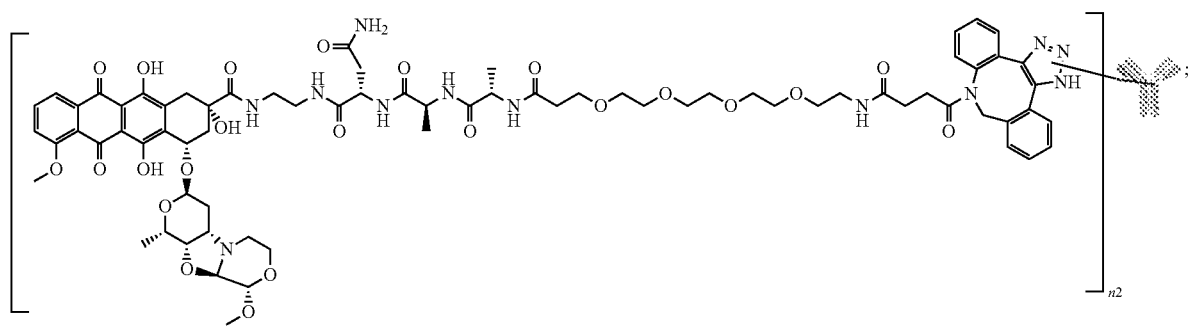

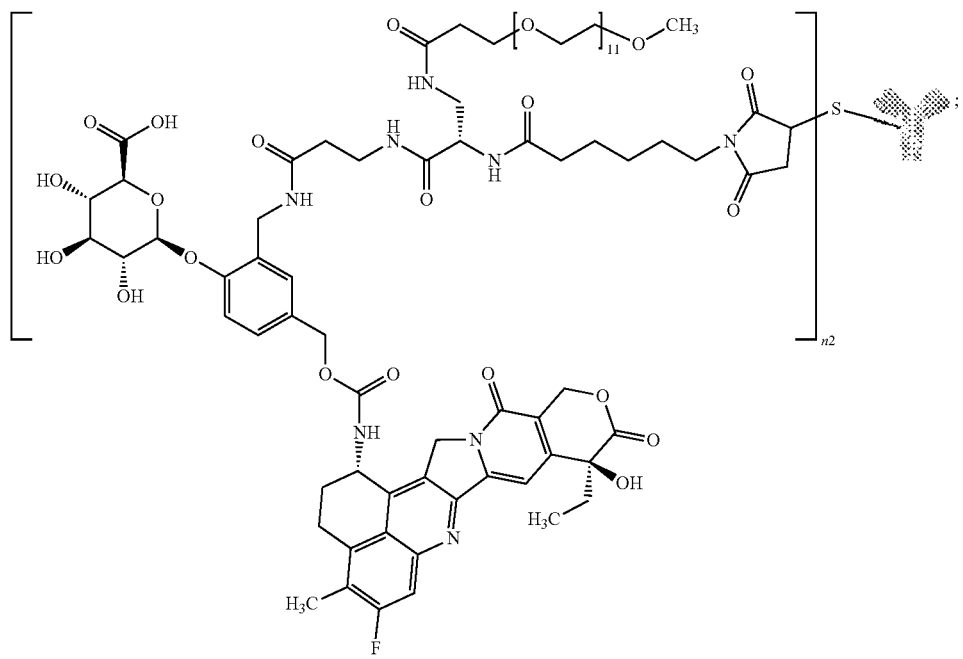
HH
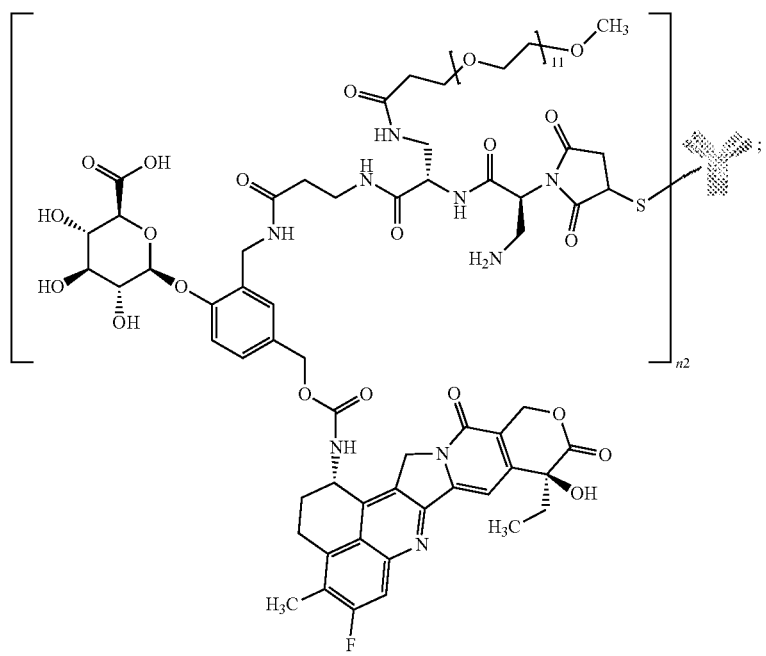
II

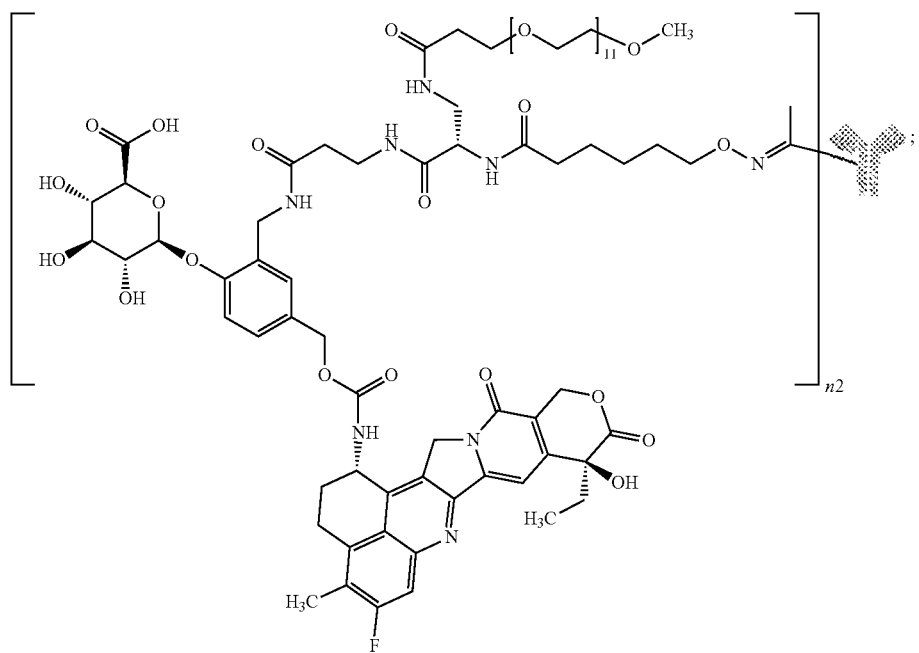
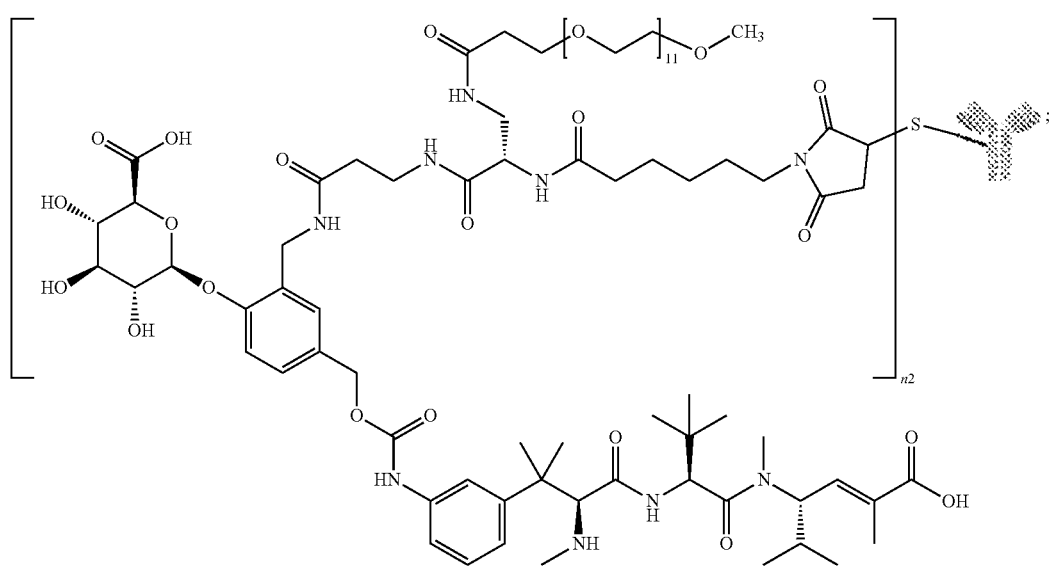

-continued
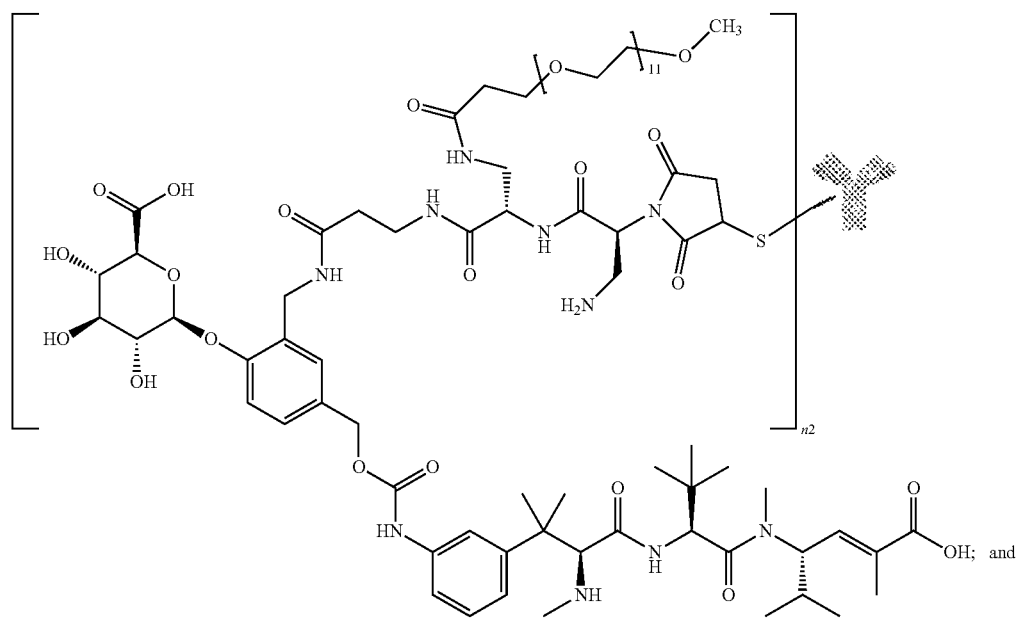
LL
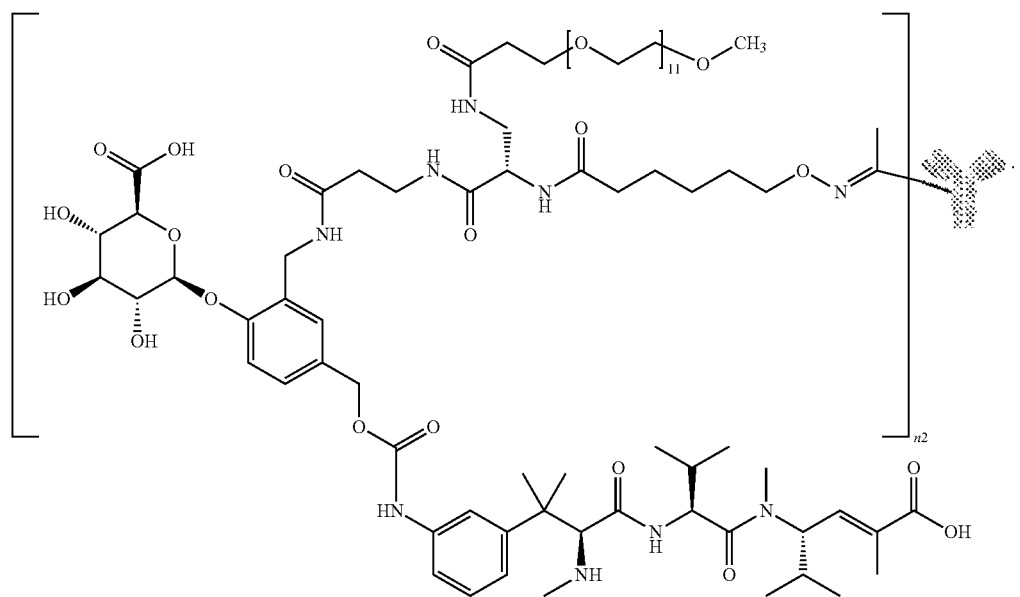
MM

In some embodiments, provided herein are anti-ROR1 conjugates having the structure of any of Conjugates A1-MM1 in the table below. In some embodiments, n2 is an integer from 1 to 8. In some embodiments, n2 is 2. In some embodiments, n2 is 4. In some embodiments, n2 is 6. In some embodiments, n2 is 8. The present disclosure encompasses each and every regioisomer of the conjugate structures depicted below.

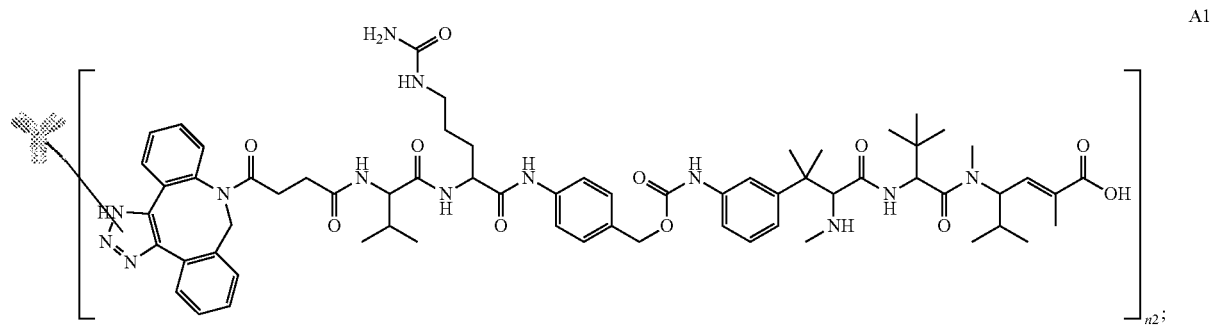

A1

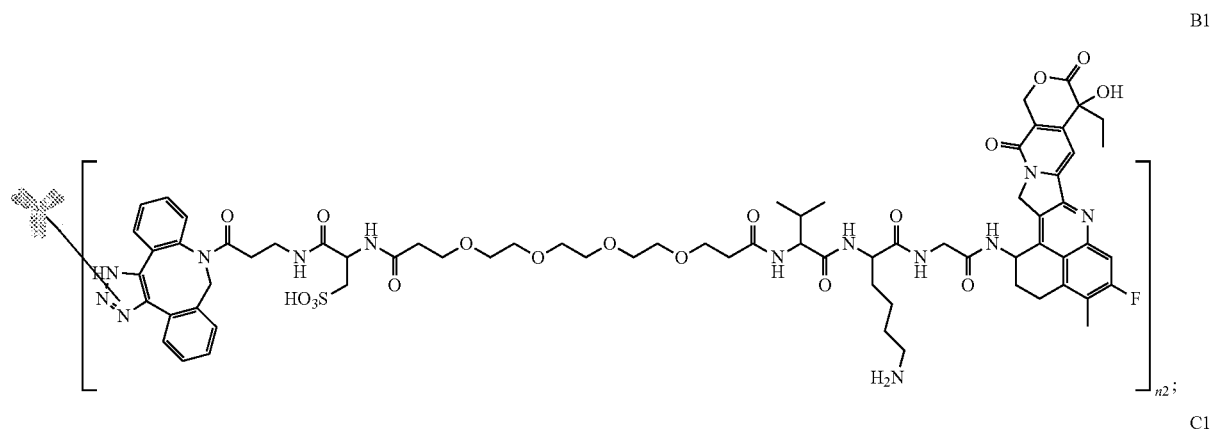

B1

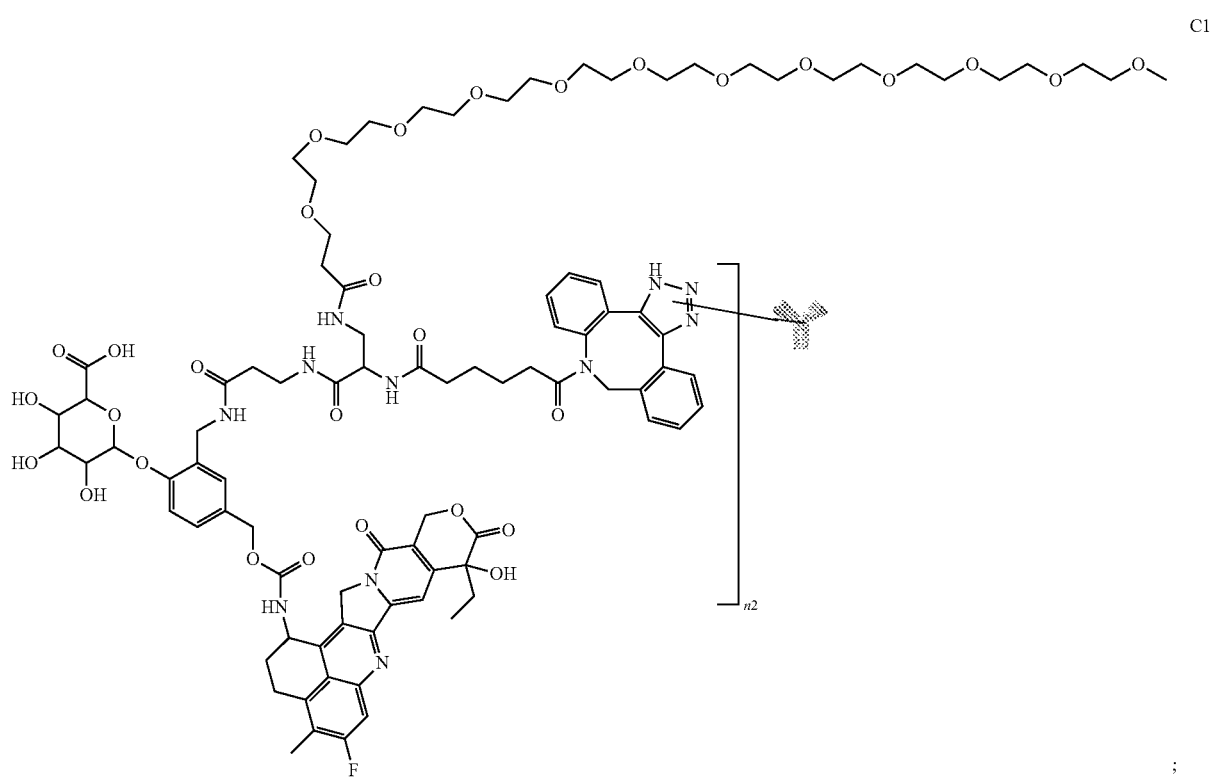

C1

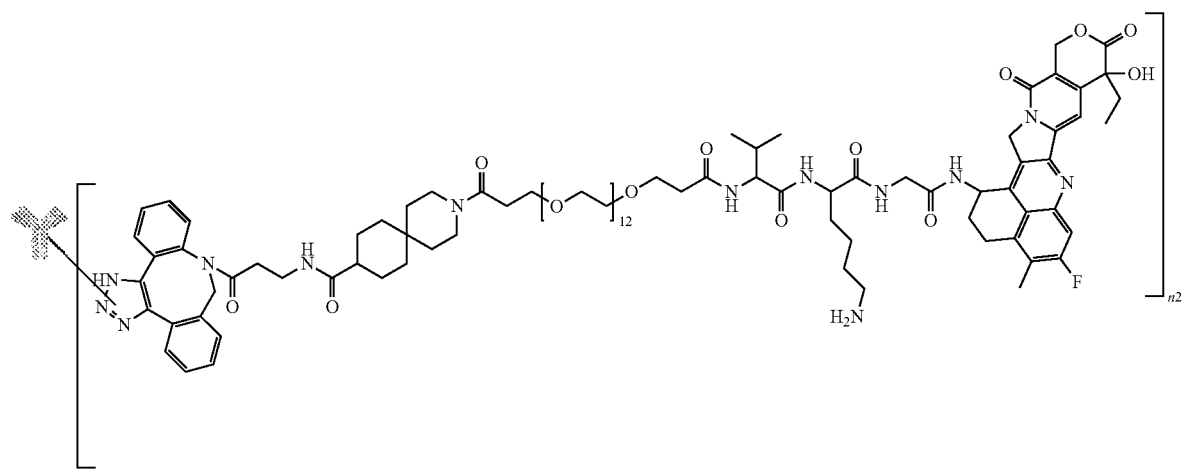
D1;
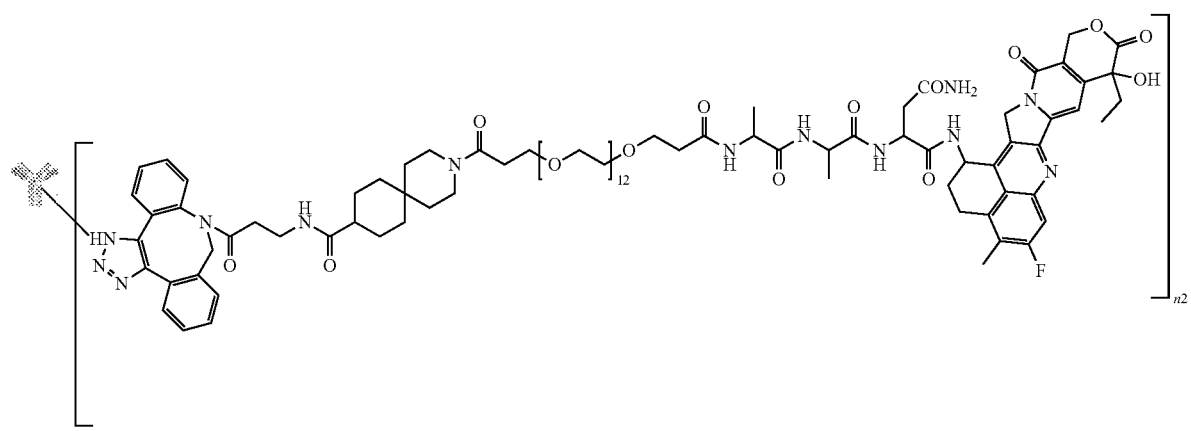
E1;
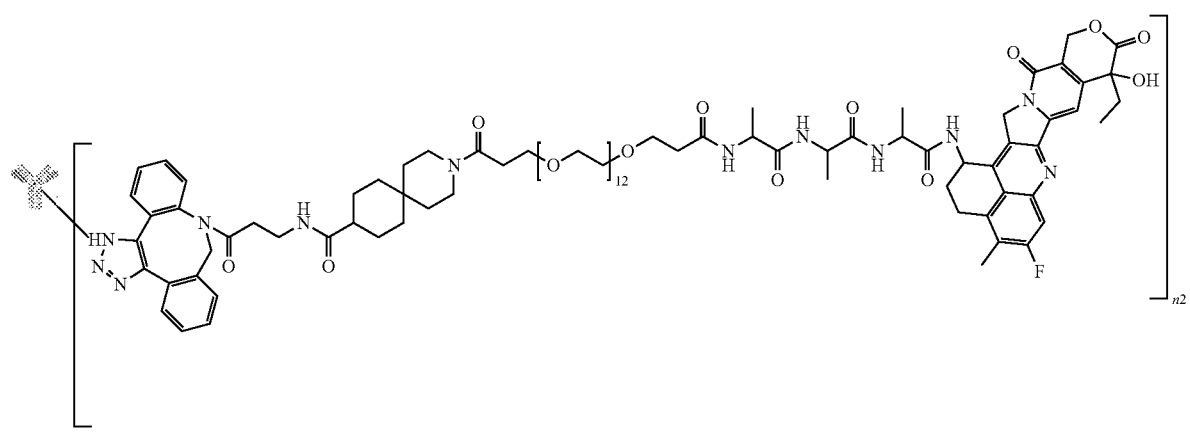
F1;

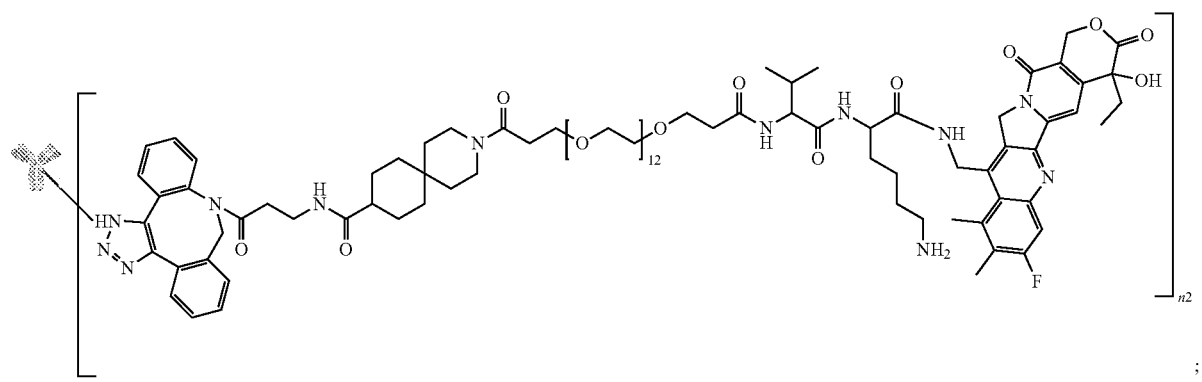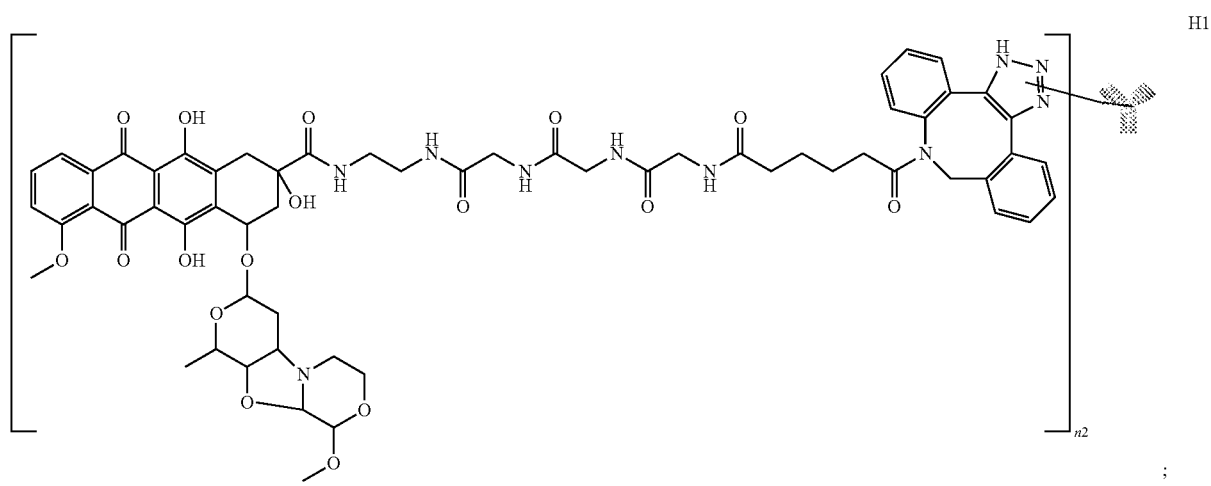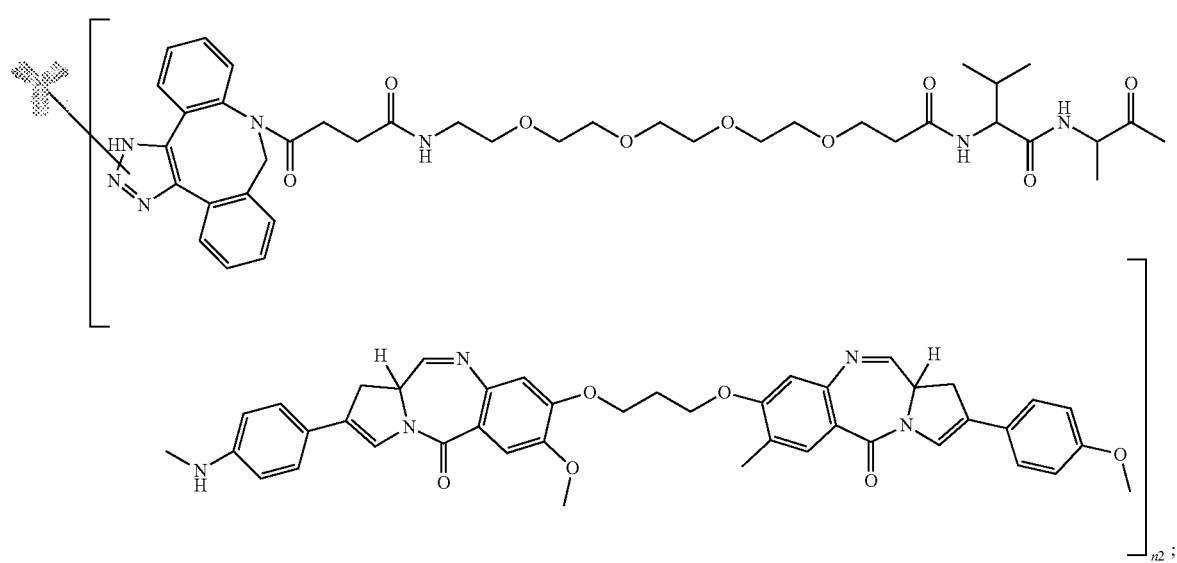

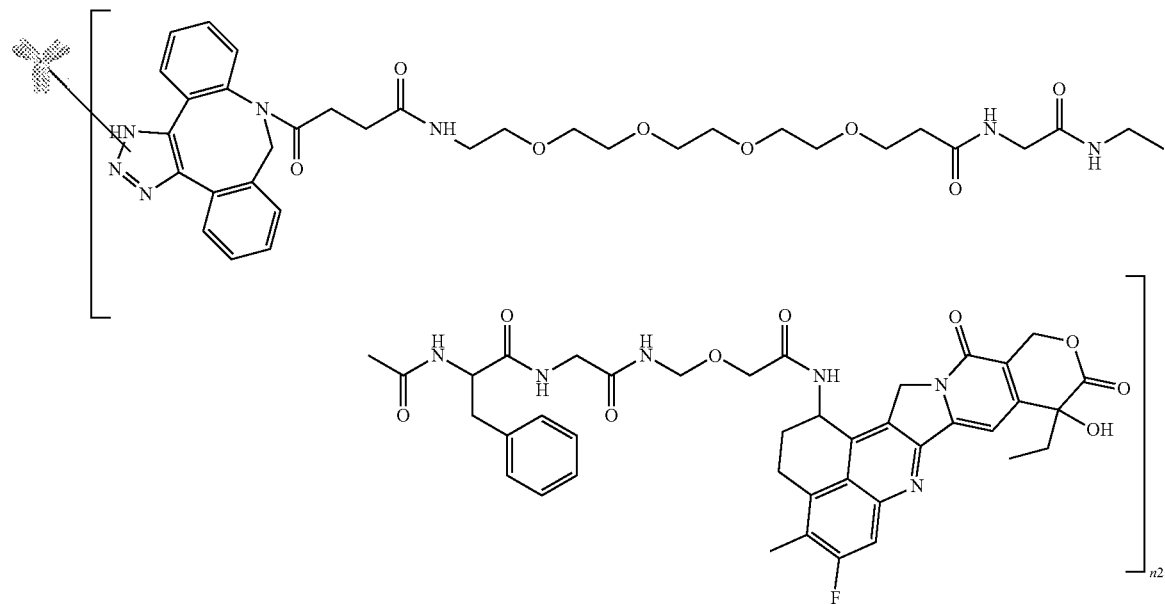
J1
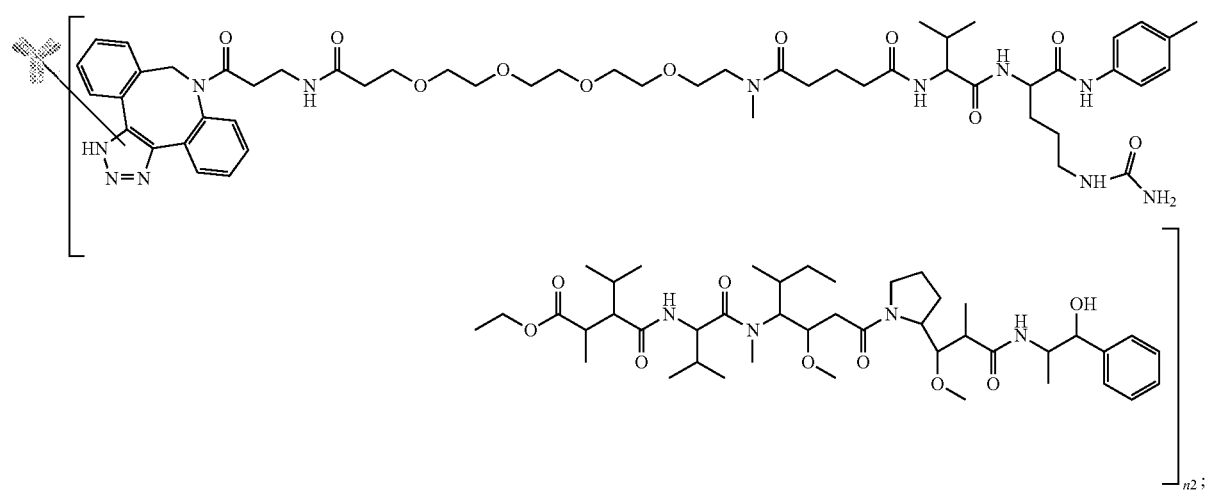
K1
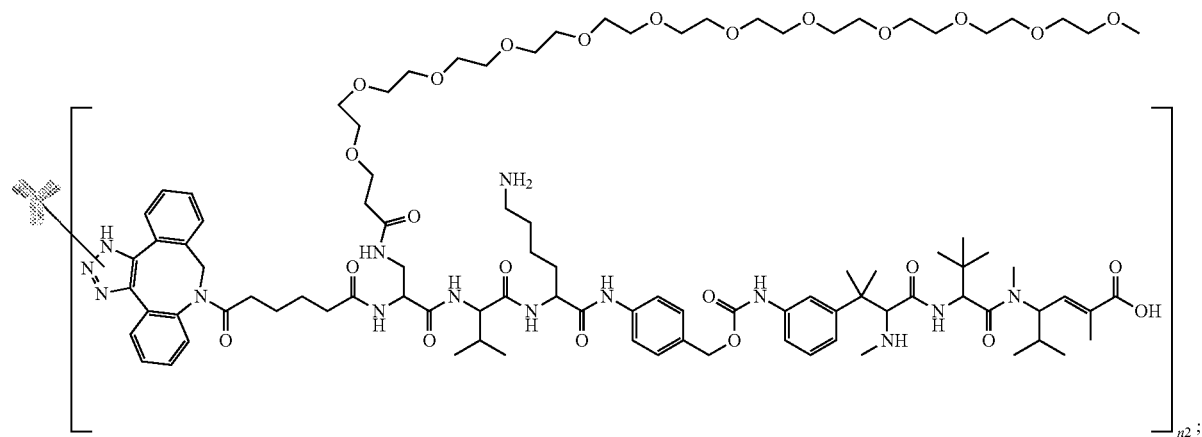
L1

M1
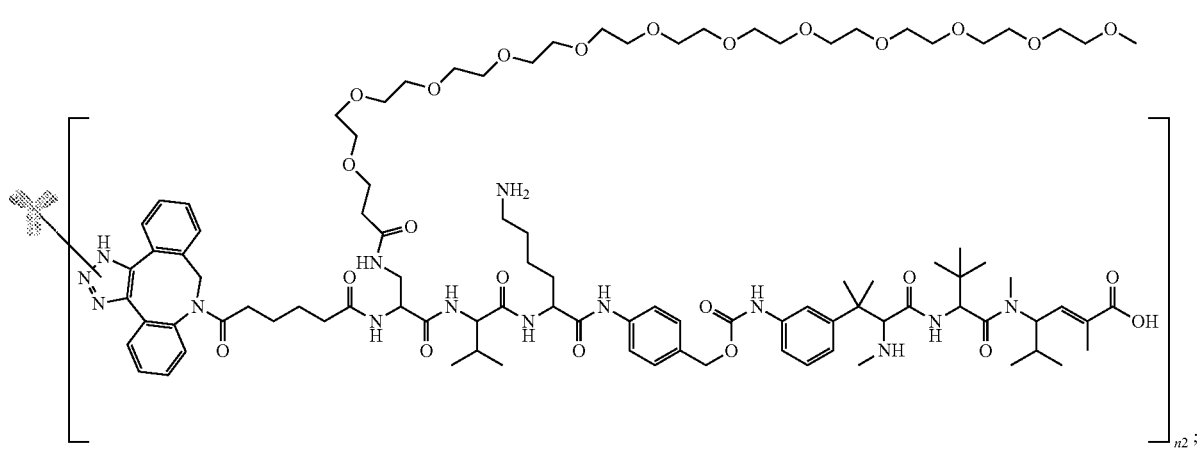
N1
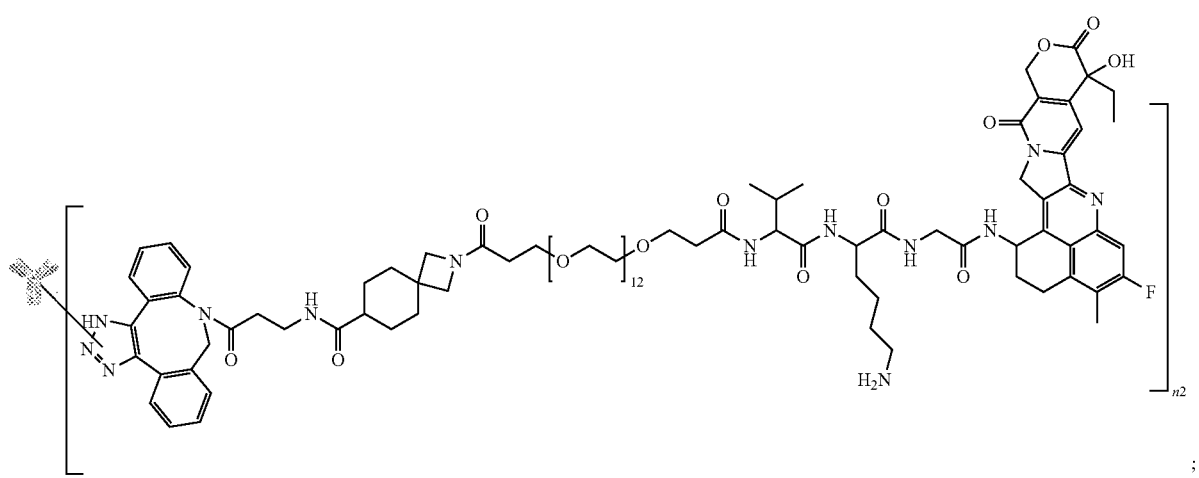
O1
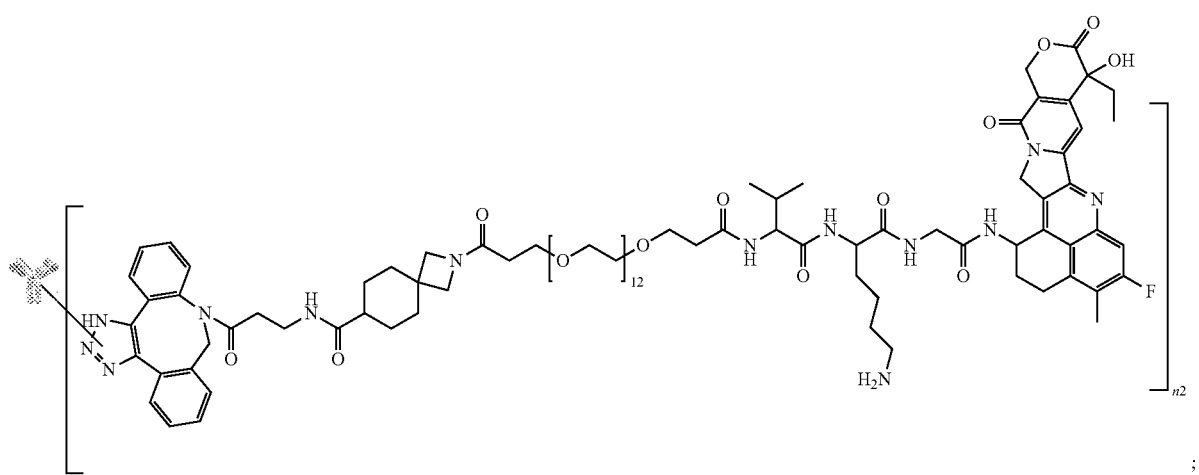

-continued
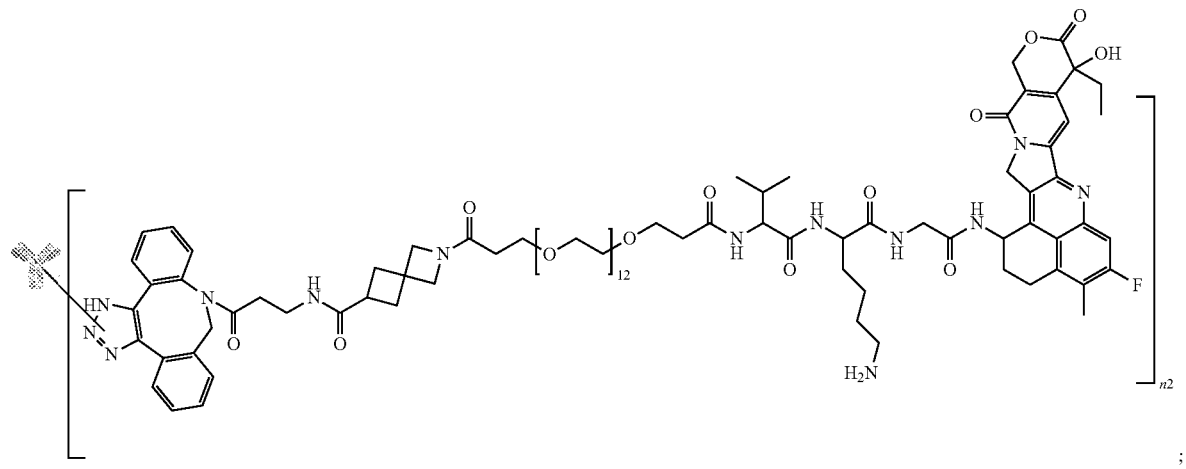
P1
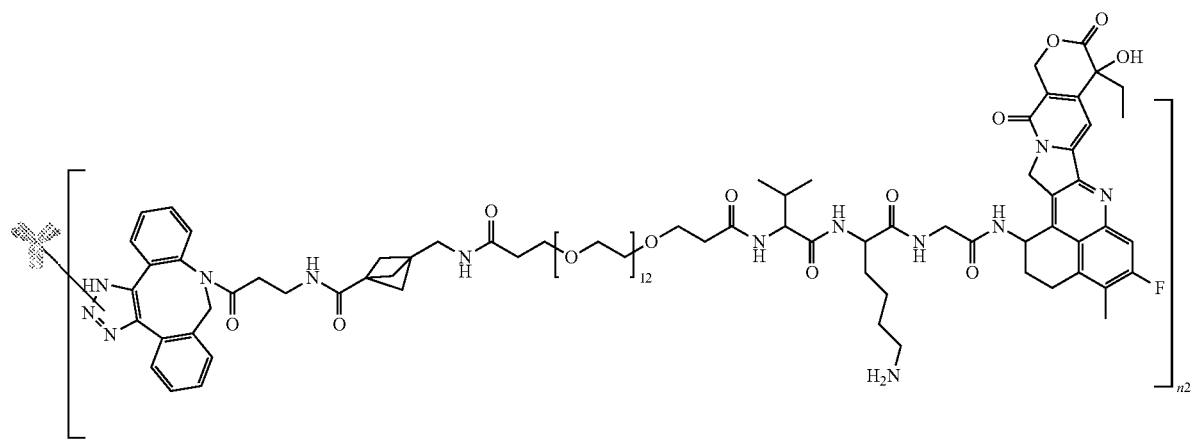
Q1

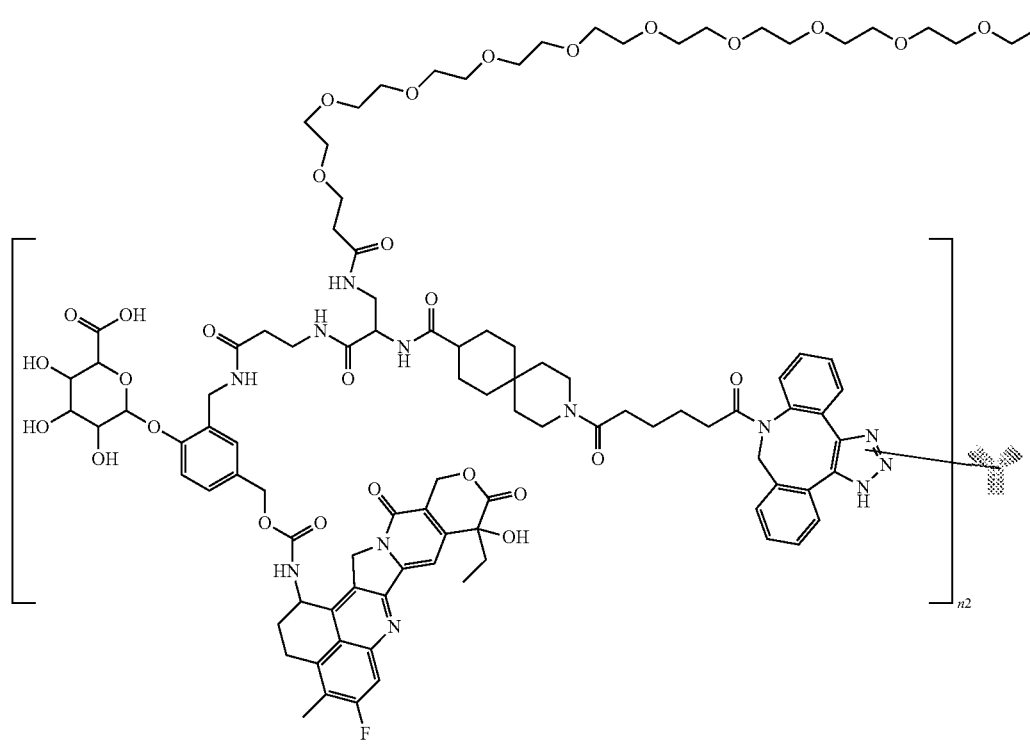
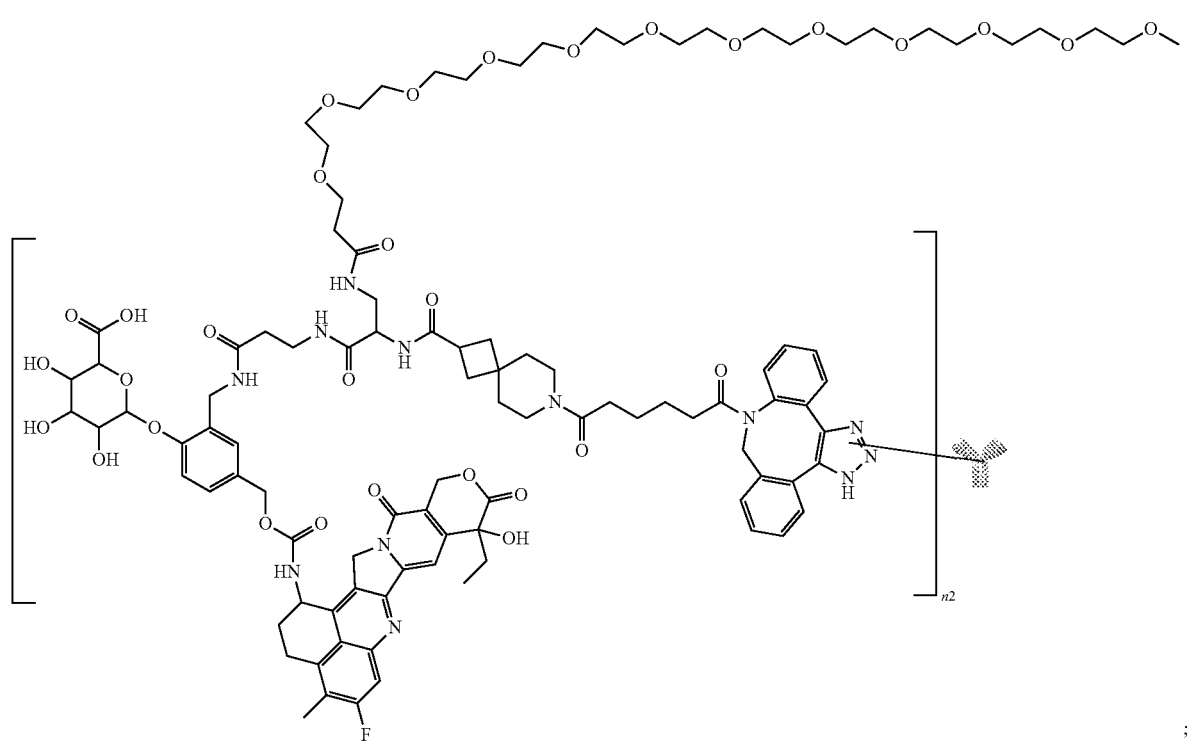

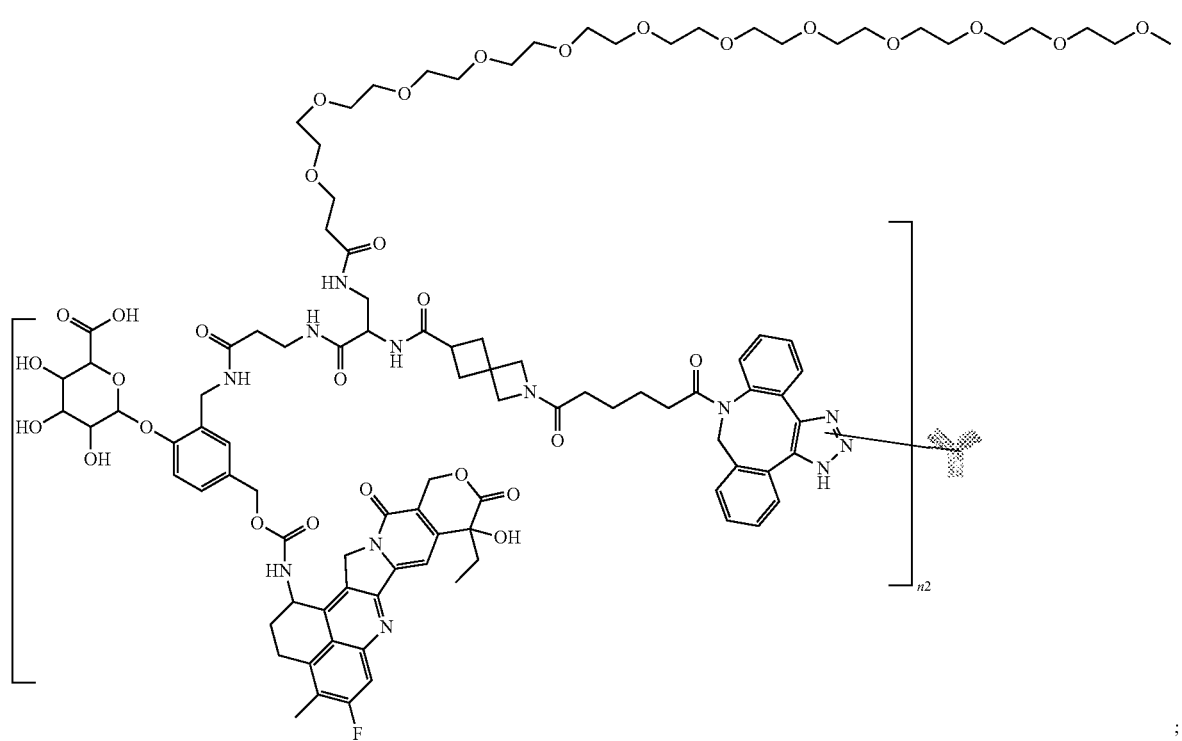
T1
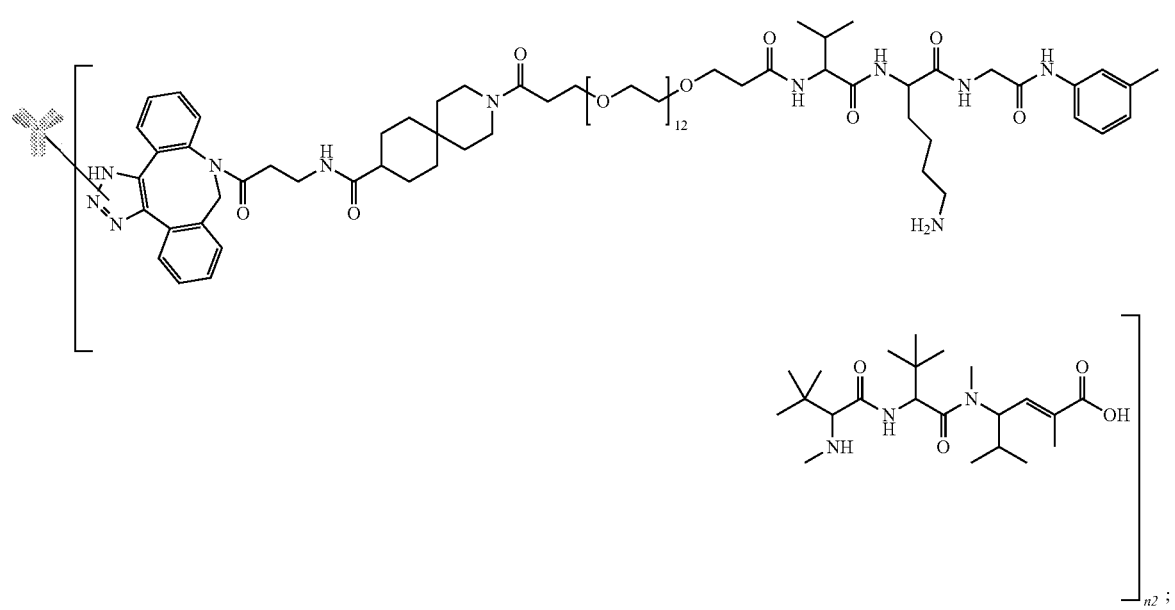
U1

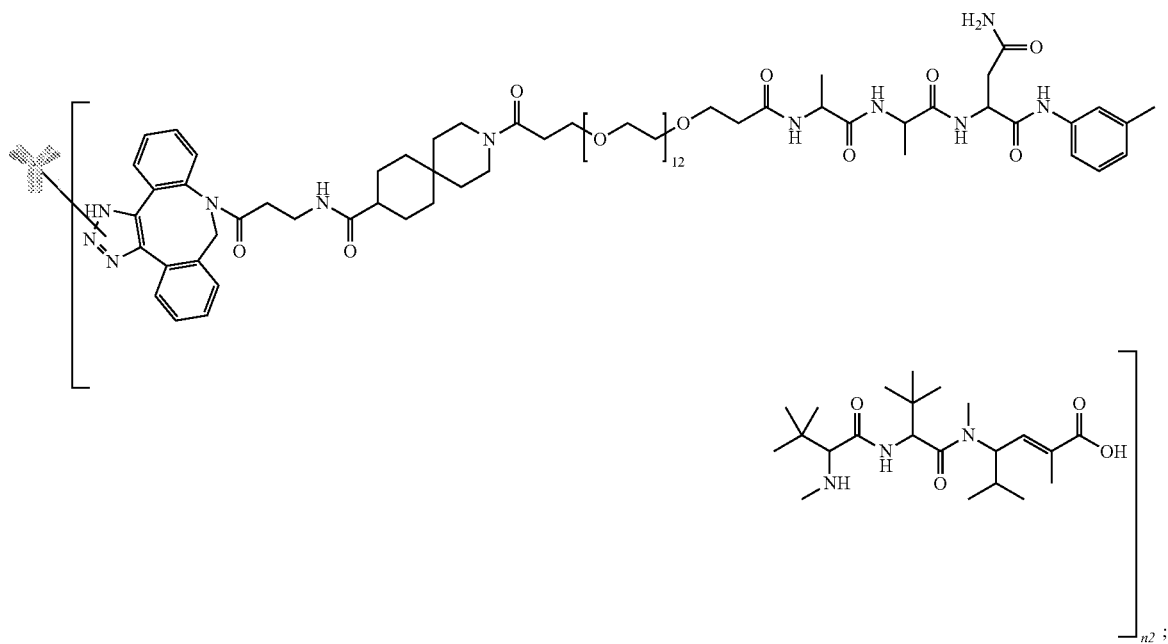
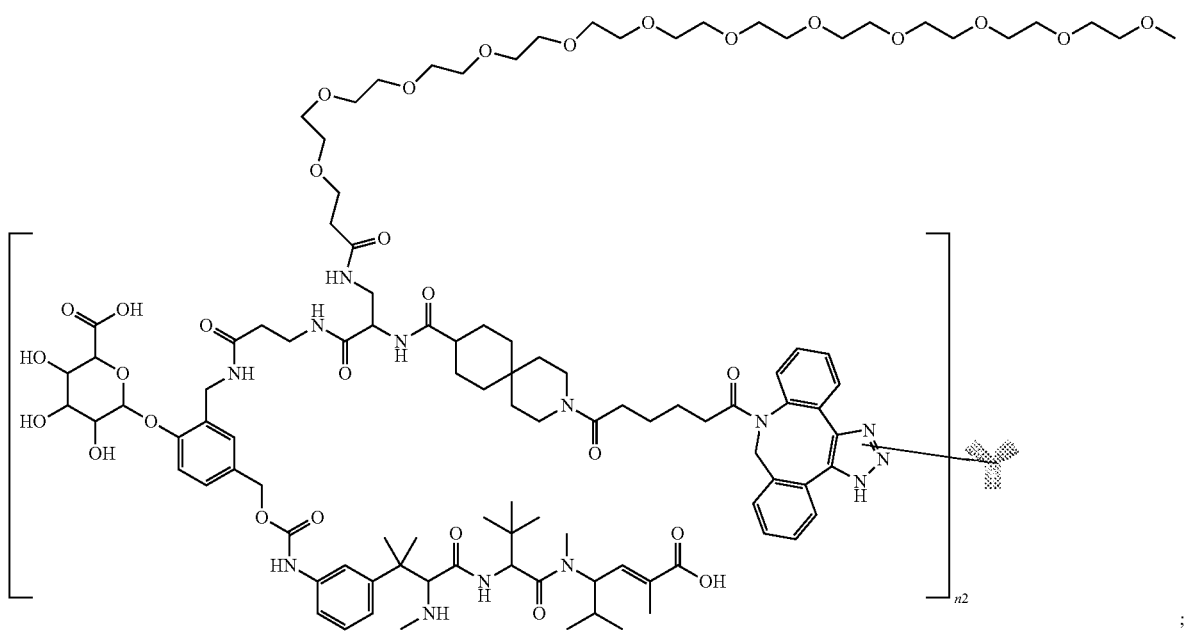

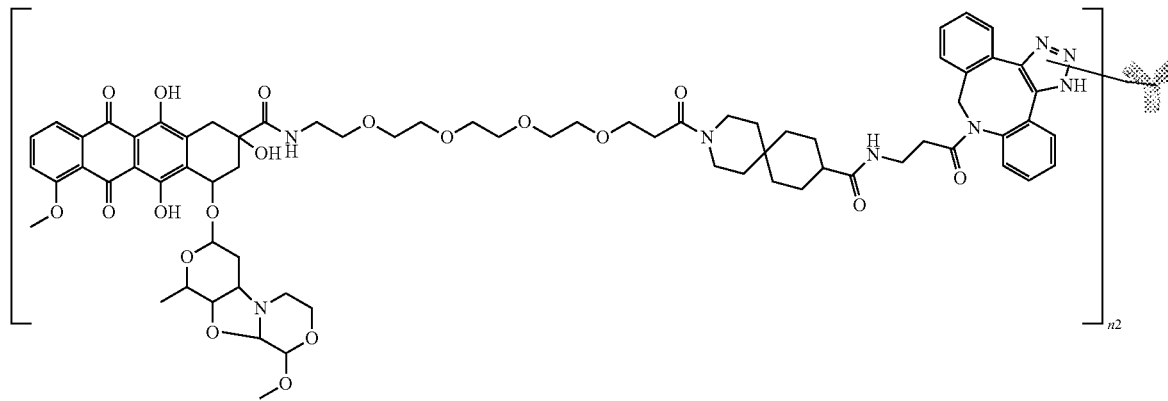
;
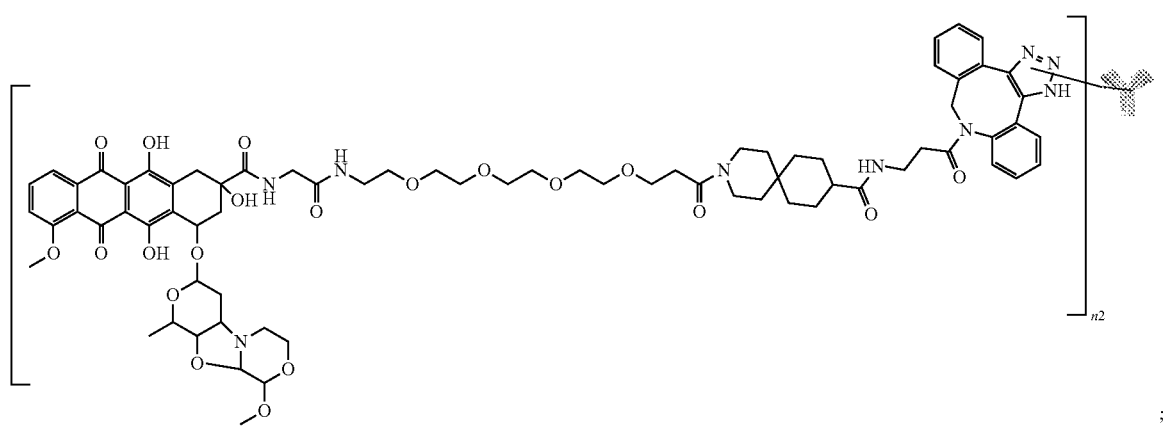
;
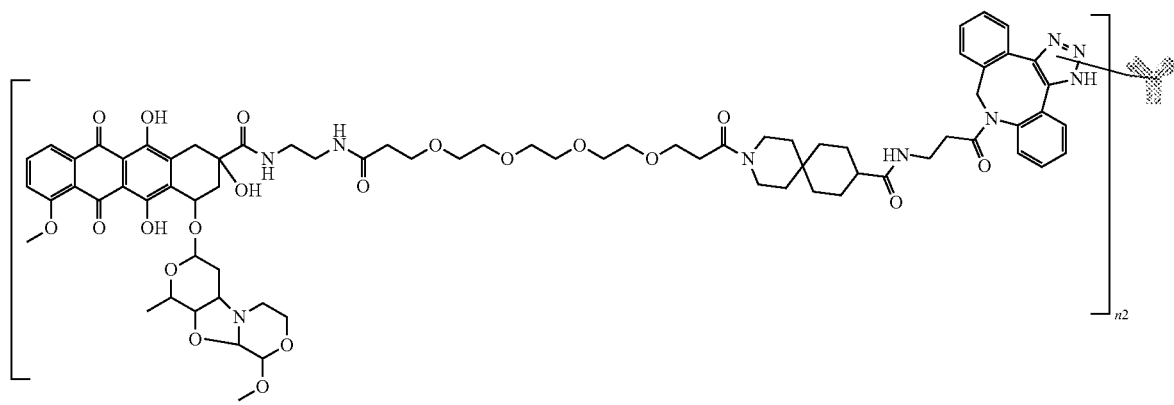
;

-continued
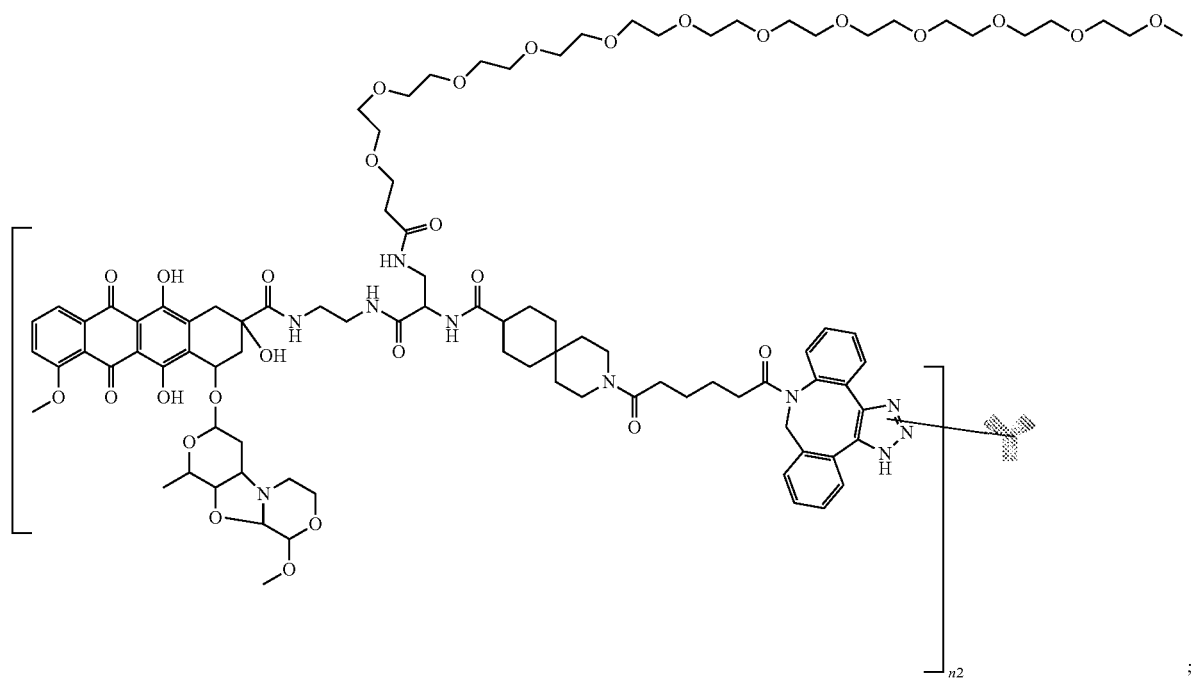
AA1
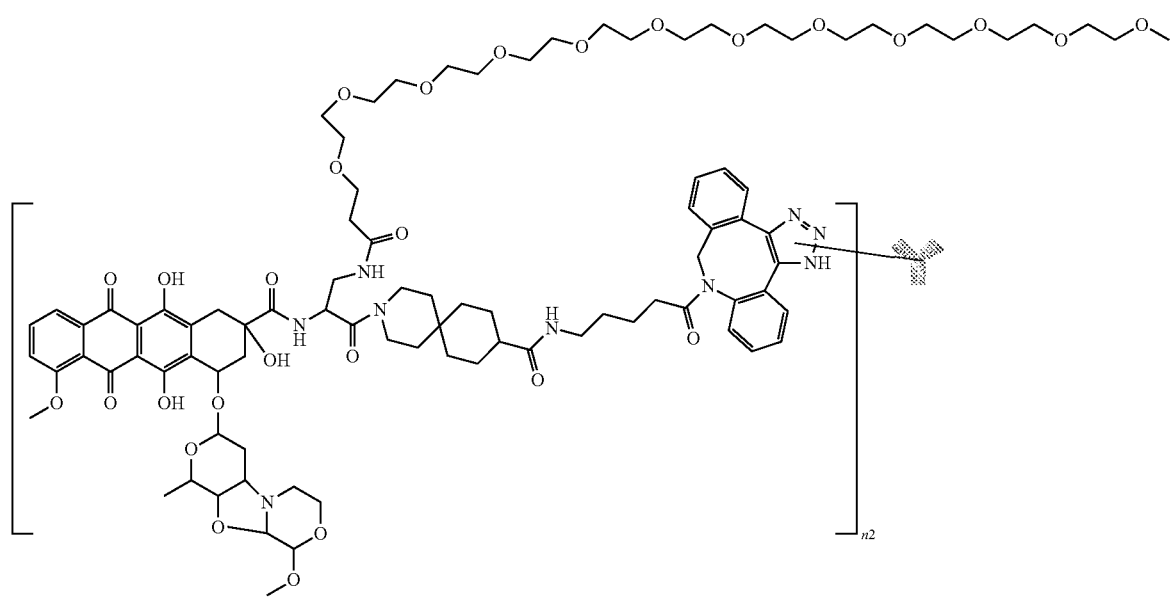
BB1

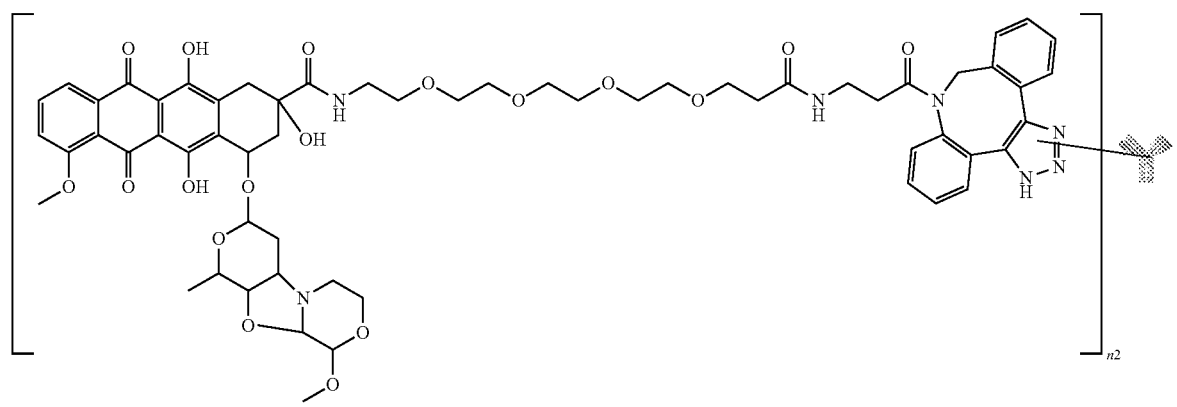
CC1
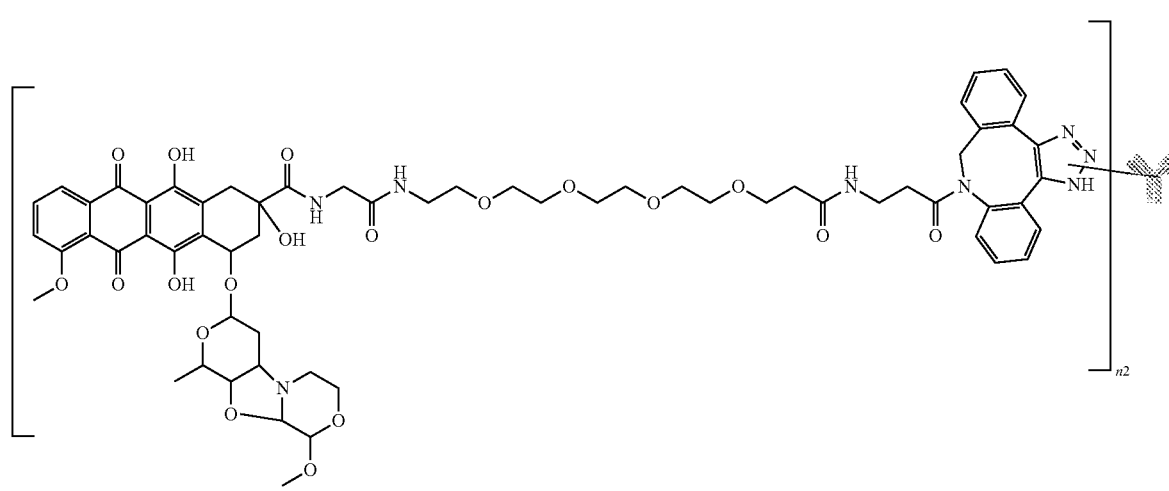
DD1
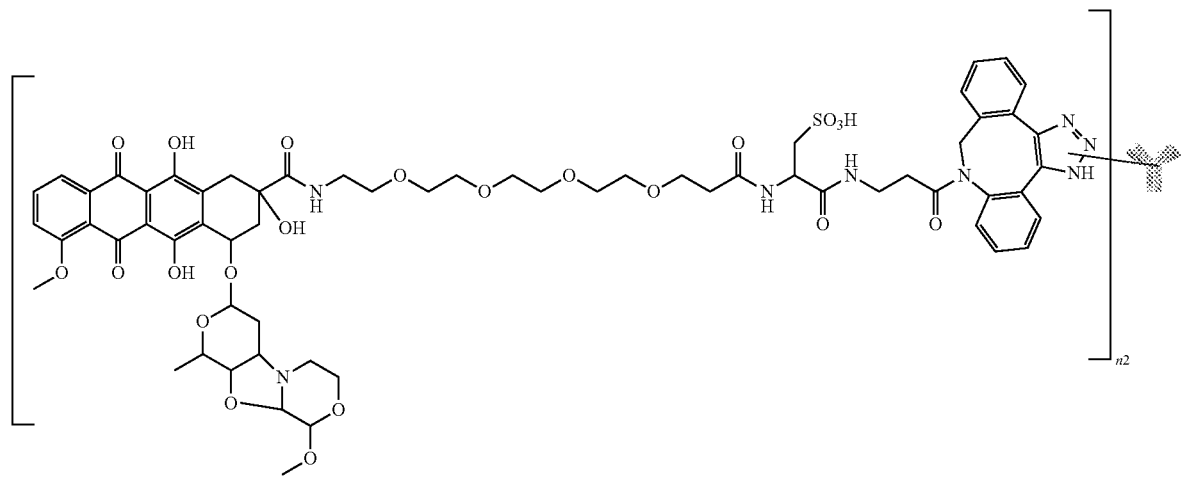
EE1

FF1
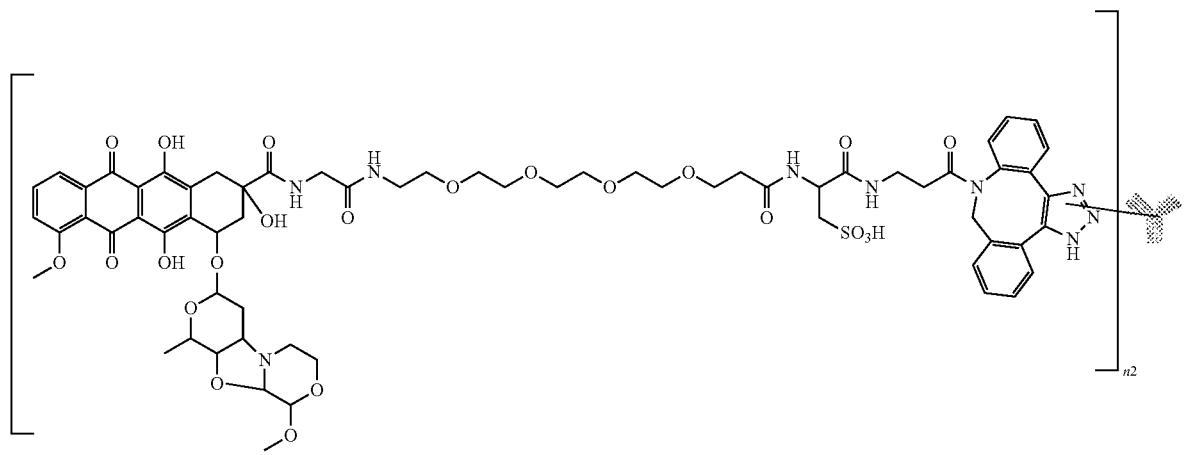
;
GG1
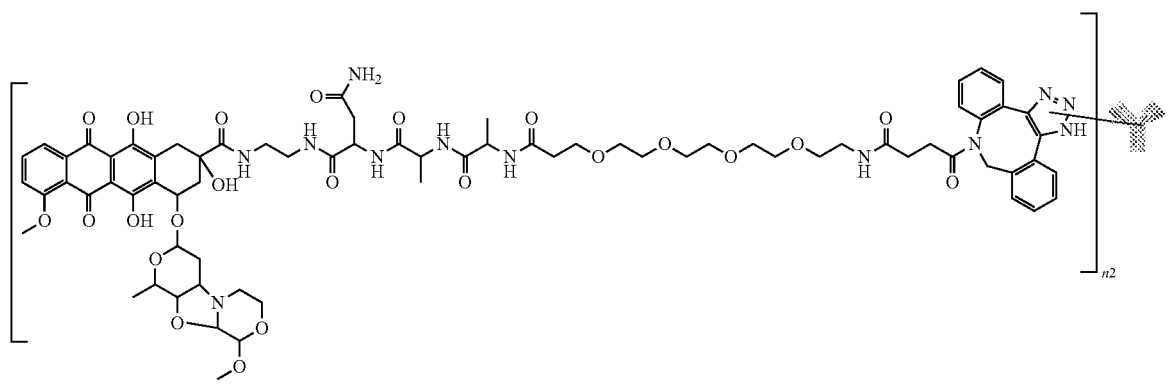
;
HH1
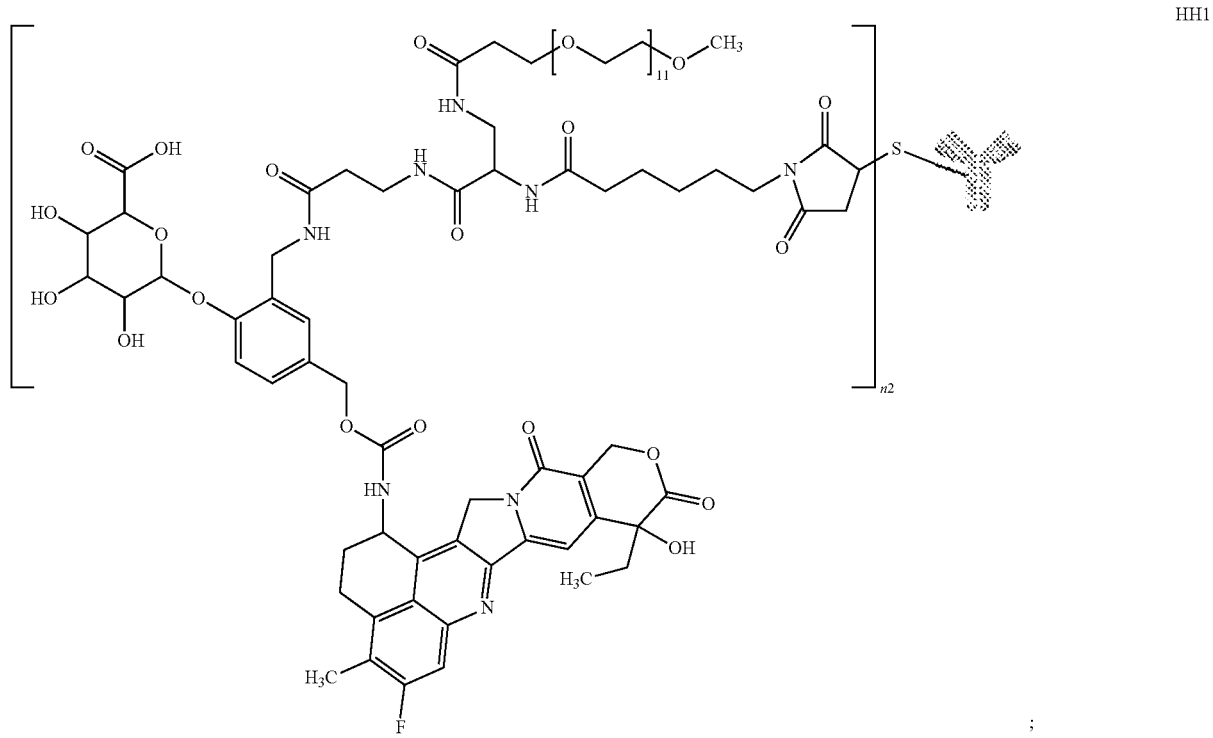
;

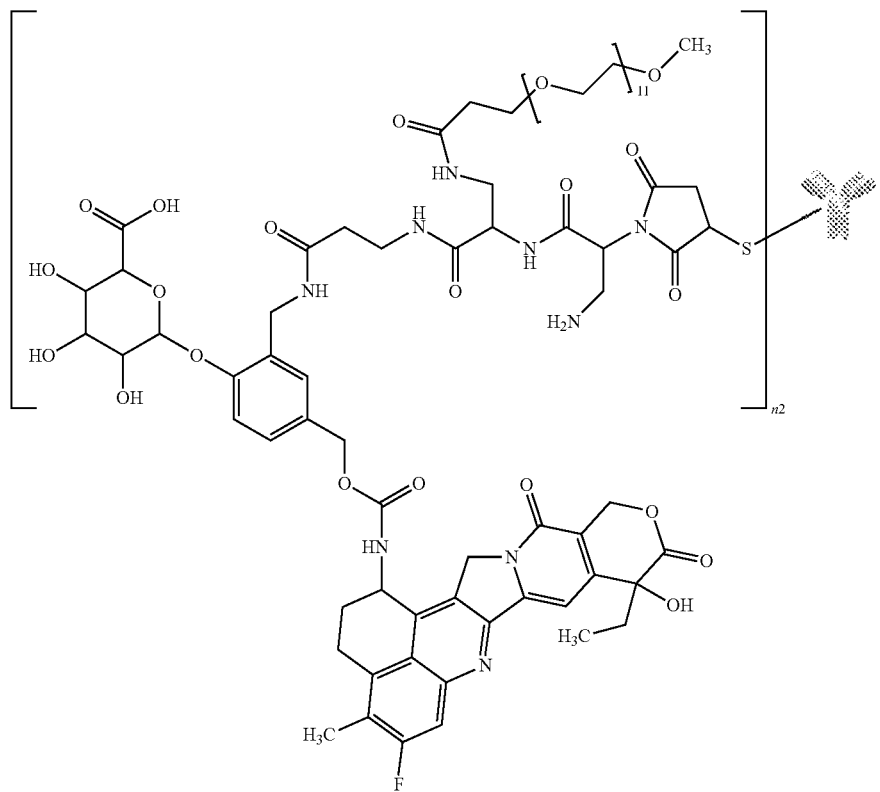
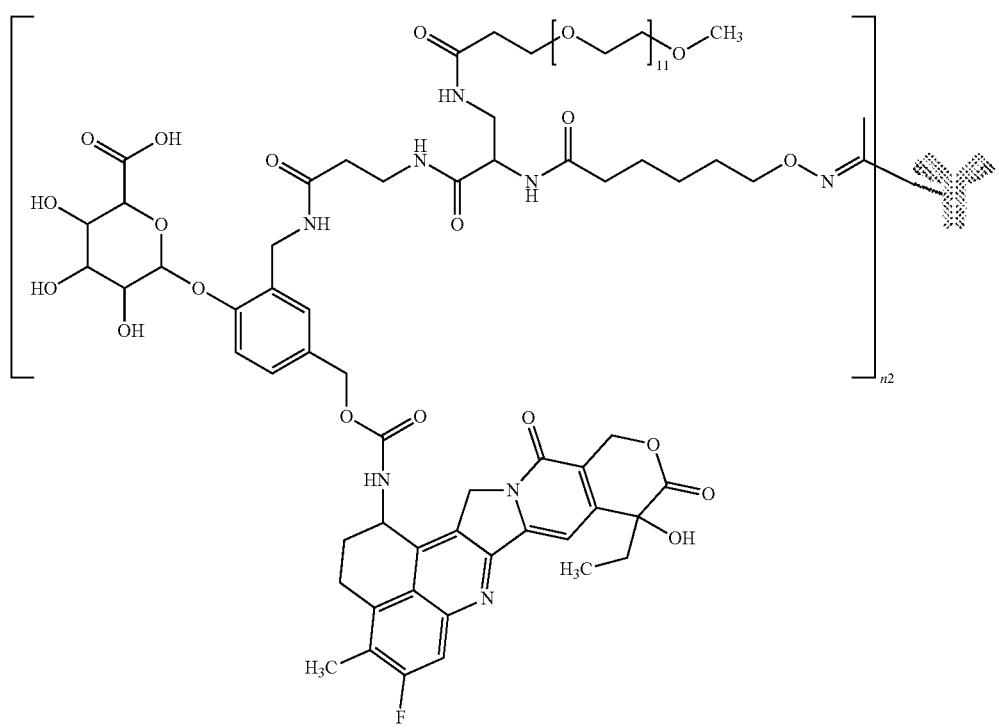

KK1
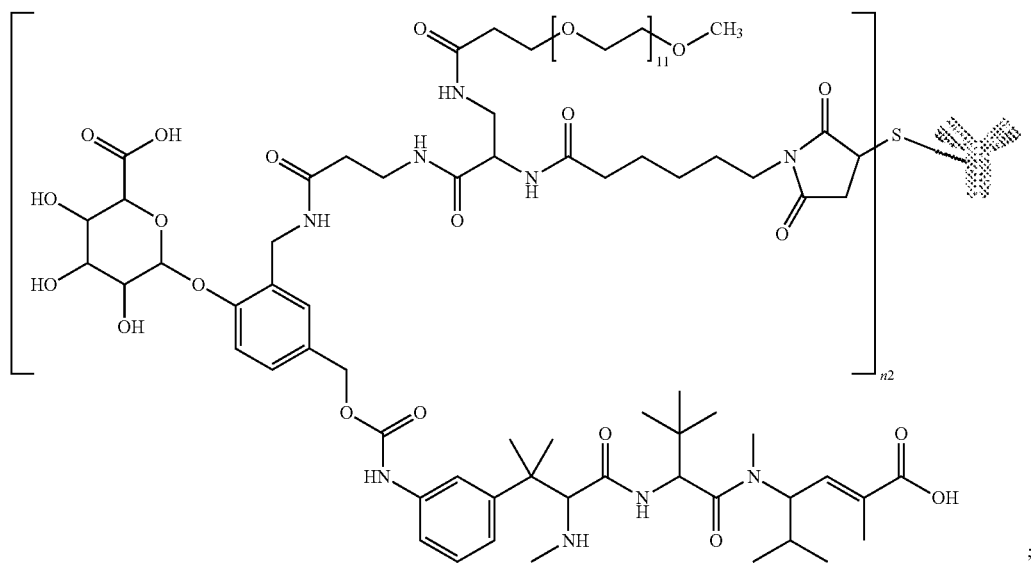
;
LL1
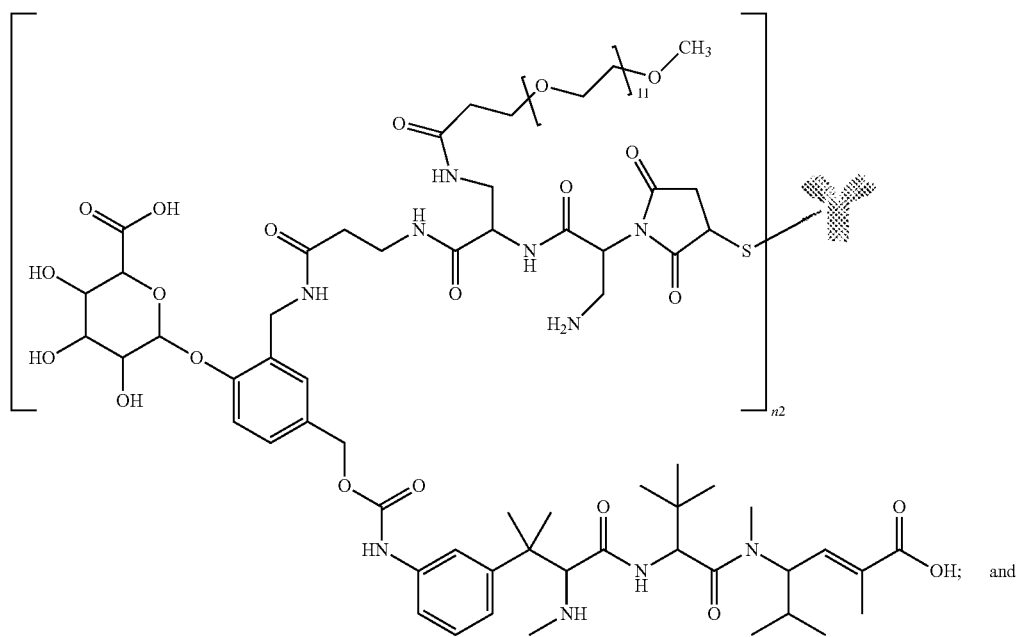
; and

-continued

MM1

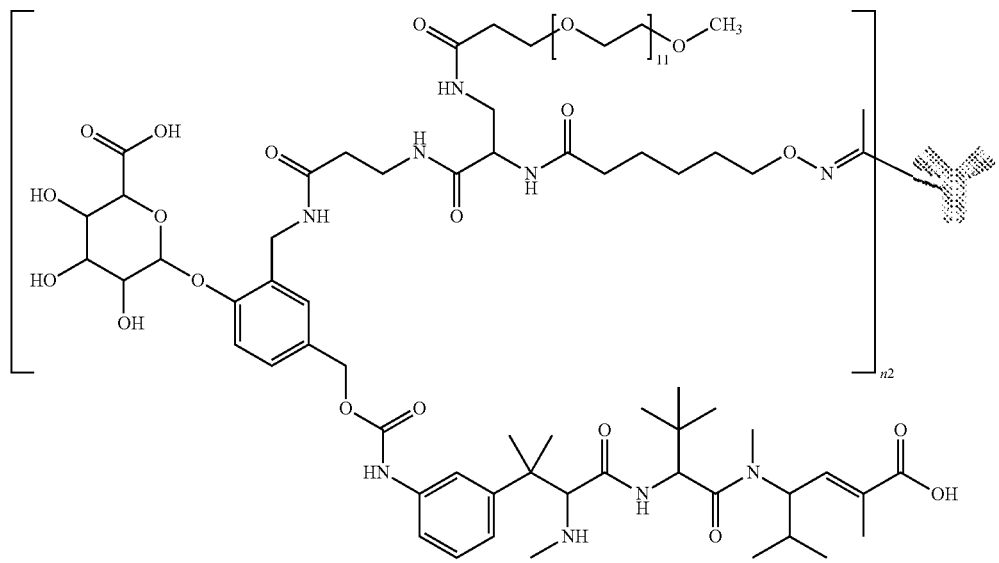

In any of the foregoing embodiments wherein the anti-ROR1 conjugate has a structure according to any one of Conjugates A-GG, the bracketed structure can be covalently bonded to one or more non-natural amino acids of the antibody, wherein the one or more non-natural amino acids are located at sites selected from the group consisting of: HC-F404, HC-Y180, HC-F241, LC-K42, and LC-E161, according to the Kabat or EU numbering scheme of Kabat. In some embodiments, the bracketed structure is covalently bonded to one or more non-natural amino acids at site HC-F404 of the antibody. In some embodiments, the bracketed structure is covalently bonded to one or more non-natural amino acids at site HC-Y180 of the antibody. In some embodiments, the bracketed structure is covalently bonded to one or more non-natural amino acids at site HC-F241 of the antibody. In some embodiments, the bracketed structure is covalently bonded to one or more non-natural amino acids at site LC-K42 of the antibody. In some embodiments, the bracketed structure is covalently bonded to one or more non-natural amino acids at site LC-E161 of the antibody. In some embodiments, the bracketed structures are covalently bonded to non-natural amino acids at sites HC-F404 and HC-Y180 of the antibody. In some embodiments, the bracketed structures are covalently bonded to non-natural amino acids at sites HC-F404, HC-Y180, and LC-K42 of the antibody. In some embodiments, the bracketed structures are covalently bonded to non-natural amino acids at sites HC-F404, HC-Y180, LC-K42, and LC-E161 of the antibody. In some embodiments, the bracketed structures are covalently bonded to non-natural amino acids at sites HC-F404, HC-Y180, and HC-F241 of the antibody. In some embodiments, the bracketed structures are covalently bonded to non-natural amino acids at sites HC-F404, HC-Y180, HC-F241, and LC-K42 of the antibody.

In particular embodiments, provided herein are anti-ROR1 conjugates according to any of the conjugates described herein wherein COMP indicates a residue of the non-natural amino acid according to Formula (30), below. In particular embodiments, provided herein are anti-ROR1 conjugates according to any of the conjugates described herein wherein COMP indicates a residue of the non-natural amino acid according to Formula (30), below, at heavy chain position 404 according to the EU numbering system. In particular embodiments, provided herein are anti-ROR1 conjugates according to any of the conjugates described herein wherein COMP indicates a residue of the non-natural amino acid according to Formula (30), below, at heavy chain position 180 according to the EU numbering system. In particular embodiments, provided herein are anti-ROR1 conjugates according to any of the conjugates described herein wherein COMP indicates a residue of the non-natural amino acid according to Formula (30), below, at heavy chain position 241 according to the EU numbering system. In particular embodiments, provided herein are anti-ROR1 conjugates according to any of the conjugates described herein wherein COMP indicates a residue of the non-natural amino acid according to Formula (30), below, at heavy chain position 222 according to the EU numbering system. In particular embodiments, provided herein are anti-ROR1 conjugates according to any of the conjugates described herein wherein COMP indicates a residue of the non-natural amino acid according to Formula (30), below, at light chain position 7 according to the Kabat or Chothia numbering system. In particular embodiments, provided herein are anti-ROR1 conjugates according to any of the conjugates described herein wherein COMP indicates a residue of the non-natural amino acid according to Formula (30), below, at light chain position 42 according to the Kabat or Chothia numbering system. In certain embodiments, PAY is selected from the group consisting of maytansine, hemiasterlin, amanitin, camptothecan, exatecan, exatecan derivative (DXd), SN-38, anthracycline, PNU-159682, PNU derivative (PNU-EDA), pyrrolobenzodiazepine (PBD), MMAF, and MMAE. In certain embodiments, PAY is maytansine. In certain embodiments, PAY is hemiasterlin. In certain embodiments, PAY is amanitin. In certain embodiments, PAY is exutecan. In certain embodiments, PAY is exatecan derivative Dxd. In certain embodiments, PAY is anthracycline. In certain embodiments, PAY is PNU-159682. In certain embodiments, PAY is PNU derivative (PNU-EDA). In certain embodiments, PAY is pyrrolobenzodiazepine. In certain embodiments, PAY is MMAF. In certain embodiments, PAY is MMAE.

(30)

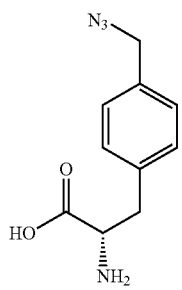

In particular embodiments, provided herein are anti-ROR1 conjugates according to any of the conjugates described herein wherein COMP indicates a residue of the non-natural amino acid according to Formula (56), below. In particular embodiments, provided herein are anti-ROR1 conjugates according to any of the conjugates described herein wherein COMP indicates a residue of the non-natural amino acid according to Formula (56), below, at heavy chain position 404 according to the EU numbering system. In particular embodiments, provided herein are anti-ROR1 conjugates according to any of the conjugates described herein wherein COMP indicates a residue of the non-natural amino acid according to Formula (56), below, at heavy chain position 180 according to the EU numbering system. In particular embodiments, provided herein are anti-ROR1 conjugates according to any of the conjugates described herein wherein COMP indicates a residue of the non-natural amino acid according to Formula (56), below, at heavy chain position 241 according to the EU numbering system. In particular embodiments, provided herein are anti-ROR1 conjugates according to any of the conjugates described herein wherein COMP indicates a residue of the non-natural amino acid according to Formula (56), below, at heavy chain position 222 according to the EU numbering system. In particular embodiments, provided herein are anti-ROR1 conjugates according to any of the conjugates described herein wherein COMP indicates a residue of the non-natural amino acid according to Formula (56), below, at light chain position 7 according to the Kabat or Chothia numbering system. In particular embodiments, provided herein are anti-ROR1 conjugates according to any of the conjugates described herein wherein COMP indicates a residue of the non-natural amino acid according to Formula (56), below, at light chain position 42 according to the Kabat or Chothia numbering system. In certain embodiments, PAY is selected from the group consisting of maytansine, hemiasterlin, amanitin, camptothecan, exatecan, exatecan derivative (DXd), SN-38, anthracycline, PNU-159682, PNU derivative (PNU-EDA), pyrrolobenzodiazepine (PBD), MMAF, and MMAE. In certain embodiments, PAY is maytansine. In certain embodiments, PAY is hemiasterlin. In certain embodiments, PAY is amanitin. In certain embodiments, PAY is exatecan. In certain embodiments, PAY is exatecan derivative (Dxd). In certain embodiments, PAY is deruxtecan. In certain embodiments, PAY is anthracycline. In certain embodiments, PAY is PNU-159682. In certain embodiments, PAY is PNU derivative (PNU-EDA). In certain embodiments, PAY is pyrrolobenzodiazepine. In certain embodiments, PAY is MMAF. In certain embodiments, PAY is MMAE.

(56)

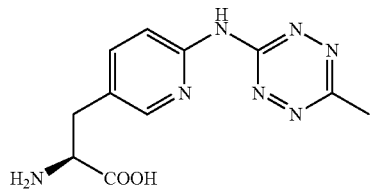

In particular embodiments, provided herein are anti-ROR1 conjugates according to any of the conjugates described herein wherein COMP indicates a non-natural amino acid residue of para-azido-L-phenylalanine. In particular embodiments, provided herein are anti-ROR1 conjugates according to any of the conjugates described herein wherein COMP indicates the non-natural amino acid residue para-azido-phenylalanine at heavy chain position 404 according to the EU numbering system. In particular embodiments, provided herein are anti-ROR1 conjugates according to any of the conjugates described herein wherein COMP indicates a non-natural amino acid residue of para-azido-L-phenylalanine at heavy chain position 180 according to the EU numbering system. In particular embodiments, provided herein are anti-ROR1 conjugates according to any of the conjugates described herein wherein COMP indicates a non-natural amino acid residue para-azido-L-phenylalanine at heavy chain position 241 according to the EU numbering system. In particular embodiments, provided herein are anti-ROR1 conjugates according to any of the conjugates described herein wherein COMP indicates a non-natural amino acid residue para-azido-L-phenylalanine at heavy chain position 222 according to the EU numbering system. In particular embodiments, provided herein are anti-ROR1 conjugates according to any of the conjugates described herein wherein COMP indicates a non-natural amino acid residue para-azido-L-phenylalanine at light chain position 7 according to the Kabat or Chothia numbering system. In particular embodiments, provided herein are anti-ROR1 conjugates according to any of the conjugates described herein wherein COMP indicates a non-natural amino acid residue para-azido-L-phenylalanine at light chain position 42 according to the Kabat or Chothia numbering system. In certain embodiments, PAY is selected from the group consisting of maytansine, hemiasterlin, amanitin, camptothecan, exatecan, exatecan derivative (DXd), SN-38, anthracycline, PNU-159682, pyrrolobenzodiazepine (PBD), MMAF, and MMAE. In certain embodiments, PAY is maytansine. In certain embodiments, PAY is hemiasterlin. In certain embodiments, PAY is amanitin. In certain embodiments, PAY is exatecan. In certain embodiments, PAY is exatecan derivative (Dxd). In certain embodiments, PAY is anthracycline. In certain embodiments, PAY is PNU-159682. In certain embodiments, PAY is PNU derivative (PNU-EDA). In certain embodiments, PAY is pyrrolobenzodiazepine. In certain embodiments, PAY is MMAF. In certain embodiments, PAY is MMAE.

3. Payloads

In addition to the payloads described above, the molecular payload can be any molecular entity that one of skill in the art might desire to conjugate to the polypeptide. In certain embodiments, the payload is a therapeutic moiety. In such embodiment, the antibody conjugate can be used to target the therapeutic moiety to its molecular target. In certain embodiments, the payload is a labeling moiety. In such embodiments, the antibody conjugate can be used to detect binding of the polypeptide to its target. In certain embodiments, the payload is a cytotoxic moiety. In such embodiments, the antibody conjugate can be used target the cytotoxic moiety to a diseased cell, for example a cancer cell, to initiate destruction or elimination of the cell. Conjugates comprising other molecular payloads apparent to those of skill in the art are within the scope of the conjugates described herein.

In certain embodiments, an antibody conjugate can have a payload selected from the group consisting of a label, a dye, a polymer, a water-soluble polymer, polyethylene glycol, a derivative of polyethylene glycol, a photocrosslinker, a cytotoxic compound, a radionuclide, a drug, an affinity label, a photoaffinity label, a reactive compound, a resin, a second protein or polypeptide or polypeptide analog, an antibody or antibody fragment, a metal chelator, a cofactor, a fatty acid, a carbohydrate, a polynucleotide, a DNA, a RNA, an antisense polynucleotide, a peptide, a water-soluble dendrimer, a cyclodextrin, an inhibitory ribonucleic acid, a biomaterial, a nanoparticle, a spin label, a fluorophore, a metal-containing moiety, a radioactive moiety, a novel functional group, a group that covalently or noncovalently interacts with other molecules, a photocaged moiety, a photoisomerizable moiety, biotin, a derivative of biotin, a biotin analogue, a moiety incorporating a heavy atom, a chemically cleavable group, a photocleavable group, an elongated side chain, a carbon-linked sugar, a redox-active agent, an amino thioacid, a toxic moiety, an isotopically labeled moiety, a biophysical probe, a phosphorescent group, a chemiluminescent group, an electron dense group, a magnetic group, an intercalating group, a chromophore, an energy transfer agent, a biologically active agent, a detectable label, a small molecule, or any combination thereof. In an embodiment, the payload is a label, a dye, a polymer, a cytotoxic compound, a radionuclide, a drug, an affinity label, a resin, a protein, a polypeptide, a polypeptide analog, an antibody, antibody fragment, a metal chelator, a cofactor, a fatty acid, a carbohydrate, a polynucleotide, a DNA, a RNA, a peptide, a fluorophore, or a carbon-linked sugar. In another embodiment, the payload is a label, a dye, a polymer, a drug, an antibody, antibody fragment, a DNA, an RNA, or a peptide.

Useful drug payloads include any cytotoxic or cytostatic agent. Useful classes of cytotoxic agents include, for example, antitubulin agents, auristatins, DNA minor groove binders, DNA replication inhibitors, alkylating agents (e.g., platinum complexes such as cis-platin, mono(platinum), bis(platinum) and tri-nuclear platinum complexes and carboplatin), anthracyclines, antibiotics, antifolates, antimetabolites, calmodulin inhibitors, chemotherapy sensitizers, duocarmycins, etoposides, fluorinated pyrimidines, ionophores, lexitropsins, maytansinoids, nitrosoureas, platinols, pore-forming compounds, purine antimetabolites, puromycins, radiation sensitizers, rapamycins, steroids, taxanes, topoisomerase inhibitors, vinca alkaloids, or the like.

Individual cytotoxic agents include, for example, an androgen, anthramycin (AMC), asparaginase, 5-azacytidine, azathioprine, bleomycin, busulfan, buthionine sulfoximine, calicheamicin, calicheamicin derivatives, camptothecin, carboplatin, carmustine (BSNU), CC-1065, chlorambucil, cis-platin, colchicine, cyclophosphamide, cytarabine, cytidine arabinoside, cytochalasin B, dacarbazine, dactinomycin (formerly actinomycin), daunorubicin, decarbazine, DM1, DM4, docetaxel, doxorubicin, etoposide, an estrogen, 5-fluordeoxyuridine, 5-fluorouracil, gemcitabine, gramicidin D, hydroxyurea, idarubicin, ifosfamide, irinotecan, lomustine (CCNU), maytansine, mechlorethamine, melphalan, 6-mercaptopurine, methotrexate, mithramycin, mitomycin C, mitoxantrone, nitroimidazole, paclitaxel, palytoxin, plicamycin, procarbizine, rhizoxin, streptozotocin, tenoposide, 6-thioguanine, thioTEPA, topotecan, vinblastine, vincristine, vinorelbine, VP-16 and VM-26.

In some embodiments, suitable cytotoxic agents include, for example, DNA minor groove binders (e.g., enediynes and lexitropsins, a CBI compound; see also U.S. Pat. No. 6,130,237), duocarmycins, taxanes (e.g., paclitaxel and docetaxel), puromycins, vinca alkaloids, CC-1065, SN-38, topotecan, morpholino-doxorubicin, rhizoxin, cyanomorpholino-doxorubicin, echinomycin, combretastatin, netropsin, epothilone A and B, estramustine, cryptophycins, cemadotin, maytansinoids, discodermolide, eleutherobin, and mitoxantrone.

In some embodiments, the payload is an anti-tubulin agent. Examples of anti-tubulin agents include, but are not limited to, taxanes (e.g., Taxol® (paclitaxel), Taxotere® (docetaxel)), T67 (Tularik) and vinca alkyloids (e.g., vincristine, vinblastine, vindesine, and vinorelbine). Other antitubulin agents include, for example, baccatin derivatives, taxane analogs, epothilones (e.g., epothilone A and B), nocodazole, colchicine and colcimid, estramustine, cryptophycins, cemadotin, maytansinoids, combretastatins, discodermolide, and eleutherobin.

In certain embodiments, the cytotoxic agent is a maytansinoid, another group of anti-tubulin agents. For example, in specific embodiments, the maytansinoid can be maytansine or DM1 (ImmunoGen, Inc.; see also Chari et al., 1992, Cancer Res. 52:127-131).

In some embodiments, the payload is an auristatin, such as auristatin E or a derivative thereof. For example, the auristatin E derivative can be an ester formed between auristatin E and a keto acid. For example, auristatin E can be reacted with paraacetyl benzoic acid or benzoylvaleric acid to produce AEB and AEVB, respectively. Other typical auristatin derivatives include AFP (auristatin phenylalanine phenylenediamine), MMAF (monomethyl auristatin F), and MMAE (monomethyl auristatin E). The synthesis and structure of auristatin derivatives are described in U.S. Patent Application Publication Nos. 2003-0083263, 2005-0238649 and 2005-0009751; International Patent Publication No. WO 04/010957, International Patent Publication No. WO 02/088172, and U.S. Pat. Nos. 6,323,315; 6,239,104; 6,034,065; 5,780,588; 5,665,860; 5,635,483; 5,599,902; 5,554,725; 5,530,097; 5,521,284; 5,504,191; 5,410,024; 5,076,973; 4,986,988; 4,978,744; 4,879,278; 4,816,444; and 4,486,414.

In some embodiments, the payload is a hemiasterlin. Hemiasterlins suitable for use in the antibody-drug conjugates described herein are described, for example, in International Patent Publication No. WO 2016/2016/123582, which is incorporated herein by reference in its entirety.

In some embodiments, the payload is not a radioisotope. In some embodiments, the payload is not radioactive.

In some embodiments, the payload is an antimetabolite. The antimetabolite can be, for example, a purine antagonist (e.g., azothioprine or mycophenolate mofetil), a dihydrofolate reductase inhibitor (e.g., methotrexate), acyclovir, gangcyclovir, zidovudine, vidarabine, ribavarin, azidothymidine, cytidine arabinoside, amantadine, dideoxyuridine, iododeoxyuridine, poscarnet, or trifluridine.

In other embodiments, the payload is tacrolimus, cyclosporine, FU506 or rapamycin. In further embodiments, the Drug is aldesleukin, alemtuzumab, alitretinoin, allopurinol, altretamine, amifostine, anastrozole, arsenic trioxide, bexarotene, bexarotene, calusterone, capecitabine, celecoxib, cladribine, Darbepoetin alfa, Denileukin diftitox, dexrazoxane, dromostanolone propionate, epirubicin, Epoetin alfa, estramustine, exemestane, Filgrastim, floxuridine, fludarabine, fulvestrant, gemcitabine, gemtuzumab ozogamicin (MYLOTARG), goserelin, idarubicin, ifosfamide, imatinib mesylate, Interferon alfa-2a, irinotecan, letrozole, leucovorin, levamisole, meclorethamine or nitrogen mustard, megestrol, mesna, methotrexate, methoxsalen, mitomycin C, mitotane, nandrolone phenpropionate, oprelvekin, oxaliplatin, pamidronate, pegademase, pegaspargase, pegfilgrastim, pentostatin, pipobroman, a pladienolide, plicamycin, porfimer sodium, procarbazine, quinacrine, rasburicase, Rituximab, Sargramostim, streptozocin, tamoxifen, temozolomide, teniposide, testolactone, thioguanine, toremifene, Tositumomab, Trastuzumab (HERCEPTIN), tretinoin, uracil mustard, valrubicin, vinblastine, vincristine, vinorelbine or zoledronate.

Other useful drug payloads include chemical compounds useful in the treatment of cancer. Examples of chemotherapeutic agents include Erlotinib (TARCEVA®, Genentech/OSI Pharm.), Bortezomib (VELCADE®, Millennium Pharm.), Fulvestrant (FASLODEX®, AstraZeneca), Sutent (SU11248, Pfizer), Letrozole (FEMARA®, Novartis), Imatinib mesylate (GLEEVEC®, Novartis), PTK787/ZK 222584 (Novartis), Oxaliplatin (Eloxatin®, Sanofi), 5-FU (5-fluorouracil), Leucovorin, Rapamycin (Sirolimus, RAPAMUNE®, Wyeth), Lapatinib (TYKERB 0, GSK572016, Glaxo Smith Kline), Lonafarnib (SCH 66336), Sorafenib (BAY43-9006, Bayer Labs), and Gefitinib (IRESSA®, AstraZeneca), AG1478, AG1571 (SU 5271; Sugen), alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including the synthetic analog topotecan); bryostatin; callystatin; CC-1065 (including its adozelesin, carzelesin and bizelesin synthetic analogs); cryptophycins (particularly cryptophycin 1 and cryptophycin 8); dolastatin; duocarmycin (including the synthetic analogs, KW-2189 and CB1-TM1); eleutherobin; pancratistatin; a sarcodictyin; spongistatin; nitrogen mustards such as chlorambucil, chlomaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially uncialamycin, calicheamicin gammaII, and calicheamicin omegaII (Angew Chem. Intl. Ed. Engl. (1994) 33:183-186); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® (doxorubicin), morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pladienolide B, pteropterin, trimetrexate; purine analogs such as fludarabine, 6-mercaptopurine, thiamniprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2''-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® (paclitaxel; Bristol-Myers Squibb Oncology, Princeton, N.J.), ABRAXANE® (Cremophor-free), albumin-engineered nanoparticle formulations of paclitaxel (American Pharmaceutical Partners, Schaumberg, Ill.), and TAXOTERE® (doxetaxel; Rhone-Poulenc Rorer, Antony, France); chloranmbucil; GEMZAR® (gemcitabine); 6-thioguanine; mercaptopurine; methotrexate; platinum analogs such as cisplatin and carboplatin; vinblastine; etoposide (VP-16); ifosfamide; mitoxantrone; vincristine; NAVELBINE® (vinorelbine); novantrone; teniposide; edatrexate; daunomycin; aminopterin; capecitabine (XELODA®); ibandronate; CPT-11; topoisomerase inhibitor RFS 2000; difluoromethylornithine (DMFO); retinoids such as retinoic acid; and pharmaceutically acceptable salts, acids and derivatives of any of the above.

Other useful payloads include: (i) anti-hormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, 4-hydroxytamoxifen, trioxifene, keoxifene, LY117018, onapristone, and FARESTON® (toremifene citrate); (ii) aromatase inhibitors that inhibit the enzyme aromatase, which regulates estrogen production in the adrenal glands, such as, for example, 4(5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); (iii) anti-androgens such as flutamide, nilutamide, bicalutamide, leuprolide, and goserelin; as well as troxacitabine (a 1,3-dioxolane nucleoside cytosine analog); (iv) protein kinase inhibitors; (v) lipid kinase inhibitors; (vi) antisense oligonucleotides, particularly those which inhibit expression of genes in signaling pathways implicated in aberrant cell proliferation, such as, for example, PKC-alpha, Ralf and H-Ras; (vii) ribozymes such as VEGF expression inhibitors (e.g., ANGIOZYMEO) and HER2 expression inhibitors; (viii) vaccines such as gene therapy vaccines, for example, ALLOVECTIN®, LEU- VECTIN®, and VAXID®; PROLEUKIN® rIL-2; a topoisomerase 1 inhibitor such as LURTOTECAN®; ABARELIX® rmRH; (ix) anti-angiogenic agents such as bevacizumab (AVASTIN®, Genentech); (x) agents that act to regulate or inhibit activity of members of the poly(ADP-ribose) polymerase (PARP) family in tumors (e.g., Talazoparib (BMN-673), Iniparib (BSI 201), Veliparib (ABT-888), Olaparib (AZD-2281, trade name LYNPARZA™), Rucaparib (AG 014699), BGB-290, E7016, E7449, and CEP-9722); (xi) agents that act to regulate or inhibit activity of members of the histone deacetylase (HDAC) family in tumors (e.g., abexinostat, entinostat, gavinostat, 4SC-202, ACY-241, AR-42, CG200745, CHR-2845, CHR-3996, CXD101, MPT0E028, OBP-801, SHP-141, CUDC-101, KA2507, panobinostat, pracinostat, quisinostat, resminostat, ricolinostat); (xii) agents that act to regulate or inhibit activity of mitochondrial enzyme isocitrate dehydrogenase type 2 (IDH2) in tumors (e.g., enasidenib mesylate (CC-90007, AG-221 mesylate); and (xiii) pharmaceutically acceptable salts, acids and derivatives of any of the above. Other useful payloads include anti-angiogenic agents, including, e.g., MMP-2 (matrix-metalloproteinase 2) inhibitors, MMP-9 (matrix-metalloproteinase 9) inhibitors, COX-II (cyclooxygenase II) inhibitors, and VEGF receptor tyrosine kinase inhibitors. Examples of such useful matrix metalloproteinase inhibitors that can be used in combination with the present compounds/compositions are described in WO 96/33172, WO 96/27583, EP 818442, EP 1004578, WO 98/07697, WO 98/03516, WO 98/34918, WO 98/34915, WO 98/33768, WO 98/30566, EP 606,046, EP 931,788, WO 90/05719, WO 99/52910, WO 99/52889, WO 99/29667, WO 99/07675, EP 945864, U.S. Pat. Nos. 5,863,949, 5,861, 510, and EP 780,386, all of which are incorporated herein in their entireties by reference. Examples of VEGF receptor tyrosine kinase inhibitors include 4-(4-bromo-2-fluoroanilino)-6-methoxy-7-(1-methylpiperidin-4-ylmethoxy)quinazoline (ZD6474; Example 2 within WO 01/32651), 4-(4-fluoro-2-methylindol-5-yloxy)-6-methoxy-7-(3-pyrrolidin-1-ylpropoxy)quinazoline (AZD2171; Example 240 within WO vatalanib (PTK787; WO 98/35985) and SU11248 (sunitinib; WO 01/60814), and compounds such as those disclosed in PCT Publication Nos. WO 97/22596, WO 97/30035, WO 97/32856, and WO 98/13354).

In certain embodiments, the payload is selected from the group consisting of maytansine, hemiasterlin, amanitin, exatecan, deruxtecan (DXd), anthracycline, PNU-159682, pyrrolobenzodiazepine (PBD), MMAF, and MMAE. In certain embodiments, the payload is maytansine. In certain embodiments, the payload is hemiasterlin. In certain embodiments, the payload is amanitin. In certain embodiments, the payload is hemiasterlin. In certain embodiments, the payload is amanitin. In certain embodiments, the payload is hemiasterlin. In certain embodiments, the payload is deruxtecan. In certain embodiments, the payload is hemiasterlin. In certain embodiments, the payload is anthracycline. In certain embodiments, the payload is hemiasterlin. In certain embodiments, the payload is PNU-159682. In certain embodiments, the payload is hemiasterlin. In certain embodiments, the payload is pyrrolobenzodiazepine. In certain embodiments, the payload is MMAF. In certain embodiments, the payload is MMAE.

In certain embodiments, the payload is an antibody or an antibody fragment. In certain embodiments, the payload antibody or fragment can be encoded by any of the immunoglobulin genes recognized by those of skill in the art. The immunoglobulin genes include, but are not limited to, the κ, λ, α, γ (IgG1, IgG2, IgG3, and IgG4), δ, ε and μ constant region genes, as well as the immunoglobulin variable region genes. The term includes full-length antibody and antibody fragments recognized by those of skill in the art, and variants thereof. Exemplary fragments include but are not limited to Fv, Fc, Fab, and (Fab)$_2$, single chain Fv (scFv), diabodies, triabodies, tetrabodies, bifunctional hybrid polypeptides, CDR1, CDR2, CDR3, combinations of CDR's, variable regions, framework regions, constant regions, and the like.

In certain embodiments, the payload is one or more water-soluble polymers. A wide variety of macromolecular polymers and other molecules can be linked to the polypeptides described herein to modulate biological properties of the polypeptide, and/or provide new biological properties to the polypeptide. These macromolecular polymers can be linked to the polypeptide via a naturally encoded amino acid, via a non-naturally encoded amino acid, or any functional substituent of a natural or modified amino acid, or any substituent or functional group added to a natural or modified amino acid. The molecular weight of the polymer may be of a wide range, including but not limited to, between about 100 Da and about 100,000 Da or more.

The polymer selected may be water soluble so that a protein to which it is attached does not precipitate in an aqueous environment, such as a physiological environment. The polymer may be branched or unbranched. Preferably, for therapeutic use of the end-product preparation, the polymer will be pharmaceutically acceptable.

In certain embodiments, the proportion of polyethylene glycol molecules to polypeptide molecules will vary, as will their concentrations in the reaction mixture. In general, the optimum ratio (in terms of efficiency of reaction in that there is minimal excess unreacted protein or polymer) may be determined by the molecular weight of the polyethylene glycol selected and on the number of available reactive groups available. As relates to molecular weight, typically the higher the molecular weight of the polymer, the fewer number of polymer molecules which may be attached to the protein. Similarly, branching of the polymer should be taken into account when optimizing these parameters. Generally, the higher the molecular weight (or the more branches) the higher the polymer:protein ratio.

The water-soluble polymer may be any structural form including but not limited to linear, forked or branched. Typically, the water soluble polymer is a poly(alkylene glycol), such as poly(ethylene glycol) (PEG), but other water soluble polymers can also be employed. By way of example, PEG is used to describe certain embodiments.

PEG is a well-known, water-soluble polymer that is commercially available or can be prepared by ring-opening polymerization of ethylene glycol according to methods well known in the art (Sandler and Karo, Polymer Synthesis, Academic Press, New York, Vol. 3, pages 138-161). The term "PEG" is used broadly to encompass any polyethylene glycol molecule, without regard to size or to modification at an end of the PEG, and can be represented as linked to a polypeptide by the formula: XO—(CH$_2$CH$_2$O)$_n$—CH$_2$CH$_2$—Y where n is 2 to 10,000, X is H or a terminal modification, including but not limited to, a C$_{1-4}$ alkyl, and Y is the attachment point to the polypeptide.

In some cases, a PEG terminates on one end with hydroxy or methoxy, i.e., X is H or CH$_3$ ("methoxy PEG"). Alternatively, the PEG can terminate with a reactive group, thereby forming a bifunctional polymer. Typical reactive groups can include those reactive groups that are commonly used to react with the functional groups found in the 20 common amino acids (including but not limited to, maleimide groups, activated carbonates (including but not limited to, p-nitrophenyl ester), activated esters (including but not limited to, N-hydroxysuccinimide, p-nitrophenyl ester, and aldehydes) as well as functional groups that are inert to the 20 common amino acids but that react specifically with complementary functional groups present in non-naturally encoded amino acids (including but not limited to, azide groups, alkyne groups). It is noted that the other end of the PEG, which is shown in the above formula by Y, will attach either directly or indirectly to a polypeptide via a naturally-occurring or non-naturally encoded amino acid. For instance, Y may be an amide, carbamate, or urea linkage to an amine group (including but not limited to, the epsilon amine of lysine or the N-terminus) of the polypeptide. Alternatively, Y may be a maleimide linkage to a thiol group (including but not limited to, the thiol group of cysteine). Alternatively, Y may be a linkage to a residue not commonly accessible via the 20 common amino acids. For example, an azide group on the PEG can be reacted with an alkyne group on the polypeptide to form a Huisgen [3+2] cycloaddition product. Alternatively, an alkyne group on the PEG can be reacted with an azide group present in a non-naturally encoded amino acid, such as the modified amino acids described herein, to form a similar product. In some embodiments, a strong nucleophile (including but not limited to, hydrazine, hydrazide, hydroxylamine, semicarbazide) can be reacted with an aldehyde or ketone group present in a non-naturally encoded amino acid to form a hydrazone, oxime or semicarbazone, as applicable, which in some cases can be further reduced by treatment with an appropriate reducing agent. Alternatively, the strong nucleophile can be incorporated into the polypeptide via a non-naturally encoded amino acid and used to react preferentially with a ketone or aldehyde group present in the water-soluble polymer.

Any molecular mass for a PEG can be used as practically desired, including but not limited to, from about 100 Daltons (Da) to 100,000 Da or more as desired (including but not limited to, sometimes 0.1-50 kDa or 10-40 kDa). Branched chain PEGs, including but not limited to, PEG molecules with each chain having a MW ranging from 1-100 kDa (including but not limited to, 1-50 kDa or 5-20 kDa) can also be used. A wide range of PEG molecules are described in, including but not limited to, the Shearwater Polymers, Inc. catalog, and the Nektar Therapeutics catalog, incorporated herein by reference.

Generally, at least one terminus of the PEG molecule is available for reaction with the antibody. For example, PEG derivatives bearing alkyne and azide moieties for reaction with amino acid side chains can be used to attach PEG to non-naturally encoded amino acids as described herein. If the non-naturally encoded amino acid comprises an azide, then the PEG will typically contain either an alkyne moiety to effect formation of the [3+2] cycloaddition product or an activated PEG species (i.e., ester, carbonate) containing a phosphine group to effect formation of the amide linkage. Alternatively, if the non-naturally encoded amino acid comprises an alkyne, then the PEG will typically contain an azide moiety to effect formation of the [3+2] Huisgen cycloaddition product. If the non-naturally encoded amino acid comprises a carbonyl group, the PEG will typically comprise a potent nucleophile (including but not limited to, a hydrazide, hydrazine, hydroxylamine, or semicarbazide functionality) in order to effect formation of corresponding hydrazone, oxime, and semicarbazone linkages, respectively. In other alternatives, a reverse of the orientation of the reactive groups described herein can be used, i.e., an azide moiety in the non-naturally encoded amino acid can be reacted with a PEG derivative containing an alkyne.

In some embodiments, the polypeptide variant with a PEG derivative contains a chemical functionality that is reactive with the chemical functionality present on the side chain of the non-naturally encoded amino acid.

In certain embodiments, the payload is an azide- or acetylene-containing polymer comprising a water-soluble polymer backbone having an average molecular weight from about 800 Da to about 100,000 Da. The polymer backbone of the water-soluble polymer can be poly(ethylene glycol). However, it should be understood that a wide variety of water soluble polymers including but not limited to poly(ethylene)glycol and other related polymers, including poly(dextran) and poly(propylene glycol), are also suitable for use and that the use of the term PEG or poly(ethylene glycol) is intended to encompass and include all such molecules. The term PEG includes, but is not limited to, poly(ethylene glycol) in any of its forms, including bifunctional PEG, multiarmed PEG, derivatized PEG, forked PEG, branched PEG, pendent PEG (i.e. PEG or related polymers having one or more functional groups pendent to the polymer backbone), or PEG with degradable linkages therein.

The polymer backbone can be linear or branched. Branched polymer backbones are generally known in the art. Typically, a branched polymer has a central branch core moiety and a plurality of linear polymer chains linked to the central branch core. PEG is commonly used in branched forms that can be prepared by addition of ethylene oxide to various polyols, such as glycerol, glycerol oligomers, pentaerythritol and sorbitol. The central branch moiety can also be derived from several amino acids, such as lysine. The branched poly(ethylene glycol) can be represented in general form as R(-PEG-OH)$_m$ in which R is derived from a core moiety, such as glycerol, glycerol oligomers, or pentaerythritol, and m represents the number of arms. Multi-armed PEG molecules, such as those described in U.S. Pat. Nos. 5,932,462 5,643,575; 5,229,490; 4,289,872; U.S. Pat. Appl. 2003/0143596; WO 96/21469; and WO 93/21259, each of which is incorporated by reference herein in its entirety, can also be used as the polymer backbone.

Branched PEG can also be in the form of a forked PEG represented by PEG(-YCHZ$_2$)$_n$, where Y is a linking group and Z is an activated terminal group linked to CH by a chain of atoms of defined length.

Yet another branched form, the pendant PEG, has reactive groups, such as carboxyl, along the PEG backbone rather than at the end of PEG chains.

In addition to these forms of PEG, the polymer can also be prepared with weak or degradable linkages in the backbone. For example, PEG can be prepared with ester linkages in the polymer backbone that are subject to hydrolysis. As shown herein, this hydrolysis results in cleavage of the polymer into fragments of lower molecular weight: -PEG-CO$_2$-PEG-+H$_2$O→PEG-CO$_2$H+HO-PEG- It is understood by those skilled in the art that the term poly(ethylene glycol) or PEG represents or includes all the forms known in the art including but not limited to those disclosed herein.

Many other polymers are also suitable for use. In some embodiments, polymer backbones that are water-soluble, with from 2 to about 300 termini, are particularly suitable. Examples of suitable polymers include, but are not limited to, other poly(alkylene glycols), such as poly(propylene glycol) ("PPG"), copolymers thereof (including but not limited to copolymers of ethylene glycol and propylene glycol), terpolymers thereof, mixtures thereof, and the like. Although the molecular weight of each chain of the polymer backbone can vary, it is typically in the range of from about 800 Da to about 100,000 Da, often from about 6,000 Da to about 80,000 Da.

Those of ordinary skill in the art will recognize that the foregoing list for substantially water-soluble backbones is by no means exhaustive and is merely illustrative, and that all polymeric materials having the qualities described herein are contemplated as being suitable for use.

In some embodiments the polymer derivatives are "multifunctional", meaning that the polymer backbone has at least two termini, and possibly as many as about 300 termini, functionalized or activated with a functional group. Multifunctional polymer derivatives include, but are not limited to, linear polymers having two termini, each terminus being bonded to a functional group which may be the same or different.

4. Linkers

In certain embodiments, the antibodies can be linked to the payloads with one or more linkers capable of reacting with an antibody amino acid and with a payload group. The one or more linkers can be any linkers apparent to those of skill in the art.

The term "linker" is used herein to refer to groups or bonds that normally are formed as the result of a chemical reaction and typically are covalent linkages.

Useful linkers include those described herein. In certain embodiments, the linker is any divalent or multivalent linker known to those of skill in the art. Useful divalent linkers include alkylene, substituted alkylene, heteroalkylene, substituted heteroalkylene, arylene, substituted arylene, heteroarlyene, and substituted heteroarylene. In certain embodiments, the linker is $C_{1-10}$ alkylene or $C_{1-10}$ heteroalkylene. In some embodiments, the $C_{1-10}$heteoalkylene is PEG.

In certain embodiments, the linker is hydrolytically stable. Hydrolytically stable linkages means that the linkages are substantially stable in water and do not react with water at useful pH values, including but not limited to, under physiological conditions for an extended period of time, perhaps even indefinitely. In certain embodiments, the linker is hydrolytically unstable. Hydrolytically unstable or degradable linkages mean that the linkages are degradable in water or in aqueous solutions, including for example, blood. Enzymatically unstable or degradable linkages mean that the linkage can be degraded by one or more enzymes.

As understood in the art, PEG and related polymers may include degradable linkages in the polymer backbone or in the linker group between the polymer backbone and one or more of the terminal functional groups of the polymer molecule. For example, ester linkages formed by the reaction of PEG carboxylic acids or activated PEG carboxylic acids with alcohol groups on a biologically active agent generally hydrolyze under physiological conditions to release the agent.

Other hydrolytically degradable linkages include, but are not limited to, carbonate linkages; imine linkages resulted from reaction of an amine and an aldehyde; phosphate ester linkages formed by reacting an alcohol with a phosphate group; hydrazone linkages which are reaction product of a hydrazide and an aldehyde; acetal linkages that are the reaction product of an aldehyde and an alcohol; orthoester linkages that are the reaction product of a formate and an alcohol; peptide linkages formed by an amine group, including but not limited to, at an end of a polymer such as PEG, and a carboxyl group of a peptide; and oligonucleotide linkages formed by a phosphoramidite group, including but not limited to, at the end of a polymer, and a 5' hydroxyl group of an oligonucleotide.

A number of different cleavable linkers are known to those of skill in the art. See U.S. Pat. Nos. 4,618,492; 4,542,225, and 4,625,014. The mechanisms for release of an agent from these linker groups include, for example, irradiation of a photolabile bond and acid-catalyzed hydrolysis. U.S. Pat. No. 4,671,958, for example, includes a description of immunoconjugates comprising linkers which are cleaved at the target site in vivo by the proteolytic enzymes of the patient's complement system. The length of the linker may be predetermined or selected depending upon a desired spatial relationship between the polypeptide and the molecule linked to it. In view of the large number of methods that have been reported for attaching a variety of radiodiagnostic compounds, radiotherapeutic compounds, drugs, toxins, and other agents to polypeptides one skilled in the art will be able to determine a suitable method for attaching a given agent to a polypeptide.

The linker may have a wide range of molecular weight or molecular length. Larger or smaller molecular weight linkers may be used to provide a desired spatial relationship or conformation between the polypeptide and the linked entity. Linkers having longer or shorter molecular length may also be used to provide a desired space or flexibility between the polypeptide and the linked entity. Similarly, a linker having a particular shape or conformation may be utilized to impart a particular shape or conformation to the polypeptide or the linked entity, either before or after the polypeptide reaches its target. The functional groups present on each end of the linker may be selected to modulate the release of a polypeptide or a payload under desired conditions. This optimization of the spatial relationship between the polypeptide and the linked entity may provide new, modulated, or desired properties to the molecule.

In some embodiments, provided herein are water-soluble bifunctional linkers that have a dumbbell structure that includes: a) an azide, an alkyne, a hydrazine, a hydrazide, a hydroxylamine, or a carbonyl-containing moiety on at least a first end of a polymer backbone; and b) at least a second functional group on a second end of the polymer backbone. The second functional group can be the same or different as the first functional group. The second functional group, in some embodiments, is not reactive with the first functional group. In some embodiments, water-soluble compounds that comprise at least one arm of a branched molecular structure are provided. For example, the branched molecular structure can be a dendritic structure.

In some embodiments, the linker is derived from a linker precursor selected from the group consisting of: N-succinimidyl-3-(2-pyridyldithio)propionate (SPDP), N-succinimidyl 4-(2-pyridyldithio)pentanoate (SPP), N-succinimidyl 4-(2-pyridyldithio)butanoate (SPDB), N-succinimidyl-4-(2-pyridyldithio)-2-sulfo-butanoate (sulfo-SPDB), N-succinimidyl iodoacetate (SIA), N-succinimidyl(4-iodoacetyl) aminobenzoate (STAB), maleimide PEG NHS, N-succinimidyl 4-(maleimidomethyl)cyclohexanecarboxylate (SMCC), N-sulfosuccinimidyl 4-(maleimidomethyl)cyclohexanecarboxylate (sulfo-SMCC) or 2,5-dioxopyrrolidin-1-yl 17-(2,5-dioxo-2,5-dihydro-1H-pyrrol-1-yl)-5,8,11,14-tetraoxo-4,7,10,13-tetraazaheptadecan-1-oate (CX1-1). In a specific embodiment, the linker is derived from the linker precursor N-succinimidyl 4-(maleimidomethyl)cyclohexanecarboxylate (SMCC).

In some embodiments, the linker is derived from a linker precursor selected from the group consisting of dipeptides, tripeptides, tetrapeptides, and pentapeptides. In such embodiments, the linker can be cleaved by a protease. Exemplary dipeptides include, but are not limited to, valine-citrulline (vc or val-cit), alanine-phenylalanine (af or ala-phe); phenylalanine-lysine (fk or phe-lys); phenylalanine-homolysine (phe-homolys); and N-methyl-valine-citrulline (Me-val-cit). Exemplary tripeptides include, but are not limited to, glycine-valine-citrulline (gly-val-cit), glycine-glycine-glycine (gly-gly-gly), and glycine-methoxyethoxy-ethyl)serine-valine (gly-val-citalanine OMESerValAla).

In some embodiments, a linker comprises a self-immolative spacer. In certain embodiments, the self-immolative spacer comprises p-aminobenzyl. In some embodiments, a p-aminobenzyl alcohol is attached to an amino acid unit via an amide bond, and a carbamate, methylcarbamate, or carbonate is made between the benzyl alcohol and the payload (Hamann et al. (2005) Expert Opin. Ther. Patents (2005) 15:1087-1103). In some embodiments, the linker comprises p-aminobenzyloxycarbonyl (PAB). Other examples of self-immolative spacers include, but are not limited to, aromatic compounds that are electronically similar to the PAB group, such as 2-aminoimidazol-5-methanol derivatives (U.S. Pat. No. 7,375,078; Hay et al. (1999) Bioorg. Med. Chem. Lett. 9:2237) and ortho- or para-aminobenzylacetals. In some embodiments, spacers can be used that undergo cyclization upon amide bond hydrolysis, such as substituted and unsubstituted 4-aminobutyric acid amides (Rodrigues et al. (1995) Chemistry Biology 2:223), appropriately substituted bicyclo[2.2.1] and bicyclo[2.2.2] ring systems (Storm et al. (1972) J. Amer. Chem. Soc. 94:5815) and 2-aminophenylpropionic acid amides (Amsberry, et al. (1990) J. Org. Chem. Linkage of a drug to the α-carbon of a glycine residue is another example of a self-immolative spacer that may be useful in conjugates (Kingsbury et al. (1984) J. Med. Chem. 27:1447).

In certain embodiments, linker precursors can be combined to form larger linkers. For instance, in certain embodiments, linkers comprise the dipeptide valine-citrulline and p-aminobenzyloxycarbonyl. These are also referenced as citValCit-PAB linkers.

In certain embodiments, the payloads can be linked to the linkers, referred to herein as a linker-payload, with one or more linker groups capable of reacting with an antibody amino acid group. The one or more linkers can be any linkers apparent to those of skill in the art or those set forth herein.

Additional linkers are disclosed herein, such as, for example, the linker precursors (A)-(L) described below.

5. Antibodies and Antibody Specificity

Provided herein are antibodies that selectively bind human ROR1. In some aspects, the antibody selectively binds to the extracellular domain of human ROR1 (human ROR1).

Also provided herein are conjugates that comprise antibodies that selectively bind human receptor tyrosine kinase orphan receptor 1. In some aspects, the antibody of the conjugate selectively binds to the extracellular domain of human receptor tyrosine kinase orphan receptor 1 (human ROR1).

In some embodiments, the antibody binds to a homolog of human ROR1. In some aspects, the antibody binds to a homolog of human ROR1 from a species selected from monkeys, mice, dogs, cats, rats, cows, horses, goats and sheep. In some aspects, the homolog is a cynomolgus monkey homolog. In some aspects, the homolog is a mouse or murine analog.

In some embodiments, the antibody has one or more CDRs having particular lengths, in terms of the number of amino acid residues. In some embodiments, the Chothia CDR-H1 of the antibody is 6, 7, or 8 residues in length. In some embodiments, the Kabat CDR-H1 of the antibody is 4, 5, or 6 residues in length. In some embodiments, the Chothia CDR-H2 of the antibody is 5, 6, or 7 residues in length. In some embodiments, the Kabat CDR-H2 of the antibody is 16, 17, or 18 residues in length. In some embodiments, the Kabat/Chothia CDR-H3 of the antibody is 7, 8, 9, 11, 12, 13, 14, 15, or 16 residues in length.

In some aspects, the Kabat/Chothia CDR-L1 of the antibody is 10, 11, 12, 13, 14, 15, or 16 residues in length. In some aspects, the Kabat/Chothia CDR-L2 of the antibody is 6, 7, or 8 residues in length. In some aspects, the Kabat/Chothia CDR-L3 of the antibody is 8, 9, or 10 residues in length.

In some embodiments, the antibody comprises a light chain. In some aspects, the light chain is a kappa light chain. In some aspects, the light chain is a lambda light chain.

In some embodiments, the antibody comprises a heavy chain. In some aspects, the heavy chain is an IgA. In some aspects, the heavy chain is an IgD. In some aspects, the heavy chain is an IgE. In some aspects, the heavy chain is an IgG. In some aspects, the heavy chain is an IgM. In some aspects, the heavy chain is an IgG1. In some aspects, the heavy chain is an IgG2. In some aspects, the heavy chain is an IgG3. In some aspects, the heavy chain is an IgG4. In some aspects, the heavy chain is an IgA1. In some aspects, the heavy chain is an IgA2.

In some embodiments, the antibody is an antibody fragment. In some aspects, the antibody fragment is an Fv fragment. In some aspects, the antibody fragment is a Fab fragment. In some aspects, the antibody fragment is a F(ab')2 fragment. In some aspects, the antibody fragment is a Fab' fragment. In some aspects, the antibody fragment is an scFv (sFv) fragment. In some aspects, the antibody fragment is an scFv-Fc fragment.

In some embodiments, the antibody is a monoclonal antibody. In some embodiments, the antibody is a polyclonal antibody.

In some embodiments, the antibody is a chimeric antibody. In some embodiments, the antibody is a humanized antibody. In some embodiments, the antibody is a human antibody.

In some embodiments, the antibody is an affinity matured antibody. In some aspects, the antibody is an affinity matured antibody derived from an illustrative sequence provided in this disclosure.

The antibodies provided herein may be useful for the treatment of a variety of diseases and conditions including cancers. In some embodiments, the antibodies provided herein may be useful for the treatment of cancers of solid tumors. For example, the antibodies provided herein can be useful for the treatment of colorectal cancer.

5.1 CDR-H3 Sequences

In some embodiments, the antibody comprises a CDR-H3 sequence comprising, consisting of, or consisting essentially of a CDR-H3 sequence of an illustrative antibody or $V_H$ sequence provided herein. In some aspects, the CDR-H3 sequence is a CDR-H3 sequence of a $V_H$ sequence provided in SEQ ID NOs: 854-1020.

In some embodiments, the antibody comprises a CDR-H3 sequence comprising, consisting of, or consisting essentially of a sequence selected from SEQ ID NOs: 672-838. In some aspects, the antibody comprises a CDR-H3 sequence comprising, consisting of, or consisting essentially of SEQ ID NO:672. In some aspects, the antibody comprises a CDR-H3 sequence comprising, consisting of, or consisting essentially of SEQ ID NO:673. In some aspects, the antibody comprises a CDR-H3 sequence comprising, consisting of, or consisting essentially of SEQ ID NO:674. In some aspects, the antibody comprises a CDR-H3 sequence comprising, consisting of, or consisting essentially of SEQ ID NO:675. In some aspects, the antibody comprises a CDR-H3 sequence comprising, consisting of, or consisting essentially of SEQ ID NO:676. In some aspects, the antibody comprises a CDR-H3 sequence comprising, consisting of, or consisting essentially of SEQ ID NO:677. In some aspects, the antibody comprises a CDR-H3 sequence comprising, consisting of, or consisting essentially of SEQ ID NO:678. In some aspects, the antibody comprises a CDR-H3 sequence comprising, consisting of, or consisting essentially of SEQ ID NO:679. In some aspects, the antibody comprises a CDR-H3 sequence comprising, consisting of, or consisting essentially of SEQ ID NO:680. In some aspects, the antibody comprises a CDR-H3 sequence comprising, consisting of, or consisting essentially of SEQ ID NO:681. In some aspects, the antibody comprises a CDR-H3 sequence comprising, consisting of, or consisting essentially of SEQ ID NO:682. In some aspects, the antibody comprises a CDR-H3 sequence comprising, consisting of, or consisting essentially of SEQ ID NO:683. In some aspects, the antibody comprises a CDR-H3 sequence comprising, consisting of, or consisting essentially of SEQ ID NO:684. In some aspects, the antibody comprises a CDR-H3 sequence comprising, consisting of, or consisting essentially of SEQ ID NO:685. In some aspects, the antibody comprises a CDR-H3 sequence comprising, consisting of, or consisting essentially of SEQ ID NO:686. In some aspects, the antibody comprises a CDR-H3 sequence comprising, consisting of, or consisting essentially of SEQ ID NO:687. In some aspects, the antibody comprises a CDR-H3 sequence comprising, consisting of, or consisting essentially of SEQ ID NO:688. In some aspects, the antibody comprises a CDR-H3 sequence comprising, consisting of, or consisting essentially of SEQ ID NO:689. In some aspects, the antibody comprises a CDR-H3 sequence comprising, consisting of, or consisting essentially of SEQ ID NO:690. In some aspects, the antibody comprises a CDR-H3 sequence comprising, consisting of, or consisting essentially of SEQ ID NO:691. In some aspects, the antibody comprises a CDR-H3 sequence comprising, consisting of, or consisting essentially of SEQ ID NO:692. In some aspects, the antibody comprises a CDR-H3 sequence comprising, consisting of, or consisting essentially of SEQ ID NO:693. In some aspects, the antibody comprises a CDR-H3 sequence comprising, consisting of, or consisting essentially of SEQ ID NO:694. In some aspects, the antibody comprises a CDR-H3 sequence comprising, consisting of, or consisting essentially of SEQ ID NO:695. In some aspects, the antibody comprises a CDR-H3 sequence comprising, consisting of, or consisting essentially of SEQ ID NO:696. In some aspects, the antibody comprises a CDR-H3 sequence comprising, consisting of, or consisting essentially of SEQ ID NO:697. In some aspects, the antibody comprises a CDR-H3 sequence comprising, consisting of, or consisting essentially of SEQ ID NO:698. In some aspects, the antibody comprises a CDR-H3 sequence comprising, consisting of, or consisting essentially of SEQ ID NO:699.

In some aspects, the antibody comprises a CDR-H3 sequence comprising, consisting of, or consisting essentially of SEQ ID NO:700. In some aspects, the antibody comprises a CDR-H3 sequence comprising, consisting of, or consisting essentially of SEQ ID NO:701. In some aspects, the antibody comprises a CDR-H3 sequence comprising, consisting of, or consisting essentially of SEQ ID NO:702. In some aspects, the antibody comprises a CDR-H3 sequence comprising, consisting of, or consisting essentially of SEQ ID NO:703. In some aspects, the antibody comprises a CDR-H3 sequence comprising, consisting of, or consisting essentially of SEQ ID NO:704. In some aspects, the antibody comprises a CDR-H3 sequence comprising, consisting of, or consisting essentially of SEQ ID NO:705. In some aspects, the antibody comprises a CDR-H3 sequence comprising, consisting of, or consisting essentially of SEQ ID NO:706. In some aspects, the antibody comprises a CDR-H3 sequence comprising, consisting of, or consisting essentially of SEQ ID NO:707. In some aspects, the antibody comprises a CDR-H3 sequence comprising, consisting of, or consisting essentially of SEQ ID NO:708. In some aspects, the antibody comprises a CDR-H3 sequence comprising, consisting of, or consisting essentially of SEQ ID NO:709. In some aspects, the antibody comprises a CDR-H3 sequence comprising, consisting of, or consisting essentially of SEQ ID NO:710. In some aspects, the antibody comprises a CDR-H3 sequence comprising, consisting of, or consisting essentially of SEQ ID NO:711. In some aspects, the antibody comprises a CDR-H3 sequence comprising, consisting of, or consisting essentially of SEQ ID NO:712. In some aspects, the antibody comprises a CDR-H3 sequence comprising, consisting of, or consisting essentially of SEQ ID NO:713. In some aspects, the antibody comprises a CDR-H3 sequence comprising, consisting of, or consisting essentially of SEQ ID NO:714. In some aspects, the antibody comprises a CDR-H3 sequence comprising, consisting of, or consisting essentially of SEQ ID NO:715. In some aspects, the antibody comprises a CDR-H3 sequence comprising, consisting of, or consisting essentially of SEQ ID NO:716. In some aspects, the antibody comprises a CDR-H3 sequence comprising, consisting of, or consisting essentially of SEQ ID NO:717. In some aspects, the antibody comprises a CDR-H3 sequence comprising, consisting of, or consisting essentially of SEQ ID NO:718. In some aspects, the antibody comprises a CDR-H3 sequence comprising, consisting of, or consisting essentially of SEQ ID NO:719. In some aspects, the antibody comprises a CDR-H3 sequence comprising, consisting of, or consisting essentially of SEQ ID NO:720. In some aspects, the antibody comprises a CDR-H3 sequence comprising, consisting of, or consisting essentially of SEQ ID NO:721. In some aspects, the antibody comprises a CDR-H3 sequence comprising, consisting of, or consisting essentially of SEQ ID NO:722. In some aspects, the antibody comprises a CDR-H3 sequence comprising, consisting of, or consisting essentially of SEQ ID NO:723. In some aspects, the antibody comprises a CDR-H3 sequence comprising, consisting of, or consisting essentially of SEQ ID NO:724. In some aspects, the antibody comprises a CDR-H3 sequence comprising, consisting of, or consisting essentially of SEQ ID NO:725. In some aspects, the antibody comprises a CDR-H3 sequence comprising, consisting of, or consisting essentially of SEQ ID NO:726. In some aspects, the antibody comprises a CDR-H3 sequence comprising, consisting of, or consisting essentially of SEQ ID NO:727. In some aspects, the antibody comprises a CDR-H3 sequence comprising, consisting of, or consisting essentially of SEQ ID NO:728. In some aspects, the antibody comprises a CDR-H3 sequence comprising, consisting of, or consisting essentially of SEQ ID NO:729. In some aspects, the antibody comprises a CDR-H3 sequence comprising, consisting of, or consisting essentially of SEQ ID NO:730. In some aspects, the antibody comprises a CDR-H3 sequence comprising, consisting of, or consisting essentially of SEQ ID NO:731. In some aspects, the antibody comprises a CDR-H3 sequence comprising, consisting of, or consisting essentially of SEQ ID NO:732. In some aspects, the antibody comprises a CDR-H3 sequence comprising, consisting of, or consisting essentially of SEQ ID NO:733. In some aspects, the antibody comprises a CDR-H3 sequence comprising, consisting of, or consisting essentially of SEQ ID NO:734. In some aspects, the antibody comprises a CDR-H3 sequence comprising, consisting of, or consisting essentially of SEQ ID NO:735. In some aspects, the antibody comprises a CDR-H3 sequence comprising, consisting of, or consisting essentially of SEQ ID NO:736. In some aspects, the antibody comprises a CDR-H3 sequence comprising, consisting of, or consisting essentially of SEQ ID NO:737. In some aspects, the antibody comprises a CDR-H3 sequence comprising, consisting of, or consisting essentially of SEQ ID NO:738. In some aspects, the antibody comprises a CDR-H3 sequence comprising, consisting of, or consisting essentially of SEQ ID NO:739. In some aspects, the antibody comprises a CDR-H3 sequence comprising, consisting of, or consisting essentially of SEQ ID NO:740. In some aspects, the antibody comprises a CDR-H3 sequence comprising, consisting of, or consisting essentially of SEQ ID NO:741. In some aspects, the antibody comprises a CDR-H3 sequence comprising, consisting of, or consisting essentially of SEQ ID NO:742. In some aspects, the antibody comprises a CDR-H3 sequence comprising, consisting of, or consisting essentially of SEQ ID NO:743. In some aspects, the antibody comprises a CDR-H3 sequence comprising, consisting of, or consisting essentially of SEQ ID NO:744. In some aspects, the antibody comprises a CDR-H3 sequence comprising, consisting of, or consisting essentially of SEQ ID NO:745. In some aspects, the antibody comprises a CDR-H3 sequence comprising, consisting of, or consisting essentially of SEQ ID NO:746. In some aspects, the antibody comprises a CDR-H3 sequence comprising, consisting of, or consisting essentially of SEQ ID NO:747. In some aspects, the antibody comprises a CDR-H3 sequence comprising, consisting of, or consisting essentially of SEQ ID NO:748. In some aspects, the antibody comprises a CDR-H3 sequence comprising, consisting of, or consisting essentially of SEQ ID NO:749.

In some aspects, the antibody comprises a CDR-H3 sequence comprising, consisting of, or consisting essentially of SEQ ID NO:750. In some aspects, the antibody comprises a CDR-H3 sequence comprising, consisting of, or consisting essentially of SEQ ID NO:751. In some aspects, the antibody comprises a CDR-H3 sequence comprising, consisting of, or consisting essentially of SEQ ID NO:752. In some aspects, the antibody comprises a CDR-H3 sequence comprising, consisting of, or consisting essentially of SEQ ID NO:753. In some aspects, the antibody comprises a CDR-H3 sequence comprising, consisting of, or consisting essentially of SEQ ID NO:754. In some aspects, the antibody comprises a CDR-H3 sequence comprising, consisting of, or consisting essentially of SEQ ID NO:755. In some aspects, the antibody comprises a CDR-H3 sequence comprising, consisting of, or consisting essentially of SEQ ID NO:756. In some aspects, the antibody comprises a CDR-H3 sequence comprising, consisting of, or consisting essentially of SEQ ID NO:757. In some aspects, the antibody comprises a CDR-H3 sequence comprising, consisting of, or consisting essentially of SEQ ID NO:758. In some aspects, the antibody comprises a CDR-H3 sequence comprising, consisting of, or consisting essentially of SEQ ID NO:759. In some aspects, the antibody comprises a CDR-H3 sequence comprising, consisting of, or consisting essentially of SEQ ID NO:760. In some aspects, the antibody comprises a CDR-H3 sequence comprising, consisting of, or consisting essentially of SEQ ID NO:761. In some aspects, the antibody comprises a CDR-H3 sequence comprising, consisting of, or consisting essentially of SEQ ID NO:762. In some aspects, the antibody comprises a CDR-H3 sequence comprising, consisting of, or consisting essentially of SEQ ID NO:763. In some aspects, the antibody comprises a CDR-H3 sequence comprising, consisting of, or consisting essentially of SEQ ID NO:764. In some aspects, the antibody comprises a CDR-H3 sequence comprising, consisting of, or consisting essentially of SEQ ID NO:765. In some aspects, the antibody comprises a CDR-H3 sequence comprising, consisting of, or consisting essentially of SEQ ID NO:766. In some aspects, the antibody comprises a CDR-H3 sequence comprising, consisting of, or consisting essentially of SEQ ID NO:767. In some aspects, the antibody comprises a CDR-H3 sequence comprising, consisting of, or consisting essentially of SEQ ID NO:768. In some aspects, the antibody comprises a CDR-H3 sequence comprising, consisting of, or consisting essentially of SEQ ID NO:769. In some aspects, the antibody comprises a CDR-H3 sequence comprising, consisting of, or consisting essentially of SEQ ID NO:770. In some aspects, the antibody comprises a CDR-H3 sequence comprising, consisting of, or consisting essentially of SEQ ID NO:771. In some aspects, the antibody comprises a CDR-H3 sequence comprising, consisting of, or consisting essentially of SEQ ID NO:772. In some aspects, the antibody comprises a CDR-H3 sequence comprising, consisting of, or consisting essentially of SEQ ID NO:773. In some aspects, the antibody comprises a CDR-H3 sequence comprising, consisting of, or consisting essentially of SEQ ID NO:774. In some aspects, the antibody comprises a CDR-H3 sequence comprising, consisting of, or consisting essentially of SEQ ID NO:775. In some aspects, the antibody comprises a CDR-H3 sequence comprising, consisting of, or consisting essentially of SEQ ID NO:776. In some aspects, the antibody comprises a CDR-H3 sequence comprising, consisting of, or consisting essentially of SEQ ID NO:777. In some aspects, the antibody comprises a CDR-H3 sequence comprising, consisting of, or consisting essentially of SEQ ID NO:778. In some aspects, the antibody comprises a CDR-H3 sequence comprising, consisting of, or consisting essentially of SEQ ID NO:779. In some aspects, the antibody comprises a CDR-H3 sequence comprising, consisting of, or consisting essentially of SEQ ID NO:780. In some aspects, the antibody comprises a CDR-H3 sequence comprising, consisting of, or consisting essentially of SEQ ID NO:781. In some aspects, the antibody comprises a CDR-H3 sequence comprising, consisting of, or consisting essentially of SEQ ID NO:782. In some aspects, the antibody comprises a CDR-H3 sequence comprising, consisting of, or consisting essentially of SEQ ID NO:783. In some aspects, the antibody comprises a CDR-H3 sequence comprising, consisting of, or consisting essentially of SEQ ID NO:784. In some aspects, the antibody comprises a CDR-H3 sequence comprising, consisting of, or consisting essentially of SEQ ID NO:785. In some aspects, the antibody comprises a CDR-H3 sequence comprising, consisting of, or consisting essentially of SEQ ID NO:786. In some aspects, the antibody comprises a CDR-H3 sequence comprising, consisting of, or consisting essentially of SEQ ID NO:787. In some aspects, the antibody comprises a CDR-H3 sequence comprising, consisting of, or consisting essentially of SEQ ID NO:788. In some aspects, the antibody comprises a CDR-H3 sequence comprising, consisting of, or consisting essentially of SEQ ID NO:789. In some aspects, the antibody comprises a CDR-H3 sequence comprising, consisting of, or consisting essentially of SEQ ID NO:790. In some aspects, the antibody comprises a CDR-H3 sequence comprising, consisting of, or consisting essentially of SEQ ID NO:791. In some aspects, the antibody comprises a CDR-H3 sequence comprising, consisting of, or consisting essentially of SEQ ID NO:792. In some aspects, the antibody comprises a CDR-H3 sequence comprising, consisting of, or consisting essentially of SEQ ID NO:793. In some aspects, the antibody comprises a CDR-H3 sequence comprising, consisting of, or consisting essentially of SEQ ID NO:794. In some aspects, the antibody comprises a CDR-H3 sequence comprising, consisting of, or consisting essentially of SEQ ID NO:795. In some aspects, the antibody comprises a CDR-H3 sequence comprising, consisting of, or consisting essentially of SEQ ID NO:796. In some aspects, the antibody comprises a CDR-H3 sequence comprising, consisting of, or consisting essentially of SEQ ID NO:797. In some aspects, the antibody comprises a CDR-H3 sequence comprising, consisting of, or consisting essentially of SEQ ID NO:798. In some aspects, the antibody comprises a CDR-H3 sequence comprising, consisting of, or consisting essentially of SEQ ID NO:799.

In some aspects, the antibody comprises a CDR-H3 sequence comprising, consisting of, or consisting essentially of SEQ ID NO:800. In some aspects, the antibody comprises a CDR-H3 sequence comprising, consisting of, or consisting essentially of SEQ ID NO:801. In some aspects, the antibody comprises a CDR-H3 sequence comprising, consisting of, or consisting essentially of SEQ ID NO:802. In some aspects, the antibody comprises a CDR-H3 sequence comprising, consisting of, or consisting essentially of SEQ ID NO:803. In some aspects, the antibody comprises a CDR-H3 sequence comprising, consisting of, or consisting essentially of SEQ ID NO:804. In some aspects, the antibody comprises a CDR-H3 sequence comprising, consisting of, or consisting essentially of SEQ ID NO:805. In some aspects, the antibody comprises a CDR-H3 sequence comprising, consisting of, or consisting essentially of SEQ ID NO:806. In some aspects, the antibody comprises a CDR-H3 sequence comprising, consisting of, or consisting essentially of SEQ ID NO:807. In some aspects, the antibody comprises a CDR-H3 sequence comprising, consisting of, or consisting essentially of SEQ ID NO:808. In some aspects, the antibody comprises a CDR-H3 sequence comprising, consisting of, or consisting essentially of SEQ ID NO:809. In some aspects, the antibody comprises a CDR-H3 sequence comprising, consisting of, or consisting essentially of SEQ ID NO:810. In some aspects, the antibody comprises a CDR-H3 sequence comprising, consisting of, or consisting essentially of SEQ ID NO:811. In some aspects, the antibody comprises a CDR-H3 sequence comprising, consisting of, or consisting essentially of SEQ ID NO:812. In some aspects, the antibody comprises a CDR-H3 sequence comprising, consisting of, or consisting essentially of SEQ ID NO:813. In some aspects, the antibody comprises a CDR-H3 sequence comprising, consisting of, or consisting essentially of SEQ ID NO:814. In some aspects, the antibody comprises a CDR-H3 sequence comprising, consisting of, or consisting essentially of SEQ ID NO:815. In some aspects, the antibody comprises a CDR-H3 sequence comprising, consisting of, or consisting essentially of SEQ ID NO:816. In some aspects, the antibody comprises a CDR-H3 sequence comprising, consisting of, or consisting essentially of SEQ ID NO:817. In some aspects, the antibody comprises a CDR-H3 sequence comprising, consisting of, or consisting essentially of SEQ ID NO:818. In some aspects, the antibody comprises a CDR-H3 sequence comprising, consisting of, or consisting essentially of SEQ ID NO:819. In some aspects, the antibody comprises a CDR-H3 sequence comprising, consisting of, or consisting essentially of SEQ ID NO:820. In some aspects, the antibody comprises a CDR-H3 sequence comprising, consisting of, or consisting essentially of SEQ ID NO:821. In some aspects, the antibody comprises a CDR-H3 sequence comprising, consisting of, or consisting essentially of SEQ ID NO:822. In some aspects, the antibody comprises a CDR-H3 sequence comprising, consisting of, or consisting essentially of SEQ ID NO:823. In some aspects, the antibody comprises a CDR-H3 sequence comprising, consisting of, or consisting essentially of SEQ ID NO:824. In some aspects, the antibody comprises a CDR-H3 sequence comprising, consisting of, or consisting essentially of SEQ ID NO:825. In some aspects, the antibody comprises a CDR-H3 sequence comprising, consisting of, or consisting essentially of SEQ ID NO:826. In some aspects, the antibody comprises a CDR-H3 sequence comprising, consisting of, or consisting essentially of SEQ ID NO:827. In some aspects, the antibody comprises a CDR-H3 sequence comprising, consisting of, or consisting essentially of SEQ ID NO:828. In some aspects, the antibody comprises a CDR-H3 sequence comprising, consisting of, or consisting essentially of SEQ ID NO:829. In some aspects, the antibody comprises a CDR-H3 sequence comprising, consisting of, or consisting essentially of SEQ ID NO:830. In some aspects, the antibody comprises a CDR-H3 sequence comprising, consisting of, or consisting essentially of SEQ ID NO:831. In some aspects, the antibody comprises a CDR-H3 sequence comprising, consisting of, or consisting essentially of SEQ ID NO:832. In some aspects, the antibody comprises a CDR-H3 sequence comprising, consisting of, or consisting essentially of SEQ ID NO:833. In some aspects, the antibody comprises a CDR-H3 sequence comprising, consisting of, or consisting essentially of SEQ ID NO:834. In some aspects, the antibody comprises a CDR-H3 sequence comprising, consisting of, or consisting essentially of SEQ ID NO:835. In some aspects, the antibody comprises a CDR-H3 sequence comprising, consisting of, or consisting essentially of SEQ ID NO:836. In some aspects, the antibody comprises a CDR-H3 sequence comprising, consisting of, or consisting essentially of SEQ ID NO:837. In some aspects, the antibody comprises a CDR-H3 sequence comprising, consisting of, or consisting essentially of SEQ ID NO:838.

In some aspects, the CDR-H3 sequence comprises, consists of, or consists essentially of a variant of an illustrative CDR-H3 sequence provided in this disclosure. In some aspects, the CDR-H3 sequence comprises, consists of, or consists essentially of a sequence having at least 70%, 75%, 80%, 85%, 90%, or 95% identity with any of the illustrative CDR-H3 sequences provided in this disclosure. In some aspects, the CDR-H3 sequence comprises, consists of, or consists essentially of any of the illustrative CDR-H3 sequences provided in this disclosure, with 1, 2, or 3 amino acid substitutions. In some aspects, the amino acid substitutions are conservative amino acid substitutions.

5.2 $V_H$ Sequences Comprising Illustrative CDRs

In some embodiments, the antibody comprises a $V_H$ sequence comprising one or more CDR-H3 sequences comprising, consisting of, or consisting essentially of one or more illustrative CDR-H3 sequences provided in this disclosure, and variants thereof. In some embodiments, the CDR-H3 sequences comprise, consist of, or consist essentially of one or more CDR-H3 sequences provided in a $V_H$ sequence selected from SEQ ID NOs: 854-1020.

5.2.1. $V_H$ Sequences Comprising Illustrative Kabat CDRs

In some embodiments, the antibody comprises a $V_H$ sequence comprising one or more Kabat CDR-H3 sequences comprising, consisting of, or consisting essentially of one or more illustrative Kabat CDR-H3 sequences provided in this disclosure, and variants thereof.

5.2.1.1. Kabat CDR-H3

In some embodiments, the antibody comprises a $V_H$ sequence comprising a CDR-H3 sequence, wherein the CDR-H3 sequence comprises, consists of, or consists essentially of a Kabat CDR-H3 sequence of an illustrative antibody or $V_H$ sequence provided herein. In some aspects, the Kabat CDR-H3 sequence is a Kabat CDR-H3 sequence of a $V_H$ sequence provided in SEQ ID NOs: 854-1020.

In some embodiments, the antibody comprises a $V_H$ sequence comprising a Kabat CDR-H3 sequence comprising, consisting of, or consisting essentially of a sequence selected from SEQ ID NOs: 672-838. In some aspects, the antibody comprises a CDR-H3 sequence comprising, consisting of, or consisting essentially of SEQ ID NO:672. In some aspects, the antibody comprises a CDR-H3 sequence comprising, consisting of, or consisting essentially of SEQ ID NO:673. In some aspects, the antibody comprises a CDR-H3 sequence comprising, consisting of, or consisting essentially of SEQ ID NO:674. In some aspects, the antibody comprises a CDR-H3 sequence comprising, consisting of, or consisting essentially of SEQ ID NO:675. In some aspects, the antibody comprises a CDR-H3 sequence comprising, consisting of, or consisting essentially of SEQ ID NO:676. In some aspects, the antibody comprises a CDR-H3 sequence comprising, consisting of, or consisting essentially of SEQ ID NO:677. In some aspects, the antibody comprises a CDR-H3 sequence comprising, consisting of, or consisting essentially of SEQ ID NO:678. In some aspects, the antibody comprises a CDR-H3 sequence comprising, consisting of, or consisting essentially of SEQ ID NO:679. In some aspects, the antibody comprises a CDR-H3 sequence comprising, consisting of, or consisting essentially of SEQ ID NO:680. In some aspects, the antibody comprises a CDR-H3 sequence comprising, consisting of, or consisting essentially of SEQ ID NO:681. In some aspects, the antibody comprises a CDR-H3 sequence comprising, consisting of, or consisting essentially of SEQ ID NO:682. In some aspects, the antibody comprises a CDR-H3 sequence comprising, consisting of, or consisting essentially of SEQ ID NO:683. In some aspects, the antibody comprises a CDR-H3 sequence comprising, consisting of, or consisting essentially of SEQ ID NO:684. In some aspects, the antibody comprises a CDR-H3 sequence comprising, consisting of, or consisting essentially of SEQ ID NO:685. In some aspects, the antibody comprises a CDR-H3 sequence comprising, consisting of, or consisting essentially of SEQ ID NO:686. In some aspects, the antibody comprises a CDR-H3 sequence comprising, consisting of, or consisting essentially of SEQ ID NO:687. In some aspects, the antibody comprises a CDR-H3 sequence comprising, consisting of, or consisting essentially of SEQ ID NO:688. In some aspects, the antibody comprises a CDR-H3 sequence comprising, consisting of, or consisting essentially of SEQ ID NO:689. In some aspects, the antibody comprises a CDR-H3 sequence comprising, consisting of, or consisting essentially of SEQ ID NO:690. In some aspects, the antibody comprises a CDR-H3 sequence comprising, consisting of, or consisting essentially of SEQ ID NO:691. In some aspects, the antibody comprises a CDR-H3 sequence comprising, consisting of, or consisting essentially of SEQ ID NO:692. In some aspects, the antibody comprises a CDR-H3 sequence comprising, consisting of, or consisting essentially of SEQ ID NO:693. In some aspects, the antibody comprises a CDR-H3 sequence comprising, consisting of, or consisting essentially of SEQ ID NO:694. In some aspects, the antibody comprises a CDR-H3 sequence comprising, consisting of, or consisting essentially of SEQ ID NO:695. In some aspects, the antibody comprises a CDR-H3 sequence comprising, consisting of, or consisting essentially of SEQ ID NO:696. In some aspects, the antibody comprises a CDR-H3 sequence comprising, consisting of, or consisting essentially of SEQ ID NO:697. In some aspects, the antibody comprises a CDR-H3 sequence comprising, consisting of, or consisting essentially of SEQ ID NO:698. In some aspects, the antibody comprises a CDR-H3 sequence comprising, consisting of, or consisting essentially of SEQ ID NO:699.

In some aspects, the antibody comprises a CDR-H3 sequence comprising, consisting of, or consisting essentially of SEQ ID NO:700. In some aspects, the antibody comprises a CDR-H3 sequence comprising, consisting of, or consisting essentially of SEQ ID NO:701. In some aspects, the antibody comprises a CDR-H3 sequence comprising, consisting of, or consisting essentially of SEQ ID NO:702. In some aspects, the antibody comprises a CDR-H3 sequence comprising, consisting of, or consisting essentially of SEQ ID NO:703. In some aspects, the antibody comprises a CDR-H3 sequence comprising, consisting of, or consisting essentially of SEQ ID NO:704. In some aspects, the antibody comprises a CDR-H3 sequence comprising, consisting of, or consisting essentially of SEQ ID NO:705. In some aspects, the antibody comprises a CDR-H3 sequence comprising, consisting of, or consisting essentially of SEQ ID NO:706. In some aspects, the antibody comprises a CDR-H3 sequence comprising, consisting of, or consisting essentially of SEQ ID NO:707. In some aspects, the antibody comprises a CDR-H3 sequence comprising, consisting of, or consisting essentially of SEQ ID NO:708. In some aspects, the antibody comprises a CDR-H3 sequence comprising, consisting of, or consisting essentially of SEQ ID NO:709. In some aspects, the antibody comprises a CDR-H3 sequence comprising, consisting of, or consisting essentially of SEQ ID NO:710. In some aspects, the antibody comprises a CDR-H3 sequence comprising, consisting of, or consisting essentially of SEQ ID NO:711. In some aspects, the antibody comprises a CDR-H3 sequence comprising, consisting of, or consisting essentially of SEQ ID NO:712. In some aspects, the antibody comprises a CDR-H3 sequence comprising, consisting of, or consisting essentially of SEQ ID NO:713. In some aspects, the antibody comprises a CDR-H3 sequence comprising, consisting of, or consisting essentially of SEQ ID NO:714. In some aspects, the antibody comprises a CDR-H3 sequence comprising, consisting of, or consisting essentially of SEQ ID NO:715. In some aspects, the antibody comprises a CDR-H3 sequence comprising, consisting of, or consisting essentially of SEQ ID NO:716. In some aspects, the antibody comprises a CDR-H3 sequence comprising, consisting of, or consisting essentially of SEQ ID NO:717. In some aspects, the antibody comprises a CDR-H3 sequence comprising, consisting of, or consisting essentially of SEQ ID NO:718. In some aspects, the antibody comprises a CDR-H3 sequence comprising, consisting of, or consisting essentially of SEQ ID NO:719. In some aspects, the antibody comprises a CDR-H3 sequence comprising, consisting of, or consisting essentially of SEQ ID NO:720. In some aspects, the antibody comprises a CDR-H3 sequence comprising, consisting of, or consisting essentially of SEQ ID NO:721. In some aspects, the antibody comprises a CDR-H3 sequence comprising, consisting of, or consisting essentially of SEQ ID NO:722. In some aspects, the antibody comprises a CDR-H3 sequence comprising, consisting of, or consisting essentially of SEQ ID NO:723. In some aspects, the antibody comprises a CDR-H3 sequence comprising, consisting of, or consisting essentially of SEQ ID NO:724. In some aspects, the antibody comprises a CDR-H3 sequence comprising, consisting of, or consisting essentially of SEQ ID NO:725. In some aspects, the antibody comprises a CDR-H3 sequence comprising, consisting of, or consisting essentially of SEQ ID NO:726. In some aspects, the antibody comprises a CDR-H3 sequence comprising, consisting of, or consisting essentially of SEQ ID NO:727. In some aspects, the antibody comprises a CDR-H3 sequence comprising, consisting of, or consisting essentially of SEQ ID NO:728. In some aspects, the antibody comprises a CDR-H3 sequence comprising, consisting of, or consisting essentially of SEQ ID NO:729. In some aspects, the antibody comprises a CDR-H3 sequence comprising, consisting of, or consisting essentially of SEQ ID NO:730. In some aspects, the antibody comprises a CDR-H3 sequence comprising, consisting of, or consisting essentially of SEQ ID NO:731. In some aspects, the antibody comprises a CDR-H3 sequence comprising, consisting of, or consisting essentially of SEQ ID NO:732. In some aspects, the antibody comprises a CDR-H3 sequence comprising, consisting of, or consisting essentially of SEQ ID NO:733. In some aspects, the antibody comprises a CDR-H3 sequence comprising, consisting of, or consisting essentially of SEQ ID NO:734. In some aspects, the antibody comprises a CDR-H3 sequence comprising, consisting of, or consisting essentially of SEQ ID NO:735. In some aspects, the antibody comprises a CDR-H3 sequence comprising, consisting of, or consisting essentially of SEQ ID NO:736. In some aspects, the antibody comprises a CDR-H3 sequence comprising, consisting of, or consisting essentially of SEQ ID NO:737. In some aspects, the antibody comprises a CDR-H3 sequence comprising, consisting of, or consisting essentially of SEQ ID NO:738. In some aspects, the antibody comprises a CDR-H3 sequence comprising, consisting of, or consisting essentially of SEQ ID NO:739. In some aspects, the antibody comprises a CDR-H3 sequence comprising, consisting of, or consisting essentially of SEQ ID NO:740. In some aspects, the antibody comprises a CDR-H3 sequence comprising, consisting of, or consisting essentially of SEQ ID NO:741. In some aspects, the antibody comprises a CDR-H3 sequence comprising, consisting of, or consisting essentially of SEQ ID NO:742. In some aspects, the antibody comprises a CDR-H3 sequence comprising, consisting of, or consisting essentially of SEQ ID NO:743. In some aspects, the antibody comprises a CDR-H3 sequence comprising, consisting of, or consisting essentially of SEQ ID NO:744. In some aspects, the antibody comprises a CDR-H3 sequence comprising, consisting of, or consisting essentially of SEQ ID NO:745. In some aspects, the antibody comprises a CDR-H3 sequence comprising, consisting of, or consisting essentially of SEQ ID NO:746. In some aspects, the antibody comprises a CDR-H3 sequence comprising, consisting of, or consisting essentially of SEQ ID NO:747. In some aspects, the antibody comprises a CDR-H3 sequence comprising, consisting of, or consisting essentially of SEQ ID NO:748. In some aspects, the antibody comprises a CDR-H3 sequence comprising, consisting of, or consisting essentially of SEQ ID NO:749.

In some aspects, the antibody comprises a CDR-H3 sequence comprising, consisting of, or consisting essentially of SEQ ID NO:750. In some aspects, the antibody comprises a CDR-H3 sequence comprising, consisting of, or consisting essentially of SEQ ID NO:751. In some aspects, the antibody comprises a CDR-H3 sequence comprising, consisting of, or consisting essentially of SEQ ID NO:752. In some aspects, the antibody comprises a CDR-H3 sequence comprising, consisting of, or consisting essentially of SEQ ID NO:753. In some aspects, the antibody comprises a CDR-H3 sequence comprising, consisting of, or consisting essentially of SEQ ID NO:754. In some aspects, the antibody comprises a CDR-H3 sequence comprising, consisting of, or consisting essentially of SEQ ID NO:755. In some aspects, the antibody comprises a CDR-H3 sequence comprising, consisting of, or consisting essentially of SEQ ID NO:756. In some aspects, the antibody comprises a CDR-H3 sequence comprising, consisting of, or consisting essentially of SEQ ID NO:757. In some aspects, the antibody comprises a CDR-H3 sequence comprising, consisting of, or consisting essentially of SEQ ID NO:758. In some aspects, the antibody comprises a CDR-H3 sequence comprising, consisting of, or consisting essentially of SEQ ID NO:759. In some aspects, the antibody comprises a CDR-H3 sequence comprising, consisting of, or consisting essentially of SEQ ID NO:760. In some aspects, the antibody comprises a CDR-H3 sequence comprising, consisting of, or consisting essentially of SEQ ID NO:761. In some aspects, the antibody comprises a CDR-H3 sequence comprising, consisting of, or consisting essentially of SEQ ID NO:762. In some aspects, the antibody comprises a CDR-H3 sequence comprising, consisting of, or consisting essentially of SEQ ID NO:763. In some aspects, the antibody comprises a CDR-H3 sequence comprising, consisting of, or consisting essentially of SEQ ID NO:764. In some aspects, the antibody comprises a CDR-H3 sequence comprising, consisting of, or consisting essentially of SEQ ID NO:765. In some aspects, the antibody comprises a CDR-H3 sequence comprising, consisting of, or consisting essentially of SEQ ID NO:766. In some aspects, the antibody comprises a CDR-H3 sequence comprising, consisting of, or consisting essentially of SEQ ID NO:767. In some aspects, the antibody comprises a CDR-H3 sequence comprising, consisting of, or consisting essentially of SEQ ID NO:768. In some aspects, the antibody comprises a CDR-H3 sequence comprising, consisting of, or consisting essentially of SEQ ID NO:769. In some aspects, the antibody comprises a CDR-H3 sequence comprising, consisting of, or consisting essentially of SEQ ID NO:770. In some aspects, the antibody comprises a CDR-H3 sequence comprising, consisting of, or consisting essentially of SEQ ID NO:771. In some aspects, the antibody comprises a CDR-H3 sequence comprising, consisting of, or consisting essentially of SEQ ID NO:772. In some aspects, the antibody comprises a CDR-H3 sequence comprising, consisting of, or consisting essentially of SEQ ID NO:773. In some aspects, the antibody comprises a CDR-H3 sequence comprising, consisting of, or consisting essentially of SEQ ID NO:774. In some aspects, the antibody comprises a CDR-H3 sequence comprising, consisting of, or consisting essentially of SEQ ID NO:775. In some aspects, the antibody comprises a CDR-H3 sequence comprising, consisting of, or consisting essentially of SEQ ID NO:776. In some aspects, the antibody comprises a CDR-H3 sequence comprising, consisting of, or consisting essentially of SEQ ID NO:777. In some aspects, the antibody comprises a CDR-H3 sequence comprising, consisting of, or consisting essentially of SEQ ID NO:778. In some aspects, the antibody comprises a CDR-H3 sequence comprising, consisting of, or consisting essentially of SEQ ID NO:779. In some aspects, the antibody comprises a CDR-H3 sequence comprising, consisting of, or consisting essentially of SEQ ID NO:780. In some aspects, the antibody comprises a CDR-H3 sequence comprising, consisting of, or consisting essentially of SEQ ID NO:781. In some aspects, the antibody comprises a CDR-H3 sequence comprising, consisting of, or consisting essentially of SEQ ID NO:782. In some aspects, the antibody comprises a CDR-H3 sequence comprising, consisting of, or consisting essentially of SEQ ID NO:783. In some aspects, the antibody comprises a CDR-H3 sequence comprising, consisting of, or consisting essentially of SEQ ID NO:784. In some aspects, the antibody comprises a CDR-H3 sequence comprising, consisting of, or consisting essentially of SEQ ID NO:785. In some aspects, the antibody comprises a CDR-H3 sequence comprising, consisting of, or consisting essentially of SEQ ID NO:786. In some aspects, the antibody comprises a CDR-H3 sequence comprising, consisting of, or consisting essentially of SEQ ID NO:787. In some aspects, the antibody comprises a CDR-H3 sequence comprising, consisting of, or consisting essentially of SEQ ID NO:788. In some aspects, the antibody comprises a CDR-H3 sequence comprising, consisting of, or consisting essentially of SEQ ID NO:789. In some aspects, the antibody comprises a CDR-H3 sequence comprising, consisting of, or consisting essentially of SEQ ID NO:790. In some aspects, the antibody comprises a CDR-H3 sequence comprising, consisting of, or consisting essentially of SEQ ID NO:791. In some aspects, the antibody comprises a CDR-H3 sequence comprising, consisting of, or consisting essentially of SEQ ID NO:792. In some aspects, the antibody comprises a CDR-H3 sequence comprising, consisting of, or consisting essentially of SEQ ID NO:793. In some aspects, the antibody comprises a CDR-H3 sequence comprising, consisting of, or consisting essentially of SEQ ID NO:794. In some aspects, the antibody comprises a CDR-H3 sequence comprising, consisting of, or consisting essentially of SEQ ID NO:795. In some aspects, the antibody comprises a CDR-H3 sequence comprising, consisting of, or consisting essentially of SEQ ID NO:796. In some aspects, the antibody comprises a CDR-H3 sequence comprising, consisting of, or consisting essentially of SEQ ID NO:797. In some aspects, the antibody comprises a CDR-H3 sequence comprising, consisting of, or consisting essentially of SEQ ID NO:798. In some aspects, the antibody comprises a CDR-H3 sequence comprising, consisting of, or consisting essentially of SEQ ID NO:799.

In some aspects, the antibody comprises a CDR-H3 sequence comprising, consisting of, or consisting essentially of SEQ ID NO:800. In some aspects, the antibody comprises a CDR-H3 sequence comprising, consisting of, or consisting essentially of SEQ ID NO:801. In some aspects, the antibody comprises a CDR-H3 sequence comprising, consisting of, or consisting essentially of SEQ ID NO:802. In some aspects, the antibody comprises a CDR-H3 sequence comprising, consisting of, or consisting essentially of SEQ ID NO:803. In some aspects, the antibody comprises a CDR-H3 sequence comprising, consisting of, or consisting essentially of SEQ ID NO:804. In some aspects, the antibody comprises a CDR-H3 sequence comprising, consisting of, or consisting essentially of SEQ ID NO:805. In some aspects, the antibody comprises a CDR-H3 sequence comprising, consisting of, or consisting essentially of SEQ ID NO:806. In some aspects, the antibody comprises a CDR-H3 sequence comprising, consisting of, or consisting essentially of SEQ ID NO:807. In some aspects, the antibody comprises a CDR-H3 sequence comprising, consisting of, or consisting essentially of SEQ ID NO:808. In some aspects, the antibody comprises a CDR-H3 sequence comprising, consisting of, or consisting essentially of SEQ ID NO:809. In some aspects, the antibody comprises a CDR-H3 sequence comprising, consisting of, or consisting essentially of SEQ ID NO:810. In some aspects, the antibody comprises a CDR-H3 sequence comprising, consisting of, or consisting essentially of SEQ ID NO:811. In some aspects, the antibody comprises a CDR-H3 sequence comprising, consisting of, or consisting essentially of SEQ ID NO:812. In some aspects, the antibody comprises a CDR-H3 sequence comprising, consisting of, or consisting essentially of SEQ ID NO:813. In some aspects, the antibody comprises a CDR-H3 sequence comprising, consisting of, or consisting essentially of SEQ ID NO:814. In some aspects, the antibody comprises a CDR-H3 sequence comprising, consisting of, or consisting essentially of SEQ ID NO:815. In some aspects, the antibody comprises a CDR-H3 sequence comprising, consisting of, or consisting essentially of SEQ ID NO:816. In some aspects, the antibody comprises a CDR-H3 sequence comprising, consisting of, or consisting essentially of SEQ ID NO:817. In some aspects, the antibody comprises a CDR-H3 sequence comprising, consisting of, or consisting essentially of SEQ ID NO:818. In some aspects, the antibody comprises a CDR-H3 sequence comprising, consisting of, or consisting essentially of SEQ ID NO:819. In some aspects, the antibody comprises a CDR-H3 sequence comprising, consisting of, or consisting essentially of SEQ ID NO:820. In some aspects, the antibody comprises a CDR-H3 sequence comprising, consisting of, or consisting essentially of SEQ ID NO:821. In some aspects, the antibody comprises a CDR-H3 sequence comprising, consisting of, or consisting essentially of SEQ ID NO:822. In some aspects, the antibody comprises a CDR-H3 sequence comprising, consisting of, or consisting essentially of SEQ ID NO:823. In some aspects, the antibody comprises a CDR-H3 sequence comprising, consisting of, or consisting essentially of SEQ ID NO:824. In some aspects, the antibody comprises a CDR-H3 sequence comprising, consisting of, or consisting essentially of SEQ ID NO:825. In some aspects, the antibody comprises a CDR-H3 sequence comprising, consisting of, or consisting essentially of SEQ ID NO:826. In some aspects, the antibody comprises a CDR-H3 sequence comprising, consisting of, or consisting essentially of SEQ ID NO:827. In some aspects, the antibody comprises a CDR-H3 sequence comprising, consisting of, or consisting essentially of SEQ ID NO:828. In some aspects, the antibody comprises a CDR-H3 sequence comprising, consisting of, or consisting essentially of SEQ ID NO:829. In some aspects, the antibody comprises a CDR-H3 sequence comprising, consisting of, or consisting essentially of SEQ ID NO:830. In some aspects, the antibody comprises a CDR-H3 sequence comprising, consisting of, or consisting essentially of SEQ ID NO:831. In some aspects, the antibody comprises a CDR-H3 sequence comprising, consisting of, or consisting essentially of SEQ ID NO:832. In some aspects, the antibody comprises a CDR-H3 sequence comprising, consisting of, or consisting essentially of SEQ ID NO:833. In some aspects, the antibody comprises a CDR-H3 sequence comprising, consisting of, or consisting essentially of SEQ ID NO:834. In some aspects, the antibody comprises a CDR-H3 sequence comprising, consisting of, or consisting essentially of SEQ ID NO:835. In some aspects, the antibody comprises a CDR-H3 sequence comprising, consisting of, or consisting essentially of SEQ ID NO:836. In some aspects, the antibody comprises a CDR-H3 sequence comprising, consisting of, or consisting essentially of SEQ ID NO:837. In some aspects, the antibody comprises a CDR-H3 sequence comprising, consisting of, or consisting essentially of SEQ ID NO:838.

5.2.1.2. Kabat CDR-H2

In some embodiments, the antibody comprises a $V_H$ sequence comprising a CDR-H2 sequence, wherein the CDR-H2 sequence comprises, consists of, or consists essentially of a Kabat CDR-H2 sequence of an illustrative antibody or $V_H$ sequence provided herein. In some aspects, the Kabat CDR-H2 sequence is a Kabat CDR-H2 sequence of a $V_H$ sequence provided in SEQ ID NOs: 854-1020.

In some embodiments, the antibody comprises a $V_H$ sequence comprising a Kabat CDR-H2 sequence comprising, consisting of, or consisting essentially of a sequence selected from SEQ ID NOs: 505-671. In some aspects, the antibody comprises a Kabat CDR-H2 sequence comprising, consisting of, or consisting essentially of SEQ ID NO:505. In some aspects, the antibody comprises a Kabat CDR-H2 sequence comprising, consisting of, or consisting essentially of SEQ ID NO:506. In some aspects, the antibody comprises a Kabat CDR-H2 sequence comprising, consisting of, or consisting essentially of SEQ ID NO:507. In some aspects, the antibody comprises a Kabat CDR-H2 sequence comprising, consisting of, or consisting essentially of SEQ ID NO:508. In some aspects, the antibody comprises a Kabat CDR-H2 sequence comprising, consisting of, or consisting essentially of SEQ ID NO:509. In some aspects, the antibody comprises a Kabat CDR-H2 sequence comprising, consisting of, or consisting essentially of SEQ ID NO:510. In some aspects, the antibody comprises a Kabat CDR-H2 sequence comprising, consisting of, or consisting essentially of SEQ ID NO:511. In some aspects, the antibody comprises a Kabat CDR-H2 sequence comprising, consisting of, or consisting essentially of SEQ ID NO:512. In some aspects, the antibody comprises a Kabat CDR-H2 sequence comprising, consisting of, or consisting essentially of SEQ ID NO:513. In some aspects, the antibody comprises a Kabat CDR-H2 sequence comprising, consisting of, or consisting essentially of SEQ ID NO:514. In some aspects, the antibody comprises a Kabat CDR-H2 sequence comprising, consisting of, or consisting essentially of SEQ ID NO:515. In some aspects, the antibody comprises a Kabat CDR-H2 sequence comprising, consisting of, or consisting essentially of SEQ ID NO:516. In some aspects, the antibody comprises a Kabat CDR-H2 sequence comprising, consisting of, or consisting essentially of SEQ ID NO:517. In some aspects, the antibody comprises a Kabat CDR-H2 sequence comprising, consisting of, or consisting essentially of SEQ ID NO:518. In some aspects, the antibody comprises a Kabat CDR-H2 sequence comprising, consisting of, or consisting essentially of SEQ ID NO:519. In some aspects, the antibody comprises a Kabat CDR-H2 sequence comprising, consisting of, or consisting essentially of SEQ ID NO:520. In some aspects, the antibody comprises a Kabat CDR-H2 sequence comprising, consisting of, or consisting essentially of SEQ ID NO:521. In some aspects, the antibody comprises a Kabat CDR-H2 sequence comprising, consisting of, or consisting essentially of SEQ ID NO:522. In some aspects, the antibody comprises a Kabat CDR-H2 sequence comprising, consisting of, or consisting essentially of SEQ ID NO:523. In some aspects, the antibody comprises a Kabat CDR-H2 sequence comprising, consisting of, or consisting essentially of SEQ ID NO:524. In some aspects, the antibody comprises a Kabat CDR-H2 sequence comprising, consisting of, or consisting essentially of SEQ ID NO:525. In some aspects, the antibody comprises a Kabat CDR-H2 sequence comprising, consisting of, or consisting essentially of SEQ ID NO:526. In some aspects, the antibody comprises a Kabat CDR-H2 sequence comprising, consisting of, or consisting essentially of SEQ ID NO:527. In some aspects, the antibody comprises a Kabat CDR-H2 sequence comprising, consisting of, or consisting essentially of SEQ ID NO:528. In some aspects, the antibody comprises a Kabat CDR-H2 sequence comprising, consisting of, or consisting essentially of SEQ ID NO:529. In some aspects, the antibody comprises a Kabat CDR-H2 sequence comprising, consisting of, or consisting essentially of SEQ ID NO:530. In some aspects, the antibody comprises a Kabat CDR-H2 sequence comprising, consisting of, or consisting essentially of SEQ ID NO:531. In some aspects, the antibody comprises a Kabat CDR-H2 sequence comprising, consisting of, or consisting essentially of SEQ ID NO:532. In some aspects, the antibody comprises a Kabat CDR-H2 sequence comprising, consisting of, or consisting essentially of SEQ ID NO:533. In some aspects, the antibody comprises a Kabat CDR-H2 sequence comprising, consisting of, or consisting essentially of SEQ ID NO:534. In some aspects, the antibody comprises a Kabat CDR-H2 sequence comprising, consisting of, or consisting essentially of SEQ ID NO:535. In some aspects, the antibody comprises a Kabat CDR-H2 sequence comprising, consisting of, or consisting essentially of SEQ ID NO:536. In some aspects, the antibody comprises a Kabat CDR-H2 sequence comprising, consisting of, or consisting essentially of SEQ ID NO:537. In some aspects, the antibody comprises a Kabat CDR-H2 sequence comprising, consisting of, or consisting essentially of SEQ ID NO:538. In some aspects, the antibody comprises a Kabat CDR-H2 sequence comprising, consisting of, or consisting essentially of SEQ ID NO:539. In some aspects, the antibody comprises a Kabat CDR-H2 sequence comprising, consisting of, or consisting essentially of SEQ ID NO:540. In some aspects, the antibody comprises a Kabat CDR-H2 sequence comprising, consisting of, or consisting essentially of SEQ ID NO:541. In some aspects, the antibody comprises a Kabat CDR-H2 sequence comprising, consisting of, or consisting essentially of SEQ ID NO:542. In some aspects, the antibody comprises a Kabat CDR-H2 sequence comprising, consisting of, or consisting essentially of SEQ ID NO:543. In some aspects, the antibody comprises a Kabat CDR-H2 sequence comprising, consisting of, or consisting essentially of SEQ ID NO:544. In some aspects, the antibody comprises a Kabat CDR-H2 sequence comprising, consisting of, or consisting essentially of SEQ ID NO:545. In some aspects, the antibody comprises a Kabat CDR-H2 sequence comprising, consisting of, or consisting essentially of SEQ ID NO:546. In some aspects, the antibody comprises a Kabat CDR-H2 sequence comprising, consisting of, or consisting essentially of SEQ ID NO:547. In some aspects, the antibody comprises a Kabat CDR-H2 sequence comprising, consisting of, or consisting essentially of SEQ ID NO:548. In some aspects, the antibody comprises a Kabat CDR-H2 sequence comprising, consisting of, or consisting essentially of SEQ ID NO:549.

In some aspects, the antibody comprises a Kabat CDR-H2 sequence comprising, consisting of, or consisting essentially of SEQ ID NO:550. In some aspects, the antibody comprises a Kabat CDR-H2 sequence comprising, consisting of, or consisting essentially of SEQ ID NO:551. In some aspects, the antibody comprises a Kabat CDR-H2 sequence comprising, consisting of, or consisting essentially of SEQ ID NO:552. In some aspects, the antibody comprises a Kabat CDR-H2 sequence comprising, consisting of, or consisting essentially of SEQ ID NO:553. In some aspects, the antibody comprises a Kabat CDR-H2 sequence comprising, consisting of, or consisting essentially of SEQ ID NO:554. In some aspects, the antibody comprises a Kabat CDR-H2 sequence comprising, consisting of, or consisting essentially of SEQ ID NO:555. In some aspects, the antibody comprises a Kabat CDR-H2 sequence comprising, consisting of, or consisting essentially of SEQ ID NO:556. In some aspects, the antibody comprises a Kabat CDR-H2 sequence comprising, consisting of, or consisting essentially of SEQ ID NO:557. In some aspects, the antibody comprises a Kabat CDR-H2 sequence comprising, consisting of, or consisting essentially of SEQ ID NO:558. In some aspects, the antibody comprises a Kabat CDR-H2 sequence comprising, consisting of, or consisting essentially of SEQ ID NO:559.

In some aspects, the antibody comprises a Kabat CDR-H2 sequence comprising, consisting of, or consisting essentially of SEQ ID NO:560. In some aspects, the antibody comprises a Kabat CDR-H2 sequence comprising, consisting of, or consisting essentially of SEQ ID NO:561. In some aspects, the antibody comprises a Kabat CDR-H2 sequence comprising, consisting of, or consisting essentially of SEQ ID NO:562. In some aspects, the antibody comprises a Kabat CDR-H2 sequence comprising, consisting of, or consisting essentially of SEQ ID NO:563. In some aspects, the antibody comprises a Kabat CDR-H2 sequence comprising, consisting of, or consisting essentially of SEQ ID NO:564. In some aspects, the antibody comprises a Kabat CDR-H2 sequence comprising, consisting of, or consisting essentially of SEQ ID NO:565. In some aspects, the antibody comprises a Kabat CDR-H2 sequence comprising, consisting of, or consisting essentially of SEQ ID NO:566. In some aspects, the antibody comprises a Kabat CDR-H2 sequence comprising, consisting of, or consisting essentially of SEQ ID NO:567. In some aspects, the antibody comprises a Kabat CDR-H2 sequence comprising, consisting of, or consisting essentially of SEQ ID NO:568. In some aspects, the antibody comprises a Kabat CDR-H2 sequence comprising, consisting of, or consisting essentially of SEQ ID NO:569. In some aspects, the antibody comprises a Kabat CDR-H2 sequence comprising, consisting of, or consisting essentially of SEQ ID NO:570. In some aspects, the antibody comprises a Kabat CDR-H2 sequence comprising, consisting of, or consisting essentially of SEQ ID NO:571. In some aspects, the antibody comprises a Kabat CDR-H2 sequence comprising, consisting of, or consisting essentially of SEQ ID NO:572. In some aspects, the antibody comprises a Kabat CDR-H2 sequence comprising, consisting of, or consisting essentially of SEQ ID NO:573. In some aspects, the antibody comprises a Kabat CDR-H2 sequence comprising, consisting of, or consisting essentially of SEQ ID NO:574. In some aspects, the antibody comprises a Kabat CDR-H2 sequence comprising, consisting of, or consisting essentially of SEQ ID NO:575. In some aspects, the antibody comprises a Kabat CDR-H2 sequence comprising, consisting of, or consisting essentially of SEQ ID NO:576. In some aspects, the antibody comprises a Kabat CDR-H2 sequence comprising, consisting of, or consisting essentially of SEQ ID NO:577. In some aspects, the antibody comprises a Kabat CDR-H2 sequence comprising, consisting of, or consisting essentially of SEQ ID NO:578. In some aspects, the antibody comprises a Kabat CDR-H2 sequence comprising, consisting of, or consisting essentially of SEQ ID NO:579. In some aspects, the antibody comprises a Kabat CDR-H2 sequence comprising, consisting of, or consisting essentially of SEQ ID NO:580. In some aspects, the antibody comprises a Kabat CDR-H2 sequence comprising, consisting of, or consisting essentially of SEQ ID NO:581. In some aspects, the antibody comprises a Kabat CDR-H2 sequence comprising, consisting of, or consisting essentially of SEQ ID NO:582. In some aspects, the antibody comprises a Kabat CDR-H2 sequence comprising, consisting of, or consisting essentially of SEQ ID NO:583. In some aspects, the antibody comprises a Kabat CDR-H2 sequence comprising, consisting of, or consisting essentially of SEQ ID NO:584. In some aspects, the antibody comprises a Kabat CDR-H2 sequence comprising, consisting of, or consisting essentially of SEQ ID NO:585. In some aspects, the antibody comprises a Kabat CDR-H2 sequence comprising, consisting of, or consisting essentially of SEQ ID NO:586. In some aspects, the antibody comprises a Kabat CDR-H2 sequence comprising, consisting of, or consisting essentially of SEQ ID NO:587. In some aspects, the antibody comprises a Kabat CDR-H2 sequence comprising, consisting of, or consisting essentially of SEQ ID NO:588. In some aspects, the antibody comprises a Kabat CDR-H2 sequence comprising, consisting of, or consisting essentially of SEQ ID NO:589. In some aspects, the antibody comprises a Kabat CDR-H2 sequence comprising, consisting of, or consisting essentially of SEQ ID NO:590. In some aspects, the antibody comprises a Kabat CDR-H2 sequence comprising, consisting of, or consisting essentially of SEQ ID NO:591. In some aspects, the antibody comprises a Kabat CDR-H2 sequence comprising, consisting of, or consisting essentially of SEQ ID NO:592. In some aspects, the antibody comprises a Kabat CDR-H2 sequence comprising, consisting of, or consisting essentially of SEQ ID NO:593. In some aspects, the antibody comprises a Kabat CDR-H2 sequence comprising, consisting of, or consisting essentially of SEQ ID NO:594. In some aspects, the antibody comprises a Kabat CDR-H2 sequence comprising, consisting of, or consisting essentially of SEQ ID NO:595. In some aspects, the antibody comprises a Kabat CDR-H2 sequence comprising, consisting of, or consisting essentially of SEQ ID NO:596. In some aspects, the antibody comprises a Kabat CDR-H2 sequence comprising, consisting of, or consisting essentially of SEQ ID NO:597. In some aspects, the antibody comprises a Kabat CDR-H2 sequence comprising, consisting of, or consisting essentially of SEQ ID NO:598. In some aspects, the antibody comprises a Kabat CDR-H2 sequence comprising, consisting of, or consisting essentially of SEQ ID NO:599.

In some aspects, the antibody comprises a Kabat CDR-H2 sequence comprising, consisting of, or consisting essentially of SEQ ID NO:600. In some aspects, the antibody comprises a Kabat CDR-H2 sequence comprising, consisting of, or consisting essentially of SEQ ID NO:601. In some aspects, the antibody comprises a Kabat CDR-H2 sequence comprising, consisting of, or consisting essentially of SEQ ID NO:602. In some aspects, the antibody comprises a Kabat CDR-H2 sequence comprising, consisting of, or consisting essentially of SEQ ID NO:603. In some aspects, the antibody comprises a Kabat CDR-H2 sequence comprising, consisting of, or consisting essentially of SEQ ID NO:604. In some aspects, the antibody comprises a Kabat CDR-H2 sequence comprising, consisting of, or consisting essentially of SEQ ID NO:605. In some aspects, the antibody comprises a Kabat CDR-H2 sequence comprising, consisting of, or consisting essentially of SEQ ID NO:606. In some aspects, the antibody comprises a Kabat CDR-H2 sequence comprising, consisting of, or consisting essentially of SEQ ID NO:607. In some aspects, the antibody comprises a Kabat CDR-H2 sequence comprising, consisting of, or consisting essentially of SEQ ID NO:608. In some aspects, the antibody comprises a Kabat CDR-H2 sequence comprising, consisting of, or consisting essentially of SEQ ID NO:609. In some aspects, the antibody comprises a Kabat CDR-H2 sequence comprising, consisting of, or consisting essentially of SEQ ID NO:610. In some aspects, the antibody comprises a Kabat CDR-H2 sequence comprising, consisting of, or consisting essentially of SEQ ID NO:611. In some aspects, the antibody comprises a Kabat CDR-H2 sequence comprising, consisting of, or consisting essentially of SEQ ID NO:612. In some aspects, the antibody comprises a Kabat CDR-H2 sequence comprising, consisting of, or consisting essentially of SEQ ID NO:613. In some aspects, the antibody comprises a Kabat CDR-H2 sequence comprising, consisting of, or consisting essentially of SEQ ID NO:614. In some aspects, the antibody comprises a Kabat CDR-H2 sequence comprising, consisting of, or consisting essentially of SEQ ID NO:615. In some aspects, the antibody comprises a Kabat CDR-H2 sequence comprising, consisting of, or consisting essentially of SEQ ID NO:616. In some aspects, the antibody comprises a Kabat CDR-H2 sequence comprising, consisting of, or consisting essentially of SEQ ID NO:617. In some aspects, the antibody comprises a Kabat CDR-H2 sequence comprising, consisting of, or consisting essentially of SEQ ID NO:618. In some aspects, the antibody comprises a Kabat CDR-H2 sequence comprising, consisting of, or consisting essentially of SEQ ID NO:619. In some aspects, the antibody comprises a Kabat CDR-H2 sequence comprising, consisting of, or consisting essentially of SEQ ID NO:620. In some aspects, the antibody comprises a Kabat CDR-H2 sequence comprising, consisting of, or consisting essentially of SEQ ID NO:621. In some aspects, the antibody comprises a Kabat CDR-H2 sequence comprising, consisting of, or consisting essentially of SEQ ID NO:622. In some aspects, the antibody comprises a Kabat CDR-H2 sequence comprising, consisting of, or consisting essentially of SEQ ID NO:623. In some aspects, the antibody comprises a Kabat CDR-H2 sequence comprising, consisting of, or consisting essentially of SEQ ID NO:624. In some aspects, the antibody comprises a Kabat CDR-H2 sequence comprising, consisting of, or consisting essentially of SEQ ID NO:625. In some aspects, the antibody comprises a Kabat CDR-H2 sequence comprising, consisting of, or consisting essentially of SEQ ID NO:626. In some aspects, the antibody comprises a Kabat CDR-H2 sequence comprising, consisting of, or consisting essentially of SEQ ID NO:627. In some aspects, the antibody comprises a Kabat CDR-H2 sequence comprising, consisting of, or consisting essentially of SEQ ID NO:628. In some aspects, the antibody comprises a Kabat CDR-H2 sequence comprising, consisting of, or consisting essentially of SEQ ID NO:629. In some aspects, the antibody comprises a Kabat CDR-H2 sequence comprising, consisting of, or consisting essentially of SEQ ID NO:630. In some aspects, the antibody comprises a Kabat CDR-H2 sequence comprising, consisting of, or consisting essentially of SEQ ID NO:631. In some aspects, the antibody comprises a Kabat CDR-H2 sequence comprising, consisting of, or consisting essentially of SEQ ID NO:632. In some aspects, the antibody comprises a Kabat CDR-H2 sequence comprising, consisting of, or consisting essentially of SEQ ID NO:633. In some aspects, the antibody comprises a Kabat CDR-H2 sequence comprising, consisting of, or consisting essentially of SEQ ID NO:634. In some aspects, the antibody comprises a Kabat CDR-H2 sequence comprising, consisting of, or consisting essentially of SEQ ID NO:635. In some aspects, the antibody comprises a Kabat CDR-H2 sequence comprising, consisting of, or consisting essentially of SEQ ID NO:636. In some aspects, the antibody comprises a Kabat CDR-H2 sequence comprising, consisting of, or consisting essentially of SEQ ID NO:637. In some aspects, the antibody comprises a Kabat CDR-H2 sequence comprising, consisting of, or consisting essentially of SEQ ID NO:638. In some aspects, the antibody comprises a Kabat CDR-H2 sequence comprising, consisting of, or consisting essentially of SEQ ID NO:639. In some aspects, the antibody comprises a Kabat CDR-H2 sequence comprising, consisting of, or consisting essentially of SEQ ID NO:640. In some aspects, the antibody comprises a Kabat CDR-H2 sequence comprising, consisting of, or consisting essentially of SEQ ID NO:641. In some aspects, the antibody comprises a Kabat CDR-H2 sequence comprising, consisting of, or consisting essentially of SEQ ID NO:642. In some aspects, the antibody comprises a Kabat CDR-H2 sequence comprising, consisting of, or consisting essentially of SEQ ID NO:643. In some aspects, the antibody comprises a Kabat CDR-H2 sequence comprising, consisting of, or consisting essentially of SEQ ID NO:644. In some aspects, the antibody comprises a Kabat CDR-H2 sequence comprising, consisting of, or consisting essentially of SEQ ID NO:645. In some aspects, the antibody comprises a Kabat CDR-H2 sequence comprising, consisting of, or consisting essentially of SEQ ID NO:646. In some aspects, the antibody comprises a Kabat CDR-H2 sequence comprising, consisting of, or consisting essentially of SEQ ID NO:647. In some aspects, the antibody comprises a Kabat CDR-H2 sequence comprising, consisting of, or consisting essentially of SEQ ID NO:648. In some aspects, the antibody comprises a Kabat CDR-H2 sequence comprising, consisting of, or consisting essentially of SEQ ID NO:649.

In some aspects, the antibody comprises a Kabat CDR-H2 sequence comprising, consisting of, or consisting essentially of SEQ ID NO:650. In some aspects, the antibody comprises a Kabat CDR-H2 sequence comprising, consisting of, or consisting essentially of SEQ ID NO:651. In some aspects, the antibody comprises a Kabat CDR-H2 sequence comprising, consisting of, or consisting essentially of SEQ ID NO:652. In some aspects, the antibody comprises a Kabat CDR-H2 sequence comprising, consisting of, or consisting essentially of SEQ ID NO:653. In some aspects, the antibody comprises a Kabat CDR-H2 sequence comprising, consisting of, or consisting essentially of SEQ ID NO:654. In some aspects, the antibody comprises a Kabat CDR-H2 sequence comprising, consisting of, or consisting essentially of SEQ ID NO:655. In some aspects, the antibody comprises a Kabat CDR-H2 sequence comprising, consisting of, or consisting essentially of SEQ ID NO:656. In some aspects, the antibody comprises a Kabat CDR-H2 sequence comprising, consisting of, or consisting essentially of SEQ ID NO:657. In some aspects, the antibody comprises a Kabat CDR-H2 sequence comprising, consisting of, or consisting essentially of SEQ ID NO:658. In some aspects, the antibody comprises a Kabat CDR-H2 sequence comprising, consisting of, or consisting essentially of SEQ ID NO:659. In some aspects, the antibody comprises a Kabat CDR-H2 sequence comprising, consisting of, or consisting essentially of SEQ ID NO:660. In some aspects, the antibody comprises a Kabat CDR-H2 sequence comprising, consisting of, or consisting essentially of SEQ ID NO:661. In some aspects, the antibody comprises a Kabat CDR-H2 sequence comprising, consisting of, or consisting essentially of SEQ ID NO:662. In some aspects, the antibody comprises a Kabat CDR-H2 sequence comprising, consisting of, or consisting essentially of SEQ ID NO:663. In some aspects, the antibody comprises a Kabat CDR-H2 sequence comprising, consisting of, or consisting essentially of SEQ ID NO:664. In some aspects, the antibody comprises a Kabat CDR-H2 sequence comprising, consisting of, or consisting essentially of SEQ ID NO:665. In some aspects, the antibody comprises a Kabat CDR-H2 sequence comprising, consisting of, or consisting essentially of SEQ ID NO:666. In some aspects, the antibody comprises a Kabat CDR-H2 sequence comprising, consisting of, or consisting essentially of SEQ ID NO:667. In some aspects, the antibody comprises a Kabat CDR-H2 sequence comprising, consisting of, or consisting essentially of SEQ ID NO:668. In some aspects, the antibody comprises a Kabat CDR-H2 sequence comprising, consisting of, or consisting essentially of SEQ ID NO:669. In some aspects, the antibody comprises a Kabat CDR-H2 sequence comprising, consisting of, or consisting essentially of SEQ ID NO:670. In some aspects, the antibody comprises a Kabat CDR-H2 sequence comprising, consisting of, or consisting essentially of SEQ ID NO:671.

5.2.1.3. Kabat CDR-H1

In some embodiments, the antibody comprises a $V_H$ sequence comprising a CDR-H1 sequence, wherein the CDR-H1 sequence comprises, consists of, or consists essentially of a Kabat CDR-H1 sequence of an illustrative antibody or $V_H$ sequence provided herein. In some aspects, the Kabat CDR-H1 sequence is a Kabat CDR-H1 sequence of a $V_H$ sequence provided in SEQ ID NOs: 854-1020.

In some embodiments, the antibody comprises a $V_H$ sequence comprising a Kabat CDR-H1 sequence comprising, consisting of, or consisting essentially of a sequence selected from SEQ ID NOs: 171-337. In some aspects, the antibody comprises a Kabat CDR-H1 sequence comprising, consisting of, or consisting essentially of SEQ ID NO:171. In some aspects, the antibody comprises a Kabat CDR-H1 sequence comprising, consisting of, or consisting essentially of SEQ ID NO:172. In some aspects, the antibody comprises a Kabat CDR-H1 sequence comprising, consisting of, or consisting essentially of SEQ ID NO:173. In some aspects, the antibody comprises a Kabat CDR-H1 sequence comprising, consisting of, or consisting essentially of SEQ ID NO:174. In some aspects, the antibody comprises a Kabat CDR-H1 sequence comprising, consisting of, or consisting essentially of SEQ ID NO:175. In some aspects, the antibody comprises a Kabat CDR-H1 sequence comprising, consisting of, or consisting essentially of SEQ ID NO:176. In some aspects, the antibody comprises a Kabat CDR-H1 sequence comprising, consisting of, or consisting essentially of SEQ ID NO:177. In some aspects, the antibody comprises a Kabat CDR-H1 sequence comprising, consisting of, or consisting essentially of SEQ ID NO:178. In some aspects, the antibody comprises a Kabat CDR-H1 sequence comprising, consisting of, or consisting essentially of SEQ ID NO:179. In some aspects, the antibody comprises a Kabat CDR-H1 sequence comprising, consisting of, or consisting essentially of SEQ ID NO:180. In some aspects, the antibody comprises a Kabat CDR-H1 sequence comprising, consisting of, or consisting essentially of SEQ ID NO:181. In some aspects, the antibody comprises a Kabat CDR-H1 sequence comprising, consisting of, or consisting essentially of SEQ ID NO:182. In some aspects, the antibody comprises a Kabat CDR-H1 sequence comprising, consisting of, or consisting essentially of SEQ ID NO:183. In some aspects, the antibody comprises a Kabat CDR-H1 sequence comprising, consisting of, or consisting essentially of SEQ ID NO:184. In some aspects, the antibody comprises a Kabat CDR-H1 sequence comprising, consisting of, or consisting essentially of SEQ ID NO:185. In some aspects, the antibody comprises a Kabat CDR-H1 sequence comprising, consisting of, or consisting essentially of SEQ ID NO:186. In some aspects, the antibody comprises a Kabat CDR-H1 sequence comprising, consisting of, or consisting essentially of SEQ ID NO:187. In some aspects, the antibody comprises a Kabat CDR-H1 sequence comprising, consisting of, or consisting essentially of SEQ ID NO:188. In some aspects, the antibody comprises a Kabat CDR-H1 sequence comprising, consisting of, or consisting essentially of SEQ ID NO:189. In some aspects, the antibody comprises a Kabat CDR-H1 sequence comprising, consisting of, or consisting essentially of SEQ ID NO:190. In some aspects, the antibody comprises a Kabat CDR-H1 sequence comprising, consisting of, or consisting essentially of SEQ ID NO:191. In some aspects, the antibody comprises a Kabat CDR-H1 sequence comprising, consisting of, or consisting essentially of SEQ ID NO:192. In some aspects, the antibody comprises a Kabat CDR-H1 sequence comprising, consisting of, or consisting essentially of SEQ ID NO:193. In some aspects, the antibody comprises a Kabat CDR-H1 sequence comprising, consisting of, or consisting essentially of SEQ ID NO:194. In some aspects, the antibody comprises a Kabat CDR-H1 sequence comprising, consisting of, or consisting essentially of SEQ ID NO:195. In some aspects, the antibody comprises a Kabat CDR-H1 sequence comprising, consisting of, or consisting essentially of SEQ ID NO:196. In some aspects, the antibody comprises a Kabat CDR-H1 sequence comprising, consisting of, or consisting essentially of SEQ ID NO:197. In some aspects, the antibody comprises a Kabat CDR-H1 sequence comprising, consisting of, or consisting essentially of SEQ ID NO:198. In some aspects, the antibody comprises a Kabat CDR-H1 sequence comprising, consisting of, or consisting essentially of SEQ ID NO:199.

In some aspects, the antibody comprises a Kabat CDR-H1 sequence comprising, consisting of, or consisting essentially of SEQ ID NO:200. In some aspects, the antibody comprises a Kabat CDR-H1 sequence comprising, consisting of, or consisting essentially of SEQ ID NO:201. In some aspects, the antibody comprises a Kabat CDR-H1 sequence comprising, consisting of, or consisting essentially of SEQ ID NO:202. In some aspects, the antibody comprises a Kabat CDR-H1 sequence comprising, consisting of, or consisting essentially of SEQ ID NO:203. In some aspects, the antibody comprises a Kabat CDR-H1 sequence comprising, consisting of, or consisting essentially of SEQ ID NO:204. In some aspects, the antibody comprises a Kabat CDR-H1 sequence comprising, consisting of, or consisting essentially of SEQ ID NO:205. In some aspects, the antibody comprises a Kabat CDR-H1 sequence comprising, consisting of, or consisting essentially of SEQ ID NO:206. In some aspects, the antibody comprises a Kabat CDR-H1 sequence comprising, consisting of, or consisting essentially of SEQ ID NO:207. In some aspects, the antibody comprises a Kabat CDR-H1 sequence comprising, consisting of, or consisting essentially of SEQ ID NO:208. In some aspects, the antibody comprises a Kabat CDR-H1 sequence comprising, consisting of, or consisting essentially of SEQ ID NO:209. In some aspects, the antibody comprises a Kabat CDR-H1 sequence comprising, consisting of, or consisting essentially of SEQ ID NO:210. In some aspects, the antibody comprises a Kabat CDR-H1 sequence comprising, consisting of, or consisting essentially of SEQ ID NO:211. In some aspects, the antibody comprises a Kabat CDR-H1 sequence comprising, consisting of, or consisting essentially of SEQ ID NO:212. In some aspects, the antibody comprises a Kabat CDR-H1 sequence comprising, consisting of, or consisting essentially of SEQ ID NO:213. In some aspects, the antibody comprises a Kabat CDR-H1 sequence comprising, consisting of, or consisting essentially of SEQ ID NO:214. In some aspects, the antibody comprises a Kabat CDR-H1 sequence comprising, consisting of, or consisting essentially of SEQ ID NO:215. In some aspects, the antibody comprises a Kabat CDR-H1 sequence comprising, consisting of, or consisting essentially of SEQ ID NO:216. In some aspects, the antibody comprises a Kabat CDR-H1 sequence comprising, consisting of, or consisting essentially of SEQ ID NO:217. In some aspects, the antibody comprises a Kabat CDR-H1 sequence comprising, consisting of, or consisting essentially of SEQ ID NO:218. In some aspects, the antibody comprises a Kabat CDR-H1 sequence comprising, consisting of, or consisting essentially of SEQ ID NO:219. In some aspects, the antibody comprises a Kabat CDR-H1 sequence comprising, consisting of, or consisting essentially of SEQ ID NO:220. In some aspects, the antibody comprises a Kabat CDR-H1 sequence comprising, consisting of, or consisting essentially of SEQ ID NO:221. In some aspects, the antibody comprises a Kabat CDR-H1 sequence comprising, consisting of, or consisting essentially of SEQ ID NO:222. In some aspects, the antibody comprises a Kabat CDR-H1 sequence comprising, consisting of, or consisting essentially of SEQ ID NO:223. In some aspects, the antibody comprises a Kabat CDR-H1 sequence comprising, consisting of, or consisting essentially of SEQ ID NO:224. In some aspects, the antibody comprises a Kabat CDR-H1 sequence comprising, consisting of, or consisting essentially of SEQ ID NO:225. In some aspects, the antibody comprises a Kabat CDR-H1 sequence comprising, consisting of, or consisting essentially of SEQ ID NO:226. In some aspects, the antibody comprises a Kabat CDR-H1 sequence comprising, consisting of, or consisting essentially of SEQ ID NO:227. In some aspects, the antibody comprises a Kabat CDR-H1 sequence comprising, consisting of, or consisting essentially of SEQ ID NO:228. In some aspects, the antibody comprises a Kabat CDR-H1 sequence comprising, consisting of, or consisting essentially of SEQ ID NO:229. In some aspects, the antibody comprises a Kabat CDR-H1 sequence comprising, consisting of, or consisting essentially of SEQ ID NO:230. In some aspects, the antibody comprises a Kabat CDR-H1 sequence comprising, consisting of, or consisting essentially of SEQ ID NO:231. In some aspects, the antibody comprises a Kabat CDR-H1 sequence comprising, consisting of, or consisting essentially of SEQ ID NO:232. In some aspects, the antibody comprises a Kabat CDR-H1 sequence comprising, consisting of, or consisting essentially of SEQ ID NO:233. In some aspects, the antibody comprises a Kabat CDR-H1 sequence comprising, consisting of, or consisting essentially of SEQ ID NO:234. In some aspects, the antibody comprises a Kabat CDR-H1 sequence comprising, consisting of, or consisting essentially of SEQ ID NO:235. In some aspects, the antibody comprises a Kabat CDR-H1 sequence comprising, consisting of, or consisting essentially of SEQ ID NO:236. In some aspects, the antibody comprises a Kabat CDR-H1 sequence comprising, consisting of, or consisting essentially of SEQ ID NO:237. In some aspects, the antibody comprises a Kabat CDR-H1 sequence comprising, consisting of, or consisting essentially of SEQ ID NO:238. In some aspects, the antibody comprises a Kabat CDR-H1 sequence comprising, consisting of, or consisting essentially of SEQ ID NO:239. In some aspects, the antibody comprises a Kabat CDR-H1 sequence comprising, consisting of, or consisting essentially of SEQ ID NO:240. In some aspects, the antibody comprises a Kabat CDR-H1 sequence comprising, consisting of, or consisting essentially of SEQ ID NO:241. In some aspects, the antibody comprises a Kabat CDR-H1 sequence comprising, consisting of, or consisting essentially of SEQ ID NO:242. In some aspects, the antibody comprises a Kabat CDR-H1 sequence comprising, consisting of, or consisting essentially of SEQ ID NO:243. In some aspects, the antibody comprises a Kabat CDR-H1 sequence comprising, consisting of, or consisting essentially of SEQ ID NO:244. In some aspects, the antibody comprises a Kabat CDR-H1 sequence comprising, consisting of, or consisting essentially of SEQ ID NO:245. In some aspects, the antibody comprises a Kabat CDR-H1 sequence comprising, consisting of, or consisting essentially of SEQ ID NO:246. In some aspects, the antibody comprises a Kabat CDR-H1 sequence comprising, consisting of, or consisting essentially of SEQ ID NO:247. In some aspects, the antibody comprises a Kabat CDR-H1 sequence comprising, consisting of, or consisting essentially of SEQ ID NO:248. In some aspects, the antibody comprises a Kabat CDR-H1 sequence comprising, consisting of, or consisting essentially of SEQ ID NO:249.

In some aspects, the antibody comprises a Kabat CDR-H1 sequence comprising, consisting of, or consisting essentially of SEQ ID NO:250. In some aspects, the antibody comprises a Kabat CDR-H1 sequence comprising, consisting of, or consisting essentially of SEQ ID NO:251. In some aspects, the antibody comprises a Kabat CDR-H1 sequence comprising, consisting of, or consisting essentially of SEQ ID NO:252. In some aspects, the antibody comprises a Kabat CDR-H1 sequence comprising, consisting of, or consisting essentially of SEQ ID NO:253. In some aspects, the antibody comprises a Kabat CDR-H1 sequence comprising, consisting of, or consisting essentially of SEQ ID NO:254. In some aspects, the antibody comprises a Kabat CDR-H1 sequence comprising, consisting of, or consisting essentially of SEQ ID NO:255. In some aspects, the antibody comprises a Kabat CDR-H1 sequence comprising, consisting of, or consisting essentially of SEQ ID NO:256. In some aspects, the antibody comprises a Kabat CDR-H1 sequence comprising, consisting of, or consisting essentially of SEQ ID NO:257. In some aspects, the antibody comprises a Kabat CDR-H1 sequence comprising, consisting of, or consisting essentially of SEQ ID NO:258. In some aspects, the antibody comprises a Kabat CDR-H1 sequence comprising, consisting of, or consisting essentially of SEQ ID NO:259. In some aspects, the antibody comprises a Kabat CDR-H1 sequence comprising, consisting of, or consisting essentially of SEQ ID NO:260. In some aspects, the antibody comprises a Kabat CDR-H1 sequence comprising, consisting of, or consisting essentially of SEQ ID NO:261. In some aspects, the antibody comprises a Kabat CDR-H1 sequence comprising, consisting of, or consisting essentially of SEQ ID NO:262. In some aspects, the antibody comprises a Kabat CDR-H1 sequence comprising, consisting of, or consisting essentially of SEQ ID NO:263. In some aspects, the antibody comprises a Kabat CDR-H1 sequence comprising, consisting of, or consisting essentially of SEQ ID NO:264. In some aspects, the antibody comprises a Kabat CDR-H1 sequence comprising, consisting of, or consisting essentially of SEQ ID NO:265. In some aspects, the antibody comprises a Kabat CDR-H1 sequence comprising, consisting of, or consisting essentially of SEQ ID NO:266. In some aspects, the antibody comprises a Kabat CDR-H1 sequence comprising, consisting of, or consisting essentially of SEQ ID NO:267. In some aspects, the antibody comprises a Kabat CDR-H1 sequence comprising, consisting of, or consisting essentially of SEQ ID NO:268. In some aspects, the antibody comprises a Kabat CDR-H1 sequence comprising, consisting of, or consisting essentially of SEQ ID NO:269. In some aspects, the antibody comprises a Kabat CDR-H1 sequence comprising, consisting of, or consisting essentially of SEQ ID NO:270. In some aspects, the antibody comprises a Kabat CDR-H1 sequence comprising, consisting of, or consisting essentially of SEQ ID NO:271. In some aspects, the antibody comprises a Kabat CDR-H1 sequence comprising, consisting of, or consisting essentially of SEQ ID NO:272. In some aspects, the antibody comprises a Kabat CDR-H1 sequence comprising, consisting of, or consisting essentially of SEQ ID NO:273. In some aspects, the antibody comprises a Kabat CDR-H1 sequence comprising, consisting of, or consisting essentially of SEQ ID NO:274. In some aspects, the antibody comprises a Kabat CDR-H1 sequence comprising, consisting of, or consisting essentially of SEQ ID NO:275. In some aspects, the antibody comprises a Kabat CDR-H1 sequence comprising, consisting of, or consisting essentially of SEQ ID NO:276. In some aspects, the antibody comprises a Kabat CDR-H1 sequence comprising, consisting of, or consisting essentially of SEQ ID NO:277. In some aspects, the antibody comprises a Kabat CDR-H1 sequence comprising, consisting of, or consisting essentially of SEQ ID NO:278. In some aspects, the antibody comprises a Kabat CDR-H1 sequence comprising, consisting of, or consisting essentially of SEQ ID NO:279. In some aspects, the antibody comprises a Kabat CDR-H1 sequence comprising, consisting of, or consisting essentially of SEQ ID NO:280. In some aspects, the antibody comprises a Kabat CDR-H1 sequence comprising, consisting of, or consisting essentially of SEQ ID NO:281. In some aspects, the antibody comprises a Kabat CDR-H1 sequence comprising, consisting of, or consisting essentially of SEQ ID NO:282. In some aspects, the antibody comprises a Kabat CDR-H1 sequence comprising, consisting of, or consisting essentially of SEQ ID NO:283. In some aspects, the antibody comprises a Kabat CDR-H1 sequence comprising, consisting of, or consisting essentially of SEQ ID NO:284. In some aspects, the antibody comprises a Kabat CDR-H1 sequence comprising, consisting of, or consisting essentially of SEQ ID NO:285. In some aspects, the antibody comprises a Kabat CDR-H1 sequence comprising, consisting of, or consisting essentially of SEQ ID NO:286. In some aspects, the antibody comprises a Kabat CDR-H1 sequence comprising, consisting of, or consisting essentially of SEQ ID NO:287. In some aspects, the antibody comprises a Kabat CDR-H1 sequence comprising, consisting of, or consisting essentially of SEQ ID NO:288. In some aspects, the antibody comprises a Kabat CDR-H1 sequence comprising, consisting of, or consisting essentially of SEQ ID NO:289. In some aspects, the antibody comprises a Kabat CDR-H1 sequence comprising, consisting of, or consisting essentially of SEQ ID NO:290. In some aspects, the antibody comprises a Kabat CDR-H1 sequence comprising, consisting of, or consisting essentially of SEQ ID NO:291. In some aspects, the antibody comprises a Kabat CDR-H1 sequence comprising, consisting of, or consisting essentially of SEQ ID NO:292. In some aspects, the antibody comprises a Kabat CDR-H1 sequence comprising, consisting of, or consisting essentially of SEQ ID NO:293. In some aspects, the antibody comprises a Kabat CDR-H1 sequence comprising, consisting of, or consisting essentially of SEQ ID NO:294. In some aspects, the antibody comprises a Kabat CDR-H1 sequence comprising, consisting of, or consisting essentially of SEQ ID NO:295. In some aspects, the antibody comprises a Kabat CDR-H1 sequence comprising, consisting of, or consisting essentially of SEQ ID NO:296. In some aspects, the antibody comprises a Kabat CDR-H1 sequence comprising, consisting of, or consisting essentially of SEQ ID NO:297. In some aspects, the antibody comprises a Kabat CDR-H1 sequence comprising, consisting of, or consisting essentially of SEQ ID NO:298. In some aspects, the antibody comprises a Kabat CDR-H1 sequence comprising, consisting of, or consisting essentially of SEQ ID NO:299.

In some aspects, the antibody comprises a Kabat CDR-H1 sequence comprising, consisting of, or consisting essentially of SEQ ID NO:300. In some aspects, the antibody comprises a Kabat CDR-H1 sequence comprising, consisting of, or consisting essentially of SEQ ID NO:301. In some aspects, the antibody comprises a Kabat CDR-H1 sequence comprising, consisting of, or consisting essentially of SEQ ID NO:302. In some aspects, the antibody comprises a Kabat CDR-H1 sequence comprising, consisting of, or consisting essentially of SEQ ID NO:303. In some aspects, the antibody comprises a Kabat CDR-H1 sequence comprising, consisting of, or consisting essentially of SEQ ID NO:304. In some aspects, the antibody comprises a Kabat CDR-H1 sequence comprising, consisting of, or consisting essentially of SEQ ID NO:305. In some aspects, the antibody comprises a Kabat CDR-H1 sequence comprising, consisting of, or consisting essentially of SEQ ID NO:306. In some aspects, the antibody comprises a Kabat CDR-H1 sequence comprising, consisting of, or consisting essentially of SEQ ID NO:307. In some aspects, the antibody comprises a Kabat CDR-H1 sequence comprising, consisting of, or consisting essentially of SEQ ID NO:308. In some aspects, the antibody comprises a Kabat CDR-H1 sequence comprising, consisting of, or consisting essentially of SEQ ID NO:309. In some aspects, the antibody comprises a Kabat CDR-H1 sequence comprising, consisting of, or consisting essentially of SEQ ID NO:310. In some aspects, the antibody comprises a Kabat CDR-H1 sequence comprising, consisting of, or consisting essentially of SEQ ID NO:311. In some aspects, the antibody comprises a Kabat CDR-H1 sequence comprising, consisting of, or consisting essentially of SEQ ID NO:312. In some aspects, the antibody comprises a Kabat CDR-H1 sequence comprising, consisting of, or consisting essentially of SEQ ID NO:313. In some aspects, the antibody comprises a Kabat CDR-H1 sequence comprising, consisting of, or consisting essentially of SEQ ID NO:314. In some aspects, the antibody comprises a Kabat CDR-H1 sequence comprising, consisting of, or consisting essentially of SEQ ID NO:315. In some aspects, the antibody comprises a Kabat CDR-H1 sequence comprising, consisting of, or consisting essentially of SEQ ID NO:316. In some aspects, the antibody comprises a Kabat CDR-H1 sequence comprising, consisting of, or consisting essentially of SEQ ID NO:317. In some aspects, the antibody comprises a Kabat CDR-H1 sequence comprising, consisting of, or consisting essentially of SEQ ID NO:318. In some aspects, the antibody comprises a Kabat CDR-H1 sequence comprising, consisting of, or consisting essentially of SEQ ID NO:319. In some aspects, the antibody comprises a Kabat CDR-H1 sequence comprising, consisting of, or consisting essentially of SEQ ID NO:320. In some aspects, the antibody comprises a Kabat CDR-H1 sequence comprising, consisting of, or consisting essentially of SEQ ID NO:321. In some aspects, the antibody comprises a Kabat CDR-H1 sequence comprising, consisting of, or consisting essentially of SEQ ID NO:322. In some aspects, the antibody comprises a Kabat CDR-H1 sequence comprising, consisting of, or consisting essentially of SEQ ID NO:323. In some aspects, the antibody comprises a Kabat CDR-H1 sequence comprising, consisting of, or consisting essentially of SEQ ID NO:324. In some aspects, the antibody comprises a Kabat CDR-H1 sequence comprising, consisting of, or consisting essentially of SEQ ID NO:325. In some aspects, the antibody comprises a Kabat CDR-H1 sequence comprising, consisting of, or consisting essentially of SEQ ID NO:326. In some aspects, the antibody comprises a Kabat CDR-H1 sequence comprising, consisting of, or consisting essentially of SEQ ID NO:327. In some aspects, the antibody comprises a Kabat CDR-H1 sequence comprising, consisting of, or consisting essentially of SEQ ID NO:328. In some aspects, the antibody comprises a Kabat CDR-H1 sequence comprising, consisting of, or consisting essentially of SEQ ID NO:329. In some aspects, the antibody comprises a Kabat CDR-H1 sequence comprising, consisting of, or consisting essentially of SEQ ID NO:330. In some aspects, the antibody comprises a Kabat CDR-H1 sequence comprising, consisting of, or consisting essentially of SEQ ID NO:331. In some aspects, the antibody comprises a Kabat CDR-H1 sequence comprising, consisting of, or consisting essentially of SEQ ID NO:332. In some aspects, the antibody comprises a Kabat CDR-H1 sequence comprising, consisting of, or consisting essentially of SEQ ID NO:333. In some aspects, the antibody comprises a Kabat CDR-H1 sequence comprising, consisting of, or consisting essentially of SEQ ID NO:334. In some aspects, the antibody comprises a Kabat CDR-H1 sequence comprising, consisting of, or consisting essentially of SEQ ID NO:335. In some aspects, the antibody comprises a Kabat CDR-H1 sequence comprising, consisting of, or consisting essentially of SEQ ID NO:336. In some aspects, the antibody comprises a Kabat CDR-H1 sequence comprising, consisting of, or consisting essentially of SEQ ID NO:337.

5.2.1.4. Kabat CDR-H3+Kabat CDR-H2

In some embodiments, the antibody comprises a $V_H$ sequence comprising a Kabat CDR-H3 sequence comprising, consisting of, or consisting essentially of a sequence selected from SEQ ID NOs: 672-838, and a Kabat CDR-H2 sequence comprising, consisting of, or consisting essentially of a sequence selected from SEQ ID NOs: 505-671. In some aspects, the Kabat CDR-H3 sequence and the Kabat CDR-H2 sequence are both from a single illustrative $V_H$ sequence provided in this disclosure. For example, in some aspects, the Kabat CDR-H3 and Kabat CDR-H2 are both from a single illustrative $V_H$ sequence selected from SEQ ID NOs: 854-1020.

5.2.1.5. Kabat CDR-H3+Kabat CDR-H1

In some embodiments, the antibody comprises a $V_H$ sequence comprising a Kabat CDR-H3 sequence comprising, consisting of, or consisting essentially of a sequence selected from SEQ ID NOs: 672-838, and a Kabat CDR-H1 sequence comprising, consisting of, or consisting essentially of a sequence selected from SEQ ID NOs: 171-337. In some aspects, the Kabat CDR-H3 sequence and the Kabat CDR-H1 sequence are both from a single illustrative $V_H$ sequence provided in this disclosure. For example, in some aspects, the Kabat CDR-H3 and Kabat CDR-H1 are both from a single illustrative $V_H$ sequence selected from SEQ ID NOs: 854-1020.

5.2.1.6. Kabat CDR H1+Kabat CDR-H2

In some embodiments, the antibody comprises a $V_H$ sequence comprising a Kabat CDR-H1 sequence comprising, consisting of, or consisting essentially of a sequence selected from SEQ ID NOs: 171-337 and a Kabat CDR-H2 sequence comprising, consisting of, or consisting essentially of a sequence selected from SEQ ID NOs: 505-671. In some aspects, the Kabat CDR-H1 sequence and the Kabat CDR-H2 sequence are both from a single illustrative $V_H$ sequence provided in this disclosure. For example, in some aspects, the Kabat CDR-H1 and Kabat CDR-H2 are both from a single illustrative $V_H$ sequence selected from SEQ ID NOs: 854-1020.

5.2.1.7. Kabat CDR-H1+Kabat CDR-H2+Kabat CDR-H3

In some embodiments, the antibody comprises a $V_H$ sequence comprising a Kabat CDR-H1 sequence comprising, consisting of, or consisting essentially of a sequence selected from SEQ ID NOs: 171-337, a Kabat CDR-H2 sequence comprising, consisting of, or consisting essentially of a sequence selected from SEQ ID NOs: 505-671, and a Kabat CDR-H3 sequence comprising, consisting of, or consisting essentially of a sequence selected from SEQ ID NOs: 672-838. In some aspects, the Kabat CDR-H1 sequence, Kabat CDR-H2 sequence, and Kabat CDR-H3 sequence are all from a single illustrative $V_H$ sequence provided in this disclosure. For example, in some aspects, the Kabat CDR-H1, Kabat CDR-H2, and Kabat CDR-H3 are all from a single illustrative $V_H$ sequence selected from SEQ ID NOs: 854-1020.

5.2.1.8. Variants of $V_H$ Sequences Comprising Illustrative Kabat CDRs

In some embodiments, the $V_H$ sequences provided herein comprise a variant of an illustrative Kabat CDR-H3, CDR-H2, and/or CDR-H1 sequence provided in this disclosure.

In some aspects, the Kabat CDR-H3 sequence comprises, consists of, or consists essentially of a variant of an illustrative Kabat CDR-H3 sequence provided in this disclosure. In some aspects, the Kabat CDR-H3 sequence comprises, consists of, or consists essentially of a sequence having at least 70%, 75%, 80%, 85%, 90%, 95%, 96%, 97%, 98%, or 99% identity with any of the illustrative Kabat CDR-H3 sequences provided in this disclosure. In some aspects, the Kabat CDR-H3 sequence comprises, consists of, or consists essentially of any of the illustrative Kabat CDR-H3 sequences provided in this disclosure, with 1, 2, or 3 amino acid substitutions. In some aspects, the amino acid substitutions are conservative amino acid substitutions.

In some aspects, the Kabat CDR-H2 sequence comprises, consists of, or consists essentially of a variant of an illustrative Kabat CDR-H2 sequence provided in this disclosure. In some aspects, the Kabat CDR-H2 sequence comprises, consists of, or consists essentially of a sequence having at least 70%, 75%, 80%, 85%, 90%, 95%, 96%, 97%, 98%, or 99% identity with any of the illustrative Kabat CDR-H2 sequences provided in this disclosure. In some aspects, the Kabat CDR-H2 sequence comprises, consists of, or consists essentially of any of the illustrative Kabat CDR-H2 sequences provided in this disclosure, with 1, 2, or 3 amino acid substitutions. In some aspects, the amino acid substitutions are conservative amino acid substitutions.

In some aspects, the Kabat CDR-H1 sequence comprises, consists of, or consists essentially of a variant of an illustrative Kabat CDR-H1 sequence provided in this disclosure. In some aspects, the Kabat CDR-H1 sequence comprises, consists of, or consists essentially of a sequence having at least 70%, 75%, 80%, 85%, 90%, 95%, 96%, 97%, 98%, or 99% identity with any of the illustrative Kabat CDR-H1 sequences provided in this disclosure. In some aspects, the Kabat CDR-H1 sequence comprises, consists of, or consists essentially of any of the illustrative Kabat CDR-H1 sequences provided in this disclosure, with 1, 2, or 3 amino acid substitutions. In some aspects, the amino acid substitutions are conservative amino acid substitutions.

5.2.2. $V_H$ Sequences Comprising Illustrative Chothia CDRs

In some embodiments, the antibody comprises a $V_H$ sequence comprising one or more Chothia CDR-H sequences comprising, consisting of, or consisting essentially of one or more illustrative Chothia CDR-H sequences provided in this disclosure, and variants thereof.

5.2.2.1. Chothia CDR-H3

In some embodiments, the antibody comprises a $V_H$ sequence comprising a CDR-H3 sequence, wherein the CDR-H3 sequence comprises, consists of, or consists essentially of a Chothia CDR-H3 sequence of an illustrative antibody or $V_H$ sequence provided herein. In some aspects, the Chothia CDR-H3 sequence is a Chothia CDR-H3 sequence of a $V_H$ sequence provided in SEQ ID NOs: 854-1020.

In some embodiments, the antibody comprises a $V_H$ sequence comprising a Chothia CDR-H3 sequence comprising, consisting of, or consisting essentially of a sequence selected from SEQ ID NOs: 672-838. In some aspects, the antibody comprises a Chothia CDR-H3 sequence comprising, consisting of, or consisting essentially of SEQ ID NO:672. In some aspects, the antibody comprises a Chothia CDR-H3 sequence comprising, consisting of, or consisting essentially of SEQ ID NO:673. In some aspects, the antibody comprises a Chothia CDR-H3 sequence comprising, consisting of, or consisting essentially of SEQ ID NO:674. In some aspects, the antibody comprises a Chothia CDR-H3 sequence comprising, consisting of, or consisting essentially of SEQ ID NO:675. In some aspects, the antibody comprises a Chothia CDR-H3 sequence comprising, consisting of, or consisting essentially of SEQ ID NO:676. In some aspects, the antibody comprises a Chothia CDR-H3 sequence comprising, consisting of, or consisting essentially of SEQ ID NO:677. In some aspects, the antibody comprises a Chothia CDR-H3 sequence comprising, consisting of, or consisting essentially of SEQ ID NO:678. In some aspects, the antibody comprises a Chothia CDR-H3 sequence comprising, consisting of, or consisting essentially of SEQ ID NO:679. In some aspects, the antibody comprises a Chothia CDR-H3 sequence comprising, consisting of, or consisting essentially of SEQ ID NO:680. In some aspects, the antibody comprises a Chothia CDR-H3 sequence comprising, consisting of, or consisting essentially of SEQ ID NO:681. In some aspects, the antibody comprises a Chothia CDR-H3 sequence comprising, consisting of, or consisting essentially of SEQ ID NO:682. In some aspects, the antibody comprises a Chothia CDR-H3 sequence comprising, consisting of, or consisting essentially of SEQ ID NO:683. In some aspects, the antibody comprises a Chothia CDR-H3 sequence comprising, consisting of, or consisting essentially of SEQ ID NO:684. In some aspects, the antibody comprises a Chothia CDR-H3 sequence comprising, consisting of, or consisting essentially of SEQ ID NO:685. In some aspects, the antibody comprises a Chothia CDR-H3 sequence comprising, consisting of, or consisting essentially of SEQ ID NO:686. In some aspects, the antibody comprises a Chothia CDR-H3 sequence comprising, consisting of, or consisting essentially of SEQ ID NO:687. In some aspects, the antibody comprises a Chothia CDR-H3 sequence comprising, consisting of, or consisting essentially of SEQ ID NO:688. In some aspects, the antibody comprises a Chothia CDR-H3 sequence comprising, consisting of, or consisting essentially of SEQ ID NO:689. In some aspects, the antibody comprises a Chothia CDR-H3 sequence comprising, consisting of, or consisting essentially of SEQ ID NO:690. In some aspects, the antibody comprises a Chothia CDR-H3 sequence comprising, consisting of, or consisting essentially of SEQ ID NO:691. In some aspects, the antibody comprises a Chothia CDR-H3 sequence comprising, consisting of, or consisting essentially of SEQ ID NO:692. In some aspects, the antibody comprises a Chothia CDR-H3 sequence comprising, consisting of, or consisting essentially of SEQ ID NO:693. In some aspects, the antibody comprises a Chothia CDR-H3 sequence comprising, consisting of, or consisting essentially of SEQ ID NO:694. In some aspects, the antibody comprises a Chothia CDR-H3 sequence comprising, consisting of, or consisting essentially of SEQ ID NO:695. In some aspects, the antibody comprises a Chothia CDR-H3 sequence comprising, consisting of, or consisting essentially of SEQ ID NO:696. In some aspects, the antibody comprises a Chothia CDR-H3 sequence comprising, consisting of, or consisting essentially of SEQ ID NO:697. In some aspects, the antibody comprises a Chothia CDR-H3 sequence comprising, consisting of, or consisting essentially of SEQ ID NO:698. In some aspects, the antibody comprises a Chothia CDR-H3 sequence comprising, consisting of, or consisting essentially of SEQ ID NO:699.

In some aspects, the antibody comprises a Chothia CDR-H3 sequence comprising, consisting of, or consisting essentially of SEQ ID NO:700. In some aspects, the antibody comprises a Chothia CDR-H3 sequence comprising, consisting of, or consisting essentially of SEQ ID NO:701. In some aspects, the antibody comprises a Chothia CDR-H3 sequence comprising, consisting of, or consisting essentially of SEQ ID NO:702. In some aspects, the antibody comprises a Chothia CDR-H3 sequence comprising, consisting of, or consisting essentially of SEQ ID NO:703. In some aspects, the antibody comprises a Chothia CDR-H3 sequence comprising, consisting of, or consisting essentially of SEQ ID NO:704. In some aspects, the antibody comprises a Chothia CDR-H3 sequence comprising, consisting of, or consisting essentially of SEQ ID NO:705. In some aspects, the antibody comprises a Chothia CDR-H3 sequence comprising, consisting of, or consisting essentially of SEQ ID NO:706. In some aspects, the antibody comprises a Chothia CDR-H3 sequence comprising, consisting of, or consisting essentially of SEQ ID NO:707. In some aspects, the antibody comprises a Chothia CDR-H3 sequence comprising, consisting of, or consisting essentially of SEQ ID NO:708. In some aspects, the antibody comprises a Chothia CDR-H3 sequence comprising, consisting of, or consisting essentially of SEQ ID NO:709. In some aspects, the antibody comprises a Chothia CDR-H3 sequence comprising, consisting of, or consisting essentially of SEQ ID NO:710. In some aspects, the antibody comprises a Chothia CDR-H3 sequence comprising, consisting of, or consisting essentially of SEQ ID NO:711. In some aspects, the antibody comprises a Chothia CDR-H3 sequence comprising, consisting of, or consisting essentially of SEQ ID NO:712. In some aspects, the antibody comprises a Chothia CDR-H3 sequence comprising, consisting of, or consisting essentially of SEQ ID NO:713. In some aspects, the antibody comprises a Chothia CDR-H3 sequence comprising, consisting of, or consisting essentially of SEQ ID NO:714. In some aspects, the antibody comprises a Chothia CDR-H3 sequence comprising, consisting of, or consisting essentially of SEQ ID NO:715. In some aspects, the antibody comprises a Chothia CDR-H3 sequence comprising, consisting of, or consisting essentially of SEQ ID NO:716. In some aspects, the antibody comprises a Chothia CDR-H3 sequence comprising, consisting of, or consisting essentially of SEQ ID NO:717. In some aspects, the antibody comprises a Chothia CDR-H3 sequence comprising, consisting of, or consisting essentially of SEQ ID NO:718. In some aspects, the antibody comprises a Chothia CDR-H3 sequence comprising, consisting of, or consisting essentially of SEQ ID NO:719. In some aspects, the antibody comprises a Chothia CDR-H3 sequence comprising, consisting of, or consisting essentially of SEQ ID NO:720. In some aspects, the antibody comprises a Chothia CDR-H3 sequence comprising, consisting of, or consisting essentially of SEQ ID NO:721. In some aspects, the antibody comprises a Chothia CDR-H3 sequence comprising, consisting of, or consisting essentially of SEQ ID NO:722. In some aspects, the antibody comprises a Chothia CDR-H3 sequence comprising, consisting of, or consisting essentially of SEQ ID NO:723. In some aspects, the antibody comprises a Chothia CDR-H3 sequence comprising, consisting of, or consisting essentially of SEQ ID NO:724. In some aspects, the antibody comprises a Chothia CDR-H3 sequence comprising, consisting of, or consisting essentially of SEQ ID NO:725. In some aspects, the antibody comprises a Chothia CDR-H3 sequence comprising, consisting of, or consisting essentially of SEQ ID NO:726. In some aspects, the antibody comprises a Chothia CDR-H3 sequence comprising, consisting of, or consisting essentially of SEQ ID NO:727. In some aspects, the antibody comprises a Chothia CDR-H3 sequence comprising, consisting of, or consisting essentially of SEQ ID NO:728. In some aspects, the antibody comprises a Chothia CDR-H3 sequence comprising, consisting of, or consisting essentially of SEQ ID NO:729. In some aspects, the antibody comprises a Chothia CDR-H3 sequence comprising, consisting of, or consisting essentially of SEQ ID NO:730. In some aspects, the antibody comprises a Chothia CDR-H3 sequence comprising, consisting of, or consisting essentially of SEQ ID NO:731. In some aspects, the antibody comprises a Chothia CDR-H3 sequence comprising, consisting of, or consisting essentially of SEQ ID NO:732. In some aspects, the antibody comprises a Chothia CDR-H3 sequence comprising, consisting of, or consisting essentially of SEQ ID NO:733. In some aspects, the antibody comprises a Chothia CDR-H3 sequence comprising, consisting of, or consisting essentially of SEQ ID NO:734. In some aspects, the antibody comprises a Chothia CDR-H3 sequence comprising, consisting of, or consisting essentially of SEQ ID NO:735. In some aspects, the antibody comprises a Chothia CDR-H3 sequence comprising, consisting of, or consisting essentially of SEQ ID NO:736. In some aspects, the antibody comprises a Chothia CDR-H3 sequence comprising, consisting of, or consisting essentially of SEQ ID NO:737. In some aspects, the antibody comprises a Chothia CDR-H3 sequence comprising, consisting of, or consisting essentially of SEQ ID NO:738. In some aspects, the antibody comprises a Chothia CDR-H3 sequence comprising, consisting of, or consisting essentially of SEQ ID NO:739. In some aspects, the antibody comprises a Chothia CDR-H3 sequence comprising, consisting of, or consisting essentially of SEQ ID NO:740. In some aspects, the antibody comprises a Chothia CDR-H3 sequence comprising, consisting of, or consisting essentially of SEQ ID NO:741. In some aspects, the antibody comprises a Chothia CDR-H3 sequence comprising, consisting of, or consisting essentially of SEQ ID NO:742. In some aspects, the antibody comprises a Chothia CDR-H3 sequence comprising, consisting of, or consisting essentially of SEQ ID NO:743. In some aspects, the antibody comprises a Chothia CDR-H3 sequence comprising, consisting of, or consisting essentially of SEQ ID NO:744. In some aspects, the antibody comprises a Chothia CDR-H3 sequence comprising, consisting of, or consisting essentially of SEQ ID NO:745. In some aspects, the antibody comprises a Chothia CDR-H3 sequence comprising, consisting of, or consisting essentially of SEQ ID NO:746. In some aspects, the antibody comprises a Chothia CDR-H3 sequence comprising, consisting of, or consisting essentially of SEQ ID NO:747. In some aspects, the antibody comprises a Chothia CDR-H3 sequence comprising, consisting of, or consisting essentially of SEQ ID NO:748. In some aspects, the antibody comprises a Chothia CDR-H3 sequence comprising, consisting of, or consisting essentially of SEQ ID NO:749.

In some aspects, the antibody comprises a Chothia CDR-H3 sequence comprising, consisting of, or consisting essentially of SEQ ID NO:750. In some aspects, the antibody comprises a Chothia CDR-H3 sequence comprising, consisting of, or consisting essentially of SEQ ID NO:751. In some aspects, the antibody comprises a Chothia CDR-H3 sequence comprising, consisting of, or consisting essentially of SEQ ID NO:752. In some aspects, the antibody comprises a Chothia CDR-H3 sequence comprising, consisting of, or consisting essentially of SEQ ID NO:753. In some aspects, the antibody comprises a Chothia CDR-H3 sequence comprising, consisting of, or consisting essentially of SEQ ID NO:754. In some aspects, the antibody comprises a Chothia CDR-H3 sequence comprising, consisting of, or consisting essentially of SEQ ID NO:755. In some aspects, the antibody comprises a Chothia CDR-H3 sequence comprising, consisting of, or consisting essentially of SEQ ID NO:756. In some aspects, the antibody comprises a Chothia CDR-H3 sequence comprising, consisting of, or consisting essentially of SEQ ID NO:757. In some aspects, the antibody comprises a Chothia CDR-H3 sequence comprising, consisting of, or consisting essentially of SEQ ID NO:758. In some aspects, the antibody comprises a Chothia CDR-H3 sequence comprising, consisting of, or consisting essentially of SEQ ID NO:759. In some aspects, the antibody comprises a Chothia CDR-H3 sequence comprising, consisting of, or consisting essentially of SEQ ID NO:760. In some aspects, the antibody comprises a Chothia CDR-H3 sequence comprising, consisting of, or consisting essentially of SEQ ID NO:761. In some aspects, the antibody comprises a Chothia CDR-H3 sequence comprising, consisting of, or consisting essentially of SEQ ID NO:762. In some aspects, the antibody comprises a Chothia CDR-H3 sequence comprising, consisting of, or consisting essentially of SEQ ID NO:763. In some aspects, the antibody comprises a Chothia CDR-H3 sequence comprising, consisting of, or consisting essentially of SEQ ID NO:764. In some aspects, the antibody comprises a Chothia CDR-H3 sequence comprising, consisting of, or consisting essentially of SEQ ID NO:765. In some aspects, the antibody comprises a Chothia CDR-H3 sequence comprising, consisting of, or consisting essentially of SEQ ID NO:766. In some aspects, the antibody comprises a Chothia CDR-H3 sequence comprising, consisting of, or consisting essentially of SEQ ID NO:767. In some aspects, the antibody comprises a Chothia CDR-H3 sequence comprising, consisting of, or consisting essentially of SEQ ID NO:768. In some aspects, the antibody comprises a Chothia CDR-H3 sequence comprising, consisting of, or consisting essentially of SEQ ID NO:769. In some aspects, the antibody comprises a Chothia CDR-H3 sequence comprising, consisting of, or consisting essentially of SEQ ID NO:770. In some aspects, the antibody comprises a Chothia CDR-H3 sequence comprising, consisting of, or consisting essentially of SEQ ID NO:771. In some aspects, the antibody comprises a Chothia CDR-H3 sequence comprising, consisting of, or consisting essentially of SEQ ID NO:772. In some aspects, the antibody comprises a Chothia CDR-H3 sequence comprising, consisting of, or consisting essentially of SEQ ID NO:773. In some aspects, the antibody comprises a Chothia CDR-H3 sequence comprising, consisting of, or consisting essentially of SEQ ID NO:774. In some aspects, the antibody comprises a Chothia CDR-H3 sequence comprising, consisting of, or consisting essentially of SEQ ID NO:775. In some aspects, the antibody comprises a Chothia CDR-H3 sequence comprising, consisting of, or consisting essentially of SEQ ID NO:776. In some aspects, the antibody comprises a Chothia CDR-H3 sequence comprising, consisting of, or consisting essentially of SEQ ID NO:777. In some aspects, the antibody comprises a Chothia CDR-H3 sequence comprising, consisting of, or consisting essentially of SEQ ID NO:778. In some aspects, the antibody comprises a Chothia CDR-H3 sequence comprising, consisting of, or consisting essentially of SEQ ID NO:779. In some aspects, the antibody comprises a Chothia CDR-H3 sequence comprising, consisting of, or consisting essentially of SEQ ID NO:780. In some aspects, the antibody comprises a Chothia CDR-H3 sequence comprising, consisting of, or consisting essentially of SEQ ID NO:781. In some aspects, the antibody comprises a Chothia CDR-H3 sequence comprising, consisting of, or consisting essentially of SEQ ID NO:782. In some aspects, the antibody comprises a Chothia CDR-H3 sequence comprising, consisting of, or consisting essentially of SEQ ID NO:783. In some aspects, the antibody comprises a Chothia CDR-H3 sequence comprising, consisting of, or consisting essentially of SEQ ID NO:784. In some aspects, the antibody comprises a Chothia CDR-H3 sequence comprising, consisting of, or consisting essentially of SEQ ID NO:785. In some aspects, the antibody comprises a Chothia CDR-H3 sequence comprising, consisting of, or consisting essentially of SEQ ID NO:786. In some aspects, the antibody comprises a Chothia CDR-H3 sequence comprising, consisting of, or consisting essentially of SEQ ID NO:787. In some aspects, the antibody comprises a Chothia CDR-H3 sequence comprising, consisting of, or consisting essentially of SEQ ID NO:788. In some aspects, the antibody comprises a Chothia CDR-H3 sequence comprising, consisting of, or consisting essentially of SEQ ID NO:789. In some aspects, the antibody comprises a Chothia CDR-H3 sequence comprising, consisting of, or consisting essentially of SEQ ID NO:790. In some aspects, the antibody comprises a Chothia CDR-H3 sequence comprising, consisting of, or consisting essentially of SEQ ID NO:791. In some aspects, the antibody comprises a Chothia CDR-H3 sequence comprising, consisting of, or consisting essentially of SEQ ID NO:792. In some aspects, the antibody comprises a Chothia CDR-H3 sequence comprising, consisting of, or consisting essentially of SEQ ID NO:793. In some aspects, the antibody comprises a Chothia CDR-H3 sequence comprising, consisting of, or consisting essentially of SEQ ID NO:794. In some aspects, the antibody comprises a Chothia CDR-H3 sequence comprising, consisting of, or consisting essentially of SEQ ID NO:795. In some aspects, the antibody comprises a Chothia CDR-H3 sequence comprising, consisting of, or consisting essentially of SEQ ID NO:796. In some aspects, the antibody comprises a Chothia CDR-H3 sequence comprising, consisting of, or consisting essentially of SEQ ID NO:797. In some aspects, the antibody comprises a Chothia CDR-H3 sequence comprising, consisting of, or consisting essentially of SEQ ID NO:798. In some aspects, the antibody comprises a Chothia CDR-H3 sequence comprising, consisting of, or consisting essentially of SEQ ID NO:799.

In some aspects, the antibody comprises a Chothia CDR-H3 sequence comprising, consisting of, or consisting essentially of SEQ ID NO:800. In some aspects, the antibody comprises a Chothia CDR-H3 sequence comprising, consisting of, or consisting essentially of SEQ ID NO:801. In some aspects, the antibody comprises a Chothia CDR-H3 sequence comprising, consisting of, or consisting essentially of SEQ ID NO:802. In some aspects, the antibody comprises a Chothia CDR-H3 sequence comprising, consisting of, or consisting essentially of SEQ ID NO:803. In some aspects, the antibody comprises a Chothia CDR-H3 sequence comprising, consisting of, or consisting essentially of SEQ ID NO:804. In some aspects, the antibody comprises a Chothia CDR-H3 sequence comprising, consisting of, or consisting essentially of SEQ ID NO:805. In some aspects, the antibody comprises a Chothia CDR-H3 sequence comprising, consisting of, or consisting essentially of SEQ ID NO:806. In some aspects, the antibody comprises a Chothia CDR-H3 sequence comprising, consisting of, or consisting essentially of SEQ ID NO:807. In some aspects, the antibody comprises a Chothia CDR-H3 sequence comprising, consisting of, or consisting essentially of SEQ ID NO:808. In some aspects, the antibody comprises a Chothia CDR-H3 sequence comprising, consisting of, or consisting essentially of SEQ ID NO:809. In some aspects, the antibody comprises a Chothia CDR-H3 sequence comprising, consisting of, or consisting essentially of SEQ ID NO:810. In some aspects, the antibody comprises a Chothia CDR-H3 sequence comprising, consisting of, or consisting essentially of SEQ ID NO:811. In some aspects, the antibody comprises a Chothia CDR-H3 sequence comprising, consisting of, or consisting essentially of SEQ ID NO:812. In some aspects, the antibody comprises a Chothia CDR-H3 sequence comprising, consisting of, or consisting essentially of SEQ ID NO:813. In some aspects, the antibody comprises a Chothia CDR-H3 sequence comprising, consisting of, or consisting essentially of SEQ ID NO:814. In some aspects, the antibody comprises a Chothia CDR-H3 sequence comprising, consisting of, or consisting essentially of SEQ ID NO:815. In some aspects, the antibody comprises a Chothia CDR-H3 sequence comprising, consisting of, or consisting essentially of SEQ ID NO:816. In some aspects, the antibody comprises a Chothia CDR-H3 sequence comprising, consisting of, or consisting essentially of SEQ ID NO:817. In some aspects, the antibody comprises a Chothia CDR-H3 sequence comprising, consisting of, or consisting essentially of SEQ ID NO:818. In some aspects, the antibody comprises a Chothia CDR-H3 sequence comprising, consisting of, or consisting essentially of SEQ ID NO:819. In some aspects, the antibody comprises a Chothia CDR-H3 sequence comprising, consisting of, or consisting essentially of SEQ ID NO:820. In some aspects, the antibody comprises a Chothia CDR-H3 sequence comprising, consisting of, or consisting essentially of SEQ ID NO:821. In some aspects, the antibody comprises a Chothia CDR-H3 sequence comprising, consisting of, or consisting essentially of SEQ ID NO:822. In some aspects, the antibody comprises a Chothia CDR-H3 sequence comprising, consisting of, or consisting essentially of SEQ ID NO:823. In some aspects, the antibody comprises a Chothia CDR-H3 sequence comprising, consisting of, or consisting essentially of SEQ ID NO:824. In some aspects, the antibody comprises a Chothia CDR-H3 sequence comprising, consisting of, or consisting essentially of SEQ ID NO:825. In some aspects, the antibody comprises a Chothia CDR-H3 sequence comprising, consisting of, or consisting essentially of SEQ ID NO:826. In some aspects, the antibody comprises a Chothia CDR-H3 sequence comprising, consisting of, or consisting essentially of SEQ ID NO:827. In some aspects, the antibody comprises a Chothia CDR-H3 sequence comprising, consisting of, or consisting essentially of SEQ ID NO:828. In some aspects, the antibody comprises a Chothia CDR-H3 sequence comprising, consisting of, or consisting essentially of SEQ ID NO:829. In some aspects, the antibody comprises a Chothia CDR-H3 sequence comprising, consisting of, or consisting essentially of SEQ ID NO:830. In some aspects, the antibody comprises a Chothia CDR-H3 sequence comprising, consisting of, or consisting essentially of SEQ ID NO:831. In some aspects, the antibody comprises a Chothia CDR-H3 sequence comprising, consisting of, or consisting essentially of SEQ ID NO:832. In some aspects, the antibody comprises a Chothia CDR-H3 sequence comprising, consisting of, or consisting essentially of SEQ ID NO:833. In some aspects, the antibody comprises a Chothia CDR-H3 sequence comprising, consisting of, or consisting essentially of SEQ ID NO:834. In some aspects, the antibody comprises a Chothia CDR-H3 sequence comprising, consisting of, or consisting essentially of SEQ ID NO:835. In some aspects, the antibody comprises a Chothia CDR-H3 sequence comprising, consisting of, or consisting essentially of SEQ ID NO:836. In some aspects, the antibody comprises a Chothia CDR-H3 sequence comprising, consisting of, or consisting essentially of SEQ ID NO:837. In some aspects, the antibody comprises a Chothia CDR-H3 sequence comprising, consisting of, or consisting essentially of SEQ ID NO:838.

5.2.2.2. Chothia CDR-H2

In some embodiments, the antibody comprises a $V_H$ sequence comprising a CDR-H2 sequence, wherein the CDR-H2 sequence comprises, consists of, or consists essentially of a Chothia CDR-H2 sequence of an illustrative antibody or $V_H$ sequence provided herein. In some aspects, the Chothia CDR-H2 sequence is a Chothia CDR-H2 sequence of a $V_H$ sequence provided in SEQ ID NOs: 854-1020.

In some embodiments, the antibody comprises a $V_H$ sequence comprising a Chothia CDR-H2 sequence comprising, consisting of, or consisting essentially of a sequence selected from SEQ ID NOs: 338-504. In some aspects, the antibody comprises a Chothia CDR-H2 sequence comprising, consisting of, or consisting essentially of SEQ ID NO:338. In some aspects, the antibody comprises a Chothia CDR-H2 sequence comprising, consisting of, or consisting essentially of SEQ ID NO:339. In some aspects, the antibody comprises a Chothia CDR-H2 sequence comprising, consisting of, or consisting essentially of SEQ ID NO:340. In some aspects, the antibody comprises a Chothia CDR-H2 sequence comprising, consisting of, or consisting essentially of SEQ ID NO:341. In some aspects, the antibody comprises a Chothia CDR-H2 sequence comprising, consisting of, or consisting essentially of SEQ ID NO:342. In some aspects, the antibody comprises a Chothia CDR-H2 sequence comprising, consisting of, or consisting essentially of SEQ ID NO:343. In some aspects, the antibody comprises a Chothia CDR-H2 sequence comprising, consisting of, or consisting essentially of SEQ ID NO:344. In some aspects, the antibody comprises a Chothia CDR-H2 sequence comprising, consisting of, or consisting essentially of SEQ ID NO:345. In some aspects, the antibody comprises a Chothia CDR-H2 sequence comprising, consisting of, or consisting essentially of SEQ ID NO:346. In some aspects, the antibody comprises a Chothia CDR-H2 sequence comprising, consisting of, or consisting essentially of SEQ ID NO:347. In some aspects, the antibody comprises a Chothia CDR-H2 sequence comprising, consisting of, or consisting essentially of SEQ ID NO:348. In some aspects, the antibody comprises a Chothia CDR-H2 sequence comprising, consisting of, or consisting essentially of SEQ ID NO:349.

In some aspects, the antibody comprises a Chothia CDR-H2 sequence comprising, consisting of, or consisting essentially of SEQ ID NO:350. In some aspects, the antibody comprises a Chothia CDR-H2 sequence comprising, consisting of, or consisting essentially of SEQ ID NO:351. In some aspects, the antibody comprises a Chothia CDR-H2 sequence comprising, consisting of, or consisting essentially of SEQ ID NO:352. In some aspects, the antibody comprises a Chothia CDR-H2 sequence comprising, consisting of, or consisting essentially of SEQ ID NO:353. In some aspects, the antibody comprises a Chothia CDR-H2 sequence comprising, consisting of, or consisting essentially of SEQ ID NO:354. In some aspects, the antibody comprises a Chothia CDR-H2 sequence comprising, consisting of, or consisting essentially of SEQ ID NO:355. In some aspects, the antibody comprises a Chothia CDR-H2 sequence comprising, consisting of, or consisting essentially of SEQ ID NO:356. In some aspects, the antibody comprises a Chothia CDR-H2 sequence comprising, consisting of, or consisting essentially of SEQ ID NO:357. In some aspects, the antibody comprises a Chothia CDR-H2 sequence comprising, consisting of, or consisting essentially of SEQ ID NO:358. In some aspects, the antibody comprises a Chothia CDR-H2 sequence comprising, consisting of, or consisting essentially of SEQ ID NO:359. In some aspects, the antibody comprises a Chothia CDR-H2 sequence comprising, consisting of, or consisting essentially of SEQ ID NO:360. In some aspects, the antibody comprises a Chothia CDR-H2 sequence comprising, consisting of, or consisting essentially of SEQ ID NO:361. In some aspects, the antibody comprises a Chothia CDR-H2 sequence comprising, consisting of, or consisting essentially of SEQ ID NO:362. In some aspects, the antibody comprises a Chothia CDR-H2 sequence comprising, consisting of, or consisting essentially of SEQ ID NO:363. In some aspects, the antibody comprises a Chothia CDR-H2 sequence comprising, consisting of, or consisting essentially of SEQ ID NO:364. In some aspects, the antibody comprises a Chothia CDR-H2 sequence comprising, consisting of, or consisting essentially of SEQ ID NO:365. In some aspects, the antibody comprises a Chothia CDR-H2 sequence comprising, consisting of, or consisting essentially of SEQ ID NO:366. In some aspects, the antibody comprises a Chothia CDR-H2 sequence comprising, consisting of, or consisting essentially of SEQ ID NO:367. In some aspects, the antibody comprises a Chothia CDR-H2 sequence comprising, consisting of, or consisting essentially of SEQ ID NO:368. In some aspects, the antibody comprises a Chothia CDR-H2 sequence comprising, consisting of, or consisting essentially of SEQ ID NO:369. In some aspects, the antibody comprises a Chothia CDR-H2 sequence comprising, consisting of, or consisting essentially of SEQ ID NO:370. In some aspects, the antibody comprises a Chothia CDR-H2 sequence comprising, consisting of, or consisting essentially of SEQ ID NO:371. In some aspects, the antibody comprises a Chothia CDR-H2 sequence comprising, consisting of, or consisting essentially of SEQ ID NO:372. In some aspects, the antibody comprises a Chothia CDR-H2 sequence comprising, consisting of, or consisting essentially of SEQ ID NO:373. In some aspects, the antibody comprises a Chothia CDR-H2 sequence comprising, consisting of, or consisting essentially of SEQ ID NO:374. In some aspects, the antibody comprises a Chothia CDR-H2 sequence comprising, consisting of, or consisting essentially of SEQ ID NO:375. In some aspects, the antibody comprises a Chothia CDR-H2 sequence comprising, consisting of, or consisting essentially of SEQ ID NO:376. In some aspects, the antibody comprises a Chothia CDR-H2 sequence comprising, consisting of, or consisting essentially of SEQ ID NO:377. In some aspects, the antibody comprises a Chothia CDR-H2 sequence comprising, consisting of, or consisting essentially of SEQ ID NO:378. In some aspects, the antibody comprises a Chothia CDR-H2 sequence comprising, consisting of, or consisting essentially of SEQ ID NO:379. In some aspects, the antibody comprises a Chothia CDR-H2 sequence comprising, consisting of, or consisting essentially of SEQ ID NO:380. In some aspects, the antibody comprises a Chothia CDR-H2 sequence comprising, consisting of, or consisting essentially of SEQ ID NO:381. In some aspects, the antibody comprises a Chothia CDR-H2 sequence comprising, consisting of, or consisting essentially of SEQ ID NO:382. In some aspects, the antibody comprises a Chothia CDR-H2 sequence comprising, consisting of, or consisting essentially of SEQ ID NO:383. In some aspects, the antibody comprises a Chothia CDR-H2 sequence comprising, consisting of, or consisting essentially of SEQ ID NO:384. In some aspects, the antibody comprises a Chothia CDR-H2 sequence comprising, consisting of, or consisting essentially of SEQ ID NO:385. In some aspects, the antibody comprises a Chothia CDR-H2 sequence comprising, consisting of, or consisting essentially of SEQ ID NO:386. In some aspects, the antibody comprises a Chothia CDR-H2 sequence comprising, consisting of, or consisting essentially of SEQ ID NO:387. In some aspects, the antibody comprises a Chothia CDR-H2 sequence comprising, consisting of, or consisting essentially of SEQ ID NO:388. In some aspects, the antibody comprises a Chothia CDR-H2 sequence comprising, consisting of, or consisting essentially of SEQ ID NO:389. In some aspects, the antibody comprises a Chothia CDR-H2 sequence comprising, consisting of, or consisting essentially of SEQ ID NO:390. In some aspects, the antibody comprises a Chothia CDR-H2 sequence comprising, consisting of, or consisting essentially of SEQ ID NO:391. In some aspects, the antibody comprises a Chothia CDR-H2 sequence comprising, consisting of, or consisting essentially of SEQ ID NO:392. In some aspects, the antibody comprises a Chothia CDR-H2 sequence comprising, consisting of, or consisting essentially of SEQ ID NO:393. In some aspects, the antibody comprises a Chothia CDR-H2 sequence comprising, consisting of, or consisting essentially of SEQ ID NO:394. In some aspects, the antibody comprises a Chothia CDR-H2 sequence comprising, consisting of, or consisting essentially of SEQ ID NO:395. In some aspects, the antibody comprises a Chothia CDR-H2 sequence comprising, consisting of, or consisting essentially of SEQ ID NO:396. In some aspects, the antibody comprises a Chothia CDR-H2 sequence comprising, consisting of, or consisting essentially of SEQ ID NO:397. In some aspects, the antibody comprises a Chothia CDR-H2 sequence comprising, consisting of, or consisting essentially of SEQ ID NO:398. In some aspects, the antibody comprises a Chothia CDR-H2 sequence comprising, consisting of, or consisting essentially of SEQ ID NO:399.

In some aspects, the antibody comprises a Chothia CDR-H2 sequence comprising, consisting of, or consisting essentially of SEQ ID NO:400. In some aspects, the antibody comprises a Chothia CDR-H2 sequence comprising, consisting of, or consisting essentially of SEQ ID NO:401. In some aspects, the antibody comprises a Chothia CDR-H2 sequence comprising, consisting of, or consisting essentially of SEQ ID NO:402. In some aspects, the antibody comprises a Chothia CDR-H2 sequence comprising, consisting of, or consisting essentially of SEQ ID NO:403. In some aspects, the antibody comprises a Chothia CDR-H2 sequence comprising, consisting of, or consisting essentially of SEQ ID NO:404. In some aspects, the antibody comprises a Chothia CDR-H2 sequence comprising, consisting of, or consisting essentially of SEQ ID NO:405. In some aspects, the antibody comprises a Chothia CDR-H2 sequence comprising, consisting of, or consisting essentially of SEQ ID NO:406. In some aspects, the antibody comprises a Chothia CDR-H2 sequence comprising, consisting of, or consisting essentially of SEQ ID NO:407. In some aspects, the antibody comprises a Chothia CDR-H2 sequence comprising, consisting of, or consisting essentially of SEQ ID NO:408. In some aspects, the antibody comprises a Chothia CDR-H2 sequence comprising, consisting of, or consisting essentially of SEQ ID NO:409. In some aspects, the antibody comprises a Chothia CDR-H2 sequence comprising, consisting of, or consisting essentially of SEQ ID NO:410. In some aspects, the antibody comprises a Chothia CDR-H2 sequence comprising, consisting of, or consisting essentially of SEQ ID NO:411. In some aspects, the antibody comprises a Chothia CDR-H2 sequence comprising, consisting of, or consisting essentially of SEQ ID NO:412. In some aspects, the antibody comprises a Chothia CDR-H2 sequence comprising, consisting of, or consisting essentially of SEQ ID NO:413. In some aspects, the antibody comprises a Chothia CDR-H2 sequence comprising, consisting of, or consisting essentially of SEQ ID NO:414. In some aspects, the antibody comprises a Chothia CDR-H2 sequence comprising, consisting of, or consisting essentially of SEQ ID NO:415. In some aspects, the antibody comprises a Chothia CDR-H2 sequence comprising, consisting of, or consisting essentially of SEQ ID NO:416. In some aspects, the antibody comprises a Chothia CDR-H2 sequence comprising, consisting of, or consisting essentially of SEQ ID NO:417. In some aspects, the antibody comprises a Chothia CDR-H2 sequence comprising, consisting of, or consisting essentially of SEQ ID NO:418. In some aspects, the antibody comprises a Chothia CDR-H2 sequence comprising, consisting of, or consisting essentially of SEQ ID NO:419. In some aspects, the antibody comprises a Chothia CDR-H2 sequence comprising, consisting of, or consisting essentially of SEQ ID NO:420. In some aspects, the antibody comprises a Chothia CDR-H2 sequence comprising, consisting of, or consisting essentially of SEQ ID NO:421. In some aspects, the antibody comprises a Chothia CDR-H2 sequence comprising, consisting of, or consisting essentially of SEQ ID NO:422. In some aspects, the antibody comprises a Chothia CDR-H2 sequence comprising, consisting of, or consisting essentially of SEQ ID NO:423. In some aspects, the antibody comprises a Chothia CDR-H2 sequence comprising, consisting of, or consisting essentially of SEQ ID NO:424. In some aspects, the antibody comprises a Chothia CDR-H2 sequence comprising, consisting of, or consisting essentially of SEQ ID NO:425. In some aspects, the antibody comprises a Chothia CDR-H2 sequence comprising, consisting of, or consisting essentially of SEQ ID NO:426. In some aspects, the antibody comprises a Chothia CDR-H2 sequence comprising, consisting of, or consisting essentially of SEQ ID NO:427. In some aspects, the antibody comprises a Chothia CDR-H2 sequence comprising, consisting of, or consisting essentially of SEQ ID NO:428. In some aspects, the antibody comprises a Chothia CDR-H2 sequence comprising, consisting of, or consisting essentially of SEQ ID NO:429. In some aspects, the antibody comprises a Chothia CDR-H2 sequence comprising, consisting of, or consisting essentially of SEQ ID NO:430. In some aspects, the antibody comprises a Chothia CDR-H2 sequence comprising, consisting of, or consisting essentially of SEQ ID NO:431. In some aspects, the antibody comprises a Chothia CDR-H2 sequence comprising, consisting of, or consisting essentially of SEQ ID NO:432. In some aspects, the antibody comprises a Chothia CDR-H2 sequence comprising, consisting of, or consisting essentially of SEQ ID NO:433. In some aspects, the antibody comprises a Chothia CDR-H2 sequence comprising, consisting of, or consisting essentially of SEQ ID NO:434. In some aspects, the antibody comprises a Chothia CDR-H2 sequence comprising, consisting of, or consisting essentially of SEQ ID NO:435. In some aspects, the antibody comprises a Chothia CDR-H2 sequence comprising, consisting of, or consisting essentially of SEQ ID NO:436. In some aspects, the antibody comprises a Chothia CDR-H2 sequence comprising, consisting of, or consisting essentially of SEQ ID NO:437. In some aspects, the antibody comprises a Chothia CDR-H2 sequence comprising, consisting of, or consisting essentially of SEQ ID NO:438. In some aspects, the antibody comprises a Chothia CDR-H2 sequence comprising, consisting of, or consisting essentially of SEQ ID NO:439. In some aspects, the antibody comprises a Chothia CDR-H2 sequence comprising, consisting of, or consisting essentially of SEQ ID NO:440. In some aspects, the antibody comprises a Chothia CDR-H2 sequence comprising, consisting of, or consisting essentially of SEQ ID NO:441. In some aspects, the antibody comprises a Chothia CDR-H2 sequence comprising, consisting of, or consisting essentially of SEQ ID NO:442. In some aspects, the antibody comprises a Chothia CDR-H2 sequence comprising, consisting of, or consisting essentially of SEQ ID NO:443. In some aspects, the antibody comprises a Chothia CDR-H2 sequence comprising, consisting of, or consisting essentially of SEQ ID NO:444. In some aspects, the antibody comprises a Chothia CDR-H2 sequence comprising, consisting of, or consisting essentially of SEQ ID NO:445. In some aspects, the antibody comprises a Chothia CDR-H2 sequence comprising, consisting of, or consisting essentially of SEQ ID NO:446. In some aspects, the antibody comprises a Chothia CDR-H2 sequence comprising, consisting of, or consisting essentially of SEQ ID NO:447. In some aspects, the antibody comprises a Chothia CDR-H2 sequence comprising, consisting of, or consisting essentially of SEQ ID NO:448. In some aspects, the antibody comprises a Chothia CDR-H2 sequence comprising, consisting of, or consisting essentially of SEQ ID NO:449.

In some aspects, the antibody comprises a Chothia CDR-H2 sequence comprising, consisting of, or consisting essentially of SEQ ID NO:450. In some aspects, the antibody comprises a Chothia CDR-H2 sequence comprising, consisting of, or consisting essentially of SEQ ID NO:451. In some aspects, the antibody comprises a Chothia CDR-H2 sequence comprising, consisting of, or consisting essentially of SEQ ID NO:452. In some aspects, the antibody comprises a Chothia CDR-H2 sequence comprising, consisting of, or consisting essentially of SEQ ID NO:453. In some aspects, the antibody comprises a Chothia CDR-H2 sequence comprising, consisting of, or consisting essentially of SEQ ID NO:454. In some aspects, the antibody comprises a Chothia CDR-H2 sequence comprising, consisting of, or consisting essentially of SEQ ID NO:455. In some aspects, the antibody comprises a Chothia CDR-H2 sequence comprising, consisting of, or consisting essentially of SEQ ID NO:456. In some aspects, the antibody comprises a Chothia CDR-H2 sequence comprising, consisting of, or consisting essentially of SEQ ID NO:457. In some aspects, the antibody comprises a Chothia CDR-H2 sequence comprising, consisting of, or consisting essentially of SEQ ID NO:458. In some aspects, the antibody comprises a Chothia CDR-H2 sequence comprising, consisting of, or consisting essentially of SEQ ID NO:459. In some aspects, the antibody comprises a Chothia CDR-H2 sequence comprising, consisting of, or consisting essentially of SEQ ID NO:460. In some aspects, the antibody comprises a Chothia CDR-H2 sequence comprising, consisting of, or consisting essentially of SEQ ID NO:461. In some aspects, the antibody comprises a Chothia CDR-H2 sequence comprising, consisting of, or consisting essentially of SEQ ID NO:462. In some aspects, the antibody comprises a Chothia CDR-H2 sequence comprising, consisting of, or consisting essentially of SEQ ID NO:463. In some aspects, the antibody comprises a Chothia CDR-H2 sequence comprising, consisting of, or consisting essentially of SEQ ID NO:464. In some aspects, the antibody comprises a Chothia CDR-H2 sequence comprising, consisting of, or consisting essentially of SEQ ID NO:465. In some aspects, the antibody comprises a Chothia CDR-H2 sequence comprising, consisting of, or consisting essentially of SEQ ID NO:466. In some aspects, the antibody comprises a Chothia CDR-H2 sequence comprising, consisting of, or consisting essentially of SEQ ID NO:467. In some aspects, the antibody comprises a Chothia CDR-H2 sequence comprising, consisting of, or consisting essentially of SEQ ID NO:468. In some aspects, the antibody comprises a Chothia CDR-H2 sequence comprising, consisting of, or consisting essentially of SEQ ID NO:469. In some aspects, the antibody comprises a Chothia CDR-H2 sequence comprising, consisting of, or consisting essentially of SEQ ID NO:470. In some aspects, the antibody comprises a Chothia CDR-H2 sequence comprising, consisting of, or consisting essentially of SEQ ID NO:471. In some aspects, the antibody comprises a Chothia CDR-H2 sequence comprising, consisting of, or consisting essentially of SEQ ID NO:472. In some aspects, the antibody comprises a Chothia CDR-H2 sequence comprising, consisting of, or consisting essentially of SEQ ID NO:473. In some aspects, the antibody comprises a Chothia CDR-H2 sequence comprising, consisting of, or consisting essentially of SEQ ID NO:474. In some aspects, the antibody comprises a Chothia CDR-H2 sequence comprising, consisting of, or consisting essentially of SEQ ID NO:475. In some aspects, the antibody comprises a Chothia CDR-H2 sequence comprising, consisting of, or consisting essentially of SEQ ID NO:476. In some aspects, the antibody comprises a Chothia CDR-H2 sequence comprising, consisting of, or consisting essentially of SEQ ID NO:477. In some aspects, the antibody comprises a Chothia CDR-H2 sequence comprising, consisting of, or consisting essentially of SEQ ID NO:478. In some aspects, the antibody comprises a Chothia CDR-H2 sequence comprising, consisting of, or consisting essentially of SEQ ID NO:479. In some aspects, the antibody comprises a Chothia CDR-H2 sequence comprising, consisting of, or consisting essentially of SEQ ID NO:480. In some aspects, the antibody comprises a Chothia CDR-H2 sequence comprising, consisting of, or consisting essentially of SEQ ID NO:481. In some aspects, the antibody comprises a Chothia CDR-H2 sequence comprising, consisting of, or consisting essentially of SEQ ID NO:482. In some aspects, the antibody comprises a Chothia CDR-H2 sequence comprising, consisting of, or consisting essentially of SEQ ID NO:483. In some aspects, the antibody comprises a Chothia CDR-H2 sequence comprising, consisting of, or consisting essentially of SEQ ID NO:484. In some aspects, the antibody comprises a Chothia CDR-H2 sequence comprising, consisting of, or consisting essentially of SEQ ID NO:485. In some aspects, the antibody comprises a Chothia CDR-H2 sequence comprising, consisting of, or consisting essentially of SEQ ID NO:486. In some aspects, the antibody comprises a Chothia CDR-H2 sequence comprising, consisting of, or consisting essentially of SEQ ID NO:487. In some aspects, the antibody comprises a Chothia CDR-H2 sequence comprising, consisting of, or consisting essentially of SEQ ID NO:488. In some aspects, the antibody comprises a Chothia CDR-H2 sequence comprising, consisting of, or consisting essentially of SEQ ID NO:489. In some aspects, the antibody comprises a Chothia CDR-H2 sequence comprising, consisting of, or consisting essentially of SEQ ID NO:490. In some aspects, the antibody comprises a Chothia CDR-H2 sequence comprising, consisting of, or consisting essentially of SEQ ID NO:491. In some aspects, the antibody comprises a Chothia CDR-H2 sequence comprising, consisting of, or consisting essentially of SEQ ID NO:492. In some aspects, the antibody comprises a Chothia CDR-H2 sequence comprising, consisting of, or consisting essentially of SEQ ID NO:493. In some aspects, the antibody comprises a Chothia CDR-H2 sequence comprising, consisting of, or consisting essentially of SEQ ID NO:494. In some aspects, the antibody comprises a Chothia CDR-H2 sequence comprising, consisting of, or consisting essentially of SEQ ID NO:495. In some aspects, the antibody comprises a Chothia CDR-H2 sequence comprising, consisting of, or consisting essentially of SEQ ID NO:496. In some aspects, the antibody comprises a Chothia CDR-H2 sequence comprising, consisting of, or consisting essentially of SEQ ID NO:497. In some aspects, the antibody comprises a Chothia CDR-H2 sequence comprising, consisting of, or consisting essentially of SEQ ID NO:498. In some aspects, the antibody comprises a Chothia CDR-H2 sequence comprising, consisting of, or consisting essentially of SEQ ID NO:499. In some aspects, the antibody comprises a Chothia CDR-H2 sequence comprising, consisting of, or consisting essentially of SEQ ID NO:500. In some aspects, the antibody comprises a Chothia CDR-H2 sequence comprising, consisting of, or consisting essentially of SEQ ID NO:501. In some aspects, the antibody comprises a Chothia CDR-H2 sequence comprising, consisting of, or consisting essentially of SEQ ID NO:502. In some aspects, the antibody comprises a Chothia CDR-H2 sequence comprising, consisting of, or consisting essentially of SEQ ID NO:503. In some aspects, the antibody comprises a Chothia CDR-H2 sequence comprising, consisting of, or consisting essentially of SEQ ID NO:504.

5.2.2.3. Chothia CDR-H1

In some embodiments, the antibody comprises a $V_H$ sequence comprising a CDR-H1 sequence, wherein the CDR-H1 sequence comprises, consists of, or consists essentially of a Chothia CDR-H1 sequence of an illustrative antibody or $V_H$ sequence provided herein. In some aspects, the Chothia CDR-H1 sequence is a Chothia CDR-H1 sequence of a $V_H$ sequence provided in SEQ ID NOs: 854-1020.

In some embodiments, the antibody comprises a $V_H$ sequence comprising a Chothia CDR-H1 sequence comprising, consisting of, or consisting essentially of a sequence selected from SEQ ID NOs: 4-170. In some aspects, the antibody comprises a Chothia CDR-H1 sequence comprising, consisting of, or consisting essentially of SEQ ID NO:4. In some aspects, the antibody comprises a Chothia CDR-H1 sequence comprising, consisting of, or consisting essentially of SEQ ID NO:5. In some aspects, the antibody comprises a Chothia CDR-H1 sequence comprising, consisting of, or consisting essentially of SEQ ID NO:6. In some aspects, the antibody comprises a Chothia CDR-H1 sequence comprising, consisting of, or consisting essentially of SEQ ID NO:7. In some aspects, the antibody comprises a Chothia CDR-H1 sequence comprising, consisting of, or consisting essentially of SEQ ID NO:8. In some aspects, the antibody comprises a Chothia CDR-H1 sequence comprising, consisting of, or consisting essentially of SEQ ID NO:9. In some aspects, the antibody comprises a Chothia CDR-H1 sequence comprising, consisting of, or consisting essentially of SEQ ID NO:10. In some aspects, the antibody comprises a Chothia CDR-H1 sequence comprising, consisting of, or consisting essentially of SEQ ID NO:11. In some aspects, the antibody comprises a Chothia CDR-H1 sequence comprising, consisting of, or consisting essentially of SEQ ID NO:12. In some aspects, the antibody comprises a Chothia CDR-H1 sequence comprising, consisting of, or consisting essentially of SEQ ID NO:13. In some aspects, the antibody comprises a Chothia CDR-H1 sequence comprising, consisting of, or consisting essentially of SEQ ID NO:14. In some aspects, the antibody comprises a Chothia CDR-H1 sequence comprising, consisting of, or consisting essentially of SEQ ID NO:15. In some aspects, the antibody comprises a Chothia CDR-H1 sequence comprising, consisting of, or consisting essentially of SEQ ID NO:16. In some aspects, the antibody comprises a Chothia CDR-H1 sequence comprising, consisting of, or consisting essentially of SEQ ID NO:17. In some aspects, the antibody comprises a Chothia CDR-H1 sequence comprising, consisting of, or consisting essentially of SEQ ID NO:18. In some aspects, the antibody comprises a Chothia CDR-H1 sequence comprising, consisting of, or consisting essentially of SEQ ID NO:19. In some aspects, the antibody comprises a Chothia CDR-H1 sequence comprising, consisting of, or consisting essentially of SEQ ID NO:20. In some aspects, the antibody comprises a Chothia CDR-H1 sequence comprising, consisting of, or consisting essentially of SEQ ID NO:21. In some aspects, the antibody comprises a Chothia CDR-H1 sequence comprising, consisting of, or consisting essentially of SEQ ID NO:22. In some aspects, the antibody comprises a Chothia CDR-H1 sequence comprising, consisting of, or consisting essentially of SEQ ID NO:23. In some aspects, the antibody comprises a Chothia CDR-H1 sequence comprising, consisting of, or consisting essentially of SEQ ID NO:24. In some aspects, the antibody comprises a Chothia CDR-H1 sequence comprising, consisting of, or consisting essentially of SEQ ID NO:25. In some aspects, the antibody comprises a Chothia CDR-H1 sequence comprising, consisting of, or consisting essentially of SEQ ID NO:26. In some aspects, the antibody comprises a Chothia CDR-H1 sequence comprising, consisting of, or consisting essentially of SEQ ID NO:27. In some aspects, the antibody comprises a Chothia CDR-H1 sequence comprising, consisting of, or consisting essentially of SEQ ID NO:28. In some aspects, the antibody comprises a Chothia CDR-H1 sequence comprising, consisting of, or consisting essentially of SEQ ID NO:29. In some aspects, the antibody comprises a Chothia CDR-H1 sequence comprising, consisting of, or consisting essentially of SEQ ID NO:30. In some aspects, the antibody comprises a Chothia CDR-H1 sequence comprising, consisting of, or consisting essentially of SEQ ID NO:31. In some aspects, the antibody comprises a Chothia CDR-H1 sequence comprising, consisting of, or consisting essentially of SEQ ID NO:32. In some aspects, the antibody comprises a Chothia CDR-H1 sequence comprising, consisting of, or consisting essentially of SEQ ID NO:33. In some aspects, the antibody comprises a Chothia CDR-H1 sequence comprising, consisting of, or consisting essentially of SEQ ID NO:34. In some aspects, the antibody comprises a Chothia CDR-H1 sequence comprising, consisting of, or consisting essentially of SEQ ID NO:35. In some aspects, the antibody comprises a Chothia CDR-H1 sequence comprising, consisting of, or consisting essentially of SEQ ID NO:36. In some aspects, the antibody comprises a Chothia CDR-H1 sequence comprising, consisting of, or consisting essentially of SEQ ID NO:37. In some aspects, the antibody comprises a Chothia CDR-H1 sequence comprising, consisting of, or consisting essentially of SEQ ID NO:38. In some aspects, the antibody comprises a Chothia CDR-H1 sequence comprising, consisting of, or consisting essentially of SEQ ID NO:39. In some aspects, the antibody comprises a Chothia CDR-H1 sequence comprising, consisting of, or consisting essentially of SEQ ID NO:40. In some aspects, the antibody comprises a Chothia CDR-H1 sequence comprising, consisting of, or consisting essentially of SEQ ID NO:41. In some aspects, the antibody comprises a Chothia CDR-H1 sequence comprising, consisting of, or consisting essentially of SEQ ID NO:42. In some aspects, the antibody comprises a Chothia CDR-H1 sequence comprising, consisting of, or consisting essentially of SEQ ID NO:43. In some aspects, the antibody comprises a Chothia CDR-H1 sequence comprising, consisting of, or consisting essentially of SEQ ID NO:44. In some aspects, the antibody comprises a Chothia CDR-H1 sequence comprising, consisting of, or consisting essentially of SEQ ID NO:45. In some aspects, the antibody comprises a Chothia CDR-H1 sequence comprising, consisting of, or consisting essentially of SEQ ID NO:46. In some aspects, the antibody comprises a Chothia CDR-H1 sequence comprising, consisting of, or consisting essentially of SEQ ID NO:47. In some aspects, the antibody comprises a Chothia CDR-H1 sequence comprising, consisting of, or consisting essentially of SEQ ID NO:48. In some aspects, the antibody comprises a Chothia CDR-H1 sequence comprising, consisting of, or consisting essentially of SEQ ID NO:49.

In some aspects, the antibody comprises a Chothia CDR-H1 sequence comprising, consisting of, or consisting essentially of SEQ ID NO:50. In some aspects, the antibody comprises a Chothia CDR-H1 sequence comprising, consisting of, or consisting essentially of SEQ ID NO:51. In some aspects, the antibody comprises a Chothia CDR-H1 sequence comprising, consisting of, or consisting essentially of SEQ ID NO:52. In some aspects, the antibody comprises a Chothia CDR-H1 sequence comprising, consisting of, or consisting essentially of SEQ ID NO:53. In some aspects, the antibody comprises a Chothia CDR-H1 sequence comprising, consisting of, or consisting essentially of SEQ ID NO:54. In some aspects, the antibody comprises a Chothia CDR-H1 sequence comprising, consisting of, or consisting essentially of SEQ ID NO:55. In some aspects, the antibody comprises a Chothia CDR-H1 sequence comprising, consisting of, or consisting essentially of SEQ ID NO:56. In some aspects, the antibody comprises a Chothia CDR-H1 sequence comprising, consisting of, or consisting essentially of SEQ ID NO:57. In some aspects, the antibody comprises a Chothia CDR-H1 sequence comprising, consisting of, or consisting essentially of SEQ ID NO:58. In some aspects, the antibody comprises a Chothia CDR-H1 sequence comprising, consisting of, or consisting essentially of SEQ ID NO:59. In some aspects, the antibody comprises a Chothia CDR-H1 sequence comprising, consisting of, or consisting essentially of SEQ ID NO:60. In some aspects, the antibody comprises a Chothia CDR-H1 sequence comprising, consisting of, or consisting essentially of SEQ ID NO:61. In some aspects, the antibody comprises a Chothia CDR-H1 sequence comprising, consisting of, or consisting essentially of SEQ ID NO:62. In some aspects, the antibody comprises a Chothia CDR-H1 sequence comprising, consisting of, or consisting essentially of SEQ ID NO:63. In some aspects, the antibody comprises a Chothia CDR-H1 sequence comprising, consisting of, or consisting essentially of SEQ ID NO:64. In some aspects, the antibody comprises a Chothia CDR-H1 sequence comprising, consisting of, or consisting essentially of SEQ ID NO:65. In some aspects, the antibody comprises a Chothia CDR-H1 sequence comprising, consisting of, or consisting essentially of SEQ ID NO:66. In some aspects, the antibody comprises a Chothia CDR-H1 sequence comprising, consisting of, or consisting essentially of SEQ ID NO:67. In some aspects, the antibody comprises a Chothia CDR-H1 sequence comprising, consisting of, or consisting essentially of SEQ ID NO:68. In some aspects, the antibody comprises a Chothia CDR-H1 sequence comprising, consisting of, or consisting essentially of SEQ ID NO:69. In some aspects, the antibody comprises a Chothia CDR-H1 sequence comprising, consisting of, or consisting essentially of SEQ ID NO:70. In some aspects, the antibody comprises a Chothia CDR-H1 sequence comprising, consisting of, or consisting essentially of SEQ ID NO:71. In some aspects, the antibody comprises a Chothia CDR-H1 sequence comprising, consisting of, or consisting essentially of SEQ ID NO:72. In some aspects, the antibody comprises a Chothia CDR-H1 sequence comprising, consisting of, or consisting essentially of SEQ ID NO:73. In some aspects, the antibody comprises a Chothia CDR-H1 sequence comprising, consisting of, or consisting essentially of SEQ ID NO:74. In some aspects, the antibody comprises a Chothia CDR-H1 sequence comprising, consisting of, or consisting essentially of SEQ ID NO:75. In some aspects, the antibody comprises a Chothia CDR-H1 sequence comprising, consisting of, or consisting essentially of SEQ ID NO:76. In some aspects, the antibody comprises a Chothia CDR-H1 sequence comprising, consisting of, or consisting essentially of SEQ ID NO:77. In some aspects, the antibody comprises a Chothia CDR-H1 sequence comprising, consisting of, or consisting essentially of SEQ ID NO:78. In some aspects, the antibody comprises a Chothia CDR-H1 sequence comprising, consisting of, or consisting essentially of SEQ ID NO:79. In some aspects, the antibody comprises a Chothia CDR-H1 sequence comprising, consisting of, or consisting essentially of SEQ ID NO:80. In some aspects, the antibody comprises a Chothia CDR-H1 sequence comprising, consisting of, or consisting essentially of SEQ ID NO:81. In some aspects, the antibody comprises a Chothia CDR-H1 sequence comprising, consisting of, or consisting essentially of SEQ ID NO:82. In some aspects, the antibody comprises a Chothia CDR-H1 sequence comprising, consisting of, or consisting essentially of SEQ ID NO:83. In some aspects, the antibody comprises a Chothia CDR-H1 sequence comprising, consisting of, or consisting essentially of SEQ ID NO:84. In some aspects, the antibody comprises a Chothia CDR-H1 sequence comprising, consisting of, or consisting essentially of SEQ ID NO:85. In some aspects, the antibody comprises a Chothia CDR-H1 sequence comprising, consisting of, or consisting essentially of SEQ ID NO:86. In some aspects, the antibody comprises a Chothia CDR-H1 sequence comprising, consisting of, or consisting essentially of SEQ ID NO:87. In some aspects, the antibody comprises a Chothia CDR-H1 sequence comprising, consisting of, or consisting essentially of SEQ ID NO:88. In some aspects, the antibody comprises a Chothia CDR-H1 sequence comprising, consisting of, or consisting essentially of SEQ ID NO:89. In some aspects, the antibody comprises a Chothia CDR-H1 sequence comprising, consisting of, or consisting essentially of SEQ ID NO:90. In some aspects, the antibody comprises a Chothia CDR-H1 sequence comprising, consisting of, or consisting essentially of SEQ ID NO:91. In some aspects, the antibody comprises a Chothia CDR-H1 sequence comprising, consisting of, or consisting essentially of SEQ ID NO:92. In some aspects, the antibody comprises a Chothia CDR-H1 sequence comprising, consisting of, or consisting essentially of SEQ ID NO:93. In some aspects, the antibody comprises a Chothia CDR-H1 sequence comprising, consisting of, or consisting essentially of SEQ ID NO:94. In some aspects, the antibody comprises a Chothia CDR-H1 sequence comprising, consisting of, or consisting essentially of SEQ ID NO:95. In some aspects, the antibody comprises a Chothia CDR-H1 sequence comprising, consisting of, or consisting essentially of SEQ ID NO:96. In some aspects, the antibody comprises a Chothia CDR-H1 sequence comprising, consisting of, or consisting essentially of SEQ ID NO:97. In some aspects, the antibody comprises a Chothia CDR-H1 sequence comprising, consisting of, or consisting essentially of SEQ ID NO:98. In some aspects, the antibody comprises a Chothia CDR-H1 sequence comprising, consisting of, or consisting essentially of SEQ ID NO:99.

In some aspects, the antibody comprises a Chothia CDR-H1 sequence comprising, consisting of, or consisting essentially of SEQ ID NO:100. In some aspects, the antibody comprises a Chothia CDR-H1 sequence comprising, consisting of, or consisting essentially of SEQ ID NO:101. In some aspects, the antibody comprises a Chothia CDR-H1 sequence comprising, consisting of, or consisting essentially of SEQ ID NO:102. In some aspects, the antibody comprises a Chothia CDR-H1 sequence comprising, consisting of, or consisting essentially of SEQ ID NO:103. In some aspects, the antibody comprises a Chothia CDR-H1 sequence comprising, consisting of, or consisting essentially of SEQ ID NO:104. In some aspects, the antibody comprises a Chothia CDR-H1 sequence comprising, consisting of, or consisting essentially of SEQ ID NO:105. In some aspects, the antibody comprises a Chothia CDR-H1 sequence comprising, consisting of, or consisting essentially of SEQ ID NO:106. In some aspects, the antibody comprises a Chothia CDR-H1 sequence comprising, consisting of, or consisting essentially of SEQ ID NO:107. In some aspects, the antibody comprises a Chothia CDR-H1 sequence comprising, consisting of, or consisting essentially of SEQ ID NO:108. In some aspects, the antibody comprises a Chothia CDR-H1 sequence comprising, consisting of, or consisting essentially of SEQ ID NO:109. In some aspects, the antibody comprises a Chothia CDR-H1 sequence comprising, consisting of, or consisting essentially of SEQ ID NO:110. In some aspects, the antibody comprises a Chothia CDR-H1 sequence comprising, consisting of, or consisting essentially of SEQ ID NO:111. In some aspects, the antibody comprises a Chothia CDR-H1 sequence comprising, consisting of, or consisting essentially of SEQ ID NO:112. In some aspects, the antibody comprises a Chothia CDR-H1 sequence comprising, consisting of, or consisting essentially of SEQ ID NO:113. In some aspects, the antibody comprises a Chothia CDR-H1 sequence comprising, consisting of, or consisting essentially of SEQ ID NO:114. In some aspects, the antibody comprises a Chothia CDR-H1 sequence comprising, consisting of, or consisting essentially of SEQ ID NO:115. In some aspects, the antibody comprises a Chothia CDR-H1 sequence comprising, consisting of, or consisting essentially of SEQ ID NO:116. In some aspects, the antibody comprises a Chothia CDR-H1 sequence comprising, consisting of, or consisting essentially of SEQ ID NO:117. In some aspects, the antibody comprises a Chothia CDR-H1 sequence comprising, consisting of, or consisting essentially of SEQ ID NO:118. In some aspects, the antibody comprises a Chothia CDR-H1 sequence comprising, consisting of, or consisting essentially of SEQ ID NO:119. In some aspects, the antibody comprises a Chothia CDR-H1 sequence comprising, consisting of, or consisting essentially of SEQ ID NO:120. In some aspects, the antibody comprises a Chothia CDR-H1 sequence comprising, consisting of, or consisting essentially of SEQ ID NO:121. In some aspects, the antibody comprises a Chothia CDR-H1 sequence comprising, consisting of, or consisting essentially of SEQ ID NO:122. In some aspects, the antibody comprises a Chothia CDR-H1 sequence comprising, consisting of, or consisting essentially of SEQ ID NO:123. In some aspects, the antibody comprises a Chothia CDR-H1 sequence comprising, consisting of, or consisting essentially of SEQ ID NO:124. In some aspects, the antibody comprises a Chothia CDR-H1 sequence comprising, consisting of, or consisting essentially of SEQ ID NO:125. In some aspects, the antibody comprises a Chothia CDR-H1 sequence comprising, consisting of, or consisting essentially of SEQ ID NO:126. In some aspects, the antibody comprises a Chothia CDR-H1 sequence comprising, consisting of, or consisting essentially of SEQ ID NO:127. In some aspects, the antibody comprises a Chothia CDR-H1 sequence comprising, consisting of, or consisting essentially of SEQ ID NO:128. In some aspects, the antibody comprises a Chothia CDR-H1 sequence comprising, consisting of, or consisting essentially of SEQ ID NO:129. In some aspects, the antibody comprises a Chothia CDR-H1 sequence comprising, consisting of, or consisting essentially of SEQ ID NO:130. In some aspects, the antibody comprises a Chothia CDR-H1 sequence comprising, consisting of, or consisting essentially of SEQ ID NO:131. In some aspects, the antibody comprises a Chothia CDR-H1 sequence comprising, consisting of, or consisting essentially of SEQ ID NO:132. In some aspects, the antibody comprises a Chothia CDR-H1 sequence comprising, consisting of, or consisting essentially of SEQ ID NO:133. In some aspects, the antibody comprises a Chothia CDR-H1 sequence comprising, consisting of, or consisting essentially of SEQ ID NO:134. In some aspects, the antibody comprises a Chothia CDR-H1 sequence comprising, consisting of, or consisting essentially of SEQ ID NO:135. In some aspects, the antibody comprises a Chothia CDR-H1 sequence comprising, consisting of, or consisting essentially of SEQ ID NO:136. In some aspects, the antibody comprises a Chothia CDR-H1 sequence comprising, consisting of, or consisting essentially of SEQ ID NO:137. In some aspects, the antibody comprises a Chothia CDR-H1 sequence comprising, consisting of, or consisting essentially of SEQ ID NO:138. In some aspects, the antibody comprises a Chothia CDR-H1 sequence comprising, consisting of, or consisting essentially of SEQ ID NO:139. In some aspects, the antibody comprises a Chothia CDR-H1 sequence comprising, consisting of, or consisting essentially of SEQ ID NO:140. In some aspects, the antibody comprises a Chothia CDR-H1 sequence comprising, consisting of, or consisting essentially of SEQ ID NO:141. In some aspects, the antibody comprises a Chothia CDR-H1 sequence comprising, consisting of, or consisting essentially of SEQ ID NO:142. In some aspects, the antibody comprises a Chothia CDR-H1 sequence comprising, consisting of, or consisting essentially of SEQ ID NO:143. In some aspects, the antibody comprises a Chothia CDR-H1 sequence comprising, consisting of, or consisting essentially of SEQ ID NO:144. In some aspects, the antibody comprises a Chothia CDR-H1 sequence comprising, consisting of, or consisting essentially of SEQ ID NO:145. In some aspects, the antibody comprises a Chothia CDR-H1 sequence comprising, consisting of, or consisting essentially of SEQ ID NO:146. In some aspects, the antibody comprises a Chothia CDR-H1 sequence comprising, consisting of, or consisting essentially of SEQ ID NO:147. In some aspects, the antibody comprises a Chothia CDR-H1 sequence comprising, consisting of, or consisting essentially of SEQ ID NO:148. In some aspects, the antibody comprises a Chothia CDR-H1 sequence comprising, consisting of, or consisting essentially of SEQ ID NO:149.

In some aspects, the antibody comprises a Chothia CDR-H1 sequence comprising, consisting of, or consisting essentially of SEQ ID NO:150. In some aspects, the antibody comprises a Chothia CDR-H1 sequence comprising, consisting of, or consisting essentially of SEQ ID NO:151. In some aspects, the antibody comprises a Chothia CDR-H1 sequence comprising, consisting of, or consisting essentially of SEQ ID NO:152. In some aspects, the antibody comprises a Chothia CDR-H1 sequence comprising, consisting of, or consisting essentially of SEQ ID NO:153. In some aspects, the antibody comprises a Chothia CDR-H1 sequence comprising, consisting of, or consisting essentially of SEQ ID NO:154. In some aspects, the antibody comprises a Chothia CDR-H1 sequence comprising, consisting of, or consisting essentially of SEQ ID NO:155. In some aspects, the antibody comprises a Chothia CDR-H1 sequence comprising, consisting of, or consisting essentially of SEQ ID NO:156. In some aspects, the antibody comprises a Chothia CDR-H1 sequence comprising, consisting of, or consisting essentially of SEQ ID NO:157. In some aspects, the antibody comprises a Chothia CDR-H1 sequence comprising, consisting of, or consisting essentially of SEQ ID NO:158. In some aspects, the antibody comprises a Chothia CDR-H1 sequence comprising, consisting of, or consisting essentially of SEQ ID NO:159. In some aspects, the antibody comprises a Chothia CDR-H1 sequence comprising, consisting of, or consisting essentially of SEQ ID NO:160. In some aspects, the antibody comprises a Chothia CDR-H1 sequence comprising, consisting of, or consisting essentially of SEQ ID NO:161. In some aspects, the antibody comprises a Chothia CDR-H1 sequence comprising, consisting of, or consisting essentially of SEQ ID NO:162. In some aspects, the antibody comprises a Chothia CDR-H1 sequence comprising, consisting of, or consisting essentially of SEQ ID NO:163. In some aspects, the antibody comprises a Chothia CDR-H1 sequence comprising, consisting of, or consisting essentially of SEQ ID NO:164. In some aspects, the antibody comprises a Chothia CDR-H1 sequence comprising, consisting of, or consisting essentially of SEQ ID NO:165. In some aspects, the antibody comprises a Chothia CDR-H1 sequence comprising, consisting of, or consisting essentially of SEQ ID NO:166. In some aspects, the antibody comprises a Chothia CDR-H1 sequence comprising, consisting of, or consisting essentially of SEQ ID NO:167. In some aspects, the antibody comprises a Chothia CDR-H1 sequence comprising, consisting of, or consisting essentially of SEQ ID NO:168. In some aspects, the antibody comprises a Chothia CDR-H1 sequence comprising, consisting of, or consisting essentially of SEQ ID NO:169. In some aspects, the antibody comprises a Chothia CDR-H1 sequence comprising, consisting of, or consisting essentially of SEQ ID NO:170.

5.2.2.4. Chothia CDR-H3+Chothia CDR-H2

In some embodiments, the antibody comprises a $V_H$ sequence comprising a Chothia CDR-H3 sequence comprising, consisting of, or consisting essentially of a sequence selected from SEQ ID NOs:672-838, and a Chothia CDR-H2 sequence comprising, consisting of, or consisting essentially of a sequence selected from SEQ ID NOs:338-504. In some aspects, the Chothia CDR-H3 sequence and the Chothia CDR-H2 sequence are both from a single illustrative $V_H$ sequence provided in this disclosure. For example, in some aspects, the Chothia CDR-H3 and Chothia CDR-H2 are both from a single illustrative $V_H$ sequence selected from SEQ ID NOs: 854-1020.

5.2.2.5. Chothia CDR-H3+Chothia CDR-H1

In some embodiments, the antibody comprises a $V_H$ sequence comprising a Chothia CDR-H3 sequence comprising, consisting of, or consisting essentially of a sequence selected from SEQ ID NOs: 672-838, and a Chothia CDR-H1 sequence comprising, consisting of, or consisting essentially of a sequence selected from SEQ ID NOs: 4-170. In some aspects, the Chothia CDR-H3 sequence and the Chothia CDR-H1 sequence are both from a single illustrative $V_H$ sequence provided in this disclosure. For example, in some aspects, the Chothia CDR-H3 and Chothia CDR-H1 are both from a single illustrative $V_H$ sequence selected from SEQ ID NOs: 854-1020.

5.2.2.6. Chothia CDR-H1+Chothia CDR-H2

In some embodiments, the antibody comprises a $V_H$ sequence comprising a Chothia CDR-H1 sequence comprising, consisting of, or consisting essentially of a sequence selected from SEQ ID NOs: 4-170 and a Chothia CDR-H2 sequence comprising, consisting of, or consisting essentially of a sequence selected from SEQ ID NOs: 338-504. In some aspects, the Chothia CDR-H1 sequence and the Chothia CDR-H2 sequence are both from a single illustrative $V_H$ sequence provided in this disclosure. For example, in some aspects, the Chothia CDR-H1 and Chothia CDR-H2 are both from a single illustrative $V_H$ sequence selected from SEQ ID NOs: 854-1020.

5.2.2.7. Chothia CDR-H1+Chothia CDR-H2+Chothia CDR-H3

In some embodiments, the antibody comprises a $V_H$ sequence comprising a Chothia CDR-H1 sequence comprising, consisting of, or consisting essentially of a sequence selected from SEQ ID NOs: 4-170, a Chothia CDR-H2 sequence comprising, consisting of, or consisting essentially of a sequence selected from SEQ ID NOs: 1338-504, and a Chothia CDR-H3 sequence comprising, consisting of, or consisting essentially of a sequence selected from SEQ ID NOs: 672-838. In some aspects, the Chothia CDR-H1 sequence, Chothia CDR-H2 sequence, and Chothia CDR-H3 sequence are all from a single illustrative $V_H$ sequence provided in this disclosure. For example, in some aspects, the Chothia CDR-H1, Chothia CDR-H2, and Chothia CDR-H3 are all from a single illustrative $V_H$ sequence selected from SEQ ID NOs: 854-1020.

5.2.2.8. Variants of $V_H$ Sequences Comprising Illustrative Chothia CDRs

In some embodiments, the $V_H$ sequences provided herein comprise a variant of an illustrative Chothia CDR-H3, CDR-H2, and/or CDR-H1 sequence provided in this disclosure.

In some aspects, the Chothia CDR-H3 sequence comprises, consists of, or consists essentially of a variant of an illustrative Chothia CDR-H3 sequence provided in this disclosure. In some aspects, the Chothia CDR-H3 sequence comprises, consists of, or consists essentially of a sequence having at least 70%, 75%, 80%, 85%, 90%, 95%, 96%, 97%, 98%, or 99% identity with any of the illustrative Chothia CDR-H3 sequences provided in this disclosure. In some aspects, the Chothia CDR-H3 sequence comprises, consists of, or consists essentially of any of the illustrative Chothia CDR-H3 sequences provided in this disclosure, with 1, 2, or 3 amino acid substitutions. In some aspects, the amino acid substitutions are conservative amino acid substitutions.

In some aspects, the Chothia CDR-H2 sequence comprises, consists of, or consists essentially of a variant of an illustrative Chothia CDR-H2 sequence provided in this disclosure. In some aspects, the Chothia CDR-H2 sequence comprises, consists of, or consists essentially of a sequence having at least 70%, 75%, 80%, 85%, 90%, 95%, 96%, 97%, 98%, or 99% identity with any of the illustrative Chothia CDR-H2 sequences provided in this disclosure. In some aspects, the Chothia CDR-H2 sequence comprises, consists of, or consists essentially of any of the illustrative Chothia CDR-H2 sequences provided in this disclosure, with 1, 2, or 3 amino acid substitutions. In some aspects, the amino acid substitutions are conservative amino acid substitutions.

In some aspects, the Chothia CDR-H1 sequence comprises, consists of, or consists essentially of a variant of an illustrative Chothia CDR-H1 sequence provided in this disclosure. In some aspects, the Chothia CDR-H1 sequence comprises, consists of, or consists essentially of a sequence having at least 70%, 75%, 80%, 85%, 90%, 95%, 96%, 97%, 98%, or 99% identity with any of the illustrative Chothia CDR-H1 sequences provided in this disclosure. In some aspects, the Chothia CDR-H1 sequence comprises, consists of, or consists essentially of any of the illustrative Chothia CDR-H1 sequences provided in this disclosure, with 1, 2, or 3 amino acid substitutions. In some aspects, the amino acid substitutions are conservative amino acid substitutions.

5.3. $V_H$ Sequences

In some embodiments, the antibody comprises, consists of, or consists essentially of a $V_H$ sequence provided in SEQ ID NOs: 854-1020.

In some embodiments, the antibody comprises a $V_H$ sequence comprising, consisting of, or consisting essentially of a sequence selected from SEQ ID NOs: 854-1020. In some aspects, the antibody comprises a $V_H$ sequence comprising, consisting of, or consisting essentially of SEQ ID NO:854. In some aspects, the antibody comprises a $V_H$ sequence comprising, consisting of, or consisting essentially of SEQ ID NO:855. In some aspects, the antibody comprises a $V_H$ sequence comprising, consisting of, or consisting essentially of SEQ ID NO:856. In some aspects, the antibody comprises a $V_H$ sequence comprising, consisting of, or consisting essentially of SEQ ID NO:857. In some aspects, the antibody comprises a $V_H$ sequence comprising, consisting of, or consisting essentially of SEQ ID NO:858. In some aspects, the antibody comprises a $V_H$ sequence comprising, consisting of, or consisting essentially of SEQ ID NO:859. In some aspects, the antibody comprises a $V_H$ sequence comprising, consisting of, or consisting essentially of SEQ ID NO:860. In some aspects, the antibody comprises a $V_H$ sequence comprising, consisting of, or consisting essentially of SEQ ID NO:861. In some aspects, the antibody comprises a $V_H$ sequence comprising, consisting of, or consisting essentially of SEQ ID NO:862. In some aspects, the antibody comprises a $V_H$ sequence comprising, consisting of, or consisting essentially of SEQ ID NO:863. In some aspects, the antibody comprises a $V_H$ sequence comprising, consisting of, or consisting essentially of SEQ ID NO:864. In some aspects, the antibody comprises a $V_H$ sequence comprising, consisting of, or consisting essentially of SEQ ID NO:865. In some aspects, the antibody comprises a $V_H$ sequence comprising, consisting of, or consisting essentially of SEQ ID NO:866. In some aspects, the antibody comprises a $V_H$ sequence comprising, consisting of, or consisting essentially of SEQ ID NO:867. In some aspects, the antibody comprises a $V_H$ sequence comprising, consisting of, or consisting essentially of SEQ ID NO:868. In some aspects, the antibody comprises a $V_H$ sequence comprising, consisting of, or consisting essentially of SEQ ID NO:869. In some aspects, the antibody comprises a $V_H$ sequence comprising, consisting of, or consisting essentially of SEQ ID NO:870. In some aspects, the antibody comprises a $V_H$ sequence comprising, consisting of, or consisting essentially of SEQ ID NO:871. In some aspects, the antibody comprises a $V_H$ sequence comprising, consisting of, or consisting essentially of SEQ ID NO:872. In some aspects, the antibody comprises a $V_H$ sequence comprising, consisting of, or consisting essentially of SEQ ID NO:873. In some aspects, the antibody comprises a $V_H$ sequence comprising, consisting of, or consisting essentially of SEQ ID NO:874. In some aspects, the antibody comprises a $V_H$ sequence comprising, consisting of, or consisting essentially of SEQ ID NO:875. In some aspects, the antibody comprises a $V_H$ sequence comprising, consisting of, or consisting essentially of SEQ ID NO:876. In some aspects, the antibody comprises a $V_H$ sequence comprising, consisting of, or consisting essentially of SEQ ID NO:877. In some aspects, the antibody comprises a $V_H$ sequence comprising, consisting of, or consisting essentially of SEQ ID NO:878. In some aspects, the antibody comprises a $V_H$ sequence comprising, consisting of, or consisting essentially of SEQ ID NO:879. In some aspects, the antibody comprises a $V_H$ sequence comprising, consisting of, or consisting essentially of SEQ ID NO:880. In some aspects, the antibody comprises a $V_H$ sequence comprising, consisting of, or consisting essentially of SEQ ID NO:881. In some aspects, the antibody comprises a $V_H$ sequence comprising, consisting of, or consisting essentially of SEQ ID NO:882. In some aspects, the antibody comprises a $V_H$ sequence comprising, consisting of, or consisting essentially of SEQ ID NO:883. In some aspects, the antibody comprises a $V_H$ sequence comprising, consisting of, or consisting essentially of SEQ ID NO:884. In some aspects, the antibody comprises a $V_H$ sequence comprising, consisting of, or consisting essentially of SEQ ID NO:885. In some aspects, the antibody comprises a $V_H$ sequence comprising, consisting of, or consisting essentially of SEQ ID NO:886. In some aspects, the antibody comprises a $V_H$ sequence comprising, consisting of, or consisting essentially of SEQ ID NO:887. In some aspects, the antibody comprises a $V_H$ sequence comprising, consisting of, or consisting essentially of SEQ ID NO:888. In some aspects, the antibody comprises a $V_H$ sequence comprising, consisting of, or consisting essentially of SEQ ID NO:889. In some aspects, the antibody comprises a $V_H$ sequence comprising, consisting of, or consisting essentially of SEQ ID NO:890. In some aspects, the antibody comprises a $V_H$ sequence comprising, consisting of, or consisting essentially of SEQ ID NO:891. In some aspects, the antibody comprises a $V_H$ sequence comprising, consisting of, or consisting essentially of SEQ ID NO:892. In some aspects, the antibody comprises a $V_H$ sequence comprising, consisting of, or consisting essentially of SEQ ID NO:893. In some aspects, the antibody comprises a $V_H$ sequence comprising, consisting of, or consisting essentially of SEQ ID NO:894. In some aspects, the antibody comprises a $V_H$ sequence comprising, consisting of, or consisting essentially of SEQ ID NO:895. In some aspects, the antibody comprises a $V_H$ sequence comprising, consisting of, or consisting essentially of SEQ ID NO:896. In some aspects, the antibody comprises a $V_H$ sequence comprising, consisting of, or consisting essentially of SEQ ID NO:897. In some aspects, the antibody comprises a $V_H$ sequence comprising, consisting of, or consisting essentially of SEQ ID NO:898. In some aspects, the antibody comprises a $V_H$ sequence comprising, consisting of, or consisting essentially of SEQ ID NO:899.

In some aspects, the antibody comprises a $V_H$ sequence comprising, consisting of, or consisting essentially of SEQ ID NO:900. In some aspects, the antibody comprises a $V_H$ sequence comprising, consisting of, or consisting essentially of SEQ ID NO:901. In some aspects, the antibody comprises a $V_H$ sequence comprising, consisting of, or consisting essentially of SEQ ID NO:902. In some aspects, the antibody comprises a $V_H$ sequence comprising, consisting of, or consisting essentially of SEQ ID NO:903. In some aspects, the antibody comprises a $V_H$ sequence comprising, consisting of, or consisting essentially of SEQ ID NO:904. In some aspects, the antibody comprises a $V_H$ sequence comprising, consisting of, or consisting essentially of SEQ ID NO:905. In some aspects, the antibody comprises a $V_H$ sequence comprising, consisting of, or consisting essentially of SEQ ID NO:906. In some aspects, the antibody comprises a $V_H$ sequence comprising, consisting of, or consisting essentially of SEQ ID NO:907. In some aspects, the antibody comprises a $V_H$ sequence comprising, consisting of, or consisting essentially of SEQ ID NO:908. In some aspects, the antibody comprises a $V_H$ sequence comprising, consisting of, or consisting essentially of SEQ ID NO:909. In some aspects, the antibody comprises a $V_H$ sequence comprising, consisting of, or consisting essentially of SEQ ID NO:910. In some aspects, the antibody comprises a $V_H$ sequence comprising, consisting of, or consisting essentially of SEQ ID NO:911. In some aspects, the antibody comprises a $V_H$ sequence comprising, consisting of, or consisting essentially of SEQ ID NO:912. In some aspects, the antibody comprises a $V_H$ sequence comprising, consisting of, or consisting essentially of SEQ ID NO:913. In some aspects, the antibody comprises a $V_H$ sequence comprising, consisting of, or consisting essentially of SEQ ID NO:914. In some aspects, the antibody comprises a $V_H$ sequence comprising, consisting of, or consisting essentially of SEQ ID NO:915. In some aspects, the antibody comprises a $V_H$ sequence comprising, consisting of, or consisting essentially of SEQ ID NO:916. In some aspects, the antibody comprises a $V_H$ sequence comprising, consisting of, or consisting essentially of SEQ ID NO:917. In some aspects, the antibody comprises a $V_H$ sequence comprising, consisting of, or consisting essentially of SEQ ID NO:918. In some aspects, the antibody comprises a $V_H$ sequence comprising, consisting of, or consisting essentially of SEQ ID NO:919. In some aspects, the antibody comprises a $V_H$ sequence comprising, consisting of, or consisting essentially of SEQ ID NO:920. In some aspects, the antibody comprises a $V_H$ sequence comprising, consisting of, or consisting essentially of SEQ ID NO:921. In some aspects, the antibody comprises a $V_H$ sequence comprising, consisting of, or consisting essentially of SEQ ID NO:922. In some aspects, the antibody comprises a $V_H$ sequence comprising, consisting of, or consisting essentially of SEQ ID NO:923. In some aspects, the antibody comprises a $V_H$ sequence comprising, consisting of, or consisting essentially of SEQ ID NO:924. In some aspects, the antibody comprises a $V_H$ sequence comprising, consisting of, or consisting essentially of SEQ ID NO:925. In some aspects, the antibody comprises a $V_H$ sequence comprising, consisting of, or consisting essentially of SEQ ID NO:926. In some aspects, the antibody comprises a $V_H$ sequence comprising, consisting of, or consisting essentially of SEQ ID NO:927. In some aspects, the antibody comprises a $V_H$ sequence comprising, consisting of, or consisting essentially of SEQ ID NO:928. In some aspects, the antibody comprises a $V_H$ sequence comprising, consisting of, or consisting essentially of SEQ ID NO:929. In some aspects, the antibody comprises a $V_H$ sequence comprising, consisting of, or consisting essentially of SEQ ID NO:930. In some aspects, the antibody comprises a $V_H$ sequence comprising, consisting of, or consisting essentially of SEQ ID NO:931. In some aspects, the antibody comprises a $V_H$ sequence comprising, consisting of, or consisting essentially of SEQ ID NO:932. In some aspects, the antibody comprises a $V_H$ sequence comprising, consisting of, or consisting essentially of SEQ ID NO:933. In some aspects, the antibody comprises a $V_H$ sequence comprising, consisting of, or consisting essentially of SEQ ID NO:934. In some aspects, the antibody comprises a $V_H$ sequence comprising, consisting of, or consisting essentially of SEQ ID NO:935. In some aspects, the antibody comprises a $V_H$ sequence comprising, consisting of, or consisting essentially of SEQ ID NO:936. In some aspects, the antibody comprises a $V_H$ sequence comprising, consisting of, or consisting essentially of SEQ ID NO:937. In some aspects, the antibody comprises a $V_H$ sequence comprising, consisting of, or consisting essentially of SEQ ID NO:938. In some aspects, the antibody comprises a $V_H$ sequence comprising, consisting of, or consisting essentially of SEQ ID NO:939. In some aspects, the antibody comprises a $V_H$ sequence comprising, consisting of, or consisting essentially of SEQ ID NO:940. In some aspects, the antibody comprises a $V_H$ sequence comprising, consisting of, or consisting essentially of SEQ ID NO:941. In some aspects, the antibody comprises a $V_H$ sequence comprising, consisting of, or consisting essentially of SEQ ID NO:942. In some aspects, the antibody comprises a $V_H$ sequence comprising, consisting of, or consisting essentially of SEQ ID NO:943. In some aspects, the antibody comprises a $V_H$ sequence comprising, consisting of, or consisting essentially of SEQ ID NO:944. In some aspects, the antibody comprises a $V_H$ sequence comprising, consisting of, or consisting essentially of SEQ ID NO:945. In some aspects, the antibody comprises a $V_H$ sequence comprising, consisting of, or consisting essentially of SEQ ID NO:946. In some aspects, the antibody comprises a $V_H$ sequence comprising, consisting of, or consisting essentially of SEQ ID NO:947. In some aspects, the antibody comprises a $V_H$ sequence comprising, consisting of, or consisting essentially of SEQ ID NO:948. In some aspects, the antibody comprises a $V_H$ sequence comprising, consisting of, or consisting essentially of SEQ ID NO:949.

In some aspects, the antibody comprises a $V_H$ sequence comprising, consisting of, or consisting essentially of SEQ ID NO:950. In some aspects, the antibody comprises a $V_H$ sequence comprising, consisting of, or consisting essentially of SEQ ID NO:951. In some aspects, the antibody comprises a $V_H$ sequence comprising, consisting of, or consisting essentially of SEQ ID NO:952. In some aspects, the antibody comprises a $V_H$ sequence comprising, consisting of, or consisting essentially of SEQ ID NO:953. In some aspects, the antibody comprises a $V_H$ sequence comprising, consisting of, or consisting essentially of SEQ ID NO:954. In some aspects, the antibody comprises a $V_H$ sequence comprising, consisting of, or consisting essentially of SEQ ID NO:955. In some aspects, the antibody comprises a $V_H$ sequence comprising, consisting of, or consisting essentially of SEQ ID NO:956. In some aspects, the antibody comprises a $V_H$ sequence comprising, consisting of, or consisting essentially of SEQ ID NO:957. In some aspects, the antibody comprises a $V_H$ sequence comprising, consisting of, or consisting essentially of SEQ ID NO:958. In some aspects, the antibody comprises a $V_H$ sequence comprising, consisting of, or consisting essentially of SEQ ID NO:959. In some aspects, the antibody comprises a $V_H$ sequence comprising, consisting of, or consisting essentially of SEQ ID NO:960. In some aspects, the antibody comprises a $V_H$ sequence comprising, consisting of, or consisting essentially of SEQ ID NO:961. In some aspects, the antibody comprises a $V_H$ sequence comprising, consisting of, or consisting essentially of SEQ ID NO:962. In some aspects, the antibody comprises a $V_H$ sequence comprising, consisting of, or consisting essentially of SEQ ID NO:963. In some aspects, the antibody comprises a $V_H$ sequence comprising, consisting of, or consisting essentially of SEQ ID NO:964. In some aspects, the antibody comprises a $V_H$ sequence comprising, consisting of, or consisting essentially of SEQ ID NO:965. In some aspects, the antibody comprises a $V_H$ sequence comprising, consisting of, or consisting essentially of SEQ ID NO:966. In some aspects, the antibody comprises a $V_H$ sequence comprising, consisting of, or consisting essentially of SEQ ID NO:967. In some aspects, the antibody comprises a $V_H$ sequence comprising, consisting of, or consisting essentially of SEQ ID NO:968. In some aspects, the antibody comprises a $V_H$ sequence comprising, consisting of, or consisting essentially of SEQ ID NO:969. In some aspects, the antibody comprises a $V_H$ sequence comprising, consisting of, or consisting essentially of SEQ ID NO:970. In some aspects, the antibody comprises a $V_H$ sequence comprising, consisting of, or consisting essentially of SEQ ID NO:971. In some aspects, the antibody comprises a $V_H$ sequence comprising, consisting of, or consisting essentially of SEQ ID NO:972. In some aspects, the antibody comprises a $V_H$ sequence comprising, consisting of, or consisting essentially of SEQ ID NO:973.

In some aspects, the antibody comprises a $V_H$ sequence comprising, consisting of, or consisting essentially of SEQ ID NO:974. In some aspects, the antibody comprises a $V_H$ sequence comprising, consisting of, or consisting essentially of SEQ ID NO:975. In some aspects, the antibody comprises a $V_H$ sequence comprising, consisting of, or consisting essentially of SEQ ID NO:976. In some aspects, the antibody comprises a $V_H$ sequence comprising, consisting of, or consisting essentially of SEQ ID NO:977. In some aspects, the antibody comprises a $V_H$ sequence comprising, consisting of, or consisting essentially of SEQ ID NO:978. In some aspects, the antibody comprises a $V_H$ sequence comprising, consisting of, or consisting essentially of SEQ ID NO:979. In some aspects, the antibody comprises a $V_H$ sequence comprising, consisting of, or consisting essentially of SEQ ID NO:980. In some aspects, the antibody comprises a $V_H$ sequence comprising, consisting of, or consisting essentially of SEQ ID NO:981. In some aspects, the antibody comprises a $V_H$ sequence comprising, consisting of, or consisting essentially of SEQ ID NO:982. In some aspects, the antibody comprises a $V_H$ sequence comprising, consisting of, or consisting essentially of SEQ ID NO:983. In some aspects, the antibody comprises a $V_H$ sequence comprising, consisting of, or consisting essentially of SEQ ID NO:984. In some aspects, the antibody comprises a $V_H$ sequence comprising, consisting of, or consisting essentially of SEQ ID NO:985. In some aspects, the antibody comprises a $V_H$ sequence comprising, consisting of, or consisting essentially of SEQ ID NO:986. In some aspects, the antibody comprises a $V_H$ sequence comprising, consisting of, or consisting essentially of SEQ ID NO:987. In some aspects, the antibody comprises a $V_H$ sequence comprising, consisting of, or consisting essentially of SEQ ID NO:988. In some aspects, the antibody comprises a $V_H$ sequence comprising, consisting of, or consisting essentially of SEQ ID NO:989. In some aspects, the antibody comprises a $V_H$ sequence comprising, consisting of, or consisting essentially of SEQ ID NO:990. In some aspects, the antibody comprises a $V_H$ sequence comprising, consisting of, or consisting essentially of SEQ ID NO:991. In some aspects, the antibody comprises a $V_H$ sequence comprising, consisting of, or consisting essentially of SEQ ID NO:992. In some aspects, the antibody comprises a $V_H$ sequence comprising, consisting of, or consisting essentially of SEQ ID NO:993. In some aspects, the antibody comprises a $V_H$ sequence comprising, consisting of, or consisting essentially of SEQ ID NO:994. In some aspects, the antibody comprises a $V_H$ sequence comprising, consisting of, or consisting essentially of SEQ ID NO:995. In some aspects, the antibody comprises a $V_H$ sequence comprising, consisting of, or consisting essentially of SEQ ID NO:996. In some aspects, the antibody comprises a $V_H$ sequence comprising, consisting of, or consisting essentially of SEQ ID NO:997. In some aspects, the antibody comprises a $V_H$ sequence comprising, consisting of, or consisting essentially of SEQ ID NO:998. In some aspects, the antibody comprises a $V_H$ sequence comprising, consisting of, or consisting essentially of SEQ ID NO:999.

In some aspects, the antibody comprises a $V_H$ sequence comprising, consisting of, or consisting essentially of SEQ ID NO:1000. In some aspects, the antibody comprises a $V_H$ sequence comprising, consisting of, or consisting essentially of SEQ ID NO:1001. In some aspects, the antibody comprises a $V_H$ sequence comprising, consisting of, or consisting essentially of SEQ ID NO:1002. In some aspects, the antibody comprises a $V_H$ sequence comprising, consisting of, or consisting essentially of SEQ ID NO:1003. In some aspects, the antibody comprises a $V_H$ sequence comprising, consisting of, or consisting essentially of SEQ ID NO:1004. In some aspects, the antibody comprises a $V_H$ sequence comprising, consisting of, or consisting essentially of SEQ ID NO:1005. In some aspects, the antibody comprises a $V_H$ sequence comprising, consisting of, or consisting essentially of SEQ ID NO:1006. In some aspects, the antibody comprises a $V_H$ sequence comprising, consisting of, or consisting essentially of SEQ ID NO:1007. In some aspects, the antibody comprises a $V_H$ sequence comprising, consisting of, or consisting essentially of SEQ ID NO:1008. In some aspects, the antibody comprises a $V_H$ sequence comprising, consisting of, or consisting essentially of SEQ ID NO:1009. In some aspects, the antibody comprises a $V_H$ sequence comprising, consisting of, or consisting essentially of SEQ ID NO:1010. In some aspects, the antibody comprises a $V_H$ sequence comprising, consisting of, or consisting essentially of SEQ ID NO:1011. In some aspects, the antibody comprises a $V_H$ sequence comprising, consisting of, or consisting essentially of SEQ ID NO:1012. In some aspects, the antibody comprises a $V_H$ sequence comprising, consisting of, or consisting essentially of SEQ ID NO:1013. In some aspects, the antibody comprises a $V_H$ sequence comprising, consisting of, or consisting essentially of SEQ ID NO:1014. In some aspects, the antibody comprises a $V_H$ sequence comprising, consisting of, or consisting essentially of SEQ ID NO:1015. In some aspects, the antibody comprises a $V_H$ sequence comprising, consisting of, or consisting essentially of SEQ ID NO:1016. In some aspects, the antibody comprises a $V_H$ sequence comprising, consisting of, or consisting essentially of SEQ ID NO:1017. In some aspects, the antibody comprises a $V_H$ sequence comprising, consisting of, or consisting essentially of SEQ ID NO:1018. In some aspects, the antibody comprises a $V_H$ sequence comprising, consisting of, or consisting essentially of SEQ ID NO:1019. In some aspects, the antibody comprises a $V_H$ sequence comprising, consisting of, or consisting essentially of SEQ ID NO:1020.

5.3.1. Variants of $V_H$ Sequences

In some embodiments, the $V_H$ sequences provided herein comprise, consist of, or consist essentially of a variant of an illustrative $V_H$ sequence provided in this disclosure.

In some aspects, the $V_H$ sequence comprises, consists of, or consists essentially of a variant of an illustrative $V_H$ sequence provided in this disclosure. In some aspects, the $V_H$ sequence comprises, consists of, or consists essentially of a sequence having at least 85%, 90%, 95%, 96%, 97%, 98%, 99%, or 99.5% identity with any of the illustrative $V_H$ sequences provided in this disclosure.

In some embodiments, the $V_H$ sequence comprises, consists of, or consists essentially of any of the illustrative $V_H$ sequences provided in this disclosure having 20 or fewer, 19 or fewer, 18 or fewer, 17 or fewer, 16 or fewer, 15 or fewer, 14 or fewer, 13 or fewer, 12 or fewer, 11 or fewer, 10 or fewer, 9 or fewer, 8 or fewer, 7 or fewer, 6 or fewer, 5 or fewer, 4 or fewer, 3 or fewer, 2 or fewer, or 1 or fewer amino acid substitutions. In some aspects, the amino acid substitutions are conservative amino acid substitutions.

5.4. CDR-L3 Sequences

In some embodiments, the antibody comprises a CDR-L3 sequence comprising, consisting of, or consisting essentially of a CDR-L3 sequence of an illustrative antibody or $V_L$ sequence provided herein. In some aspects, the CDR-L3 sequence is a CDR-L3 sequence of a $V_L$ sequence provided in SEQ ID NOs: 1021-1026.

In some embodiments, the antibody comprises a CDR-L3 sequence comprising, consisting of, or consisting essentially of a sequence selected from SEQ ID NOs: 849-853. In some aspects, the antibody comprises a CDR-L3 sequence comprising, consisting of, or consisting essentially of SEQ ID NO: 849. In some aspects, the antibody comprises a CDR-L3 sequence comprising, consisting of, or consisting essentially of SEQ ID NO: 850. In some aspects, the antibody comprises a CDR-L3 sequence comprising, consisting of, or consisting essentially of SEQ ID NO: 851. In some aspects, the antibody comprises a CDR-L3 sequence comprising, consisting of, or consisting essentially of SEQ ID NO: 852. In some aspects, the antibody comprises a CDR-L3 sequence comprising, consisting of, or consisting essentially of SEQ ID NO: 853.

In some aspects, the CDR-L3 sequence comprises, consists of, or consists essentially of a variant of an illustrative CDR-L3 sequence provided in this disclosure. In some aspects, the CDR-L3 sequence comprises, consists of, or consists essentially of a sequence having at least 70%, 75%, 80%, 85%, 90%, 95%, 96%, 97%, 98%, or 99% identity with any of the illustrative CDR-L3 sequences provided in this disclosure. In some aspects, the CDR-L3 sequence comprises, consists of, or consists essentially of any of the illustrative CDR-L3 sequences provided in this disclosure, with 1, 2, or 3 amino acid substitutions. In some aspects, the amino acid substitutions are conservative amino acid substitutions.

5.5. $V_L$ Sequences Comprising Illustrative CDRs

In some embodiments, the antibody comprises a $V_L$ sequence comprising one or more CDR-L sequences comprising, consisting of, or consisting essentially of one or more illustrative CDR-L sequences provided in this disclosure, and variants thereof.

5.5.1. CDR-L3

In some embodiments, the antibody comprises a $V_L$ sequence comprising a CDR-L3 sequence, wherein the CDR-L3 sequence comprises, consists of, or consists essentially of a CDR-L3 sequence of an illustrative antibody or $V_L$ sequence provided herein. In some aspects, the CDR-L3 sequence is a CDR-L3 sequence of a V L sequence provided in SEQ ID NOs: 1021-1026.

In some embodiments, the antibody comprises a $V_L$ sequence comprising a CDR-L3 sequence comprising, consisting of, or consisting essentially of a sequence selected from SEQ ID NOs: 849-853. In some aspects, the antibody comprises a CDR-L3 sequence comprising, consisting of, or consisting essentially of SEQ ID NO: 849. In some aspects, the antibody comprises a CDR-L3 sequence comprising, consisting of, or consisting essentially of SEQ ID NO: 850. In some aspects, the antibody comprises a CDR-L3 sequence comprising, consisting of, or consisting essentially of SEQ ID NO: 851. In some aspects, the antibody comprises a CDR-L3 sequence comprising, consisting of, or consisting essentially of SEQ ID NO: 852. In some aspects, the antibody comprises a CDR-L3 sequence comprising, consisting of, or consisting essentially of SEQ ID NO: 853.

5.5.2. CDR-L2

In some embodiments, the antibody comprises a $V_L$ sequence comprising a CDR-L2 sequence, wherein the CDR-L2 sequence comprises, consists of, or consists essentially of a CDR-L2 sequence of an illustrative antibody or $V_L$ sequence provided herein. In some aspects, the CDR-L2 sequence is a CDR-L2 sequence of a V L sequence provided in SEQ ID NOs: 1021-1026.

In some embodiments, the antibody comprises a $V_L$ sequence comprising a CDR-L2 sequence comprising, consisting of, or consisting essentially of a sequence selected from SEQ ID NOs: 844-848. In some aspects, the antibody comprises a $V_L$ sequence comprising a CDR-L2 sequence comprising, consisting of, or consisting essentially of SEQ ID NO: 844. In some aspects, the antibody comprises a $V_L$ sequence comprising a CDR-L2 sequence comprising, consisting of, or consisting essentially of SEQ ID NO: 845. In some aspects, the antibody comprises a $V_L$ sequence comprising a CDR-L2 sequence comprising, consisting of, or consisting essentially of SEQ ID NO: 846. In some aspects, the antibody comprises a $V_L$ sequence comprising a CDR-L2 sequence comprising, consisting of, or consisting essentially of SEQ ID NO: 847. In some aspects, the antibody comprises a $V_L$ sequence comprising a CDR-L2 sequence comprising, consisting of, or consisting essentially of SEQ ID NO: 848.

5.5.3. CDR-L1

In some embodiments, the antibody comprises a $V_L$ sequence comprising a CDR-L1 sequence, wherein the CDR-L1 sequence comprises, consists of, or consists essentially of a CDR-L1 sequence of an illustrative antibody or $V_L$ sequence provided herein. In some aspects, the CDR-L1 sequence is a CDR-L1 sequence of a V L sequence provided in SEQ ID NOs: 1021-1026.

In some embodiments, the antibody comprises a $V_L$ sequence comprising a CDR-L1 sequence comprising, consisting of, or consisting essentially of a sequence selected from SEQ ID NOs: 839-843. In some aspects, the antibody comprises a $V_L$ sequence comprising a CDR-L1 sequence comprising, consisting of, or consisting essentially of SEQ ID NO: 839. In some aspects, the antibody comprises a $V_L$ sequence comprising a CDR-L1 sequence comprising, consisting of, or consisting essentially of SEQ ID NO: 840. In some aspects, the antibody comprises a $V_L$ sequence comprising a CDR-L1 sequence comprising, consisting of, or consisting essentially of SEQ ID NO: 841. In some aspects, the antibody comprises a $V_L$ sequence comprising a CDR-L1 sequence comprising, consisting of, or consisting essentially of SEQ ID NO: 842. In some aspects, the antibody comprises a $V_L$ sequence comprising a CDR-L1 sequence comprising, consisting of, or consisting essentially of SEQ ID NO: 843.

5.5.4. CDR-L3+CDR-L2

In some embodiments, the antibody comprises a $V_L$ sequence comprising a CDR-L3 sequence comprising, consisting of, or consisting essentially of a sequence selected from SEQ ID NOs: 849-853 and a CDR-L2 sequence comprising, consisting of, or consisting essentially of a sequence selected from SEQ ID NOs: 844-848. In some aspects, the CDR-L3 sequence and the CDR-L2 sequence are both from a single illustrative $V_L$ sequence provided in this disclosure. For example, in some aspects, the CDR-L3 and CDR-L2 are both from a single illustrative $V_L$ sequence selected from SEQ ID NOs: 1021-1026.

5.5.5. CDR-L3+CDR-L1

In some embodiments, the antibody comprises a $V_L$ sequence comprising a CDR-L3 sequence comprising, consisting of, or consisting essentially of a sequence selected from SEQ ID NOs: 849-853 and a CDR-L1 sequence comprising, consisting of, or consisting essentially of a sequence selected from SEQ ID NOs: 839-843. In some aspects, the CDR-L3 sequence and the CDR-L1 sequence are both from a single illustrative $V_L$ sequence provided in this disclosure. For example, in some aspects, the CDR-L3 and CDR-L1 are both from a single illustrative $V_L$ sequence selected from SEQ ID NOs: 1021-1026.

5.5.6. CDR-L1+CDR-L2

In some embodiments, the antibody comprises a $V_L$ sequence comprising a CDR-L1 sequence comprising, consisting of, or consisting essentially of a sequence selected from SEQ ID NOs: 839-843 and a CDR-L2 sequence comprising, consisting of, or consisting essentially of a sequence selected from SEQ ID NOs: 844-848. In some aspects, the CDR-L1 sequence and the CDR-L2 sequence are both from a single illustrative $V_L$ sequence provided in this disclosure. For example, in some aspects, the CDR-L1 and CDR-L2 are both from a single illustrative $V_L$ sequence selected from SEQ ID NOs: 1021-1026.

5.5.7. CDR-L1+CDR-L2+CDR-L3

In some embodiments, the antibody comprises a $V_L$ sequence comprising a CDR-L1 sequence comprising, consisting of, or consisting essentially of a sequence selected from SEQ ID NOs: 839-843, a CDR-L2 sequence comprising, consisting of, or consisting essentially of a sequence selected from SEQ ID NOs: 844-848, and a CDR-L3 sequence comprising, consisting of, or consisting essentially of a sequence selected from SEQ ID NOs: 849-853. In some aspects, the CDR-L1 sequence, CDR-L2 sequence, and CDR-L3 sequence are all from a single illustrative $V_L$ sequence provided in this disclosure. For example, in some aspects, the CDR-L1, CDR-L2, and CDR-L3 are all from a single illustrative $V_L$ sequence selected from SEQ ID NOs: 1021-1026.

5.5.8. Variants of $V_L$ Sequences Comprising Illustrative CDR-Ls

In some embodiments, the $V_L$ sequences provided herein comprise a variant of an illustrative CDR-L3, CDR-L2, and/or CDR-L1 sequence provided in this disclosure.

In some aspects, the CDR-L3 sequence comprises, consists of, or consists essentially of a variant of an illustrative CDR-L3 sequence provided in this disclosure. In some aspects, the CDR-L3 sequence comprises, consists of, or consists essentially of a sequence having at least 70%, 75%, 80%, 85%, 90%, 95%, 96%, 97%, 98%, or 99% identity with any of the illustrative CDR-L3 sequences provided in this disclosure. In some aspects, the CDR-L3 sequence comprises, consists of, or consists essentially of any of the illustrative CDR-L3 sequences provided in this disclosure, with 1, 2, or 3 amino acid substitutions. In some aspects, the amino acid substitutions are conservative amino acid substitutions.

In some aspects, the CDR-L2 sequence comprises, consists of, or consists essentially of a variant of an illustrative CDR-L2 sequence provided in this disclosure. In some aspects, the CDR-L2 sequence comprises, consists of, or consists essentially of a sequence having at least 70%, 75%, 80%, 85%, 90%, 95%, 96%, 97%, 98%, or 99% identity with any of the illustrative CDR-L2 sequences provided in this disclosure. In some aspects, the CDR-L2 sequence comprises, consists of, or consists essentially of any of the illustrative CDR-L2 sequences provided in this disclosure, with 1, 2, or 3 amino acid substitutions. In some aspects, the amino acid substitutions are conservative amino acid substitutions.

In some aspects, the CDR-L1 sequence comprises, consists of, or consists essentially of a variant of an illustrative CDR-L1 sequence provided in this disclosure. In some aspects, the CDR-L1 sequence comprises, consists of, or consists essentially of a sequence having at least 70%, 75%, 80%, 85%, 90%, 95%, 96%, 97%, 98%, or 99% identity with any of the illustrative CDR-L1 sequences provided in this disclosure. In some aspects, the CDR-L1 sequence comprises, consists of, or consists essentially of any of the illustrative CDR-L1 sequences provided in this disclosure, with 1, 2, or 3 amino acid substitutions. In some aspects, the amino acid substitutions are conservative amino acid substitutions.

5.6. $V_L$ Sequences

In some embodiments, the antibody comprises, consists of, or consists essentially of a $V_L$ sequence provided in SEQ ID NOs: 1021-1026.

In some embodiments, the antibody comprises a $V_L$ sequence comprising, consisting of, or consisting essentially of a sequence selected from SEQ ID NOs: 1021-1026. In some aspects, the antibody comprises a $V_L$ sequence comprising, consisting of, or consisting essentially of SEQ ID NO: 1021. In some aspects, the antibody comprises a $V_L$ sequence comprising, consisting of, or consisting essentially of SEQ ID NO: 1022. In some aspects, the antibody comprises a $V_L$ sequence comprising, consisting of, or consisting essentially of SEQ ID NO: 1023. In some aspects, the antibody comprises a $V_L$ sequence comprising, consisting of, or consisting essentially of SEQ ID NO: 1024. In some aspects, the antibody comprises a $V_L$ sequence comprising, consisting of, or consisting essentially of SEQ ID NO: 1025. In some aspects, the antibody comprises a $V_L$ sequence comprising, consisting of, or consisting essentially of SEQ ID NO: 1026.

5.6.1. Variants of $V_L$ Sequences

In some embodiments, the $V_L$ sequences provided herein comprise, consist of, or consist essentially of a variant of an illustrative $V_L$ sequence provided in this disclosure.

In some aspects, the $V_L$ sequence comprises, consists of, or consists essentially of a variant of an illustrative $V_L$ sequence provided in this disclosure. In some aspects, the $V_L$ sequence comprises, consists of, or consists essentially of a sequence having at least 85%, 90%, 95%, 96%, 97%, 98%, 99%, or 99.5% identity with any of the illustrative $V_L$ sequences provided in this disclosure.

In some embodiments, the $V_L$ sequence comprises, consists of, or consists essentially of any of the illustrative $V_L$ sequences provided in this disclosure having 20 or fewer, 19 or fewer, 18 or fewer, 17 or fewer, 16 or fewer, 15 or fewer, 14 or fewer, 13 or fewer, 12 or fewer, 11 or fewer, 10 or fewer, 9 or fewer, 8 or fewer, 7 or fewer, 6 or fewer, 5 or fewer, 4 or fewer, 3 or fewer, 2 or fewer, or 1 or fewer amino acid substitutions. In some aspects, the amino acid substitutions are conservative amino acid substitutions.

5.7. Pairs 5.7.1. CDR-H3-CDR-L3 Pairs

In some embodiments, the antibody comprises a CDR-H3 sequence and a CDR-L3 sequence. In some aspects, the CDR-H3 sequence is part of a $V_H$ and the CDR-L3 sequence is part of a $V_L$.

In some aspects, the CDR-H3 sequence is a CDR-H3 sequence comprising, consisting of, or consisting essentially of any one of SEQ ID NOs: 672-838, and the CDR-L3 sequence is a CDR-L3 sequence comprising, consisting of, or consisting essentially of any one of SEQ ID NOs: 849-853.

In some aspects, the CDR-H3-CDR-L3 pairs are selected from SEQ ID NO:357 and SEQ ID NO:849; SEQ ID NO:358 and SEQ ID NO:849; SEQ ID NO:359 and SEQ ID NO:849; SEQ ID NO:360 and SEQ ID NO:849; SEQ ID NO:361 and SEQ ID NO:362 and SEQ ID NO:849; SEQ ID NO:363 and SEQ ID NO:849; SEQ ID NO:364 and SEQ ID NO:849; SEQ ID NO:365 and SEQ ID NO:849; SEQ ID NO:366 and SEQ ID NO:849; SEQ ID NO:367 and SEQ ID NO:849; SEQ ID NO:368 and SEQ ID NO:849; SEQ ID NO:369 and SEQ ID NO:849; SEQ ID NO:370 and SEQ ID NO:849; SEQ ID NO:371 and SEQ ID NO:849; SEQ ID NO:372 and SEQ ID NO:849; SEQ ID NO:373 and SEQ ID NO:849; SEQ ID NO:374 and SEQ ID NO:849; SEQ ID NO:375 and SEQ ID NO:849; SEQ ID NO:376 and SEQ ID NO:849; SEQ ID NO:377 and SEQ ID NO:849; SEQ ID NO:378 and SEQ ID NO:849; SEQ ID NO:379 and SEQ ID NO:849; SEQ ID NO:380 and SEQ ID NO:849; SEQ ID NO:381 and SEQ ID NO:849; SEQ ID NO:382 and SEQ ID NO:849; SEQ ID NO:383 and SEQ ID NO:849; SEQ ID NO:384 and SEQ ID NO:849; SEQ ID NO:385 and SEQ ID NO:849; SEQ ID NO:386 and SEQ ID NO:849; SEQ ID NO:387 and SEQ ID NO:849; SEQ ID NO:388 and SEQ ID NO:849; SEQ ID NO:389 and SEQ ID NO:849; SEQ ID NO:390 and SEQ ID NO:849; SEQ ID NO:391 and SEQ ID NO:849; SEQ ID NO:392 and SEQ ID NO:849; SEQ ID NO:393 and SEQ ID NO:849; SEQ ID NO:394 and SEQ ID NO:849; SEQ ID NO:395 and SEQ ID NO:849; SEQ ID NO:396 and SEQ ID NO:849; SEQ ID NO:397 and SEQ ID NO:849; SEQ ID NO:398 and SEQ ID NO:849; SEQ ID NO:399 and SEQ ID NO:849; SEQ ID NO:400 and SEQ ID NO:849; SEQ ID NO:401 and SEQ ID NO:849; SEQ ID NO:402 and SEQ ID NO:849; SEQ ID NO:403 and SEQ ID NO:849; SEQ ID NO:404 and SEQ ID NO:849; SEQ ID NO:405 and SEQ ID NO:849; SEQ ID NO:406 and SEQ ID NO:849; SEQ ID NO:407 and SEQ ID NO:849; SEQ ID NO:408 and SEQ ID NO:849; SEQ ID NO:409 and SEQ ID NO:849; SEQ ID NO:410 and SEQ ID NO:849; SEQ ID NO:411 and SEQ ID NO:849; SEQ ID NO:412 and SEQ ID NO:849; SEQ ID NO:413 and SEQ ID NO:849; SEQ ID NO:414 and SEQ ID NO:849; SEQ ID NO:415 and SEQ ID NO:849; SEQ ID NO:416 and SEQ ID NO:849; SEQ ID NO:417 and SEQ ID NO:849; SEQ ID NO:418 and SEQ ID NO:849; SEQ ID NO:419 and SEQ ID NO:849; SEQ ID NO:420 and SEQ ID NO:849; SEQ ID NO:421 and SEQ ID NO:849; SEQ ID NO:422 and SEQ ID NO:849; SEQ ID NO:423 and SEQ ID NO:849; SEQ ID NO:424 and SEQ ID NO:849; SEQ ID NO:425 and SEQ ID NO:849; SEQ ID NO:426 and SEQ ID NO:849; SEQ ID NO:427 and SEQ ID NO:849; SEQ ID NO:428 and SEQ ID NO:849; SEQ ID NO:429 and SEQ ID NO:849; SEQ ID NO:430 and SEQ ID NO:849; SEQ ID NO:431 and SEQ ID NO:849; SEQ ID NO:432 and SEQ ID NO:849; SEQ ID NO:433 and SEQ ID NO:849; SEQ ID NO:434 and SEQ ID NO:849; SEQ ID NO:435 and SEQ ID NO:849; SEQ ID NO:436 and SEQ ID NO:849; SEQ ID NO:437 and SEQ ID NO:849; SEQ ID NO:438 and SEQ ID NO:849; SEQ ID NO:439 and SEQ ID NO:849; SEQ ID NO:440 and SEQ ID NO:849; SEQ ID NO:441 and SEQ ID NO:849; SEQ ID NO:442 and SEQ ID NO:849; SEQ ID NO:443 and SEQ ID NO:849; SEQ ID NO:444 and SEQ ID NO:849; SEQ ID NO:445 and SEQ ID NO:849; SEQ ID NO:446 and SEQ ID NO:849; SEQ ID NO:447 and SEQ ID NO:849; SEQ ID NO:448 and SEQ ID NO:849; SEQ ID NO:449 and SEQ ID NO:849; SEQ ID NO:450 and SEQ ID NO:849; SEQ ID NO:451 and SEQ ID NO:849; SEQ ID NO:452 and SEQ ID NO:849; SEQ ID NO:453 and SEQ ID NO:849; SEQ ID NO:454 and SEQ ID NO:849; SEQ ID NO:455 and SEQ ID NO:849; SEQ ID NO:456 and SEQ ID NO:849; SEQ ID NO:457 and SEQ ID NO:849; SEQ ID NO:458 and SEQ ID NO:849; SEQ ID NO:459 and SEQ ID NO:849; SEQ ID NO:460 and SEQ ID NO:849; SEQ ID NO:461 and SEQ ID NO:849; SEQ ID NO:462 and SEQ ID NO:849; SEQ ID NO:463 and SEQ ID NO:849; SEQ ID NO:464 and SEQ ID NO:849; SEQ ID NO:465 and SEQ ID NO:849; SEQ ID NO:466 and SEQ ID NO:849; SEQ ID NO:467 and SEQ ID NO:849; SEQ ID NO:468 and SEQ ID NO:849; SEQ ID NO:469 and SEQ ID NO:849; SEQ ID NO:470 and SEQ ID NO:849; SEQ ID NO:471 and SEQ ID NO:849; SEQ ID NO:472 and SEQ ID NO:849; SEQ ID NO:473 and SEQ ID NO:849; SEQ ID NO:474 and SEQ ID NO:849; SEQ ID NO:475 and SEQ ID NO:849; SEQ ID NO:476 and SEQ ID NO:849; SEQ ID NO:477 and SEQ ID NO:849; SEQ ID NO:478 and SEQ ID NO:849; SEQ ID NO:479 and SEQ ID NO:849; SEQ ID NO:480 and SEQ ID NO:849; SEQ ID NO:481 and SEQ ID NO:849; SEQ ID NO:482 and SEQ ID NO:849; SEQ ID NO:483 and SEQ ID NO:849; SEQ ID NO:484 and SEQ ID NO:849; SEQ ID NO:485 and SEQ ID NO:849; SEQ ID NO:486 and SEQ ID NO:849; SEQ ID NO:487 and SEQ ID NO:849; SEQ ID NO:488 and SEQ ID NO:849; SEQ ID NO:489 and SEQ ID NO:849; SEQ ID NO:490 and SEQ ID NO:849; SEQ ID NO:491 and SEQ ID NO:849; SEQ ID NO:492 and SEQ ID NO:849; SEQ ID NO:493 and SEQ ID NO:849; SEQ ID NO:494 and SEQ ID NO:849; SEQ ID NO:495 and SEQ ID NO:849; SEQ ID NO:496 and SEQ ID NO:849; SEQ ID NO:497 and SEQ ID NO:849; SEQ ID NO:498 and SEQ ID NO:849; SEQ ID NO:499 and SEQ ID NO:849; SEQ ID NO:500 and SEQ ID NO:849; SEQ ID NO:501 and SEQ ID NO:849; SEQ ID NO:502 and SEQ ID NO:849; SEQ ID NO:503 and SEQ ID NO:849; SEQ ID NO:504 and SEQ ID NO:849; SEQ ID NO:505 and SEQ ID NO:849; SEQ ID NO:506 and SEQ ID NO:849; SEQ ID NO:507 and SEQ ID NO:849; SEQ ID NO:508 and SEQ ID NO:849; SEQ ID NO:509 and SEQ ID NO:849; SEQ ID NO:510 and SEQ ID NO:849; SEQ ID NO:511 and SEQ ID NO:849; SEQ ID NO:512 and SEQ ID NO:849; SEQ ID NO:513 and SEQ ID NO:849; SEQ ID NO:514 and SEQ ID NO:849; SEQ ID NO:515 and SEQ ID NO:849; SEQ ID NO:516 and SEQ ID NO:849; SEQ ID NO:517 and SEQ ID NO:849; SEQ ID NO:518 and SEQ ID NO:849; SEQ ID NO:519 and SEQ ID NO:849; SEQ ID NO:520 and SEQ ID NO:849; SEQ ID NO:521 and SEQ ID NO:849; SEQ ID NO:522 and SEQ ID NO:849; and SEQ ID NO:523 and SEQ ID NO:849.

In some aspects, the CDR-H3-CDR-L3 pairs are selected from SEQ ID NO:357 and SEQ ID NO:850; SEQ ID NO:358 and SEQ ID NO:850; SEQ ID NO:359 and SEQ ID NO:850; SEQ ID NO:360 and SEQ ID NO:850; SEQ ID NO:361 and SEQ ID NO:850; SEQ ID NO:362 and SEQ ID NO:850; SEQ ID NO:363 and SEQ ID NO:850; SEQ ID NO:364 and SEQ ID NO:850; SEQ ID NO:365 and SEQ ID NO:850; SEQ ID NO:366 and SEQ ID NO:850; SEQ ID NO:367 and SEQ ID NO:850; SEQ ID NO:368 and SEQ ID NO:850; SEQ ID NO:369 and SEQ ID NO:850; SEQ ID NO:370 and SEQ ID NO:850; SEQ ID NO:371 and SEQ ID NO:850; SEQ ID NO:372 and SEQ ID NO:850; SEQ ID NO:373 and SEQ ID NO:850; SEQ ID NO:374 and SEQ ID NO:850; SEQ ID NO:375 and SEQ ID NO:850; SEQ ID NO:376 and SEQ ID NO:850; SEQ ID NO:377 and SEQ ID NO:850; SEQ ID NO:378 and SEQ ID NO:850; SEQ ID NO:379 and SEQ ID NO:850; SEQ ID NO:380 and SEQ ID NO:850; SEQ ID NO:381 and SEQ ID NO:850; SEQ ID NO:382 and SEQ ID NO:850; SEQ ID NO:383 and SEQ ID NO:850; SEQ ID NO:384 and SEQ ID NO:850; SEQ ID NO:385 and SEQ ID NO:850; SEQ ID NO:386 and SEQ ID NO:850; SEQ ID NO:387 and SEQ ID NO:850; SEQ ID NO:388 and SEQ ID NO:850; SEQ ID NO:389 and SEQ ID NO:850; SEQ ID NO:390 and SEQ ID NO:850; SEQ ID NO:391 and SEQ ID NO:850; SEQ ID NO:392 and SEQ ID NO:850; SEQ ID NO:393 and SEQ ID NO:850; SEQ ID NO:394 and SEQ ID NO:850; SEQ ID NO:395 and SEQ ID NO:850; SEQ ID NO:396 and SEQ ID NO:850; SEQ ID NO:397 and SEQ ID NO:850; SEQ ID NO:398 and SEQ ID NO:850; SEQ ID NO:399 and SEQ ID NO:850; SEQ ID NO:400 and SEQ ID NO:850; SEQ ID NO:401 and SEQ ID NO:850; SEQ ID NO:402 and SEQ ID NO:850; SEQ ID NO:403 and SEQ ID NO:850; SEQ ID NO:404 and SEQ ID NO:850; SEQ ID NO:405 and SEQ ID NO:850; SEQ ID NO:406 and SEQ ID NO:850; SEQ ID NO:407 and SEQ ID NO:850; SEQ ID NO:408 and SEQ ID NO:850; SEQ ID NO:409 and SEQ ID NO:850; SEQ ID NO:410 and SEQ ID NO:850; SEQ ID NO:411 and SEQ ID NO:850; SEQ ID NO:412 and SEQ ID NO:850; SEQ ID NO:413 and SEQ ID NO:850; SEQ ID NO:414 and SEQ ID NO:850; SEQ ID NO:415 and SEQ ID NO:850; SEQ ID NO:416 and SEQ ID NO:850; SEQ ID NO:417 and SEQ ID NO:850; SEQ ID NO:418 and SEQ ID NO:850; SEQ ID NO:419 and SEQ ID NO:850; SEQ ID NO:420 and SEQ ID NO:850; SEQ ID NO:421 and SEQ ID NO:850; SEQ ID NO:422 and SEQ ID NO:850; SEQ ID NO:423 and SEQ ID NO:850; SEQ ID NO:424 and SEQ ID NO:850; SEQ ID NO:425 and SEQ ID NO:850; SEQ ID NO:426 and SEQ ID NO:850; SEQ ID NO:427 and SEQ ID NO:850; SEQ ID NO:428 and SEQ ID NO:850; SEQ ID NO:429 and SEQ ID NO:850; SEQ ID NO:430 and SEQ ID NO:850; SEQ ID NO:431 and SEQ ID NO:850; SEQ ID NO:432 and SEQ ID NO:850; SEQ ID NO:433 and SEQ ID NO:850; SEQ ID NO:434 and SEQ ID NO:850; SEQ ID NO:435 and SEQ ID NO:850; SEQ ID NO:436 and SEQ ID NO:850; SEQ ID NO:437 and SEQ ID NO:850; SEQ ID NO:438 and SEQ ID NO:850; SEQ ID NO:439 and SEQ ID NO:850; SEQ ID NO:440 and SEQ ID NO:850; SEQ ID NO:441 and SEQ ID NO:850; SEQ ID NO:442 and SEQ ID NO:850; SEQ ID NO:443 and SEQ ID NO:850; SEQ ID NO:444 and SEQ ID NO:850; SEQ ID NO:445 and SEQ ID NO:850; SEQ ID NO:446 and SEQ ID NO:850; SEQ ID NO:447 and SEQ ID NO:850; SEQ ID NO:448 and SEQ ID NO:850; SEQ ID NO:449 and SEQ ID NO:850; SEQ ID NO:450 and SEQ ID NO:850; SEQ ID NO:451 and SEQ ID NO:850; SEQ ID NO:452 and SEQ ID NO:850; SEQ ID NO:453 and SEQ ID NO:850; SEQ ID NO:454 and SEQ ID NO:850; SEQ ID NO:455 and SEQ ID NO:850; SEQ ID NO:456 and SEQ ID NO:850; SEQ ID NO:457 and SEQ ID NO:850; SEQ ID NO:458 and SEQ ID NO:850; SEQ ID NO:459 and SEQ ID NO:850; SEQ ID NO:460 and SEQ ID NO:850; SEQ ID NO:461 and SEQ ID NO:850; SEQ ID NO:462 and SEQ ID NO:850; SEQ ID NO:463 and SEQ ID NO:850; SEQ ID NO:464 and SEQ ID NO:850; SEQ ID NO:465 and SEQ ID NO:850; SEQ ID NO:466 and SEQ ID NO:850; SEQ ID NO:467 and SEQ ID NO:850; SEQ ID NO:468 and SEQ ID NO:850; SEQ ID NO:469 and SEQ ID NO:850; SEQ ID NO:470 and SEQ ID NO:850; SEQ ID NO:471 and SEQ ID NO:850; SEQ ID NO:472 and SEQ ID NO:850; SEQ ID NO:473 and SEQ ID NO:850; SEQ ID NO:474 and SEQ ID NO:850; SEQ ID NO:475 and SEQ ID NO:850; SEQ ID NO:476 and SEQ ID NO:850; SEQ ID NO:477 and SEQ ID NO:850; SEQ ID NO:478 and SEQ ID NO:850; SEQ ID NO:479 and SEQ ID NO:850; SEQ ID NO:480 and SEQ ID NO:850; SEQ ID NO:481 and SEQ ID NO:850; SEQ ID NO:482 and SEQ ID NO:850; SEQ ID NO:483 and SEQ ID NO:850; SEQ ID NO:484 and SEQ ID NO:850; SEQ ID NO:485 and SEQ ID NO:850; SEQ ID NO:486 and SEQ ID NO:850; SEQ ID NO:487 and SEQ ID NO:850; SEQ ID NO:488 and SEQ ID NO:850; SEQ ID NO:489 and SEQ ID NO:850; SEQ ID NO:490 and SEQ ID NO:850; SEQ ID NO:491 and SEQ ID NO:850; SEQ ID NO:492 and SEQ ID NO:850; SEQ ID NO:493 and SEQ ID NO:850; SEQ ID NO:494 and SEQ ID NO:850; SEQ ID NO:495 and SEQ ID NO:850; SEQ ID NO:496 and SEQ ID NO:850; SEQ ID NO:497 and SEQ ID NO:850; SEQ ID NO:498 and SEQ ID NO:850; SEQ ID NO:499 and SEQ ID NO:850; SEQ ID NO:500 and SEQ ID NO:850; SEQ ID NO:501 and SEQ ID NO:850; SEQ ID NO:502 and SEQ ID NO:850; SEQ ID NO:503 and SEQ ID NO:850; SEQ ID NO:504 and SEQ ID NO:850; SEQ ID NO:505 and SEQ ID NO:850; SEQ ID NO:506 and SEQ ID NO:850; SEQ ID NO:507 and SEQ ID NO:850; SEQ ID NO:508 and SEQ ID NO:850; SEQ ID NO:509 and SEQ ID NO:850; SEQ ID NO:510 and SEQ ID NO:850; SEQ ID NO:511 and SEQ ID NO:850; SEQ ID NO:512 and SEQ ID NO:850; SEQ ID NO:513 and SEQ ID NO:850; SEQ ID NO:514 and SEQ ID NO:850; SEQ ID NO:515 and SEQ ID NO:850; SEQ ID NO:516 and SEQ ID NO:850; SEQ ID NO:517 and SEQ ID NO:850; SEQ ID NO:518 and SEQ ID NO:850; SEQ ID NO:519 and SEQ ID NO:850; SEQ ID NO:520 and SEQ ID NO:850; SEQ ID NO:521 and SEQ ID NO:850; SEQ ID NO:522 and SEQ ID NO:850; and SEQ ID NO:523 and SEQ ID NO:850.

In some aspects, the CDR-H3-CDR-L3 pairs are selected from SEQ ID NO:357 and SEQ ID NO:851; SEQ ID NO:358 and SEQ ID NO:851; SEQ ID NO:359 and SEQ ID NO:851; SEQ ID NO:360 and SEQ ID NO:851; SEQ ID NO:361 and SEQ ID NO:851; SEQ ID NO:362 and SEQ ID NO:851; SEQ ID NO:363 and SEQ ID NO:851; SEQ ID NO:364 and SEQ ID NO:851; SEQ ID NO:365 and SEQ ID NO:851; SEQ ID NO:366 and SEQ ID NO:851; SEQ ID NO:367 and SEQ ID NO:851; SEQ ID NO:368 and SEQ ID NO:851; SEQ ID NO:369 and SEQ ID NO:851; SEQ ID NO:370 and SEQ ID NO:851; SEQ ID NO:371 and SEQ ID NO:851; SEQ ID NO:372 and SEQ ID NO:851; SEQ ID NO:373 and SEQ ID NO:851; SEQ ID NO:374 and SEQ ID NO:851; SEQ ID NO:375 and SEQ ID NO:851; SEQ ID NO:376 and SEQ ID NO:851; SEQ ID NO:377 and SEQ ID NO:851; SEQ ID NO:378 and SEQ ID NO:851; SEQ ID NO:379 and SEQ ID NO:851; SEQ ID NO:380 and SEQ ID NO:851; SEQ ID NO:381 and SEQ ID NO:851; SEQ ID NO:382 and SEQ ID NO:851; SEQ ID NO:383 and SEQ ID NO:851; SEQ ID NO:384 and SEQ ID NO:851; SEQ ID NO:385 and SEQ ID NO:851; SEQ ID NO:386 and SEQ ID NO:851; SEQ ID NO:387 and SEQ ID NO:851; SEQ ID NO:388 and SEQ ID NO:851; SEQ ID NO:389 and SEQ ID NO:851; SEQ ID NO:390 and SEQ ID NO:851; SEQ ID NO:391 and SEQ ID NO:851; SEQ ID NO:392 and SEQ ID NO:851; SEQ ID NO:393 and SEQ ID NO:851; SEQ ID NO:394 and SEQ ID NO:851; SEQ ID NO:395 and SEQ ID NO:851; SEQ ID NO:396 and SEQ ID NO:851; SEQ ID NO:397 and SEQ ID NO:851; SEQ ID NO:398 and SEQ ID NO:851; SEQ ID NO:399 and SEQ ID NO:851; SEQ ID NO:400 and SEQ ID NO:851; SEQ ID NO:401 and SEQ ID NO:851; SEQ ID NO:402 and SEQ ID NO:851; SEQ ID NO:403 and SEQ ID NO:851; SEQ ID NO:404 and SEQ ID NO:851; SEQ ID NO:405 and SEQ ID NO:851; SEQ ID NO:406 and SEQ ID NO:851; SEQ ID NO:407 and SEQ ID NO:851; SEQ ID NO:408 and SEQ ID NO:851; SEQ ID NO:409 and SEQ ID NO:851; SEQ ID NO:410 and SEQ ID NO:851; SEQ ID NO:411 and SEQ ID NO:851; SEQ ID NO:412 and SEQ ID NO:851; SEQ ID NO:413 and SEQ ID NO:851; SEQ ID NO:414 and SEQ ID NO:851; SEQ ID NO:415 and SEQ ID NO:851; SEQ ID NO:416 and SEQ ID NO:851; SEQ ID NO:417 and SEQ ID NO:851; SEQ ID NO:418 and SEQ ID NO:851; SEQ ID NO:419 and SEQ ID NO:851; SEQ ID NO:420 and SEQ ID NO:851; SEQ ID NO:421 and SEQ ID NO:851; SEQ ID NO:422 and SEQ ID NO:851; SEQ ID NO:423 and SEQ ID NO:851; SEQ ID NO:424 and SEQ ID NO:851; SEQ ID NO:425 and SEQ ID NO:851; SEQ ID NO:426 and SEQ ID NO:851; SEQ ID NO:427 and SEQ ID NO:851; SEQ ID NO:428 and SEQ ID NO:851; SEQ ID NO:429 and SEQ ID NO:851; SEQ ID NO:430 and SEQ ID NO:851; SEQ ID NO:431 and SEQ ID NO:851; SEQ ID NO:432 and SEQ ID NO:851; SEQ ID NO:433 and SEQ ID NO:851; SEQ ID NO:434 and SEQ ID NO:851; SEQ ID NO:435 and SEQ ID NO:851; SEQ ID NO:436 and SEQ ID NO:851; SEQ ID NO:437 and SEQ ID NO:851; SEQ ID NO:438 and SEQ ID NO:851; SEQ ID NO:439 and SEQ ID NO:851; SEQ ID NO:440 and SEQ ID NO:851; SEQ ID NO:441 and SEQ ID NO:851; SEQ ID NO:442 and SEQ ID NO:851; SEQ ID NO:443 and SEQ ID NO:851; SEQ ID NO:444 and SEQ ID NO:851; SEQ ID NO:445 and SEQ ID NO:851; SEQ ID NO:446 and SEQ ID NO:851; SEQ ID NO:447 and SEQ ID NO:851; SEQ ID NO:448 and SEQ ID NO:851; SEQ ID NO:449 and SEQ ID NO:851; SEQ ID NO:450 and SEQ ID NO:851; SEQ ID NO:451 and SEQ ID NO:851; SEQ ID NO:452 and SEQ ID NO:851; SEQ ID NO:453 and SEQ ID NO:851; SEQ ID NO:454 and SEQ ID NO:851; SEQ ID NO:455 and SEQ ID NO:851; SEQ ID NO:456 and SEQ ID NO:851; SEQ ID NO:457 and SEQ ID NO:851; SEQ ID NO:458 and SEQ ID NO:851; SEQ ID NO:459 and SEQ ID NO:851; SEQ ID NO:460 and SEQ ID NO:851; SEQ ID NO:461 and SEQ ID NO:851; SEQ ID NO:462 and SEQ ID NO:851; SEQ ID NO:463 and SEQ ID NO:851; SEQ ID NO:464 and SEQ ID NO:851; SEQ ID NO:465 and SEQ ID NO:851; SEQ ID NO:466 and SEQ ID NO:851; SEQ ID NO:467 and SEQ ID NO:851; SEQ ID NO:468 and SEQ ID NO:851; SEQ ID NO:469 and SEQ ID NO:851; SEQ ID NO:470 and SEQ ID NO:851; SEQ ID NO:471 and SEQ ID NO:851; SEQ ID NO:472 and SEQ ID NO:851; SEQ ID NO:473 and SEQ ID NO:851; SEQ ID NO:474 and SEQ ID NO:851; SEQ ID NO:475 and SEQ ID NO:851; SEQ ID NO:476 and SEQ ID NO:851; SEQ ID NO:477 and SEQ ID NO:851; SEQ ID NO:478 and SEQ ID NO:851; SEQ ID NO:479 and SEQ ID NO:851; SEQ ID NO:480 and SEQ ID NO:851; SEQ ID NO:481 and SEQ ID NO:851; SEQ ID NO:482 and SEQ ID NO:851; SEQ ID NO:483 and SEQ ID NO:851; SEQ ID NO:484 and SEQ ID NO:851; SEQ ID NO:485 and SEQ ID NO:851; SEQ ID NO:486 and SEQ ID NO:851; SEQ ID NO:487 and SEQ ID NO:851; SEQ ID NO:488 and SEQ ID NO:851; SEQ ID NO:489 and SEQ ID NO:851; SEQ ID NO:490 and SEQ ID NO:851; SEQ ID NO:491 and SEQ ID NO:851; SEQ ID NO:492 and SEQ ID NO:851; SEQ ID NO:493 and SEQ ID NO:851; SEQ ID NO:494 and SEQ ID NO:851; SEQ ID NO:495 and SEQ ID NO:851; SEQ ID NO:496 and SEQ ID NO:851; SEQ ID NO:497 and SEQ ID NO:851; SEQ ID NO:498 and SEQ ID NO:851; SEQ ID NO:499 and SEQ ID NO:851; SEQ ID NO:500 and SEQ ID NO:851; SEQ ID NO:501 and SEQ ID NO:851; SEQ ID NO:502 and SEQ ID NO:851; SEQ ID NO:503 and SEQ ID NO:851; SEQ ID NO:504 and SEQ ID NO:851; SEQ ID NO:505 and SEQ ID NO:851; SEQ ID NO:506 and SEQ ID NO:851; SEQ ID NO:507 and SEQ ID NO:851; SEQ ID NO:508 and SEQ ID NO:851; SEQ ID NO:509 and SEQ ID NO:851; SEQ ID NO:510 and SEQ ID NO:851; SEQ ID NO:511 and SEQ ID NO:851; SEQ ID NO:512 and SEQ ID NO:851; SEQ ID NO:513 and SEQ ID NO:851; SEQ ID NO:514 and SEQ ID NO:851; SEQ ID NO:515 and SEQ ID NO:851; SEQ ID NO:516 and SEQ ID NO:851; SEQ ID NO:517 and SEQ ID NO:851; SEQ ID NO:518 and SEQ ID NO:851; SEQ ID NO:519 and SEQ ID NO:851; SEQ ID NO:520 and SEQ ID NO:851; SEQ ID NO:521 and SEQ ID NO:851; SEQ ID NO:522 and SEQ ID NO:851; and SEQ ID NO:523 and SEQ ID NO:851.

In some aspects, the CDR-H3-CDR-L3 pairs are selected from SEQ ID NO:357 and SEQ ID NO:852; SEQ ID NO:358 and SEQ ID NO:852; SEQ ID NO:359 and SEQ ID NO:852; SEQ ID NO:360 and SEQ ID NO:852; SEQ ID NO:361 and SEQ ID NO:852; SEQ ID NO:362 and SEQ ID NO:852; SEQ ID NO:363 and SEQ ID NO:852; SEQ ID NO:364 and SEQ ID NO:852; SEQ ID NO:365 and SEQ ID NO:852; SEQ ID NO:366 and SEQ ID NO:852; SEQ ID NO:367 and SEQ ID NO:852; SEQ ID NO:368 and SEQ ID NO:852; SEQ ID NO:369 and SEQ ID NO:852; SEQ ID NO:370 and SEQ ID NO:852; SEQ ID NO:371 and SEQ ID NO:852; SEQ ID NO:372 and SEQ ID NO:852; SEQ ID NO:373 and SEQ ID NO:852; SEQ ID NO:374 and SEQ ID NO:852; SEQ ID NO:375 and SEQ ID NO:852; SEQ ID NO:376 and SEQ ID NO:852; SEQ ID NO:377 and SEQ ID NO:852; SEQ ID NO:378 and SEQ ID NO:852; SEQ ID NO:379 and SEQ ID NO:852; SEQ ID NO:380 and SEQ ID NO:852; SEQ ID NO:381 and SEQ ID NO:852; SEQ ID NO:382 and SEQ ID NO:852; SEQ ID NO:383 and SEQ ID NO:852; SEQ ID NO:384 and SEQ ID NO:852; SEQ ID NO:385 and SEQ ID NO:852; SEQ ID NO:386 and SEQ ID NO:852; SEQ ID NO:387 and SEQ ID NO:852; SEQ ID NO:388 and SEQ ID NO:852; SEQ ID NO:389 and SEQ ID NO:852; SEQ ID NO:390 and SEQ ID NO:852; SEQ ID NO:391 and SEQ ID NO:852; SEQ ID NO:392 and SEQ ID NO:852; SEQ ID NO:393 and SEQ ID NO:852; SEQ ID NO:394 and SEQ ID NO:852; SEQ ID NO:395 and SEQ ID NO:852; SEQ ID NO:396 and SEQ ID NO:852; SEQ ID NO:397 and SEQ ID NO:852; SEQ ID NO:398 and SEQ ID NO:852; SEQ ID NO:399 and SEQ ID NO:852; SEQ ID NO:400 and SEQ ID NO:852; SEQ ID NO:401 and SEQ ID NO:852; SEQ ID NO:402 and SEQ ID NO:852; SEQ ID NO:403 and SEQ ID NO:852; SEQ ID NO:404 and SEQ ID NO:852; SEQ ID NO:405 and SEQ ID NO:852; SEQ ID NO:406 and SEQ ID NO:852; SEQ ID NO:407 and SEQ ID NO:852; SEQ ID NO:408 and SEQ ID NO:852; SEQ ID NO:409 and SEQ ID NO:852; SEQ ID NO:410 and SEQ ID NO:852; SEQ ID NO:411 and SEQ ID NO:852; SEQ ID NO:412 and SEQ ID NO:852; SEQ ID NO:413 and SEQ ID NO:852; SEQ ID NO:414 and SEQ ID NO:852; SEQ ID NO:415 and SEQ ID NO:852; SEQ ID NO:416 and SEQ ID NO:852; SEQ ID NO:417 and SEQ ID NO:852; SEQ ID NO:418 and SEQ ID NO:852; SEQ ID NO:419 and SEQ ID NO:852; SEQ ID NO:420 and SEQ ID NO:852; SEQ ID NO:421 and SEQ ID NO:852; SEQ ID NO:422 and SEQ ID NO:852; SEQ ID NO:423 and SEQ ID NO:852; SEQ ID NO:424 and SEQ ID NO:852; SEQ ID NO:425 and SEQ ID NO:852; SEQ ID NO:426 and SEQ ID NO:852; SEQ ID NO:427 and SEQ ID NO:852; SEQ ID NO:428 and SEQ ID NO:852; SEQ ID NO:429 and SEQ ID NO:852; SEQ ID NO:430 and SEQ ID NO:852; SEQ ID NO:431 and SEQ ID NO:852; SEQ ID NO:432 and SEQ ID NO:852; SEQ ID NO:433 and SEQ ID NO:852; SEQ ID NO:434 and SEQ ID NO:852; SEQ ID NO:435 and SEQ ID NO:852; SEQ ID NO:436 and SEQ ID NO:852; SEQ ID NO:437 and SEQ ID NO:852; SEQ ID NO:438 and SEQ ID NO:852; SEQ ID NO:439 and SEQ ID NO:852; SEQ ID NO:440 and SEQ ID NO:852; SEQ ID NO:441 and SEQ ID NO:852; SEQ ID NO:442 and SEQ ID NO:852; SEQ ID NO:443 and SEQ ID NO:852; SEQ ID NO:444 and SEQ ID NO:852; SEQ ID NO:445 and SEQ ID NO:852; SEQ ID NO:446 and SEQ ID NO:852; SEQ ID NO:447 and SEQ ID NO:852; SEQ ID NO:448 and SEQ ID NO:852; SEQ ID NO:449 and SEQ ID NO:852; SEQ ID NO:450 and SEQ ID NO:852; SEQ ID NO:451 and SEQ ID NO:852; SEQ ID NO:452 and SEQ ID NO:852; SEQ ID NO:453 and SEQ ID NO:852; SEQ ID NO:454 and SEQ ID NO:852; SEQ ID NO:455 and SEQ ID NO:852; SEQ ID NO:456 and SEQ ID NO:852; SEQ ID NO:457 and SEQ ID NO:852; SEQ ID NO:458 and SEQ ID NO:852; SEQ ID NO:459 and SEQ ID NO:852; SEQ ID NO:460 and SEQ ID NO:852; SEQ ID NO:461 and SEQ ID NO:852; SEQ ID NO:462 and SEQ ID NO:852; SEQ ID NO:463 and SEQ ID NO:852; SEQ ID NO:464 and SEQ ID NO:852; SEQ ID NO:465 and SEQ ID NO:852; SEQ ID NO:466 and SEQ ID NO:852; SEQ ID NO:467 and SEQ ID NO:852; SEQ ID NO:468 and SEQ ID NO:852; SEQ ID NO:469 and SEQ ID NO:852; SEQ ID NO:470 and SEQ ID NO:852; SEQ ID NO:471 and SEQ ID NO:852; SEQ ID NO:472 and SEQ ID NO:852; SEQ ID NO:473 and SEQ ID NO:852; SEQ ID NO:474 and SEQ ID NO:852; SEQ ID NO:475 and SEQ ID NO:852; SEQ ID NO:476 and SEQ ID NO:852; SEQ ID NO:477 and SEQ ID NO:852; SEQ ID NO:478 and SEQ ID NO:852; SEQ ID NO:479 and SEQ ID NO:852; SEQ ID NO:480 and SEQ ID NO:852; SEQ ID NO:481 and SEQ ID NO:852; SEQ ID NO:482 and SEQ ID NO:852; SEQ ID NO:483 and SEQ ID NO:852; SEQ ID NO:484 and SEQ ID NO:852; SEQ ID NO:485 and SEQ ID NO:852; SEQ ID NO:486 and SEQ ID NO:852; SEQ ID NO:487 and SEQ ID NO:852; SEQ ID NO:488 and SEQ ID NO:852; SEQ ID NO:489 and SEQ ID NO:852; SEQ ID NO:490 and SEQ ID NO:852; SEQ ID NO:491 and SEQ ID NO:852; SEQ ID NO:492 and SEQ ID NO:852; SEQ ID NO:493 and SEQ ID NO:852; SEQ ID NO:494 and SEQ ID NO:852; SEQ ID NO:495 and SEQ ID NO:852; SEQ ID NO:496 and SEQ ID NO:852; SEQ ID NO:497 and SEQ ID NO:852; SEQ ID NO:498 and SEQ ID NO:852; SEQ ID NO:499 and SEQ ID NO:852; SEQ ID NO:500 and SEQ ID NO:852; SEQ ID NO:501 and SEQ ID NO:852; SEQ ID NO:502 and SEQ ID NO:852; SEQ ID NO:503 and SEQ ID NO:852; SEQ ID NO:504 and SEQ ID NO:852; SEQ ID NO:505 and SEQ ID NO:852; SEQ ID NO:506 and SEQ ID NO:852; SEQ ID NO:507 and SEQ ID NO:852; SEQ ID NO:508 and SEQ ID NO:852; SEQ ID NO:509 and SEQ ID NO:852; SEQ ID NO:510 and SEQ ID NO:852; SEQ ID NO:511 and SEQ ID NO:852; SEQ ID NO:512 and SEQ ID NO:852; SEQ ID NO:513 and SEQ ID NO:852; SEQ ID NO:514 and SEQ ID NO:852; SEQ ID NO:515 and SEQ ID NO:852; SEQ ID NO:516 and SEQ ID NO:852; SEQ ID NO:517 and SEQ ID NO:852; SEQ ID NO:518 and SEQ ID NO:852; SEQ ID NO:519 and SEQ ID NO:852; SEQ ID NO:520 and SEQ ID NO:852; SEQ ID NO:521 and SEQ ID NO:852; SEQ ID NO:522 and SEQ ID NO:852; and SEQ ID NO:523 and SEQ ID NO:852.

In some aspects, the CDR-H3-CDR-L3 pairs are selected from SEQ ID NO:357 and SEQ ID NO:853; SEQ ID NO:358 and SEQ ID NO:853; SEQ ID NO:359 and SEQ ID NO:853; SEQ ID NO:360 and SEQ ID NO:853; SEQ ID NO:361 and SEQ ID NO:853; SEQ ID NO:362 and SEQ ID NO:853; SEQ ID NO:363 and SEQ ID NO:853; SEQ ID NO:364 and SEQ ID NO:853; SEQ ID NO:365 and SEQ ID NO:853; SEQ ID NO:366 and SEQ ID NO:853; SEQ ID NO:367 and SEQ ID NO:853; SEQ ID NO:368 and SEQ ID NO:853; SEQ ID NO:369 and SEQ ID NO:853; SEQ ID NO:370 and SEQ ID NO:853; SEQ ID NO:371 and SEQ ID NO:853; SEQ ID NO:372 and SEQ ID NO:853; SEQ ID NO:373 and SEQ ID NO:853; SEQ ID NO:374 and SEQ ID NO:853; SEQ ID NO:375 and SEQ ID NO:853; SEQ ID NO:376 and SEQ ID NO:853; SEQ ID NO:377 and SEQ ID NO:853; SEQ ID NO:378 and SEQ ID NO:853; SEQ ID NO:379 and SEQ ID NO:853; SEQ ID NO:380 and SEQ ID NO:853; SEQ ID NO:381 and SEQ ID NO:853; SEQ ID NO:382 and SEQ ID NO:853; SEQ ID NO:383 and SEQ ID NO:853; SEQ ID NO:384 and SEQ ID NO:853; SEQ ID NO:385 and SEQ ID NO:853; SEQ ID NO:386 and SEQ ID NO:853; SEQ ID NO:387 and SEQ ID NO:853; SEQ ID NO:388 and SEQ ID NO:853; SEQ ID NO:389 and SEQ ID NO:853; SEQ ID NO:390 and SEQ ID NO:853; SEQ ID NO:391 and SEQ ID NO:853; SEQ ID NO:392 and SEQ ID NO:853; SEQ ID NO:393 and SEQ ID NO:853; SEQ ID NO:394 and SEQ ID NO:853; SEQ ID NO:395 and SEQ ID NO:853; SEQ ID NO:396 and SEQ ID NO:853; SEQ ID NO:397 and SEQ ID NO:853; SEQ ID NO:398 and SEQ ID NO:853; SEQ ID NO:399 and SEQ ID NO:853; SEQ ID NO:400 and SEQ ID NO:853; SEQ ID NO:401 and SEQ ID NO:853; SEQ ID NO:402 and SEQ ID NO:853; SEQ ID NO:403 and SEQ ID NO:853; SEQ ID NO:404 and SEQ ID NO:853; SEQ ID NO:405 and SEQ ID NO:853; SEQ ID NO:406 and SEQ ID NO:853; SEQ ID NO:407 and SEQ ID NO:853; SEQ ID NO:408 and SEQ ID NO:853; SEQ ID NO:409 and SEQ ID NO:853; SEQ ID NO:410 and SEQ ID NO:853; SEQ ID NO:411 and SEQ ID NO:853; SEQ ID NO:412 and SEQ ID NO:853; SEQ ID NO:413 and SEQ ID NO:853; SEQ ID NO:414 and SEQ ID NO:853; SEQ ID NO:415 and SEQ ID NO:853; SEQ ID NO:416 and SEQ ID NO:853; SEQ ID NO:417 and SEQ ID NO:853; SEQ ID NO:418 and SEQ ID NO:853; SEQ ID NO:419 and SEQ ID NO:853; SEQ ID NO:420 and SEQ ID NO:853; SEQ ID NO:421 and SEQ ID NO:853; SEQ ID NO:422 and SEQ ID NO:853; SEQ ID NO:423 and SEQ ID NO:853; SEQ ID NO:424 and SEQ ID NO:853; SEQ ID NO:425 and SEQ ID NO:853; SEQ ID NO:426 and SEQ ID NO:853; SEQ ID NO:427 and SEQ ID NO:853; SEQ ID NO:428 and SEQ ID NO:853; SEQ ID NO:429 and SEQ ID NO:853; SEQ ID NO:430 and SEQ ID NO:853; SEQ ID NO:431 and SEQ ID NO:853; SEQ ID NO:432 and SEQ ID NO:853; SEQ ID NO:433 and SEQ ID NO:853; SEQ ID NO:434 and SEQ ID NO:853; SEQ ID NO:435 and SEQ ID NO:853; SEQ ID NO:436 and SEQ ID NO:853; SEQ ID NO:437 and SEQ ID NO:853; SEQ ID NO:438 and SEQ ID NO:853; SEQ ID NO:439 and SEQ ID NO:853; SEQ ID NO:440 and SEQ ID NO:853; SEQ ID NO:441 and SEQ ID NO:853; SEQ ID NO:442 and SEQ ID NO:853; SEQ ID NO:443 and SEQ ID NO:853; SEQ ID NO:444 and SEQ ID NO:853; SEQ ID NO:445 and SEQ ID NO:853; SEQ ID NO:446 and SEQ ID NO:853; SEQ ID NO:447 and SEQ ID NO:853; SEQ ID NO:448 and SEQ ID NO:853; SEQ ID NO:449 and SEQ ID NO:853; SEQ ID NO:450 and SEQ ID NO:853; SEQ ID NO:451 and SEQ ID NO:853; SEQ ID NO:452 and SEQ ID NO:853; SEQ ID NO:453 and SEQ ID NO:853; SEQ ID NO:454 and SEQ ID NO:853; SEQ ID NO:455 and SEQ ID NO:853; SEQ ID NO:456 and SEQ ID NO:853; SEQ ID NO:457 and SEQ ID NO:853; SEQ ID NO:458 and SEQ ID NO:853; SEQ ID NO:459 and SEQ ID NO:853; SEQ ID NO:460 and SEQ ID NO:853; SEQ ID NO:461 and SEQ ID NO:853; SEQ ID NO:462 and SEQ ID NO:853; SEQ ID NO:463 and SEQ ID NO:853; SEQ ID NO:464 and SEQ ID NO:853; SEQ ID NO:465 and SEQ ID NO:853; SEQ ID NO:466 and SEQ ID NO:853; SEQ ID NO:467 and SEQ ID NO:853; SEQ ID NO:468 and SEQ ID NO:853; SEQ ID NO:469 and SEQ ID NO:853; SEQ ID NO:470 and SEQ ID NO:853; SEQ ID NO:471 and SEQ ID NO:853; SEQ ID NO:472 and SEQ ID NO:853; SEQ ID NO:473 and SEQ ID NO:853; SEQ ID NO:474 and SEQ ID NO:853; SEQ ID NO:475 and SEQ ID NO:853; SEQ ID NO:476 and SEQ ID NO:853; SEQ ID NO:477 and SEQ ID NO:853; SEQ ID NO:478 and SEQ ID NO:853; SEQ ID NO:479 and SEQ ID NO:853; SEQ ID NO:480 and SEQ ID NO:853; SEQ ID NO:481 and SEQ ID NO:853; SEQ ID NO:482 and SEQ ID NO:853; SEQ ID NO:483 and SEQ ID NO:853; SEQ ID NO:484 and SEQ ID NO:853; SEQ ID NO:485 and SEQ ID NO:853; SEQ ID NO:486 and SEQ ID NO:853; SEQ ID NO:487 and SEQ ID NO:853; SEQ ID NO:488 and SEQ ID NO:853; SEQ ID NO:489 and SEQ ID NO:853; SEQ ID NO:490 and SEQ ID NO:853; SEQ ID NO:491 and SEQ ID NO:853; SEQ ID NO:492 and SEQ ID NO:853; SEQ ID NO:493 and SEQ ID NO:853; SEQ ID NO:494 and SEQ ID NO:853; SEQ ID NO:495 and SEQ ID NO:853; SEQ ID NO:496 and SEQ ID NO:853; SEQ ID NO:497 and SEQ ID NO:853; SEQ ID NO:498 and SEQ ID NO:853; SEQ ID NO:499 and SEQ ID NO:853; SEQ ID NO:500 and SEQ ID NO:853; SEQ ID NO:501 and SEQ ID NO:853; SEQ ID NO:502 and SEQ ID NO:853; SEQ ID NO:503 and SEQ ID NO:853; SEQ ID NO:504 and SEQ ID NO:853; SEQ ID NO:505 and SEQ ID NO:853; SEQ ID NO:506 and SEQ ID NO:853; SEQ ID NO:507 and SEQ ID NO:853; SEQ ID NO:508 and SEQ ID NO:853; SEQ ID NO:509 and SEQ ID NO:853; SEQ ID NO:510 and SEQ ID NO:853; SEQ ID NO:511 and SEQ ID NO:853; SEQ ID NO:512 and SEQ ID NO:853; SEQ ID NO:513 and SEQ ID NO:853; SEQ ID NO:514 and SEQ ID NO:853; SEQ ID NO:515 and SEQ ID NO:853; SEQ ID NO:516 and SEQ ID NO:853; SEQ ID NO:517 and SEQ ID NO:853; SEQ ID NO:518 and SEQ ID NO:853; SEQ ID NO:519 and SEQ ID NO:853; SEQ ID NO:520 and SEQ ID NO:853; SEQ ID NO:521 and SEQ ID NO:853; SEQ ID NO:522 and SEQ ID NO:853; and SEQ ID NO:523 and SEQ ID NO:853.

5.7.1.1. Variants of CDR-H3-CDR-L3 Pairs

In some embodiments, the CDR-H3-CDR-L3 pairs provided herein comprise a variant of an illustrative CDR-H3 and/or CDR-L1 sequence provided in this disclosure.

In some aspects, the CDR-H3 sequence comprises, consists of, or consists essentially of a variant of an illustrative CDR-H3 sequence provided in this disclosure. In some aspects, the CDR-H3 sequence comprises, consists of, or consists essentially of a sequence having at least 70%, 75%, 80%, 85%, 90%, 95%, 96%, 97%, 98%, or 99% identity with any of the illustrative CDR-H3 sequences provided in this disclosure. In some aspects, the CDR-H3 sequence comprises, consists of, or consists essentially of any of the illustrative CDR-H3 sequences provided in this disclosure, with 1, 2, or 3 amino acid substitutions. In some aspects, the amino acid substitutions are conservative amino acid substitutions.

In some aspects, the CDR-L3 sequence comprises, consists of, or consists essentially of a variant of an illustrative CDR-L3 sequence provided in this disclosure. In some aspects, the CDR-L3 sequence comprises, consists of, or consists essentially of a sequence having at least 70%, 75%, 80%, 85%, 90%, 95%, 96%, 97%, 98%, or 99% identity with any of the illustrative CDR-L3 sequences provided in this disclosure. In some aspects, the CDR-L3 sequence comprises, consists of, or consists essentially of any of the illustrative CDR-L3 sequences provided in this disclosure, with 1, 2, or 3 amino acid substitutions. In some aspects, the amino acid substitutions are conservative amino acid substitutions.

5.7.2. CDR-H1-CDR-L1 Pairs

In some embodiments, the antibody comprises a CDR-H1 sequence and a CDR-L1 sequence. In some aspects, the CDR-H1 sequence is part of a $V_H$ and the CDR-L1 sequence is part of a $V_L$.

In some aspects, the CDR-H1 sequence is a Chothia CDR-H1 sequence comprising, consisting of, or consisting essentially of any one of SEQ ID NOs: 4-170, and the CDR-L1 sequence is a CDR-L1 sequence comprising, consisting of, or consisting essentially of any one of SEQ ID NOs: 839-843.

In some aspects, the CDR-H1 sequence is a Kabat CDR-H1 sequence comprising, consisting of, or consisting essentially of any one of SEQ ID NOs: 171-337, and the CDR-L1 sequence is a CDR-L1 sequence comprising, consisting of, or consisting essentially of any one of SEQ ID NOs: 839-843.

5.7.2.1. Variants of CDR-H1-CDR-L1 Pairs

In some embodiments, the CDR-H1-CDR-L1 pairs provided herein comprise a variant of an illustrative CDR-H1 and/or CDR-L1 sequence provided in this disclosure.

In some aspects, the CDR-H1 sequence comprises, consists of, or consists essentially of a variant of an illustrative CDR-H1 sequence provided in this disclosure. In some aspects, the CDR-H1 sequence comprises, consists of, or consists essentially of a sequence having at least 70%, 75%, 80%, 85%, 90%, 95%, 96%, 97%, 98%, or 99% identity with any of the illustrative CDR-H1 sequences provided in this disclosure. In some aspects, the CDR-H1 sequence comprises, consists of, or consists essentially of any of the illustrative CDR-H1 sequences provided in this disclosure, with 1, 2, or 3 amino acid substitutions. In some aspects, the amino acid substitutions are conservative amino acid substitutions.

In some aspects, the CDR-L1 sequence comprises, consists of, or consists essentially of a variant of an illustrative CDR-L1 sequence provided in this disclosure. In some aspects, the CDR-L1 sequence comprises, consists of, or consists essentially of a sequence having at least 70%, 75%, 80%, 85%, 90%, 95%, 96%, 97%, 98%, or 99% identity with any of the illustrative CDR-L1 sequences provided in this disclosure. In some aspects, the CDR-L1 sequence comprises, consists of, or consists essentially of any of the illustrative CDR-L1 sequences provided in this disclosure, with 1, 2, or 3 amino acid substitutions. In some aspects, the amino acid substitutions are conservative amino acid substitutions.

5.7.3. CDR-H2-CDR-L2 Pairs

In some embodiments, the antibody comprises a CDR-H2 sequence and a CDR-L2 sequence. In some aspects, the CDR-H2 sequence is part of a $V_H$ and the CDR-L2 sequence is part of a $V_L$.

In some aspects, the CDR-H2 sequence is a Chothia CDR-H2 sequence comprising, consisting of, or consisting essentially of any one of SEQ ID NOs: 338-504, and the CDR-L2 sequence is a CDR-L2 sequence comprising, consisting of, or consisting essentially of any one of SEQ ID NOs: 844-848.

In some aspects, the CDR-H1 sequence is a Kabat CDR-H2 sequence comprising, consisting of, or consisting essentially of any one of SEQ ID NOs: 505-671, and the CDR-L2 sequence is a CDR-L2 sequence comprising, consisting of, or consisting essentially of any one of SEQ ID NOs: 844-848.

5.7.3.1. Variants of CDR-H2-CDR-L2 Pairs

In some embodiments, the CDR-H2-CDR-L2 pairs provided herein comprise a variant of an illustrative CDR-H2 and/or CDR-L2 sequence provided in this disclosure.

In some aspects, the CDR-H2 sequence comprises, consists of, or consists essentially of a variant of an illustrative CDR-H2 sequence provided in this disclosure. In some aspects, the CDR-H2 sequence comprises, consists of, or consists essentially of a sequence having at least 70%, 75%, 80%, 85%, 90%, 95%, 96%, 97%, 98%, or 99% identity with any of the illustrative CDR-H2 sequences provided in this disclosure. In some aspects, the CDR-H2 sequence comprises, consists of, or consists essentially of any of the illustrative CDR-H2 sequences provided in this disclosure, with 1, 2, or 3 amino acid substitutions. In some aspects, the amino acid substitutions are conservative amino acid substitutions.

In some aspects, the CDR-L2 sequence comprises, consists of, or consists essentially of a variant of an illustrative CDR-L2 sequence provided in this disclosure. In some aspects, the CDR-L2 sequence comprises, consists of, or consists essentially of a sequence having at least 70%, 75%, 80%, 85%, 90%, 95%, 96%, 97%, 98%, or 99% identity with any of the illustrative CDR-L2 sequences provided in this disclosure. In some aspects, the CDR-L2 sequence comprises, consists of, or consists essentially of any of the illustrative CDR-L2 sequences provided in this disclosure, with 1, 2, or 3 amino acid substitutions. In some aspects, the amino acid substitutions are conservative amino acid substitutions.

5.7.4. $V_H$-$V_L$ Pairs

In some embodiments, the antibody comprises a $V_H$ sequence and a $V_L$ sequence.

In some aspects, the $V_H$ sequence is a $V_H$ sequence comprising, consisting of, or consisting essentially of any one of SEQ ID NOs: 854-1020, and the $V_L$ sequence is a $V_L$ sequence comprising, consisting of, or consisting essentially of any one of SEQ ID NOs: 1021-1026.

In some aspects, the $V_H$-$V_L$ pairs are selected from SEQ ID NO:854 and SEQ ID NO:1021; SEQ ID NO:855 and SEQ ID NO:1021; SEQ ID NO:856 and SEQ ID NO:1021; SEQ ID NO:857 and SEQ ID NO:1021; SEQ ID NO:858 and SEQ ID NO:1021; SEQ ID NO:859 and SEQ ID NO:1021; SEQ ID NO:860 and SEQ ID NO:1021; SEQ ID NO:861 and SEQ ID NO:1021; SEQ ID NO:862 and SEQ ID NO:1021; SEQ ID NO:863 and SEQ ID NO:1021; SEQ ID NO:864 and SEQ ID NO:1021; SEQ ID NO:865 and SEQ ID NO:1021; SEQ ID NO:866 and SEQ ID NO:1021; SEQ ID NO:867 and SEQ ID NO:1021; SEQ ID NO:868 and SEQ ID NO:1021; SEQ ID NO:869 and SEQ ID NO:1021; SEQ ID NO:870 and SEQ ID NO:1021; SEQ ID NO:871 and SEQ ID NO:1021; SEQ ID NO:872 and SEQ ID NO:1021; SEQ ID NO:873 and SEQ ID NO:1021; SEQ ID NO:874 and SEQ ID NO:1021; SEQ ID NO:875 and SEQ ID NO:1021; SEQ ID NO:876 and SEQ ID NO:1021; SEQ ID NO:877 and SEQ ID NO:1021; SEQ ID NO:878 and SEQ ID NO:1021; SEQ ID NO:879 and SEQ ID NO:1021; SEQ ID NO:880 and SEQ ID NO:1021; SEQ ID NO:881 and SEQ ID NO:1021; SEQ ID NO:882 and SEQ ID NO:1021; SEQ ID NO:883 and SEQ ID NO:1021; SEQ ID NO:884 and SEQ ID NO:1021; SEQ ID NO:885 and SEQ ID NO:1021; SEQ ID NO:886 and SEQ ID NO:1021; SEQ ID NO:887 and SEQ ID NO:1021; SEQ ID NO:888 and SEQ ID NO:1021; SEQ ID NO:889 and SEQ ID NO:1021; SEQ ID NO:890 and SEQ ID NO:1021; SEQ ID NO:891 and SEQ ID NO:1021; SEQ ID NO:892 and SEQ ID NO:1021; SEQ ID NO:893 and SEQ ID NO:1021; SEQ ID NO:894 and SEQ ID NO:1021; SEQ ID NO:895 and SEQ ID NO:1021; SEQ ID NO:896 and SEQ ID NO:1021; SEQ ID NO:897 and SEQ ID NO:1021; SEQ ID NO:898 and SEQ ID NO:1021; SEQ ID NO:899 and SEQ ID NO:1021; SEQ ID NO:900 and SEQ ID NO:1021; SEQ ID NO:901 and SEQ ID NO:1021; SEQ ID NO:902 and SEQ ID NO:1021; SEQ ID NO:903 and SEQ ID NO:1021; SEQ ID NO:904 and SEQ ID NO:1021; SEQ ID NO:905 and SEQ ID NO:1021; SEQ ID NO:906 and SEQ ID NO:1021; SEQ ID NO:907 and SEQ ID NO:1021; SEQ ID NO:908 and SEQ ID NO:1021; SEQ ID NO:909 and SEQ ID NO:1021; SEQ ID NO:910 and SEQ ID NO:1021; SEQ ID NO:911 and SEQ ID NO:1021; SEQ ID NO:912 and SEQ ID NO:1021; SEQ ID NO:913 and SEQ ID NO:1021; SEQ ID NO:914 and SEQ ID NO:1021; SEQ ID NO:915 and SEQ ID NO:1021; SEQ ID NO:916 and SEQ ID NO:1021; SEQ ID NO:917 and SEQ ID NO:1021; SEQ ID NO:918 and SEQ ID NO:1021; SEQ ID NO:919 and SEQ ID NO:1021; SEQ ID NO:920 and SEQ ID NO:1021; SEQ ID NO:921 and SEQ ID NO:1021; SEQ ID NO:922 and SEQ ID NO:1021; SEQ ID NO:923 and SEQ ID NO:1021; SEQ ID NO:924 and SEQ ID NO:1021; SEQ ID NO:925 and SEQ ID NO:1021; SEQ ID NO:926 and SEQ ID NO:1021; SEQ ID NO:927 and SEQ ID NO:1021; SEQ ID NO:928 and SEQ ID NO:1021; SEQ ID NO:929 and SEQ ID NO:1021; SEQ ID NO:930 and SEQ ID NO:1021; SEQ ID NO:931 and SEQ ID NO:1021; SEQ ID NO:932 and SEQ ID NO:1021; SEQ ID NO:933 and SEQ ID NO:1021; SEQ ID NO:934 and SEQ ID NO:1021; SEQ ID NO:935 and SEQ ID NO:1021; SEQ ID NO:936 and SEQ ID NO:1021; SEQ ID NO:937 and SEQ ID NO:1021; SEQ ID NO:938 and SEQ ID NO:1021; SEQ ID NO:939 and SEQ ID NO:1021; SEQ ID NO:940 and SEQ ID NO:1021; SEQ ID NO:941 and SEQ ID NO:1021; SEQ ID NO:942 and SEQ ID NO:1021; SEQ ID NO:943 and SEQ ID NO:1021; SEQ ID NO:944 and SEQ ID NO:1021; SEQ ID NO:945 and SEQ ID NO:1021; SEQ ID NO:946 and SEQ ID NO:1021; SEQ ID NO:947 and SEQ ID NO:1021; SEQ ID NO:948 and SEQ ID NO:1021; SEQ ID NO:949 and SEQ ID NO:1021; SEQ ID NO:950 and SEQ ID NO:1021; SEQ ID NO:951 and SEQ ID NO:1021; SEQ ID NO:952 and SEQ ID NO:1021; SEQ ID NO:953 and SEQ ID NO:1021; SEQ ID NO:954 and SEQ ID NO:1021; SEQ ID NO:955 and SEQ ID NO:1021; SEQ ID NO:956 and SEQ ID NO:1021; SEQ ID NO:957 and SEQ ID NO:1021; SEQ ID NO:958 and SEQ ID NO:1021; SEQ ID NO:959 and SEQ ID NO:1021; SEQ ID NO:960 and SEQ ID NO:1021; SEQ ID NO:961 and SEQ ID NO:1021; SEQ ID NO:962 and SEQ ID NO:1021; SEQ ID NO:963 and SEQ ID NO:1021; SEQ ID NO:964 and SEQ ID NO:1021; SEQ ID NO:965 and SEQ ID NO:1021; SEQ ID NO:966 and SEQ ID NO:1021; SEQ ID NO:967 and SEQ ID NO:1021; SEQ ID NO:968 and SEQ ID NO:1021; SEQ ID NO:969 and SEQ ID NO:1021; SEQ ID NO:970 and SEQ ID NO:1021; SEQ ID NO:971 and SEQ ID NO:1021; SEQ ID NO:972 and SEQ ID NO:1021; SEQ ID NO:973 and SEQ ID NO:1021; SEQ ID NO:974 and SEQ ID NO:1021; SEQ ID NO:975 and SEQ ID NO:1021; SEQ ID NO:976 and SEQ ID NO:1021; SEQ ID NO:977 and SEQ ID NO:1021; SEQ ID NO:978 and SEQ ID NO:1021; SEQ ID NO:979 and SEQ ID NO:1021; SEQ ID NO:980 and SEQ ID NO:1021; SEQ ID NO:981 and SEQ ID NO:1021; SEQ ID NO:982 and SEQ ID NO:1021; SEQ ID NO:983 and SEQ ID NO:1021; SEQ ID NO:984 and SEQ ID NO:1021; SEQ ID NO:985 and SEQ ID NO:1021; SEQ ID NO:986 and SEQ ID NO:1021; SEQ ID NO:987 and SEQ ID NO:1021; SEQ ID NO:988 and SEQ ID NO:1021; SEQ ID NO:989 and SEQ ID NO:1021; SEQ ID NO:990 and SEQ ID NO:1021; SEQ ID NO:991 and SEQ ID NO:1021; SEQ ID NO:992 and SEQ ID NO:1021; SEQ ID NO:993 and SEQ ID NO:1021; SEQ ID NO:994 and SEQ ID NO:1021; SEQ ID NO:995 and SEQ ID NO:1021; SEQ ID NO:996 and SEQ ID NO:1021; SEQ ID NO:997 and SEQ ID NO:1021; SEQ ID NO:998 and SEQ ID NO:1021; SEQ ID NO:999 and SEQ ID NO:1021; SEQ ID NO:1000 and SEQ ID NO:1021; SEQ ID NO:1001 and SEQ ID NO:1021; SEQ ID NO:1002 and SEQ ID NO:1021; SEQ ID NO:1003 and SEQ ID NO:1021; SEQ ID NO:1004 and SEQ ID NO:1021; SEQ ID NO:1005 and SEQ ID NO:1021; SEQ ID NO:1006 and SEQ ID NO:1021; SEQ ID NO:1007 and SEQ ID NO:1021; SEQ ID NO:1008 and SEQ ID NO:1021; SEQ ID NO:1009 and SEQ ID NO:1021; SEQ ID NO:1010 and SEQ ID NO:1021; SEQ ID NO:1011 and SEQ ID NO:1021; SEQ ID NO:1012 and SEQ ID NO:1021; SEQ ID NO:1013 and SEQ ID NO:1021; SEQ ID NO:1014 and SEQ ID NO:1021; SEQ ID NO:1015 and SEQ ID NO:1021; SEQ ID NO:1016 and SEQ ID NO:1021; SEQ ID NO:1017 and SEQ ID NO:1021; SEQ ID NO:1018 and SEQ ID NO:1021; SEQ ID NO:1019 and SEQ ID NO:1021; and SEQ ID NO:1020 and SEQ ID NO:1021.

In some aspects, the $V_H$-$V_L$ pairs are selected from SEQ ID NO:854 and SEQ ID NO:1022; SEQ ID NO:855 and SEQ ID NO:1022; SEQ ID NO:856 and SEQ ID NO:1022; SEQ ID NO:857 and SEQ ID NO:1022; SEQ ID NO:858 and SEQ ID NO:1022; SEQ ID NO:859 and SEQ ID NO:1022; SEQ ID NO:860 and SEQ ID NO:1022; SEQ ID NO:861 and SEQ ID NO:1022; SEQ ID NO:862 and SEQ ID NO:1022; SEQ ID NO:863 and SEQ ID NO:1022; SEQ ID NO:864 and SEQ ID NO:1022; SEQ ID NO:865 and SEQ ID NO:1022; SEQ ID NO:866 and SEQ ID NO:1022; SEQ ID NO:867 and SEQ ID NO:1022; SEQ ID NO:868 and SEQ ID NO:1022; SEQ ID NO:869 and SEQ ID NO:1022; SEQ ID NO:870 and SEQ ID NO:1022; SEQ ID NO:871 and SEQ ID NO:1022; SEQ ID NO:872 and SEQ ID NO:1022; SEQ ID NO:873 and SEQ ID NO:1022; SEQ ID NO:874 and SEQ ID NO:1022; SEQ ID NO:875 and SEQ ID NO:1022; SEQ ID NO:876 and SEQ ID NO:1022; SEQ ID NO:877 and SEQ ID NO:1022; SEQ ID NO:878 and SEQ ID NO:1022; SEQ ID NO:879 and SEQ ID NO:1022; SEQ ID NO:880 and SEQ ID NO:1022; SEQ ID NO:881 and SEQ ID NO:1022; SEQ ID NO:882 and SEQ ID NO:1022; SEQ ID NO:883 and SEQ ID NO:1022; SEQ ID NO:884 and SEQ ID NO:1022; SEQ ID NO:885 and SEQ ID NO:1022; SEQ ID NO:886 and SEQ ID NO:1022; SEQ ID NO:887 and SEQ ID NO:1022; SEQ ID NO:888 and SEQ ID NO:1022; SEQ ID NO:889 and SEQ ID NO:1022; SEQ ID NO:890 and SEQ ID NO:1022; SEQ ID NO:891 and SEQ ID NO:1022; SEQ ID NO:892 and SEQ ID NO:1022; SEQ ID NO:893 and SEQ ID NO:1022; SEQ ID NO:894 and SEQ ID NO:1022; SEQ ID NO:895 and SEQ ID NO:1022; SEQ ID NO:896 and SEQ ID NO:1022; SEQ ID NO:897 and SEQ ID NO:1022; SEQ ID NO:898 and SEQ ID NO:1022; SEQ ID NO:899 and SEQ ID NO:1022; SEQ ID NO:900 and SEQ ID NO:1022; SEQ ID NO:901 and SEQ ID NO:1022; SEQ ID NO:902 and SEQ ID NO:1022; SEQ ID NO:903 and SEQ ID NO:1022; SEQ ID NO:904 and SEQ ID NO:1022; SEQ ID NO:905 and SEQ ID NO:1022; SEQ ID NO:906 and SEQ ID NO:1022; SEQ ID NO:907 and SEQ ID NO:1022; SEQ ID NO:908 and SEQ ID NO:1022; SEQ ID NO:909 and SEQ ID NO:1022; SEQ ID NO:910 and SEQ ID NO:1022; SEQ ID NO:911 and SEQ ID NO:1022; SEQ ID NO:912 and SEQ ID NO:1022; SEQ ID NO:913 and SEQ ID NO:1022; SEQ ID NO:914 and SEQ ID NO:1022; SEQ ID NO:915 and SEQ ID NO:1022; SEQ ID NO:916 and SEQ ID NO:1022; SEQ ID NO:917 and SEQ ID NO:1022; SEQ ID NO:918 and SEQ ID NO:1022; SEQ ID NO:919 and SEQ ID NO:1022; SEQ ID NO:920 and SEQ ID NO:1022; SEQ ID NO:921 and SEQ ID NO:1022; SEQ ID NO:922 and SEQ ID NO:1022; SEQ ID NO:923 and SEQ ID NO:1022; SEQ ID NO:924 and SEQ ID NO:1022; SEQ ID NO:925 and SEQ ID NO:1022; SEQ ID NO:926 and SEQ ID NO:1022; SEQ ID NO:927 and SEQ ID NO:1022; SEQ ID NO:928 and SEQ ID NO:1022; SEQ ID NO:929 and SEQ ID NO:1022; SEQ ID NO:930 and SEQ ID NO:1022; SEQ ID NO:931 and SEQ ID NO:1022; SEQ ID NO:932 and SEQ ID NO:1022; SEQ ID NO:933 and SEQ ID NO:1022; SEQ ID NO:934 and SEQ ID NO:1022; SEQ ID NO:935 and SEQ ID NO:1022; SEQ ID NO:936 and SEQ ID NO:1022; SEQ ID NO:937 and SEQ ID NO:1022; SEQ ID NO:938 and SEQ ID NO:1022; SEQ ID NO:939 and SEQ ID NO:1022; SEQ ID NO:940 and SEQ ID NO:1022; SEQ ID NO:941 and SEQ ID NO:1022; SEQ ID NO:942 and SEQ ID NO:1022; SEQ ID NO:943 and SEQ ID NO:1022; SEQ ID NO:944 and SEQ ID NO:1022; SEQ ID NO:945 and SEQ ID NO:1022; SEQ ID NO:946 and SEQ ID NO:1022; SEQ ID NO:947 and SEQ ID NO:1022; SEQ ID NO:948 and SEQ ID NO:1022; SEQ ID NO:949 and SEQ ID NO:1022; SEQ ID NO:950 and SEQ ID NO:1022; SEQ ID NO:951 and SEQ ID NO:1022; SEQ ID NO:952 and SEQ ID NO:1022; SEQ ID NO:953 and SEQ ID NO:1022; SEQ ID NO:954 and SEQ ID NO:1022; SEQ ID NO:955 and SEQ ID NO:1022; SEQ ID NO:956 and SEQ ID NO:1022; SEQ ID NO:957 and SEQ ID NO:1022; SEQ ID NO:958 and SEQ ID NO:1022; SEQ ID NO:959 and SEQ ID NO:1022; SEQ ID NO:960 and SEQ ID NO:1022; SEQ ID NO:961 and SEQ ID NO:1022; SEQ ID NO:962 and SEQ ID NO:1022; SEQ ID NO:963 and SEQ ID NO:1022; SEQ ID NO:964 and SEQ ID NO:1022; SEQ ID NO:965 and SEQ ID NO:1022; SEQ ID NO:966 and SEQ ID NO:1022; SEQ ID NO:967 and SEQ ID NO:1022; SEQ ID NO:968 and SEQ ID NO:1022; SEQ ID NO:969 and SEQ ID NO:1022; SEQ ID NO:970 and SEQ ID NO:1022; SEQ ID NO:971 and SEQ ID NO:1022; SEQ ID NO:972 and SEQ ID NO:1022; SEQ ID NO:973 and SEQ ID NO:1022; SEQ ID NO:974 and SEQ ID NO:1022; SEQ ID NO:975 and SEQ ID NO:1022; SEQ ID NO:976 and SEQ ID NO:1022; SEQ ID NO:977 and SEQ ID NO:1022; SEQ ID NO:978 and SEQ ID NO:1022; SEQ ID NO:979 and SEQ ID NO:1022; SEQ ID NO:980 and SEQ ID NO:1022; SEQ ID NO:981 and SEQ ID NO:1022; SEQ ID NO:982 and SEQ ID NO:1022; SEQ ID NO:983 and SEQ ID NO:1022; SEQ ID NO:984 and SEQ ID NO:1022; SEQ ID NO:985 and SEQ ID NO:1022; SEQ ID NO:986 and SEQ ID NO:1022; SEQ ID NO:987 and SEQ ID NO:1022; SEQ ID NO:988 and SEQ ID NO:1022; SEQ ID NO:989 and SEQ ID NO:1022; SEQ ID NO:990 and SEQ ID NO:1022; SEQ ID NO:991 and SEQ ID NO:1022; SEQ ID NO:992 and SEQ ID NO:1022; SEQ ID NO:993 and SEQ ID NO:1022; SEQ ID NO:994 and SEQ ID NO:1022; SEQ ID NO:995 and SEQ ID NO:1022; SEQ ID NO:996 and SEQ ID NO:1022; SEQ ID NO:997 and SEQ ID NO:1022; SEQ ID NO:998 and SEQ ID NO:1022; SEQ ID NO:999 and SEQ ID NO:1022; SEQ ID NO:1000 and SEQ ID NO:1022; SEQ ID NO:1001 and SEQ ID NO:1022; SEQ ID NO:1002 and SEQ ID NO:1022; SEQ ID NO:1003 and SEQ ID NO:1022; SEQ ID NO:1004 and SEQ ID NO:1022; SEQ ID NO:1005 and SEQ ID NO:1022; SEQ ID NO:1006 and SEQ ID NO:1022; SEQ ID NO:1007 and SEQ ID NO:1022; SEQ ID NO:1008 and SEQ ID NO:1022; SEQ ID NO:1009 and SEQ ID NO:1022; SEQ ID NO:1010 and SEQ ID NO:1022; SEQ ID NO:1011 and SEQ ID NO:1022; SEQ ID NO:1012 and SEQ ID NO:1022; SEQ ID NO:1013 and SEQ ID NO:1022; SEQ ID NO:1014 and SEQ ID NO:1022; SEQ ID NO:1015 and SEQ ID NO:1022; SEQ ID NO:1016 and SEQ ID NO:1022; SEQ ID NO:1017 and SEQ ID NO:1022; SEQ ID NO:1018 and SEQ ID NO:1022; SEQ ID NO:1019 and SEQ ID NO:1022; and SEQ ID NO:1020 and SEQ ID NO:1022.

In some aspects, the $V_H$-$V_L$ pairs are selected from SEQ ID NO:854 and SEQ ID NO:1023; SEQ ID NO:855 and SEQ ID NO:1023; SEQ ID NO:856 and SEQ ID NO:1023; SEQ ID NO:857 and SEQ ID NO:1023; SEQ ID NO:858 and SEQ ID NO:1023; SEQ ID NO:859 and SEQ ID NO:1023; SEQ ID NO:860 and SEQ ID NO:1023; SEQ ID NO:861 and SEQ ID NO:1023; SEQ ID NO:862 and SEQ ID NO:1023; SEQ ID NO:863 and SEQ ID NO:1023; SEQ ID NO:864 and SEQ ID NO:1023; SEQ ID NO:865 and SEQ ID NO:1023; SEQ ID NO:866 and SEQ ID NO:1023; SEQ ID NO:867 and SEQ ID NO:1023; SEQ ID NO:868 and SEQ ID NO:1023; SEQ ID NO:869 and SEQ ID NO:1023; SEQ ID NO:870 and SEQ ID NO:1023; SEQ ID NO:871 and SEQ ID NO:1023; SEQ ID NO:872 and SEQ ID NO:1023; SEQ ID NO:873 and SEQ ID NO:1023; SEQ ID NO:874 and SEQ ID NO:1023; SEQ ID NO:875 and SEQ ID NO:1023; SEQ ID NO:876 and SEQ ID NO:1023; SEQ ID NO:877 and SEQ ID NO:1023; SEQ ID NO:878 and SEQ ID NO:1023; SEQ ID NO:879 and SEQ ID NO:1023; SEQ ID NO:880 and SEQ ID NO:1023; SEQ ID NO:881 and SEQ ID NO:1023; SEQ ID NO:882 and SEQ ID NO:1023; SEQ ID NO:883 and SEQ ID NO:1023; SEQ ID NO:884 and SEQ ID NO:1023; SEQ ID NO:885 and SEQ ID NO:1023; SEQ ID NO:886 and SEQ ID NO:1023; SEQ ID NO:887 and SEQ ID NO:1023; SEQ ID NO:888 and SEQ ID NO:1023; SEQ ID NO:889 and SEQ ID NO:1023; SEQ ID NO:890 and SEQ ID NO:1023; SEQ ID NO:891 and SEQ ID NO:1023; SEQ ID NO:892 and SEQ ID NO:1023; SEQ ID NO:893 and SEQ ID NO:1023; SEQ ID NO:894 and SEQ ID NO:1023; SEQ ID NO:895 and SEQ ID NO:1023; SEQ ID NO:896 and SEQ ID NO:1023; SEQ ID NO:897 and SEQ ID NO:1023; SEQ ID NO:898 and SEQ ID NO:1023; SEQ ID NO:899 and SEQ ID NO:1023; SEQ ID NO:900 and SEQ ID NO:1023; SEQ ID NO:901 and SEQ ID NO:1023; SEQ ID NO:902 and SEQ ID NO:1023; SEQ ID NO:903 and SEQ ID NO:1023; SEQ ID NO:904 and SEQ ID NO:1023; SEQ ID NO:905 and SEQ ID NO:1023; SEQ ID NO:906 and SEQ ID NO:1023; SEQ ID NO:907 and SEQ ID NO:1023; SEQ ID NO:908 and SEQ ID NO:1023; SEQ ID NO:909 and SEQ ID NO:1023; SEQ ID NO:910 and SEQ ID NO:1023; SEQ ID NO:911 and SEQ ID NO:1023; SEQ ID NO:912 and SEQ ID NO:1023; SEQ ID NO:913 and SEQ ID NO:1023; SEQ ID NO:914 and SEQ ID NO:1023; SEQ ID NO:915 and SEQ ID NO:1023; SEQ ID NO:916 and SEQ ID NO:1023; SEQ ID NO:917 and SEQ ID NO:1023; SEQ ID NO:918 and SEQ ID NO:1023; SEQ ID NO:919 and SEQ ID NO:1023; SEQ ID NO:920 and SEQ ID NO:1023; SEQ ID NO:921 and SEQ ID NO:1023; SEQ ID NO:922 and SEQ ID NO:1023; SEQ ID NO:923 and SEQ ID NO:1023; SEQ ID NO:924 and SEQ ID NO:1023; SEQ ID NO:925 and SEQ ID NO:1023; SEQ ID NO:926 and SEQ ID NO:1023; SEQ ID NO:927 and SEQ ID NO:1023; SEQ ID NO:928 and SEQ ID NO:1023; SEQ ID NO:929 and SEQ ID NO:1023; SEQ ID NO:930 and SEQ ID NO:1023; SEQ ID NO:931 and SEQ ID NO:1023; SEQ ID NO:932 and SEQ ID NO:1023; SEQ ID NO:933 and SEQ ID NO:1023; SEQ ID NO:934 and SEQ ID NO:1023; SEQ ID NO:935 and SEQ ID NO:1023; SEQ ID NO:936 and SEQ ID NO:1023; SEQ ID NO:937 and SEQ ID NO:1023; SEQ ID NO:938 and SEQ ID NO:1023; SEQ ID NO:939 and SEQ ID NO:1023; SEQ ID NO:940 and SEQ ID NO:1023; SEQ ID NO:941 and SEQ ID NO:1023; SEQ ID NO:942 and SEQ ID NO:1023; SEQ ID NO:943 and SEQ ID NO:1023; SEQ ID NO:944 and SEQ ID NO:1023; SEQ ID NO:945 and SEQ ID NO:1023; SEQ ID NO:946 and SEQ ID NO:1023; SEQ ID NO:947 and SEQ ID NO:1023; SEQ ID NO:948 and SEQ ID NO:1023; SEQ ID NO:949 and SEQ ID NO:1023; SEQ ID NO:950 and SEQ ID NO:1023; SEQ ID NO:951 and SEQ ID NO:1023; SEQ ID NO:952 and SEQ ID NO:1023; SEQ ID NO:953 and SEQ ID NO:1023; SEQ ID NO:954 and SEQ ID NO:1023; SEQ ID NO:955 and SEQ ID NO:1023; SEQ ID NO:956 and SEQ ID NO:1023; SEQ ID NO:957 and SEQ ID NO:1023; SEQ ID NO:958 and SEQ ID NO:1023; SEQ ID NO:959 and SEQ ID NO:1023; SEQ ID NO:960 and SEQ ID NO:1023; SEQ ID NO:961 and SEQ ID NO:1023; SEQ ID NO:962 and SEQ ID NO:1023; SEQ ID NO:963 and SEQ ID NO:1023; SEQ ID NO:964 and SEQ ID NO:1023; SEQ ID NO:965 and SEQ ID NO:1023; SEQ ID NO:966 and SEQ ID NO:1023; SEQ ID NO:967 and SEQ ID NO:1023; SEQ ID NO:968 and SEQ ID NO:1023; SEQ ID NO:969 and SEQ ID NO:1023; SEQ ID NO:970 and SEQ ID NO:1023; SEQ ID NO:971 and SEQ ID NO:1023; SEQ ID NO:972 and SEQ ID NO:1023; SEQ ID NO:973 and SEQ ID NO:1023; SEQ ID NO:974 and SEQ ID NO:1023; SEQ ID NO:975 and SEQ ID NO:1023; SEQ ID NO:976 and SEQ ID NO:1023; SEQ ID NO:977 and SEQ ID NO:1023; SEQ ID NO:978 and SEQ ID NO:1023; SEQ ID NO:979 and SEQ ID NO:1023; SEQ ID NO:980 and SEQ ID NO:1023; SEQ ID NO:981 and SEQ ID NO:1023; SEQ ID NO:982 and SEQ ID NO:1023; SEQ ID NO:983 and SEQ ID NO:1023; SEQ ID NO:984 and SEQ ID NO:1023; SEQ ID NO:985 and SEQ ID NO:1023; SEQ ID NO:986 and SEQ ID NO:1023; SEQ ID NO:987 and SEQ ID NO:1023; SEQ ID NO:988 and SEQ ID NO:1023; SEQ ID NO:989 and SEQ ID NO:1023; SEQ ID NO:990 and SEQ ID NO:1023; SEQ ID NO:991 and SEQ ID NO:1023; SEQ ID NO:992 and SEQ ID NO:1023; SEQ ID NO:993 and SEQ ID NO:1023; SEQ ID NO:994 and SEQ ID NO:1023; SEQ ID NO:995 and SEQ ID NO:1023; SEQ ID NO:996 and SEQ ID NO:1023; SEQ ID NO:997 and SEQ ID NO:1023; SEQ ID NO:998 and SEQ ID NO:1023; SEQ ID NO:999 and SEQ ID NO:1023; SEQ ID NO:1000 and SEQ ID NO:1023; SEQ ID NO:1001 and SEQ ID NO:1023; SEQ ID NO:1002 and SEQ ID NO:1023; SEQ ID NO:1003 and SEQ ID NO:1023; SEQ ID NO:1004 and SEQ ID NO:1023; SEQ ID NO:1005 and SEQ ID NO:1023; SEQ ID NO:1006 and SEQ ID NO:1023; SEQ ID NO:1007 and SEQ ID NO:1023; SEQ ID NO:1008 and SEQ ID NO:1023; SEQ ID NO:1009 and SEQ ID NO:1023; SEQ ID NO:1010 and SEQ ID NO:1023; SEQ ID NO:1011 and SEQ ID NO:1023; SEQ ID NO:1012 and SEQ ID NO:1023; SEQ ID NO:1013 and SEQ ID NO:1023; SEQ ID NO:1014 and SEQ ID NO:1023; SEQ ID NO:1015 and SEQ ID NO:1023; SEQ ID NO:1016 and SEQ ID NO:1023; SEQ ID NO:1017 and SEQ ID NO:1023; SEQ ID NO:1018 and SEQ ID NO:1023; SEQ ID NO:1019 and SEQ ID NO:1023; and SEQ ID NO:1020 and SEQ ID NO:1023.

In some aspects, the $V_H$-$V_L$ pairs are selected from SEQ ID NO:854 and SEQ ID NO:1024; SEQ ID NO:855 and SEQ ID NO:1024; SEQ ID NO:856 and SEQ ID NO:1024; SEQ ID NO:857 and SEQ ID NO:1024; SEQ ID NO:858 and SEQ ID NO:1024; SEQ ID NO:859 and SEQ ID NO:1024; SEQ ID NO:860 and SEQ ID NO:1024; SEQ ID NO:861 and SEQ ID NO:1024; SEQ ID NO:862 and SEQ ID NO:1024; SEQ ID NO:863 and SEQ ID NO:1024; SEQ ID NO:864 and SEQ ID NO:1024; SEQ ID NO:865 and SEQ ID NO:1024; SEQ ID NO:866 and SEQ ID NO:1024; SEQ ID NO:867 and SEQ ID NO:1024; SEQ ID NO:868 and SEQ ID NO:1024; SEQ ID NO:869 and SEQ ID NO:1024; SEQ ID NO:870 and SEQ ID NO:1024; SEQ ID NO:871 and SEQ ID NO:1024; SEQ ID NO:872 and SEQ ID NO:1024; SEQ ID NO:873 and SEQ ID NO:1024; SEQ ID NO:874 and SEQ ID NO:1024; SEQ ID NO:875 and SEQ ID NO:1024; SEQ ID NO:876 and SEQ ID NO:1024; SEQ ID NO:877 and SEQ ID NO:1024; SEQ ID NO:878 and SEQ ID NO:1024; SEQ ID NO:879 and SEQ ID NO:1024; SEQ ID NO:880 and SEQ ID NO:1024; SEQ ID NO:881 and SEQ ID NO:1024; SEQ ID NO:882 and SEQ ID NO:1024; SEQ ID NO:883 and SEQ ID NO:1024; SEQ ID NO:884 and SEQ ID NO:1024; SEQ ID NO:885 and SEQ ID NO:1024; SEQ ID NO:886 and SEQ ID NO:1024; SEQ ID NO:887 and SEQ ID NO:1024; SEQ ID NO:888 and SEQ ID NO:1024; SEQ ID NO:889 and SEQ ID NO:1024; SEQ ID NO:890 and SEQ ID NO:1024; SEQ ID NO:891 and SEQ ID NO:1024; SEQ ID NO:892 and SEQ ID NO:1024; SEQ ID NO:893 and SEQ ID NO:1024; SEQ ID NO:894 and SEQ ID NO:1024; SEQ ID NO:895 and SEQ ID NO:1024; SEQ ID NO:896 and SEQ ID NO:1024; SEQ ID NO:897 and SEQ ID NO:1024; SEQ ID NO:898 and SEQ ID NO:1024; SEQ ID NO:899 and SEQ ID NO:1024; SEQ ID NO:900 and SEQ ID NO:1024; SEQ ID NO:901 and SEQ ID NO:1024; SEQ ID NO:902 and SEQ ID NO:1024; SEQ ID NO:903 and SEQ ID NO:1024; SEQ ID NO:904 and SEQ ID NO:1024; SEQ ID NO:905 and SEQ ID NO:1024; SEQ ID NO:906 and SEQ ID NO:1024; SEQ ID NO:907 and SEQ ID NO:1024; SEQ ID NO:908 and SEQ ID NO:1024; SEQ ID NO:909 and SEQ ID NO:1024; SEQ ID NO:910 and SEQ ID NO:1024; SEQ ID NO:911 and SEQ ID NO:1024; SEQ ID NO:912 and SEQ ID NO:1024; SEQ ID NO:913 and SEQ ID NO:1024; SEQ ID NO:914 and SEQ ID NO:1024; SEQ ID NO:915 and SEQ ID NO:1024; SEQ ID NO:916 and SEQ ID NO:1024; SEQ ID NO:917 and SEQ ID NO:1024; SEQ ID NO:918 and SEQ ID NO:1024; SEQ ID NO:919 and SEQ ID NO:1024; SEQ ID NO:920 and SEQ ID NO:1024; SEQ ID NO:921 and SEQ ID NO:1024; SEQ ID NO:922 and SEQ ID NO:1024; SEQ ID NO:923 and SEQ ID NO:1024; SEQ ID NO:924 and SEQ ID NO:1024; SEQ ID NO:925 and SEQ ID NO:1024; SEQ ID NO:926 and SEQ ID NO:1024; SEQ ID NO:927 and SEQ ID NO:1024; SEQ ID NO:928 and SEQ ID NO:1024; SEQ ID NO:929 and SEQ ID NO:1024; SEQ ID NO:930 and SEQ ID NO:1024; SEQ ID NO:931 and SEQ ID NO:1024; SEQ ID NO:932 and SEQ ID NO:1024; SEQ ID NO:933 and SEQ ID NO:1024; SEQ ID NO:934 and SEQ ID NO:1024; SEQ ID NO:935 and SEQ ID NO:1024; SEQ ID NO:936 and SEQ ID NO:1024; SEQ ID NO:937 and SEQ ID NO:1024; SEQ ID NO:938 and SEQ ID NO:1024; SEQ ID NO:939 and SEQ ID NO:1024; SEQ ID NO:940 and SEQ ID NO:1024; SEQ ID NO:941 and SEQ ID NO:1024; SEQ ID NO:942 and SEQ ID NO:1024; SEQ ID NO:943 and SEQ ID NO:1024; SEQ ID NO:944 and SEQ ID NO:1024; SEQ ID NO:945 and SEQ ID NO:1024; SEQ ID NO:946 and SEQ ID NO:1024; SEQ ID NO:947 and SEQ ID NO:1024; SEQ ID NO:948 and SEQ ID NO:1024; SEQ ID NO:949 and SEQ ID NO:1024; SEQ ID NO:950 and SEQ ID NO:1024; SEQ ID NO:951 and SEQ ID NO:1024; SEQ ID NO:952 and SEQ ID NO:1024; SEQ ID NO:953 and SEQ ID NO:1024; SEQ ID NO:954 and SEQ ID NO:1024; SEQ ID NO:955 and SEQ ID NO:1024; SEQ ID NO:956 and SEQ ID NO:1024; SEQ ID NO:957 and SEQ ID NO:1024; SEQ ID NO:958 and SEQ ID NO:1024; SEQ ID NO:959 and SEQ ID NO:1024; SEQ ID NO:960 and SEQ ID NO:1024; SEQ ID NO:961 and SEQ ID NO:1024; SEQ ID NO:962 and SEQ ID NO:1024; SEQ ID NO:963 and SEQ ID NO:1024; SEQ ID NO:964 and SEQ ID NO:1024; SEQ ID NO:965 and SEQ ID NO:1024; SEQ ID NO:966 and SEQ ID NO:1024; SEQ ID NO:967 and SEQ ID NO:1024; SEQ ID NO:968 and SEQ ID NO:1024; SEQ ID NO:969 and SEQ ID NO:1024; SEQ ID NO:970 and SEQ ID NO:1024; SEQ ID NO:971 and SEQ ID NO:1024; SEQ ID NO:972 and SEQ ID NO:1024; SEQ ID NO:973 and SEQ ID NO:1024; SEQ ID NO:974 and SEQ ID NO:1024; SEQ ID NO:975 and SEQ ID NO:1024; SEQ ID NO:976 and SEQ ID NO:1024; SEQ ID NO:977 and SEQ ID NO:1024; SEQ ID NO:978 and SEQ ID NO:1024; SEQ ID NO:979 and SEQ ID NO:1024; SEQ ID NO:980 and SEQ ID NO:1024; SEQ ID NO:981 and SEQ ID NO:1024; SEQ ID NO:982 and SEQ ID NO:1024; SEQ ID NO:983 and SEQ ID NO:1024; SEQ ID NO:984 and SEQ ID NO:1024; SEQ ID NO:985 and SEQ ID NO:1024; SEQ ID NO:986 and SEQ ID NO:1024; SEQ ID NO:987 and SEQ ID NO:1024; SEQ ID NO:988 and SEQ ID NO:1024; SEQ ID NO:989 and SEQ ID NO:1024; SEQ ID NO:990 and SEQ ID NO:1024; SEQ ID NO:991 and SEQ ID NO:1024; SEQ ID NO:992 and SEQ ID NO:1024; SEQ ID NO:993 and SEQ ID NO:1024; SEQ ID NO:994 and SEQ ID NO:1024; SEQ ID NO:995 and SEQ ID NO:1024; SEQ ID NO:996 and SEQ ID NO:1024; SEQ ID NO:997 and SEQ ID NO:1024; SEQ ID NO:998 and SEQ ID NO:1024; SEQ ID NO:999 and SEQ ID NO:1024; SEQ ID NO:1000 and SEQ ID NO:1024; SEQ ID NO:1001 and SEQ ID NO:1024; SEQ ID NO:1002 and SEQ ID NO:1024; SEQ ID NO:1003 and SEQ ID NO:1024; SEQ ID NO:1004 and SEQ ID NO:1024; SEQ ID NO:1005 and SEQ ID NO:1024; SEQ ID NO:1006 and SEQ ID NO:1024; SEQ ID NO:1007 and SEQ ID NO:1024; SEQ ID NO:1008 and SEQ ID NO:1024; SEQ ID NO:1009 and SEQ ID NO:1024; SEQ ID NO:1010 and SEQ ID NO:1024; SEQ ID NO:1011 and SEQ ID NO:1024; SEQ ID NO:1012 and SEQ ID NO:1024; SEQ ID NO:1013 and SEQ ID NO:1024; SEQ ID NO:1014 and SEQ ID NO:1024; SEQ ID NO:1015 and SEQ ID NO:1024; SEQ ID NO:1016 and SEQ ID NO:1024; SEQ ID NO:1017 and SEQ ID NO:1024; SEQ ID NO:1018 and SEQ ID NO:1024; SEQ ID NO:1019 and SEQ ID NO:1024; and SEQ ID NO:1020 and SEQ ID NO:1024.

In some aspects, the $V_H$-$V_L$ pairs are selected from SEQ ID NO:854 and SEQ ID NO:1025; SEQ ID NO:855 and SEQ ID NO:1025; SEQ ID NO:856 and SEQ ID NO:1025; SEQ ID NO:857 and SEQ ID NO:1025; SEQ ID NO:858 and SEQ ID NO:1025; SEQ ID NO:859 and SEQ ID NO:1025; SEQ ID NO:860 and SEQ ID NO:1025; SEQ ID NO:861 and SEQ ID NO:1025; SEQ ID NO:862 and SEQ ID NO:1025; SEQ ID NO:863 and SEQ ID NO:1025; SEQ ID NO:864 and SEQ ID NO:1025; SEQ ID NO:865 and SEQ ID NO:1025; SEQ ID NO:866 and SEQ ID NO:1025; SEQ ID NO:867 and SEQ ID NO:1025; SEQ ID NO:868 and SEQ ID NO:1025; SEQ ID NO:869 and SEQ ID NO:1025; SEQ ID NO:870 and SEQ ID NO:1025; SEQ ID NO:871 and SEQ ID NO:1025; SEQ ID NO:872 and SEQ ID NO:1025; SEQ ID NO:873 and SEQ ID NO:1025; SEQ ID NO:874 and SEQ ID NO:1025; SEQ ID NO:875 and SEQ ID NO:1025; SEQ ID NO:876 and SEQ ID NO:1025; SEQ ID NO:877 and SEQ ID NO:1025; SEQ ID NO:878 and SEQ ID NO:1025; SEQ ID NO:879 and SEQ ID NO:1025; SEQ ID NO:880 and SEQ ID NO:1025; SEQ ID NO:881 and SEQ ID NO:1025; SEQ ID NO:882 and SEQ ID NO:1025; SEQ ID NO:883 and SEQ ID NO:1025; SEQ ID NO:884 and SEQ ID NO:1025; SEQ ID NO:885 and SEQ ID NO:1025; SEQ ID NO:886 and SEQ ID NO:1025; SEQ ID NO:887 and SEQ ID NO:1025; SEQ ID NO:888 and SEQ ID NO:1025; SEQ ID NO:889 and SEQ ID NO:1025; SEQ ID NO:890 and SEQ ID NO:1025; SEQ ID NO:891 and SEQ ID NO:1025; SEQ ID NO:892 and SEQ ID NO:1025; SEQ ID NO:893 and SEQ ID NO:1025; SEQ ID NO:894 and SEQ ID NO:1025; SEQ ID NO:895 and SEQ ID NO:1025; SEQ ID NO:896 and SEQ ID NO:1025; SEQ ID NO:897 and SEQ ID NO:1025; SEQ ID NO:898 and SEQ ID NO:1025; SEQ ID NO:899 and SEQ ID NO:1025; SEQ ID NO:900 and SEQ ID NO:1025; SEQ ID NO:901 and SEQ ID NO:1025; SEQ ID NO:902 and SEQ ID NO:1025; SEQ ID NO:903 and SEQ ID NO:1025; SEQ ID NO:904 and SEQ ID NO:1025; SEQ ID NO:905 and SEQ ID NO:1025; SEQ ID NO:906 and SEQ ID NO:1025; SEQ ID NO:907 and SEQ ID NO:1025; SEQ ID NO:908 and SEQ ID NO:1025; SEQ ID NO:909 and SEQ ID NO:1025; SEQ ID NO:910 and SEQ ID NO:1025; SEQ ID NO:911 and SEQ ID NO:1025; SEQ ID NO:912 and SEQ ID NO:1025; SEQ ID NO:913 and SEQ ID NO:1025; SEQ ID NO:914 and SEQ ID NO:1025; SEQ ID NO:915 and SEQ ID NO:1025; SEQ ID NO:916 and SEQ ID NO:1025; SEQ ID NO:917 and SEQ ID NO:1025; SEQ ID NO:918 and SEQ ID NO:1025; SEQ ID NO:919 and SEQ ID NO:1025; SEQ ID NO:920 and SEQ ID NO:1025; SEQ ID NO:921 and SEQ ID NO:1025; SEQ ID NO:922 and SEQ ID NO:1025; SEQ ID NO:923 and SEQ ID NO:1025; SEQ ID NO:924 and SEQ ID NO:1025; SEQ ID NO:925 and SEQ ID NO:1025; SEQ ID NO:926 and SEQ ID NO:1025; SEQ ID NO:927 and SEQ ID NO:1025; SEQ ID NO:928 and SEQ ID NO:1025; SEQ ID NO:929 and SEQ ID NO:1025; SEQ ID NO:930 and SEQ ID NO:1025; SEQ ID NO:931 and SEQ ID NO:1025; SEQ ID NO:932 and SEQ ID NO:1025; SEQ ID NO:933 and SEQ ID NO:1025; SEQ ID NO:934 and SEQ ID NO:1025; SEQ ID NO:935 and SEQ ID NO:1025; SEQ ID NO:936 and SEQ ID NO:1025; SEQ ID NO:937 and SEQ ID NO:1025; SEQ ID NO:938 and SEQ ID NO:1025; SEQ ID NO:939 and SEQ ID NO:1025; SEQ ID NO:940 and SEQ ID NO:1025; SEQ ID NO:941 and SEQ ID NO:1025; SEQ ID NO:942 and SEQ ID NO:1025; SEQ ID NO:943 and SEQ ID NO:1025; SEQ ID NO:944 and SEQ ID NO:1025; SEQ ID NO:945 and SEQ ID NO:1025; SEQ ID NO:946 and SEQ ID NO:1025; SEQ ID NO:947 and SEQ ID NO:1025; SEQ ID NO:948 and SEQ ID NO:1025; SEQ ID NO:949 and SEQ ID NO:1025; SEQ ID NO:950 and SEQ ID NO:1025; SEQ ID NO:951 and SEQ ID NO:1025; SEQ ID NO:952 and SEQ ID NO:1025; SEQ ID NO:953 and SEQ ID NO:1025; SEQ ID NO:954 and SEQ ID NO:1025; SEQ ID NO:955 and SEQ ID NO:1025; SEQ ID NO:956 and SEQ ID NO:1025; SEQ ID NO:957 and SEQ ID NO:1025; SEQ ID NO:958 and SEQ ID NO:1025; SEQ ID NO:959 and SEQ ID NO:1025; SEQ ID NO:960 and SEQ ID NO:1025; SEQ ID NO:961 and SEQ ID NO:1025; SEQ ID NO:962 and SEQ ID NO:1025; SEQ ID NO:963 and SEQ ID NO:1025; SEQ ID NO:964 and SEQ ID NO:1025; SEQ ID NO:965 and SEQ ID NO:1025; SEQ ID NO:966 and SEQ ID NO:1025; SEQ ID NO:967 and SEQ ID NO:1025; SEQ ID NO:968 and SEQ ID NO:1025; SEQ ID NO:969 and SEQ ID NO:1025; SEQ ID NO:970 and SEQ ID NO:1025; SEQ ID NO:971 and SEQ ID NO:1025; SEQ ID NO:972 and SEQ ID NO:1025; SEQ ID NO:973 and SEQ ID NO:1025; SEQ ID NO:974 and SEQ ID NO:1025; SEQ ID NO:975 and SEQ ID NO:1025; SEQ ID NO:976 and SEQ ID NO:1025; SEQ ID NO:977 and SEQ ID NO:1025; SEQ ID NO:978 and SEQ ID NO:1025; SEQ ID NO:979 and SEQ ID NO:1025; SEQ ID NO:980 and SEQ ID NO:1025; SEQ ID NO:981 and SEQ ID NO:1025; SEQ ID NO:982 and SEQ ID NO:1025; SEQ ID NO:983 and SEQ ID NO:1025; SEQ ID NO:984 and SEQ ID NO:1025; SEQ ID NO:985 and SEQ ID NO:1025; SEQ ID NO:986 and SEQ ID NO:1025; SEQ ID NO:987 and SEQ ID NO:1025; SEQ ID NO:988 and SEQ ID NO:1025; SEQ ID NO:989 and SEQ ID NO:1025; SEQ ID NO:990 and SEQ ID NO:1025; SEQ ID NO:991 and SEQ ID NO:1025; SEQ ID NO:992 and SEQ ID NO:1025; SEQ ID NO:993 and SEQ ID NO:1025; SEQ ID NO:994 and SEQ ID NO:1025; SEQ ID NO:995 and SEQ ID NO:1025; SEQ ID NO:996 and SEQ ID NO:1025; SEQ ID NO:997 and SEQ ID NO:1025; SEQ ID NO:998 and SEQ ID NO:1025; SEQ ID NO:999 and SEQ ID NO:1025; SEQ ID NO:1000 and SEQ ID NO:1025; SEQ ID NO:1001 and SEQ ID NO:1025; SEQ ID NO:1002 and SEQ ID NO:1025; SEQ ID NO:1003 and SEQ ID NO:1025; SEQ ID NO:1004 and SEQ ID NO:1025; SEQ ID NO:1005 and SEQ ID NO:1025; SEQ ID NO:1006 and SEQ ID NO:1025; SEQ ID NO:1007 and SEQ ID NO:1025; SEQ ID NO:1008 and SEQ ID NO:1025; SEQ ID NO:1009 and SEQ ID NO:1025; SEQ ID NO:1010 and SEQ ID NO:1025; SEQ ID NO:1011 and SEQ ID NO:1025; SEQ ID NO:1012 and SEQ ID NO:1025; SEQ ID NO:1013 and SEQ ID NO:1025; SEQ ID NO:1014 and SEQ ID NO:1025; SEQ ID NO:1015 and SEQ ID NO:1025; SEQ ID NO:1016 and SEQ ID NO:1025; SEQ ID NO:1017 and SEQ ID NO:1025; SEQ ID NO:1018 and SEQ ID NO:1025; SEQ ID NO:1019 and SEQ ID NO:1025; and SEQ ID NO:1020 and SEQ ID NO:1025.

In some aspects, the $V_H$-$V_L$ pairs are selected from SEQ ID NO:854 and SEQ ID NO:1026; SEQ ID NO:855 and SEQ ID NO:1026; SEQ ID NO:856 and SEQ ID NO:1026; SEQ ID NO:857 and SEQ ID NO:1026; SEQ ID NO:858 and SEQ ID NO:1026; SEQ ID NO:859 and SEQ ID NO:1026; SEQ ID NO:860 and SEQ ID NO:1026; SEQ ID NO:861 and SEQ ID NO:1026; SEQ ID NO:862 and SEQ ID NO:1026; SEQ ID NO:863 and SEQ ID NO:1026; SEQ ID NO:864 and SEQ ID NO:1026; SEQ ID NO:865 and SEQ ID NO:1026; SEQ ID NO:866 and SEQ ID NO:1026; SEQ ID NO:867 and SEQ ID NO:1026; SEQ ID NO:868 and SEQ ID NO:1026; SEQ ID NO:869 and SEQ ID NO:1026; SEQ ID NO:870 and SEQ ID NO:1026; SEQ ID NO:871 and SEQ ID NO:1026; SEQ ID NO:872 and SEQ ID NO:1026; SEQ ID NO:873 and SEQ ID NO:1026; SEQ ID NO:874 and SEQ ID NO:1026; SEQ ID NO:875 and SEQ ID NO:1026; SEQ ID NO:876 and SEQ ID NO:1026; SEQ ID NO:877 and SEQ ID NO:1026; SEQ ID NO:878 and SEQ ID NO:1026; SEQ ID NO:879 and SEQ ID NO:1026; SEQ ID NO:880 and SEQ ID NO:1026; SEQ ID NO:881 and SEQ ID NO:1026; SEQ ID NO:882 and SEQ ID NO:1026; SEQ ID NO:883 and SEQ ID NO:1026; SEQ ID NO:884 and SEQ ID NO:1026; SEQ ID NO:885 and SEQ ID NO:1026; SEQ ID NO:886 and SEQ ID NO:1026; SEQ ID NO:887 and SEQ ID NO:1026; SEQ ID NO:888 and SEQ ID NO:1026; SEQ ID NO:889 and SEQ ID NO:1026; SEQ ID NO:890 and SEQ ID NO:1026; SEQ ID NO:891 and SEQ ID NO:1026; SEQ ID NO:892 and SEQ ID NO:1026; SEQ ID NO:893 and SEQ ID NO:1026; SEQ ID NO:894 and SEQ ID NO:1026; SEQ ID NO:895 and SEQ ID NO:1026; SEQ ID NO:896 and SEQ ID NO:1026; SEQ ID NO:897 and SEQ ID NO:1026; SEQ ID NO:898 and SEQ ID NO:1026; SEQ ID NO:899 and SEQ ID NO:1026; SEQ ID NO:900 and SEQ ID NO:1026; SEQ ID NO:901 and SEQ ID NO:1026; SEQ ID NO:902 and SEQ ID NO:1026; SEQ ID NO:903 and SEQ ID NO:1026; SEQ ID NO:904 and SEQ ID NO:1026; SEQ ID NO:905 and SEQ ID NO:1026; SEQ ID NO:906 and SEQ ID NO:1026; SEQ ID NO:907 and SEQ ID NO:1026; SEQ ID NO:908 and SEQ ID NO:1026; SEQ ID NO:909 and SEQ ID NO:1026; SEQ ID NO:910 and SEQ ID NO:1026; SEQ ID NO:911 and SEQ ID NO:1026; SEQ ID NO:912 and SEQ ID NO:1026; SEQ ID NO:913 and SEQ ID NO:1026; SEQ ID NO:914 and SEQ ID NO:1026; SEQ ID NO:915 and SEQ ID NO:1026; SEQ ID NO:916 and SEQ ID NO:1026; SEQ ID NO:917 and SEQ ID NO:1026; SEQ ID NO:918 and SEQ ID NO:1026; SEQ ID NO:919 and SEQ ID NO:1026; SEQ ID NO:920 and SEQ ID NO:1026; SEQ ID NO:921 and SEQ ID NO:1026; SEQ ID NO:922 and SEQ ID NO:1026; SEQ ID NO:923 and SEQ ID NO:1026; SEQ ID NO:924 and SEQ ID NO:1026; SEQ ID NO:925 and SEQ ID NO:1026; SEQ ID NO:926 and SEQ ID NO:1026; SEQ ID NO:927 and SEQ ID NO:1026; SEQ ID NO:928 and SEQ ID NO:1026; SEQ ID NO:929 and SEQ ID NO:1026; SEQ ID NO:930 and SEQ ID NO:1026; SEQ ID NO:931 and SEQ ID NO:1026; SEQ ID NO:932 and SEQ ID NO:1026; SEQ ID NO:933 and SEQ ID NO:1026; SEQ ID NO:934 and SEQ ID NO:1026; SEQ ID NO:935 and SEQ ID NO:1026; SEQ ID NO:936 and SEQ ID NO:1026; SEQ ID NO:937 and SEQ ID NO:1026; SEQ ID NO:938 and SEQ ID NO:1026; SEQ ID NO:939 and SEQ ID NO:1026; SEQ ID NO:940 and SEQ ID NO:1026; SEQ ID NO:941 and SEQ ID NO:1026; SEQ ID NO:942 and SEQ ID NO:1026; SEQ ID NO:943 and SEQ ID NO:1026; SEQ ID NO:944 and SEQ ID NO:1026; SEQ ID NO:945 and SEQ ID NO:1026; SEQ ID NO:946 and SEQ ID NO:1026; SEQ ID NO:947 and SEQ ID NO:1026; SEQ ID NO:948 and SEQ ID NO:1026; SEQ ID NO:949 and SEQ ID NO:1026; SEQ ID NO:950 and SEQ ID NO:1026; SEQ ID NO:951 and SEQ ID NO:1026; SEQ ID NO:952 and SEQ ID NO:1026; SEQ ID NO:953 and SEQ ID NO:1026; SEQ ID NO:954 and SEQ ID NO:1026; SEQ ID NO:955 and SEQ ID NO:1026; SEQ ID NO:956 and SEQ ID NO:1026; SEQ ID NO:957 and SEQ ID NO:1026; SEQ ID NO:958 and SEQ ID NO:1026; SEQ ID NO:959 and SEQ ID NO:1026; SEQ ID NO:960 and SEQ ID NO:1026; SEQ ID NO:961 and SEQ ID NO:1026; SEQ ID NO:962 and SEQ ID NO:1026; SEQ ID NO:963 and SEQ ID NO:1026; SEQ ID NO:964 and SEQ ID NO:1026; SEQ ID NO:965 and SEQ ID NO:1026; SEQ ID NO:966 and SEQ ID NO:1026; SEQ ID NO:967 and SEQ ID NO:1026; SEQ ID NO:968 and SEQ ID NO:1026; SEQ ID NO:969 and SEQ ID NO:1026; SEQ ID NO:970 and SEQ ID NO:1026; SEQ ID NO:971 and SEQ ID NO:1026; SEQ ID NO:972 and SEQ ID NO:1026; SEQ ID NO:973 and SEQ ID NO:1026; SEQ ID NO:974 and SEQ ID NO:1026; SEQ ID NO:975 and SEQ ID NO:1026; SEQ ID NO:976 and SEQ ID NO:1026; SEQ ID NO:977 and SEQ ID NO:1026; SEQ ID NO:978 and SEQ ID NO:1026; SEQ ID NO:979 and SEQ ID NO:1026; SEQ ID NO:980 and SEQ ID NO:1026; SEQ ID NO:981 and SEQ ID NO:1026; SEQ ID NO:982 and SEQ ID NO:1026; SEQ ID NO:983 and SEQ ID NO:1026; SEQ ID NO:984 and SEQ ID NO:1026; SEQ ID NO:985 and SEQ ID NO:1026; SEQ ID NO:986 and SEQ ID NO:1026; SEQ ID NO:987 and SEQ ID NO:1026; SEQ ID NO:988 and SEQ ID NO:1026; SEQ ID NO:989 and SEQ ID NO:1026; SEQ ID NO:990 and SEQ ID NO:1026; SEQ ID NO:991 and SEQ ID NO:1026; SEQ ID NO:992 and SEQ ID NO:1026; SEQ ID NO:993 and SEQ ID NO:1026; SEQ ID NO:994 and SEQ ID NO:1026; SEQ ID NO:995 and SEQ ID NO:1026; SEQ ID NO:996 and SEQ ID NO:1026; SEQ ID NO:997 and SEQ ID NO:1026; SEQ ID NO:998 and SEQ ID NO:1026; SEQ ID NO:999 and SEQ ID NO:1026; SEQ ID NO:1000 and SEQ ID NO:1026; SEQ ID NO:1001 and SEQ ID NO:1026; SEQ ID NO:1002 and SEQ ID NO:1026; SEQ ID NO:1003 and SEQ ID NO:1026; SEQ ID NO:1004 and SEQ ID NO:1026; SEQ ID NO:1005 and SEQ ID NO:1026; SEQ ID NO:1006 and SEQ ID NO:1026; SEQ ID NO:1007 and SEQ ID NO:1026; SEQ ID NO:1008 and SEQ ID NO:1026; SEQ ID NO:1009 and SEQ ID NO:1026; SEQ ID NO:1010 and SEQ ID NO:1026; SEQ ID NO:1011 and SEQ ID NO:1026; SEQ ID NO:1012 and SEQ ID NO:1026; SEQ ID NO:1013 and SEQ ID NO:1026; SEQ ID NO:1014 and SEQ ID NO:1026; SEQ ID NO:1015 and SEQ ID NO:1026; SEQ ID NO:1016 and SEQ ID NO:1026; SEQ ID NO:1017 and SEQ ID NO:1026; SEQ ID NO:1018 and SEQ ID NO:1026; SEQ ID NO:1019 and SEQ ID NO:1026; and SEQ ID NO:1020 and SEQ ID NO:1026.

5.7.4.1. Variants of $V_H$-$V_L$ Pairs

In some embodiments, the $V_H$-$V_L$ pairs provided herein comprise a variant of an illustrative $V_H$ and/or $V_L$ sequence provided in this disclosure.

In some aspects, the $V_H$ sequence comprises, consists of, or consists essentially of a variant of an illustrative $V_H$ sequence provided in this disclosure. In some aspects, the $V_H$ sequence comprises, consists of, or consists essentially of a sequence having at least 85%, 90%, 95%, 96%, 97%, 98%, 99%, or 99.5% identity with any of the illustrative $V_H$ sequences provided in this disclosure.

In some embodiments, the $V_H$ sequence comprises, consists of, or consists essentially of any of the illustrative $V_H$ sequences provided in this disclosure having 20 or fewer, 19 or fewer, 18 or fewer, 17 or fewer, 16 or fewer, 15 or fewer, 14 or fewer, 13 or fewer, 12 or fewer, 11 or fewer, 10 or fewer, 9 or fewer, 8 or fewer, 7 or fewer, 6 or fewer, 5 or fewer, 4 or fewer, 3 or fewer, 2 or fewer, or 1 or fewer amino acid substitutions. In some aspects, the amino acid substitutions are conservative amino acid substitutions.

In some aspects, the $V_L$ sequence comprises, consists of, or consists essentially of a variant of an illustrative $V_L$ sequence provided in this disclosure. In some aspects, the $V_L$ sequence comprises, consists of, or consists essentially of a sequence having at least 85%, 90%, 95%, 96%, 97%, 98%, 99%, or 99.5% identity with any of the illustrative $V_L$ sequences provided in this disclosure.

In some embodiments, the $V_L$ sequence comprises, consists of, or consists essentially of any of the illustrative $V_L$ sequences provided in this disclosure having 20 or fewer, 19 or fewer, 18 or fewer, 17 or fewer, 16 or fewer, 15 or fewer, 14 or fewer, 13 or fewer, 12 or fewer, 11 or fewer, 10 or fewer, 9 or fewer, 8 or fewer, 7 or fewer, 6 or fewer, 5 or fewer, 4 or fewer, 3 or fewer, 2 or fewer, or 1 or fewer amino acid substitutions. In some aspects, the amino acid substitutions are conservative amino acid substitutions.

5.7.5. Heavy Chain-Light Chain Pairs

In some embodiments, the antibody comprises a heavy chain sequence of an antibody disclosed herein and a light chain sequence of a suitable antibody. In some embodiments, the antibody comprises a heavy chain sequence of an antibody disclosed herein and a light chain sequence of an antibody disclosed herein.

In some embodiments, the heavy chain comprises a $V_H$ sequence comprising, consisting of, or consisting essentially of any one of SEQ ID NOs: 854-1020, and the light chain comprises a light chain sequence of any suitable antibody. Techniques for determining whether a particular light chain will pair with a heavy chain as described herein are well known to those of skill in the art. For example, a cell-free protein synthesis reaction comprising a nucleic acid encoding the heavy chain of interest and a nucleic acid encoding the light chain to be assessed may be performed as described, for example, in Example 1.

In some embodiments, the heavy chain comprises a $V_H$ sequence comprising, consisting of, or consisting essentially of any one of SEQ ID NOs: 854-1020, and the light chain comprises a $V_L$ sequence comprising, consisting of, or consisting essentially of any one of SEQ ID NOs: 1021-1026.

In some embodiments, the heavy chain comprises a $V_H$ sequence comprising, consisting of, or consisting essentially of any one of SEQ ID NOs: 979-1020, and the light chain comprises a $V_L$ sequence comprising, consisting of, or consisting essentially of any one of SEQ ID NOs: 1021-1026.

In some embodiments, the heavy chain comprises a $V_H$ sequence comprising, consisting of, or consisting essentially of any one of SEQ ID NOs: 979-1020, and the light chain comprises a $V_L$ sequence comprising, consisting of, or consisting essentially of SEQ ID NO: 1022 or 1023.

In some embodiments, the antibody comprises a $V_H$/$V_L$ pair together comprising, consisting of, or consisting essentially of the sequences of any pair selected from the group consisting of SEQ ID NOS: 854/1021, 855/1021, 856/1021, 857/1021, 858/1021, 859/1021, 860/1021, 861/1021, 862/1021, 863/1021, 864/1021, 865/1021, 866/1021, 867/1021, 868/1021, 869/1021, 870/1021, 871/1021, 872/1021, 873/1021, 874/1021, 875/1021, 876/1021, 877/1021, 878/1021, 879/1021, 880/1021, 881/1021, 882/1021, 883/1021, 884/1021, 885/1021, 886/1021, 887/1021, 888/1021, 889/1021, 890/1021, 891/1021, 892/1021, 893/1021, 894/1021, 895/1021, 896/1021, 897/1021, 898/1021, 899/1021, 900/1021, 901/1021, 902/1021, 903/1021, 904/1021, 905/1021, 906/1021, 907/1021, 908/1021, 909/1021, 910/1021, 911/1021, 912/1021, 913/1021, 914/1021, 915/1021, 916/1021, 917/1021, 918/1021, 919/1021, 920/1021, 921/1021, 922/1021, 923/1021, 924/1021, 925/1021, 926/1021, 927/1021, 928/1021, 929/1021, 930/1021, 931/1021, 932/1021, 933/1021, 934/1021, 935/1021, 936/1021, 937/1021, 938/1021, 939/1021, 940/1021, 941/1021, 942/1021, 943/1021, 944/1021, 945/1021, 946/1021, 947/1021, 948/1021, 949/1021, 950/1021, 951/1021, 952/1021, 953/1021, 954/1021, 955/1021, 956/1021, 957/1021, 958/1021, 959/1021, 960/1021, 961/1021, 962/1021, 963/1021, 964/1021, 965/1021, 966/1021, 967/1021, 968/1021, 969/1021, 970/1021, 971/1021, 972/1021, 973/1021, 974/1021, 975/1021, 976/1021, 977/1021, 978/1021, 979/1021, 980/1021, 981/1021, 982/1021, 983/1021, 984/1021, 985/1021, 986/1021, 987/1021, 988/1021, 989/1021, 990/1021, 991/1021, 992/1021, 993/1021, 994/1021, 995/1021, 996/1021, 997/1021, 998/1021, 999/1021, 1000/1021, 1001/1021, 1002/1021, 1003/1021, 1004/1021, 1005/1021, 1006/1021, 1007/1021, 1008/1021, 1009/1021, 1010/1021, 1011/1021, 1012/1021, 1013/1021, 1014/1021, 1015/1021, 1016/1021, 1017/1021, 1018/1021, 1019/1021, and 1020/1021.

In some embodiments, the antibody comprises a $V_H/V_L$ pair together comprising, consisting of, or consisting essentially of the sequences of any pair selected from the group consisting of SEQ ID NOS: 854/1022, 855/1022, 856/1022, 857/1022, 858/1022, 859/1022, 860/1022, 861/1022, 862/1022, 863/1022, 864/1022, 865/1022, 866/1022, 867/1022, 868/1022, 869/1022, 870/1022, 871/1022, 872/1022, 873/1022, 874/1022, 875/1022, 876/1022, 877/1022, 878/1022, 879/1022, 880/1022, 881/1022, 882/1022, 883/1022, 884/1022, 885/1022, 886/1022, 887/1022, 888/1022, 889/1022, 890/1022, 891/1022, 892/1022, 893/1022, 894/1022, 895/1022, 896/1022, 897/1022, 898/1022, 899/1022, 900/1022, 901/1022, 902/1022, 903/1022, 904/1022, 905/1022, 906/1022, 907/1022, 908/1022, 909/1022, 910/1022, 911/1022, 912/1022, 913/1022, 914/1022, 915/1022, 916/1022, 917/1022, 918/1022, 919/1022, 920/1022, 921/1022, 922/1022, 923/1022, 924/1022, 925/1022, 926/1022, 927/1022, 928/1022, 929/1022, 930/1022, 931/1022, 932/1022, 933/1022, 934/1022, 935/1022, 936/1022, 937/1022, 938/1022, 939/1022, 940/1022, 941/1022, 942/1022, 943/1022, 944/1022, 945/1022, 946/1022, 947/1022, 948/1022, 949/1022, 950/1022, 951/1022, 952/1022, 953/1022, 954/1022, 955/1022, 956/1022, 957/1022, 958/1022, 959/1022, 960/1022, 961/1022, 962/1022, 963/1022, 964/1022, 965/1022, 966/1022, 967/1022, 968/1022, 969/1022, 970/1022, 971/1022, 972/1022, 973/1022, 974/1022, 975/1022, 976/1022, 977/1022, 978/1022, 979/1022, 980/1022, 981/1022, 982/1022, 983/1022, 984/1022, 985/1022, 986/1022, 987/1022, 988/1022, 989/1022, 990/1022, 991/1022, 992/1022, 993/1022, 994/1022, 995/1022, 996/1022, 997/1022, 998/1022, 999/1022, 1000/1022, 1001/1022, 1002/1022, 1003/1022, 1004/1022, 1005/1022, 1006/1022, 1007/1022, 1008/1022, 1009/1022, 1010/1022, 1011/1022, 1012/1022, 1013/1022, 1014/1022, 1015/1022, 1016/1022, 1017/1022, 1018/1022, 1019/1022, and 1020/1022.

In some embodiments, the antibody comprises a $V_H/V_L$ pair together comprising, consisting of, or consisting essentially of the sequences of any pair selected from the group consisting of SEQ ID NOS: 854/1023, 855/1023, 856/1023, 857/1023, 858/1023, 859/1023, 860/1023, 861/1023, 862/1023, 863/1023, 864/1023, 865/1023, 866/1023, 867/1023, 868/1023, 869/1023, 870/1023, 871/1023, 872/1023, 873/1023, 874/1023, 875/1023, 876/1023, 877/1023, 878/1023, 879/1023, 880/1023, 881/1023, 882/1023, 883/1023, 884/1023, 885/1023, 886/1023, 887/1023, 888/1023, 889/1023, 890/1023, 891/1023, 892/1023, 893/1023, 894/1023, 895/1023, 896/1023, 897/1023, 898/1023, 899/1023, 900/1023, 901/1023, 902/1023, 903/1023, 904/1023, 905/1023, 906/1023, 907/1023, 908/1023, 909/1023, 910/1023, 911/1023, 912/1023, 913/1023, 914/1023, 915/1023, 916/1023, 917/1023, 918/1023, 919/1023, 920/1023, 921/1023, 922/1023, 923/1023, 924/1023, 925/1023, 926/1023, 927/1023, 928/1023, 929/1023, 930/1023, 931/1023, 932/1023, 933/1023, 934/1023, 935/1023, 936/1023, 937/1023, 938/1023, 939/1023, 940/1023, 941/1023, 942/1023, 943/1023, 944/1023, 945/1023, 946/1023, 947/1023, 948/1023, 949/1023, 950/1023, 951/1023, 952/1023, 953/1023, 954/1023, 955/1023, 956/1023, 957/1023, 958/1023, 959/1023, 960/1023, 961/1023, 962/1023, 963/1023, 964/1023, 965/1023, 966/1023, 967/1023, 968/1023, 969/1023, 970/1023, 971/1023, 972/1023, 973/1023, 974/1023, 975/1023, 976/1023, 977/1023, 978/1023, 979/1023, 980/1023, 981/1023, 982/1023, 983/1023, 984/1023, 985/1023, 986/1023, 987/1023, 988/1023, 989/1023, 990/1023, 991/1023, 992/1023, 993/1023, 994/1023, 995/1023, 996/1023, 997/1023, 998/1023, 999/1023, 1000/1023, 1001/1023, 1002/1023, 1003/1023, 1004/1023, 1005/1023, 1006/1023, 1007/1023, 1008/1023, 1009/1023, 1010/1023, 1011/1023, 1012/1023, 1013/1023, 1014/1023, 1015/1023, 1016/1023, 1017/1023, 1018/1023, 1019/1023, and 1020/1023.

5.8. Antibodies Comprising all Six CDRs

In some embodiments, the antibody comprises a CDR-H1 sequence, a CDR-H2 sequence, a CDR-H3 sequence, a CDR-L1 sequence, and a CDR-L3 sequence. In some aspects, the CDR sequences are part of a $V_H$ (for CDR-H) or $V_L$ (for CDR-L).

In some aspects, the CDR-H1 sequence is a Chothia CDR-H1 sequence comprising, consisting of, or consisting essentially of SEQ ID NOs: 4-170; the CDR-H2 sequence is a Chothia CDR-H2 sequence comprising, consisting of, or consisting essentially of SEQ ID NOs: 338-504; the CDR-H3 sequence is a CDR-H3 sequence comprising, consisting of, or consisting essentially of SEQ ID NOs: 672-838; the CDR-L1 sequence is a CDR-L1 sequence comprising, consisting of, or consisting essentially of SEQ ID NOs: 839-843; the CDR-L2 sequence is a CDR-L2 sequence comprising, consisting of, or consisting essentially of SEQ ID NOs: 844-848; and the CDR-L3 sequence is a CDR-L3 sequence comprising, consisting of, or consisting essentially of SEQ ID NOs: 849-853.

In some aspects, the CDR-H1 sequence is a Kabat CDR-H1 sequence comprising, consisting of, or consisting essentially of SEQ ID NOs: 171-337; the CDR-H2 sequence is a Kabat CDR-H2 sequence comprising, consisting of, or consisting essentially of SEQ ID NOs: 505-671; the CDR-H3 sequence is a CDR-H3 sequence comprising, consisting of, or consisting essentially of SEQ ID NOs: 672-838; the CDR-L1 sequence is a CDR-L1 sequence comprising, consisting of, or consisting essentially of SEQ ID NOs: 839-843; the CDR-L2 sequence is a CDR-L2 sequence comprising, consisting of, or consisting essentially of SEQ ID NOs: 844-848; and the CDR-L3 sequence is a CDR-L3 sequence comprising, consisting of, or consisting essentially of SEQ ID NOs: 849-853.

In some aspects, the antibody comprises three heavy chain CDRs from a $V_H$ sequence selected from SEQ ID NOs:854-1020, or variants thereof, and three light chain CDRs from a $V_L$ sequence selected from SEQ ID NOs: 1021-1026, or variants thereof. The CDRs can be according to any CDR scheme known to the person of skill. In certain embodiments, the CDRs are Kabat CDRs. In certain embodiments, the CDRs are Chothia CDRs.

In some embodiments, the antibody comprises three heavy chain CDRs, or variants thereof, and three light chain CDRs, or variants thereof, from a $V_H/V_L$ pair selected from the group consisting of SEQ ID NOS: 854/1021, 855/1021, 856/1021, 857/1021, 858/1021, 859/1021, 860/1021, 861/1021, 862/1021, 863/1021, 864/1021, 865/1021, 866/1021, 867/1021, 868/1021, 869/1021, 870/1021, 871/1021, 872/1021, 873/1021, 874/1021, 875/1021, 876/1021, 877/1021, 878/1021, 879/1021, 880/1021, 881/1021, 882/1021, 883/1021, 884/1021, 885/1021, 886/1021, 887/1021, 888/1021, 889/1021, 890/1021, 891/1021, 892/1021, 893/1021, 894/1021, 895/1021, 896/1021, 897/1021, 898/1021, 899/1021, 900/1021, 901/1021, 902/1021, 903/1021, 904/1021, 905/1021, 906/1021, 907/1021, 908/1021, 909/1021, 910/1021, 911/1021, 912/1021, 913/1021, 914/1021, 915/1021, 916/1021, 917/1021, 918/1021, 919/1021, 920/1021, 921/1021, 922/1021, 923/1021, 924/1021, 925/1021, 926/1021, 927/1021, 928/1021, 929/1021, 930/1021, 931/1021, 932/1021, 933/1021, 934/1021, 935/1021, 936/1021, 937/1021, 938/1021, 939/1021, 940/1021, 941/1021, 942/1021, 943/1021, 944/1021, 945/1021, 946/1021, 947/1021, 948/1021, 949/1021, 950/1021, 951/1021, 952/1021, 953/1021, 954/1021, 955/1021, 956/1021, 957/1021, 958/1021, 959/1021, 960/1021, 961/1021, 962/1021, 963/1021, 964/1021, 965/1021, 966/1021, 967/1021, 968/1021, 969/1021, 970/1021, 971/1021, 972/1021, 973/1021, 974/1021, 975/1021, 976/1021, 977/1021, 978/1021, 979/1021, 980/1021, 981/1021, 982/1021, 983/1021, 984/1021, 985/1021, 986/1021, 987/1021, 988/1021, 989/1021, 990/1021, 991/1021, 992/1021, 993/1021, 994/1021, 995/1021, 996/1021, 997/1021, 998/1021, 999/1021, 1000/1021, 1001/1021, 1002/1021, 1003/1021, 1004/1021, 1005/1021, 1006/1021, 1007/1021, 1008/1021, 1009/1021, 1010/1021, 1011/1021, 1012/1021, 1013/1021, 1014/1021, 1015/1021, 1016/1021, 1017/1021, 1018/1021, 1019/1021, and 1020/1021. The CDRs can be according to any CDR scheme known to the person of skill. In certain embodiments, the CDRs are Kabat CDRs. In certain embodiments, the CDRs are Chothia CDRs. In certain embodiments, the antibody further comprises the framework regions of the $V_H/V_L$ pair.

In some embodiments, the antibody comprises three heavy chain CDRs, or variants thereof, and three light chain CDRs, or variants thereof, from a $V_H/V_L$ pair selected from the group consisting of: 854/1022, 855/1022, 856/1022, 857/1022, 858/1022, 859/1022, 860/1022, 861/1022, 862/1022, 863/1022, 864/1022, 865/1022, 866/1022, 867/1022, 868/1022, 869/1022, 870/1022, 871/1022, 872/1022, 873/1022, 874/1022, 875/1022, 876/1022, 877/1022, 878/1022, 879/1022, 880/1022, 881/1022, 882/1022, 883/1022, 884/1022, 885/1022, 886/1022, 887/1022, 888/1022, 889/1022, 890/1022, 891/1022, 892/1022, 893/1022, 894/1022, 895/1022, 896/1022, 897/1022, 898/1022, 899/1022, 900/1022, 901/1022, 902/1022, 903/1022, 904/1022, 905/1022, 906/1022, 907/1022, 908/1022, 909/1022, 910/1022, 911/1022, 912/1022, 913/1022, 914/1022, 915/1022, 916/1022, 917/1022, 918/1022, 919/1022, 920/1022, 921/1022, 922/1022, 923/1022, 924/1022, 925/1022, 926/1022, 927/1022, 928/1022, 929/1022, 930/1022, 931/1022, 932/1022, 933/1022, 934/1022, 935/1022, 936/1022, 937/1022, 938/1022, 939/1022, 940/1022, 941/1022, 942/1022, 943/1022, 944/1022, 945/1022, 946/1022, 947/1022, 948/1022, 949/1022, 950/1022, 951/1022, 952/1022, 953/1022, 954/1022, 955/1022, 956/1022, 957/1022, 958/1022, 959/1022, 960/1022, 961/1022, 962/1022, 963/1022, 964/1022, 965/1022, 966/1022, 967/1022, 968/1022, 969/1022, 970/1022, 971/1022, 972/1022, 973/1022, 974/1022, 975/1022, 976/1022, 977/1022, 978/1022, 979/1022, 980/1022, 981/1022, 982/1022, 983/1022, 984/1022, 985/1022, 986/1022, 987/1022, 988/1022, 989/1022, 990/1022, 991/1022, 992/1022, 993/1022, 994/1022, 995/1022, 996/1022, 997/1022, 998/1022, 999/1022, 1000/1022, 1001/1022, 1002/1022, 1003/1022, 1004/1022, 1005/1022, 1006/1022, 1007/1022, 1008/1022, 1009/1022, 1010/1022, 1011/1022, 1012/1022, 1013/1022, 1014/1022, 1015/1022, 1016/1022, 1017/1022, 1018/1022, 1019/1022, and 1020/1022. The CDRs can be according to any CDR scheme known to the person of skill. In certain embodiments, the CDRs are Kabat CDRs. In certain embodiments, the CDRs are Chothia CDRs. In certain embodiments, the antibody further comprises the framework regions of the $V_H/V_L$ pair.

In some embodiments, the antibody comprises three heavy chain CDRs, or variants thereof, and three light chain CDRs, or variants thereof, from a $V_H/V_L$ pair selected from the group consisting of: 854/1023, 855/1023, 856/1023, 857/1023, 858/1023, 859/1023, 860/1023, 861/1023, 862/1023, 863/1023, 864/1023, 865/1023, 866/1023, 867/1023, 868/1023, 869/1023, 870/1023, 871/1023, 872/1023, 873/1023, 874/1023, 875/1023, 876/1023, 877/1023, 878/1023, 879/1023, 880/1023, 881/1023, 882/1023, 883/1023, 884/1023, 885/1023, 886/1023, 887/1023, 888/1023, 889/1023, 890/1023, 891/1023, 892/1023, 893/1023, 894/1023, 895/1023, 896/1023, 897/1023, 898/1023, 899/1023, 900/1023, 901/1023, 902/1023, 903/1023, 904/1023, 905/1023, 906/1023, 907/1023, 908/1023, 909/1023, 910/1023, 911/1023, 912/1023, 913/1023, 914/1023, 915/1023, 916/1023, 917/1023, 918/1023, 919/1023, 920/1023, 921/1023, 922/1023, 923/1023, 924/1023, 925/1023, 926/1023, 927/1023, 928/1023, 929/1023, 930/1023, 931/1023, 932/1023, 933/1023, 934/1023, 935/1023, 936/1023, 937/1023, 938/1023, 939/1023, 940/1023, 941/1023, 942/1023, 943/1023, 944/1023, 945/1023, 946/1023, 947/1023, 948/1023, 949/1023, 950/1023, 951/1023, 952/1023, 953/1023, 954/1023, 955/1023, 956/1023, 957/1023, 958/1023, 959/1023, 960/1023, 961/1023, 962/1023, 963/1023, 964/1023, 965/1023, 966/1023, 967/1023, 968/1023, 969/1023, 970/1023, 971/1023, 972/1023, 973/1023, 974/1023, 975/1023, 976/1023, 977/1023, 978/1023, 979/1023, 980/1023, 981/1023, 982/1023, 983/1023, 984/1023, 985/1023, 986/1023, 987/1023, 988/1023, 989/1023, 990/1023, 991/1023, 992/1023, 993/1023, 994/1023, 995/1023, 996/1023, 997/1023, 998/1023, 999/1023, 1000/1023, 1001/1023, 1002/1023, 1003/1023, 1004/1023, 1005/1023, 1006/1023, 1007/1023, 1008/1023, 1009/1023, 1010/1023, 1011/1023, 1012/1023, 1013/1023, 1014/1023, 1015/1023, 1016/1023, 1017/1023, 1018/1023, 1019/1023, and 1020/1023.

In some embodiments, the antibody comprises three Chothia heavy chain CDRs according to one of the following groups of heavy chain CDR SEQ ID NOs: 4/338/672; 6/340/674; 7/341/675; 8/342/676; 9/343/677; 10/344/678; 11/345/679; 12/346/680; 13/347/681; 14/348/682; 15/349/683; 16/350/684; 17/351/685; 18/352/686; 19/353/687; 20/354/688; 21/355/689; 22/356/690; 23/357/691; 24/358/692; 25/359/693; 26/360/694; 27/361/695; 28/362/696; 29/363/697; 30/364/698; 31/365/699; 32/366/700; 33/367/701; 34/368/702; 35/369/703; 36/370/704; 37/371/705; 38/372/706; 39/373/707; 40/374/708; 41/375/709; 42/376/710; 43/377/711; 44/378/712; 45/379/713; 46/380/714; 47/381/715; 48/382/716; 49/383/717; 50/384/718; 51/385/719; 52/386/720; 53/387/721; 54/388/722; 55/389/723; 56/390/724; 57/391/725; 58/392/726; 59/393/727; 60/394/728; 61/395/729; 62/396/730; 63/397/731; 64/398/732;

65/399/733; 66/400/734; 67/401/735; 68/402/736; 69/403/737; 70/404/738; 71/405/739; 72/406/740; 73/407/741; 74/408/742; 75/409/743; 76/410/744; 77/411/745; 78/412/746; 79/413/747; 80/414/748; 81/415/749; 82/416/750; 83/417/751; 84/418/752; 85/419/753; 86/420/754; 87/421/755; 88/422/756; 89/423/757; 90/424/758; 91/425/759; 92/426/760; 93/427/761; 94/428/762; 95/429/763; 96/430/764; 97/431/765; 98/432/766; 99/433/767; 100/434/768; 101/435/769; 102/436/770; 103/437/771; 104/438/772; 105/439/773; 106/440/774; 107/441/775; 108/442/776; 109/443/777; 110/444/778; 111/445/779; 112/446/780; 113/447/781; 114/448/782; 115/449/783; 116/450/784; 117/451/785; 118/452/786; 119/453/787; 120/454/788; 121/455/789; 122/456/790; 123/457/791; 124/458/792; 125/459/793; 126/460/794; 127/461/795; 128/462/796; 129/463/797; 130/464/798; 131/465/799; 132/466/800; 133/467/801; 134/468/802; 135/469/803; 136/470/804; 137/471/805; 138/472/806; 139/473/807; 140/474/808; 141/475/809; 142/476/810; 143/477/811; 144/478/812; 145/479/813; 146/480/814; 147/481/815; 148/482/816; 149/483/817; 150/484/818; 151/485/819; 152/486/820; 153/487/821; 154/488/822; 155/489/823; 156/490/824; 157/491/825; 158/492/826; 159/493/827; 160/494/828; 161/495/829; 162/496/830; 163/497/831; 164/498/832; 165/499/833; 166/500/834; 167/501/835; 168/502/836; 169/503/837; and 170/504/838.

In some embodiments, the antibody comprises six CDRs according to one of the following groups of CDR SEQ ID NOs: 4/338/672/839/844/849; 5/339/673/839/844/849; 6/340/674/839/844/849; 7/341/675/839/844/849; 8/342/676/839/844/849; 9/343/677/839/844/849; 10/344/678/839/844/849; 11/345/679/839/844/849; 12/346/680/839/844/849; 13/347/681/839/844/849; 14/348/682/839/844/849; 15/349/683/839/844/849; 16/350/684/839/844/849; 17/351/685/839/844/849; 18/352/686/839/844/849; 19/353/687/839/844/849; 20/354/688/839/844/849; 21/355/689/839/844/849; 22/356/690/839/844/849; 23/357/691/839/844/849; 24/358/692/839/844/849; 25/359/693/839/844/849; 26/360/694/839/844/849; 27/361/695/839/844/849; 28/362/696/839/844/849; 29/363/697/839/844/849; 30/364/698/839/844/849; 31/365/699/839/844/849; 32/366/700/839/844/849; 33/367/701/839/844/849; 34/368/702/839/844/849; 35/369/703/839/844/849; 36/370/704/839/844/849; 37/371/705/839/844/849; 38/372/706/839/844/849; 39/373/707/839/844/849; 40/374/708/839/844/849; 41/375/709/839/844/849; 42/376/710/839/844/849; 43/377/711/839/844/849; 44/378/712/839/844/849; 45/379/713/839/844/849; 46/380/714/839/844/849; 47/381/715/839/844/849; 48/382/716/839/844/849; 49/383/717/839/844/849; 50/384/718/839/844/849; 51/385/719/839/844/849; 52/386/720/839/844/849; 53/387/721/839/844/849; 54/388/722/839/844/849; 55/389/723/839/844/849; 56/390/724/839/844/849; 57/391/725/839/844/849; 58/392/726/839/844/849; 59/393/727/839/844/849; 60/394/728/839/844/849; 61/395/729/839/844/849; 62/396/730/839/844/849; 63/397/731/839/844/849; 64/398/732/839/844/849; 65/399/733/839/844/849; 66/400/734/839/844/849; 67/401/735/839/844/849; 68/402/736/839/844/849; 69/403/737/839/844/849; 70/404/738/839/844/849; 71/405/739/839/844/849; 72/406/740/839/844/849; 73/407/741/839/844/849; 74/408/742/839/844/849; 75/409/743/839/844/849; 76/410/744/839/844/849; 77/411/745/839/844/849; 78/412/746/839/844/849; 79/413/747/839/844/849; 80/414/748/839/844/849; 81/415/749/839/844/849; 82/416/750/839/844/849; 83/417/751/839/844/849; 84/418/752/839/844/849; 85/419/753/839/844/849; 86/420/754/839/844/849; 87/421/755/839/844/849; 88/422/756/839/844/849; 89/423/757/839/844/849; 90/424/758/839/844/849; 91/425/759/839/844/849; 92/426/760/839/844/849; 93/427/761/839/844/849; 94/428/762/839/844/849; 95/429/763/839/844/849; 96/430/764/839/844/849; 97/431/765/839/844/849; 98/432/766/839/844/849; 99/433/767/839/844/849; 100/434/768/839/844/849; 101/435/769/839/844/849; 102/436/770/839/844/849; 103/437/771/839/844/849; 104/438/772/839/844/849; 105/439/773/839/844/849; 106/440/774/839/844/849; 107/441/775/839/844/849; 108/442/776/839/844/849; 109/443/777/839/844/849; 110/444/778/839/844/849; 111/445/779/839/844/849; 112/446/780/839/844/849; 113/447/781/839/844/849; 114/448/782/839/844/849; 115/449/783/839/844/849; 116/450/784/839/844/849; 117/451/785/839/844/849; 118/452/786/839/844/849; 119/453/787/839/844/849; 120/454/788/839/844/849; 121/455/789/839/844/849; 122/456/790/839/844/849; 123/457/791/839/844/849; 124/458/792/839/844/849; 125/459/793/839/844/849; 126/460/794/839/844/849; 127/461/795/839/844/849; 128/462/796/839/844/849; 129/463/797/839/844/849; 130/464/798/839/844/849; 131/465/799/839/844/849; 132/466/800/839/844/849; 133/467/801/839/844/849; 134/468/802/839/844/849; 135/469/803/839/844/849; 136/470/804/839/844/849; 137/471/805/839/844/849; 138/472/806/839/844/849; 139/473/807/839/844/849; 140/474/808/839/844/849; 141/475/809/839/844/849; 142/476/810/839/844/849; 143/477/811/839/844/849; 144/478/812/839/844/849; 145/479/813/840/845/850; 146/480/814/840/845/850; 147/481/815/840/845/850; 148/482/816/840/845/850; 149/483/817/840/845/850; 150/484/818/840/845/850; 151/485/819/840/845/850; 152/486/820/840/845/850; 153/487/821/840/845/850; 154/488/822/840/845/850; 155/489/823/840/845/850; 156/490/824/840/845/850; 157/491/825/840/845/850; 158/492/826/840/845/850; 159/493/827/840/845/850; 160/494/828/840/845/850; 161/495/829/840/845/850; 162/496/830/840/845/850; 163/497/831/840/845/850; 164/498/832/840/845/850; 165/499/833/840/845/850; 166/500/834/840/845/850; 167/501/835/840/845/850; 168/502/836/840/845/850; 169/503/837/840/845/850; 170/504/838/840/845/850; 145/479/813/841/846/851; 146/480/814/841/846/851; 147/481/815/841/846/851; 148/482/816/841/846/851; 149/483/817/841/846/851; 150/484/818/841/846/851; 151/485/819/841/846/851; 152/486/820/841/846/851; 153/487/821/841/846/851; 154/488/822/841/846/851; 155/489/823/841/846/851; 156/490/824/841/846/851; 157/491/825/841/846/851; 158/492/826/841/846/851; 159/493/827/841/846/851; 160/494/828/841/846/851; 161/495/829/841/846/851; 162/496/830/841/846/851; 163/497/831/841/846/851; 164/498/832/841/846/851; 165/499/833/841/846/851; 166/500/834/841/846/851; 167/501/835/841/846/851; 168/502/836/841/846/851; 169/503/837/841/846/851; and 170/504/838/841/846/851.

In some embodiments, the isolated antibody comprises three Kabat HC CDRs according to one of the following groups of HC CDR SEQ ID NOs: 171/505/672; 172/506/673; 173/507/674; 174/508/675; 175/509/676; 176/510/677; 177/511/678; 178/512/679; 179/513/680; 180/514/681; 181/515/682; 182/516/683; 183/517/684; 184/518/685; 185/519/686; 186/520/687; 187/521/688; 188/522/689; 189/523/690; 190/524/691; 191/525/692; 192/526/693; 193/527/694; 194/528/695; 195/529/696; 196/530/697; 197/531/698; 198/532/699; 199/533/700; 200/534/701; 201/535/702; 202/536/703; 203/537/704; 204/538/705; 205/539/706; 206/540/707; 207/541/708; 208/542/709; 209/543/710; 210/544/711; 211/545/712; 212/546/713; 213/547/714; 214/548/715; 215/549/716; 216/550/717; 217/551/718; 218/552/719; 219/553/720; 220/554/721; 221/555/722; 222/556/723; 223/557/724; 224/558/725; 225/559/726; 226/560/727; 227/561/728; 228/562/729; 229/563/730; 230/564/731; 231/565/732; 232/566/733; 233/567/734; 234/568/735; 235/569/736; 236/570/737; 237/571/

738; 238/572/739; 239/573/740; 240/574/741; 241/575/742; 242/576/743; 243/577/744; 244/578/745; 245/579/746; 246/580/747; 247/581/748; 248/582/749; 249/583/750; 250/584/751; 251/585/752; 252/586/753; 253/587/754; 254/588/755; 255/589/756; 256/590/757; 257/591/758; 258/592/759; 259/593/760; 260/594/761; 261/595/762; 262/596/763; 263/597/764; 264/598/765; 265/599/766; 266/600/767; 267/601/768; 268/602/769; 269/603/770; 270/604/771; 271/605/772; 272/606/773; 273/607/774; 274/608/775; 275/609/776; 276/610/777; 277/611/778; 278/612/779; 279/613/780; 280/614/781; 281/615/782; 282/616/783; 283/617/784; 284/618/785; 285/619/786; 286/620/787; 287/621/788; 288/622/789; 289/623/790; 290/624/791; 291/625/792; 292/626/793; 293/627/794; 294/628/795; 295/629/796; 296/630/797; 297/631/798; 298/632/799; 299/633/800; 300/634/801; 301/635/802; 302/636/803; 303/637/804; 304/638/805; 305/639/806; 306/640/807; 307/641/808; 308/642/809; 309/643/810; 310/644/811; 311/645/812; 312/646/813; 313/647/814; 314/648/815; 315/649/816; 316/650/817; 317/651/818; 318/652/819; 319/653/820; 320/654/821; 321/655/822; 322/656/823; 323/657/824; 324/658/825; 325/659/826; 326/660/827; 327/661/828; 328/662/829; 329/663/830; 330/664/831; 331/665/832; 332/666/833; 333/667/834; 334/668/835; 335/669/836; 336/670/837; and 337/671/838.

In some embodiments, the isolated antibody comprises six CDRs according to one of the following groups of CDR SEQ ID NOs: 171/505/672/839/844/849; 172/506/673/839/844/849; 173/507/674/839/844/849; 174/508/675/839/844/849; 175/509/676/839/844/849; 176/510/677/839/844/849; 177/511/678/839/844/849; 178/512/679/839/844/849; 179/513/680/839/844/849; 180/514/681/839/844/849; 181/515/682/839/844/849; 182/516/683/839/844/849; 183/517/684/839/844/849; 184/518/685/839/844/849; 185/519/686/839/844/849; 186/520/687/839/844/849; 187/521/688/839/844/849; 188/522/689/839/844/849; 189/523/690/839/844/849; 190/524/691/839/844/849; 191/525/692/839/844/849; 192/526/693/839/844/849; 193/527/694/839/844/849; 194/528/695/839/844/849; 195/529/696/839/844/849; 196/530/697/839/844/849; 197/531/698/839/844/849; 198/532/699/839/844/849; 199/533/700/839/844/849; 200/534/701/839/844/849; 201/535/702/839/844/849; 202/536/703/839/844/849; 203/537/704/839/844/849; 204/538/705/839/844/849; 205/539/706/839/844/849; 206/540/707/839/844/849; 207/541/708/839/844/849; 208/542/709/839/844/849; 209/543/710/839/844/849; 210/544/711/839/844/849; 211/545/712/839/844/849; 212/546/713/839/844/849; 213/547/714/839/844/849; 214/548/715/839/844/849; 215/549/716/839/844/849; 216/550/717/839/844/849; 217/551/718/839/844/849; 218/552/719/839/844/849; 219/553/720/839/844/849; 220/554/721/839/844/849; 221/555/722/839/844/849; 222/556/723/839/844/849; 223/557/724/839/844/849; 224/558/725/839/844/849; 225/559/726/839/844/849; 226/560/727/839/844/849; 227/561/728/839/844/849; 228/562/729/839/844/849; 229/563/730/839/844/849; 230/564/731/839/844/849; 231/565/732/839/844/849; 232/566/733/839/844/849; 233/567/734/839/844/849; 234/568/735/839/844/849; 235/569/736/839/844/849; 236/570/737/839/844/849; 237/571/738/839/844/849; 238/572/739/839/844/849; 239/573/740/839/844/849; 240/574/741/839/844/849; 241/575/742/839/844/849; 242/576/743/839/844/849; 243/577/744/839/844/849; 244/578/745/839/844/849; 245/579/746/839/844/849; 246/580/747/839/844/849; 247/581/748/839/844/849; 248/582/749/839/844/849; 249/583/750/839/844/849; 250/584/751/839/844/849; 251/585/752/839/844/849; 252/586/753/839/844/849; 253/587/754/839/844/849; 254/588/755/839/844/849; 255/589/756/839/844/849; 256/590/757/839/844/849; 257/591/758/839/844/849; 258/592/759/839/844/849; 259/593/760/839/844/849; 260/594/761/839/844/849; 261/595/762/839/844/849; 262/596/763/839/844/849; 263/597/764/839/844/849; 264/598/765/839/844/849; 265/599/766/839/844/849; 266/600/767/839/844/849; 267/601/768/839/844/849; 268/602/769/839/844/849; 269/603/770/839/844/849; 270/604/771/839/844/849; 271/605/772/839/844/849; 272/606/773/839/844/849; 273/607/774/839/844/849; 274/608/775/839/844/849; 275/609/776/839/844/849; 276/610/777/839/844/849; 277/611/778/839/844/849; 278/612/779/839/844/849; 279/613/780/839/844/849; 280/614/781/839/844/849; 281/615/782/839/844/849; 282/616/783/839/844/849; 283/617/784/839/844/849; 284/618/785/839/844/849; 285/619/786/839/844/849; 286/620/787/839/844/849; 287/621/788/839/844/849; 288/622/789/839/844/849; 289/623/790/839/844/849; 290/624/791/839/844/849; 291/625/792/839/844/849; 292/626/793/839/844/849; 293/627/794/839/844/849; 294/628/795/839/844/849; 295/629/796/839/844/849; 296/630/797/839/844/849; 297/631/798/839/844/849; 298/632/799/839/844/849; 299/633/800/839/844/849; 300/634/801/839/844/849; 301/635/802/839/844/849; 302/636/803/839/844/849; 303/637/804/839/844/849; 304/638/805/839/844/849; 305/639/806/839/844/849; 306/640/807/839/844/849; 307/641/808/839/844/849; 308/642/809/839/844/849; 309/643/810/839/844/849; 310/644/811/839/844/849; 311/645/812/840/845/850; 312/646/813/840/845/850; 313/647/814/840/845/850; 314/648/815/840/845/850; 315/649/816/840/845/850; 316/650/817/840/845/850; 317/651/818/840/845/850; 318/652/819/840/845/850; 319/653/820/840/845/850; 320/654/821/840/845/850; 321/655/822/840/845/850; 322/656/823/840/845/850; 323/657/824/840/845/850; 324/658/825/840/845/850; 325/659/826/840/845/850; 326/660/827/840/845/850; 327/661/828/840/845/850; 328/662/829/840/845/850; 329/663/830/840/845/850; 330/664/831/840/845/850; 331/665/832/840/845/850; 332/666/833/840/845/850; 333/667/834/840/845/850; 334/668/835/840/845/850; 335/669/836/840/845/850; 336/670/837/840/845/850; 337/671/838/840/845/850; 311/645/812/841/846/851; 312/646/813/841/846/851; 313/647/814/841/846/851; 314/648/815/841/846/851; 315/649/816/841/846/851; 316/650/817/841/846/851; 317/651/818/841/846/851; 318/652/819/841/846/851; 319/653/820/841/846/851; 320/654/821/841/846/851; 321/655/822/841/846/851; 322/656/823/841/846/851; 323/657/824/841/846/851; 324/658/825/841/846/851; 325/659/826/841/846/851; 326/660/827/841/846/851; 327/661/828/841/846/851; 328/662/829/841/846/851; 329/663/830/841/846/851; 330/664/831/841/846/851; 331/665/832/841/846/851; 332/666/833/841/846/851; 333/667/834/841/846/851; 334/668/835/841/846/851; 335/669/836/841/846/851; 336/670/837/841/846/851; and 337/671/838/841/846/851.

In certain embodiments, the CDRs can be according to any CDR scheme known to the person of skill. In certain embodiments, the CDRs are Kabat CDRs. In certain embodiments, the CDRs are Chothia CDRs. In certain embodiments, the antibody further comprises the framework regions of the $V_H$/$V_L$ pair.

5.8.1. Variants of Antibodies Comprising all Six CDRs

In some embodiments, the CDR-H1, CDR-H2, CDR-H3, CDR-L1, CDR-L2, and CDR-L3 provided herein comprise a variant of an illustrative CDR-H1, CDR-H2, CDR-H3, CDR-L1, CDR-L2, and/or CDR-L3 sequence provided in this disclosure.

In some aspects, the CDR-H1 sequence comprises, consists of, or consists essentially of a variant of an illustrative Chothia or Kabat CDR-H1 sequence provided in this disclosure. In some aspects, the CDR-H1 sequence comprises, consists of, or consists essentially of a sequence having at least 70%, 75%, 80%, 85%, 95%, 96%, 97%, 98%, or 99% identity with any of the illustrative Chothia or Kabat CDR-H1 sequences provided in this disclosure. In some aspects, the CDR-H1 sequence comprises, consists of, or consists essentially of any of the illustrative Chothia or Kabat CDR-H1 sequences provided in this disclosure, with 1, 2, or 3 amino acid substitutions. In some aspects, the amino acid substitutions are conservative amino acid substitutions.

In some aspects, the CDR-H2 sequence comprises, consists of, or consists essentially of a variant of an illustrative Chothia or Kabat CDR-H2 sequence provided in this disclosure. In some aspects, the CDR-H2 sequence comprises, consists of, or consists essentially of a sequence having at least 70%, 75%, 80%, 85%, 90%, 95%, 96%, 97%, 98%, or 99% identity with any of the illustrative Chothia or Kabat CDR-H2 sequences provided in this disclosure. In some aspects, the CDR-H2 sequence comprises, consists of, or consists essentially of any of the illustrative Chothia or Kabat CDR-H2 sequences provided in this disclosure, with 1, 2, or 3 amino acid substitutions. In some aspects, the amino acid substitutions are conservative amino acid substitutions.

In some aspects, the CDR-H3 sequence comprises, consists of, or consists essentially of a variant of an illustrative CDR-H3 sequence provided in this disclosure. In some aspects, the CDR-H3 sequence comprises, consists of, or consists essentially of a sequence having at least 70%, 75%, 80%, 85%, 90%, 95%, 96%, 97%, 98%, or 99% identity with any of the illustrative CDR-H3 sequences provided in this disclosure. In some aspects, the CDR-H3 sequence comprises, consists of, or consists essentially of any of the illustrative CDR-H3 sequences provided in this disclosure, with 1, 2, or 3 amino acid substitutions. In some aspects, the amino acid substitutions are conservative amino acid substitutions.

In some aspects, the CDR-L1 sequence comprises, consists of, or consists essentially of a variant of an illustrative CDR-L1 sequence provided in this disclosure. In some aspects, the CDR-L1 sequence comprises, consists of, or consists essentially of a sequence having at least 70%, 75%, 80%, 85%, 90%, 95%, 96%, 97%, 98%, or 99% identity with any of the illustrative CDR-L1 sequences provided in this disclosure. In some aspects, the CDR-L1 sequence comprises, consists of, or consists essentially of any of the illustrative CDR-L1 sequences provided in this disclosure, with 1, 2, or 3 amino acid substitutions. In some aspects, the amino acid substitutions are conservative amino acid substitutions.

In some aspects, the CDR-L2 sequence comprises, consists of, or consists essentially of a variant of an illustrative CDR-L2 sequence provided in this disclosure. In some aspects, the CDR-L2 sequence comprises, consists of, or consists essentially of a sequence having at least 70%, 75%, 80%, 85%, 90%, 95%, 96%, 97%, 98%, or 99% identity with any of the illustrative CDR-L2 sequences provided in this disclosure. In some aspects, the CDR-L2 sequence comprises, consists of, or consists essentially of any of the illustrative CDR-L2 sequences provided in this disclosure, with 1, 2, or 3 amino acid substitutions. In some aspects, the amino acid substitutions are conservative amino acid substitutions.

In some aspects, the CDR-L3 sequence comprises, consists of, or consists essentially of a variant of an illustrative CDR-L3 sequence provided in this disclosure. In some aspects, the CDR-L3 sequence comprises, consists of, or consists essentially of a sequence having at least 70%, 75%, 80%, 85%, 90%, 95%, 96%, 97%, 98%, or 99% identity with any of the illustrative CDR-L3 sequences provided in this disclosure. In some aspects, the CDR-L3 sequence comprises, consists of, or consists essentially of any of the illustrative CDR-L3 sequences provided in this disclosure, with 1, 2, or 3 amino acid substitutions. In some aspects, the amino acid substitutions are conservative amino acid substitutions.

6. Germline

In some embodiments, the antibody or antibody of the conjugate that specifically binds ROR1 is an antibody comprising a variable region that is encoded by a particular germline gene, or a variant thereof. The illustrative antibodies provided herein comprise variable regions that are encoded by the heavy chain variable region germline genes VH1-18, VH3-33, VH2-5, VH2-70, and VH4-30-4. or variants thereof; and the light chain variable region germline genes Vκ1-5, Vκ3-11, Vκ2-20, Vκ1-33, and Vκ1-16, or variants thereof.

One of skill in the art would recognize that the CDR sequences provided herein may also be useful when combined with variable regions encoded by other variable region germline genes, or variants thereof. In particular, the CDR sequences provided herein may be useful when combined with variable regions encoded by variable region germline genes, or variants thereof, that are structurally similar to the variable region germline genes recited above. For example, in some embodiments, a CDR-H sequence provided herein may be combined with a variable region encoded by a variable region germline gene selected from the $V_H1$, $V_H2$, $V_H3$, or $V_H4$ families, or a variant thereof. In some embodiments, a CDR-L sequence provided herein may be combined with a variable region encoded by a variable region germline gene selected from the Vκ1, Vκ2, or Vκ3, or a variant thereof.

7. Affinity

In some embodiments, the affinity of the antibody for ROR1 as indicated by $K_D$, is less than about $10^{-5}$ M, less than about $10^{-6}$ M, less than about $10^{-7}$ M, less than about $10^{-8}$ M, less than about $10^{-9}$ M, or less than about $10^{-10}$ M. In some embodiments, the affinity of the antibody is between about $10^{-7}$ M and $10^{-11}$ M. In some embodiments, the affinity of the antibody is between about $10^{-7}$ M and $10^{-10}$ M. In some embodiments, the affinity of the antibody is between about $10^{-7}$ M and $10^{-9}$ M. In some embodiments, the affinity of the antibody is between about $10^{-7}$ M and $10^{-8}$ M. In some embodiments, the affinity of the antibody is between about $10^{-8}$ M and $10^{-11}$ M. In some embodiments, the affinity of the antibody is between about $10^{-8}$ M and $10^{-10}$ M. In some embodiments, the affinity of the antibody is between about $10^{-9}$ M and $10^{-11}$ M. In some embodiments, the affinity of the antibody is between about $10^{-9}$ M and $10^{-10}$ M.

In some embodiments, the affinity of the antibody for human ROR1, human ROR1 extracellular domain, or for individual domains within human ROR1, as determined by surface plasmon resonance at 25° C., and as indicated by $K_D$, is from about $1.39\times10^{-10}$ M to about $1.01\times10^{-7}$ M. In some embodiments, the affinity of the antibody for human ROR1, as determined by surface plasmon resonance at 25° C., and as indicated by $K_D$, is from about $5.04\times10^{-10}$ M to about $9.76\times10^{-8}$ M. In some embodiments, the affinity of the antibody for human ROR1, as determined by surface plasmon resonance at 25° C., and as indicated by $K_D$, is from about $1.06\times10^{-9}$ M to about $2.45\times10^{-8}$ M. In some embodiments, the affinity of the antibody for human ROR1 is about any of the $K_D$ values reported for human ROR1 in the examples below.

In some embodiments the antibody has a $k_a$ of at least about $10^4$ $M^{-1} \times sec^{-1}$. In some embodiments the antibody has a $k_a$ of at least about $10^5$ $M^{-1} \times sec^{-1}$. In some embodiments the antibody has a $k_a$ of at least about $10^6$ $M^{-1} \times sec^{-1}$. In some embodiments the antibody has a $k_a$ of between about $10^4$ $M^{-1} \times sec^{-1}$ and about $10^7$ $M^{-1} \times sec^{-1}$. In some embodiments the antibody has a $k_a$ of between about $10^5$ $M^{-1} \times sec^{-1}$ and about $10^7$ $M^{-1} \times sec^{-1}$. In some embodiments the antibody has a $k_a$ of between about $10^6$ $M^{-1} \times sec^{-1}$ and about $10^7$ $M^{-1} \times sec^{-1}$.

In some embodiments the antibody has a $k_a$ when associating with human ROR1, human ROR1 extracellular domain, or for individual domains within human ROR1, as determined by surface plasmon resonance at 25° C., of from about $9.17 \times 10^4$ $M^{-1} \times sec^{-1}$ to about $5.94 \times 10^6$ $M^{-1} \times sec^{-1}$. In some embodiments the antibody has a $k_a$ when associating with human ROR1, as determined by surface plasmon resonance at 25° C., of from about $1.71 \times 10^5$ $M^{-1} \times sec^{-1}$ to about $1.17 \times 10^6$ $M^{-1} \times sec^{-1}$. In some embodiments the antibody has a $k_a$ when associating with human ROR1, as determined by surface plasmon resonance at 25° C., of from about $2.56 \times 10^5$ $M^{-1} \times sec^{-1}$ to about $7.75 \times 10^5$ $M^{-1} \times sec^{-1}$. In some embodiments the antibody has a $k_a$ when associating with human ROR1 of about any of the $k_a$ values reported for human ROR1 in the examples below.

In some embodiments the antibody has a $k_d$ of about $10^{-5}$ $sec^{-1}$ or less. In some embodiments the antibody has a $k_d$ of about $10^{-4}$ $sec^{-1}$ or less. In some embodiments the antibody has a $k_d$ of about $10^{-3}$ $sec^{-1}$ or less. In some embodiments the antibody has a $k_d$ of between about $10^{-2}$ $sec^{-1}$ and about $10^{-5}$ $sec^{-1}$. In some embodiments the antibody has a $k_d$ of between about $10^{-2}$ $sec^{-1}$ and about $10^{-4}$ $sec^{-1}$. In some embodiments the antibody has a $k_d$ of between about $10^{-3}$ $sec^{-1}$ and about $10^{-5}$ $sec^{-1}$.

In some embodiments the antibody has a $k_d$ when dissociating from human ROR1, human ROR1 extracellular domain, or for individual domains within human ROR1, as determined by surface plasmon resonance at 25° C., of from about $1.01 \times 10^{-4}$ $sec^{-1}$ to about $0.05$ $sec^{-1}$. In some embodiments the antibody has a $k_d$ when dissociating from human ROR1, as determined by surface plasmon resonance at 25° C., of from about $2.27 \times 10^{-4}$ $sec^{-1}$ to about $0.01$ $sec^{-1}$. In some embodiments the antibody has a $k_d$ when dissociating from human ROR1, as determined by surface plasmon resonance at 25° C., of from about $5.05 \times 10^{-4}$ $sec^{-1}$ to about $8.50 \times 10^{-3}$ $sec^{-1}$. In some embodiments the antibody has a $k_d$ when dissociating from human ROR1 of about any of the $k_d$ values reported for human ROR1 in the examples below.

In some aspects, the $K_D$, $k_a$, and $k_d$ are determined at 25° C. In some embodiments, the $K_D$, $k_a$, and $k_d$ are determined by surface plasmon resonance. In some embodiments, the $K_D$, $k_a$, and $k_d$ are determined according to the methods described in the Examples provided herein.

8. Epitope Bins

In some embodiments, the antibody binds the same epitope as an antibody encompassing any of SEQ ID NOs: 854-1020. In some embodiments, the antibody binds the same epitope as an antibody comprising any of the $V_H$-$V_L$ pairs, above. In some embodiments, the antibody competes for epitope binding with an antibody encompassing any of SEQ ID NOs: 854-1020. In some embodiments, the antibody competes for epitope binding with an antibody comprising any of the $V_H$-$V_L$ pairs, above.

9. Glycosylation Variants

In certain embodiments, an antibody may be altered to increase, decrease or eliminate the extent to which it is glycosylated. Glycosylation of polypeptides is typically either "N-linked" or "O-linked."

"N-linked" glycosylation refers to the attachment of a carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site.

"O-linked" glycosylation refers to the attachment of one of the sugars N-acetylgalactosamine, galactose, or xylose to a hydroxyamino acid, most commonly serine or threonine, although 5-hydroxyproline or 5-hydroxylysine may also be used.

Addition or deletion of N-linked glycosylation sites to the antibody may be accomplished by altering the amino acid sequence such that one or more of the above-described tripeptide sequences is created or removed. Addition or deletion of O-linked glycosylation sites may be accomplished by addition, deletion, or substitution of one or more serine or threonine residues in or to (as the case may be) the sequence of an antibody.

10. Fc Variants

In certain embodiments, amino acid modifications may be introduced into the Fc region of an antibody provided herein to generate an Fc region variant. In certain embodiments, the Fc region variant possesses some, but not all, effector functions. Such antibodies may be useful, for example, in applications in which the half-life of the antibody in vivo is important, yet certain effector functions are unnecessary or deleterious. Examples of effector functions include complement-dependent cytotoxicity (CDC) and antibody-directed complement-mediated cytotoxicity (ADCC). Numerous substitutions or substitutions or deletions with altered effector function are known in the art.

In some embodiments, the Fc comprises one or more modifications in at least one of the $C_H3$ sequences. In some embodiments, the Fc comprises one or more modifications in at least one of the $C_H2$ sequences. For example, the Fc can include one or modifications selected from the group consisting of: V262E, V262D, V262K, V262R, V262S, V264S, V303R, and V305R. In some embodiments, an Fc is a single polypeptide. In some embodiments, an Fc is multiple peptides, e.g., two polypeptides. Exemplary modifications in the Fc region are described, for example, in International Patent Application No. PCT/US2017/037545, filed Jun. 14, 2017.

An alteration in in CDC and/or ADCC activity can be confirmed using in vitro and/or in vivo assays. For example, Fc receptor (FcR) binding assays can be conducted to measure FcγR binding. The primary cells for mediating ADCC, NK cells, express FcγRIII only, whereas monocytes express FcγRI, FcγRII and FcγRIII FcR expression on hematopoietic cells is summarized in Ravetch and Kinet, *Ann. Rev. Immunol.*, 1991, 9:457-492, incorporated by reference in its entirety.

Non-limiting examples of in vitro assays to assess ADCC activity of a molecule of interest are provided in U.S. Pat. Nos. 5,500,362 and 5,821,337; Hellstrom et al., *Proc. Natl. Acad. Sci. U.S.A.*, 1986, 83:7059-7063; Hellstrom et al., *Proc. Natl. Acad. Sci. U.S.A.*, 1985, 82:1499-1502; and Bruggemann et al., *J. Exp. Med.*, 1987, 166:1351-1361; each of which is incorporated by reference in its entirety. Useful effector cells for such assays include peripheral blood mononuclear cells (PBMC) and Natural Killer (NK) cells. Alternatively, or additionally, ADCC activity of the molecule of interest may be assessed in vivo, using an animal model such as that disclosed in Clynes et al. *Proc. Natl. Acad. Sci. U.S.A.*, 1998, 95:652-656, incorporated by reference in its entirety.

C1q binding assays may also be carried out to confirm that the antibody is unable to bind C1q and hence lacks CDC activity. Examples of C1q binding assays include those described in WO 2006/029879 and WO 2005/100402, each of which is incorporated by reference in its entirety.

Complement activation assays include those described, for example, in Gazzano-Santoro et al., *J. Immunol. Methods*, 1996, 202:163-171; Cragg et al., *Blood*, 2003, 101:1045-1052; and Cragg and Glennie, *Blood*, 2004, 103:2738-2743; each of which is incorporated by reference in its entirety.

FcRn binding and in vivo clearance (half-life determination) can also be measured, for example, using the methods described in Petkova et al., *Intl. Immunol.*, 2006, 18:1759-1769, incorporated by reference in its entirety.

11. Modified Amino Acids

When the antibody conjugate comprises a modified amino acid, the modified amino acid can be any modified amino acid deemed suitable by the practitioner. In particular embodiments, the modified amino acid comprises a reactive group useful for forming a covalent bond to a linker precursor or to a payload precursor. In certain embodiments, the modified amino acid is a non-natural amino acid. In certain embodiments, the reactive group is selected from the group consisting of amino, carboxy, acetyl, hydrazino, hydrazido, semicarbazido, sulfanyl, azido and alkynyl. Modified amino acids are also described in, for example, WO 2013/185115 and WO 2015/006555, each of which is incorporated herein by reference in its entirety.

In certain embodiments, the amino acid residue is according to any of the following formulas:

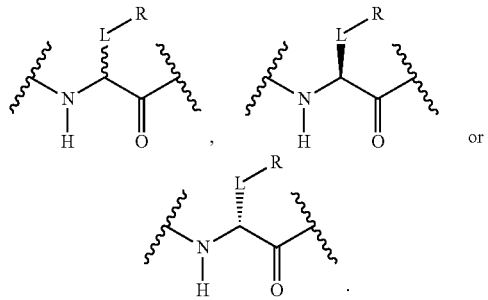

Those of skill in the art will recognize that antibodies are generally comprised of L-amino acids However, with non-natural amino acids, the present methods and compositions provide the practitioner with the ability to use L-, D- or racemic non-natural amino acids at the site-specific positions. In certain embodiments, the non-natural amino acids described herein include D-versions of the natural amino acids and racemic versions of the natural amino acids.

In the above formulas, the wavy lines indicate bonds that connect to the remainder of the polypeptide chains of the antibodies. These non-natural amino acids can be incorporated into polypeptide chains just as natural amino acids are incorporated into the same polypeptide chains. In certain embodiments, the non-natural amino acids are incorporated into the polypeptide chain via amide bonds as indicated in the formulas.

In the above formulas, R designates any functional group without limitation, so long as the amino acid residue is not identical to a natural amino acid residue. In certain embodiments, R can be a hydrophobic group, a hydrophilic group, a polar group, an acidic group, a basic group, a chelating group, a reactive group, a therapeutic moiety or a labeling moiety. In certain embodiments, R is selected from the group consisting of $R^{1a}NR^{2a}R^{3a}$, $R^{1a}C(O)R^{2a}$, $R^{1a}C(=O)OR^{2a}$, $R^{1a}N_3$, $R^{1a}C(\equiv CH)$. In these embodiments, $R^{1a}$ is selected from the group consisting of a bond, alkylene, heteroalkylene, arylene, heteroarylene. $R^{2a}$ and $R^{3a}$ are each independently selected from the group consisting of hydrogen, alkyl and heteroalkyl.

In some embodiments, the non-naturally encoded amino acids include side chain functional groups that react efficiently and selectively with functional groups not found in the 20 common amino acids (including but not limited to, azido, ketone, aldehyde and aminooxy groups) to form stable conjugates. For example, antigen-binding polypeptide that includes a non-naturally encoded amino acid containing an azido functional group can be reacted with a polymer (including but not limited to, poly(ethylene glycol) or, alternatively, a second polypeptide containing an alkyne moiety to form a stable conjugate resulting for the selective reaction of the azide and the alkyne functional groups to form a Huisgen [3+2] cycloaddition product.

Exemplary non-naturally encoded amino acids that may be suitable for use in the present invention and that are useful for reactions with water soluble polymers include, but are not limited to, those with carbonyl, aminooxy, hydrazine, hydrazide, semicarbazide, azide and alkyne reactive groups. In some embodiments, non-naturally encoded amino acids comprise a saccharide moiety. Examples of such amino acids include N-acetyl-L-glucosaminyl-L-serine, N-acetyl-L-galactosaminyl-L-serine, N-acetyl-L-glucosaminyl-L-threonine, N-acetyl-L-glucosaminyl-L-asparagine and O-mannosaminyl-L-serine. Examples of such amino acids also include examples where the naturally-occurring N- or O-linkage between the amino acid and the saccharide is replaced by a covalent linkage not commonly found in nature—including but not limited to, an alkene, an oxime, a thioether, an amide and the like. Examples of such amino acids also include saccharides that are not commonly found in naturally-occurring proteins such as 2-deoxy-glucose, 2-deoxygalactose and the like.

Many of the non-naturally encoded amino acids provided herein are commercially available, e.g., from Sigma-Aldrich (St. Louis, Mo., USA), Novabiochem (a division of EMD Biosciences, Darmstadt, Germany), or Peptech (Burlington, Mass., USA). Those that are not commercially available are optionally synthesized as provided herein or using standard methods known to those of skill in the art. For organic synthesis techniques, see, e.g., Organic Chemistry by Fessendon and Fessendon, (1982, Second Edition, Willard Grant Press, Boston Mass.); Advanced Organic Chemistry by March (Third Edition, 1985, Wiley and Sons, New York);

and Advanced Organic Chemistry by Carey and Sundberg (Third Edition, Parts A and B, 1990, Plenum Press, New York). See, also, U.S. Patent Application Publications 2003/0082575 and 2003/0108885, which is incorporated by reference herein. In addition to unnatural amino acids that contain unnatural side chains, unnatural amino acids that may be suitable for use in the present invention also optionally comprise modified backbone structures, including but not limited to, as illustrated by the structures of Formula II-1 and III-1:

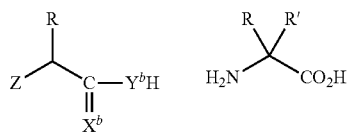

wherein Z typically comprises OH, $NH_2$, SH, NH—R', or S—R'; $X^b$ and $Y^b$, which can be the same or different, typically comprise S or O, and R and R', which are optionally the same or different, are typically selected from the same list of constituents for the R group described herein for the unnatural amino acids having Formula I-I as well as hydrogen. For example, unnatural amino acids of the invention optionally comprise substitutions in the amino or carboxyl group as illustrated by Formulas II-I and III-I. Unnatural amino acids of this type include, but are not limited to, α-hydroxy acids, α-thioacids, α-aminothiocarboxylates, including but not limited to, with side chains corresponding to the common twenty natural amino acids or unnatural side chains. In addition, substitutions at the α-carbon optionally include, but are not limited to, L, D, or α-α-disubstituted amino acids such as D-glutamate, D-alanine, D-methyl-O-tyrosine, aminobutyric acid, and the like. Other structural alternatives include cyclic amino acids, such as proline analogues as well as 3, 4, 6, 7, 8, and 9 membered ring proline analogues, β and γ amino acids such as substituted β-alanine and γ-amino butyric acid.

Many unnatural amino acids are based on natural amino acids, such as tyrosine, glutamine, phenylalanine, and the like, and are suitable for use in the present invention. Tyrosine analogs include, but are not limited to, para-substituted tyrosines, ortho-substituted tyrosines, and meta substituted tyrosines, where the substituted tyrosine comprises, including but not limited to, a keto group (including but not limited to, an acetyl group), a benzoyl group, an amino group, a hydrazine, an hydroxyamine, a thiol group, a carboxy group, an isopropyl group, a methyl group, a $C_6$-$C_{20}$ straight chain or branched hydrocarbon, a saturated or unsaturated hydrocarbon, an O-methyl group, a polyether group, a nitro group, an alkynyl group or the like. In addition, multiply substituted aryl rings are also contemplated. Glutamine analogs that may be suitable for use in the present invention include, but are not limited to, α-hydroxy derivatives, γ-substituted derivatives, cyclic derivatives, and amide substituted glutamine derivatives. Example phenylalanine analogs that may be suitable for use in the present invention include, but are not limited to, para-substituted phenylalanines, ortho-substituted phenylalanines, and meta-substituted phenylalanines, where the substituent comprises, including but not limited to, a hydroxy group, a methoxy group, a methyl group, an allyl group, an aldehyde, an azido, an iodo, a bromo, a keto group (including but not limited to, an acetyl group), a benzoyl, an alkynyl group, or the like. Specific examples of unnatural amino acids that may be suitable for use in the present invention include, but are not limited to, a p-acetyl-L-phenylalanine, an O-methyl-L-tyrosine, an L-3-(2-naphthyl)alanine, a 3-methyl-phenylalanine, an O-4-allyl-L-tyrosine, a 4-propyl-L-tyrosine, a tri-O-acetyl-GlcNAcβ-serine, an L-Dopa, a fluorinated phenylalanine, an isopropyl-L-phenylalanine, a p-azido-L-phenylalanine, a p-azido-methyl-L-phenylalanine, a p-acyl-L-phenylalanine, a p-benzoyl-L-phenylalanine, an L-phosphoserine, a phosphonoserine, a phosphonotyrosine, a p-iodo-phenylalanine, a p-bromophenylalanine, a p-amino-L-phenylalanine, an isopropyl-L-phenylalanine, and a p-propargyloxy-phenylalanine, and the like. Examples of structures of a variety of unnatural amino acids that may be suitable for use in the present invention are provided in, for example, WO 2002/085923 entitled "In vivo incorporation of unnatural amino acids." See also Kiick et al., (2002) Incorporation of azides into recombinant proteins for chemoselective modification by the Staudinger ligation, PNAS 99:19-24, for additional methionine analogs.

Many of the unnatural amino acids suitable for use in the present invention are commercially available, e.g., from Sigma (USA) or Aldrich (Milwaukee, Wis., USA). Those that are not commercially available are optionally synthesized as provided herein or as provided in various publications or using standard methods known to those of skill in the art. For organic synthesis techniques, see, e.g., Organic Chemistry by Fessendon and Fessendon, (1982, Second Edition, Willard Grant Press, Boston Mass.); Advanced Organic Chemistry by March (Third Edition, 1985, Wiley and Sons, New York); and Advanced Organic Chemistry by Carey and Sundberg (Third Edition, Parts A and B, 1990, Plenum Press, New York). Additional publications describing the synthesis of unnatural amino acids include, e.g., WO 2002/085923 entitled "In vivo incorporation of Unnatural Amino Acids;" Matsoukas et al., (1995) J. Med. Chem., 38, 4660-4669; King, F. E. & Kidd, D. A. A. (1949) A New Synthesis of Glutamine and of γ-Dipeptides of Glutamic Acid from Phthylated Intermediates. J. Chem. Soc., 3315-3319; Friedman, 0. M. & Chatterrji, R. (1959) Synthesis of Derivatives of Glutamine as Model Substrates for Anti-Tumor Agents. J. Am. Chem. Soc. 81, 3750-3752; Craig, J. C. et al. (1988) Absolute Configuration of the Enantiomers of 7-Chloro-4 [[4-(diethylamino)-1-methylbutyl]amino]quinoline (Chloroquine). J. Org. Chem. 53, 1167-1170; Azoulay, M., Vilmont, M. & Frappier, F. (1991) Glutamine analogues as Potential Antimalarials, Eur. J. Med. Chem. 26, 201-5; Koskinen, A. M. P. & Rapoport, H. (1989) Synthesis of 4-Substituted Prolines as Conformationally Constrained Amino Acid Analogues. J. Org. Chem. 54, 1859-1866; Christie, B. D. & Rapoport, H. (1985) Synthesis of Optically Pure Pipecolates from L-Asparagine. Application to the Total Synthesis of (+)-Apovincamine through Amino Acid Decarbonylation and Iminium Ion Cyclization. J. Org. Chem. 1989:1859-1866; Barton et al., (1987) Synthesis of Novel a-Amino-Acids and Derivatives Using Radical Chemistry: Synthesis of L- and D-a-Amino-Adipic Acids, L-a-aminopimelic Acid and Appropriate Unsaturated Derivatives. Tetrahedron Lett. 43:4297-4308; and, Subasinghe et al., (1992) Quisqualic acid analogues: synthesis of beta-heterocyclic 2-aminopropanoic acid derivatives and their activity at a novel quisqualate-sensitized site. J. Med. Chem. 35:4602-7. See also, patent applications entitled "Protein Arrays," filed Dec. 22, 2003, Ser. No. 10/744,899 and Ser. No. 60/435,821 filed on Dec. 22, 2002.

Amino acids with a carbonyl reactive group allow for a variety of reactions to link molecules (including but not limited to, PEG or other water soluble molecules) via nucleophilic addition or aldol condensation reactions among others.

Exemplary carbonyl-containing amino acids can be represented as follows:

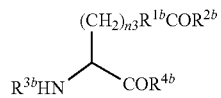

wherein n3 is 0-10; $R^{1b}$ is an alkyl, aryl, substituted alkyl, or substituted aryl; $R^{2b}$ is H, alkyl, aryl, substituted alkyl, and substituted aryl; and $R^{3b}$ is H, an amino acid, a polypeptide, or an amino terminus modification group, and $R^{4b}$ is H, an amino acid, a polypeptide, or a carboxy terminus modification group. In some embodiments, n3 is 1, $R^{1b}$ is phenyl and $R^{2b}$ is a simple alkyl (i.e., methyl, ethyl, or propyl) and the ketone moiety is positioned in the para position relative to the alkyl side chain. In some embodiments, n3 is 1, $R^{1b}$ is phenyl and $R^{2b}$ is a simple alkyl (i.e., methyl, ethyl, or propyl) and the ketone moiety is positioned in the meta position relative to the alkyl side chain.

In some examples, a non-naturally encoded amino acid bearing adjacent hydroxyl and amino groups can be incorporated into the polypeptide as a "masked" aldehyde functionality. For example, 5-hydroxylysine bears a hydroxyl group adjacent to the epsilon amine. Reaction conditions for generating the aldehyde typically involve addition of molar excess of sodium metaperiodate under mild conditions to avoid oxidation at other sites within the polypeptide. The pH of the oxidation reaction is typically about 7.0. A typical reaction involves the addition of about 1.5 molar excess of sodium meta periodate to a buffered solution of the polypeptide, followed by incubation for about 10 minutes in the dark. See, e.g. U.S. Pat. No. 6,423,685, which is incorporated by reference herein.

The carbonyl functionality can be reacted selectively with a hydrazine-, hydrazide-, hydroxylamine-, or semicarbazide-containing reagent under mild conditions in aqueous solution to form the corresponding hydrazone, oxime, or semicarbazone linkages, respectively, that are stable under physiological conditions. See, e.g., Jencks, W. P., J. Am. Chem. Soc. 81, 475-481 (1959); Shao, J. and Tam, J. P., J. Am. Chem. Soc. 117:3893-3899 (1995). Moreover, the unique reactivity of the carbonyl group allows for selective modification in the presence of the other amino acid side chains. See, e.g., Cornish, V. W., et al., J. Am. Chem. Soc. 118:8150-8151 (1996); Geoghegan, K. F. & Stroh, J. G., Bioconjug. Chem. 3:138-146 (1992); Mahal, L. K., et al., Science 276:1125-1128 (1997).

Non-naturally encoded amino acids containing a nucleophilic group, such as a hydrazine, hydrazide or semicarbazide, allow for reaction with a variety of electrophilic groups to form conjugates (including but not limited to, with PEG or other water soluble polymers).

Exemplary hydrazine, hydrazide or semicarbazide-containing amino acids can be represented as follows:

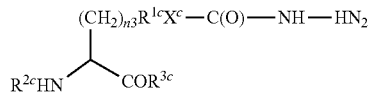

wherein n3 is 0-10; $R^{1c}$ is an alkyl, aryl, substituted alkyl, or substituted aryl or not present; $X^c$, is N, or S or not present; $R^{2c}$ is H, an amino acid, a polypeptide, or an amino terminus modification group, and $R^{3c}$ is H, an amino acid, a polypeptide, or a carboxy terminus modification group.

In some embodiments, n3 is 4, $R^{1c}$ is not present, and X is N. In some embodiments, n3 is 2, $R^{1c}$ is not present, and X is not present. In some embodiments, n3 is 1, $R^{1c}$ is phenyl, X is O, and the oxygen atom is positioned para to the aliphatic group on the aryl ring.

Hydrazide-, hydrazine-, and semicarbazide-containing amino acids are available from commercial sources. For instance, L-glutamate-γ-hydrazide is available from Sigma Chemical (St. Louis, Mo.). Other amino acids not available commercially can be prepared by one skilled in the art. See, e.g., U.S. Pat. No. 6,281,211, which is incorporated by reference herein.

Polypeptides containing non-naturally encoded amino acids that bear hydrazide, hydrazine or semicarbazide functionalities can be reacted efficiently and selectively with a variety of molecules that contain aldehydes or other functional groups with similar chemical reactivity. See, e.g., Shao, J. and Tam, J., J. Am. Chem. Soc. 117:3893-3899 (1995). The unique reactivity of hydrazide, hydrazine and semicarbazide functional groups makes them significantly more reactive toward aldehydes, ketones and other electrophilic groups as compared to the nucleophilic groups present on the 20 common amino acids (including but not limited to, the hydroxyl group of serine or threonine or the amino groups of lysine and the N-terminus).

Non-naturally encoded amino acids containing an aminooxy (also called a hydroxylamine) group allow for reaction with a variety of electrophilic groups to form conjugates (including but not limited to, with PEG or other water soluble polymers). Like hydrazines, hydrazides and semicarbazides, the enhanced nucleophilicity of the aminooxy group permits it to react efficiently and selectively with a variety of molecules that contain aldehydes or other functional groups with similar chemical reactivity. See, e.g., Shao, J. and Tam, J., J. Am. Chem. Soc. 117:3893-3899 (1995); H. Hang and C. Bertozzi, Acc. Chem. Res. 34: 727-736 (2001). Whereas the result of reaction with a hydrazine group is the corresponding hydrazone, however, an oxime results generally from the reaction of an aminooxy group with a carbonyl-containing group such as a ketone.

Exemplary amino acids containing aminooxy groups can be represented as follows:

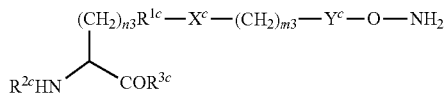

wherein n3 is 0-10; $R^{1c}$ is an alkyl, aryl, substituted alkyl, or substituted aryl or not present; $X^c$ is O, N, S or not present; m3 is 0-10; $Y^c$ is =C(O) or not present; $R^{2c}$ is H, an amino acid, a polypeptide, or an amino terminus modification group, and $R^{3c}$ is H, an amino acid, a polypeptide, or a carboxy terminus modification group. In some embodiments, n3 is 1, $R^{1a}$ is phenyl, $X^c$ is O, m is 1, and $Y^c$ is present. In some embodiments, n3 is 2, $R^{1c}$ and $X^c$ are not present, m3 is 0, and $Y^c$ is not present.

Aminooxy-containing amino acids can be prepared from readily available amino acid precursors (homoserine, serine and threonine). See, e.g., M. Carrasco and R. Brown, J. Org. Chem. 68: 8853-8858 (2003). Certain aminooxy-containing amino acids, such as L-2-amino-4-(aminooxy)butyric acid), have been isolated from natural sources (Rosenthal, G. et al., Life Sci. 60: 1635-1641 (1997). Other aminooxy-containing amino acids can be prepared by one skilled in the art.

The unique reactivity of azide and alkyne functional groups makes them extremely useful for the selective modification of polypeptides and other biological molecules. Organic azides, particularly aliphatic azides, and alkynes are generally stable toward common reactive chemical conditions. In particular, both the azide and the alkyne functional groups are inert toward the side chains (i.e., R groups) of the 20 common amino acids found in naturally-occurring polypeptides. When brought into close proximity, however, the "spring-loaded" nature of the azide and alkyne groups is revealed and they react selectively and efficiently via Huisgen [3+2] cycloaddition reaction to generate the corresponding triazole. See, e.g., Chin J., et al., Science 301:964-7 (2003); Wang, Q., et al., J. Am. Chem. Soc. 125, 3192-3193 (2003); Chin, J. W., et al., J. Am. Chem. Soc. 124:9026-9027 (2002).

Because the Huisgen cycloaddition reaction involves a selective cycloaddition reaction (see, e.g., Padwa, A., in COMPREHENSIVE ORGANIC SYNTHESIS, Vol. 4, (ed. Trost, B. M., 1991), p. 1069-1109; Huisgen, R. in 1,3-DIPOLAR CYCLOADDITION CHEMISTRY, (ed. Padwa, A., 1984), p. 1-176) rather than a nucleophilic substitution, the incorporation of non-naturally encoded amino acids bearing azide and alkyne-containing side chains permits the resultant polypeptides to be modified selectively at the position of the non-naturally encoded amino acid. Cycloaddition reaction involving azide or alkyne-containing antibody can be carried out at room temperature under aqueous conditions by the addition of Cu(II) (including but not limited to, in the form of a catalytic amount of $CuSO_4$) in the presence of a reducing agent for reducing Cu(II) to Cu(I), in situ, in catalytic amount. See, e.g., Wang, Q., et al., J. Am. Chem. Soc. 125, 3192-3193 (2003); Tornoe, C. W., et al., J. Org. Chem. 67:3057-3064 (2002); Rostovtsev, et al., Angew. Chem. Int. Ed. 41:2596-2599 (2002). Exemplary reducing agents include, including but not limited to, ascorbate, metallic copper, quinine, hydroquinone, vitamin K, glutathione, cysteine, $Fe^{2+}$, $Co^{2+}$, and an applied electric potential.

In some cases, where a Huisgen [3+2] cycloaddition reaction between an azide and an alkyne is desired, the antigen-binding polypeptide comprises a non-naturally encoded amino acid comprising an alkyne moiety and the water soluble polymer to be attached to the amino acid comprises an azide moiety. Alternatively, the converse reaction (i.e., with the azide moiety on the amino acid and the alkyne moiety present on the water soluble polymer) can also be performed.

The azide functional group can also be reacted selectively with a water soluble polymer containing an aryl ester and appropriately functionalized with an aryl phosphine moiety to generate an amide linkage. The aryl phosphine group reduces the azide in situ and the resulting amine then reacts efficiently with a proximal ester linkage to generate the corresponding amide. See, e.g., E. Saxon and C. Bertozzi, Science 287, 2007-2010 (2000). The azide-containing amino acid can be either an alkyl azide (including but not limited to, 2-amino-6-azido-1-hexanoic acid) or an aryl azide (p-azido-phenylalanine).

Exemplary water soluble polymers containing an aryl ester and a phosphine moiety can be represented as follows:

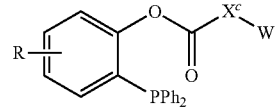

wherein $X^c$ can be O, N, S or not present, Ph is phenyl, W is a water soluble polymer and R can be H, alkyl, aryl, substituted alkyl and substituted aryl groups. Exemplary R groups include but are not limited to —$CH_2$, —$C(CH_3)_3$, —OR', —NR'R", —SR', -halogen, —C(O)R', —CONR'R", —$S(O)_2R'$, —$S(O)_2NR'R"$, —CN and —$NO_2$. R', R", R'" and R"" each independently refer to hydrogen, substituted or unsubstituted heteroalkyl, substituted or unsubstituted aryl, including but not limited to, aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R'" and R"" groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (including but not limited to, —$CF_3$ and —$CH_2CF_3$) and acyl (including but not limited to, —$C(O)CH_3$, —$C(O)CF_3$, —$C(O)CH_2OCH_3$, and the like).

The azide functional group can also be reacted selectively with a water soluble polymer containing a thioester and appropriately functionalized with an aryl phosphine moiety to generate an amide linkage. The aryl phosphine group reduces the azide in situ and the resulting amine then reacts efficiently with the thioester linkage to generate the corresponding amide. Exemplary water soluble polymers containing a thioester and a phosphine moiety can be represented as follows:

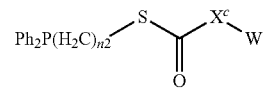

wherein n2 is 1-10; Xc can be O, N, S or not present, Ph is phenyl, and W is a water soluble polymer.

Exemplary alkyne-containing amino acids can be represented as follows:

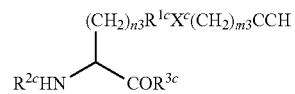

wherein n3 is 0-10; $R^{1c}$ is an alkyl, aryl, substituted alkyl, or substituted aryl or not present; $X^c$ is O, N, S or not present; m3 is 0-10, $R^{2c}$ is H, an amino acid, a polypeptide, or an amino terminus modification group, and $R^{3c}$ is H, an amino acid, a polypeptide, or a carboxy terminus modification group. In some embodiments, n3 is 1, $R^{1c}$ is phenyl, $X^c$ is not present, m3 is 0 and the acetylene moiety is positioned in the para position relative to the alkyl side chain. In some embodiments, n3 is 1, $R^{1c}$ is phenyl, $X^c$ is O, m3 is 1 and the propargyloxy group is positioned in the para position relative to the alkyl side chain (i.e., 0-propargyl-tyrosine). In some embodiments, n3 is 1, $R^{1c}$ and $X^c$ are not present and m3 is 0 (i.e., proparylglycine).

Alkyne-containing amino acids are commercially available. For example, propargylglycine is commercially available from Peptech (Burlington, Mass.). Alternatively, alkyne-containing amino acids can be prepared according to standard methods. For instance, p-propargyloxyphenylalanine can be synthesized, for example, as described in Deiters, A., et al., J. Am. Chem. Soc. 125: 11782-11783 (2003), and 4-alkynyl-L-phenylalanine can be synthesized as described in Kayser, B., et al., Tetrahedron 53(7): 2475-2484 (1997). Other alkyne-containing amino acids can be prepared by one skilled in the art.

Exemplary azide-containing amino acids can be represented as follows:

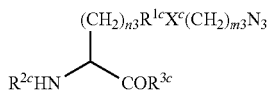

wherein n3 is 0-10; $R^{1c}$ is an alkyl, aryl, substituted alkyl, substituted aryl or not present; $X^c$ is O, N, S or not present; m3 is 0-10; $R^{2c}$ is H, an amino acid, a polypeptide, or an amino terminus modification group, and $R^{3c}$ is H, an amino acid, a polypeptide, or a carboxy terminus modification group. In some embodiments, n3 is 1, $R^{1c}$ is phenyl, $X^c$ is not present, m3 is 0 and the azide moiety is positioned para to the alkyl side chain. In some embodiments, n3 is 0-4 and $R^{1c}$ and $X^c$ are not present, and m3=0. In some embodiments, n3 is 1, $R^{1c}$ is phenyl, $X^c$ is O, m3 is 2 and the P-azidoethoxy moiety is positioned in the para position relative to the alkyl side chain.

Azide-containing amino acids are available from commercial sources. For instance, 4-azidophenylalanine can be obtained from Chem-Impex International, Inc. (Wood Dale, Ill.). For those azide-containing amino acids that are not commercially available, the azide group can be prepared relatively readily using standard methods known to those of skill in the art, including but not limited to, via displacement of a suitable leaving group (including but not limited to, halide, mesylate, tosylate) or via opening of a suitably protected lactone. See, e.g., Advanced Organic Chemistry by March (Third Edition, 1985, Wiley and Sons, New York).

The unique reactivity of beta-substituted aminothiol functional groups makes them extremely useful for the selective modification of polypeptides and other biological molecules that contain aldehyde groups via formation of the thiazolidine. See, e.g., J. Shao and J. Tam, J. Am. Chem. Soc. 1995, 117 (14) 3893-3899. In some embodiments, beta-substituted aminothiol amino acids can be incorporated into antibodies and then reacted with water soluble polymers comprising an aldehyde functionality. In some embodiments, a water soluble polymer, drug conjugate or other payload can be coupled to an antibody polypeptide comprising a beta-substituted aminothiol amino acid via formation of the thiazolidine.

Particular examples of useful non-natural amino acids include, but are not limited to, p-acetyl-L-phenylalanine, O-methyl-L-tyrosine, L-3-(2-naphthyl)alanine, 3-methyl-phenylalanine, O-4-allyl-L-tyrosine, 4-propyl-L-tyrosine, tri-O-acetyl-GlcNAc b-serine, L-Dopa, fluorinated phenylalanine, isopropyl-L-phenylalanine, p-azido-methyl-L-phenylalanine, p-azido-L-phenylalanine, p-acyl-L-phenylalanine, p-benzoyl-L-phenylalanine, L-phosphoserine, phosphonoserine, phosphonotyrosine, p-iodo-phenylalanine, p-bromophenylalanine, p-amino-L-phenylalanine, isopropyl-L-phenylalanine, and p-propargyloxy-phenylalanine. Further useful examples include N-acetyl-L-glucosaminyl-L-serine, N-acetyl-L-galactosaminyl-L-serine, N-acetyl-L-glucosaminyl-L-threonine, N-acetyl-L-glucosaminyl-L-asparagine and O-mannosaminyl-L-serine.

In particular embodiments, the non-natural amino acids are selected from p-acetyl-phenylalanine, p-ethynyl-phenylalanine, p-propargyloxyphenylalanine, p-azido-methyl-phenylalanine, and p-azido-phenylalanine. One particularly useful non-natural amino acid is p-azido phenylalanine. This amino acid residue is known to those of skill in the art to facilitate Huisgen [3+2] cyloaddition reactions (so-called "click" chemistry reactions) with, for example, compounds bearing alkynyl groups. This reaction enables one of skill in the art to readily and rapidly conjugate to the antibody at the site-specific location of the non-natural amino acid.

In certain embodiments, the first reactive group is an alkynyl moiety (including but not limited to, in the unnatural amino acid p-propargyloxyphenylalanine, where the propargyl group is also sometimes referred to as an acetylene moiety) and the second reactive group is an azido moiety, and [3+2] cycloaddition chemistry can be used. In certain embodiments, the first reactive group is the azido moiety (including but not limited to, in the unnatural amino acid p-azido-L-phenylalanine) and the second reactive group is the alkynyl moiety.

In the above formulas, each L represents a divalent linker. The divalent linker can be any divalent linker known to those of skill in the art. Generally, the divalent linker is capable of forming covalent bonds to the functional moiety R and the cognate reactive group (e.g., alpha carbon) of the non-natural amino acid. Useful divalent linkers a bond, alkylene, substituted alkylene, heteroalkylene, substituted heteroalkylene, arylene, substituted arylene, heteroarlyene and substituted heteroarylene. In certain embodiments, L is $C_{1-10}$ alkylene or $C_{1-10}$ heteroalkylene.

The non-natural amino acids used in the methods and compositions described herein have at least one of the following four properties: (1) at least one functional group on the sidechain of the non-natural amino acid has at least one characteristics and/or activity and/or reactivity orthogonal to the chemical reactivity of the 20 common, genetically-encoded amino acids (i.e., alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine), or at least orthogonal to the chemical reactivity of the naturally occurring amino acids present in the polypeptide that includes the non-natural amino acid; (2) the introduced non-natural amino acids are substantially chemically inert toward the 20 common, genetically-encoded amino acids; (3) the non-natural amino acid can be stably incorporated into a polypeptide, preferably with the stability commensurate with the naturally-occurring amino acids or under typical physiological conditions, and further preferably such incorporation can occur via an in vivo system; and (4) the non-natural amino acid includes an oxime functional group or a functional group that can be transformed into an oxime group by reacting with a reagent, preferably under conditions that do not destroy the biological properties of the polypeptide that includes the non-natural amino acid (unless of course such a destruction of biological properties is the purpose of the modification/transformation), or where the transformation can occur under aqueous conditions at a pH between about 4 and about 8, or where the reactive site on the non-natural amino acid is an electrophilic site. Any number of non-natural amino acids can be introduced into the polypeptide. Non-natural amino acids may also include protected or masked oximes or protected or masked groups that can be transformed into an oxime group after deprotection of the protected group or unmasking of the masked group. Non-natural amino acids may also include protected or masked carbonyl or dicarbonyl groups, which can be transformed into a carbonyl or dicarbonyl group after deprotection of the protected group or unmasking of the masked group and thereby are available to react with hydroxylamines or oximes to form oxime groups.

In further embodiments, non-natural amino acids that may be used in the methods and compositions described herein include, but are not limited to, amino acids comprising a photoactivatable cross-linker, spin-labeled amino acids, fluorescent amino acids, metal binding amino acids, metal-containing amino acids, radioactive amino acids, amino acids with novel functional groups, amino acids that covalently or non-covalently interact with other molecules, photocaged and/or photoisomerizable amino acids, amino acids comprising biotin or a biotin analogue, glycosylated amino acids such as a sugar substituted serine, other carbohydrate modified amino acids, keto-containing amino acids, aldehyde-containing amino acids, amino acids comprising polyethylene glycol or other polyethers, heavy atom substituted amino acids, chemically cleavable and/or photocleavable amino acids, amino acids with an elongated side chains as compared to natural amino acids, including but not limited to, polyethers or long chain hydrocarbons, including but not limited to, greater than about 5 or greater than about 10 carbons, carbon-linked sugar-containing amino acids, redox-active amino acids, amino thioacid containing amino acids, and amino acids comprising one or more toxic moiety.

In some embodiments, non-natural amino acids comprise a saccharide moiety. Examples of such amino acids include N-acetyl-L-glucosaminyl-L-serine, N-acetyl-L-galactosaminyl-L-serine, N-acetyl-L-glucosaminyl-L-threonine, N-acetyl-L-glucosaminyl-L-asparagine and O-mannosaminyl-L-serine. Examples of such amino acids also include examples where the naturally-occurring N- or O-linkage between the amino acid and the saccharide is replaced by a covalent linkage not commonly found in nature—including but not limited to, an alkene, an oxime, a thioether, an amide and the like. Examples of such amino acids also include saccharides that are not commonly found in naturally-occurring proteins such as 2-deoxy-glucose, 2-deoxygalactose and the like.

The chemical moieties incorporated into antibodies via incorporation of non-natural amino acids offer a variety of advantages and manipulations of polypeptides. For example, the unique reactivity of a carbonyl or dicarbonyl functional group (including a keto- or aldehyde-functional group) allows selective modification of antibodies with any of a number of hydrazine- or hydroxylamine-containing reagents in vivo and in vitro. A heavy atom non-natural amino acid, for example, can be useful for phasing x-ray structure data. The site-specific introduction of heavy atoms using non-natural amino acids also provides selectivity and flexibility in choosing positions for heavy atoms. Photoreactive non-natural amino acids (including but not limited to, amino acids with benzophenone and arylazides (including but not limited to, phenylazide) side chains), for example, allow for efficient in vivo and in vitro photocrosslinking of polypeptides. Examples of photoreactive non-natural amino acids include, but are not limited to, p-azido-phenylalanine and p-benzoyl-phenylalanine. The antibodies with the photoreactive non-natural amino acids may then be crosslinked at will by excitation of the photoreactive group-providing temporal control. In a non-limiting example, the methyl group of a non-natural amino can be substituted with an isotopically labeled, including but not limited to, with a methyl group, as a probe of local structure and dynamics, including but not limited to, with the use of nuclear magnetic resonance and vibrational spectroscopy.

Amino acids with an electrophilic reactive group allow for a variety of reactions to link molecules via various chemical reactions, including, but not limited to, nucleophilic addition reactions. Such electrophilic reactive groups include a carbonyl- or dicarbonyl-group (including a keto- or aldehyde group), a carbonyl-like- or dicarbonyl-like-group (which has reactivity similar to a carbonyl- or dicarbonyl-group and is structurally similar to a carbonyl- or dicarbonyl-group), a masked carbonyl- or masked dicarbonyl-group (which can be readily converted into a carbonyl- or dicarbonyl-group), or a protected carbonyl- or protected dicarbonyl-group (which has reactivity similar to a carbonyl- or dicarbonyl-group upon deprotection). Such amino acids include amino acids having the structure of Formula (I-1):

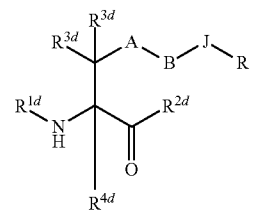

wherein: A is optional, and when present is lower alkylene, substituted lower alkylene, lower cycloalkylene, substituted lower cycloalkylene, lower alkenylene, substituted lower alkenylene, alkynylene, lower hetero alkylene, substituted heteroalkylene, lower heterocycloalkylene, substituted lower heterocycloalkylene, arylene, substituted arylene, heteroarylene, substituted heteroarylene, alkarylene, substituted alkarylene, aralkylene, or substituted aralkylene; B is optional, and when present is a linker selected from the group consisting of lower alkylene, substituted lower alkylene, lower alkenylene, substituted lower alkenylene, lower heteroalkylene, substituted lower heteroalkylene, —O—, —O-(alkylene or substituted alkylene)-, —S—, —S-(alkylene or substituted alkylene)-, —S(O)$_k$— where k is 1, 2, or 3, —S(O)$_k$(alkylene or substituted alkylene)-, —C(O)—, —NS(O)$_2$—, —OS(O)$_2$—, —C(O)-(alkylene or substituted alkylene)-, —C(S)—, —C(S)-(alkylene or substituted alkylene)-, —N(R')—, —NR'-(alkylene or substituted alkylene)-, —C(O)N(R')—, —CON(R')-(alkylene or substituted alkylene)-, —CSN(R')—, —CSN(R')— (alkyl ene or substituted alkylene)-, —N(R')CO-(alkylene or substituted alkylene)-, —N(R')C(O)O—, —S(O)$_k$N(R')—, —N(R')C(O)N (R')—, —N(R')C(S)N(R')—, —N(R')S(O)$_k$N(R')—, —N(R')—N═, —C(R')═N—, —C(R')═N—N (R')—, —C(R')═N—N═, —C(R')$_2$—N═N—, and —C(R')₂—N(R')—N(R')—, where each R' is independently H, alkyl, or substituted alkyl; J is

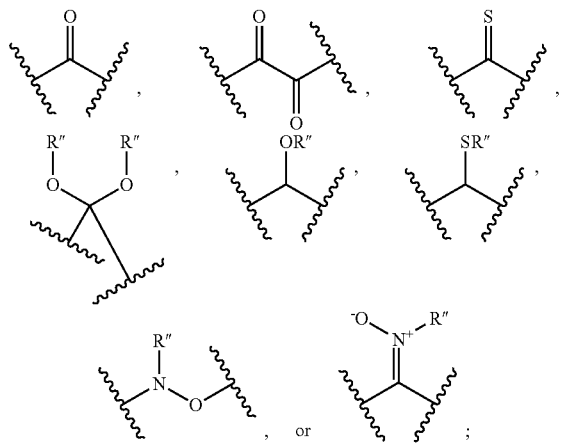

R is H, alkyl, substituted alkyl, cycloalkyl, or substituted cycloalkyl; each R" is independently H, alkyl, substituted alkyl, or a protecting group, or when more than one R" group is present, two R" optionally form a heterocycloalkyl; $R^{1d}$ is H, an amino protecting group, resin, amino acid, polypeptide, or polynucleotide; and $R^{2d}$ is OH, an ester protecting group, resin, amino acid, polypeptide, or polynucleotide; each of $R^{3d}$ and $R^{4d}$ is independently H, halogen, lower alkyl, or substituted lower alkyl, or $R^{3d}$ and $R^{4d}$ or two $R^{3d}$ groups optionally form a cycloalkyl or a heterocycloalkyl; or the -A-B-J-R groups together form a bicyclic or tricyclic cycloalkyl or heterocycloalkyl comprising at least one carbonyl group, including a dicarbonyl group, protected carbonyl group, including a protected dicarbonyl group, or masked carbonyl group, including a masked dicarbonyl group; or the -J-R group together forms a monocyclic or bicyclic cycloalkyl or heterocycloalkyl comprising at least one carbonyl group, including a dicarbonyl group, protected carbonyl group, including a protected dicarbonyl group, or masked carbonyl group, including a masked dicarbonyl group; with a proviso that when A is phenylene and each $R^{3d}$ is H, B is present; and that when A is —(CH₂)₄— and each $R^{3d}$ is H, B is not —NHC(O)(CH₂CH₂)—; and that when A and B are absent and each $R^{3d}$ is H, R is not methyl. Such non-natural amino acids may be in the form of a salt, or may be incorporated into a non-natural amino acid polypeptide, polymer, polysaccharide, or a polynucleotide and optionally post translationally modified.

In certain embodiments, compounds of Formula (I-1) are stable in aqueous solution for at least 1 month under mildly acidic conditions. In certain embodiments, compounds of Formula (I-1) are stable for at least 2 weeks under mildly acidic conditions. In certain embodiments, compound of Formula (I-1) are stable for at least 5 days under mildly acidic conditions. In certain embodiments, such acidic conditions are pH 2 to 8.

In certain embodiments of compounds of Formula (I-1), B is lower alkylene, substituted lower alkylene, —O-(alkylene or substituted alkylene)-, —C(R')=N—N(R')—, —N(R')CO—, —C(O)—, —C(R')=N—, —C(O)-(alkylene or substituted alkylene)-, —CON(R')-(alkylene or substituted alkylene)-, —S(alkylene or substituted alkylene)-, —S(O)(alkylene or substituted alkylene)-, or —S(O)₂(alkylene or substituted alkylene)-. In certain embodiments of compounds of Formula (I-1), B is —O(CH₂)—, —CH=N—, —CH=N—NH—, —NHCH₂—, —NHCO—, —C(O)—, —C(O)—(CH₂)—, —CONH—(CH₂)—, —SCH₂—, —S(=O)CH₂—, or —S(O)₂CH₂—. In certain embodiments of compounds of Formula (I-1), R is $C_{1-6}$ alkyl or cycloalkyl. In certain embodiments of compounds of Formula (I-1) R is —CH₃, —CH(CH₃)₂, or cyclopropyl. In certain embodiments of compounds of Formula (I-1), $R^{1d}$ is H, tert-butyloxycarbonyl (Boc), 9-Fluorenylmethoxycarbonyl (Fmoc), N-acetyl, tetrafluoroacetyl (TFA), or benzyloxycarbonyl (Cbz). In certain embodiments of compounds of Formula (I-1), $R^{1d}$ is a resin, amino acid, polypeptide, or polynucleotide. In certain embodiments of compounds of Formula (I-1), $R^{2d}$ is OH, O-methyl, O-ethyl, or O-t-butyl. In certain embodiments of compounds of Formula (I-1), $R^{2d}$ is a resin, amino acid, polypeptide, or polynucleotide. In certain embodiments of compounds of Formula (I-1), $R^{2d}$ is a polynucleotide. In certain embodiments of compounds of Formula (I-1), $R^{2d}$ is ribonucleic acid (RNA). In certain embodiments of compounds of Formula (I-1), $R^{2d}$ is tRNA. In certain embodiments of compounds of Formula (I-1), the tRNA specifically recognizes a selector codon. In certain embodiments of compounds of Formula (I-1) the selector codon is selected from the group consisting of an amber codon, ochre codon, opal codon, a unique codon, a rare codon, an unnatural codon, a five-base codon, and a four-base codon. In certain embodiments of compounds of Formula (I-1), $R^{2d}$ is a suppressor tRNA.

In certain embodiments of compounds of Formula (I-2),

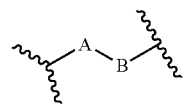

is selected from the group consisting of: (i) A is substituted lower alkylene, C₄-arylene, substituted arylene, heteroarylene, substituted heteroarylene, alkarylene, substituted alkarylene, aralkylene, or substituted aralkylene; B is optional, and when present is a divalent linker selected from the group consisting of lower alkylene, substituted lower alkylene, lower alkenylene, substituted lower alkenylene, —O—, —O-(alkylene or substituted alkylene)-, —S—, —S(O)—, —S(O)₂—, —NS(O)₂—, —OS(O)₂—, —C(O)—, —C(O)-(alkylene or substituted alkylene)-, —C(S)—, —C(O)N(R')—, —CON(R')-(alkylene or substituted alkylene)-, —CSN(R')—, —N(R')CO-(alkylene or substituted alkylene)-, —N(R')C(O)O—, —N(R')C(S)—, —S(O)N(R'), —S(O)₂N(R'), —N(R')C(O)N(R')—, —N(R') C(S)N(R')—, —N(R')S(O)N(R')—, —N(R')S(O)₂N(R')—, —N(R')—N=, —C(R')=N—N(R')—, —C(R')=N—N=, —C(R')₂—N=N—, and —C(R')₂—N(R')—N(R')—; (ii) A is optional, and when present is substituted lower alkylene, C₄-arylene, substituted arylene, heteroarylene, substituted heteroarylene, alkarylene, substituted alkarylene, aralkylene, or substituted aralkylene; B is a divalent linker selected from the group consisting of lower alkylene, substituted lower alkylene, lower alkenylene, substituted lower alkenylene, —O—, —O-(alkylene or substituted alkylene)-, —S—, —S(O)—, —S(O)₂—, —NS(O)₂—, —OS(O)₂—, —C(O)—, —C(O)-(alkylene or substituted alkylene)-, —C(S)—, —N(R')—, —C(O)N(R')—, —CON(R')-(alkylene or substituted alkylene)-, —CSN(R')—, —N(R')CO-(alkylene or substituted alkylene)-, —N(R')C(O)O—, —N(R')C(S)—, —S(O)N(R'), —S(O)₂N(R'), —N(R')C(O)

N(R')—, —N(R')C(S)N(R')—, —N(R')S(O)N(R')—, —N(R')S(O)₂N(R')—, —N(R')—N═, —C(R')═N—N(R')—, —C(R')═N—N═, —C(R')₂—N═N—, and —C(R')₂—N(R')—N(R')—; (iii) A is lower alkylene; B is optional, and when present is a divalent linker selected from the group consisting of lower alkylene, substituted lower alkylene, lower alkenylene, substituted lower alkenylene, —O—, —O-(alkylene or substituted alkylene)-, —S—, —S(O)—, —S(O)₂—, —NS(O)₂—, —OS(O)₂—, —C(O)—, —C(O)-(alkylene or substituted alkylene)-, —C(S)—, —C(O)N(R')—, —CSN(R')—, —CON(R')-(alkylene or substituted alkylene)-, —N(R')C(O)O—, —N(R')C(S)—, —S(O)N(R'), —S(O)₂N(R'), —N(R')C(O)N(R')—, —N(R')C(S)N(R')—, —N(R')S(O)N(R')—, —N(R')S(O)₂N(R')—, —N(R')—N═, —C(R')═N—N(R')—, —C(R')═N—N═, —C(R')₂—N═N—, and —C(R')₂—N(R')—N(R')—; and (iv) A is phenylene; B is a divalent linker selected from the group consisting of lower alkylene, substituted lower alkylene, lower alkenylene, substituted lower alkenylene, —O—, —O-(alkylene or substituted alkylene)-, —S—, —S(O)—, —S(O)₂—, —NS(O)₂—, —OS(O)₂—, —C(O)—, —C(O)-(alkylene or substituted alkylene)-, —C(S)—, —C(O)N(R')—, —CON(R')-(alkylene or substituted alkylene)-, —CSN(R')—, —N(R')CO-(alkylene or substituted alkylene)-, —N(R')C(O)O—, —N(R')C(S)—, —S(O)N(R'), —S(O)₂N(R'), —N(R')C(O)N(R')—, —N(R') C(S)N(R')—, —N(R')S(O)N(R')—, —N(R')S(O)₂N(R')—, —N(R')—N═, —C(R')'N—N(R')—, —C(R')═N—N═, —C(R')₂—N═N—, and —C(R')₂—N(R')—N(R')—; J is

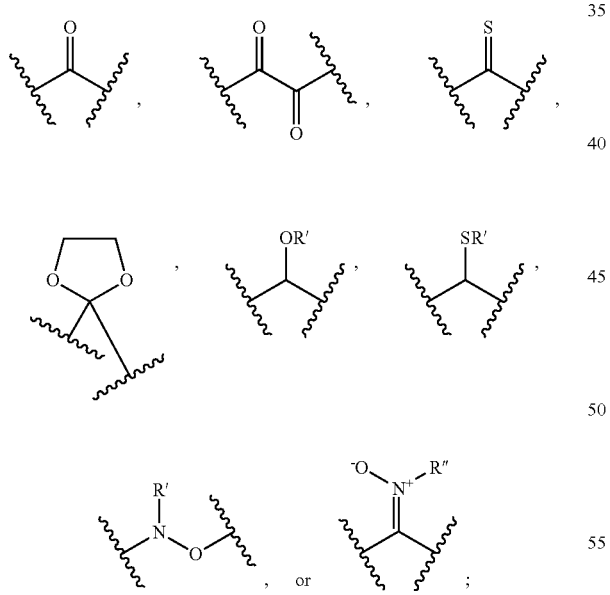

each R' is independently H, alkyl, or substituted alkyl; $R^{1d}$ is optional, and when present, is H, an amino protecting group, resin, amino acid, polypeptide, or polynucleotide; and $R^{2d}$ is optional, and when present, is OH, an ester protecting group, resin, amino acid, polypeptide, or polynucleotide; and each $R^{3d}$ and $R^{4d}$ is independently H, halogen, lower alkyl, or substituted lower alkyl; and R is H, alkyl, substituted alkyl, cycloalkyl, or substituted cycloalkyl.

In certain embodiments, the non-natural amino acid can be according to formula XIX:

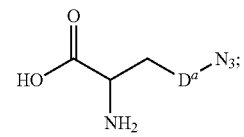

Formula XIX or a salt thereof, wherein: $D^a$ is —Ar—$W^{3a}$— or —$W^{1a}$—$Y^1$—C(O)—$Y^{2a}$—$W^{2a}$—; Ar is

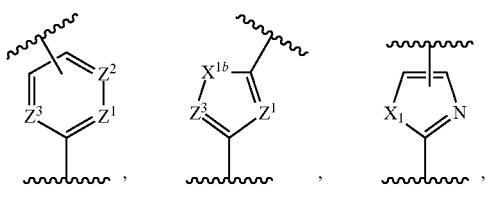

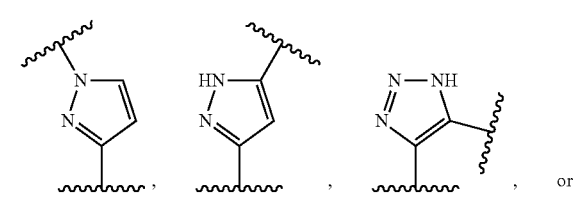

, or

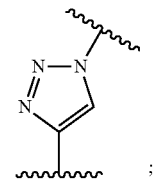

;

each of $W^{1a}$, $W^{2a}$, and $W^{3a}$ is independently a single bond or lower alkylene; each $X^{1b}$ is independently —NH—, —O—, or —S—; each $Y^{1a}$ is independently a single bond, —NH—, or —O—; each $Y^{2a}$ is independently a single bond, —NH—, —O—, or an N-linked or C-linked pyrrolidinylene; and one of $Z^1$, $Z^2$, and $Z^3$ is —N— and the others of $Z^1$, $Z^2$, and $Z^3$ are independently —CH—. In certain embodiments, the non-natural amino acid is according to formula XIXa:

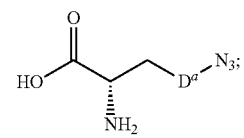

Formula XIX where $D^a$ is a defined in the context of formula XIX. In certain embodiments, the non-natural amino acid is according formula XIXb:

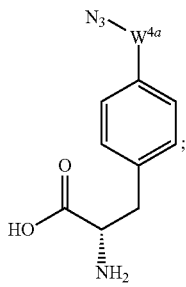

Formula XIXb or a salt thereof, wherein $W^{1a}$ is $C_1$-$C_{10}$ alkylene. In a further embodiment, $W^{4a}$ is $C_1$-$C_5$ alkylene. In an embodiment, $W^{4a}$ is $C_1$-$C_3$ alkylene. In an embodiment, $W^{4a}$ is $C_1$ alkylene. In particular embodiments, the non-natural amino acid is selected from the group consisting of:

(1)

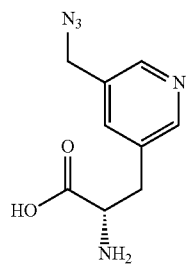

(2)

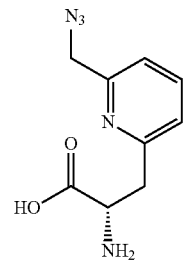

(3)

(4)

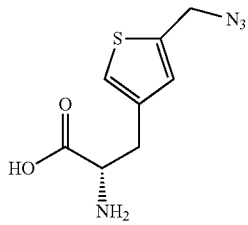

(5)

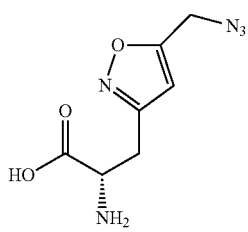

(6)

(7)

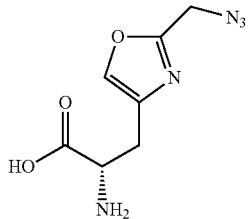

(8)

(9)

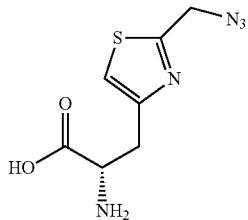

331
-continued
(10)
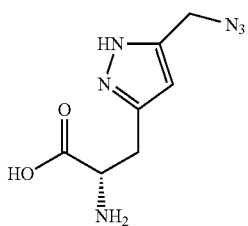
(11)
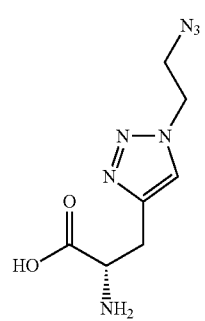
(12)
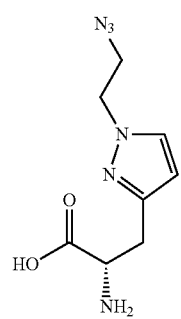
(13)
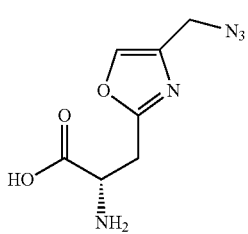
(14)
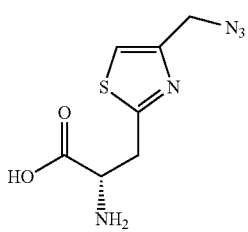
(15)
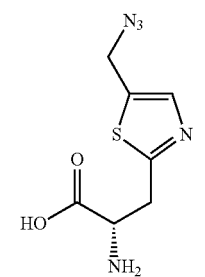
332
-continued
(16)
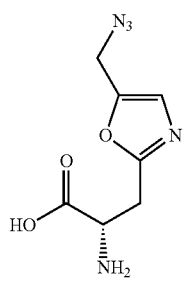
(17)
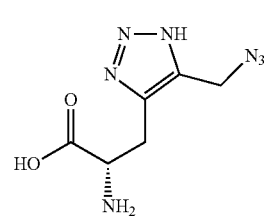
(18)
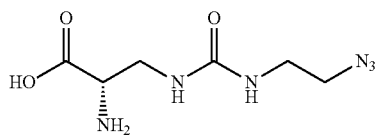
(19)
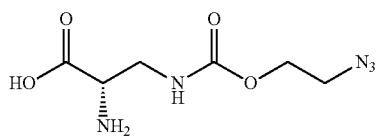
(20)
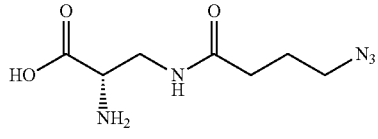
(21)
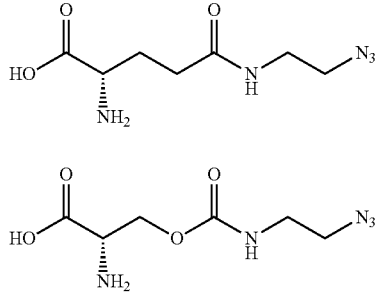
(22)
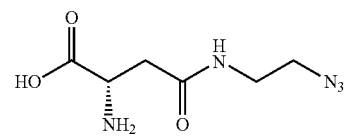
(23)
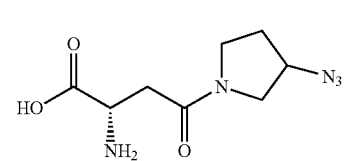
(24)

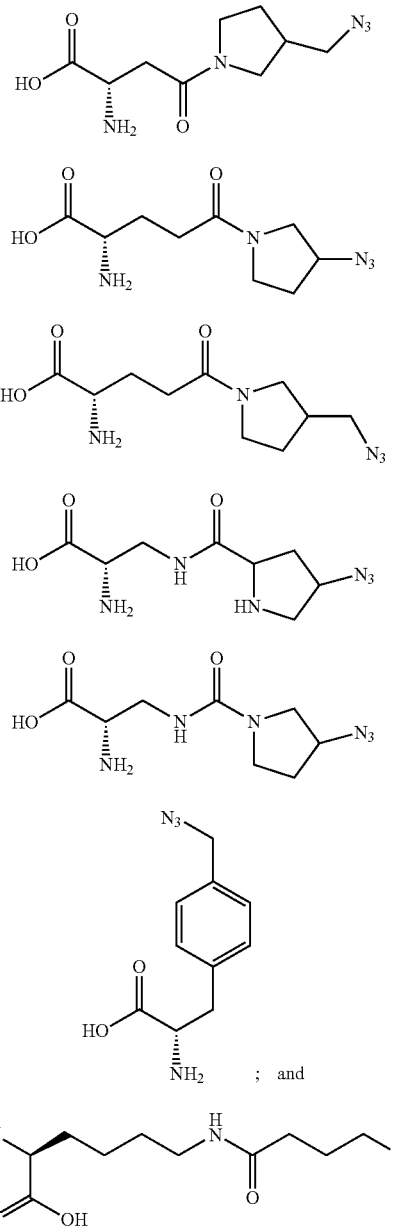

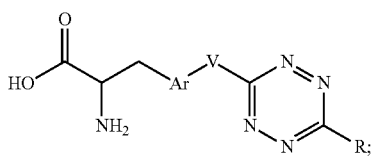

or a salt thereof. Such non-natural amino acids may be in the form of a salt, or may be incorporated into a non-natural amino acid polypeptide, polymer, polysaccharide, or a polynucleotide and optionally post translationally modified.

In certain embodiments, the modified amino acid is according to formula I:

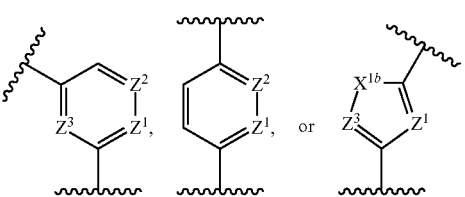

Formula I or a salt thereof, wherein Ar is:

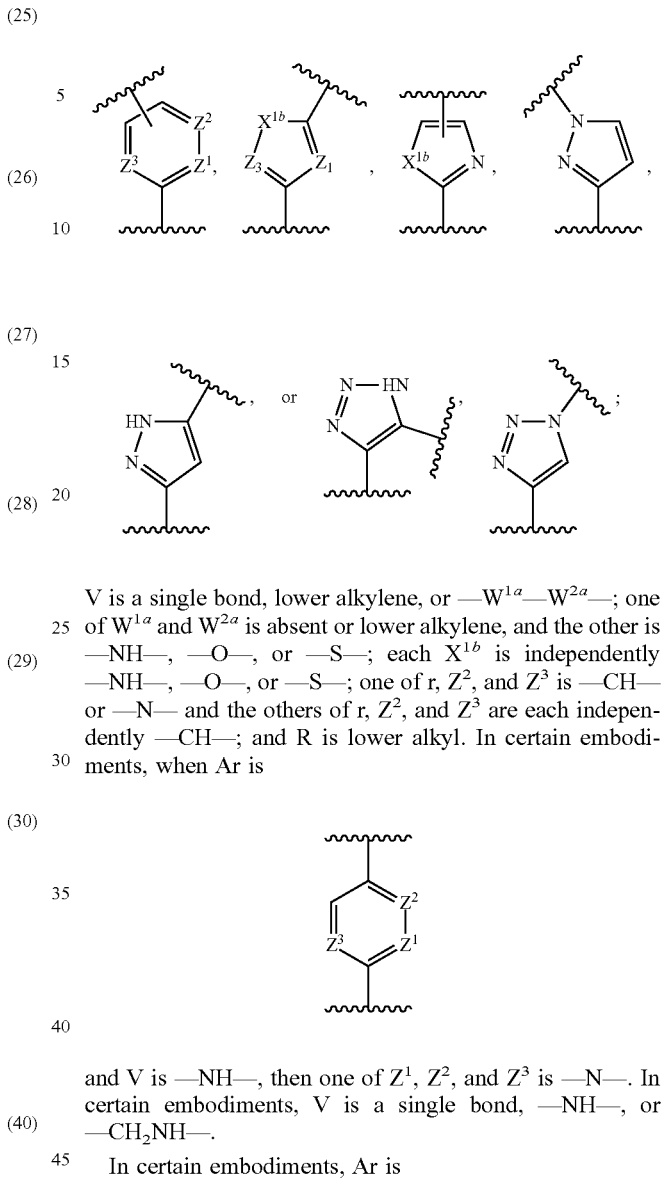

V is a single bond, lower alkylene, or $-W^{1a}-W^{2a}-$; one of $W^{1a}$ and $W^{2a}$ is absent or lower alkylene, and the other is $-NH-$, $-O-$, or $-S-$; each $X^{1b}$ is independently $-NH-$, $-O-$, or $-S-$; one of r, $Z^2$, and $Z^3$ is $-CH-$ or $-N-$ and the others of r, $Z^2$, and $Z^3$ are each independently $-CH-$; and R is lower alkyl. In certain embodiments, when Ar is and V is $-NH-$, then one of $Z^1$, $Z^2$, and $Z^3$ is $-N-$. In certain embodiments, V is a single bond, $-NH-$, or $-CH_2NH-$.

In certain embodiments, Ar is and $Z^1$, $Z^2$, $Z^3$ and $X^{1b}$ are as defined in the context of formula I. In certain embodiments according to this paragraph, V is $-W^{1a}-W^{2a}-$; one of $W^{1a}$ and $W^{2a}$ is absent or $-CH_2-$, and the other is $-NH-$, $-O-$, or $-S-$. In certain embodiments according to this paragraph, V is a single bond, $-NH-$, or $-CH_2NH-$. In certain embodiments according to this paragraph, $Z^1$ is N. In certain embodiments according to this paragraph, $Z^2$ is N. In certain embodiments according to this paragraph, $Z^3$ is N. In certain embodiments according to this paragraph, $Z^1$ is CH, $Z^3$ is CH and $X^{1b}$ is S.

In certain embodiments, Ar is

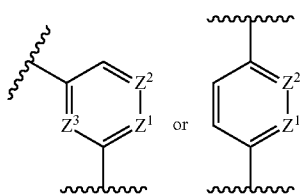

and $Z^1$, $Z^2$, and $Z^3$ are as defined in the context of formula I. In certain embodiments according to this paragraph, V is —$W^{1a}$—$W^{2a}$—; one of $W^{1a}$ and $W^{2a}$ is absent or —$CH_2$—, and the other is —NH—, —O—, or —S—. In certain embodiments according to this paragraph, V is a single bond, —NH—, or —$CH_2NH$—. In certain embodiments according to this paragraph, $Z^1$ is N. In certain embodiments according to this paragraph, $Z^2$ is N. In certain embodiments according to this paragraph, $Z^3$ is N.

In certain embodiments, Ar is

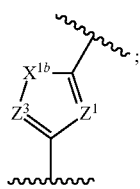

and $Z^1$, $Z^3$ and $X^1$ are as defined in the context of Formula I-1. In certain embodiments according to this paragraph, V is —$W^{1a}$—$W^{2a}$—; one of $W^{1a}$ and $W^{2a}$ is absent or —$CH_2$—, and the other is —NH—, —O—, or —S—. In certain embodiments according to this paragraph, V is a single bond, —NH—, or —$CH_2NH$—. In certain embodiments according to this paragraph, $Z^1$ is N. In certain embodiments according to this paragraph, $Z^3$ is N. In certain embodiments according to this paragraph, $Z^1$ is CH, $Z^3$ is CH and $X^{1b}$ is S.

In certain embodiments, the modified amino acid is according to Formula Ia:

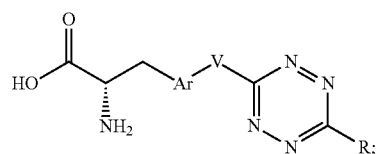

Formula I-1a where Ar, V, and R are defined in the context of Formula I-1.

In an embodiment, compounds of either of Formulas I-1 and I-1a are provided wherein V is a single bond. In another embodiment, compounds of either of Formulas I-1 and I-1a are provided wherein V is —NH—. In another embodiment, compounds of either of Formulas I-1 and I-1a are provided wherein V is —$CH_2NH$—.

In certain embodiments, the modified amino acid is according to Formula II-1:

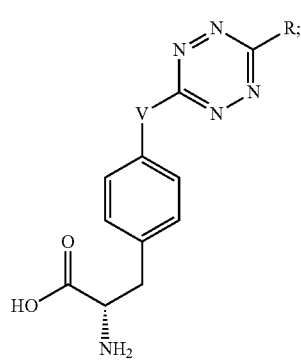

Formula II-1 or a salt thereof, wherein V and R are as defined in Formula I-1. In certain embodiments according to this paragraph, V is —$W^{1a}$—$W^{2a}$—; one of $W^{1a}$ and $W^{2a}$ is absent or —$CH_2$—, and the other is —NH—, —O—, or —S—. In certain embodiments, V is a single bond, —NH—, or —$CH_2NH$—. In certain embodiments, V is a single bond or —$CH_2NH$—; and R is methyl.

In certain embodiments, the modified amino acid is according to Formula III-1:

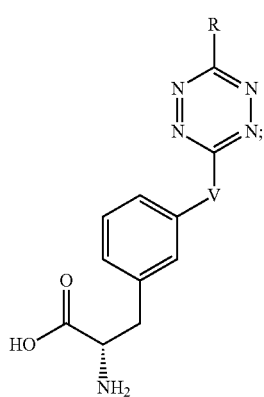

Formula III-1 or a salt thereof, wherein V and R are as defined in Formula I-1. In certain embodiments according to this paragraph, V is —$W^{1a}$—$W^{2a}$—; one of $W^{1a}$ and $W^{2a}$ is absent or —$CH_2$—, and the other is —NH—, —O—, or —S—. In certain embodiments, V is a single bond, —NH—, or —$CH_2NH$—. In certain embodiments, V is a single bond, —NH—, or —$CH_2NH$—; and R is methyl.

337

In certain embodiments, the modified amino acid is according to Formula IV-1:

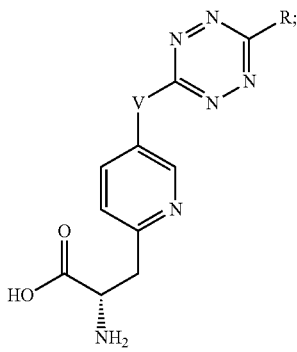

Formula IV-1 or a salt thereof, wherein V and R are as defined in Formula I-1. In certain embodiments according to this paragraph, V is —$W^{1a}$—$W^{2a}$—; one of $W^{1a}$ and $W^{2a}$ is absent or —$CH_2$—, and the other is —NH—, —O—, or —S—. In certain embodiments, V is a single bond, —NH—, or —$CH_2NH$—. In certain embodiments, V is a single bond, —NH—, or —$CH_2NH$—; and R is methyl.

In certain embodiments, the modified amino acid is according to Formula V-1:

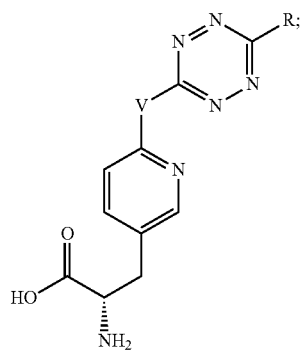

Formula V-1 or a salt thereof, wherein V and R are as defined in Formula I. In certain embodiments according to this paragraph, V is —$W^{1a}$—$W^{2a}$—; one of $W^{1a}$ and $W^{2a}$ is absent or —$CH_2$—, and the other is —NH—, —O—, or —S—. In certain embodiments, V is a single bond, —NH—, or —$CH_2NH$—. In certain embodiments, V is a single bond, —NH—, or —$CH_2NH$—; and R is methyl.

338

In certain embodiments, the modified amino acid is according to Formula VI-1:

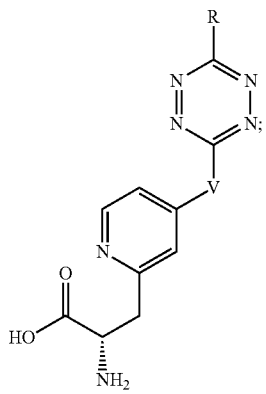

Formula VI-1 or a salt thereof, wherein V and R are as defined in Formula I. In certain embodiments according to this paragraph, V is —$W^{1a}$—$W^{2a}$—; one of $W^{1a}$ and $W^{2a}$ is absent or —$CH_2$—, and the other is —NH—, —O—, or —S—. In certain embodiments, V is a single bond, —NH—, or —$CH_2NH$—. In certain embodiments, V is a single bond, —NH—, or —$CH_2NH$—; and R is methyl.

In certain embodiments, the modified amino acid is according to Formula

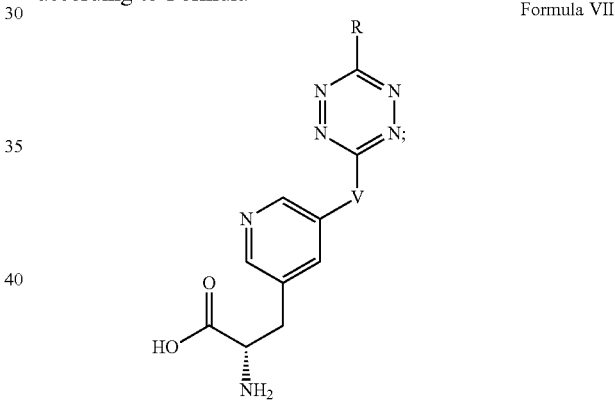

Formula VII or a salt thereof, wherein V and R are as defined in Formula I. In certain embodiments according to this paragraph, V is —$W^{1a}$—$W^{2a}$—; one of $W^{1a}$ and $W^{2a}$ is absent or —$CH_2$—, and the other is —NH—, —O—, or —S—. In certain embodiments, V is a single bond, —NH—, or —$CH_2NH$—. In certain embodiments, V is a single bond, —NH—, or —$CH_2NH$—; and R is methyl.

In certain embodiments, the modified amino acid is according to Formula VIII-1:

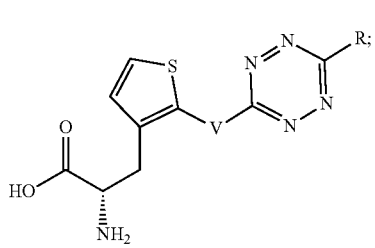

Formula VIII-1

Or a salt thereof, wherein V and R are as defined in Formula I. In certain embodiments according to this paragraph, V is —$W^{1a}$—$W^{2a}$—; one of $W^{1a}$ and $W^{2a}$ is absent or —$CH_2$—, and the other is —NH—, —O—, or —S—. In certain embodiments, V is a single bond, —NH—, or —$CH_2NH$—. In certain embodiments, V is a single bond, —NH—, or —$CH_2NH$—; and R is methyl.

In certain embodiments, the modified amino acid is according to Formula IX-1:

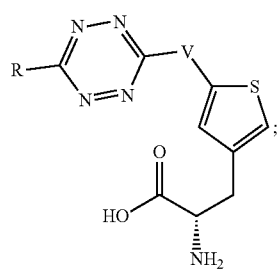

Formula IX-1 or a salt thereof, wherein V and R are as defined in Formula I-1. In certain embodiments according to this paragraph, V is —$W^{1a}$—$W^{2a}$—; one of $W^{1a}$ and $W^{2a}$ is absent or —$CH_2$—, and the other is —NH—, —O—, or —S—. In certain embodiments, V is a single bond, —NH—, or —$CH_2NH$—. In certain embodiments, V is a single bond, —NH—, or —$CH_2NH$—; and R is methyl.

In certain embodiments, the modified amino acid is according to any of formulas 51-62:

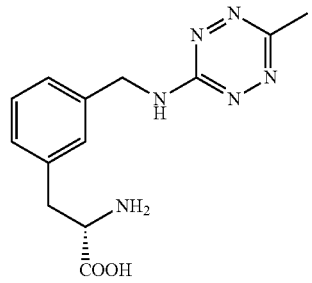

(51)

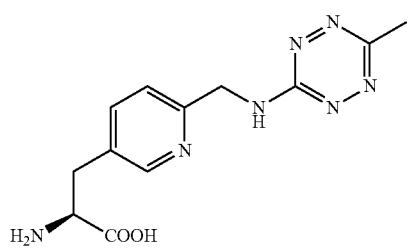

(52)

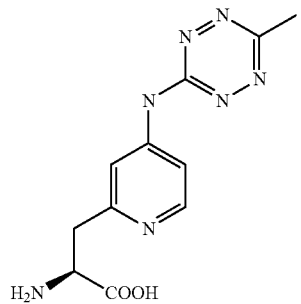

(53)

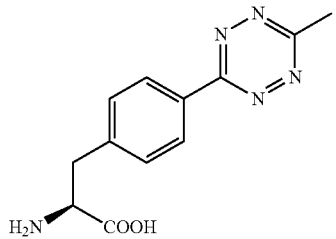

(54)

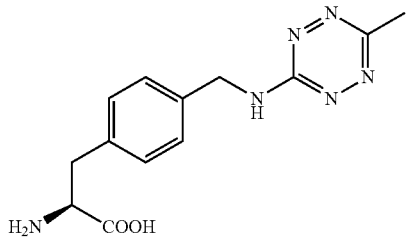

(55)

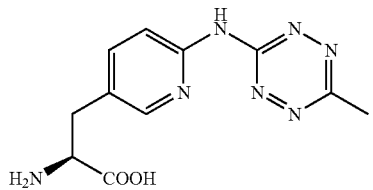

(56)

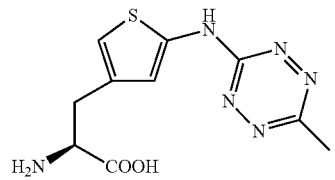

(57)

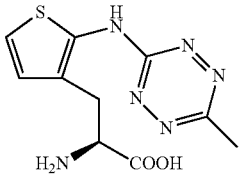

(58)

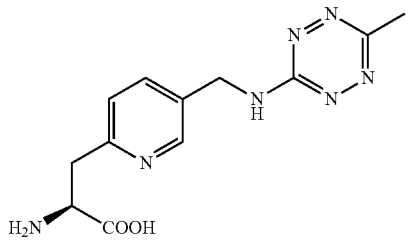

(59)

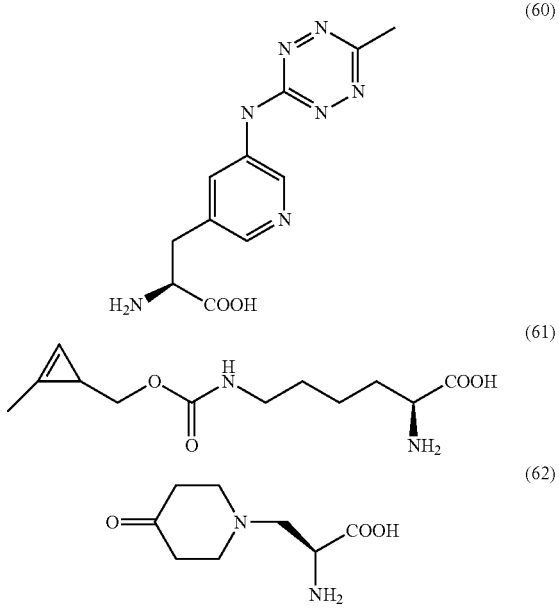

or a salt thereof.

In certain embodiments, the non-natural amino acid is selected from the group consisting of compounds 30, 53, 56, 59, 60, 61, and 62 above. In certain embodiments, the non-natural amino acid is compound 30. In certain embodiments, the non-natural amino acid is compound 56. In some embodiments, the non-natural amino acid is compound 61. In some embodiments, the non-natural amino acid is compound 62.

12. Preparation of Antibodies and Antibody Conjugates

12.1. Antigen Preparation

The ROR1 protein to be used for isolation of the antibodies may be intact ROR1 or a fragment of ROR1. The intact ROR1 protein, or fragment of ROR1, may be in the form of an isolated protein or protein expressed by a cell. Other forms of ROR1 useful for generating antibodies will be apparent to those skilled in the art.

12.2. Monoclonal Antibodies

Monoclonal antibodies may be obtained, for example, using the hybridoma method first described by Kohler et al., *Nature*, 1975, 256:495-497 (incorporated by reference in its entirety), and/or by recombinant DNA methods (see e.g., U.S. Pat. No. 4,816,567, incorporated by reference in its entirety). Monoclonal antibodies may also be obtained, for example, using phage or yeast-based libraries. See e.g., U.S. Pat. Nos. 8,258,082 and 8,691,730, each of which is incorporated by reference in its entirety.

In the hybridoma method, a mouse or other appropriate host animal is immunized to elicit lymphocytes that produce or are capable of producing antibodies that will specifically bind to the protein used for immunization. Alternatively, lymphocytes may be immunized in vitro. Lymphocytes are then fused with myeloma cells using a suitable fusing agent, such as polyethylene glycol, to form a hybridoma cell. See Goding J. W., *Monoclonal Antibodies: Principles and Practice* 3$^{rd}$ ed. (1986) Academic Press, San Diego, CA, incorporated by reference in its entirety.

The hybridoma cells are seeded and grown in a suitable culture medium that contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Useful myeloma cells are those that fuse efficiently, support stable high-level production of antibody by the selected antibody-producing cells, and are sensitive media conditions, such as the presence or absence of HAT medium. Among these, preferred myeloma cell lines are murine myeloma lines, such as those derived from MOP-21 and MC-11 mouse tumors (available from the Salk Institute Cell Distribution Center, San Diego, CA), and SP-2 or X63-Ag8-653 cells (available from the American Type Culture Collection, Rockville, MD). Human myeloma and mouse-human heteromyeloma cell lines also have been described for the production of human monoclonal antibodies. See e.g., Kozbor, *J. Immunol.*, 1984, 133:3001, incorporated by reference in its entirety.

After the identification of hybridoma cells that produce antibodies of the desired specificity, affinity, and/or biological activity, selected clones may be subcloned by limiting dilution procedures and grown by standard methods. See Goding, supra. Suitable culture media for this purpose include, for example, D-MEM or RPMI-1640 medium. In addition, the hybridoma cells may be grown in vivo as ascites tumors in an animal.

DNA encoding the monoclonal antibodies may be readily isolated and sequenced using conventional procedures (e.g., by using oligonucleotide probes that are capable of binding specifically to genes encoding the heavy and light chains of the monoclonal antibodies). Thus, the hybridoma cells can serve as a useful source of DNA encoding antibodies with the desired properties. Once isolated, the DNA may be placed into expression vectors, which are then transfected into host cells such as bacteria (e.g., *E. coli*), yeast (e.g., *Saccharomyces* or *Pichia* sp.), COS cells, Chinese hamster ovary (CHO) cells, or myeloma cells that do not otherwise produce antibody, to produce the monoclonal antibodies.

12.3. Humanized Antibodies

Humanized antibodies may be generated by replacing most, or all, of the structural portions of a non-human monoclonal antibody with corresponding human antibody sequences. Consequently, a hybrid molecule is generated in which only the antigen-specific variable, or CDR, is composed of non-human sequence. Methods to obtain humanized antibodies include those described in, for example, Winter and Milstein, *Nature*, 1991, 349:293-299; Rader et al., *Proc. Nat. Acad. Sci. U.S.A.*, 1998, 95:8910-8915; Steinberger et al., *J. Biol. Chem.*, 2000, 275:36073-36078; Queen et al., *Proc. Natl. Acad. Sci. U.S.A.*, 1989, 86:10029-10033; and U.S. Pat. Nos. 5,585,089, 5,693,762, and 6,180,370; each of which is incorporated by reference in its entirety.

12.4. Human Antibodies

Human antibodies can be generated by a variety of techniques known in the art, for example by using transgenic animals (e.g., humanized mice). See, e.g., Jakobovits et al., *Proc. Natl. Acad. Sci. U.S.A.*, 1993, 90:2551; Jakobovits et al., *Nature*, 1993, 362:255-258; Bruggermann et al., *Year in Immuno.*, 1993, 7:33; and U.S. Pat. Nos. 5,591,669, 5,589, 369 and 5,545,807; each of which is incorporated by reference in its entirety. Human antibodies can also be derived from phage-display libraries (see e.g., Hoogenboom et al., *J.*

Mol. Biol., 1991, 227:381-388; Marks et al., J. Mol. Biol., 1991, 222:581-597; and U.S. Pat. Nos. 5,565,332 and 5,573,905; each of which is incorporated by reference in its entirety). Human antibodies may also be generated by in vitro activated B cells (see e.g., U.S. Pat. Nos. 5,567,610 and 5,229,275, each of which is incorporated by reference in its entirety). Human antibodies may also be derived from yeast-based libraries (see e.g., U.S. Pat. No. 8,691,730, incorporated by reference in its entirety).

12.5. Conjugation

The antibody conjugates can be prepared by standard techniques. In certain embodiments, an antibody is contacted with a payload precursor under conditions suitable for forming a bond from the antibody to the payload to form an antibody-payload conjugate. In certain embodiments, an antibody is contacted with a linker precursor under conditions suitable for forming a bond from the antibody to the linker. The resulting antibody-linker is contacted with a payload precursor under conditions suitable for forming a bond from the antibody-linker to the payload to form an antibody-linker-payload conjugate. In certain embodiments, a payload precursor is contacted with a linker precursor under conditions suitable for forming a bond from the payload to the linker. The resulting payload-linker is contacted with an antibody under conditions suitable for forming a bond from the payload-linker to the antibody to form an antibody-linker-payload conjugate. Suitable linkers for preparing the antibody conjugates are disclosed herein, and exemplary conditions for conjugation are described in the Examples below.

In some embodiments, an anti-ROR1 conjugate is prepared by contacting an anti-ROR1 antibody as disclosed herein with a linker precursor having a structure of any of LP1-LP39:

LP1
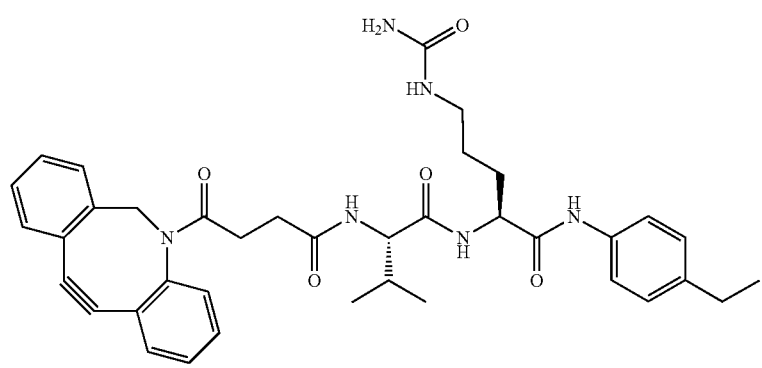

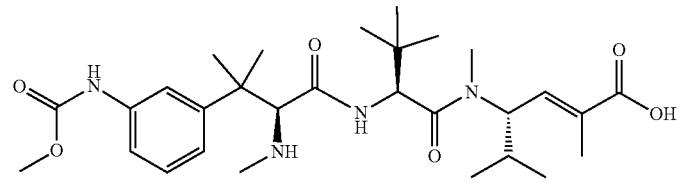

LP2
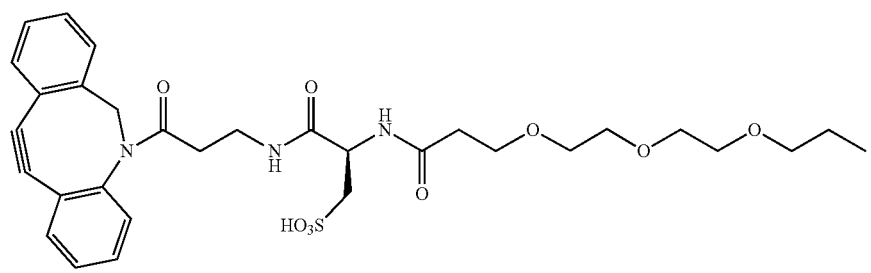

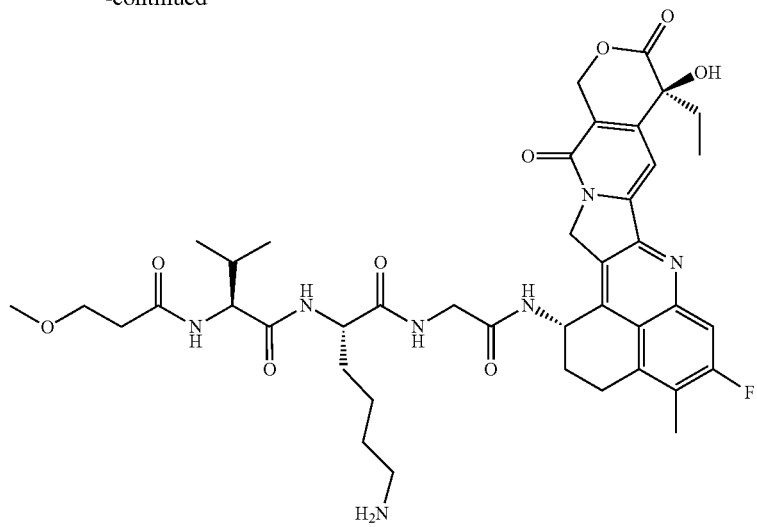
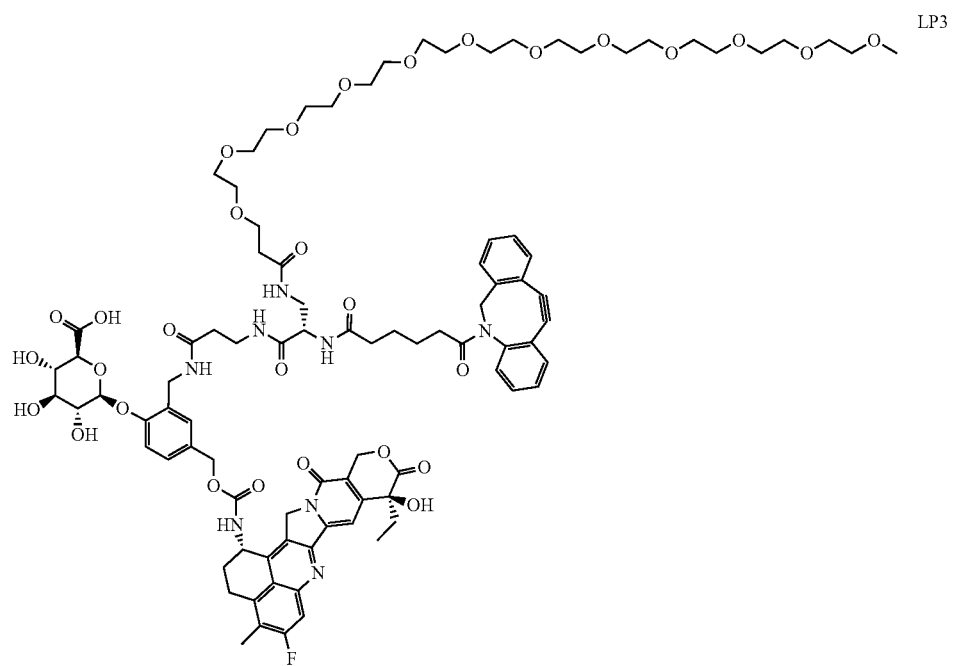 [SMILES: CC[C@@]1(O)C(=O)OCc2c1cc1n(c2=O)Cc2c-1nc1cc(F)c(C)c3c1c2[C@@H](NC(=O)OCc1ccc(O[C@@H]2O[C@H](C(=O)O)[C@@H](O)[C@H](O)[C@H]2O)c(CNC(=O)CCNC(=O)[C@H](CNC(=O)CCOCCOCCOCCOCCOCCOCCOCCOCCOCCOCCOCCOC)NC(=O)CCCCC(=O)N2Cc4ccccc4C#Cc4ccccc42)c1)CC3]
LP3
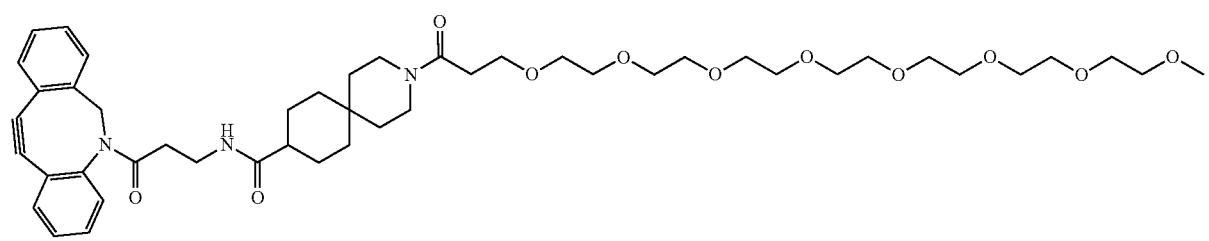
LP4

-continued
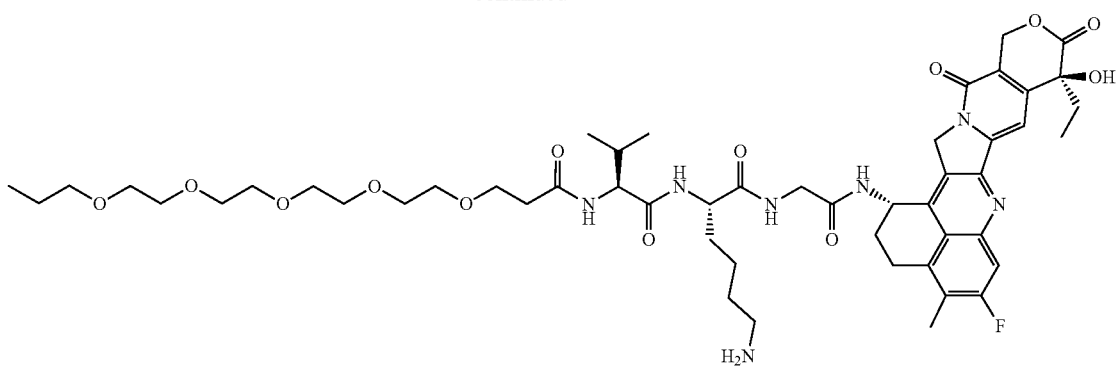
LP5
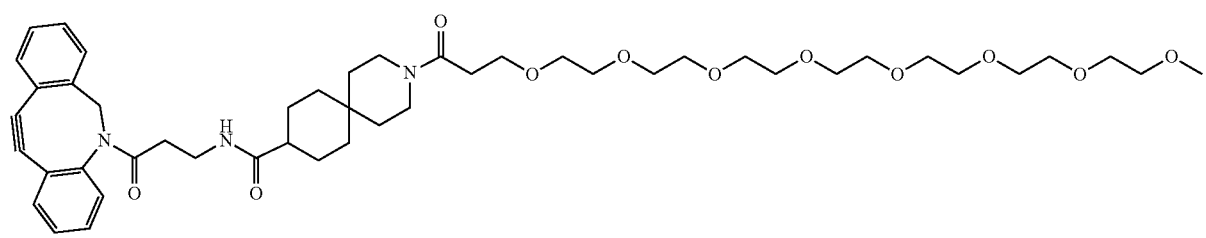
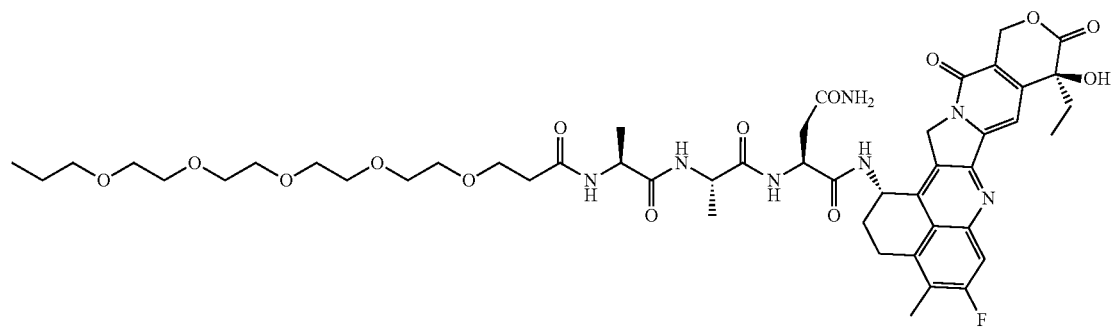
LP6
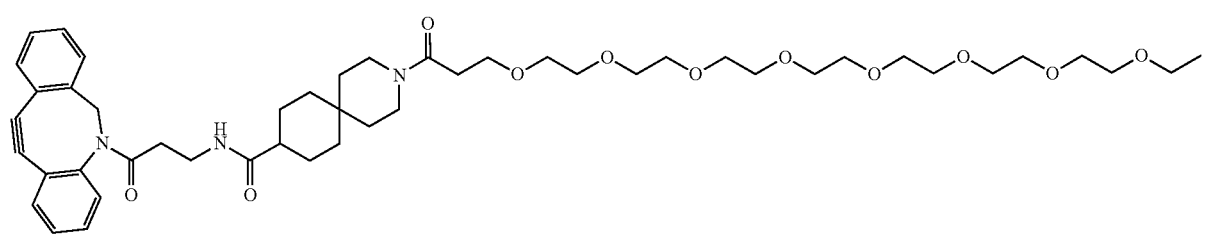
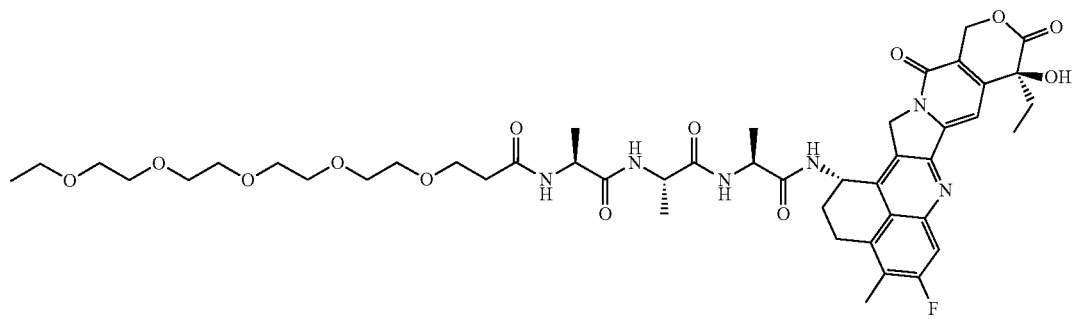

-continued
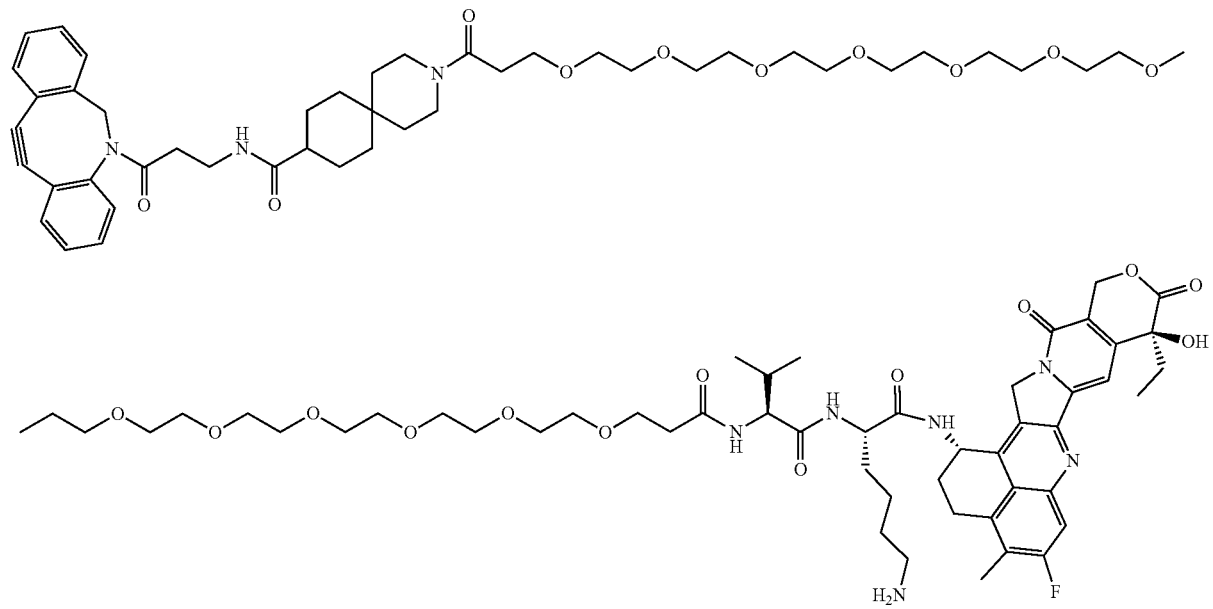
LP7
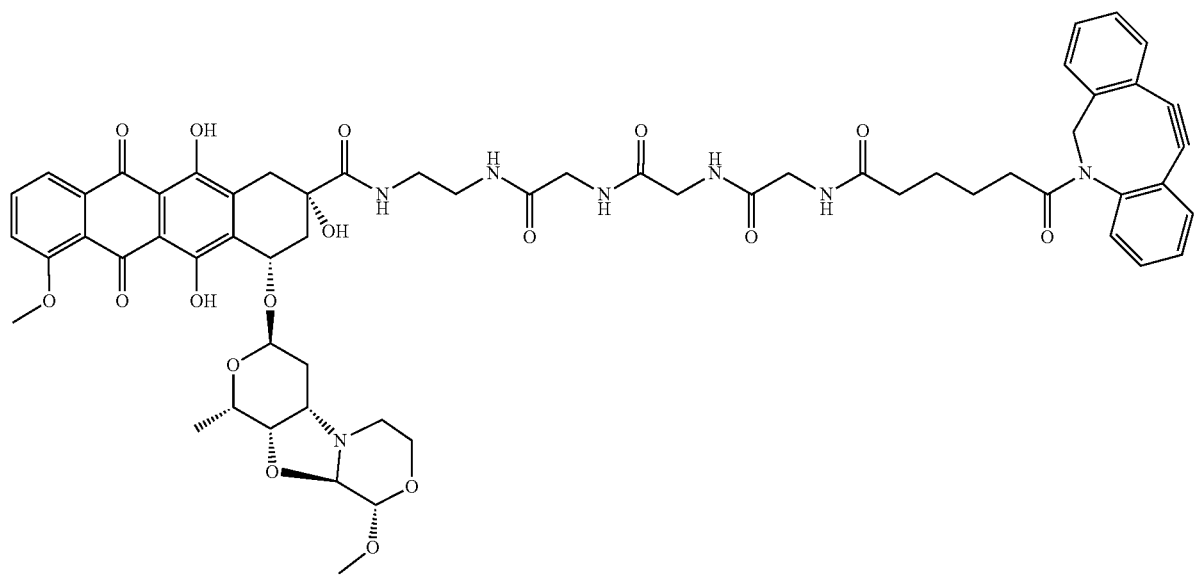
LP8
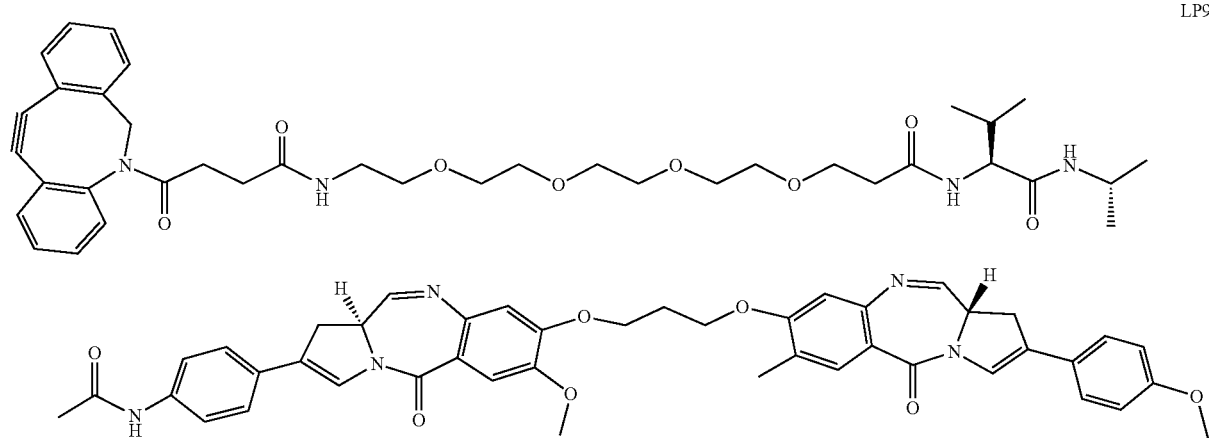
LP9

LP10
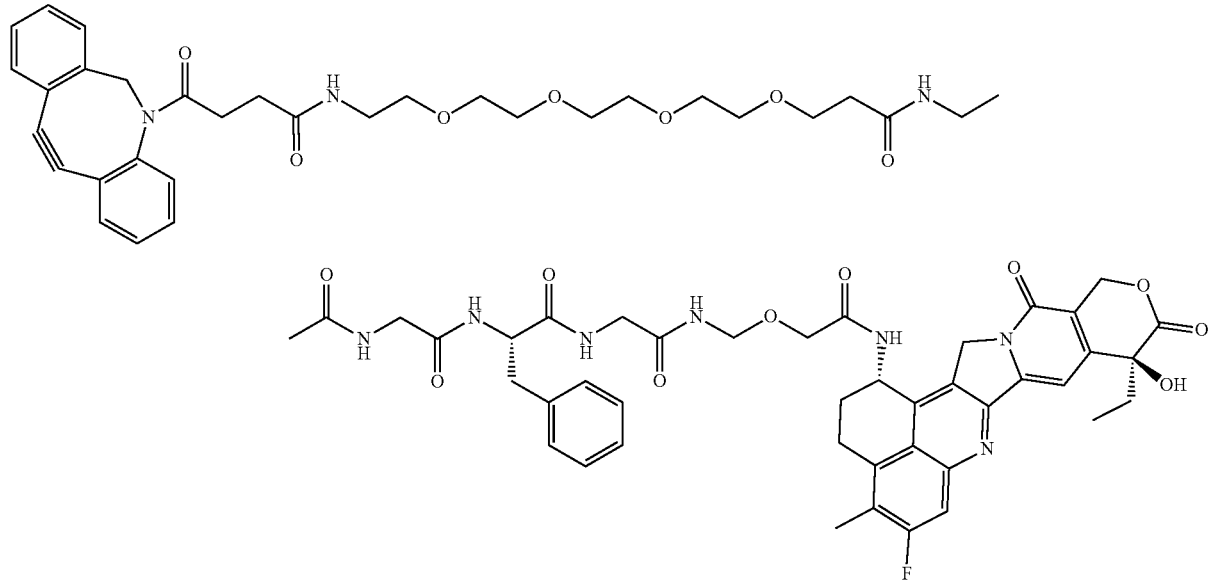
LP11
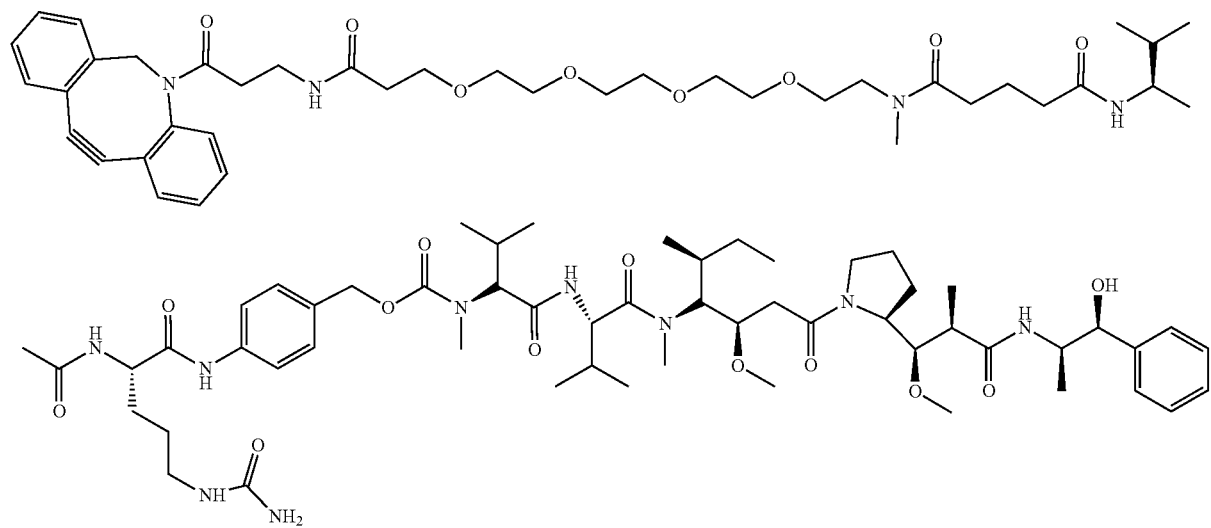
LP12
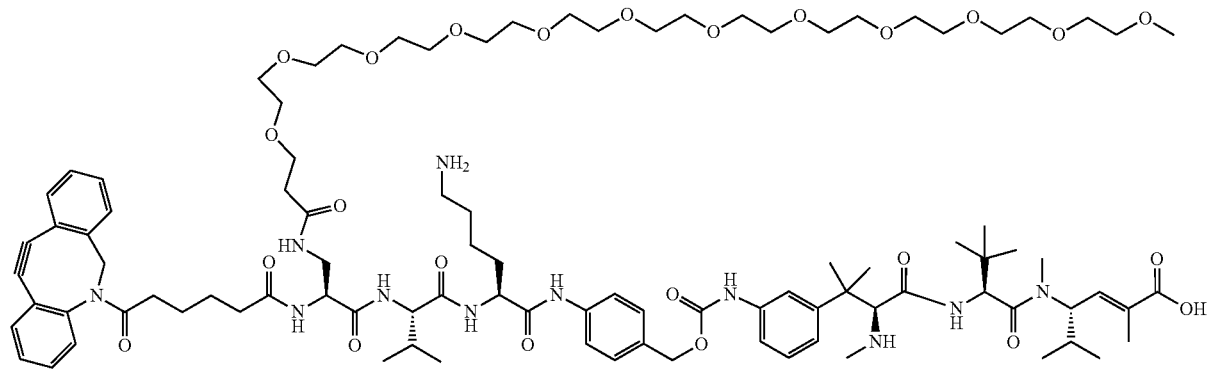

-continued
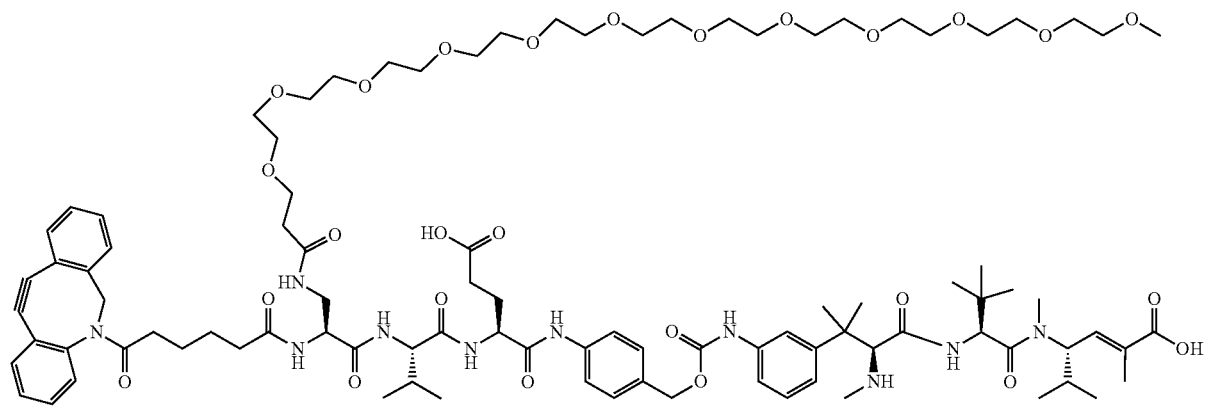
LP13
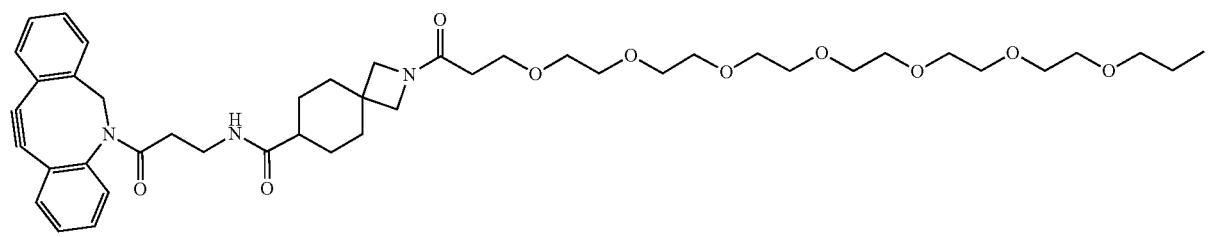
LP14
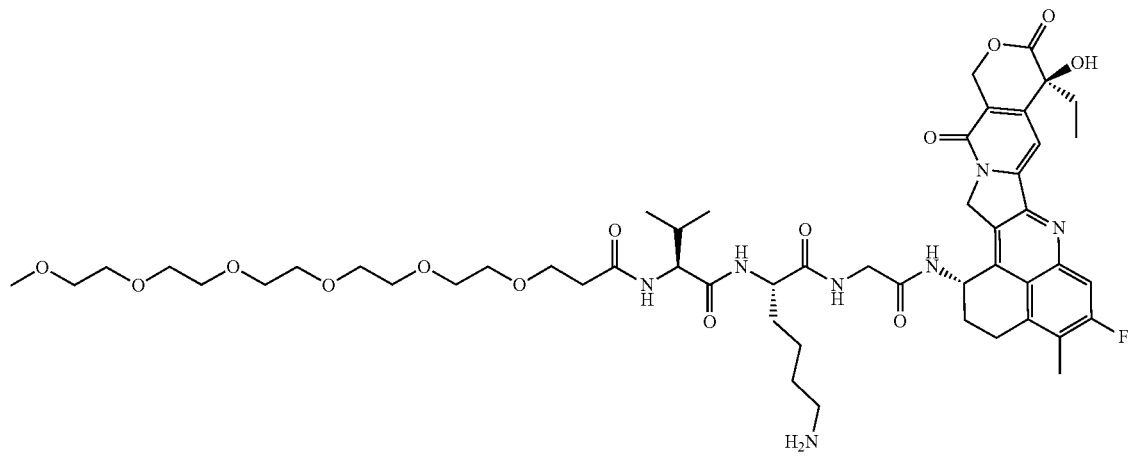
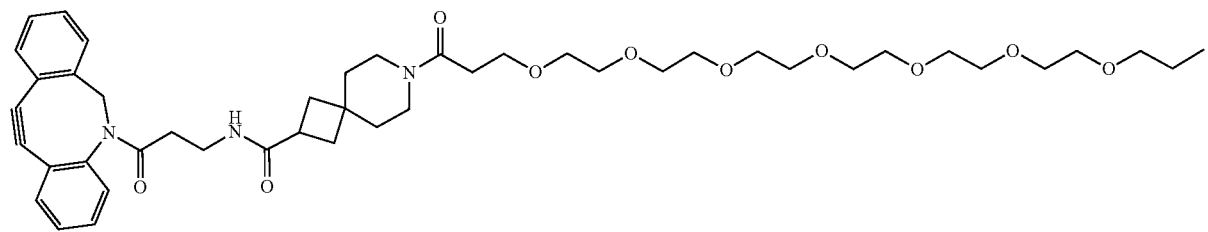
LP15

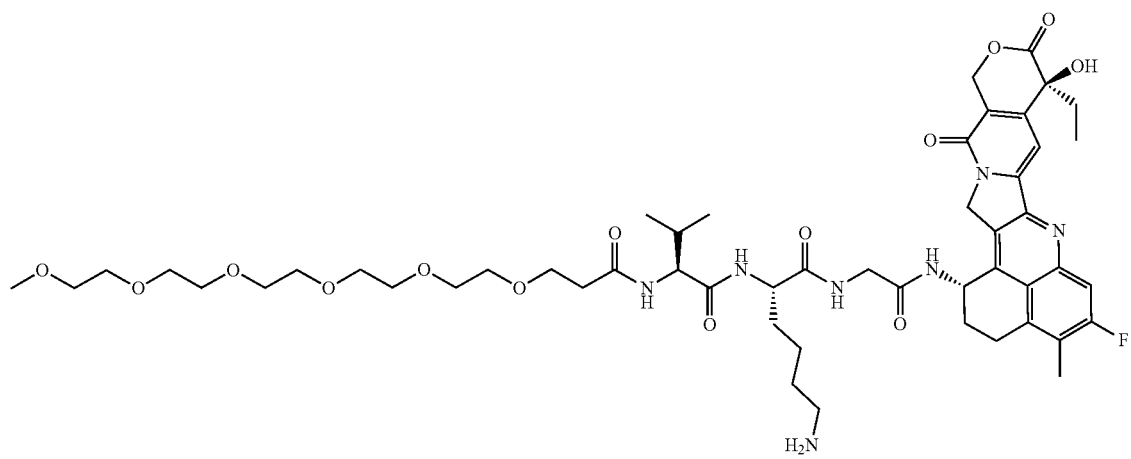
LP16
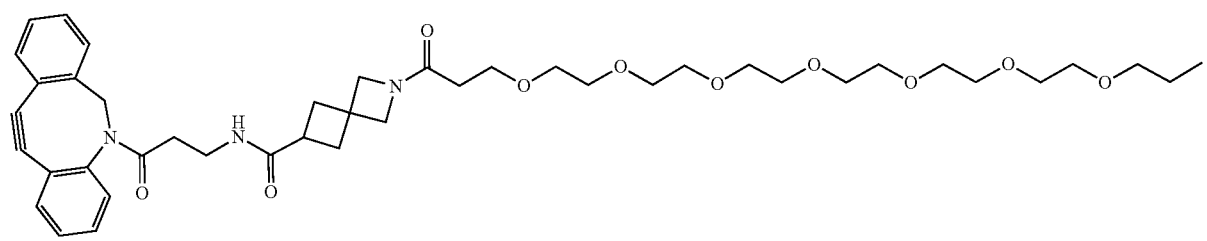
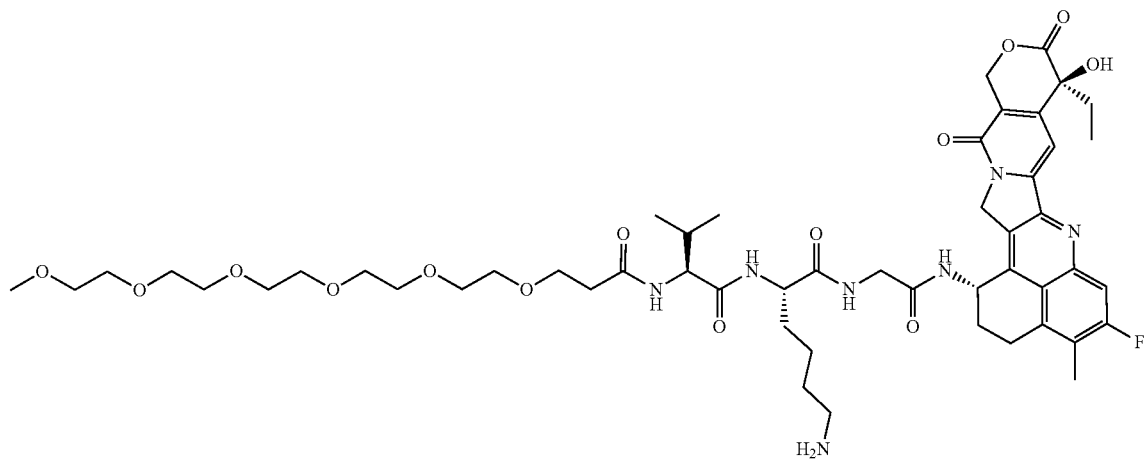
LP17
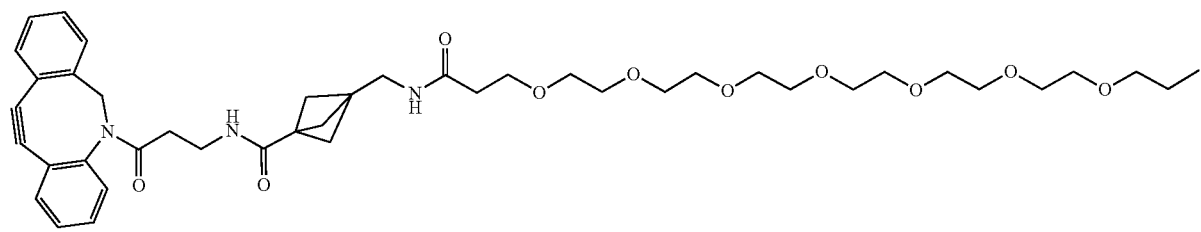

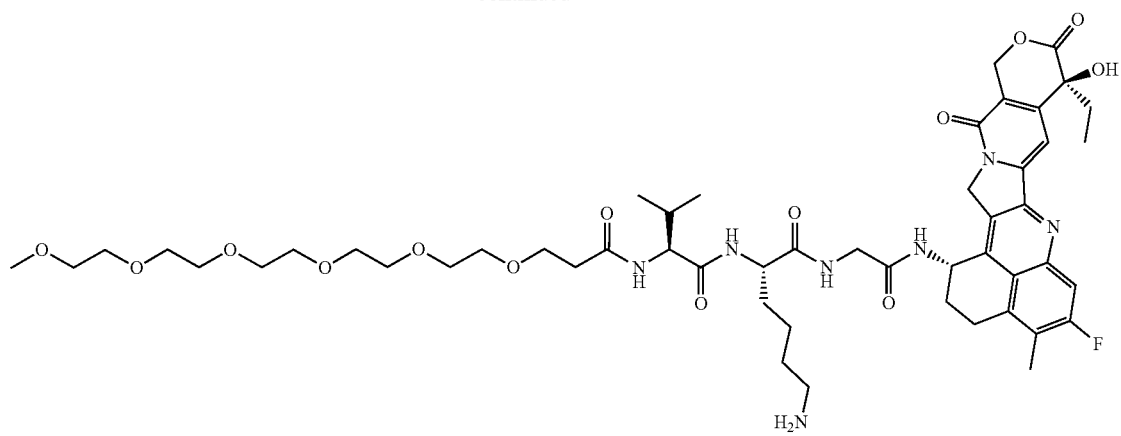
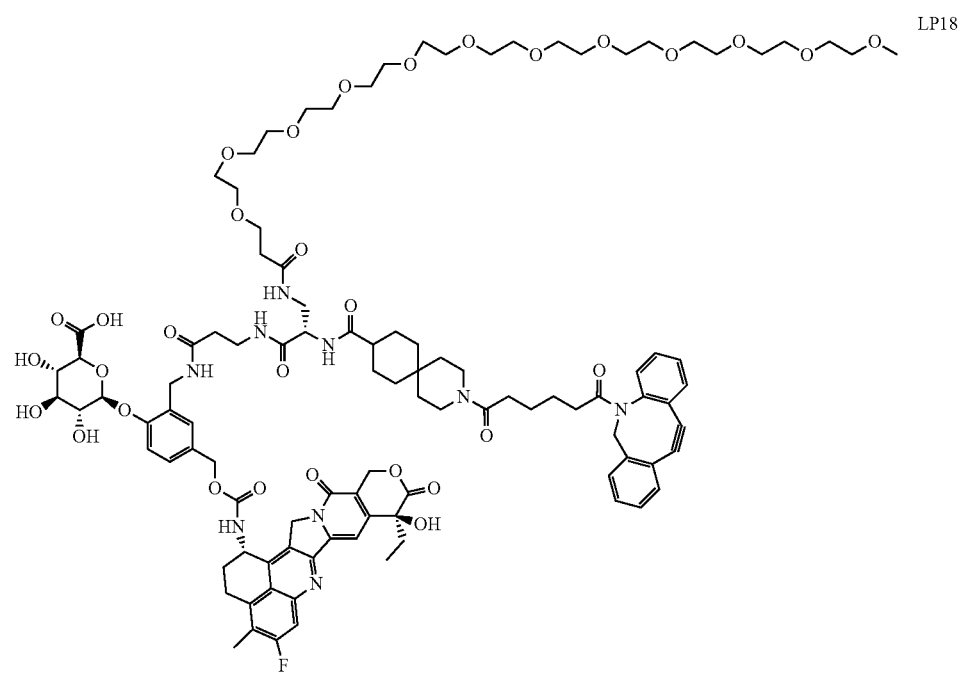
LP18

-continued
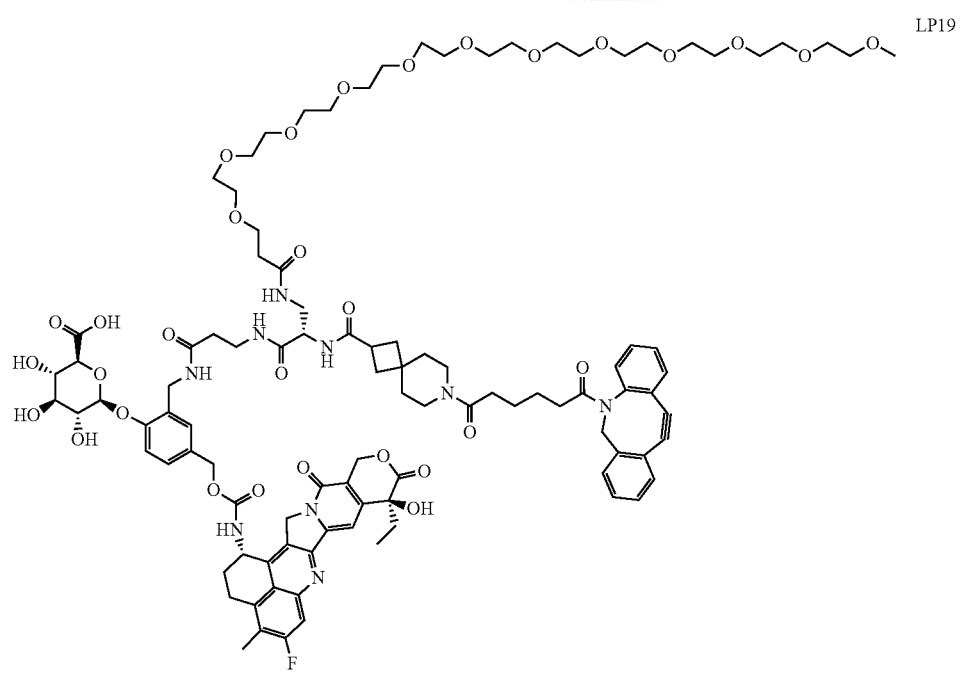
LP19
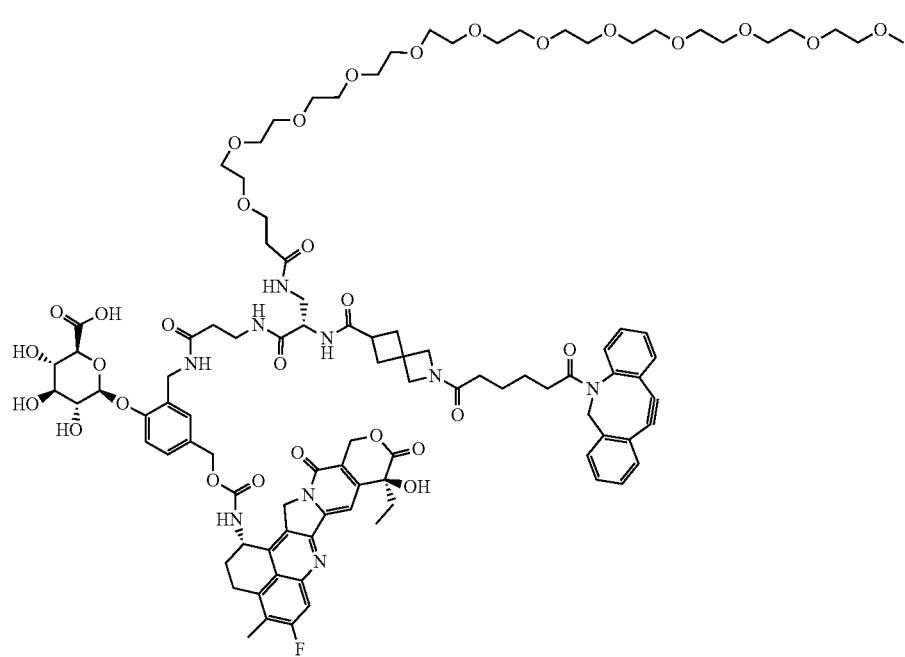
LP20
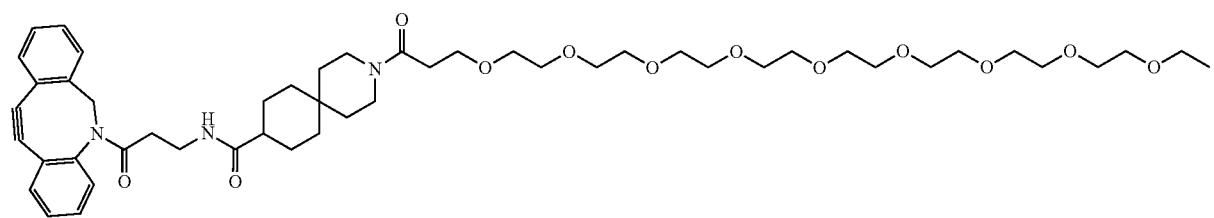
(LP21)

361 362
-continued
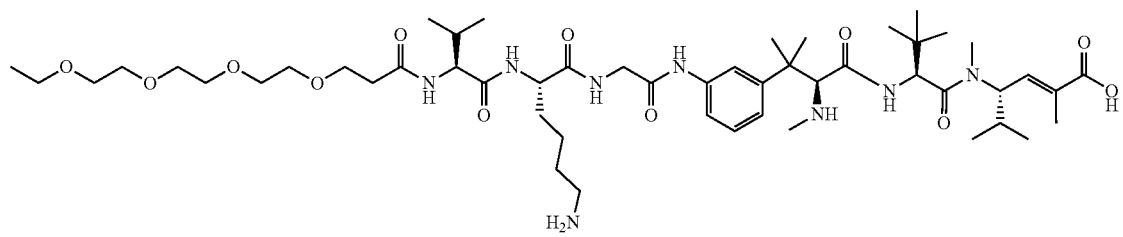
LP22
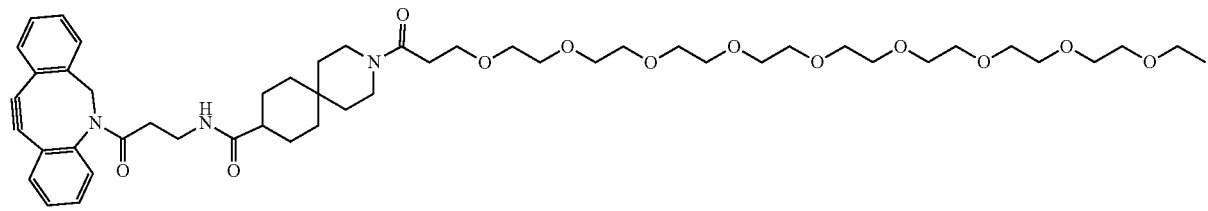
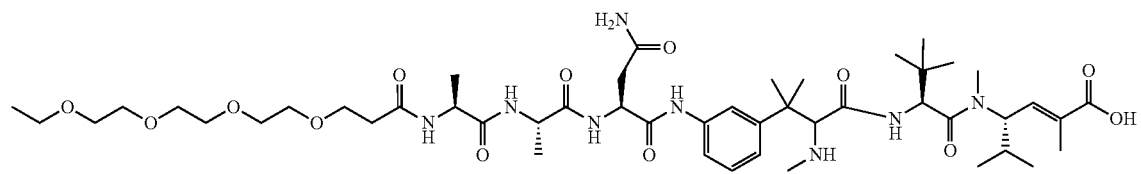
LP23
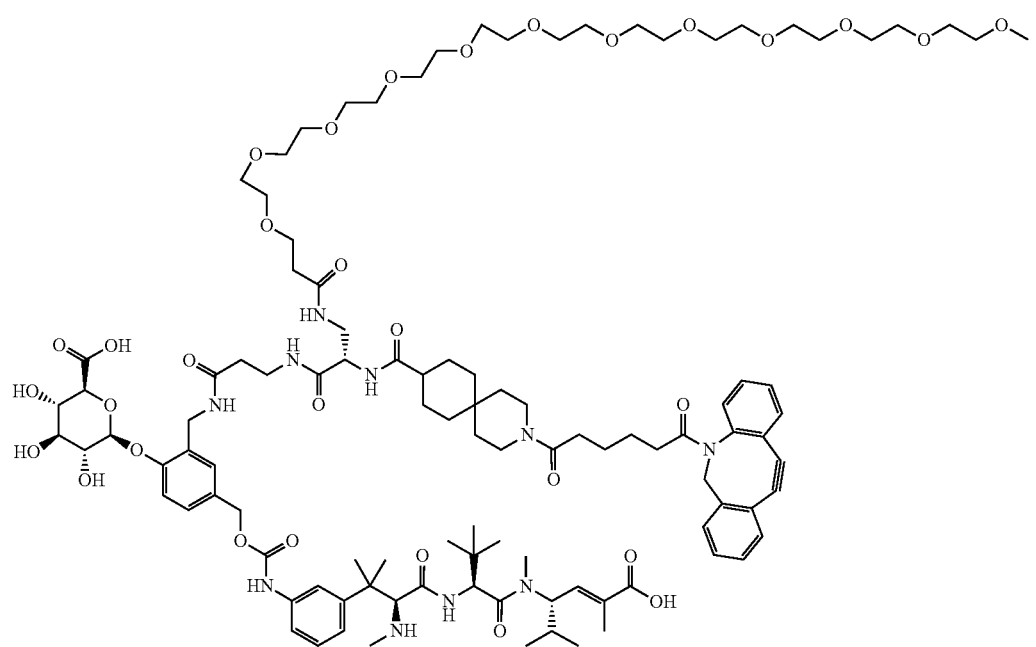

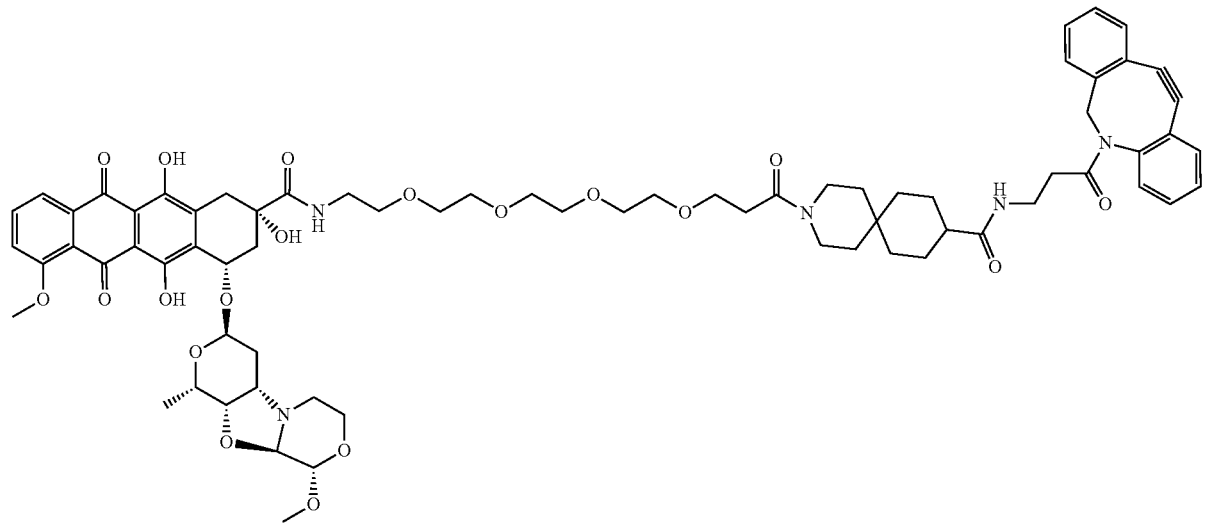
LP24
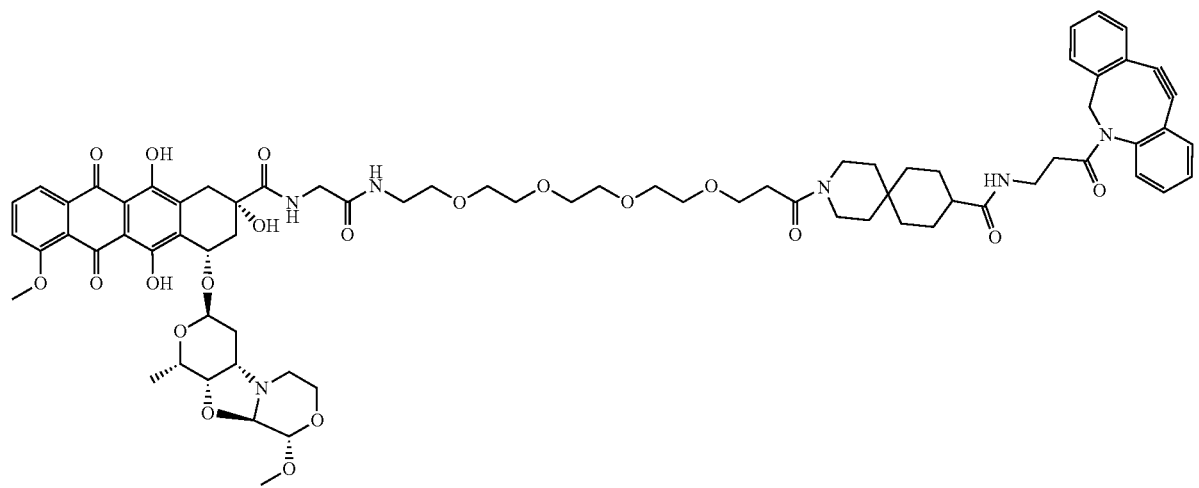
LP25
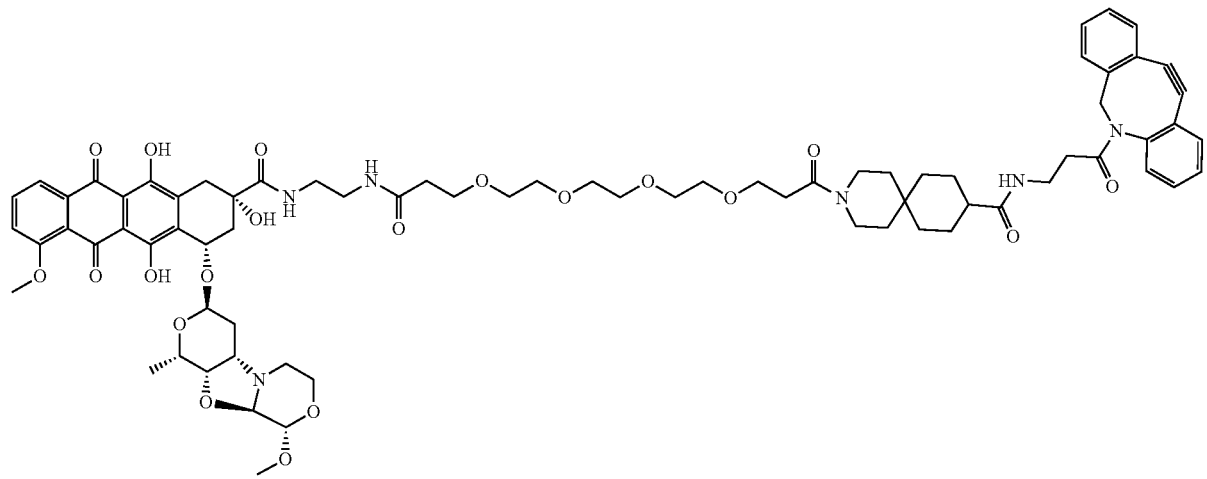
LP26

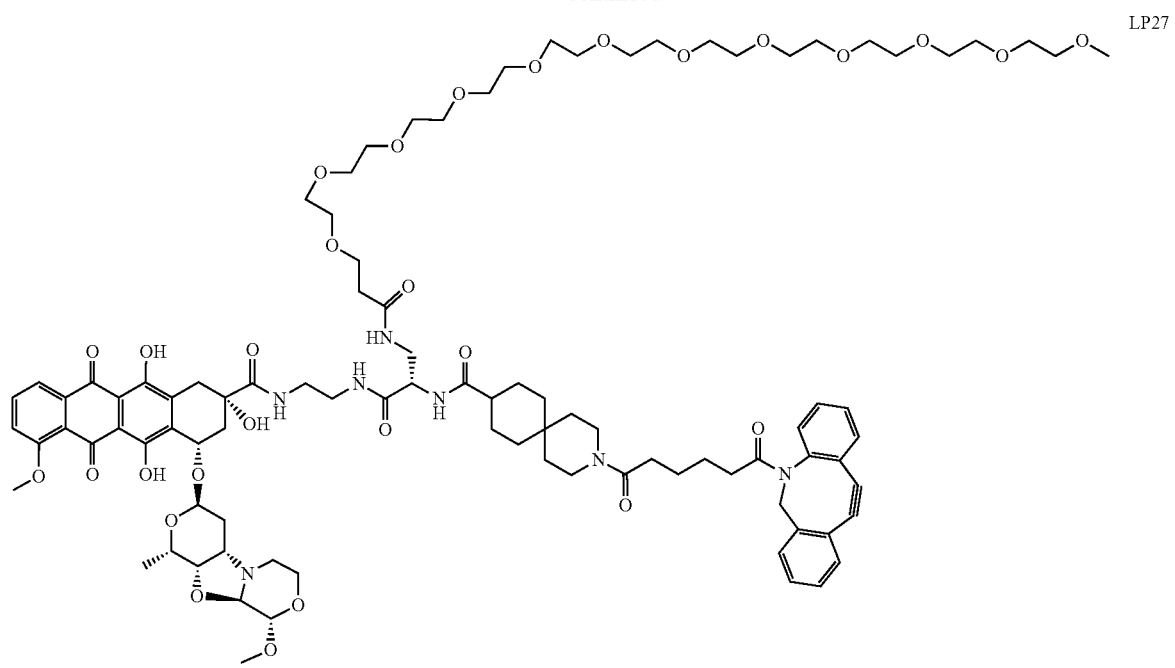
LP27
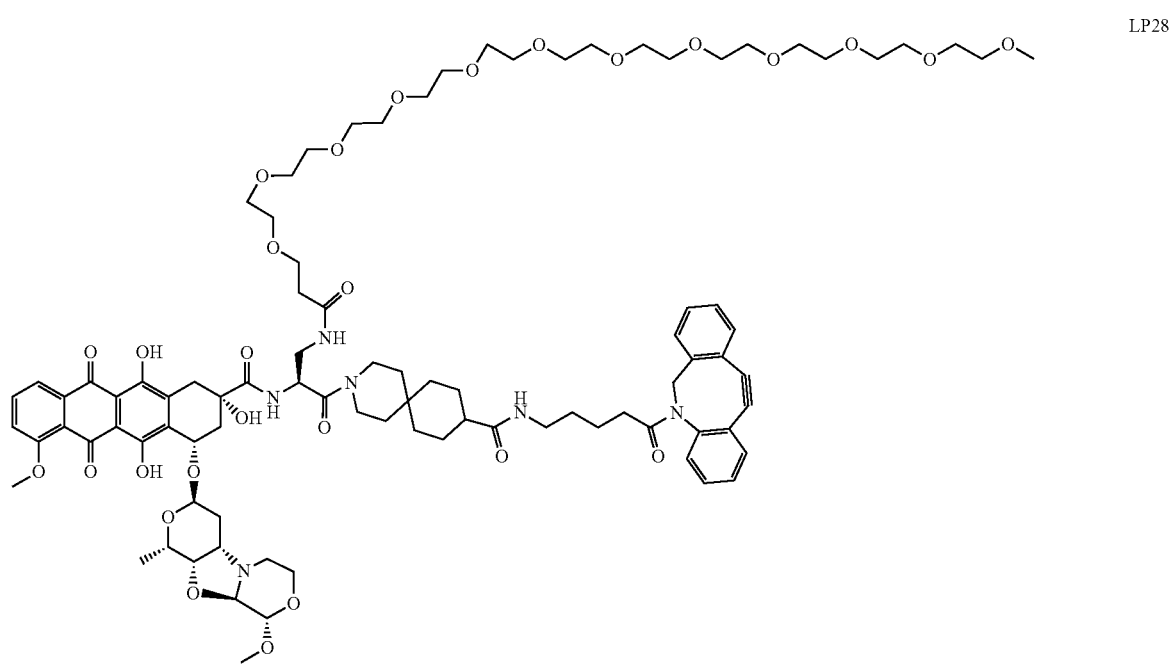
LP28

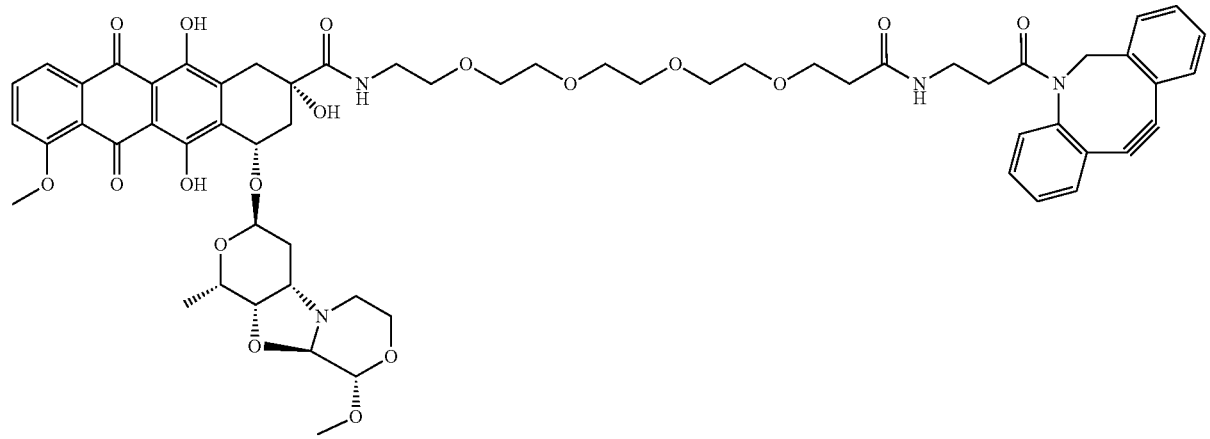
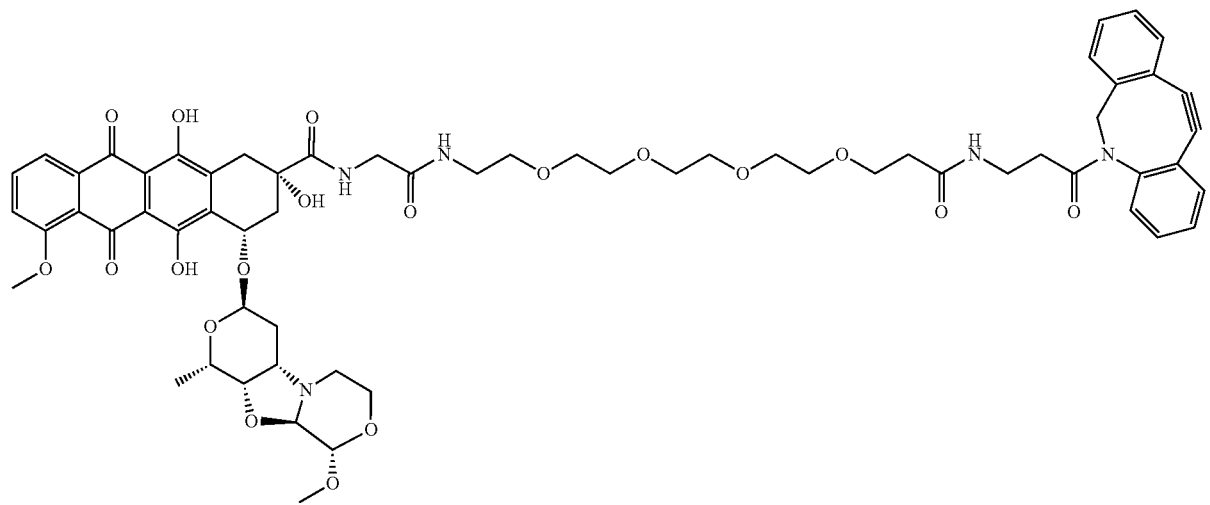
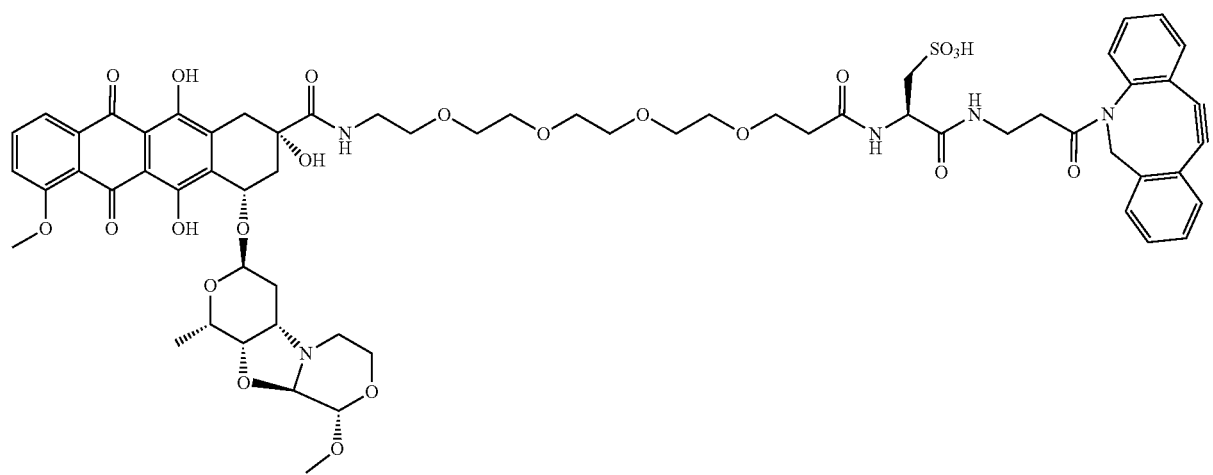

-continued
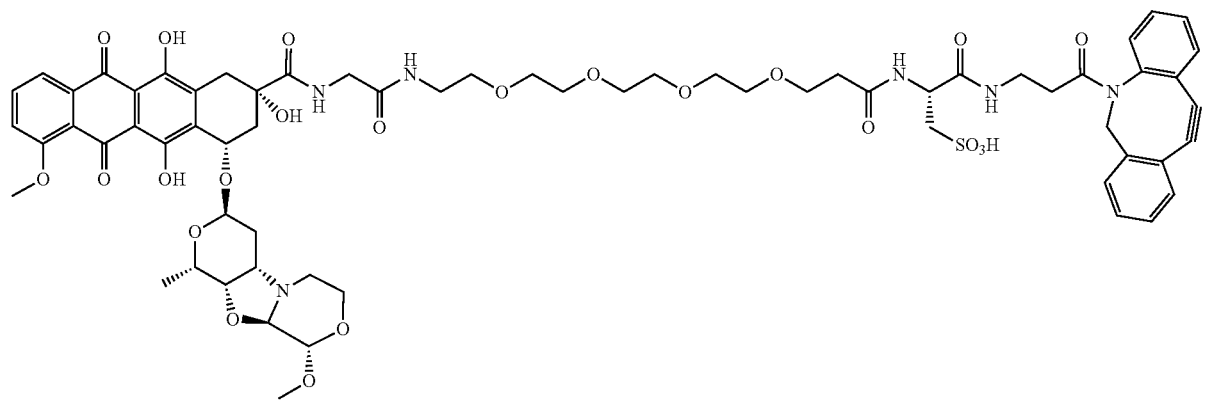
LP32
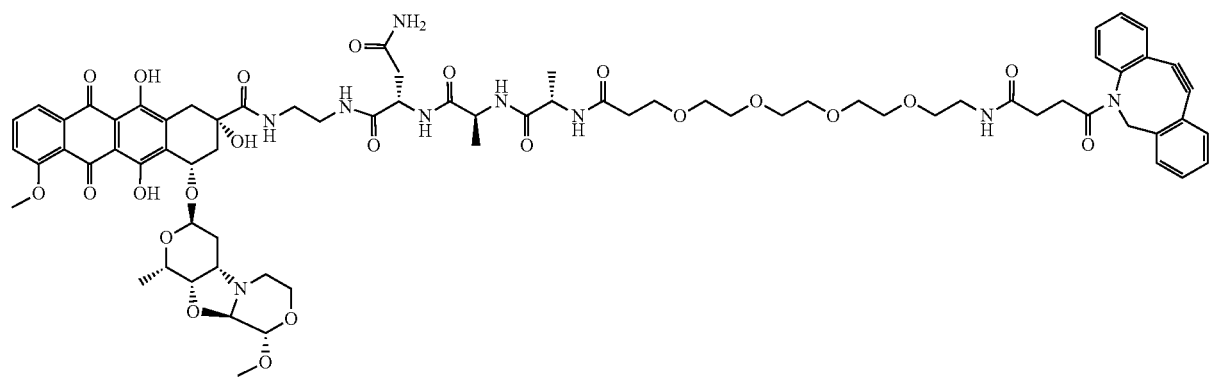
LP33
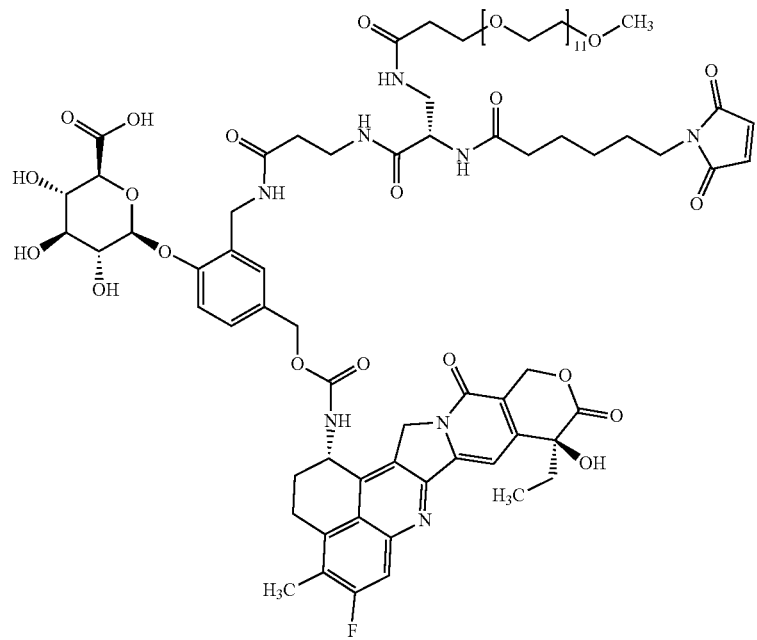
LP34

-continued
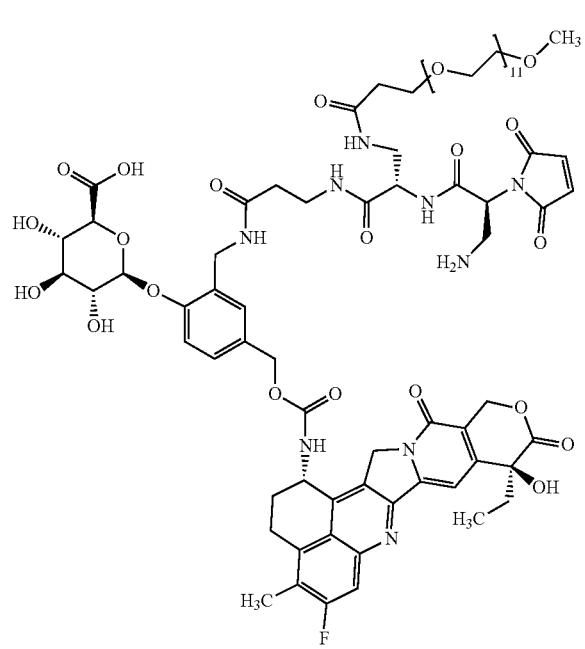
LP35
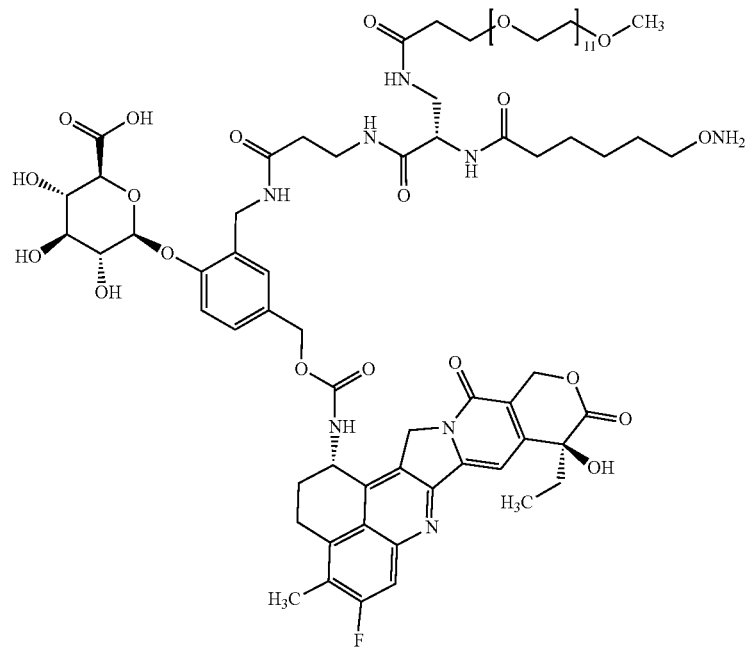
LP36

-continued
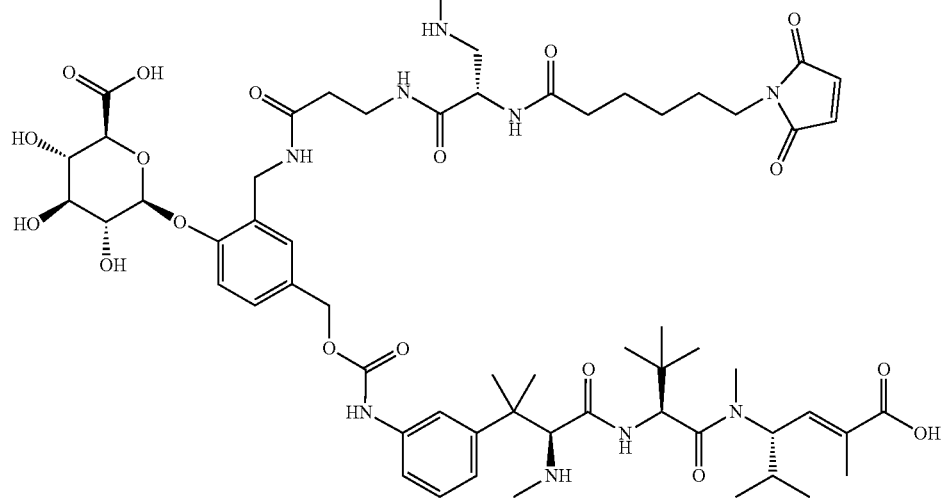
LP37
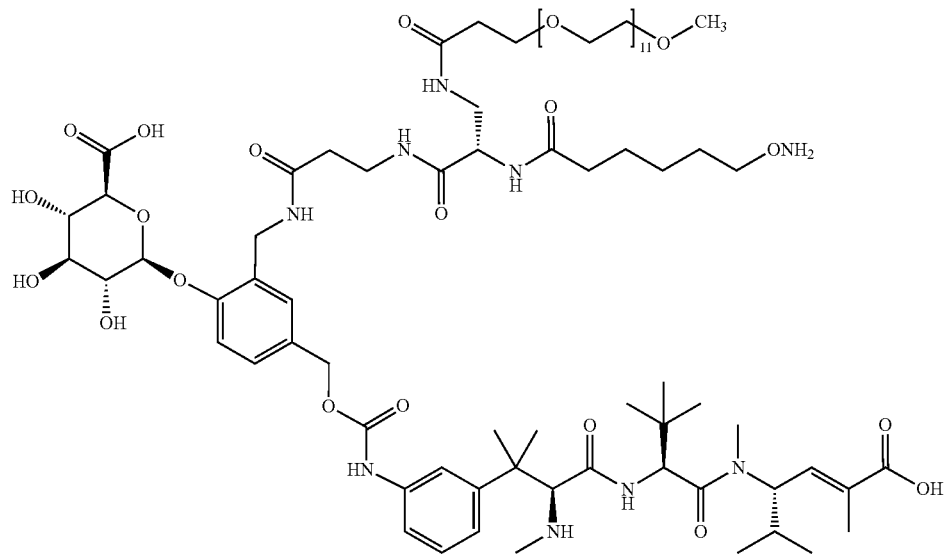
LP38

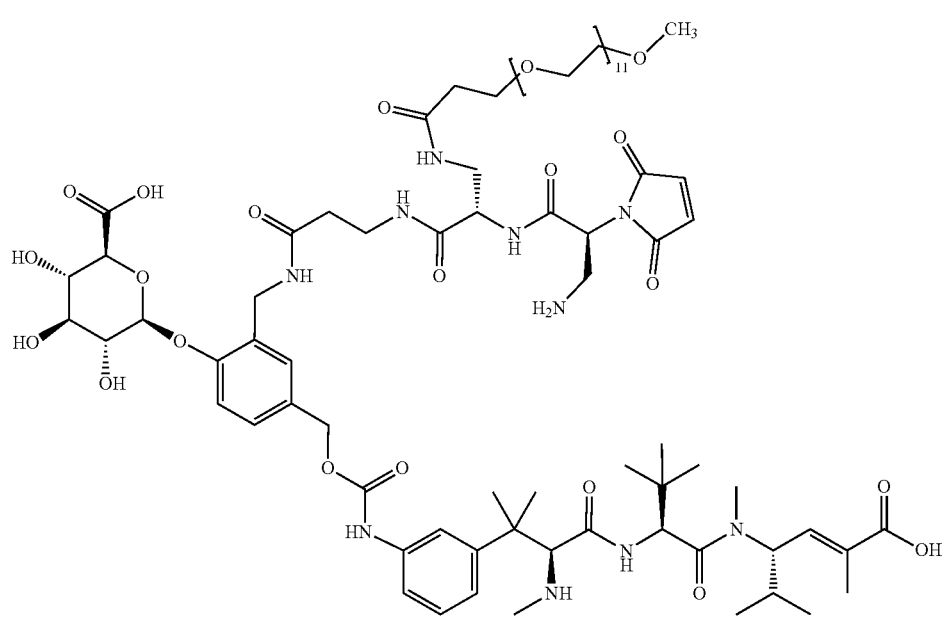
LP39
In some embodiments, an anti-ROR1 conjugate is prepared by contacting an anti-ROR1 antibody as disclosed herein with a linker precursor having a structure of any of LP1A-LP39A:
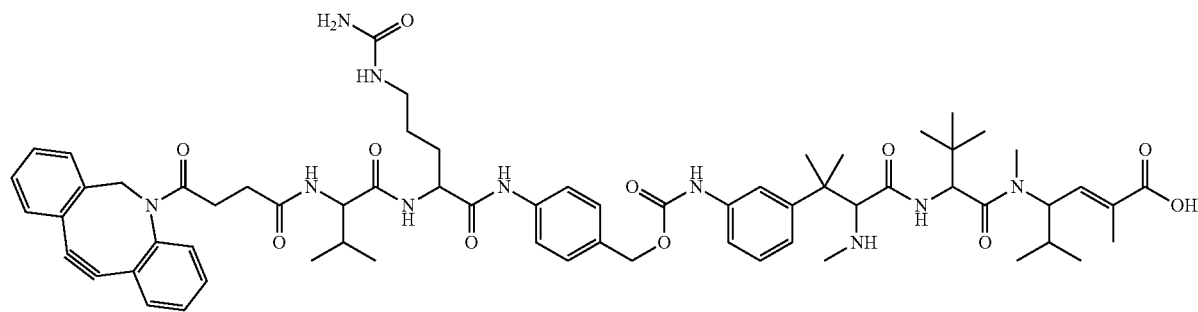
LP1A
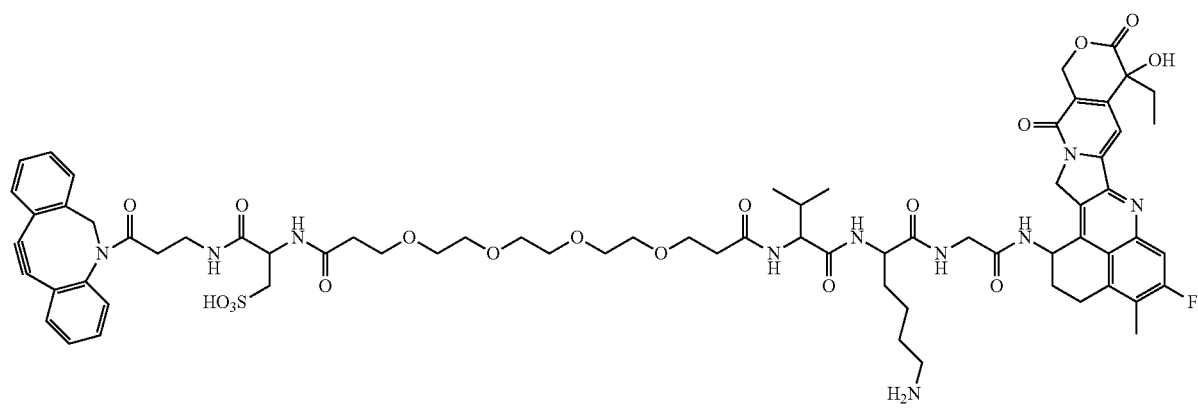
LP2A -continued
LP3A
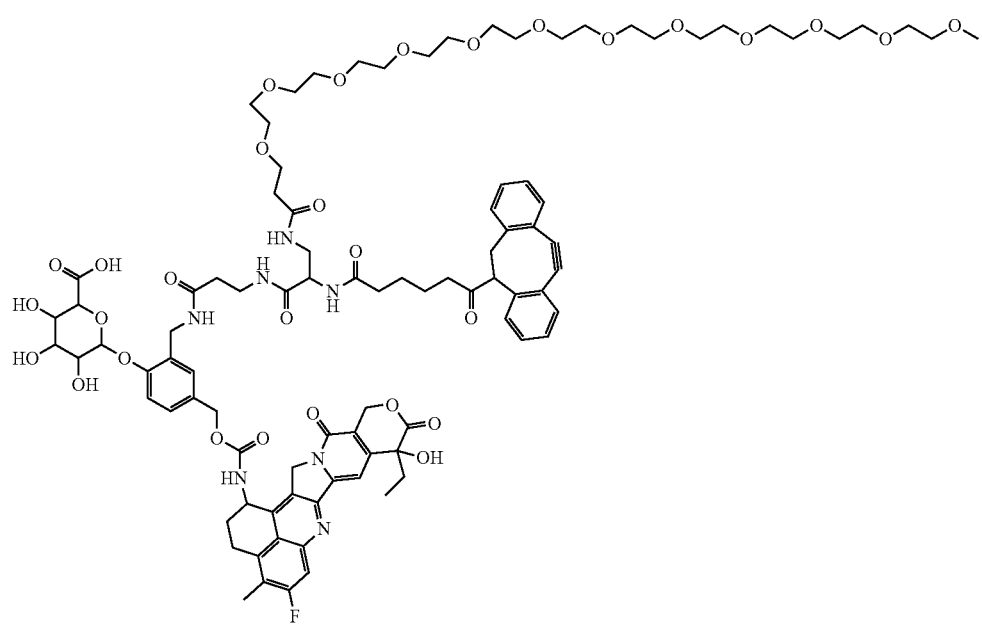
LP4A
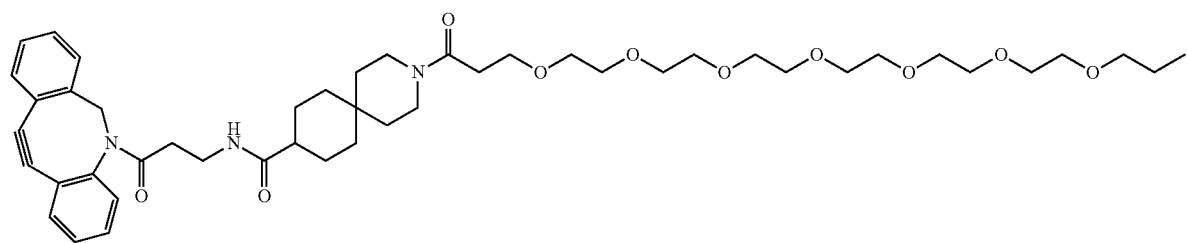
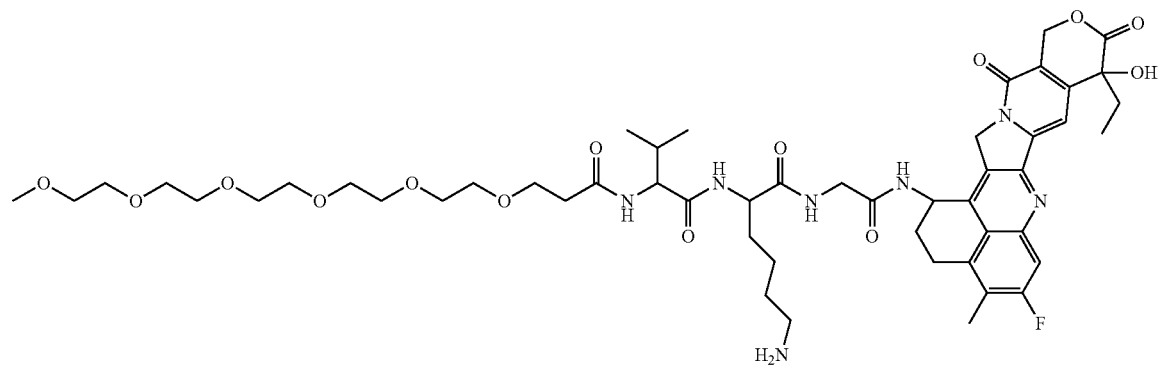
LP5A
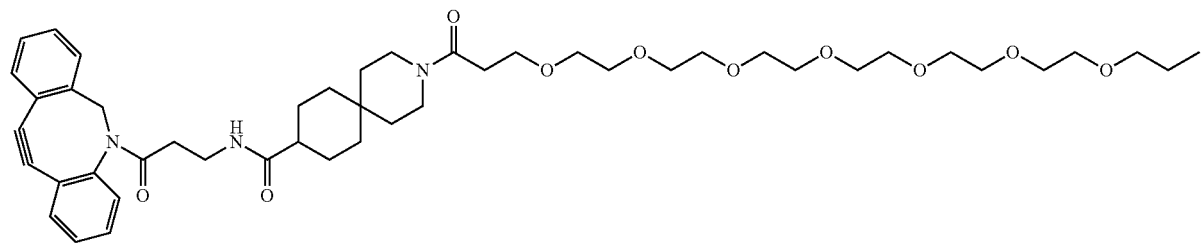

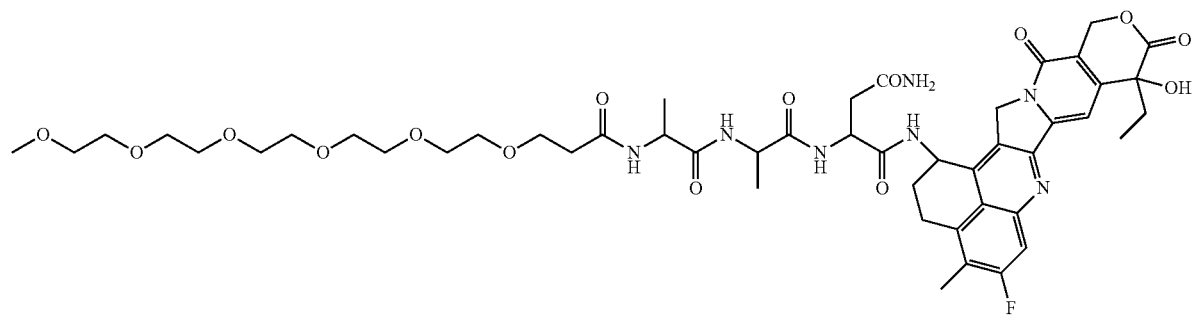
LP6A
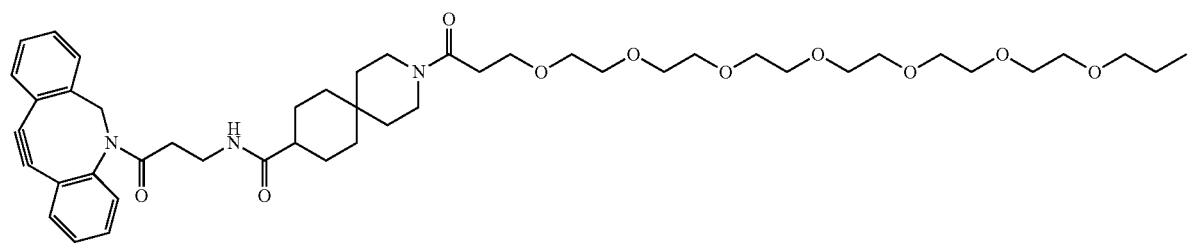
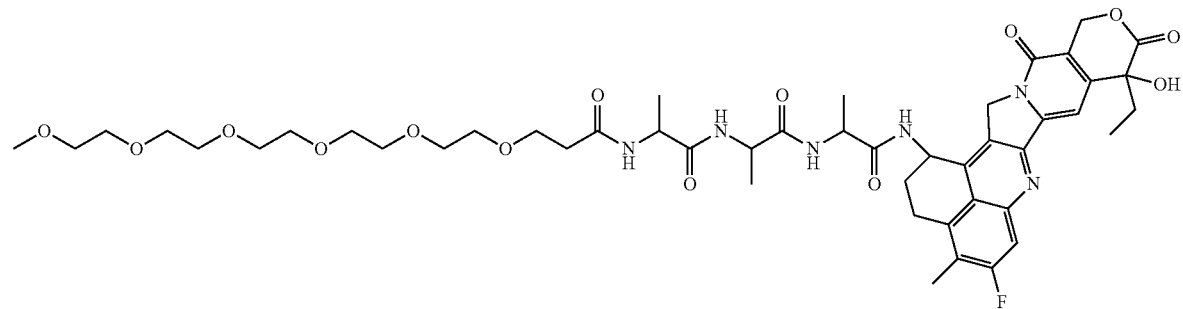
LP7A
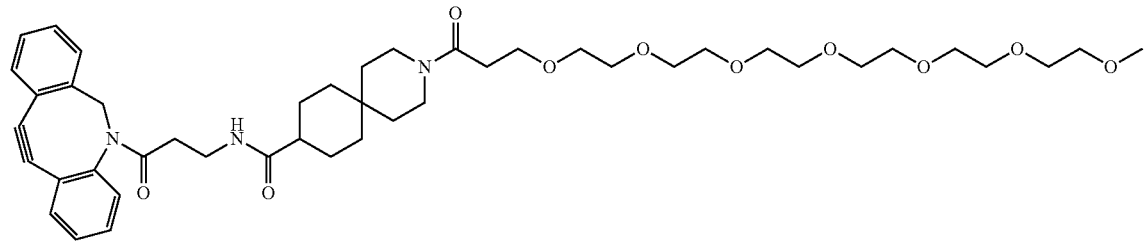
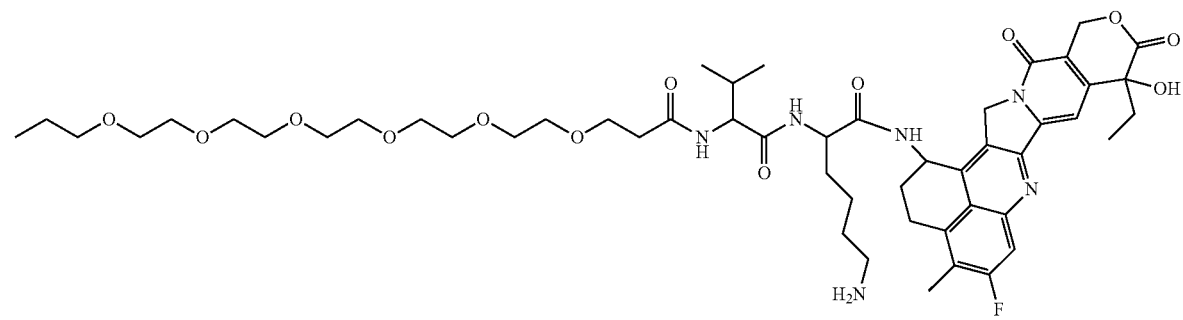

-continued
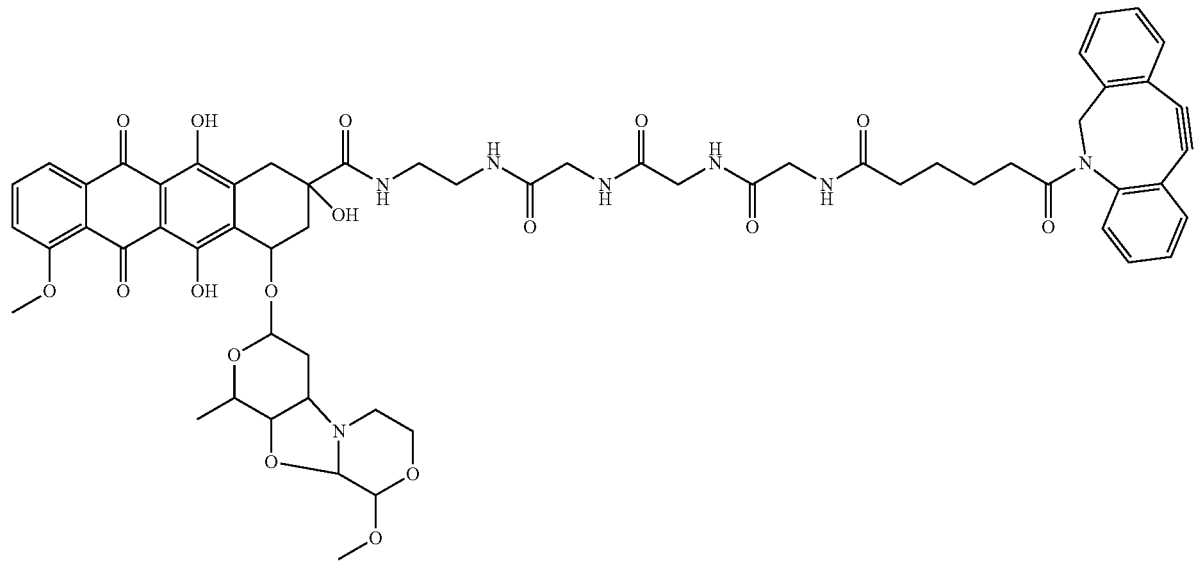
LP8A
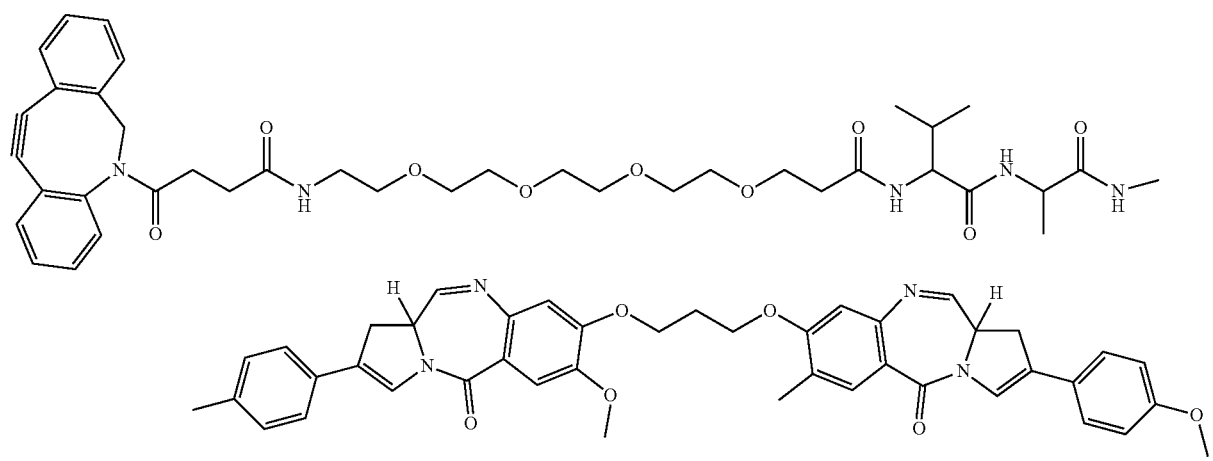
LP9A
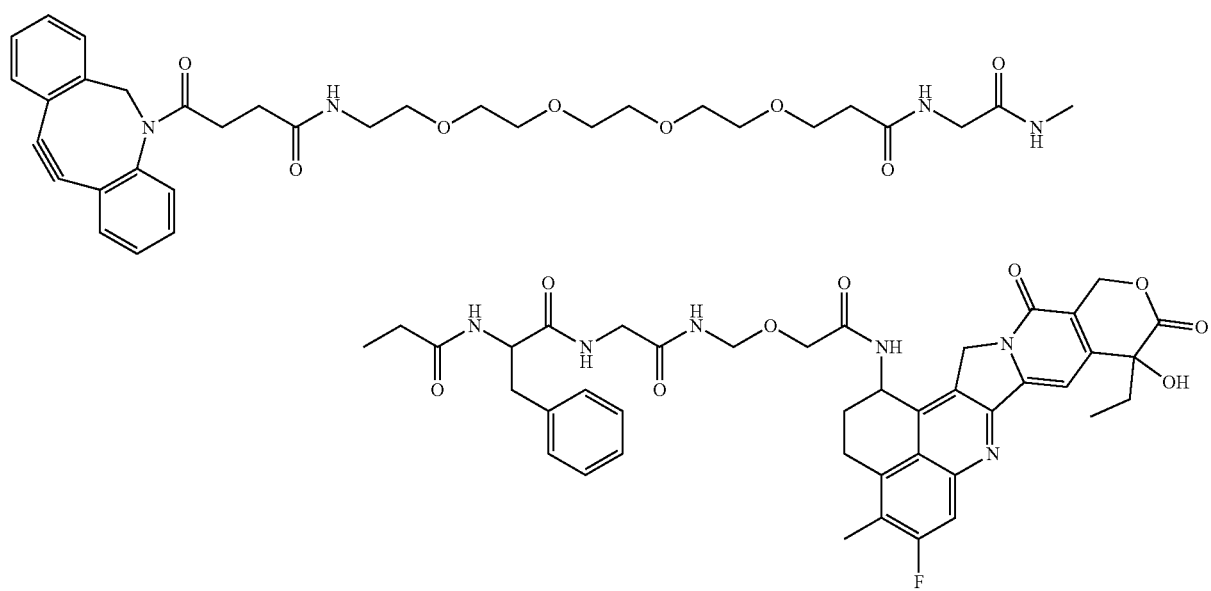
LP10A

-continued
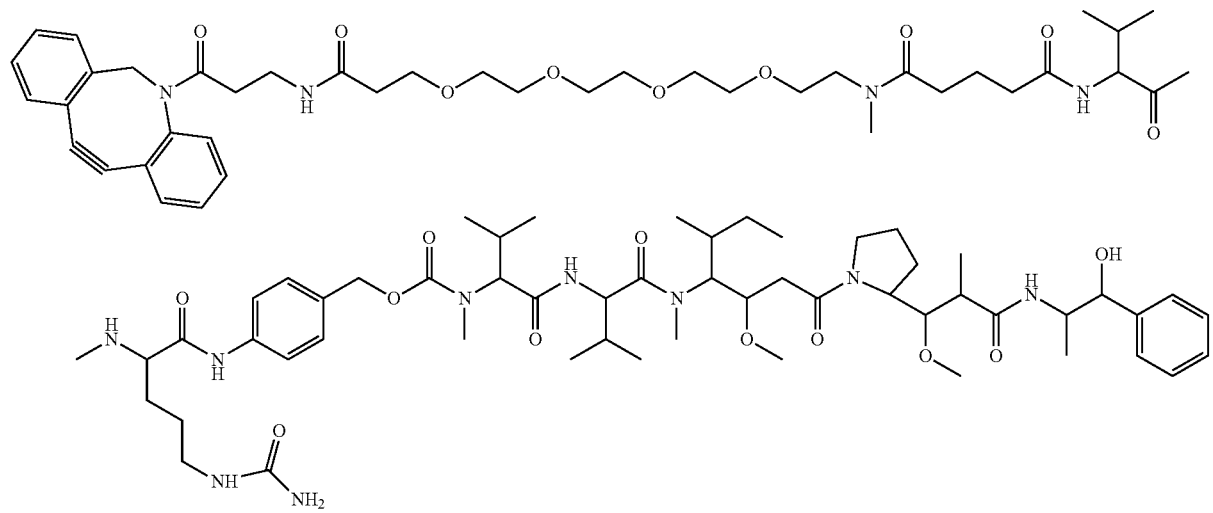
LP11A
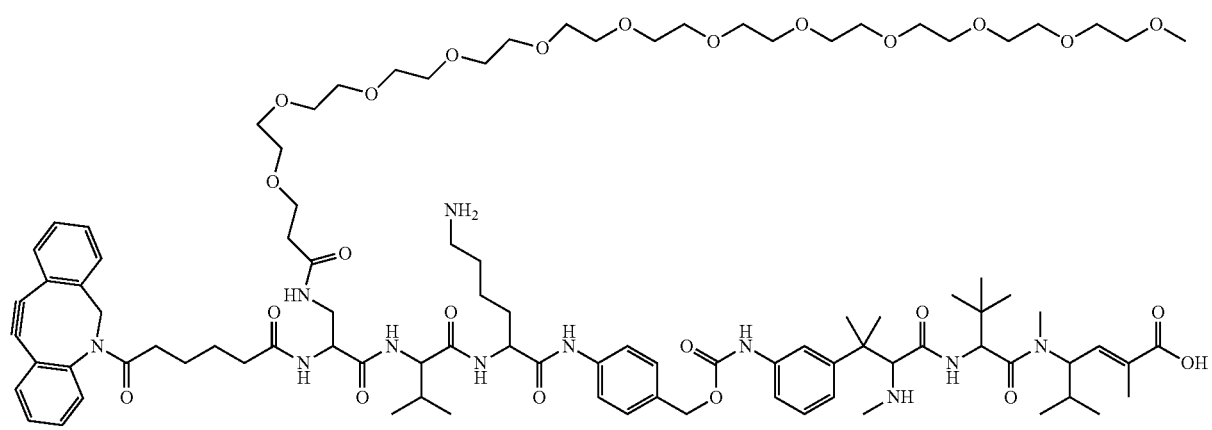
LP12A
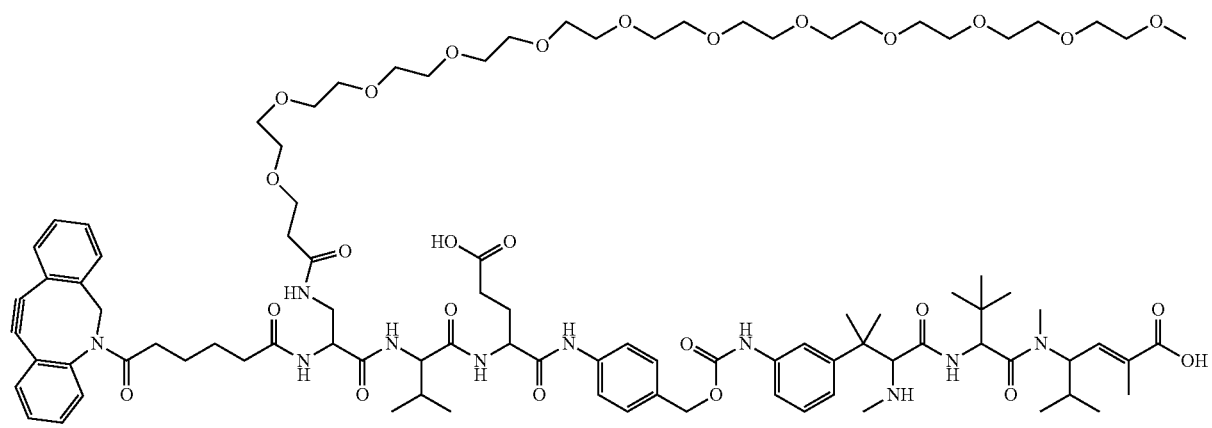
LP13A

-continued
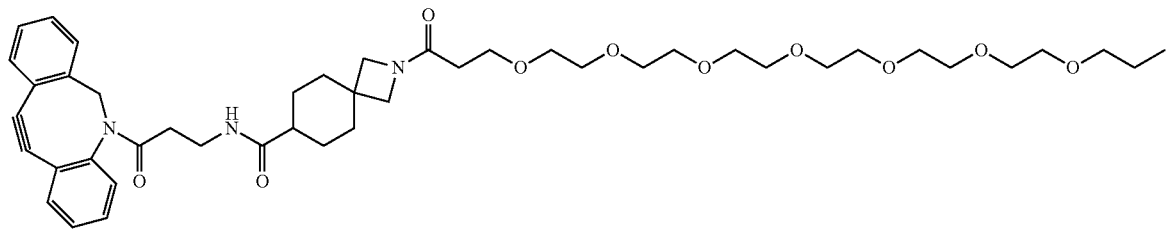
LP14A
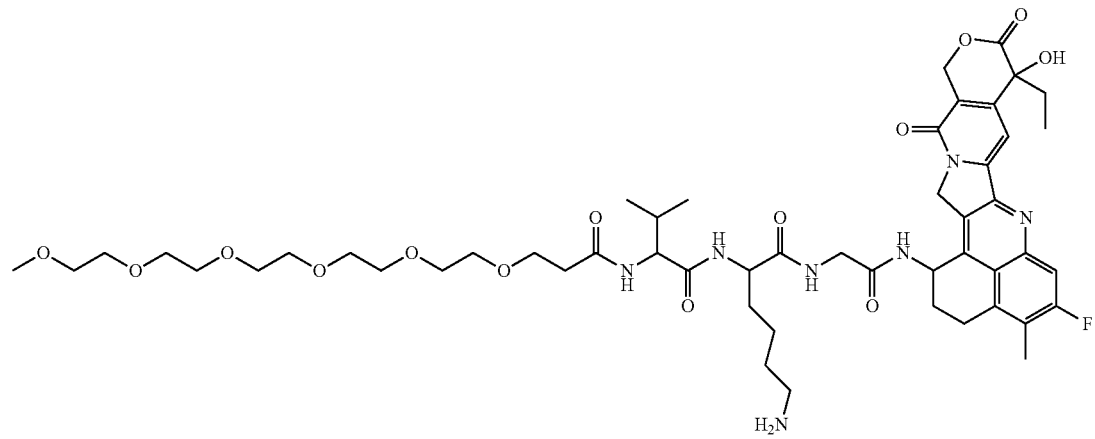
LP15A
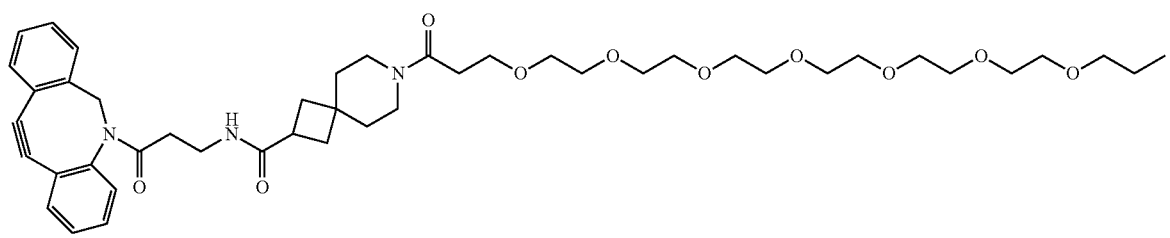
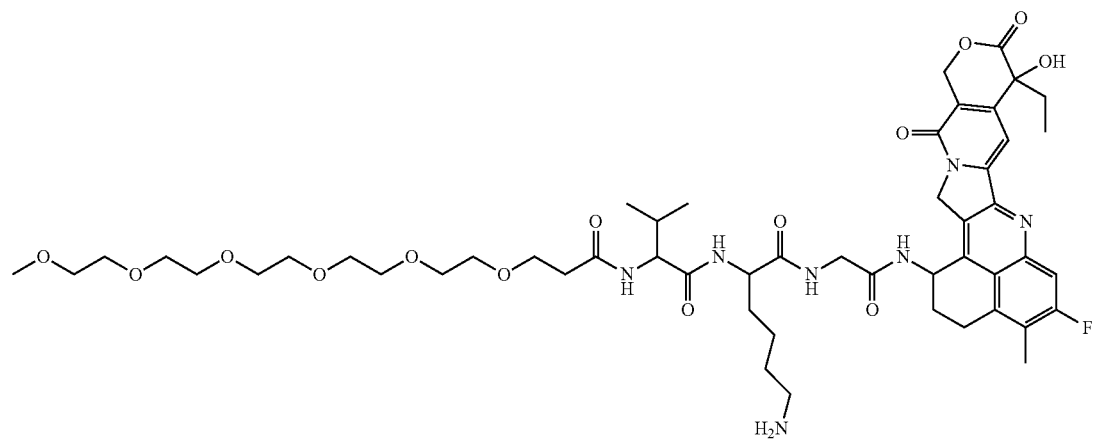
LP16A
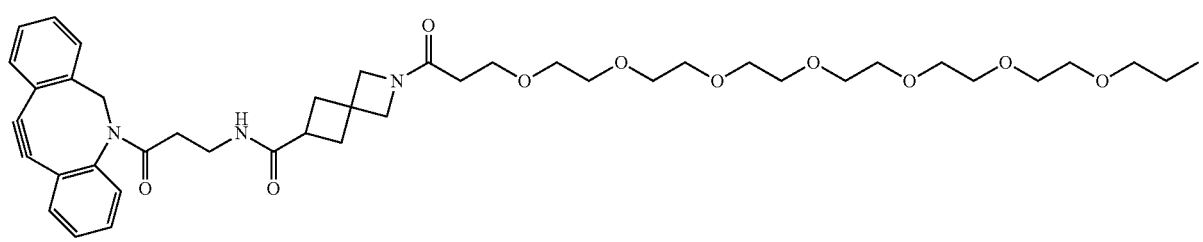

387
388
-continued
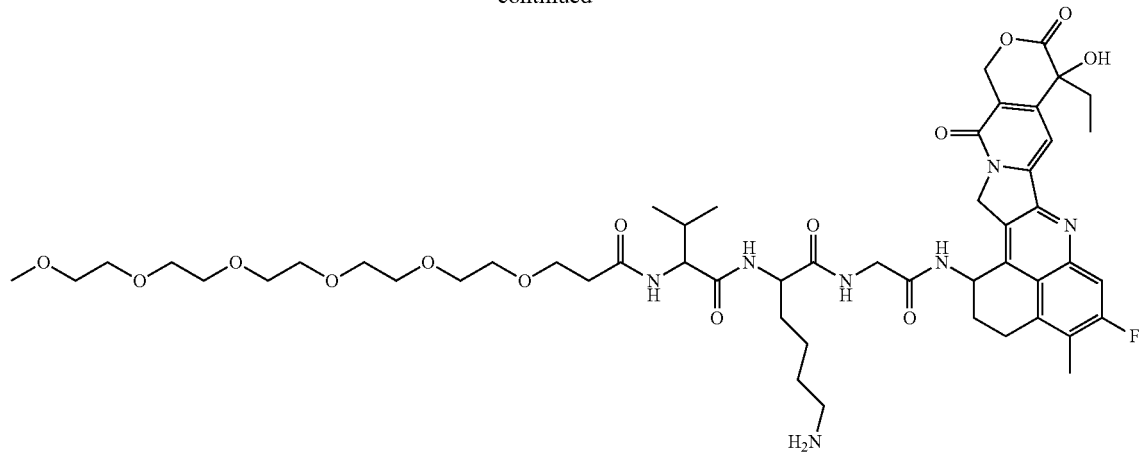
LP17A
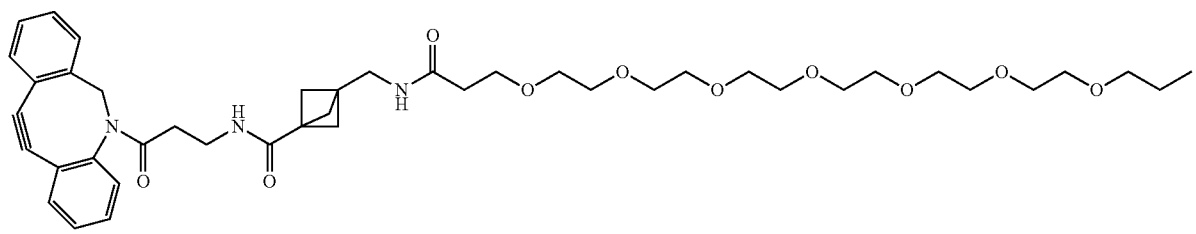
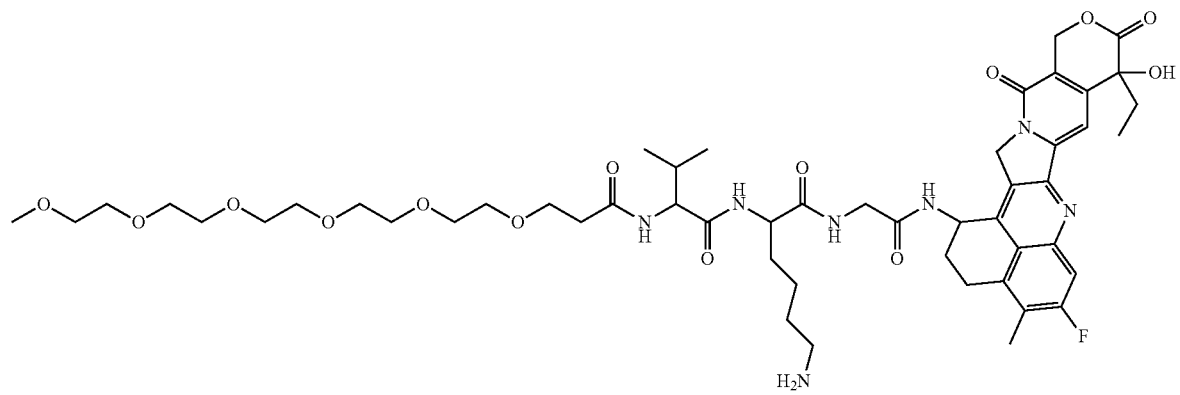

389 390
-continued
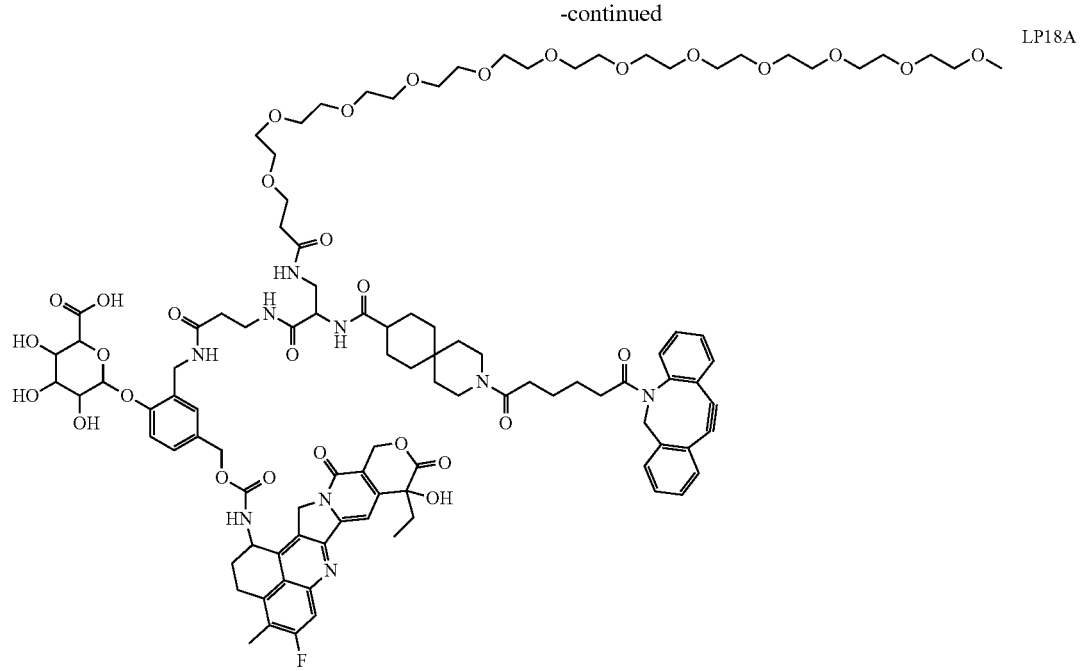
LP18A
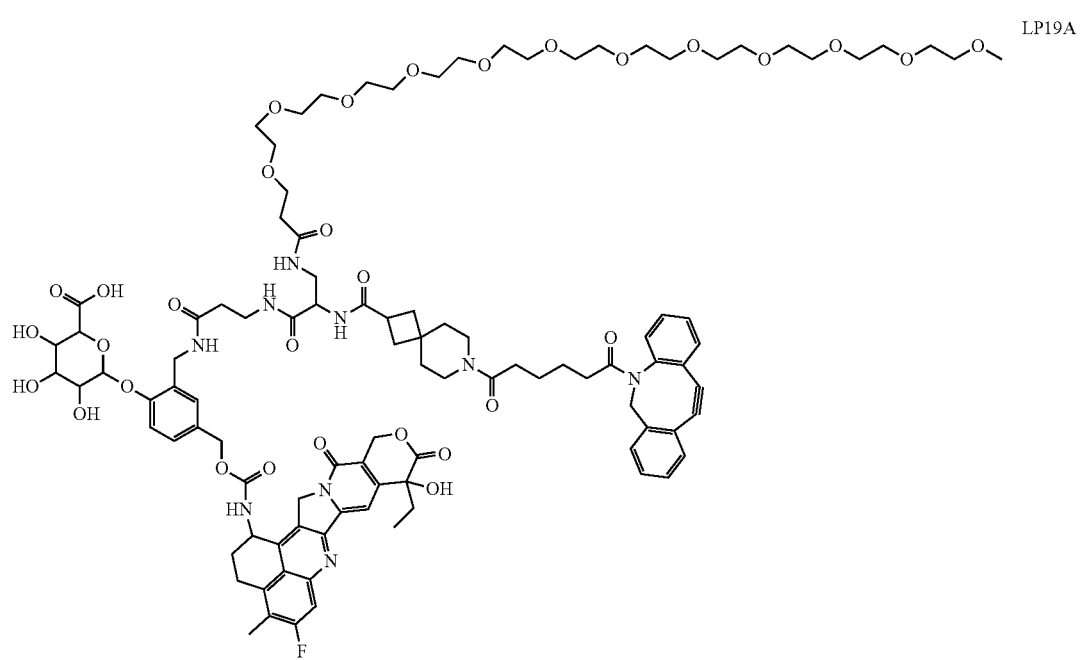
LP19A 391 392
-continued
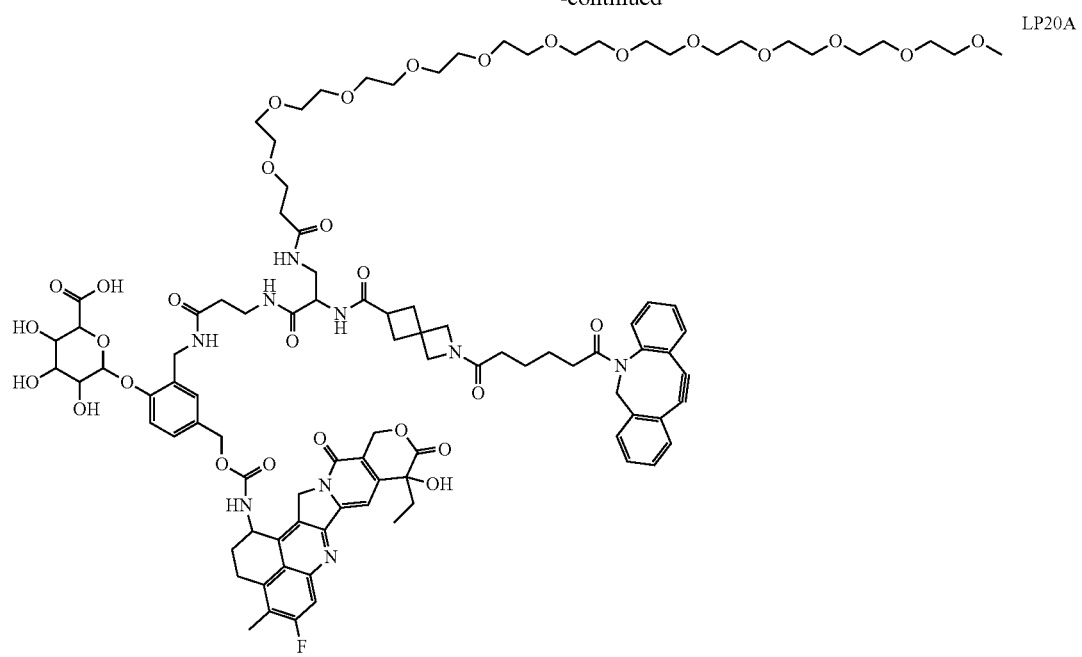
LP20A
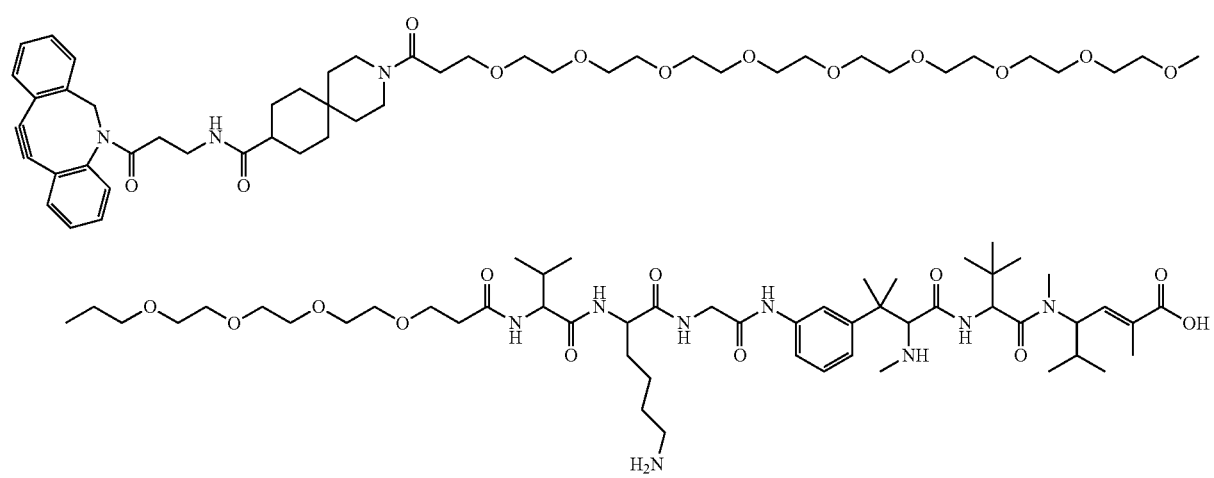
LP21A
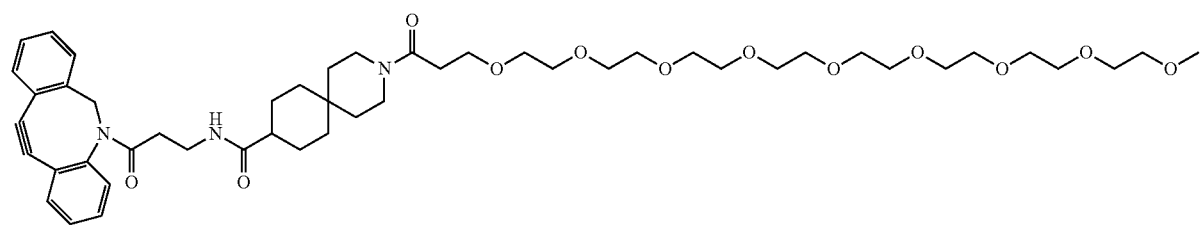
LP22A
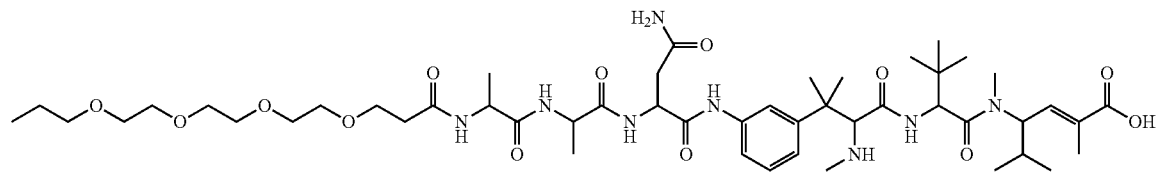

393
394
-continued
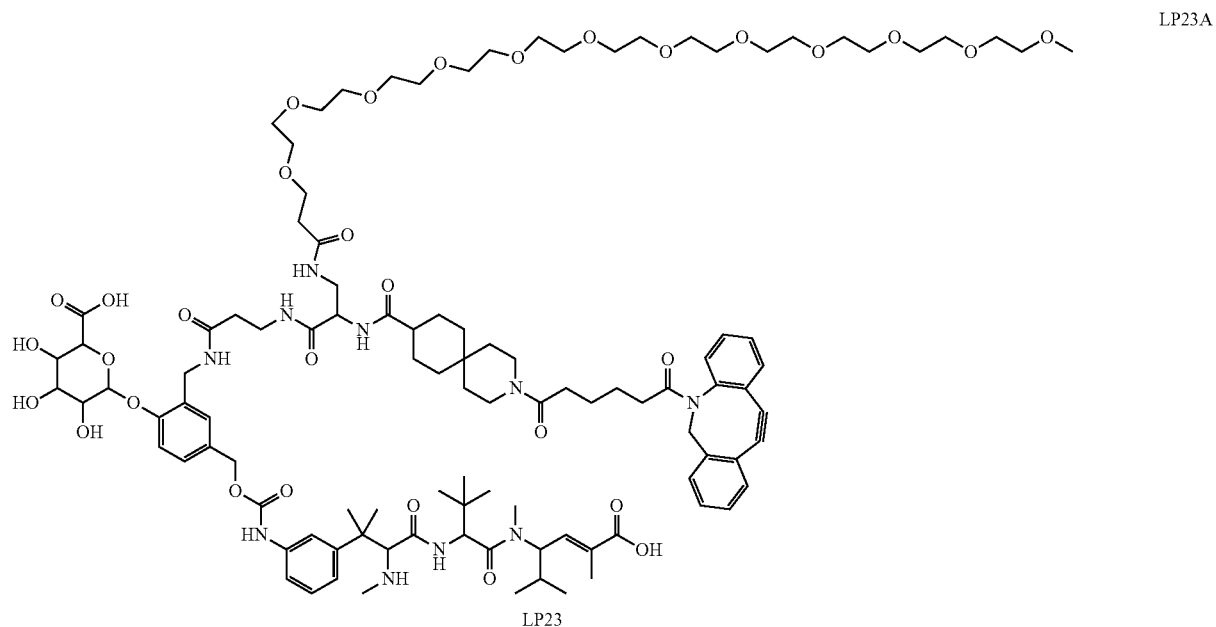
LP23A
LP23
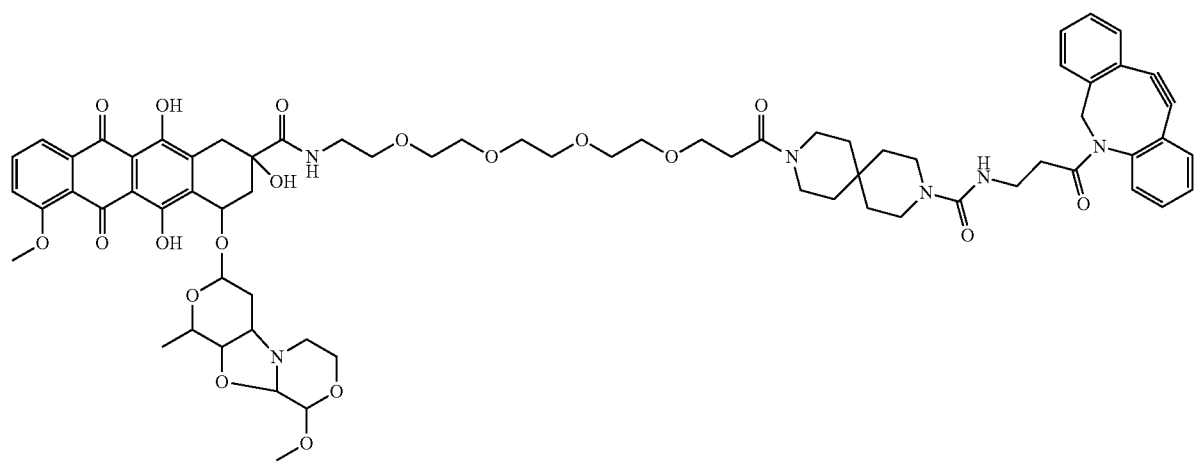
LP24A
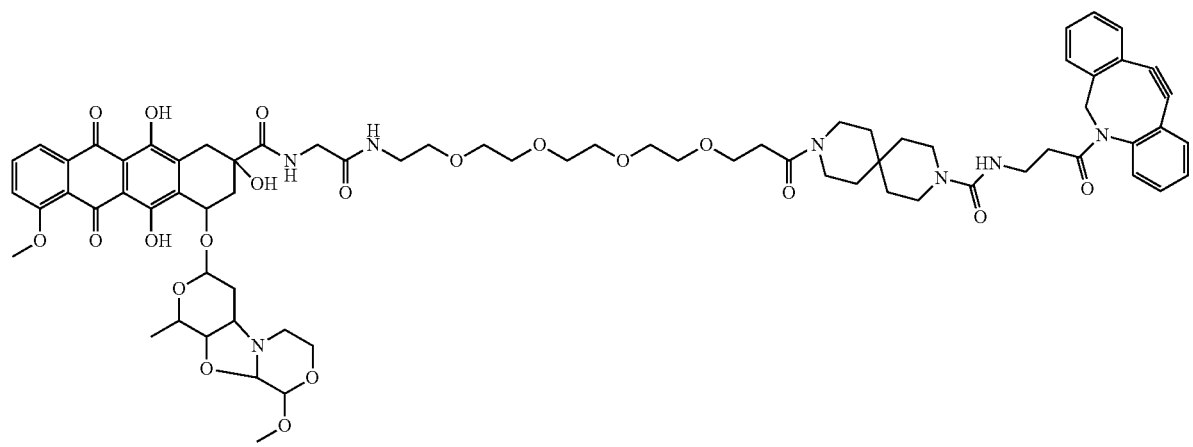
LP25A

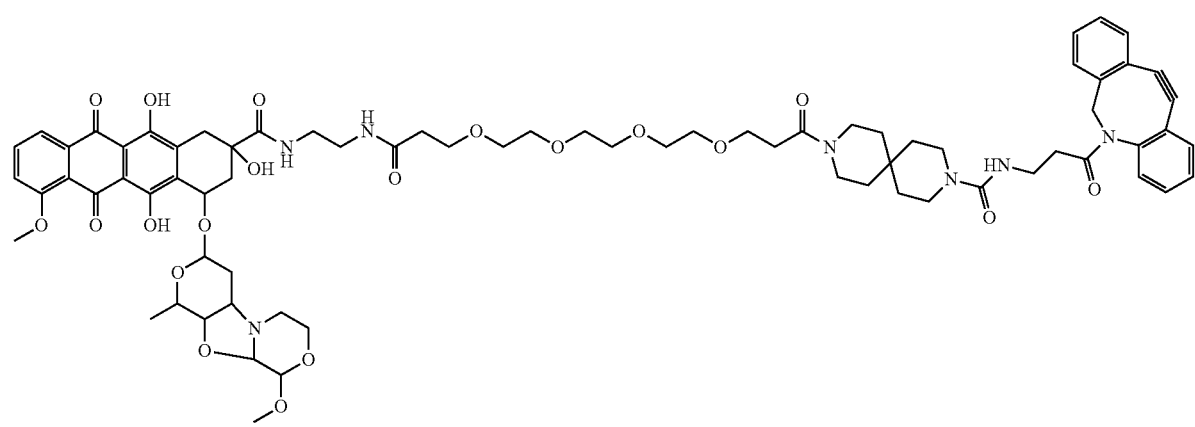
LP26A
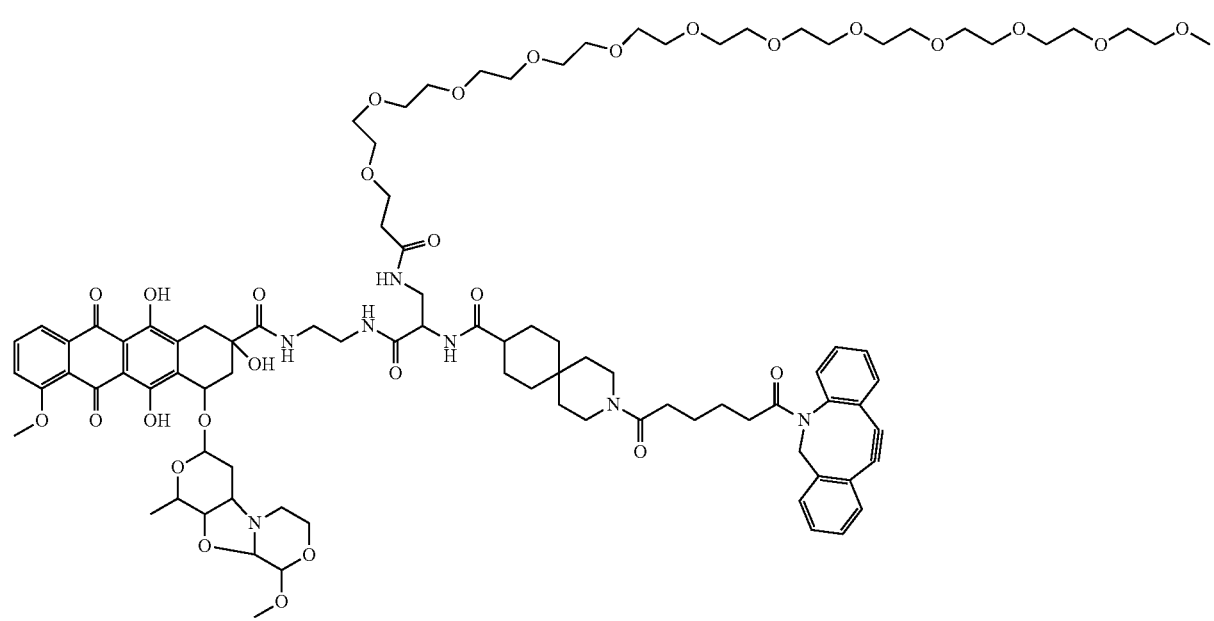
LP27A

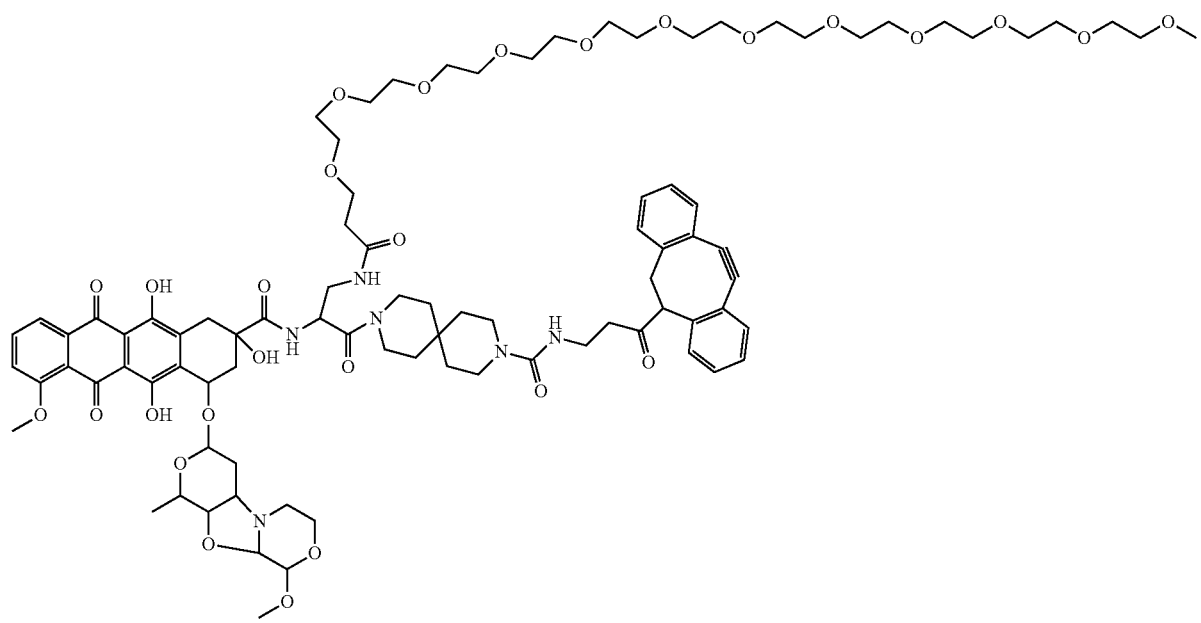
LP28A
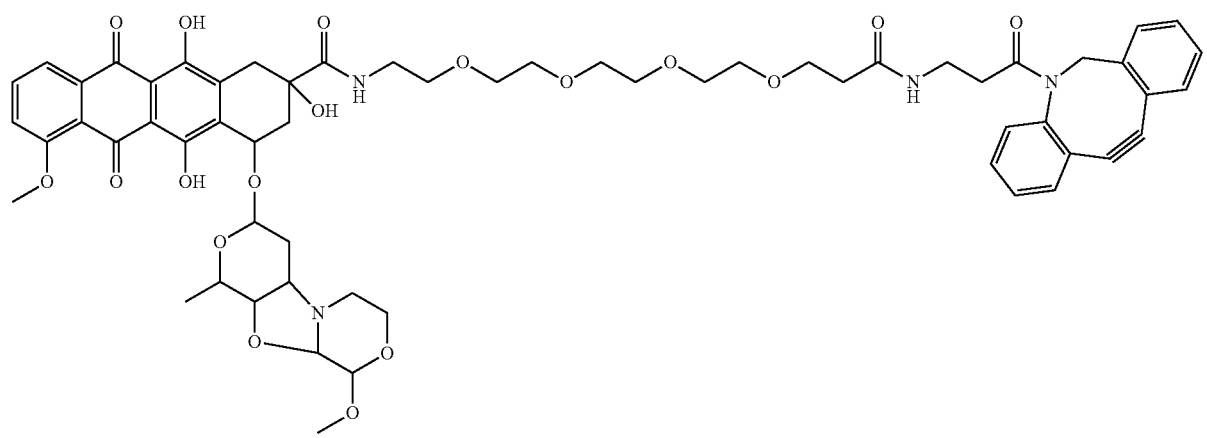
LP29A
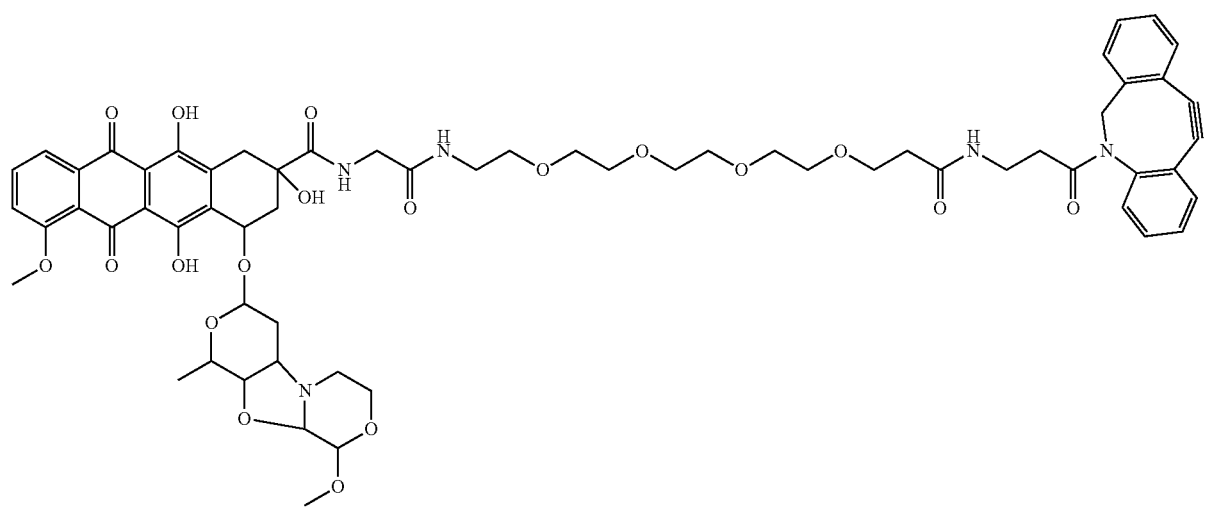
LP30A

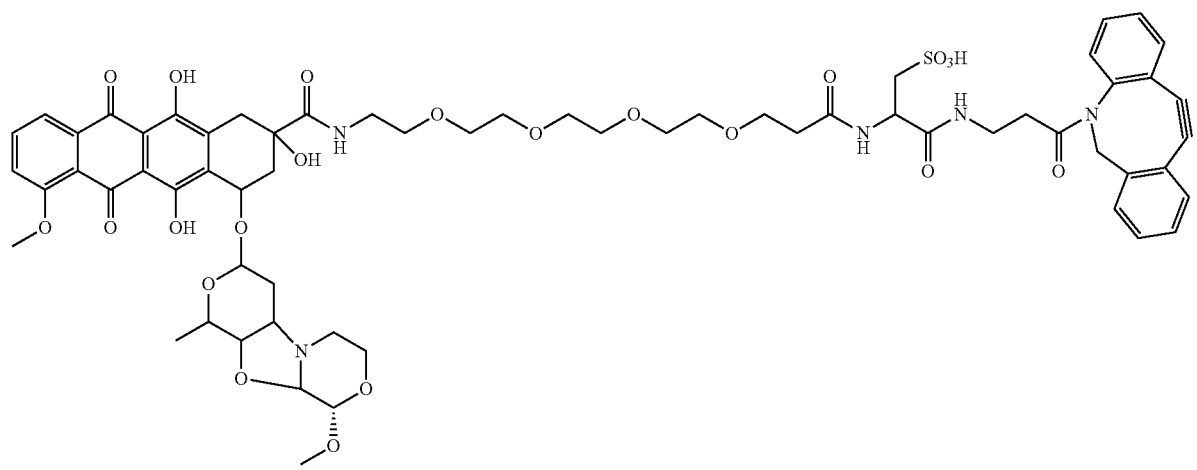
LP31A
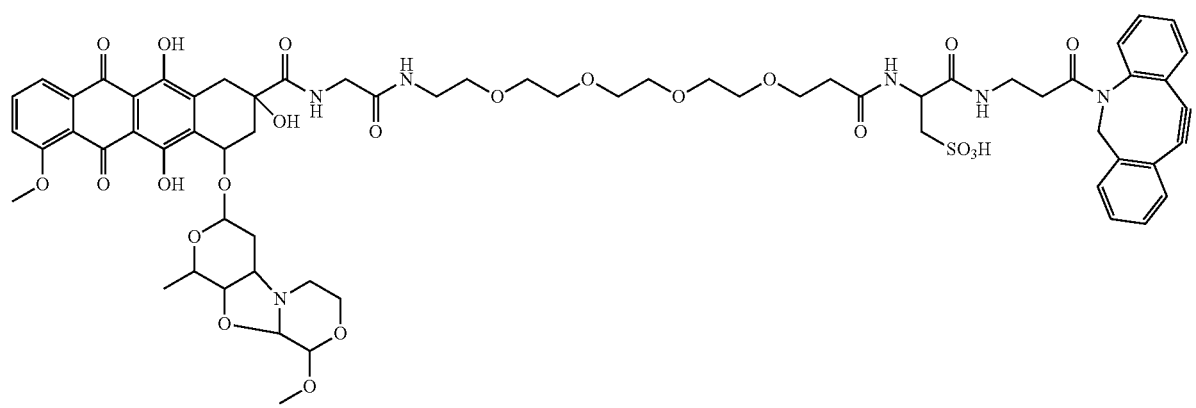
LP32A
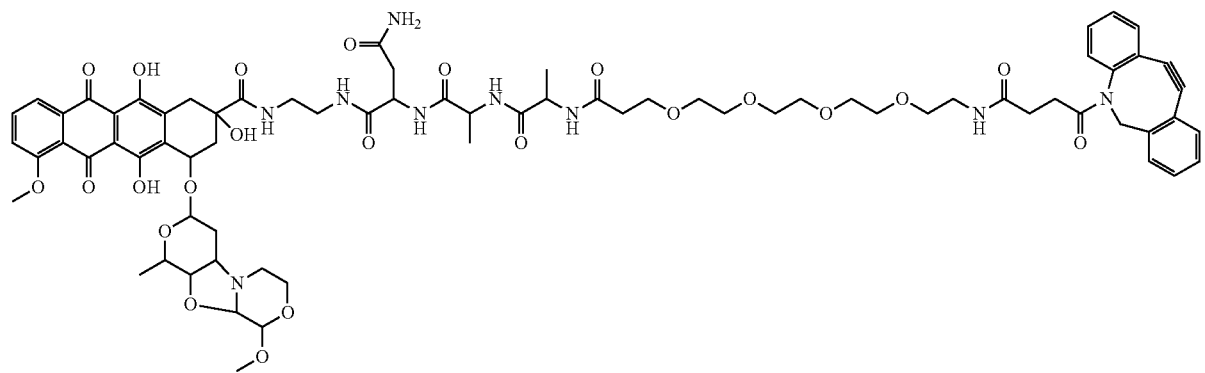
LP33A

-continued
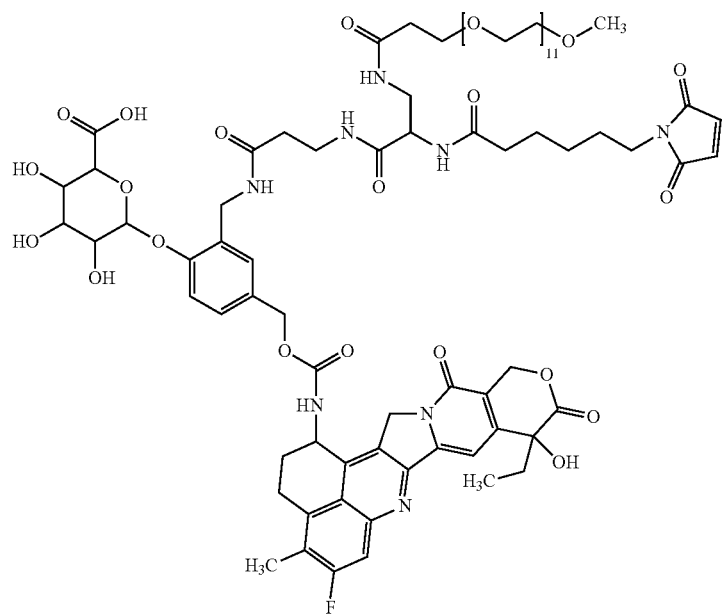
LP34A
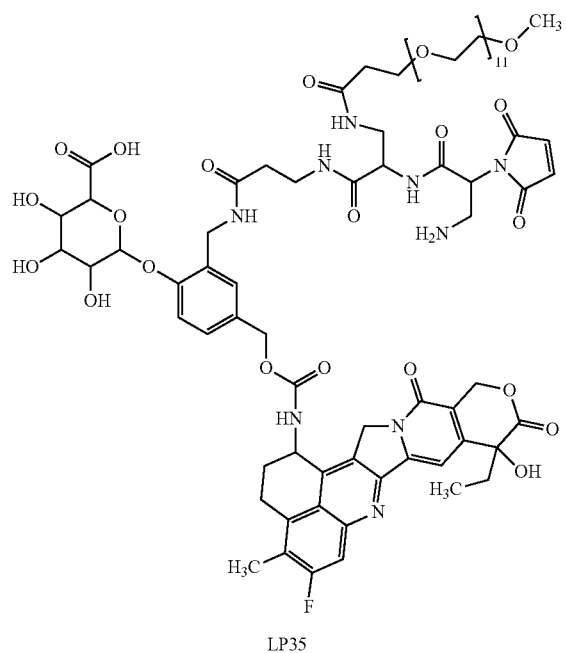
LP35
LP35A

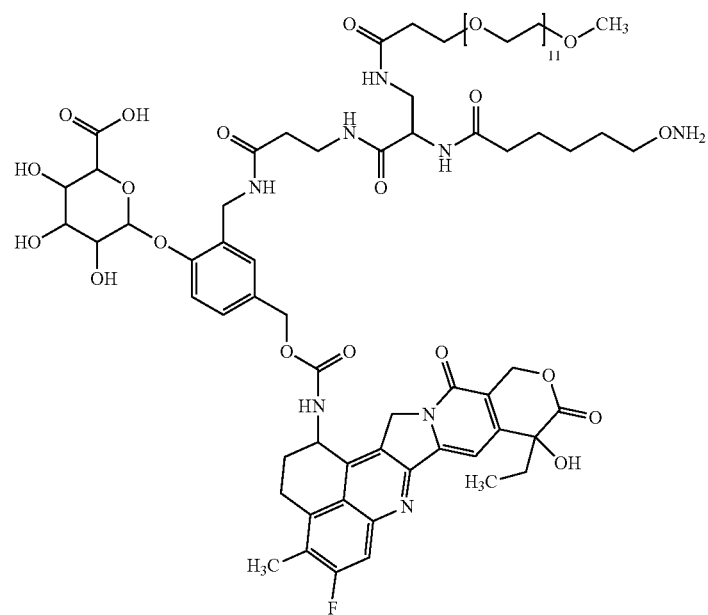
LP36A
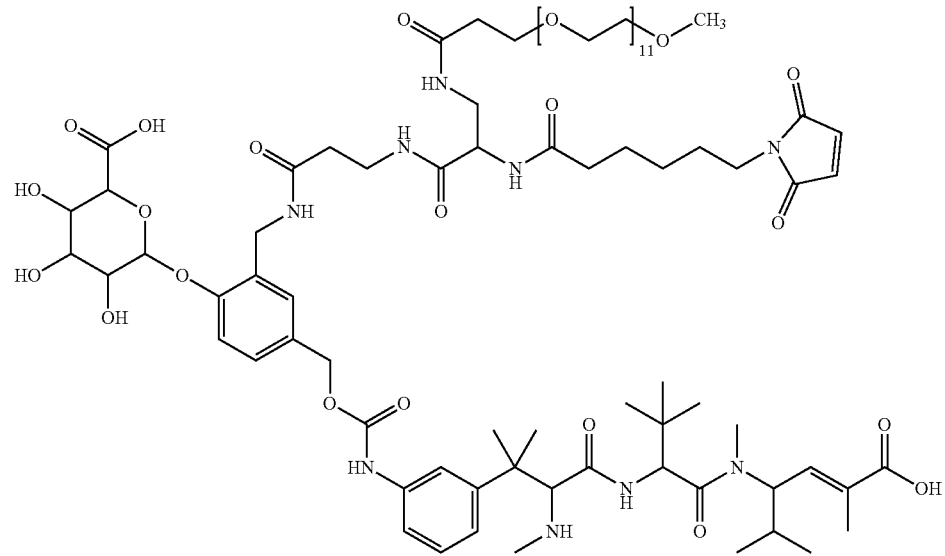
LP37A

-continued

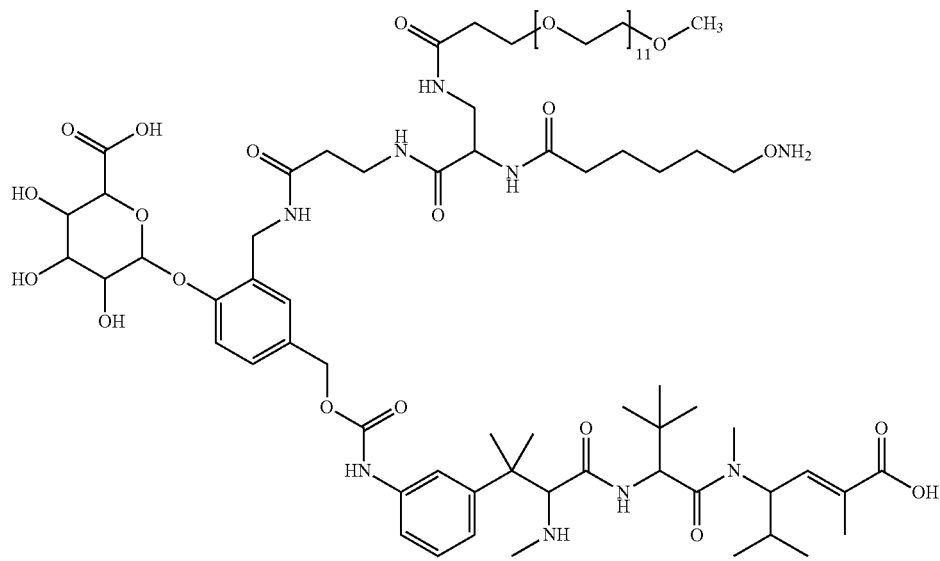

LP38A

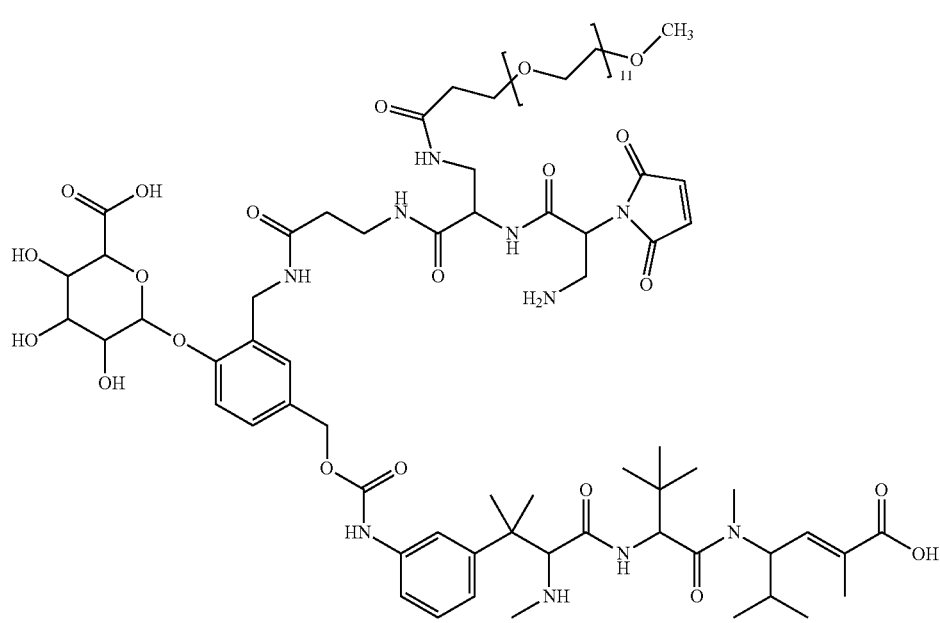

LP39A

13. Vectors, Host Cells, and Recombinant Methods

The invention also provides isolated nucleic acids encoding anti-ROR1 antibodies, vectors and host cells comprising the nucleic acids, and recombinant techniques for the production of the antibodies.

The ROR1 antibodies can be prepared according to techniques apparent to the person of skill. In certain embodiments, the ROR1 antibodies are prepared from isolated nucleic acids encoding anti-ROR1 antibodies, vectors, and host cells comprising the nucleic acids, and recombinant techniques for the production of the antibodies.

For recombinant production of the antibody, the nucleic acid(s) encoding it may be isolated and inserted into a replicable vector for further cloning (i.e., amplification of the DNA) or expression. In some aspects, the nucleic acid may be produced by homologous recombination, for example as described in U.S. Pat. No. 5,204,244, incorporated by reference in its entirety.

Many different vectors are known in the art. The vector components generally include, but are not limited to, one or more of the following: a signal sequence, an origin of replication, one or more marker genes, an enhancer element, a promoter, and a transcription termination sequence, for example as described in U.S. Pat. No. 5,534,615, incorporated by reference in its entirety.

Illustrative examples of suitable host cells are provided below. These host cells are not meant to be limiting.

Suitable host cells include any prokaryotic (e.g., bacterial), lower eukaryotic (e.g., yeast), or higher eukaryotic (e.g., mammalian) cells. Suitable prokaryotes include eubacteria, such as Gram-negative or Gram-positive organisms, for example, Enterobacteriaceae such as *Escherichia* (*E. coli*), *Enterobacter, Erwinia, Klebsiella, Proteus, Salmo-* nella (*S. typhimurium*), *Serratia* (*S. marcescans*), *Shigella*, Bacilli (*B. subtilis* and *B. licheniformis*), *Pseudomonas* (*P. aeruginosa*), and *Streptomyces*. One useful *E. coli* cloning host is *E. coli* 294, although other strains such as *E. coli* B, *E. coli* X1776, and *E. coli* W3110 are suitable.

In addition to prokaryotes, eukaryotic microbes such as filamentous fungi or yeast are also suitable cloning or expression hosts for anti-ROR1 antibody-encoding vectors. *Saccharomyces cerevisiae*, or common baker's yeast, is a commonly used lower eukaryotic host microorganism. However, a number of other genera, species, and strains are available and useful, such as *Spodoptera frugiperda* (e.g., SF9), *Schizosaccharomyces pombe*, *Kluyveromyces* (*K. lactis*, *K fragilis*, *K bulgaricus K. wickeramii*, *K. waltii*, *K. drosophilarum*, *K. thermotolerans*, and *K. marxianus*), *Yarrowia*, *Pichia pastoris*, *Candida* (*C. albicans*), *Trichoderma reesia*, *Neurospora crassa*, *Schwanniomyces* (*S. occidentalis*), and filamentous fungi such as, for example *Penicillium*, *Tolypocladium*, and *Aspergillus* (*A. nidulans* and *A. niger*).

Useful mammalian host cells include COS-7 cells, HEK293 cells; baby hamster kidney (BHK) cells; Chinese hamster ovary (CHO); mouse sertoli cells; African green monkey kidney cells (VERO-76), and the like.

The host cells used to produce the anti-ROR1 antibody of this invention may be cultured in a variety of media. Commercially available media such as, for example, Ham's F10, Minimal Essential Medium (MEM), RPMI-1640, and Dulbecco's Modified Eagle's Medium (DMEM) are suitable for culturing the host cells. In addition, any of the media described in Ham et al., *Meth. Enz.*, 1979, 58:44; Barnes et al., *Anal. Biochem.*, 1980, 102:255; and U.S. Pat. Nos. 4,767,704, 4,657,866, 4,927,762, 4,560,655, and 5,122,469, or WO 90/03430 and WO 87/00195 may be used. Each of the foregoing references is incorporated by reference in its entirety.

Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics, trace elements (defined as inorganic compounds usually present at final concentrations in the micromolar range), and glucose or an equivalent energy source. Any other necessary supplements may also be included at appropriate concentrations that would be known to those skilled in the art.

The culture conditions, such as temperature, pH, and the like, are those previously used with the host cell selected for expression, and will be apparent to the ordinarily skilled artisan.

When using recombinant techniques, the antibody can be produced intracellularly, in the periplasmic space, or directly secreted into the medium. If the antibody is produced intracellularly, as a first step, the particulate debris, either host cells or lysed fragments, is removed, for example, by centrifugation or ultrafiltration. For example, Carter et al. (*Bio/Technology*, 1992, 10:163-167) describes a procedure for isolating antibodies which are secreted to the periplasmic space of *E. coli*. Briefly, cell paste is thawed in the presence of sodium acetate (pH 3.5), EDTA, and phenylmethylsulfonylfluoride (PMSF) over about 30 min. Cell debris can be removed by centrifugation.

In some embodiments, the antibody is produced in a cell-free system. In some aspects, the cell-free system is an in vitro transcription and translation system as described in Yin et al., *mAbs*, 2012, 4:217-225, incorporated by reference in its entirety. In some aspects, the cell-free system utilizes a cell-free extract from a eukaryotic cell or from a prokaryotic cell. In some aspects, the prokaryotic cell is *E. coli*. Cell-free expression of the antibody may be useful, for example, where the antibody accumulates in a cell as an insoluble aggregate, or where yields from periplasmic expression are low. The antibodies produced in a cell-free system may be aglycosylated depending on the source of the cells.

Where the antibody is secreted into the medium, supernatants from such expression systems are generally first concentrated using a commercially available protein concentration filter, for example, an Amicon® or Millipore® Pellcon® ultrafiltration unit. A protease inhibitor such as PMSF may be included in any of the foregoing steps to inhibit proteolysis and antibiotics may be included to prevent the growth of adventitious contaminants.

The antibody composition prepared from the cells can be purified using, for example, hydroxyapatite chromatography, gel electrophoresis, dialysis, and affinity chromatography, with affinity chromatography being a particularly useful purification technique. The suitability of protein A as an affinity ligand depends on the species and isotype of any immunoglobulin Fc domain that is present in the antibody. Protein A can be used to purify antibodies that are based on human γ1, γ2, or γ4 heavy chains (Lindmark et al., *J. Immunol. Meth.*, 1983, 62:1-13, incorporated by reference in its entirety). Protein G is useful for all mouse isotypes and for human γ3 (Guss et al., *EMBO J.*, 1986, 5:1567-1575, incorporated by reference in its entirety).

The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a $C_{H3}$ domain, the BakerBond ABX® resin is useful for purification.

Other techniques for protein purification, such as fractionation on an ion-exchange column, ethanol precipitation, Reverse Phase HPLC, chromatography on silica, chromatography on heparin Sepharose®, chromatofocusing, SDS-PAGE, and ammonium sulfate precipitation are also available, and can be applied by one of skill in the art.

Following any preliminary purification step(s), the mixture comprising the antibody of interest and contaminants may be subjected to low pH hydrophobic interaction chromatography using an elution buffer at a pH between about 2.5 to about 4.5, generally performed at low salt concentrations (e.g., from about 0 to about 0.25 M salt).

14. Pharmaceutical Compositions and Methods of Administration

The antibodies or the antibody conjugates provided herein can be formulated into pharmaceutical compositions using methods available in the art and those disclosed herein. Any of the antibodies or the antibody conjugates provided herein can be provided in the appropriate pharmaceutical composition and be administered by a suitable route of administration.

The methods provided herein encompass administering pharmaceutical compositions comprising at least one antibody or antibody conjugate provided herein and one or more compatible and pharmaceutically acceptable carriers. In this context, the term "pharmaceutically acceptable" means approved by a regulatory agency of the Federal or a state government or listed in the U.S. Pharmacopeia or other generally recognized pharmacopeia for use in animals, and more particularly in humans. The term "carrier" includes a diluent, adjuvant (e.g., Freund's adjuvant (complete and incomplete)), excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water can be used as a carrier when the pharmaceutical composition is administered intravenously. Saline solutions and aqueous dextrose and glycerol solutions can also be employed as liquid carriers, particularly for injectable solutions. Examples of suitable pharmaceutical carriers are described in Martin, E. W., *Remington's Pharmaceutical Sciences*.

In clinical practice the pharmaceutical compositions, antibodies, or antibody conjugates provided herein may be administered by any route known in the art. Exemplary routes of administration include, but are not limited to, the inhalation, intraarterial, intradermal, intramuscular, intraperitoneal, intravenous, nasal, parenteral, pulmonary, and subcutaneous routes. In some embodiments, a pharmaceutical composition, antibody, or antibody conjugate provided herein is administered parenterally.

The compositions for parenteral administration can be emulsions or sterile solutions. Parenteral compositions may include, for example, propylene glycol, polyethylene glycol, vegetable oils, and injectable organic esters (e.g., ethyl oleate). These compositions can also contain wetting, isotonizing, emulsifying, dispersing and stabilizing agents. Sterilization can be carried out in several ways, for example using a bacteriological filter, by radiation or by heating. Parenteral compositions can also be prepared in the form of sterile solid compositions which can be dissolved at the time of use in sterile water or any other injectable sterile medium.

In some embodiments, a composition provided herein is a pharmaceutical composition or a single unit dosage form. Pharmaceutical compositions and single unit dosage forms provided herein comprise a prophylactically or therapeutically effective amount of one or more prophylactic or therapeutic antibody conjugates.

The pharmaceutical composition may comprise one or more pharmaceutical excipients. Any suitable pharmaceutical excipient may be used, and one of ordinary skill in the art is capable of selecting suitable pharmaceutical excipients. Non-limiting examples of suitable excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Whether a particular excipient is suitable for incorporation into a pharmaceutical composition or dosage form depends on a variety of factors well known in the art including, but not limited to, the way in which the dosage form will be administered to a subject and the specific antibody in the dosage form. The composition or single unit dosage form, if desired, can also contain minor amounts of wetting or emulsifying agents, or pH buffering agents. Accordingly, the pharmaceutical excipients provided below are intended to be illustrative, and not limiting. Additional pharmaceutical excipients include, for example, those described in the *Handbook of Pharmaceutical Excipients*, Rowe et al. (Eds.) 6$^{th}$ Ed. (2009), incorporated by reference in its entirety.

In some embodiments, the pharmaceutical composition comprises an anti-foaming agent. Any suitable anti-foaming agent may be used. In some aspects, the anti-foaming agent is selected from an alcohol, an ether, an oil, a wax, a silicone, a surfactant, and combinations thereof. In some aspects, the anti-foaming agent is selected from a mineral oil, a vegetable oil, ethylene bis stearamide, a paraffin wax, an ester wax, a fatty alcohol wax, a long chain fatty alcohol, a fatty acid soap, a fatty acid ester, a silicon glycol, a fluorosilicone, a polyethylene glycol-polypropylene glycol copolymer, polydimethylsiloxane-silicon dioxide, ether, octyl alcohol, capryl alcohol, sorbitan trioleate, ethyl alcohol, 2-ethylhexanol, dimethicone, oleyl alcohol, simethicone, and combinations thereof.

In some embodiments, the pharmaceutical composition comprises a co-solvent. Illustrative examples of co-solvents include ethanol, poly(ethylene) glycol, butylene glycol, dimethylacetamide, glycerin, and propylene glycol.

In some embodiments, the pharmaceutical composition comprises a buffer. Illustrative examples of buffers include acetate, borate, carbonate, lactate, malate, phosphate, citrate, hydroxide, diethanolamine, monoethanolamine, glycine, methionine, guar gum, and monosodium glutamate.

In some embodiments, the pharmaceutical composition comprises a carrier or filler. Illustrative examples of carriers or fillers include lactose, maltodextrin, mannitol, sorbitol, chitosan, stearic acid, xanthan gum, and guar gum.

In some embodiments, the pharmaceutical composition comprises a surfactant. Illustrative examples of surfactants include d-alpha tocopherol, benzalkonium chloride, benzethonium chloride, cetrimide, cetylpyridinium chloride, docusate sodium, glyceryl behenate, glyceryl monooleate, lauric acid, macrogol 15 hydroxystearate, myristyl alcohol, phospholipids, polyoxyethylene alkyl ethers, polyoxyethylene sorbitan fatty acid esters, polyoxyethylene stearates, polyoxylglycerides, sodium lauryl sulfate, sorbitan esters, and vitamin E polyethylene(glycol) succinate.

In some embodiments, the pharmaceutical composition comprises an anti-caking agent. Illustrative examples of anti-caking agents include calcium phosphate (tribasic), hydroxymethyl cellulose, hydroxypropyl cellulose, and magnesium oxide.

Other excipients that may be used with the pharmaceutical compositions include, for example, albumin, antioxidants, antibacterial agents, antifungal agents, bioabsorbable polymers, chelating agents, controlled release agents, diluents, dispersing agents, dissolution enhancers, emulsifying agents, gelling agents, ointment bases, penetration enhancers, preservatives, solubilizing agents, solvents, stabilizing agents, and sugars. Specific examples of each of these agents are described, for example, in the *Handbook of Pharmaceutical Excipients*, Rowe et al. (Eds.) 6$^{th}$ Ed. (2009), The Pharmaceutical Press, incorporated by reference in its entirety.

In some embodiments, the pharmaceutical composition comprises a solvent. In some aspects, the solvent is saline solution, such as a sterile isotonic saline solution or dextrose solution. In some aspects, the solvent is water for injection.

In some embodiments, the pharmaceutical compositions are in a particulate form, such as a microparticle or a nanoparticle. Microparticles and nanoparticles may be formed from any suitable material, such as a polymer or a lipid. In some aspects, the microparticles or nanoparticles are micelles, liposomes, or polymersomes.

Further provided herein are anhydrous pharmaceutical compositions and dosage forms comprising an antibody or antibody conjugate, since, in some embodiments, water can facilitate the degradation of some antibodies.

Anhydrous pharmaceutical compositions and dosage forms provided herein can be prepared using anhydrous or low moisture containing ingredients and low moisture or low humidity conditions. Pharmaceutical compositions and dosage forms that comprise lactose and at least one active ingredient that comprises a primary or secondary amine can be anhydrous if substantial contact with moisture and/or humidity during manufacturing, packaging, and/or storage is expected.

An anhydrous pharmaceutical composition can be prepared and stored such that its anhydrous nature is maintained. Accordingly, anhydrous compositions can be packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

Lactose-free compositions provided herein can comprise excipients that are well known in the art and are listed, for example, in the U.S. Pharmocopia (USP) SP (XXI)/NF (XVI). In general, lactose-free compositions comprise an active ingredient, a binder/filler, and a lubricant in pharmaceutically compatible and pharmaceutically acceptable amounts. Exemplary lactose-free dosage forms comprise an active ingredient, microcrystalline cellulose, pre gelatinized starch, and magnesium stearate.

Also provided are pharmaceutical compositions and dosage forms that comprise one or more excipients that reduce the rate by which an antibody or antibody-conjugate will decompose. Such excipients, which are referred to herein as "stabilizers," include, but are not limited to, antioxidants such as ascorbic acid, pH buffers, or salt buffers.

14.1. Parenteral Dosage Forms

In certain embodiments, provided are parenteral dosage forms. Parenteral dosage forms can be administered to subjects by various routes including, but not limited to, subcutaneous, intravenous (including bolus injection), intramuscular, and intraarterial. Because their administration typically bypasses subjects' natural defenses against contaminants, parenteral dosage forms are typically, sterile or capable of being sterilized prior to administration to a subject. Examples of parenteral dosage forms include, but are not limited to, solutions ready for injection, dry products ready to be dissolved or suspended in a pharmaceutically acceptable vehicle for injection, suspensions ready for injection, and emulsions.

Suitable vehicles that can be used to provide parenteral dosage forms are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

Excipients that increase the solubility of one or more of the antibodies disclosed herein can also be incorporated into the parenteral dosage forms.

14.2. Dosage and Unit Dosage Forms

In human therapeutics, the doctor will determine the posology which he considers most appropriate according to a preventive or curative treatment and according to the age, weight, condition and other factors specific to the subject to be treated.

In certain embodiments, a composition provided herein is a pharmaceutical composition or a single unit dosage form. Pharmaceutical compositions and single unit dosage forms provided herein comprise a prophylactically or therapeutically effective amount of one or more prophylactic or therapeutic antibodies.

The amount of the antibody or antibody conjugate or composition which will be effective in the prevention or treatment of a disorder or one or more symptoms thereof will vary with the nature and severity of the disease or condition, and the route by which the antibody is administered. The frequency and dosage will also vary according to factors specific for each subject depending on the specific therapy (e.g., therapeutic or prophylactic agents) administered, the severity of the disorder, disease, or condition, the route of administration, as well as age, body, weight, response, and the past medical history of the subject. Effective doses may be extrapolated from dose-response curves derived from in vitro or animal model test systems.

In certain embodiments, exemplary doses of a composition include milligram or microgram amounts of the antibody per kilogram of subject or sample weight (e.g., about 10 micrograms per kilogram to about 50 milligrams per kilogram, about 100 micrograms per kilogram to about 25 milligrams per kilogram, or about 100 microgram per kilogram to about 10 milligrams per kilogram).

In certain embodiment, the dosage of the antibody provided herein, based on weight of the antibody, administered to prevent, treat, manage, or ameliorate a disorder, or one or more symptoms thereof in a subject is 0.1 mg/kg, 1 mg/kg, 2 mg/kg, 3 mg/kg, 4 mg/kg, 5 mg/kg, 6 mg/kg, mg/kg, or 15 mg/kg or more of a subject's body weight. In another embodiment, the dosage of the composition or a composition provided herein administered to prevent, treat, manage, or ameliorate a disorder, or one or more symptoms thereof in a subject is 0.1 mg to 200 mg, 0.1 mg to 100 mg, 0.1 mg to 50 mg, 0.1 mg to 25 mg, 0.1 mg to 20 mg, 0.1 mg to 15 mg, 0.1 mg to 10 mg, mg to 7.5 mg, 0.1 mg to 5 mg, 0.1 to 2.5 mg, 0.25 mg to 20 mg, 0.25 to 15 mg, 0.25 to 12 mg, to 10 mg, 0.25 mg to 7.5 mg, 0.25 mg to 5 mg, 0.25 mg to 2.5 mg, 0.5 mg to 20 mg, 0.5 to 15 mg, 0.5 to 12 mg, 0.5 to 10 mg, 0.5 mg to 7.5 mg, 0.5 mg to 5 mg, 0.5 mg to 2.5 mg, 1 mg to 20 mg, 1 mg to 15 mg, 1 mg to 12 mg, 1 mg to 10 mg, 1 mg to 7.5 mg, 1 mg to 5 mg, or 1 mg to 2.5 mg.

The dose can be administered according to a suitable schedule. In certain embodiments, the dose is administered once, two times, three times, or for times weekly. It may be necessary to use dosages of the antibody or antibody conjugate outside the ranges disclosed herein in some cases, as will be apparent to those of ordinary skill in the art. Furthermore, it is noted that the clinician or treating physician will know how and when to interrupt, adjust, or terminate therapy in conjunction with subject response.

Different therapeutically effective amounts may be applicable for different diseases and conditions, as will be readily known by those of ordinary skill in the art. Similarly, amounts sufficient to prevent, manage, treat or ameliorate such disorders, but insufficient to cause, or sufficient to reduce, adverse effects associated with the antibodies provided herein are also encompassed by the herein described dosage amounts and dose frequency schedules. Further, when a subject is administered multiple dosages of a composition provided herein, not all of the dosages need be the same. For example, the dosage administered to the subject may be increased to improve the prophylactic or therapeutic effect of the composition or it may be decreased to reduce one or more side effects that a particular subject is experiencing.

In certain embodiments, treatment or prevention can be initiated with one or more loading doses of an antibody or antibody conjugate or composition provided herein followed by one or more maintenance doses.

In certain embodiments, a dose of an antibody or antibody conjugate or composition provided herein can be administered to achieve a steady-state concentration of the antibody in blood or serum of the subject. The steady-state concentration can be determined by measurement according to techniques available to those of skill or can be based on the physical characteristics of the subject such as height, weight and age.

In certain embodiments, administration of the same composition may be repeated and the administrations may be separated by at least 1 day, 2 days, 3 days, 5 days, 10 days, 15 days, 30 days, 45 days, 2 months, 75 days, 3 months, or 6 months. In other embodiments, administration of the same prophylactic or therapeutic agent may be repeated and the administration may be separated by at least 1 day, 2 days, 3 days, 5 days, 10 days, 15 days, 30 days, 45 days, 2 months, days, 3 months, or 6 months.

14.3. Combination Therapies and Formulations

In certain embodiments, provided are methods for treatment and/or compositions and therapeutic formulations comprising any of the antibodies or antibody conjugates provided herein in combination with one or more chemotherapeutic agents disclosed herein, and methods of treatment comprising administering such combinations to subjects in need thereof. Examples of chemotherapeutic agents include, but are not limited to, Erlotinib (TARCEVA®, Genentech/OSI Pharm.), Bortezomib (VELCADE®, Millennium Pharm.), Fulvestrant (FASLODEX®, AstraZeneca), Sutent (SU11248, Pfizer), Letrozole (FEMARA®, Novartis), Imatinib mesylate (GLEEVEC®, Novartis), PTK787/ZK 222584 (Novartis), Oxaliplatin (Eloxatin®, Sanofi), 5-FU (5-fluorouracil), Leucovorin, Rapamycin (Sirolimus, RAPAMUNE®, Wyeth), Lapatinib (TYKERB 0, GSK572016, Glaxo Smith Kline), Lonafarnib (SCH 66336), Sorafenib (BAY43-9006, Bayer Labs), and Gefitinib (IRESSA®, AstraZeneca), AG1478, AG1571 (SU 5271; Sugen), alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylolomelamine; acetogenins (especially bullatacin and bullatacinone); a camptothecin (including the synthetic analog topotecan); bryostatin; callystatin; CC-1065 (including its adozelesin, carzelesin and bizelesin synthetic analogs); cryptophycins (particularly cryptophycin 1 and cryptophycin 8); dolastatin; duocarmycin (including the synthetic analogs, KW-2189 and CB1-TM1); eleutherobin; pancratistatin; a sarcodictyin; spongistatin; nitrogen mustards such as chlorambucil, chlomaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially uncialamycin, calicheamicin gammaII, and calicheamicin omegaII (Angew Chem. Intl. Ed. Engl. (1994) 33:183-186); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® (doxorubicin), morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pladienolide B, pteropterin, trimetrexate; purine analogs such as fludarabine, 6-mercaptopurine, thiamniprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® (paclitaxel; Bristol-Myers Squibb Oncology, Princeton, N.J.), ABRAXANE® (Cremophor-free), albumin-engineered nanoparticle formulations of paclitaxel (American Pharmaceutical Partners, Schaumberg, Ill.), and TAXOTERE® (doxetaxel; Rhone-Poulenc Rorer, Antony, France); chloranmbucil; GEMZAR® (gemcitabine); 6-thioguanine; mercaptopurine; methotrexate; platinum analogs such as cisplatin and carboplatin; vinblastine; etoposide (VP-16); ifosfamide; mitoxantrone; vincristine; NAVELBINE® (vinorelbine); novantrone; teniposide; edatrexate; daunomycin; aminopterin; capecitabine (XELODA®); ibandronate; CPT-11; topoisomerase inhibitor RFS 2000; difluoromethylornithine (DMFO); retinoids such as retinoic acid; and pharmaceutically acceptable salts, acids and derivatives of any of the above.

In certain embodiments, provided are methods for treatment and/or compositions and therapeutic formulations comprising any of the antibodies or antibody conjugates provided herein in combination with a checkpoint inhibitor, for example, a PD-1 inhibitor, PD-L1 inhibitor, PD-L2 inhibitor, CTLA-4 inhibitor, LAG-3 inhibitor, TIM-3 inhibitor, V-domain Ig suppressor of T-cell activation (VISTA) inhibitors, small molecule, peptide, nucleotide, or other inhibitor.

In certain embodiments, provided are methods for treatment and/or compositions and therapeutic formulations comprising any of the antibodies or antibody conjugates provided herein in combination with one or more PD-1 or PD-L1 inhibitors, and methods of treatment comprising administering such combinations to subjects in need thereof. In some embodiments, the one or more PD-1 or PD-L1 inhibitors comprise a small molecule blocker of the PD-1 or PD-L1 pathway. In some embodiments, the one or more PD-1 or PD-L1 inhibitors comprise an antibody that inhibits PD-1 or PD-L1 activity. In some embodiments, the one or more PD-1 or PD-L1 inhibitors are selected from the group consisting of: CA-170, BMS-8, BMS-202, BMS-936558, CK-301, and AUNP12. In some embodiments, the one or more PD-1 or PD-L1 inhibitors are selected from the group consisting of: avelumab, nivolumab, pembrolizumab, atezolizumab, durvalumab, AMP-224 (GlaxoSmithKline), MEDI0680/AMP-514 (AstraZeneca), PDR001 (Novartis), cemiplimab, TSR-042 (Tesaro), Tizlelizumab/BGB-A317 (Beigene), CK-301 (Checkpoint Therapeutics), BMS-936559 (Bristol-Meyers Squibb), camrelizumab, sintilimab, toripalimab, genolimzumab, and A167 (Sichuan Kelun-Biotech Biopharmaceutical). In some embodiments, the one or more PD-1 or PD-L1 inhibitors are selected from the group consisting of: MGA012 (Incyte/MacroGenics), PF-06801591 (Pfizer/Merck KGaA), LY3300054 (Eli Lilly), FAZ053 (Novartis), PD-11 (Novartis), CX-072 (CytomX), BGB-A333 (Beigene), BI 754091 (Boehringer Ingelheim), JNJ-63723283 (Johnson and Johnson/Jannsen), AGEN2034 (Agenus), CA-327 (Curis), CX-188 (CytomX), STI-A1110 (Servier), JTX-4014 (Jounce), (LLY) AM0001 (Armo Biosciences), CBT-502 (CBT Pharmaceuticals), FS118 (F-Star/Merck KGaA), XmAb20717 (Xencor), XmAb23104 (Xencor), AB122 (Arcus Biosciences), KY1003 (Kymab), RXI-762 (RXi). In some embodiments, the one or more PD-1 or PD-L1 inhibitors are selected from the group consisting of: PRS-332 (Pieris Pharmaceuticals), ALPN-202 (Alpine Immune Science), TSR-075 (Tesaro/Anaptys Bio), MCLA-145 (Merus), MGD013 (Macrogenics), MGD019 (Macrogenics). An additional PD-1 inhibitor is Pidilizumab (CT-011). In some embodiments, the one or more PD-1 or PD-L1 inhibitors are selected from an anti-PD1 mono-specific or bi-specific antibody described in, for example, WO 2016/077397, WO 2018/156777, and International Application No. PCT/US2013/034213, filed May 23, 2018.

In some embodiments, the one or more PD-1 or PD-L1 inhibitors are selected from the group consisting of CA-170, BMS-8, BMS-202, BMS-936558, CK-301, AUNP12, avelumab, nivolumab, pembrolizumab, atezolizumab, durvalumab, AMP-224, MEDI0680/AMP-514, PDR001, cemiplimab, TSR-042, Tizlelizumab/BGB-A317, CK-301, BMS-936559, camrelizumab, sintilimab, toripalimab, genolimzumab, A167, MGA012, PF-06801591, LY3300054, FAZ053, PD-11, CX-072, BGB-A333, BI 754091, JNJ-63723283, AGEN2034, CA-327, CX-188, STI-A1110, JTX-4014, (LLY) AM0001, CBT-502, FS118, XmAb20717, XmAb23104, AB122, KY1003, RXI-762, PRS-33, ALPN-202, TSR-075, MCLA-145, MGD013, and MGD019.

In certain embodiments, provided are methods for treatment and/or compositions and therapeutic formulations comprising any of the antibodies or antibody conjugates provided herein in combination with one or more CTLA-4 inhibitors, and methods of treatment comprising administering such combinations to subjects in need thereof. CTLA-4 inhibitors include, but are not limited to, ipilimumab (Yervoy®), tremelimumab (AstraZeneca and MedImmune), AGEN1884 and AGEN2041 (Agenus).

In certain embodiments, provided are methods for treatment and/or compositions and therapeutic formulations comprising any of the antibodies or antibody conjugates provided herein in combination with one or more LAG-3 inhibitors, and methods of treatment comprising administering such combinations to subjects in need thereof. Examples of LAG-3 immune checkpoint inhibitors include, but are not limited to, BMS-986016 (Bristol-Myers Squibb), GSK2831781 (GaxoSmithKline), IMP321 (Prima BioMed), LAG525 (Novartis), and the dual PD-1 and LAG-3 inhibitor MGD013 (MacroGenics).

In certain embodiments, provided are methods for treatment and/or compositions and therapeutic formulations comprising any of the antibodies or antibody conjugates provided herein in combination with one or more TIM-3 inhibitors, and methods of treatment comprising administering such combinations to subjects in need thereof. A specific TIM-3 inhibitor includes, but is not limited to, TSR-022 (Tesaro).

Other immune checkpoint inhibitors for use in the invention described herein include, but are not limited to, B7-H3/CD276 immune checkpoint inhibitors such as MGA217; indoleamine 2,3-dioxygenase (IDO) immune checkpoint inhibitors such as Indoximod and INCB024360; killer immunoglobulin-like receptors (KIRs) immune checkpoint inhibitors such as Lirilumab (BMS-986015); and, carcinoembryonic antigen cell adhesion molecule (CEACAM) inhibitors (e.g., CEACAM-1, -3 and/or -5).

In certain embodiments, provided are methods for treatment and/or compositions or therapeutic formulations comprising any of the antibody conjugates provided herein in combination with a PARP inhibitor, including, but not limited to olaparib (AZD-2281, Lynparza®), rucaparib (AG 014699, Rubraca®), niraparib (Zejula®), talazoparib (BMN-673, Talzenna®), veliparib (ABT-888), fluzoparib (HS10160), Iniparib (BSI 201), BGB-290, E7016, E7449, and CEP-9722. In one embodiment, an antibody conjugate provided herein is administered in combination with olaparib, rucaparib, niraparib, or talazoparib. In one embodiment, an antibody conjugate provided herein is administered in combination with olaparib.

The agents administered in combination with the antibodies or antibody conjugates disclosed herein can be administered just prior to, sequentially, concurrent with, or shortly after the administration of the antibodies or antibody conjugates. In one embodiment, the agents administered in combination with the antibodies or antibody conjugates disclosed herein are administered sequentially after the administration of the antibody conjugates. In one embodiment, the agents administered in combination with the antibodies or antibody conjugates disclosed herein are administered concurrently after the administration of the antibody conjugates. For purposes of the present disclosure, such administration regimens are considered the administration of an antibody conjugate "in combination with" an additional therapeutically active component. Embodiments include pharmaceutical compositions in which an antibody conjugate disclosed herein is co-formulated with one or more of the chemotherapeutic agents, PD-1 inhibitors, PD-L1 inhibitors, or PARP inhibitors disclosed herein.

15. Therapeutic Applications

For therapeutic applications, the antibodies or antibody conjugates provided herein can be administered to a mammal, generally a human, in a pharmaceutically acceptable dosage form such as those known in the art and those discussed above. For example, the antibodies or antibody conjugates may be administered to a human intravenously as a bolus or by continuous infusion over a period of time, by intramuscular, intraperitoneal, intra-cerebrospinal, subcutaneous, intra-articular, intrasynovial, intrathecal, or intratumoral routes. The antibodies or antibody conjugates also are suitably administered by peritumoral, intralesional, or perilesional routes, to exert local as well as systemic therapeutic effects. The intraperitoneal route may be particularly useful, for example, in the treatment of ovarian tumors.

The antibodies or antibody conjugates provided herein may be useful for the treatment of any disease or condition involving receptor ROR1. In some embodiments, the disease or condition is a disease or condition that can be diagnosed by overexpression of ROR1. In some embodiments, the disease or condition is a disease or condition that can benefit from treatment with an anti-ROR1 antibody. In some embodiments, the disease or condition is a cancer.

Any suitable cancer may be treated with the antibodies or antibody conjugates provided herein. Illustrative suitable cancers include, for example, acute lymphoblastic leukemia (ALL), acute myeloid leukemia (AML), adrenocortical carcinoma, anal cancer, appendix cancer, astrocytoma, basal cell carcinoma, brain tumor, bile duct cancer, bladder cancer, bone cancer, breast cancer (including triple-negative breast cancer, or TNBC), bronchial tumor, carcinoma of unknown primary origin, cardiac tumor, cervical cancer, chordoma, colon cancer, colorectal cancer, craniopharyngioma, ductal carcinoma, embryonal tumor, endometrial cancer, ependymoma, esophageal cancer, esthesioneuroblastoma, fallopian tube carcinoma, fibrous histiocytoma, Ewing sarcoma, eye cancer, germ cell tumor, gallbladder cancer, gastric cancer, gastrointestinal carcinoid tumor, gastrointestinal stromal tumor, gestational trophoblastic disease, glioma, head and neck cancer, hepatocellular cancer, histiocytosis, Hodgkin lymphoma, hypopharyngeal cancer, intraocular melanoma, islet cell tumor, Kaposi sarcoma, kidney cancer, Langerhans cell histiocytosis, laryngeal cancer, lip and oral cavity cancer, liver cancer, lobular carcinoma in situ, lung cancer, macroglobulinemia, malignant fibrous histiocytoma, melanoma, Merkel cell carcinoma, mesothelioma, metastatic squamous neck cancer with occult primary, midline tract carcinoma involving NUT gene, mouth cancer, multiple endocrine neoplasia syndrome, multiple myeloma, mycosis fungoides, myelodysplastic syndrome, myelodysplastic/myeloproliferative neoplasm, nasal cavity and par nasal sinus cancer, nasopharyngeal cancer, neuroblastoma, non-small cell lung cancer (NSCLC), oropharyngeal cancer, osteosarcoma, ovarian cancer, pancreatic cancer, papillomatosis, paraganglioma, parathyroid cancer, penile cancer, pharyngeal cancer, pheochromocytomas, pituitary tumor, pleuropulmonary blastoma, primary central nervous system lymphoma, primary peritoneal carcinoma, prostate cancer, rectal cancer, renal cell cancer, renal pelvis and ureter cancer, retinoblastoma, rhabdoid tumor, salivary gland cancer, Sezary syndrome, skin cancer, small cell lung cancer, small intestine cancer, soft tissue sarcoma, spinal cord tumor, stomach cancer, T-cell lymphoma, teratoid tumor, testicular cancer, throat cancer, thymoma and thymic carcinoma, thyroid cancer, urethral cancer, uterine cancer, vaginal cancer, vulvar cancer, and Wilms tumor.

In some embodiments, the disease to be treated with the antibodies or antibody conjugates provided herein is gastric cancer, colorectal cancer, renal cell carcinoma, cervical cancer, non-small cell lung carcinoma, ovarian cancer, uterine cancer, fallopian tube carcinoma, primary peritoneal carcinoma, uterine corpus carcinoma, endometrial carcinoma, prostate cancer, breast cancer, head and neck cancer, brain carcinoma, liver cancer, pancreatic cancer, mesothelioma, and/or a cancer of epithelial origin. In particular embodiments, the disease is colorectal cancer. In some embodiments, the disease is ovarian cancer. In some embodiments, the disease is breast cancer. In some embodiments, the disease is triple-negative breast cancer (TNBC). In some embodiments, the disease is PARP inhibitor-resistant triple-negative breast cancer (TNBC). In some embodiments, the disease is lung cancer. In some embodiments, the disease is non-small cell lung cancer (NSCLC). In some embodiments, the disease is head and neck cancer. In some embodiments, the disease is renal cell carcinoma. In some embodiments, the disease is brain carcinoma. In some embodiments, the disease is endometrial cancer.

In certain embodiments, the cancer is selected from ovarian cancer, endometrial cancer, breast cancer, triple negative breast cancer, colorectal cancer, prostate cancer, gastric cancer, non-Hodgkin's lymphoma, melanoma, renal cancer, and pancreatic cancer. In certain embodiments, the cancer is a hematological cancer. In certain embodiments, the cancer is selected from lymphomas, leukemias, and myelomas. In certain embodiments, the cancer is selected from CLL, MCL, DLBCL, and ALL.

In certain embodiments, the antibodies or antibody conjugates provided herein treat the disease, including cancer, by inducing immunogenic cell death. In certain embodiments, cells treated with an antibody or antibody conjugate provided herein are characterized by cell-surface calreticulin and/or by release of HMGB1. In certain embodiments, cells treated with an antibody or an antibody conjugate provided herein elicited monocyte activation.

In certain embodiments, the antibodies or antibody conjugates provided herein treat the disease, for example cancer, by activating anti-tumor immunity or protective immunity. In certain embodiments, tumor cells pre-treated with an antibody or antibody conjugate provided herein undergo immunogenic cell damage, which can, in turn mount protective immunity in vivo.

In other embodiments, the antibodies or antibody conjugates provided herein in combination with a checkpoint inhibitor described herein treat the disease, for example cancer, by activating anti-tumor immunity or protective immunity. In certain embodiments, tumor cells pre-treated with an antibody or antibody conjugate provided herein undergo immunogenic cell damage, which can, in turn mount protective immunity in vivo. In certain embodiments, the checkpoint inhibitor is a PD-1 or PD-L1 inhibitor.

16. Diagnostic Applications

In some embodiments, the antibody or antibody conjugates provided herein are used in diagnostic applications. For example, an anti-ROR1 antibody or antibody conjugate may be useful in assays for ROR1 protein. In some aspects the antibody or antibody conjugate can be used to detect the expression of ROR1 in various cells and tissues. These assays may be useful, for example, in making a diagnosis and/or prognosis for a disease, such as a cancer.

In some diagnostic and prognostic applications, the antibody or antibody conjugate may be labeled with a detectable moiety. Suitable detectable moieties include, but are not limited to radioisotopes, fluorescent labels, and enzyme-substrate labels. In another embodiment, the anti-ROR1 antibody or antibody conjugate need not be labeled, and the presence of the antibody or antibody conjugate can be detected using a labeled antibody which specifically binds to the anti-ROR1 antibody or antibody conjugate.

Also provided herein is a method of diagnosing cancer in a subject in need thereof, comprising:
a) administering to the subject an effective amount of an antibody conjugate described herein, an antibody described herein, or a pharmaceutical composition described herein, wherein the antibody drug conjugate or antibody optionally comprises a label; and b) detecting the antibody drug conjugate or the antibody or detecting the label comprised in the antibody drug conjugate or antibody.

Also provided herein is a method of diagnosing cancer in a subject in need thereof, comprising detecting the expression of ROR1 in a cell or tissue wherein the method comprises:
- a) administering to the subject an effective amount of an antibody conjugate described herein, an antibody described herein, or a pharmaceutical composition described herein, wherein the antibody drug conjugate or antibody optionally comprises a label; and
- b) detecting the antibody drug conjugate or antibody or detecting the label comprised in the antibody drug conjugate or antibody.

Also provided herein is a method of diagnosing cancer in a subject in need thereof, comprising:
- a) detecting the expression of ROR1 in a cell or tissue of the subject; and
- b) administering to the subject an effective amount of an antibody conjugate described herein, an antibody described herein, or a pharmaceutical composition described herein.

17. Affinity Purification Reagents

The antibodies or antibody conjugates provided herein may be used as affinity purification agents. In this process, the antibodies or antibody conjugates may be immobilized on a solid phase such a resin or filter paper, using methods well known in the art. The immobilized antibodies or antibody conjugate is contacted with a sample containing the ROR1 protein (or fragment thereof) to be purified, and thereafter the support is washed with a suitable solvent that will remove substantially all the material in the sample except the ROR1 protein, which is bound to the immobilized antibody. Finally, the support is washed with another suitable solvent, such as glycine buffer, pH 5.0 that will release the ROR1 protein from the antibody.

18. Kits

In some embodiments, an anti-ROR1 antibodies or antibody conjugate provided herein is provided in the form of a kit, i.e., a packaged combination of reagents in predetermined amounts with instructions for performing a procedure. In some embodiments, the procedure is a diagnostic assay. In other embodiments, the procedure is a therapeutic procedure.

In some embodiments, the kit further comprises a solvent for the reconstitution of the anti-ROR1 antibodies or antibody conjugate. In some embodiments, the anti-ROR1 antibodies or antibody conjugate is provided in the form of a pharmaceutical composition.

SYNTHETIC EXAMPLES

The present examples describe the preparation and testing of the following linker-payloads and conjugates.

Linker-Payloads.

| LP No. | Linker payload description | Linker release mechanism |
|---|---|---|
| 1 | DBCO-Valcit-pAB-hemiasterlin | Cathepsin cleavable |
| 2 | DBCO-L-cysteic acid-PEG4-VKG-Exatecan | Cathepsin cleavable |
| 3 | DBCO-β-Glucuronide-PEG12-Exatecan | bGlucuronidase cleavable |
| 4 | DBCO-nnAA-PEG13-VKG-Exatecan | Cathepsin cleavable |
| 5 | DBCO-nnAA-PEG13-AAN-Exatecan | Legumain (LGMN) cleavable |
| 6 | DBCO-nnAA-PEG13-AAA-Exatecan | Cathepsin cleavable |
| 7 | DBCO-nnAA-PEG13-VK-Exatecan | Cathepsin cleavable |
| 8 | DBCO-GGG-EDA PNU | Non cleavable |
| 9 | DBCO-PEG4-VA-PBD | Cathepsin cleavable |
| 10 | DBCO-PEG4-GGFG-aminol-Dxd | Cathepsin followed by pH release |
| 11 | DBCO-Valcit-pAB-MMAE | Cathepsin cleavable |
| 12 | DBCO sidechain PEG12 ValLys-pAB-hemiasterlin | Cathepsin cleavable |
| 13 | DBCO sidechain PEG12 ValGlu-pAB-hemiasterlin | Cathepsin cleavable |
| 14 | DBCO-6,4 nnAA-PEG-VKG-Exatecan | Cathepsin cleavable |
| 15 | DBCO-4,6 nnAA-PEG-VKG-Exatecan | Cathepsin cleavable |
| 17 | DBCO-bridged nnAA-PEG-VKG-Exatecan | Cathepsin cleavable |
| 18 | DBCO-6,6 nnAA-β-Glucuronide-PEG12-Exatecan | bGlucuronidase cleavable |
| 19 | DBCO-6,4 nnAA-β-Glucuronide-PEG12-Exatecan | bGlucuronidase cleavable |
| 20 | DBCO-4,4 nnAA-β-Glucuronide-PEG12-Exatecan | bGlucuronidase cleavable |
| 21 | DBCO-nnAA-PEG13-VKG-hemiasterlin | Cathepsin cleavable |
| 22 | DBCO-nnAA-PEG13-AAN-hemiasterlin | Legumain (LGMN) cleavable |
| 23 | DBCO-6,4 nnAA-β-Glucuronide-PEG12-hemiasterlin | bGlucuronidase cleavable |
| 24 | DBCO-nnAA-PEG4-PNU | Non cleavable |
| 25 | DBCO-nnAA-PEG4-Gly-PNU | Non cleavable |
| 26 | DBCO-nnAA-PEG4-EDA-PNU | Non cleavable |
| 27 | DBCO-nnAA-sidechain PEG12-EDA-PNU | Non cleavable |
| 28 | DBCO-nnAA-sidechain PEG12-PNU | Non cleavable |
| 29 | DBCO-PEG4-PNU | Non cleavable |
| 30 | DBCO-PEG4-Gly-PNU | Non cleavable |
| 31 | DBCO-L-Cysteic acid-PEG4-PNU | Non cleavable |
| 32 | DBCO-L-Cysteic acid-PEG4-Gly-PNU | Non cleavable |
| 33 | DBCO-PEG4-AAN-PNU EDA | Legumain (LGMN) cleavable |

Antibody-Drug Conjugates.

| Conjugate | Conjugation site on HC 2188-D04 SEQ ID NO: 895 | Conjugation site on LC SEQ ID NO: 1021 | mAb | LP |
|---|---|---|---|---|
| 1 | Y180/F404 |  | 42 | LP1 |
| 2 | Y180/F404 | K42 | 42 | LP1 |
| 3 | Y180 |  | 42 | LP9 |
| 4 | Y180F404 | K42/E161 | 42 | LP1 |
| 5 | F404 |  | 42 | LP8 |
| 6 | Y180/F404 |  | 42 | LP10 |
| 7 | Y180/F404 | K42/E161 | 42 | LP10 |
| 8 | Y180/F404 | K42/E161 | 42 | LP2 |
| 9 | Y180/F404 | K42/E161 | 42 | LP3 |
| 10 | Y180F404 | K42/E161 | 42 | LP4 |
| 11 | Y180/F404 | K42/E161 | 42 | LP7 |
| 12 | Y180/F404 | K42/E161 | 42 | LP5 |
| 13 | Y180/F404 | K42/E161 | 42 | LP6 |
| 14 | Y180/F404 | K42/E161 | 42 | LP12 |
| 15 | Y180/F404 | K42/E161 | 42 | LP13 |
| 16 | Y180/F404 | K42/E161 | 42 | LP34 |
| 17 | Y180/F404 |  | 42 | LP14 |
| 18 | F404 |  | 42 | LP29 |
| 19 | F404 |  | 42 | LP30 |
| 20 | F404 |  | 42 | LP31 |
| 21 | F404 |  | 42 | LP32 |
| 22 | Y180/F404 |  | 42 | LP11 |
| 23 | F404 |  | 42 x 42 | LP8 |
| 24 | F404 |  | 42 x C01 | LP8 |

-continued

| Con-jugate | Conjugation site on HC 2188-D04 SEQ ID NO: 895 | Conjugation site on LC SEQ ID NO: 1021 | mAb | LP |
|---|---|---|---|---|
| 25 | F404 | | 42 x B09 | LP8 |
| 26 | F404 | | 42 x A05 | LP8 |
| 27 | F404 | | 42 x B04 | LP8 |
| 28 | F404 | | A05 x B04 | LP8 |
| 29 | F404 | | A05 x C06 | LP8 |
| 30 | Y180F404 | K42/E161 | 42 | LP14 |
| 31 | Y180F404 | K42/E161 | 42 | LP15 |
| 32 | Y180F404 | K42/E161 | 42 | LP16 |
| 33 | Y180F404 | K42/E161 | 42 | LP17 |
| 34 | Y180F404 | K42/E161 | 42 | LP18 |
| 35 | Y180F404 | K42/E161 | 42 | LP19 |
| 36 | Y180F404 | K42/E161 | 42 | LP20 |
| 37 | F404 | | 42 | LP33 |
| 38 | Y180F404 | K42/E161 | 42 | LP23 |
| 39 | Y180F404 | K42/E161 | 42 | LP22 |
| 40 | Y180F404 | K42/E161 | 42 | LP21 |
| 41 | F404 | | 42 | LP24 |
| 42 | F404 | | 42 | LP25 |
| 43 | F404 | | 42 | LP26 |
| 44 | F404 | | 42 | LP27 |
| 45 | F404 | | 42 | LP28 |
| 46 | Y180/F241/F404 | K42 | 42 | LP3 |
| 47 | Y180/F241/F404 | K42 | 42 | LP4 |
| 48 | Y180/F241/F404 | K42 | 42 | LP5 |
| 49 | Y180/F241/F404 | | 42 | LP3 |
| 50 | Y180/F241/F404 | | 42 | LP4 |
| 51 | Y180/F241/F404 | K42 | 42 | LP1 |
| 52 | Anti-GFP Y180/F241/F404 | K42 | Anti GFP | LP3 |
| 53 | Anti-GFP Y180/F241/F404 | K42 | Anti GFP | LP4 |

Biparatopic Conjugates.

| Conjugate | HC-knob | HC-hole | LC | LP |
|---|---|---|---|---|
| 23 | aROR1_2188-D04_HC_F404T AG_Knob | aROR1_2188-D04_HC_F404 TAG_Hole | SD-012277 Trastuzumab LC SerOpt | LP8 |
| 24 | aROR1_2188-D04_HC_F404T AG_Knob | aROR1_1943-C01_HC_F404 TAG_Hole | SD-012277 Trastuzumab LC SerOpt | LP8 |
| 25 | aROR1_2188-D04_HC_F404T AG_Knob | aROR1_2193-B09_HC_F404 TAG_Hole | SD-012277 Trastuzumab LC SerOpt | LP8 |
| 26 | aROR1_2188-D04_HC_F404T AG_Knob | aROR1_2194-A05_HC_F404 TAG_Hole | SD-012277 Trastuzumab LC SerOpt | LP8 |
| 27 | aROR1_2188-D04_HC_F404T AG_Knob | aROR1_2186-B04_HC_F404 TAG_Hole | SD-012277 Trastuzumab LC SerOpt | LP8 |
| 28 | aROR1_2194-A05_HC_F404T AG_Knob | aROR1_2186-B04_HC_F404 TAG_Hole | SD-012277 Trastuzumab LC SerOpt | LP8 |
| 29 | aROR1_2194-A05_HC_F404T AG_Knob | aROR1_1987-C06_HC_F404 TAG_Hole | SD-012277 Trastuzumab LC SerOpt | LP8 |

Synthetic Example 1: LP1
(DBCO-Valcit-pAB-Hemiasterlin)

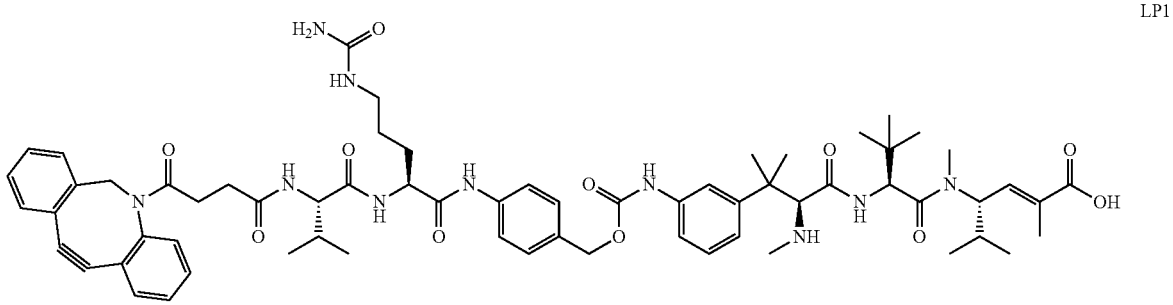 [SMILES: CN[C@H](C(=O)N[C@H](C(=O)N(C)[C@H](/C=C(\C)C(=O)O)C(C)C)C(C)(C)C)C(C)(C)c1cccc(NC(=O)OCc2ccc(NC(=O)[C@H](CCCNC(N)=O)NC(=O)[C@@H](NC(=O)CCC(=O)N3Cc4ccccc4C#Cc4ccccc43)C(C)C)cc2)c1]

Scheme 1
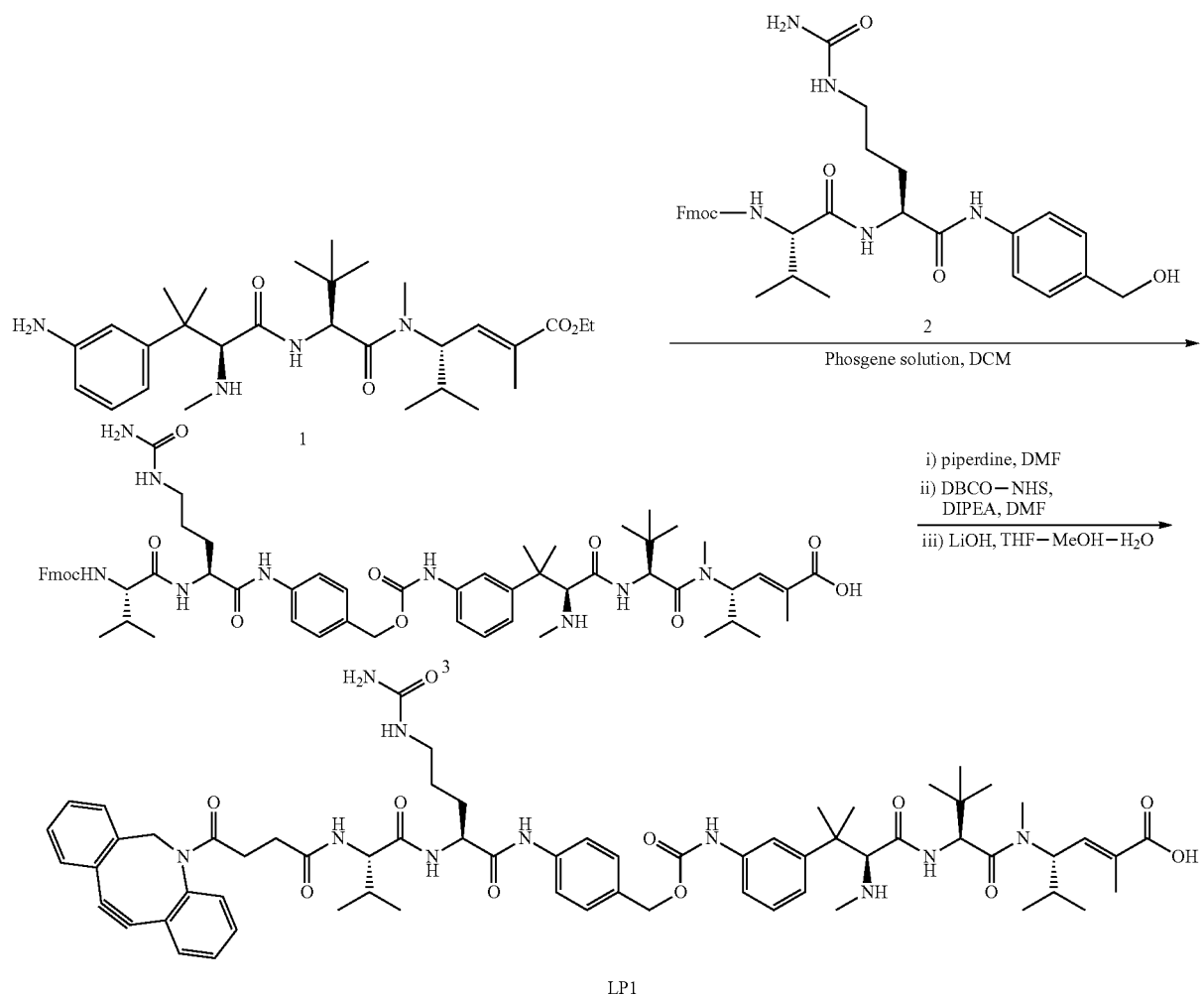
LP1 DBCO-Valcit-pAB-hemiasterlin Linker payload is synthesized as described in PCT/US2016/15844, WO 2020/252015 A1, the contents of which are hereby incorporated by reference in their entirety.
Synthetic Example 2: LP2 (DBCO-L-Cysteic acid-PEG4-VKG-Exatecan)
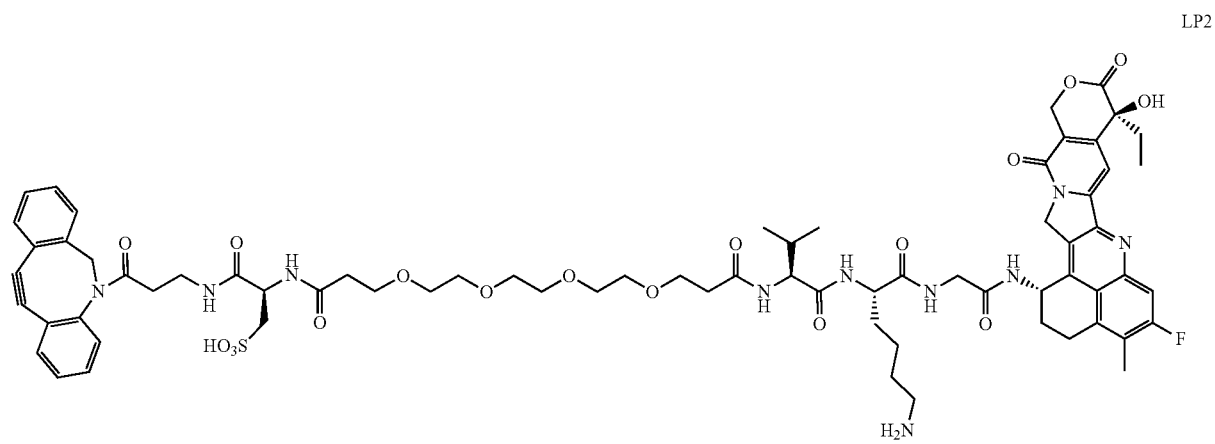 [SMILES: CC[C@@]1(O)C(=O)OCc2c1cc1n(c2=O)Cc2c-1nc1cc(F)c(C)c3c1c2[C@@H](NC(=O)CNC(=O)[C@H](CCCCN)NC(=O)[C@@H](NC(=O)CCOCCOCCOCCOCCC(=O)N[C@@H](CS(=O)(=O)O)C(=O)NCCC(=O)N1Cc2ccccc2C#Cc2ccccc21)C(C)C)CC3]

Scheme 2
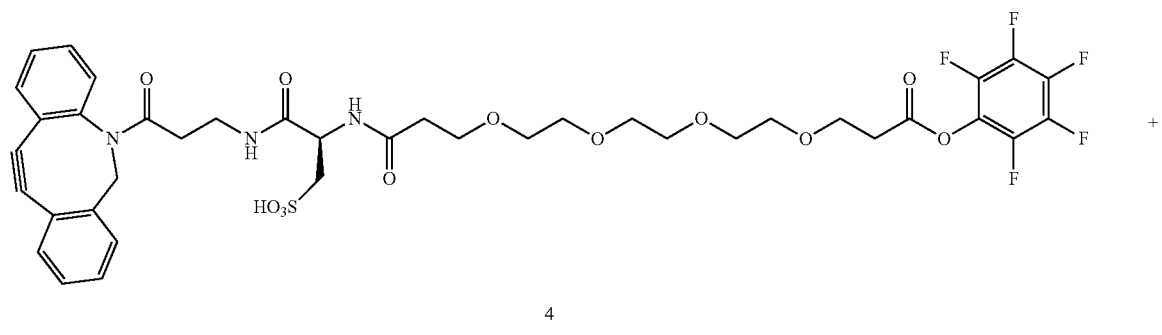
4
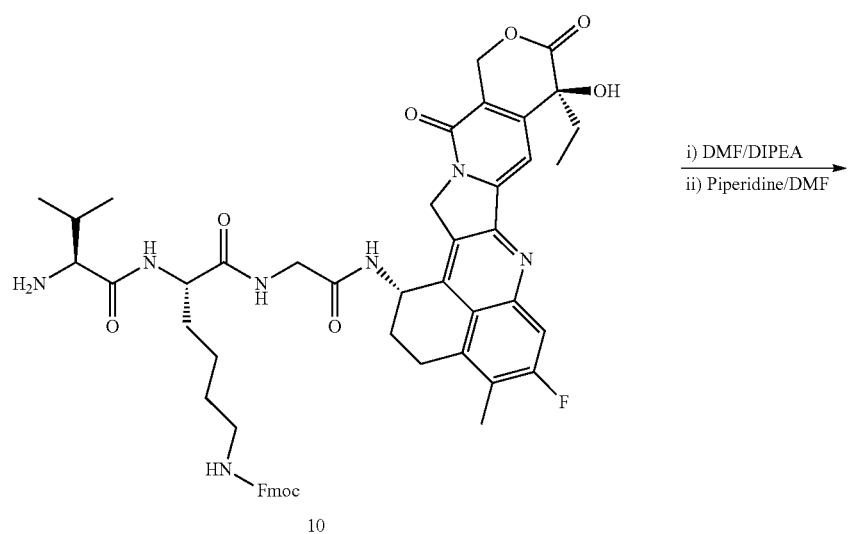
10
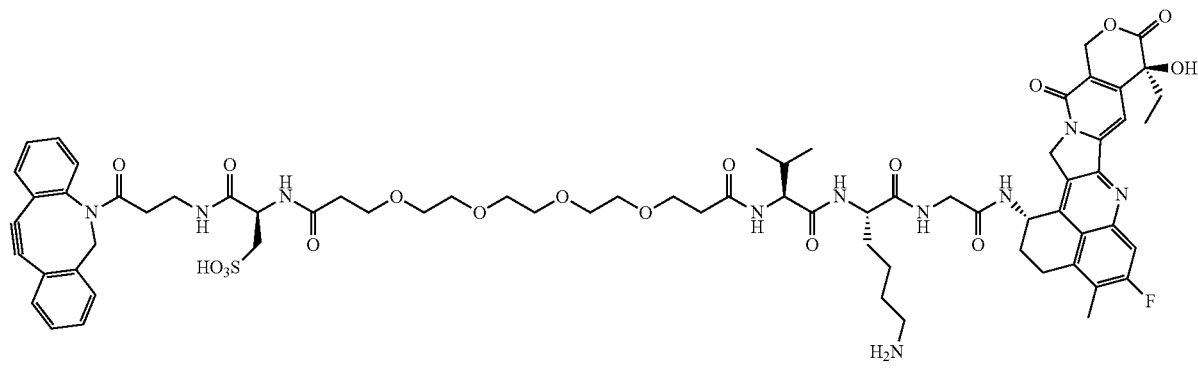
LP2
LP2 DBCO-L-cysteic acid-PEG4-VKG-Exatecan linker payload is synthesized consistent with the methods as described in Synthetic Example 4.

Synthetic Example 3: LP3
(DBCO-B-Glucuronide-PEG12-Exatecan)
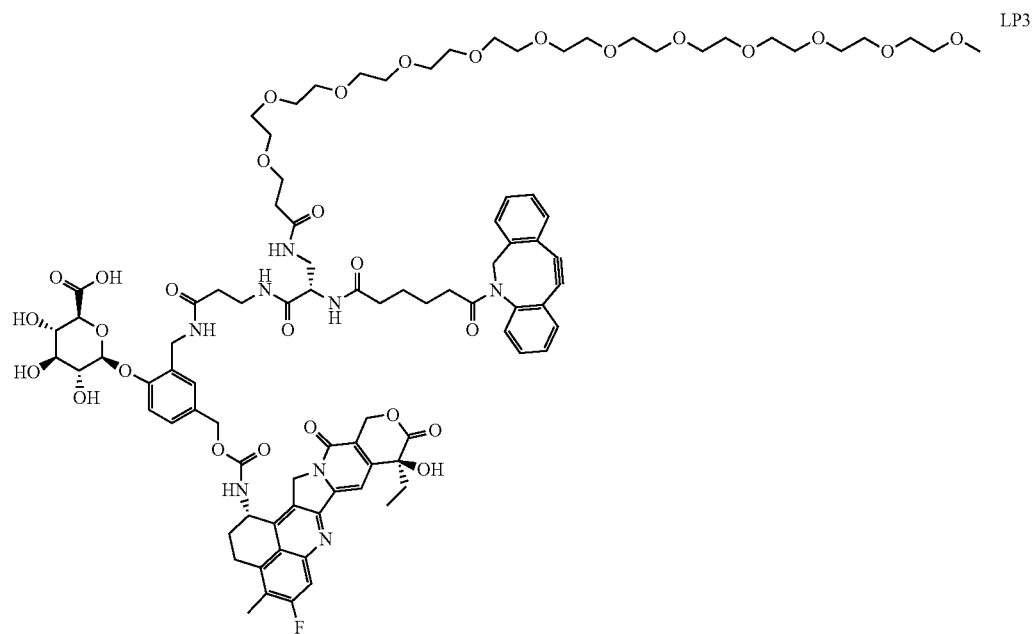 [SMILES: CC[C@@]1(O)C(=O)OCc2c1cc1n(c2=O)Cc2c-1nc1cc(F)c(C)c3c1c2[C@@H](NC(=O)OCc1ccc(O[C@@H]2O[C@H](C(=O)O)[C@@H](O)[C@H](O)[C@H]2O)c(CNC(=O)CCNC(=O)[C@H](CNC(=O)CCOCCOCCOCCOCCOCCOCCOCCOCCOCCOCCOCCOC)NC(=O)CCCCC(=O)N2Cc4ccccc4C#Cc4ccccc42)c1)CC3]
(40)
Scheme 3: Synthetic Scheme for β-Glu-Exatecan Benzylamine (Compound (19))
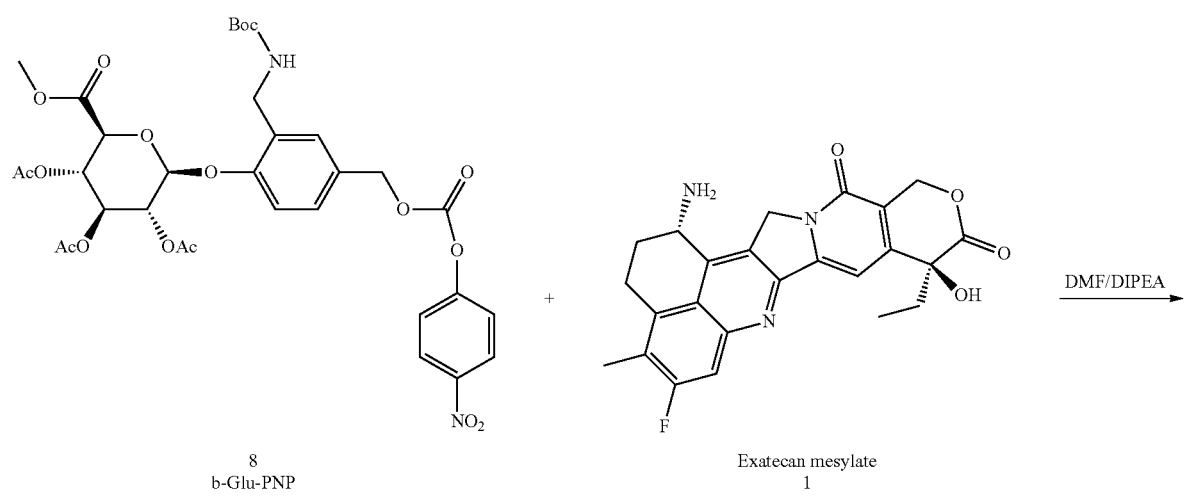

-continued
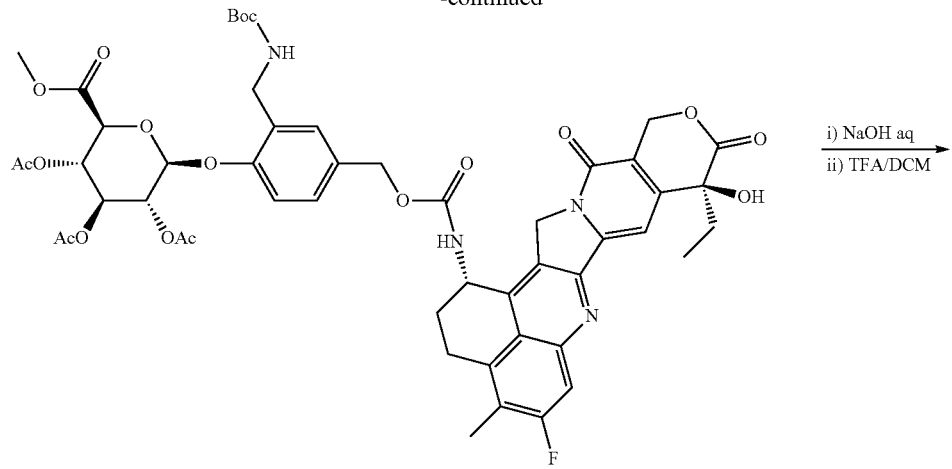
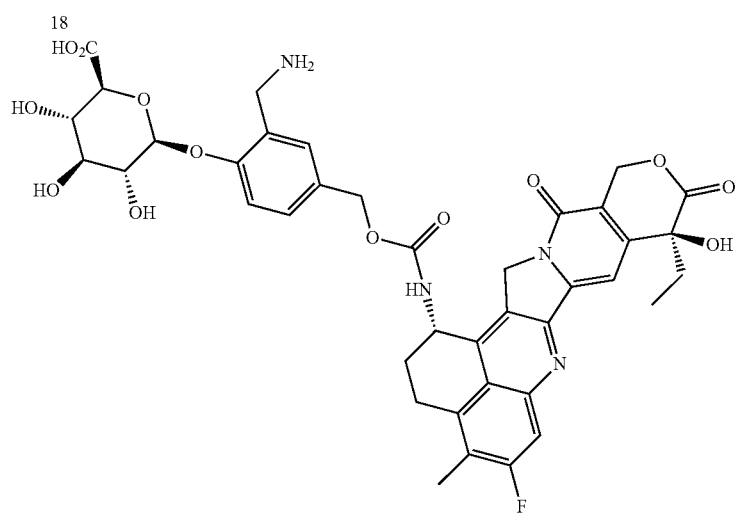
Scheme 5: Synthesis of β-Glu PNP linker (8)
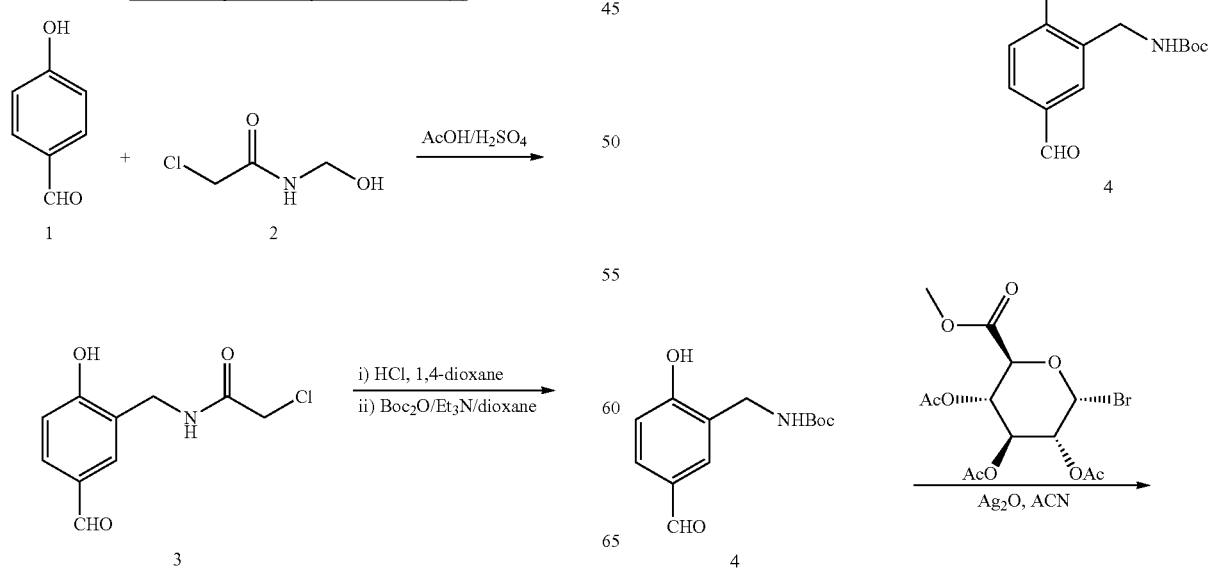

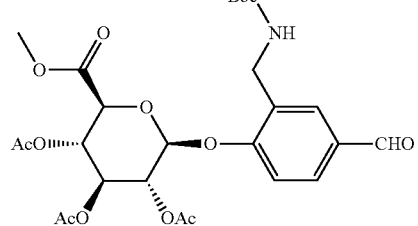
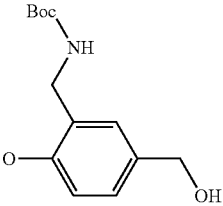
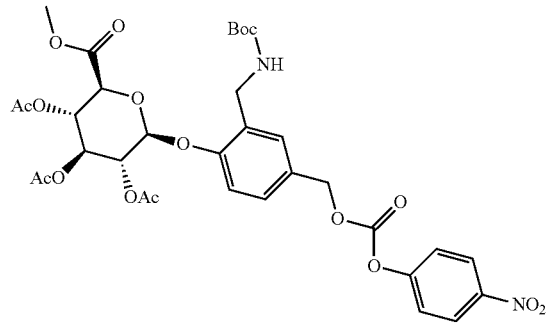
Scheme 6: Synthesis of m-PEG12-DBCO-PFP linker (16)
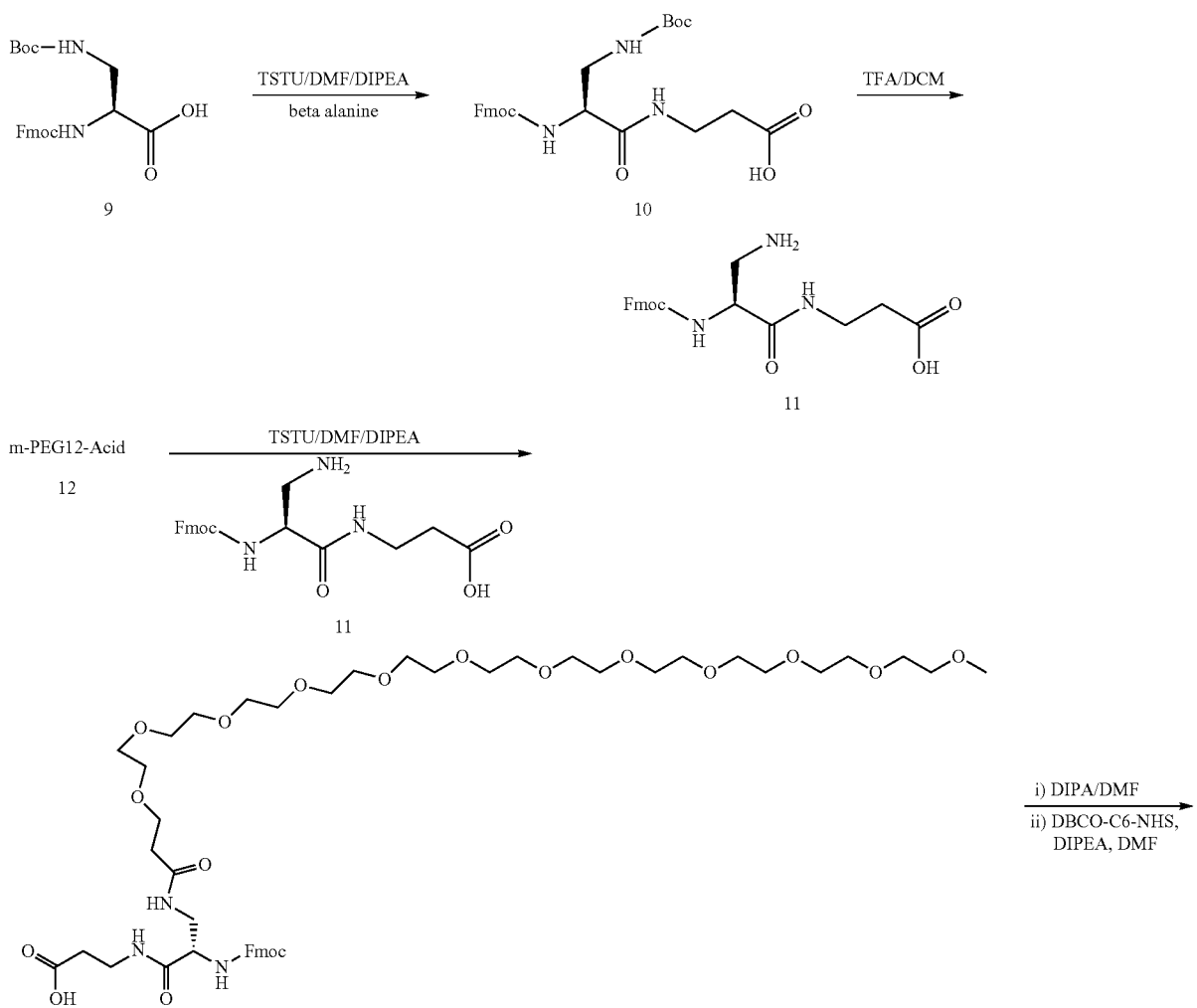

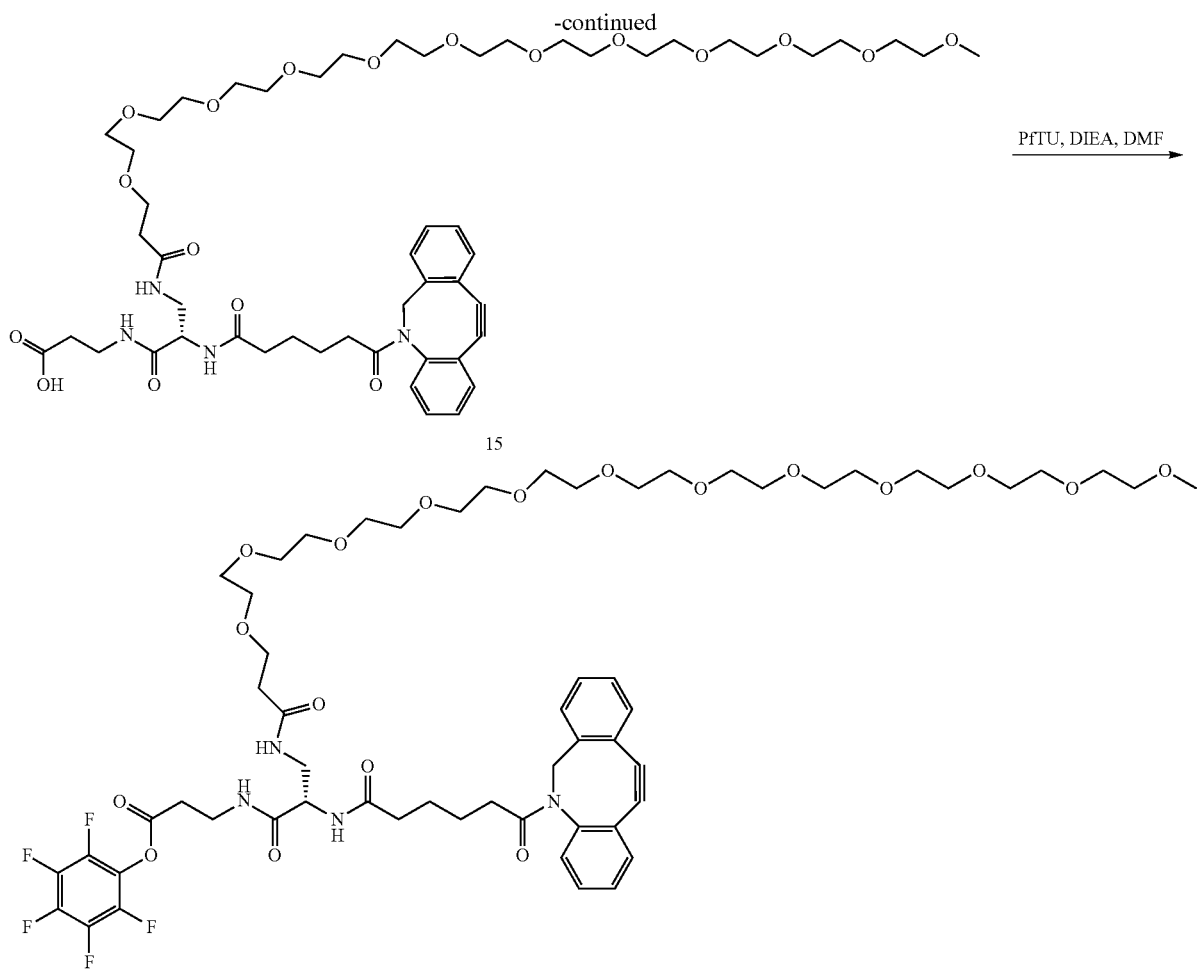

16 (m-PEG12-DBCO-PFP linker)

Synthesis of b-Glu PNP Linker Fragment (8)
Synthesis of Compound (4)

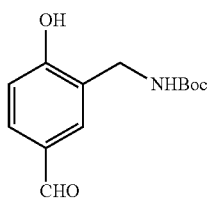

4

To a suspension of 4-hydroxybenzaldehyde (1) (5.3 g, 43.4 mmol) and 2-Chloro-N-(hydroxymethyl)acetamide (2) (5 g, 40.6 mmol) in AcOH (20 mL) was slowly added concentrated H$_2$SO$_4$ (32 mL). The mixture was stirred at room temperature (22° C.) for 16 h. The resulting viscous liquid was poured into ice water (300 mL) and extracted with EtOAc (100 mL×5). The organic layer was dried over Na$_2$SO$_4$ and concentrated under reduced pressure to give crude compound (3), which was dissolved in 1,4-dioxane (40 mL). To this solution was added concentrated hydrochloric acid (40 mL). The mixture was heated under reflux for one hour and then concentrated in vacuo to give a residue. The residue was dissolved in dioxane:H$_2$O (1:1, 50 mL). To this mixture was added Et$_3$N (9 mL), followed by Boc$_2$O (10 g, 46 mmol). The reaction mixture was stirred at room temperature for 16 h and partitioned between EtOAc (300 mL) and water (100 mL). The organic layer was dried over Na$_2$SO$_4$ and concentrated to dryness under reduced pressure. The residue was purified by silica gel chromatography (220 g column, 20-30% EtOAc:hexane in 30 mins, flow rate: mL/min) to furnish compound (4) as an off-white solid (5.3 g). MS calculated for C$_{13}$H$_{17}$NO$_4$, 251.3; found 252.2 [M+H]$^+$; $^1$H NMR (500 MHz, DMSO-d$_6$) δ10.75 (s, 1H), 9.77 (s, 1H), 7.69-7.62 (m, 2H), 7.31 (t, J=6.2 Hz, 1H), 6.96 (d, J=8.1 Hz, 1H), 4.11 (d, J=6.1 Hz, 2H), 1.41 (s, 9H).

Synthesis of Compound (7)

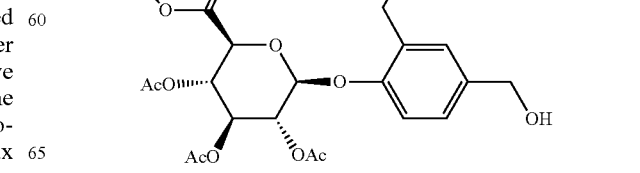

7

To a solution of compound (4) (2.2 g, 8.8 mmol) and (2R,3R,4S,5S,6S)-2-bromo-6-(methoxycarbonyl)tetrahydro-2H-pyran-3,4,5-triyl triacetate (5) (3.2 g, 8.1 mmol) in anhydrous acetonitrile (50 mL) was added Ag$_2$O (3.7 g, 16 mmol). The suspension was stirred under argon atmosphere for 16 h. The solids were filtered off and washed with acetonitrile (10 mL). To the combined acetonitrile solution was added i-PrOH (10 mL) and NaBH$_4$ (300 mg, 8.1 mmol), and the mixture was stirred at room temperature. After 30 min, the reaction was quenched with water (100 mL) and extracted with EtOAc (3×100 mL). The organic layer was dried over Na$_2$SO$_4$ and concentrated to dryness under reduced pressure. The residue was purified by silica gel chromatography (220 g column, 40-70% EtOAc:hexane in 30 min, flow rate: 40 mL/min) to furnish compound (7) as a white foam (3.0 g, 5.2 mmol). MS calculated for C$_{26}$H$_{35}$NO$_{13}$, 569.2; found 570.4 [M+H]$^+$; $^1$H NMR (500 MHz, DMSO-d$_6$) δ7.15 (q, J=6.0 Hz, 3H), 6.98 (d, J=8.7 Hz, 1H), 5.61-5.41 (m, 2H), 5.25-5.03 (m, 3H), 4.73 (d, J=9.9 Hz, 1H), 4.42 (d, J=5.3 Hz, 2H), 4.03 (tt, J=16.4, 8.3 Hz, 2H), 3.65 (s, 3H), 2.14-1.92 (m, 10H), 1.41 (s, 9H), 1.33-1.14 (m, 2H).

Synthesis of Compound (8)

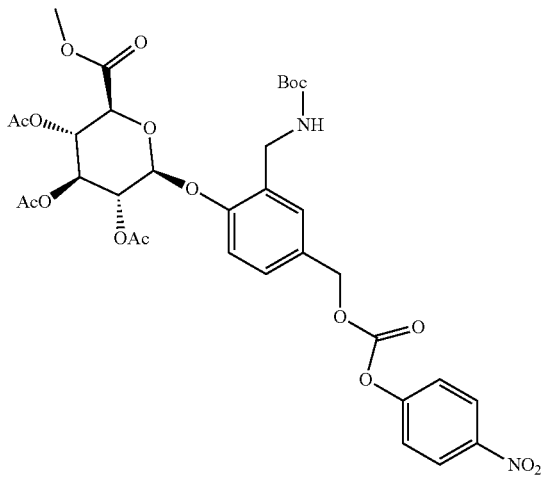

8

To a solution of compound (7) (2.6 g, 4.56 mmol) in anhydrous DMF (15 mL) was added DIEA (1.1 mL) and bis-PNP carbonate (2 g, 6.57 mmol). The mixture was stirred at room temperature for 16 h and purified directly by reverse phase HPLC (Phenomenex Gemini NX 5μ, C18, 110 Å, 150×50 mm, Mobile phase: A: 0.1% TFA in water, B: acetonitrile, Gradient: 20-90% B over 20 min, flow 50 mL/min) to give compound (8) (1.8 g) as a white solid after lyophilization. MS calculated for C$_{33}$H$_{38}$N$_2$O$_{17}$, 734.2; found 735.5 [M+H]$^+$; $^1$H NMR (500 MHz, DMSO-d$_6$) δ 8.35-8.29 (m, 2H), 7.60-7.53 (m, 2H), 7.36 (dd, J=8.4, 2.2 Hz, 1H), 7.29 (d, J=2.3 Hz, 1H), 7.22 (t, J=6.2 Hz, 1H), 7.09 (d, J=8.4 Hz, 1H), 5.65 (d, J=7.9 Hz, 1H), 5.52 (t, J=9.6 Hz, 1H), 5.26 (s, 2H), 5.19 (dd, J=9.8, 7.9 Hz, 1H), 5.10 (t, J=9.7 Hz, 1H), 4.76 (d, J=9.9 Hz, 1H), 4.03 (qd, J=16.7, 6.2 Hz, 3H), 3.66 (s, 3H), 2.06 (s, 3H), 2.02 (d, J=2.6 Hz, 6H), 1.39 (s, 8H), 1.30 (s, 1H).

Synthesis of m-PEG12-DBCO-PFP (16)

Synthesis of Compound (11)

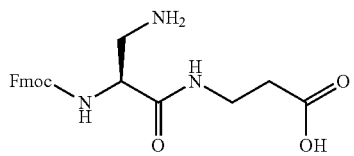

11

To a solution of Fmoc-Dap (Boc)-COOH (9) (853 mg, 2 mmol) in anhydrous DMF (10 mL) was added N,N,N',N'-Tetramethyl-O—(N-succinimidyl)uronium tetrafluoroborate (TSTU) (608 mg, 2 mmol), followed by DIPEA (0.7 mL). The mixture was stirred at room temperature for 10 min. A solution of beta-alanine (0.2 g) in acetonitrile:water (1:1, 3 mL) was added, followed by DIPEA (0.4 mL). The reaction mixture was stirred at room temperature for 30 min, and then acidified with 0.5 N hydrochloric acid (50 mL). The mixture was extracted with EtOAc (200 mL) and the organic layer was dried over Na$_2$SO$_4$ and concentrated to dryness under reduced pressure to give crude compound (10) as white powder. Crude compound (10) was treated with TFA:DCM (1:4, v/v, 20 mL) at room temperature for one hour. The mixture was evaporated to dryness under reduced pressure to give crude compound (11) which was used directly in the next step. MS calculated for C$_{21}$H$_{23}$N$_3$O$_5$, 397.16; found 398.2 [M+H]$^+$.

Synthesis of Compound (14)

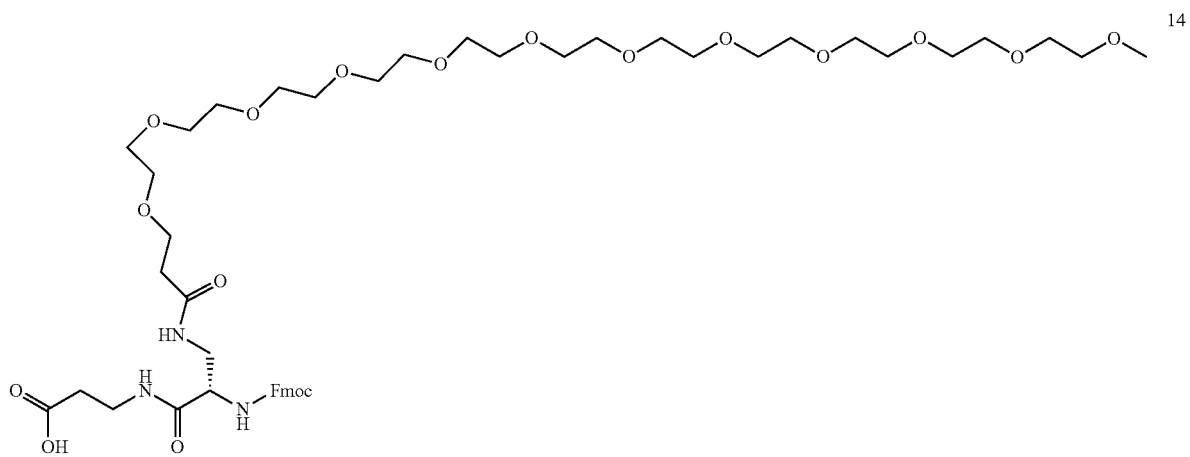

14 m-PEG12-acid (12) (1.18 g, 2 mmol) was dissolved in DMF (10 mL) and TSTU (610 mg, 2 mmol) was added, followed by DIPEA (700 After 5 min, a solution of compound (11) in DMF (10 mL) with DIPEA (0.7 mL) was added. The reaction mixture was stirred at room temperature for 30 mins and purified directly by reverse phase HPLC to give compound (14) as a viscous foam (1.27 g). MS calculated for $C_{47}H_{73}N_3O^{18}$, 967.5; found 968.8 $[M+H]^+$; $^1H$ NMR (500 MHz, DMSO-$d_6$) δ8.35-8.29 (m, 2H), 7.60-7.53 (m, 2H), 7.36 (dd, J=8.4, 2.2 Hz, 1H), 7.29 (d, J=2.3 Hz, 1H), 7.22 (t, J=6.2 Hz, 1H), 7.09 (d, J=8.4 Hz, 1H), 5.65 (d, J=7.9 Hz, 1H), 5.52 (t, J=9.6 Hz, 1H), 5.26 (s, 2H), 5.19 (dd, J=9.8, 7.9 Hz, 1H), 5.10 (t, J=9.7 Hz, 1H), 4.76 (d, J=9.9 Hz, 1H), 4.03 (qd, J=16.7, 6.2 Hz, 3H), 3.66 (s, 3H), 2.06 (s, 3H), 2.02 (d, J=2.6 Hz, 6H), 1.39 (s, 8H), 1.30 (s, 1H).

Synthesis of Compound (15)

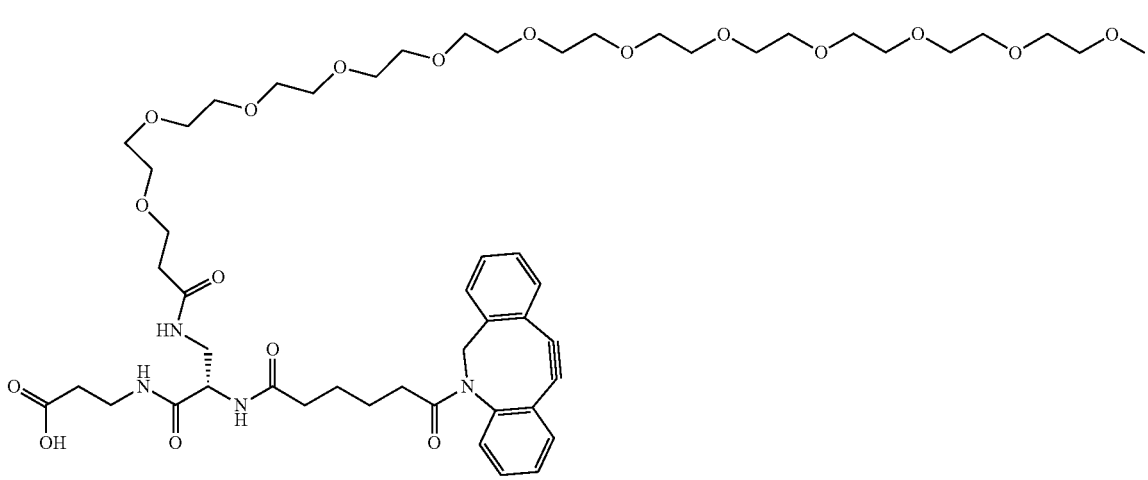

To a solution of compound (14) (1.24 g) in DMF (10 mL) was added i-Pr$_2$NH (DIPEA) (10 mL) and the reaction mixture was stirred at room temperature for 2 h. The mixture was then concentrated under reduced pressure to about 9 mL. To this solution, DBCO-C6-NHS (0.55 g) was added followed by DIPEA (0.23 mL). The mixture was stirred at room temperature for 2 h and then purified directly by reverse phase HPLC to give compound (15) as a colorless syrup (1.17 g). MS calculated for $C_{53}H_{80}N_4O_{18}$, 1060.6; found 1061.9 $[M+H]^+$.

Synthesis of Compound (16)

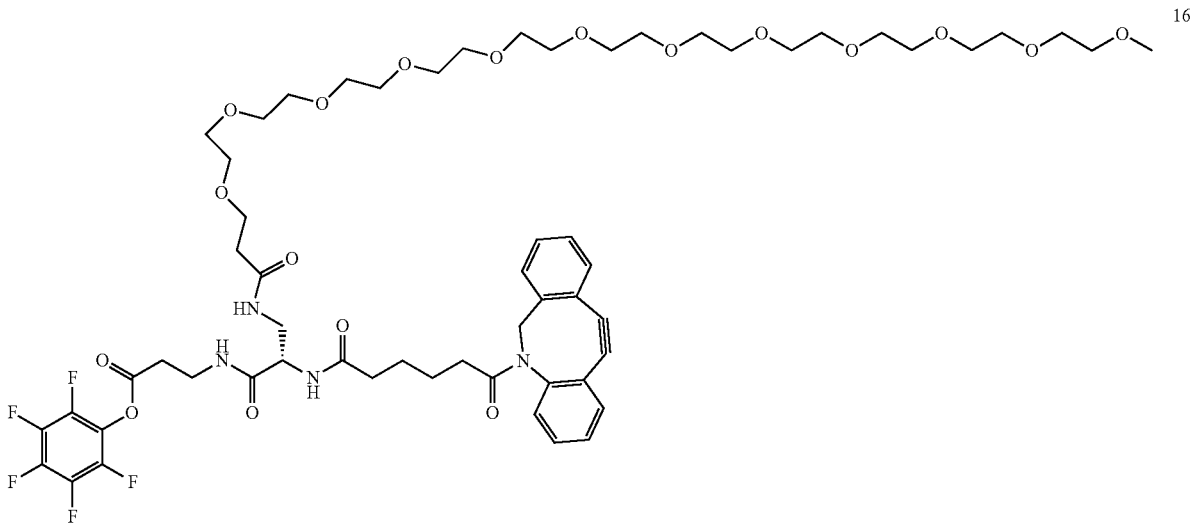

(m-PEG12-DBCO-PFP linker)

To a solution of compound (15) (1.1 g) in DMF (8 mL) was added Pentafluorophenol-tetramethyluronium hexafluorophosphate (PfTU) (0.5 g) followed by DIEA (0.4 mL) and the reaction mixture was stirred at room temperature for 10 min. The mixture was purified directly by RP-HPLC to give compound (16) as a colorless syrup (1.0 g). MS calculated for $C_{59}H_{79}F_5N_4O_{18}$, 1226.5; found 1227.8 [M+H]$^+$. Compound (16) was used in the next reaction.

Synthesis of Compound (19)

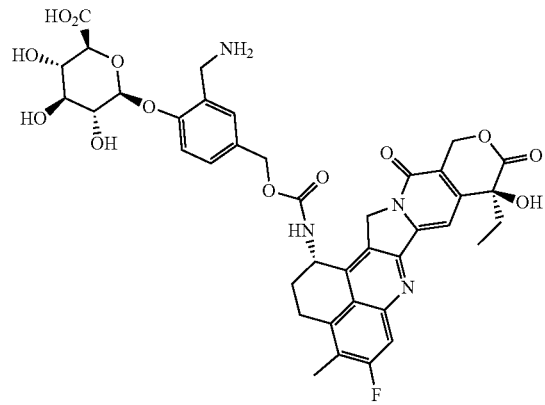

19

To a solution of compound (8) (735 mg, 1 mmol) and Exatecan mesylate 1, 531 mg, 1 mmol) in DMF (10 mL) was added DIPEA (350 µL). The reaction mixture was stirred at room temperature (22° C.) for 5 hours and then diluted with EtOAc (200 mL). The mixture was washed with 0.5 N hydrochloric acid (100 mL), water (100 mL), and brine (50 mL). The organic layer was dried over $Na_2SO_4$ and concentrated to dryness under reduced pressure to give crude compound (18) which was suspended in acetonitrile:water (2:1, 50 mL). To this mixture, 1 N aq. NaOH (7 mL) was added and the reaction was stirred at room temperature. After 3 h, 1 N hydrochloric acid (7 mL) was added and the mixture was evaporated to dryness under reduced pressure. The resulting residue was treated with TFA:DCM (1:4, v/v, 20 mL) at room temperature for one hour. The mixture was diluted with toluene (30 mL) and then evaporated to dryness under reduced pressure. The residue was purified by reverse phase HPLC to give compound (19) as a yellow solid (745 mg). MS calculated for $C_{39}H_{39}FN_4O_{13}$, 790.3; found 791.6 [M+H]$^+$; $^1$H NMR (500 MHz, DMSO-d$_6$) δ 8.09 (d, J=8.0 Hz, 4H), 7.73 (dd, J=10.7, 3.2 Hz, 1H), 7.54 (d, J=2.1 Hz, 1H), 7.49 (dd, J=8.5, 2.2 Hz, 1H), 7.32 (s, 1H), 7.22 (d, J=8.5 Hz, 1H), 6.55 (s, 1H), 5.75 (s, 1H), 5.48 (d, J=16.3 Hz, 1H), 5.46-5.37 (m, 3H), 5.31-5.13 (m, 4H), 5.08-5.02 (m, 2H), 4.19-4.07 (m, 2H), 3.95 (d, J=9.5 Hz, 1H), 3.44 (dd, J=8.8, 2.6 Hz, 1H), 3.28-3.19 (m, 2H), 3.14-3.04 (m, 1H), 2.34 (s, 3H), 2.26 (dd, J=12.5, 6.4 Hz, 1H), 2.12 (qd, J=9.0, 4.6 Hz, 1H), 1.87 (dh, J=21.5, 7.2 Hz, 2H), 0.89 (t, J=7.2 Hz, 3H).

Final Coupling of Synthesis LP3:

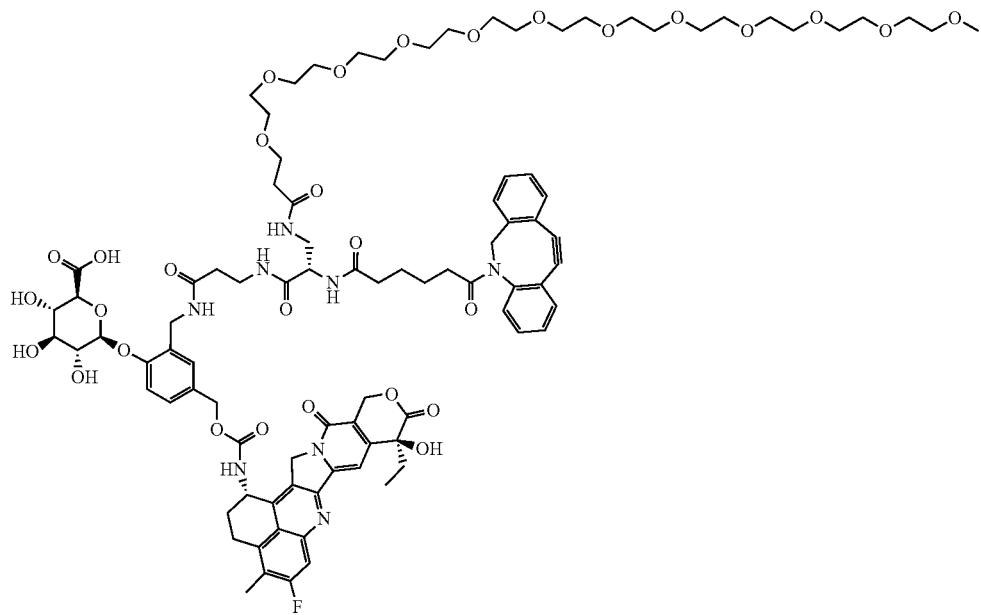 [SMILES: CC[C@@]1(O)C(=O)OCc2c1cc1n(c2=O)Cc2c-1nc1cc(F)c(C)c3c1c2[C@@H](NC(=O)OCc1ccc(O[C@@H]2O[C@H](C(=O)O)[C@@H](O)[C@H](O)[C@H]2O)c(CNC(=O)CCNC(=O)[C@H](CNC(=O)CCOCCOCCOCCOCCOCCOCCOCCOCCOCCOCCOCCOC)NC(=O)CCCCC(=O)N2Cc4ccccc4C#Cc4ccccc42)c1)CC3]

The compound b-Glu-Exatecan benzyl amine (19) (540 mg, 0.68 mmol) was dissolved in DMF (4 mL) and compound m-PEG12-DBCO-PFP (16) (750 mg, 0.6 mmol) was added, followed by DIPEA (0.32 mL). The reaction mixture was stirred at room temperature for 30 min and purified directly by reverse phase HPLC (Phenomenex Gemini NX 5μ, C18, 110 Å, 150×50 mm, Mobile phase: A: 0.1% TFA in water, B: acetonitrile, Gradient: 20-90% B over 20 min, flow 50 mL/min) to give compound LP3 as a pale-yellow solid (704 mg). HRMS m/z (ESI+): calculated for $C_{92}H_{117}FN_8O_{30}$, 1832.78; found 1833.79 [M+H]+; 1H NMR (500 MHz, DMSO-$d_6$) δ12.84 (s, 1H), 8.20 (t, J=6.2 Hz, 1H), 8.02 (d, J=8.8 Hz, 1H), 7.75 (td, J=6.1, 3.4 Hz, 2H), 7.62-7.52 (m, 1H), 7.50-7.39 (m, 2H), 7.32-7.25 (m, 2H), 6.52 (s, 1H), 5.50-5.39 (m, 2H), 5.27 (d, J=13.6 Hz, 3H), 5.01-4.94 (m, 1H), 4.29 (t, J=6.3 Hz, 2H), 3.57 (d, J=14.0 Hz, 1H), 3.56-3.46 (m, 35H), 3.48-3.40 (m, 5H), 3.35 (td, J=12.8, 6.5 Hz, 5H), 3.24 (s, 2H), 3.22 (s, 3H), 2.36 (d, J=1.8 Hz, 3H), 2.27 (dq, J=13.4, 6.3 Hz, 3H), 2.16 (ddd, J=21.5, 11.0, 6.0 Hz, 2H), 1.87 (dp, J=21.0, 7.2 Hz, 4H), 1.17 (s, 3H), 0.88 (t, J=7.3 Hz, 3H).

Synthetic Example 4: LP4
(DBCO-NNAA-PEG13-VKG-Exatecan)

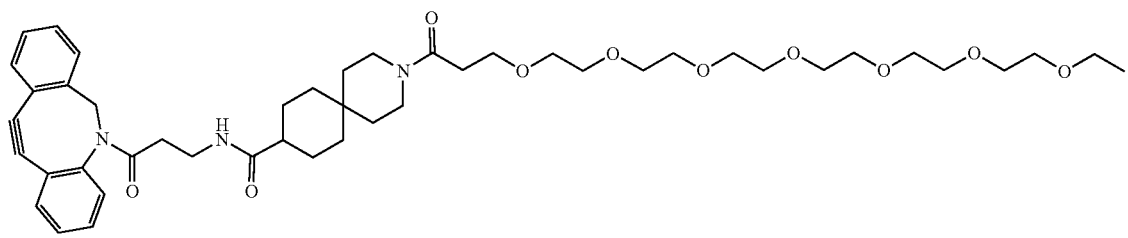

LP4

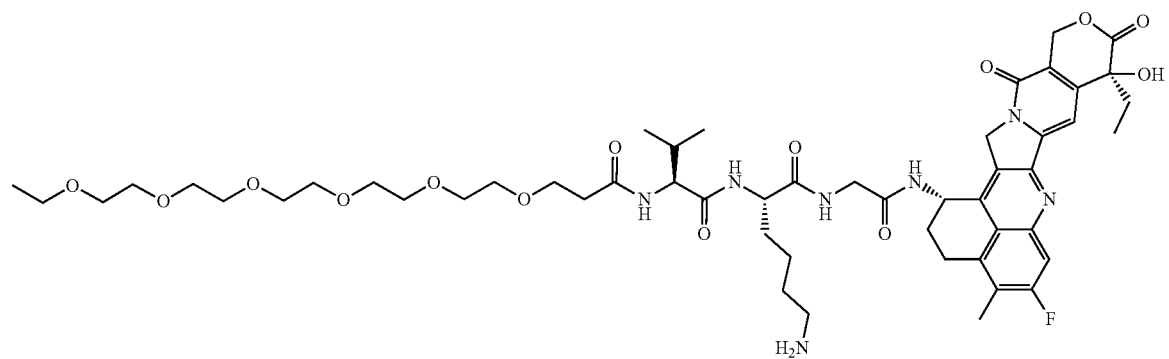

Scheme 7: synthesis of VK(Fmoc)G-Exatecan (10)
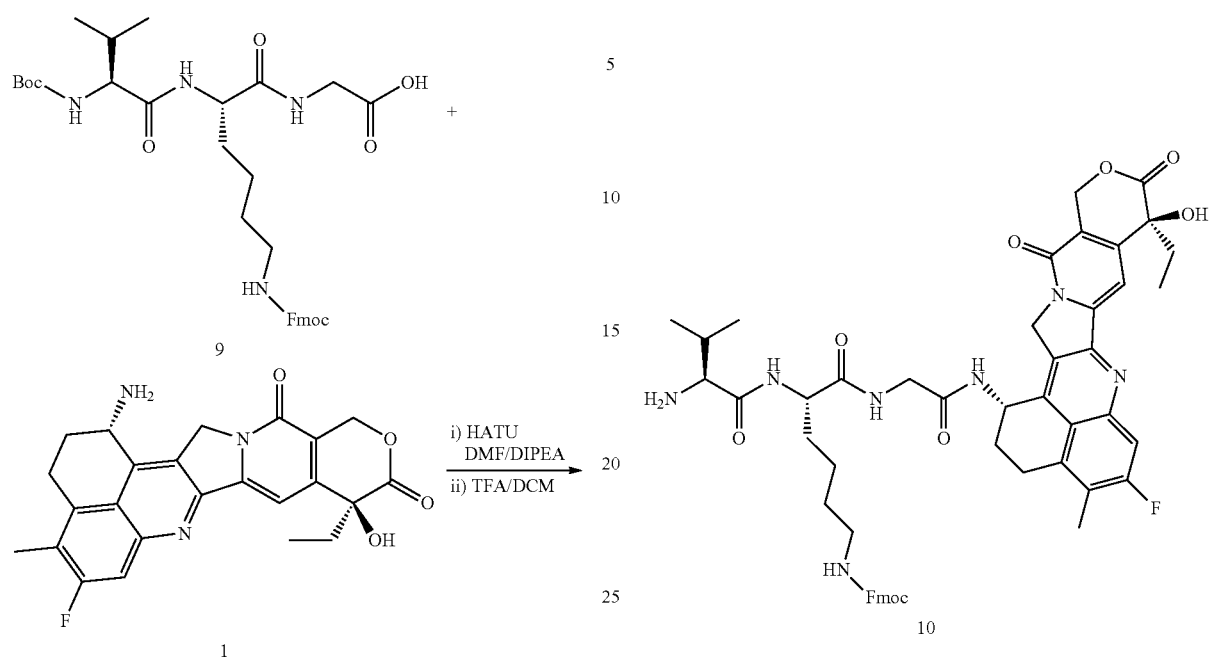
Scheme 8: final couplings and deprotection of the synthesis LP4
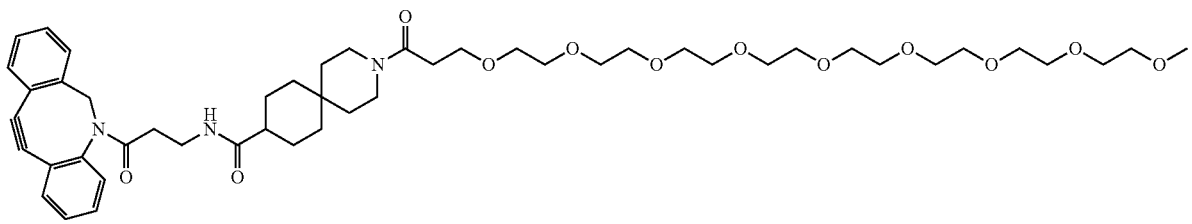
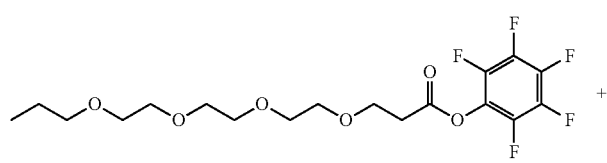

-continued

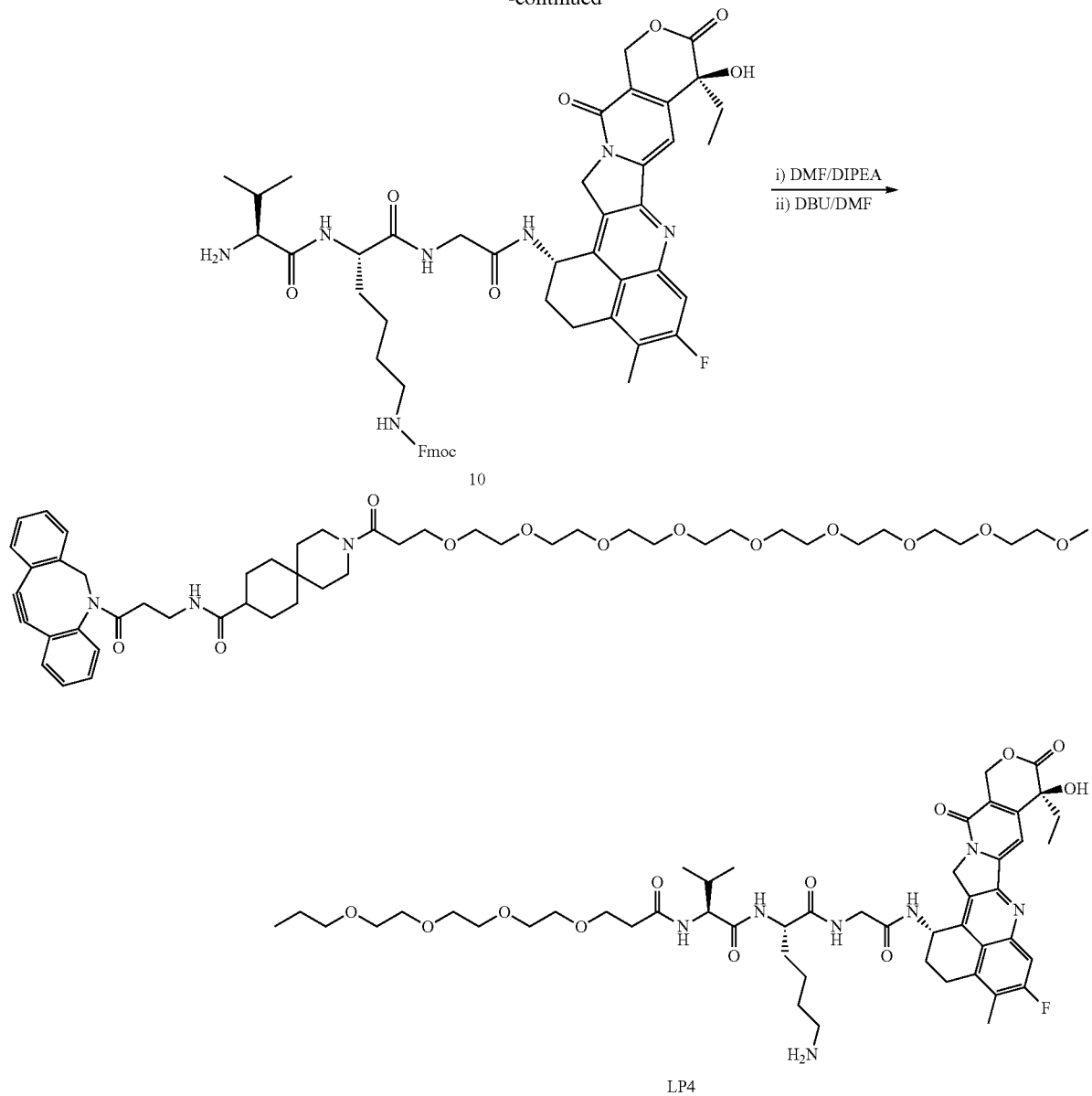

LP4

Synthesis of Compound 10:

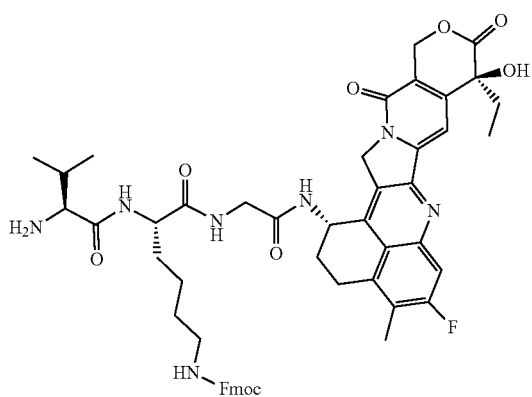

To a solution of compound Boc-VK(Fmoc)-G-OH 9 (562 mg, 0.9 mmol) in anhydrous DMF (10 mL) was added Exatecan mesylate (1) (478 mg, 0.9 mmol) and DIPEA (470 µL). After all components dissolved, HATU (342 mg, 0.9 mmol) was added, and the mixture was stirred at room temperature for 10 min. The reaction was then diluted with water (80 mL) and extracted with EtOAc (150 mL). The organic layer was washed with hydrochloric acid (0.2 M, 50 mL) and brine (50 mL), dried over $Na_2SO_4$ and evaporated to dryness under reduced pressure. The residue obtained was treated with TFA/DCM (1/4, 20 mL) at room temperature for 30 min and the reaction was evaporated to dryness under reduced pressure. The crude mixture was dissolved in 5 mL of DMF and purified by reverse phase HPLC to give compound 10 as a yellowish solid (771 mg). MS calculated for $C_{52}H_{56}FN_7O_9$, 941.4; found 942.9 $[M+H]^+$.

Synthesis of LP4

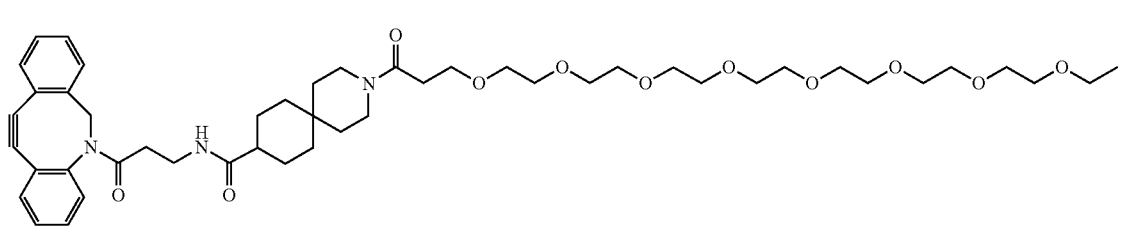

LP4

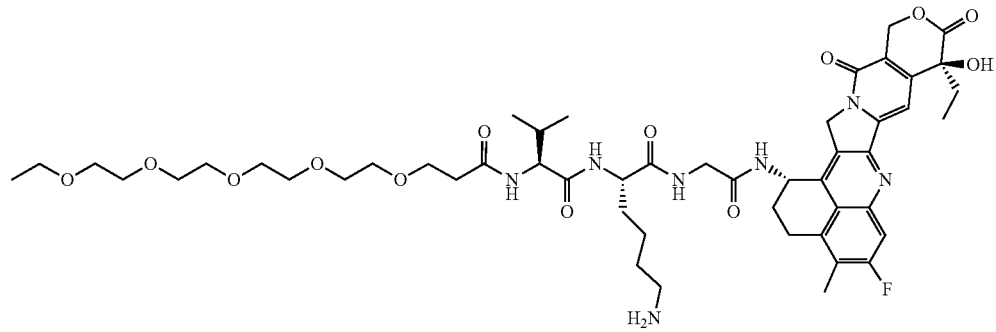

To a solution of compound 4 (426 mg, 0.33 mmol) in anhydrous DMF (3 mL) was added compound 10 (TFA salt, 347 mg, 0.33 mmol) and DIPEA (130 The mixture was stirred at room temperature for 15 min, the LCMS showed the desired product formation. Then DBU (366 µL) was added dropwise, and the mixture was stirred at room temperature for additional 10 min. LCMS showed completion of the reaction. Then the mixture was purified directly by reverse phase HPLC to give LP4 as a yellowish solid (350 mg); HRMS m/z (ESI$^+$): calculated for $C_{96}H_{133}FN_{10}O_{24}$, 1828.94; found 1829.95 [M+H]$^+$; $^1$H NMR (500 MHz, DMSO) δ 8.43 (d, J=8.5 Hz, 1H), 8.14 (t, J=5.6 Hz, 1H), 7.98 (d, J=7.4 Hz, 1H), 7.81 (d, J=10.9 Hz, 1H), 7.77-7.53 (m, 7H), 7.54-7.23 (m, 10H), 5.57 (dt, J=8.7, 4.4 Hz, 1H), 5.47-5.38 (m, 2H), 5.25 (d, J=3.3 Hz, 2H), 5.04 (d, J=14.1 Hz, 2H), 4.16 (td, J=8.1, 5.9 Hz, 3H), 4.08 (dd, J=8.5, 6.8 Hz, 3H), 3.88-3.68 (m, 13H), 3.50 (d, J=3.6 Hz, 71H), 3.25-3.13 (m, 4H), 3.13-3.03 (m, 2H), 2.92 (dq, J=13.4, 6.8 Hz, 2H), 2.78 (q, J=6.8 Hz, 3H), 2.60-2.26 (m, 18H), 2.26-2.03 (m, 3H), 1.98-1.74 (m, 6H), 1.74-1.46 (m, 8H), 1.46-1.09 (m, 12H), 0.97 (s, 2H), 0.88 (t, J=7.3 Hz, 3H), 0.78 (dd, J=14.1, 6.7 Hz, 7H).

Synthetic Example 5: LP5
(DBCO-NNAA-PEG13-AAN-Exatecan)

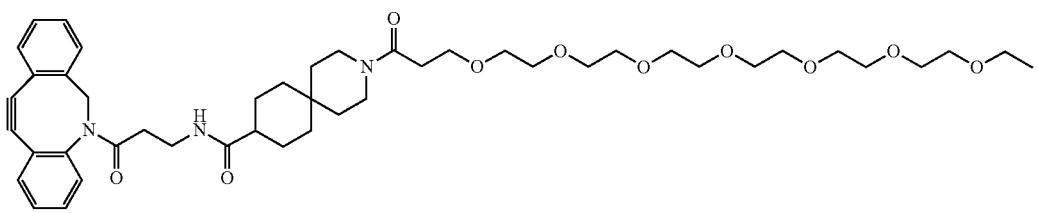

LP5

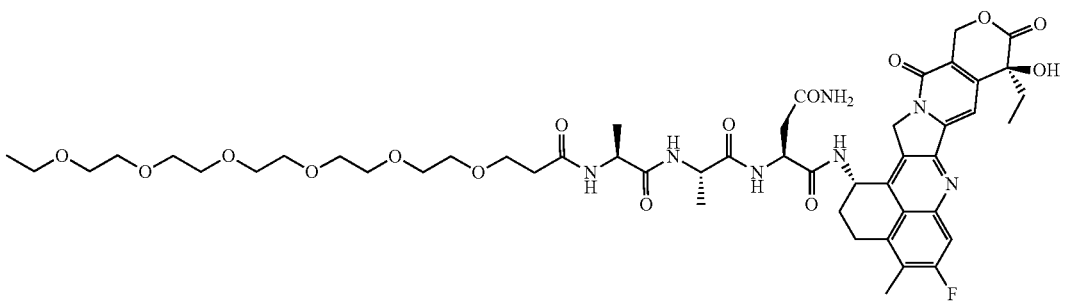

Scheme 9: synthesis of AAN-Exatecan (3)
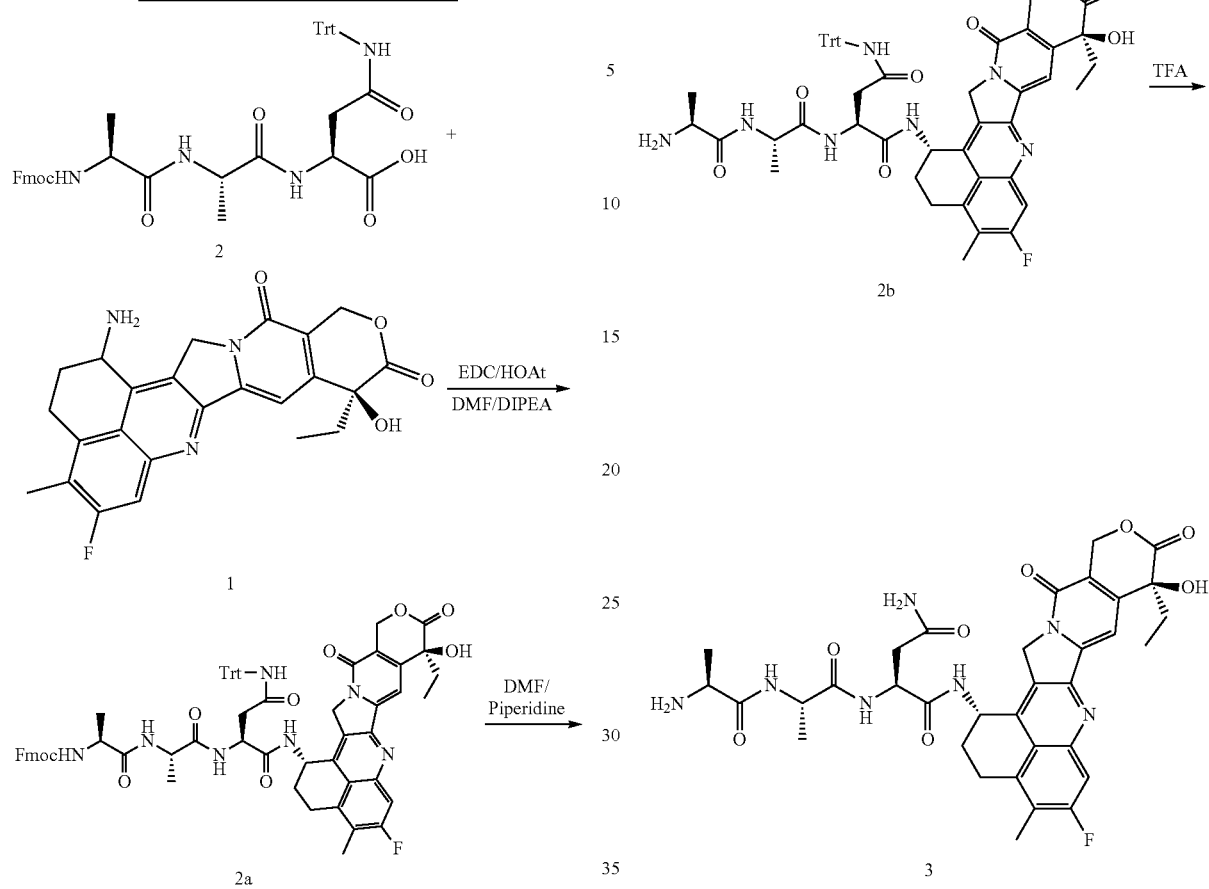
Scheme 10: Synthesis of DBCO-nnAA-PEG13-PFP linker (4)
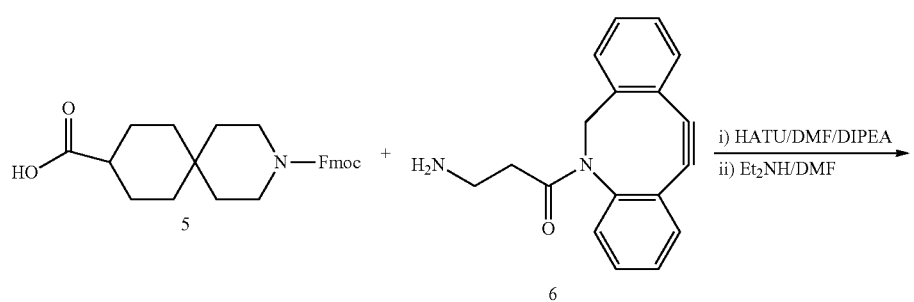
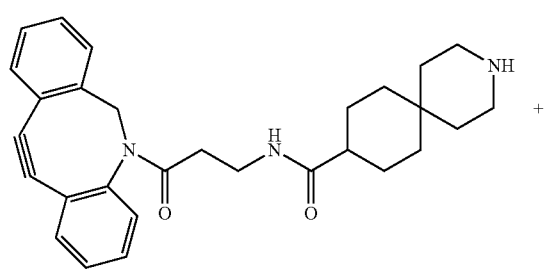

-continued
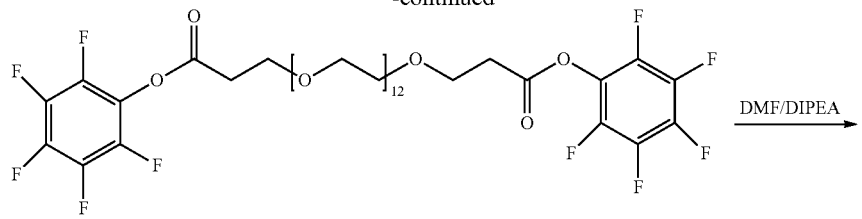
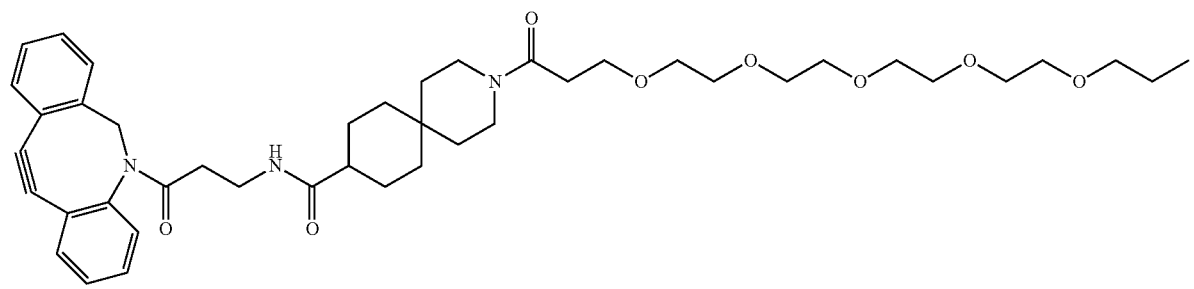
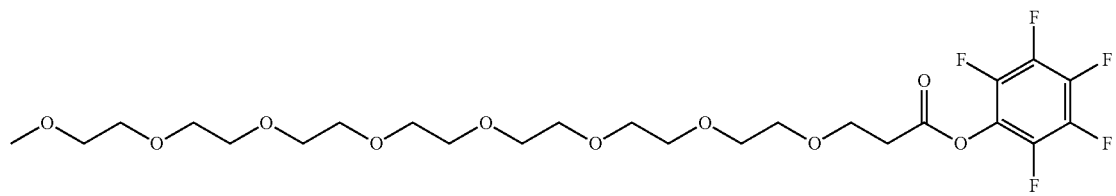
Scheme 11: final coupling for the synthesis of LP5
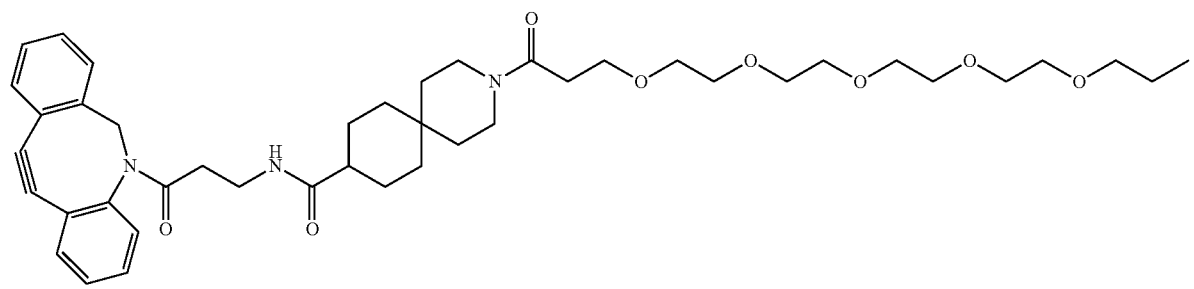
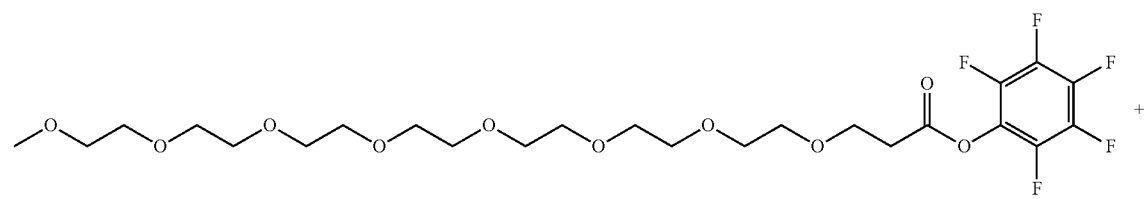

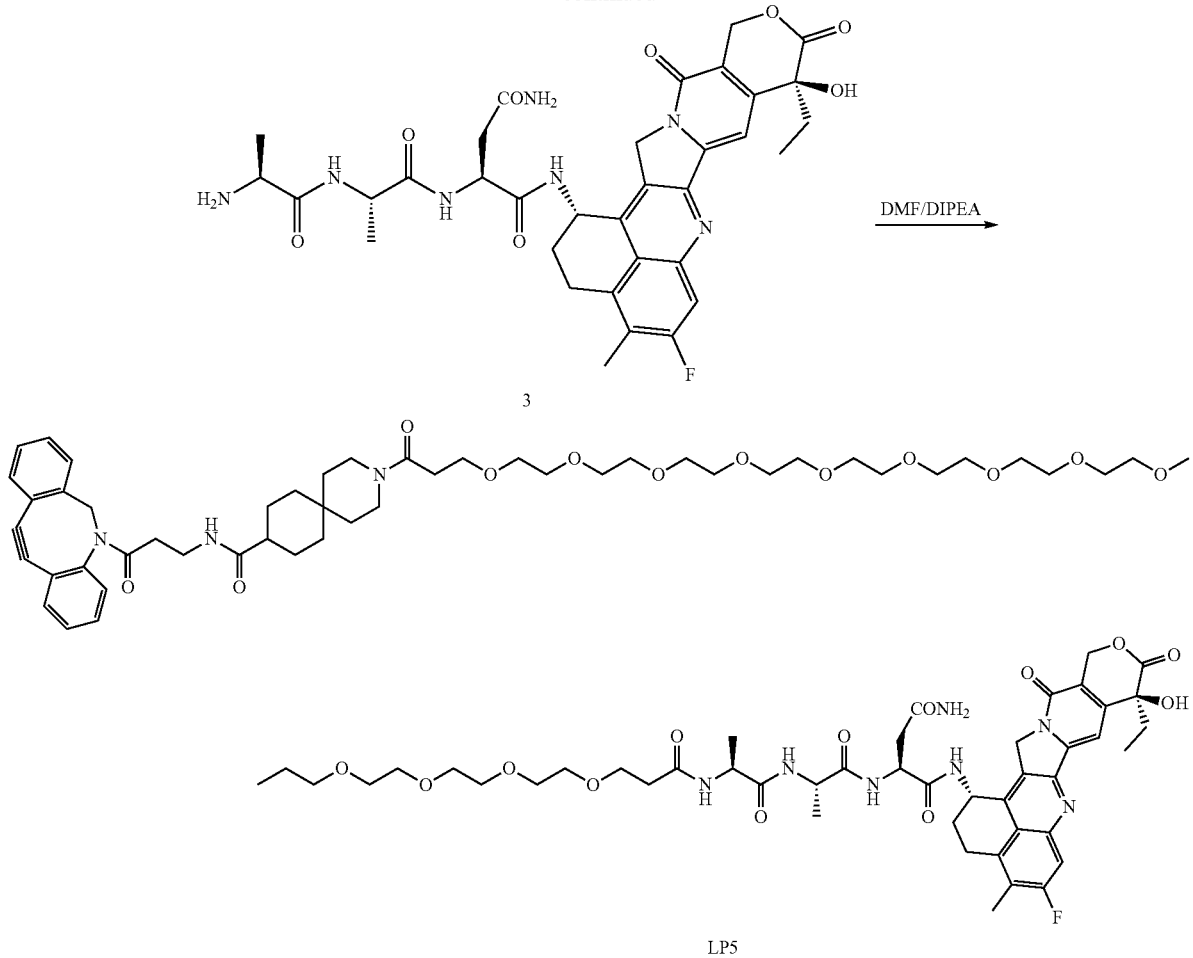

3

LP5

Synthesis of Compound 3:

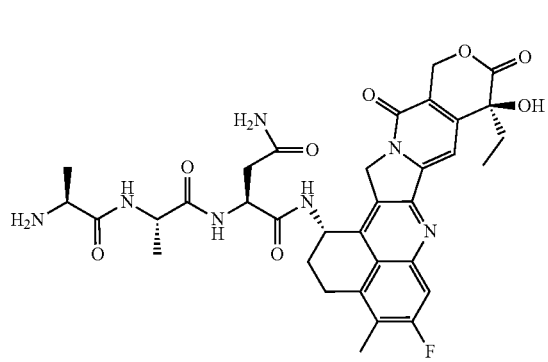

3

To a suspension of exatecan mesylate 1 (MsOH salt, 150 mg, 0.28 mmol) in anhydrous DMF (3 mL) at room temperature was added Fmoc-AAN(Trt)-OH 2 (250 mg, 0.33 mmol), EDC (65 mg, 0.34 mmol), HOAt (46 mg, 0.34 mmol), and DIPEA (53 μL). The reaction was stirred at RT for 1 h, LCMS showed the desired product, then 0.3 mL of piperidine was added. The mixture was stirred for 5 min, and then added to a 1/1 mixture of hexane/diethyl ether (45 mL). The precipitate was collected by centrifugation and the solvent was removed by decantation to give the compound 2b. The residue 2b was dissolved in 3 mL of TFA and the mixture was stirred for 10 min at RT. Then the TFA was removed under reduced pressure, the crude mixture was purified by reverse phase HPLC. Pure Fractions were lyophilized to give compound 3 as a TFA salt (63 mg); LCMS m/z (ESI$^+$): calculated for $C_{34}H_{38}FN_7O_8$, 691.28; found 692.4 (M+H).

Synthesis of Compound 7:

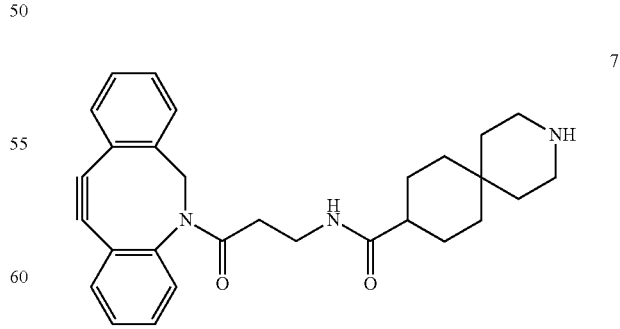

7

Compound 5 (1.4 g, 3.34 mmol) was dissolved in DMF (10 mL). To the clear solution was added HATU (1.2 g, 3.34 mmol) and DIPEA (861 mg, 6.68 mmol). The solution was stirred at room temperature for about 30 sec. followed by the addition of DBCO-amine 7 (922 mg, 3.34 mmol) in DMF (2 mL). After the mixture was stirred at room temperature for 20 minutes, diethyl amine (2 mL) was added into and allowed to stir for another 30 minutes, LCMS showed completion of the reaction. The reaction solution was concentrated under reduced pressure and purified by reverse phase HPLC to afford compound 7 (790 mg); LCMS m/z (ESI$^+$): calculated for $C_{29}H_{33}N_3O_2$, 455.26; found 456.4 (M+H).

Synthesis of Compound 4:

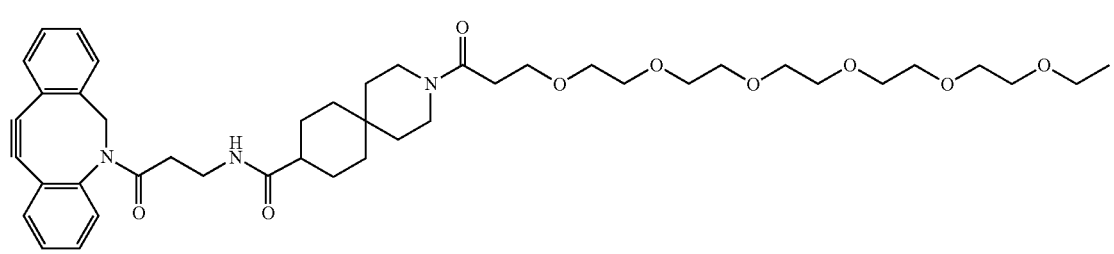

4

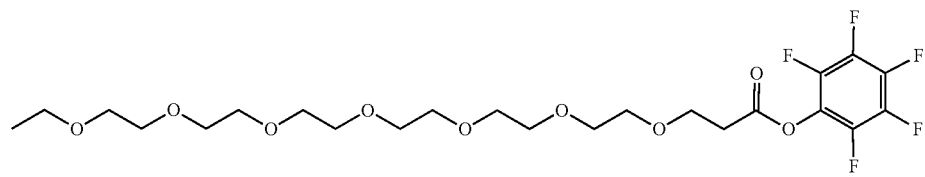

A solution of compound 8 (3 g, 2.9 mmol), compound 7 (780 mg, 1.37 mmol) and DIPEA (353 mg, 2.74 mmol) in DMF (20 mL) was stirred for 20 minutes, LCMS showed completion of the reaction. The reaction mixture was directly purified by reverse phase HPLC to give compound 4 (1.52 g); LCMS m/z (ESI$^+$): calculated for $C_{65}H_{88}F_5N_3O_{18}$, 1293.60; found 1293.7 (M+H).

Synthesis of LP5:

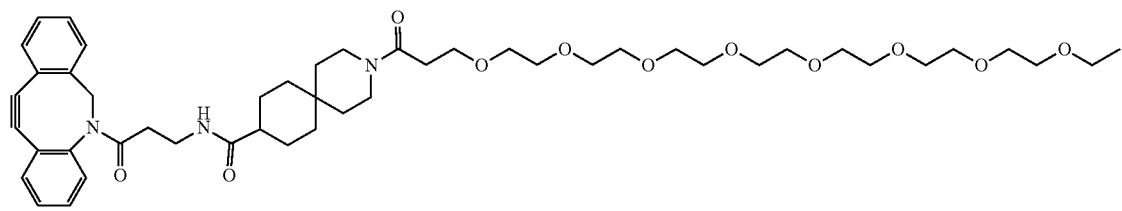

LP5

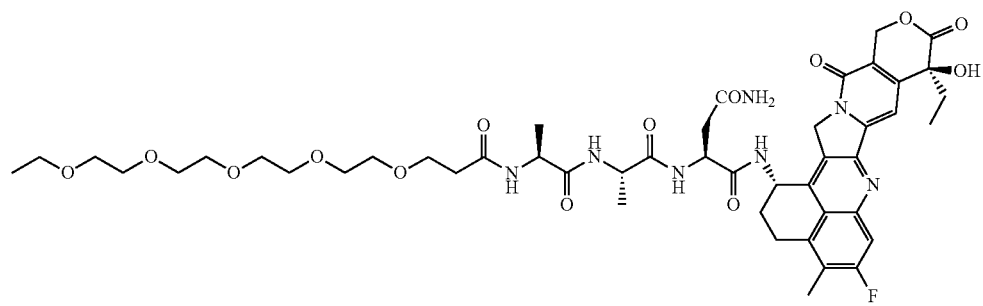

To a solution of compound 4 (770 mg, 0.6 mmol) in anhydrous DMF (3 mL) was added compound 3 (TFA salt, 478 mg, 0.6 mmol) and DIPEA (206 The mixture was stirred at room temperature for 10 min, LCMS showed completion of the reaction. Then the mixture was purified directly by reverse phase HPLC to give LP5 as a light yellowish solid (710 mg); $^1$H NMR (500 MHz, DMSO-d6) δ 11.41 (s, 1H), 8.25 (d, J=8.5 Hz, 1H), 8.07-7.91 (m, 3H), 7.77 (d, J=10.9 Hz, 1H), 7.68-7.54 (m, 2H), 7.47 (dddd, J=13.4, 7.6, 4.9, 2.8 Hz, 4H), 7.43-7.22 (m, 5H), 6.98-6.83 (m, 1H), 5.51 (dt, J=8.8, 4.5 Hz, 1H), 5.43 (s, 2H), 5.22 (s, 2H), 5.04 (d, J=14.0 Hz, 1H), 4.47 (q, J=6.8 Hz, 1H), 4.09 (dp, J=18.0, 7.1 Hz, 3H), 3.73 (s, 10H), 3.67-3.27 (m, 61H), 3.22-3.01 (m, 3H), 2.92 (dq, J=13.3, 6.7 Hz, 1H), 2.68-2.45 (m, 8H), 2.45-2.28 (m, 6H), 2.19 (dq, J=9.3, 4.8 Hz, 1H), 1.87 (qd, J=13.8, 7.1 Hz, 4H), 1.61 (d, J=13.1 Hz, 2H), 1.49-1.21 (m, 7H), 1.13 (dd, J=26.8, 7.1 Hz, 7H), 0.97 (ddd, J=16.1, 11.6, 6.4 Hz, 2H), 0.88 (t, J=7.3 Hz, 3H); LCMS m/z (ESI$^+$): calculated for $C_{93}H_{125}FN_{10}O_{25}$, 1801.9; found 1802.9 [M+H]$^+$.

Synthetic Example 6: LP6
(DBCO-NNAA-PEG13-AAA-Exatecan)

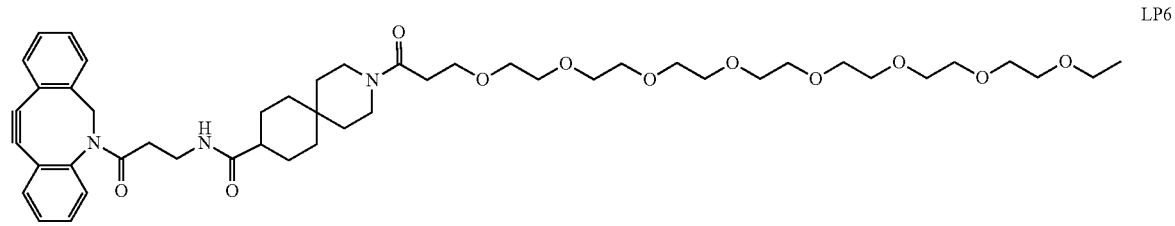

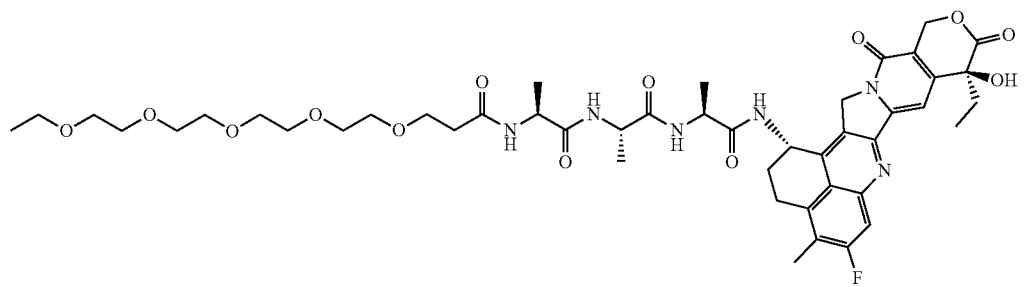

Scheme 12: Synthesis of AAA-Exatecan
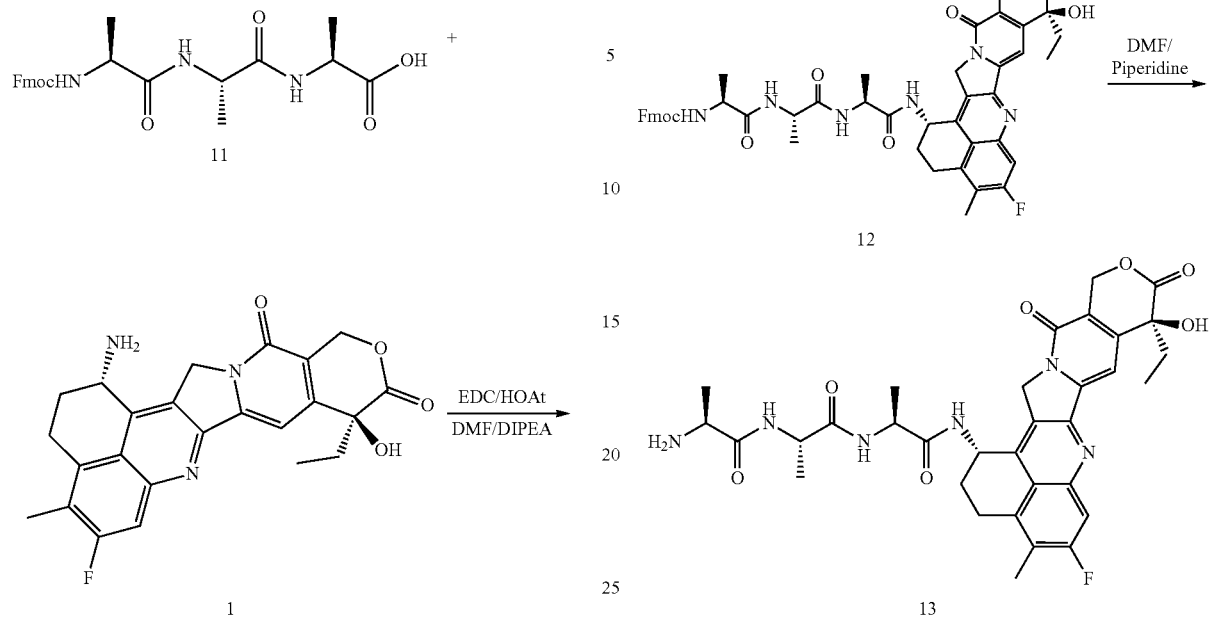
Scheme 13: Synthesis of DBCO-nnAA-PEG13-AAA-Exatecan (LP6)
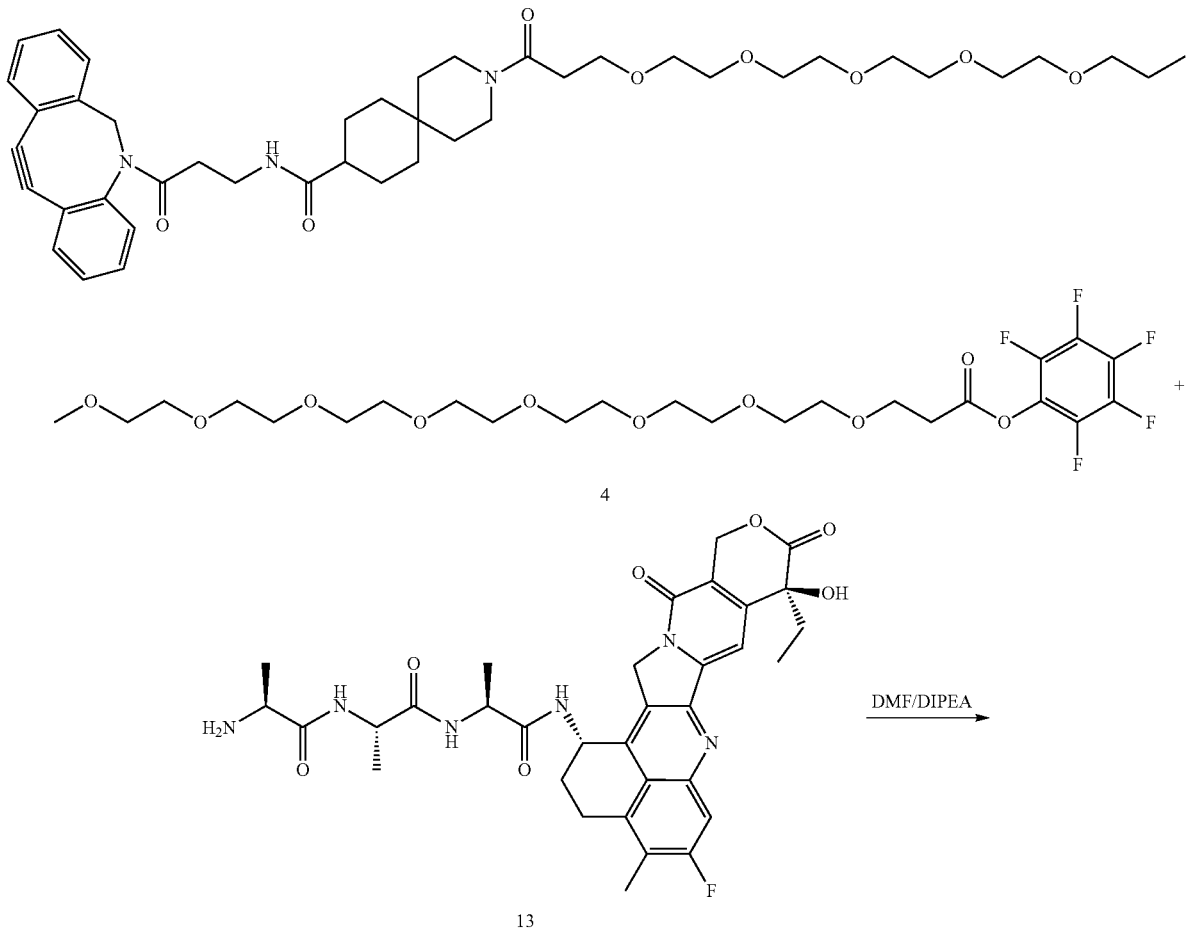

-continued
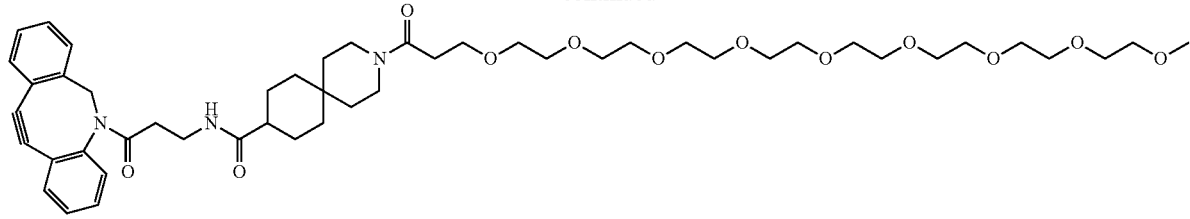
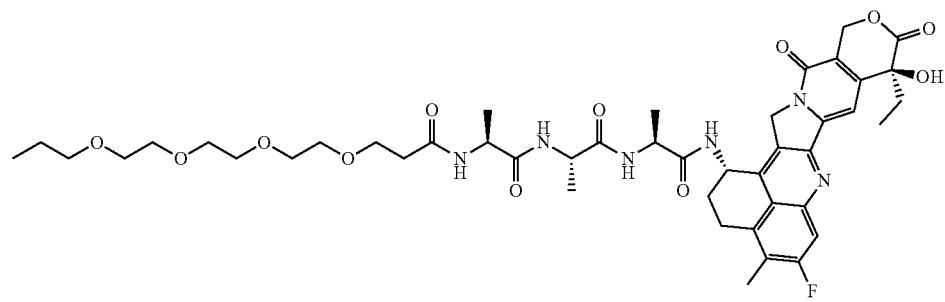
LP6
LP6 was synthesized in an analogous fashion using the same methods as described above. LCMS m/z (ESI⁺): calculated for $C_{92}H_{124}FN_9O_{24}$, 1757.87; found 1759.1 $[M+H]^+$
Synthetic Example 7
Synthesis of DBCO-NNAA-PEG13-VK-Exatecan LP7
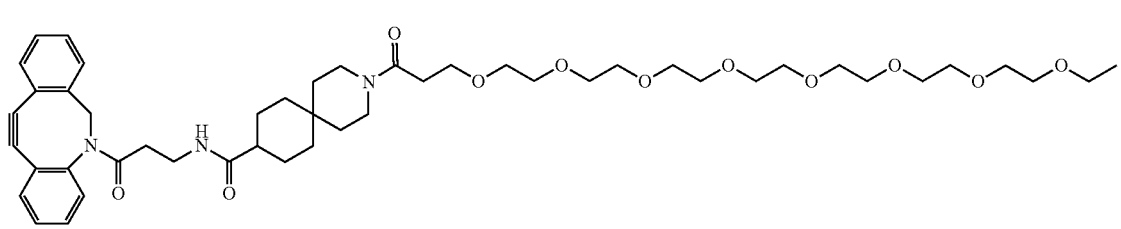
LP7
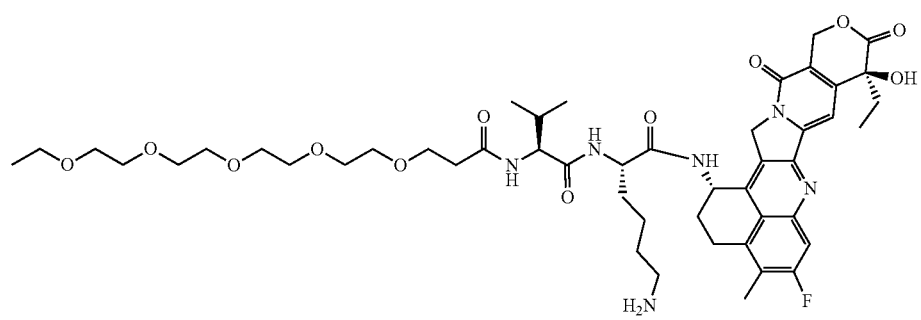

Scheme 14: Synthesis of VK(Fmoc)-Exatecan (15)
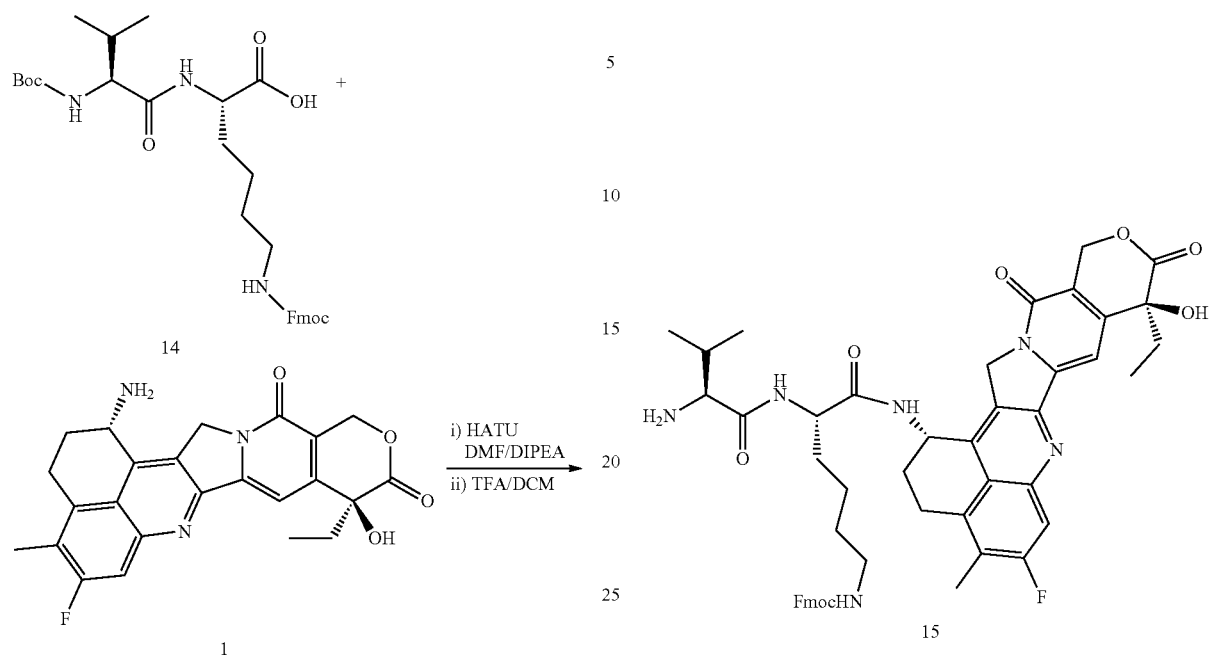
Scheme 15: final coupling and deprotection of DBCO-PEG13-VK-Exatecan (LP7)
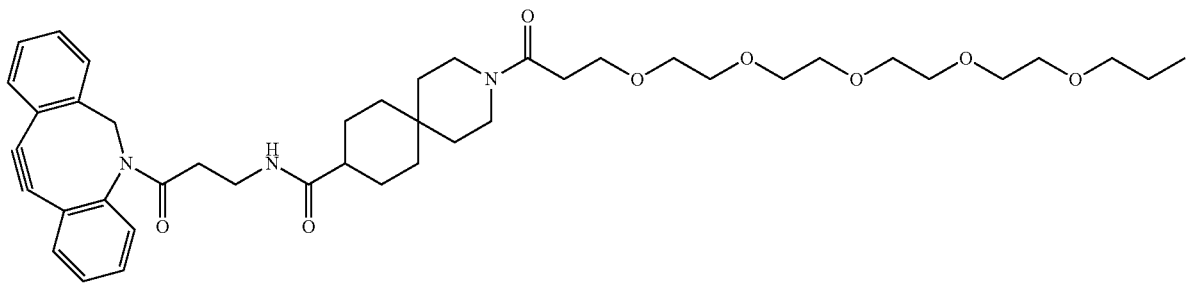
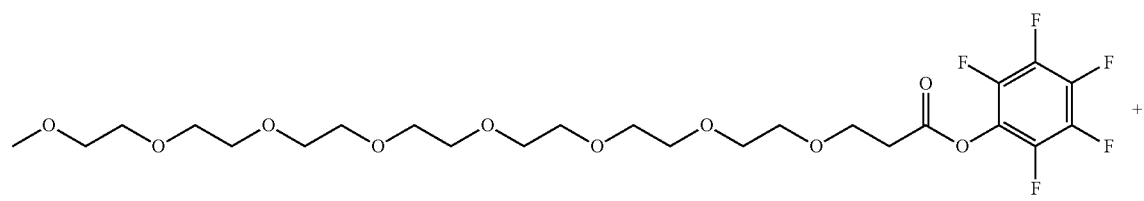

-continued
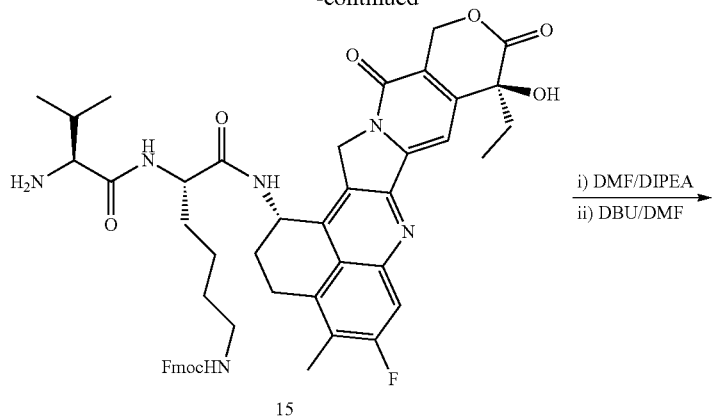
15
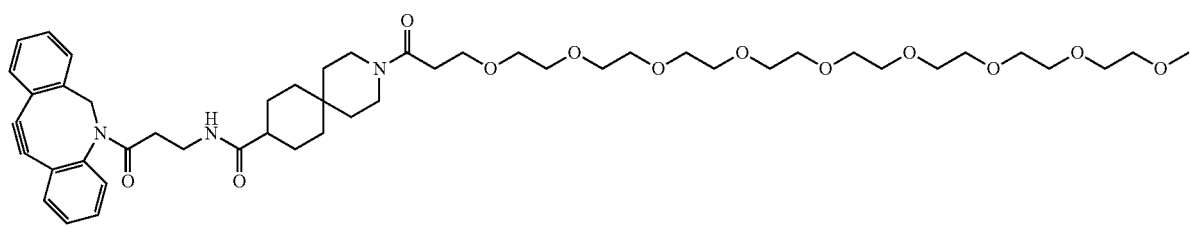
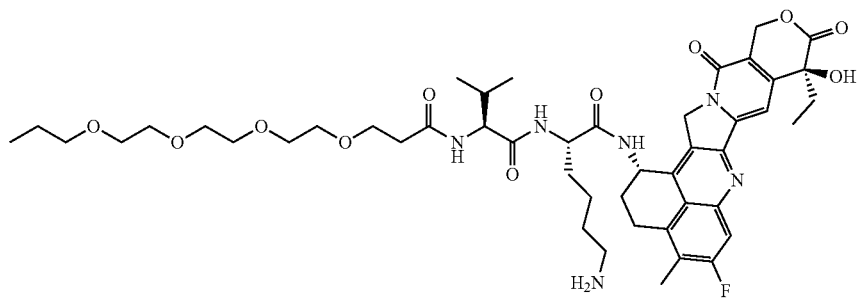
LP7
LP7 was synthesized in an analogous fashion using the same methods as described above. LCMS m/z (ESI$^+$): calculated for $C_{94}H_{130}FN_9O_{23}$, 1771.93; found 1773.1 [M+H]$^+$.

Synthetic Example 8: LP8 (DBCO-GGG-EDA PNU)
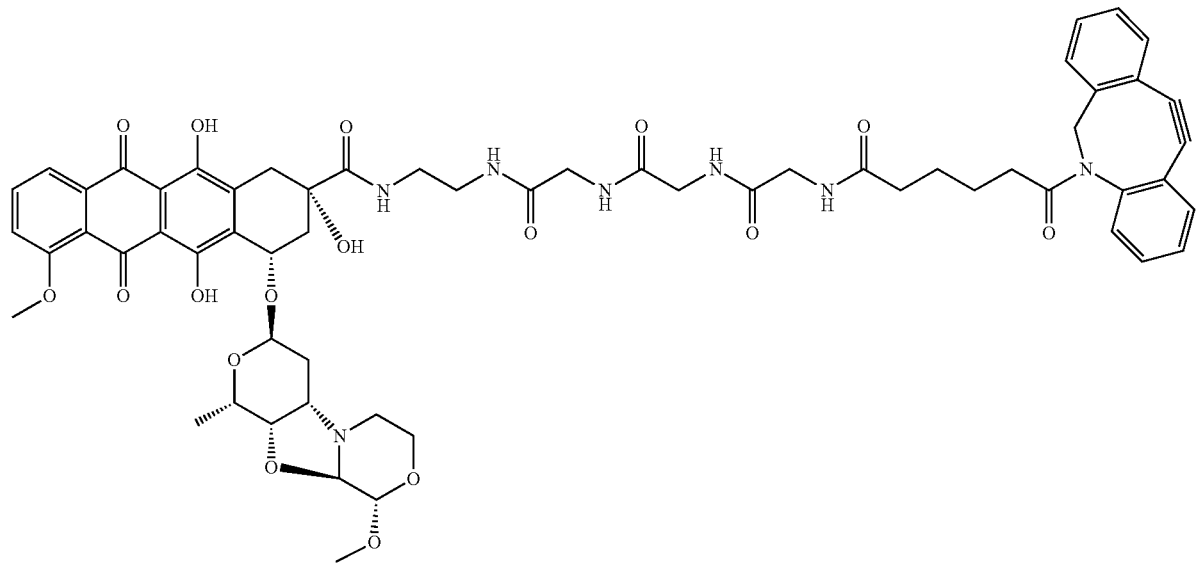 [SMILES: COc1cccc2c1C(=O)c1c(O)c3c(c(O)c1C2=O)C[C@@](O)(C(=O)NCCNC(=O)CNC(=O)CNC(=O)CNC(=O)CCCCC(=O)N1Cc2ccccc2C#Cc2ccccc21)C[C@@H]3O[C@H]1C[C@H]2[C@H](O[C@@H]3[C@@H](OC)OCCN32)[C@H](C)O1]
LP8 is synthesized according to the literature published methods, for example WO 2016/102679 A1, incorporated by reference herein in its entirety.
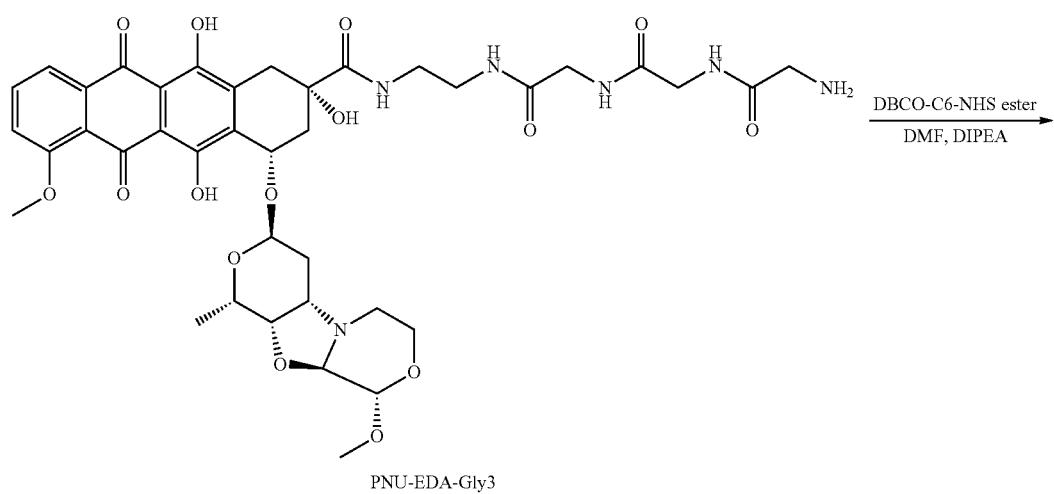
PNU-EDA-Gly3

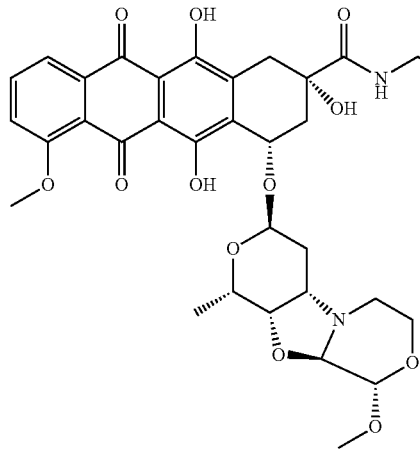
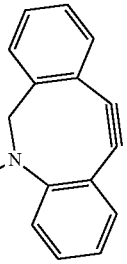

PNU-EDA-Gly3 (1 eq) and DBCO-C6-NHS (1 eq) was dissolved in DMF and added 1.2 eq of DIPEA, the reaction mixture was stirred for 1 h, LCMS showed the desired product. The crude material was purified by preparative HPLC.

Synthetic Example 9: LP9 (DBCO-PEG4-VA-PBD)

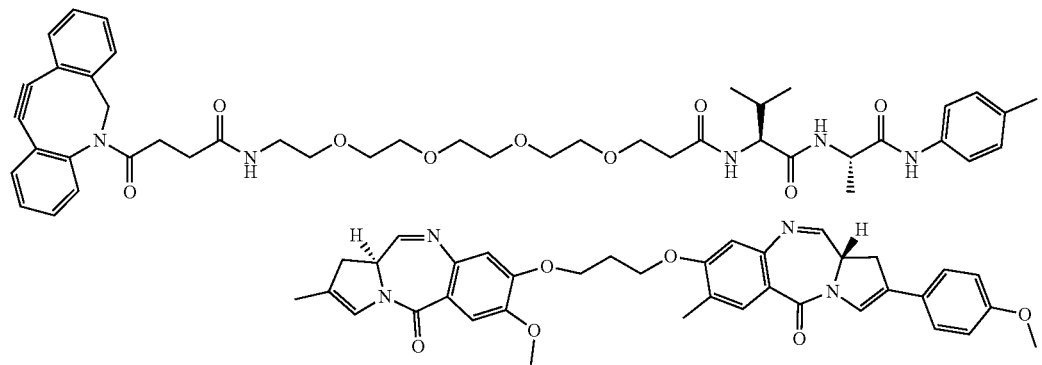

LP9 is synthesized according to the literature published methods, for example WO 2016/102679 A1, incorporated by reference herein in its entirety.

Synthetic Example 10: LP10 (DBCO-PEG4-GGFG-Aminol-DXD)

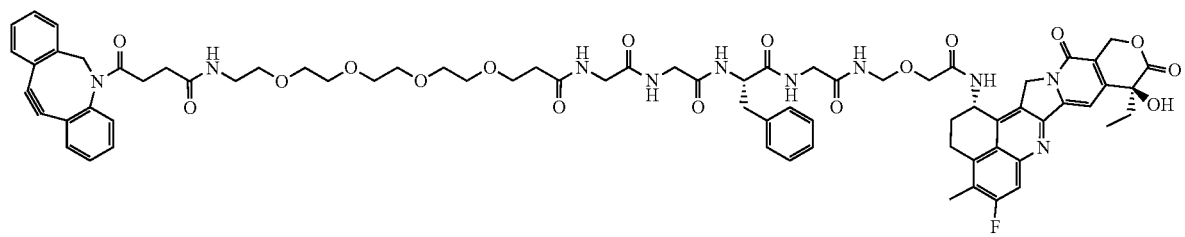 [SMILES: CC[C@@]1(O)C(=O)OCc2c1cc1n(c2=O)Cc2c-1nc1cc(F)c(C)c3c1c2[C@@H](NC(=O)COCNC(=O)CNC(=O)[C@H](Cc1ccccc1)NC(=O)CNC(=O)CNC(=O)CCOCCOCCOCCOCCNC(=O)CCC(=O)N1Cc2ccccc2C#Cc2ccccc21)CC3]

LP10 is synthesized as shown below scheme from GGFG-aminol-Dxd (synthesized according to the literature published methods WO 2015/115091 A1, incorporated by reference herein in its entirety)

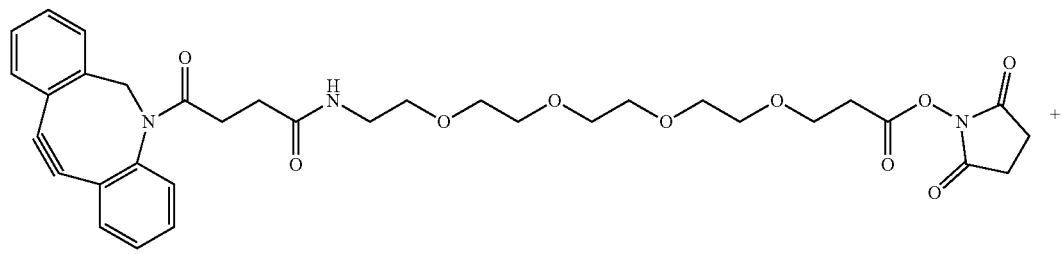

DBCO-PEG4-NHS

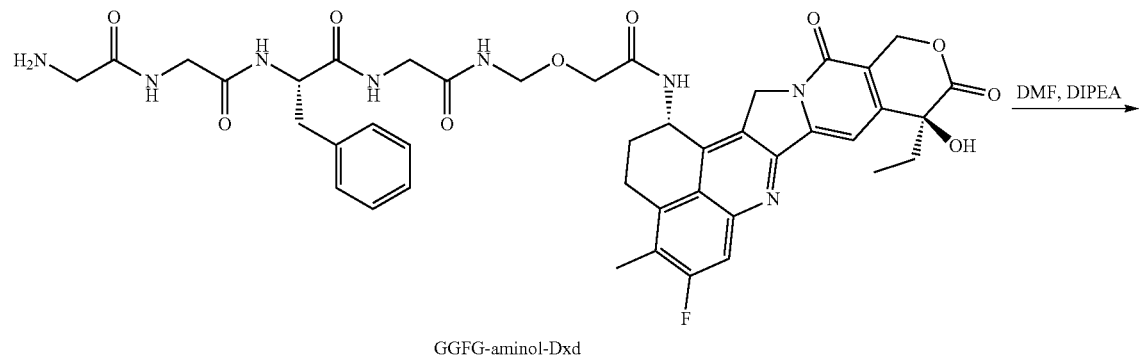

GGFG-aminol-Dxd

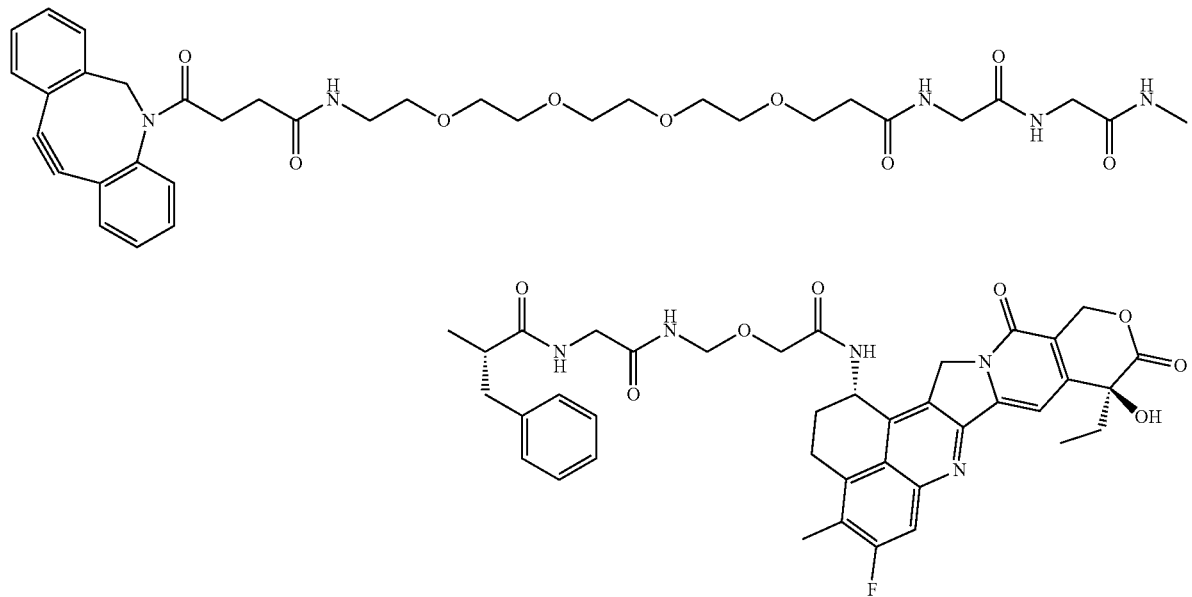

GGFG-aminol-Dxd (1 eq) and DBCO-PEG4-NHS (1 eq) was dissolved in DMF and added 1.2 eq of DIPEA, the reaction mixture was stirred for 1 h, LCMS showed completion of the reaction. The crude compound was purified by preparative HPLC. LCMS m/z (ESI$^+$): calculated for $C_{52}H_{56}FN_9O_{13}$, 1374.56; found 1375.7 [M+H]$^+$.

Synthetic Example 11: LP11 DBCO-VALCIT-PAB-MMAE

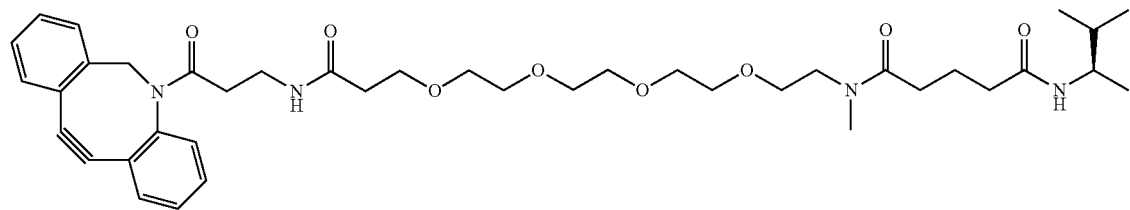

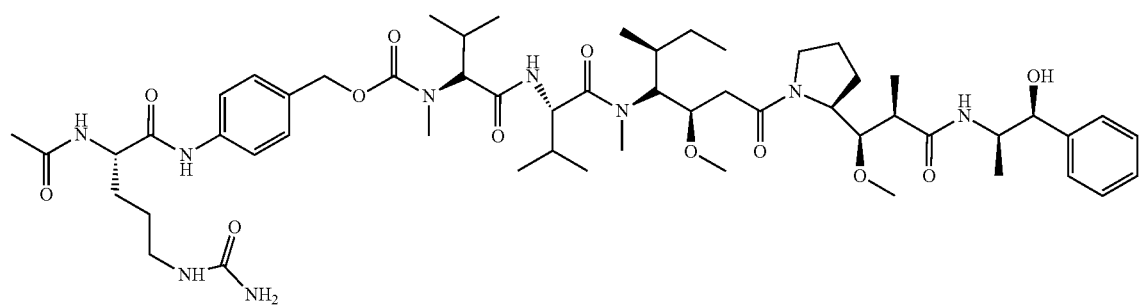

LP11 DBCO-Valcit-pAB-MMAE linker payload synthesized using methods consistent with Synthetic Example 1. LCMS m/z (ESI$^+$): calculated for $C_{93}H_{137}N_{13}O_{20}$, 1756.01; found 1756.1 [M+H]$^+$.

Synthetic Example 12: LP12 DBCO Sidechain PEG12 VALLYS-pAB-Hemiasterlin

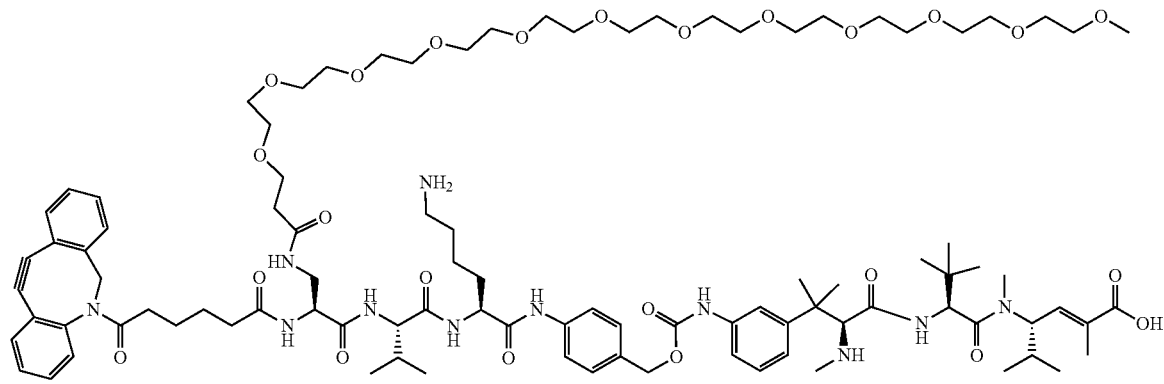 [SMILES: CN[C@H](C(=O)N[C@H](C(=O)N(C)[C@H](/C=C(\C)C(=O)O)C(C)C)C(C)(C)C)C(C)(C)c1cccc(NC(=O)OCc2ccc(NC(=O)[C@H](CCCCN)NC(=O)[C@@H](NC(=O)[C@H](CNC(=O)CCOCCOCCOCCOCCOCCOCCOCCOCCOCCOCCOCCOC)NC(=O)CCCCC(=O)N3Cc4ccccc4C#Cc4ccccc43)C(C)C)cc2)c1]

LP12 DBCO sidechain PEG12 Val-Lys-pAB-hemiasterlin linker payload synthesized using methods consistent with Synthetic Example 1.

Synthetic Example 13: LP13 DBCO Sidechain PEG12 VALGLU-pAB-Hemiasterlin
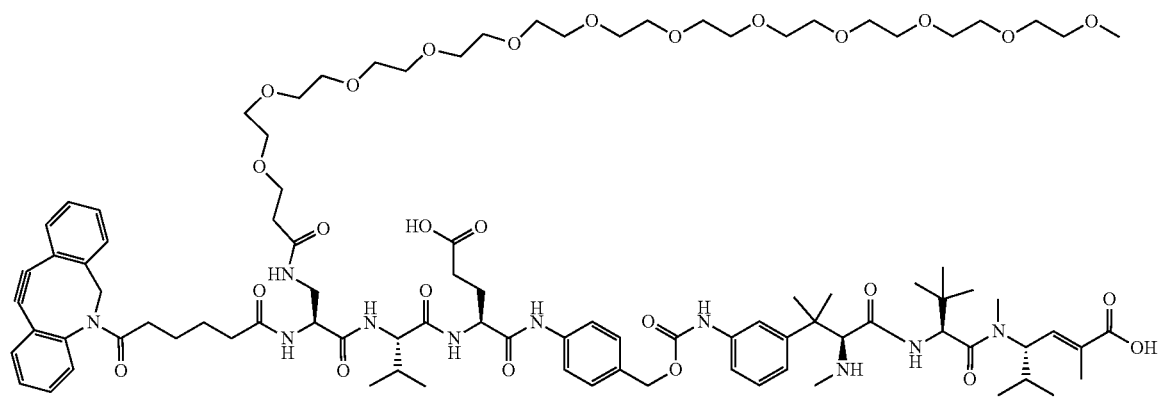 [SMILES: CN[C@H](C(=O)N[C@H](C(=O)N(C)[C@H](/C=C(\C)C(=O)O)C(C)C)C(C)(C)C)C(C)(C)c1cccc(NC(=O)OCc2ccc(NC(=O)[C@H](CCC(=O)O)NC(=O)[C@@H](NC(=O)[C@H](CNC(=O)CCOCCOCCOCCOCCOCCOCCOCCOCCOCCOCCOCCOC)NC(=O)CCCCC(=O)N3Cc4ccccc4C#Cc4ccccc43)C(C)C)cc2)c1]
LP13 DBCO sidechain PEG12 ValGlu-pAB-hemiasterlin linker payload synthesized using methods consistent with Synthetic Example 1.
Synthetic Example 14: LP14 DBCO-6,4 NNAA-PEG-VKG-Exatecan
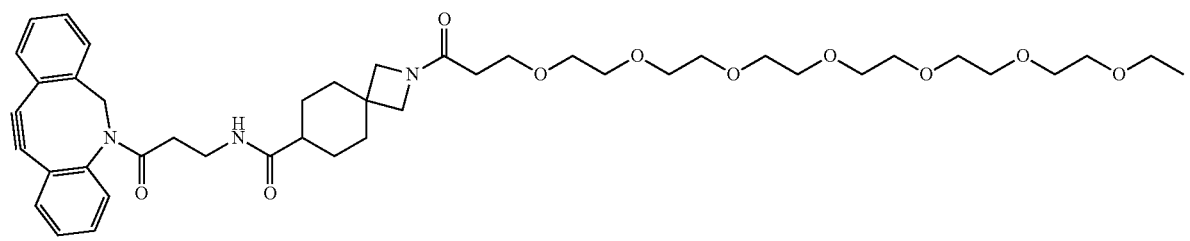
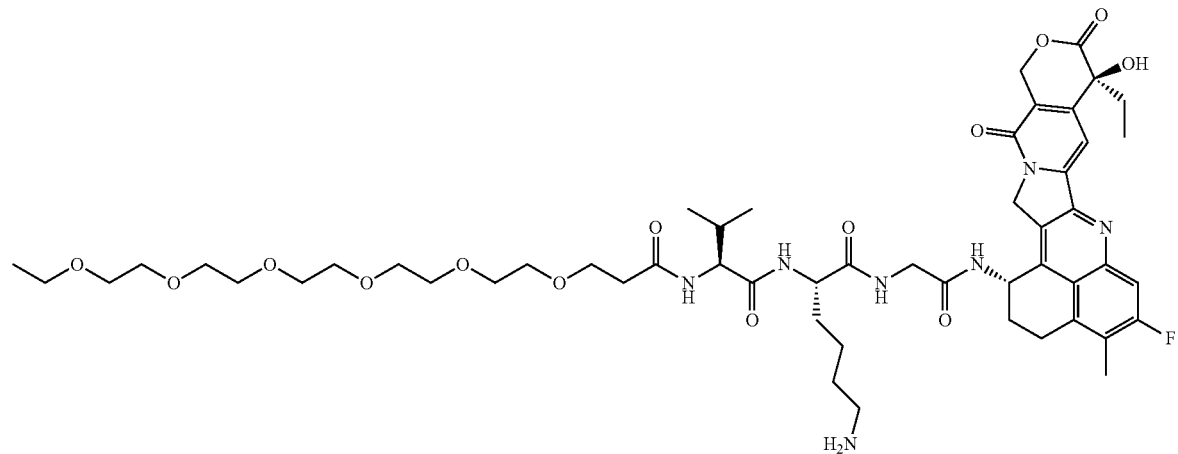
LP14 is synthesized consistent with the methods from the common intermediate compound 10.

Synthetic Example 15: LP15 DBCO-4,6 NNAA-PEG-VKG-Exatecan
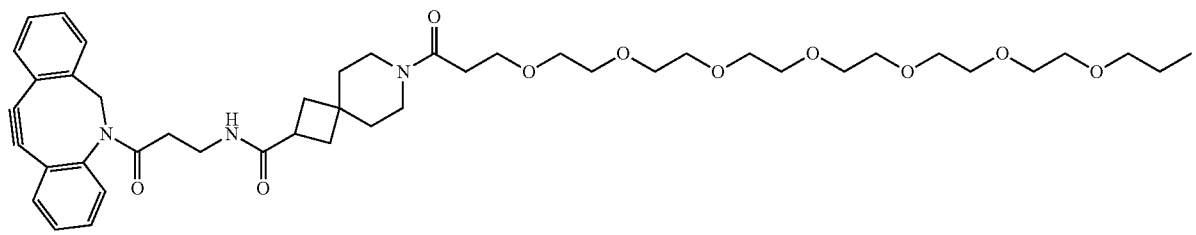
LP15 is synthesized consistent with the methods from the common intermediate compound 10.
Synthetic Example 16: LP16 DBCO-4,4 NNAA-PEG-VKG-Exatecan
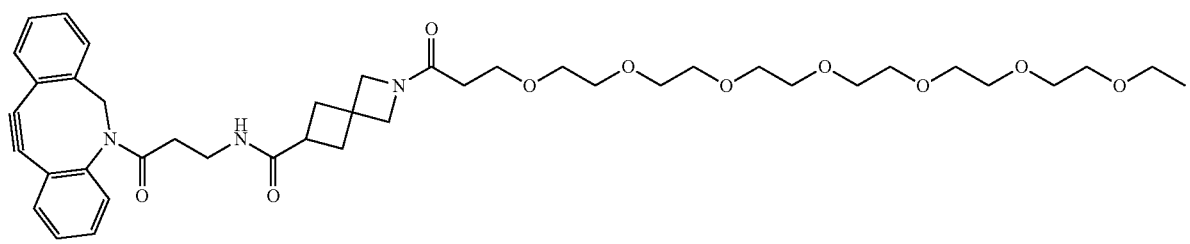

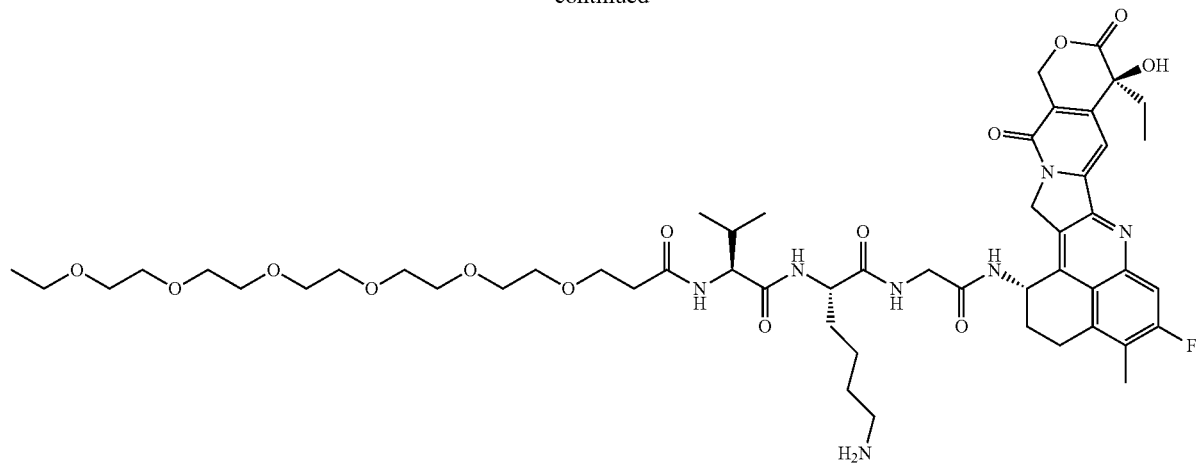
LP16 is synthesized consistent with the methods from the common intermediate compound 10.
Synthetic Example 17: LP17 DBCO-BRIDGED NNAA-PEG-VKG-Exatecan
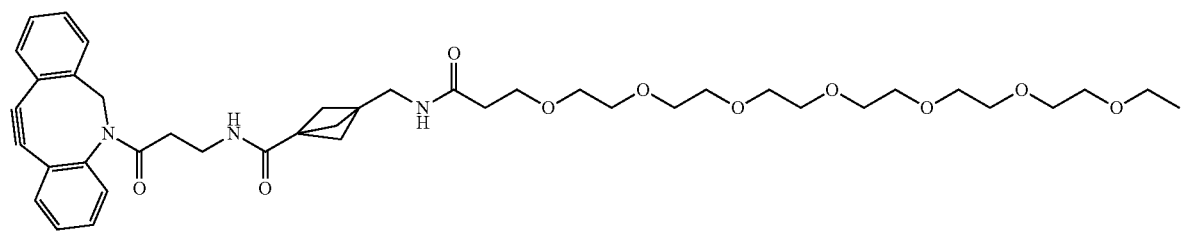
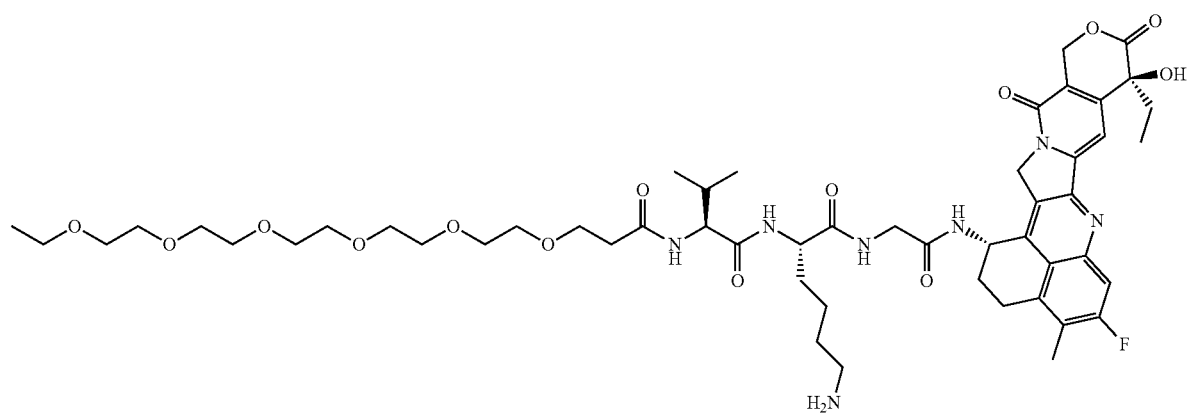

LP17 IS synthesized, purified, and characterized consistent with the methods from the common intermediate compound 10.
Synthetic Example 18: Synthesis of LP18 (DBCO-6,6 NNAA-B-Glucuronide-PEG12-Exatecan)
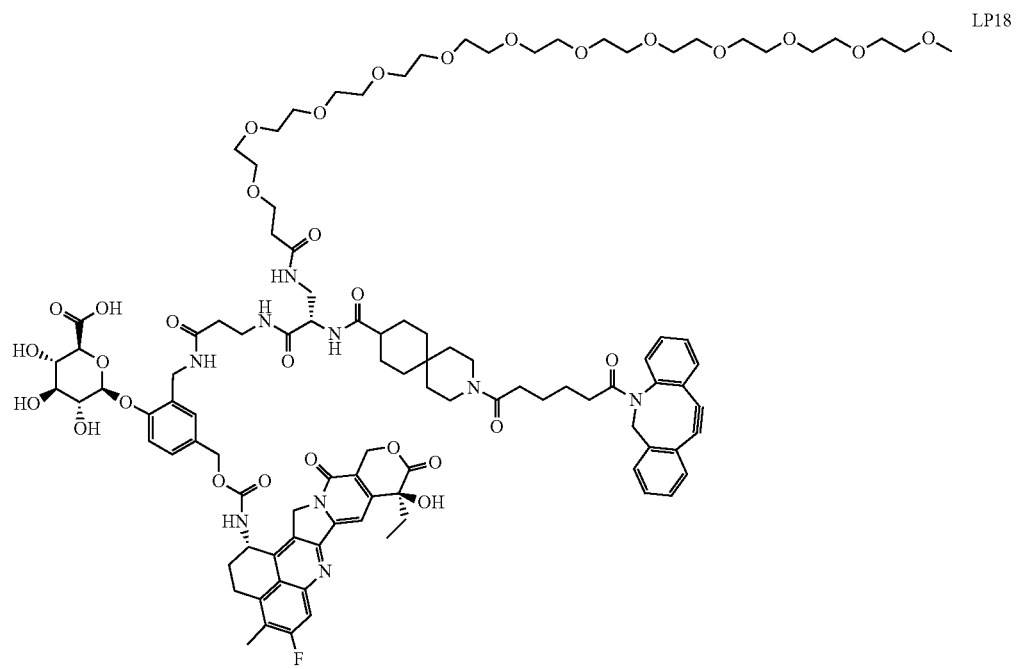 [SMILES: CC[C@@]1(O)C(=O)OCc2c1cc1n(c2=O)Cc2c-1nc1cc(F)c(C)c3c1c2[C@@H](NC(=O)OCc1ccc(O[C@@H]2O[C@H](C(=O)O)[C@@H](O)[C@H](O)[C@H]2O)c(CNC(=O)CCNC(=O)[C@H](CNC(=O)CCOCCOCCOCCOCCOCCOCCOCCOCCOCCOCCOCCOC)NC(=O)C2CCC4(CC2)CCN(C(=O)CCCCC(=O)N2Cc5ccccc5C#Cc5ccccc52)CC4)c1)CC3]
LP18
Scheme 16: synthesis of DBCO linker (compound 21)
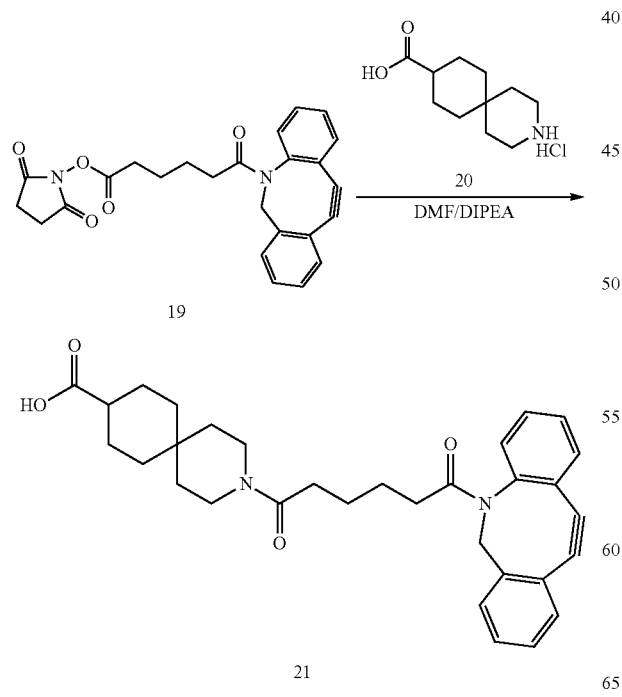

Scheme 17: synthesis Fmoc mPEG12 linker (24)
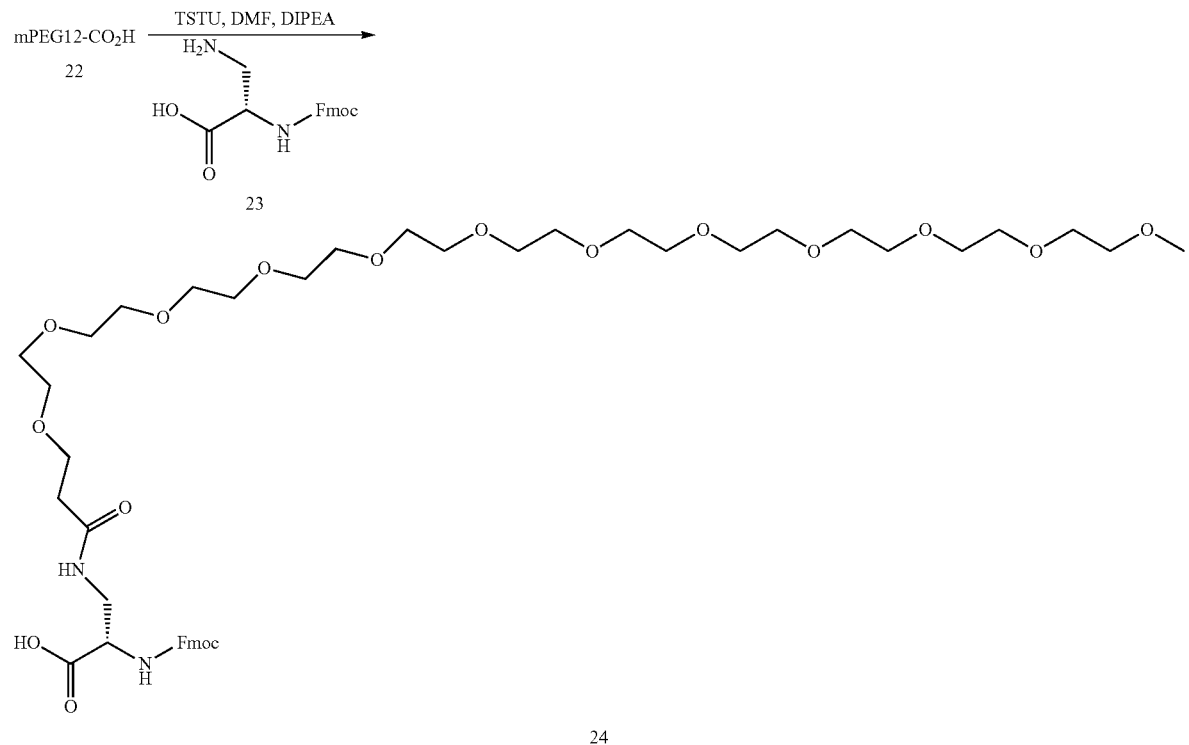
Scheme 18: synthesis of DBCO-mPEG12-Pfp ester linker (27)
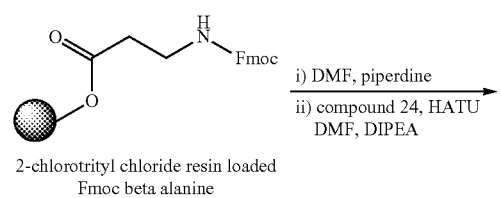
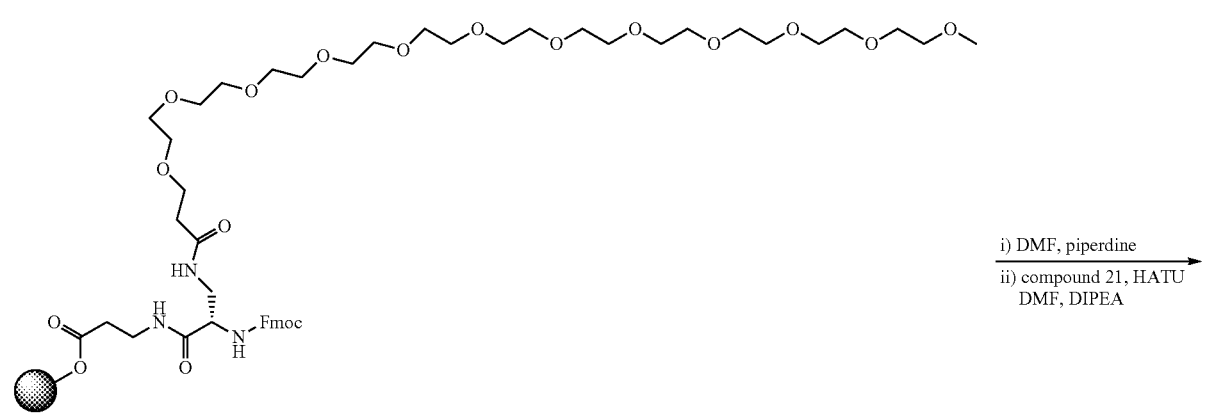

485
486
-continued
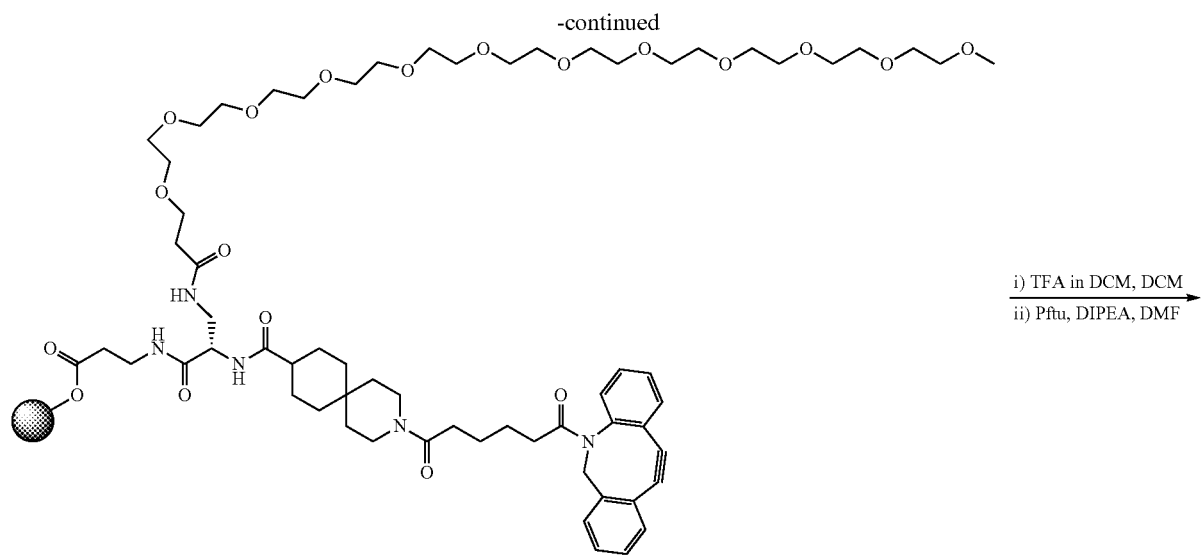
26
i) TFA in DCM, DCM
ii) Pftu, DIPEA, DMF
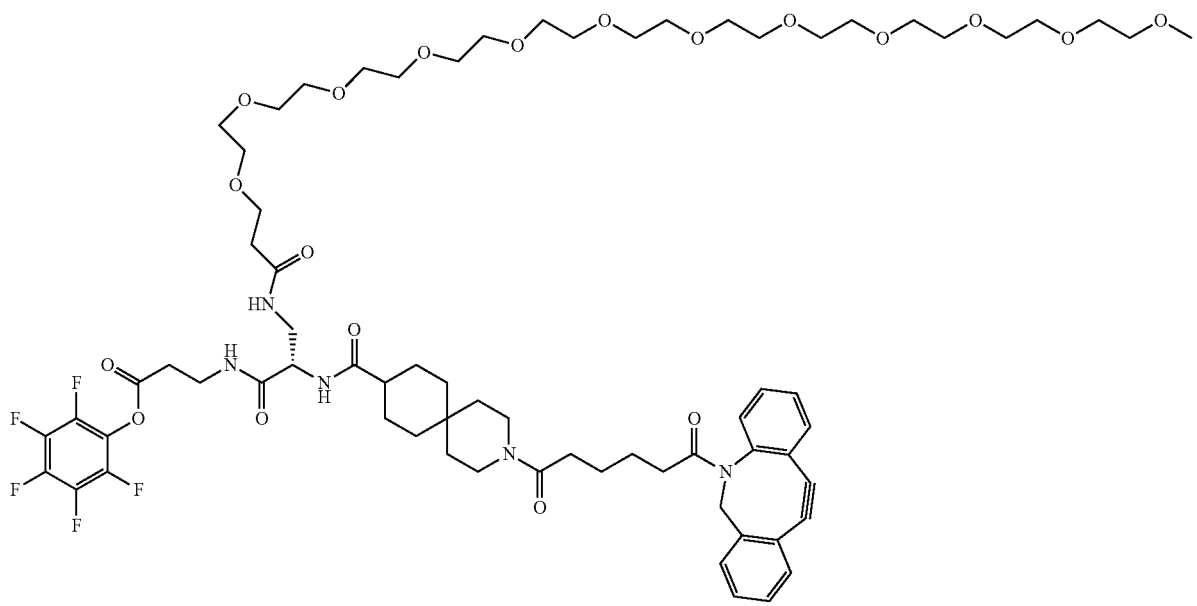
27

Scheme 19: final coupling to make LP18
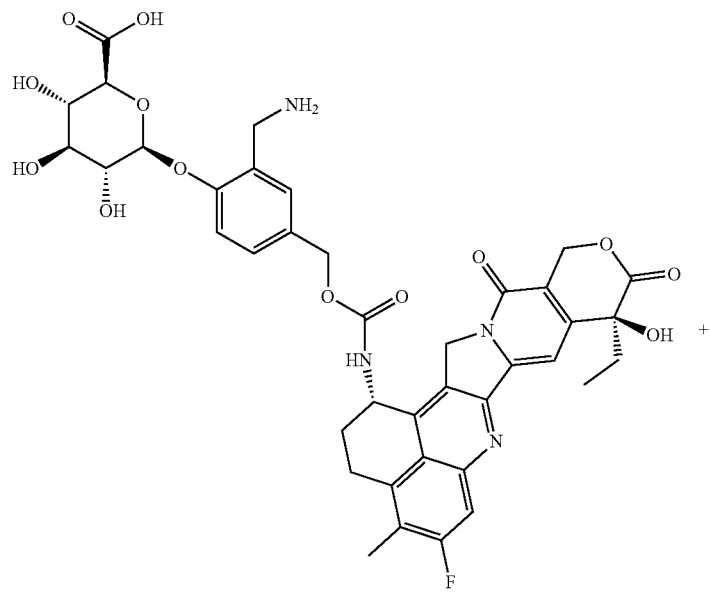
29
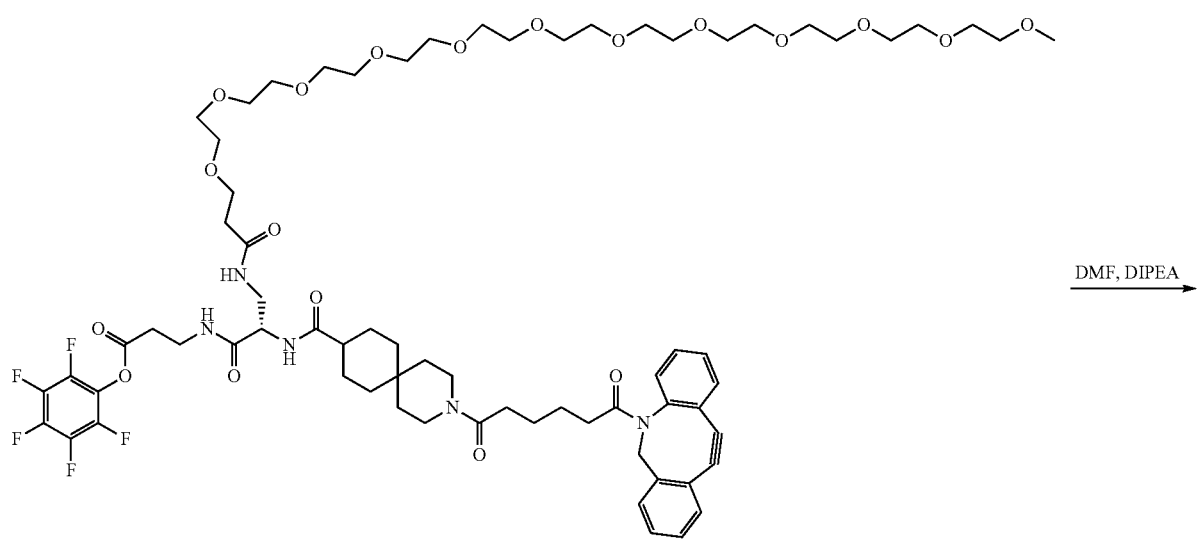
27
DMF, DIPEA →

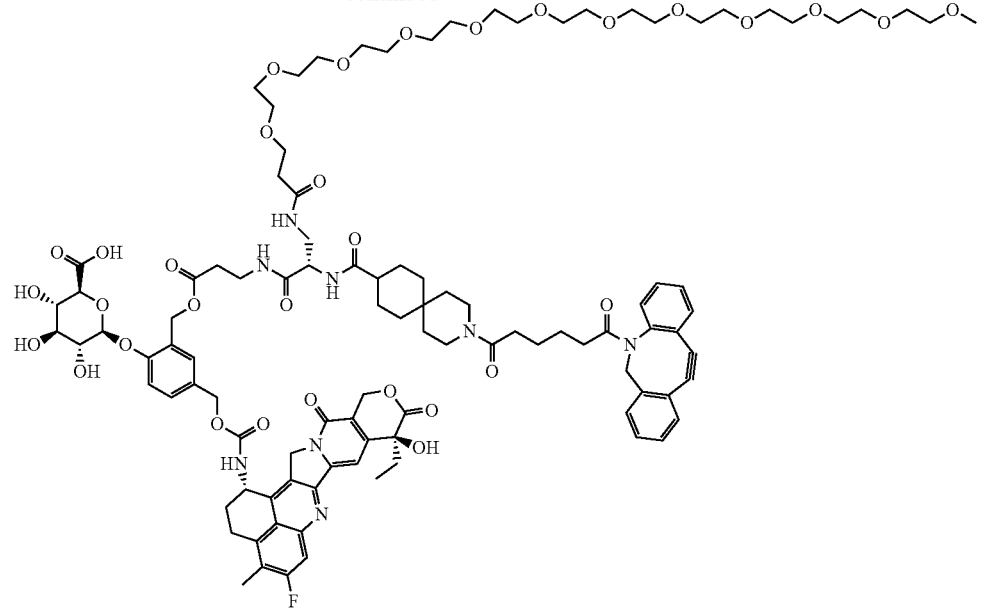
LP18
Synthetic Examples 19 and 20: LP19 (DBCO-6,4 NNAA-B-Glucuronide-PEG12-Exatecan) and LP20 (DBCO-4,4 NNAA-B-Glucuronide-PEG12-Exatecan)
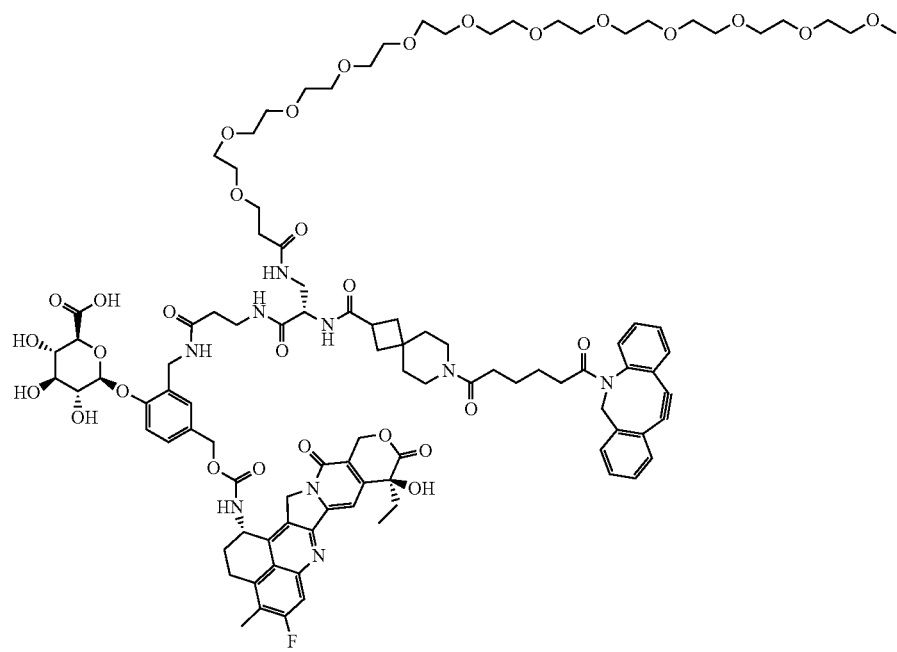

-continued
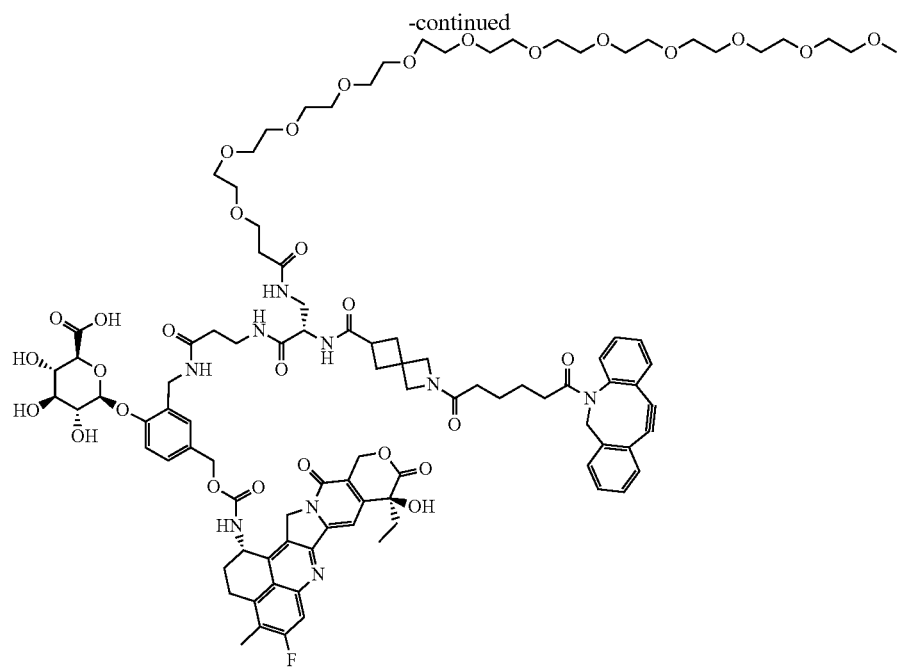
LP19 and LP20 are synthesized, purified, and characterized consistent with the methods of Synthetic Example 18 from the common intermediate compound 29.
Synthetic Example 21: Synthesis of LP21 (DBCO-NNAA-PEG13-VKG-Hemiasterlin)
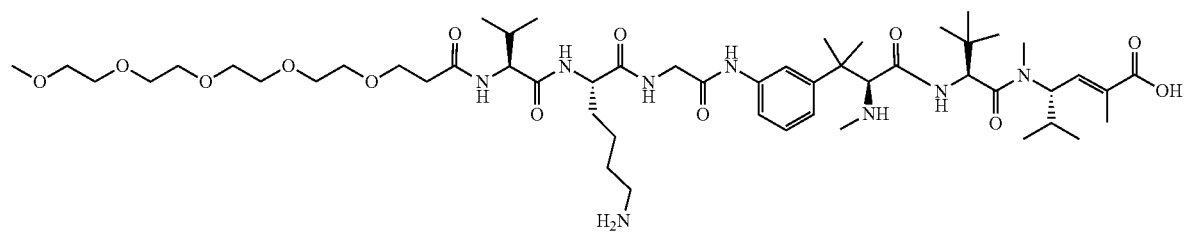

LP21 is synthesized in an analogous fashion using methods consistent with Synthetic Example 4.

Synthetic Example 22: Synthesis of LP22 (DBCO-NNAA-PEG13-AAN-Hemiasterlin)

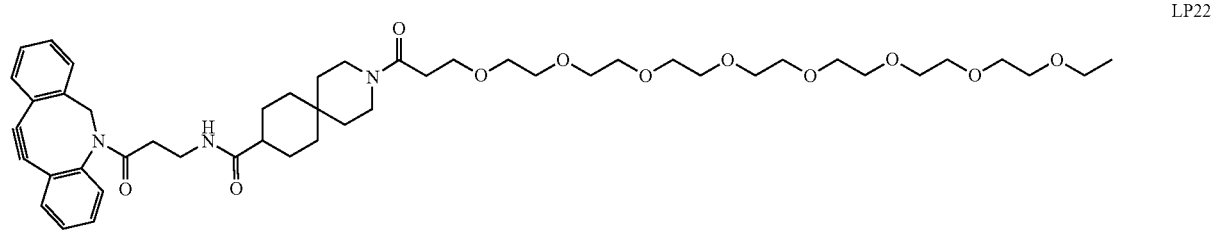

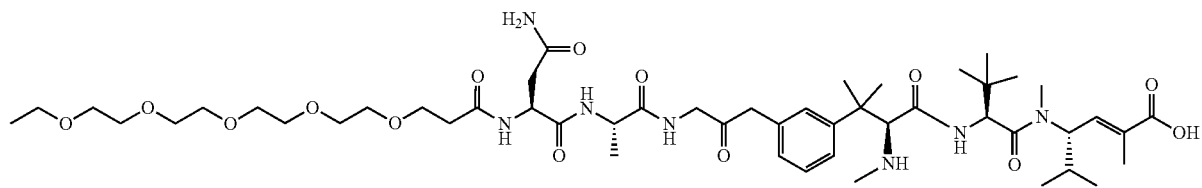

LP22 is synthesized in an analogous fashion using methods consistent with Synthetic Example 5.

Synthetic Example 23: Synthesis of LP23 (DBCO-6,4 NNAA-B-Glucuronide-PEG12-Hemiasterlin)

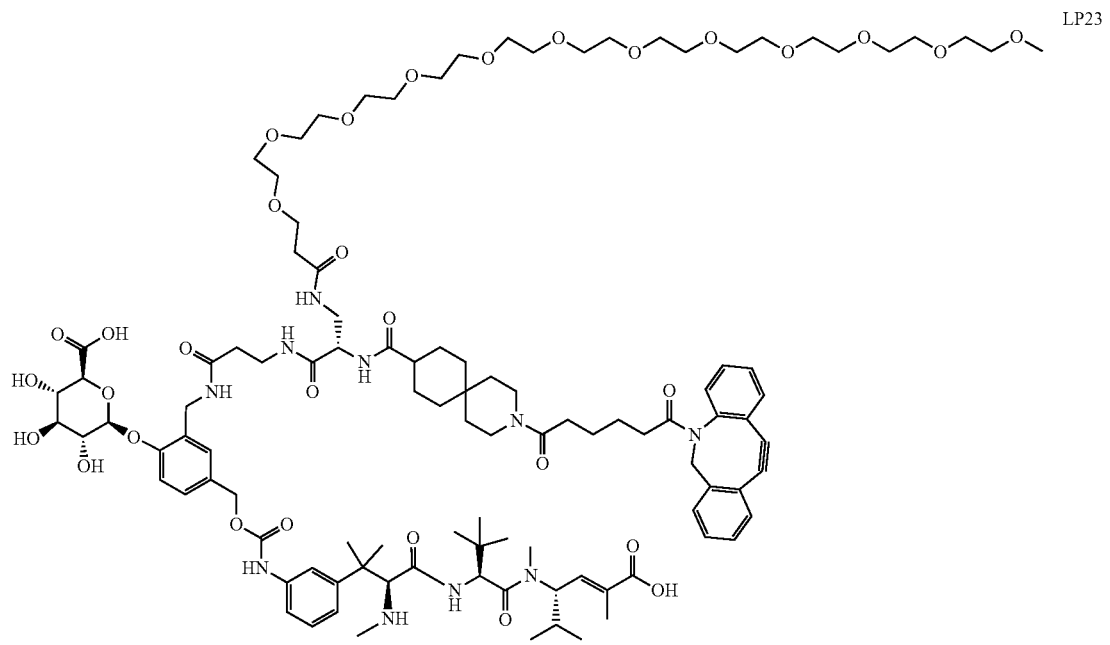 [SMILES: CN[C@H](C(=O)N[C@H](C(=O)N(C)[C@H](/C=C(\C)C(=O)O)C(C)C)C(C)(C)C)C(C)(C)c1cccc(NC(=O)OCc2ccc(O[C@@H]3O[C@H](C(=O)O)[C@@H](O)[C@H](O)[C@H]3O)c(CNC(=O)CCNC(=O)[C@H](CNC(=O)CCOCCOCCOCCOCCOCCOCCOCCOCCOCCOCCOCCOC)NC(=O)C3CCC4(CC3)CCN(C(=O)CCCCC(=O)N3Cc5ccccc5C#Cc5ccccc53)CC4)c2)c1]

LP23 is synthesized in an analogous fashion using methods consistent with Synthetic Example 18.

Synthetic Examples 24-28: P Anthracycline Based Non-Cleavable Linker Payloads (LP24, LP25, LP26, LP27, LP28)
LP24, LP25, LP26, LP27, and LP28 PNU based non cleavable linker payloads are synthesized consistent with the methods as described above.
DBCO-nnAA-PEG4-PNU (LP24):
DBCO-nnAA-PEG4-Gly-PNU (LP25):
DBCO-nnAA-PEG4-EDA-PNU (LP26):
LP24
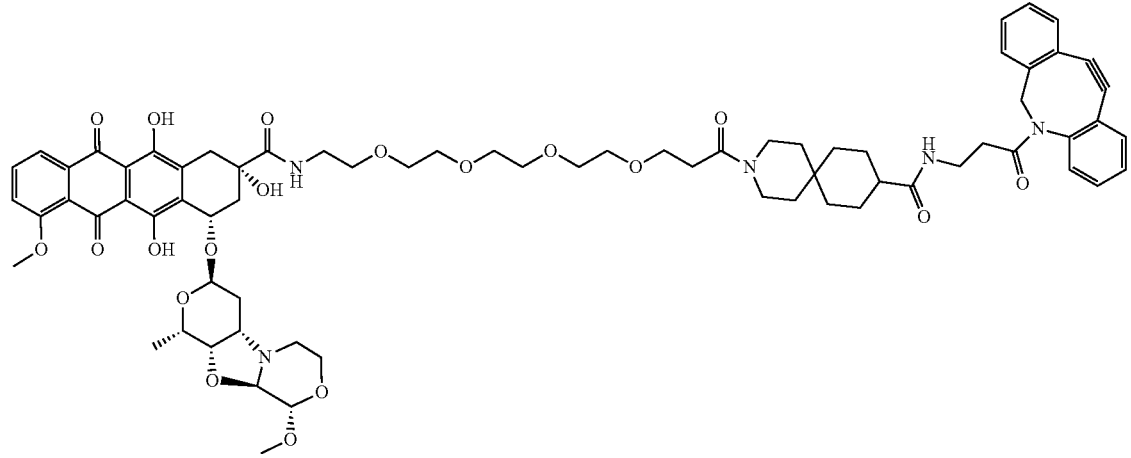
LP25
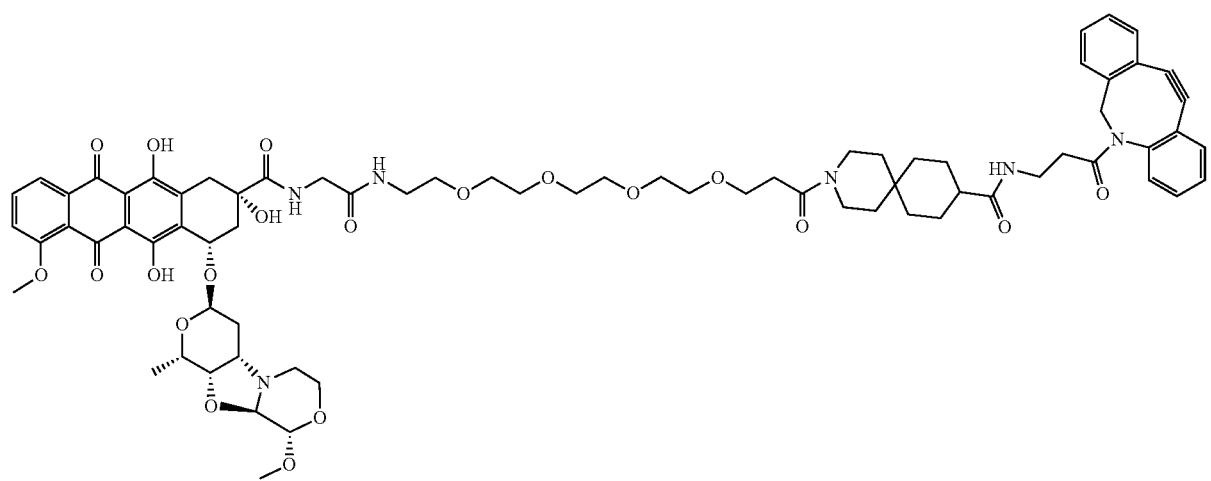

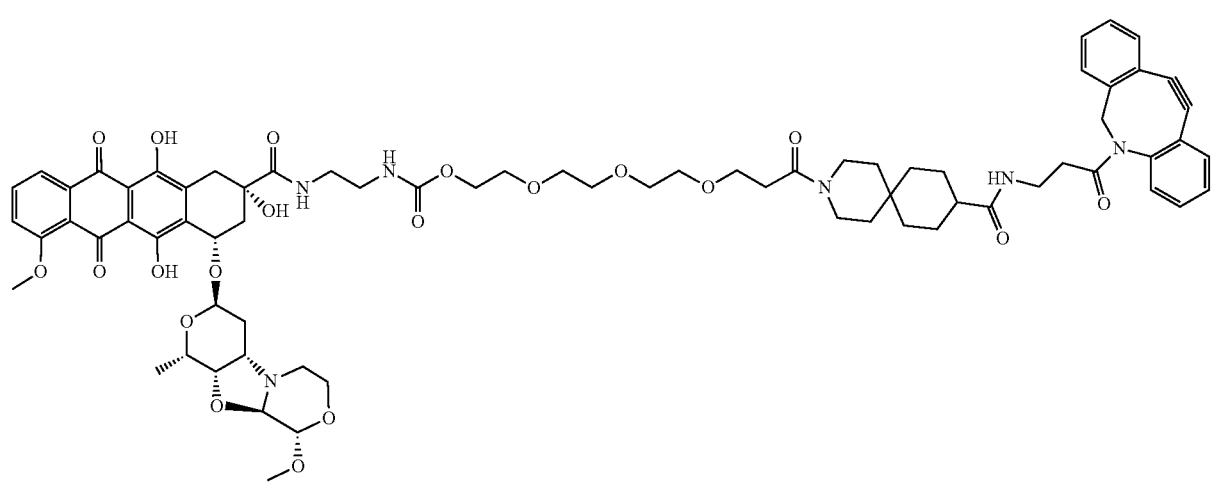
DBCO-nnAA-sidechain PEG12-EDA-PNU (LP27):
DBCO-nnAA-sidechain PEG12-PNU (LP28):
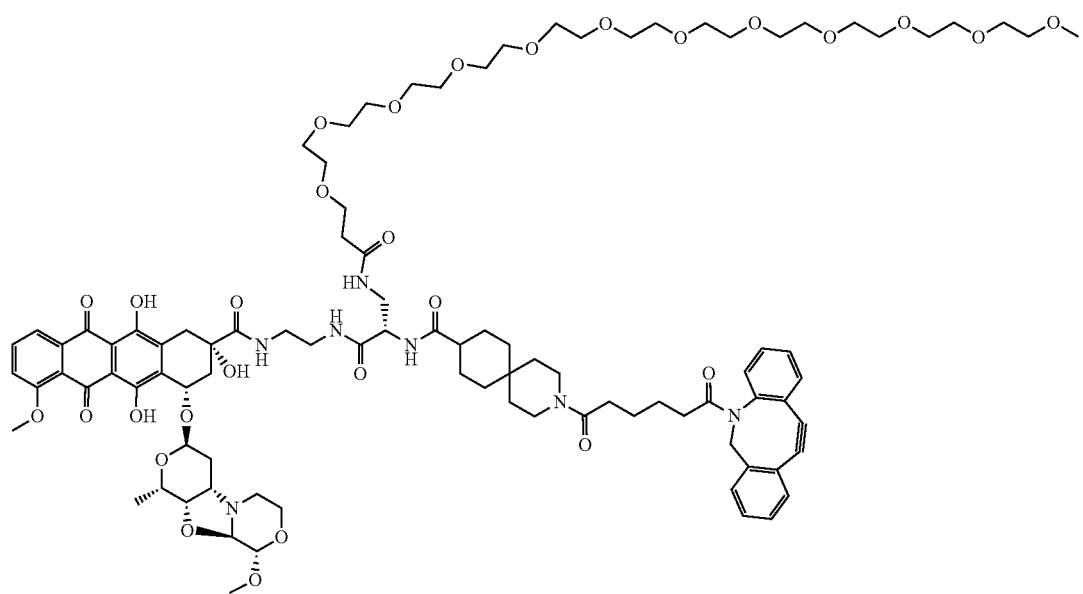

-continued
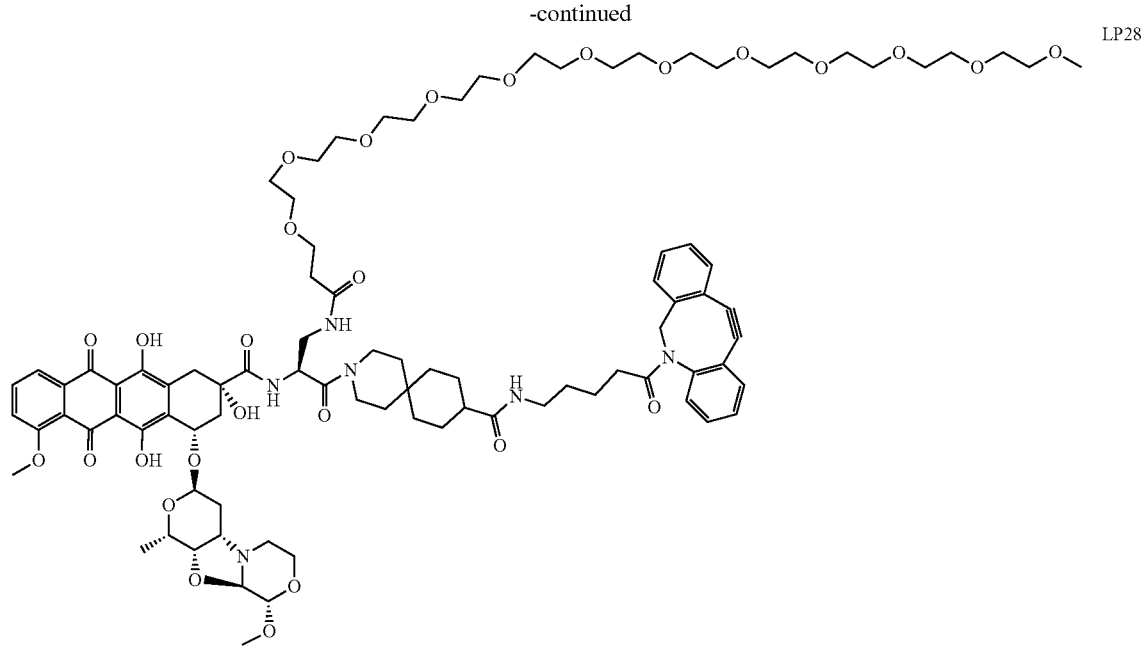
LP28
Synthetic Examples 29-33: PNU Anthracycline Non-Cleavable and Cleavable Linker Payloads
LP29, LP30, LP31, and LP32, LP33 PNU based non-cleavable and cleavable linker payloads are synthesized in analogous fashion using the methods consistent with those described above.
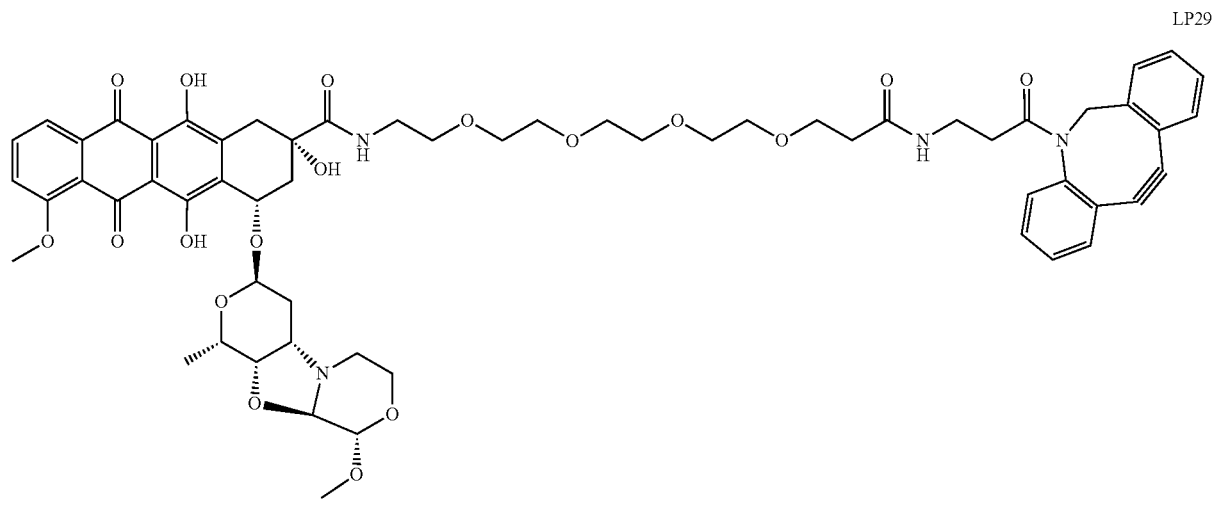
LP29
DBCO-PEG4-PNU -continued
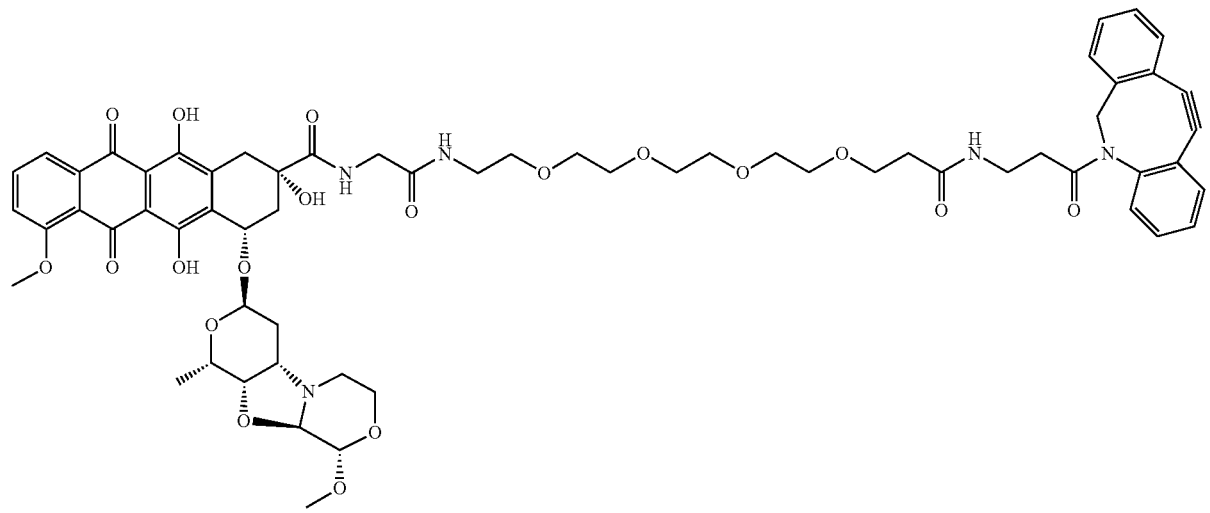
DBCO-PEG4-Gly-PNU
LP30
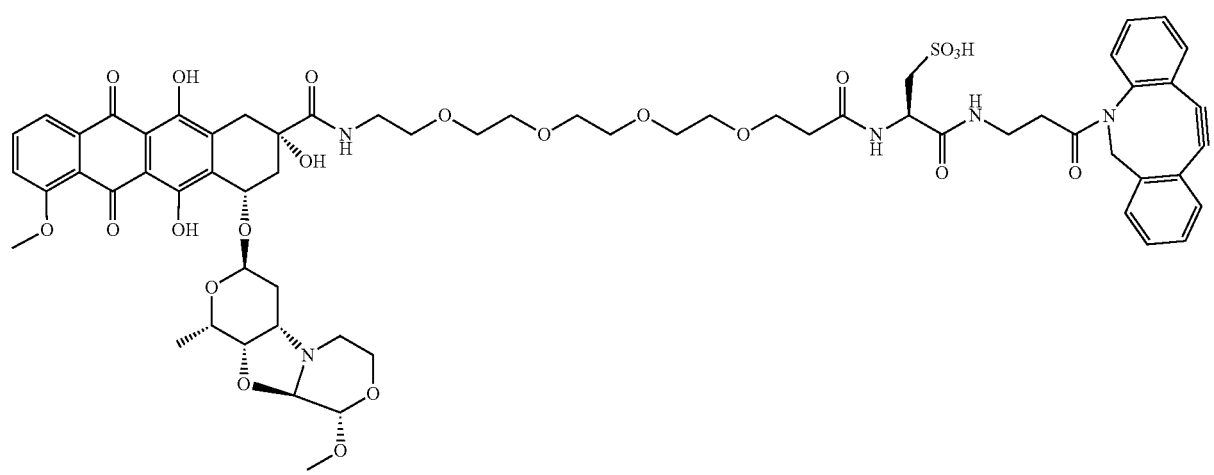
DBCO-L-Cysteic acid-PEG4-PNU
LP31
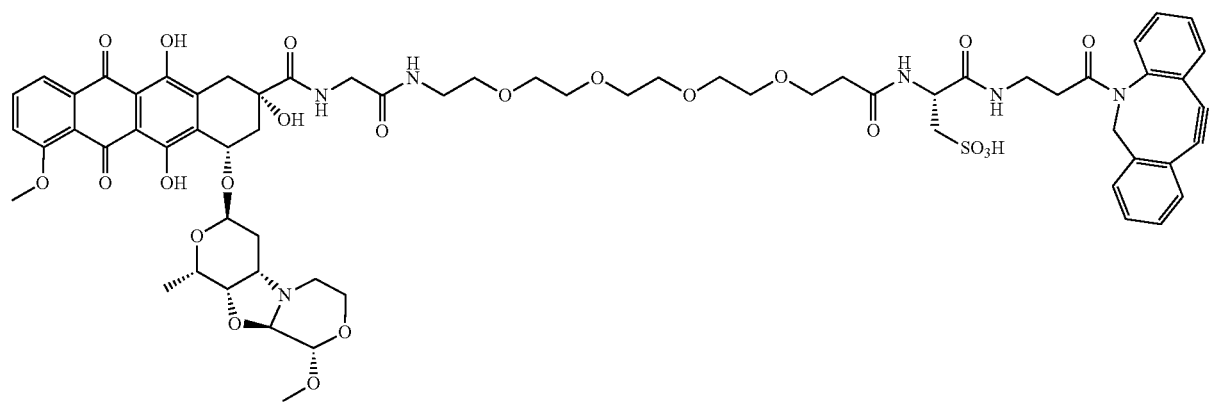
DBCO-L-Cysteic acid-PEG4-Gly-PNU
LP32

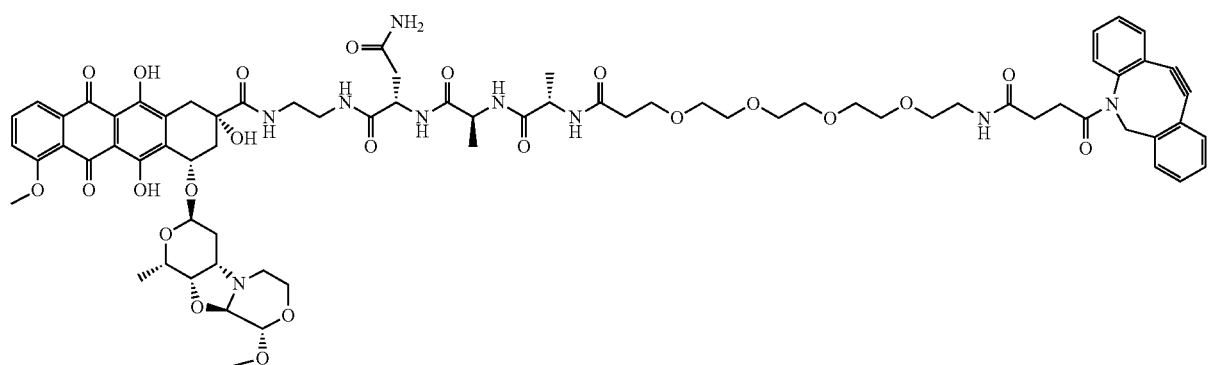

DBCO-PEG4-AAN-PNU EDA

Synthetic Examples—Payloads

Hemiasterlin:

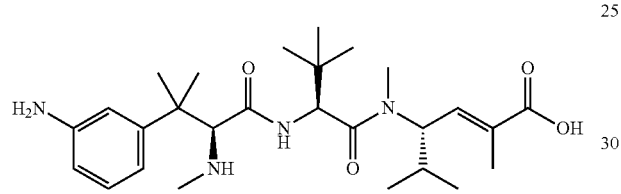

Hemiasterlin payload is synthesized as described in PCT/US2016/15844, WO 2020/252015 A1, which is incorporated by reference in its entirety.

Exatecan:

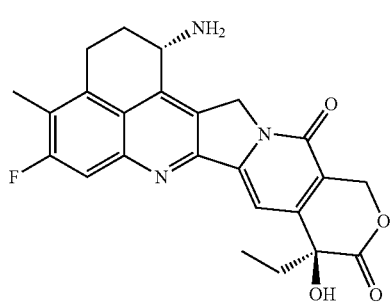 [SMILES: CC[C@@]1(O)C(=O)OCc2c1cc1n(c2=O)Cc2c-1nc1cc(F)c(C)c3c1c2[C@@H](N)CC3]

Exatecan is obtained from a commercial source.

Gly-Exatecan:

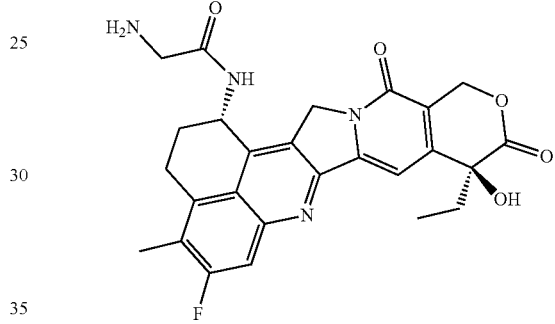

Gly exatecan is synthesized from Exatecan (1 eq), Fmoc-Gly-OH (1 eq) in DMF added 1.2 eq of DIPEA and HATU (1 eq), the reaction mixture was stirred for 5 h, LCMS showed completion of the reaction. 5 eq of piperdine was added and stirred for 1 h, and the reaction was concentrated and purified by preparative HPLC.

PNU-159682:

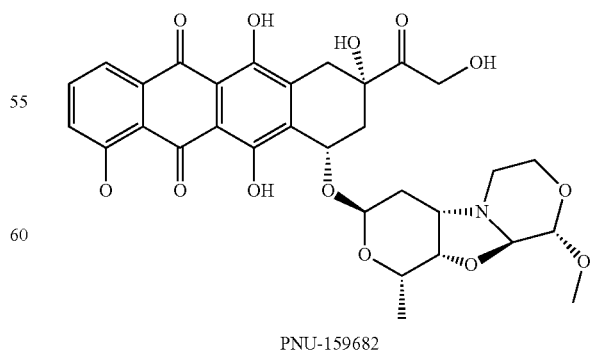

PNU-159682

PNU-159682 is obtained from a commercial source.

PNU-EDA:

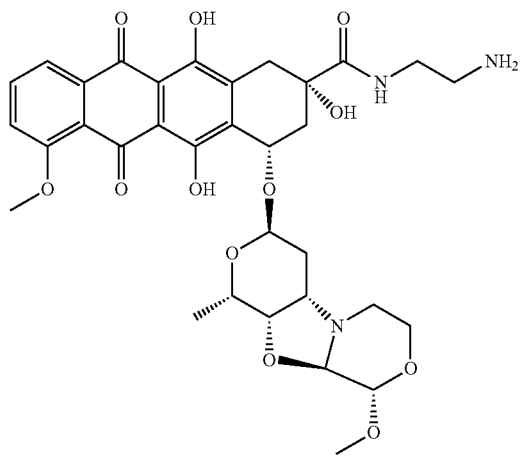 [SMILES: COc1cccc2c1C(=O)c1c(O)c3c(c(O)c1C2=O)C[C@@](O)(C(=O)NCCN)C[C@@H]3O[C@H]1C[C@H]2[C@H](O[C@@H]3[C@@H](OC)OCCN32)[C@H](C)O1]

PNU-EDA is synthesized according to the literature published methods WO 2016/102679 A1, which is incorporated by reference in its entirety.

Example 1

Generation and Primary Screening of Anti-ROR1 Antibodies

Generation and Phage Display Selection

Antibody Fab libraries were constructed using an optimized trastuzumab Fab sequence codon optimized in a modified, commercially available p3 phagemid vector (Antibody Design Labs). Briefly, the phagemid vector was modified to express Fab heavy chains as C-terminal p3 fusion proteins, and regulatory regions (start codons, restriction enzyme sites, periplasmic leader sequences) were optimized for Fab display levels. Libraries were constructed using a standard overlap extension PCR protocol with mutagenic primers targeting heavy chain complementary determining regions (CDRs). See Heckman and Pease, Nat. Protoc., 2007, 2:924-932. Libraries were rescued through electroporation in M13-K07 infected SS320 E. coli cells. See Raj an & Sidhu, Methods Enzymol., 2012, 502:3-23; Marks & Bradbury, Methods Mol Biol., 2004, 248:161-76. Following multiple selection rounds, Fab heavy chain pools were transferred into cell-free expression vectors for expression as His6 and FLAG-tagged IgG1.

Ribosome Display Selections

Antibody Fab libraries were constructed using a standard overlap extension PCR protocol with mutagenic primers targeting complementary determining regions (CDRs). See Heckman & Pease, supra. Selections for novel antibodies were performed using standard ribosome display protocols. See Hanes & Plückthun, Proc. Natl. Acad. Sci. U.S.A, 1997, 94:4937-4942. Specifically, Fab-based ribosome display selections were performed according to published protocols. See Stafford et al., 2014, Protein Eng. Des. Sel. 27:97-109; Dreier and Plückthun, 2011, Methods Mol Biol 687:283-306. After multiple rounds of selection, the DNA from RT-PCR output was cloned into an optimized vector for cell-free expression using standard molecular biology techniques. See Yin et al., 2012, mAbs 4. All constructs were HIS- and FLAG-tagged to streamline purification and testing during screening Primary Screening of Antibody Variants Libraries of antibody variants generated by selection workflow were transformed into E. coli and grown on agar plates with antibiotic (Kanamycin). Individual colonies were grown in liquid broth (TB+antibiotic Kanamycin), and used as a template for DNA amplification via rolling circle amplification (RCA). The variants were then expressed in a cell-free protein synthesis reaction as described. See Yin et al., mAbs, 2012, 4:217-225. Briefly, cell-free extracts were treated with 50 μM iodoacetamide for 30 min at RT (20° C.) and added to a premix containing cell-free components (see Cai et al., Biotechnol Prg, 2015, 3:823-831), 10% (v/v) RCA DNA template (approximately 10 μg/mL DNA) for HC variants of interest, and 2.5 μg/mL of the trastuzumab LC. 60 μL cell free (CF) reactions were incubated at 30° C. for 12 hr on a shaker at 650 rpm in 96-well plates. 400-1500 colonies were screened, depending on the predicted diversity of different selection campaigns. Following synthesis, each reaction was diluted 1-200, 1-400 secondary antibody, 0.2 million CHO (stained with Oregon Green), and 0.2 million CHO-hROR1.

Secondary Screening of Antibody Variants

The top leads from the initial round of screening were cultured and miniprepped via the Qiaprep 96 Turbo miniprep kit (Qiagen) according to manufacturer's instructions. 5 μg/mL miniprepped HC DNA and 5 μg/mL of the trastuzumab LC was added to 4 mL cell-free reactions and incubated overnight for 12 hr at 30° C., 650 rpm. Expressed variants from clarified cell-free reactions were purified via IMAC purification using a semi-automated high throughput batch purification method. Briefly, purifications were performed in a 96-well plate format where 50 μL/well of IMAC resin (Ni Sepharose High Performance, GE Healthcare) was equilibrated in IMAC binding buffer (50 mM Tris pH 8.0, 300 mM NaCl, 10 mM imidazole), incubated with 1 mL cell-free reaction for 15 minutes followed by two washes in IMAC binding buffer. His-tagged antibody variants were then eluted using 200 μL IMAC elution buffer (50 mM Tris pH 8.0, 300 mM NaCl, 500 mM imidazole) and buffer exchanged into PBS using a 96-well Zeba plate (7 kD MWCO, Thermofisher). Purified antibodies were quantified via high throughput capillary electrophoresis using the Labchip GXII (Perkin Elmer) against a Herceptin standard curve, according to manufacturer's instructions.

Exemplary affinity-matured antibodies are reported in Table 5, below.

TABLE 5

Affinity Matured Antibodies

| Antibody | $V_H$ | SEQ ID NO. | $V_L$ | SEQ ID NO. |
|---|---|---|---|---|
| 1 | 1987-C05 | 854 | Trastuzumab | 1021 |
| 2 | 2188-D11 | 855 | Trastuzumab | 1021 |
| 3 | 2188-B04 | 856 | Trastuzumab | 1021 |
| 4 | 2188-C09 | 857 | Trastuzumab | 1021 |
| 5 | 2188-G03 | 858 | Trastuzumab | 1021 |
| 6 | 2188-E03 | 859 | Trastuzumab | 1021 |
| 7 | 2188-B11 | 860 | Trastuzumab | 1021 |
| 8 | 2188-E07 | 861 | Trastuzumab | 1021 |
| 9 | 2188-B02 | 862 | Trastuzumab | 1021 |
| 10 | 2188-C07 | 863 | Trastuzumab | 1021 |
| 11 | 2188-A03 | 864 | Trastuzumab | 1021 |
| 12 | 2188-F03 | 865 | Trastuzumab | 1021 |
| 13 | 2188-D03 | 866 | Trastuzumab | 1021 |
| 14 | 2188-C04 | 867 | Trastuzumab | 1021 |
| 15 | 2188-D10 | 868 | Trastuzumab | 1021 |
| 16 | 2188-A06 | 869 | Trastuzumab | 1021 |

TABLE 5-continued

Affinity Matured Antibodies

| Antibody | $V_H$ | SEQ ID NO. | $V_L$ | SEQ ID NO. |
|---|---|---|---|---|
| 17 | 2188-C11 | 870 | Trastuzumab | 1021 |
| 18 | 2188-F01 | 871 | Trastuzumab | 1021 |
| 19 | 2188-E11 | 872 | Trastuzumab | 1021 |
| 20 | 2188-A07 | 873 | Trastuzumab | 1021 |
| 21 | 2188-C01 | 874 | Trastuzumab | 1021 |
| 22 | 2188-F08 | 875 | Trastuzumab | 1021 |
| 23 | 2188-E04 | 876 | Trastuzumab | 1021 |
| 24 | 2188-B01 | 877 | Trastuzumab | 1021 |
| 25 | 2188-F11 | 878 | Trastuzumab | 1021 |
| 26 | 2188-B08 | 879 | Trastuzumab | 1021 |
| 27 | 2188-C10 | 880 | Trastuzumab | 1021 |
| 28 | 2188-C02 | 881 | Trastuzumab | 1021 |
| 29 | 2188-B07 | 882 | Trastuzumab | 1021 |
| 30 | 2188-A11 | 883 | Trastuzumab | 1021 |
| 31 | 2188-D01 | 884 | Trastuzumab | 1021 |
| 32 | 2188-E09 | 885 | Trastuzumab | 1021 |
| 33 | 2188-E06 | 886 | Trastuzumab | 1021 |
| 34 | 2188-B03 | 887 | Trastuzumab | 1021 |
| 35 | 2188-F06 | 888 | Trastuzumab | 1021 |
| 36 | 2188-D02 | 889 | Trastuzumab | 1021 |
| 37 | 2188-B06 | 890 | Trastuzumab | 1021 |
| 38 | 2188-D09 | 891 | Trastuzumab | 1021 |
| 39 | 2188-F02 | 892 | Trastuzumab | 1021 |
| 40 | 2188-E10 | 893 | Trastuzumab | 1021 |
| 41 | 2188-A09 | 894 | Trastuzumab | 1021 |
| 42 | 2188-D04 | 895 | Trastuzumab | 1021 |
| 43 | 2188-A05 | 896 | Trastuzumab | 1021 |
| 44 | 2188-E01 | 897 | Trastuzumab | 1021 |
| 45 | 2188-G01 | 898 | Trastuzumab | 1021 |
| 46 | 2188-B09 | 899 | Trastuzumab | 1021 |
| 47 | 2188-F07 | 900 | Trastuzumab | 1021 |
| 48 | 2188-D08 | 901 | Trastuzumab | 1021 |
| 49 | 2188-D05 | 902 | Trastuzumab | 1021 |
| 50 | 2188-C03 | 903 | Trastuzumab | 1021 |
| 51 | 2188-E08 | 904 | Trastuzumab | 1021 |
| 52 | 2188-C06 | 905 | Trastuzumab | 1021 |
| 53 | 2188-A08 | 906 | Trastuzumab | 1021 |
| 54 | 2188-B10 | 907 | Trastuzumab | 1021 |
| 55 | 2188-G02 | 908 | Trastuzumab | 1021 |
| 56 | 2188-C05 | 909 | Trastuzumab | 1021 |
| 57 | 2188-A10 | 910 | Trastuzumab | 1021 |
| 58 | 2188-G04 | 911 | Trastuzumab | 1021 |
| 59 | 2188-C08 | 912 | Trastuzumab | 1021 |
| 60 | 2188-E05 | 913 | Trastuzumab | 1021 |
| 61 | 2188-A02 | 914 | Trastuzumab | 1021 |
| 62 | 2188-F04 | 915 | Trastuzumab | 1021 |
| 63 | 2188-F05 | 916 | Trastuzumab | 1021 |
| 64 | 2188-D07 | 917 | Trastuzumab | 1021 |
| 65 | 2188-E02 | 918 | Trastuzumab | 1021 |
| 66 | 2188-D06 | 919 | Trastuzumab | 1021 |
| 67 | 2188-F09 | 920 | Trastuzumab | 1021 |
| 68 | 2188-F10 | 921 | Trastuzumab | 1021 |
| 69 | 2188-B05 | 922 | Trastuzumab | 1021 |
| 70 | 1943-C02 | 923 | Trastuzumab | 1021 |
| 71 | 2193-D04 | 924 | Trastuzumab | 1021 |
| 72 | 2193-E10 | 925 | Trastuzumab | 1021 |
| 73 | 2193-E06 | 926 | Trastuzumab | 1021 |
| 74 | 2193-E04 | 927 | Trastuzumab | 1021 |
| 75 | 2193-B09 | 928 | Trastuzumab | 1021 |
| 76 | 2193-D11 | 929 | Trastuzumab | 1021 |
| 77 | 2193-B02 | 930 | Trastuzumab | 1021 |
| 78 | 2193-D05 | 931 | Trastuzumab | 1021 |
| 79 | 2193-E11 | 932 | Trastuzumab | 1021 |
| 80 | 2193-D06 | 933 | Trastuzumab | 1021 |
| 81 | 2193-C02 | 934 | Trastuzumab | 1021 |
| 82 | 2193-B03 | 935 | Trastuzumab | 1021 |
| 83 | 2193-A02 | 936 | Trastuzumab | 1021 |
| 84 | 2193-E05 | 937 | Trastuzumab | 1021 |
| 85 | 2193-A06 | 938 | Trastuzumab | 1021 |
| 86 | 2193-C04 | 939 | Trastuzumab | 1021 |
| 87 | 2193-E08 | 940 | Trastuzumab | 1021 |
| 88 | 2193-B10 | 941 | Trastuzumab | 1021 |
| 89 | 2193-D08 | 942 | Trastuzumab | 1021 |
| 90 | 2193-B08 | 943 | Trastuzumab | 1021 |
| 91 | 2193-C05 | 944 | Trastuzumab | 1021 |
| 92 | 2193-D10 | 945 | Trastuzumab | 1021 |
| 93 | 2193-D03 | 946 | Trastuzumab | 1021 |
| 94 | 2193-A09 | 947 | Trastuzumab | 1021 |
| 95 | 2193-A10 | 948 | Trastuzumab | 1021 |
| 96 | 2193-E07 | 949 | Trastuzumab | 1021 |
| 97 | 2193-A07 | 950 | Trastuzumab | 1021 |
| 98 | 2193-E03 | 951 | Trastuzumab | 1021 |
| 99 | 2193-C08 | 952 | Trastuzumab | 1021 |
| 100 | 2193-B11 | 953 | Trastuzumab | 1021 |
| 101 | 2193-A03 | 954 | Trastuzumab | 1021 |
| 102 | 2193-D02 | 955 | Trastuzumab | 1021 |
| 103 | 2193-B06 | 956 | Trastuzumab | 1021 |
| 104 | 2193-B01 | 957 | Trastuzumab | 1021 |
| 105 | 2193-D09 | 958 | Trastuzumab | 1021 |
| 106 | 2193-E09 | 959 | Trastuzumab | 1021 |
| 107 | 2193-B07 | 960 | Trastuzumab | 1021 |
| 108 | 2193-C06 | 961 | Trastuzumab | 1021 |
| 109 | 2193-B05 | 962 | Trastuzumab | 1021 |
| 110 | 2193-A11 | 963 | Trastuzumab | 1021 |
| 111 | 2193-E02 | 964 | Trastuzumab | 1021 |
| 112 | 2193-A08 | 965 | Trastuzumab | 1021 |
| 113 | 2193-C11 | 966 | Trastuzumab | 1021 |
| 114 | 2193-A01 | 967 | Trastuzumab | 1021 |
| 115 | 2193-D07 | 968 | Trastuzumab | 1021 |
| 116 | 2193-A05 | 969 | Trastuzumab | 1021 |
| 117 | 2193-C03 | 970 | Trastuzumab | 1021 |
| 118 | 2193-C09 | 971 | Trastuzumab | 1021 |
| 119 | 2193-D01 | 972 | Trastuzumab | 1021 |
| 120 | 2193-E01 | 973 | Trastuzumab | 1021 |
| 121 | 2193-C07 | 974 | Trastuzumab | 1021 |
| 122 | 2193-B04 | 975 | Trastuzumab | 1021 |
| 123 | 2193-C10 | 976 | Trastuzumab | 1021 |
| 124 | 2193-C01 | 977 | Trastuzumab | 1021 |
| 125 | 2193-A04 | 978 | Trastuzumab | 1021 |
| 126 | 1944-A07 | 979 | Trastuzumab | 1021 |
| 127 | 2194-A02 | 980 | Trastuzumab | 1021 |
| 128 | 2194-A05 | 981 | Trastuzumab | 1021 |
| 129 | 2194-B04 | 982 | Trastuzumab | 1021 |
| 130 | 2194-A09 | 983 | Trastuzumab | 1021 |
| 131 | 2194-A01 | 984 | Trastuzumab | 1021 |
| 132 | 2194-B03 | 985 | Trastuzumab | 1021 |
| 133 | 2194-B02 | 986 | Trastuzumab | 1021 |
| 134 | 2194-A03 | 987 | Trastuzumab | 1021 |
| 135 | 2194-A11 | 988 | Trastuzumab | 1021 |
| 136 | 2194-A08 | 989 | Trastuzumab | 1021 |
| 137 | 2194-A04 | 990 | Trastuzumab | 1021 |
| 138 | 2194-A10 | 991 | Trastuzumab | 1021 |
| 139 | 2194-A07 | 992 | Trastuzumab | 1021 |
| 140 | 2194-B01 | 993 | Trastuzumab | 1021 |
| 141 | 2194-A06 | 994 | Trastuzumab | 1021 |
| 142 | 2196-C01 | 995 | SP34 or 2037-B10 | 1022 or 1023 |
| 143 | 2196-A02 | 996 | SP34 or 2037-B10 | 1022 or 1023 |
| 144 | 2196-B03 | 997 | SP34 or 2037-B10 | 1022 or 1023 |
| 145 | 2196-A05 | 998 | SP34 or 2037-B10 | 1022 or 1023 |
| 146 | 2196-C02 | 999 | SP34 or 2037-B10 | 1022 or 1023 |
| 147 | 2196-B11 | 1000 | SP34 or 2037-B10 | 1022 or 1023 |
| 148 | 2196-B08 | 1001 | SP34 or 2037-B10 | 1022 or 1023 |
| 149 | 2196-A04 | 1002 | SP34 or 2037-B10 | 1022 or 1023 |
| 150 | 2196-A03 | 1003 | SP34 or 2037-B10 | 1022 or 1023 |
| 151 | 2196-B07 | 1004 | SP34 or 2037-B10 | 1022 or 1023 |
| 152 | 2196-A06 | 1005 | SP34 or 2037-B10 | 1022 or 1023 |
| 153 | 2196-B05 | 1006 | SP34 or 2037-B10 | 1022 or 1023 |
| 154 | 2196-A01 | 1007 | SP34 or 2037-B10 | 1022 or 1023 |
| 155 | 2196-B01 | 1008 | SP34 or 2037-B10 | 1022 or 1023 |
| 156 | 2196-A09 | 1009 | SP34 or 2037-B10 | 1022 or 1023 |
| 157 | 2196-A08 | 1010 | SP34 or 2037-B10 | 1022 or 1023 |
| 158 | 2196-A10 | 1011 | SP34 or 2037-B10 | 1022 or 1023 |
| 159 | 2196-B06 | 1012 | SP34 or 2037-B10 | 1022 or 1023 |
| 160 | 2196-B09 | 1013 | SP34 or 2037-B10 | 1022 or 1023 |
| 161 | 2196-C03 | 1014 | SP34 or 2037-B10 | 1022 or 1023 |
| 162 | 2196-C04 | 1015 | SP34 or 2037-B10 | 1022 or 1023 |

TABLE 5-continued

Affinity Matured Antibodies

| Antibody | V$_H$ | SEQ ID NO. | V$_L$ | SEQ ID NO. |
|---|---|---|---|---|
| 163 | 2196-A07 | 1016 | SP34 or 2037-B10 | 1022 or 1023 |
| 164 | 2196-A11 | 1017 | SP34 or 2037-B10 | 1022 or 1023 |
| 165 | 2196-B02 | 1018 | SP34 or 2037-B10 | 1022 or 1023 |
| 166 | 2196-B04 | 1019 | SP34 or 2037-B10 | 1022 or 1023 |
| 167 | 2196-B10 | 1020 | SP34 or 2037-B10 | 1022 or 1023 |

Example 2

Preparation of SCFVS

A single-chain antibody is made in either the V$_H$V$_L$ or V$_L$V$_H$ orientation with a linker sequence between the V$_H$ and V$_L$ domains. Typically scFv linkers are composed of (GGGGS)n repeats where n=3, 4, 5, or 6 for linkers of 15, 20, 25, or 30 residues respectively. For cell-free expression, an N-terminal Met is added, but for mammalian expression a leader peptide is added. On the C-terminal end of the scFv, an Fc sequence can be added to extend in vivo half-life or the scFv can be used directly. An optional linker sequence can be incorporated between the scFv and the Fc. An exemplary scFv-Fc linker sequence is AAGSDQEPKSS (SEQ ID NO: 1035). C-terminal affinity tags can optionally be added to facilitate purification and assay development. An exemplary affinity tag is a C-terminal FlagHis tag GSGDYKDDDDKGSGHHHHHH (SEQ ID NO: 1033). A stop codon is typically inserted at the end of the sequence. An exemplary scFv can include an N-terminal Met residue, a V$_H$ domain, a GGGGSGGGGSGGGGS (SEQ ID NO: 1034) linker, a V$_L$ domain, an AAGSDQEPKSS (SEQ ID NO: 1035) linker, an Fc domain, a FlagHis tag, and a stop codon.

Example 3

Differential Scanning Fluorimetry

A protein thermal shift assay was carried out by mixing the protein to be assayed with an environmentally sensitive dye (SYPRO Orange, Life Technologies Cat #S-6650) in a phosphate buffered solution (PBS), and monitoring the fluorescence of the mixture in real time as it underwent controlled thermal denaturation. Protein solutions between 0.2-2 mg/mL were mixed at a 1-1 volumetric ratio with a 1-500 PBS-diluted solution of SYPRO Orange (SYPRO Orange stock dye is 5000× in DMSO). 10 µL aliquots of the protein-dye mixture were dispensed in quadruplicate in a 384-well microplate (Bio-Rad Cat #MSP-3852), and the plate was sealed with an optically clear sealing film (Bio-Rad Cat #MSB-1001) and placed in a 384-well plate real-time thermocycler (Bio-Rad CFX384 Real Time System). The protein-dye mixture was heated from to 95° C., at increments of 0.1° C. per cycle (~1.5° C. per minute), allowing 3 seconds of equilibration at each temperature before taking a fluorescence measurement. At the end of the experiment, the transition melting temperatures (TM1 and TM2) were determined using the Bio-Rad CFX manager software. TM1 represents the melting temperature of the Fc domain. TM2 represents the melting temperature of the Fab domain.

Example 4

High-Throughput Primary Screening of Cell Binding

A high-throughput primary screen was performed to rapidly assess cell binding of antibodies produced in small-scale (60 µL) cell-free reactions. In this screen, four components were combined in equal volumes to a final volume of 100 µL/well in a U-bottom 96-well plate (Greiner Cat #650201) or flat bottom 384 well plate (Greiner Cat #781201). These components are: 1) ROR1-expressing CHO cells (CHO-hROR1) diluted in assay buffer (1×PBS+ 0.2% BSA, sterile filtered) to achieve a final concentration of 500,000 cells/well, 2) a CHO hROR1-negative cell line stained with CellTrace Oregon Green (Invitrogen Cat #34555) and diluted in assay buffer to achieve a final concentration of 500,000 cells/well, 3) a 1-50 dilution of cell-free reaction producing the antibody of interest diluted in assay buffer, and 4) a secondary anti-human antibody (AlexaFluor 647 AffiniPure F(ab')$_2$ Donkey anti-human IgG, Fc specific; Jackson ImmunoResearch Cat #709-606-098) diluted 1-100 in assay buffer. Plates were then incubated on ice for one hour. Cells were pelleted by spinning at 1500×g for 5 minutes and resuspended in assay buffer. High-throughput flow cytometry was then performed on resuspended cells on a FACS instrument (BDBiosciences FACSCanto II or BDBiosciences LSR II), and data was analyzed with FlowJo software. Antibody binding was assessed by the proportional level of secondary antibody signal (presumably due to binding to our antibody of interest) on CHO-hROR1 cells compared to the signal on CHO hROR1-negative cells.

Example 5

Epitope Binning

Immunoglobulin (Ig, residues 39-151), Frizzled (Fz, residues 165-305), and Kringle (Kr, residues 308-395) domains of ROR1 were constructed with a C-terminal HIS6 tag, expressed in HEK293 cells, and purified (Acro Biosystems). Antibodies were tested for their ability to bind to each of these domains via ELISA. Briefly, 2 µg/mL of Ig, Fz, or Kr were coated to 384-well polystyrene plates for 1 hr at 30° C. in 0.1 M bicarbonate pH8.9 buffer before they were washed and blocked with 2% BSA in PBST (PBS, 0.1% Tween20) for 1 hr. Antibody variants were diluted to 10 µg/mL and further serially diluted 3-fold before 30 µL was applied to the ELISA plates for binding (1 hr at 30° C.). Antibody binding was detected via HRP-conjugated anti-human Fc antibodies (Jackson Immunoresearch) and detection with SuperSignal ELISA Pico Chemiluminescent Substrate (Pierce).

Example 6

ROR2 Cross-Reactivity

Antibodies were tested for their ability to bind to either ROR1 or ROR2 via ELISA. Briefly, 2 µg/mL of ROR1 or ROR2 (Acro Biosystems) were coated to 384-well polystyrene plates for 1 hr at 30° C. in 0.1 M bicarbonate pH8.9 buffer before they were washed and blocked with 2% BSA in PBST (PBS, 0.1% Tween20) for 1 hr. Antibody variants were diluted to 2.5 µg/mL and further serially diluted 3-fold before 30 µL was applied to the ELISA plates for binding (1 hr at 30° C.). Antibody binding was detected via HRP-conjugated anti-human Fc antibodies (Jackson Immunoresearch) and detection with SuperSignal ELISA Pico Chemiluminescent Substrate (Pierce). Cross-reactivity was reported as a ratio of ROR1-ELISA signal over ROR2-ELISA signal at the highest dilution tested.

Example 7

Biacore Off-Rate and Kinetic Analysis

Anti-Fc polyclonal antibodies were immobilized onto a CMS chip (GE Life Sciences) using amine coupling chemistry (from Amine Coupling Kit, GE Life Sciences). The immobilization steps were carried out at a flow rate of 25 µL/min in 1×HBS-EP+buffer (GE Life Sciences; 10× Stock diluted before use). The sensor surfaces were activated for 7 min with a mixture of NHS (0.05 M) and EDC (0.2 M). The Anti-Fc antibodies were injected over all 4 flow cells at a concentration of 25 ug/ml in 10 mM sodium acetate, pH 4.5, for 7 min. Ethanolamine (1 M, pH 8.5) was injected for 7 min to block any remaining activated groups. An average of 12,000 response units (RU) of capture antibody was immobilized on each flow cell.

Off-rate and kinetic binding experiments were performed at 25° C. using 1×HBS-EP+buffer. Test and control antibodies were injected over the anti-Fc surface at concentrations of 5-10 µg/mL for 12 seconds at a flow rate of 10 µL/min on flow cells 2, 3 and 4, followed by a buffer wash for 30 seconds at the same flow rate. Kinetic characterization of antibody samples was carried out with a range of antigen concentrations from 1-100 nM and 1 injection of 0 nM antigen (for example, 100, 50, 25, 6.25, 1.56 and 0 nM). After capturing ligand (antibody) on the anti-Fc surface, the analyte (hROR1, Fz or Kr domains, Acro Biosystems, Delaware) was bound for 180 seconds, followed by a 600 second dissociation phase at a flow rate of 50 µL/min. Between each ligand capture and analyte binding cycle, regeneration was carried out using 2 injections of 10 mM Glycine pH 2.0 for 30 seconds at 30 µL/min, followed by a 30 second buffer wash step.

The data was fit with the Biacore T200 Evaluation software, using a 1-1 Langmuir binding model. $K_D$ (affinity, nM) was determined as a ratio of the kinetic rate constants calculated from the fits of the association and dissociation phases.

Example 8

Cell Lines and Cell Culture Conditions

Ntera-2, MDA-MB-231, MCF7, HCT116 and Mino cells were obtained from ATCC. HCT116-hRor1-D02 clone was generated by transfecting HCT116 cells with a plasmid containing human Ror1 cDNA sequence and selected for highest stable expression of hRor1 on the cell surface. MDA-MB-231, MCF7, HCT116 and HCT116-Ror1 cell were maintained in Ham's F-12 high glucose DMEM (50-50) (Cellgro-Mediatech; Manassas, VA) supplemented with 10% heat-inactivated fetal bovine serum (Hyclone; Thermo Scientific; Waltham, MA), 1% Penicillin/Streptomycin (Cellgro-Mediatech; Manassas, VA) and 2 mmol/L-glutamax (Life Technology; Carlsbad, CA). Mino cells were maintained in RPMI-1640 medium (Cellgro-Mediatech; Manassas, VA) supplemented with 20% heat-inactivated fetal bovine serum (Hyclone; Thermo Scientific; Waltham, MA), 1% Penicillin/Streptomycin (Cellgro-Mediatech; Manassas, VA) and 2 mmol/L-glutamax (Life Technology; Carlsbad, CA).

Example 9

Cell Binding Experiments

Variants with expression levels>250 nM were tested in a fluorescence-activated cell sorting (FACS) cell-binding assay. For leads from naïve library selection, ROR1 positive MDA-MB-231 cell and ROR1 negative MCF7 cell were used to screen for FACS binders. For leads from affinity maturation library selection, HCT116 cells overexpressing human ROR1 (HCT116-hRor1) and HCT116 parent cells were used to screen for FACS binders.

A mix of ROR1 positive and negative cells was prepared as follows. Ror1 negative cells were washed 2× in PBS then incubated in PBS containing 1 nM CellTrace™ Oregon Green488® (Life Technologies) at 37° C. for 30 minutes. Cells were then washed 2× with RPMI w/10% fetal calf serum (or FCS), washed 2× with FACS buffer (PBS+0.5% BSA), suspended thoroughly in ice-cold FACS buffer at a final concentration of 4×10 6 cells/ml and kept on ice. ROR1 positive cells were washed 2× in PBS and suspended with ice-cold FACS buffer at 4×10 6 cells/ml. ROR1 positive and negative cells were then mixed to obtain a 1-1 cell suspension and seeded at 50 µl per well on 96 well polypropylene plates. 50 µl of 6-12 point dilutions of anti-ROR1 variants starting from concentrations of ~100-200 nM antibody was dispensed using BioMekFX (Beckman Coulter) into each well. Cells were then incubated on ice for 1 hr, washed with FACS buffer and incubated for 1 hr on ice with 50 µl FACS buffer containing 2.5 µg/ml Alexa647-conjugated Goat Anti-Human IgG dispensed using BioMekFX (Beckman Coulter). Cells were then washed 2× with FACS buffer and fixed for 10 minutes in 200 µl PBS with 2% PFA prior to fluorescence detection. Samples were acquired using a Beckton Dickinson LSRII FACS. Mean Fluorescence Intensity of ROR1 antibody binding was analyzed using FlowJo® software (Tree Star, Inc.).

Example 10

Cell Killing Analysis

The internalization of the antibodies was evaluated by drugs conjugated to secondary antibodies in a cell killing assay on target positive cells. For leads from naïve library selection, HCT116 cells overexpressing human ROR1 (HCT116-hRor1-D02) were used to screen for internalizing leads. Cells were washed twice with calcium and magnesium-free Hanks Balanced Salt Solution (HBSS), harvested with HYQ® TASE™ (Hyclone; Thermo Scientific; Waltham, MA) and counted by the Vi-CELL Cell Viability Analyzers (Beckman Coulter, Brea, CA). A total of 625 cells in a volume of 25 µL were seeded in each well of a 384-well half area flat bottom white polystyrene plate. Lead antibodies were formulated at 4× starting concentration in the cell culture medium and filtered through MultiScreenHTs 96-Well Filter Plates (Millipore; Billerica, MA). 12.5 µL of the serial diluted antibody (1-3 serial dilution starting from 10 nM) was added into treatment wells and 12.5 µL of a Fab anti-human Fc conjugated to Duocarmycin SA (Moradec, San Diego) via a cleavable linker was then added into each well at a fixed final concentration of 5 nM. Assay plates were cultured at 37° C. in a $CO_2$ incubator for 120 hrs before assay. For cell viability measurement, 30 μL of Cell Titer-Gb® reagent (Promega Corp. Madison, WI) was added into each well, and plates were processed as per product instructions. Relative luminescence was measured on an ENVISION® plate reader (Perkin-Elmer; Waltham, MA). Relative luminescence readings were converted to % viability using untreated cells as controls. Data was fitted with non-linear regression analysis, using a log(inhibitor) vs. response-variable slope, 4 parameter fit with GraphPad Prism (GraphPad v 5.0, Software; San Diego, CA). Data was expressed as relative cell viability (ATP content) % vs. dose of antibody.

For leads from affinity maturation library selection, target positive Mino cells were used to screen for internalizing leads. Cells were harvested and counted by the Vi-CELL Cell Viability Analyzers (Beckman Coulter, Brea, CA). A total of 12500 cells in a volume of 25 μl were seeded in each well of a 384-well half area flat bottom white polystyrene plate. Lead antibodies were formulated at 4× starting concentration in the cell culture medium and filtered through MultiScreenHTs 96-Well Filter Plates (Millipore; Billerica, MA). 12.5 μL of the serial diluted antibody (1-3 serial dilution starting from 10 nM) was added into treatment wells and 12.5 μL of a nanobody anti-human Fc conjugated to a PBD dimer compound via a val-cit linker, and was then added into each well at a fixed final concentration of 5 nM. Assay plates were cultured at 37° C. in a $CO_2$ incubator for 72 hrs before assay. The cell viability was then measured and data plotted as previous described.

Example 11

Permissiveness of Different Light Chains

The anti-ROR1 lead antibodies were discovered from a Fab ribosome display library that contained CDR H1, H2, and H3 diversity and utilized a constant LC (trastuzumab LC). In this example, the HCs of the lead antibodies were co-expressed with trastuzumab LC or different LCs derived from anti-CD3 antibodies: hOKT3-LC1, hSP34-LC3, hUCHT1-LC3 to determine if the anti-ROR1 HC leads would retain binding to ROR1 when assembled with anti-CD3 LCs. The HCs of lead antibodies 1944-A07, 1987-C05, and 1943-B03 were co-expressed with either trastuzumab LC (parental antibody control) or the LCs of hSP34-LC3, hUCHT1-LC3, or hOKT3-LC1. The antibodies were then purified and tested for ROR1 binding by ELISA. The ELISA assay was carried out as follows. Briefly, 2 μg/mL of ROR1 was coated to a 384-well polystyrene plate for 1 hr at 30° C. in 0.1 M bicarbonate pH8.9 buffer before it was washed and blocked with 2% BSA in PBST (PBS, 0.1% Tween20) for 1 hr. Antibody variants were diluted to 5 μg/mL and further serially diluted 3-fold before 30 μL was applied to the ELISA plates for binding (1 hr at Antibody binding was detected via HRP-conjugated anti-human Fc antibodies (Jackson Immunoresearch) and detection with SuperSignal ELISA Pico Chemiluminescent Substrate (Pierce).

Figure 8A:
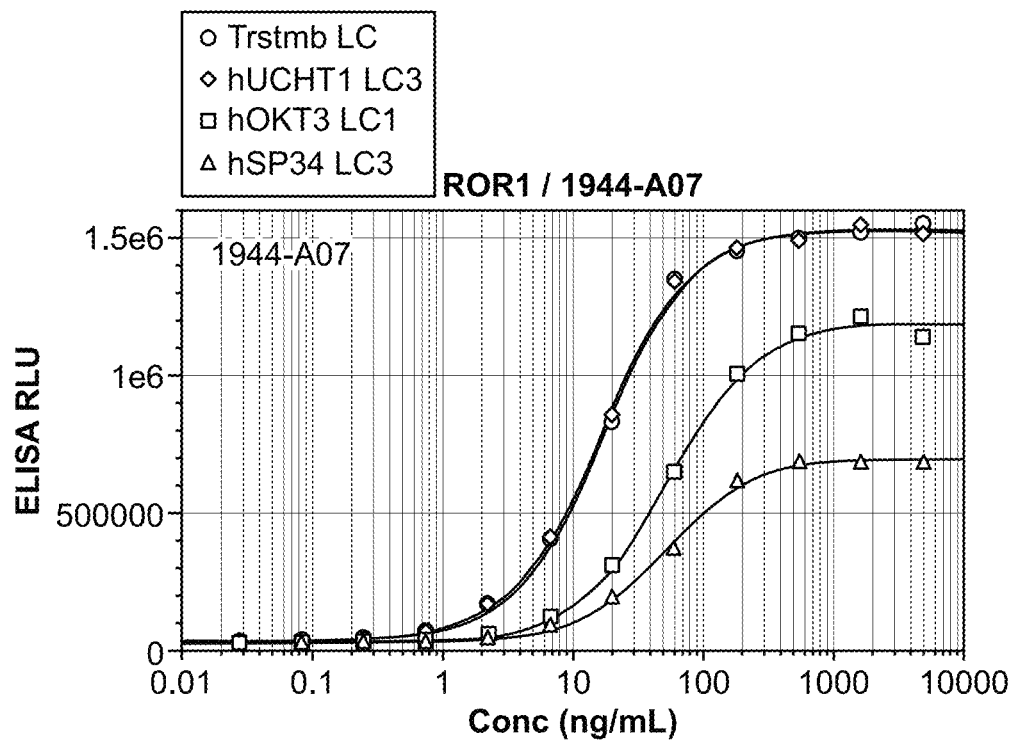
FIGS. 8A-8C provide ELISA binding curves for select heavy chains with three different light chains.
Figure 8B:
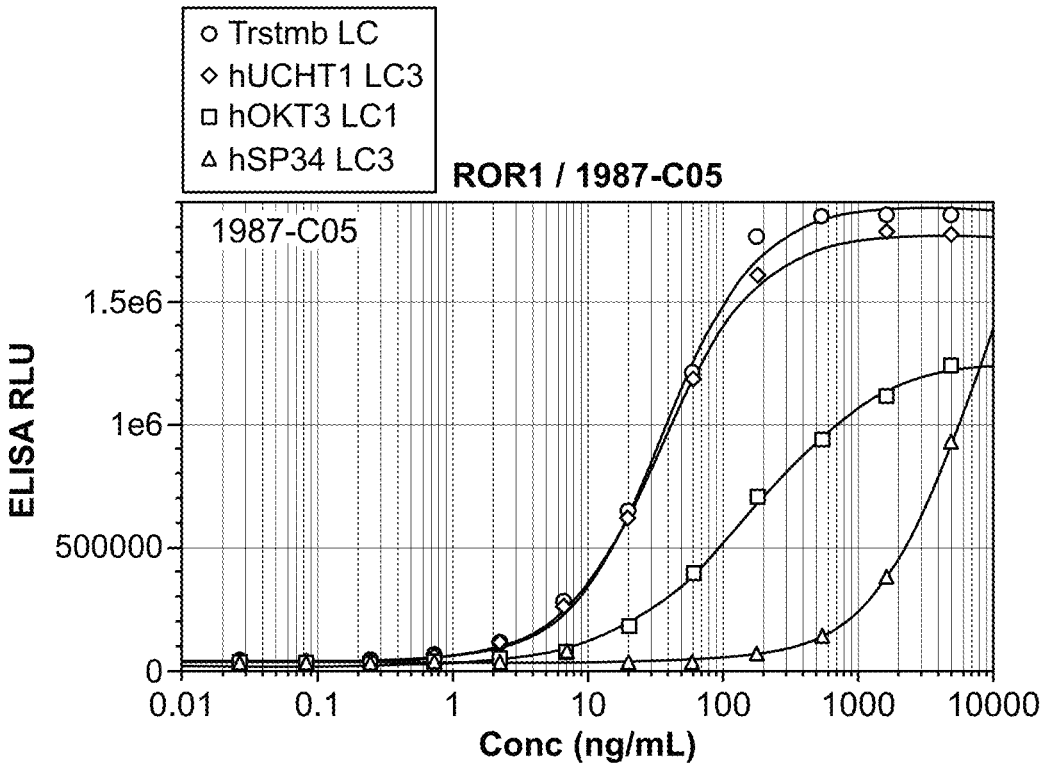
Figure 8C:
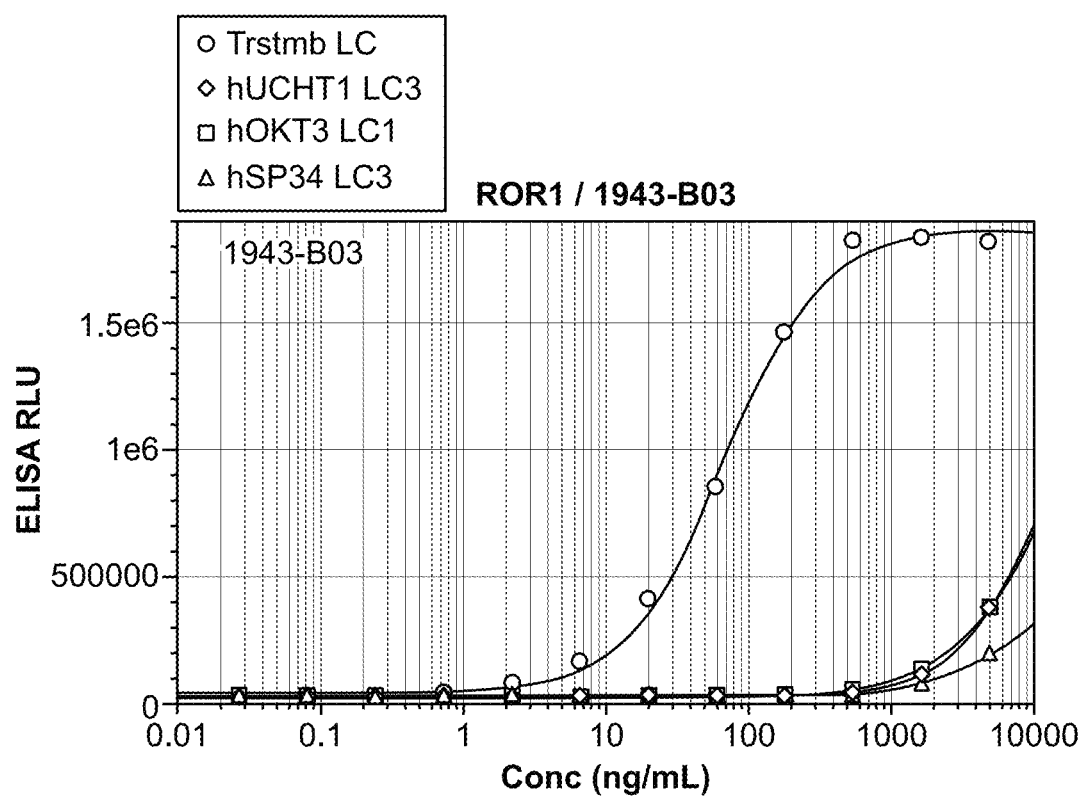
Figure 9A:
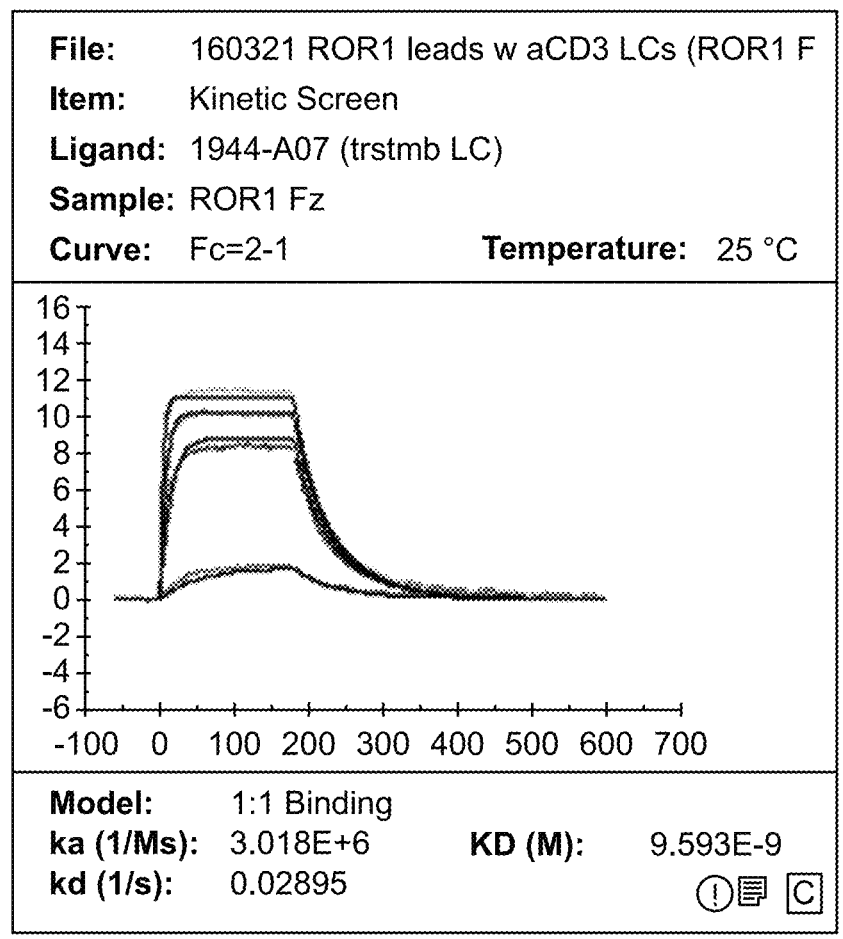
FIGS. 9A-9H provide the results of kinetic screens for select heavy chains with four different light chains.
Figure 9B:
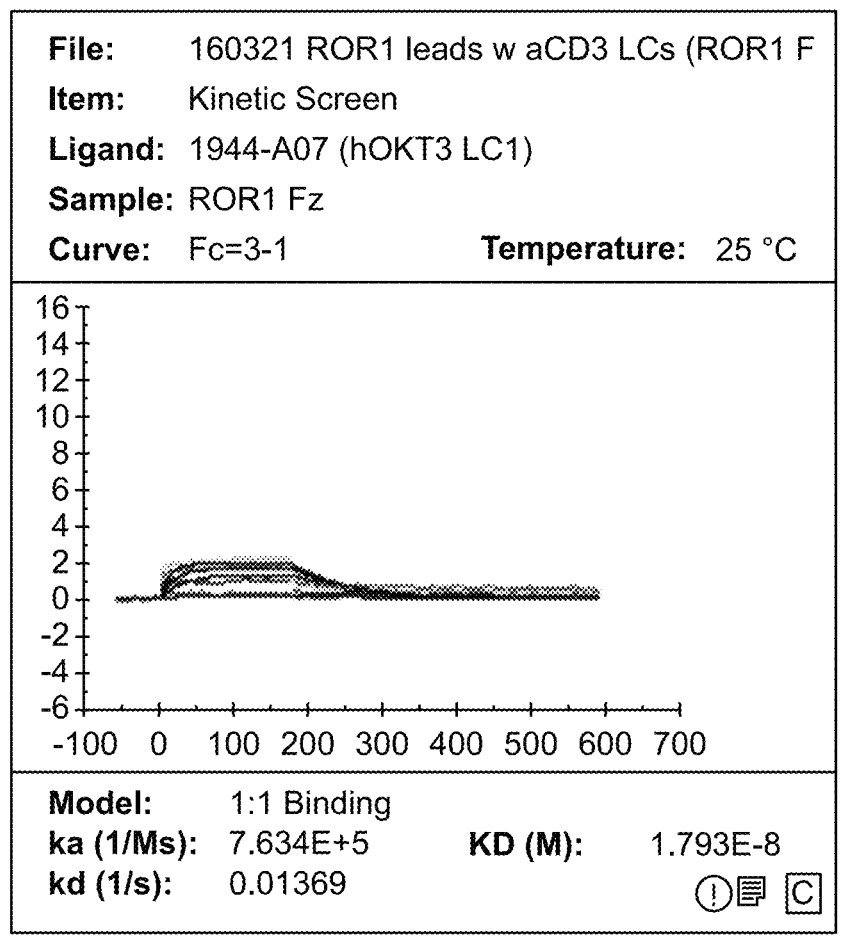
Figure 9C:
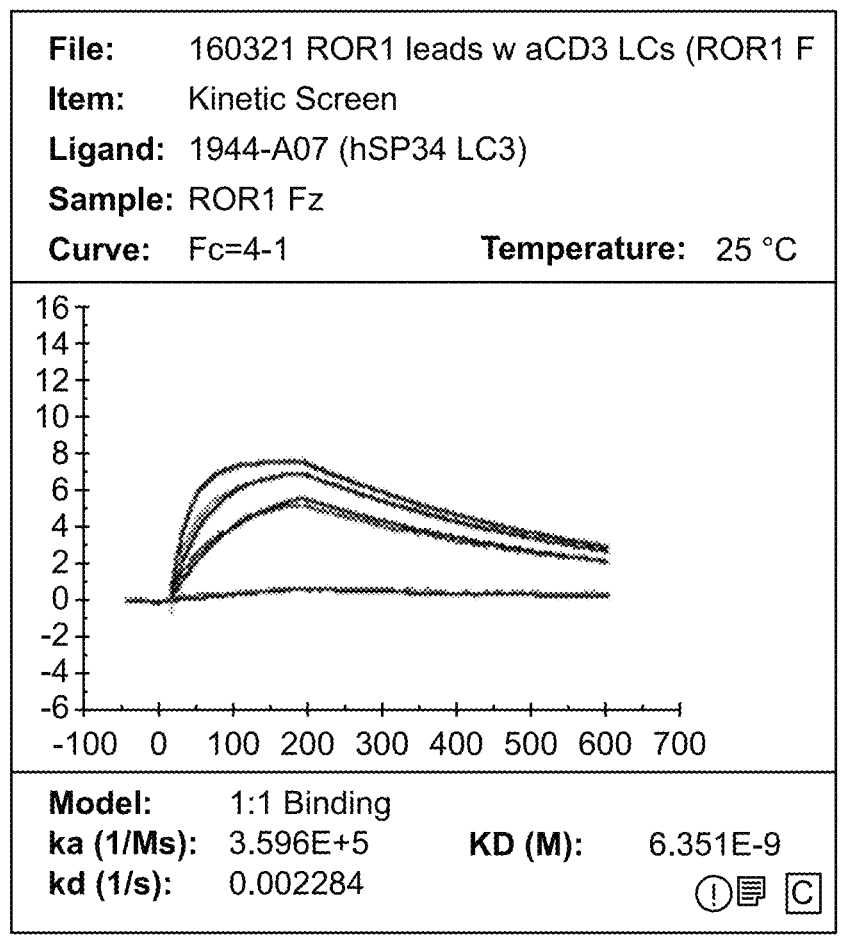
Figure 9D:
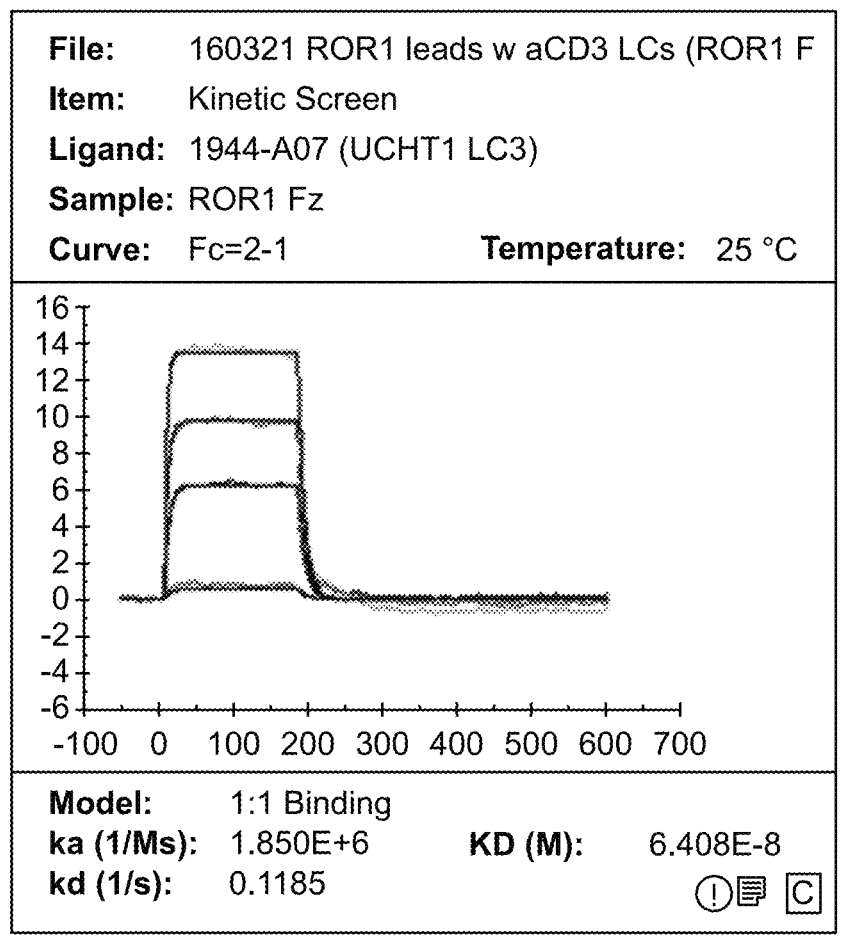
Figure 9E:
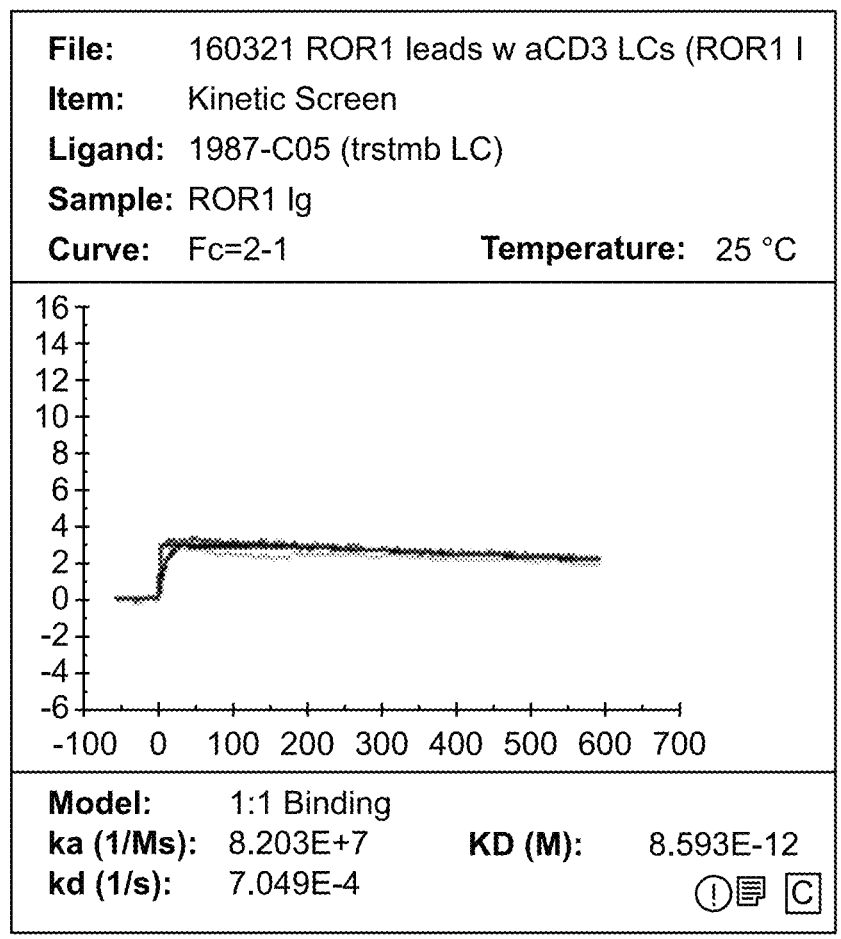
Figure 9F:
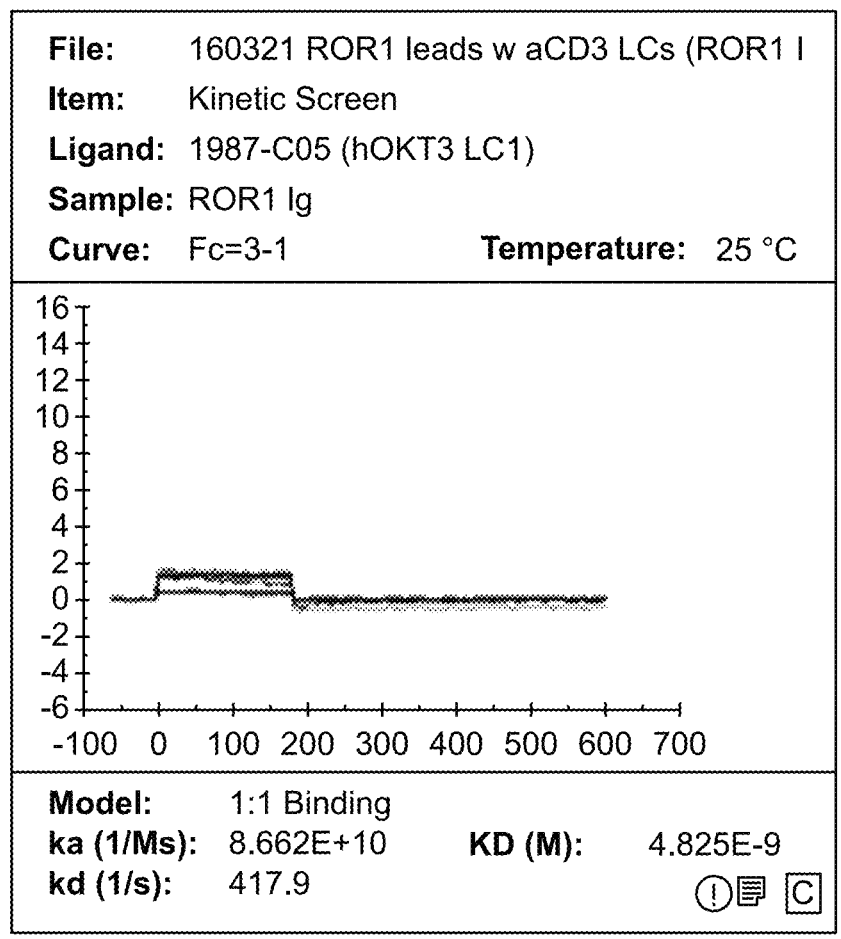
Figure 9G:
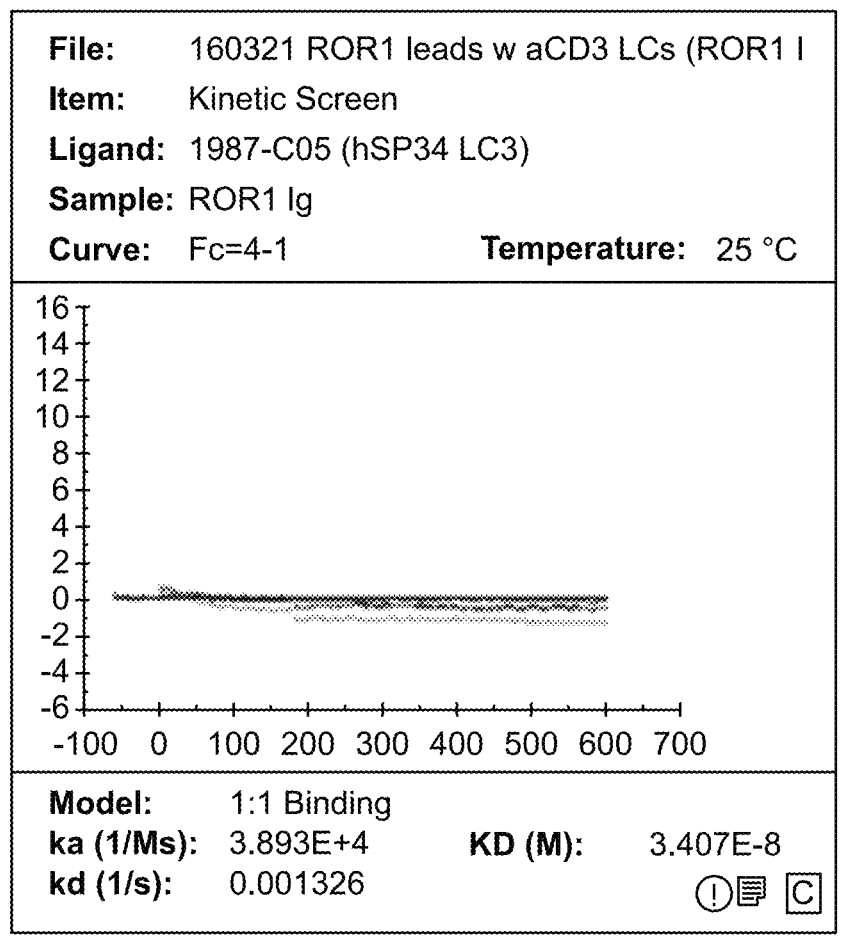
Figure 9H:
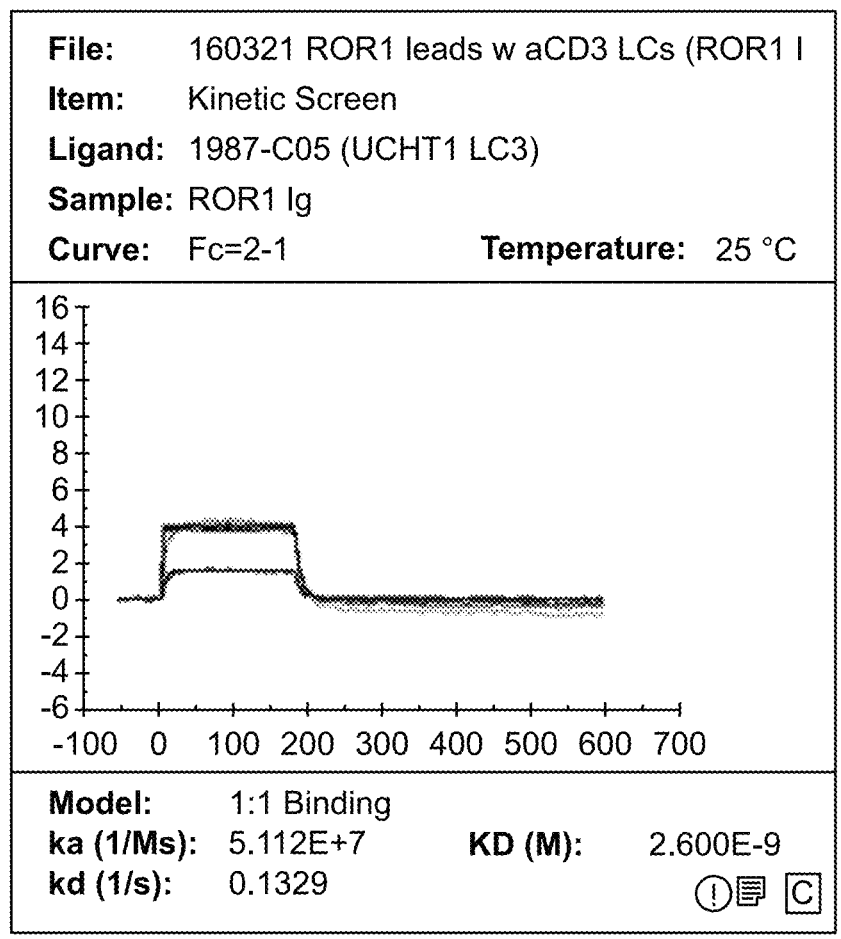

Both 1944-A07 and 1987-C05 maintained varying degrees of binding to ROR1 when combined with different anti-CD3 LCs. However, most ROR1 binding was lost for 1943-B03 when assembled with LCs other than trastuzumab LC. See FIGS. 8A-8C.

For anti-CD3-LC-containing IgGs that had detectable ROR1-binding in ELISA (1944-A07 and 1987-C05 variants), those antibodies were further tested for binding by surface plasmon resonance (SPR). Binding kinetics were assessed to the ROR1-frizzled domain (hROR1-Fz) or the ROR1-extracellular domain (hROR1) for 1944-A07 and 1987-C05 variants, respectively. Briefly, anti-ROR1 antibodies were captured via anti-human Fc polyclonal antibodies immobilized to a CM5 chip, and ROR1 recombinant proteins were flowed across the surface to assess binding kinetics. hROR1 or hROR1-Fz domain (Acro Biosystems, Delaware) binding was tested at 100, 50, 25, 6.25, 1.5625 nM. The data was fit with the Biacore™ T200 Evaluation software, using a 1-1 Langmuir binding model. $K_D$ (affinity, nM) was determined as a ratio of the kinetic rate constants calculated from the fits of the association and dissociation phases. See Tables 6 and 7.

Binding kinetics fell in a similar range ($K_D$~5-10 nM) for the 1944-A07 variants, with the exception of hUCHT1-LC-containing antibodies for which binding was not detected. Binding kinetics of 1987-C05 variants also fell into the 1-2 nM $K_D$ range, with no detectable binding when combined with hSP34-LC3 or hOKT3-LC1. The kinetic results differed slightly from the ELISA-based results which may be attributed to differences in assay format, whereas SPR detects monovalent affinities and ELISA measures equilibrium binding of a bivalent antibody. See FIGS. 9A-9H.

TABLE 6

Binding domain of affinity-matured antibodies.

| | Parent Molecule | | | | Domain |
|---|---|---|---|---|---|
| Matured lead | HC-LC Pairing | VH | SEQ ID NO. | VL | SEQ ID NO. | binding by ELISA |
| SRP2188 | 1987-C05 HC with Trastuzumab LC | 1987-C05 | 854 | Trstmb | 1021 | Ig |
| SRP2193 | 1943-C02 with Trastuzumab LC | 1943-C02 | 923 | Trstmb | 1021 | Fz |
| SRP2194 | 1944-A07 with Trastuzumab LC | 1944-A07 | 979 | Trstmb | 1021 | Fz |
| SRP2196 | 1944-A07 with aCD3 SP34 LC | 1944-A07 | 979 | SP34 | 1022 | Fz |

TABLE 7

Binding kinetics to hROR1-Fz or hROR1 of affinity-matured humanized antibodies (SRP2060).

| | Sample | ka1 (1/Ms) | kd1 (1/s) | KD (M) |
|---|---|---|---|---|
| 1944-A07 HC | | | | |
| w/trstmb LC (parent IgG) | ROR1 Fz | 3.02E+06 | 2.90E−02 | 9.59E−09 |
| w/hSP34 LC3 | ROR1 Fz | 3.60E+05 | 2.28E−03 | 6.35E−09 |
| w/hUCHT1 LC3 | ROR1 Fz | 1.85E+06 | 1.19E−01 | 6.41E−08 |
| w/hOKT3 LC1 | ROR1 Fz | | Not detected | |
| 1987-C05 HC | | | | |
| w/trstmb LC (parent IgG) | ROR1 ECD | 2.43E+06 | 6.73E−04 | 2.77E−10 |
| w/hSP34 LC3 | ROR1 ECD | | Not detected | |
| w/hUCHT1 LC3 | ROR1 ECD | 5.66E+05 | 6.45E−04 | 1.14E−09 |
| w/hOKT3 LC1 | ROR1 ECD | | Not detected | |

Accordingly, this example indicates that an anti-ROR1 antibody can be provided, wherein the antibody includes a heavy chain containing a $V_H$ sequence comprising, consisting of, or consisting essentially of any one of SEQ ID NOs: 979-1020, and wherein the light chain contains a $V_L$ comprising, consisting of, or consisting essentially of any one of SEQ ID NOs: 1021-1026. In addition, anti-ROR1 antibody can be provided, wherein the antibody includes a heavy chain containing a $V_H$ sequence comprising, consisting of, or consisting essentially of any one of SEQ ID NOs: 1021-1026, and wherein the light chain is obtained from the light chain of any suitable antibody.

Example 12

Characteristics of Illustrative Anti-ROR1 Antibodies

Tables 8 through 11 show results obtained using the illustrative antibodies described herein. Tables 8 and 9 show results obtained with antibodies isolated with affinity maturation of initial leads. Table 10 shows results obtained with antibodies isolated from affinity maturation of initial antibody leads constructed with a trastuzumab light chain. Table 11 shows results obtained with antibodies isolated from affinity maturation of initial antibody leads constructed with an SP34 light chain.

TABLE 8

Affinity-matured antibodies from initial leads (Trastuzumab HC framework).

| Fab-HC Variant ID | HCT 116-hROR1 Binding | | Mino Nb-PBD, drug-conjugated 2° antibody Cell Killing | | Biacore human ROR1-ECD | | | ROR1/ROR2 ELISA ratio | TM2 (° C.) |
|---|---|---|---|---|---|---|---|---|---|
| | Bmax (MFI) | Kd (nM) | IC50 (nM) | Span (%) | ka (1/Ms) | kd (1/s) | KD (M) | | |
| SRP1987-C05 parent | 9497 | 0.04 | 7.7E-04 | 68.0 | 9.81E+05 | 6.81E-04 | 6.94E-10 | ND | 83 |
| SRP2188-A02 | 9388 | 0.03 | 7.0E-04 | 65.0 | ND | ND | ND | 33 | 79 |
| SRP2188-A03 | 9704 | 0.03 | 1.0E-03 | 71.0 | 7.66E+05 | 3.89E-04 | 5.08E-10 | 24 | 81 |
| SRP2188-A05 | 9029 | 0.04 | 1.0E-03 | 71.0 | 1.07E+06 | 2.43E-04 | 2.27E-10 | 31 | 77 |
| SRP2188-A06 | 8953 | 0.02 | ND | ND | ND | ND | ND | ND | 75 |
| SRP2188-A07 | 9328 | 0.07 | 4.8E-04 | 75.0 | 6.66E+05 | 4.06E-04 | 6.09E-10 | 24 | 77 |
| SRP2188-A08 | 8127 | 0.18 | 2.0E-02 | 75.0 | ND | ND | ND | 27 | 74 |
| SRP2188-A09 | 9384 | 0.03 | 8.8E-04 | 71.0 | 9.44E+05 | 4.01E-04 | 4.24E-10 | 23 | 78 |
| SRP2188-A10 | 9148 | 0.03 | ND | ND | 5.22E+05 | 2.22E-04 | 4.26E-10 | ND | 74 |
| SRP2188-A11 | 8338 | 0.06 | ND | ND | 1.07E+06 | 3.79E-04 | 3.54E-10 | ND | 70 |
| SRP2188-B01 | 9470 | 0.04 | 6.9E-04 | 75.0 | ND | ND | ND | 23 | 76 |
| SRP2188-B02 | 9765 | 0.03 | ND | ND | ND | ND | ND | ND | 75 |
| SRP2188-B03 | 9559 | 0.04 | 1.7E-03 | 71.0 | 9.65E+05 | 3.34E-04 | 3.46E-10 | 16 | 79 |
| SRP2188-B04 | 9664 | 0.05 | 1.2E-03 | 73.0 | ND | ND | ND | 47 | 76 |
| SRP2188-B05 | 8512 | 0.03 | 1.1E-03 | 70.0 | 8.87E+05 | 6.71E-04 | 7.57E-10 | 12 | 77 |
| SRP2188-B06 | 9126 | 0.06 | ND | ND | 9.27E+05 | 4.67E-04 | 5.04E-10 | ND | 69 |
| SRP2188-B07 | 8755 | 0.07 | 1.4E-03 | 72.0 | 8.80E+05 | 1.94E-04 | 2.21E-10 | 58 | 72 |
| SRP2188-B08 | 9207 | 0.09 | 6.2E-03 | 71.0 | ND | ND | ND | 25 | 76 |
| SRP2188-B09 | 9415 | 0.05 | ND | ND | 8.82E+05 | 5.79E-04 | 6.57E-10 | ND | 77 |
| SRP2188-B10 | 9002 | 0.04 | ND | ND | 1.17E+06 | 5.39E-04 | 4.62E-10 | ND | 74 |
| SRP2188-B11 | 8734 | 0.04 | ND | ND | ND | ND | ND | ND | 74 |
| SRP2188-C01 | 10149 | 0.38 | ND | ND | ND | ND | ND | ND | 72 |
| SRP2188-C02 | 9925 | 0.13 | 1.0E-02 | 73.0 | ND | ND | ND | 28 | 72 |
| SRP2188-C03 | 9595 | 0.03 | 1.1E-03 | 71.0 | ND | ND | ND | 34 | 77 |
| SRP2188-C04 | 9503 | 0.03 | ND | ND | 7.23E+05 | 1.01E-04 | 1.39E-10 | ND | 72 |
| SRP2188-C05 | 9507 | 0.06 | ND | ND | 1.06E+06 | 4.53E-04 | 4.27E-10 | ND | 76 |
| SRP2188-C06 | 9581 | 0.03 | ND | ND | ND | ND | ND | ND | 79 |
| SRP2188-C07 | 9160 | 0.04 | 8.5E-04 | 71.0 | ND | ND | ND | 20 | 76 |
| SRP2188-C08 | 8566 | 0.03 | ND | ND | ND | ND | ND | ND | 73 |
| SRP2188-C09 | 9081 | 0.03 | 9.1E-04 | 71.0 | 8.33E+05 | 4.20E-04 | 5.04E-10 | 19 | 76 |
| SRP2188-C10 | 9310 | 0.05 | ND | ND | ND | ND | ND | ND | 73 |
| SRP2188-C11 | 9207 | 0.04 | ND | ND | 7.07E+05 | 6.17E-04 | 8.73E-10 | ND | 79 |
| SRP2188-D01 | 8936 | 0.04 | 1.1E-03 | 72.0 | ND | ND | ND | 25 | 77 |
| SRP2188-D02 | 10039 | 0.04 | 1.4E-03 | 72.0 | ND | ND | ND | 27 | 83 |
| SRP2188-D03 | 9107 | 0.04 | 8.9E-04 | 72.0 | 6.56E+05 | 5.50E-04 | 8.38E-10 | 16 | 81 |
| SRP2188-D04 | 9689 | 0.04 | 1.4E-03 | 69.0 | 9.94E+05 | 4.23E-04 | 4.26E-10 | 15 | 82 |
| SRP2188-D05 | 9840 | 0.04 | ND | ND | 7.47E+05 | 3.59E-04 | 4.80E-10 | ND | 76 |
| SRP2188-D06 | 9808 | 0.04 | 1.5E-03 | 69.0 | 8.97E+05 | 5.63E-04 | 6.28E-10 | 18 | 82 |
| SRP2188-D07 | 8989 | 0.04 | 1.7E-03 | 70.0 | ND | ND | ND | 38 | 75 |
| SRP2188-D08 | 9598 | 0.05 | ND | ND | 7.03E+05 | 2.68E-04 | 3.81E-10 | ND | 72 |
| SRP2188-D09 | 8974 | 0.06 | 1.3E-03 | 70.0 | 7.66E+05 | 2.80E-04 | 3.66E-10 | 21 | 76 |
| SRP2188-D10 | 9071 | 0.05 | 1.0E-03 | 65.0 | ND | ND | ND | 26 | 83 |
| SRP2188-D11 | 9599 | 0.02 | ND | ND | 7.43E+05 | 5.50E-04 | 7.41E-10 | ND | 73 |
| SRP2188-E01 | 9369 | 0.06 | 1.5E-03 | 69.0 | 4.68E+05 | 3.87E-04 | 8.27E-10 | 25 | 74 |
| SRP2188-E02 | 10522 | 0.07 | 7.5E-04 | 76.0 | ND | ND | ND | 15 | 76 |

TABLE 8-continued

Affinity-matured antibodies from initial leads (Trastuzumab HC framework).

| Fab-HC Variant ID | HCT 116-hROR1 Binding | | Mino Nb-PBD, drug-conjugated 2° antibody Cell Killing | | Biacore human ROR1-ECD | | | ROR1/ROR2 ELISA ratio | TM2 (° C.) |
|---|---|---|---|---|---|---|---|---|---|
| | Bmax (MFI) | Kd (nM) | IC50 (nM) | Span (%) | ka (1/Ms) | kd (1/s) | KD (M) | | |
| SRP2188-E03 | 10336 | 0.02 | 1.3E−03 | 65.0 | 7.18E+05 | 3.33E−04 | 4.64E−10 | 14 | 80 |
| SRP2188-E04 | 9857 | 0.03 | 8.7E−04 | 66.0 | 7.75E+05 | 4.68E−04 | 6.04E−10 | 15 | 81 |
| SRP2188-E05 | 10620 | 0.05 | ND | ND | 8.40E+05 | 3.10E−04 | 3.69E−10 | ND | 75 |
| SRP2188-E06 | 9967 | 0.04 | ND | ND | 7.90E+05 | 3.46E−04 | 4.38E−10 | ND | 79 |
| SRP2188-E07 | 7597 | 0.02 | ND | ND | ND | ND | ND | ND | 82 |
| SRP2188-E08 | 9329 | 0.03 | ND | ND | ND | ND | ND | ND | 76 |
| SRP2188-E09 | 9781 | 0.02 | ND | ND | ND | ND | ND | ND | 73 |
| SRP2188-E10 | 9116 | 0.04 | 9.9E−04 | 73.0 | ND | ND | ND | 14 | 82 |
| SRP2188-E11 | 9248 | 0.03 | ND | ND | ND | ND | ND | ND | 72 |
| SRP2188-F01 | 8665 | 0.02 | ND | ND | 5.78E+05 | 3.16E−04 | 5.46E−10 | ND | 77 |
| SRP2188-F02 | 9848 | 0.03 | ND | ND | ND | ND | ND | ND | 78 |
| SRP2188-F03 | 10074 | 0.04 | 1.1E−03 | 71.0 | ND | ND | ND | 18 | 75 |
| SRP2188-F04 | 10030 | 0.03 | 7.2E−04 | 71.0 | ND | ND | ND | 17 | 73 |
| SRP2188-F05 | 9619 | 0.04 | ND | ND | 8.70E+05 | 5.10E−04 | 5.87E−10 | ND | 78 |
| SRP2188-F06 | 10150 | 0.03 | 5.5E−04 | 75.0 | 9.31E+05 | 3.57E−04 | 3.84E−10 | 11 | 80 |
| SRP2188-F07 | 9872 | 0.03 | ND | ND | ND | ND | ND | ND | 78 |
| SRP2188-F08 | 9032 | 0.02 | 7.1E−04 | 75.0 | 9.87E+05 | 4.22E−04 | 4.28E−10 | 25 | 76 |
| SRP2188-F09 | 8764 | 0.02 | 1.8E−03 | 59.0 | ND | ND | ND | 25 | 76 |
| SRP2188-F10 | 8477 | 0.03 | ND | ND | 1.00E+06 | 3.99E−04 | 3.99E−10 | ND | 74 |
| SRP2188-F11 | 9477 | 0.03 | 9.9E−04 | 68.0 | 7.94E+05 | 2.49E−04 | 3.13E−10 | 14 | 79 |
| SRP2188-G01 | 9749 | 0.05 | 1.5E−03 | 61.0 | ND | ND | ND | 26 | 82 |
| SRP2188-G02 | 8919 | 0.02 | 4.7E−04 | 74.0 | 9.05E+05 | 4.43E−04 | 4.90E−10 | 16 | 78 |
| SRP2188-G03 | 8959 | 0.03 | 9.7E−04 | 70.0 | 8.46E+05 | 3.16E−04 | 3.73E−10 | 17 | 78 |
| SRP2188-G04 | 8994 | 0.02 | ND | ND | 6.39E+05 | 2.59E−04 | 4.06E−10 | ND | 77 |

ND = not determined,
Nb = anti-Fc nanobody

TABLE 9

Affinity-matured antibodies from initial leads (Trastuzumab HC framework).

| Fab-HC Variant ID | HCT 116-hROR1 Binding | | Mino Nb-PBD, drug-conjugated 2° antibody Cell Killing | | Biacore human ROR1-Fz | | | ROR1/ROR2 ELISA ratio | TM2 (° C.) |
|---|---|---|---|---|---|---|---|---|---|
| | Bmax (MFI) | Kd (nM) | EC50 (nM) | Span (%) | ka (1/Ms) | kd (1/s) | KD (M) | | |
| SRP1943-C02 | ND | ND | NC | NC | 5.39E+05 | 0.05 | 9.76E−08 | ND | ND |
| SRP2193-A01 | NSB | NSB | ND | ND | ND | ND | ND | ND | 85 |
| SRP2193-A02 | NSB | NSB | ND | ND | ND | ND | ND | ND | 85 |
| SRP2193-A03 | NSB | NSB | ND | ND | ND | ND | ND | ND | 81 |
| SRP2193-A04 | NSB | NSB | ND | ND | ND | ND | ND | ND | 83 |
| SRP2193-A05 | NSB | NSB | ND | ND | ND | ND | ND | ND | 85 |
| SRP2193-A06 | NSB | NSB | ND | ND | ND | ND | ND | ND | 79 |
| SRP2193-A07 | NSB | NSB | ND | ND | ND | ND | ND | ND | 85 |
| SRP2193-A08 | NSB | NSB | ND | ND | ND | ND | ND | ND | 85 |
| SRP2193-A09 | NSB | NSB | ND | ND | ND | ND | ND | ND | 85 |
| SRP2193-A10 | NSB | NSB | ND | ND | ND | ND | ND | ND | 84 |
| SRP2193-A11 | NSB | NSB | ND | ND | ND | ND | ND | ND | 85 |
| SRP2193-B01 | 15290 | 0.15 | 2.30E−03 | 66 | 1.58E+05 | 1.78E−04 | 1.13E−09 | 365 | 84 |
| SRP2193-B02 | 15591 | 0.28 | ND | ND | 2.18E+05 | 5.11E−04 | 2.35E−09 | ND | 81 |
| SRP2193-B03 | 15523 | 0.67 | ND | ND | 1.70E+05 | 5.05E−04 | 2.96E−09 | ND | 81 |
| SRP2193-B04 | 15611 | 0.4 | ND | ND | 1.72E+05 | 1.34E−04 | 7.78E−10 | ND | 82 |
| SRP2193-B05 | 15434 | 0.47 | ND | ND | ND | ND | ND | ND | 85 |
| SRP2193-B06 | 14589 | 1.7 | 2.70E−03 | 65 | 9.17E+04 | 4.87E−04 | 5.31E−09 | 220 | 79 |
| SRP2193-B07 | 15478 | 0.6 | ND | ND | ND | ND | ND | ND | 81 |
| SRP2193-B08 | 14261 | 1.15 | ND | ND | ND | ND | ND | ND | 78 |
| SRP2193-B09 | 15175 | 0.23 | 2.90E−03 | 67 | 1.19E+05 | 2.26E−04 | 1.90E−09 | 179 | 83 |
| SRP2193-B10 | 14689 | 1.08 | ND | ND | ND | ND | ND | ND | 83 |
| SRP2193-B11 | 15182 | 0.46 | 1.30E−03 | 66 | 1.58E+05 | 2.51E−04 | 1.59E−09 | 134 | 85 |
| SRP2193-C01 | 15857 | 0.39 | ND | ND | ND | ND | ND | ND | 83 |
| SRP2193-C02 | 15847 | 0.85 | 3.40E−03 | 62 | 2.78E+05 | 1.73E−03 | 6.20E−09 | 133 | 84 |
| SRP2193-C03 | 15749 | 0.14 | ND | ND | ND | ND | ND | ND | 84 |
| SRP2193-C04 | 14909 | 0.18 | ND | ND | 1.73E+05 | 2.07E−04 | 1.19E−09 | ND | 85 |
| SRP2193-C05 | 15074 | 1.75 | ND | ND | ND | ND | ND | ND | NA |

TABLE 9-continued

Affinity-matured antibodies from initial leads (Trastuzumab HC framework).

| Fab-HC Variant ID | HCT 116-hROR1 Binding | | Mino Nb-PBD, drug-conjugated 2° antibody Cell Killing | | Biacore human ROR1-Fz | | | ROR1/ROR2 ELISA ratio | TM2 (° C.) |
|---|---|---|---|---|---|---|---|---|---|
| | Bmax (MFI) | Kd (nM) | EC50 (nM) | Span (%) | ka (1/Ms) | kd (1/s) | KD (M) | | |
| SRP2193-C06 | 14480 | 4.16 | ND | ND | ND | ND | ND | ND | NA |
| SRP2193-C07 | NSB | NSB | NK | NK | not detected | not detected | not detected | 316 | NA |
| SRP2193-C08 | 14985 | 0.72 | ND | ND | ND | ND | ND | ND | 79 |
| SRP2193-C09 | 15509 | 0.35 | 1.60E−03 | 64 | 1.78E+05 | 3.94E−04 | 2.22E−09 | 89 | 84 |
| SRP2193-C10 | 16589 | 0.32 | ND | ND | ND | ND | ND | ND | NA |
| SRP2193-C11 | 15735 | 0.64 | 1.50E−03 | 63 | 1.15E+05 | 2.73E−04 | 2.37E−09 | 159 | 83 |
| SRP2193-D01 | 15966 | 1.3 | 5.10E−03 | 66 | not detected | not detected | not detected | 205 | 84 |
| SRP2193-D02 | 15477 | 1.22 | 3.80E−03 | 61 | 1.46E+05 | 1.01E−03 | 6.94E−09 | 151 | 83 |
| SRP2193-D03 | 15749 | 0.93 | ND | ND | ND | ND | ND | ND | 85 |
| SRP2193-D04 | 15008 | 0.7 | 4.50E−03 | 65 | 1.04E+05 | 2.92E−04 | 2.81E−09 | 136 | 83 |
| SRP2193-D05 | 15763 | 1.64 | 4.20E−03 | 59 | 1.14E+05 | 3.31E−04 | 2.89E−09 | 107 | 84 |
| SRP2193-D06 | 14315 | 0.28 | 5.70E−03 | 68 | 5.94E+06 | 0.6 | 1.01E−07 | 157 | 82 |
| SRP2193-D07 | 15430 | 3.11 | ND | ND | ND | ND | ND | ND | 83 |
| SRP2193-D08 | 14818 | 0.41 | ND | ND | not detected | not detected | not detected | ND | ND |
| SRP2193-D09 | 14680 | 0.83 | ND | ND | not detected | not detected | not detected | ND | 83 |
| SRP2193-D10 | 14785 | 0.64 | ND | ND | 1.05E+05 | 3.79E−04 | 3.62E−09 | ND | 82 |
| SRP2193-D11 | 15218 | 1.25 | ND | ND | ND | ND | ND | ND | 84 |
| SRP2193-E01 | 16998 | 0.13 | ND | ND | 2.28E+05 | 2.42E−04 | 1.06E−09 | ND | 81 |
| SRP2193-E02 | 16434 | 8.13 | ND | ND | ND | ND | ND | ND | 83 |
| SRP2193-E03 | 14834 | 0.19 | ND | ND | 2.59E+05 | 2.94E−04 | 1.14E−09 | ND | 85 |
| SRP2193-E04 | 14375 | 15.56 | ND | ND | ND | ND | ND | ND | 79 |
| SRP2193-E05 | 18303 | 0.1 | 3.40E−04 | 70 | 2.95E+05 | 1.99E−04 | 6.74E−10 | 165 | 83 |
| SRP2193-E06 | 14658 | 5.82 | 2.50E−03 | 63 | 1.11E+05 | 2.46E−04 | 2.23E−09 | 244 | 84 |
| SRP2193-E07 | 15154 | 0.68 | ND | ND | not detected | not detected | not detected | ND | ND |
| SRP2193-E08 | 15092 | 4.28 | ND | ND | 1.64E+05 | 6.51E−04 | 3.96E−09 | ND | 85 |
| SRP2193-E09 | 16298 | 0.46 | ND | ND | ND | ND | ND | ND | 82 |
| SRP2193-E10 | 15936 | 7.14 | ND | ND | ND | ND | ND | ND | 82 |
| SRP2193-E11 | 25400 | 1.33 | ND | ND | 3.70E+05 | 4.74E−04 | 1.28E−09 | ND | 81 |

ND = not determined,
NSB = non-saturating binding

TABLE 10

Affinity-matured antibodies from initial leads (Trastuzumab HC framework).

| Fab-HC Variant ID | HCT 116-hROR1 Binding | | Mino Nb-PBD, drug-conjugated 2° antibody Cell Killing | | Biacore human ROR1-Fz | | | ROR1/ROR2 ELISA ratio | TM2 (° C.) |
|---|---|---|---|---|---|---|---|---|---|
| | Bmax (MFI) | Kd (nM) | EC50 (nM) | Span (%) | ka (1/Ms) | kd (1/s) | KD (M) | | |
| SRP1944-A07 | ND | ND | 0.01 | 52 | 5.59E+05 | 0.01 | 2.45E−08 | ND | ND |
| SRP2194-A01 | 9009 | 0.12 | ND | ND | 3.04E+05 | 3.25E−04 | 1.07E−09 | ND | 78 |
| SRP2194-A02 | 9219 | 0.14 | ND | ND | 3.08E+05 | 4.29E−04 | 1.39E−09 | ND | 79 |
| SRP2194-A03 | 7614 | 5.35 | ND | ND | ND | ND | ND | ND | ND |
| SRP2194-A04 | 9047 | 0.16 | ND | ND | 1.98E+05 | 3.64E−04 | 1.84E−09 | ND | 79 |
| SRP2194-A05 | 8810 | 0.31 | 2.00E−03 | 65 | 2.06E+05 | 3.17E−04 | 1.54E−09 | 75.4 | 82 |
| SRP2194-A06 | 9050 | 0.49 | ND | ND | 5.16E+05 | 1.93E−03 | 3.75E−09 | ND | ND |
| SRP2194-A07 | 8768 | 0.41 | ND | ND | 1.71E+05 | 2.75E−04 | 1.61E−09 | ND | 79 |
| SRP2194-A08 | 8248 | 0.3 | ND | ND | ND | ND | ND | ND | 78 |
| SRP2194-A09 | 8240 | 0.13 | ND | ND | ND | ND | ND | ND | ND |
| SRP2194-A10 | 8247 | 0.16 | ND | ND | ND | ND | ND | ND | ND |
| SRP2194-A11 | 8664 | 0.1 | ND | ND | ND | ND | ND | ND | ND |
| SRP2194-B01 | 8863 | 0.14 | ND | ND | 2.74E+05 | 8.57E−04 | 3.12E−09 | ND | 79 |
| SRP2194-B02 | 9328 | 0.15 | ND | ND | 2.56E+05 | 7.10E−04 | 2.77E−09 | ND | 77 |
| SRP2194-B03 | 9482 | 0.18 | ND | ND | 2.07E+05 | 2.95E−04 | 1.42E−09 | ND | 79 |
| SRP2194-B04 | 9302 | 0.2 | ND | ND | 2.71E+05 | 3.92E−04 | 1.44E−09 | ND | 77 |

ND = not determined

TABLE 11

Affinity-matured antibodies from initial leads (Trastuzumab HC framework)

| | HCT 116-hROR1 Binding | | Biacore human ROR1-Fz | | | ROR1/ROR2 | |
|---|---|---|---|---|---|---|---|
| Fab-HC Variant ID | Bmax (MFI) | Kd (nM) | ka (1/Ms) | kd (1/s) | KD (M) | ELISA ratio | TM2 (° C.) |
| SRP2196-A01 | 15821 | 0.3 | ND | ND | ND | ND | 74 |
| SRP2196-A02 | 15153 | 0.2 | ND | ND | ND | ND | 71 |
| SRP2196-A03 | 15374 | 0.3 | 1.69E+05 | 2.75E−04 | 1.63E−09 | ND | 70 |
| SRP2196-A04 | 14237 | 0.1 | 1.39E+05 | 3.43E−04 | 2.46E−09 | ND | ND |
| SRP2196-A05 | 14805 | 0.3 | 1.75E+05 | 6.82E−04 | 3.90E−09 | ND | 71 |
| SRP2196-A06 | 14555 | 0.2 | 1.80E+05 | 6.90E−04 | 3.82E−09 | ND | 70 |
| SRP2196-A07 | 14058 | 0.2 | 1.86E+05 | 6.40E−04 | 3.44E−09 | 16.3 | 74 |
| SRP2196-A08 | 13900 | 0.2 | 1.83E+05 | 7.80E−04 | 4.26E−09 | ND | 69 |
| SRP2196-A09 | 14622 | 0.2 | 1.50E+05 | 5.68E−04 | 3.79E−09 | 20.1 | 75 |
| SRP2196-A10 | 14442 | 0.3 | 1.72E+05 | 4.79E−04 | 2.78E−09 | ND | 68 |
| SRP2196-A11 | 14023 | 0.0 | 1.91E+05 | 7.92E−04 | 4.16E−09 | ND | 73 |
| SRP2196-B01 | 15306 | 0.3 | 1.31E+05 | 4.01E−04 | 3.06E−09 | 17.2 | 75 |
| SRP2196-B02 | 14863 | 0.3 | 1.63E+05 | 2.27E−04 | 1.39E−09 | ND | 69 |
| SRP2196-B03 | 15628 | 0.6 | 1.24E+05 | 9.45E−04 | 7.64E−09 | 22.8 | 71 |
| SRP2196-B04 | 14363 | 0.5 | 1.27E+05 | 3.52E−04 | 2.78E−09 | ND | 72 |
| SRP2196-B05 | 14781 | 0.2 | ND | ND | ND | ND | 73 |
| SRP2196-B06 | 14791 | 0.4 | 1.42E+05 | 4.23E−04 | 2.98E−09 | ND | 70 |
| SRP2196-B07 | 15139 | 0.3 | 1.85E+05 | 2.69E−04 | 1.45E−09 | ND | 69 |
| SRP2196-B08 | 14390 | 0.2 | 1.56E+05 | 4.88E−04 | 3.13E−09 | ND | 75 |
| SRP2196-B09 | 15036 | 0.6 | 1.30E+05 | 4.27E−04 | 3.28E−09 | 27.3 | 72 |
| SRP2196-B10 | 14677 | 0.3 | 1.28E+05 | 3.34E−04 | 2.61E−09 | ND | 70 |
| SRP2196-B11 | 14663 | 0.2 | 1.37E+05 | 5.97E−04 | 4.36E−09 | 19.1 | 74 |
| SRP2196-C01 | 15699 | 0.3 | 1.25E+05 | 4.57E−04 | 3.66E−09 | ND | 70 |
| SRP2196-C02 | 15341 | 0.6 | 1.19E+05 | 3.60E−04 | 3.02E−09 | ND | 67 |
| SRP2196-C03 | 14962 | 0.4 | 1.43E+05 | 4.61E−04 | 3.23E−09 | ND | 69 |
| SRP2196-C04 | 13798 | 0.5 | 1.31E+05 | 7.04E−04 | 5.35E−09 | ND | 70 |
| SRP1944-A07 w SP34 LC3 | 13189 | 0.1 | 5.97E+05 | 8.50E−03 | 1.43E−08 | ND | ND |

ND = not determined

Example 13

Para-Azidomethylphenylalanine (pAMF) Incorporation

Non-natural para-azidomethylphenylalanine (pAMF) residues were incorporated in monoclonal antibodies (mAbs) in place of specific residues using XpressCF+® cell-free expression platform (Yin et al., 2017, Sci Rep 7(1):3026). Sites were chosen for pAMF incorporation to enable the conjugation of cytotoxin moieties via copper-catalyzed azide-alkyne cycloaddition (CuAAC) or a copper-free conjugation method, e.g., strain-promoted azide-alkyne cycloaddition (SPAAC) through dibenzocyclooctyne (DBCO or MO). mAbs were purified through affinity chromatography column followed by ion exchange chromatography columns.

Example 14

General Method for Conjugation of Compounds to Antibodies

Dibenzocylcooctyne (DBCO) compound was dissolved in dimethylsulfoxide (DMSO) to a final concentration of 5 mM. The conjugation was carried out in 1×PBS at antibody concentration of 1-30 mg/mL, DBCO compound to pAMF ratio of 1.5-3, and with 25% DMSO. The reaction mixture was incubated at room temperature for overnight. The conjugation efficiency was measured by LC/MS. Unconjugated DBCO compound was removed by cation exchange. The conjugate was formulated in formulation buffer supplemented with 9% sucrose. The drug to antibody ratio (DAR) was measured by LC/MS.

Example 15

Thermostability and Colloidal Stability

Thermal and colloidal stability of mAb 42 (HC 2188-D04 SEQ ID NO:895; LC SEQ ID NO:1021; unconjugated aROR1) and Conjugate 46 (aROR1 ADC) were measured by differential scanning fluorimetry (DSF) and dynamic light scattering (DLS), respectively. The values from these measurements are provided in Table 12. For the thermal stability of an antibody, the first melting peak (Tm1) coincides with the unfolding of the CH2 domain (FC stability), while the second melting peak (Tm2) occurs upon unfolding of the Fab domain. There is an improvement of FC stability after conjugation as the Tm1 shifts from 63.1° C. to 70.4° C., while the Fab stability (Tm2) remains stable.

For the colloidal stability of an antibody, the average particle radius (smaller radius=more tightly folded) and polydispersity (range of measured radii—an indicator of homogeneity) were measured in 1×PBS+10% sucrose buffer. While the radius and polydispersity did increase after conjugation, both measurements are within acceptable parameters (radius of an antibody is typically ~5-6 nm, while polydispersity<15% is considered a homogeneous product) and indicate that Conjugate 46 is a well-behaved antibody in this buffer.

TABLE 12

Biophysical characterization of mAb 42 and Conjugate 46 by DSF and DLS

| | Thermal Stability (DSF) | | Colloidal Stability (DLS) | |
|---|---|---|---|---|
| | Tm1 (° C.) | Tm2 (° C.) | Radius (nm) | Polydispersity (%) |
| mAb 42 | 63.1 | 81.7 | 4.9 | 6.7 |
| Conjugate 46 | 70.4 | 80.3 | 5.4 | 11.8 |

Example 16

Conjugates 46 & 47 Stability Assessment

Stability assessment for Conjugate 46 and Conjugate 47 were evaluated under various stress conditions in several different formulation buffers. Study 1: Accelerated short term temperature stability was tested for signs of aggregation/degradation at 4° C., 25° C., and 37° C. and evaluated over a 2-week period. Study 2: Freeze/thaw stability was evaluated over five freeze/thaw cycles. Study 3: Determine the effect of protein aggregation induced through high concentrations at >40 mg/mL and prolonged hold times at 4° C. The formulations used in this study include:
Buffer #1: 10 mM citrate, 9% sucrose, pH 6.0
Buffer #2: 10 mM citrate, 150 mM NaCl, 9% sucrose, pH 6.0
Buffer #3: 10 mM histidine, 9% sucrose, pH 7.0

Figure 10A:
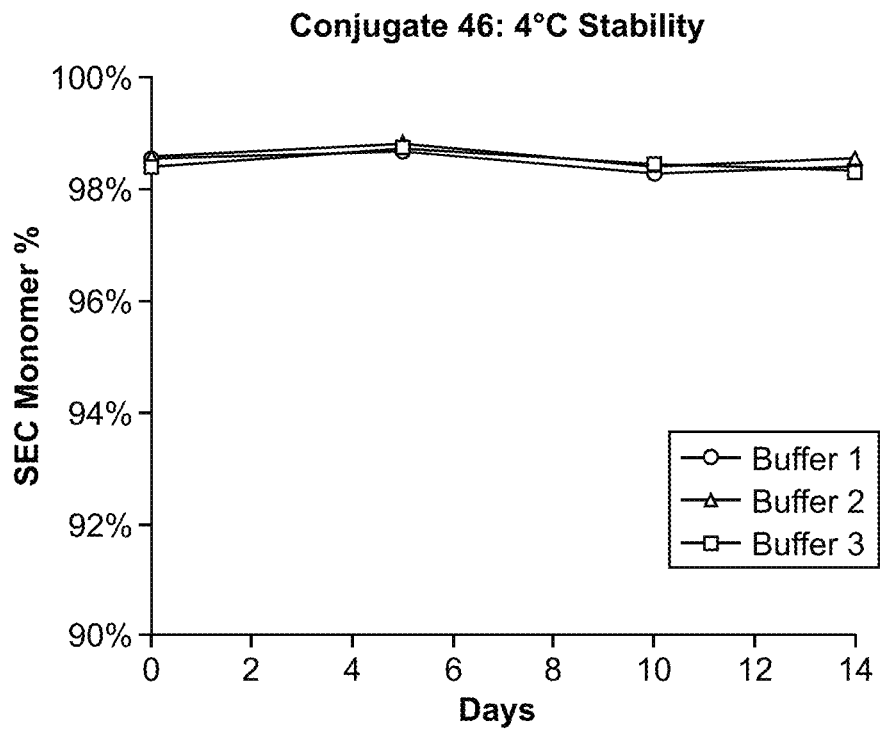
FIG. 10A provides formulation buffer comparison for Conjugate 46 at 4° C. conditions.
Figure 10B:
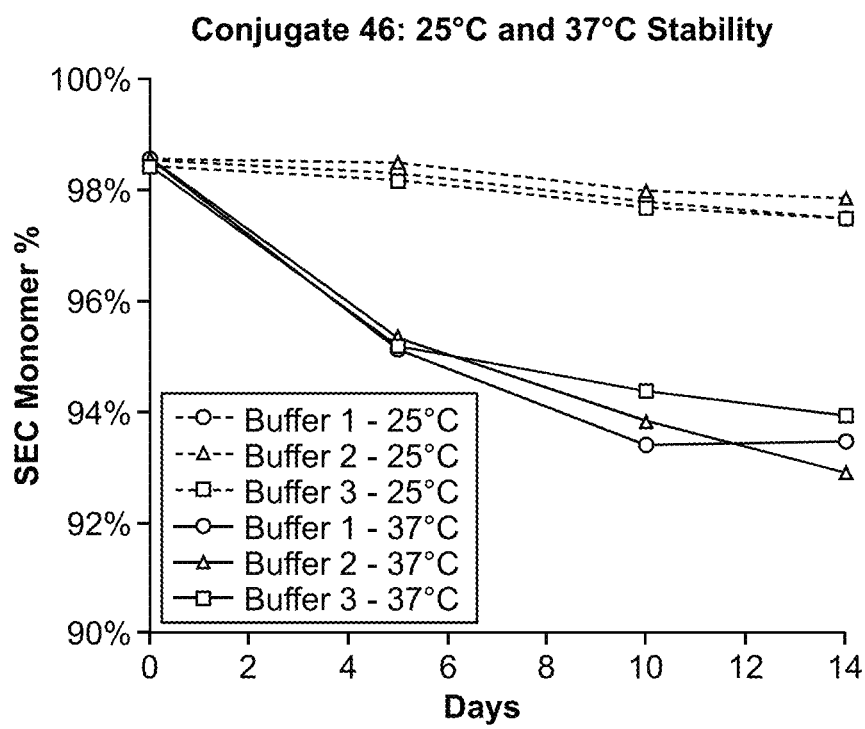
FIG. 10B provides formulation buffer comparison for Conjugate 46 at 25° C. and 37° C. conditions.
Figure 10C:
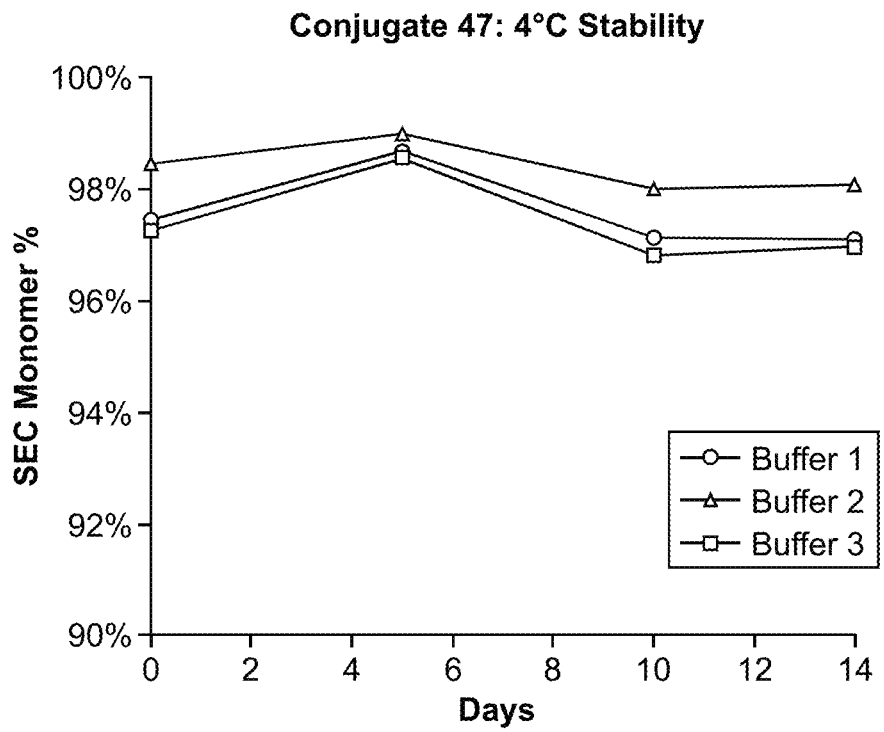
FIG. 10C provides formulation buffer comparison for Conjugate 47 at 4° C. conditions.
Figure 10D:
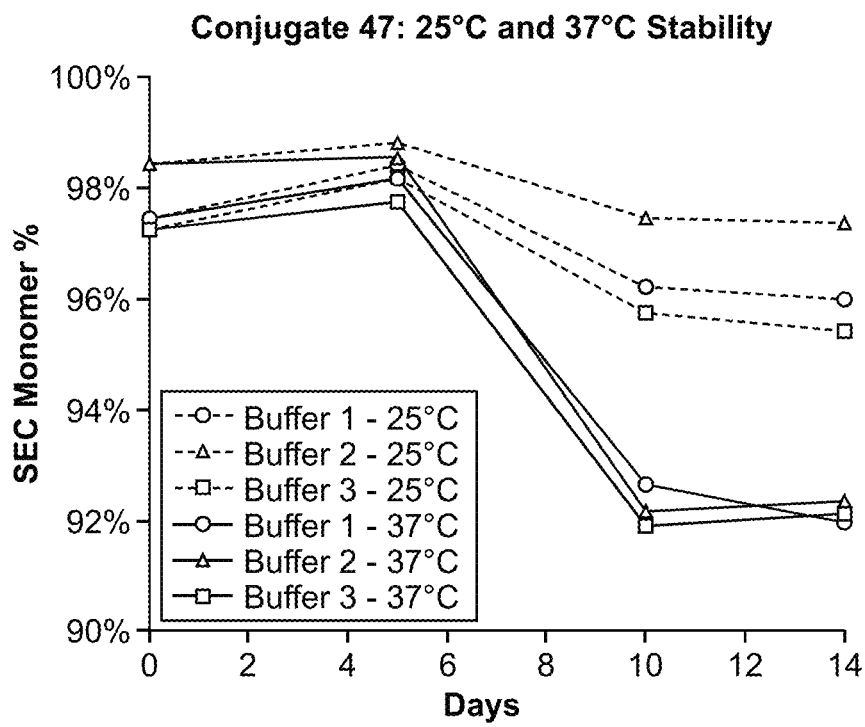
FIG. 10D provides formulation buffer comparison for Conjugate 47 at 25° C. and 37° C. conditions.

As shown in FIG. 10A and FIG. 10B, Conjugate 46 at 4° C. and 25° C. did not show significant biophysical changes in any of the formulation buffers, however at 37° C. Conjugate 46 was aggregated which resulted in a decrease of monomer percentage. Conjugate 47 showed comparable results in FIG. 10C and FIG. 10D, no significant changes in overall product quality at 4° C. and 25° C., but significantly impacted over the 2-week hold at 37° C.

Figure 10E:
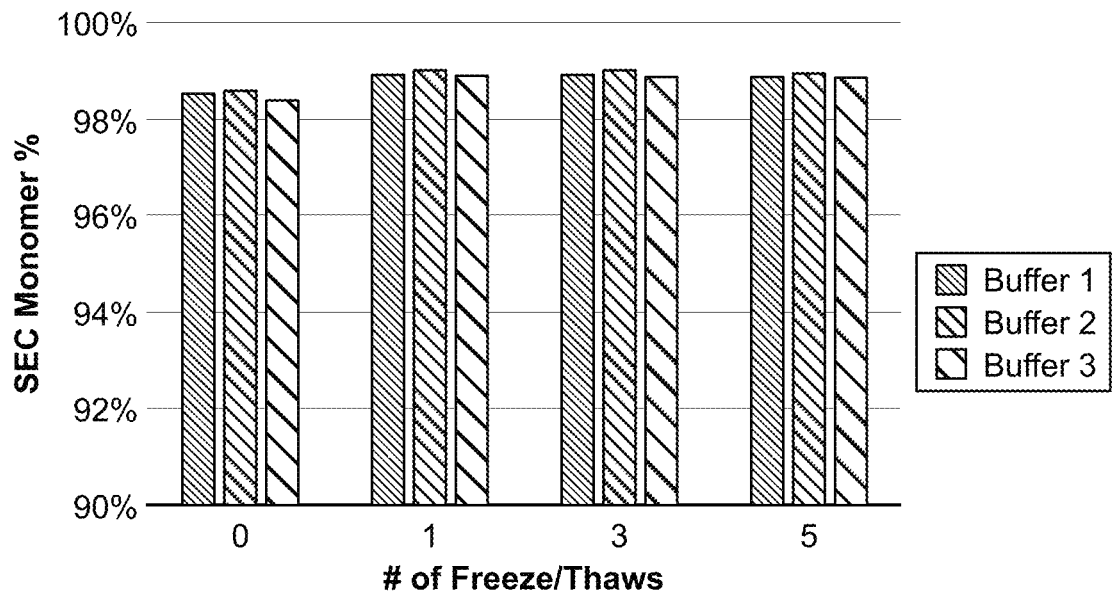
FIG. 10E provides HPLC-SEC results over 5× freeze/thaw cycles for Conjugate 46.
Figure 10F:
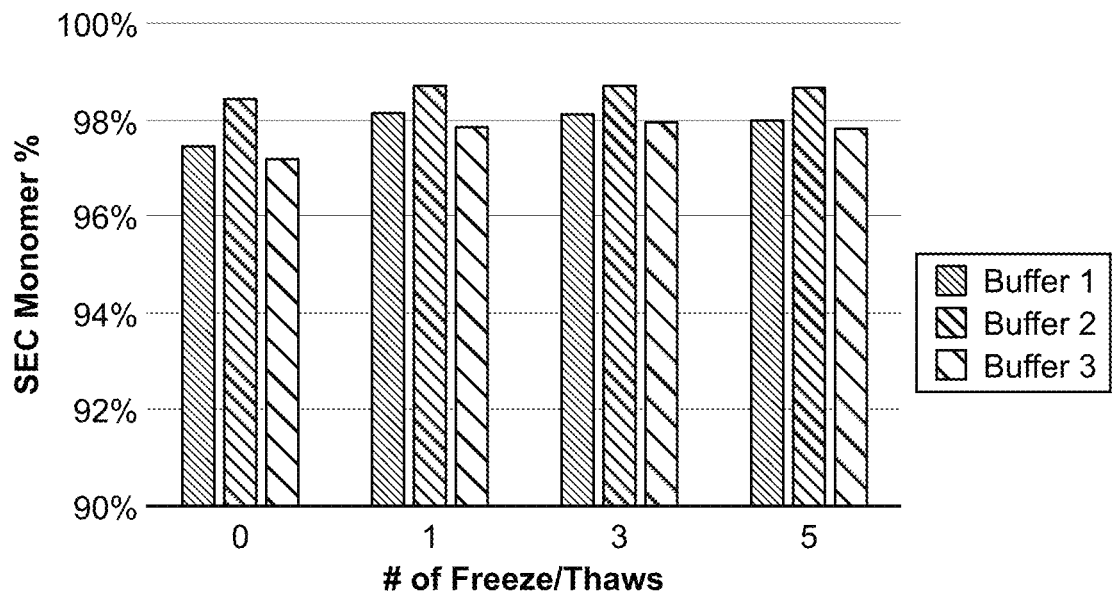
FIG. 10F provides HPLC-SEC results over 5× freeze/thaw cycles for Conjugate 47.
Figure 10G:
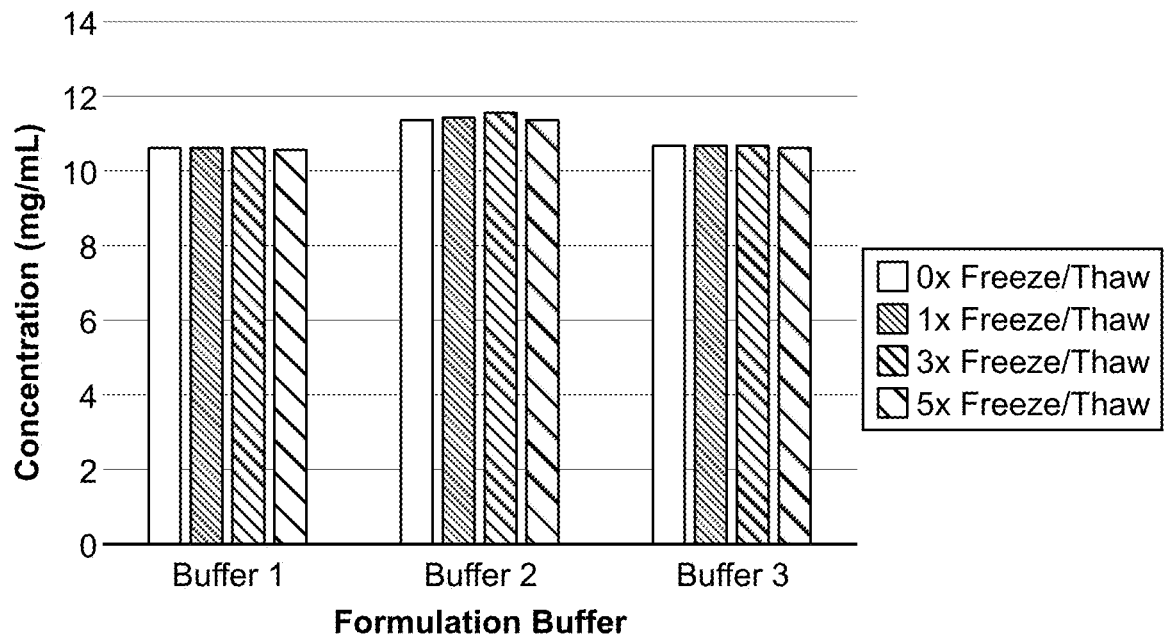
FIG. 10G provides protein concentration results over 5× freeze/thaw cycles for Conjugate 46.
Figure 10H:
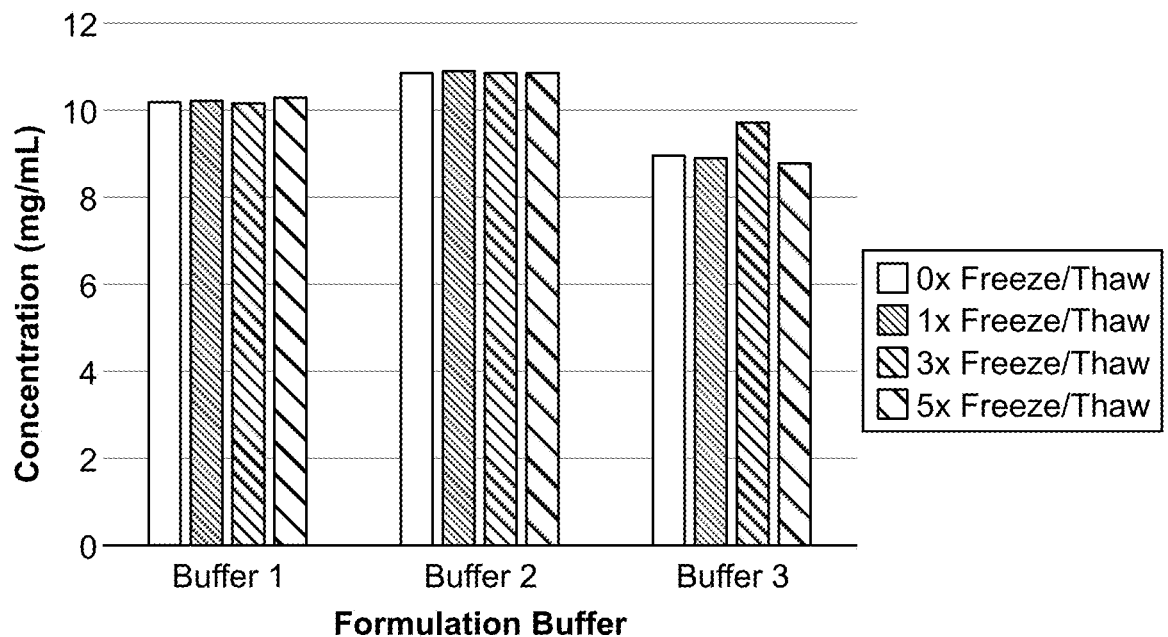
FIG. 10H provides protein concentration results over 5× freeze/thaw cycles for Conjugate 47.

Five freeze/thaw cycles were performed on Conjugate 46 and Conjugate 47. After one, three, and five freeze/thaw cycles, an aliquot from both samples was assayed by A280 and HPLC-SEC. HPLC-SEC (FIG. 10E and FIG. 10F) and protein concentration (FIG. 10G and FIG. 10H) results were consistent across all five freeze/thaw cycles and in all three formulation buffers.

Figure 10I:
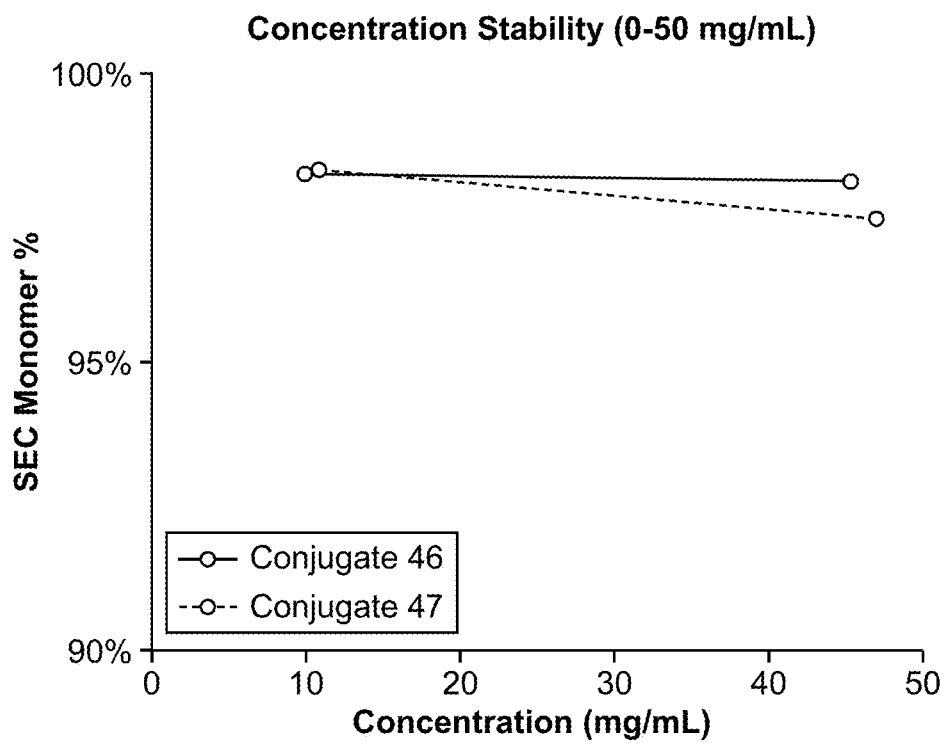
FIG. 10I and FIG. 10J provide SEC monomer % with increasing protein concentrations, 3-week hold at 4° C.
Figure 10J:
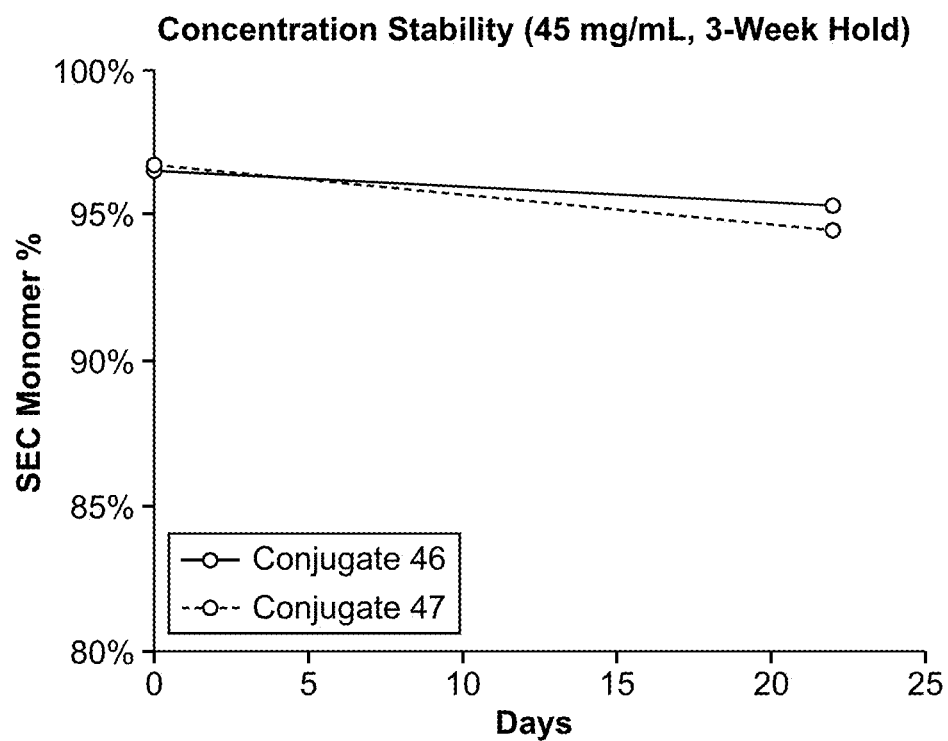
Figure 11A:
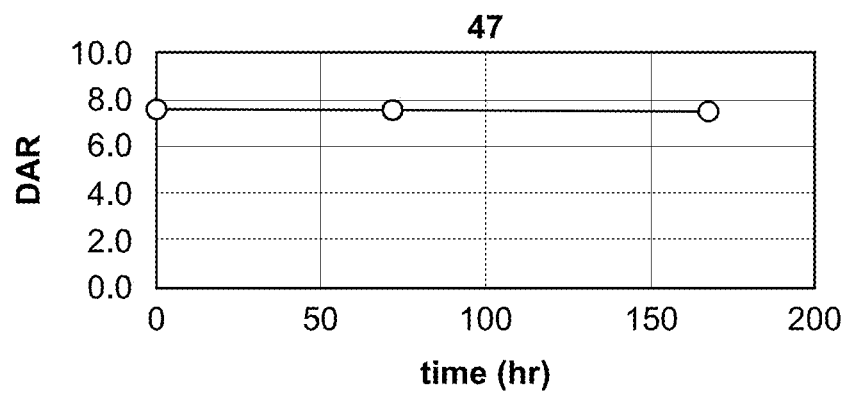
FIG. 11A provides calculated DAR of Conjugate 47 over 7 days.
Figure 11B:
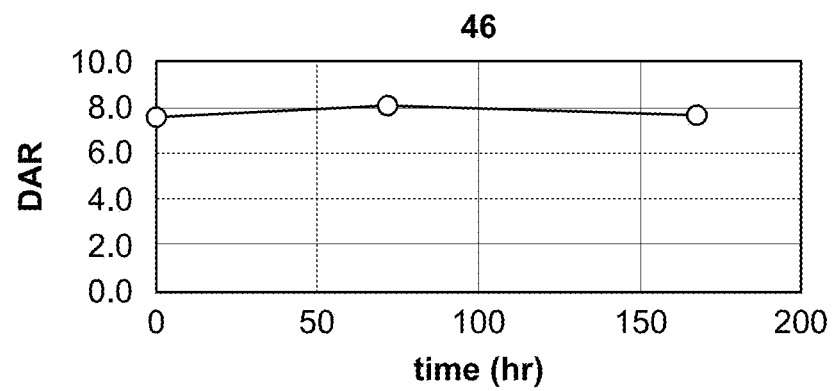
FIG. 11B provides calculated DAR of Conjugate 46 over 7 days.
Figure 11C:
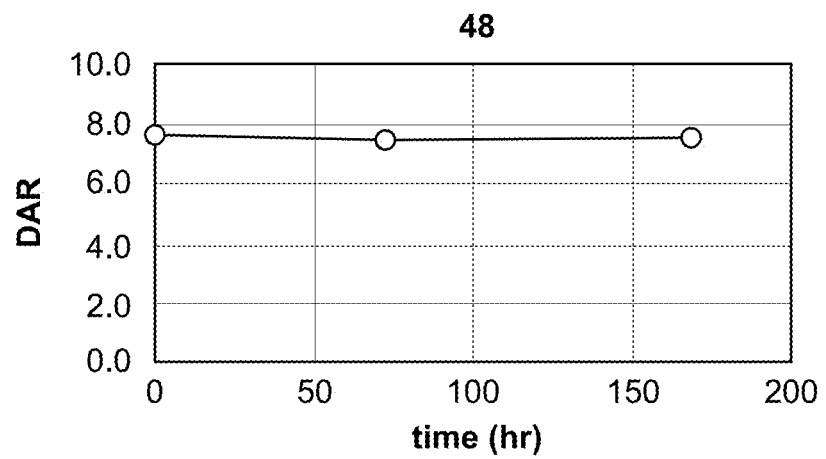
FIG. 11C provides calculated DAR of Conjugate 48 over 7 days.
Figure 11D:
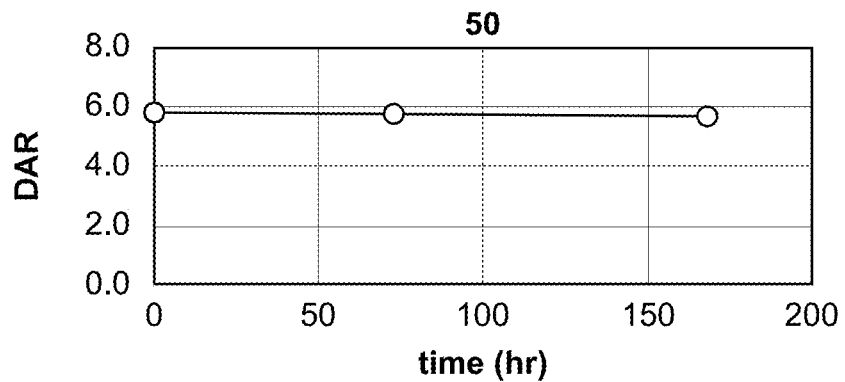
FIG. 11D provides calculated DAR of Conjugate 50 over 7 days.
Figure 11E:
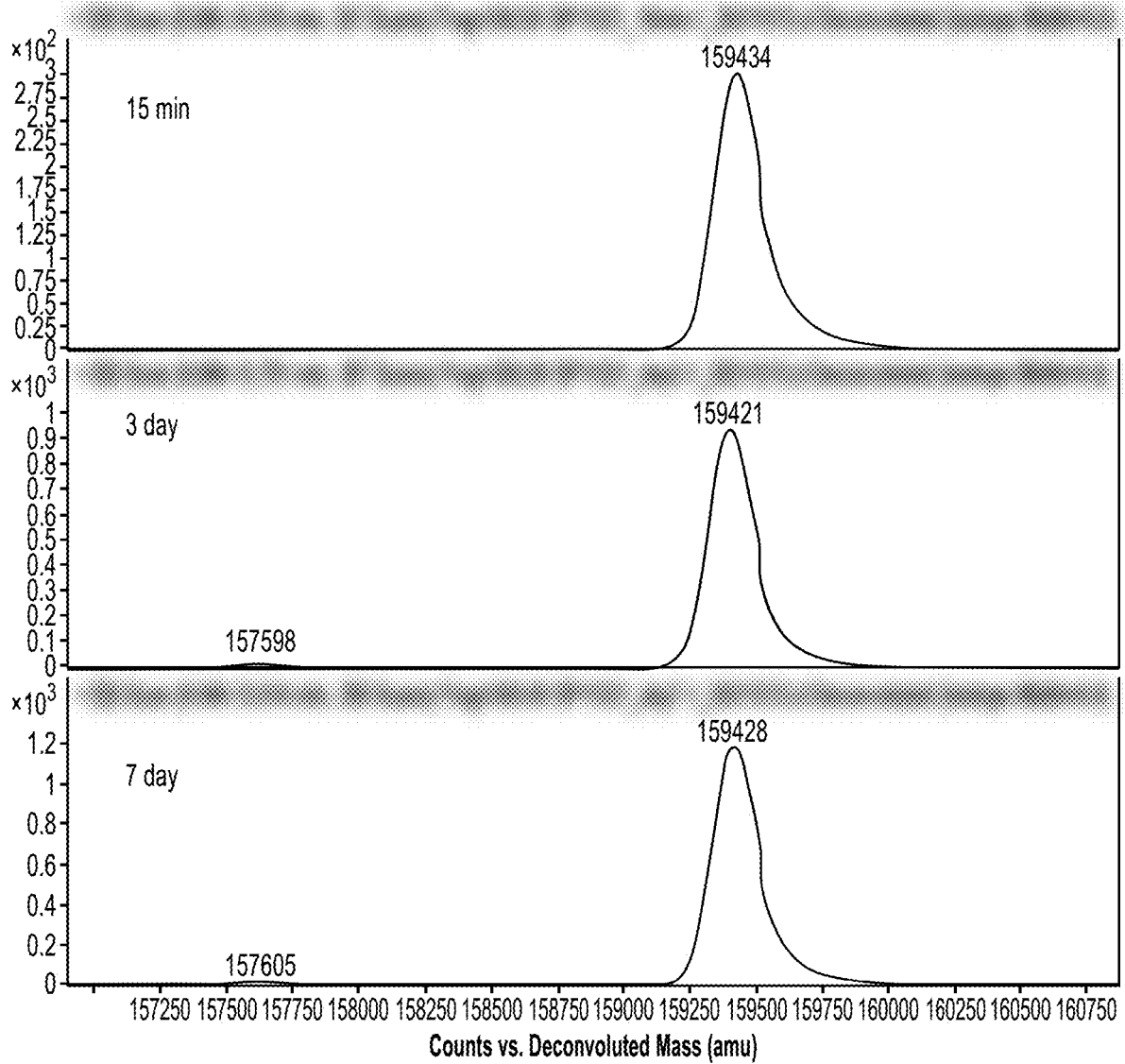
FIG. 11E provides deconvoluted mass spectra of aROR1 ADC samples from in vivo linker payload stability study for Conjugate 46.
Figure 11F:
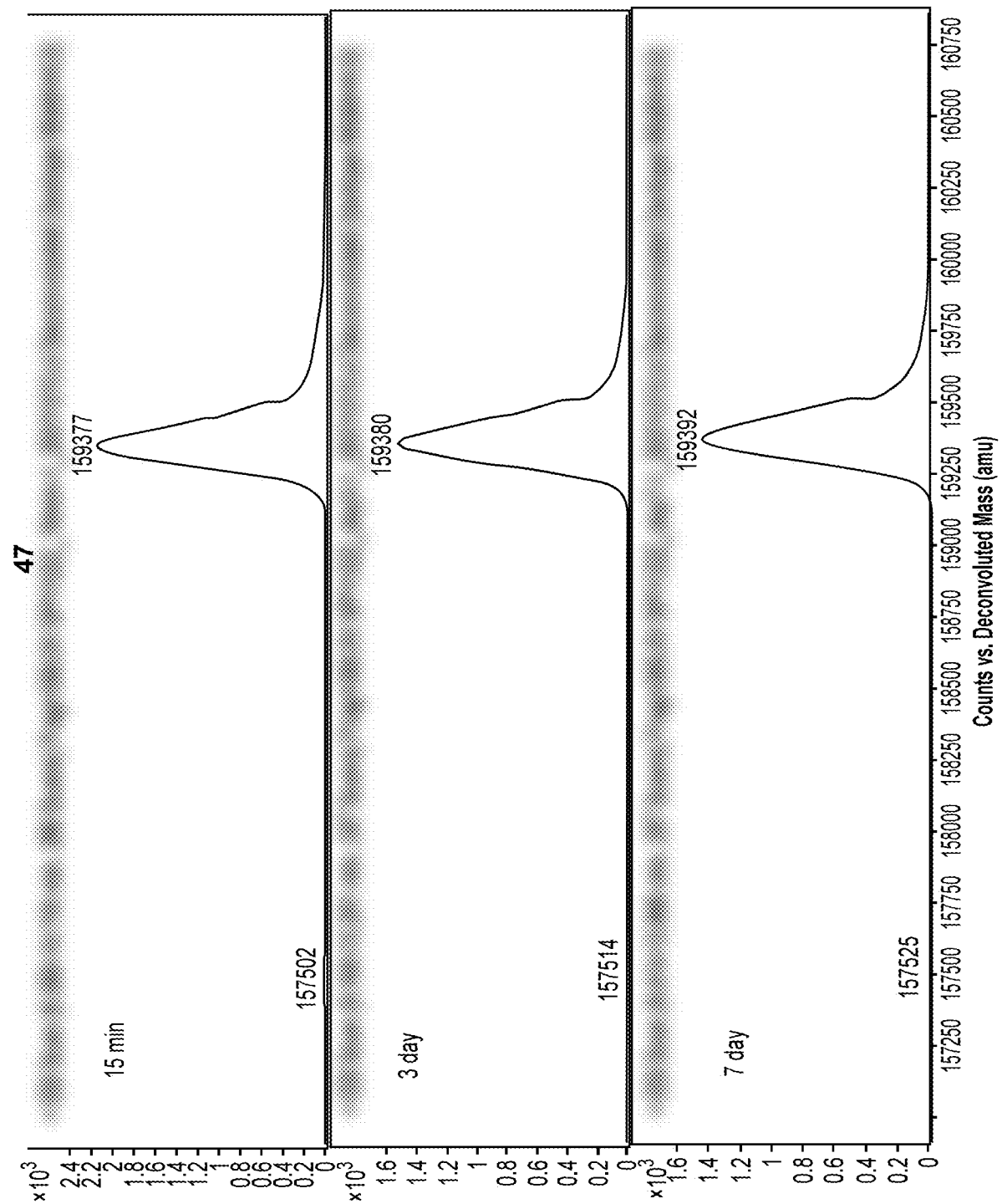
FIG. 11F provides deconvoluted mass spectra of aROR1 ADC samples from in vivo linker payload stability study for Conjugates 47.
Figure 11G:
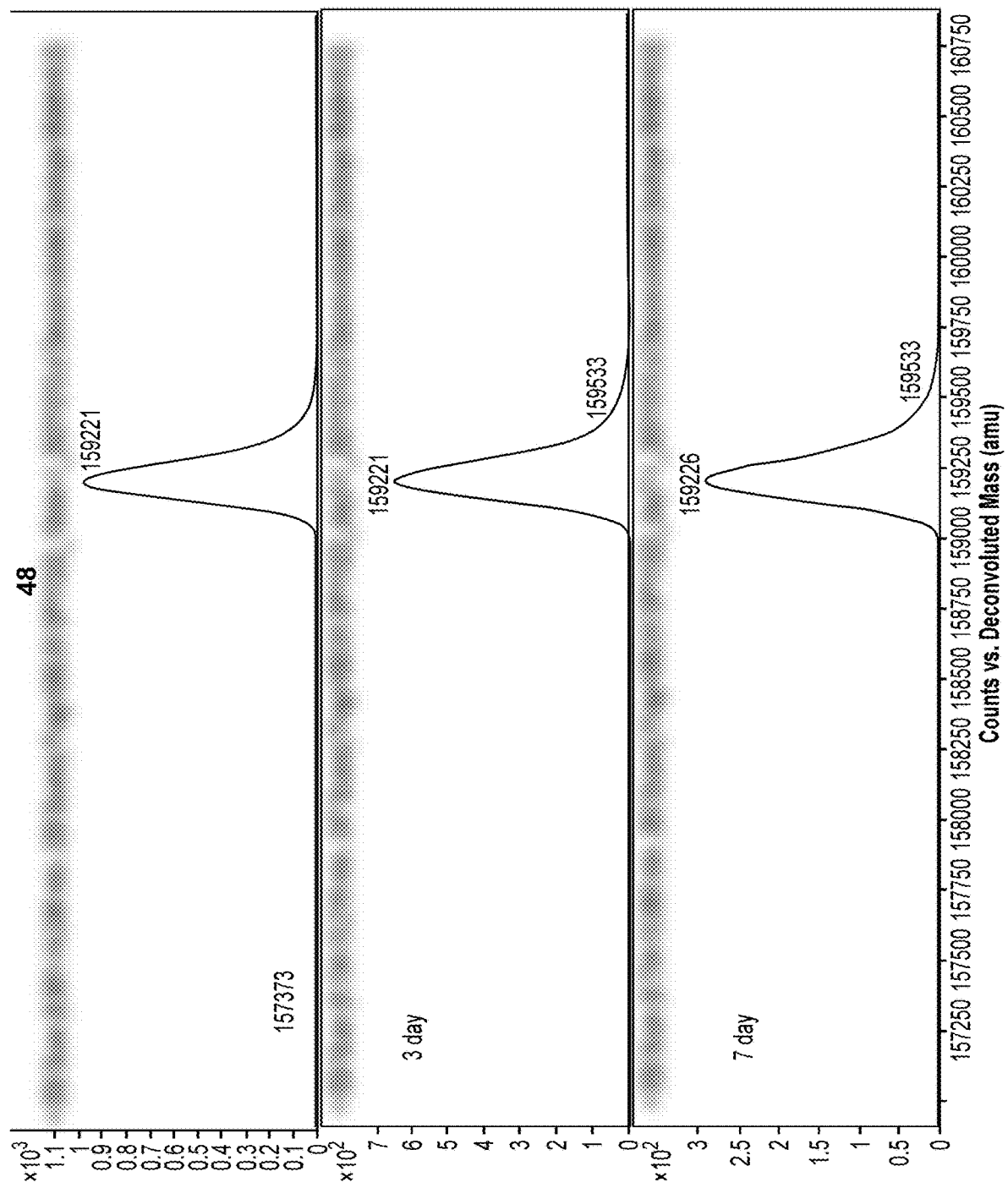
FIG. 11G provides deconvoluted mass spectra of aROR1 ADC samples from in vivo linker payload stability study for Conjugate 48.
Figure 11H:
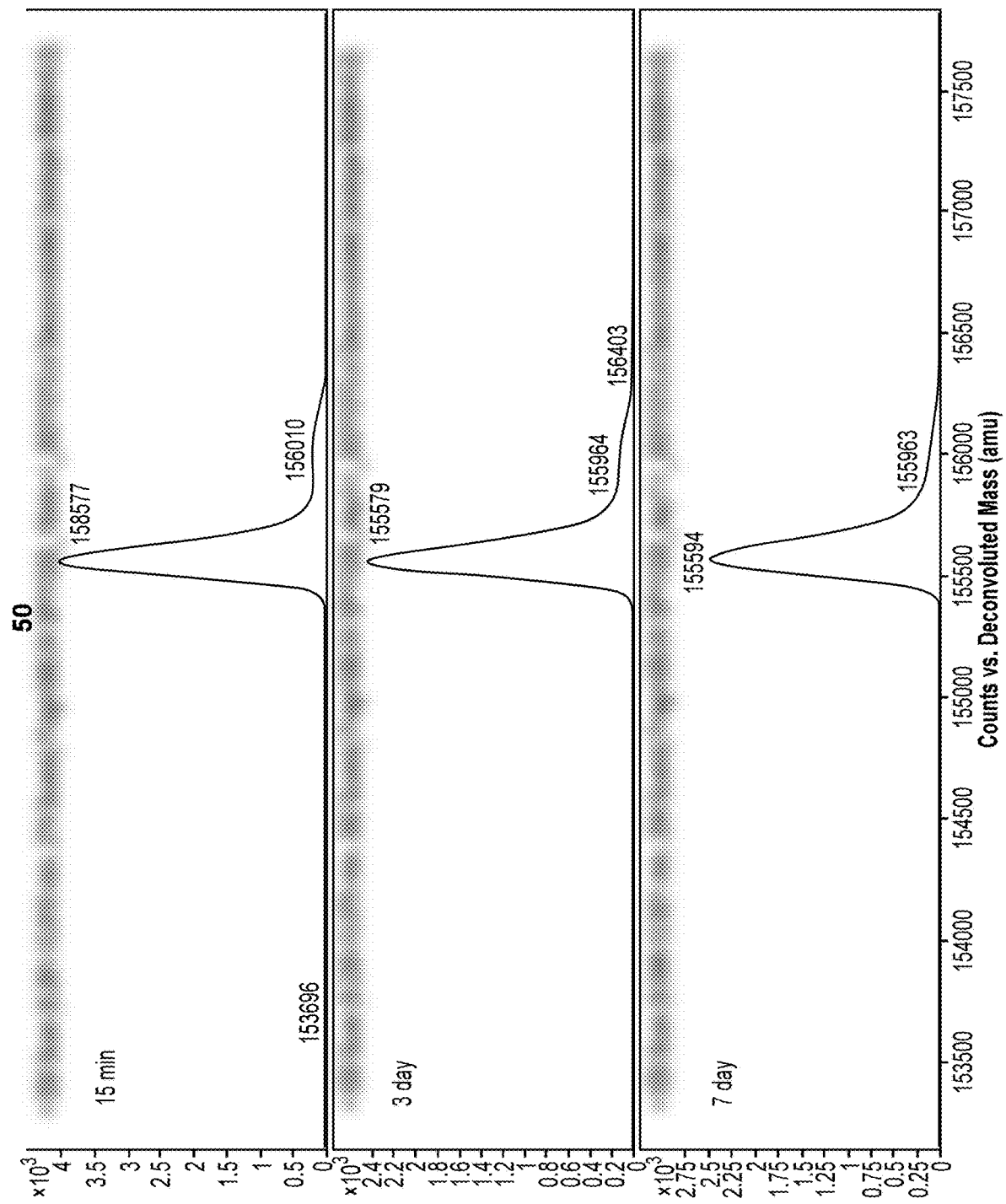
FIG. 11H provides deconvoluted mass spectra of aROR1 ADC samples from in vivo linker payload stability study for Conjugates 50.

As shown in FIG. 10I and FIG. 10J, Conjugate 46 and Conjugate 47 maintained a consistent monomer percentage throughout the elevated protein concentration assessment. After the 3-week hold at 4° C., both Conjugate 46 and Conjugate 47 demonstrated product stability and had a ≤3% decrease in monomer percentage.

Example 17

Linker Payload Stability of ADC in C57BL/6 Mice

In vivo linker payload stability of four ROR1 ADC was investigated in non-tumor bearing C57BL/6 mice in a single dose study. Briefly, Conjugates 46, 47, 48, and 50 were injected through $R^a$ at 5 mg/kg dose. Plasma samples were collected from 3 animals at 15 min, 3 days and 7 days after dosing and were kept frozen until ready to be analyzed. aROR1 ADC was pulled down from plasma using anti-hFc and then injected on to Agilent QToF for intact mass analysis. DAR was calculated based on deconvoluted peak area. As shown in FIGS. 11A-11D, the four ADCs tested were all stable over 7 days. As shown in FIGS. 11E-11H, no degradation products were observed in the deconvoluted mass spectra.

Example 18

In Vitro Cell Killing Activity of ROR1 ADCs

Anti-ROR1 antibody was conjugated to different linker-warheads described herein at different DARs and the cell killing activity of the ADCs were evaluated on ROR1 positive Ntera-2 cell and ROR1 negative MCF7 cells.

Ntera-2 or MCF7 cell at 625 cells/25 µL were seeded in a 384-well flat bottom white polystyrene plate one day before the assay start. ADCs were formulated at 2× starting concentration. Filter sterilized samples were serial diluted (1:3) under sterile conditions and added onto cells in triplicates. Plates were cultured at 37° C. in a $CO_2$ incubator for 120 hours. For cell viability measurement, 30 microliter of Cell Titer-Glo® reagent (Promega Corp, Madison, WI) was added into each well, and plates processed as per product instructions. Relative luminescence was measured on an ENVISION® plate reader (Perkin-Elmer; Waltham, MA). Relative luminescence readings were converted to % viability using untreated cells as controls. Data was fitted with non-linear regression analysis, using log (inhibitor) vs. response, variable slope, 4-parameter fit equation using GraphPad Prism.

The cell killing $EC_{50}$ and Span for ROR1 ADCs conjugated to different linker-warheads at different DARs on ROR1 positive Ntera-2 cell and ROR1 negative MCF7 cells are summarized in Tables 13-16.

TABLE 13

| | | | NTERA-2 | | MCF-7 | |
|---|---|---|---|---|---|---|
| Conjugate | Name | DAR | EC50 (nM) | Span (%) | EC50 (nM) | Span (%) |
| 5 | 2188-D04-F404-LP8 | 1.99 | 0.0101 | 83 | >10 | <10 |
| 3 | 2188-D04-Y180-LP9 | 1.7 | 0.0003 | 95 | >10 | <10 |
| 1 | 2188-D04-Y180/F404-LP1 | 3.99 | >10 | <20 | >10 | <10 |
| 2 | 2188-D04-Y180/F404/K42-LP1 | 5.98 | 0.082 | 49 | >10 | <10 |
| 4 | 2188-D04-Y180/F404/K42/E161-LP1 | 7.99 | 0.022 | 63 | >10 | <10 |
| 6 | 2188-D04-Y180/F404-LP10 | 3.99 | 0.08 | 53 | >10 | >40 |
| 7 | 2188-D04-Y180/F404/K42/E161-LP10 | 7.97 | 0.048 | 94 | >10 | >60 |
| | Exatecan | | 0.074 | 98 | 0.466 | 91 |
| | Gly-Exatecan | | 6.72 | 98 | 0.169 | 73 |
| | Dxd | | 0.26 | 99 | 0.83 | 63 |
| | Hemiasterlin | | 0.317 | 98 | 0.977 | 87 |
| | PNU-159682 | | 0.0025 | 99 | 0.016 | 92 |
| | PNU-EDA | | 0.026 | 99 | 0.3 | 85 |

TABLE 14

| | | | NTERA-2 | | MCF-7 | |
|---|---|---|---|---|---|---|
| Conjugate | Sample | DAR | EC50 (nM) | Span (%) | EC50 (nM) | Span (%) |
| 8 | D04-Y180/F404/K42/E161-LP2 | 8 | >10 | <10 | >10 | <10 |
| 9 | D04-Y180/F404/K42/E161-LP3 | 8 | 0.027 | 94 | >10 | <10 |

TABLE 14-continued

| Conjugate | Sample | DAR | NTERA-2 EC50 (nM) | NTERA-2 Span (%) | MCF-7 EC50 (nM) | MCF-7 Span (%) |
|---|---|---|---|---|---|---|
| 10 | D04-Y180/F404/K42/E161-LP4 | 8 | 0.004 | 77 | >10 | <10 |
| 11 | D04-Y180/F404/K42/E161-LP7 | 7.82 | >10 | <10 | >10 | <10 |
| 12 | D04-Y180/F404/K42/E161-LP5 | 7.77 | 0.008 | 94 | >10 | <10 |
| 13 | D04-Y180/F404/K42/E161-LP6 | 7.97 | 0.028 | 38 | >10 | <10 |
| 14 | D04-Y180/F404/K42/E161-LP12 | 8 | 0.036 | 56 | >10 | <10 |
| 15 | D04-Y180/F404/K42/E161-LP13 | 7.98 | 0.072 | 51 | >10 | <10 |
| 4 | D04-Y180/F404/K42/E161-LP1 | 7.99 | 0.023 | 58 | >10 | <10 |
| 16 | D04-Y180/F404/K42/E161-LP34 | 8 | >10 | <10 | >10 | <10 |

TABLE 14

| Conjugate | Sample | DAR | NTERA-2 EC50 (nM) | NTERA-2 Span (%) | MCF-7 EC50 (nM) | MCF-7 Span (%) |
|---|---|---|---|---|---|---|
| 4 | D04-Y180/F404/K42/E161-LP1 | 7.95 | 0.067 | 60 | >10 | <20 |
| 10 | D04-Y180/F404/K42/E161-LP4 | 7.52 | 0.019 | 86 | >10 | <20 |
| 22 | D04-Y180/F404-LP11 | 3.97 | >10 | <20 | >10 | <20 |
| 1 | D04-Y180/F404-LP1 | 3.99 | 0.085 | 56 | >10 | <20 |
| 21 | D04-Y180/F404-LP32 | 3.85 | >10 | <20 | >10 | <20 |
| 5 | D04-F404-LP8 | 1.87 | 0.021 | 85 | >10 | <20 |
| 21 | D04-F404-LP32 | 1.85 | 2.955 | 97 | >10 | >80 |
| 19 | D04-F404-LP30 | 1.84 | 0.043 | 83 | >10 | >40 |
| 20 | D04-F404-LP31 | 1.89 | >10 | >60 | >10 | >40 |
| 17 | D04-F404-LP14 | 1.91 | 0.030 | 77 | >10 | <20 |
| 23 | D04 x D04-F404-LP8 | 1.99 | 0.022 | 83 | >10 | <20 |
| 24 | D04 x C01-F404-LP8 biparatopic | 1.99 | 0.017 | 85 | >10 | <20 |
| 25 | D04 x B09-F404- LP8 biparatopic | 1.99 | 0.018 | 87 | >10 | <20 |
| 26 | D04 x A05-F404- LP8 biparatopic | 1.99 | 0.028 | 84 | >10 | <20 |
| 27 | D04 x B04-F404- LP8 biparatopic | 1.99 | 0.024 | 89 | >10 | <20 |
| 28 | A05 x B04-F404- LP8 biparatopic | 1.99 | 0.028 | 88 | >10 | <20 |
| 29 | A05 x C06-F404- LP8 biparatopic | 1.99 | 0.027 | 88 | >10 | <20 |

TABLE 15

| Conjugate | Sample Name | DAR | NTERA-2 EC50 (nM) | NTERA-2 Span (%) | MCF-7 EC50 (nM) | MCF-7 Span (%) |
|---|---|---|---|---|---|---|
| 30 | D04-Y180F404/K42/E161-LP14 | 7.87 | 0.020 | 88 | >10 | <10 |
| 31 | D04-Y180F404/K42/E161-LP15 | 7.97 | 0.018 | 87 | >10 | <10 |
| 32 | D04-Y180F404/K42/E161-LP16 | 7.94 | 0.023 | 86 | >10 | <10 |
| 33 | D04-Y180F404/K42/E161-LP17 | 7.91 | 0.019 | 87 | >10 | <10 |
| 34 | D04-Y180F404/K42/E161-LP18 | 7.69 | 0.373 | 73 | >10 | <10 |
| 35 | D04-Y180F404/K42/E161-LP19 | 7.84 | 0.236 | 77 | >10 | <10 |

TABLE 15-continued

| Conjugate | Sample Name | DAR | NTERA-2 EC50 (nM) | NTERA-2 Span (%) | MCF-7 EC50 (nM) | MCF-7 Span (%) |
|---|---|---|---|---|---|---|
| 36 | D04-Y180F404/K42/E161-LP20 | 7.83 | 0.222 | 72 | >10 | <10 |
| 37 | D04-F404-LP33 | 1.97 | 0.010 | 89 | >10 | <10 |
| 38 | D04-Y180F404/K42/E161-LP23 | 7.82 | 0.108 | 64 | >10 | <10 |
| 39 | D04-Y180F404/K42/E161-LP22 | 7.93 | 0.215 | 54 | >10 | <10 |
| 40 | D04-Y180F404/K42/E161-LP21 | 7.93 | 0.076 | 68 | >10 | <10 |
| 41 | D04-F404-LP24 | 1.99 | >10 | <10 | >10 | <10 |
| 42 | D04-F404-LP25 | 1.99 | 0.075 | 58 | >10 | <10 |
| 43 | D04-F404-LP26 | 1.99 | >10 | <10 | >10 | <10 |
| 44 | D04-F404-LP27 | 1.99 | 0.017 | 80 | >10 | <10 |
| 45 | D04-F404-LP28 | 1.99 | >10 | <10 | >10 | <10 |
| 4 | D04-Y180F404/K42/E161-LP1 | 7.96 | 0.050 | 65 | >10 | <10 |
| 10 | D04-Y180F404/K42/E161-LP4 | 7.97 | 0.013 | 89 | >10 | <10 |
| 5 | D04-F404- LP8 | 1.99 | 0.013 | 83 | >10 | <10 |
| | PNU-EDA payload | | 0.027 | 98 | 0.25 | 85 |

TABLE 16

| Conjugate | Sample Name | DAR | NTERA-2 EC50 (nM) | NTERA-2 Span (%) | MCF-7 EC50 (nM) | MCF-7 Span (%) |
|---|---|---|---|---|---|---|
| 46 | D04-Y180/F241/F404/K42-LP3 | 7.98 | 0.042 | 51 | >10 | <10 |
| 9 | D04-Y180/F404/K42/E161-LP3 | 7.46 | 0.119 | 63 | >10 | <10 |
| 47 | D04-Y180/F241/F404/K42-LP4 | 7.97 | 0.005 | 96 | >10 | <10 |
| 10 | D04-Y180/F404/K42/E161-LP4 | 8 | 0.003 | 96 | >10 | <10 |
| 52 | aGFP-Y180/F241/F404/K42-LP3 | 7.76 | >10 | <10 | >10 | <10 |
| 53 | aGFP-Y180/F241/F404/K42-LP4 | 7.82 | >10 | <10 | >10 | <10 |

Example 19

Cell Killing Activity of ROR1 ADCs is Dependent on Antibody Binding to ROR1 Antigen on the Cell Surface To evaluate if the cell killing activity of anti-ROR1 ADCs is dependent on antibody binding to ROR1 expressed on cell surface, the same linker-warheads (LP3, LP4) were conjugated to an anti-GFP antibody and the cell killing of the anti-ROR1 and anti-GFP ADCs were evaluated in cell killing assays on ROR1 positive Ntera-2 cell and ROR1 negative MCF7 cells.

Figure 12A:
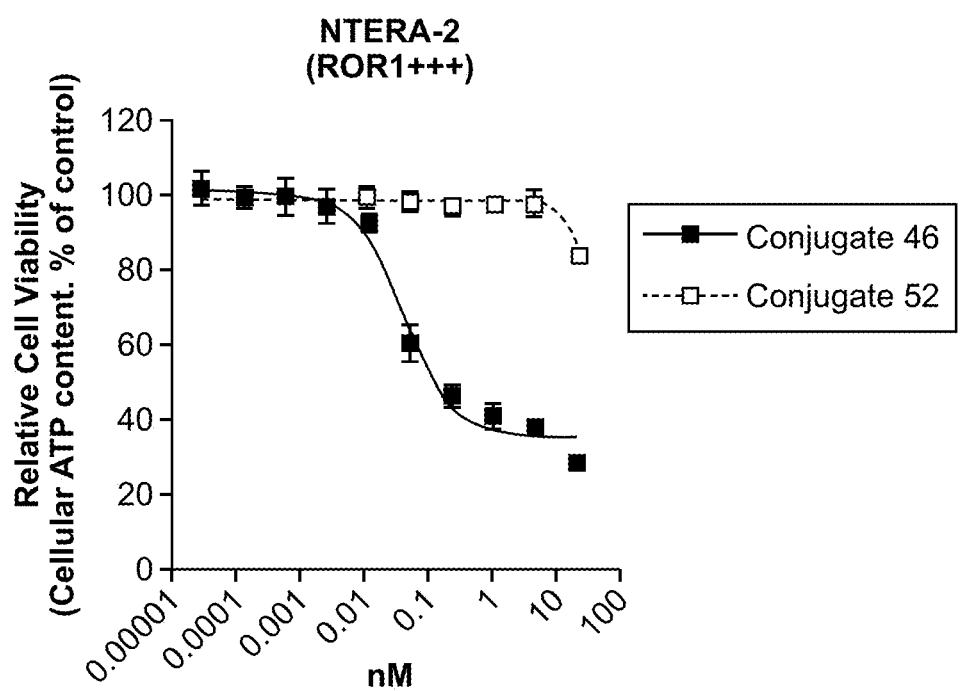
FIG. 12A and FIG. 12B demonstrate that Conjugate 46 and Conjugate 47 showed potent cell killing on ROR1 positive Ntera-2 cells, while anti-GFP antibody conjugated to LP3 or LP4 showed no detected cell killing on Ntera-2 cells at all.
Figure 12B:
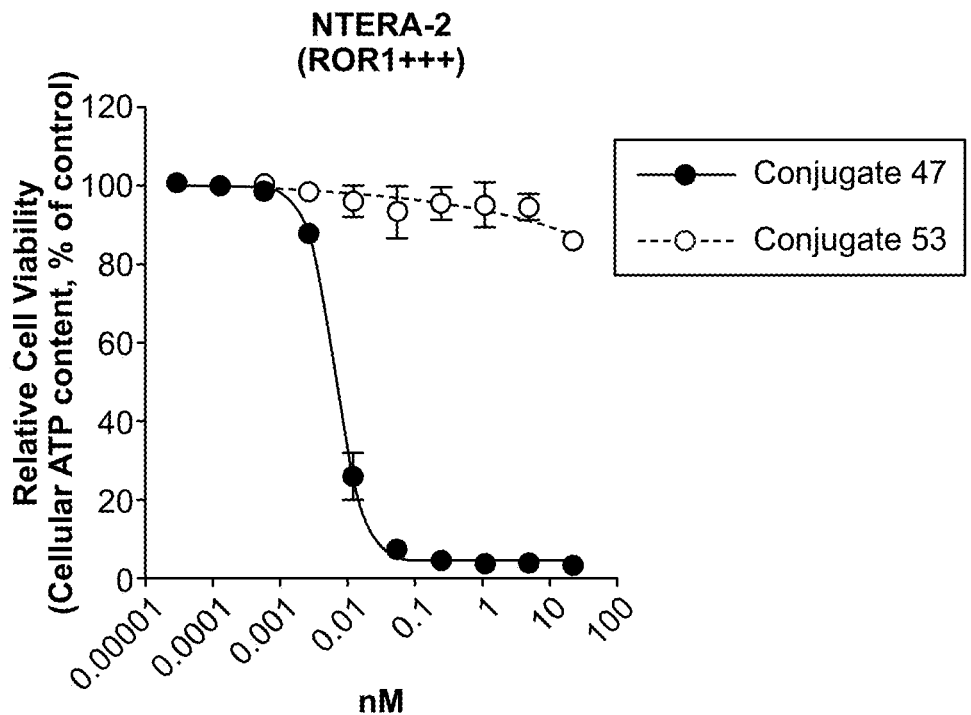

As shown in FIGS. 12A-12B and Table 17, while Conjugate 46 and Conjugate 47 showed potent cell killing on ROR1 positive Ntera-2 cells, anti-GFP antibody conjugated to LP3 or LP4 showed no cell killing on Ntera-2 cells at all, indicating that binding to ROR1 antigen expressed on Ntera-2 cells was required for the ADC cell killing activity.

Figure 12C:
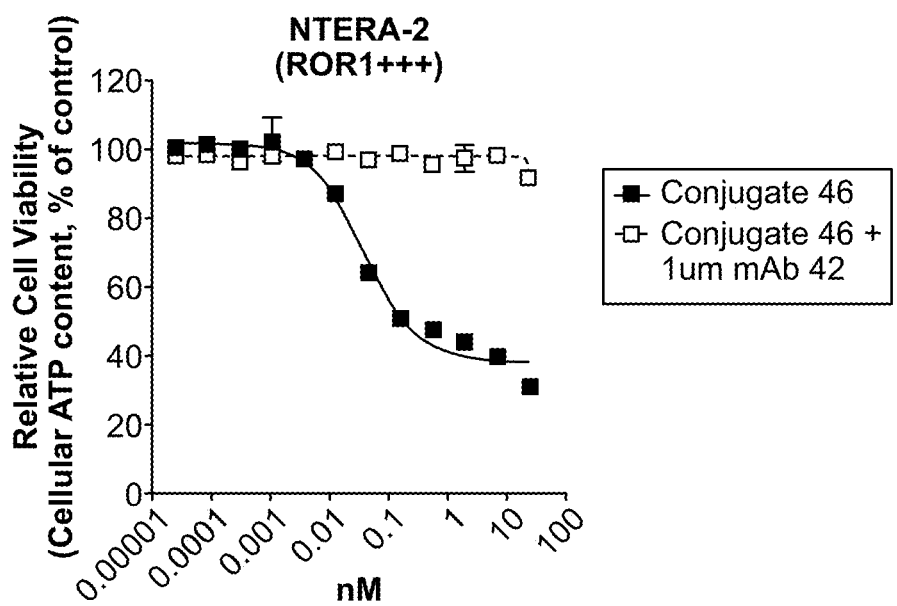
FIG. 12C and FIG. 12D demonstrate that in the presence of 1 µM of the un-conjugated anti-ROR1 antibody 2188-D04, the cell killing activity of both Conjugate 46 and Conjugate 47 was inhibited.
Figure 12D:
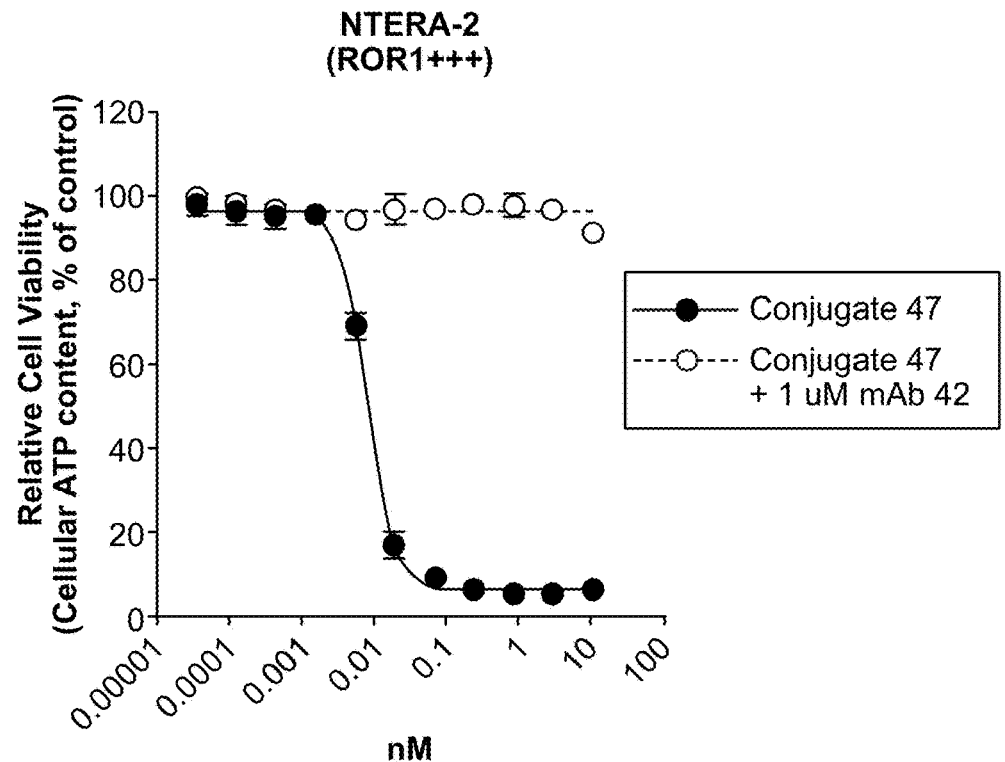

The cell killing activity of the ROR1 ADCs on ROR1 positive Ntera-2 cells was also evaluated in the presence of un-conjugated anti-ROR1 antibody, which will compete with ADC on binding to the ROR1 antigen on the cell surface. As shown in FIGS. 12C-12D and Table 18, in the presence of 1 μM of the un-conjugated anti-ROR1 antibody mAb 42, the cell killing activity of both Conjugate 46 and Conjugate 47 was completely inhibited, which further demonstrated that the ROR1 ADC cell killing activity was dependent on binding to the ROR1 antigen on the cell surface.

TABLE 17

| Conjugate | Sample | DAR | NTERA-2 EC50 (nM) | NTERA-2 Span (%) | MCF-7 EC50 (nM) | MCF-7 Span (%) |
|---|---|---|---|---|---|---|
| 46 | 2188-D04-LP3 (3 + 1) | 7.98 | 0.045 | 65 | >10 | <20 |
| 47 | 2188-D04-LP4 (3 + 1) | 7.97 | 0.007 | 96 | >10 | <20 |
| 52 | aGFP-LP3 (3 + 1) | 7.76 | >10 | <20 | >10 | <20 |
| 53 | aGFP-LP4 (3 + 1) | 7.82 | >10 | <20 | >10 | <20 |

TABLE 18

| | | | Cell Killing on Ntera2 Cells | | | |
|---|---|---|---|---|---|---|
| | | | Without 2188-D04 | | With 1 uM 2188-D04 | |
| Conjugate | Sample Name | DAR | EC50 (nM) | Span (%) | EC50 (nM) | Span (%) |
| 46 | 2188-D04-LP3 (3 + 1) | 7.98 | 0.038 | 63 | <10 | >100 |
| 47 | 2188-D04-LP4 (3 + 1) | 7.97 | 0.008 | 92 | <10 | >100 |

Example 20—In Vivo Activity of ROR1 ADCs Comparison of Payloads in MDA-MB-231

The activities of ROR1-targeted ADCs described herein were examined in a MDA-MB-231 TNBC xenograft model. Briefly, SCID/beige mice were implanted subcutaneously with $5 \times 10^6$ MDA-MB-231 tumor cells in the mammary fat pad and randomized and enrolled into the study 7 days post implant, with tumor sizes around 130 mm$^3$. Tumor-bearing mice were administered four weekly doses (qw×4) of the test articles at doses ranging from 2 mg/kg to 5 mg/kg. All treatments were well tolerated with normal body weight gain throughout the course of the study.

Figure 13A:
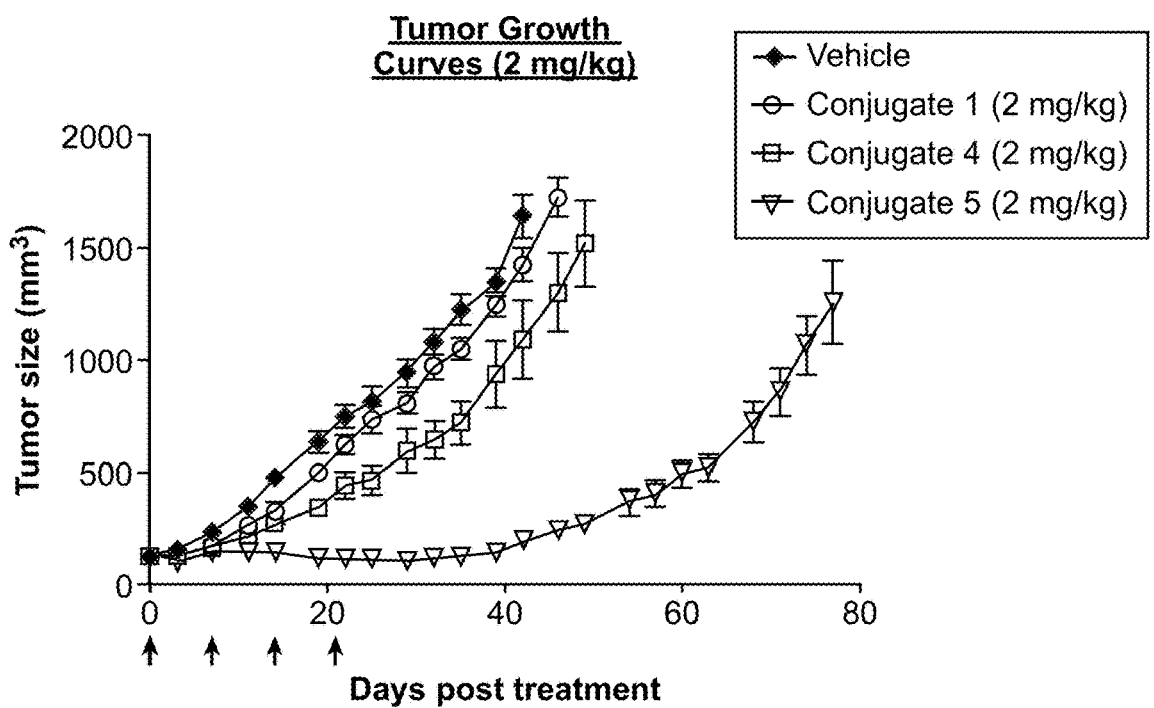
FIG. 13A-C provide MDA-MB-231 tumor growth curves in response to treatment with four weekly doses (qw×4) of ROR1-targeted ADCs, with doses ranging from (11A) 2 mg/kg to (11B) 5 mg/kg. (11C) Scatter plot of individual tumor volumes on day 42 post treatment, when control tumors reached the study endpoint. Arrows represent dosing days. Statistical analysis was performed on tumor volumes on day 42 using one-way ANOVA with Dunnett's multiple comparisons test versus the vehicle group. A probability of less than 5% ($p<0.05$) was considered significant. *=$p<0.001$; **=$p<0.0001$. All graphs are presented as individual values or mean±SEM.
Figure 13B:
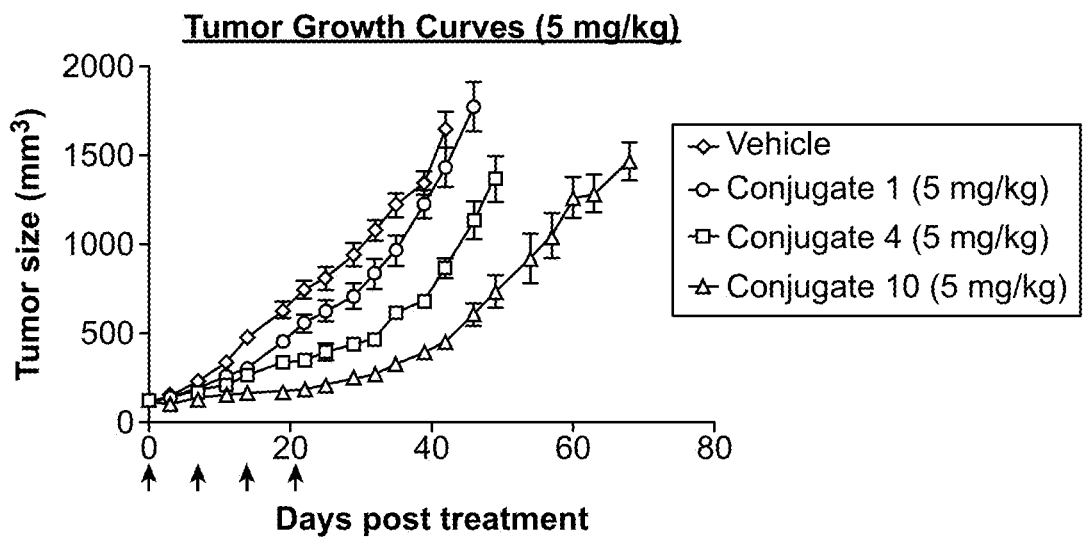
Figure 13C:
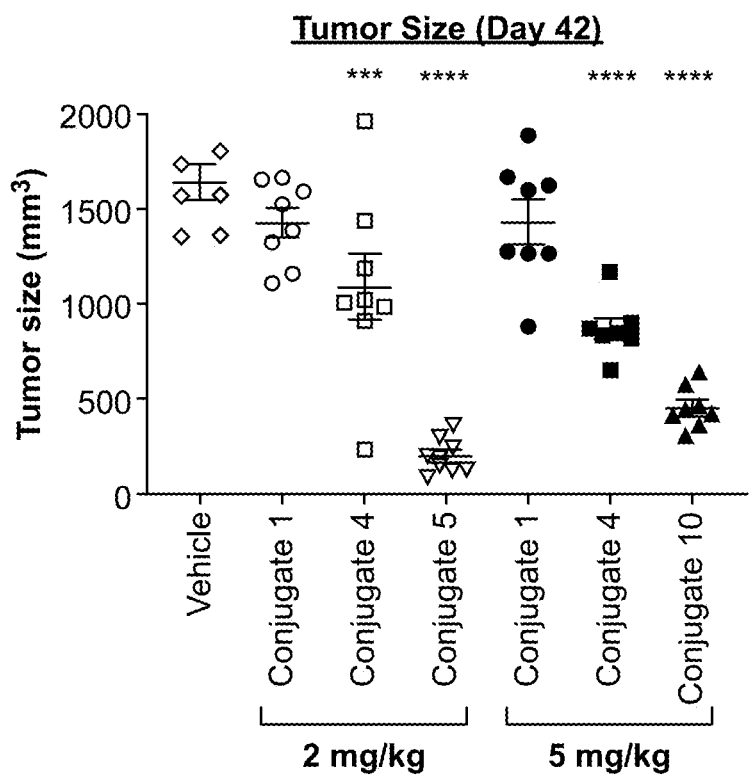

FIG. 13A and FIG. 13B illustrate the effects of the different test articles on MDA-MB-231 tumor growth up until the end of the study at day 77 post treatment. Analysis of tumor sizes on day 42, when the mean of vehicle-treated tumors reached the study endpoint (>1,500 mm$^3$), showed that Conjugate 5 at 2 mg/kg exhibited the greatest suppression of tumor growth (96% TGI), followed by Conjugate 10 at 5 mg/kg (79% TGI) (FIG. 13C). Conjugate 4 exhibited moderate tumor growth suppression when dosed at 5 mg/kg and 2 mg/kg (51% and 36% TGI, respectively), whereas Conjugate 1 did not demonstrate significant TGI compared to the vehicle-treated group at any of the tested doses.

Example 21—Comparison of Exatecan Linker-Payloads

SCID/beige mice were implanted subcutaneously with $5 \times 10^6$ MDA-MB-231 tumor cells in the mammary fat pad and randomized and enrolled into the study 7 days post implant, with tumor sizes around 130 mm$^3$. Tumor-bearing mice were administered four weekly doses (qw×4) of the test articles at doses ranging from 2 mg/kg to 5 mg/kg. All treatments were well tolerated with normal body weight gain throughout the course of the study.

Figure 14A:
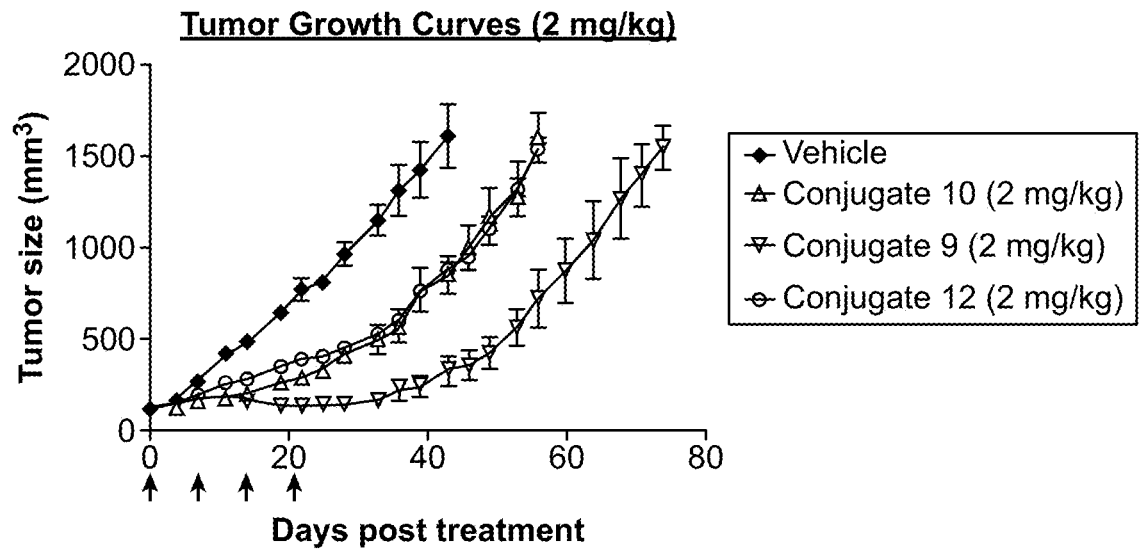
FIGS. 14A-C provide MDA-MB-231 tumor growth curves in response to treatment with four weekly doses (qw×4) of ROR1-targeted ADCs, with doses ranging from (12A) 2 mg/kg to (12B) 5 mg/kg. (12C) Scatter plot of individual tumor volumes on day 43 post treatment, when control tumors reached the study endpoint. Arrows represent dosing days. Statistical analysis was performed on tumor volumes on day 43 using one-way ANOVA with Dunnett's multiple comparisons test versus the vehicle group. A probability of less than 5% ($p<0.05$) was considered significant. ****=$p<0.0001$. All graphs are presented as individual values or mean±SEM.
Figure 14B:
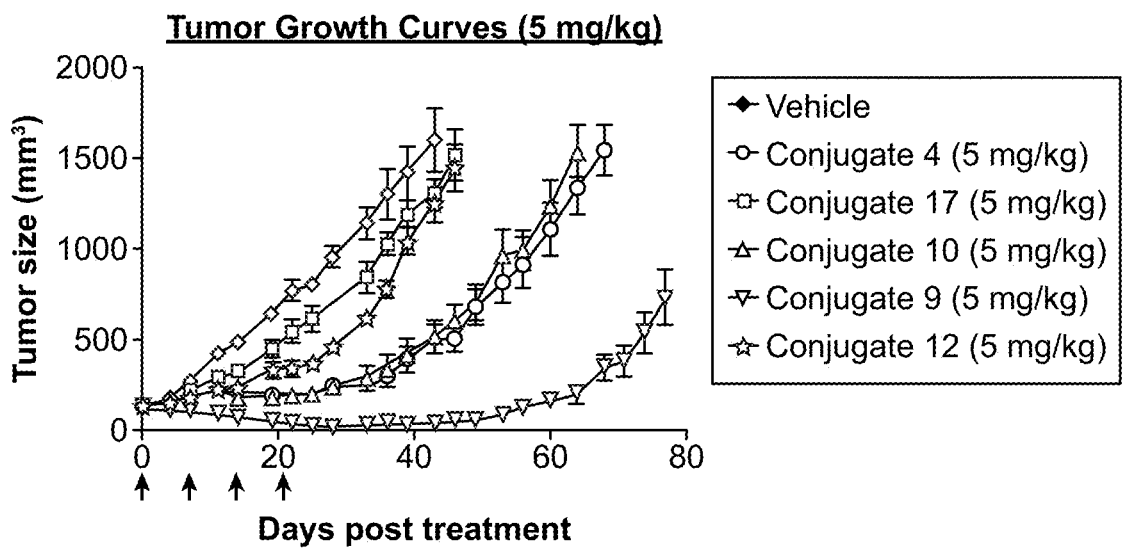
Figure 14C:
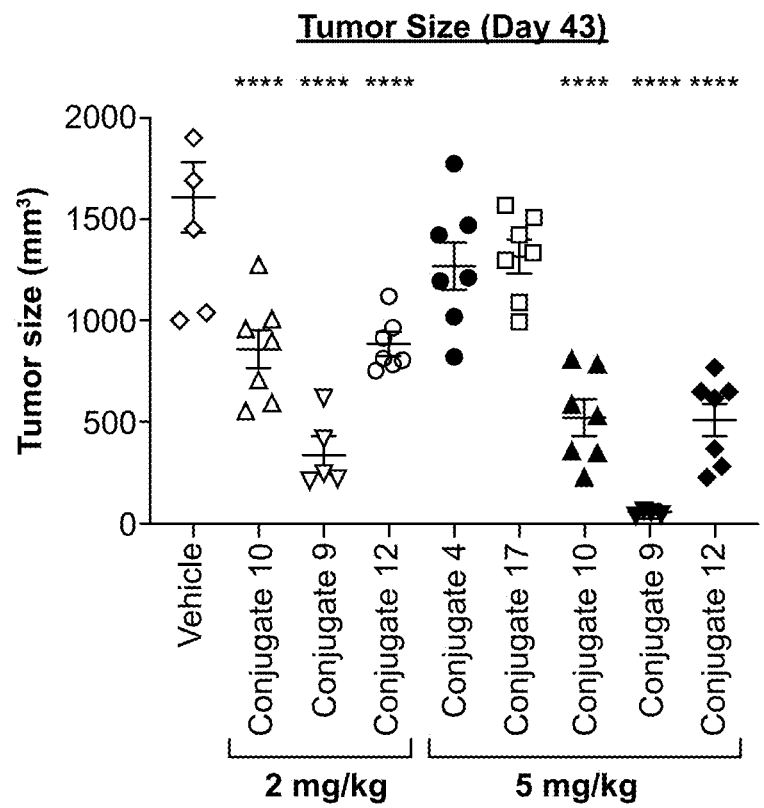

FIG. 14A and FIG. 14B illustrate the effects of the different test articles on MDA-MB-231 tumor growth up until the end of the study at day 77 post treatment. Although treatment with Conjugate 4 initially exhibited control of tumor growth, treatment with Conjugate 4 and Conjugate 17 at 5 mg/kg did not result in statistically significant TGI at day 43 post treatment (23% and 20%, respectively), when the mean of vehicle-treated tumors reached the study endpoint (>1,500 mm$^3$) (FIG. 14C). However, significant TGI, at both the 2 mg/kg and 5 mg/kg doses, was observed for all the remaining ROR1-targeted ADCs. Activity of Conjugate 10 and Conjugate 12 was nearly identical at both dosages, resulting in approximately 50% TGI at day 43 at 2 mg/kg and approximately 75% TGI at 5 mg/kg. Treatment with Conjugate 9 demonstrated the greatest TGI amongst all test articles (86% at 2 mg/kg and 106% at 5 mg/kg), with the 5 mg/kg group demonstrating prolonged tumor regression with no evidence of tumor regrowth until approximately day 49 (FIG. 14B).

Example 22—Comparison of Exatecan Linker-Payloads at Sites of Conjugation

SCID/beige mice were implanted subcutaneously with $5 \times 10^6$ MDA-MB-231 tumor cells in the mammary fat pad and randomized and enrolled into the study 7 days post implant, with tumor sizes around 130 mm$^3$. Tumor-bearing mice were administered three weekly doses (qw×3) of the test articles at doses ranging from 2 mg/kg to 5 mg/kg. All treatments were well tolerated with normal body weight gain throughout the course of the study.

Figure 15A:
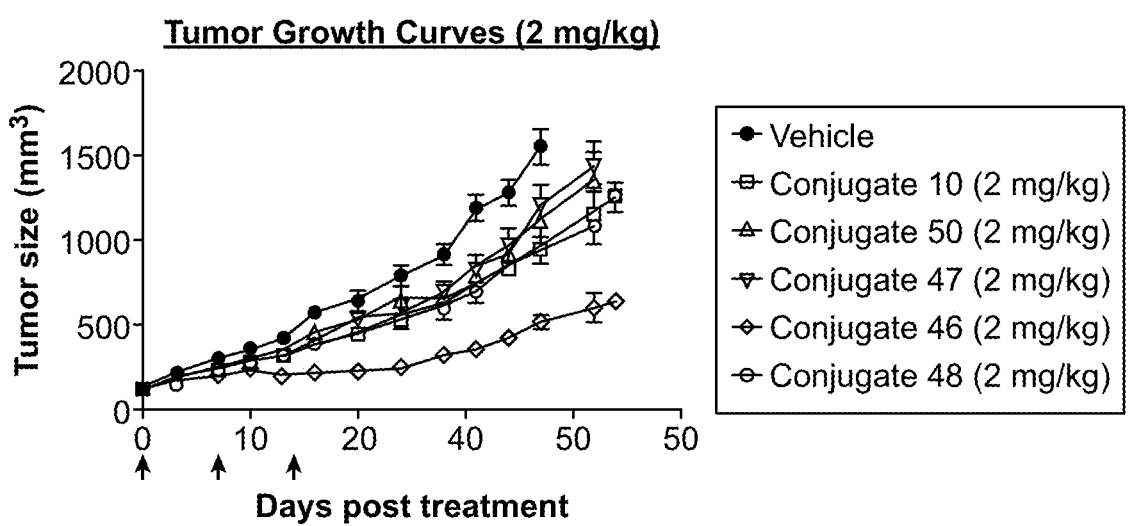
FIGS. 15A-C provide MDA-MB-231 tumor growth curves in response to treatment with three weekly doses (qw×3) of ROR1-targeted ADCs, with doses ranging from (13A) 2 mg/kg to (13B) 5 mg/kg. (13C) Scatter plot of individual tumor volumes on day 37 post treatment, when control tumors reached the study endpoint. Arrows represent dosing days. Statistical analysis was performed on tumor volumes on day 37 using one-way ANOVA with Dunnett's multiple comparisons test versus the vehicle group. A probability of less than 5% ($p<0.05$) was considered significant. *=$p<0.05$; =$p<0.01$; *=$p<0.001$; ****=$p<0.0001$. All graphs are presented as individual values or mean±SEM.
Figure 15B:
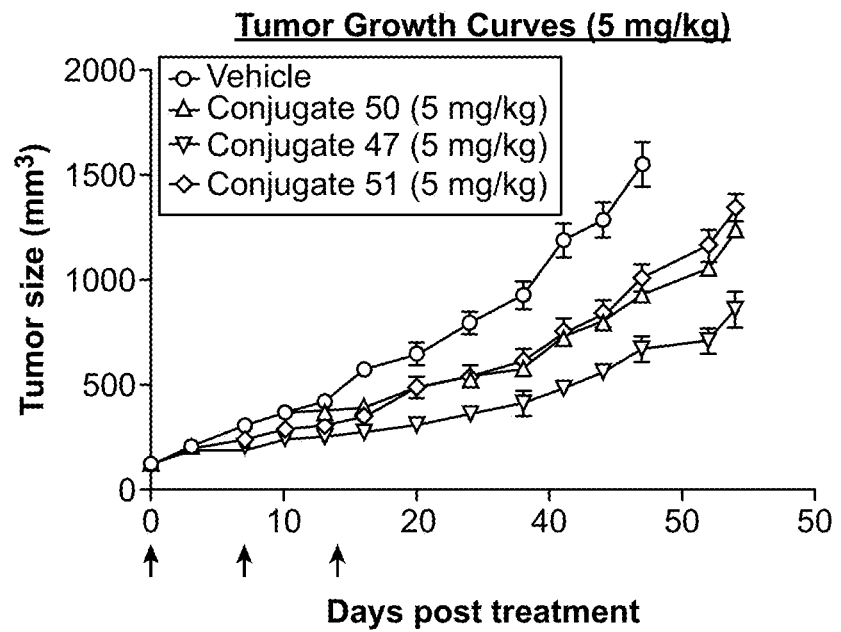
Figure 15C:
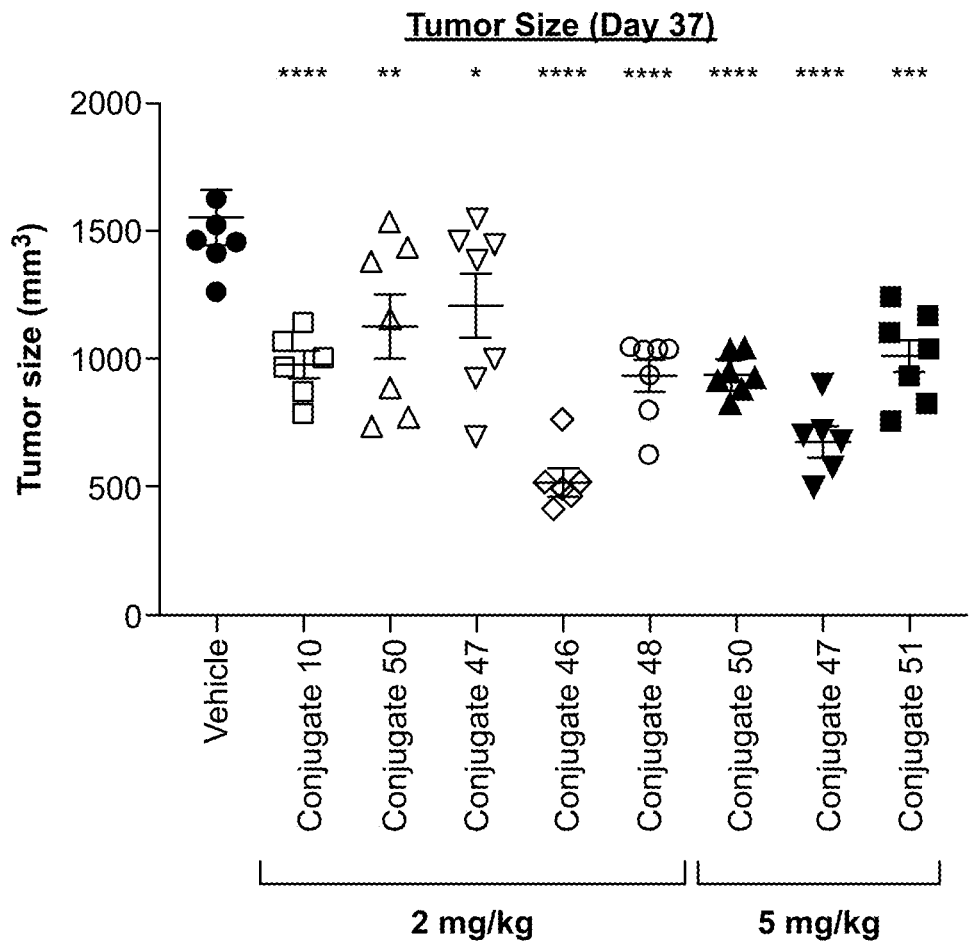

FIG. 15A and FIG. 15B illustrate the effects of the different test articles on MDA-MB-231 tumor growth up until the end of the study at day 44 post treatment. Analysis of tumor sizes on day 37 post treatment, when the mean of vehicle-treated tumors reached the study endpoint (>1,500 mm$^3$), revealed that all test articles demonstrated significant anti-tumor activity, with activities ranging from approximately 25% to 73% TGI (FIG. 15C). At the 2 mg/kg dose, Conjugate 46 demonstrated the greatest suppression of tumor growth (73% TGI), followed by Conjugate 48, Conjugate 10, Conjugate 50, and Conjugate 47(44%, 41%, 30%, and 25% TGI, respectively). TGI following treatment with the latter four molecules did not differ significantly from each other. At the 5 mg/kg dose, Conjugate 47 exhibited the greatest level of tumor suppression (62% TGI), whereas Conjugate 50 and Conjugate 51 exhibited lower control of tumor growth (43% and 38%, respectively). Notably, Conjugate 46 at 2 mg/kg achieved greater TGI than Conjugate 47 at 5 mg/kg.

Example 22—Comparison of DAR6 Vs DAR8 of Exatecan Linker-Payload

SCID/beige mice were implanted subcutaneously with $5 \times 10^6$ MDA-MB-231 tumor cells in the mammary fat pad and randomized and enrolled into the study 11 days post implant, with tumor sizes around 120 mm$^3$. Tumor-bearing mice were administered four weekly doses (qw×4) of the test articles at doses ranging from 1 mg/kg to 5 mg/kg. All treatments were well tolerated with normal body weight gain throughout the course of the study.

Figure 16A:
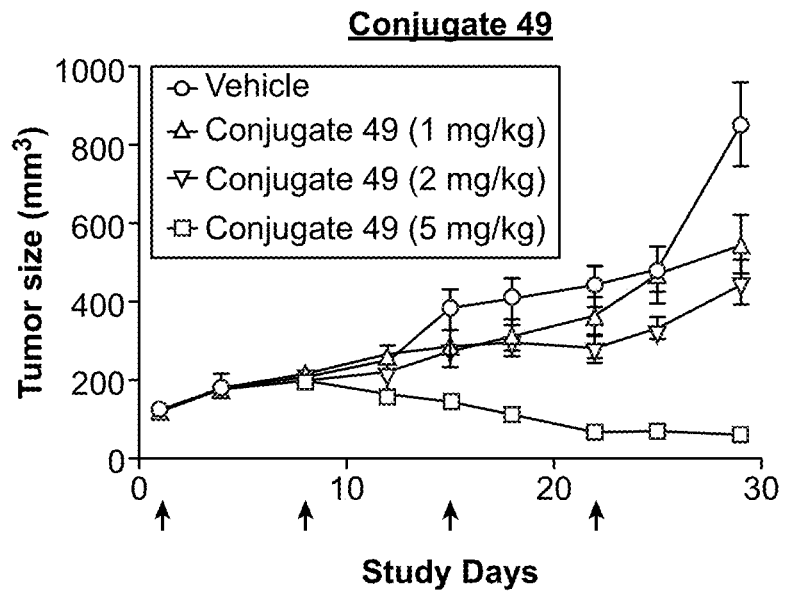
FIGS. 16A-C provide MDA-MB-231 tumor growth curves in response to treatment with four weekly doses (qw×4) of ROR1-targeted ADCs (14A) Conjugate 49 and (14B) Conjugate 46, with doses ranging from 1 mg/kg to 5 mg/kg. (14C) Scatter plot of individual tumor volumes on study day 29, when control tumors reached the study endpoint. Arrows represent dosing days. Statistical analysis was performed on tumor volumes on study day 29 using one-way ANOVA with Dunnett's multiple comparisons test versus the vehicle group. A probability of less than 5% ($p<0.05$) was considered significant. *=$p<0.05$; =$p<0.01$; *=$p<0.001$; ****=$p<0.0001$. All graphs are presented as individual values or mean±SEM.
Figure 16B:
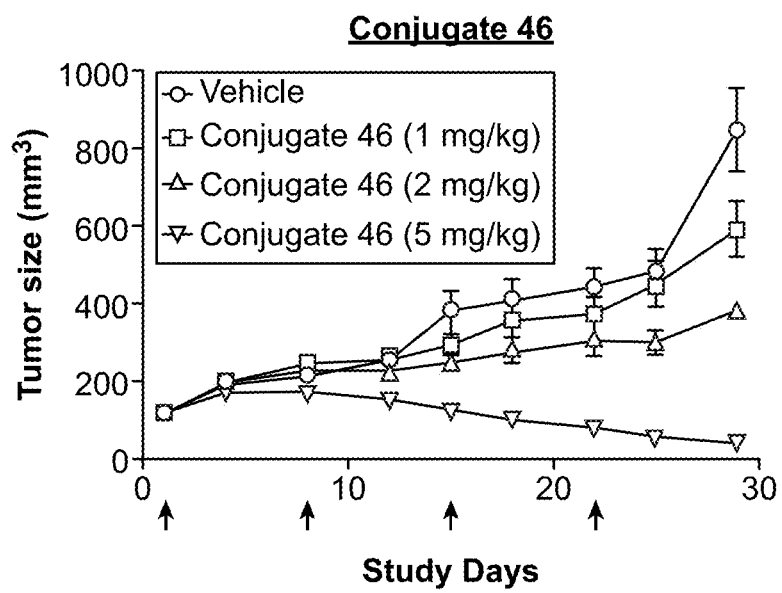
Figure 16C:
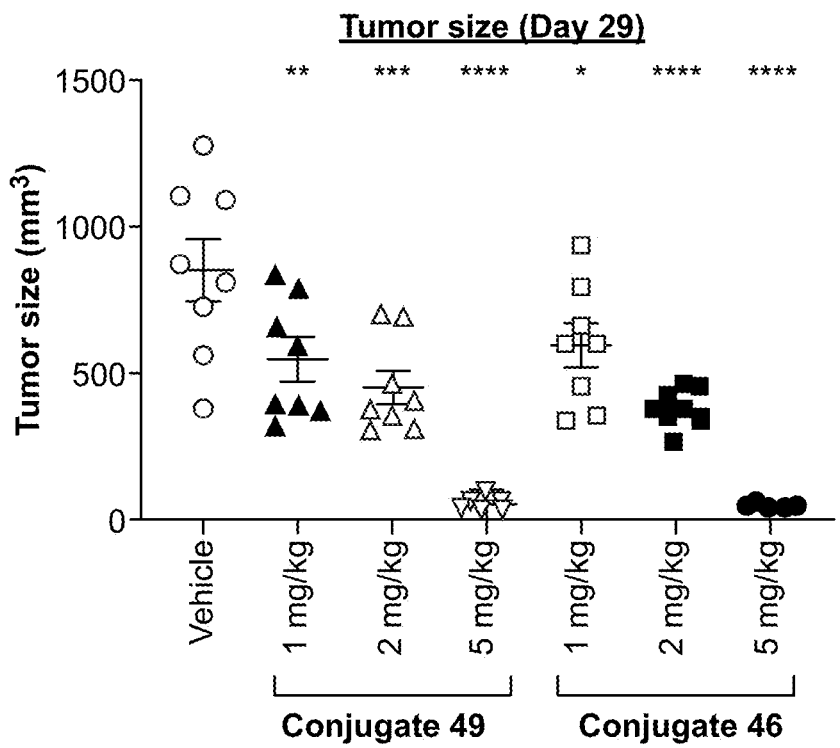

FIG. 16A and FIG. 16B illustrate the effects of the different test articles on MDA-MB-231 tumor growth up until the end of the study at study day 29. Analysis of tumor sizes on study day 29, when the mean of vehicle-treated tumors reached the study endpoint, revealed that all treatment groups exhibited anti-tumor activity compared to the vehicle-treated group, with activities ranging from approximately 35% to 111% TGI (FIG. 16C). Both Conjugate 46 and Conjugate 49 demonstrated dose-dependent activity. However, at equivalent doses, Conjugate 46 and Conjugate 49 showed no significant difference in activity: 35% and 42% TGI, respectively, at 1 mg/kg; 59% and 67% TGI, respectively, at 2 mg/kg; and 108% and 111% TGI, respectively, at 5 mg/kg. Notably, treatment with either test article at the 5 mg/kg dose was able to achieve sustained tumor regression (FIGS. 16A, 16B).

Example 23—Comparison of Linker-Payloads in H1975

The activity of the ROR1-targeted ADCs was additionally examined in the H1975 NSCLC xenograft model. Briefly, SCID/beige mice were implanted subcutaneously with $5 \times 10^6$ H1975 tumor cells in the hind flank and randomized and enrolled into the study 7 days post implant, with tumor sizes around 100 mm³. Tumor-bearing mice were administered two weekly doses (qw×2) of the test articles at doses ranging from 1 mg/kg to 10 mg/kg. All treatments were well tolerated with normal body weight gain throughout the course of the study.

Figure 17A:
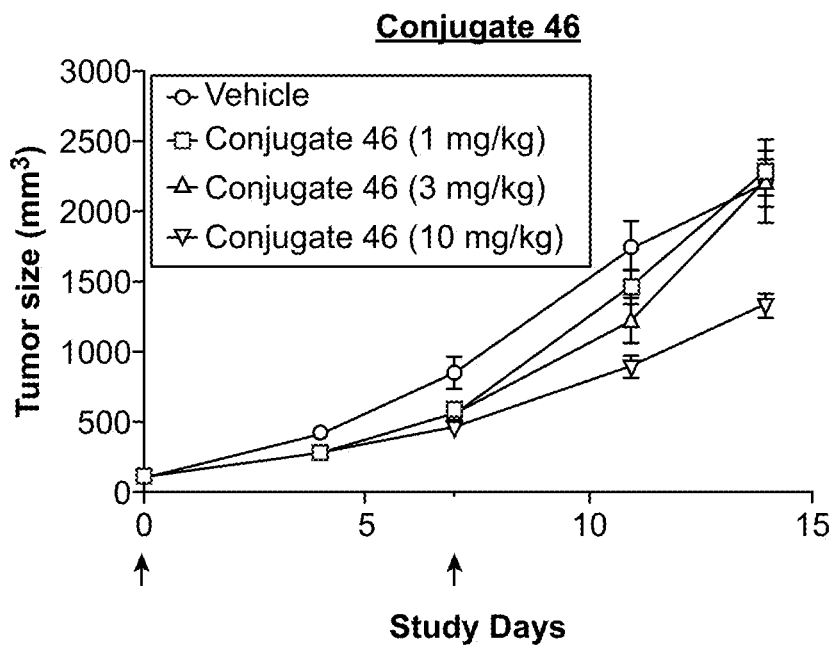
FIGS. 17A-D provide H1975 tumor growth curves in response to treatment with two weekly doses (qw×2) of ROR1-targeted ADCs (15A) Conjugate 46, (15B) Conjugate 47, and (15C) Conjugate 44, with doses ranging from 1 mg/kg to 10 mg/kg. (15D) Scatter plot of individual tumor volumes on study day 14, when control tumors reached the study endpoint. Arrows represent dosing days. Statistical analysis was performed on tumor volumes on study day 14 using one-way ANOVA with Dunnett's multiple comparisons test versus the vehicle group. A probability of less than 5% ($p<0.05$) was considered significant. **=$p<0.01$. All graphs are presented as individual values or mean±SEM.
Figure 17B:
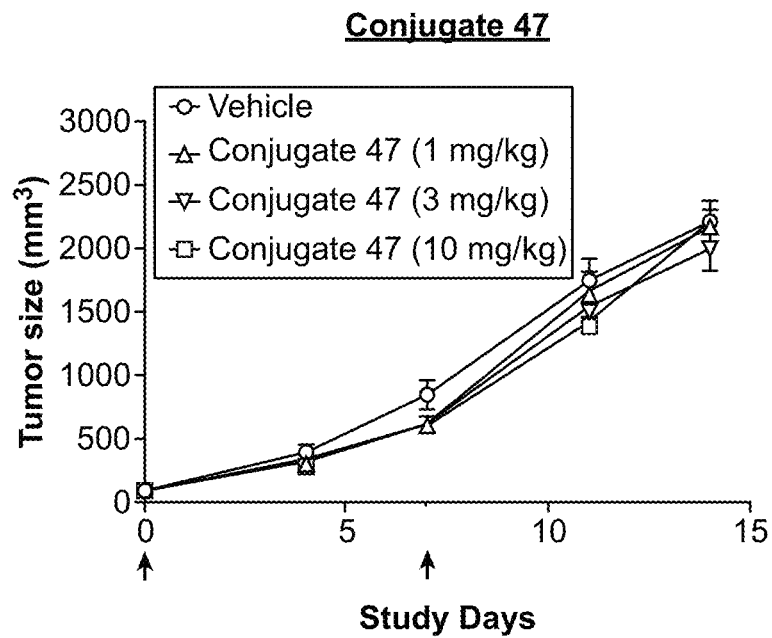
Figure 17C:
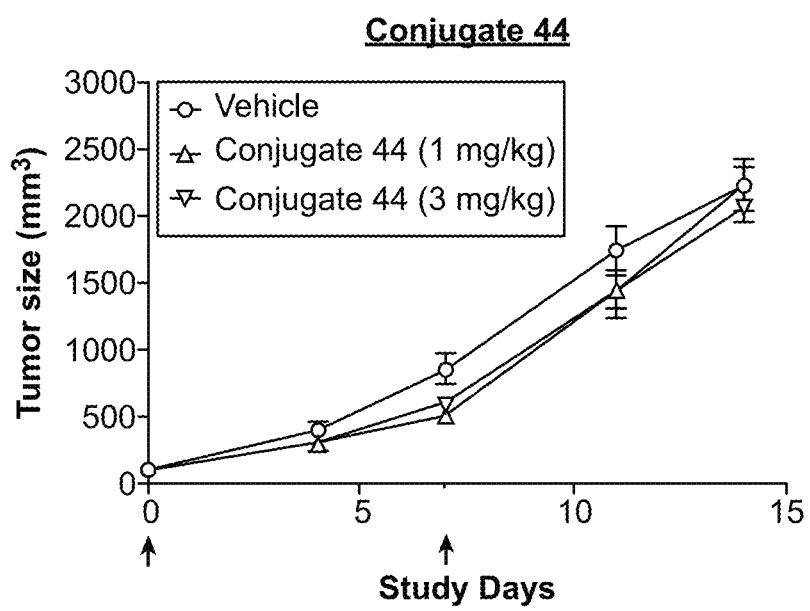
Figure 17D:
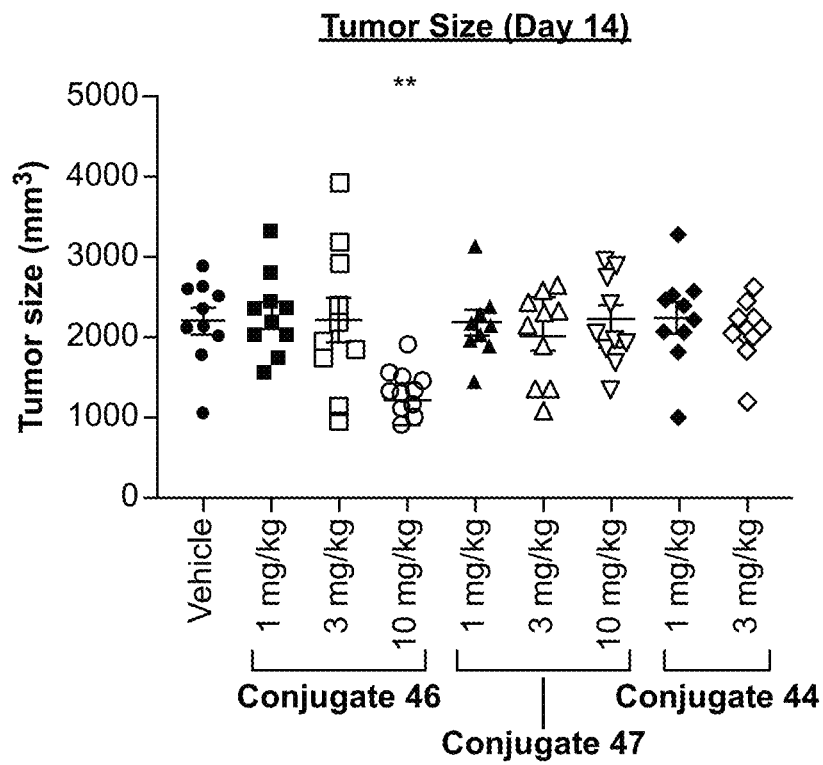

FIGS. 17A-D illustrate the effects of the different test articles on H1975 tumor growth up until the end of the study at study day 14. Analysis of tumor sizes on study day 14, when the mean of vehicle-treated tumors reached the study endpoint (>2,000 mm³), revealed that only the 10 mg/kg dose of Conjugate 46 exhibited significant tumor growth suppression (40% TGI) (FIG. 17D). All other dosages of Conjugate 46 and the other ROR1-targeted ADCs (Conjugate 47 and Conjugate 44) showed no significant effect on tumor growth compared to vehicle-treated tumors, indicating lack of anti-tumor activity.

Example 24—Comparison of Exatecan Linker-Payloads LP3 and LP4, and DAR6 Vs DAR8 in NSCLC PDX Models The activity of the different ROR1-targeted ADCs was additionally examined in NSCLC patient-derived xenograft (PDX) models. Briefly, PDX tumors, spanning varying levels of ROR1 expression, were passaged in athymic nude Fox1$^{nu}$ mice before being processed into tumor fragments for subcutaneous implantation into the hind flank of mice for study initiation. When tumors reached a volume of around 150-300 mm³, the mice were randomized and enrolled into the study. Tumor-bearing mice were administered up to five weekly doses (qw×5) of the test articles at 10 mg/kg. All treatments were well tolerated with normal body weight gain throughout the course of the study.

Figure 18A:
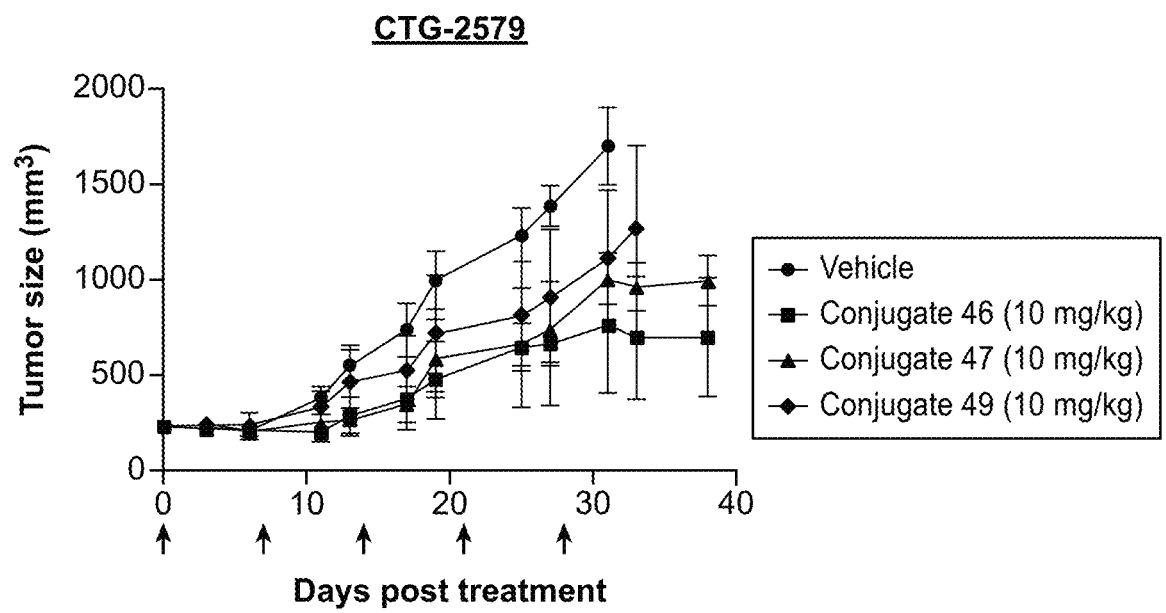
FIGS. 18A-I provide PDX tumor growth curves in response to treatment with up to five weekly doses (qw×5) of ROR1-targeted ADCs Conjugate 46, Conjugate 47, and Conjugate 49 dosed at 10 mg/kg in different NSCLC PDx models. Arrows represent dosing days. All graphs are presented as mean±SEM.
Figure 18B:
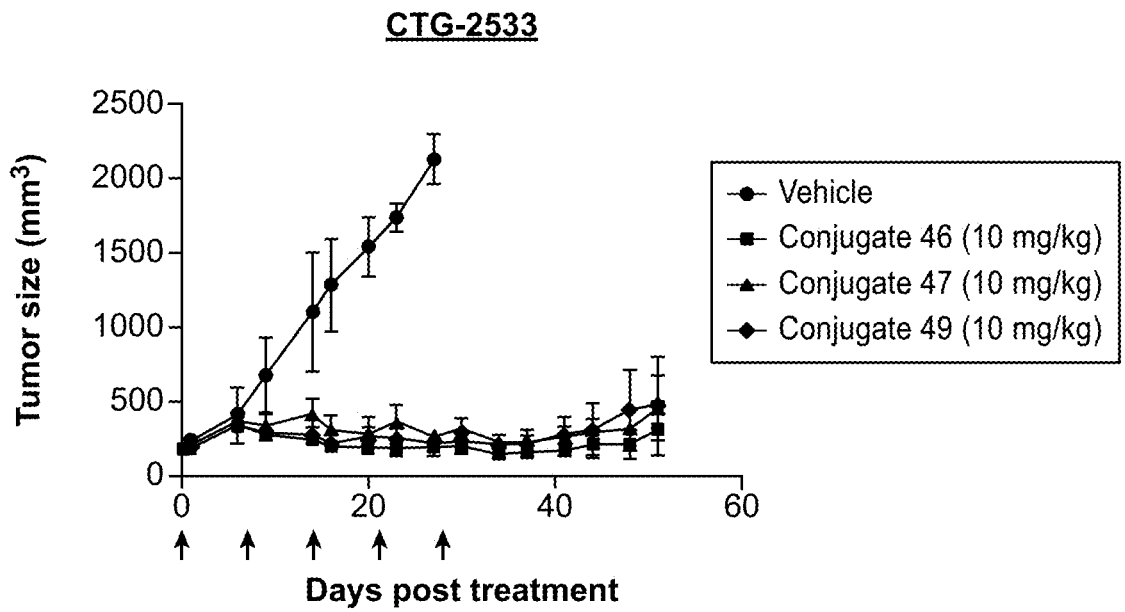
Figure 18C:
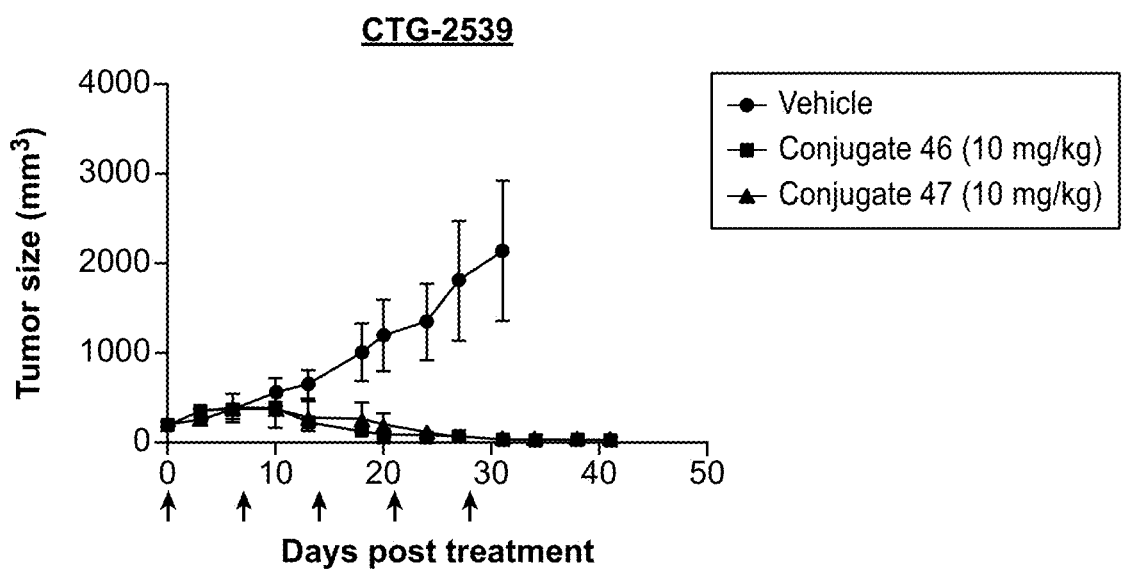
Figure 18D:
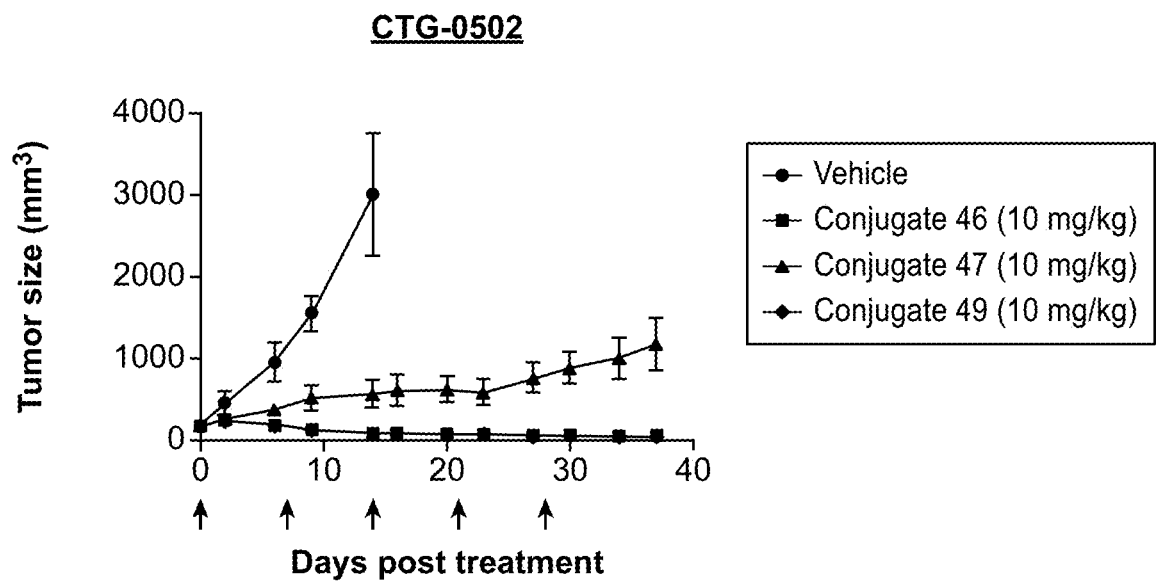
Figure 18E:
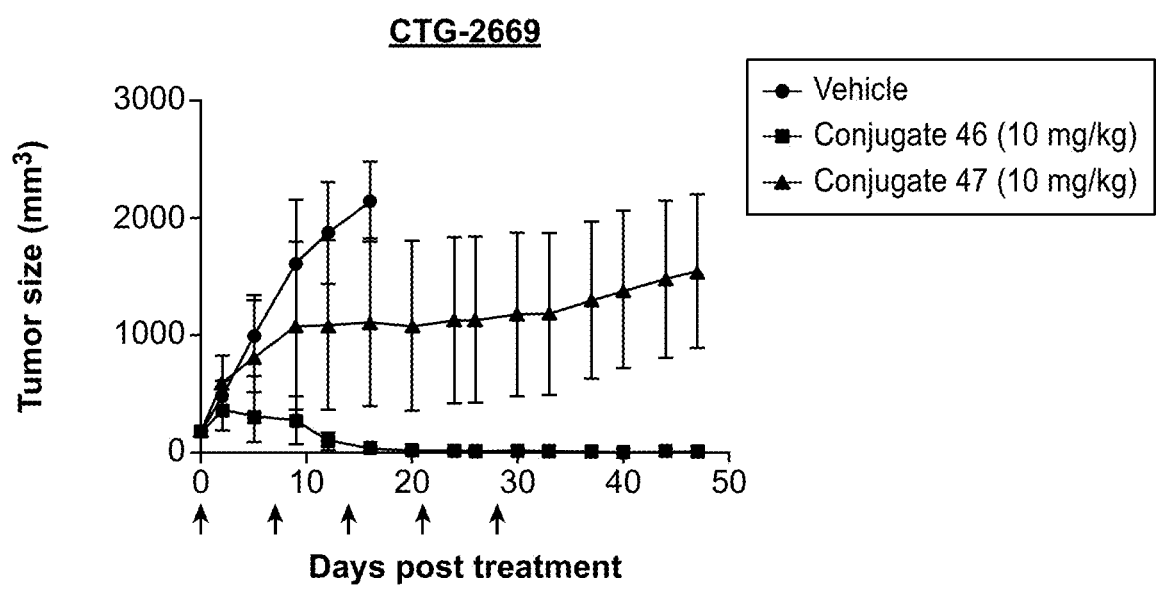
Figure 18F:
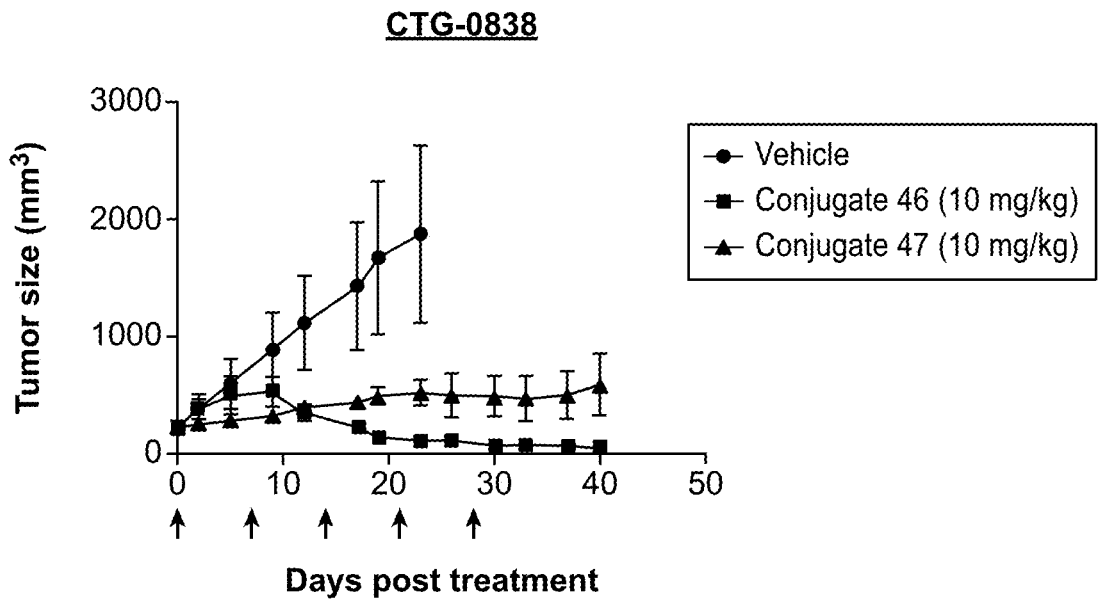
Figure 18G:
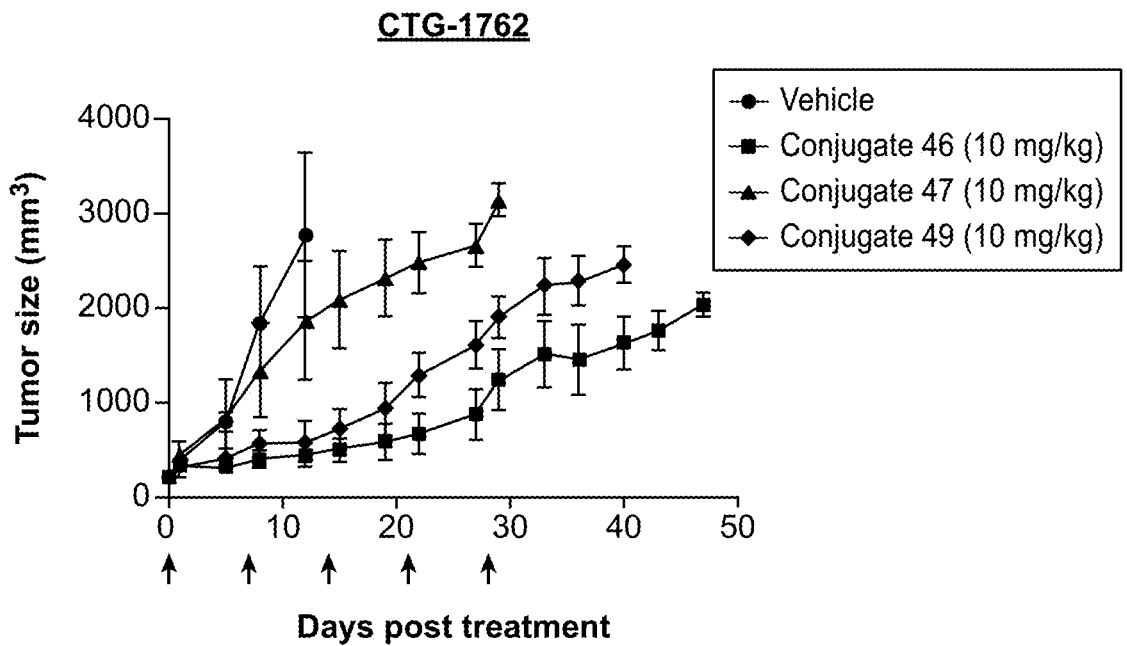
Figure 18H:
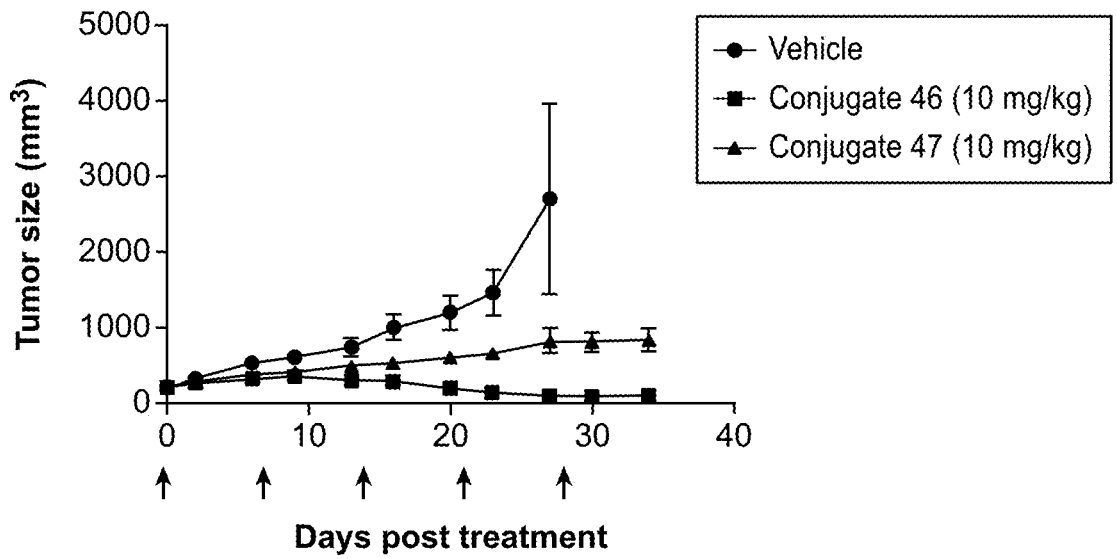
Figure 18I:
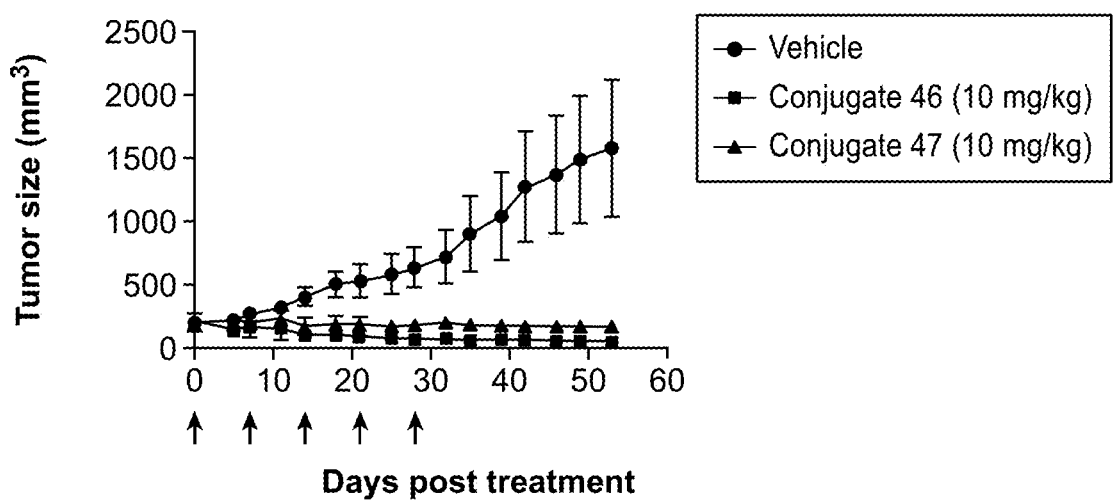
Figure 19A:
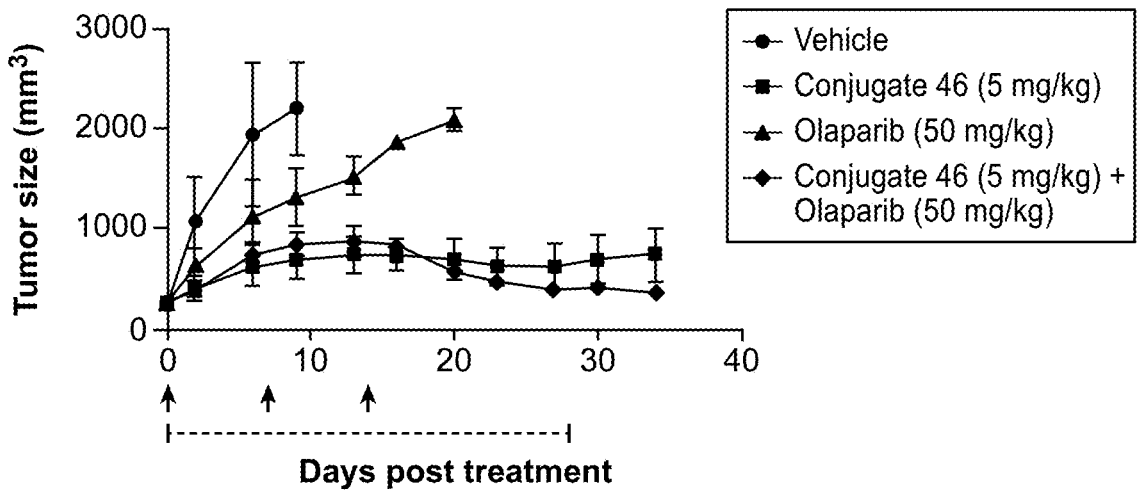
FIGS. 19A-D provide PDX tumor growth curves in response to treatment with up to three weekly doses (qw×3) of Conjugate 46 dosed at 5 mg/kg and twenty-eight daily doses (qd×28) of olaparib dosed at 50 mg/kg in different TNBC PDX models. Arrows represent dosing days for Conjugate 46; dotted line represents dosing days for olaparib. All graphs are presented as mean±SEM.
Figure 19B:
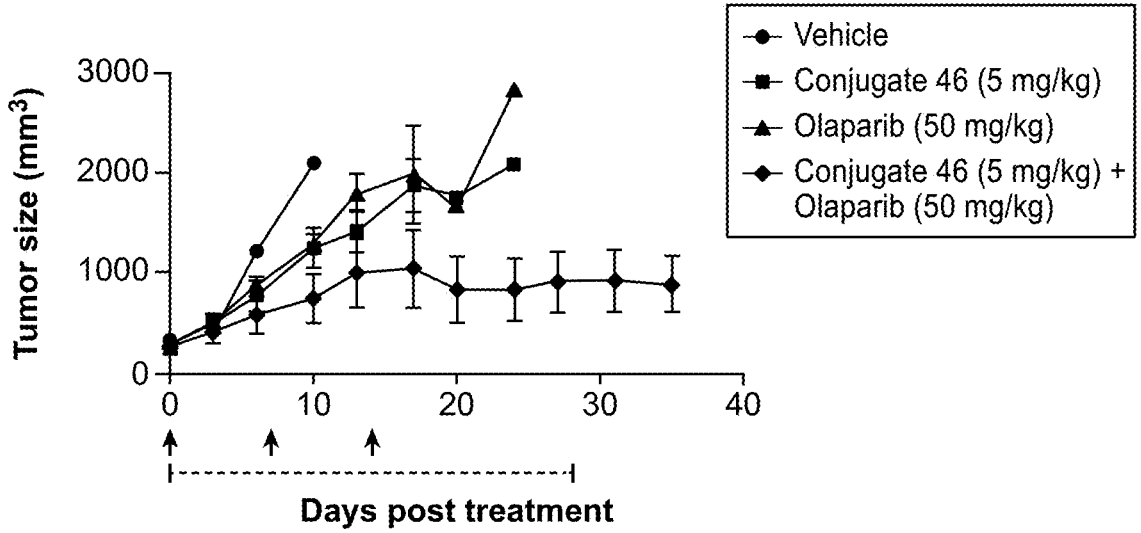
Figure 19C:
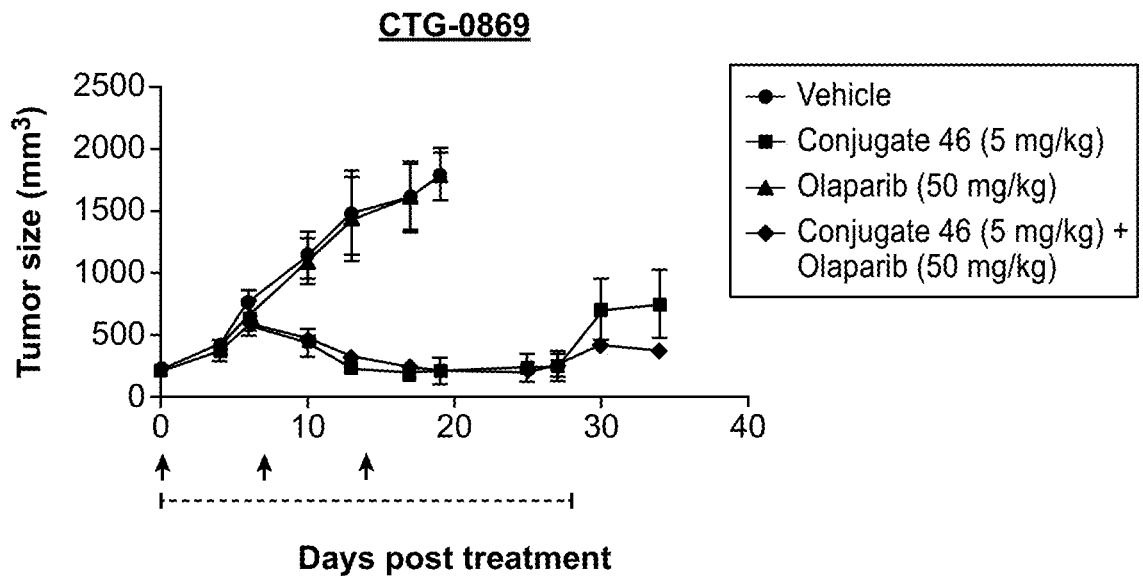
Figure 19D:
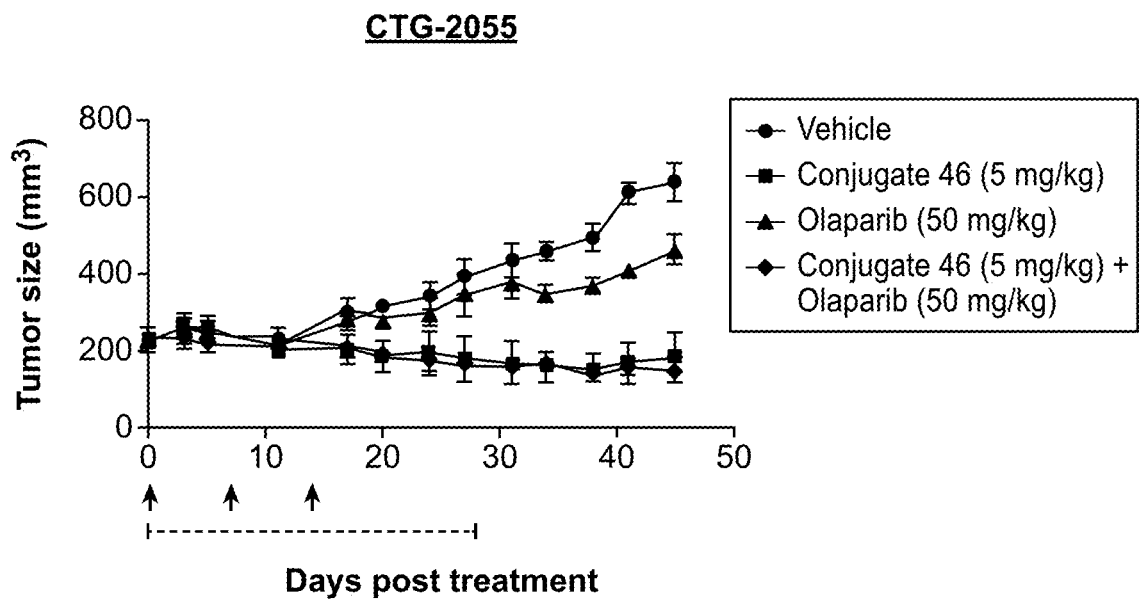

FIGS. 18A-16I illustrate the effects of the different test articles on tumor growth up until the end of the study. When the mean of vehicle-treated tumors reached the study endpoint (>1,500-2,000 mm³), TGI was calculated for each respective treatment group and PDX model (Table 19). In aggregate, Conjugate 46 demonstrated better or equivalent tumor control compared to Conjugate 47 across all NSCLC PDX models tested here (Table 19). Conjugate 49, on the other hand, exhibited roughly similar anti-tumor activity compared to Conjugate 46, with Conjugate 46 trending towards better activity in select models (e.g., CTG-2579 (FIG. 18A) and CTG-1762 (FIG. 18G)). For CTG-1762, although Conjugate 49 and Conjugate 46 exhibited similar activity early on in the tumor growth curves, as the tumors started to grow out, Conjugate 46 began to demonstrate better tumor growth suppression. For the majority of the NSCLC PDX models tested here, treatment with Conjugate 46 led to durable tumor regressions with no evidence of tumor regrowth by the end of the study whereas treatment with Conjugate 47 often demonstrated only sustained tumor stasis or slowed tumor growth (FIGS. 18A-18I).

TABLE 19

| Tumor | Day | TGI (%) 46 | 47 | 49 |
|---|---|---|---|---|
| CTG-2579 | 31 | 64 | 47 | 40 |
| CTG-2533 | 27 | 100**** | 96 | 99**** |
| CTG-2539 | 31 | 108* | 108* | — |
| CTG-0502 | 14 | 103** | 86** | 104** |
| CTG-2669 | 16 | 108* | 53 | — |
| CTG-0838 | 23 | 107* | 82 | — |
| CTG-1762 | 12 | 91* | 36 | 86* |
| CTG-2555 | 27 | 104 | 75 | — |
| CTG-0848 | 53 | 111* | 102* | — |

Table 19 provides mean TGI values reported for all molecules for each respective NSCLC PDX model when control tumors reached the study endpoint. Statistical analysis was performed on tumor volumes on the reported study day using one-way ANOVA with Dunnett's multiple comparisons test versus the vehicle group. A probability of less than 5% ($p<0.05$) was considered significant. *=$p<0.05$; =$p<0.01$; **=$p<0.0001$.

Example 25—Toxicity in Non-Human Primates

To understand the potential toxicity of the ROR1-targeted ADCs described herein prior to clinical development, drug toxicity in a non-human primate system, such as cynomolgus monkey, is tested. The ROR1-targeted ADCs described herein are dosed to cynomolgus monkeys in a repeat dose study (e.g, dosed twice, every 3 weeks) by slow intravenous infusion. The monkeys are dosed at different dose levels (e.g., 10 mg/kg, 20 mg/kg, or 45 mg/kg) to understand at which dose level toxicity occurs. Blood is drawn at various timepoints to monitor drug exposure and markers of toxicity. Ultimately, the ROR1-targeted ADCs' pharmacokinetic (PK) profile is aligned with observed toxicity to generate an understanding of the drug safety profile.

The PK profile of the drug is evaluated by measuring the component parts of an ADC: total antibody (Tab), drug-linker stability of the ADC (ADC), and free drug (free payload). Poor drug-linker stability or fast antibody clearance can contribute to drug catabolism and higher concentrations of free payload that cause toxicity. Blood clinical chemistry is evaluated to monitor for signs of liver or kidney toxicity. Blood hematology, such as various red and white blood cells, is also monitored to detect hematological toxicities. Both clinical chemistry and hematology are monitored over time to understand if toxicities are reversible.

The ADC and/or its component parts can also distribute into tissues, and therefore, have the potential to cause toxicity to specific organs. To understand tissue toxicities, animals are sacrificed at the end of the study (for example, 3 weeks following the second dose) and the organs are examined both macroscopically and microscopically for signs of drug injury. Specifically, organs are weighed and examined for differences in size, color, and/or appearance. To evaluate toxicities at the microscopic level, tissues are fixed, sectioned, and stained. Signs of microscopic injury may include mitotic arrest, necrotic or damaged tissues, and inflammation with or without signs of immune cell infiltration.

Drug safety can be partially represented by the drug's Highest Non-Severely Toxic Dose (HNSTD), or dose at which no or limited toxicities are observed. The higher the HNSTD, the more significant the drug safety.

Example 26—Anti-Tumor Activity in PARP Inhibitor-Resistant Triple Negative Breast Cancer The activity of Conjugate 46 as a single agent or in combination with the PARP inhibitor olaparib was additionally assessed in TNBC PDX models. Briefly, PDX tumors, spanning varying levels of ROR1 expression and sensitivity to olaparib, were passaged in athymic nude Fox1$^{nu}$ mice before being processed into tumor fragments for subcutaneous implantation into the hind flank of mice for study initiation. When tumors reached a volume of around 150-300 mm$^3$, the mice were randomized and enrolled into the study. Tumor-bearing mice were administered up to three weekly doses (qw×3) of Conjugate 46 i.v. at 5 mg/kg and up to twenty-eight daily doses (qd×28) of olaparib p.o. at 50 mg/kg. All treatments were well tolerated, with mice exhibiting normal body weight gain throughout the course of the study.

FIGS. 19A-D illustrate the effects of Conjugate 46 and olaparib single-agent and combination treatments on tumor growth. Overall, Conjugate 46 demonstrated robust tumor growth control in all four models evaluated here. The CTG-0437, CTG-1017, and CTG-2055 models also exhibited moderate tumor growth suppression with single-agent olaparib treatment. Combination of Conjugate 46 with olaparib showed similar efficacy as single-agent Conjugate 46 in CTG-0437, CTG-0869, and CTG-2055. In CTG-1017, however, combination treatment exhibited improved tumor growth control compared to either treatment alone. Notably, combination treatment in all four models resulted in sustained tumor stasis or tumor regression.

Example 27—Combination Therapy in PARP Inhibitor-Resistant Triple Negative Breast Cancer Combination treatment with Conjugate 46 and olaparib (50 mg/kg, qd×28) is conducted using a 2 mg/kg, qw×3 dosing regimen for Conjugate 46. The combination therapy is assessed in six TNBC PDX models as described in Example 26.

Example 28—Induction of Cell Death Markers

Figure 20A:
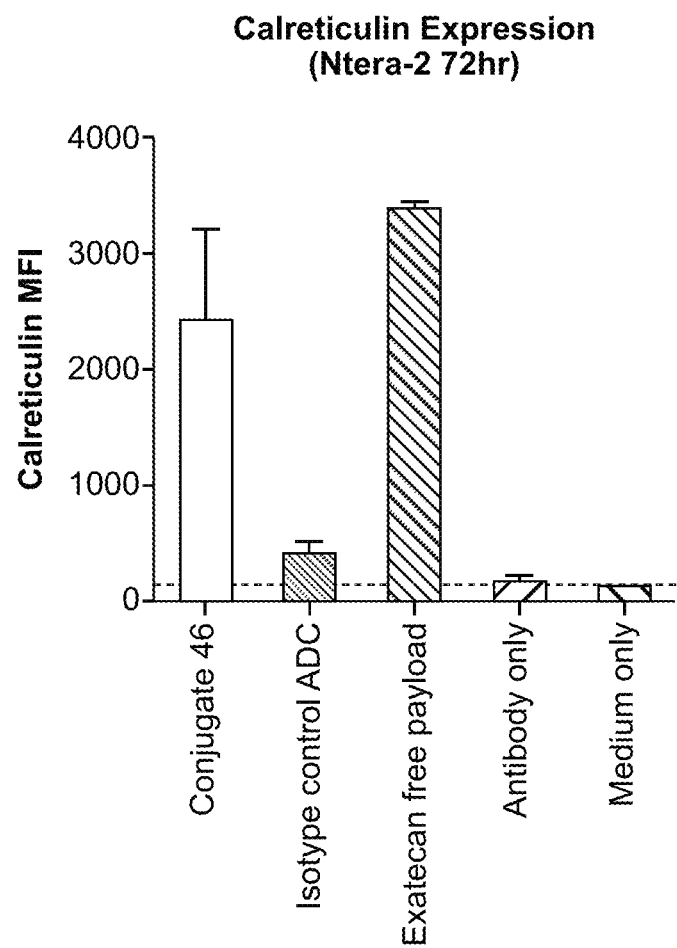
FIG. 20A provides calreticulin expression in Ntera-2 cells following treatment with Conjugate 46 or exatecan compared to the antibody alone and an isotype control of Conjugate 46.
Figure 20B:
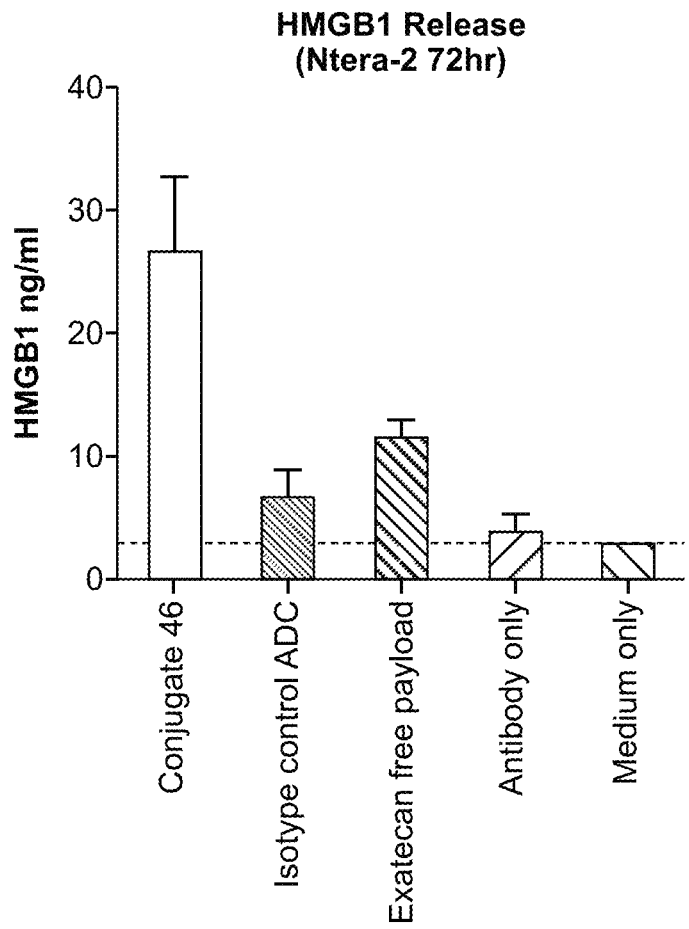
FIG. 20B provides HMGB1 release in Ntera-2 cells following treatment with Conjugate 46 or exatecan compared to the antibody alone and an isotype control of Conjugate 46.

ROR1-positive Ntera-2 cells were treated with Conjugate 46 or exatecan for 3 days. Calreticulin on the cell surface was measured by FACS and HMGB1 in the cell culture medium were measured by ELISA. Both Conjugate 46 and exatecan treatment induced markers for immunogenic cell death (calreticulin translocation to the cell surface and HMGB1 release into the cell culture medium). FIG. 20A and FIG. 20B illustrate calreticulin expression and HMGB1 release of Ntera-2 cells in the presence of Conjugate 46 or exatecan compared to the un-conjugated antibody and an isotype control of Conjugate 46.

Example 29—Induction of Target Cell Killing and Monocyte Activation

Figure 21A:
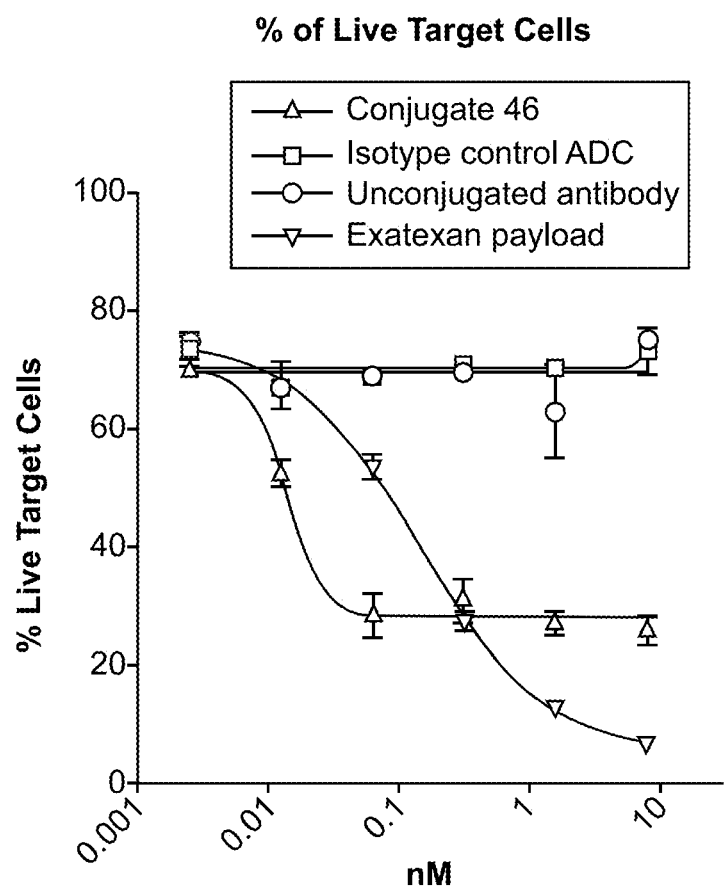
FIG. 21A provides percent of live target cells in Ntera-2 cells following treatment with Conjugate 46 or exatecan compared to the antibody alone and an isotype control of Conjugate 46.
Figure 21B:
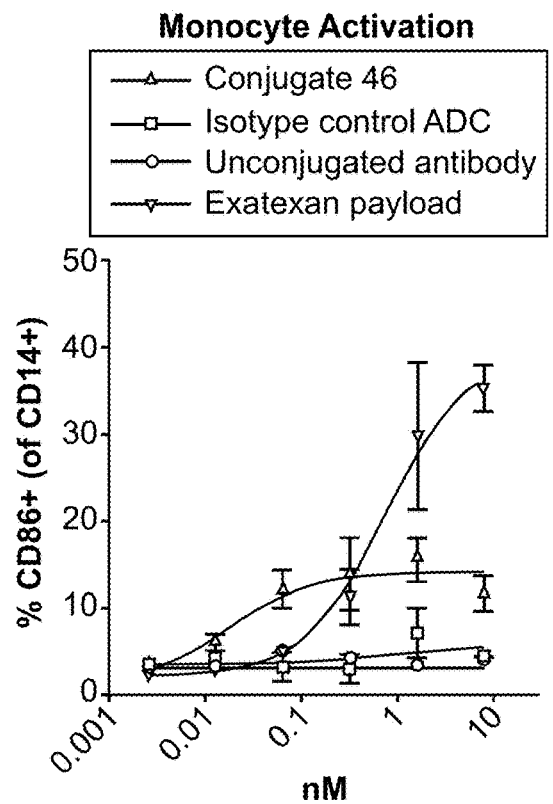
FIG. 21B is a graph showing monocyte activation in Ntera-2 cells following treatment with Conjugate 46 or exatecan compared to the antibody alone and an isotype control of Conjugate 46.
Figure 21C:
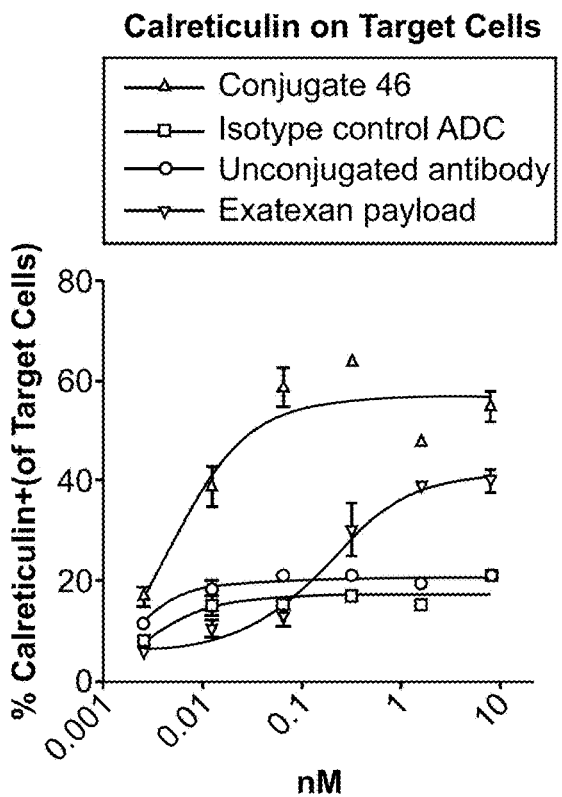
FIG. 21C is a graph showing the percent of calreticulin on the cell surface of Ntera-2 cells following treatment with Conjugate 46 or exatecan compared to the antibody alone and an isotype control of Conjugate 46. Calreticulin surface expression is measured as a percentage compared to untreated cells.

ROR1-positive Ntera-2 cells were co-cultured with PMBCS at E:T=10.1 and treated with Conjugate 46 or exatecan for 3 days. Live target cell count and monocyte activation were measured by FACS. Both Conjugate 46 and exatecan treatment induced potent cell killing of target cells as well as monocyte activation. FIG. 21A and FIG. 21B are graphs showing the percent of live target cells and monocyte activation in Ntera-2 cells following treatment with Conjugate 46 or exatecan compared to the un-conjugated antibody and an isotype control of Conjugate 46. Conjugate 46 or exatecan-treated cells potently induced monocyte activation, as demonstrated by the induction of CD86 expression (FIG. 21B). Unconjugated anti-ROR1 antibody or a non-targeted ADC had no activity. Concomitant with reduced viability, calreticulin could be detected on the cell surface of Conjugate 46 and exatecan treated cells (FIG. 21C), consistent with immunogenic cell death. Viability and calreticulin surface expression were measured and presented as a percentage compared to untreated cells.

Example 30—Anti-PD-1 Combination Therapy

The activity of Conjugate 46 as a single agent or in combination with anti-PD-1 was assessed in syngeneic models using a mouse lung cancer line engineered to express human ROR1, LLC1-hROR1. Briefly, C57BL/6 mice were implanted subcutaneously with 5×10$^5$ LLC1-hROR1 tumor cells in the hind flank and randomized and enrolled into the study 14 days post implant, with tumor sizes ranging from around 50 mm$^3$ to 120 mm$^3$. Tumor-bearing mice were administered two weekly doses (qw×2) of Conjugate 46 at 10 mg/kg and/or three doses (q3d×3) of the anti-PD-1 antibody at 8 mg/kg. All treatments were well tolerated, with mice exhibiting normal body weight gain throughout the course of the study. Two days after the final dose of Conjugate 46 (study day 9), the tumors were harvested and processed for immune phenotyping by flow cytometry.

Figure 22A:
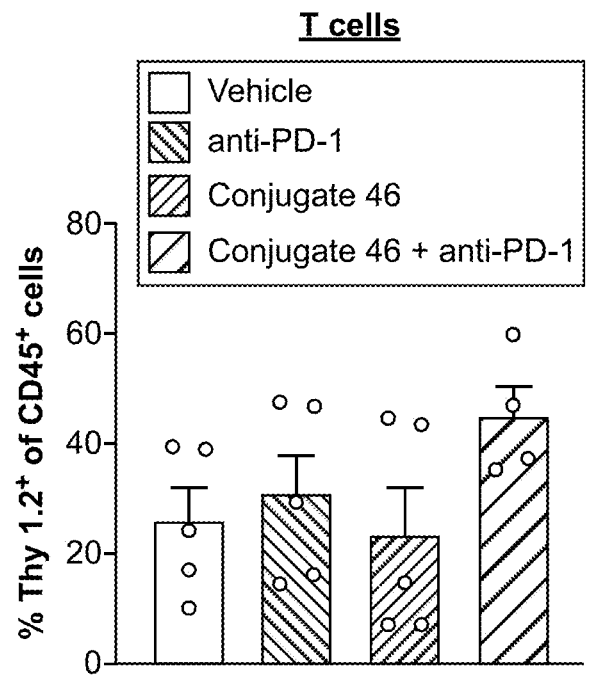
FIGS. 22A-22F provide bar graphs of proportions of (FIG. 22A) total T cells, (FIG. 22B) CD4$^+$ T cells, (FIG. 22C) CD8$^+$ T cells, (FIG. 22D) and tumor-associated macrophages (TAMs), (FIG. 22E) CD80 median fluorescence intensity (MFI) on TAMs, and proportion of (FIG. 22F) arginase 1$^+$ (Arg1$^+$) TAMs in the tumors of mice treated with vehicle or 10 mg/kg Conjugate 46 (qw×2) and/or 8 mg/kg anti-PD-1 (q3d×3). All graphs are presented as individual values and mean±SEM.
Figure 22B:
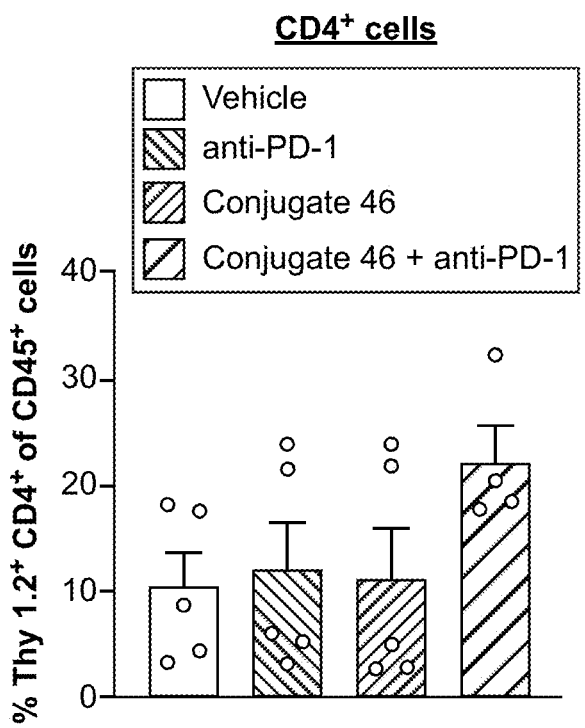
Figure 22C:
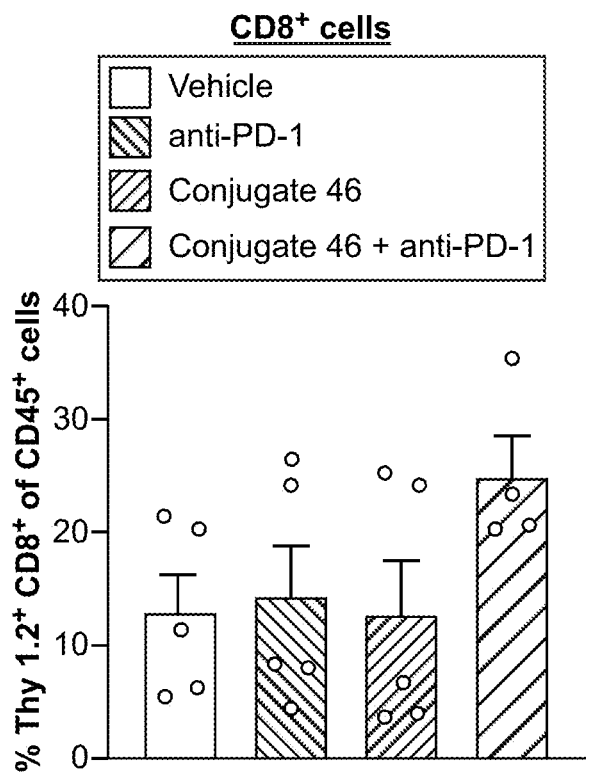
Figure 22D:
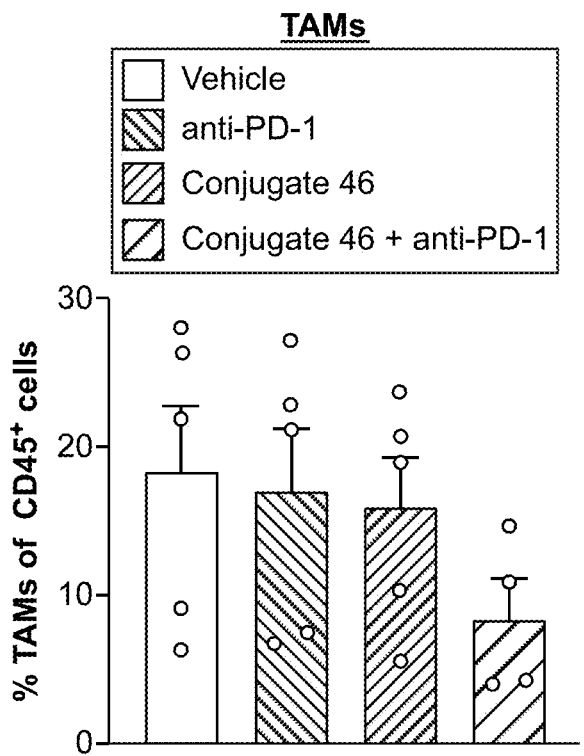
Figure 22E:
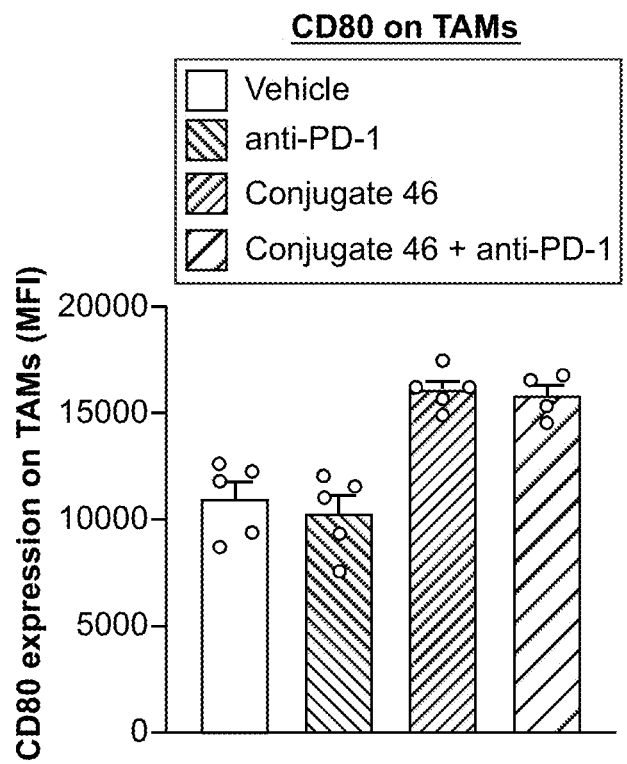
Figure 22F:
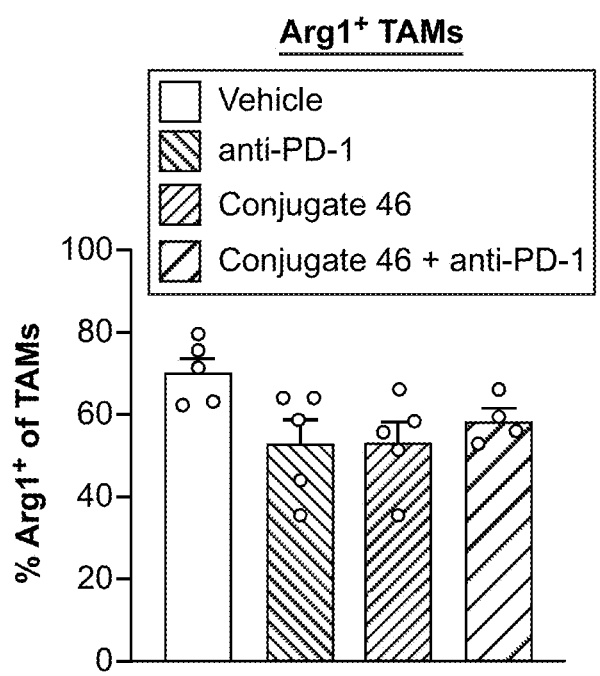

FIGS. 22A-20F illustrate the effects of Conjugate 46 and anti-PD-1 single-agent and combination treatments on the immune infiltrate in the tumor. In FIG. 22A, the tumoral infiltration of total T cells (defined by Thy1.2 positivity) of total CD45$^+$ immune cells was quantified and showed a trend towards increased numbers of total T cells in the combination treatment group compared to all other groups. If the T cells were divided into CD4$^+$ and CD8$^+$ subsets (FIG. 22B and FIG. 22C), a similar pattern was still observed, with the combination group trending towards greater CD4$^+$ and CD8$^+$ T cell infiltration in the tumor compared to the vehicle- and single-agent-treated groups. In FIG. 22D, the infiltration of total tumor-associated macrophages (TAMs) was quantified, and showed a trend towards decreased proportions of TAMs in the combination-treatment group compared to all other groups. Using the costimulatory molecule CD80 as a surrogate marker for the activation of TAMs or skewing of the TAMs towards a more anti-tumor phenotype, it was observed that both treatment with Conjugate 46 and combination treatment achieved a similar degree of increased TAM expression of CD80 (FIG. 22E). On the contrary, using arginase 1 (Arg1) as a surrogate marker for immune-suppressive TAMs, decreased proportions of immune-suppressive TAMs in all treatment groups compared to the vehicle-treated group (FIG. 22F) were observed.

Example 31

Sequences

Tables 20 and 21 provide sequences referred to herein.

TABLE 20

Sequences

| SEQ ID NO: | Molecule | Region | Scheme | Sequence |
|---|---|---|---|---|
| 1 | Human (hROR1) From UniProt Q01973 | | | MHRPRRRGTRPPLLALLAALLLAARGAA AQETELSVSAELVPTSSWNISSELNKDS YLTLDEPMNNITTSLGQTAELHCKVSGN PPPTIRWEKNDAPVVQEPRRLSERSTIY GSRLRIRNLDTTDTGYFQCVATNGKEVV SSTGVLFVKEGPPPTASPGYSDEYEEDG FCQPYRGIACARFIGNRTVYMESLHMQG EIENQITAAFTMIGTSSHLSDKCSQFAI PSLCHYAFPYCDETSSVPKPRDLCRDEC EILENVLCQTEYIFARSNPMILMRLKLP NCEDLPQPESPEAANCIRIGIPMADPIN KNHKCYNSTGVDYRGTVSVTKSGRQCQP WNSQYPHTHTFTALRFPELNGGHSYCRN PGNQKEAPWCFTLDENFKSDLCDIPACD SKDSKEKNKMEILYILVPSVAIPLAIAL LFFFICVCRNNQKSSSAPVQRQPKHVRG QNVEMSMLNAYKPKSKAKELPLSAVREM EELGECAFGKIYKGHLYLPGMDHAQLVA IKTLKDYNNPQQWTEFQQEASLMAELHH PNIVCLLGAVTQEQPVCMLFEYINQGDL HEFLIMRSPHSDVGCSSDEDGTVKSSLD HGDELHIAIQIAAGMEYLSSHFFVHKDL AARNILIGEQLHVKISDLGLSREIYSAD YYRVQSKSLLPIRWMPPEAIMYGKFSSD SDIWSFGVVLWEIFSFGLQPYYGESNQE VIEMVRKRQLLPCSEDCPPRMYSLMTEC WNEIPSRRPREKDIHVRLRSWEGLSSHT SSTTPSGGNATTQTTSLSASPVSNLSNP RYPNYMFPSQGITPQGQIAGFIGPPIPQ NQRFIPINGYPIPPGYAAFPAAHYQPTG PPRVIQHCPPPKSRSPSSASGSTSTGHV TSLPSSGSNQEANIPLLPHMSIPNHPGG MGITVFGNKSQKPYKIDSKQASLLGDAN IHGHTESMISAEL |
| 2 | Cynomolgus ROR1 From UniProt F6RUP2 | | | MHRPRRRGTRPPLLALLAALLLAARGAA AQETELSVSAELVPTSSWNISSELNKDS YLTLDEPMNNITTSLGQTAELHCKVSGN PPPTIRWEKNDAPVVQEPRRLSFRSTIY GSRLRIRNLDTTDTGYFQCVATNGKEVV SSTGVLFVKFGPPPTASPGYSDEYEEDG FCQPYRGIACARFIGNRTVYMESLHMQG EIENQITAAFTMIGTSSHLSDKCSQFAI PSLCHYAFPYCDETSSVPKPRDLCRDEC EILENVLCQTEYIFARSNPMILMRLKLP NCEDLPQPESPEAANCIRIGIPMADPIN KNHKCYNSTGVDYRGTVSVTKSGRQCQP WNSQYPHTHTFTALRFPELNGGHSYCRN PGNQKEAPWCFTLDENFKSDLCDIPACD SKDSKEKNKMEILYILVPSVAIPLAIAL LFFFICVCRNNQKSSSPPVQRQPKHVRG QNVEMSMLNAYKPKSKAKELPLSAVREM EELGECAFGKIYKGHLYLPGMDHAQLVA IKTLKDYNNPQQWTEFQQEASLMAELHH PNIVCLLGAVTQEQPVCMLFEYMNQGDL HEFLIMRSPHSDVGCSSDEDGTVKSSLD HGDELHIAIQIAAGMEYLSSHFFVHKDL AARNILIGEQLHVKISDLGLSREIYSAD YYRVQSKSLLPIRWMPPEAIMYGKFSSD SDIWSFGVVLWEIFSFGLQPYYGFSNQE VIEMVRKRQLLPCSEDCPPRMYSLMTEC WNEIPSRRPREKDIHVRLRSWEGLSSHT SSTTPSGGNATTQTTSLSASPVSNLSNP RYPNYIFPSQGITPQGQIAGFIGPPIPQ NQRFIPINGYPIPPGYAAFPAAHYQPTG |

TABLE 20-continued

Sequences

| SEQ ID NO: | Molecule | Region Scheme | Sequence |
|---|---|---|---|
| | | | PPRVIQHCPPPKSRSPSSASGSTSTGHV TSLPSSGSNQEANIPLLPHMSIPNHPGG MGITVEGNKSQKPYKIDAKQASLLGDAN IHGHTESMISAEL |
| 3 | Murine ROR1 From UniProt Q9Z139 | | MHRPRRGTRPPPLALLAALLLAARGAD AQETELSVSAELVPTSSWNTSSEIDKGS YLTLDEPMNNITTSLGQTAELHCKVSGN PPPSIRWEKNDAPVVQEPRRISFRATNY GSRLRIRNLDTTDTGYFQCVATNGKKVV STTGVLFVKFGPPPTASPGSSDEYEEDG FCQPYRGIACARFIGNRTVYMESLHMQG EIENQITAAFTMIGTSSHLSDKCSQFAI PSLCHYAFPYCDETSSVPKPRDLCRDEC EVLENVLCQTEYIFARSNPMILMRLKLP NCEDLPQPESPEAANCIRIGIPMADPIN KNHKCYNSTGVDYRGTVSVTKSGRQCQP WNSQYPHTHSFTALRFPELNGGHSYCRN PGNQKEAPWCFTLDENFKSDLCDIPACD SKDSKEKNKMEILYILVPSVAIPLAIAF LFFFICVCRNNQKSSSPPVQRQPKPVRG QNVEMSMLNAYKPKSKAKELPLSAVREM EELGECTFGKIYKGHLYLPGMDHAQLVA IKTLKDYNNPQQWTEFQQEASLMAELHH PNIVCLLGAVTQEQPVCMLFEYMNQGDL HEFLIMRSPHSDVGCSSDEDGTVKSSLD HGDELHIAIQIAAGMEYLSSHFFVHKDL AARNILIGEQLHVKISDLGLSREIYSAD YYRVQSKSSLPIRWMPPEAIMYGKFSSD SDIWSFGVVLWEIFSFGLQPYYGFSNQE VIEMVRKROLLPCSEDCPPRMYSLMTEC WNEIPSRRPREKDIHVRLRSWEGLSSHT SSTTPSGGNATTQTTSLSASPVSNLSNP RFPNYMFPSQGITPQGQIAGFIGPAIPQ NQRFIPINGYPIPPGYAAFPAAHYQPAG PPRVIQHCPPPKSRSPSSASGSTSTGHV ASLPSSGSNQEANVPLLPHMSIPNHPGG MGITVFGNKSQKPYKIDSKQSSLLGDSH IHGHTESMISAEV |
| 4 | 1987-C05 | CDR-H1 Chothia | GFNISDY |
| 5 | 2188-D11 | CDR-H1 Chothia | GFNIRDY |
| 6 | 2188-B04 | CDR-H1 Chothia | GFNITWY |
| 7 | 2188-C09 | CDR-H1 Chothia | GFNINSY |
| 8 | 2188-G03 | CDR-H1 Chothia | GFNIVDY |
| 9 | 2188-E03 | CDR-H1 Chothia | GFNIRDY |
| 10 | 2188-B11 | CDR-H1 Chothia | GFNINRY |
| 11 | 2188-E07 | CDR-H1 Chothia | GFNIGDY |
| 12 | 2188-B02 | CDR-H1 Chothia | GFNISSY |
| 13 | 2188-C07 | CDR-H1 Chothia | GFNIVRY |
| 14 | 2188-A03 | CDR-H1 Chothia | GFNIRDY |
| 15 | 2188-F03 | CDR-H1 Chothia | GFNISDY |
| 16 | 2188-D03 | CDR-H1 Chothia | GFNISDY |
| 17 | 2188-C04 | CDR-H1 Chothia | GFNINSY |
| 18 | 2188-D10 | CDR-H1 Chothia | GFNISDY |
| 19 | 2188-A06 | CDR-H1 Chothia | GFNIKSY |
| 20 | 2188-C11 | CDR-H1 Chothia | GFNIKSY |
| 21 | 2188-F01 | CDR-H1 Chothia | GFNIRYY |

TABLE 20-continued

Sequences

| SEQ ID NO: | Molecule | Region | Scheme | Sequence |
|---|---|---|---|---|
| 22 | 2188-E11 | CDR-H1 | Chothia | GFNISHY |
| 23 | 2188-A07 | CDR-H1 | Chothia | GFNIHHY |
| 24 | 2188-C01 | CDR-H1 | Chothia | GFNIISY |
| 25 | 2188-F08 | CDR-H1 | Chothia | GFNIPDF |
| 26 | 2188-E04 | CDR-H1 | Chothia | GFNISDY |
| 27 | 2188-B01 | CDR-H1 | Chothia | GFNINSH |
| 28 | 2188-F11 | CDR-H1 | Chothia | GFNITGY |
| 29 | 2188-B08 | CDR-H1 | Chothia | GFNIDSY |
| 30 | 2188-C10 | CDR-H1 | Chothia | GFNINSY |
| 31 | 2188-C02 | CDR-H1 | Chothia | GFNIFRY |
| 32 | 2188-B07 | CDR-H1 | Chothia | GFNIHSH |
| 33 | 2188-A11 | CDR-H1 | Chothia | GFNISDY |
| 34 | 2188-D01 | CDR-H1 | Chothia | GFNIKSY |
| 35 | 2188-E09 | CDR-H1 | Chothia | GFNISDF |
| 36 | 2188-E06 | CDR-H1 | Chothia | GFNIGDY |
| 37 | 2188-B03 | CDR-H1 | Chothia | GFNISSY |
| 38 | 2188-F06 | CDR-H1 | Chothia | GFNILDY |
| 39 | 2188-D02 | CDR-H1 | Chothia | GFNISDY |
| 40 | 2188-B06 | CDR-H1 | Chothia | GFNIHSY |
| 41 | 2188-D09 | CDR-H1 | Chothia | GFNIRDY |
| 42 | 2188-F02 | CDR-H1 | Chothia | GFNISDY |
| 43 | 2188-E10 | CDR-H1 | Chothia | GFNIGDF |
| 44 | 2188-A09 | CDR-H1 | Chothia | GFNIINY |
| 45 | 2188-D04 | CDR-H1 | Chothia | GFNISDY |
| 46 | 2188-A05 | CDR-H1 | Chothia | GFNIKRY |
| 47 | 2188-E01 | CDR-H1 | Chothia | GFNIGDY |
| 48 | 2188-G01 | CDR-H1 | Chothia | GFNISDY |
| 49 | 2188-B09 | CDR-H1 | Chothia | GFNINSY |
| 50 | 2188-F07 | CDR-H1 | Chothia | GFNISDY |
| 51 | 2188-D08 | CDR-H1 | Chothia | GFNIRDY |
| 52 | 2188-D05 | CDR-H1 | Chothia | GFNISEY |
| 53 | 2188-C03 | CDR-H1 | Chothia | GFNINSY |
| 54 | 2188-E08 | CDR-H1 | Chothia | GFNIIDF |
| 55 | 2188-C06 | CDR-H1 | Chothia | GFNINSY |
| 56 | 2188-A08 | CDR-H1 | Chothia | GFNIHNF |
| 57 | 2188-B10 | CDR-H1 | Chothia | GFNINSY |
| 58 | 2188-G02 | CDR-H1 | Chothia | GFNIVGY |

TABLE 20-continued

Sequences

| SEQ ID NO: | Molecule | Region | Scheme | Sequence |
|---|---|---|---|---|
| 59 | 2188-C05 | CDR-H1 | Chothia | GFNINSF |
| 60 | 2188-A10 | CDR-H1 | Chothia | GFNINSY |
| 61 | 2188-G04 | CDR-H1 | Chothia | GFNIFDY |
| 62 | 2188-C08 | CDR-H1 | Chothia | GFNIKSH |
| 63 | 2188-E05 | CDR-H1 | Chothia | GFNISDY |
| 64 | 2188-A02 | CDR-H1 | Chothia | GFNIKSY |
| 65 | 2188-F04 | CDR-H1 | Chothia | GFNISDF |
| 66 | 2188-F05 | CDR-H1 | Chothia | GFNISDY |
| 67 | 2188-D07 | CDR-H1 | Chothia | GFNISDF |
| 68 | 2188-E02 | CDR-H1 | Chothia | GFNIPDY |
| 69 | 2188-D06 | CDR-H1 | Chothia | GFNIRDY |
| 70 | 2188-F09 | CDR-H1 | Chothia | GFNIRDY |
| 71 | 2188-F10 | CDR-H1 | Chothia | GFNISVF |
| 72 | 2188-B05 | CDR-H1 | Chothia | GFNIPDY |
| 73 | 1943-C02 | CDR-H1 | Chothia | GFNINDY |
| 74 | 2193-D04 | CDR-H1 | Chothia | GFNINGF |
| 75 | 2193-E10 | CDR-H1 | Chothia | GFNIYDY |
| 76 | 2193-E06 | CDR-H1 | Chothia | GFNIDDY |
| 77 | 2193-E04 | CDR-H1 | Chothia | GFNINDR |
| 78 | 2193-B09 | CDR-H1 | Chothia | GFNINNS |
| 79 | 2193-D11 | CDR-H1 | Chothia | GFNINAY |
| 80 | 2193-B02 | CDR-H1 | Chothia | GFNIKNS |
| 81 | 2193-D05 | CDR-H1 | Chothia | GFNINDH |
| 82 | 2193-E11 | CDR-H1 | Chothia | GFNINDY |
| 83 | 2193-D06 | CDR-H1 | Chothia | GFNIRDY |
| 84 | 2193-C02 | CDR-H1 | Chothia | GFNISDY |
| 85 | 2193-B03 | CDR-H1 | Chothia | GFNIRDY |
| 86 | 2193-A02 | CDR-H1 | Chothia | GFNIHAS |
| 87 | 2193-E05 | CDR-H1 | Chothia | GFNIKRS |
| 88 | 2193-A06 | CDR-H1 | Chothia | GFNINAY |
| 89 | 2193-C04 | CDR-H1 | Chothia | GFNINTS |
| 90 | 2193-E08 | CDR-H1 | Chothia | GFNINFY |
| 91 | 2193-B10 | CDR-H1 | Chothia | GFNIADY |
| 92 | 2193-D08 | CDR-H1 | Chothia | GFNIKRS |
| 93 | 2193-B08 | CDR-H1 | Chothia | GFNIKDY |
| 94 | 2193-C05 | CDR-H1 | Chothia | GFNIKHS |
| 95 | 2193-D10 | CDR-H1 | Chothia | GFNINVS |
| 96 | 2193-D03 | CDR-H1 | Chothia | GFNINDH |

TABLE 20-continued

Sequences

| SEQ ID NO: | Molecule | Region | Scheme | Sequence |
|---|---|---|---|---|
| 97 | 2193-A09 | CDR-H1 | Chothia | GFNIGKH |
| 98 | 2193-A10 | CDR-H1 | Chothia | GFNIGDY |
| 99 | 2193-E07 | CDR-H1 | Chothia | GFNINKV |
| 100 | 2193-A07 | CDR-H1 | Chothia | GFNINAS |
| 101 | 2193-E03 | CDR-H1 | Chothia | GFNITAS |
| 102 | 2193-C08 | CDR-H1 | Chothia | GFNINHY |
| 103 | 2193-B11 | CDR-H1 | Chothia | GFNITGS |
| 104 | 2193-A03 | CDR-H1 | Chothia | GFNIANY |
| 105 | 2193-D02 | CDR-H1 | Chothia | GFNIKDY |
| 106 | 2193-B06 | CDR-H1 | Chothia | GFNIDGY |
| 107 | 2193-B01 | CDR-H1 | Chothia | GFNIGGY |
| 108 | 2193-D09 | CDR-H1 | Chothia | GFNINGY |
| 109 | 2193-E09 | CDR-H1 | Chothia | GFNIGAY |
| 110 | 2193-B07 | CDR-H1 | Chothia | GFNINNS |
| 111 | 2193-C06 | CDR-H1 | Chothia | GFNIIVH |
| 112 | 2193-B05 | CDR-H1 | Chothia | GFNINQY |
| 113 | 2193-A11 | CDR-H1 | Chothia | GFNIDAY |
| 114 | 2193-E02 | CDR-H1 | Chothia | GFNIKDY |
| 115 | 2193-A08 | CDR-H1 | Chothia | GFNIIDS |
| 116 | 2193-C11 | CDR-H1 | Chothia | GFNIADS |
| 117 | 2193-A01 | CDR-H1 | Chothia | GFNINDH |
| 118 | 2193-D07 | CDR-H1 | Chothia | GFNIIDY |
| 119 | 2193-A05 | CDR-H1 | Chothia | GFNIKGY |
| 120 | 2193-C03 | CDR-H1 | Chothia | GFNINYS |
| 121 | 2193-C09 | CDR-H1 | Chothia | GFNINHS |
| 122 | 2193-D01 | CDR-H1 | Chothia | GFNINDS |
| 123 | 2193-E01 | CDR-H1 | Chothia | GFNIKGK |
| 124 | 2193-C07 | CDR-H1 | Chothia | GFNIKDQ |
| 125 | 2193-B04 | CDR-H1 | Chothia | GFNISNS |
| 126 | 2193-C10 | CDR-H1 | Chothia | GFNINNA |
| 127 | 2193-C01 | CDR-H1 | Chothia | GLNINDH |
| 128 | 2193-A04 | CDR-H1 | Chothia | GFNIISY |
| 129 | 1944-A07 | CDR-H1 | Chothia | GFNITGY |
| 130 | 2194-A02 | CDR-H1 | Chothia | GFNITGY |
| 131 | 2194-A05 | CDR-H1 | Chothia | GFNIKEY |
| 132 | 2194-B04 | CDR-H1 | Chothia | GFNITGY |
| 133 | 2194-A09 | CDR-H1 | Chothia | GFNITGY |

TABLE 20-continued

Sequences

| SEQ ID NO: | Molecule | Region | Scheme | Sequence |
|---|---|---|---|---|
| 134 | 2194-A01 | CDR-H1 | Chothia | GFNITGY |
| 135 | 2194-B03 | CDR-H1 | Chothia | GFNITSY |
| 136 | 2194-B02 | CDR-H1 | Chothia | GFNISGY |
| 137 | 2194-A03 | CDR-H1 | Chothia | GFNITGY |
| 138 | 2194-A11 | CDR-H1 | Chothia | GFNITQY |
| 139 | 2194-A08 | CDR-H1 | Chothia | GFNITGY |
| 140 | 2194-A04 | CDR-H1 | Chothia | GFNITGY |
| 141 | 2194-A10 | CDR-H1 | Chothia | GFNITQY |
| 142 | 2194-A07 | CDR-H1 | Chothia | GFNFTDY |
| 143 | 2194-B01 | CDR-H1 | Chothia | GFNIASY |
| 144 | 2194-A06 | CDR-H1 | Chothia | GFNITDY |
| 145 | 2196-C01 | CDR-H1 | Chothia | GFNIIGY |
| 146 | 2196-A02 | CDR-H1 | Chothia | GFNITGY |
| 147 | 2196-B03 | CDR-H1 | Chothia | GFNITGY |
| 148 | 2196-A05 | CDR-H1 | Chothia | GFNITNY |
| 149 | 2196-C02 | CDR-H1 | Chothia | GFNITGY |
| 150 | 2196-B11 | CDR-H1 | Chothia | GFNITGY |
| 151 | 2196-B08 | CDR-H1 | Chothia | GFNITGY |
| 152 | 2196-A04 | CDR-H1 | Chothia | GFNISPY |
| 153 | 2196-A03 | CDR-H1 | Chothia | GFNITQY |
| 154 | 2196-B07 | CDR-H1 | Chothia | GFNITGY |
| 155 | 2196-A06 | CDR-H1 | Chothia | GFNITGY |
| 156 | 2196-B05 | CDR-H1 | Chothia | GFNITGY |
| 157 | 2196-A01 | CDR-H1 | Chothia | GFNITGY |
| 158 | 2196-B01 | CDR-H1 | Chothia | GFNITGY |
| 159 | 2196-A09 | CDR-H1 | Chothia | GFNITGY |
| 160 | 2196-A08 | CDR-H1 | Chothia | GFNITGY |
| 161 | 2196-A10 | CDR-H1 | Chothia | GFNITGY |
| 162 | 2196-B06 | CDR-H1 | Chothia | GFNITGY |
| 163 | 2196-B09 | CDR-H1 | Chothia | GFNITEY |
| 164 | 2196-C03 | CDR-H1 | Chothia | GFNITGY |
| 165 | 2196-C04 | CDR-H1 | Chothia | GFNITGY |
| 166 | 2196-A07 | CDR-H1 | Chothia | GFNITGY |
| 167 | 2196-A11 | CDR-H1 | Chothia | GFNITGY |
| 168 | 2196-B02 | CDR-H1 | Chothia | GFNITQY |
| 169 | 2196-B04 | CDR-H1 | Chothia | GFNITEY |
| 170 | 2196-B10 | CDR-H1 | Chothia | GFNITGY |
| 171 | 1987-C05 | CDR-H1 | Kabat | DYDIH |

TABLE 20-continued

Sequences

| SEQ ID NO: | Molecule | Region | Scheme | Sequence |
|---|---|---|---|---|
| 172 | 2188-D11 | CDR-H1 | Kabat | DYDIH |
| 173 | 2188-B04 | CDR-H1 | Kabat | WYDIH |
| 174 | 2188-C09 | CDR-H1 | Kabat | SYDIH |
| 175 | 2188-G03 | CDR-H1 | Kabat | DYDIH |
| 176 | 2188-E03 | CDR-H1 | Kabat | DYDIH |
| 177 | 2188-B11 | CDR-H1 | Kabat | RYDIH |
| 178 | 2188-E07 | CDR-H1 | Kabat | DYGIH |
| 179 | 2188-B02 | CDR-H1 | Kabat | SYDIH |
| 180 | 2188-C07 | CDR-H1 | Kabat | RYDIH |
| 181 | 2188-A03 | CDR-H1 | Kabat | DYDIH |
| 182 | 2188-F03 | CDR-H1 | Kabat | DYDIH |
| 183 | 2188-D03 | CDR-H1 | Kabat | DYDIH |
| 184 | 2188-C04 | CDR-H1 | Kabat | SYDIH |
| 185 | 2188-D10 | CDR-H1 | Kabat | DYDIH |
| 186 | 2188-A06 | CDR-H1 | Kabat | SYDIH |
| 187 | 2188-C11 | CDR-H1 | Kabat | SYDIH |
| 188 | 2188-F01 | CDR-H1 | Kabat | YYDIH |
| 189 | 2188-E11 | CDR-H1 | Kabat | HYDIH |
| 190 | 2188-A07 | CDR-H1 | Kabat | HYDIH |
| 191 | 2188-C01 | CDR-H1 | Kabat | SYDIH |
| 192 | 2188-F08 | CDR-H1 | Kabat | DFEIH |
| 193 | 2188-E04 | CDR-H1 | Kabat | DYDIH |
| 194 | 2188-B01 | CDR-H1 | Kabat | SHDIH |
| 195 | 2188-F11 | CDR-H1 | Kabat | GYDIH |
| 196 | 2188-B08 | CDR-H1 | Kabat | SYDIH |
| 197 | 2188-C10 | CDR-H1 | Kabat | SYDIH |
| 198 | 2188-C02 | CDR-H1 | Kabat | RYDIH |
| 199 | 2188-B07 | CDR-H1 | Kabat | SHDIH |
| 200 | 2188-A11 | CDR-H1 | Kabat | DYDIH |
| 201 | 2188-D01 | CDR-H1 | Kabat | SYDIH |
| 202 | 2188-E09 | CDR-H1 | Kabat | DFDIH |
| 203 | 2188-E06 | CDR-H1 | Kabat | DYDIH |
| 204 | 2188-B03 | CDR-H1 | Kabat | SYDIH |
| 205 | 2188-F06 | CDR-H1 | Kabat | DYDIH |
| 206 | 2188-D02 | CDR-H1 | Kabat | DYDIH |
| 207 | 2188-B06 | CDR-H1 | Kabat | SYDIH |
| 208 | 2188-D09 | CDR-H1 | Kabat | DYDIH |

TABLE 20-continued

Sequences

| SEQ ID NO: | Molecule | Region | Scheme | Sequence |
|---|---|---|---|---|
| 209 | 2188-F02 | CDR-H1 | Kabat | DYDIH |
| 210 | 2188-E10 | CDR-H1 | Kabat | DFDIH |
| 211 | 2188-A09 | CDR-H1 | Kabat | NYDIH |
| 212 | 2188-D04 | CDR-H1 | Kabat | DYDIH |
| 213 | 2188-A05 | CDR-H1 | Kabat | RYDIH |
| 214 | 2188-E01 | CDR-H1 | Kabat | DYDIH |
| 215 | 2188-G01 | CDR-H1 | Kabat | DYDIH |
| 216 | 2188-B09 | CDR-H1 | Kabat | SYDIH |
| 217 | 2188-F07 | CDR-H1 | Kabat | DYDIH |
| 218 | 2188-D08 | CDR-H1 | Kabat | DYDIH |
| 219 | 2188-D05 | CDR-H1 | Kabat | EYDIH |
| 220 | 2188-C03 | CDR-H1 | Kabat | SYDIH |
| 221 | 2188-E08 | CDR-H1 | Kabat | DFDIH |
| 222 | 2188-C06 | CDR-H1 | Kabat | SYDIH |
| 223 | 2188-A08 | CDR-H1 | Kabat | NFDIH |
| 224 | 2188-B10 | CDR-H1 | Kabat | SYDIH |
| 225 | 2188-G02 | CDR-H1 | Kabat | GYDIH |
| 226 | 2188-C05 | CDR-H1 | Kabat | SFDIH |
| 227 | 2188-A10 | CDR-H1 | Kabat | SYDIH |
| 228 | 2188-G04 | CDR-H1 | Kabat | DYDIH |
| 229 | 2188-C08 | CDR-H1 | Kabat | SHDIH |
| 230 | 2188-E05 | CDR-H1 | Kabat | DYDIH |
| 231 | 2188-A02 | CDR-H1 | Kabat | SYDIH |
| 232 | 2188-F04 | CDR-H1 | Kabat | DFDIH |
| 233 | 2188-F05 | CDR-H1 | Kabat | DYDIH |
| 234 | 2188-D07 | CDR-H1 | Kabat | DFDIH |
| 235 | 2188-E02 | CDR-H1 | Kabat | DYEIH |
| 236 | 2188-D06 | CDR-H1 | Kabat | DYDIH |
| 237 | 2188-F09 | CDR-H1 | Kabat | DYDIH |
| 238 | 2188-F10 | CDR-H1 | Kabat | VFDIH |
| 239 | 2188-B05 | CDR-H1 | Kabat | DYDIH |
| 240 | 1943-C02 | CDR-H1 | Kabat | DYYIH |
| 241 | 2193-D04 | CDR-H1 | Kabat | GFYIH |
| 242 | 2193-E10 | CDR-H1 | Kabat | DYYIH |
| 243 | 2193-E06 | CDR-H1 | Kabat | DYYIH |
| 244 | 2193-E04 | CDR-H1 | Kabat | DRYIH |
| 245 | 2193-B09 | CDR-H1 | Kabat | NSYIH |
| 246 | 2193-D11 | CDR-H1 | Kabat | AYYIH |

TABLE 20-continued

Sequences

| SEQ ID NO: | Molecule | Region | Scheme | Sequence |
|---|---|---|---|---|
| 247 | 2193-B02 | CDR-H1 | Kabat | NSYIH |
| 248 | 2193-D05 | CDR-H1 | Kabat | DHYIH |
| 249 | 2193-E11 | CDR-H1 | Kabat | DYYIH |
| 250 | 2193-D06 | CDR-H1 | Kabat | DYYIH |
| 251 | 2193-C02 | CDR-H1 | Kabat | DYYIH |
| 252 | 2193-B03 | CDR-H1 | Kabat | DYYIH |
| 253 | 2193-A02 | CDR-H1 | Kabat | ASYIH |
| 254 | 2193-E05 | CDR-H1 | Kabat | RSYIH |
| 255 | 2193-A06 | CDR-H1 | Kabat | AYYIH |
| 256 | 2193-C04 | CDR-H1 | Kabat | TSYIH |
| 257 | 2193-E08 | CDR-H1 | Kabat | EYYIH |
| 258 | 2193-B10 | CDR-H1 | Kabat | DYYVH |
| 259 | 2193-D08 | CDR-H1 | Kabat | RSYIH |
| 260 | 2193-B08 | CDR-H1 | Kabat | DYYIH |
| 261 | 2193-C05 | CDR-H1 | Kabat | HSYIH |
| 262 | 2193-D10 | CDR-H1 | Kabat | VSYIH |
| 263 | 2193-D03 | CDR-H1 | Kabat | DHYIH |
| 264 | 2193-A09 | CDR-H1 | Kabat | KHHIH |
| 265 | 2193-A10 | CDR-H1 | Kabat | DYYIH |
| 266 | 2193-E07 | CDR-H1 | Kabat | KVYIH |
| 267 | 2193-A07 | CDR-H1 | Kabat | ASDIH |
| 268 | 2193-E03 | CDR-H1 | Kabat | ASYIH |
| 269 | 2193-C08 | CDR-H1 | Kabat | HYYIH |
| 270 | 2193-B11 | CDR-H1 | Kabat | GSYIH |
| 271 | 2193-A03 | CDR-H1 | Kabat | NYHIH |
| 272 | 2193-D02 | CDR-H1 | Kabat | DYYIH |
| 273 | 2193-B06 | CDR-H1 | Kabat | GYYIH |
| 274 | 2193-B01 | CDR-H1 | Kabat | GYYIH |
| 275 | 2193-D09 | CDR-H1 | Kabat | GYYIH |
| 276 | 2193-E09 | CDR-H1 | Kabat | AYYIH |
| 277 | 2193-B07 | CDR-H1 | Kabat | NSYIH |
| 278 | 2193-C06 | CDR-H1 | Kabat | VHYIH |
| 279 | 2193-B05 | CDR-H1 | Kabat | QYYIH |
| 280 | 2193-A11 | CDR-H1 | Kabat | AYYIH |
| 281 | 2193-E02 | CDR-H1 | Kabat | DYYIH |
| 282 | 2193-A08 | CDR-H1 | Kabat | DSYIH |
| 283 | 2193-C11 | CDR-H1 | Kabat | DSYIH |

TABLE 20-continued

Sequences

| SEQ ID NO: | Molecule | Region | Scheme | Sequence |
|---|---|---|---|---|
| 284 | 2193-A01 | CDR-H1 | Kabat | DHYIH |
| 285 | 2193-D07 | CDR-H1 | Kabat | DYNIH |
| 286 | 2193-A05 | CDR-H1 | Kabat | GYYIH |
| 287 | 2193-C03 | CDR-H1 | Kabat | YSYIH |
| 288 | 2193-C09 | CDR-H1 | Kabat | HSYIH |
| 289 | 2193-D01 | CDR-H1 | Kabat | DSYIH |
| 290 | 2193-E01 | CDR-H1 | Kabat | GKYIH |
| 291 | 2193-C07 | CDR-H1 | Kabat | DQDIH |
| 292 | 2193-B04 | CDR-H1 | Kabat | NSYTH |
| 293 | 2193-C10 | CDR-H1 | Kabat | NAYIH |
| 294 | 2193-C01 | CDR-H1 | Kabat | DHYIH |
| 295 | 2193-A04 | CDR-H1 | Kabat | SYYIH |
| 296 | 1944-A07 | CDR-H1 | Kabat | GYYIH |
| 297 | 2194-A02 | CDR-H1 | Kabat | GYYIH |
| 298 | 2194-A05 | CDR-H1 | Kabat | EYHIH |
| 299 | 2194-B04 | CDR-H1 | Kabat | GYHIH |
| 300 | 2194-A09 | CDR-H1 | Kabat | GYYIH |
| 301 | 2194-A01 | CDR-H1 | Kabat | GYYIH |
| 302 | 2194-B03 | CDR-H1 | Kabat | SYYIH |
| 303 | 2194-B02 | CDR-H1 | Kabat | GYYIH |
| 304 | 2194-A03 | CDR-H1 | Kabat | GYYIH |
| 305 | 2194-A11 | CDR-H1 | Kabat | QYYIH |
| 306 | 2194-A08 | CDR-H1 | Kabat | GYHIH |
| 307 | 2194-A04 | CDR-H1 | Kabat | GYYIH |
| 308 | 2194-A10 | CDR-H1 | Kabat | QYYIH |
| 309 | 2194-A07 | CDR-H1 | Kabat | DYYIH |
| 310 | 2194-B01 | CDR-H1 | Kabat | SYYIH |
| 311 | 2194-A06 | CDR-H1 | Kabat | DYYIH |
| 312 | 2196-C01 | CDR-H1 | Kabat | GYYIH |
| 313 | 2196-A02 | CDR-H1 | Kabat | GYYIH |
| 314 | 2196-B03 | CDR-H1 | Kabat | GYYIH |
| 315 | 2196-A05 | CDR-H1 | Kabat | NYYIH |
| 316 | 2196-C02 | CDR-H1 | Kabat | GYHIH |
| 317 | 2196-B11 | CDR-H1 | Kabat | GYYIH |
| 318 | 2196-B08 | CDR-H1 | Kabat | GYYIH |
| 319 | 2196-A04 | CDR-H1 | Kabat | PYYIH |
| 320 | 2196-A03 | CDR-H1 | Kabat | QYHIH |
| 321 | 2196-B07 | CDR-H1 | Kabat | GYHIH |

TABLE 20-continued

Sequences

| SEQ ID NO: | Molecule | Region Scheme | Sequence |
|---|---|---|---|
| 322 | 2196-A06 | CDR-H1 Kabat | GYYIH |
| 323 | 2196-B05 | CDR-H1 Kabat | GYYIH |
| 324 | 2196-A01 | CDR-H1 Kabat | GYYIH |
| 325 | 2196-B01 | CDR-H1 Kabat | GYYIH |
| 326 | 2196-A09 | CDR-H1 Kabat | GYYIH |
| 327 | 2196-A08 | CDR-H1 Kabat | GYYIH |
| 328 | 2196-A10 | CDR-H1 Kabat | GYYIH |
| 329 | 2196-B06 | CDR-H1 Kabat | GYYIH |
| 330 | 2196-B09 | CDR-H1 Kabat | EYYIH |
| 331 | 2196-C03 | CDR-H1 Kabat | GYYIH |
| 332 | 2196-C04 | CDR-H1 Kabat | GYYIH |
| 333 | 2196-A07 | CDR-H1 Kabat | GYYIH |
| 334 | 2196-A11 | CDR-H1 Kabat | GYYIH |
| 335 | 2196-B02 | CDR-H1 Kabat | QYYIH |
| 336 | 2196-B04 | CDR-H1 Kabat | EYYIH |
| 337 | 2196-B10 | CDR-H1 Kabat | GYYIH |
| 338 | 1987-C05 | CDR-H2 Chothia | DPDDGS |
| 339 | 2188-D11 | CDR-H2 Chothia | DPDDGS |
| 340 | 2188-B04 | CDR-H2 Chothia | NPDDGD |
| 341 | 2188-C09 | CDR-H2 Chothia | NPHDGD |
| 342 | 2188-G03 | CDR-H2 Chothia | DPRDGS |
| 343 | 2188-E03 | CDR-H2 Chothia | DPDDGS |
| 344 | 2188-B11 | CDR-H2 Chothia | NPDDGD |
| 345 | 2188-E07 | CDR-H2 Chothia | DPEDGF |
| 346 | 2188-B02 | CDR-H2 Chothia | NPDDGD |
| 347 | 2188-C07 | CDR-H2 Chothia | NPDDGD |
| 348 | 2188-A03 | CDR-H2 Chothia | NPDDGD |
| 349 | 2188-F03 | CDR-H2 Chothia | DPDDGS |
| 350 | 2188-D03 | CDR-H2 Chothia | DPHDGS |
| 351 | 2188-C04 | CDR-H2 Chothia | NPEDGD |
| 352 | 2188-D10 | CDR-H2 Chothia | DPRDGA |
| 353 | 2188-A06 | CDR-H2 Chothia | NPDDGD |
| 354 | 2188-C11 | CDR-H2 Chothia | NPDDGD |
| 355 | 2188-F01 | CDR-H2 Chothia | DPDDGW |
| 356 | 2188-E11 | CDR-H2 Chothia | DPGDGA |
| 357 | 2188-A07 | CDR-H2 Chothia | NPDDGD |
| 358 | 2188-C01 | CDR-H2 Chothia | DPHDGS |

TABLE 20-continued

Sequences

| SEQ ID NO: | Molecule | Region | Scheme | Sequence |
|---|---|---|---|---|
| 359 | 2188-F08 | CDR-H2 | Chothia | EPDDGA |
| 360 | 2188-E04 | CDR-H2 | Chothia | DPQDGS |
| 361 | 2188-B01 | CDR-H2 | Chothia | NPDDGD |
| 362 | 2188-F11 | CDR-H2 | Chothia | DPEDGA |
| 363 | 2188-B08 | CDR-H2 | Chothia | NPDDGD |
| 364 | 2188-C10 | CDR-H2 | Chothia | NPDDGD |
| 365 | 2188-C02 | CDR-H2 | Chothia | NPDDGD |
| 366 | 2188-B07 | CDR-H2 | Chothia | NPDDGD |
| 367 | 2188-A11 | CDR-H2 | Chothia | DPKDGA |
| 368 | 2188-D01 | CDR-H2 | Chothia | NPYDGD |
| 369 | 2188-E09 | CDR-H2 | Chothia | DPQDGW |
| 370 | 2188-E06 | CDR-H2 | Chothia | DPEDGA |
| 371 | 2188-B03 | CDR-H2 | Chothia | DPGDGA |
| 372 | 2188-F06 | CDR-H2 | Chothia | DPDDGA |
| 373 | 2188-D02 | CDR-H2 | Chothia | DPEDGA |
| 374 | 2188-B06 | CDR-H2 | Chothia | NPDDGD |
| 375 | 2188-D09 | CDR-H2 | Chothia | DPGDGS |
| 376 | 2188-F02 | CDR-H2 | Chothia | DPSDGS |
| 377 | 2188-E10 | CDR-H2 | Chothia | DPRDGA |
| 378 | 2188-A09 | CDR-H2 | Chothia | NPDDGD |
| 379 | 2188-D04 | CDR-H2 | Chothia | DPADGS |
| 380 | 2188-A05 | CDR-H2 | Chothia | NPDDGD |
| 381 | 2188-E01 | CDR-H2 | Chothia | DPQDGA |
| 382 | 2188-G01 | CDR-H2 | Chothia | DPNDGA |
| 383 | 2188-B09 | CDR-H2 | Chothia | DPKDGW |
| 384 | 2188-F07 | CDR-H2 | Chothia | DPNDGS |
| 385 | 2188-D08 | CDR-H2 | Chothia | DPDDGA |
| 386 | 2188-D05 | CDR-H2 | Chothia | DPHDGW |
| 387 | 2188-C03 | CDR-H2 | Chothia | NPDDGD |
| 388 | 2188-E08 | CDR-H2 | Chothia | DPQDGS |
| 389 | 2188-C06 | CDR-H2 | Chothia | NPDDGD |
| 390 | 2188-A08 | CDR-H2 | Chothia | NPFDGD |
| 391 | 2188-B10 | CDR-H2 | Chothia | NPHDGD |
| 392 | 2188-G02 | CDR-H2 | Chothia | DPNDGA |
| 393 | 2188-C05 | CDR-H2 | Chothia | DPRDGS |
| 394 | 2188-A10 | CDR-H2 | Chothia | NPEDGD |
| 395 | 2188-G04 | CDR-H2 | Chothia | DPRDGS |
| 396 | 2188-C08 | CDR-H2 | Chothia | NPDDGD |

TABLE 20-continued

Sequences

| SEQ ID NO: | Molecule | Region | Scheme | Sequence |
|---|---|---|---|---|
| 397 | 2188-E05 | CDR-H2 | Chothia | EPWDGS |
| 398 | 2188-A02 | CDR-H2 | Chothia | NPEDGD |
| 399 | 2188-F04 | CDR-H2 | Chothia | DPDDGA |
| 400 | 2188-F05 | CDR-H2 | Chothia | DPRDGA |
| 401 | 2188-D07 | CDR-H2 | Chothia | DPTDGA |
| 402 | 2188-E02 | CDR-H2 | Chothia | EPHDGS |
| 403 | 2188-D06 | CDR-H2 | Chothia | DPNDGA |
| 404 | 2188-F09 | CDR-H2 | Chothia | DPNDGS |
| 405 | 2188-F10 | CDR-H2 | Chothia | DPNDGA |
| 406 | 2188-B05 | CDR-H2 | Chothia | DPDDGW |
| 407 | 1943-C02 | CDR-H2 | Chothia | DPNSGS |
| 408 | 2193-D04 | CDR-H2 | Chothia | DPNGGS |
| 409 | 2193-E10 | CDR-H2 | Chothia | DPVNGS |
| 410 | 2193-E06 | CDR-H2 | Chothia | DPKNGS |
| 411 | 2193-E04 | CDR-H2 | Chothia | DPSLGS |
| 412 | 2193-B09 | CDR-H2 | Chothia | DPNNGS |
| 413 | 2193-D11 | CDR-H2 | Chothia | DPNTGS |
| 414 | 2193-B02 | CDR-H2 | Chothia | DPTRGS |
| 415 | 2193-D05 | CDR-H2 | Chothia | DPNSGS |
| 416 | 2193-E11 | CDR-H2 | Chothia | EPNSGA |
| 417 | 2193-D06 | CDR-H2 | Chothia | DPHSGS |
| 418 | 2193-C02 | CDR-H2 | Chothia | DPQSGS |
| 419 | 2193-B03 | CDR-H2 | Chothia | DPVSGS |
| 420 | 2193-A02 | CDR-H2 | Chothia | DPKSGS |
| 421 | 2193-E05 | CDR-H2 | Chothia | DPNGSS |
| 422 | 2193-A06 | CDR-H2 | Chothia | DPDSGS |
| 423 | 2193-C04 | CDR-H2 | Chothia | DPKSGS |
| 424 | 2193-E08 | CDR-H2 | Chothia | DPHSGS |
| 425 | 2193-B10 | CDR-H2 | Chothia | DPNSGY |
| 426 | 2193-D08 | CDR-H2 | Chothia | DPSGGS |
| 427 | 2193-B08 | CDR-H2 | Chothia | DPSPGA |
| 428 | 2193-C05 | CDR-H2 | Chothia | DPHNGS |
| 429 | 2193-D10 | CDR-H2 | Chothia | DPNSGF |
| 430 | 2193-D03 | CDR-H2 | Chothia | DPNTGS |
| 431 | 2193-A09 | CDR-H2 | Chothia | DPKGGS |
| 432 | 2193-A10 | CDR-H2 | Chothia | DPKSGY |
| 433 | 2193-E07 | CDR-H2 | Chothia | DPTIGS |

TABLE 20-continued

Sequences

| SEQ ID NO: | Molecule | Region | Scheme | Sequence |
|---|---|---|---|---|
| 434 | 2193-A07 | CDR-H2 | Chothia | DPNTGT |
| 435 | 2193-E03 | CDR-H2 | Chothia | DPKGGS |
| 436 | 2193-C08 | CDR-H2 | Chothia | DPYPGS |
| 437 | 2193-B11 | CDR-H2 | Chothia | DPKSGF |
| 438 | 2193-A03 | CDR-H2 | Chothia | DPKSGS |
| 439 | 2193-D02 | CDR-H2 | Chothia | DPESGS |
| 440 | 2193-B06 | CDR-H2 | Chothia | DPHPGS |
| 441 | 2193-B01 | CDR-H2 | Chothia | DPRSGY |
| 442 | 2193-D09 | CDR-H2 | Chothia | DPNSGS |
| 443 | 2193-E09 | CDR-H2 | Chothia | DPGSGY |
| 444 | 2193-B07 | CDR-H2 | Chothia | DPNSGS |
| 445 | 2193-C06 | CDR-H2 | Chothia | DPISGS |
| 446 | 2193-B05 | CDR-H2 | Chothia | DPIGGS |
| 447 | 2193-A11 | CDR-H2 | Chothia | DPKSGS |
| 448 | 2193-E02 | CDR-H2 | Chothia | DPTSGS |
| 449 | 2193-A08 | CDR-H2 | Chothia | DPNAGS |
| 450 | 2193-C11 | CDR-H2 | Chothia | DPKSGS |
| 451 | 2193-A01 | CDR-H2 | Chothia | DPTSGS |
| 452 | 2193-D07 | CDR-H2 | Chothia | GPADGS |
| 453 | 2193-A05 | CDR-H2 | Chothia | DPNSGS |
| 454 | 2193-C03 | CDR-H2 | Chothia | EPKSGS |
| 455 | 2193-C09 | CDR-H2 | Chothia | DPISGS |
| 456 | 2193-D01 | CDR-H2 | Chothia | DPTSGP |
| 457 | 2193-E01 | CDR-H2 | Chothia | DPKSGS |
| 458 | 2193-C07 | CDR-H2 | Chothia | DPTRGA |
| 459 | 2193-B04 | CDR-H2 | Chothia | EPKNGS |
| 460 | 2193-C10 | CDR-H2 | Chothia | DPRSGS |
| 461 | 2193-C01 | CDR-H2 | Chothia | DPKSGS |
| 462 | 2193-A04 | CDR-H2 | Chothia | DPNSGS |
| 463 | 1944-A07 | CDR-H2 | Chothia | SPNSGS |
| 464 | 2194-A02 | CDR-H2 | Chothia | SPLAGN |
| 465 | 2194-A05 | CDR-H2 | Chothia | SPNSGS |
| 466 | 2194-B04 | CDR-H2 | Chothia | SPLAGN |
| 467 | 2194-A09 | CDR-H2 | Chothia | TPLSGA |
| 468 | 2194-A01 | CDR-H2 | Chothia | SPLAGN |
| 469 | 2194-B03 | CDR-H2 | Chothia | SPLAGN |
| 470 | 2194-B02 | CDR-H2 | Chothia | SPLAGN |
| 471 | 2194-A03 | CDR-H2 | Chothia | TPNSGT |

TABLE 20-continued

Sequences

| SEQ ID NO: | Molecule | Region | Scheme | Sequence |
|---|---|---|---|---|
| 472 | 2194-A11 | CDR-H2 | Chothia | SPNSGY |
| 473 | 2194-A08 | CDR-H2 | Chothia | APSSGY |
| 474 | 2194-A04 | CDR-H2 | Chothia | SPLAGN |
| 475 | 2194-A10 | CDR-H2 | Chothia | SPNSGS |
| 476 | 2194-A07 | CDR-H2 | Chothia | SPLAGN |
| 477 | 2194-B01 | CDR-H2 | Chothia | SPLAGN |
| 478 | 2194-A06 | CDR-H2 | Chothia | SPLAGN |
| 479 | 2196-C01 | CDR-H2 | Chothia | TPLSGA |
| 480 | 2196-A02 | CDR-H2 | Chothia | SPNSGA |
| 481 | 2196-B03 | CDR-H2 | Chothia | SPNSGA |
| 482 | 2196-A05 | CDR-H2 | Chothia | SPNSGA |
| 483 | 2196-C02 | CDR-H2 | Chothia | SPNSGW |
| 484 | 2196-B11 | CDR-H2 | Chothia | SPNSGY |
| 485 | 2196-B08 | CDR-H2 | Chothia | SPNSGY |
| 486 | 2196-A04 | CDR-H2 | Chothia | YPISGH |
| 487 | 2196-A03 | CDR-H2 | Chothia | SPNSGS |
| 488 | 2196-B07 | CDR-H2 | Chothia | SPNSGA |
| 489 | 2196-A06 | CDR-H2 | Chothia | SPNSGS |
| 490 | 2196-B05 | CDR-H2 | Chothia | SPNSGA |
| 491 | 2196-A01 | CDR-H2 | Chothia | SPNSGY |
| 492 | 2196-B01 | CDR-H2 | Chothia | SPNSGY |
| 493 | 2196-A09 | CDR-H2 | Chothia | SPNSGA |
| 494 | 2196-A08 | CDR-H2 | Chothia | SPNSGS |
| 495 | 2196-A10 | CDR-H2 | Chothia | SPNSGA |
| 496 | 2196-B06 | CDR-H2 | Chothia | SPNSGS |
| 497 | 2196-B09 | CDR-H2 | Chothia | SPNSGS |
| 498 | 2196-C03 | CDR-H2 | Chothia | SPNSGS |
| 499 | 2196-C04 | CDR-H2 | Chothia | APLSGS |
| 500 | 2196-A07 | CDR-H2 | Chothia | SPNSGS |
| 501 | 2196-A11 | CDR-H2 | Chothia | SPNSGT |
| 502 | 2196-B02 | CDR-H2 | Chothia | SPNSGQ |
| 503 | 2196-B04 | CDR-H2 | Chothia | SPNSGA |
| 504 | 2196-B10 | CDR-H2 | Chothia | TPLSGA |
| 505 | 1987-C05 | CDR-H2 | Kabat | GIDPDDGSTDYADSVKG |
| 506 | 2188-D11 | CDR-H2 | Kabat | LIDPDDGSTDEADSVKG |
| 507 | 2188-B04 | CDR-H2 | Kabat | WINPDDGDTYYADSVKG |
| 508 | 2188-C09 | CDR-H2 | Kabat | WINPHDGDTYYADSVKG |

TABLE 20-continued

Sequences

| SEQ ID NO: | Molecule | Region | Scheme | Sequence |
|---|---|---|---|---|
| 509 | 2188-G03 | CDR-H2 | Kabat | GIDPRDGSTDYADSVKG |
| 510 | 2188-E03 | CDR-H2 | Kabat | GIDPDDGSTDYADSVKG |
| 511 | 2188-B11 | CDR-H2 | Kabat | WINPDDGDTFLADSVKG |
| 512 | 2188-E07 | CDR-H2 | Kabat | GIDPEDGFTVHADSVKG |
| 513 | 2188-B02 | CDR-H2 | Kabat | WINPDDGDTYLADSVKG |
| 514 | 2188-C07 | CDR-H2 | Kabat | WINPDDGDTYYADSVKG |
| 515 | 2188-A03 | CDR-H2 | Kabat | WINPDDGDTYYADSVKG |
| 516 | 2188-F03 | CDR-H2 | Kabat | GIDPDDGSTDYADSVKG |
| 517 | 2188-D03 | CDR-H2 | Kabat | GIDPHDGSTDYADSVKG |
| 518 | 2188-C04 | CDR-H2 | Kabat | WINPEDGDTYHADSVKG |
| 519 | 2188-D10 | CDR-H2 | Kabat | RIDPRDGATDYADSVKG |
| 520 | 2188-A06 | CDR-H2 | Kabat | WINPDDGDTYHADSVKG |
| 521 | 2188-C11 | CDR-H2 | Kabat | WINPDDGDTYLADSVKG |
| 522 | 2188-F01 | CDR-H2 | Kabat | LIDPDDGWTVSADSVKG |
| 523 | 2188-E11 | CDR-H2 | Kabat | GIDPGDGATDHADSVKG |
| 524 | 2188-A07 | CDR-H2 | Kabat | WINPDDGDTYYADSVKG |
| 525 | 2188-C01 | CDR-H2 | Kabat | LIDPHDGSTDSADSVKG |
| 526 | 2188-F08 | CDR-H2 | Kabat | RIEPDDGATDYADSVKG |
| 527 | 2188-E04 | CDR-H2 | Kabat | GIDPQDGSTDYADSVKG |
| 528 | 2188-B01 | CDR-H2 | Kabat | WINPDDGDTYYADSVKG |
| 529 | 2188-F11 | CDR-H2 | Kabat | GIDPEDGATDYADSVKG |
| 530 | 2188-B08 | CDR-H2 | Kabat | WINPDDGDTFYADSVKG |
| 531 | 2188-C10 | CDR-H2 | Kabat | WINPDDGDTYHADSVKG |
| 532 | 2188-C02 | CDR-H2 | Kabat | WINPDDGDTYYADSVKG |
| 533 | 2188-B07 | CDR-H2 | Kabat | WINPDDGDTYYADSVKG |
| 534 | 2188-A11 | CDR-H2 | Kabat | LIDPKDGATDSADSVKG |
| 535 | 2188-D01 | CDR-H2 | Kabat | WINPYDGTYYADSVKG |
| 536 | 2188-E09 | CDR-H2 | Kabat | EIDPQDGWTVHADSVKG |
| 537 | 2188-E06 | CDR-H2 | Kabat | GIDPEDGATDIADSVKG |
| 538 | 2188-B03 | CDR-H2 | Kabat | AIDPGDGATDYADSVKG |
| 539 | 2188-F06 | CDR-H2 | Kabat | GIDPDDGATDYADSVKG |
| 540 | 2188-D02 | CDR-H2 | Kabat | GIDPEDGATDYADSVKG |
| 541 | 2188-B06 | CDR-H2 | Kabat | WINPDDGDTYHADSVKG |
| 542 | 2188-D09 | CDR-H2 | Kabat | GIDPGDGSTDYADSVKG |
| 543 | 2188-F02 | CDR-H2 | Kabat | WIDPSDGSTEHADSVKG |
| 544 | 2188-E10 | CDR-H2 | Kabat | GIDPRDGATDYADSVKG |
| 545 | 2188-A09 | CDR-H2 | Kabat | WINPDDGDTYYADSVKG |
| 546 | 2188-D04 | CDR-H2 | Kabat | GIDPADGSTDYADSVKG |

TABLE 20-continued

Sequences

| SEQ ID NO: | Molecule | Region | Scheme | Sequence |
|---|---|---|---|---|
| 547 | 2188-A05 | CDR-H2 | Kabat | WINPDDGDTYYADSVKG |
| 548 | 2188-E01 | CDR-H2 | Kabat | GIDPQDGATDYADSVKG |
| 549 | 2188-G01 | CDR-H2 | Kabat | GIDPNDGATDYADSVKG |
| 550 | 2188-B09 | CDR-H2 | Kabat | VIDPKDGWTDHADSVKG |
| 551 | 2188-F07 | CDR-H2 | Kabat | GIDPNDGSTDHADSVKG |
| 552 | 2188-D08 | CDR-H2 | Kabat | GIDPDDGATDEADSVKG |
| 553 | 2188-D05 | CDR-H2 | Kabat | GIDPHDGWTDHADSVKG |
| 554 | 2188-C03 | CDR-H2 | Kabat | WINPDDGDTYYADSVKG |
| 555 | 2188-E08 | CDR-H2 | Kabat | GIDPQDGSTDLADSVKG |
| 556 | 2188-C06 | CDR-H2 | Kabat | WINPDDGDTYLADSVKG |
| 557 | 2188-A08 | CDR-H2 | Kabat | WINPFDGDTYYADSVKG |
| 558 | 2188-B10 | CDR-H2 | Kabat | WINPHDGDTYHADSVKG |
| 559 | 2188-G02 | CDR-H2 | Kabat | GIDPNDGATDYADSVKG |
| 560 | 2188-C05 | CDR-H2 | Kabat | GIDPRDGSTDSADSVKG |
| 561 | 2188-A10 | CDR-H2 | Kabat | WINPEDGDTSHADSVKG |
| 562 | 2188-G04 | CDR-H2 | Kabat | GIDPRDGSTDHADSVKG |
| 563 | 2188-C08 | CDR-H2 | Kabat | WINPDDGDTYHADSVKG |
| 564 | 2188-E05 | CDR-H2 | Kabat | GIEPWDGSTDHADSVKG |
| 565 | 2188-A02 | CDR-H2 | Kabat | WINPEDGDTYYADSVKG |
| 566 | 2188-F04 | CDR-H2 | Kabat | GIDPDDGATDYADSVKG |
| 567 | 2188-F05 | CDR-H2 | Kabat | GIDPRDGATDSADSVKG |
| 568 | 2188-D07 | CDR-H2 | Kabat | GIDPTDGATDYADSVKG |
| 569 | 2188-E02 | CDR-H2 | Kabat | GIEPHDGSTDYADSVKG |
| 570 | 2188-D06 | CDR-H2 | Kabat | GIDPNDGATDYADSVKG |
| 571 | 2188-F09 | CDR-H2 | Kabat | AIDPNDGSTDYADSVKG |
| 572 | 2188-F10 | CDR-H2 | Kabat | GIDPNDGATDHADSVKG |
| 573 | 2188-B05 | CDR-H2 | Kabat | VIDPDDGWTHYADSVKG |
| 574 | 1943-C02 | CDR-H2 | Kabat | AIDPNSGSTDYADSVKG |
| 575 | 2193-D04 | CDR-H2 | Kabat | AIDPNGGSTVYADSVKG |
| 576 | 2193-E10 | CDR-H2 | Kabat | AIDPVNGSTNNADSVKG |
| 577 | 2193-E06 | CDR-H2 | Kabat | VIDPKNGSTVYADSVKG |
| 578 | 2193-E04 | CDR-H2 | Kabat | VIDPSLGSTIDADSVKG |
| 579 | 2193-B09 | CDR-H2 | Kabat | IIDPNNGSTAYADSVKG |
| 580 | 2193-D11 | CDR-H2 | Kabat | AIDPNTGSTVDADSVKG |
| 581 | 2193-B02 | CDR-H2 | Kabat | TIDPTRGSTVHADSVKG |
| 582 | 2193-D05 | CDR-H2 | Kabat | AIDPNSGSTVYADSVKG |
| 583 | 2193-E11 | CDR-H2 | Kabat | GIEPNSGATVFADSVKG |

TABLE 20-continued

Sequences

| SEQ ID NO: | Molecule | Region Scheme | Sequence |
|---|---|---|---|
| 584 | 2193-D06 | CDR-H2 Kabat | AIDPHSGSTVYADSVKG |
| 585 | 2193-C02 | CDR-H2 Kabat | TIDPQSGSTVYADSVKG |
| 586 | 2193-B03 | CDR-H2 Kabat | AIDPVSGSTLFADSVKG |
| 587 | 2193-A02 | CDR-H2 Kabat | AIDPKSGSTYYADSVKG |
| 588 | 2193-E05 | CDR-H2 Kabat | SIDPNGSSTHYADSVKG |
| 589 | 2193-A06 | CDR-H2 Kabat | AIDPDSGSTHNADSVKG |
| 590 | 2193-C04 | CDR-H2 Kabat | AIDPKSGSTNFADSVKG |
| 591 | 2193-E08 | CDR-H2 Kabat | AIDPHSGSTNFADSVKG |
| 592 | 2193-B10 | CDR-H2 Kabat | AIDPNSGYTVKADSVKG |
| 593 | 2193-D08 | CDR-H2 Kabat | AIDPSGGSTNHADSVKG |
| 594 | 2193-B08 | CDR-H2 Kabat | AIDPSPGATLDADSVKG |
| 595 | 2193-C05 | CDR-H2 Kabat | AIDPHNGSTASADSVKG |
| 596 | 2193-D10 | CDR-H2 Kabat | TIDPNSGFTVHADSVKG |
| 597 | 2193-D03 | CDR-H2 Kabat | AIDPNTGSTVNADSVKG |
| 598 | 2193-A09 | CDR-H2 Kabat | VIDPKGGSTVYADSVKG |
| 599 | 2193-A10 | CDR-H2 Kabat | AIDPKSGYTVYADSVKG |
| 600 | 2193-E07 | CDR-H2 Kabat | SIDPTIGSTHFADSVKG |
| 601 | 2193-A07 | CDR-H2 Kabat | AIDPNTGTTNYADSVKG |
| 602 | 2193-E03 | CDR-H2 Kabat | AIDPKGGSTRFADSVKG |
| 603 | 2193-C08 | CDR-H2 Kabat | AIDPYPGSTYNADSVKG |
| 604 | 2193-B11 | CDR-H2 Kabat | AIDPKSGFTSYADSVKG |
| 605 | 2193-A03 | CDR-H2 Kabat | AIDPKSGSTVHADSVKG |
| 606 | 2193-D02 | CDR-H2 Kabat | AIDPESGSTVYADSVKG |
| 607 | 2193-B06 | CDR-H2 Kabat | AIDPHPGSTVYADSVKG |
| 608 | 2193-B01 | CDR-H2 Kabat | AIDPRSGYTVYADSVKG |
| 609 | 2193-D09 | CDR-H2 Kabat | AIDPNSGSTNFADSVKG |
| 610 | 2193-E09 | CDR-H2 Kabat | AIDPGSGYTVPADSVKG |
| 611 | 2193-B07 | CDR-H2 Kabat | AIDPNSGSTLSADSVKG |
| 612 | 2193-C06 | CDR-H2 Kabat | AIDPISGSTQWADSVKG |
| 613 | 2193-B05 | CDR-H2 Kabat | AIDPIGGSTHLADSVKG |
| 614 | 2193-A11 | CDR-H2 Kabat | AIDPKSGSTVYADSVKG |
| 615 | 2193-E02 | CDR-H2 Kabat | SIDPTSGSTVIADSVKG |
| 616 | 2193-A08 | CDR-H2 Kabat | AIDPNAGSTVYADSVKG |
| 617 | 2193-C11 | CDR-H2 Kabat | VIDPKSGSTNYADSVKG |
| 618 | 2193-A01 | CDR-H2 Kabat | AIDPTSGSTVFADSVKG |
| 619 | 2193-D07 | CDR-H2 Kabat | AIGPADGSTVNADSVKG |
| 620 | 2193-A05 | CDR-H2 Kabat | VIDPNSGSTIFADSVKG |
| 621 | 2193-C03 | CDR-H2 Kabat | AIEPKSGSTASADSVKG |

TABLE 20-continued

Sequences

| SEQ ID NO: | Molecule | Region | Scheme | Sequence |
|---|---|---|---|---|
| 622 | 2193-C09 | CDR-H2 | Kabat | AIDPISGSTVYADSVKG |
| 623 | 2193-D01 | CDR-H2 | Kabat | AIDPTSGPTVYADSVKG |
| 624 | 2193-E01 | CDR-H2 | Kabat | AIDPKSGSTAHADSVKG |
| 625 | 2193-C07 | CDR-H2 | Kabat | AIDPTRGATVYADSVKG |
| 626 | 2193-B04 | CDR-H2 | Kabat | AIEPKNGSTHHADSVKG |
| 627 | 2193-C10 | CDR-H2 | Kabat | AIDPRSGSTISADSVKG |
| 628 | 2193-C01 | CDR-H2 | Kabat | TIDPKSGSTHVADSVKG |
| 629 | 2193-A04 | CDR-H2 | Kabat | AIDPNSGSTLLADSVKG |
| 630 | 1944-A07 | CDR-H2 | Kabat | YISPNSGSTYYADSVKG |
| 631 | 2194-A02 | CDR-H2 | Kabat | YISPLAGNTYHADSVKG |
| 632 | 2194-A05 | CDR-H2 | Kabat | YISPNSGSTYYADSVKG |
| 633 | 2194-B04 | CDR-H2 | Kabat | YISPLAGNTYHADSVKG |
| 634 | 2194-A09 | CDR-H2 | Kabat | YITPLSGATYRADSVKG |
| 635 | 2194-A01 | CDR-H2 | Kabat | YISPLAGNTYHADSVKG |
| 636 | 2194-B03 | CDR-H2 | Kabat | YISPLAGNTYHADSVKG |
| 637 | 2194-B02 | CDR-H2 | Kabat | YISPLAGNTYHADSVKG |
| 638 | 2194-A03 | CDR-H2 | Kabat | YITPNSGTTYSADSVKG |
| 639 | 2194-A11 | CDR-H2 | Kabat | YISPNSGYTTDADSVKG |
| 640 | 2194-A08 | CDR-H2 | Kabat | YIAPSSGYTYDADSVKG |
| 641 | 2194-A04 | CDR-H2 | Kabat | YISPLAGNTHHADSVKG |
| 642 | 2194-A10 | CDR-H2 | Kabat | YISPNSGSTHIADSVKG |
| 643 | 2194-A07 | CDR-H2 | Kabat | YISPLAGNTYHADSVKG |
| 644 | 2194-B01 | CDR-H2 | Kabat | YISPLAGNTYHADSVKG |
| 645 | 2194-A06 | CDR-H2 | Kabat | YISPLAGNTYHADSVKG |
| 646 | 2196-C01 | CDR-H2 | Kabat | SITPLSGATSKADSVKG |
| 647 | 2196-A02 | CDR-H2 | Kabat | QISPNSGATHDADSVKG |
| 648 | 2196-B03 | CDR-H2 | Kabat | YISPNSGATHYADSVKG |
| 649 | 2196-A05 | CDR-H2 | Kabat | YISPNSGATYQADSVKG |
| 650 | 2196-C02 | CDR-H2 | Kabat | FISPNSGWTYSADSVKG |
| 651 | 2196-B11 | CDR-H2 | Kabat | QISPNSGYTYYADSVKG |
| 652 | 2196-B08 | CDR-H2 | Kabat | QISPNSGYTYLADSVKG |
| 653 | 2196-A04 | CDR-H2 | Kabat | QIYPISGHTYQADSVKG |
| 654 | 2196-A03 | CDR-H2 | Kabat | YISPNSGSTHEADSVKG |
| 655 | 2196-B07 | CDR-H2 | Kabat | YISPNSGATYYADSVKG |
| 656 | 2196-A06 | CDR-H2 | Kabat | QISPNSGSTHQADSVKG |
| 657 | 2196-B05 | CDR-H2 | Kabat | QISPNSGATYHADSVKG |
| 658 | 2196-A01 | CDR-H2 | Kabat | QISPNSGYTYYADSVKG |

TABLE 20-continued

Sequences

| SEQ ID NO: | Molecule | Region | Scheme | Sequence |
|---|---|---|---|---|
| 659 | 2196-B01 | CDR-H2 | Kabat | QISPNSGYTYYADSVKG |
| 660 | 2196-A09 | CDR-H2 | Kabat | QISPNSGATHYADSVKG |
| 661 | 2196-A08 | CDR-H2 | Kabat | YISPNSGSTYKADSVKG |
| 662 | 2196-A10 | CDR-H2 | Kabat | YISPNSGATHYADSVKG |
| 663 | 2196-B06 | CDR-H2 | Kabat | QISPNSGSTYSADSVKG |
| 664 | 2196-B09 | CDR-H2 | Kabat | YISPNSGSTYYADSVKG |
| 665 | 2196-C03 | CDR-H2 | Kabat | QISPNSGSTYSADSVKG |
| 666 | 2196-C04 | CDR-H2 | Kabat | FIAPLSGSTHNADSVKG |
| 667 | 2196-A07 | CDR-H2 | Kabat | QISPNSGSTYYADSVKG |
| 668 | 2196-A11 | CDR-H2 | Kabat | QISPNSGTTYDADSVKG |
| 669 | 2196-B02 | CDR-H2 | Kabat | YISPNSGQTYDADSVKG |
| 670 | 2196-B04 | CDR-H2 | Kabat | YISPNSGATYQADSVKG |
| 671 | 2196-B10 | CDR-H2 | Kabat | SITPLSGATSKADSVKG |
| 672 | 1987-C05 | CDR-H3 | | DY------GVFDY |
| 673 | 2188-D11 | CDR-H3 | | DY------GVFDY |
| 674 | 2188-B04 | CDR-H3 | | DY------GVFDY |
| 675 | 2188-C09 | CDR-H3 | | DY------GVFDY |
| 676 | 2188-G03 | CDR-H3 | | DF------GVFDY |
| 677 | 2188-E03 | CDR-H3 | | DY------GVYDY |
| 678 | 2188-B11 | CDR-H3 | | DY------GVFDY |
| 679 | 2188-E07 | CDR-H3 | | DY------GVYDY |
| 680 | 2188-B02 | CDR-H3 | | DY------GVFDY |
| 681 | 2188-C07 | CDR-H3 | | DY------GVFDY |
| 682 | 2188-A03 | CDR-H3 | | DY------GVFDY |
| 683 | 2188-F03 | CDR-H3 | | DY------GVFDY |
| 684 | 2188-D03 | CDR-H3 | | DY------GVYDY |
| 685 | 2188-C04 | CDR-H3 | | DY------GVYDY |
| 686 | 2188-D10 | CDR-H3 | | DY------GVFDY |
| 687 | 2188-A06 | CDR-H3 | | DY------GVFDY |
| 688 | 2188-C11 | CDR-H3 | | DY------GVFDY |
| 689 | 2188-F01 | CDR-H3 | | DY------GVFDY |
| 690 | 2188-E11 | CDR-H3 | | DY------GVFDY |
| 691 | 2188-A07 | CDR-H3 | | DY------GVFDY |
| 692 | 2188-C01 | CDR-H3 | | DY------GVFDY |
| 693 | 2188-F08 | CDR-H3 | | DY------GVFDY |
| 694 | 2188-E04 | CDR-H3 | | DF------GVFDY |
| 695 | 2188-B01 | CDR-H3 | | DY------GVLDY |
| 696 | 2188-F11 | CDR-H3 | | DY------GVFDY |

TABLE 20-continued

Sequences

| SEQ ID NO: | Molecule | Region Scheme | Sequence |
|---|---|---|---|
| 697 | 2188-B08 | CDR-H3 | DY------GVFDY |
| 698 | 2188-C10 | CDR-H3 | DY------GVFDY |
| 699 | 2188-C02 | CDR-H3 | DY------GVFDY |
| 700 | 2188-B07 | CDR-H3 | DY------GVFDY |
| 701 | 2188-A11 | CDR-H3 | DY------GVFDY |
| 702 | 2188-D01 | CDR-H3 | DY------GVFDY |
| 703 | 2188-E09 | CDR-H3 | DY------GVFDY |
| 704 | 2188-E06 | CDR-H3 | DY------GVFDY |
| 705 | 2188-B03 | CDR-H3 | DY------GVFDY |
| 706 | 2188-F06 | CDR-H3 | DY------GVFDY |
| 707 | 2188-D02 | CDR-H3 | DY------GVFDY |
| 708 | 2188-B06 | CDR-H3 | DY------GVFDY |
| 709 | 2188-D09 | CDR-H3 | DY------GVFDY |
| 710 | 2188-F02 | CDR-H3 | DY------GVFDY |
| 711 | 2188-E10 | CDR-H3 | DY------GVFDY |
| 712 | 2188-A09 | CDR-H3 | DY------GVFDY |
| 713 | 2188-D04 | CDR-H3 | DY------GVFDY |
| 714 | 2188-A05 | CDR-H3 | DY------GVFDY |
| 715 | 2188-E01 | CDR-H3 | DY------GVFDY |
| 716 | 2188-G01 | CDR-H3 | DY------GVFDY |
| 717 | 2188-B09 | CDR-H3 | DY------GVFDY |
| 718 | 2188-F07 | CDR-H3 | DY------GVFDY |
| 719 | 2188-D08 | CDR-H3 | DY------GVFDY |
| 720 | 2188-D05 | CDR-H3 | DY------GVFDY |
| 721 | 2188-C03 | CDR-H3 | DY------GVFDY |
| 722 | 2188-E08 | CDR-H3 | DY------GVFDY |
| 723 | 2188-C06 | CDR-H3 | DY------GVFDY |
| 724 | 2188-A08 | CDR-H3 | DY------GVFDY |
| 725 | 2188-B10 | CDR-H3 | DY------GVFDY |
| 726 | 2188-G02 | CDR-H3 | DY------GVFDY |
| 727 | 2188-C05 | CDR-H3 | DY------GVFDY |
| 728 | 2188-A10 | CDR-H3 | DY------GVFDY |
| 729 | 2188-G04 | CDR-H3 | DY------GVFDY |
| 730 | 2188-C08 | CDR-H3 | DY------GVFDY |
| 731 | 2188-E05 | CDR-H3 | DY------GVFDY |
| 732 | 2188-A02 | CDR-H3 | DY------GVFDY |
| 733 | 2188-F04 | CDR-H3 | DY------GVFDY |

TABLE 20-continued

Sequences

| SEQ ID NO: | Molecule | Region Scheme | Sequence |
|---|---|---|---|
| 734 | 2188-F05 | CDR-H3 | DY-------GVFDY |
| 735 | 2188-D07 | CDR-H3 | DY-------GVFDY |
| 736 | 2188-E02 | CDR-H3 | DY-------GVFDY |
| 737 | 2188-D06 | CDR-H3 | DY-------GVFDY |
| 738 | 2188-F09 | CDR-H3 | DY-------GVFDY |
| 739 | 2188-F10 | CDR-H3 | DY-------GVFDY |
| 740 | 2188-B05 | CDR-H3 | DY-------GVFDY |
| 741 | 1943-C02 | CDR-H3 | SRWFRVLWSYVFDY |
| 742 | 2193-D04 | CDR-H3 | SRWYRVLWSYAFDY |
| 743 | 2193-E10 | CDR-H3 | SRWYRVLWSYVFDY |
| 744 | 2193-E06 | CDR-H3 | SRWFRVLWSYVFDY |
| 745 | 2193-E04 | CDR-H3 | SRWFRVLWSYVFDY |
| 746 | 2193-B09 | CDR-H3 | SRWYRVLWSYVLDY |
| 747 | 2193-D11 | CDR-H3 | SRWFRVLWSYVFDY |
| 748 | 2193-B02 | CDR-H3 | SRWFRVLWSYVFDY |
| 749 | 2193-D05 | CDR-H3 | SRWFRVLWSYVFDY |
| 750 | 2193-E11 | CDR-H3 | SRWYRVLWSYVFHY |
| 751 | 2193-D06 | CDR-H3 | SRWFRVLWSYVFDY |
| 752 | 2193-C02 | CDR-H3 | SRWFRVLWSFVFDY |
| 753 | 2193-B03 | CDR-H3 | SRWFRVLWSYVFDY |
| 754 | 2193-A02 | CDR-H3 | SRWLRVLWSYIFDY |
| 755 | 2193-E05 | CDR-H3 | SRWFRVLWSYVLDY |
| 756 | 2193-A06 | CDR-H3 | SRWFRVLWSYIFDY |
| 757 | 2193-C04 | CDR-H3 | SRWFRVLWSYVLDY |
| 758 | 2193-E08 | CDR-H3 | SRWYRVLWSYVFDY |
| 759 | 2193-B10 | CDR-H3 | SRWLRVLWSFVFDY |
| 760 | 2193-D08 | CDR-H3 | TRWFRVLWSYVFDY |
| 761 | 2193-B08 | CDR-H3 | SRWFRVLWSYALDY |
| 762 | 2193-C05 | CDR-H3 | SRWFRVLWSYVIDY |
| 763 | 2193-D10 | CDR-H3 | SRWFRVLWSYVFDY |
| 764 | 2193-D03 | CDR-H3 | SRWSRVLWIYVFDY |
| 765 | 2193-A09 | CDR-H3 | SRWSRVLWSYVFDY |
| 766 | 2193-A10 | CDR-H3 | SRWFRVLWSYVFDY |
| 767 | 2193-E07 | CDR-H3 | SQWFRVLWSYVFDY |
| 768 | 2193-A07 | CDR-H3 | SRWFRVLWSYVFDY |
| 769 | 2193-E03 | CDR-H3 | SRWFRVLWSYVFDY |
| 770 | 2193-C08 | CDR-H3 | SRWFRVLWSYVFDY |
| 771 | 2193-B11 | CDR-H3 | SRWFRVLWSEVFDY |

TABLE 20-continued

Sequences

| SEQ ID NO: | Molecule | Region Scheme | Sequence |
|---|---|---|---|
| 772 | 2193-A03 | CDR-H3 | SRWSRVLWTYVFDY |
| 773 | 2193-D02 | CDR-H3 | SRWFRVLWSYVFDY |
| 774 | 2193-B06 | CDR-H3 | SRWFRVLWTYVFDY |
| 775 | 2193-B01 | CDR-H3 | SRWFRVLWSFVLDY |
| 776 | 2193-D09 | CDR-H3 | SRWFRVLWSYVFDY |
| 777 | 2193-E09 | CDR-H3 | SRWYRVLWSYVFDY |
| 778 | 2193-B07 | CDR-H3 | SRWFRVLWSYIFDY |
| 779 | 2193-C06 | CDR-H3 | SRWRRALWIYVFDY |
| 780 | 2193-B05 | CDR-H3 | SRWYRVLWSYVFDY |
| 781 | 2193-A11 | CDR-H3 | SRWFRVLWSYVFDY |
| 782 | 2193-E02 | CDR-H3 | SRWWRVLWSYVFDY |
| 783 | 2193-A08 | CDR-H3 | SRWFRVLWSYVFDY |
| 784 | 2193-C11 | CDR-H3 | SRWFRVLWSYVFDY |
| 785 | 2193-A01 | CDR-H3 | SRWFRVLWSYVFDY |
| 786 | 2193-D07 | CDR-H3 | SRWLRVLWSYVFDY |
| 787 | 2193-A05 | CDR-H3 | SRWFRVLWSYVLDY |
| 788 | 2193-C03 | CDR-H3 | SRWYRVLWSYVLDY |
| 789 | 2193-C09 | CDR-H3 | SRWSRVLWSYVFDY |
| 790 | 2193-D01 | CDR-H3 | SRWFRVLWSYVFDY |
| 791 | 2193-E01 | CDR-H3 | SRWFRVLWTYVFDY |
| 792 | 2193-C07 | CDR-H3 | SRWYRVLWSFVFDY |
| 793 | 2193-B04 | CDR-H3 | SRWFRVLWTYVFDY |
| 794 | 2193-C10 | CDR-H3 | SRWFRVLWSFGEDY |
| 795 | 2193-C01 | CDR-H3 | SRWFRVLWSYVFDY |
| 796 | 2193-A04 | CDR-H3 | SRWFRVLWSYVYDY |
| 797 | 1944-A07 | CDR-H3 | DSRR---YVRPFDY |
| 798 | 2194-A02 | CDR-H3 | DSRR---YVRPFDY |
| 799 | 2194-A05 | CDR-H3 | DHRR---YVRPFDY |
| 800 | 2194-B04 | CDR-H3 | DSRR---YVRPLDY |
| 801 | 2194-A09 | CDR-H3 | DSRR---YVRPFDY |
| 802 | 2194-A01 | CDR-H3 | DSRR---YVRPMDY |
| 803 | 2194-B03 | CDR-H3 | DSRR---YVRPFDY |
| 804 | 2194-B02 | CDR-H3 | DSRR---YVRPLDY |
| 805 | 2194-A03 | CDR-H3 | DSRR---YVRPLDY |
| 806 | 2194-A11 | CDR-H3 | DSRR---YVRPFDY |
| 807 | 2194-A08 | CDR-H3 | DSRR---YVRPFDY |
| 808 | 2194-A04 | CDR-H3 | DSRR---YVRPLDY |

TABLE 20-continued

Sequences

| SEQ ID NO: | Molecule | Region Scheme | Sequence |
|---|---|---|---|
| 809 | 2194-A10 | CDR-H3 | DSRR---YVRPFDY |
| 810 | 2194-A07 | CDR-H3 | DSRR---YVRPFDY |
| 811 | 2194-B01 | CDR-H3 | DSRR---YVRPFDY |
| 812 | 2194-A06 | CDR-H3 | DSRR---YVRPFDY |
| 813 | 2196-C01 | CDR-H3 | DSRR---YIRSWDY |
| 814 | 2196-A02 | CDR-H3 | DSRR---YVRGWDY |
| 815 | 2196-B03 | CDR-H3 | DSRR---YVRPFDY |
| 816 | 2196-A05 | CDR-H3 | DSRR---YVRSWDY |
| 817 | 2196-C02 | CDR-H3 | DSRR---YVRPFDY |
| 818 | 2196-B11 | CDR-H3 | DSRR---YIRSWDY |
| 819 | 2196-B08 | CDR-H3 | DSRR---YVRGWDY |
| 820 | 2196-A04 | CDR-H3 | FSRR---YVGPFGY |
| 821 | 2196-A03 | CDR-H3 | DSRR---YVRGWDY |
| 822 | 2196-B07 | CDR-H3 | DSRR---YVRGWDY |
| 823 | 2196-A06 | CDR-H3 | DSRR---YVRGWDY |
| 824 | 2196-B05 | CDR-H3 | DSRR---YVRGWDY |
| 825 | 2196-A01 | CDR-H3 | DSRR---YVRGWDY |
| 826 | 2196-B01 | CDR-H3 | DSRR---YVRSWDY |
| 827 | 2196-A09 | CDR-H3 | DSRR---YIRSWDY |
| 828 | 2196-A08 | CDR-H3 | DSRR---YVRSWDY |
| 829 | 2196-A10 | CDR-H3 | DSRR---YVRSWDY |
| 830 | 2196-B06 | CDR-H3 | DSRR---YVLSWDY |
| 831 | 2196-B09 | CDR-H3 | DSRR---YVRSWDY |
| 832 | 2196-C03 | CDR-H3 | DSRR---YVLSWDY |
| 833 | 2196-C04 | CDR-H3 | FSRR---YVNPWDY |
| 834 | 2196-A07 | CDR-H3 | DSRR---YVRGWDY |
| 835 | 2196-A11 | CDR-H3 | DSRR---YVRGWDY |
| 836 | 2196-B02 | CDR-H3 | DSRR---YVRSWDY |
| 837 | 2196-B04 | CDR-H3 | DSRR---YVRGWDY |
| 838 | 2196-B10 | CDR-H3 | DSRR---YIRSWDY |
| 839 | trastuzumab | CDR-L1 | RASQDVNTAVA |
| 840 | SP34 | CDR-L1 | RSSTGAVTTSNYAN |
| 841 | 2037-B10 | CDR-L1 | GSSTGAVTSGYYPN |
| 842 | hUCHT1-LC3 | CDR-L1 | RASQDIRNYLN |
| 843 | hOKT3-LC1 | CDR-L1 | SASSSVSYMN |
| 844 | trastuzumab | CDR-L2 | SASFLYS |
| 845 | SP34 | CDR-L2 | GTNKRAP |
| 846 | 2037-B10 | CDR-L2 | GTKFLAP |

TABLE 20-continued

Sequences

| SEQ ID NO: | Molecule | Region Scheme | Sequence |
|---|---|---|---|
| 847 | hUCHT1-LC3 | CDR-L2 | YTSRLHS |
| 848 | hOKT3-LC1 | CDR-L2 | DTSKLAS |
| 849 | trastuzumab | CDR-L3 | QQHYTTPPT |
| 850 | SP34 | CDR-L3 | ALWYSNLWV |
| 851 | 2037-B10 | CDR-L3 | ALWYSNRWV |
| 852 | hUCHT1-LC3 | CDR-L3 | QQGNTLPWT |
| 853 | hOKT3-LC1 | CDR-L3 | QQWSSNPFT |
| 854 | 1987-C05 | VH | EVQLVESGGGLVQPGGSLRLSCAASGEN ISDYDIHWVRQAPGKGLEWVGGIDPDDG STDYADSVKGRFTISADTSKNTAYLQMN SLRAEDTAVYYCARDYGVFDYWGQGTLV TVSS |
| 855 | 2188-D11 | VH | EVQLVESGGGLVQTGGSLRLSCAASGEN IRDYDIHWVRQAPGKGLEWVGLIDPDDG STDEADSVKGRFTISADTSKNTAYLQMN SLRAEDTAVYYCARDYGVFDYWGQGTLV TVSS |
| 856 | 2188-B04 | VH | EVQLVESGGGLVQPGGSLRLSCAASGEN ITWYDIHWVRQAPGKGLEWVGWINPDDG DTYYADSVKGRFTISADTSKNTAYLQMN SLRAEDTAVYYCARDYGVFDYWGQGTLV TVSS |
| 857 | 2188-C09 | VH | EVQLVESGGGLVQPGGSLRLSCAASGEN INSYDIHWVRQAPGKGLEWVGWINPHDG DTYYADSVTGRFTISADTSKNTAYLQMN SLRAEDTAVYYCARDYGVFDYWGQGTLV TVSS |
| 858 | 2188-G03 | VH | EVQLVESGGGLVQPGGSLRLSCAASGEN IVDYDIHWVRQAPGKGLEWVGIDPRDG STDYADSVKGRFTISADTSKNTAYLQMN SLRAEDTAVYYCARDFGVFDYWGQGTLV TVSS |
| 859 | 2188-E03 | VH | EVQLVESGGGLVQPGGSLRLSCAASGEN IRDYDIHWVRQAPGKGLEWVAGIDPDDG STDYADSVKGRFTISADTSKNTAYLQMN SLRAEDTAVYYCARDYGVYDYWGQGTLV TVSS |
| 860 | 2188-B11 | VH | EVQLVESGGGLVQPGGSLRLSCAASGEN INRYDIHWVRQAPGKGLEWVGWINPDDG DTFLADSVKGRFTISADTSKSTAYLQMN SLRAEDTAVYYCARDYGVFDYWGQGTLV TVSS |
| 861 | 2188-E07 | VH | EVQLVESGGGLVQPGGSLRLSCAASGEN IGDYGIHWVRQAPGKGLEWVGGIDPEDG FTVHADSVKGRFTISADTSKNTAYLQMN SLRAEDTAVYYCARDYGVYDYWGQGTLV TVSS |
| 862 | 2188-B02 | VH | EVQLVESGGGLVQPGGSLRLSCAASGEN ISSYDIHWVRQAPGKGLEWVGWINPDDG DTYLADSVKGRFTISADTSKSTAYLQMN SLRAEDTAVYYCARDYGVFDYWGQGTLV TVSS |
| 863 | 2188-C07 | VH | EVQLVESGGGLVQPGGSLRLSCAASGEN IVRYDIHWVRQAPGKGLEWVGWINPDDG DTYYADSVKGRFTISADTSKNTAYLQMN SLRAEDTAVYYCARDYGVFDYWGQGTLV TVSS |

TABLE 20-continued

Sequences

| SEQ ID NO: | Molecule | Region Scheme | Sequence |
|---|---|---|---|
| 864 | 2188-A03 | VH | EVQLVESGGGLVQPGGSLRLSCAASGEN IRDYDIHWVRQAPGKGLEWVGWINPDDG DTYYADSVKGRFTISADTSKNTAYLQMN SLRAEDTAVYYCARDYGVFDYWGQGTLV TVSS |
| 865 | 2188-F03 | VH | EVQLVESGGGLVQPGGSLRLSCAASGEN ISDYDIHWVRQAPGKGLEWVSGIDPDDG STDYADSVKGRFTISADTSKNTAYLQMN SLRAEDTAVYYCARDYGVFDYWGQGTLV TVSS |
| 866 | 2188-D03 | VH | EVQLVESGGGLVQPGGSLRLSCAASGEN ISDYDIHWVRQAPGKGLEWVGGIDPHDG STDYADSVKGRFTISADTSKNTAYLQMN SLRAEDTAVYYCARDYGVYDYWGQGTLV TVSS |
| 867 | 2188-C04 | VH | EVQLVESGGGLVQPGGSLRLSCAASGEN INSYDIHWVRQAPGKGLEWVGWINPEDG DTYHADSVRGRFTISADTSKNTAYLQMN SLRAEDTAVYYCARDYGVYDYWGQGTLV TVSS |
| 868 | 2188-D10 | VH | EVQLVESGGGLVQPGGSLRLSCAASGEN ISDYDIHWVRQAPGKGLEWVGRIDPRDG ATDYADSVKGRFTISADTSKNTAYLQMN SLRAEDTAVYYCARDYGVFDYWGQGTLV TVSS |
| 869 | 2188-A06 | VH | EVQLVESGGGLVQPGGSLRLSCAASGEN IKSYDIHWVRQAPGKGLEWVGWINPDDG DTYHADSVKGRFTISADTSKNTAYLQMN SLRAEDTAVYYCARDYGVFDYWGQGTLV TVSS |
| 870 | 2188-C11 | VH | EVQLVESGGGLVQPGGSLRLSCAASGEN IKSYDIHWVRQAPGKGLEWVGWINPDDG DTYLADSVKGRFTISADTSKNTAYLQMN SLRAEDTAVYYCARDYGVFDYWGQGTLV TVSS |
| 871 | 2188-F01 | VH | EVQLVESGGGLVQPGGSLRLSCAASGEN IRYYDIHWVRQAPGKGLEWVGLIDPDDG WTVSADSVKGRFTISADTSKNTAYLQMN SLRAEDTAVYYCARDYGVFDYWGQGTLV TVSS |
| 872 | 2188-E11 | VH | EVQLVESGGGLVQPGGSLRLSCAASGEN ISHYDIHWVRQAPGKGLEWVSGIDPGDG ATDHADSVKGRFTISADTSKNTAYLQMN SLRAEDTAVYYCARDYGVFDYWGQGTLV TVSS |
| 873 | 2188-A07 | VH | EVQLVESGGGLVQPGGSLRLSCAASGEN IHHYDIHWVRQAPGKGLEWVGWINPDDG DTYYADSVKGRFTISADTSKNTAYLQMN SLRAEDTAVYYCARDYGVFDYWGQGTLV TVSS |
| 874 | 2188-C01 | VH | EVQLVESGGGLVQPGGSLRLSCAASGEN IISYDIHWVRQAPGKGLEWVSLIDPHDG STDSADSVKGRFTISADTSKNTAYLQMN SLRAEDTAVYYCARDYGVFDYWGQGTLV TVSS |
| 875 | 2188-F08 | VH | EVQLVESGGGLVQPGGSLRLSCAASGEN IPDFEIHWVRQAPGKGLEWVARIEPDDG ATDYADSVKGRFTISADTSKNTAYLQMN SLRAEDTAVYYCARDYGVFDYWGQGTLV TVSS |

TABLE 20-continued

Sequences

| SEQ ID NO: | Molecule | Region Scheme | Sequence |
| --- | --- | --- | --- |
| 876 | 2188-E04 | VH | EVQLVESGGGLVQPGGSLRLSCAASGEN ISDYDIHWVRQAPGKGLEWVAGIDPQDG STDYADSVKGRFTISADTSKNTAYLQMN SLRAEDAAVYYCARDFGVFDYWGQGTLV TVSS |
| 877 | 2188-B01 | VH | EVQLVESGGGLVQPGGSLRLSCAASGEN INSHDIHWVRQAPGKGLEWVGWINPDDG DTYYADSVKGRFTISADTSKNTAYLQMN SLRAEDTAVYYCARDYGVLDYWGQGTLV TVSS |
| 878 | 2188-F11 | VH | EVQLVESGGGLVQPGGSLRLSCAASGEN ITGYDIHWVRQAPGKGLEWVGGIDPEDG ATDYADSVKGRFTISADTSKNTAYLQMN SLRAEDTAVYYCARDYGVFDYWGQGTLV TVSS |
| 879 | 2188-B08 | VH | EVQLVESGGGLVQPGGSLRLSCAASGEN IDSYDIHWVRQAPGKGLEWVGWINPDDG DTFYADSVKGRFTISADTSKNTAYLQMD SLRAEDTAVYYCARDYGVFDYWGQGTLV TVSS |
| 880 | 2188-C10 | VH | EVQLVESGGGLVQPGGSLRLSCAASGEN INSYDIHWVRQAPGKGLEWVGWINPDDG DTYHADSVKGRFTISADTSKNTAYLQMN SLRAEDTAVYYCARDYGVFDYWGQGTLV TVSS |
| 881 | 2188-C02 | VH | EVQLVESGGGLVQPGGSLRLSCAASGEN IERYDIHWVRQAPGKGLEWVGWINPDDG DTYYADSVKGRFTISADTSKNTAYLQTK SLRAEDTAVYYCARDYGVFDYWGQGTLV TVSS |
| 882 | 2188-B07 | VH | EVQLVESGGGLVQPGGSLRLSCAASGEN IHSHDIHWVRQAPGKGLEWVGWINPDDG DTYYADSVKGRFAISADTSKNTAYLQMN SLRAEDTAVYYCARDYGVFDYWGRGTLV TVSS |
| 883 | 2188-A11 | VH | EVQLVESGGGLVQPGGSLRLSCAASGEN ISDYDIHWVRQAPGKGLEWVSLIDPKDG ATDSADSVKGRFTISADTSKNTAYLQMN SLRAGDTAVYYCARDYGVFDYWGQGTLV TVSS |
| 884 | 2188-D01 | VH | EVQLVESGGGLVQPGGSLRLSCAASGEN IKSYDIHWVRQAPGKGLEWVGWINPYDG DTYYADSVKGRFTISADTSKNTAYLQMN SLRAEDTAVYYCARDYGVFDYWGQGTLV TVSS |
| 885 | 2188-E09 | VH | EVQLVESGGGLVQPGGSLRLSCAASGEN ISDFDIHWVRQAPGKGLEWVAEIDPQDG WTVHADSVKGRFTISADTSKNTAYLQMN SLRAEDTAVYYCARDYGVFDYWGQGTLV TVSS |
| 886 | 2188-E06 | VH | EVQLVESGGGLVQPGGSLRLSCAASGEN IGDYDIHWVRQAPGKGLEWVGGIDPEDG ATDIADSVKGRFTISADTSKNTAYLQMD SLRAEDTAVYYCARDYGVFDYWGQGTLV TVSS |
| 887 | 2188-B03 | VH | EVQLVESGGGLVQPGGSLRLSCAASGEN ISSYDIHWVRQAPGKGLEWVGAIDPGDG ATDYADSVKGRFTISADTSKNTAYLQMN SLRAEDTAVYYCARDYGVYDYWGQGTLV TVSS |

TABLE 20-continued

Sequences

| SEQ ID NO: | Molecule | Region Scheme | Sequence |
|---|---|---|---|
| 888 | 2188-F06 | VH | EVQLVESGGGLVQPGGSLRLSCAASGEN ILDYDIHWVRQAPGKGLEWVGGIDPDDG ATDYADSVKGRFTISADTSKNTAYLQMN SLRAEDTAVYYCARDYGVFDYWGQGTLV TVSS |
| 889 | 2188-D02 | VH | EVQLVESGGGLVQPGGSLRLSCAASGEN ISDYDIHWVRQAPGKGLEWVGGIDPEDG ATDYADSVKGRFTISADTSKNTAYLQMN SLRAEDTAVYYCARDYGVFDYWGQGTLV TVSS |
| 890 | 2188-B06 | VH | EVQLVESGGGLVQPGGSLRLSCAASGEN IHSYDIHWVRQAPGEGLEWVGWINPDDG DTYHADSVKGRFTISADTSKNTAYLQMN SLRAEDTAVYYCARDYGVFDYWGQGTLV TVSS |
| 891 | 2188-D09 | VH | EVQLVESGGGLVQPGGSLRLSCAASGEN IRDYDIHWVRQAPGKGLEWVGGIDPGDG STDYADSVKGRFTISADTSKNTAYLQMN SLRAEDTAVYYCARDFGVFDYWGQGTLV TVSS |
| 892 | 2188-F02 | VH | EVQLVESGGGLVQPGGSLRLSCAASGEN ISDYDIHWVRQAPGKGLEWVAWIDPSDG STEHADSVKGRFTISADTSKNTAYLQMS SLRAEDTAVYYCARDYGVFDYWGQGTLV TVSS |
| 893 | 2188-E10 | VH | EVQLVESGGGLVQPGGSLRLSCAASGEN IGDFDIHWVRQAPGKGLEWVGGIDPRDG ATDYADSVKGRFTISADTSKNTAYLQMN SLRAEDTAVYYCARDYGVFDYWGQGTLV TVSS |
| 894 | 2188-A09 | VH | EVQLVESGGGLVQPGGSLRLSCAASGEN IINYDIHWVRQAPGKGLEWVGWINPDDG DTYYADSVKGRFTISADTSKNTAYLQMN SLRAEDTAVYYCARDYGVFDYWGQGTLV TVSS |
| 895 | 2188-D04 | VH | EVQLVESGGGLVQPGGSLRLSCAASGEN ISDYDIHWVRQAPGKGLEWVGGIDPADG STDYADSVKGRFTISADTSKNTAYLQMN SLRAEDTAVYYCARDYGVYDYWGQGTLV TVSS |
| 896 | 2188-A05 | VH | EVQLVESGGGLVQPGGSLRLSCAASGEN IKRYDIHWVRQAPGKGLEWVGWINPDDG DTYYADSVKGRFTISADTSKNTAYLQMN SLRAEDTAVYYCARDYGVFDYWGQGTLV TVSS |
| 897 | 2188-E01 | VH | EVQLVESGGGLVQPGGSLRLSCAASGEN IGDYDIHWVRQAPGKGLEWVVGIDPQDG ATDYADSVKGRFTISADTSKNTAYLQMN SLRAEDTAVYYCARDYGVFDYWGQGTLV TVSS |
| 898 | 2188-G01 | VH | EVQLVESGGGLVQPGGSLRLSCAASGEN ISDYDIHWVRQAPGKGLEWVGGIDPNDG ATDYADSVKGRFTISADTSKNTAYLQMN SLRAEDTAVYYCARDYGVFDYWGQGTLV TVSS |
| 899 | 2188-B09 | VH | EVQLVESGGGLVQPGGSLRLSCAASGEN INSYDIHWVRQAPGKGLEWVGVIDPKDG WTDHADSVKGRFTISADTSKNTAYLQMN SLRTEDTAVYYCARDYGVFDYWGQGTLV TVSS |
| 900 | 2188-F07 | VH | EVQLVESGGGLVQPGGSLRLSCAASGEN ISDYDIHWVRQAPGKGLEWVGGIDPNDG STDHADSVKGRFTISADTSKNMAYLQMN |

TABLE 20-continued

Sequences

| SEQ ID NO: | Molecule | Region Scheme | Sequence |
|---|---|---|---|
| | | | SLRAEDTAVYYCARDYGVFDYWGQGTLV TVSS |
| 901 | 2188-D08 | VH | EVQLVESGGGLVQPGGSLRLSCAASGEN IRDYDIHWVRQAPGKGLEWVVGIDPDDG ATDEADSVKGRFTISADTSKNTAYLQMN SLRAEDTAVYYCARDYGVFDYWGQGTLV TVSS |
| 902 | 2188-D05 | VH | EVQLVESGGGLVQPGGSLRLSCAASGEN ISEYDIHWVRQAPGKGLEWVGGIDPHDG WTDHADSVKGRFTISADTSKNTAYLQMN SLRAEDTAVYYCARDYGVYDYWGQGTLV TVSS |
| 903 | 2188-C03 | VH | EVQLVESGGGLVQPGGSLRLSCAASGEN INSYDIHWVRQAPGKGLEWVGWINPDDG DTYYADSVKGRFTISADTSKNTAYLQMN SLRAEDTAVYYCARDYGVFDYWGQGTLV TVSS |
| 904 | 2188-E08 | VH | EVQLVESGGGLVQPGGSLRLSCAASGEN IIDFDIHWVRQAPGKGLEWVGGIDPQDG STDLADSVKGRLTISADTSKNTAYLQMN SLRAEDTAVYYCARDYGVFDYWGQGTLV TVSS |
| 905 | 2188-C06 | VH | EVQLVESGGGLVQPGGSLRLSCAASGEN INSYDIHWVRQAPGKGLEWVGWINPDDG DTYLADSVKGRFTISADTSKNTAYLQMN SLRAEDTAVYYCARDYGVFDYWGQGTLV TVSS |
| 906 | 2188-A08 | VH | EVQLVESGGGLVQPGGSLRLSCAASGEN IHNFDIHWVRQAPGKGLEWVGWINPFDG DTYYADSVKGRFTISADTSKNTAYLRMN SLRAEDTAAYYCARDYGVFDYWGQGTLV TVSS |
| 907 | 2188-B10 | VH | EVQLVESGGGLVQPGGSLRLSCAASGEN INSYDIHWVRQAPGKGLEWVGWINPHDG DTYHADSVKGRFTISADTSKNTAYLQMN SLRAEDTAVYYCARDYGVFDYWGQGTLV TVSS |
| 908 | 2188-G02 | VH | EVQLVESGGGLVQPGGSLRLSCAASGEN IVGYDIHWVRQAPSKGLEWVGGIDPNDG ATDYADSVKGRFTISADTSKNTAYLQMN SLRAEDTAVYYCARDYGVFDYWGQGTLV TVSS |
| 909 | 2188-C05 | VH | EVQLVESGGGLVQPGGSLRLSCAASGEN INSFDIHWVRQAPGKGLEWVGGIDPRDG STDSADSVKGRFTISADTSKNTAYLQMN SLRAEDTAVYYCARDYGVFDYWGQGTLV TVSS |
| 910 | 2188-A10 | VH | EVQLVESGGGLVQPGGSLRLSCAASGEN INSYDIHWVRQAPGKGLEWVGWINPEDG DTSHADSVKGRFTISADTSKNTAYLQMN SLRAEDTAVYYCARDYGVFDYWGQGTLV TVSS |
| 911 | 2188-G04 | VH | EVQLVESGGGLVQPGGSLRLSCAASGEN IFDYDIHWVRQAPGKGLEWVGGIDPRDG STDHADSVKGRFTISADTSKNTAYLQMN SLRAEDTAVYYCARDYGVYDYWGQGTLV TVSS |
| 912 | 2188-C08 | VH | EVQLVESGGGLVQPGGSLRLSCAASGEN IKSHDIHWVRQAPGKGLEWVGWINPDDG DTYHADSVKGRFTISADTSKNTAYLQMN SLRAEDTAVYYCARDYGVFDYWGQGTLV TVSS |

TABLE 20-continued

Sequences

| SEQ ID NO: | Molecule | Region Scheme | Sequence |
|---|---|---|---|
| 913 | 2188-E05 | VH | EVQLVESGGGLVQPGGSLRLSCAASGEN ISDYDIHWVRQAPGKGLEWVAGIEPWDG STDHADSVKGRFTISADTSKNTAYLQMN SLRAEDTAVYYCARDYGVFDYWGQGTLV TVSS |
| 914 | 2188-A02 | VH | EVQLVESGGGLVQPGGSLRLSCAASGEN IKSYDIHWVRQAPGKGLEWVGWINPEDG DTYYADSVKGRFTISADTSKNTAYLQMN SLRAEDTAVYYCARDFGVFDYWGQGTLV TVSS |
| 915 | 2188-F04 | VH | EVQLVESGGSLVQPGGSLRLSCAASGEN ISDFDIHWVRQAPGKGLEWVSGIDPDDG ATDYADSVKGRFTISADTSKNTAYLQMN SLRAEDTAVYYCARDYGVFDYWGQGTLV TVSS |
| 916 | 2188-F05 | VH | EVQLVESGGGLVQPGGSLRLSCAASGEN ISDYDIHWVRQAPGKGLEWVGGIDPRDG ATDSADSVKGRFTISADTSKNTAYLQMN SLRAEDTAVYYCARDYGVFDYWGQGTLV TVSS |
| 917 | 2188-D07 | VH | EVQLVESGGGLVQPGGSLRLSCAASGEN ISDFDIHWVRQAPGKGLEWVVGIDPTDG ATDYADSVKGRFTISADTSKNTAYLQMN SLRAEDTAVYYCARDYGVFDYWGQGTLV TVSS |
| 918 | 2188-E02 | VH | EVQLVESGGGLVQPGGSLRLSCAASGEN IPDYEIHWVRQAPGKGLEWVGGIEPHDG STDYADSVKGRFTISADTSKNTAYLQMN SLRAEDTAVYYCARDYGVYDYWGQGTLV TVSS |
| 919 | 2188-D06 | VH | EVQLVESGGGLVQPGGSLRLSCAASGEN IRDYDIHWVRQAPGKGLEWVGGIDPNDG ATDYADSVKGRFTISADTSKNTAYLQMN SLRAEDTAVYYCARDYGVFDYWGQGTLV TVSS |
| 920 | 2188-F09 | VH | EVQLVESGGDLVQPGGSLRLSCAASGEN IRDYDIHWVRQAPGKGLEWVSAIDPNDG STDYADSVKGRFTISADTSKNTAYLQMN SLRAEDTAVYYCARDYGVFDYWGQGTLV TVSS |
| 921 | 2188-F10 | VH | EVQLVESGGGLVQPGGSLRLSCAASGEN ISVFDIHWVRQAPGKGLEWVGGIDPNDG ATDHADSVKGRFTISADTSKNTAYLQMN SLRAEDTAVYYCARDYGVFDYWGQGTLV TVSS |
| 922 | 2188-B05 | VH | EVQLVESGGGLVQPGGSLRLSCAASGEN IPDYDIHWVRQAPGKGLEWVGVIDPDDG WTHYADSVKGRFTISADTSKNTAYLQMN SLRAEDTAVYYCARDYGVFDYWGQGTLV TVSS |
| 923 | 1943-C02 | VH | EVQLVESGGGLAQPGGSLRLSCAAPGEN INDYYIHWVRQAPGKGLEWVGAIDPNSG STDYADSVKGRFAISADTSKNTAYLQMN SLRAEDTAVYYCARSRWFRVLWSYVFDY WGQGTLVTVSS |
| 924 | 2193-D04 | VH | EVQLVESGGGLVQPGGSLRLSCAASGEN INGFYIHWVRQAPGKGLEWVGAIDPNGG STVYADSVKGRFTISADTSKNTAYLQMN SLRAEDTAVYYCARSRWYRVLWSYAFDY WGQGTLVTVSS |
| 925 | 2193-E10 | VH | EVQLVESGGGLVQPGGSLRLSCAASGEN IYDYYIHWVRQAPGKGLEWVGAIDPVNG STNNADSVKGRFTISADTSKNTAYLQMN |

TABLE 20-continued

Sequences

| SEQ ID NO: | Molecule | Region Scheme | Sequence |
|---|---|---|---|
| | | | SLRAEDTAVYYCARSRWYRVLWSYVFDY WGQGTLVTVSS |
| 926 | 2193-E06 | VH | EVQLVESGGGLVRPGGSLRLSCAASGEN IDDYYIHWVRQAPGKGLEWVGVIDPKNG STVYADSVKGRSTISADTPKSTAYLQMN SLRAEDTAVYYCARSRWFRVLWSYVFDY WGQGTLVTVSS |
| 927 | 2193-E04 | VH | EVQLVESGGGLVQPGGSLRLSCAASGEN INDRYIHWVRQAPGKGLEWVGVIDPSLG STIDADSVKGRFTISADTSRNTAYLQMN SLRAEDTAVYYCARSRWERVLWSYVFDY WGQGTLVTVSS |
| 928 | 2193-B09 | VH | EVQLVESGGGLVQPGGSLRLSCAASGEN INNSYIHWVRQAPGKGLEWVGIIDPNNG STAYADSVKGRFTISADTSKNTAYLQMN SLRAEDTAVYYCARSRWYRVLWSYVLDY WGQGTLVTVSS |
| 929 | 2193-D11 | VH | EVQLVESGGGSVQPGGSLRLSCAASGEN INAYYIHWVRQAPGKGLEWVGAIDPNTG STVDADSVKGRFTISADTSKNTAYLQMN SLRAEDTAVYYCARSRWFRVLWSYVFDY WGQGTLVTVSS |
| 930 | 2193-B02 | VH | EVQLVESGGGLVQPGGSLRLSCAASGEN IKNSYIHWVRQAPGKGLEWVGTIDPTRG STVHADSVKGRFTISADTSKNTAYLQMN SLRAEDTAVYYCARSRWERVLWSYVFDY WGQGTLVTVSS |
| 931 | 2193-D05 | VH | EVQLVESGGGLVQPGGSLRLSCAASGEN INDHYIHWVRQAPGKGLEWVGAIDPNSG STVYADSVKGRFTISADTSKNTAYLQMN SLRAEDTAVYYCARSRWFRVLWSYVFDY WGQGTLVTVSS |
| 932 | 2193-E11 | VH | EVQLVESGGGLVQPGGSLRLSCAASGEN INDYYIHWVRQAPGKGLEWVGGIEPNSG ATVFADSVKGRFTIGADTSKNTAYLQMN SLRAEDTAVYYCARSRWYRVLWSYVFHY WGQGTLVTVSS |
| 933 | 2193-D06 | VH | EVQLVESGGGLVQPGGSLRLSCAASGEN IRDYYIHWVRQAPGKGLEWVRAIDPHSG STVYADSVKGRFTISADTSKNTAYLQMN SLRAEDTAVYYCARSRWFRVLWSYVFDY WGQGTLVTVSS |
| 934 | 2193-C02 | VH | EVQLVESGGGLVQPGGSLRLSCAASGEN ISDYYIHWVRQAPGKGLEWVGTIDPQSG STVYADSVKGRFTISADTSENTAYLQMN SLRAEDTAVYYCARSRWERVLWSFVFDY WGQGTLVTVSS |
| 935 | 2193-B03 | VH | EVQLVESGGGLVQPGGSLRLSCAASGEN IRDYYIHWVRQAPGKGLEWVGAIDPVSG STLFADSVKGRFTISADTSKNTAYLQMN SLRAEDTEVYYCARSRWFRVLWSYVFDY WGQGTLVTVSS |
| 936 | 2193-A02 | VH | EVQLVESGGGLVQPGGSLRLSCAASGEN IHASYIHWVRQAPGKGLEWVGAIDPKSG STYYADSVKGRFTISADTSKNTAYLQMN SLRAEDTAVYYCARSRWLRVLWSYIFDY WGQGTLVTVSS |
| 937 | 2193-E05 | VH | EVQLVESGGGLVQPGGSLRLSCAASGEN IKRSYIHWVRQAPGKGLEWVVSIDPNGS STHYADSVKGRFTISADTSKNTAYLQMN SLRAEDTAVYYCARSRWFRVLWSYVLDY WGQGTLVTVSS |

TABLE 20-continued

Sequences

| SEQ ID NO: | Molecule | Region Scheme | Sequence |
|---|---|---|---|
| 938 | 2193-A06 | VH | EVQLVESGGGLVQPGGSLRLSCAASGEN INAYYIHWVRQAPGKGLEWVDAIDPDSG STHNADSVKGRFTISADTSKNTAYLQMN SLRAEDTAVYYCARSRWERVLWSYIFDY WGQGTLVTVSS |
| 939 | 2193-C04 | VH | EVQLVESGGGLVQPGGSLRLSCAASGEN INTSYIHWVRQAPGKGLEWVGAIDPKSG STNFADSVKGRFTISADASKNTAYLQMN SLRAEDTAVYYCARSRWFRVLWSYVLDY WGQGTLVTVSS |
| 940 | 2193-E08 | VH | EVQLVESGGGLVQPGGSLRLSCAASGEN INEYYIHWVRQAPGKGLEWVGAIDPHSG STNFADSVKGRFTISADTSKNTAYLQMN SLRAEDTAVYYCARSRWYRVLWSYVFDY WGQGTLVTVSS |
| 941 | 2193-B10 | VH | EVQLVESGGGLVQPGGSLRLSCAASGEN IADYVHWVRQAPGKGLEWVGAIDPNSG YTVKADSVKGRFTISADTSKNTAYLQMN SLRAEDTAVYYCARSRWLRVLWSFVFDY WGQGTLVTVSS |
| 942 | 2193-D08 | VH | EVQLVESGGGLVQPGGSLRLSCAASGEN IKRSYIHWVRQAPGKGLEWVVAIDPSGG STNHADSVKGRFTISADTSKNTAYLQMN SLRAEDTAVYYCARTRWFRVLWSYVFDY WGQGTLVTVSS |
| 943 | 2193-B08 | VH | EVQLVESGGGLVQPGGSLRLSCAASGEN IKDYYIHWVRQAPGKGLEWVSAIDPSPG ATLDADSVKGRFTISADTSKNTAYLQMN SLRAEDTAVYYCARSRWERVLWSYALDY WGQGTLVTVSS |
| 944 | 2193-C05 | VH | EVQLVESGGGLVQPGGSLRLSCAASGEN IKHSYIHWVRQAPGKGLEWVGAIDPHNG STASADSVKGRFTISADTSKNTAYLQMN SLRAEDTAVHYCARSRWFRVLWSYVIDY WGQGTLVTVSS |
| 945 | 2193-D10 | VH | EVQLVESGGGLVQPGGSLRLSCAASGEN INVSYIHWVRQAPGKGLEWVATIDPNSG FTVHADSVKGRFTISADTSKNTAYLQMN SLRAEDTAVYYCARSRWERVLWSYVFDY WGQGTLVTVSS |
| 946 | 2193-D03 | VH | EVQLVESGGGLVQPGGSLRLSCAASGEN INDHYIHWVRQAPGKGLEWVSAIDPNTG STVNADSVKGRFTISADTSKNTAYLQMN SLRAEDTAVYYCARSRWSRVLWIYVFDY WGQGTLVTVSS |
| 947 | 2193-A09 | VH | EVQLVESGGGLVQPGGSLRLSCAASGEN IGKHHIHWVRQAPGKGLEWVGVIDPKGG STVYADSVKGRFTISADTSKNTAYLQMN SLRAEDTAVYYCARSRWSRVLWSYVFDY WGQGTLVTVSS |
| 948 | 2193-A10 | VH | EVQLVESGGGLVQPGGSLRLSCAASGEN IGDYIHWVRQAPGKGLEWVGAIDPKSG YTVYADSVKGRFTISADTSKNTAYLQMN SLRAEDTAVYYCARSRWERVLWSYVFDY WGQGTLVTVSS |
| 949 | 2193-E07 | VH | EVQLVESGGGLVQPGGSLRLSCAASGEN INKVYIHWVRQAPGKGLEWVVSIDPTIG STHFADSVKGRFTISADTSKSTAYLQMN SLRAEDTAVYYCARSQWERVLWSYVFDY WGQGTLVTVSS |
| 950 | 2193-A07 | VH | EVQLVESGGGLVQPGGSLRLSCAASGEN INASDIHWVRQAPGKGLGWVGAIDPNTG TTNYADSVKGRFTISADTSKNTAYLQMN |

TABLE 20-continued

Sequences

| SEQ ID NO: | Molecule | Region Scheme | Sequence |
|---|---|---|---|
| | | | SLRAEDTAVYYCARSRWFRVLWSYVFDY WGQGTLVTVSS |
| 951 | 2193-E03 | VH | EVQLVESGGGLVQPGGSLRLSCAASGEN ITASYIHWVRQAPGKGLEWVGAIDPKGG STRFADSVKGRFTISADTSKNTAYLQMN SLRAEDTAVYYCARSRWERVLWSYVFDY WGQGTLVTVSS |
| 952 | 2193-C08 | VH | EVQLVESGSGLVQPGGSLRLSCAASGEN INHYYIHWVRQAPGKGLEWVGAIDPYPG STYNADSVKGRFTISADTSKNTAYLQMN SLRAEDTAVYYCARSRWERVLWSYVFDY WGQGTLVTVSS |
| 953 | 2193-B11 | VH | EVQLVESGGGLVQPGGSLRLSCAASGEN ITGSYIHWVRQAPGKGLEWVGAIDPKSG FTSYADSAKGRFTISADTSKNTAYLQMN SLRAEDTAVYYCARSRWFRVLWSFVFDY WGQGTLVTVSS |
| 954 | 2193-A03 | VH | EVQLVESGGGLVQPGGSLRLSCAASGEN IANYHIHWVRQAPGKGLEWVGAIDPKSG STVHADSVKGRFTISADTSKNTAYLQMN SLRAEDTAVYYCARSRWSRVLWTYVFDY WGQGTLVTVSS |
| 955 | 2193-D02 | VH | EVQLVESGGGLVQPGGSLRLSCAASGEN IKDYYIHWVRQAPGKGLEWVGAIDPESG STVYADSVKGRFTISADTSKNTAYLQMN SLRAEDTAVYYCARSRWERVLWSYVFDY WGQGTLVTVSS |
| 956 | 2193-B06 | VH | EVQLVESGGGLVQPGGSLRLSCAASGEN IDGYYIHWVRQAPGKGLEWVAAIDPHPG STVYADSVKGRFTISADTSKNTAYLQMN SLRAEDTAVYYCARSRWFRVLWTYVFDY WGQGTLVTVSS |
| 957 | 2193-B01 | VH | EVQLVESGGGLVQPGGSLRLSCAASGEN IGGYYIHWVRQAPGKGLEWVGAIDPRSG YTVYADSVKGRFTISADTSKNTAYLQMN SLRAEDTAVYYCARSRWERVLWSFVLDY WGQGTLVTVSS |
| 958 | 2193-D09 | VH | EVQLVESGGGLVQPGGSLRLSCAASGEN INGYYIHWVRQAPGKGLEWVSAIDPNSG STNFADSVKGRFTISADTSKNTAYLQMN SLRAEDTAVYYCARSRWFRVLWSYVFDY WGQGTPVTVSS |
| 959 | 2193-E09 | VH | EVQLVESGGGLVQPGGSLRLPCAASGEN IGAYYIHWVRQAPGKGLEWVGAIDPGSG YTVPADSVKGRFTISADTSKNTAYLQMN SLRAEDTAVYYCARSRWYRVLWSYVFDY WGQGTLVTVSS |
| 960 | 2193-B07 | VH | EVQLVESGGGLVQPGGSLRLSCAASGEN INNSYIHWVRQAPGKGLEWVGAIDPNSG STLSADSVKGRFTISADTSKSTAYLQMN SLRAEDTAVYYCARSRWERVLWSYIFDY WGQGTLVTVSS |
| 961 | 2193-C06 | VH | EVQLVESGGGLVQPGGSLRLSCAASGEN IIVHYIHWVRQAPGKGLEWVSAIDPISG STQWADSVKGRFTISADTSKNTAYLQMN SLRAEDTAVYYCARSRWRRALWIYVFDY WGQGTLVTVSS |
| 962 | 2193-B05 | VH | EVQLVESGGGLVQPGGSLRLSCAASGEN INQYYIHWVRQAPGEGLEWVGAIDPIGG STHLADSVKGRFTISADTSKNTAYLQMN SLRAEDAAVYYCARSRWYRVLWSYVFDY WGQGTLVTVSS |

TABLE 20-continued

Sequences

| SEQ ID NO: | Molecule | Region Scheme | Sequence |
|---|---|---|---|
| 963 | 2193-A11 | VH | EVQLVESGGGLVQPGGSLRLSCAASGEN IDAYYIHWVRQAPGKGLEWVGAIDPKSG STVYADSVKGRFTTSADTSKNTAYLQMN SLRAEDTAVYYCARSRWFRVLWSYVFDY WGQGTLVTVSS |
| 964 | 2193-E02 | VH | EVQLVESGGGLVQPGGSLRLSCAASGEN IKDYYIHWVRQAPGKGLEWVGSIDPTSG STVIADSVKGRFTISADTSKNTAYLQMN SLRAEDTAVYYCARSRWWRVLWSYVFDY WGQGTLVTVSS |
| 965 | 2193-A08 | VH | EVQLVESGGGLVQPGGSLRLSCAASGEN IIDSYIHWVRQAPGKGLEWVGAIDPNAG STVYADSVRGRFTISADTSKNTAYIQMN SLRAEDTAVYYCARSRWFRVLWSYVFDY WGQGTLVTVSS |
| 966 | 2193-C11 | VH | EVQLVESGGGLVQPGGSLRLSCAASGEN IADSYIHWVRQAPGKGLEWVAVIDPKSG STNYADSVKGRFTISADTSKNTAYLQMN SLRAEDTAVYYCARSRWERVLWSYVFDY WGQGTLVTVSS |
| 967 | 2193-A01 | VH | EVQLVESGGGLVQPGGSLRLSCAASGEN INDHYIHWVRQAPGKGLEWVGAIDPTSG STVFADSVKGRFTISADTSKNTAYLQMN SLRAEDTAVYYCARSRWFRVLWSYVFDY WGQGTLVTVSS |
| 968 | 2193-D07 | VH | EVQLVESGGGLVQPGGSLRLSCAASGEN IIDYNIHWVRQAPGKGLEWVTAIGPADG STVNADSLKGRFTISADTSKNTAYLQMN SLRAEDTAVYYCARSRWLRVLWSYVFDY WGQGTLVTVSS |
| 969 | 2193-A05 | VH | EVQLVESGGGLVQPGGSLRLSCAASGEN IKGYYIHWVRQAPGKGLEWVSVIDPNSG STIFADSVKGRFTISADTSKNTAYLQMN SLRAEDTAVYYCARSRWERVLWSYVLDY WGQGTLVTVSS |
| 970 | 2193-C03 | VH | EVQLVESGGGLVQPGGSLRLSCAASGEN INYSYIHWVRQAPGKGLEWVGAIEPKSG STASADSVKGRFTISADTSKNTAYLQMN SLRAEDAAVYYCARSRWYRVLWSYVLDY WGQGTLVTVSS |
| 971 | 2193-C09 | VH | EVQLVESGGGLVQPGGPLRLSCAASGEN INHSYIHWVRQAPGKGLEWVGAIDPISG STVYADSVKGRFTISADTSKNTAYLQMN SLRAEDTAVYYCARSRWSRVLWSYVFDY WGQGTLVTVSS |
| 972 | 2193-D01 | VH | EVQLVESGGGLVQPGGSLRLSCAASGEN INDSYIHWVRQAPGKGLEWVGAIDPTSG PTVYADSVKGRFTISADTSKSTAYLQMN SLRAEDTAVYYCARSRWERVLWSYVFDY WGQGTLVTVSS |
| 973 | 2193-E01 | VH | EVQLVESGGGLVQPGGSLRLSCAASGEN IKGKYIHWVRQAPGKGLEWVGAIDPKSG STAHADSVKGRFTISADTSKNTAYLQMN SLRAEDTAAYYCARSRWFRVLWTYVFDY WGQGTLVTVSS |
| 974 | 2193-C07 | VH | EVQLVESGGGLVQPGGSLRLSCAASGEN IKQDIHWVRQAPGKGLEWVGAIDPTRG ATVYADSVKGRFTISADTSKNTAYLQMN SLRAEGTAVYYCARSRWYRVLWSFVFDY WGQGTLVTVSS |
| 975 | 2193-B04 | VH | EVQLVESGGGLVQPGGSLRLSCAASGEN ISNSYIHWVRQAPGKGLEWVGAIEPKNG STHHADSVKGRFTISADTSKNTAYLQMN |

TABLE 20-continued

Sequences

| SEQ ID NO: | Molecule | Region Scheme | Sequence |
|---|---|---|---|
| | | | SLRAEDTAVYYCARSRWFRVLWTYVFDY WGQGTLVTVSS |
| 976 | 2193-C10 | VH | EVQLVESGGGLVQPGGSLRLSCAASGEN INNAYIHWVRQAPGKGLEWVGAIDPRSG STISADSMKGRFTISADTSKNTAYLQMN SLRAEDTAVYYCARSRWERVLWSEGEDY WGQGTLVTVSS |
| 977 | 2193-C01 | VH | EVQLVESGGGLVQPGGSLRLSCAASGLN INDHYIHWVRQAPGKGLEWVGTIDPKSG STHVADSVKGRFTISADTSKNTAYLQMN SLRAEDTAVYYCARSRWFRVLWSYVFDY WGQGTLVTVSS |
| 978 | 2193-A04 | VH | EVQLVESGGGLVQPGGSLRLSCAASGEN IISYYIHWVRQAPGKGLEWVGAIDPNSG STLLADSVKGRFTISADTSKNTAYLQMN SLRAEDTAVYYCARSRWFRVLWSYVYDY WGQGTLVTVSS |
| 979 | 1944-A07 | VH | EVQLVESGGGLVQPGGSLRLSCAASGEN ITGYYIHWVRQAPGKGLEWVGYISPNSG STYYADSVKGRFTISADTSKNTAYLQMN SLRAEDTAVYYCARDSRRYVRPFDYWGQ GTLVTVSS |
| 980 | 2194-A02 | VH | EVQLVESGGGLVQPGGSLRLSCAASGEN ITGYYIHWVRQAPGKGLEWVGYISPLAG NTYHADSVKGRFTISADTSKNTAYLQMN SLRAEDTAVYYCARDSRRYVRPEDYWGQ GTLVTVSS |
| 981 | 2194-A05 | VH | EVQLVESGGGLVQPGGSLRLSCAASGEN IKEYHIHWVRQAPGKGLEWVGYISPNSG STYYADSVKGRFTISADTSKNTAYLQMN SLRAEDTAVYYCARDHRRYVRPFDYWGQ GTLVTVSS |
| 982 | 2194-B04 | VH | EVQLVESGGGLVQPGGSLRLSCAASGEN ITGYHIHWVRQAPGKGLEWVGYISPLAG NTYHADSVKGRFTISADTSKNTAYLQMN SLRAEDTAVYYCTRDSRRYVRPLDYWGQ GTLVTVSS |
| 983 | 2194-A09 | VH | EVQLVESGGGLVQPGGSLRLSCAASGEN ITGYYIHWVRQAPGKGLEWVGYITPLSG ATYRADSVKGRFTISADTSKNTAYLQMN SLRAEDTAVYYCARDSRRYVRPEDYWGQ GTLVTVSS |
| 984 | 2194-A01 | VH | EVQLVESGGGLVQPGGSLRLSCAASGEN ITGYYIHWVRQAPGKGLEWVGYISPLAG NTYHADSVKGRENISADTSKNTAYLQMN SLRAEDTAVYYCARDSRRYVRPMDYWGQ GTLVTVSS |
| 985 | 2194-B03 | VH | EVQLVESGGGLVQPGGSLRLSCAASGEN ITSYYIHWVRQAPGKGLEWVGYISPLAG NTYHADSVKGRFTISADTSKNTAYLQMN SLRAEDTAVYYCARDSRRYVRPEDYWGQ GTLVTVSS |
| 986 | 2194-B02 | VH | EVQLVESGGGLVQPGGSLRLSCAASGEN ISGYYIHWVRQTPGKGLEWVGYISPLAG NTYHADSVKGRFTISADTSKNTAYLQMN SLRAEDTAVYYCARDSRRYVRPLDYWGQ GTLVTVSS |
| 987 | 2194-A03 | VH | EVQLVESGGGLVQPGGPLRLSCAASGEN ITGYYIHWVRQAPGKGLEWVGYITPNSG TTYSADSVKGRFTISADTSKNTAYLQMN SLRAEDTAVYYCARDSRRYVRPLDYWGQ GTLVTVSS |

TABLE 20-continued

Sequences

| SEQ ID NO: | Molecule | Region Scheme | Sequence |
|---|---|---|---|
| 988 | 2194-A11 | VH | EVQLVESGGGLVQPGGSLRLSCAASGEN ITQYYIHWVRQAPGKGLEWVGYISPNSG YTTDADSVKGRFTISADTSKNTAYLQMN SLRAEDTAVYYCARDSRRYVRPFDYWGQ GTLVTVSS |
| 989 | 2194-A08 | VH | EVQLVESGGGLVQPGGSLRLSCAASGEN ITGYHIHWVRQAPGKGLEWVGYIAPSSG YTYDADSVKGRFTISADTSKNTAYLQMN SLRAEDTAVYYCARDSRRYVRPEDYWGQ GTLVTVSS |
| 990 | 2194-A04 | VH | EVQLVESGGGLVQPGGSLRLSCAASGEN ITGYYIHWVRQAPGKGLEWVGYISPLAG NTHHADSVKGRFTISADTSKNTAYLQMN SLRAEDTAVYYCARDSRRYVRPLDYWGQ GTLVTVSS |
| 991 | 2194-A10 | VH | EVQLVESGGGLVQPGGSLRLSCAASGEN ITQYYIHWVRQAPAKGLEWVGYISPNSG STHIADSVKGRFTISADTSKNTAYLQMN SLRAEDTAVYYCARDSRRYVRPEDYWGQ STLVTVSS |
| 992 | 2194-A07 | VH | EVQLVESGGGLVQPGGSLRLSCAASGEN FTDYYIHWVRQAPGKGLEWVGYISPLAG NTYHADSVKGRFTISADTSKNTAYLQMN SLRAEDTAVYYCARDSRRYVRPEDYWGQ GTLVTVSS |
| 993 | 2194-B01 | VH | EVQLVESGGGLVQPGGSLRLSCAASGEN IASYYIHWVRQAPGKGLEWVGYISPLAG NTYHADSVKGRFTISADTSKNTAYLQMN SLRAEDTAVYYCARDSRRYVRPEDYWGQ GTLVTVSS |
| 994 | 2194-A06 | VH | EVQLVESGGGLVQPGGSLRLSCAASGEN ITDYYIHWVRQAPGKGLEWVGYISPLAG NTYHADSVKGREPISADTSKNTAYLQMN SLRAEDTAVYYCARDSRRYVRPEDYWGQ GTLVTVSS |
| 995 | 2196-C01 | VH | EVQLVESGGGLVQPGGSLRLSCAASGEN IIGYYIHWVRQAPGKGLEWVGSITPLSG ATSKADSVKGRFTISADTSKNTAYLQMN SLRAEDTAVYYCARDSRRYIRSWDYWGQ GTLVTVSS |
| 996 | 2196-A02 | VH | EVQLVESGGGLVQPGGSLRLSCAASGEN ITGYYIHWVRQAPGKGLEWVGQISPNSG ATHDADSVKGRFTISADTSKNTAYLQMN SLRAEDTAVYYCARDSRRYVRGWDYWGQ GTLVTVSS |
| 997 | 2196-B03 | VH | EVQLVESGGGLAQPGGSLRLSCAASGEN ITGYYIHWVRQAPGKGLEWVGYISPNSG ATHYADSVKGRFTISADTSKNTAYLQMN SLRAEDTAVYYCARDSRRYVRPFDYWGQ GTLVTVSS |
| 998 | 2196-A05 | VH | EVQLVESGGGLVQPGGSLRLSCAASGEN ITNYIHWVRQAPGKGLEWVGYISPNSG ATYQADSVKGRFTISADTSKNTAYLQMN SLRAEDTAVYYCARDSRRYVRSWDYWGQ GTLVTVSS |
| 999 | 2196-C02 | VH | EVQLVESGGGLVQPGGSLRLSCAASGEN ITGYHIHWVRQAPGKGLEWVGFISPNSG WTYSADSVKGRFTISADTSKNTAYLQMN SLRAEDTAVYYCARDSRRYVRPFDYWGQ GTLVTVSS |
| 1000 | 2196-B11 | VH | EVQLVESGGGLVQPGGSLRLSCAASGEN ITGYYIHWVRQAPGRGLEWVGQISPNSG YTYYADSVKGRFTISADTSKNTAYLQMN |

TABLE 20-continued

| SEQ ID NO: | Molecule | Region Scheme | Sequence |
|---|---|---|---|
| | | | SLRAEDTAVYYCARDSRRYIRSWDYWGQGTLVTVSS |
| 1001 | 2196-B08 | VH | EVQLVESGGGLVQPGGSLRLSCAASGENITGYYIHWVRQAPGKGLEWVGQISPNSGYTYLADSVKGRFTISADTSKNTAYLQMNSLRAEDTAVYYCARDSRRYVRGWDYWGQGTLVTVSS |
| 1002 | 2196-A04 | VH | EVQLVESGGGLVQPGGSLRLSCAASGENISPYYIHWVRQAPGKGLEWVGQIYPISGHTYQADSVKGRFTISADTSKNTAYLQMNSLRAEDTAVYYCARESRRYVGPFGYWGQGTLVTVSS |
| 1003 | 2196-A03 | VH | EVQLVESGGGLVQPGGSLRLSCAASGENITQYHIHWVRQAPGKGLEWVGYISPNSGSTHEADSVKGRFTISADTSKNTAYLQMNSLRAEDTAVYYCARDSRRYVRGWDYWGQGTLVTVSS |
| 1004 | 2196-B07 | VH | EVQLVESGGGLVQPGGSLRLSCAASGENITGYIHWVRQAPGEGLEWVGYISPNSGATYYADSVEGRFTISADTSKNTAYLQMHSLRAEDTAVYYCTRDSRRYVRGWDYWGQGTLVTVSS |
| 1005 | 2196-A06 | VH | EVQLVESGGGLVQPGGSLRLSCAASGENITGYYIHWVRQAPGKGLEWVGQISPNSGSTHQADSVKGRFTISADTSKNTAYLQMNSLRAGDTAVYYCARDSRRYVRGWDYWGQGTLVTVSS |
| 1006 | 2196-B05 | VH | EVQLVESGGGLVQPGGSLRLSCAASGENITGYYIHWVRQAPGKGLEWVGQISPNSGATYHADSVKGRFTISADTSKNTAYLQMNSLRAEDTAVYYCARDSRRYVRGWDYWGQGTLVTVSS |
| 1007 | 2196-A01 | VH | EVQLVESGGGLVQPGGSLRLSCAASGENITGYYIHWVRQAPGKGLEWVGQISPNSGYTYYADSVKGRFTISADTSKNTAYLQMNSLRAEDTAVYYCARDSRRYVRGWDYWGQGTLVTVSS |
| 1008 | 2196-B01 | VH | EVQLVESGGGLVQPGGSLRLSCAASGENITGYYIHWVRQAPGKGLEWVGQISPNSGYTYYADSVKGRFTISADTSKNTTYLQMNSLRAEDTAVYYCARDSRRYVRSWDYWGQGTLVTVSS |
| 1009 | 2196-A09 | VH | EVQLVESGGGLVQPGGSLRLSCAASGENITGYYIHWVRQAPGKGLEWVGQISPNSGATHYADSVKGRFTISADTSKNTAYLQMNSLRAEDTAVYYCARDSRRYIRSWDYWGQGTLVTVSS |
| 1010 | 2196-A08 | VH | EVQLVESGGGLVQPGGSLRLSCAASGENITGYYIHWVRQAPGKGLEWVGYISPNSGSTYKADSVKGRFTISADTSRNTAYLQMNSLRAEDTAVYYCARDSRRYVRSWDYWGQGTLVTVSS |
| 1011 | 2196-A10 | VH | EVQLVESGGGLVQPGGSLRLSCAASGENITGYYIHWVRQAPGKGLEWVGYISPNSGATHYADSVKGRFTISADISKNTAYLQMNSLRAEDTAVHYCARDSRRYVRSWDYWGQGTLVTVSS |
| 1012 | 2196-B06 | VH | EVQLVESGGGLVQPGGSLRLSCAASGENITGYYIHWVRQAPGKGLEWVGQISPNSGSTYSADSVKGRFTISADTSKNTAYLQMNSLRAEDTAVYYCARDSRRYVLSWDYWGQGTLVTVSS |

TABLE 20-continued

Sequences

| SEQ ID NO: | Molecule | Region Scheme | Sequence |
|---|---|---|---|
| 1013 | 2196-B09 | VH | EVQLVESGGGLVQPEGSLRLSCAASGEN ITEYYIHWVRQAPGKGLEWVGYISPNSG STYYADSVKGRFTISADTSKNTAYLQMN SLRAEDTAVYYCARDSRRYVRSWDYWGQ GTLVTVSS |
| 1014 | 2196-C03 | VH | EVQLVESGGGLVQPGGSLRLSCAASGEN ITGYYIHWVRQAPGKGLEWVGQISPNSG STYSADSVKGRFTISADTSKNTAYLQMS SLRAEDTAVYYCARDSRRYVLSWDYWGQ GTLVTVSS |
| 1015 | 2196-C04 | VH | EVQLVESGGGLVQPGGSLRLSCAASGEN ITGYYIHWVRQAPGKGLEWVGFIAPLSG STHNADSVKGRFTISADTSKNTAYLQMN SLRAEDTAVYYCARESRRYVNPWDYWGQ GTLVTVSS |
| 1016 | 2196-A07 | VH | EVQLVESGGGLVQPGGSLRLSCAASGEN ITGYYIHWVRQAPGKGLEWVGQISPNSG STYYADSVKGRFTISADTSKNTAYLQMS SLRAEDTAVYYCARDSRRYVRGWDYWGQ GTLVTVSS |
| 1017 | 2196-A11 | VH | EVQLVESGGGLVQPGGSLRLSCAASGEN ITGYYIHWVRQAPGKGLEWVGQISPNSG TTYDADSVKGRFTISADTSKNTAYLQMN SLRAEDTAVYYCARDSRRYVRGWDYWGQ GTLVTVSS |
| 1018 | 2196-B02 | VH | EVQLVESGGGLVQPGGSLRLSCAASGEN ITQYYIHWVRQAPGKGLEWVGYISPNSG QTYDADSVKGRFTISADTSKNTAYLQMN SLRAEDTAVYYCARDSRRYVRSWDYWGQ GTLVTVSS |
| 1019 | 2196-B04 | VH | EVQLVESGGGLVQPGGSLRLSCAASGEN ITEYYIHWVRQAPGKGLEWVGYISPNSG ATYQADSVKGRFTISADTSKNTAYLQMN SLRAEDTAVYYCARDSRRYVRGWDYWGQ GTLVTVSS |
| 1020 | 2196-B10 | VH | EVQLVESGGGLVQPGGSLRLSCAASGEN ITGYYIHWVRQAPGKGLEWVGSITPLSG ATSKADSVKGRFTISADTSKNTAYLQMN SLRAEDTAVYYCARDSRRYIRSWDYWGQ GTLVTVSS |
| 1021 | trastuzumab | VL | DIQMTQSPSSLSASVGDRVTITCRASQD VNTAVAWYQQKPGKAPKLLIYSASFLYS GVPSRFSGSRSGTDFTLTISSLQPEDFA TYYCQQHYTTPPTFGQGTKVEIK |
| 1022 | SP34 | VL | QAVVTQESALTTSPGETVTLTCRSSTGA VTTSNYANWVQEKPDHLFTGLIGGTNKR APGVPARFSGSLIGDKAALTITGAQTED EAIYFCALWYSNLWVFGGGTKLTVL |
| 1023 | 2037-B10 | VL | QTVVTQEPSLTVSPGGTVTLTCGSSTGA VTSGYYPNWLQQKPGQAPRGLIGGTKFL APGTPARFSGSLLGGKAALTLSGVQPED EAEYYCALWYSNRWVFGGGTQLTVTG |
| 1024 | hUCHT1-LC3 | VL | DIQMTQSPSTLSASVGDRVTITCRASQD IRNYLNWYQQKPGKAPKLLIYYTSRLHS GVPSRFSGSGSGTEYTLTISSLQPDDFA TYYCQQGNTLPWTFGGGTKVEIK |
| 1025 | hOKT3-LC1 | VL | DIQMTQSPSSLSASVGDRVTITCSASSS VSYMNWYQQKPGKAPKRLIYDTSKLASG VPSRFSGSGSGTEYTLTISSLQPEDFAT YYCQQWSSNPFTFGQGTKLEIK |
| 1026 | hSP34-LC3 | VL | QTVVTQEPSLTVSPGGTVTLTCGSSTGA VTSGYYPNWFQQKPGQAPRGLIGGTKFL |

TABLE 20-continued

Sequences

| SEQ ID NO: | Molecule | Region Scheme | Sequence |
|---|---|---|---|
| | | | APGTPARFSGSLLGGKAALTLSGVQPED EAEYYCALWYSNRWVFGGGTQLTVTG |
| 1027 | Human IgG1 HC Constant | | ASTKGPSVFPLAPSSKSTSGGTAALGCL VKDYFPEPVTVSWNSGALTSGVHTFPAV LQSSGLYSLSSVVTVPSSSLGTQTYICN VNHKPSNTKVDKKVEPKSCDKTHTCPPC PAPELLGGPSVFLFPPKPKDTLMISRTP EVTCVVVDVSHEDPEVKFNWYVDGVEVH NAKTKPREEQYNSTYRVVSVLTVLHQDW LNGKEYKCKVSNKALPAPIEKTISKAKG QPREPQVYTLPPSREEMTKNQVSLTCLV KGFYPSDIAVEWESNGQPENNYKTTPPV LDSDGSFFLYSKLTVDKSRWQQGNVFSC SVMHEALHNHYTQKSLSLSPGK |
| 1028 | Human IgG LC Constant Ckappa | | RTVAAPSVFIFPPSDEQLKSGTASVVCL LNNFYPREAKVQWKVDNALQSGNSQESV TEQDSKDSTYSLSSTLTLSKADYEKHKV YACEVTHQGLSSPVTKSFNRGEC |
| 1029 | Mouse IgG1 HC Constant | | AKTTPPSVYPLAPGSAAQTNSMVTLGCL VKGYFPEPVTVTWNSGSLSSGVHTFPAV LQSDLYTLSSSVTVPSSTWPSETVTCNV AHPASSTKVDKKIVPRDCGCKPCICTVP EVSSVFIFPPKPKDVLTITLTPKVTCVV VDISKDDPEVQFSWFVDDVEVHTAQTQP REEQFNSTFRSVSELPIMHQDWLNGKEF KCRVNSAAFPAPIEKTISKTKGRPKAPQ VYTIPPPKEQMAKDKVSLTCMITDFFPE DITVEWQWNGQPAENYKNTQPIMDTDGS YFVYSKLNVQKSNWEAGNTFTCSVLHEG LHNHHTEKSLSHSPG |
| 1030 | Mouse IgG LC Constant Ckappa | | RADAAPTVSIFPPSSEQLTSGGASVVCF LNNFYPKDINVKWKIDGSERQNGVLNSW TDQDSKDSTYSMSSTLTLTKDEYERHNS YTCEATHKTSTSPIVKSENRNEC |
| 1031 | Kappa LC | | HMTVAAPSVFIFPPSDEQLKSGTASVVC LLNNFYPREAKVQWKVDNALQSGNSQES VTEQDSKDSTYSLSSTLTLSKADYEKHK VYACEVTHQGLSSPVTKSFNRGEC |
| 1032 | Lambda LD | | GQPKAAPSVTLFPPSSEELQANKATLVC LISDFYPGAVTVAWKADSSPVKAGVETT TPSKQSNNKYAASSYLSLTPEQWKSHRS YSCQVTHEGSTVEKTVAPTECS |
| 1033 | FlagHis Tag | | GSGDYKDDDDKGSGHHHHHH |
| 1034 | Linker | | GGGGSGGGGSGGGGS |
| 1035 | Linker | | AAGSDQEPKSS |

TABLE 21

Antibody Sequences

| Polypeptide description | Sequence |
|---|---|
| 2188-D04 HC SEQ ID NO: 1052 | MEVQLVESGGGLVQPGGSLRLSCAASGENISDYDIHWVRQAPGKGLEWVGGIDPADGSTD YADSVKGRFTISADTSKNTAYLQMNSLRAEDTAVYYCARDYGVYDYWGQGTLVTVSSAST KGPSVFPLAPSSKSTSGGTAALGCLVKDYFPEPVTVSWNSGALTSGVHTFPAVLQSSGLY SLSSVVTVPSSSLGTQTYICNVNHKPSNTKVDKKVEPKSCDKTHTCPPCPAPELLGGPSV FLFPPKPKDTLMISRTPEVTCVVVDVSHEDPEVKFNWYVDGVEVHNAKTKPREEQYNSTY RVVSVLTVLHQDWLNGKEYKCKVSNKALPAPIEKTISKAKGQPREPQVYTLPPSREEMTK NQVSLTCLVKGFYPSDIAVEWESNGQPENNYKTTPPVLDSDGSFFLYSKLTVDKSRWQQG NVFSCSVMHEALHNHYTQKSLSLSPGK |

TABLE 21-continued

Antibody Sequences

| Polypeptide description | Sequence |
|---|---|
| 2188-D04 LC SEQ ID NO: 1053 | MDIQMTQSPSSLSASVGDRVTITCRASQDVNTAVAWYQQKPGKAPKLLIYSASFLYSGVP SRESGSRSGTDFTLTISSLQPEDFATYYCQQHYTTPPTFGQGTKVEIKRTVAAPSVFIFP PSDEQLKSGTASVVCLLNNFYPREAKVQWKVDNALQSGNSQESVTEQDSKDSTYSLSSTL TLSKADYEKHKVYACEVTHQGLSSPVTKSENRGEC |
| 2188-D04 IgG HC Y180F404TAG SEQ ID NO: 1036 | MEVQLVESGGGLVQPGGSLRLSCAASGENISDYDIHWVRQAPGKGLEWVGGIDPADGSTD YADSVKGRFTISADTSKNTAYLQMNSLRAEDTAVYYCARDYGVYDYWGQGTLVTVSSAST KGPSVFPLAPSSKSTSGGTAALGCLVKDYFPEPVTVSWNSGALTSGVHTFPAVLQSSGL* SLSSVVTVPSSSLGTQTYICNVNHKPSNTKVDKKVEPKSCDKTHTCPPCPAPELLGGPSV FLFPPKPKDTLMISRTPEVTCVVVDVSHEDPEVKFNWYVDGVEVHNAKTKPREEQYNSTY RVVSVLTVLHQDWLNGKEYKCKVSNKALPAPIEKTISKAKGQPREPQVYTLPPSREEMTK NQVSLTCLVKGFYPSDIAVEWESNGQPENNYKTTPPVLDSDGS*FLYSKLTVDKSRWQQG NVFSCSVMHEALHNHYTQKSLSLSPGK |
| 2188-D04 Y180TAG V262E SEQ ID NO: 1037 | MEVQLVESGGGLVQPGGSLRLSCAASGENISDYDIHWVRQAPGKGLEWVGGIDPADGSTD YADSVKGRFTISADTSKNTAYLQMNSLRAEDTAVYYCARDYGVYDYWGQGTLVTVSSAST KGPSVFPLAPSSKSTSGGTAALGCLVKDYFPEPVTVSWNSGALTSGVHTFPAVLQSSGL* SLSSVVTVPSSSLGTQTYICNVNHKPSNTKVDKKVEPKSCDKTHTCPPCPAPELLGGPSV FLFPPKPKDTLMISRTPEVTCEVVDVSHEDPEVKFNWYVDGVEVHNAKTKPREEQYNSTY RVVSVLTVLHQDWLNGKEYKCKVSNKALPAPIEKTISKAKGQPREPQVYTLPPSREEMTK NQVSLTCLVKGFYPSDIAVEWESNGQPENNYKTTPPVLDSDGSFFLYSKLTVDKSRWQQG NVFSCSVMHEALHNHYTQKSLSLSPGK |
| 2188-D04 IgG HC F404TAG SEQ ID NO: 1038 | MEVQLVESGGGLVQPGGSLRLSCAASGFNISDYDIHWVRQAPGKGLEWVGGIDPADGSTD YADSVKGRFTISADTSKNTAYLQMNSLRAEDTAVYYCARDYGVYDYWGQGTLVTVSSAST KGPSVFPLAPSSKSTSGGTAALGCLVKDYFPEPVTVSWNSGALTSGVHTFPAVLQSSGLY SLSSVVTVPSSSLGTQTYICNVNHKPSNTKVDKKVEPKSCDKTHTCPPCPAPELLGGPSV FLFPPKPKDTLMISRTPEVTCVVVDVSHEDPEVKFNWYVDGVEVHNAKTKPREEQYNSTY RVVSVLTVLHQDWLNGKEYKCKVSNKALPAPIEKTISKAKGQPREPQVYTLPPSREEMTK NQVSLTCLVKGFYPSDIAVEWESNGQPENNYKTTPPVLDSDGS*FLYSKLTVDKSRWQQG NVFSCSVMHEALHNHYTQKSLSLSPGK |
| 2188-D04_HC_F404TAG_ Knob SEQ ID NO: 1039 | MEVQLVESGGGLVQPGGSLRLSCAASGENISDYDIHWVRQAPGKGLEWVGGIDPADGSTD YADSVKGRFTISADTSKNTAYLQMNSLRAEDTAVYYCARDYGVYDYWGQGTLVTVSSAST KGPSVFPLAPSSKSTSGGTAALGCLVKDYFPEPVTVSWNSGALTSGVHTFPAVLQSSGLY SLSSVVTVPSSSLGTQTYICNVNHKPSNTKVDKKVEPKSCDKTHTCPPCPAPELLGGPSV FLFPPKPKDTLMISRTPEVTCVVVDVSHEDPEVKFNWYVDGVEVHNAKTKPREEQYNSTY RVVSVLTVLHQDWLNGKEYKCKVSNKALPAPIEKTISKAKGQPREPQVYTLPPSREEMTK NQVSLWCLVKGFYPSDIAVEWESNGQPENNYKTTPPVLDSDGS*FLYSKLTVDKSRWQQG NVFSCSVMHEALHNHYTQKSLSLSPGK |
| 2188-D04_HC_F404TAG Hole SEQ ID NO: 1040 | MEVQLVESGGGLVQPGGSLRLSCAASGENISDYDIHWVRQAPGKGLEWVGGIDPADGSTD YADSVKGRFTISADTSKNTAYLQMNSLRAEDTAVYYCARDYGVYDYWGQGTLVTVSSAST KGPSVFPLAPSSKSTSGGTAALGCLVKDYFPEPVTVSWNSGALTSGVHTFPAVLQSSGLY SLSSVVTVPSSSLGTQTYICNVNHKPSNTKVDKKVEPKSCDKTHTCPPCPAPELLGGPSV FLFPPKPKDTLMISRTPEVTCVVVDVSHEDPEVKFNWYVDGVEVHNAKTKPREEQYNSTY RVVSVLTVLHQDWLNGKEYKCKVSNKALPAPIEKTISKAKGQPREPQVYTLPPSREEMTK NQVSLCAVKGFYPSDIAVEWESNGQPENNYKTTPPVLDSDGS*FLYSKLTVDKSRWQQG NVFSCSVMHEALHNHYTQKSLSLSPGK |
| 2194-A05_HC_F404TAG_ Knob SEQ ID NO: 1041 | MEVQLVESGGGLVQPGGSLRLSCAASGENIKEYHIHWVRQAPGKGLEWVGYISPNSGSTY YADSVKGRFTISADTSKNTAYLQMNSLRAEDTAVYYCARDHRRYVRPFDYWGQGTLVTVS SASTKGPSVFPLAPSSKSTSGGTAALGCLVKDYFPEPVTVSWNSGALTSGVHTFPAVLQS SGLYSLSSVVTVPSSSLGTQTYICNVNHKPSNTKVDKKVEPKSCDKTHTCPPCPAPELLG GPSVFLFPPKPKDTLMISRTPEVTCVVVDVSHEDPEVKFNWYVDGVEVHNAKTKPREEQY NSTYRVVSVLTVLHQDWLNGKEYKCKVSNKALPAPIEKTISKAKGQPREPQVYTLPPSRE EMTKNQVSLWCLVKGFYPSDIAVEWESNGQPENNYKTTPPVLDSDGS*FLYSKLTVDKSR WQQGNVFSCSVMHEALHNHYTQKSLSLSPGK |
| 1987-C06_HC_F404TAG_ Hole SEQ ID NO: 1042 | MEVQLVESGGGLVQPGGSLRLSCAASGENIKEYHIHWVRQAPGKGLEWVGYISPNSGSTY YADSVKGRFTISADTSKNTAYLQMNSLRAEDTAVYYCARDHRRYVRPFDYWGQGTLVTVS SASTKGPSVFPLAPSSKSTSGGTAALGCLVKDYFPEPVTVSWNSGALTSGVHTFPAVLQS SGLYSLSSVVTVPSSSLGTQTYICNVNHKPSNTKVDKKVEPKSCDKTHTCPPCPAPELLG GPSVFLFPPKPKDTLMISRTPEVTCVVVDVSHEDPEVKFNWYVDGVEVHNAKTKPREEQY NSTYRVVSVLTVLHQDWLNGKEYKCKVSNKALPAPIEKTISKAKGQPREPQVYTLPPSRE EMTKNQVSLWCLVKGFYPSDIAVEWESNGQPENNYKTTPPVLDSDGS*FLYSKLTVDKSR WQQGNVFSCSVMHEALHNHYTQKSLSLSPGK |
| 1943-C01_HC_F404TAG_ Hole SEQ ID NO: 1043 | MEVQLVESGGGLVQPGGSLRLSCAASGENINGYDIHWVRQAPGKGLEWVGYIDPNDGATN YADSVKGRFTISADTSKNTAYLQMNSLRAEDTAVYYCARDYGVFDYWGQGTLVTVSSAST KGPSVFPLAPSSKSTSGGTAALGCLVKDYFPEPVTVSWNSGALTSGVHTFPAVLQSSGLY SLSSVVTVPSSSLGTQTYICNVNHKPSNTKVDKKVEPKSCDKTHTCPPCPAPELLGGPSV FLFPPKPKDTLMISRTPEVTCVVVDVSHEDPEVKFNWYVDGVEVHNAKTKPREEQYNSTY RVVSVLTVLHQDWLNGKEYKCKVSNKALPAPIEKTISKAKGQPREPQVYTLPPSREEMTK |

TABLE 21-continued

Antibody Sequences

| Polypeptide description | Sequence |
|---|---|
| | NQVSLSCAVKGFYPSDIAVEWESNGQPENNYKTTPPVLDSDGS*FLVSKLTVDKSRWQQG<br>NVFSCSVMHEALHNHYTQKSLSLSPGK |
| 2193-<br>B09_HC_F404TAG_<br>Hole<br>SEQ ID NO: 1044 | MEVQLVESGGGLVQPGGSLRLSCAASGENINNSYIHWVRQAPGKGLEWVGIIDPNNGSTA<br>YADSVKGRFTISADTSKNTAYLQMNSLRAEDTAVYYCARSRWYRVLWSYVLDYWGQGTLV<br>TVSSASTKGPSVFPLAPSSKSTSGGTAALGCLVKDYFPEPVTVSWNSGALTSGVHTEPAV<br>LQSSGLYSLSSVVTVPSSSLGTQTYICNVNHKPSNTKVDKKVEPKSCDKTHTCPPCPAPE<br>LLGGPSVFLFPPKPKDTLMISRTPEVTCVVVDVSHEDPEVKENWYVDGVEVHNAKTKPRE<br>EQYNSTYRVVSVLTVLHQDWLNGKEYKCKVSNKALPAPIEKTISKAKGQPREPQVYTLPP<br>SREEMTKNQVSLSCAVKGFYPSDIAVEWESNGQPENNYKTTPPVLDSDGS*FLVSKLTVD<br>KSRWQQGNVFSCSVMHEALHNHYTQKSLSLSPGK |
| 2194-<br>A05_HC_F404TAG_<br>Hole<br>SEQ ID NO: 1045 | MEVQLVESGGGLVQPGGSLRLSCAASGENIKEYHIHWVRQAPGKGLEWVGYISPNSGSTY<br>YADSVKGRFTISADTSKNTAYLQMNSLRAEDTAVYYCARDHRRYVRPFDYWGQGTLVTVS<br>SASTKGPSVFPLAPSSKSTSGGTAALGCLVKDYFPEPVTVSWNSGALTSGVHTEPAVLQS<br>SGLYSLSSVVTVPSSSLGTQTYICNVNHKPSNTKVDKKVEPKSCDKTHTCPPCPAPELLG<br>GPSVFLFPPKPKDTLMISRTPEVTCVVVDVSHEDPEVKENWYVDGVEVHNAKTKPREEQY<br>NSTYRVVSVLTVLHQDWLNGKEYKCKVSNKALPAPIEKTISKAKGQPREPQVYTLPPSRE<br>EMTKNQVSLSCAVKGFYPSDIAVEWESNGQPENNYKTTPPVLDSDGS*FLVSKLTVDKSR<br>WQQGNVFSCSVMHEALHNHYTQKSLSLSPGK |
| 2186-<br>B04_HC_F404TAG_<br>Hole<br>SEQ ID NO: 1046 | MEVQLVESGGGLVQPGGSLRLSCAASGENIAGYAIHWVRQAPGKGLEWVGLITPTPGTSN<br>YADSVKGRFTISVDTSKNTAYLQMNSLRAEDTAAYYCARDYRGVYLYSFYYDYWGQGTLV<br>TVSSASTKGPSVFPLAPSSKSTSGGTAALGCLVKDYFPEPVTVSWNSGALTSGVHTEPAV<br>LQSSGLYSLSSVVTVPSSSLGTQTYICNVNHKPSNTKVDKKVEPKSCDKTHTCPPCPAPE<br>LLGGPSVFLFPPKPKDTLMISRTPEVTCVVVDVSHEDPEVKENWYVDGVEVHNAKTKPRE<br>EQYNSTYRVVSVLTVLHQDWLNGKEYKCKVSNKALPAPIEKTISKAKGQPREPQVYTLPP<br>SREEMTKNQVSLSCAVKGFYPSDIAVEWESNGQPENNYKTTPPVLDSDGS*FLVSKLTVD<br>KSRWQQGNVFSCSVMHEALHNHYTQKSLSLSPGK |
| 1987-<br>C06_HC_F404TAG_<br>Hole<br>SEQ ID NO: 1047 | MEVQLVESGGGLVQPGGSLRLSCAASGENITSYGIHWVRQAPGKGLEWVGWIAPNSGNTY<br>YADSVKGRFTISADTSKNTAYLQMNSLRAEDTAVYYCARDIVSTYSYYYLMDYWGQGTLV<br>TVSSASTKGPSVFPLAPSSKSTSGGTAALGCLVKDYFPEPVTVSWNSGALTSGVHTEPAV<br>LQSSGLYSLSSVVTVPSSSLGTQTYICNVNHKPSNTKVDKKVEPKSCDKTHTCPPCPAPE<br>LLGGPSVFLFPPKPKDTLMISRTPEVTCVVVDVSHEDPEVKENWYVDGVEVHNAKTKPRE<br>EQYNSTYRVVSVLTVLHQDWLNGKEYKCKVSNKALPAPIEKTISKAKGQPREPQVYTLPP<br>SREEMTKNQVSLSCAVKGFYPSDIAVEWESNGQPENNYKTTPPVLDSDGS*FLVSKLTVD<br>KSRWQQGNVFSCSVMHEALHNHYTQKSLSLSPGK |
| 2188-D04 IgG<br>HC<br>Y180/F241/F404<br>TAG P011531_0<br>SEQ ID NO: 1048 | MEVQLVESGGGLVQPGGSLRLSCAASGENISDYDIHWVRQAPGKGLEWVGGIDPADGSTD<br>YADSVKGRFTISADTSKNTAYLQMNSLRAEDTAVYYCARDYGVYDWGQGTLVTVSSAST<br>KGPSVFPLAPSSKSTSGGTAALGCLVKDYFPEPVTVSWNSGALTSGVHTFPAVLQSSGL*<br>SLSSVVTVPSSSLGTQTYICNVNHKPSNTKVDKKVEPKSCDKTHTCPPCPAPELLGGPSV<br>*LFPPKPKDTLMISRTPEVTCVVVDVSHEDPEVKENWYVDGVEVHNAKTKPREEQYNSTY<br>RVVSVLTVLHQDWLNGKEYKCKVSNKALPAPIEKTISKAKGQPREPQVYTLPPSREEMTK<br>NQVSLTCLVKGFYPSDIAVEWESNGQPENNYKTTPPVLDSDGS*FLYSKLTVDKSRWQQG<br>NVFSCSVMHEALHNHYTQKSLSLSPGK |
| (trastuzumab LC<br>SerOpt<br>K42TAG/E161TAG/<br>TCT162AGC<br>SEQ ID NO: 1049 | MDIQMTQSPSSLSASVGDRVTITCRASQDVNTAVAWYQQKPG*APKLLIYSASFLYSGVP<br>SRFSGSRSGTDFTLTISSLQPEDFATYYCQQHYTTPPTFGQGTKVEIKRTVAAPSVFIEP<br>PSDEQLKSGTASVVCLLNNFYPREAKVQWKVDNALQSGNSQ*SVTEQDSKDSTYSLSSTL<br>TLSKADYEKHKVYACEVTHQGLSSPVTKSENRGEC |
| trastuzumab LC<br>SerOpt K42TAG<br>SEQ ID NO: 1050 | MDIQMTQSPSSLSASVGDRVTITCRASQDVNTAVAWYQQKPG*APKLLIYSASFLYSGVP<br>SRFSGSRSGTDFTLTISSLQPEDFATYYCQQHYTTPPTFGQGTKVEIKRTVAAPSVFIFP<br>PSDEQLKSGTASVVCLLNNFYPREAKVQWKVDNALQSGNSQESVTEQDSKDSTYSLSSTL<br>TLSKADYEKHKVYACEVTHQGLSSPVTKSENRGEC |
| Trastuzumab LC<br>SerOpt<br>SEQ ID NO: 1051 | MDIQMTQSPSSLSASVGDRVTITCRASQDVNTAVAWYQQKPGKAPKLLIYSASFLYSGVP<br>SRESGSRSGTDFTLTISSLQPEDFATYYCQQHYTTPPTFGQGTKVEIKRTVAAPSVFIFP<br>PSDEQLKSGTASVVCLLNNFYPREAKVQWKVDNALQSGNSQESVTEQDSKDSTYSLSSTL<br>TLSKADYEKHKVYACEVTHQGLSSPVTKSENRGEC |

EQUIVALENTS

The disclosure set forth above may encompass multiple distinct inventions with independent utility. Although each of these inventions has been disclosed in its preferred form(s), the specific embodiments thereof as disclosed and illustrated herein are not to be considered in a limiting sense, because numerous variations are possible. The subject matter of the inventions includes all novel and nonobvious combinations and subcombinations of the various elements, features, functions, and/or properties disclosed herein. The following claims particularly point out certain combinations and subcombinations regarded as novel and nonobvious. Inventions embodied in other combinations and subcombinations of features, functions, elements, and/or properties may be claimed in this application, in applications claiming priority from this application, or in related applications. Such claims, whether directed to a different invention or to the same invention, and whether broader, narrower, equal, or different in scope in comparison to the original claims, also are regarded as included within the subject matter of the inventions of the present disclosure.

One or more features from any embodiments described herein or in the figures may be combined with one or more features of any other embodiments described herein or in the figures without departing from the scope of the invention.

All publications, patents and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A conjugate comprising an antibody that specifically binds to receptor tyrosine kinase orphan receptor 1 (ROR1), the antibody being linked site-specifically to at least one payload moiety and comprising one or more non-natural amino acids and:
   (a) (i) a $V_H$ region comprising: a CDR-H1 comprising at least one of SEQ ID NOs: 4 and 171; a CDR-H2 comprising at least one of SEQ ID NOs: 338 and 505; and a CDR-H3 comprising SEQ ID NO: 672; and (ii) a VL comprising: a CDR-L1 comprising SEQ ID NO: 839; a CDR-L2 comprising SEQ ID NO: 844; and a CDR-L3 comprising SEQ ID NO: 849;
   (b) (i) a $V_H$ region comprising: a CDR-H1 comprising at least one of SEQ ID NOs: 9 and 176; a CDR-H2 comprising at least one of SEQ ID NOs: 343 and 510; and a CDR-H3 comprising SEQ ID NO: 677; and (ii) a VI region comprising: a CDR-L1 comprising SEQ ID NO: 839; a CDR-L2 comprising SEQ ID NO: 844; and a CDR-L3 comprising SEQ ID NO: 849; or
   (c) (i) a $V_H$ region comprising: a CDR-H1 comprising at least one of SEQ ID NOs: 45 and 212; a CDR-H2 comprising at least one of SEQ ID NOs: 379 and 546; and a CDR-H3 comprising SEQ ID NO: 713; and (ii) a VI region comprising: a CDR-L1 comprising SEQ ID NO: 839; a CDR-L2 comprising SEQ ID NO: 844; and a CDR-L3 comprising SEQ ID NO: 849.

2. The conjugate of claim 1, wherein the one or more non-natural amino acids is at an amino acid site other than the amino terminus or the carboxy terminus of the antibody.

3. The conjugate of claim 1, wherein the one or more non-natural amino acids are selected from the group consisting of: HC-F404, HC-K121, HC-Y180, HC-F241, HC-221, LC-T22, LC-S7, LC-N152, LC-K42, LC-E161, LC-D170, HC-S136, HC-S25, HC-A40, HC-S119, HC-S190, HC-K222, HC-R19, HC-Y52, and HC-S70, according to the Kabat, Chothia, or EU numbering scheme.

4. The conjugate of claim 1, wherein the antibody comprises one or more non-natural amino acids at sites selected from the group consisting of: HC-F404, HC-Y180, HCF241, and LC-K42, according to the Kabat or EU numbering scheme of Kabat.

5. The conjugate of claim 1, wherein a residue of the one or more non-natural amino acids is linked to the payload moiety by way of a cleavable linker.

6. The conjugate of claim 1, wherein the one or more non-natural amino acids is selected from the group consisting of p-acetyl-L-phenylalanine, O-methyl-L-tyrosine, an -3-(2-naphthyl) alanine, 3-methyl-phenylalanine, O-4-allyl-L-tyrosine, 4-propyl-L-tyrosine, a tri-O-acetyl-GlcNAcß-serine, L-Dopa, fluorinated phenylalanine, isopropyl-L-phenylalanine, p-azido-L-phenylalanine, p-azido-methyl-L-phenylalanine, (2S)-2-amino-3-(3-azidopyrrolidine-1-carboxamido) propanoic acid, (S)-2-amino-3-(6-((6-methyl-1,2,4,5-tetrazin-3-yl)amino)pyridin-3-yl) propanoic acid, p-acyl-L-phenylalanine, p-benzoyl-L-phenylalanine, L-phosphoserine, phosphonoserine, phosphonotyrosine, p-iodo-phenylalanine, p-bromophenylalanine, p-amino-L-phenylalanine, isopropyl-L-phenylalanine, and p-propargyloxy-phenylalanine.

7. The conjugate of claim 1, wherein the one or more non-natural amino acids is p-azidomethylphenylalanine or p-azido-methyl-L-phenylalanine.

8. The conjugate of claim 1, wherein the payload moiety is selected from the group consisting of maytansines, hemiasterlins, amanitins, camptothecans, exatecans, anthracyclines, pyrrolobenzodiazepines, and auristatins.

9. The conjugate of claim 1, wherein the payload moiety is selected from the group consisting of DM1, hemiasterlin, amanitin, camptothecan, exatecan, exatecan derivative (Dxd), SN-38, PNU-159862, PNU derivative (PNU-EDA), pyrrolobenzodiazepine, MMAF, and MMAE.

10. The conjugate of claim 1, wherein the antibody conjugate is represented by:

(c) (i) a $V_H$ region comprising: a CDR-H1 comprising SEQ ID NO: 212; a CDR-H2 comprising SEQ ID NO: 546; and a CDR-H3 comprising SEQ ID NO: 713; and (ii) a VL region comprising: a CDR-L1 comprising SEQ ID NO: 839; a CDR-L2 comprising SEQ ID NO: 844; and a CDR-L3 comprising SEQ ID NO: 849.

12. The conjugate of claim 1, wherein the antibody comprises (a) a $V_H$ region comprising: a CDR-H1 comprising SEQ ID NO: 171; a CDR-H2 comprising SEQ ID NO: 505; and a CDR-H3 comprising SEQ ID NO: 672; and (b) a Vl comprising: a CDR-L1 comprising SEQ ID NO: 839; a CDR-L2 comprising SEQ ID NO: 844; and a CDR-L3 comprising SEQ ID NO: 849.

13. The conjugate of claim 1, wherein the antibody conjugate comprises:
an antibody comprising: a $V_H$ region comprising: a CDR-H1 comprising at least one of SEQ ID NOs: 45 and 212; a CDR-H2 comprising at least one of SEQ ID NOs: 379 and 546; and

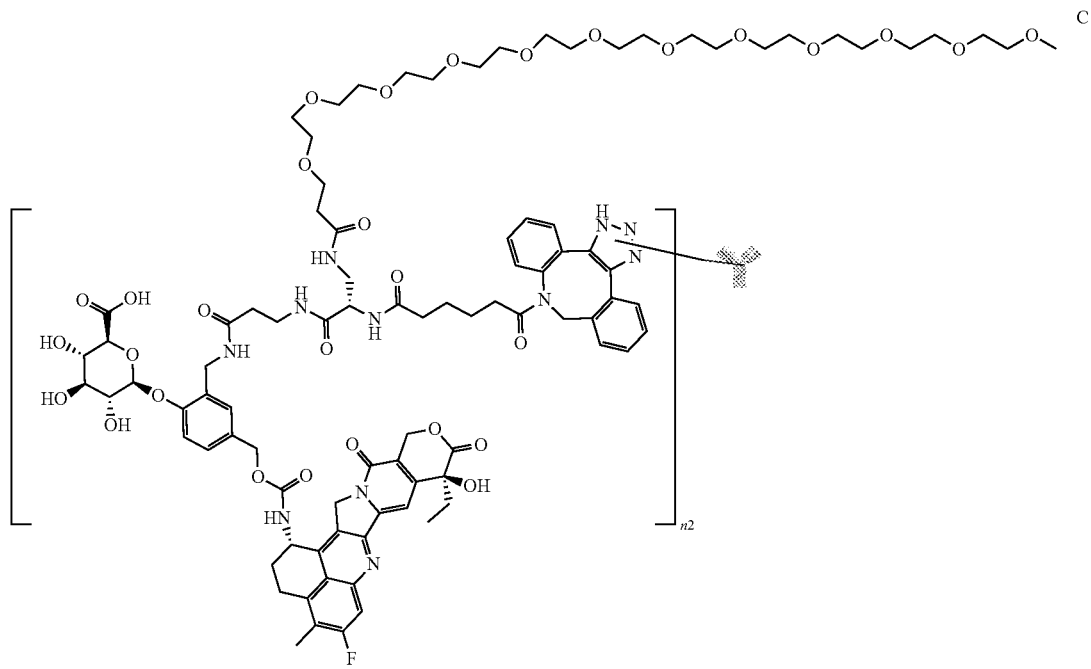

wherein n2 is an integer from 1 to 10.

11. The conjugate of claim 1, wherein the antibody comprises:
(a) (i) a $V_H$ region comprising: a CDR-H1 comprising SEQ ID NO: 171; a CDR-H2 comprising SEQ ID NO: 505; and a CDR-H3 comprising SEQ ID NO: 672; and
(ii) a VL comprising: a CDR-L1 comprising SEQ ID NO: 839; a CDR-L2 comprising SEQ ID NO: 844; and a CDR-L3 comprising SEQ ID NO: 849;
(b) (1) a $V_H$ region comprising: a CDR-H1 comprising SEQ ID NO: 176; a CDR-H2 comprising SEQ ID NO: 510; and a CDR-H3 comprising SEQ ID NO: 677; and
(ii) a VL region comprising: a CDR-L1 comprising SEQ ID NO: 839; a CDR-L2 comprising SEQ ID NO: 844; and a CDR-L3 comprising SEQ ID NO: 849; or a CDR-H3 comprising SEQ ID NO: 713; and a Vl region comprising: a CDR-L1 comprising SEQ ID NO: 839; a CDR-L2 comprising SEQ ID NO: 844; and a CDR-L3 comprising SEQ ID NO: 849; and para-azidomethylphenylalanine residues at antibody sites HC180, HC241, HC404, and LC42; and the conjugate has the following structure, wherein n2 is 8 and each linker-payload is bonded to one of the para-azidomethylphenylalanine residue side chains:

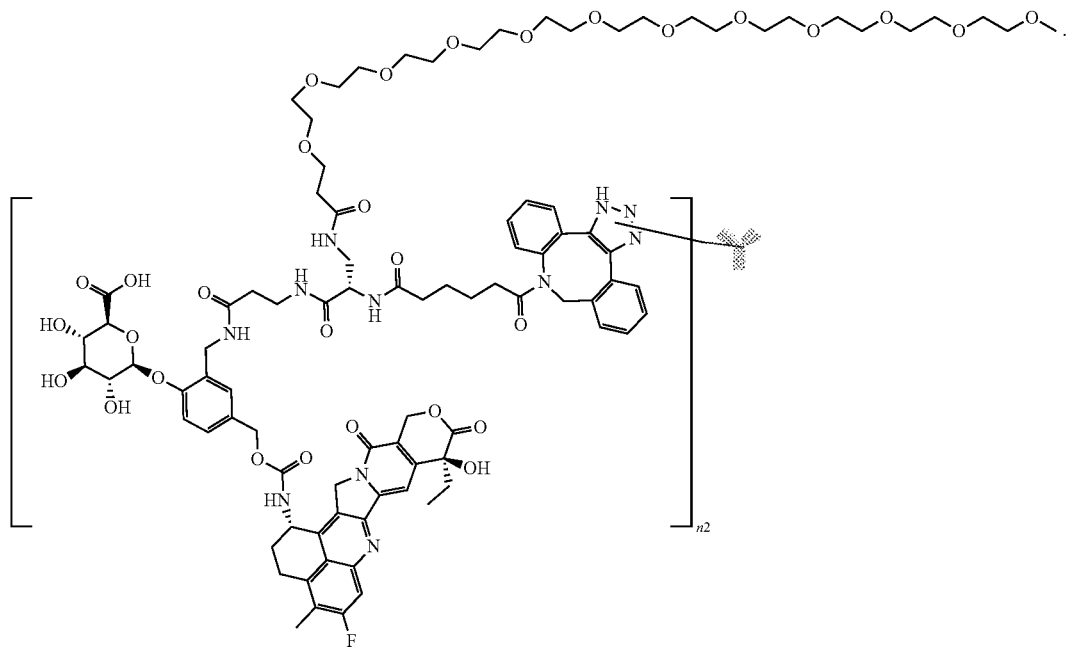

14. The conjugate of claim 1, wherein the antibody conjugate comprises:
   an antibody comprising: a $V_H$ region comprising: a CDR-H1 comprising at least one of SEQ ID NOs: 45 and 212; a CDR-H2 comprising at least one of SEQ ID NOs: 379 and 546; and
   a CDR-H3 comprising SEQ ID NO: 713; and a VI region comprising: a CDR-L1 comprising SEQ ID NO: 839; a CDR-L2 comprising SEQ ID NO: 844; and a CDR-L3 comprising SEQ ID NO: 849; and
   para-azidomethylphenylalanine residues at antibody sites HC180, HC241, and HC404; and
the conjugate has the following structure, wherein n2 is 8 and each linker-payload is bonded to one of the para-azidomethylphenylalanine residue side chains:

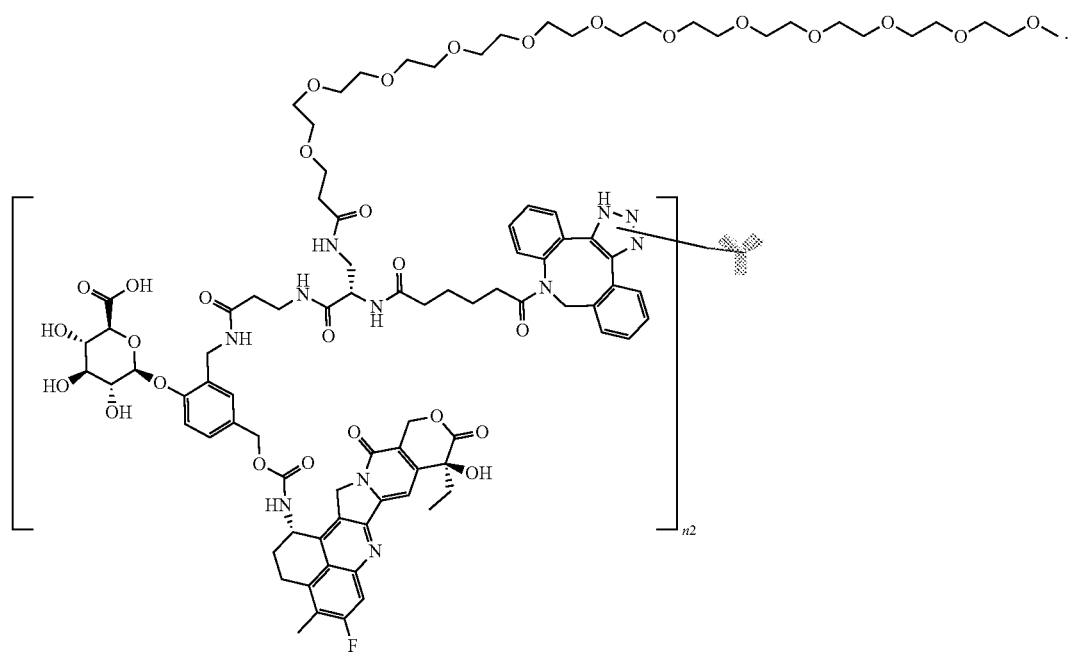

15. The conjugate of claim 1, wherein the antibody comprises: (a) a $V_H$ region comprising SEQ ID NO: 895; and (b) a Vl region comprising SEQ ID NO: 1021.

16. The conjugate of claim 1, wherein the antibody is a monoclonal antibody.

17. The conjugate of claim 1, wherein the antibody is an IgA, an IgD, an IgE, an IgG, or an IgM.

18. The conjugate of claim 1, wherein the antibody is humanized or human.

19. The conjugate of claim 1, wherein the antibody is aglycosylated.

20. The conjugate of claim 1, wherein the antibody is an antibody fragment.

21. The conjugate of claim 20, wherein the antibody fragment is selected from an Fv fragment, a Fab fragment, a F(ab')2 fragment, a Fab' fragment, an scFv (sFv) fragment, and an scFv-Fc fragment.

22. A pharmaceutical composition comprising the conjugate of claim 1 and a pharmaceutically acceptable carrier.

23. A method of reducing the proliferation of cells expressing ROR-1 in a subject in need thereof, comprising administering to the subject an effective amount of the conjugate of claim 1.

24. A method of treating a disease or condition in a subject in need thereof, comprising administering to the subject an effective amount of the conjugate of claim 1, wherein the disease or condition is a hematological cancer, a solid tumor cancer, colorectal cancer, breast cancer, ovarian cancer, cervical cancer, lung cancer, head and neck cancer, renal cell carcinoma, or endometrial carcinoma, and is characterized by the expression of ROR-1.

\* \* \* \* \*